(12) United States Patent
Meibom et al.

(10) Patent No.: US 12,398,120 B2
(45) Date of Patent: Aug. 26, 2025

(54) SUBSTITUTED HYDANTOINAMIDES AS ADAMTS7 ANTAGONISTS

(71) Applicants: BAYER AKTIENGESELLSCHAFT, Leverkusen (DE); THE BROAD INSTITUTE, INC., Cambridge, MA (US)

(72) Inventors: Daniel Meibom, Wuppertal (DE); Yolanda Cancho Grande, Leverkusen (DE); Pierre Wasnaire, Düsseldorf (DE); Sarah Anna Liesa Johannes, Hilden (DE); Kristin Beyer, Hilden (DE); Till Freudenberger, Velbert (DE); Damian Brockschnieder, Haan (DE); Dmitry Zubov, Remscheid (DE); Dzianis Menshykau, Düsseldorf (DE); Tanja Krainz, Cambridge, MA (US); Bryan MacDonald, Cambridge, MA (US); Yi Xing, Cambridge, MA (US); Nadine Elowe, Cambridge, MA (US); Guzman Sanchez, Murcia (ES)

(73) Assignees: BAYER AKTIENGESELLSCHAFT, Leverkusen (DE); THE BROAD INSTITUTE, INC., Cambridge, MA (US)

( * ) Notice: Subject to any disclaimer, the term of this patent is extended or adjusted under 35 U.S.C. 154(b) by 727 days.

(21) Appl. No.: 17/776,987

(22) PCT Filed: Nov. 12, 2020

(86) PCT No.: PCT/EP2020/081878
§ 371 (c)(1),
(2) Date: May 13, 2022

(87) PCT Pub. No.: WO2021/094436
PCT Pub. Date: May 20, 2021

(65) Prior Publication Data
US 2023/0027346 A1    Jan. 26, 2023

(30) Foreign Application Priority Data
Nov. 15, 2019 (EP) .................................. 19383014

(51) Int. Cl.
*A61P 9/00*      (2006.01)
*A61K 31/4166*   (2006.01)
*A61K 31/4174*   (2006.01)
*A61K 31/4178*   (2006.01)
*A61K 31/4245*   (2006.01)
*A61K 31/427*    (2006.01)
(Continued)

(52) U.S. Cl.
CPC ........ *C07D 403/04* (2013.01); *A61K 31/4166* (2013.01); *A61K 31/4174* (2013.01);
(Continued)

(58) Field of Classification Search
CPC .................................................... C07D 403/04
See application file for complete search history.

(56) References Cited

U.S. PATENT DOCUMENTS 3,966,781 A    6/1976 Atkinson
7,781,470 B2   8/2010 Alonso-Alija et al.
(Continued)

FOREIGN PATENT DOCUMENTS

WO    0006568 A1    2/2000
WO    0006569 A1    2/2000
(Continued)

OTHER PUBLICATIONS

Atzrodt, J. et al. (2007). "The Renaissance of H/D Exchange," Angew. Chem. Int. Ed.; 46:7744-7765.
(Continued)

*Primary Examiner* — Jennifer A Berrios
*Assistant Examiner* — Connor K English
(74) *Attorney, Agent, or Firm* — MORRISON & FOERSTER LLP

(57) ABSTRACT

The application relates to substituted hydantoinamides of formula (I) as ADAMTS7 antagonists, to processes for their preparation, their use alone or in combination for the treatment or prophylaxis of diseases, in particular of cardiovascular diseases, including atherosclerosis, coronary artery disease (CAD), peripheral vascular disease (PAD), arterial occlusive disease or restenosis after angioplasty. $R^1$ is hydrogen, alkyl, cycloalkyl, heterocycloalkyl, heteroaryl or phenyl; $R^2$ is hydrogen, cyano, halogen, alkylsulfonyl, alkyl, cycloalkyl or alkoxy; $R^3$, $R^4$, $R^5$, $R^6$, $R^7$ and $R^8$ are independently hydrogen, halogen, alkyl or alkoxy; most groups being optionally substituted; with the proviso that at least one of $R^2$, $R^3$, $R^4$ is H; $X^1$, $X^2$, $X^3$, $X^4$, $X^5$ and $X^6$ are independently N or C; with the proviso that in each ring maximal one X is N.

17 Claims, 20 Drawing Sheets
Specification includes a Sequence Listing.

(51) Int. Cl.
| | | |
|---|---|---|
| A61K 31/433 | (2006.01) | |
| A61K 31/4439 | (2006.01) | |
| A61K 31/497 | (2006.01) | |
| A61K 31/501 | (2006.01) | |
| C07D 233/02 | (2006.01) | |
| C07D 401/12 | (2006.01) | |
| C07D 401/14 | (2006.01) | |
| C07D 403/04 | (2006.01) | |
| C07D 405/04 | (2006.01) | |
| C07D 405/14 | (2006.01) | |
| C07D 417/04 | (2006.01) | |
| C07D 417/14 | (2006.01) | |

(52) U.S. Cl.
CPC ...... *A61K 31/4178* (2013.01); *A61K 31/4245* (2013.01); *A61K 31/427* (2013.01); *A61K 31/433* (2013.01); *A61K 31/4439* (2013.01); *A61K 31/497* (2013.01); *A61K 31/501* (2013.01); *A61P 9/00* (2018.01); *C07D 233/02* (2013.01); *C07D 401/12* (2013.01); *C07D 401/14* (2013.01); *C07D 405/04* (2013.01); *C07D 405/14* (2013.01); *C07D 417/04* (2013.01); *C07D 417/14* (2013.01)

(56) References Cited

U.S. PATENT DOCUMENTS

| | | |
|---|---|---|
| 8,796,324 B2 | 8/2014 | Bruggemeier et al. |
| 8,796,335 B2 | 8/2014 | Hahn et al. |
| 8,981,104 B2 | 3/2015 | Hahn et al. |
| 9,266,871 B2 | 2/2016 | Follmann et al. |
| 9,687,476 B2 | 6/2017 | Fürstner et al. |
| 9,993,476 B2 | 6/2018 | Follmann et al. |

FOREIGN PATENT DOCUMENTS

| | | |
|---|---|---|
| WO | 0119355 A2 | 3/2001 |
| WO | 0119780 A2 | 3/2001 |
| WO | 0144200 A2 | 6/2001 |
| WO | 0242301 A1 | 5/2002 |
| WO | 02096426 A1 | 12/2002 |
| WO | 03095451 A1 | 11/2003 |
| WO | 2004024715 A1 | 3/2004 |
| WO | 2004024721 A1 | 3/2004 |
| WO | 2004108086 A2 | 12/2004 |
| WO | 2010105770 A1 | 9/2010 |
| WO | 2011104322 A1 | 9/2011 |
| WO | 2011147809 A1 | 12/2011 |
| WO | 2012004258 A1 | 1/2012 |
| WO | 2012028647 A1 | 3/2012 |
| WO | 2012059549 A1 | 5/2012 |
| WO | 2012004258 A9 | 6/2012 |
| WO | 2012112363 A1 | 8/2012 |
| WO | 2012139888 A1 | 10/2012 |
| WO | 2014012934 A1 | 1/2014 |
| WO | 2014066151 A1 | 5/2014 |
| WO | 2014068099 A1 | 5/2014 |
| WO | 2014131760 A1 | 9/2014 |
| WO | 2016071212 A1 | 5/2016 |
| WO | 2017211666 A1 | 12/2017 |
| WO | 2017211667 A1 | 12/2017 |
| WO | 2018069532 A1 | 4/2018 |

OTHER PUBLICATIONS

Bengtsson, E. et al. (Jun. 16, 2017) "ADAMTS-7 is associated with ahigh-risk plaque phenotype in human atherosclerosis," Scientific Reports; 7(1):1-12.

Chan, K. et al. (Oct. 31, 2017) "Genetic Variation at the ADAMTS7 Locus is Associated With Reduced Severity of Coronary Artery Disease," Journal of the American Heart Association, 9 pages.

Chandrasekhar, S. et al. (2011) "Flow chemistry approach for partial deuteration of alkynes: synthesis of deuterated taxol side chain," Tetrahedron Letters 52:3865-3867.

Du, Y. et al. (Nov. 2012) "Upregulation of a Disintegrin and Metalloproteinase With Thrombospondin Motifs-7 by miR-29 Repression Mediates Vascular Smooth Muscle Calcification," Arterioscler Thromb Vasc Biol, 32(11):2580-2588.

Durham, T. B. et al. (2014) "Identification of Potent and Selective Hydantoin Inhibitors of Aggrecanase-1 and Aggrecanase-2 That Are Efficacious in Both Chemical and Surgical Models of Osteoarthritis," J. Med. Chem., 57:10476-10485.

Esaki, H., et al. (2006) "General method of obtaining deuterium-labeled heterocyclic compounds using neutral D20 with heterogeneous Pd/C," Tetrahedron, 62:10954-10961.

Esaki, H., et al. (2007) "Efficient H/D Exchange Reactions of Alkyl-Substituted Benzene Derivatives by Means of the Pd/C—H2—D2O System," Chem. Eur. J., 13:4052-4063.

Galis, Z. S. et al. (Feb. 22, 2002) "Matrix Metalloproteinases in Vascular Remodeling and Atherogenesis The Good, the Bad, and the Ugly," Circulation Research, 90(3):251-262.

Hanzlik, R et al. (1990). "Active Site Dynamics of Toluene Hydroxylation by Cytochrome P-4501," J. Org. Chem.; 55(13):3992-3997.

Jarman, M. (1995) "The Deuterium Isotope Effect for the α-hydroxylation of Tamoxifen by Rat Liver Microsomes Accounts for the Reduced Genotoxicity of [D5-ethyl]tamoxifen," Carcinogenesis, 16(4):683-688.

Jungbauer, L. M et al. (2009) "Preparation of fluorescently-labeledamyloid-beta peptide assemblies: the effect of fluorophore conjugation on structure and function," J. Mol. Recognit. 22:403-413.

Kelwick, R. et al. (2015) "The Adamts (A Disintegrin and Metalloproteinase with Thrombospondin motifs) family," Genome Biology; 16(113):1-16.

Kushner, D.J et al. (1999). "Pharmacological uses and perspectives of heavy water and deuterated compounds," Canadian J. of Phys. and Pharm., 77(2): 79-88. (Abstract Only).

Leis, H.J. et al. (1998). "Stable Isotope Labeled Target Compounds: Preparation and Use as Internal Standards in Quantitative Miss Spectrometry," Curr. Org. Chem.; 2(2):131-144.

Liu, C-J. (Jan. 2009) "The role of ADAMTS-7 and ADAMTS-12in the pathogenesis of arthritis," Nature Clinical Practice Rheumatology; 5(1):38-45.

Liu, C-J et al. (May 2006) "ADAMTS-7: a metalloproteinase that directly binds to and degrades cartilage oligomeric matrix protein," Faseb J.; 20(7):988-990.

Luan, Y et al. (2008) "Inhibition of ADAMTS-7 and ADAMTS-12 degradation of cartilage oligomeric matrix protein by alpha-2-macroglobulin," Osteoarthritis and Cartilage; 16:1413-1420.

Malfait, A-M. et al. (Jun. 21, 2022) "Inhibition of ADAM-TS4 and ADAM-TS5 Prevents Aggrecan Degradation in Osteoarthritic Cartilage," Journal of Biological Chemistry; 277(25):22201-22208.

Maltais, F. et al. (2009). "In Vitro and In Vivo Isotope Effects with Hepatitis C Protease Inhibitors: Enhanced Plasma Exposure of Deuterated Telaprevir versus Telaprevir in Rats," J. Med. Chem.; 52(24):7993-8001.

Matoishi, K. et al. (2000). "The first synthesis of both enantiomers of [a-2H]phenylacetic acid in high enantiomeric excess," Chem. Commun.; pp. 1519-1520.

Mutlib A. E. et al. (2000) "The Species-Dependent Metabolism of Efavirenz Produces a Nephrotoxic Glutathione Conjugate in Rats," Toxicology and Applied Pharmacology; 169:102-113.

Perrin, C. et al. (2005) "Stereochemistry of B-Deuterium Isotope Effects on Amine Basicity," J Am Chem Soc; 127:9641-9647.

Perrin, C. et al. (2007). "Secondary Deuterium Isotope Effects on the Acidity of Carboxylic Acids and Phenols," J. Am. Chem. Soc.; 129(14):4490-4497.

Perrin, C., et al. (2003) "β-Deuterium Isotope Effects on Amine Basicity, "Inductive" and Stereochemical," J. Am. Chem. Soc., 125:15008-15009.

Peterson J. T. (2006) "The importance of estimating the therapeutic index in the development of matrix metalloproteinase inhibitors," Cardiovascular Research; 69:677-687.

(56) References Cited

OTHER PUBLICATIONS

Qin W. et al. (2017) "Upregulation of ADAMTS-7 and downregulation of COMP are associated with aortic aneurysm," Molecular Medicine Reports; 16:5459-5463.
Reider, P.J. et al. (Jul. 1, 1987). "Synthesis of (R)-Serine-2-d and Its Conversion to the Broad-Spectrum Antibiotic Fludalanine," J. Org. Chem. 52:3326-3334.
Reilly; M. P. et al. (Jan. 29, 2011) "Identification of ADAMTS7 as a novel locus for coronary atherosclerosis and association of ABO with myocardial infarction in the presence of coronary atherosclerosis: two genome-wide association studies," Lancet; 377(9763):383-392.
Roy R. et al. (Oct. 15, 2008) "Tumor-Specific Urinary Matrix Metalloproteinase Fingerprinting: Identification of High Molecular Weight Urinary MatrixMetalloproteinase Species;" Clin. Cancer Res; 14(20):6610-6617.
Schneider, F. et al. (2006). Enhanced Plasma Concentration by Selective Deuteration of Rofecoxib in Rats, Arzneim.-Forsch./Drug Res.; 56(4):295-300.
Schunkert, H. et al. (Apr. 2011) "Large-scale association analysis identifies 13 new susceptibility loci for coronary artery disease," Nature Genetics; 43(4):333-338.
Sharma, A. et al. (2013). "Nevirapine Bioactivation and Covalent Binding in the Skin," Chem. Res. Toxicol.; 26:410-421.
Somerville R. P. et al. (Aug. 20, 2004) "ADAMTS7B, the Full-length Product of the ADAMTS7 Gene, Is a Chondroitin Sulfate Proteoglycan Containing a Mucin Domain," Journal of Biological Chemistry; 279(34):35159-35175.
Stanton H. et al. (2011) "Proteoglycan degradation by the ADAMTS family of proteinases," Biochimica et Biophysica Acta; 1812:1616-1629.
Wang L. et al. (2009) "ADAMTS-7 Mediates Vascular Smooth Muscle Cell Migration and Neointima Formation in Balloon-Injured Rat Arteries;" Circulation Research; 104(5):688-698.
Wang L. et al. (Aug. 25, 2010) "ADAMTS-7, a novel proteolytic culprit in vascular remodeling," Acta Physiologica Sinica, 62(4):285-294.
Wenthur, C. et al. (2013) "Discovery of (R)-(2-Fluoro-4-((-4-methoxyphenyl)ethynyl)phenyl) (3-Hydroxypiperidin-1-yl) methanone (ML337), An mGlu3 Selective and CNS Penetrant Negative Allosteric Modulator (NAM)," J Med Chem; 56:5208-5212.
Wu W. et al.(2015) "Association between plasma ADAMTS-7 levelsand ventricular remodeling in patients with acute myocardial infarction," European Journal of Medical Research; 20(27):1-6.
You L et al. (2016) "ADAMTS7 locus confers high cross-race risk for development of coronary atheromatous plaque;" Mol. Genet Genomics 291:121-128.
Zhang Y. et al.(2015) "The Function and Roles of ADAMTS-7 in Inflammatory Diseases," Mediators of Inflammation; 2015:1-11.

```
hADAMTS7_Pro  PATEGRAALDIVHPVRVDAGGSFLSYELWPRALRKRDVSVRDAPAFYELQYRGRELRFN
rADAMTS7_Pro  LPTEGRAGLDIVHPVRVDAGGSFLSYELWPRVLRKRDVSAAQSSAFYQLQYQGRELLFN hADAMTS7_Pro  LTANQHLLAPGFVSETRRRGGLGRAHIRANTPACHLLGEVQDPELEGGLAAISACDGLKG
rADAMTS7_Pro  LTTNPYLLAPGFVSEIRRRSNLSNVHIQTSVPTCHLLGDVQDPELEGGFAAISACDGLRG hADAMTS7_Pro  VFQLSNEDYFIEPLDSAPARPGHAQPHVVYKRQAPERLAQRGDSSAPSTCGVQVYPELES
rADAMTS7_Pro  VFQLSNEDYFIEPLDEVPAQPGHAQPHMVYKHK---RSGQDDSRTSGTCGVQGSPELKH hADAMTS7_Pro  RRERWEQRQQWRRPRLRRILHQR
rADAMTS7_Pro  QREHWEQRQQKRR------QQR
```

Fig. 2B

```
hADAMTS7_CD   SVSKEKWVETLVVADAKMVEYHGQPQVESYVLTIMNMVAGLFHDPSIGNPIHITIVRLVL
rADAMTS7_CD   SISKEKWVETLVVADSKMVEYHGQPQVESYVLTIMNMVAGIYHDPSIGNPIHITVVRLII
                                                                        ::

hADAMTS7_CD   LEDEEEDLKITHHADNTLKSFCKWQKSINMKGDAHPLHHDTAILLTRKDLCAAMNRPCET
rADAMTS7_CD   LEDEEEKDLKITHHADDTLKNFCRWQKNVNMKGDDHPQHHDTAILLTRKDLCATMNHPCET hADAMTS7_CD   LGLSHVAGMCQPHRSCSINEDTGLPLAFTVAHELGHSFGIQHDGSGNDCEPVGKRPFIMS
rADAMTS7_CD   LGLSHVAGLCHPQLSCSVSEDTGLPLAFTVAHELGHSFGIQHDGTGNDCESIGKRPFIMS hADAMTS7_CD   PQLLYD-ANPLTWSRCSRQYITRFLDRGWGLCLDDPPAKDIIDFPSVPPGVLYDVSHQCR
rADAMTS7_CD   PQLLYDRGIPLTWSRCSREYITRFLDRGWGLCLDDRPSKGVINFPSVLPGVLYDVNHQCR hADAMTS7_CD   LQYGAYSAFCEDMDNVCHTLWCSVGTTCHSKLDAAVDGTRCGENKWCLSGECVPVGFRPE
rADAMTS7_CD   LQYGPSAYCEDVDNVCYTLWCSVGTTCHSKMDAAVDGTSCGKNKWCLNGECVPEGFQPE hADAMTS7_CD   AV
rADAMTS7_CD   TV
```

Fig. 2C

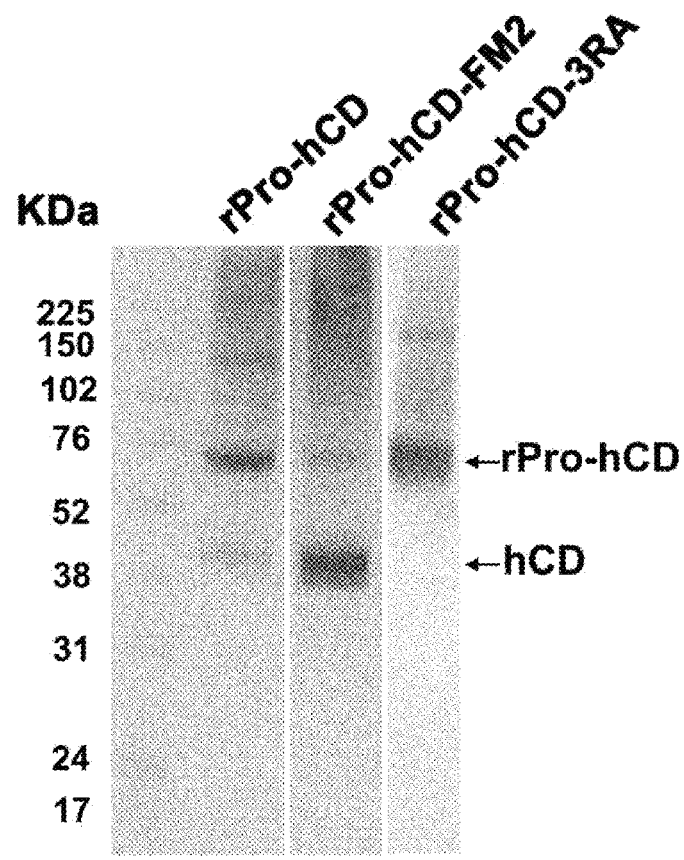

```
Rat_Pro    LPTEGRAGLDIVHPVRVDAGGSFLSYELWPRVLRKRDVSAAQASSAFYQLQYQGRELLFN
Mouse_Pro  LVTEGRAGLDIVHPVRVDAGGSFLSYELWPRVLRKRDVSTTQASSAFYQLQYQGRELLFN
           *:**********************************:*.******************

Rat_Pro    LTTNPYLLAPGFVSEIRRRSNLSNVHIQTSVPTCHLLGDVQDPELEGGFAAISACDGLRG
Mouse_Pro  LTTNPYLMAPGFVSEIRRHSTLGHAHIQTSVPTCHLLGDVQDPELEGGFAAISACDGLRG
           *******:**********:*.*..***********:************************

Rat_Pro    VFQLSNEDYFIEPLDEVPAQPGHAQPHMVYKHKRS---GQQDDSRTSGTCGVQGSPELKH
Mouse_Pro  VFQLSNEDYFIEPLDGVSAQPGHAQPHVVYKHQGSRKQAQQGDSRPSGTCGMQVPPDLEQ
           ***************.*.********:****:.*    .**.***.****:*.**:*:

Rat_Pro    QREHWEQRQQKRRQQR
Mouse_Pro  QREHWEQQQQKRRQQR
           *******:********
```

Alignment length: 196
Identity (*): 169 is 86.22%
Strongly similar (:): 12 is 6.12%
Weakly similar (.): 8 is 4.08%
Different: 7 is 3.57%

Fig. 5

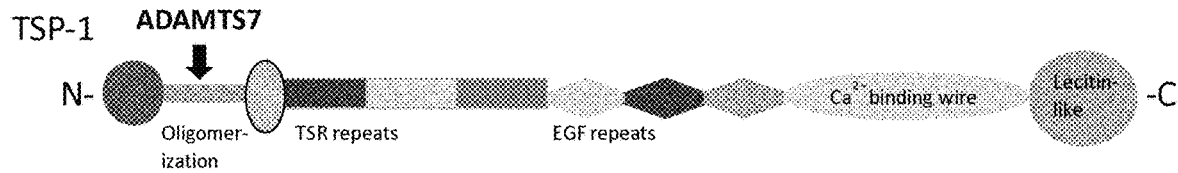

TSP1-1 (275-289) (Donor) DELSSMVLELRGLRT (K-Quencher)
TSP1-2 (278-292) (Donor) SSMVLELRGLRTIVT (K-Quencher)
TSP1-3 (300-314) (Donor) KVTEENKELANELRR (K-Quencher)
TSP1-4 (303-317) (Donor) EENKELANELRRPPL (K-Quencher)
TSP1-5 (278-289) (Donor) SSMVLELRGLRT (K-Quencher)

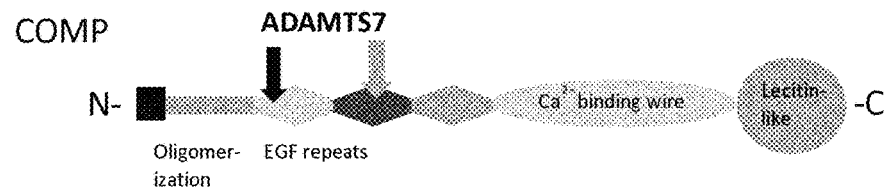

COMP1 (73-84) (Donor) GMQQSVRTGLPS (K-Quencher)
COMP2 (146-159) (Donor) SPGFRCEACPPGYS (K-Quencher)
Cysteines blocked with Acm (Acetamindomethyl)

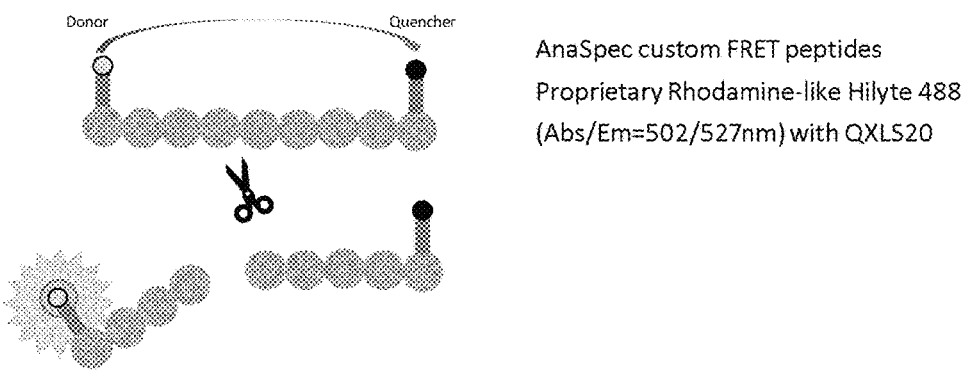

AnaSpec custom FRET peptides
Proprietary Rhodamine-like Hilyte 488
(Abs/Em=502/527nm) with QXLS20

Fig. 7A

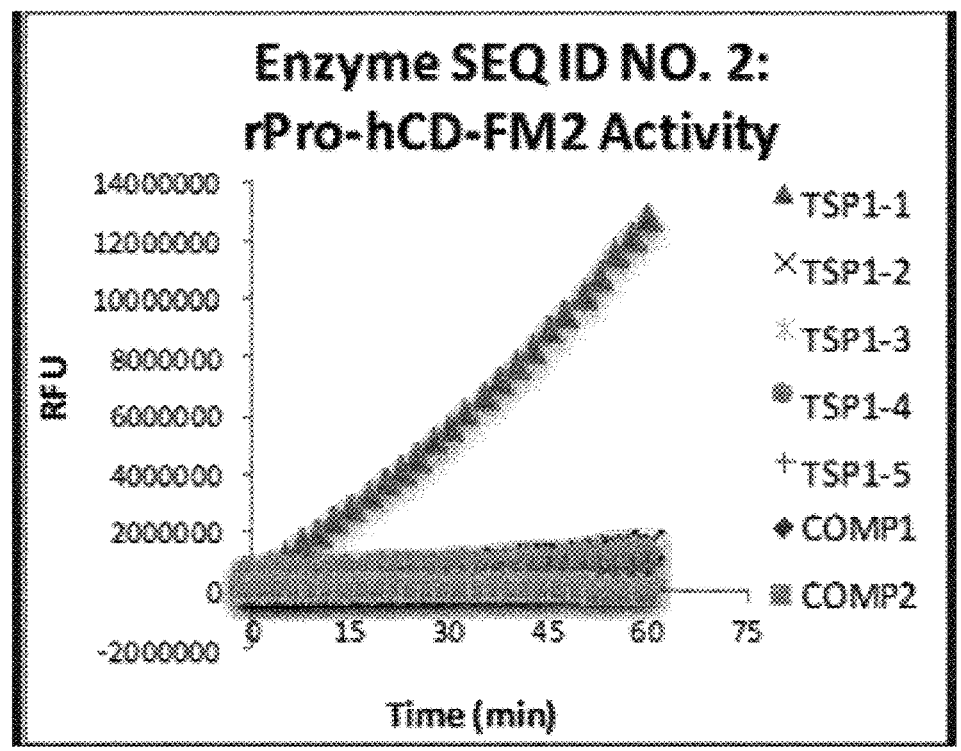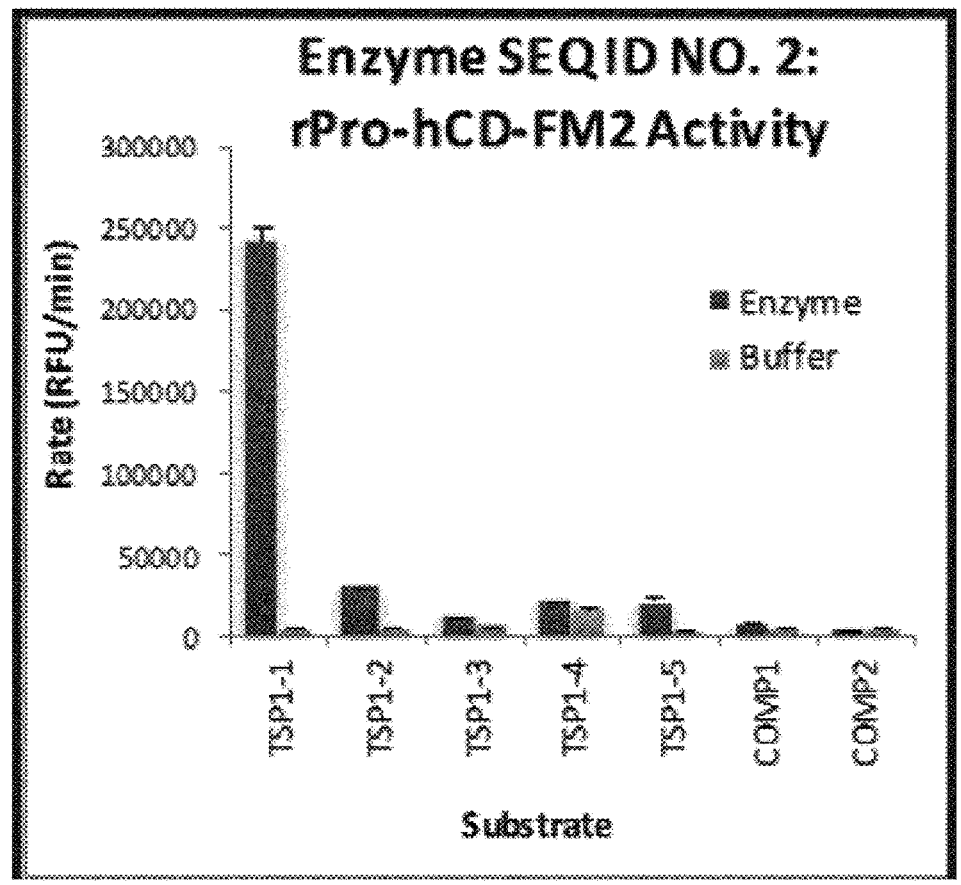
Fig. 8B

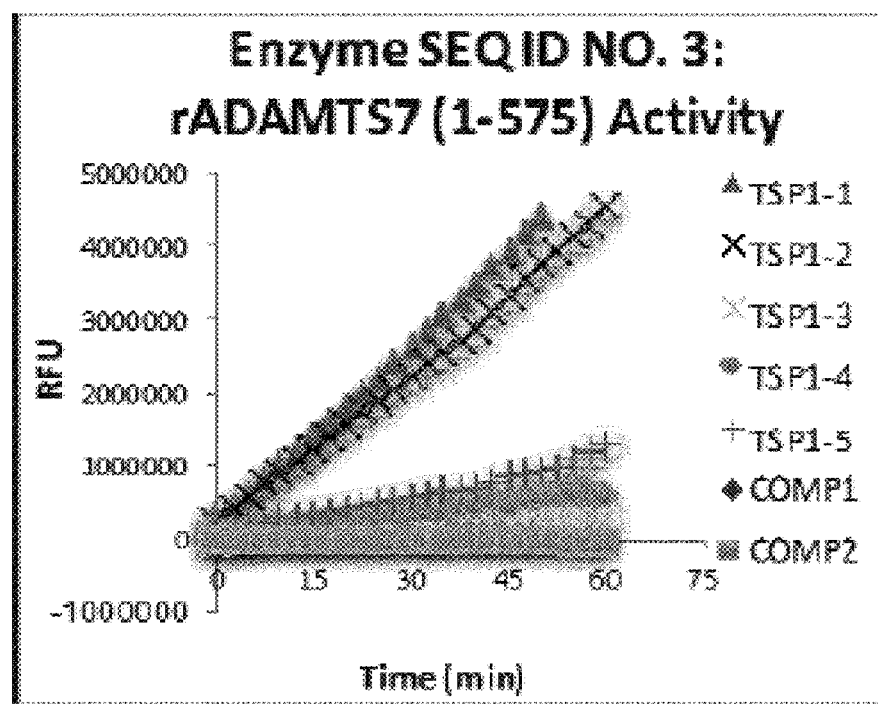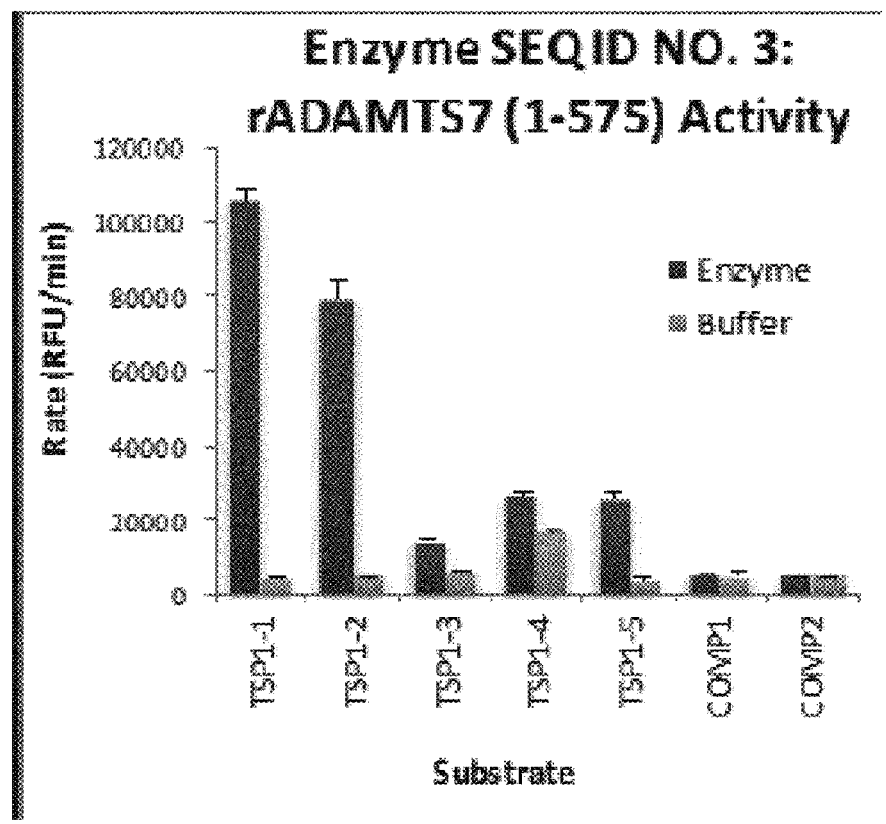
Fig. 8C

| SEQ ID NO | Substrate | aa# | Sequence | kcat (min⁻¹) | | |
|---|---|---|---|---|---|---|
| | | | | Enzyme SEQ ID NO. 1 (pPro-NCD) | Enzyme SEQ ID NO. 2 (pPro-NCD.M2) | Enzyme SEQ ID NO. 1 (L573I) |
| 4 | TSP1-1 | 275-289 | DELSSMVLELRGLRT | 2.1E-02 | 2.4E-02 | 1.0E-02 |
| 5 | TSP1-2 | 278-292 | SSMVLELRGLRTIVV | 3.2E-03 | 2.9E-03 | 7.7E-03 |
| 6 | TSP1-3 | 300-314 | KVTEENKELANELRR | 1.2E-03 | 1.2E-03 | 1.4E-03 |
| 7 | TSP1-4 | 303-317 | EENKELANELRRPPL | 2.0E-03 | 2.1E-03 | 2.6E-03 |
| 8 | TSP1-5 | 278-289 | SSMVLELRGLRT | 2.0E-03 | 2.1E-03 | 2.5E-03 |
| 9 | COMP1 | 73-84 | GMQDSVRTGLPS | 7.3E-04 | 7.6E-04 | 4.9E-04 |
| 10 | COMP2 | 146-159 | SPGFRC(Acm)EAC(Acm)PPQYS | 3.8E-04 | 3.9E-04 | 5.0E-04 |

Figure 9

SUBSTITUTED HYDANTOINAMIDES AS ADAMTS7 ANTAGONISTS

CROSS REFERENCE TO RELATED APPLICATIONS

This application is a national stage application under 35 U.S.C. § 371 of International Application No. PCT/EP2020/081878, filed internationally on Nov. 12, 2020, which claims the benefit to European Application No. 19383014.8, filed Nov. 15, 2019.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 777052064700SEQLIST.TXT, date recorded: May 13, 2022, size: 127,145 bytes).

FIELD OF THE INVENTION

The present application relates to substituted hydantoinamides, to processes for their preparation, their use alone or in combination for the treatment and/or prophylaxis of diseases as well as their use in the manufacturing-process of drugs which are used to treat and/or prophylactically treat diseases, in particular for the treatment and/or prophylaxis of heart diseases, vascular diseases, and/or cardiovascular diseases, including atherosclerosis, coronary artery disease (CAD), peripheral vascular disease (PAD)/arterial occlusive disease and/or restenosis after angioplasty (including the use of drug-coated or non drug-coated balloons and/or stent-implantation) and/or for the treatment and/or prophylaxis of lung diseases, inflammatory diseases, fibrotic diseases, metabolic diseases, cardiometabolic diseases and/or diseases/disease states affecting the kidneys and/or the central nervous and/or neurological system as well as gastrointestinal and/or urologic and/or ophthalmologic diseases/disease states.

BACKGROUND

The pathogenesis of cardiovascular diseases and/or lung diseases as well as metabolic, inflammatory and/or vascular disease states including atherosclerosis and post-angioplasty restenosis is—at least in part—characterized by vascular remodeling (Wang et al., Sheng Li Xue Bao. 2010 Aug. 25; 62(4):285-94), a process which—amongst others—involves (metallo-)proteinases (Galis & Kathri, Circ Res., 2002 Feb. 22; 90(3):251-62). Accordingly, it may be beneficial to therapeutically interfere with these proteases in the context of the aforementioned diseases/diseases states. However, a lot of clinical trials having used pan-metalloproteinase inhibitors failed, in part due to severe side effects. Peterson et al. ascribe these negative outcomes to an inadequate assessment of the therapeutic index of the drugs tested, leading to the assumption that it is even more so important to explore the role of individual pro teases (Wang et al., Sheng Li Xue Bao. 2010 Aug. 25; 62(4):285-94; Peterson, Cardiovasc. Res. 2006 Feb. 15; 69(3):677-87. Epub 2006 Jan. 17).

ADAMTS (a disintegrin and metalloproteinase with thrombospondin motifs) constitute a family of metalloproteases which consists of 19 secreted enzymes that have been described to be proteolytically active. ADAMTS play an important role in different processes such as assembly and degradation of extracellular matrix, angiogenesis, homeostasis, organogenesis, cancer, genetic disorders and arthritis (Zhang et al., Mediators Inflamm. 2015; 2015:801546. doi: 10.1155/2015/801546. Epub 2015 Nov. 30). The 19 ADAMTS enzymes (human) have been subclassified into 8 clusters.

The first 2 clusters comprise the aggrecanse- and proteoglycanase-groups (ADAMTS-1, -4, -5, -8, -15, and ADAMTS-9 & -20). The third cluster, consisting of pro-collagen N-propeptidases, is constituted by ADAMTS-2, -3 and -14 which are crucially involved in the maturation of collagen-fibrils. The only member of the fourth cluster is ADAMTS-13, a protease that cleaves von-Willebrand factor. ADAMTS-7 and ADAMTS-12 are members of the fifth cluster and they have been described to cleave cartilage oligomeric matrix protein (COMP). These two enzymes are unique inasmuch as chondroitinsulfate chains are part of these enzymes and thus confer a proteoglycan status to them (Kelwick et al., Genome Biol., 2015 May 30; 16:113. doi: 10.1186/s13059-015-0676-3). In human samples, the highest expression of ADAMTS7 was found in heart, kidney, sceletal muscle, liver and pancreas (Somerville, J. Biol. Chem., 2004 Aug. 20; 279(34):35159-75. Epub 2004 Jun. 10). Likewise, ADAMTS-7 was found to be expressed in bone, cartilage, synovium, tendons and ligaments. Additionally, it was detected in meniscus as well as fat (Liu, Nat Clin Pract Rheumatol. 2009 January; 5(1):38-45. doi: 10.1038/ncprheum0961).

The three clusters not yet referred to, contain two ADAMTS enzymes each (ADAMTS-6 and -10, ADAMTS-16 and -18, ADAMTS-17 and -19) and are characterized by the organization of the domains of their respective ADAMTS-members.

ADAMTS have been linked to divergent diseases: For example, mutations in ADAMTS13 have been associated with thrombotic, thrombozyopenic purpura (Levy et al., Nature. 2001 Oct. 4; 413(6855):488-94). ADAMTS-4 and -5 have been described to be responsible for the degradation of aggrecan in the cartilage of patients suffering from osteoarthritis (Malfait et al., J Biol Chem. 2002 Jun. 21; 277(25): 22201-8. Epub 2002 Apr. 15).

The consensus sequence HEXXHXBG(/N/S)BXHD is shared as catalytic motif by ADAMTS with the three histidine residues coordinating a $Zn^{2+}$-ion (Kelwick et al., Genome Biol., 2015 May 30; 16:113. doi: 10.1186/s13059-015-0676-3). Different from other metalloproteinases, ADAMTS family members show a narrow substrate specificity which may make ADAMTS enzymes a potentially "safe" molecular target (Wu et al., Eur J Med Res, 2015 Mar. 21; 20:27. doi: 10.1186/s40001-015-0118-4; Wang et al., Sheng Li Xue Bao. 2010 Aug. 25; 62(4):285-94).

In the context of the initially mentioned diseases/disease states ADAMTS-7 is of special interest since genome-wide association studies showed a correlation between ADAMTS-7 genetic variants and coronary artery disease (CAD). As opposed to genome-wide association studies showing variants in ADAMTS-7 to be associated with the prevalence of CAD and myocardial infarction (MI) (Chan et al., J Am Heart Assoc., 2017 Oct. 31; 6 (11). pii: e006928. doi: 10.1161/JAHA.117.006928), Reilly et al. indentified variant in the ADAMTS-7 gene as being associated with CAD, however, not with MI (Reilly et al., Lancet. 2011 Jan. 29; 377(9763):383-92. doi: 10.1016/S0140-6736 (10) 61996-4. Epub 2011 Jan. 14). Further supporting a CAD-association, also a meta-analysis of 14 genome-wide association studies identified ADAMTS-7 as locus being linked to CAD (Schunkert et al., Nat. Genet. 2011 Mar. 6; 43(4): 333-8. doi: 10.1038/ng.784).

One of the leading SNPs in the ADAMTS7 locus, rs3825807, shows an adenine (A)-to-guanine (G) exchange in the ADAMTS-7 gene with the G-allel being associated with a reduced risk for CAD. The above mentioned SNP (Single Nucleotide Polymorphism) leads to an amino acid exchange in the pro-domain of ADAMTS-7 and thereby has an impact on the maturation of ADAMTS-7. Furthermore, it has been described that the above mentioned SNP finds itself in a linkage disequilibrium with further SNPs within the ADAMTS-7 locus, such as rs1994016 and rs7178051 (Chan et al., J Am Heart Assoc., 2017 Oct. 31; 6 (11). pii: e006928. doi: 10.1161/JAHA.117.006928). Supporting the aforementioned notions, rs3825807 has also been described to be associated with the susceptibility towards CAD in a chinese population and this association persisted even after correction for clinical co-variates (You et al., Mol Genet. Genomics. 2016 February; 291(1):121-8. doi: 10.1007/s00438-015-1092-9. Epub 2015 Jul. 19).

Investigation of a potential relationship between plasma ADAMTS-7 levels and heart and/or lung function as well as analysis of ADAMTS-7 levels in patients suffering from an acute MI on the one hand showed that plasma ADAMTS-7 levels were higher in patients with a left ventricular ejection fraction (LVEF) below or equaling 35%, on the other hand revealed that plasma ADAMTS-7 levels positively correlated with i.e. (brain natriuretic peptide) BNP and left ventricular end-systolic diameter (LVESD) while showing a negative correlation with the 6-min-walking distance (Wu et al., Eur J Med Res, 2015 Mar. 21; 20:27. doi: 10.1186/s40001-015-0118-4). Furthermore, high ADAMTS-7 levels correlated with a high lipid-content and accumulation of cluster of differentiation (CD) 68 and at the same time with a low smooth muscle cell- as well as a decreased collagen-content being characteristic for vulnerable plaques. Accordingly, ADAMTS-7-levels above median were associated with an increased risk for post-surgery cardiovascular events (Bengtsson et al., Sci Rep., 2017 Jun. 16; 7(1):3753. doi: 10.1038/s41598-017-03573-4).

Opposing the above mentioned studies, one study failed to show an association between initima- or media-thickness with the G-allel of the ADAMTS-7-SNP. However, a significant association was reported between the rs3825807 G-allel and a reduced thickness of the fibrous cap as well as a decreased portion of intimal α-actin accumulation. Notably, the G-allel of the ADAMTS-7-SNP was linked to a CAD-protective effect (16%-19% reduced risk to be taken ill with each allel after correction for age and gender). Further supporting former reports, no significant association was found between the G-allel and MI.

In a hispanic subgroup, an analysis of the MESA (Multi-Ethnic Study of Artherosclerose)-cohort revealed an association of an ADAMTS-7-SNP different from the one described above and coronary artery calcification (Chan et al., J Am Heart Assoc., 2017 Oct. 31; 6 (11). pii: e006928. doi: 10.1161/JAHA.117.006928).

Taken together, the well documented association with CAD allows the conclusion that ADAMTS-7 increases the risk for CAD via effects on atherosclerosis, potentially without influencing mechanisms which are supposed to favor plaque rupture or thrombosis which themselves are drivers for MI. This assumption is underlined by the observation that the protective G-allel of the ADAMTS-7 variant had no influence on overall mortality or MI (Chan et al., J Am Heart Assoc., 2017 Oct. 31; 6 (11). pii: e006928. doi: 10.1161/JAHA.117.006928).

Experimentally, ADAMTS-7 has been described to be involved in the migration of smooth muscle cells (SMC) and the development of neointimal hyperplasia. Immunohistochemistry showed co-localisation of ADAMTS-7 with vascular smooth muscle cells (VSMC) within the neointima (Wang et al., Circ Res., 2009 Mar. 13; 104(5):688-98. doi: 10.1161/CIRCRESAHA.108.188425. Epub 2009 Jan. 22) and an increased expression of ADAMTS-7 in early- and late-stage human atherosclerotic plaques was described (Wang et al., Sheng Li Xue Bao. 2010 Aug. 25; 62(4):285-94).

Formation of a neointima is characterized by a media-to-intima migration of VSMC and their subsequent proliferation. Interestingly, migration as well as proliferation of VSMC were accelerated by ADAMTS-7 in vitro (Wang et al., Sheng Li Xue Bao. 2010 Aug. 25; 62(4):285-94). Along with this observation, overexpression of ADAMTS-7 led to an increased neointima formation in vivo, were as a knock-down reduced/delayed injury-induced intimal hyperplasia (Wang et al, Circ Res., 2009 Mar. 13; 104(5):688-98. doi: 10.1161/CIRCRESAHA.108.188425. Epub 2009 Jan. 22).

Interesting to note is that pro-inflammatory cytokines such as TNF-α, IL-1β and PDGF-BB were able to induce ADAMTS-7 expression whereas TGF-β reduced its expression. Likewise, reactive oxygen species and $H_2O_2$ increased, while oxLDL and homocysteine did not change ADAMTS-7 expression in VSMC. All of the aforementioned factors are involved in vascular injury and may contribute to induction of ADAMTS-7 in injured arteries in vivo (Wang et al, Circ Res., 2009 Mar. 13; 104(5):688-98. doi: 10.1161/CIRCRESAHA.108.188425. Epub 2009 Jan. 22).

Mechanistically, ADAMTS-7 may be involved in the pathogenesis of the above mentioned diseases/disease states such as i.e. vascular disorders by cleaving COMP and thrombospondin-1 (TSP-1), by influencing migration and proliferation of VSMC and by regulating inflammatory cytokines (Zhang et al., Mediators Inflamm. 2015; 2015: 801546. doi: 10.1155/2015/801546. Epub 2015 Nov. 30). In this context, it has been described that ADAMTS-7 directly binds to and cleaves COMP (Liu et al., FASEB J. 2006 May; 20(7):988-90. Epub2006 Apr. 3) with the catalytic domain of ADAMTS-7 being responsible for COMP-cleavage (Liu, Nat Clin Pract Rheumatol., 2009 January; 5(1):38-45. doi: 10.1038/ncprheum0961). The disintegrin-like domain may be involved in the regulation of ADAMTS-7-activity by providing substrate-surfaces (Stanton et al., Biochim Biophys Acta., 2011 December; 1812(12):1616-29. doi: 10.1016/j.bbadis.2011.08.009. Epub 2011 Sep. 2). While ADAMTS-7 accelerates VMSC-migration via COMP-degradation, COMP has no effect on VSMC-proliferation. Interestingly, ADAMTS-7-mediated COMP-degradation in response to injury accelerated VSMC-migration and neointima hyperplasia. Taking into account that during restenosis (after vessel-wall injury) VSMC de-differentiate towards a synthetic phenotype, this may—in the context of the findings described above—lead to the hypothesis that COMP preserves a contractile phenotype in VSMC. Thus, ADAMTS-7 may constitute a new molecular target in conditions of atherosclerosis and/or restenosis after angioplasty (Wang et al., Sheng Li Xue Bao. 2010 Aug. 25; 62(4):285-94).

Furthermore it has been described that ADAMTS-7 is able to contribute to endothelial repair via direct binding to TSP-1, independent of COMP (Zhang et al., Mediators Inflamm. 2015; 2015:801546. doi: 10.1155/2015/801546. Epub 2015 Nov. 30). a2-macroglobulin has also been described to associate with ADAMTS-7 and to be its substrate (Luan et al., Osteoarthritis Cartilage. 2008 November; 16(11):1413-20. doi: 10.1016/j.joca.2008.03.017. Epub 2008 May 15).

In addition, it has been described that ADAMTS7 is involved in VSMC-calcification (Du et al., Arterioscler Thromb Vasc Biol., 2012 November; 32(11):2580-8. doi: 10.1161/ATVBAHA. 112.300206. Epub 2012 Sep. 20) and that it contributes to oval cell activation as well as being an important regulator in the context of biliary fibrosis.

Furthermore, ADAMTS-7 seems to be involved in interactions of host and pathogen (Zhang et al., Mediators Inflamm. 2015; 2015:801546. doi: 10.1155/2015/801546. Epub 2015 Nov. 30.) ADAMTS-7 and ADAMTS-12 were found to be significantly increased in cartilage and synovium of patients suffering from arthritis (Liu, Nat Clin Pract Rheumatol. 2009 January; 5(1):38-45. doi: 10.1038/ncprheum0961) and ADAMTS-7 could be detected in the urine of patients with different cancer-entities such as prostate and bladder cancer (Roy et al., Clin Cancer Res. 2008 Oct. 15; 14(20):6610-7. doi: 10.1158/1078-0432.CCR-08-1136).

Additionally, ADAMTS-7 expression was increased in patients with aortic aneurysms while expression of COMP was markedly reduced in this group of patients as compared to controls. Accordingly, increased expression of ADAMTS-7 and decreased levels of COMP seem to be associated with aortic aneurysms (Qin et al., Mol Med Rep., 2017 October; 16(4):5459-5463. doi: 10.3892/mmr.2017.7293. Epub 2017 Aug. 21).

New therapeutic concepts are necessary to improve the lifes/outcomes of patients who suffer from lung diseases, heart diseases, inflammatory diseases, fibrotic diseases, metabolic diseases, cardiometabolic diseases, vascular diseases and/or cardiovascular diseases, including atherosclerosis, coronary artery disease, peripheral vascular disease/arterial occlusive disease and/or restenosis after angioplasty (including the use of drug-coated or non drug-coated balloons and/or stent-implantation).

Likewise, identification of low molecular compounds for a preventive treatment or a treatment to slow progression of these diseases are conceivable and pursued.

BRIEF DESCRIPTION OF THE FIGURES

FIG. 1A and FIG. 1B show size exclusion (SEC) profile, SDS-page, and western blot (WB) analysis of human ADAMTS-7 (hADAMTS-7) (1-537 with respect to SEQ ID NO: 21) from mammalian cell culture. FIG. 1C and FIG. 1D show SEC profile, SDS-page, and WB analysis of rat ADAMTS-7 (rADAMTS-7) (1-575 with respect to SEQ ID NO: 22) from mammalian cell culture. FIG. 1E and FIG. 1F show the domain design of human and rat hybrid ADAMTS-7 (rPro-hCD; with respect to SEQ ID NOs: 22 and 21) with amino acid position indicated below, as well as SEC profile, SDS-page, and WB analysis of purified hybrid protein from mammalian cell culture. Abbreviations: rSP: rat signal peptide; rPro: rat propeptide (the rat prodomain without the signal peptide); hCatalytic: human catalytic domain; hDis: human disintegrin domain. FIGS. 2A, 2B and 2C (consisting of panels A and B) shows the primary structure and sequence comparison of ADAMTS-7. FIG. 2A shows the primary structure of hADAMTS-7 with residue numbers labeled at the domain boundaries (SP: signal peptide; Pro: Prodomain; Dis: Disintegrin domain; TSR: thrombospondin repeat; PLAC: protease and lacunin domain. FIGS. 2B and 2C show a sequence alignment of human and rat ADAMTS-7 in the Pro and CD (catalytic+disintegrin) domains. Different residues were colored in grey, and identical residues were black. Strongly similar residues were black marked with double dots and weakly similar residues were black marked with single dots. Sequence alignment was performed using CLUSTAWL.

FIG. 3A shows that the SEC profile of hADAMTS-7 CD domain (residues 237-537) reveals production of soluble proteins (fractions B8-B12) are detectible only in the western blot. FIG. 3B shows that the SEC profile of hADAMTS-7 Pro-CD-TSR1 (residues 1-593) yielded little soluble proteins in the expected elution volumes underlined.

FIGS. 4A and 4B (consisting of panels A and B) shows that furin cleavage site mutants of ADAMTS-7 improved the yield of processed or unprocessed ADAMTS-7. FIG. 4A shows the mutations (grey) introduced into the sequence of the hybrid molecule rPro-hCD to change the furin cleavage efficiency during mammalian cell expression. Q216K mutation in a furin cleavage site and a triple mutant R58A/R61A/R217A were named as rPro-hCD-FM2 (SEQ ID No. 2) and rPro-hCD-3RA respectively. FIG. 4B shows that rPro-hCD-FM2 (SEQ ID No. 2) improved the processing to generate more hCD domains during mammalian production and rPro-hCD-3RA abolished the processing to generate unprocessed protein only. Anti-His WB that targets the 6×His tag at the C-terminus of the protein was used to analyze the raw media of the mammalian cell culture two days post-transfection.

FIG. 5 shows an alignment between mouse ADAMTS-7 prodomain and rat ADAMTS-7 prodomain.

FIGS. 7A and 7B show FRET peptide substrate evaluation for TSP-1 and COMP candidate regions.

FIG. 8A-FIG. 8C: The top panels show curves following enzymatic activity over time with different substrates. The lower panels illustrate the rates of activity for rPro-hCD (SEQ ID NO: 1), rPro-hCD-FM2 (SEQ ID NO: 2) and rADAMTS-7 (1-575) (SEQ ID NO: 3), respectively, using different substrates. TSP1-1 substrate (SEQ ID NO: 4) is most efficiently turned over by all ADAMTS-7 active constructs.

FIG. 9: Specific activities for the proteolysis of substrate SEQ ID NO: 4-10 show that TSP1-1 substrate is most efficiently turned over by the active ADAMTS-7 constructs. The TSP substrate sequences indicate the cleavage site (underlined) between glutamate and leucine as determined by mass spectrometry. COMP substrate cleavage products were below the detection limit of the mass spectrometer.

BRIEF DESCRIPTION OF THE SEQUENCE IDS

Figure 1A:
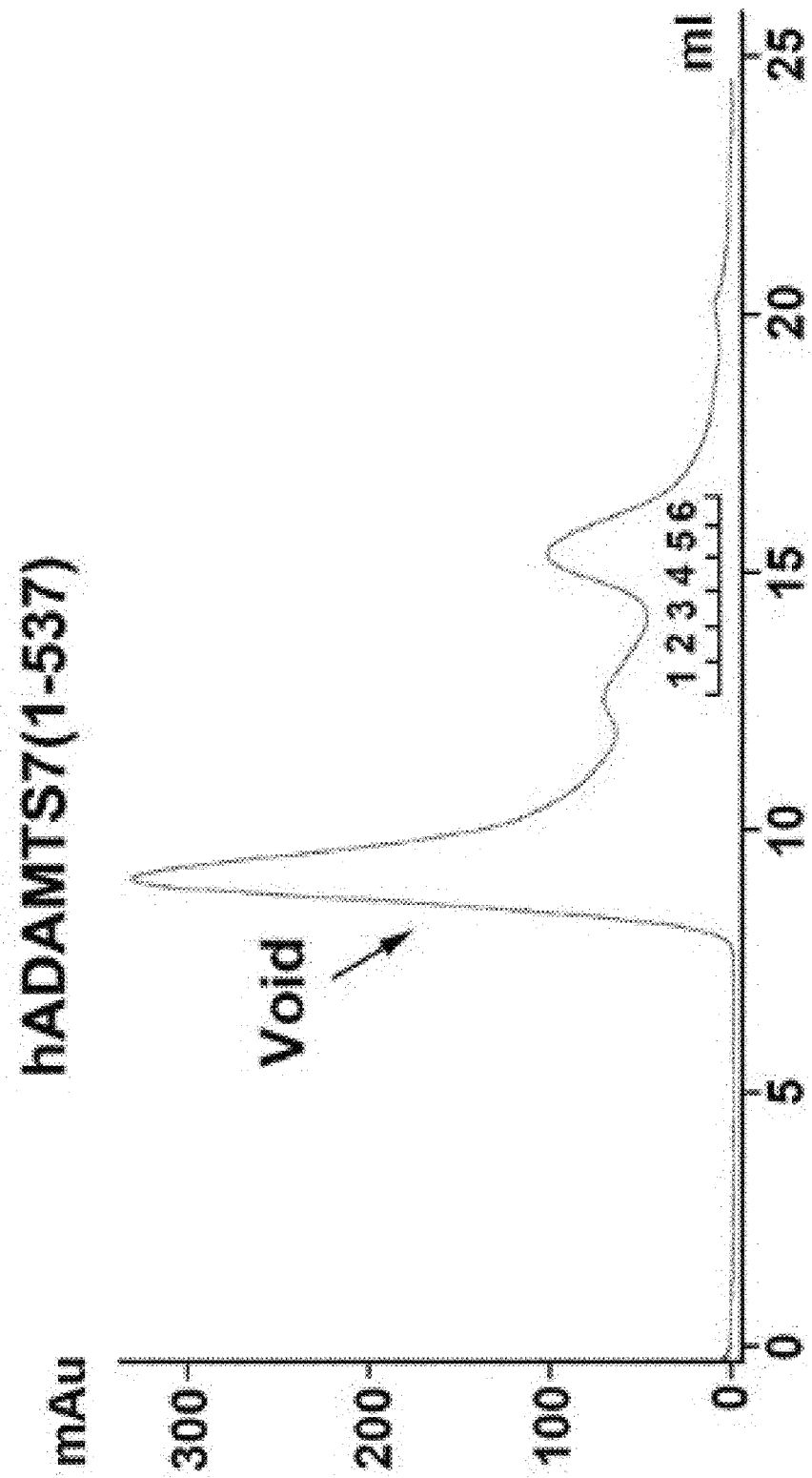
FIGS. 1A, 1B 1C, 1D, 1E and 1F (consisting of panels A, B, and C) show comparisons of recombinantly expressed wild type (WT) human ADAMTS-7, WT rat ADAMTS-7, and hybrid ADAMTS-7. Lane numbers of the SDS PAGE correspond with annotated SEC fractions.
Figure 1B:
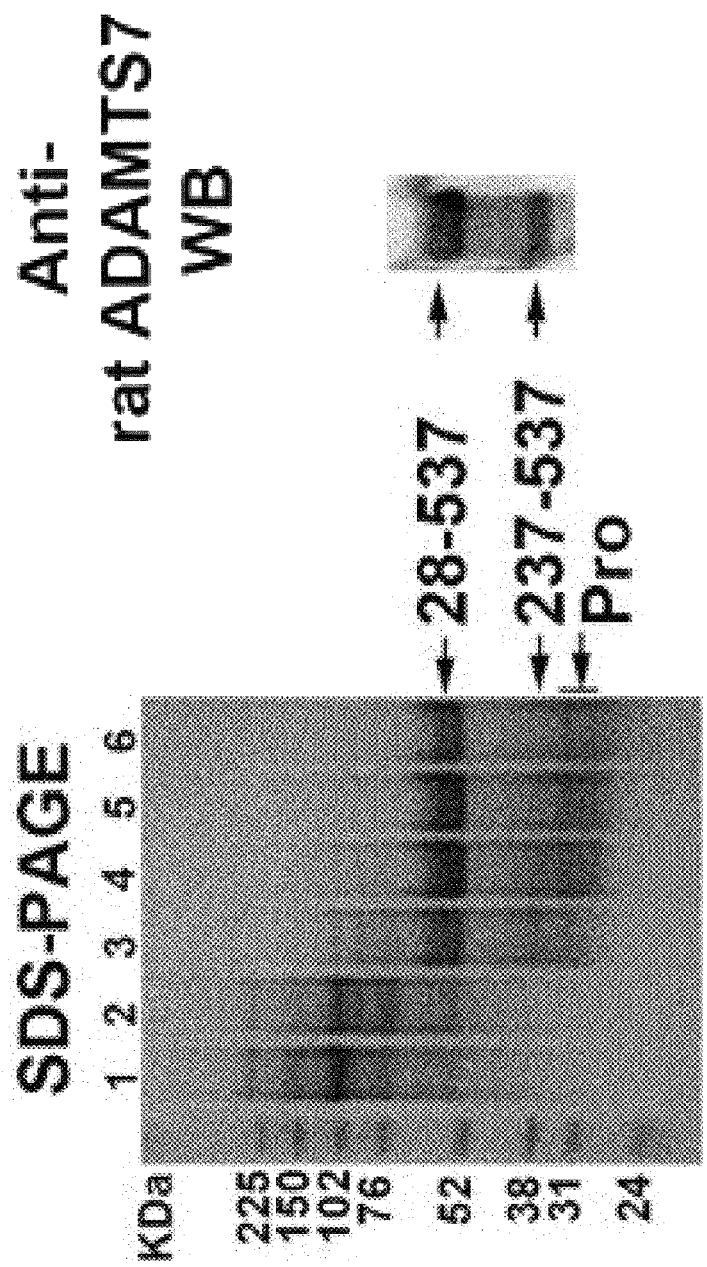
Figure 1C:
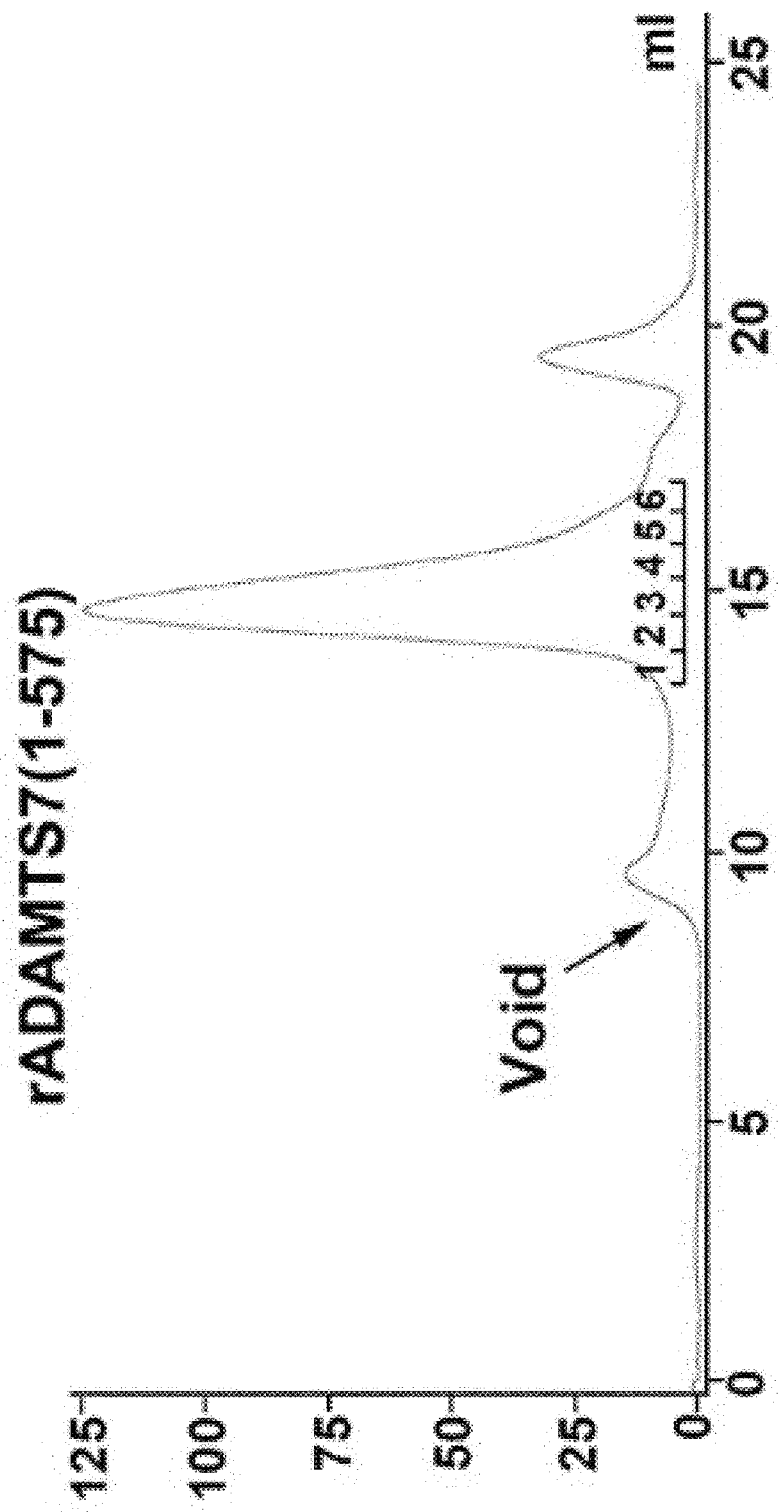
Figure 1D:
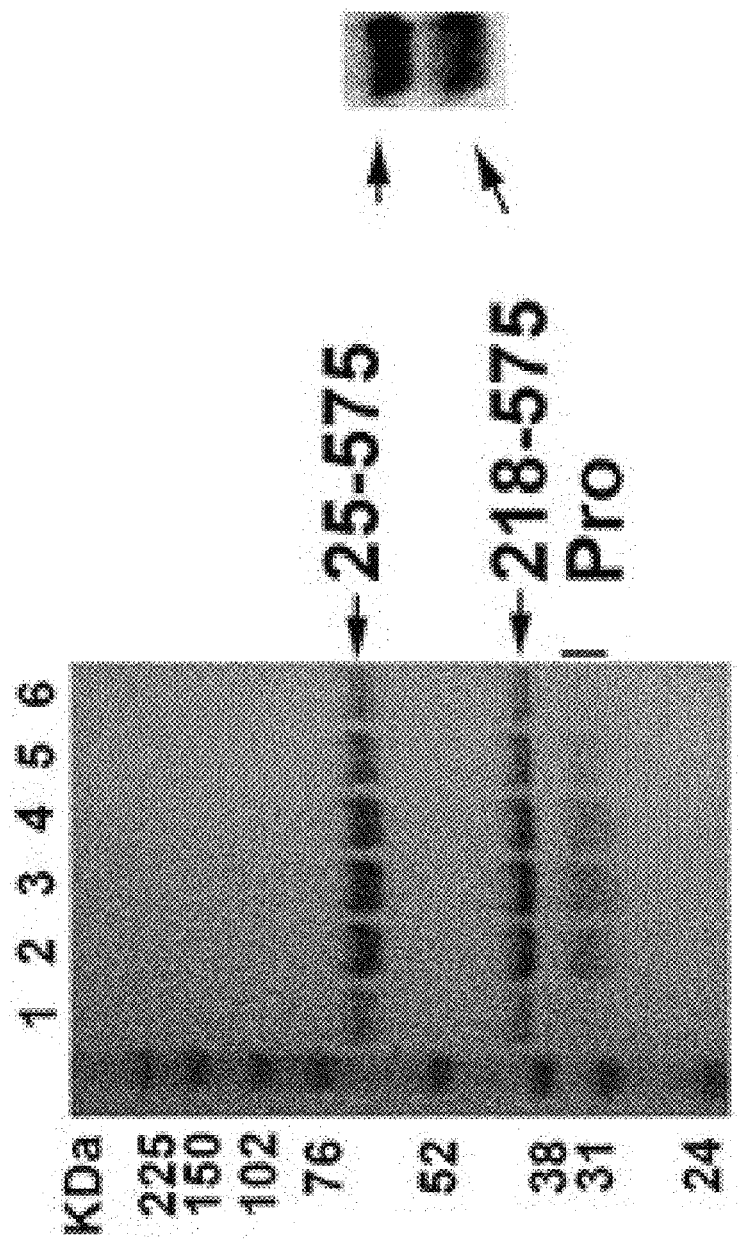
Figure 1E:
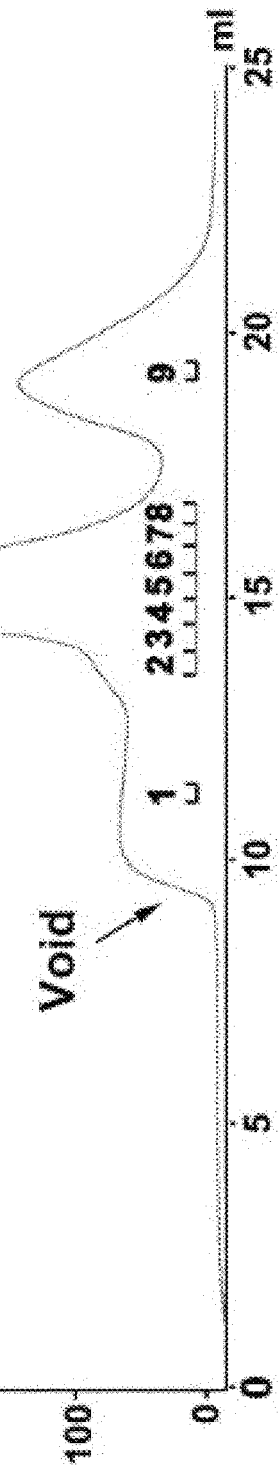
Figure 1F:
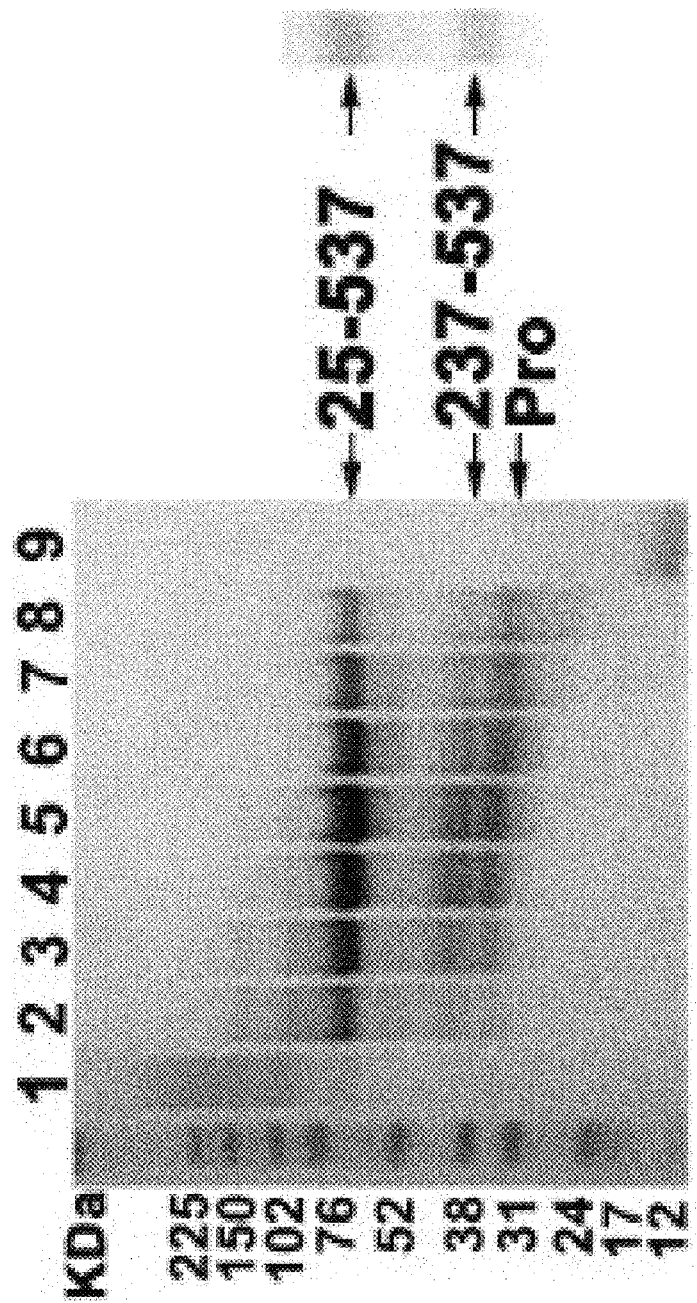

The sequence listing provided with the application via electronic filing is included herein in its entirety. Where the sequence information or listing apart from the amino acid sequence comprises modifications, fluorophores and/or quencher (i.e. within the feature data) these shall not be read restrictively but only in an exemplary way. The same holds true for non essential modifications such as tags such as FLAG tags or HIS tags.

| SEQ ID NO. | VARIANT | TYPE |
|---|---|---|
| 1 | rPro-hCD(Rat 1-217/Human 237-537)-TEV-2Strep-6His<br>MHRGLNLLLILCALAPHVLGPASGLPTEGRAGLDIVHPVRVDAGGSFLSYELWPRVLRKRDVSAAQASS<br>AFYQLQYQGRELLFNLTTNPYLLAPGFVSEIRRRSNLSNVHIQTSVPTCHLLGDVQDPELEGGFAAISAC<br>DGLRGVFQLSNEDYFIEPLDEVPAQPGHAQPHMVYKHKRSGQQDDSRTSGTCGVQGSPELKHQREHW<br>EQRQQKRRQQRSVSKEKWVETLVVADAKMVEYHGQPQVESYVLTIMNMVAGLFHDPSIGNPIHITIVRL<br>VLLEDEEEDLKITHHADNTLKSFCKWQKSINMKGDAHPLHHDTAILLTRKDLCAAMNRPCETLGLSHVAG<br>MCQPHRSCSINEDTGLPLAFTVAHELGHSFGIQHDGSGNDCEPVGKRPFIMSPQLLYDAAPLTWSRCSR<br>QYITRFLDRGWGLCLDDPPAKDIIDFPSVPPGVLYDVSHQCRLQYGAYSAFCEDMDNVCHTLWCSVGTT<br>CHSKLDAAVDGTRCGENKWCLSGECVPVGFRPEAVGSENLYFQSGWSHPQFEKGGGSGGGSGGGS<br>WSHPQFEKHHHHHH | PRT |
| 2 | rPro-hCD-FM2 (Rat 1-217/Human 237-537 FM2 (Q216K))-TEV-2Strep-6His<br>MHRGLNLLLILCALAPHVLGPASGLPTEGRAGLDIVHPVRVDAGGSFLSYELWPRVLRKRDVSAAQASS<br>AFYQLQYQGRELLFNLTTNPYLLAPGFVSEIRRRSNLSNVHIQTSVPTCHLLGDVQDPELEGGFAAISAC<br>DGLRGVFQLSNEDYFIEPLDEVPAQPGHAQPHMVYKHKRSGQQDDSRTSGTCGVQGSPELKHQREHW<br>EQRQQKRRQKRSVSKEKWVETLVVADAKMVEYHGQPQVESYVLTIMNMVAGLFHDPSIGNPIHITIVRLV<br>LLEDEEEDLKITHHADNTLKSFCKWQKSINMKGDAHPLHHDTAILLTRKDLCAAMNRPCETLGLSHVAGM<br>CQPHRSCSINEDTGLPLAFTVAHELGHSFGIQHDGSGNDCEPVGKRPFIMSPQLLYDAAPLTWSRCSRQ<br>YITRFLDRGWGLCLDDPPAKDIIDFPSVPPGVLYDVSHQCRLQYGAYSAFCEDMDNVCHTLWCSVGTTC<br>HSKLDAAVDGTRCGENKWCLSGECVPVGFRPEAVGSENLYFQSGWSHPQFEKGGGSGGGSGGGSW<br>SHPQFEKHHHHHH | PRT |
| 3 | rADAMTS-7 (Rat 1-575)-Flag<br>MHRGLNLLLILCALAPHVLGPASGLPTEGRAGLDIVHPVRVDAGGSFLSYELWPRVLRKRDVSAAQASS<br>AFYQLQYQGRELLFNLTTNPYLLAPGFVSEIRRRSNLSNVHIQTSVPTCHLLGDVQDPELEGGFAAISAC<br>DGLRGVFQLSNEDYFIEPLDEVPAQPGHAQPHMVYKHKRSGQQDDSRTSGTCGVQGSPELKHQREHW<br>EQRQQKRRQQRSISKEKWVETLVVADSKMVEYHGQPQVESYVLTIMNMVAGLYHDPSIGNPIHITVVRLI<br>ILEDEEKDLKITHHADDTLKNFCRWQKNVNMKGDDHPQHHDTAILLTRKDLCATMNHPCETLGLSHVAG<br>LCHPQLSCSVSEDTGLPLAFTVAHELGHSFGIQHDGTGNDCESIGKRPFIMSPQLLYDRGIPLTWSRCSR<br>EYITRFLDRGWGLCLDDRPSKGVINFPSVLPGVLYDVNHQCRLQYGPSSAYCEDVDNVCYTLWCSVGT<br>TCHSKMDAAVDGTSCGKNKWCLNGECVPEGFQPETVDGGWSGWSAWSVCSRSCGVGVRSSERQCT<br>QPVPKNKGKYCVGERKRYRLCNLQACPENLYFQGDYKDDDDK | PRT |
| 4 | Peptide Substrate for ADAMTS-7/12<br>(HiLyteFluor-488)-DELSSMVLELRGLRT-K(QXL520)-NH2 | PRT |
| 5 | Peptide Substrate for ADAMTS-7/12<br>(HiLyteFluor-488)-SSMVLELRGLRTIVT-K(QXL520)-NH2 | PRT |
| 6 | Peptide Substrate for ADAMTS-7/12:<br>(HiLyteFluor-488)-KVTEENKELANELRR-K(QXL520)-NH2 | PRT |
| 7 | Peptide Substrate for ADAMTS-7/12:<br>(HiLyteFluor-488)-EENKELANELRRPPL-K(QXL520)-NH2 | PRT |
| 8 | Peptide Substrate for ADAMTS-7/12:<br>(HiLyteFluor-488)-SSMVLELRGLRT-K(QXL520)-NH2 | PRT |
| 9 | Peptide Substrate for ADAMTS-7/12:<br>(Donor) GMQQSVRTGLPS (K-Quencher) | PRT |
| 10 | Peptide Substrate for ADAMTS-7/12:<br>(Donor) SPGFRCEACPPGYS (K-Quencher) | PRT |
| 11 | Peptide Substrate for ADAMTS-7 and ADAMTS-12:<br>(HiLyteFluor-488)-DELSSMVLELRGLRT-K(QXL520)-E-NH2 | PRT |
| 12 | Peptide Substrate for ADAMTS-7/12:<br>(HiLyteFluor-488)-DELSSMVLELRGLRT-K(QXL520)-K-NH2 | PRT |
| 13 | Peptide Substrate for ADAMTS-7/12:<br>(HiLyteFluor-488)-DELSSMVLELRGLRT-K(QXL520)-OH | PRT |
| 14 | Peptide Substrate for ADAMTS4 and for ADAMTS5:<br>Dabcyl-EEVKAKVQPY-Glu(Edans)-NH2 | PRT |
| 15 | rPro-hCD for ADAMTS-12<br>MPCAQGNWMAKLSMVAQLLNFGAFCHGRQAQPWPVRFPDPKQEHFIKSLPEYHIVSPVQVDASGHFL | PRT |

| SEQ ID NO. | VARIANT | TYPE |
|---|---|---|
| | SYGLHHPVTGSRKKRAAGGSGDQVYYRISHEEKNLFFNLTVNWEFLSNGYVVERRYGNLSHVKMAASS GQPCHLRGTVLQQGPTIRMGTAALSACQGLTGFFHLPHGDFFIEPVKKHPLTEEGYQPHVIYRRQSYRV PETKEPTCGLKDSLDNSVKQELQREKWERKNWPSRSLSRRSISKERWVETLVVADTKMIEYHGSENVE SYILTIMNMVTGLFHNPSIGNAIHIVWRLILLEEEQGLKIVHHAEKTLSSFCKWQKSINPKSDLNPVHH DVAVLLTRKDICAGFNRPCETLGLSHLSGMCQPHRSCNINEDSGLPLAFTIAHELGHSFGIQHDGKENDC EPVGRHPYIMSRQLQYDPTPLTWSKCSEEYITRFLDRGWGFCLDDIPKKKGLKSKVIAPGVIYDVHHQCQ LQYGPNATFCQEVENVCQTLWCSVKGFCRSKLDAAADGTQCGEKKWCMAGKCITVGKKPESIPGGGGSD YKDHDGDYKDHDIDYKDDDDK | |
| 16 | ADAMTS Catalytic Motif Consensus Sequence: HEXXHXBG(/N/S)BXHD | PRT |
| 17 | Peptide Substrate for MMP12 Mca-Pro-Leu-Gly-Leu-Glu-Glu-Ala-Dap(Dnp)-NH2 | PRT |
| 18 | Peptide Substrate for MMP15 MCA-Lys-Pro-Leu-Gly-Leu-DPA-Ala-Arg-NH2 | PRT |
| 19 | Peptide Substrate for MMP2 MCA-Pro-Leu-Gly-Leu-DPA-Ala-Arg-NH2 | PRT |
| 20 | Peptide Substrate for ADAM17 Mca-Pro-Leu-Ala-Gln-Ala-Val-Dap(Dnp)-Arg-Ser-Ser-Ser-Arg-NH2 | PRT |
| 21 | Human ADAMTS-7 from Q9UKP4 MPGGPSPRSPAPLLRPLLLLLCALAPGAPGPAPGRATEGRAALDIVHPVRVDAGGSFLSY ELWPRALRKRDVSVRRDAPAFYELQYRGRELRFNLTANQHLLAPGFVSETRRRGGLGRAH IRAHTPACHLLGEVQDPELEGGLAAISACDGLKGVFQLSNEDYFIEPLDSAPARPGHAQP HVVYKRQAPERLAQRGDSSAPSTCGVQVYPELESRRERWEQRQQWRRPRLRRLHQRSVSK EKWVETLVVADAKMVEYHGQPQVESYVLTIMNMVAGLFHDPSIGNPIHITIVRLVLLEDE EEDLKITHHADNTLKSFCKWQKSINMKGDAHPLHHDTAILLTRKDLCAAMNRPCETLGLS HVAGMCQPHRSCSINEDTGLPLAFTVAHELGHSFGIQHDGSGNDCEPVGKRPFIMSPQLL YDAAPLTWSRCSRQYITRFLDRGWGLCLDDPPAKDIIDFPSVPPGVLYDVSHQCRLQYGA YSAFCEDMDNVCHTLWCSVGTTCHSKLDAAVDGTRCGENKWCLSGECVPVGFRPEAVDGG WSGWSAWSICSRSCGMGVQSAERQCTQPTPKYKGRYCVGERKRFRLCNLQACPAGRPSFR HVQCSHFDAMLYKGQLHTWVPVVNDVNPCELHCRPANEYFAEKLRDAVVDGTPCYQVRAS RDLCINGICKNVGCDFEIDSGAMEDRCGVCHGNGSTCHTVSGTFEEAEGLGYVDVGLIPA GAREIRIQEVAEAANFLALRSEDPEKYFLNGGWTIQWNGDYQVAGTTFTYARRGNWENLT SPGPTKEPVWIQLLFQESNPGVHYEYTIHREAGGHDEVPPPVFSWHYGPWTKCTVTCGRG VQRQNVYCLERQAGPVDEEHCDPLGRPDDQQRKCSEQPCPARWWAGEWQLCSSSCGPGGL SRRAVLCIRSVGLDEQSALEPPACEHLPRPPTETPCNRHVPCPATWAVGNWSQCSVTCGE GTQRRNVLCTNDTGVPCDEAQQPASEVTCSLPLCRWPLGTLGPEGSGSGSSSHELFNEAD FIPHHLAPRPSPASSPKPGTMGNAIEEEAPELDLPGPVFVDDFYYDYNFINFHEDLSYGP SEEPDLDLAGTGDRTPPPHSHPAAPSTGSPVPATEPPAAKEEGVLGPWSPSPWPSQAGRS PPPPSEQTPGNPLINFLPEEDTPIGAPDLGLPSLSWPRVSTDGLQTPATPESQNDFPVGK DSQSQLPPPWRDRTNEVFKDDEEPKGRGAPHLPRPSSTLPPLSPVGSTHSSSPSPDVAEL WTGGTVAWEPALEGGLGPVDSELWPTVGVASLLPPPIAPLPEMKVRDSSLEPGTPSFPTP GPGSWDLQTVAVWGTFLPTTLTGLGHMPEPALNPGPKGQPESLSPEVPLSSRLLSTPAWD SPANSHRVPETQPLAPSLAEAGPPADPLVVRNAGWQAGNWSECSTTCGLGAVWRPVRCSS GRDEDCAPAGRPQPARRCHLRPCATWHSGNWSKCSRSCGGGSSVRDVQCVDTRDLRPLRP FHCQPGPAKPPAHRPCGAQPCLSWYTSSWRECSEACGGGEQQRLVTCPEPGLCEEALRPN TTRPCNTHPCTQWVVGPWGQCSGPCGGGVQRRLVKCVNTQTGLPEEDSDQCGHEAWPESS RPCGTEDCEPVEPPRCERDRLSFGFCETLRLLGRCQLPTIRTQCCRSCSPPSHGAPSRGH QRVARR | PRT |
| 22 | Rat ADAMTS-7 from Q1EHB3 MHRGLNLLLILCALAPHVLGPASGLPTEGRAGLDIVHPVRVDAGGSFLSYELWPRVLRKR DVSAAQASSAFYQLQYQGRELLFNLTTNPYLLAPGFVSEIRRRSNLSNVHIQTSVPTCHL LGDVQDPELEGGFAAISACDGLRGVFQLSNEDYFIEPLDEVPAQPGHAQPHMVYKHKRSG QQDDSRTSGTCGVQGSPELKHQREHWEQRQQKRRQQRSISKEKWVETLVVADSKMVEYHG QPQVESYVLTIMNMVAGLYHDPSIGNPIHITVVRLIILEDEEKDLKITHHADDTLKNFCR WQKNVNMKGDDHPQHHDTAILLTRKDLCATMNHPCETLGLSHVAGLCHPQLSCSVSEDTG LPLAFTVAHELGHSFGIQHDGTGNDCESIGKRPFIMSPQLLYDRGIPLTWSRCSREYITR FLDRGWGLCLDDRPSKGVINFPSVLPGVLYDVNHQCRLQYGPSSAYCEDVDNVCYTLWCS VGTTCHSKMDAAVDGTSCGKNKWCLNGECVPEGFQPETVDGGWSGWSAWSVCSRSCGVGV RSSERQCTQPVPKNKGKYCVGERKRYRLCNLQACPPDRPSFRHTQCSQFDSMLYKGKLHK WVPVLNDENPCELHCRPFNYSNREKLRDAVMDGTPCYQGRISRDICIDGICKKVGCDFEL DSGAEEDRCGVCRGDSTCHTVSRTFKEAEGMGYVDVGLIPAGAREILIEEVAEAANFLA LRSEDPDKYFLNGGWTIQWNGDYQVAGTTFTYTRKGNWETLTSPGPTTEPVWIQLLFQER NPGVHYKYTIQRASHSEAQPPEFSWHYGPWSKCPVTCGTGVQRQSLYCMEKQAGIVDEGH CDHLSRPRDRKRKCNEEPCPARWWVGDWQPCSRSCGPGGFFRRAVFCTRSVGLDEQRALE PSACGHLPRPLAEIPCYHYVACPSSWGVGNWSQCSVTCGAGIRQRSVLCINNTGVPCDGA ERPITETFCFLQPCQYSTYIVDTGASGSGSSSPELFNEVDFDPHQPVPRPSPASSPKPVS ISNAIDEEDPELDPPGPVFVDDFYYDYNFINFHEDLSYGSFEESHSDLVDIGGQTVPPHI RPTEPPSDSPVPTAGAPGAEEEGIQGSWSPSPLLSEASHSPPVLLENTPVNPLANFLTEE | PRT |

| SEQ ID NO. | VARIANT | | TYPE |
|---|---|---|---|
| | ESPIGAPELGLPSVSWPPASVDGMVTSVAPGNPDELLVREDTQSQPSTPWSDRNKLSKDG<br>NPLGPTSPALPKSPFPTQPSSPSNSTTQASLSPDAVEVSTGWNVALDPVLEADLKPVHAP<br>TDPGLLDQIQTPHTEGTQSPGLLPRPAQETQTNSSKDPAVQPLQPSLVEDGAPTDLLPAK<br>NASWQVGNWSQCSTTCGLGAIWRLVRCSSGNDEDCTLSSRPQPARHCHLRPCAAWRAGNW<br>SKCSRNCGGGSATRDVQCVDTRDLRPLRPFHCQPGPTKPPTRQLCGTQPCLPWYTSSWRE<br>CSEACGGGEQQRLVTCPEPGLCEESLRPNNTRPCNTHPCTQWVVGPWGQCSAPCGGGVQR<br>RLVKCVNTQTGLAEEDSDLCSHEAWPESSRPCATEDCELVEPSRCERDRLPFNFCETLRL<br>LGRCQLPTIRAQCCRSCPPLSRGVPSRGHQRVARR | | |
| 23 | Mouse ADAMTS-7 from Q68SA9 | | PRT |
| | MHRGPSLLLILCALASRVLGPASGLVTEGRAGLDIVHPVRVDAGGSFLSYELWPRVLRKR<br>DVSTTQASSAFYQLQYQGRELLFNLTTNPYLMAPGFVSEIRRHSTLGHAHIQTSVPTCHL<br>LGDVQDPELEGGFAAISACDGLRGVFQLSNEDYFIEPLDGVSAQPGHAQPHVVYKHQGSR<br>KQAQQGDSRPSGTCGMQVPPDLEQQREHWEQQQQKRRQQRSVSKEKWVETLVVADSKMVE<br>YHGQPQVESYVLTIMNMVAGLFHDPSIGNPIHISIVRLIILEDEEKDLKITHHAEETLKN<br>FCRWQKNINIKGDDHPQHHDTAILLTRKDLCASMNQPCETLGLSHVSGLCHPQLSCSVSE<br>DTGMPLAFTVAHELGHSFGIQHDGTGNDCESIGKRPFIMSPQLLYDRGIPLTWSRCSREY<br>ITRFLDRGWGLCLDDRPSKDVIALPSVLPGVLYDVNHQCRLQYGSHSAYCEDMDDVCHTL<br>WCSVGTTCHSKLDAAVDGTSCGKNKWCLKGECVPEGFQPEAVDGGWSGWSAWSDCSRSCG<br>VGVRSSERQCTQPVPKNRGKYCVGERKRSQLCNLPACPPDRPSFRHTQCSQFDGMLYKGK<br>LHKWVPVPNDDNPCELHCRPSNSSNTEKLRDAVVDGTPCYQSRISRDICLNGICKNVGCD<br>FVIDSGAEEDRCGVCRGDGSTCQTVSRTFKETEGQGYVDIGLIPAGAREILIEEVAEAAN<br>FLALRSEDPDKYFLNGGWTIQWNGDYRVAGTTFTYARKGNWENLTSPGPTSEPVWIQLLF<br>QEKNPGVHYQYTIQRDSHDQVRPPEFSWHYGPWSKCTVTCGTGVQRQSLYCMERQAGVVA<br>EEYCNTLNRPDERQRKCSEEPCPPRWWAGEWQPCSRSCGPEGLSRRAVFCIRSMGLDEQR<br>ALELSACEHLPRPLAETPCNRHVICPSTWGVGNWSQCSVTCGAGIRQRSVLCINNTDVPC<br>DEAERPITETFCFLQPCQYPMYIVDTGASGSGSSSPELFNEVDFIPNQLAPRPSPASSPK<br>PVSISNAIDEEELDPPGPVFVDDFYYDYNFINFHEDLSYGSFEEPHPDLVDNGGWTAPPH<br>IRPTESPSDTPVPTAGALGAEAEDIQGSWSPSPLLSEASYSPPGLEQTSINPLANFLTEE<br>DTPMGAPELGFPSLPWPPASVDDMMTPVGPGNPDELLVKEDEQSPPSTPWSDRNKLSTDG<br>NPLGHTSPALPQSPIPTQPSPPS1SPTQASPSPDVVEVSTGWNAAWDPVLEADLKPGHGE<br>LPSTVEVASPPLLPMATVPGIWGRDSPLEPGTPTFSSPELSSQHLKTLTMPGTLLLTVPT<br>DLRSPGPSGQPQTPNLEGTQSPGLLPTPARETQTNSSKDPEVQPLQPSLEEDGDPADPLP<br>ARNASWQVGNWSQCSTTCGLGAIWRLVSCSSGNDEDCTLASRPQPARHCHLRPCAAWRTG<br>NWSKCSRNCGGGSSTRDVQCVDTRDLRPLRPFHCQPGPTKPPNRQLCGTQPCLPWYTSSW<br>RECSEACGGGEQQRLVTCPEPGLCEESLRPNNSRPCNTHPCTQWVVGPWGQCSAPCGGGV<br>QRRLVRCVNTQTGLAEEDSDLCSHEAWPESSRPCATEDCELVEPPRCERDRLSFNFCETL<br>RLLGRCQLPTIRAQCCRSCPPLSRGVPSRGHQRVARR | | |
| 24 | Human ADAMTS-12 from P58397 | | PRT |
| | MPCAQRSWLANLSVVAQLLNFGALCYGRQPQPGPVRFPDRRQEHFIKGLPEYHVVGPVRV<br>DASGHFLSYGLHYPITSSRRKRDLDGSEDWVYYRISHEEKDLFFNLTVNQGFLSNSYIME<br>KRYGNLSHVKMMASSAPLCHLSGTVLQQGTRVGTAALSACHGLTGFFQLPHGDFFIEPVK<br>KHPLVEGGYHPHIVYRRQKVPETKEPTCGLKDSVNISQKQELWREKWERHNLPSRSLSRR<br>SISKERWVETLVVADTKMIEYHGSENVESYILTIMNMVTGLFHNPSIGNAIHIVVVRLIL<br>LEEEEQGLKIVHHAEKTLSSFCKWQKSINPKSDLNPVHHDVAVLLTRKDICAGFNRPCET<br>LGLSHLSGMCQPHRSCNINEDSGLPLAFTIAHELGHSFGIQHDGKENDCEPVGRHPYIMS<br>RQLQYDPTPLTWSKCSEEYITRFLDRGWGFCLDDIPKKKGLKSKVIAPGVIYDVHHQCQL<br>QYGPNATFCQEVENVCQTLWCSVKGFCRSKLDAAADGTQCGEKKWCMAGKCITVGKKPES<br>IPGGWGRWSPWSHCSRTCGAGVQSAERLCNNPEPKFGGKYCTGERKRYRLCNVHPCRSEA<br>PTFRQMQCSEFDTVPYKNELYHWFPIFNPAHPCELYCRPIDGQPFSEKMLDAVIDGTPCE<br>GGNSRNVCINGICKMVGCDYEIDSNATEDRCGVCLGDGSSCQTVRKMFKQKEGSGYVDIG<br>LIPKGARDIRVMEIEGAGNFLAIRSEDPEKYYLNGGFIIQWNGNYKLAGTVFQYDRKGDL<br>EKLMATGPTNESVWIQLLFQVTNPGIKYEYTIQKDGLDNDVEQQMYFWQYGHWTECSVTC<br>GTGIRRQTAHCIKKGRGMVKATFCDPETQPNGRQKKCHEKACPPRWWAGEWEACSATCGP<br>HGEKKRTVLCIQTMVSDEQALPPTDCQHLLKPKTLLSCNRDILCPSDWTVGNWSECSVSC<br>GGGVRIRSVTCAKNHDEPCDVTRKPNSRALCGLQQCPSSRRVLKPNKGTISNGKNPPTLK<br>PVPPPTSRPRMLTTPTGPESMSTSTPAISSPSPTTASKEGDLGGKQWQDSSTQPELSSRY<br>LISTGSTSQPILTSQSLSIQPSEENVSSSDTGPTSEGGLVATTTSGSGLSSRRNPITWPV<br>TPFYNTLTKGPEMEIHSGSGEEREQPEDKDESNPVIWTKIRVPGNDAPVESTEMPLAPPL<br>TPDLSRESWWPPFSTVMEGLLPSQRPTTSETGTPRVEGMVTEKPANTLLPLGGDHQPEPS<br>GKTANRNHLKLPNNMNQTKSSEPVLTEEDATSLITEGFLLNASNYKQLTNGHGSAHWIVG<br>NWSECSTTCGLGAYWRRVECSTQMDSDCAAIQRPDPAKRCHLRPCAGWKVGNWSKCSRNC<br>SGGFKIREIQCVDSRDHRNLRPFHCQFLAGIPPPLSMSCNPEPCEAWQVEPWSQCSRSCG<br>GGVQERGVFCPGGLCDWTKRPTSTMSCNEHLCCHWATGNWDLCSTSCGGGFQKRTVQCVP<br>SEGENKTEDQDQCLCDHKPRPPEFKKCNQQACKKSADLLCTKDKLSASFCQTLKAMKKCSV<br>PTVRAECCFSCPQTHITHTQRQRRQRLLQKSKEL | | |
| 25 | Rat ADAMTS-12 from D3ZTJ3 | | PRT |
| | MPCAQGNWMAKLSMVAQLLNFGAFCHGRQAQPWPVRFPDPKQEHFIKSLPEYHIVSPVQV<br>DASGHFLSYGLHHPVTGSRKKRAAGGSGDQVYYRISHEEKNLFFNLTVNWEFLSNGYVVE<br>RRYGNLSHVKMAASSGQPCHLRGTVLQQGPTIRMGTAALSACQGLTGFFHLPHGDFFIEP<br>VKKHPLTEEGYQPHVIYRRQSYRVPETKEPTCGLKDSLDNSVKQELQREKWERKNWPSRS<br>LSRRSISKERWVETLVVADTKMVEYHGSENVESYILTIMNMVTGLFHNPSIGNAVHIVVV<br>RLILLEEEEQGLKIVHHAEKTLSSFCKWQKSINPKSDLNPVHHDVAVLITRKDICAGVNR |

| SEQ ID NO. | VARIANT | TYPE |
|---|---|---|
| | PCETLGLSQLSGMCQPHRSCNINEDSGLPLAFTIAHELGHSFGIQHDGKENDCEPVGRHP<br>YIMSQQIQYDPTPLTWSKCSKEYITRFLDRGRGFCLDDVPRKKGLKSNVIAPGVIYDVHH<br>QCQLQYGPNATFCQEVENVCQTLWCSVKGFCRSKLDAAADGTRCGEKKWCMAGKCITVGK<br>KPESIPGGWGRWSPWSHCSRTCGAGAQSAERLCNNPEPKFGGKYCTGERKRYRLCNVHPC<br>RSDTPTFRQMQCSEFDTVPYKNQFYRWFPVFNPAHPCELYCRPIDEQFSERMLEAVIDGT<br>PCFEGGNSRNVCINGICKRVGCDYEIDSNATEDRCGVCLGDGSACQTVKKVFRQKEGSGY<br>IDIGLIPKGARDIRVMEIKAAGNFLAIRSEDPEKYYLNGGFIIQWNGNYKLAGTVFQYDR<br>KGDLERLMAPGPTNESVWLQLLFQVTNPGIKYEYTVRKDGLDNDVEKLLYFWQFGRWTEC<br>SVTCGTGIRRQTAHCVKKGHGIVKTTFCNPETQPSVRQKKCYEKDCPPRWWAGEWEACSM<br>TCGPYGEKKRTVLCIQTMGSDEQALPATDCQHLLKPKTLVSCNRDILCPSDWTVGNWSEC<br>SVSCGGGVRIRSVTCAKNLNEPCDKTRKPNSRALCGLQQCPFSRRVLKPNKDTVPSGKNP<br>TTSEHDHFKPIPASTSRPTPLSTPTVPESVSTSTPTINSLGSTITSQEEPDGIGWQNNST<br>QAEEDSHIPTSVGSTSQTPLTSWSWSMQPDDENVSSSAIGPTSESDFWATTSDSGLSSSN<br>AMTWQVTPFYSTATTEPEVEIHSGSGEDSDQPLNKEENNSVLWNKIRVPERDAPMEMDAE<br>IPLGPPPTSYVTEESSWPPFSTMMKSSLPAWSFKNETPRDEGMITEKSGNIPLPLGGDHQ<br>TTSPEKLGNNDQLASANSTNPTQGSGPVLTEEDASTLIEEGFLLNASNYKHLMKDHSPAH<br>WIVGNWSKCSTTCGLGAYWRSVECSTGMNADCAAIQRPDPAKKCHLRPCAGWRVGNWSKC<br>SRNCSGGFKIREVQCMDGVDHHRSLRPFHCQFLAGVPPPLSMSCNLEPCEEWKVEPWSQC<br>SRSCGGGVQERGVFCPGGLCDWTKRPASTVPCNRHLCCHWATGNWELCTTSCGGGSQKRT<br>VHCIPSENSTTEDQDQCFCDHQARPPEFQNCNQQACRKSADLTCTKDRLSTSFCQTLKSM<br>KKCSVPSVRVQCCLSCPQTQSIHTQRQRKQQMLQNHDTL | |
| 26 | Mouse ADAMTS-12 from Q811B3<br>MPCARGSWLAKLSIVAQLINFGAFCHGRQTQPWPVRFPDPRQEHFIKSLPEYHIVSPVQV<br>DAGGHVLSYGLHHPVTSSRKKRAAGGSGDQLYYRISHEEKDLFFNLTVNWEFLSNGYVVE<br>KRYGNLSHVKMVASSGQPCHLRGTVLQQGTTVGIGTAALSACQGLTGFFHLPHGDFFIEP<br>VKKHPLTEEGSYPHVVYRRQSIRAPETKEPICGLKDSLDNSVKQELQREKWERKTLRSRS<br>LSRRSISKERWVETLVVADTKTVEYHGSENVESYILTIMNMVTGLFHSPSIGNLVHIVVV<br>RLILLEEEEQGLKIVHHAEKTLSSFCKWQKSINPKSDLNPVHHDVAVLITRKDICAGVNR<br>PCETLGLSQLSGMCQPHRSCNINEDSGLPLAFTIAHELGHSFGIQHDGKENDCEPVGRHP<br>YIMSQQIQYDPTPLTWSKCSKEYITRFLDRGRGFCLDDIPSKKGLKSNVIAPGVIYDVHH<br>QCQLQYGPNATFCQEVENVCQTLWCSVKGFCRSKLDAAADGTRCGEKKWCMAGKCITVGK<br>KPESIPGGWGRWSPWSHCSRTCGAGAQSAERLCNNPEPKFGGKYCTGERKRYRLCNVHPC<br>RSDTPTFRQMQCSEFDTVPYKNQFYRWFPVFNAAHPCELYCRPIDEQFSERMLEAVIDGT<br>PCFEGGNSRNVCINGICKRVGCDYEIDSNATEDRCGVCLGDGSACQTVKKLFRQKEGSGY<br>VDIGLIPKGARDIRVMEIKAAGNFLAIRSEDPEKYYLNGGFIIQWNGNYKLAGTVFQYDR<br>KGDLEKLIAPGPTNESVWLQLLFQVTNPGIKYEYTVRKDGLDNDVEKLLYFWQFGRWTEC<br>SVTCGTGIRRQAAHCVKKGHGIVKTTFCNPETQPSVRQKKCHEKDCPPRWWAGEWEACST<br>TCGPYGEKKRTVLCIQTMGSDEQALPATDCQHLLKPKALVSCNRDILCPSDWTVGNWSEC<br>SVSCGGGVRIRSVTCAKNLNEPCDKTRKPNSRALCGLQQCPFSRRVLKPNKDIAPSGKNQ<br>STAEHDPFKPIPAPTSRPTPLSTPTVPESMSTSTPTINSLGSTIASQEDANGMGWQNNST<br>QAEEGSHFPTSSGSTSQVPVTSWSLSIQPDDENVSSSAIGPTSEGDFWATTTSDSGLSSS<br>DAMTWQVTPFYSTMTTDPEVEIHSGSGEDSDQPLNKDKSNSVIWNKIGVPEHDAPMETDA<br>ELPLGPPPTSYMGEEPSWPPFSTKMEGSLPAWSFKNETPRDDGMIAEKSRKIPLPLAGDH<br>HPATSEKLENHDKLALPNTTNPTQGFGPVLTEEDASNLIAEGFLLNASDYKHLMKDHSPA<br>YWIVGNWSKCSTTCGLGAYWRSVECSSGVDADCTTIQRPDPAKKCHLRPCAGWRVGNWSK<br>CSRNCSGGFKIREVQCMDSLDHHRSLRPFHCQFLAGAPPPLSMSCNLEPCGEWQVEPWSQ<br>CSRSCGGGVQERGVSCPGGLCDWTKRPATTVPCNRHLCCHWATGNWELCNTSCGGGSQKR<br>TIHCIPSENSTTEDQDQCLCDHQVKPPEFQTCNQQACRKSADLTCLKDRLSISFCQTLKS<br>MRKCSVPSVRAQCCLSCPQAPSIHTQRQRKQQLLQNHDML | PRT |

According to a first aspect the present invention provides novel low-molecular-weight compounds which act as potent antagonists of the ADAMTS7 receptor and are thus suitable for treatment and/or prevention of lung diseases, heart diseases, inflammatory diseases, fibrotic diseases, metabolic diseases, cardiometabolic diseases, vascular diseases and/or cardiovascular diseases.

Further embodiments relate to the identification of ADAMTS7 antagonists that are suitable for treatment and/or prevention of atherosclerosis, athersderosis-related diseases such as coronary artery disease or peripheral vascular disease/arterial occlusive disease as well as post-surgery complications of these diseases such as restenosis after angioplasty.

Further embodiments relate to the identification of selective ADAMTS7 antagonists in respect to ADAMTS4 antagonistic effect.

WO 2014/06651 discloses substituted hydantoinamides as ADAMTS4 and 5 inhibitors for use in the treatment of arthritis in particular osteoarthritis.

WO 2004/024721 and WO2004024715 describe hydantoin derivatives and their use as TACE (ADAMT17) inhibitors.

WO2004/108086 and WO2002/096426 disclose Hydantoin derivatives as TACE inhibitors.

WO 2017/211666 and WO2017/211667 disclose Hydantoin derivatives as ADAMTS4 and 5 inhibitors for the treatment of inflammatory diseases preferably osteoarthritis.

WO01/44200 generically discloses a broad range of compounds as selective neurokinin antagonists.

WO2018/069532 discloses inhibitors of alpha-amino-beta carboxymuconic acid semialdehyde decarboxylase.

9 distinct compounds with the following CAS numbers 2224459-87-2, 2224418-23-7, 2224397-97-9, 2224363-23-7, 2224363-22-6, 2224237-51-6, 2224237-28-7, 2224196-43-2 and 2224145-02-0 have been published without further information with regard to any pharmaceutical use.

It has now been found that compounds of the present invention have surprising and advantageous properties.

Compounds of the present invention are ADAMTS7, and ADAMTS12 antagonists but are selective against MMP12.

In particular, it has been found that compounds of the present invention are ADAMTS7 antagonists. Moreover, many of the compounds of the invention are selective with respect to ADAMTS4—preferably 10 times, or even 50 times more selective against ADAMTS7 relative to ADAMTS4.

The present invention provides compounds of general formula (I):

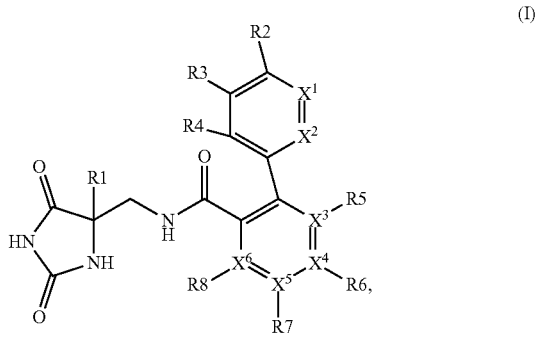

in which
R$^1$ represents a group selected from hydrogen, (C$_1$-C$_6$)-alkyl, (C$_3$-C$_6$)-cycloalkyl, 5- to 6-membered heterocycloalkyl, 5- to 10-membered heteroaryl (such as 5- to 6-membered heteroaryl), and phenyl
wherein said (C$_1$-C$_6$)-alkyl, (C$_3$-C$_6$)-cycloalkyl, 5- to 6-membered heterocycloalkyl, 5- to 10-membered heteroaryl, and phenyl are optionally substituted with one or two groups independently selected from cyano, halogen, amino, hydroxy, oxo, C$_1$-C$_3$-alkyl, (C$_1$-C$_4$)-alkoxy, (C$_1$-C$_4$)-alkylcarbonyl, mono-(C$_1$-C$_4$)-alkylamino, di-(C$_1$-C$_4$)-alkylamino, phenyl, (C$_1$-C$_4$)-alkylsulfonyl, and (C$_3$-C$_6$)-cycloalkyl,
wherein each said C$_1$-C$_3$-alkyl, (C$_3$-C$_6$)-cycloalkyl, and (C$_1$-C$_4$)-alkoxy is optionally substituted with up to 5 fluorine atoms
R$^2$ represents a group independently selected from hydrogen, cyano, halogen, (C$_1$-C$_4$)-alkylsulfonyl, (C$_1$-C$_4$)-alkyl, (C$_3$-C$_6$)-cycloalkyl, and (C$_1$-C$_4$)-alkoxy
wherein said (C$_1$-C$_4$)-alkyl, (C$_3$-C$_6$)-cycloalkyl, and (C$_1$-04)-alkoxy each is optionally independently substituted with up to five fluorine atoms, cyano, or (C$_1$-C$_2$)alkyl, wherein said (C$_1$-C$_2$)alkyl is optionally substituted with up to five fluorine atoms
R$^3$, R$^4$, R$^5$, R$^6$, R$^7$ and R$^8$ represent a group independently selected from hydrogen, halogen, (C$_1$-C$_4$)-alkyl and (C$_1$-C$_4$)-alkoxy
wherein said (C$_1$-C$_4$)-alkyl and (C$_1$-C$_4$)-alkoxy each is optionally independently substituted with up to five fluorine atoms,
with the proviso that at least one of R$^2$, R$^3$, R$^4$ represents H,
X$^1$, X$^2$, X$^3$, X$^4$, X$^5$, X$^6$, represent N or C with the provisio that in each ring system maximal one X stands for N and R$^5$, R$^6$, R$^7$ and R$^8$ are present provided that the designated atom's normal valency under the existing circumstances is not exceeded,
and pharmaceutically acceptable salts thereof, solvates thereof and the solvates of the salts thereof.

The term "substituted" means that one or more hydrogen atoms on the designated atom or group are replaced with a selection from the indicated group, provided that the designated atom's normal valency under the existing circumstances is not exceeded. Combinations of substituents and/or variables are permissible.

The term "optionally substituted" means that the number of non-hydrogen substituents can be equal to or different from zero. Unless otherwise indicated, optionally substituted groups may be substituted with as many optional substituents as can be accommodated by replacing a hydrogen atom with a non-hydrogen substituent on any available carbon atom or heteroatom.

When groups in the compounds according to the invention are substituted, said groups may be mono-substituted or poly-substituted with substituent(s), unless otherwise specified. Within the scope of the present invention, the meanings of all groups which occur repeatedly are independent from one another. Groups in the compounds according to the invention may, for example, be substituted with one, two or three identical or different substituents.

As used herein, an "oxo" substituent represents an oxygen atom, which is bound to a carbon atom or to a sulfur atom via a double bond.

As used herein "allyl" is a substituent with the structural formula H$_2$C=CH—CH$_2$*, where * is the connection to the rest of the molecule. It consists of a methylene bridge (—CH$_2$—) attached to a vinyl group (—CH=CH$_2$).

The term "ring substituent" means a non-hydrogen substituent attached to an aromatic or nonaromatic ring which replaces an available hydrogen atom on the ring.

The term "comprising" when used in the specification includes "consisting of".

If within the present text any item is referred to as "as mentioned herein", it means that it may be mentioned anywhere in the present text.

The terms as mentioned in the present text have the following meanings:

The term "halogen" or "halogen atom" means a fluorine, chlorine, bromine or iodine atom, preferably a fluorine, chlorine or bromine atom, even more preferably fluorine or chlorine most preferred fluorine.

The term "C$_1$-C$_3$-alkyl", "C$_1$-C$_4$-alkyl" and "C$_1$-C$_6$-alkyl" means a linear or branched, saturated, monovalent hydrocarbon group having 1, 2 or 3, 1, 2, 3, or 4 carbon atoms, and 1, 2, 3, 4, 5 or 6 carbon atoms, e.g. a methyl, ethyl, propyl, isopropyl, butyl, sec-butyl, isobutyl, tert-butyl, pentyl, isopentyl, 2-methylbutyl, 1-methylbutyl, 1-ethylpropyl, 1,2-dimethylpropyl, neo-pentyl, 1,1-dimethylpropyl, hexyl, 1-methylpentyl, 2-methylpentyl, 3-methylpentyl, 4-methylpentyl, 1-ethylbutyl, 2-ethylbutyl, 1,1-dimethylbutyl, 2,2-dimethylbutyl, 3,3-dimethylbutyl, 2,3-dimethylbutyl, 1,2-dimethylbutyl or 1,3-dimethylbutyl group, or an isomer thereof. Preferably, said group has 1, 2, 3 or 4 carbon atoms ("C$_1$-C$_4$-alkyl"), e.g., a methyl, ethyl, propyl, isopropyl, butyl, sec-butyl isobutyl, or tert-butyl group, more preferably 1, 2 or 3 carbon atoms ("C$_1$-C$_3$-alkyl"), e.g., a methyl, ethyl, n-propyl or isopropyl group.

The terms "C$_1$-C$_4$-alkoxy" means a linear or branched, saturated, monovalent group of formula (C$_1$-C$_4$-alkyl)-O—, in which the term "C$_1$-C$_4$-alkyl" is as defined supra, e.g., a methoxy, ethoxy, n-propoxy, isopropoxy, butoxy or an isomer thereof, preferably a methoxy-group or ethoxy-group.

The term "C$_3$-C$_6$-cycloalkyl" means a saturated, monovalent, mono- or bicyclic hydrocarbon ring which contains 3, 4, 5 or 6 carbon atoms, respectively. Said C$_3$-C$_6$-cycloalkyl group may be for example, a monocyclic hydrocarbon ring, e.g., a cyclopropyl, cyclobutyl, cyclopentyl or cyclohexyl group, or a bicyclic hydrocarbon ring. The term "3- to 6-membered cycloalkyl" is equivalent to a "$C_3$-$C_6$-cycloalkyl". Thus a "4-membered cycloalkyl group" has the same meaning as a "$C_4$-cycloalkyl group", and a "$C_3$-cycloalkyl" is a cyclopropyl-group.

The term "5- to 6-membered heterocycloalkyl means a monocyclic, saturated heterocycloalkyl with 5 or 6 ring atoms in total, respectively, which contains one or two identical or different ring heteroatoms from the series N, S or O. The heterocycloalkyl group may be attached to the rest of the molecule via any one of the carbon or nitrogen atoms. A heterocycloalkyl group which contains at least one ring nitrogen atom may be referred to as aza-heterocycloalkyl, and a heterocycloalkyl group which contains at least one ring oxygen atom may be referred to as oxa-heterocycloalkyl. Preferably, an aza-heterocycloalkyl group contains only nitrogen and carbon atoms in the ring, and an oxa-heterocycloalkyl group contains only ring oxygen and carbon atoms in the ring.

Said heterocycloalkyl without being limited thereto, can be a 5-membered ring, such as tetrahydrofuranyl, 1,3-dioxolanyl, thiolanyl, pyrrolidinyl, imidazolidinyl, pyrazolidinyl, 1,1-dioxidothiolanyl, 1,2-oxazolidinyl, 1,3-oxazolidinyl or 1,3-thiazolidinyl, for example; or a 6-membered ring, such as tetrahydropyranyl, tetrahydrothiopyranyl, piperidinyl, morpholinyl, dithianyl, thiomorpholinyl, piperazinyl, 1,3-dioxanyl, 1,4-dioxanyl or 1,2-oxazinanyl, for example.

The term "5- to 10-membered heteroaryl", "5-membered heteroaryl," "6-membered heteroaryl," "7-membered heteroaryl," "8-membered heteroaryl," "9-membered heteroaryl," and "10-membered heteroaryl" means a mono- or optionally bicyclic aromatic ring with 5 to 10, 5, 6, 7, 8, 9, or 10 ring atoms in total, respectively, which contains at least one ring heteroatom and optionally one, two or three further ring heteroatoms from the series: N, O and/or S, and which is attached to the rest of the molecule via a ring carbon atom or optionally via a ring nitrogen atom (if allowed by valency).

The following representative heteroaryls may be mentioned by way of example: furyl, pyrrolyl, thienyl, pyrazolyl, imidazolyl, thiazolyl, oxazolyl, isoxazolyl, isothiazolyl, triazolyl, oxadiazolyl, thiadiazolyl, pyridyl, pyrimidinyl, pyridazinyl, pyrazinyl, triazinyl, benzofuranyl, benzothienyl, benzimidazolyl, benzoxazolyl, benzothiazolyl, benzotriazolyl, benzopyrazolyl, indolyl, indazolyl, quinolinyl, isoquinolinyl, naphthyridinyl, quinazolinyl, quinoxalinyl, phthalazinyl, and pyrazolo[3,4-b]pyridinyl,1,2,4-oxadiazolyl and 1,3,4-oxadiazolyl.

6-membered heteroaryl groups, such as, for example, pyridinyl, pyridazinyl, pyrimidinyl, pyrazinyl or triazinyl; or a tricyclic heteroaryl group, such as, for example, carbazolyl, acridinyl or phenazinyl.

mono-($C_1$-$C_4$)-alkylamino in the context of the invention means an amino group with one straight-chain or branched alkyl substituent which contains 1, 2, 3 or 4 carbon atoms, such as: methylamino, ethylamino, n-propylamino, isopropylamino, n-butylamino, and tert-butylamino, for example.

di-($C_1$-$C_4$)-alkylamino in the context of the invention means an amino group with two identical or different straight-chain or branched alkyl substituents which each contain 1, 2, 3 or 4 carbon atoms, such as: N,N-dimethylamino, N,N-diethylamino, N-ethyl-N-methylamino, N-methyl-N-n-propylamino, N-isopropyl-N-methylamino, N-isopropyl-N-n-propylamino, N,N-diisopropylamino, N-n-butyl-N-methylamino, and N-tert-butyl-N-methylamino, for example.

($C_1$-$C_4$)-Alkylcarbonyl in the context of the invention means a straight-chain or branched alkyl group having 1, 2, 3 or 4 carbon atoms which is bound to the rest of the molecule via a carbonyl group [—C(═O)—], such as: acetyl, propionyl, n-butyryl, isobutyryl, n-pentanoyl, and pivaloyl, for example.

($C_1$-$C_4$)-alkylsulfonyl in the context of the invention means a group which is bound to the rest of the molecule via a sulfonyl group [—S(═O)$_2$—] and which has one straight-chain or branched alkyl substituent having 1, 2, 3 or 4 carbon atoms, such as: methylsulfonyl, ethylsulfonyl, n-propylsulfonyl, isopropylsulfonyl, n-butylsulfonyl, and tert-butylsulfonyl, for example.

An oxo substituent in the context of the invention means an oxygen atom which is bound to a carbon atom via a double bond.

In general, and unless otherwise mentioned, the heteroaryl or heteroarylene groups include all possible isomeric forms thereof, e.g.: tautomers and positional isomers with respect to the point of linkage to the rest of the molecule. Thus, for some illustrative non-restricting examples, the term pyridinyl includes pyridin-2-yl, pyridin-3-yl and pyridin-4-yl; or the term thienyl includes thien-2-yl and thien-3-yl.

The term "$C_1$-$C_4$", as used in the present text, e.g., in the context of the definition of "$C_1$-$C_4$-alkyl", "$C_1$-$C_4$-alkoxy"," or "$C_1$-$C_4$-alkylsulfanyl", means an alkyl group having 1 to 4 carbon atoms, i.e., 1, 2, 3, or 4 carbon atoms.

The term "$C_1$-$C_6$", as used in the present text, e.g., in the context of the definition of "$C_1$-$C_6$-alkyl", means an alkyl group having 1 to 6 carbon atoms, i.e., 1, 2, 3, 4, 5 or 6 carbon atoms.

Further, as used herein, the term "$C_3$-$C_6$", as used in the present text, e.g., in the context of the definition of "$C_3$-$C_6$-cycloalkyl", means a cycloalkyl group having 3 to 6 carbon atoms, i.e., 3, 4, 5 or 6 carbon atoms.

When a range of values is given, said range encompasses each value and sub-range within said range.

For example:

"$C_1$-$C_4$" encompasses $C_1$, $C_2$, $C_3$, $C_4$, $C_1$-$C_4$, $C_1$-$C_3$, $C_1$-$C_2$, $C_2$-$C_4$, $C_2$-$C_3$, and $C_3$-$C_4$;

"$C_1$-$C_3$" encompasses $C_1$, $C_2$, $C_3$, $C_1$-$C_3$, $C_1$-$C_2$, and $C_2$-$C_3$;

"$C_2$-$C_4$" encompasses $C_2$, $C_3$, $C_4$, $C_2$-$C_4$, $C_2$-$C_3$, and $C_3$-$C_4$;

"$C_3$-$C_6$" encompasses $C_3$, $C_4$, $C_5$, $C_6$, $C_3$-$C_6$, $C_3$-$C_5$, $C_3$-$C_4$, $C_4$-$C_6$, $C_4$-$C_5$, and $C_5$-$C_6$;

As used herein, the term "leaving group" means an atom or a group of atoms that is displaced in a chemical reaction as stable species taking with it the bonding electrons. Preferred such leaving groups include halide (e.g., fluoride, chloride, bromide or iodide), and sulfonate (e.g., (methylsulfonyl)oxy (mesyl(ate), Ms), [(trifluoromethyl)sulfonyl] oxy (triflyl/(ate), Tf), [(nonafluoro-butyl)sulfonyl]oxy (nonaflate, Nf), (phenylsulfonyl)oxy, [(4-methylphenyl) sulfonyl]oxy, [(4-bromo-phenyl)sulfonyl]oxy, [(4-nitrophenyl)sulfonyl]oxy, [(2-nitrophenyl)sulfonyl]oxy, [(4-isopropyl-phenyl)sulfonyl]oxy, [(2,4,6-triisopropylphenyl) sulfonyl]oxy, [(2,4,6-trimethylphenyl)sulfonyl]oxy, [(4-tert-butylphenyl)sulfonyl]oxy and [(4-methoxyphenyl)sulfonyl] oxy).

It is possible for the compounds of general formula (I) to exist as isotopic variants. The invention therefore includes one or more isotopic variant(s) of the compounds of general formula (I), particularly deuterium-containing compounds of general formula (I).

The term "Isotopic variant" of a compound or a reagent is defined as a compound exhibiting an unnatural proportion of one or more of the isotopes of the atoms that constitute such a compound.

The term "Isotopic variant of the compound of general formula (I)" is defined as a compound of general formula (I) exhibiting an unnatural proportion of one or more of the isotopes of the atoms that constitute such a compound.

The expression "unnatural proportion" means a proportion of such isotope which is higher than its natural abundance. The natural abundances of isotopes to be applied in this context are described in "Isotopic Compositions of the Elements 1997", Pure Appl. Chem., 70(1), 217-235, 1998.

Examples of such isotopes include stable and radioactive isotopes of hydrogen, carbon, nitrogen, oxygen, phosphorus, sulfur, fluorine, chlorine, bromine and iodine, such as $^2H$ (deuterium), $^3H$ (tritium), $^{11}C$, $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{125}I$, $^{129}I$ and $^{131}I$, respectively.

With respect to the treatment and/or prophylaxis of the disorders specified herein, isotopic variant(s) of the compounds of general formula (I) preferably contain elevated levels of deuterium ("deuterium-containing compounds of general formula (I)"). Isotopic variants of the compounds of general formula (I) in which one or more radioactive isotopes, such as $^3H$ or $^{14}C$, are incorporated are useful, e.g., in drug and/or substrate tissue distribution studies. These isotopes are particularly preferred for the ease of their incorporation and detectability. Positron-emitting isotopes such as $^{18}F$ or $^{11}C$ may be incorporated into a compound of general formula (I). These isotopic variants of the compounds of general formula (I) are useful for in vivo imaging applications. Deuterium-containing and $^{13}C$-containing compounds of general formula (I) can be used in mass spectrometry analyses in the context of preclinical or clinical studies.

Isotopic variants of the compounds of general formula (I) can generally be prepared by methods known to a person skilled in the art, such as those described in the schemes and/or examples herein, e.g., by substituting a reagent for an isotopic variant of said reagent, preferably for a deuterium-containing reagent. Depending on the desired sites of deuteration, in some cases deuterium from $D_2O$ can be incorporated either directly into the compounds or into reagents that are useful for synthesizing such compounds (Esaki et al., Tetrahedron, 2006, 62, 10954; Esaki et al., Chem. Eur. J., 2007, 13, 4052). Deuterium gas is also a useful reagent for incorporating deuterium into molecules. Catalytic deuteration of olefinic bonds (H. J. Leis et al., Curr. Org. Chem., 1998, 2, 131; J. R. Morandi et al., J. Org. Chem., 1969, 34 (6), 1889) and acetylenic bonds (N. H. Khan, J. Am. Chem. Soc., 1952, 74 (12), 3018; S. Chandrasekhar et al., Tetrahedron Letters, 2011, 52, 3865) is a rapid route for incorporation of deuterium. Metal catalysts (e.g., Pd, Pt, and Rh) in the presence of deuterium gas can be used to directly exchange deuterium for hydrogen in functional groups containing hydrocarbons (J. G. Atkinson et al., U.S. Pat. No. 3,966,781). A variety of deuterated reagents and synthetic building blocks are commercially available from companies such as for example C/D/N Isotopes, Quebec, Canada; Cambridge Isotope Laboratories Inc., Andover, MA, USA; and CombiPhos Catalysts, Inc., Princeton, NJ, USA. Further information on the state of the art with respect to deuterium-hydrogen exchange is given for example in Hanzlik et al., J. Org. Chem. 55, 3992-3997, 1990; R. P. Hanzlik et al., Biochem. Biophys. Res. Commun. 160,844,1989; P. J. Reideretal., J. Org. Chem. 52, 3326-3334, 1987; M. Jarman et al., Carcinogenesis 16 (4), 683-688, 1995; J. Atzrodt et al., Angew. Chem., Int. Ed. 2007, 46, 7744; K. Matoishi et al., Chem. Commun. 2000, 1519-1520; K. Kassahun et al., WO2012/112363.

The term "deuterium-containing compound of general formula (I)" is defined as a compound of general formula (I), in which one or more hydrogen atom(s) is/are replaced by one or more deuterium atom(s) and in which the abundance of deuterium at each deuterated position of the compound of general formula (I) is higher than the natural abundance of deuterium, which is about 0.015%. Particularly, in a deuterium-containing compound of general formula (I) the abundance of deuterium at each deuterated position of the compound of general formula (I) is higher than 10%, 20%, 30%, 40%, 50%, 60%, 70% or 80%, preferably higher than 90%, 95%, 96% or 97%, even more preferably higher than 98% or 99% at said position(s). It is understood that the abundance of deuterium at each deuterated position is independent of the abundance of deuterium at other deuterated position(s).

The selective incorporation of one or more deuterium atom(s) into a compound of general formula (I) may alter the physicochemical properties (such as for example acidity [C. L. Perrin, et al., J. Am. Chem. Soc., 2007, 129, 4490; A. Streitwieser et al., J. Am. Chem. Soc., 1963, 85, 2759;], basicity [C. L. Perrin et al., J. Am. Chem. Soc., 2005, 127, 9641; C. L. Perrin, et al., J. Am. Chem. Soc., 2003, 125, 15008; C. L. Perrin in Advances in Physical Organic Chemistry, 44, 144], lipophilicity [B. Testa et al., Int. J. Pharm., 1984, 19(3), 271]) and/or the metabolic profile of the molecule and may result in changes in the ratio of parent compound to metabolites or in the amounts of metabolites formed. Such changes may result in certain therapeutic advantages and hence may be preferred in some circumstances. Reduced rates of metabolism and metabolic switching, where the ratio of metabolites is changed, have been reported (A. E. Mutlib et al., Toxicol. Appl. Pharmacol., 2000, 169, 102; D. J. Kushner et al., Can. J. Physiol. Pharmacol., 1999, 77, 79). These changes in the exposure to parent drug and metabolites can have important consequences with respect to the pharmacodynamics, tolerability and efficacy of a deuterium-containing compound of general formula (I). In some cases deuterium substitution reduces or eliminates the formation of an undesired or toxic metabolite and/or enhances the formation of a desired metabolite (e.g., Nevirapine: A. M. Sharma et al., Chem. Res. Toxicol., 2013, 26, 410; Efavirenz: A. E. Mutlib et al., Toxicol. Appl. Pharmacol., 2000, 169, 102). In other cases the major effect of deuteration is to reduce the rate of systemic clearance. As a result, the biological half-life of the compound is increased. The potential clinical benefits would include the ability to maintain similar systemic exposure with decreased peak levels and increased trough levels, i.e., reduced peak-trough variation. This could result in lowerside effects and/or enhanced efficacy, depending on the particular compound's pharmacokinetic/pharmacodynamic relationship. ML-337 (C. J. Wenthur et al., J. Med. Chem., 2013, 56, 5208) and Odanacatib (K. Kassahun et al., WO2012/112363) are examples of this deuterium effect. Still other cases have been reported in which reduced rates of metabolism result in an increase in exposure of the drug without changing the rate of systemic clearance (e.g., Rofecoxib: F. Schneider et al., Arzneim. Forsch./Drug. Res., 2006, 56, 295; Telaprevir: F. Maltais et al., J. Med. Chem., 2009, 52, 7993). Deuterated drugs showing this effect may have reduced dosing requirements (e.g., lower number of doses or lower dosage to achieve the desired effect) and/or may produce lower metabolite loads.

A compound of general formula (I) may have multiple potential sites of attack for metabolism. To optimize the above-described effects on physicochemical properties and metabolic profile, deuterium-containing compounds of general formula (I) having a certain pattern of one or more deuterium-hydrogen exchange(s) can be selected. Particularly, the deuterium atom(s) of deuterium-containing compound(s) of general formula (I) is/are attached to a carbon atom and/or is/are located at those positions of the compound of general formula (I) which are sites of attack for metabolizing enzymes such as, e.g., cytochrome $P_{450}$.

In certain embodiments, the present invention concerns a deuterium-containing compound of general formula (I) having 1, 2, 3 or 4 deuterium atoms (i.e., 1, 2, 3, or 4 sites where the isotopic balance of hydrogen is enriched for deuterium), preferably with 1, 2 or 3 deuterium atoms.

Where the plural form of the word compounds, salts, polymorphs, hydrates, solvates and the like, is used herein, this is taken to include also a single compound, salt, polymorph, isomer, hydrate, solvate or the like.

By "stable compound' or "stable structure" is meant a compound that is sufficiently robust to survive isolation to a useful degree of purity from a reaction mixture, and is capable of being subjected to further chemical transformation or, preferably, formulation into an efficacious therapeutic agent.

The compounds of the present invention optionally contain one or more asymmetric centres, depending upon the location and nature of the various substituents desired. It is possible that one or more asymmetric carbon atoms are present in the (R) or (S) configuration, which can result in racemic mixtures in the case of a single asymmetric centre, and in diastereomeric mixtures in the case of multiple asymmetric centres. In certain instances, it is possible that asymmetry also be present due to restricted rotation about a given bond, for example, the central bond adjoining two substituted aromatic rings of the specified compounds (i.e., atropisomers).

Preferred compounds are those which produce the more desirable biological activity. Separated, pure or partially purified isomers and stereoisomers or racemic or diastereomeric mixtures of the compounds of the present invention are also included within the scope of the present invention. The purification and the separation of such materials can be accomplished by standard techniques known in the art.

Separated optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., HPLC columns using a chiral phase), with or without conventional derivatisation, optimally chosen to maximise the separation of the enantiomers. Suitable HPLC columns using a chiral phase are commercially available, such as those manufactured by Daicel, e.g., Chiracel OD and Chiracel OJ, for example, among many others, which are all routinely selectable. Enzymatic separations, with or without derivatisation, are also useful. The optically active compounds of the present invention can likewise be obtained by chiral syntheses utilizing optically active starting materials or optically active catalysts. +

In order to distinguish different types of isomers from each other, reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g., (R)- or (S)-isomers, in any ratio. Isolation of a single stereoisomer, e.g., a single enantiomer or a single diastereomer, of a compound of the present invention is achieved by any suitable state of the art method, such as chromatography, especially chiral chromatography, for example.

Further, it is possible for the compounds of the present invention to exist as tautomers. For example, a compound of the present invention which contains an imidazopyridine moiety as a heteroaryl group for example can exist as a 1H tautomer, or a 3H tautomer, or even a mixture in any amount of the two tautomers, namely:

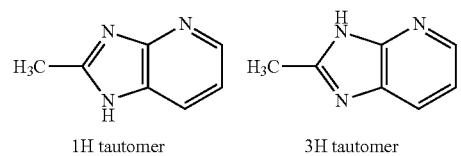

1H tautomer        3H tautomer

Moreover, in the course of the synthesis of a 1H-pyrazole group, the 1H-pyrazol-3-yl tautomer as well as the 1H-pyrazol-5-yl tautomer are formed.

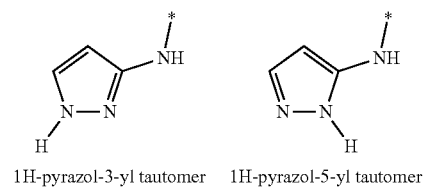 [SMILES: *Nc1cc[nH]n1 ; *Nc1ccn[nH]1]

1H-pyrazol-3-yl tautomer    1H-pyrazol-5-yl tautomer

The present invention includes all possible tautomers of the compounds of the present invention as single tautomers, or as any mixture of said tautomers, in any ratio.

The present invention also covers useful forms of the compounds of the present invention, such as metabolites, hydrates, solvates, prodrugs, salts, in particular pharmaceutically acceptable salts, and/or co-precipitates.

The compounds of the present invention can exist as a hydrate, or as a solvate, wherein the compounds of the present invention contain polar solvents, preferably water, methanol or ethanol, for example, as a structural element of the crystal lattice of the compounds. It is possible for the amount of polar solvents, in particular water, to exist in a stoichiometric or non-stoichiometric ratio. In the case of stoichiometric solvates, e.g., a hydrate, hemi-, (semi-), mono-, sesqui-, di-, tri-, tetra-, penta- etc. solvates or hydrates, respectively, are possible. The present invention includes all such hydrates or solvates.

Further, it is possible for the compounds of the present invention to exist in free form, e.g., as a free base, or as a free acid, or as a zwitterion, or to exist in the form of a salt, preferably as a free acid. Said salt may be any salt, either an organic or inorganic addition salt, particularly any pharmaceutically acceptable organic or inorganic addition salt, which is customarily used in pharmacy, or which is used, for example, for isolating or purifying the compounds of the present invention.

The term "pharmaceutically acceptable salt" refers to an inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, or "mineral acid", such as hydrochloric, hydrobromic, hydroiodic, sulfuric, sulfamic, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, 3-phenylpropionic, pivalic, 2-hydroxyethanesulfonic, itaconic, trifluoromethanesulfonic, dodecylsulfuric, ethanesulfonic, benzenesulfonic, para- toluenesulfonic, methanesulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, or thio cyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium, magnesium or strontium salt, or an aluminium or a zinc salt, or an ammonium salt derived from ammonia or from an organic primary, secondary or tertiary amine having 1 to 20 carbon atoms, such as ethylamine, diethylamine, triethylamine, ethyldiisopropylamine, monoethanolamine, diethanolamine, triethanolamine, dicyclohexylamine, dimethylaminoethanol, diethylaminoethanol, tris(hydroxymethyl)aminomethane, procaine, dibenzylamine, N-methylmorpholine, arginine, lysine, 1,2-ethylenediamine, N-methylpiperidine, N-methyl-glucamine, N,N-dimethyl-glucamine, N-ethyl-glucamine, 1,6-hexanediamine, glucosamine, sarcosine, serinol, 2-amino-1,3-propanediol, 3-amino-1,2-propanediol, 4-amino-1,2,3-butanetriol, or a salt with a quaternary ammonium ion having 1 to 20 carbon atoms, such as tetramethylammonium, tetraethylammonium, tetra(n-propyl)ammonium, tetra(n-butyl)ammonium, N-benzyl-N,N,N-trimethylammonium, choline or benzalkonium.

In accordance with preferred embodiments of the first aspect, the present invention covers a pharmaceutically acceptable salt of compounds of general formula (I), supra, which is an alkali metal salt, in particular a sodium or potassium salt, or an ammonium salt derived from an organic tertiary amine, in particular choline.

Those skilled in the art will further recognise that it is possible for acid addition salts of the claimed compounds to be prepared by reaction of the compounds with the appropriate inorganic or organic acid via any of a number of known methods. Alternatively, alkali and alkaline earth metal salts of acidic compounds of the present invention are prepared by reacting the compounds of the present invention with the appropriate base via a variety of known methods.

The present invention includes all possible salts of the compounds of the present invention as single salts, or as any mixture of said salts, in any ratio.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae relating to salts, such as "hydrochloride", "trifluoroacetate", "sodium salt", or "x HCl", "x $CF_3COOH$", "x Na", for example, mean a salt form, the stoichiometry of which salt form not being specified.

This applies analogously to cases in which synthesis intermediates or example compounds or salts thereof have been obtained, by the preparation and/or purification processes described, as solvates, such as hydrates, with (if defined) unknown stoichiometric composition.

As used herein, the term "in vivo hydrolysable ester" means an in vivo hydrolysable ester of a compound of the present invention containing a carboxy or hydroxy group, for example, a pharmaceutically acceptable ester which is hydrolysed in the human or animal body to produce the parent acid or alcohol. Suitable pharmaceutically acceptable esters for carboxy include for example alkyl, cycloalkyl and optionally substituted phenylalkyl, in particular benzyl esters, $C_1$-$C_6$ alkoxymethyl esters, e.g., methoxymethyl, $C_1$-$C_6$ alkanoyloxymethyl esters, e.g., pivaloyloxymethyl, phthalidyl esters, $C_3$-$C_8$ cycloalkoxy-carbonyloxy-$C_1$-$C_6$ alkyl esters, e.g. 1-cyclohexylcarbonyloxyethyl; 1,3-dioxolen-2-onylmethyl esters, e.g., 5-methyl-1,3-dioxolen-2-onylmethyl; and $C_1$-$C_6$-alkoxycarbonyloxyethyl esters, e.g., 1-methoxycarbonyloxyethyl, it being possible for said esters to be formed at any carboxy group in the compounds of the present invention.

An in vivo hydrolysable ester of a compound of the present invention containing a hydroxy group includes inorganic esters such as phosphate esters and [alpha]-acyloxyalkyl ethers and related compounds which as a result of the in vivo hydrolysis of the ester breakdown to give the parent hydroxy group. Examples of [alpha]-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. The present invention covers all such esters.

Furthermore, the present invention includes all possible crystalline forms, or polymorphs, of the compounds of the present invention, either as single polymorph, or as a mixture of more than one polymorph, in any ratio.

Moreover, the present invention also includes prodrugs of the compounds according to the invention. The term "prodrugs" here designates compounds which themselves can be biologically active or inactive, but are converted (for example metabolically or hydrolytically) into compounds according to the invention during their residence time in the body. Typical examples of prodrugs would be e.g. esters.

Preference is given to compounds of formula (I) in which
$R^1$ represents a group selected from hydrogen, ($C_1$-$C_6$)-alkyl, ($C_3$-$C_6$)-cycloalkyl, 5- to 6-membered heterocycloalkyl, 5- to 10-membered heteroaryl and phenyl wherein said $(C_1-C_6)$-alkyl, $(C_3-C_6)$-cycloalkyl, 5- to 6-membered heterocycloalkyl, and 5- to 10-membered heteroaryl, and phenyl are optionally substituted with one or two groups independently selected from cyano, halogen, amino, hydroxy, oxo, $C_1$-$C_3$-alkyl, $(C_1-C_4)$-alkoxy, $(C_1-C_4)$-alkylcarbonyl, mono-$(C_1-C_4)$-alkylamino, di-$(C_1-C_4)$-alkylamino, phenyl, $(C_1-C_4)$-alkylsulfonyl, and $(C_3-C_6)$-cycloalkyl, wherein each said $C_1$-$C_3$-alkyl, $(C_3-C_6)$-cycloalkyl, and $(C_1-C_4)$-alkoxy is optionally substituted with up to 5 fluorine atoms $R^2$ represents a group independently selected from hydrogen cyano, halogen, $(C_1-C_4)$-alkylsulfonyl, $(C_1-C_4)$-alkyl, $(C_3-C_6)$-cycloalkyl and $(C_1-C_4)$-alkoxy wherein said $(C_1-C_4)$-alkyl$(C_3-C_6)$-cycloalkyl and $(C_1-O_4)$-alkoxy each is optionally independently substituted with up to five fluorine atoms, cyano, or $(C_1-C_2)$alkyl, wherein said $(C_1-C_2)$alkyl is optionally substituted with up to five fluorine atoms.

$R^3$ and $R^4$ represent hydrogen and $R^5$, $R^6$, $R^7$ and $R^8$ represent a group independently selected from hydrogen, halogen, $(C_1-C_4)$-alkyl and $(C_1-C_4)$-alkoxy wherein said $(C_1-C_4)$-alkyl and $(C_1-C_4)$-alkoxy each is optionally independently substituted with up to five fluorine atoms, $X^1$, $X^2$, $X^3$, $X^4$, $X^5$, $X^6$, represent N or C with the provisio that in each ring system maximal one X stands for N and $R^5$, $R^6$, $R^7$ and $R^8$ are present provided that the designated atom's normal valency under the existing circumstances is not exceeded and pharmaceutically acceptable salts thereof, solvates thereof and the solvates of the salts thereof.

In certain such embodiments, $R^1$ is a 5- to 6-membered heteroaryl, optionally substituted with one or two groups independently selected from cyano, halogen, amino, hydroxy, oxo, $C_1$-$C_3$-alkyl, $(C_1-C_4)$-alkoxy, $(C_1-C_4)$-alkylcarbonyl, mono-$(C_1-C_4)$-alkylamino, di-$(C_1-C_4)$-alkylamino, phenyl, $(C_1-C_4)$-alkylsulfonyl, and $(C_3-C_6)$-cycloalkyl, wherein each said $C_1$-$C_3$-alkyl, $(C_3-C_6)$-cycloalkyl, and $(C_1-C_4)$-alkoxy is optionally substituted with up to 5 fluorine atoms.

Preference is further given to compounds of the formula (I) in which $R^1$ represents a group selected from hydrogen, $(C_1-C_6)$-alkyl, $(C_3-C_6)$-cycloalkyl, 5- to 6-membered heterocycloalkyl, 5- to 10-membered heteroaryl and phenyl wherein said $(C_1-C_6)$-alkyl, $(C_3-C_6)$-cycloalkyl, 5- to 6-membered heterocycloalkyl, and 5- to 10-membered heteroaryl, and phenyl are optionally substituted with one or two groups independently selected from cyano, halogen, amino, hydroxy, oxo, $C_1$-$C_3$-alkyl, $(C_1-C_4)$-alkoxy, $(C_1-C_4)$-alkylcarbonyl, mono-$(C_1-C_4)$-alkylamino, di-$(C_1-C_4)$-alkylamino, phenyl, $(C_1-C_4)$-alkylsulfonyl, and $(C_3-C_6)$-cycloalkyl, wherein each said $C_1$-$C_3$-alkyl, $(C_3-C_6)$-cycloalkyl, and $(C_1-C_4)$-alkoxy is optionally substituted with up to 5 fluorine atoms $R^2$ represents a group independently selected from hydrogen cyano, halogen, $(C_1-C_4)$-alkylsulfonyl, $(C_1-C_4)$-alkyl, $(C_3-C_6)$-cycloalkyl, and $(C_1-C_4)$-alkoxy wherein said $(C_1-C_4)$-alkyl$(C_3-C_6)$-cycloalkyl and $(C_1-O_4)$-alkoxy each is optionally independently substituted with up to five fluorine atoms, cyano, or $(C_1-C_2)$alkyl, wherein said $(C_1-C_2)$alkyl is optionally substituted with up to five fluorine atoms.

$R^3$, $R^4$, $R^5$, $R^6$, $R^7$ and $R^8$ represent a group independently selected from hydrogen, halogen, $(C_1-C_4)$-alkyl and $(C_1-C_4)$-alkoxy wherein said $(C_1-C_4)$-alkyl and $(C_1-C_4)$-alkoxy each is optionally independently substituted with up to five fluorine atoms, with the provision that at least two from $R^5$, $R^6$, $R^7$ and $R^8$ represent hydrogen, $X^1$, $X^2$, $X^3$, $X^4$, $X^5$, $X^6$, represent N or C with the provisio that in each ring system maximal one X stands for N and $R^5$, $R^6$, $R^7$ and $R^8$ are present provided that the designated atom's normal valency under the existing circumstances is not exceeded.

and pharmaceutically acceptable salts thereof, solvates thereof and the solvates of the salts thereof.

In certain such embodiments, $R^1$ is a 5- to 6-membered heteroaryl, optionally substituted with one or two groups independently selected from cyano, halogen, amino, hydroxy, oxo, $C_1$-$C_3$-alkyl, $(C_1-C_4)$-alkoxy, $(C_1-C_4)$-alkylcarbonyl, mono-$(C_1-C_4)$-alkylamino, di-$(C_1-C_4)$-alkylamino, phenyl, $(C_1-C_4)$-alkylsulfonyl, and $(C_3-C_6)$-cycloalkyl, wherein each said $C_1$-$C_3$-alkyl, $(C_3-C_6)$-cycloalkyl, and $(C_1-C_4)$-alkoxy is optionally substituted with up to 5 fluorine atoms.

Preference is given to compounds of the formula (Ia), (Ib), (Ic), (Id) and (Ie)

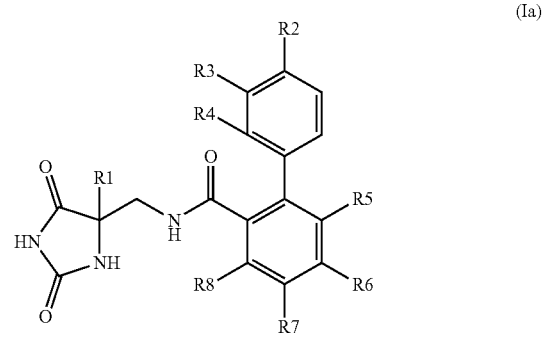

(Ia)

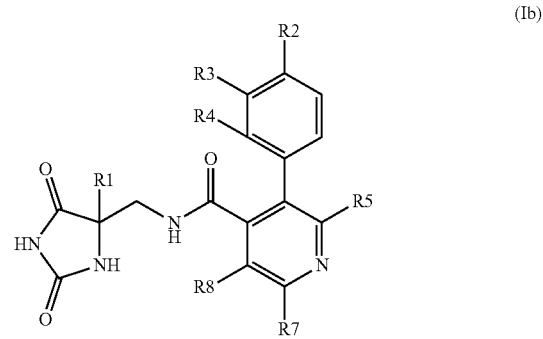

(Ib)

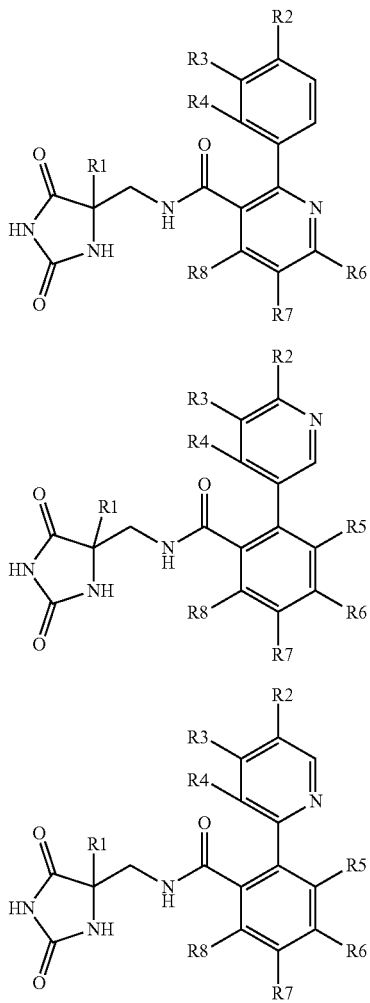

In which
R¹ represents a group selected from hydrogen, $(C_1-C_6)$-alkyl, $(C_3-C_6)$-cycloalkyl, 5- to 6-membered heterocycloalkyl, 5- to 10-membered heteroaryl and phenyl
  wherein said $(C_1-C_6)$-alkyl, $(C_3-C_6)$-cycloalkyl, 5- to 6-membered heterocycloalkyl, and 5- to 10-membered heteroaryl, phenyl are optionally substituted with one or two groups independently selected from cyano, halogen, amino, hydroxy, oxo, $C_1-C_3$-alkyl, $(C_1-C_4)$-alkoxy, $(C_1-C_4)$-alkylcarbonyl, mono-$(C_1-C_4)$-alkylamino, di-$(C_1-C_4)$-alkylamino, phenyl, $(C_1-C_4)$-alkylsulfonyl, $(C_3-C_6)$-cycloalkyl,
  wherein each said $C_1-C_3$-alkyl, $(C_3-C_6)$-cycloalkyl, and $(C_1-C_4)$-alkoxy is optionally substituted with up to 5 fluorine atoms
R² represents a group independently selected from hydrogen cyano, halogen, $(C_1-C_4)$-alkylsulfonyl, $(C_1-C_4)$-alkyl, $(C_3-C_6)$-cycloalkyl and $(C_1-C_4)$-alkoxy
  wherein said $(C_1-C_4)$-alkyl $(C_3-C_6)$-cycloalkyl and $(C_1-O4)$-alkoxy each is optionally independently substituted with up to five fluorine atoms, cyano, or $(C_1-C_2)$alkyl, wherein said $(C_1-C_2)$alkyl is optionally substituted with up to five fluorine atoms.
$R^3, R^4, R^5, R^6, R^7$ and $R^8$ represent a group independently selected from hydrogen, halogen, $(C_1-C_4)$-alkyl and $(C_1-C_4)$-alkoxy wherein said $(C_1-C_4)$-alkyl and $(C_1-C_4)$-alkoxy each is optionally independently substituted with up to five fluorine atoms,
  with the provision that at least two from $R^5, R^6, R^7$ and $R^8$ represent hydrogen,
and pharmaceutically acceptable salts thereof, solvates thereof and the solvates of the salts thereof.

In certain such embodiments, $R^1$ is a 5- to 6-membered heteroaryl, optionally substituted with one or two groups independently selected from cyano, halogen, amino, hydroxy, oxo, $C_1-C_3$-alkyl, $(C_1-C_4)$-alkoxy, $(C_1-C_4)$-alkylcarbonyl, mono-$(C_1-C_4)$-alkylamino, di-$(C_1-C_4)$-alkylamino, phenyl, $(C_1-C_4)$-alkylsulfonyl, and $(C_3-C_6)$-cycloalkyl,
  wherein each said $C_1-C_3$-alkyl, $(C_3-C_6)$-cycloalkyl, and $(C_1-C_4)$-alkoxy is optionally substituted with up to 5 fluorine atoms.

Preference is given to compounds of the formula (I) selected from the group consisting of ent-6-fluoro-N-{[4-(1-methyl-1H-pyrazol-5-yl)-2,5-dioxo-imidazolidin-4-yl]methyl}-4'-(trifluoromethyl)[biphenyl]-2-carboxamide

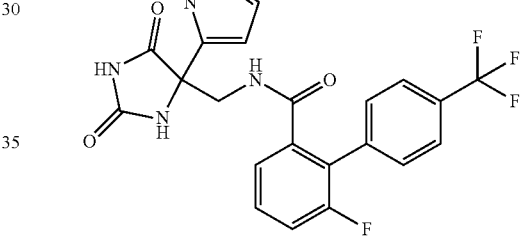

ent-5,6-difluoro-N-{[4-(1-methyl-1H-pyrazol-5-yl)-2,5-dioxoimidazolidin-4-yl]methyl}-4'-(trifluoromethyl)[biphenyl]-2-carboxamide

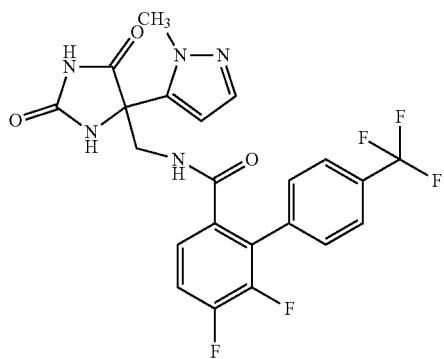 [SMILES: Cn1nccc1C1(CNC(=O)c2ccc(F)c(F)c2-c2ccc(C(F)(F)F)cc2)NC(=O)NC1=O]

ent-4'-chloro-N-{[4-(1-methyl-1H-pyrazol-5-yl)-2,5-dioxo-imidazolidin-4-yl]methyl}[biphenyl]-2-carboxamide

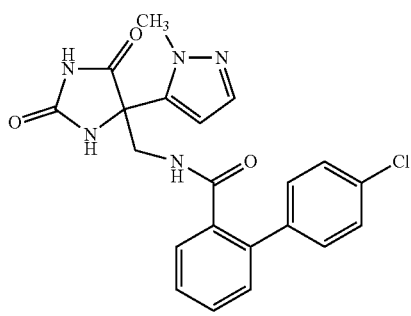 [SMILES: Cn1nccc1C1(CNC(=O)c2ccccc2-c2ccc(Cl)cc2)NC(=O)NC1=O]

ent-4'-chloro-5-fluoro-N-{[4-(1-methyl-1H-pyrazol-5-yl)-2,5-dioxoimidazolidin-4-yl]methyl}[biphenyl]-2-carboxamide

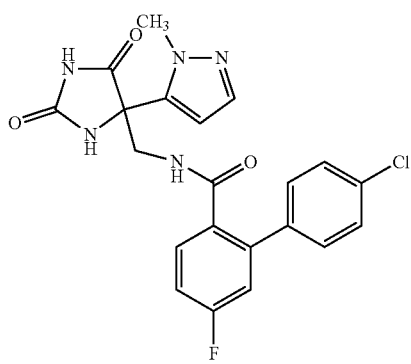 [SMILES: Cn1nccc1C1(CNC(=O)c2ccc(F)cc2-c2ccc(Cl)cc2)NC(=O)NC1=O]

ent-N-{[4-(1-methyl-1H-pyrazol-5-yl)-2,5-dioxoimidazolidin-4-yl]methyl}-4'-(trifluoromethyl)[biphenyl]-2-carboxamide

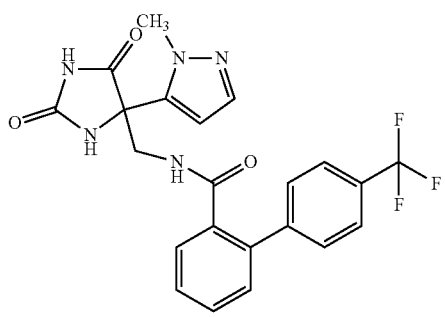 [SMILES: Cn1nccc1C1(CNC(=O)c2ccccc2-c2ccc(C(F)(F)F)cc2)NC(=O)NC1=O]

ent-4,5-difluoro-N-{[4-(1-methyl-1H-pyrazol-5-yl)-2,5-dioxoimidazolidin-4-yl]methyl}-4'-(trifluoromethyl)[biphenyl]-2-carboxamide

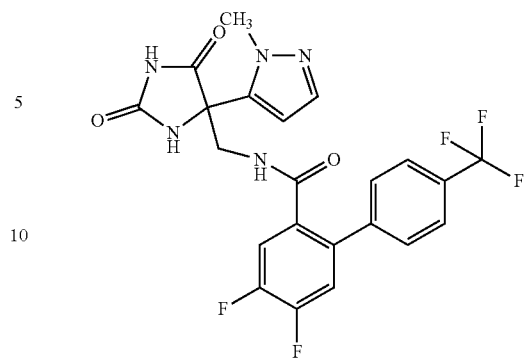

ent-N-{[4-(4-methyl-1,2-oxazol-3-yl)-2,5-dioxoimidazolidin-4-yl]methyl}-4'-(trifluoromethyl)[biphenyl]-2-carboxamide

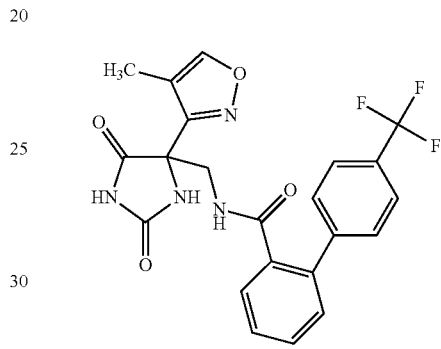

Preference is also given to compounds of formula (I) in which $R^1$ represents cyclopropyl, cyclobutyl, isopropyl, t-butyl, cyclopentyl or methylimidazole, methylpyrazole, oxazole, oxadiazole, trifluorethylpyrazole, difluormethylpyrazole, isoxazole, thiazole.

Particular preference is also given to compounds of formula (I) in which $R^1$ represents methylpyrazole, cyclopropyl.

Preference is also given to compounds of formula (1) in which $R^2$ represents methyl, trifluormethyl, trifluormethoxy, cyclopropyl, cyclobutyl, difluorethyl, difluorcyclopropyl, difluormethyl, difluorcyclopropyl, methylsulfonyl, cyanopropanyl, cyano, chloro, t-butyl and ethyl.

Particular preference is also given to compounds of formula (I) in which $R^2$ represents trifluormethyl, difluorcyclopropyl.

Preference is also given to compounds of formula (I) in which only $X^1$ represents N and $X^2$, $X^3$, $X^4$, $X^5$ and $X^6$ represent C.

Preference is also given to compounds of formula (I) in which only $X^2$ represents N and $X^1$, $X^3$, $X^4$, $X^5$ and $X^6$ represent C.

Preference is also given to compounds of formula (I) in which only $X^3$ represents N and $X^2$, $X^1$, $X^4$, $X^5$ and $X^6$ represent C.

Preference is also given to compounds of formula (I) in which only $X^4$ represents N and $X^2$, $X^3$, $X^1$, $X^5$ and $X^6$ represent C.

Particular preference is also given to compounds of formula (Ib).

Preference is also given to compounds of formula (Ib) in which at least one of $R^3$ and $R^4$ represents hydrogen.

Preference is also given to compounds of formula (Ib) in which at least one of $R^5$ $R^7$ and Ra represents hydrogen.

Particular preference is also given to compounds of formula (Ic).

Preference is also given to compounds of formula (Ic) in which at least one of $R^3$ and $R^4$ represents hydrogen.

Preference is also given to compounds of formula (Ic) in which at least one of $R^6$ and $R^7$ represents hydrogen.

Particular preference is also given to compounds of formula (Id).

Preference is also given to compounds of formula (Id) in which at least one of $R^3$ and $R^4$ represents hydrogen.

Preference is also given to compounds of formula (Id) in which at least two of $R^5$ $R^6$ $R^7$ and Ra represent hydrogen.

Particular preference is also given to compounds of formula (Ie).

Preference is also given to compounds of formula (Ie) in which at least one of $R^3$ and $R^4$ represents hydrogen.

Preference is also given to compounds of formula (Ie) in which at least two of $R^5$ $R^6$ $R^7$ and $R^8$ represent hydrogen.

Particular preference is also given to compounds of formula (Ia).

Particular preference is given to compounds of formula (Ia) in which $R^2$ represents trifluormethane, difluorcyclopropane.

Particular preference is given to compounds of formula (Ia) in which $R^1$ represents methylpyrazole, cyclopropane.

Particular preference is given to compounds of formula (Ia) in which $R^5$ and $R^6$ represent fluoro or $R^5$ represents fluoro.

Another object of the present invention is a process for the preparation of the compounds of formula (I) characterized by reacting a compound of formula (II)

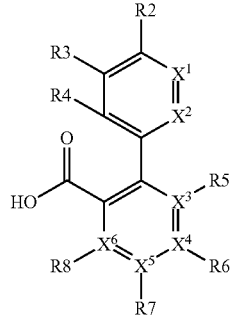

(II)

in which $R_2$, $R_3$, $R_4$, $R_5$, $R_6$, $R_7$, $R_8$ and $X^1$, $X^2$, $X^3$, $X^4$, $X^5$, $X^6$ have the meaning given above, in an inert solvent with a condensing agent such as 1-(3-dimethylaminopropyl)-3-ethylcarbodiimide hydrochloride in the presence of a base such as N,N-diisopropylethylamine and an auxiliary reagent such as HOBt with a compound of formula (III) which may be used as salt (e.g. hydrochloride)

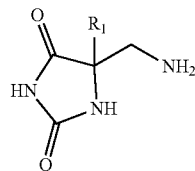

(III)

in which $R_1$ has the meaning given above.

Inert solvents for process step (II)+(III)→(I) are, for example, halogenated hydrocarbons, such as dichloromethane, trichlorethylene, chloroform orchlorobenzene, ethers, such as diethyl ether, dioxane, tetrahydrofuran, 1,2-dimethoxyethane or diglyme, hydrocarbons such as benzene, toluene, xylene, hexane, cyclohexane or petroleum fractions or other solvents such as acetonitrile, N,N-dimethylformamide, N,N-dimethylacetamide, dimethyl sulfoxide, N,N-dimethylpropyleneurea (DMPU), N-methyl-2-pyrrolidone (NMP) or pyridine. It is also possible to use mixtures of the said solvents. Preference is given to using dichloromethane or N,N-dimethylformamide. Dichloromethane is particularly preferably used.

Suitable condensing agents for amide formation in process step (II)+(III)→(I) are, for example, carbodiimides such as N,N'-diethyl-, N,N'-dipropyl-, N,N'-diisopropyl-, N,N'-dicyclohexylcarbodiimide (DCC) or N-(3-dimethylaminopropyl)-N'-ethylcarbodiimide hydrochloride (EDC), phosgene derivatives such as N,N'-carbonyldiimidazole (CDI), 1,2-oxazolium compounds such as 2-ethyl-5-phenyl-1,2-oxazolium-3-sulfate or 2-tert-butyl-5-methyl-isoxazolinium perchlorate, acylamino compounds such as 2-ethoxy-1-ethoxy-carbonyl-1,2-dihydrohydroquinoline, or isobutyl chloroformate, propanephosphonic acid anhydride (T3P), 1-chloro-N,N,2-trimethylprop-1-en-1-amine, cyanophosphonic acid diethyl ester, (2-oxo-3-oxazolidinyl)-phosphoryl chloride, benzotriazazol-1-yloxy-tris(dimethylamino) phosphonium-hexafluorophosphate, benzotriazol-1-yloxytripyrrolidinophosphonium hexafluorophosphate (PyBOP), 2-(1H-Benzotriazole-1-yl)-1,1,3,3-tetramethylaminium tetrafluoroborate (TBTU), 2-(1H-benzotriazol-1-yl)-1,1,3,3-tetramethyluronium hexafluorophosphate (HBTU), 0-(1,2-Dihydro-2-oxo-1-pyridyl)-N,N,N'—N'-tetramethyluronium tetrafluoroborate (TPTU), 1-[Bis(dimethylamino) methylene]-1H-1,2,3-triazolo[4,5-b]pyridinium 3-oxid hexafluorophosphate (HATU) or O-(6-Chloro-1-hydrocibenzotriazol-1-yl)-1,1,3,3-tetramethyluroniumtetrafluoroborate (TCTU), if appropriate in combination with other excipients such as 1 hydroxybenzotriazole (HOBt), 1-hydroxy-7-azabenzotriazole (HOAt) or N-hydroxysuccinimide (HOSu). Preferably EDC and HATU is used. Particular preference is given to using EDC.

Suitable bases for amide formation in process step (II)+(III)→(I) are, for example, alkali metal carbonates, e.g. sodium or potassium carbonate or hydrogen carbonate, or organic bases such as trialkylamines, e.g. triethylamine (TEA), trimethylamine, N methylmorpholine, N-methylpiperidine or N,N-diisopropylethylamine (DIPEA) or 4-(dimethylamino) pyridine (DMAP). Preferably, DIPEA, trimethylamine and TEA are used. Particular preference is given to using DIPEA.

The condensations (II)+(III)→(I) is generally carried out in a temperature range from −20° C. to +100° C., preferably at 0° C. to +60° C. The reaction can be carried out at normal, elevated or reduced pressure (for example from 0.5 to 5 bar). In general, one works at room temperature and normal pressure.

Alternatively, the carboxylic acid of the formula (II) can also first be converted into the corresponding carboxylic acid chloride and then reacted directly or in a separate reaction with a compound of the formula (III) to give the compounds according to the invention. The formation of carboxylic acid chlorides from carboxylic acids is carried out by the methods known to those skilled in the art, for example by treating (II) or the corresponding carboxylate with thionyl chloride, sulfuryl chloride or oxalyl chloride in the presence of a suitable base, for example in the presence of pyridine, and optionally with the addition of dimethylformamide, optionally in a suitable inert solvent.

The compounds used are commercially available, known from the literature or can be prepared analogously to processes known from the literature.

The general procedure is exemplified by the scheme below (Scheme 1)

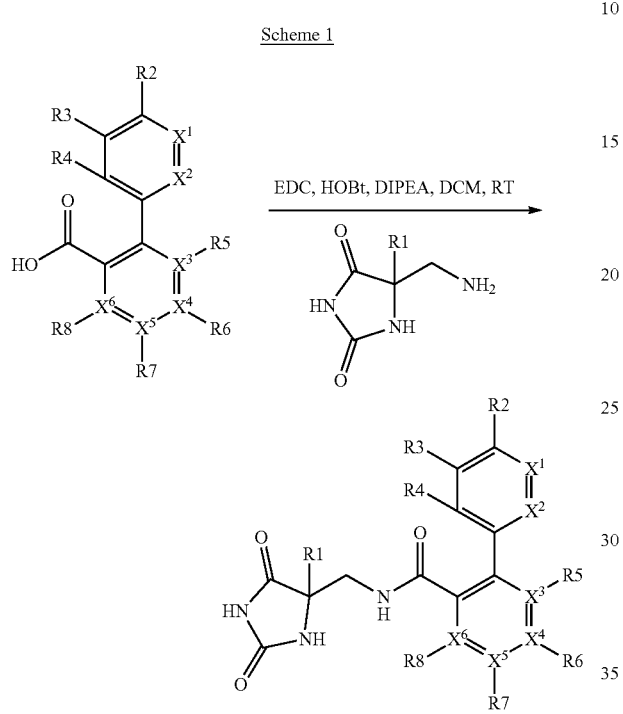

wherein $R_2$, $R_3$, $R_4$, $R_5$, $R_6$, $R_7$, $R_8$ and $X^1$, $X^2$, $X^3$, $X^4$, $X^5$, $X^6$ are as defined above.

Amines of the formula (III) can be prepared by the process exemplified in Scheme 2

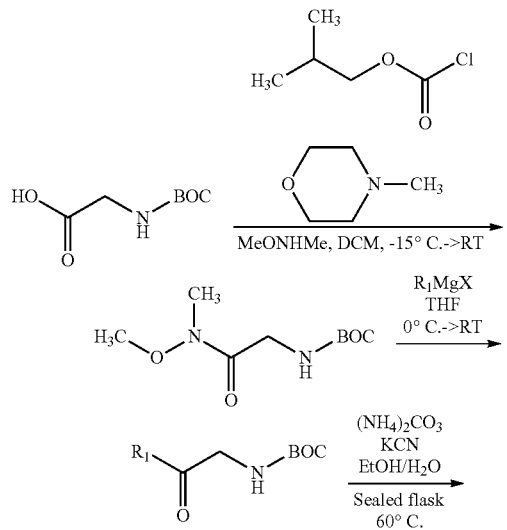

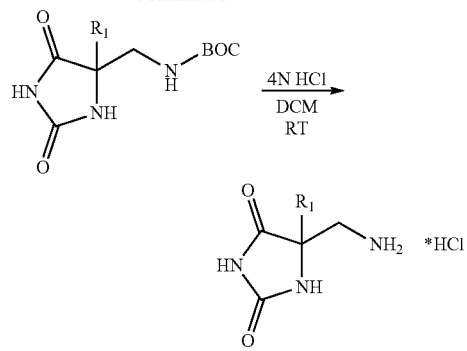

wherein $R_1$ is as defined above.

Another alternative process variant is shown in Scheme 3

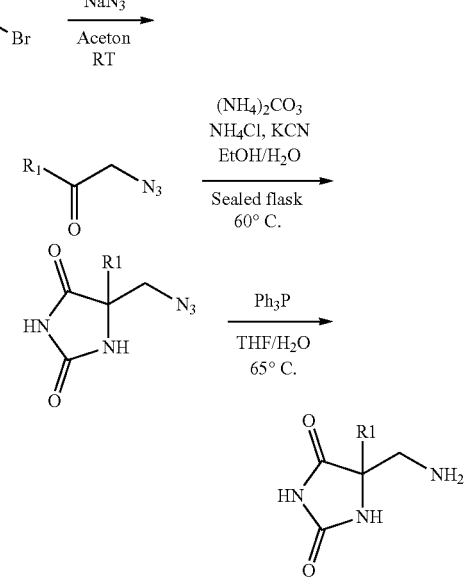

wherein $R_1$ is as defined above.

Another alternative process variant is shown in Scheme 4

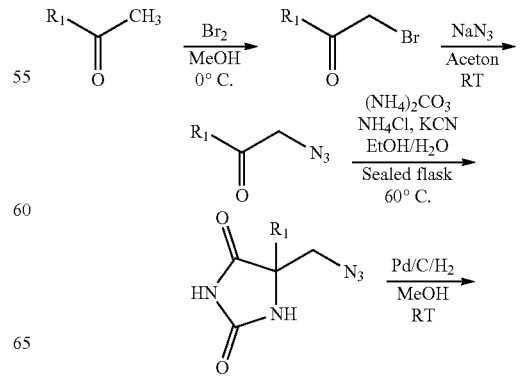

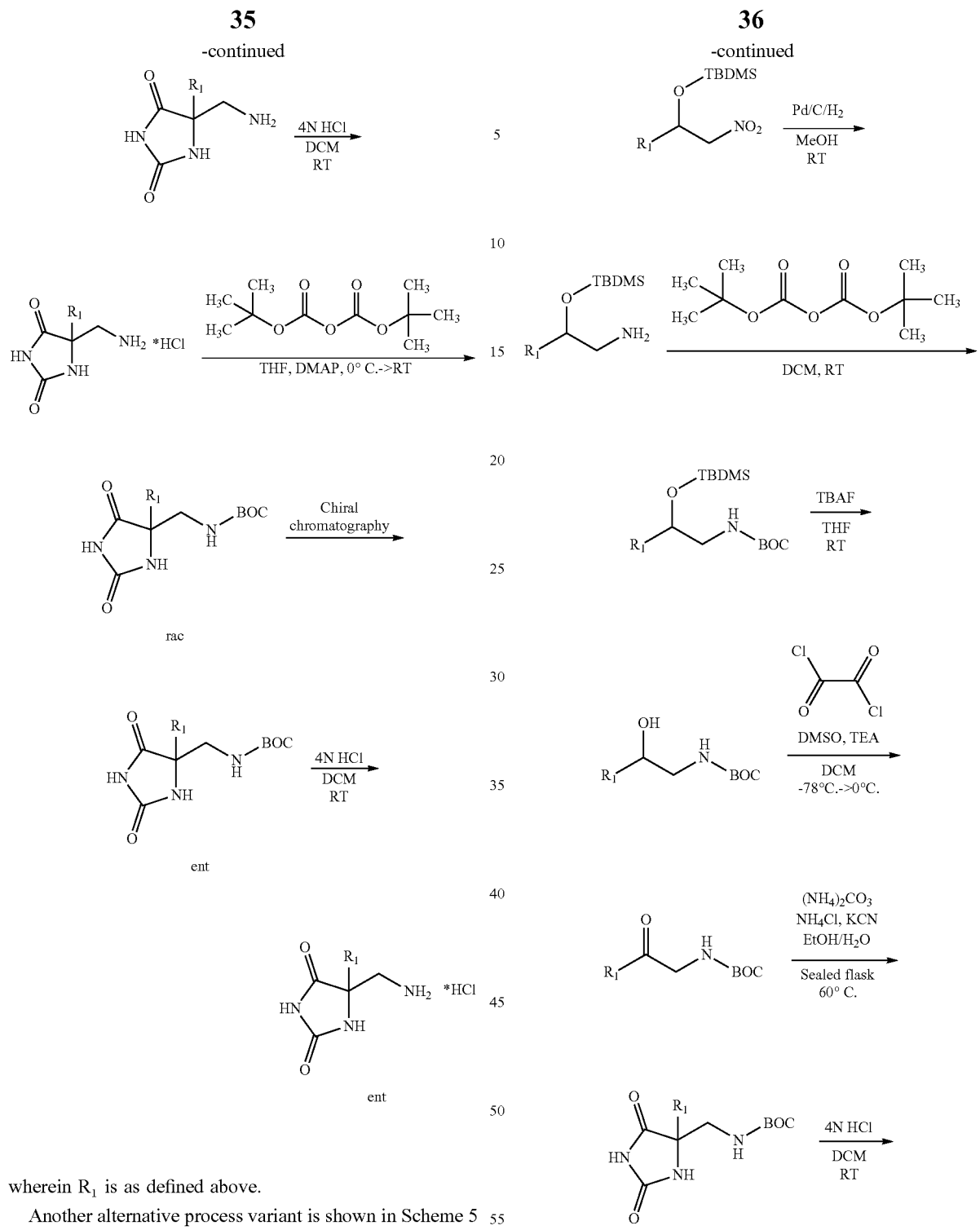
wherein $R_1$ is as defined above.
Another alternative process variant is shown in Scheme 5
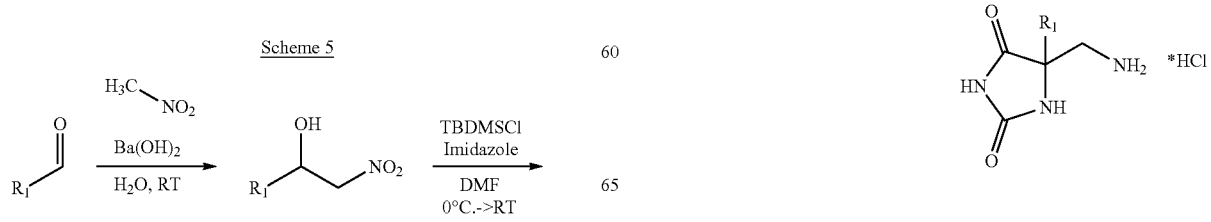
wherein $R_1$ is as defined above.

Another alternative process variant is shown in Scheme 6
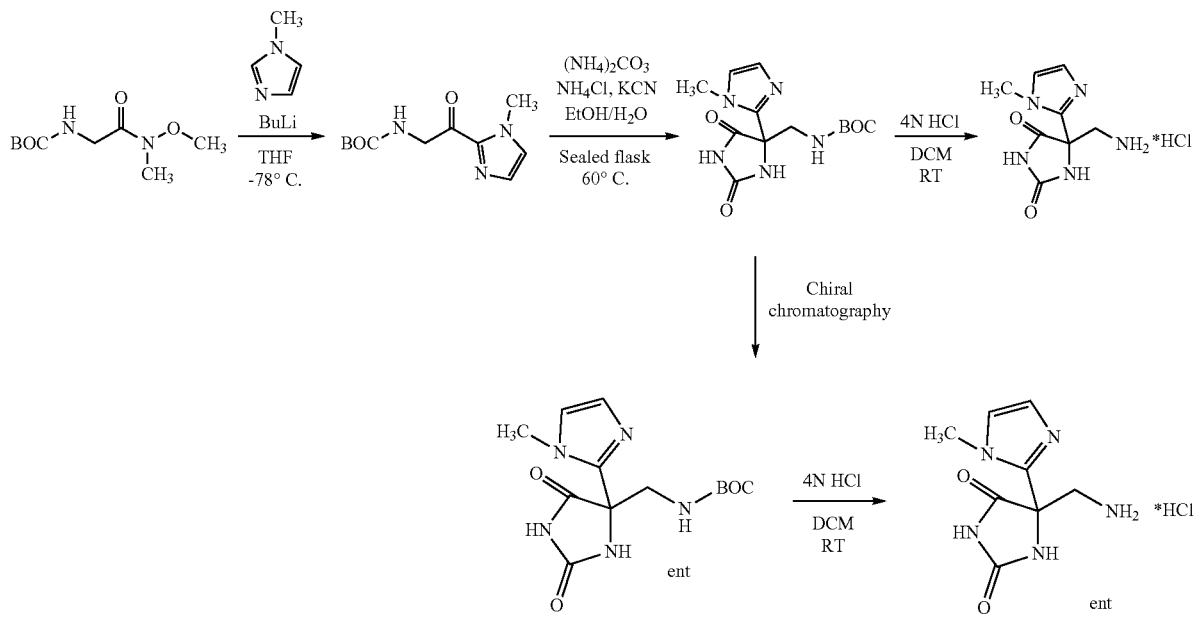
Another alternative process variant is shown in Scheme 7
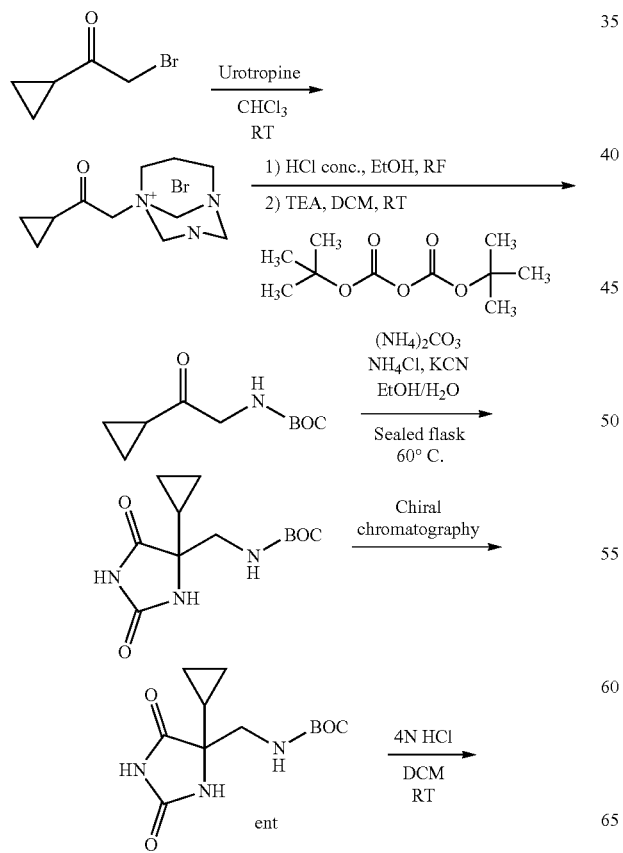
Another alternative process variant is shown in Scheme 8
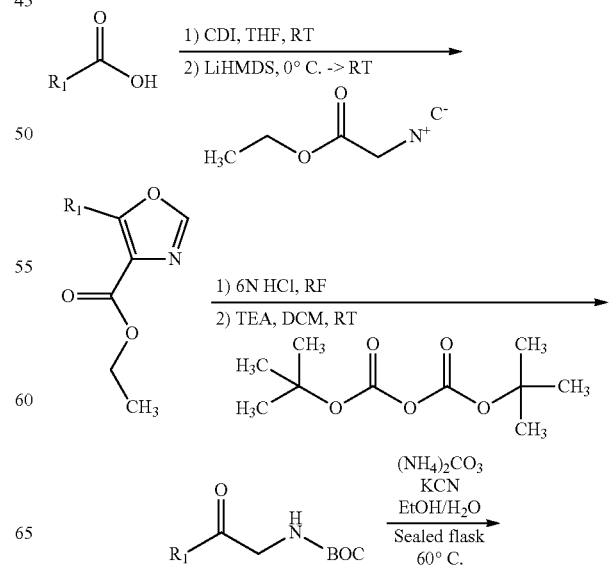

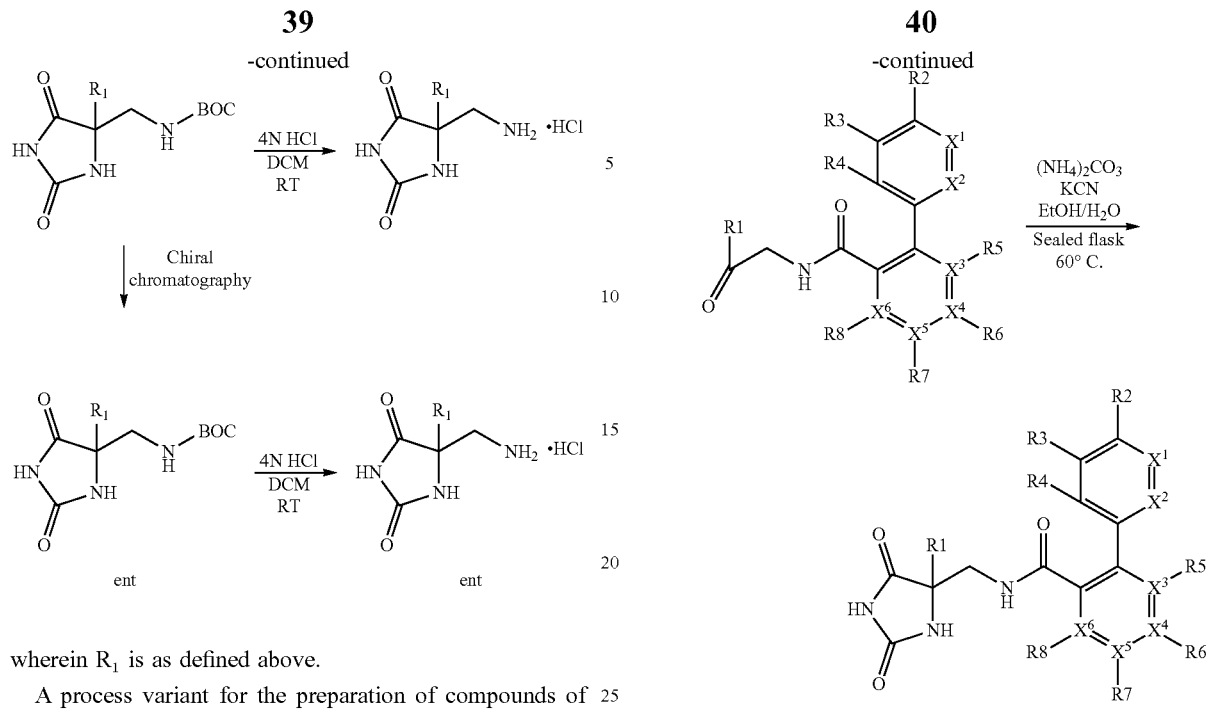

wherein $R_1$ is as defined above.

A process variant for the preparation of compounds of formula (I) is shown in Scheme 9

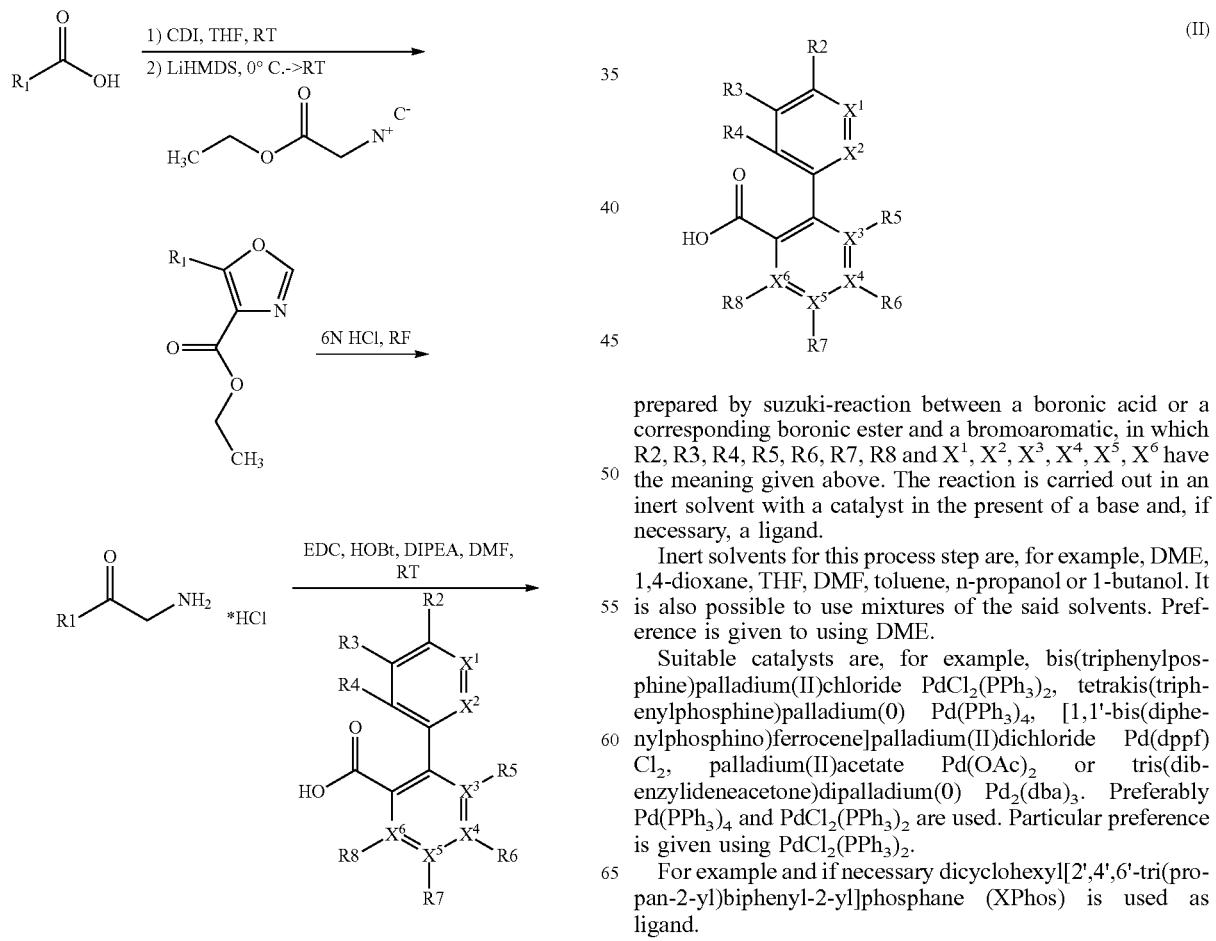

wherein $R_2$, $R_3$, $R_4$, $R_5$, $R_6$, $R_7$, $R_8$ and $X^1$, $X^2$, $X^3$, $X^4$, $X^5$, $X^6$ are as defined above.

Another object of the invention is a process for the preparation of the compounds of formula (II)

(II)

prepared by suzuki-reaction between a boronic acid or a corresponding boronic ester and a bromoaromatic, in which R2, R3, R4, R5, R6, R7, R8 and $X^1$, $X^2$, $X^3$, $X^4$, $X^5$, $X^6$ have the meaning given above. The reaction is carried out in an inert solvent with a catalyst in the present of a base and, if necessary, a ligand.

Inert solvents for this process step are, for example, DME, 1,4-dioxane, THF, DMF, toluene, n-propanol or 1-butanol. It is also possible to use mixtures of the said solvents. Preference is given to using DME.

Suitable catalysts are, for example, bis(triphenylposphine)palladium(II)chloride $PdCl_2(PPh_3)_2$, tetrakis(triphenylphosphine)palladium(0) $Pd(PPh_3)_4$, [1,1'-bis(diphenylphosphino)ferrocene]palladium(II)dichloride Pd(dppf)$Cl_2$, palladium(II)acetate $Pd(OAc)_2$ or tris(dibenzylideneacetone)dipalladium(0) $Pd_2(dba)_3$. Preferably $Pd(PPh_3)_4$ and $PdCl_2(PPh_3)_2$ are used. Particular preference is given using $PdCl_2(PPh_3)_2$.

For example and if necessary dicyclohexyl[2',4',6'-tri(propan-2-yl)biphenyl-2-yl]phosphane (XPhos) is used as ligand.

Suitable bases are, for example, aqueous solutions of sodium carbonate ($Na_2CO_3$), sodium bicarbonate ($NaHCO_3$), potassium fluoride (KF), potassium phosphate ($K_3PO_4$), potassium carbonate ($K_2CO_3$) or cesium fluoride (CsF). Organic bases like triethylamine ($Et_3N$) or diisopropylethylamine (DIPEA) could also be used. Preferably a 2M aqueous solution of sodium carbonate is used.

The Suzuki reaction is generally carried out in a temperature range from RT to +200° C., preferably in a temperature range from 80° C. to 90° C. under an argon atmosphere. The reaction can be carried out at normal, elevated or reduced pressure (for example from 0.5 to 5 bar). In general, one works at normal pressure.

If carboxylic acid esters were used in the suzuki-reaction they must be converted into the carboxylic acids bevor they can be used in the next step. For this, the carboxylic acid esters are dissolved in an organic solvent like THE and treated with an aqueous solution of an alkali metal hydroxide like lithium hydroxide or an acid like hydrochloric acid in case of tert.butyl esters.

The compounds used are commercially available, known from the literature or can be prepared analogously to processes known from the literature.

Acids of formula (II) can be prepared by the method exemplified in Scheme 10

Scheme 10

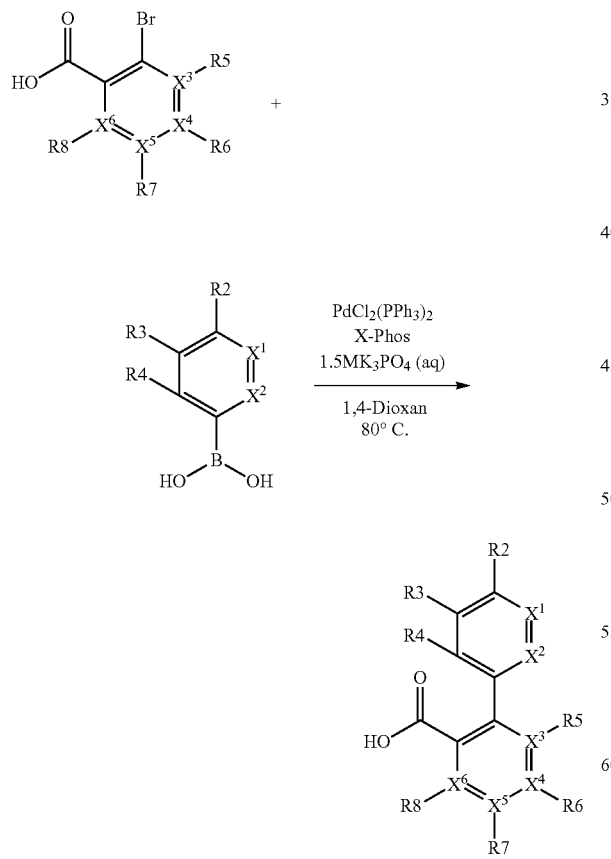

wherein $R_2$, $R_3$, $R_4$, $R_5$, $R_6$, $R_7$, $R_8$ and $X^1$, $X^2$, $X^3$, $X^4$, $X^5$, $X^6$ are as defined above.

An alternative process variant is shown in Scheme 11

Scheme 11

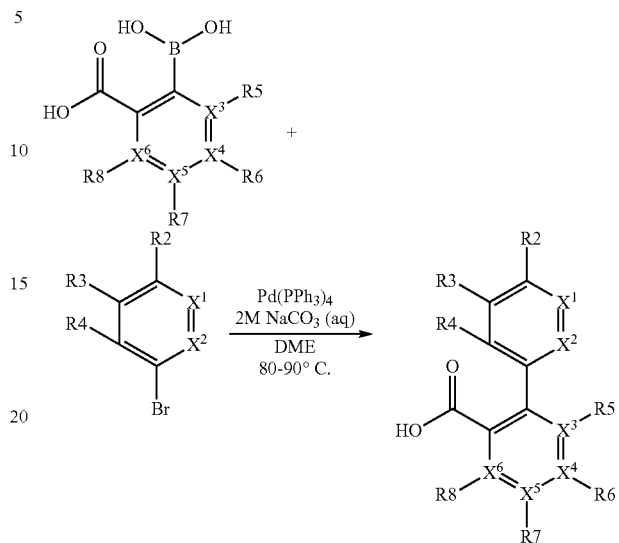

wherein $R_2$, $R_3$, $R_4$, $R_5$, $R_6$, $R_7$, $R_8$ and $X^1$, $X^2$, $X^3$, $X^4$, $X^5$, $X^6$ are as defined above.

Another alternative process variant is shown in Scheme 12

Scheme 12

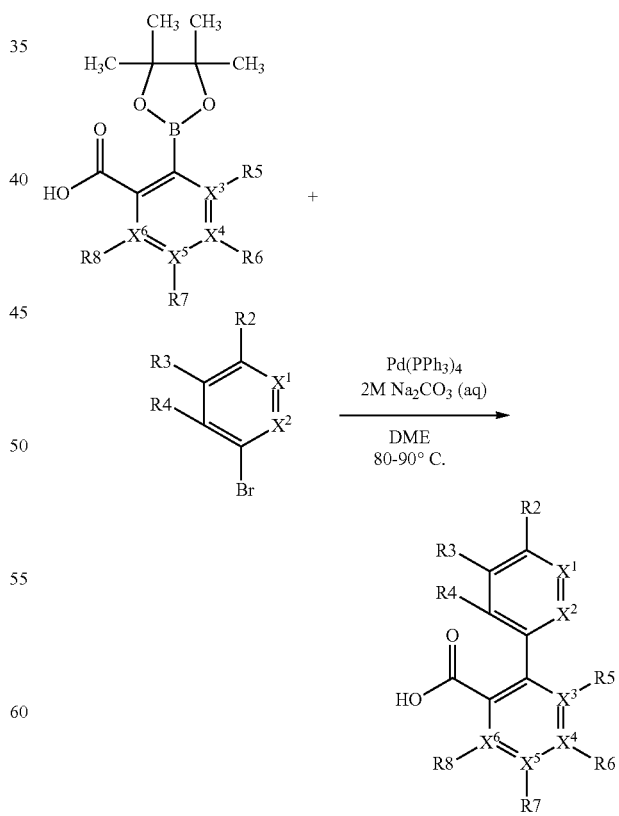

wherein $R_2$, $R_3$, $R_4$, $R_5$, $R_6$, $R_7$, $R_8$ and $X^1$, $X^2$, $X^3$, $X^4$, $X^5$, $X^6$ are as defined above.

Another alternative process variant is shown in Scheme 13

Scheme 13

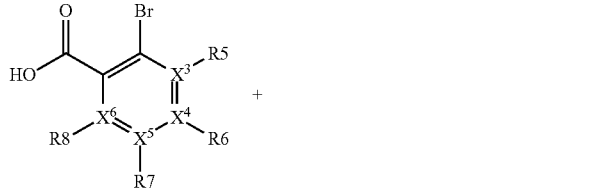

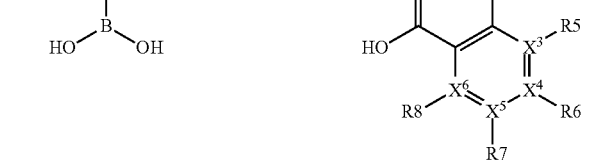

wherein $R_2$, $R_3$, $R_4$, $R_5$, $R_6$, $R_7$, $R_8$ and $X^1$, $X^2$, $X^3$, $X^4$, $X^5$, $X^6$ are as defined above.

Another alternative process variant is shown in Scheme 14

Scheme 14

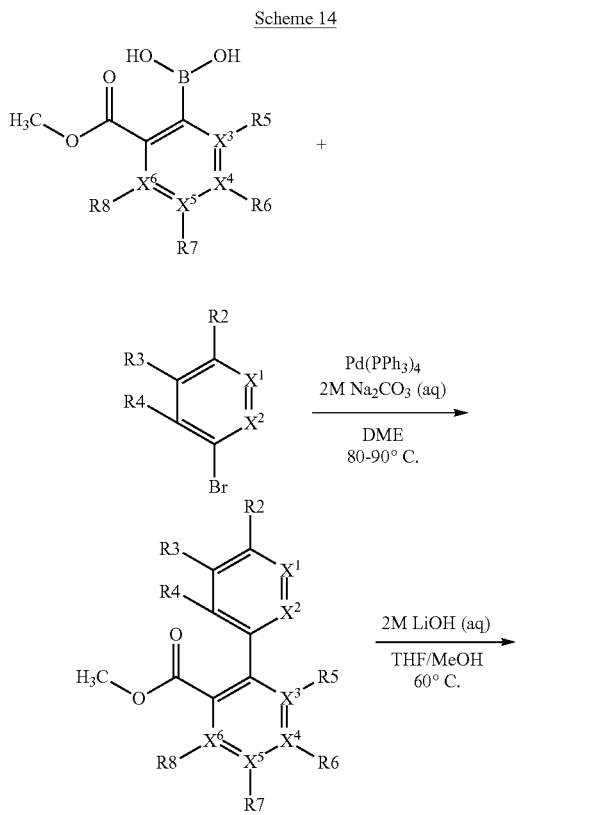

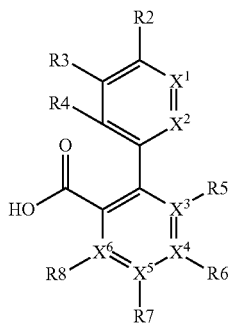

wherein $R_2$, $R_3$, $R_4$, $R_5$, $R_6$, $R_7$, $R_8$ and $X^1$, $X^2$, $X^3$, $X^4$, $X^5$, $X^6$ are as defined above.

Another alternative process variant is shown in Scheme 15

Scheme 15

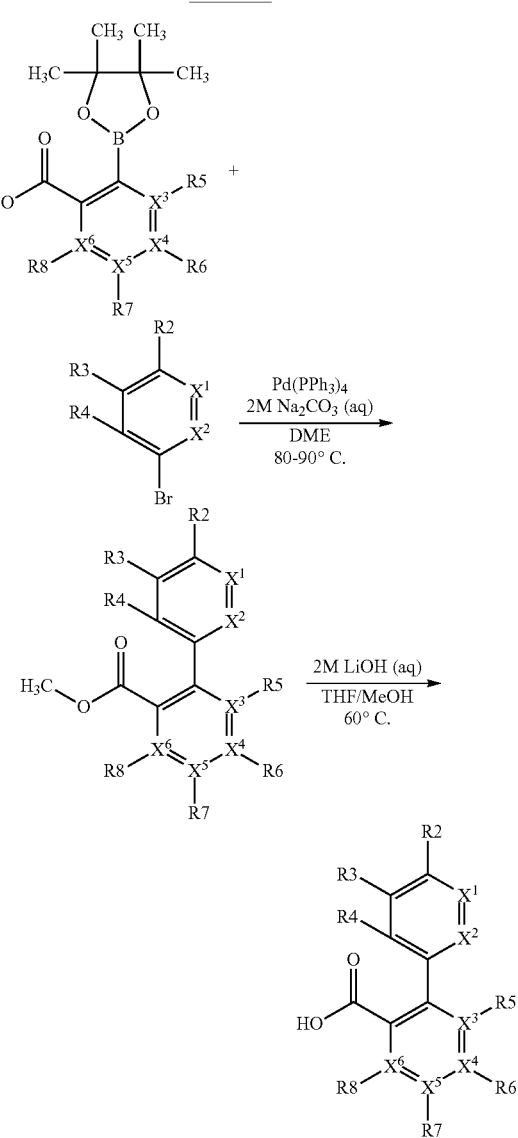

wherein $R_2$, $R_3$, $R_4$, $R_5$, $R_6$, $R_7$, $R_8$ and $X^1$, $X^2$, $X^3$, $X^4$, $X^5$, $X^6$ are as defined above.

Another alternative process variant is shown in Scheme 16

Scheme 16

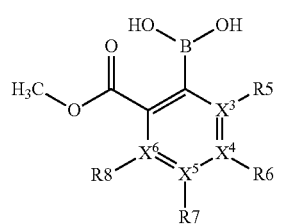

+

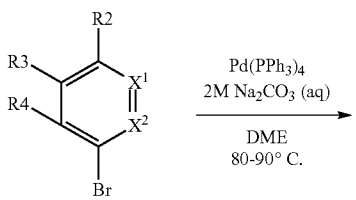

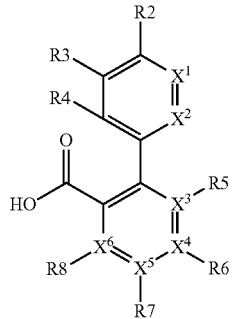

wherein $R_2$, $R_3$, $R_4$, $R_5$, $R_6$, $R_7$, $R_8$ and $X^1$, $X^2$, $X^3$, $X^4$, $X^5$, $X^6$ are as defined above.

Another alternative process variant is shown in Scheme 17

Scheme 17

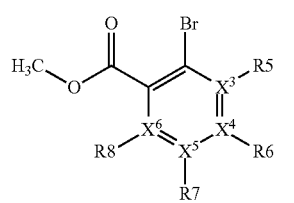

+

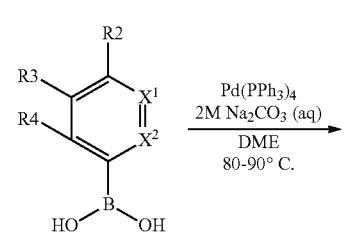

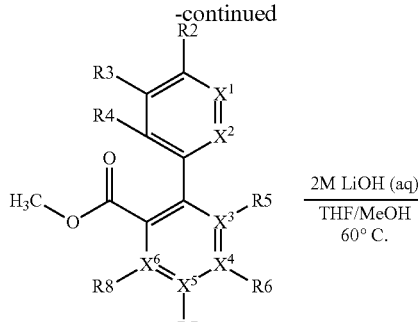

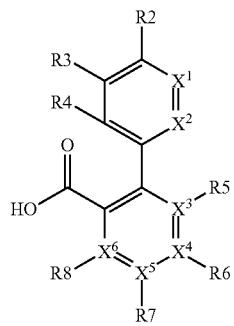

wherein $R_2$, $R_3$, $R_4$, $R_5$, $R_6$, $R_7$, $R_8$ and $X^1$, $X^2$, $X^3$, $X^4$, $X^5$, $X^6$ are as defined above.

Another alternative process variant is shown in Scheme 18

Scheme 18

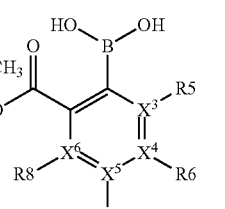

+

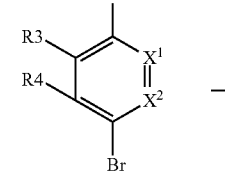

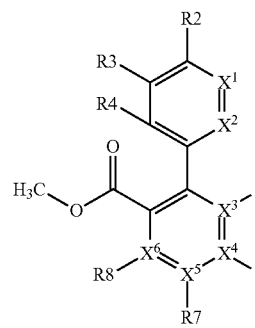

-continued

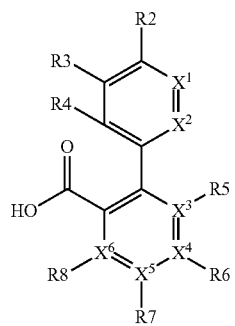

wherein $R_2$, $R_3$, $R_4$, $R_5$, $R_6$, $R_7$, $R_8$ and $X^1$, $X^2$, $X^3$, $X^4$, $X^5$, $X^6$ are as defined above.

Another alternative process variant is shown in Scheme 19

Scheme 19

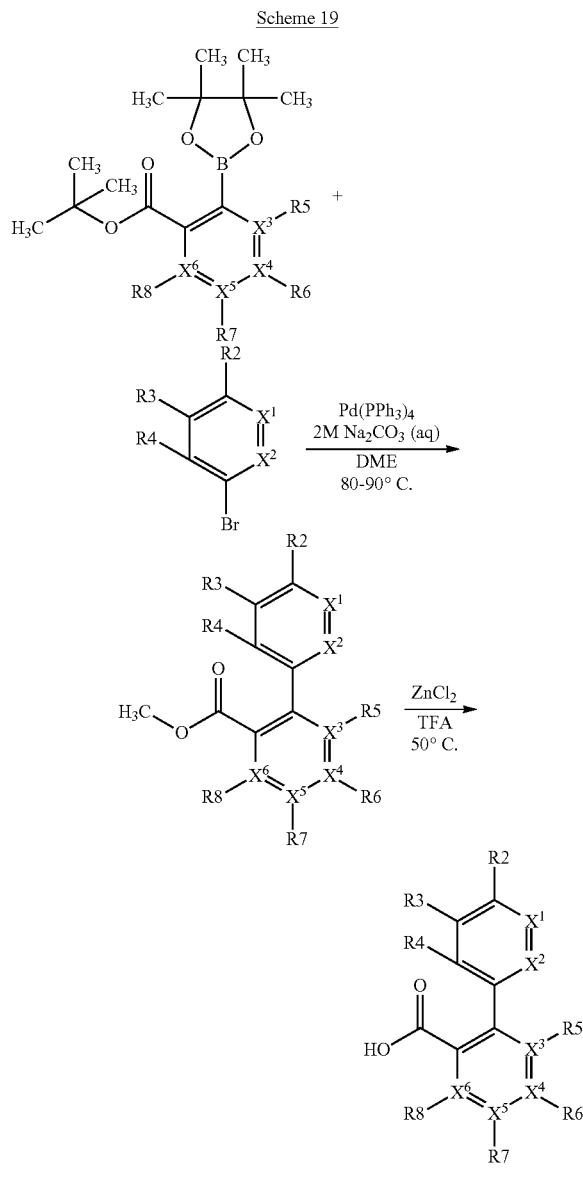

wherein $R_2$, $R_3$, $R_4$, $R_5$, $R_6$, $R_7$, $R_8$ and $X^1$, $X^2$, $X^3$, $X^4$, $X^5$, $X^6$ are as defined above.

Another object of the invention is a process for the preparation of hydantoins (III)

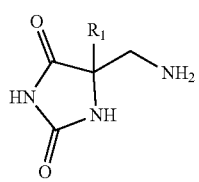

(III)

in which $R_1$ has the meaning given above.

Hydantoins can be prepared by reacting a for example BOC or Z protected α-amino ketone or aldehyde with a mixture of ammonium carbonate, alkali cyanide like potassium cyanide in ethanol and water, preferably in a sealed flask. In some cases ammonium chloride is added to the mixture as well. Instead of ethanol, methanal may be used. Example processes are shown in scheme 2, scheme 3, scheme 4, scheme 5, scheme 6, scheme 7, scheme 8 and scheme 9.

The reaction is generally carried out at a temperature between room temperature and 200° C. Preferably a temperature between 40° C. to 80° C. is used. The reaction can be performed at normal pressure. Preferably the reaction is performed in a sealed flask.

The compounds used are commercially available, known from the literature or can be prepared analogously to processes known from the literature.

Detailed instructions are also to be found in the experimental part in the section for preparing the starting compounds and intermediates.

Compounds of the current invention possess valuable pharmacological properties and can be used for the treatment and/or prophylaxis of diseases/disease state affecting human beings and animals.

Compounds concerning the present invention are potent, chemically stable antagonists of the ADAMTS7 metalloprotease and are suited for the treatment and/or prevention of diseases in human beings and animals such as, heart diseases, vascular diseases, and/or cardiovascular diseases, including atherosclerosis, coronary artery disease (CAD), peripheral vascular disease (PAD)/arterial occlusive disease and/or restenosis after angioplasty (including the use of drug-coated or non drug-coated balloons and/or stent-implantation) and/or for the treatment and/or prophylaxis of lung diseases, inflammatory diseases, fibrotic diseases, metabolic diseases, cardiometabolic diseases and/or diseases/disease states affecting the kidneys and/or the central nervous and/or neurological system as well as gastrointestinal and/or urologic and/or ophthalmologic diseases/disease states.

In the context of the present invention heart diseases, vascular diseases and/or cardiovascular diseases or disease of the cardiovascular system include, e.g., acute and chronic heart failure, arterial hypertension, coronary heart disease, stable and instable angina pectoris, myocardial ischemia, myocardial infarction, coronary microvascular dysfunction, microvascular obstruction, no-reflow-phenomenon, shock, atherosclerosis, coronary artery disease, peripheral artery disease, peripheral arterial disease, intermittent claudication, severe intermittent claudication, limb ischemia, critical limb ischemia, hypertrophy of the heart, cardiomyopathies of any etiology (such as, e.g., dilatative cardiomyopathy, restrictive cardiomyopathy, hypertrophic cardiomyopathy, ischemic cardiomyopathy), fibrosis of the heart, atrial and ventricular arrhythmias, transitory and/or ischemic attacks, apoplexy, ischemic and/or hemorrhagic stroke, preeclampsia, inflammatory cardiovascular diseases, metabolic diseases, diabetes, type-I-diabetes, type-II-diabetes, diabetes mellitus, peripheral and autonomic neuropathies, diabetic neuropathies, diabetic microangiopathies, diabetic retinopathy, diabetic ulceraat the extremities, gangrene, CREST-syndrome, hypercholesterolemia, hypertriglyceridemia, lipometabolic disorder, metabolic syndrome, increased levels of fibrinogen and low-density lipoproteins (i.e. LDL), increased concentrations of plasminogen-activator inhibitor 1 (PAI-1), as well as peripheral vascular and cardiac vascular diseases, peripheral circulatory disorders, primary and secondary Raynaud syndrome, disturbances of the microcirculation, arterial pulmonary hypertension, spasms of coronary and peripheral arteries, thromboses, thromboembolic diseases, edema-formation, such as pulmonary edema, brain-edema, renal edema, myocardial edema, myocardial edema associated with heart failure, restenosis after i.e. thrombolytic therapies, percutaneous-transluminal angioplasties (PTA), transluminal coronary angioplasties (PTCA), heart transplantations, bypass-surgeries as well as micro- and macrovascular injuries (e.g., vasculitis), reperfusion-damage, arterial and venous thromboses, microalbuminuria, cardiac insufficiency, endothelial dysfunction.

In the light of the present invention, heart failure includes more specific or related kinds of diseases such as acute decompensated heart failure, right heart failure, left heart failure, global insufficiency, ischemic cardiomyopathy, dilatative cardiomyopathy, congenital heart defect(s), valve diseases, heart failure related to valve diseases, mitral valve stenosis, mitral valve insufficiency, aortic valve stenosis, aortic valve insufficiency, tricuspid valve stenosis, tricuspid valve insufficiency, pulmonary valve stenosis, pulmonary valve insufficiency, combined valvular defects, inflammation of the heart muscle (myocarditis), chronic myocarditis, acute myocarditis, viral myocarditis, bacterial myocarditis, diabetic heart failure, alcohol- toxic cardiomyopathy, cardiac storage diseases, heart failure with preserved ejection fraction (HFpEF), diastolic heart failure, heart failure with reduced ejection fraction (HFrEF), systolic heart failure.

In the context of the present invention, the terms atrial arrhythmias and ventricular arrhythmias also include more specific and related disease-entitites, such as: Atrial fibrillation, paroxysmal atrial fibrillation, intermittent atrial fibrillation, persistent atrial fibrillation, permanent atrial fibrillation, atrial flutter, sinus arrhythmia, sinus tachycardia, passive heterotopy, active heterotopy, replacement systoles, extrasystoles, disturbances in the conduction of impulses, sick-sinus syndrome, hypersensitive carotis-sinus, tachycardias, AV-node re-entry tachycardias, atrioventricular re-entry tachycardia, WPW-syndrome (Wolff-Parkinson-White syndrome), Mahaim-tachycardia, hidden accessory pathways/tracts, permanent junctional re-entry tachycardia, focal atrial tachycardia, junctional ectopic tachycardia, atrial re-entry tachycardia, ventricular tachycardia, ventricular flutter, ventricular fibrillation, sudden cardiac death.

In the context of the present invention, the term coronary heart disease also includes more specific or related diseases entities, such as: Ischemic heart disease, stable angina pectoris, acute coronary syndrome, instable angina pectoris, NSTEMI (non-ST-segement-elevation myocardial infarction), STEMI (ST-segement-elevation myocardial infarction), ischemic damage of the heart, arrhythmias, and myocardial infarction.

In the context of the present invention, diseases of the central nervous and neurological system or central nervous and neurological diseases/diseases states refer to, e.g., the following diseases/diseases states: Transitory and ischemic attacks, stroke/apoplexy, ischemic and hemorrhagic stroke, depression, anxiety disorder, post-traumatic stress-disorder, poly-neuropathy, diabetic poly-neuropathy, stress-induced hypertension.

Compounds concerning the present invention are furthermore suited for the prophylaxis and/or treatment of polycystic kidney-disease (PCKD) and the syndrome of inadequate ADH-secretion (SIADH). Furthermore, the compounds described in the present invention are suited for the treatment and/or prophylaxis of kidney diseases, especially of acute and chronic renal insufficiency as well as of acute and chronic renal failure.

In the context of the present invention, the term acute renal insufficiency/renal failure includes acute presentations of kidney diseases, kidney failure and/or renal insufficiency with or without the dependency on dialysis as well as underlying or related kidney diseases such as renal hypoperfusion, hypotension during dialysis, lack of volume (i.e. dehydration, blood-loss), shock, acute glomerulonephritis, hemolytic-uremic syndrome (HUS), vascular catastrophe (arterial or venous thrombosis or embolism), cholesterol-embolism, acute Bence-Jones-kidney associated with plasmacytoma, acute supravesical or subvesical outlow obstructions, immunologic kidney diseases such as kidney transplant rejection, immuncomplex-induced kidney diseases, tubular dilatation, hyperphosphatemia and/or akute kidney diseases which may be characterized by the need for dialysis. Also included are conditions of partial nephrectomy, dehydration caused by force diuresis, uncontrolled increase in blood pressure accompanied by malignant hypertension, urinary tract obstructions and infections and amyloidosis as well as systemic disorders with glomerular participation such as rheumatologic-immunologic systemic disorders, such as Lupus erythematodes, renal artery thrombosis, renal vein thrombosis, analgesics-induced nephropathy and renal-tubular acidosis as well as radio-opaque substance- as well as drug-induced acute interstitial kidney diseases.

In the context of the present invention the term chronic renal insufficiency/chronic renal failure includes chronic manifestations/presentations of kidney diseases, renal failure and/or renal insufficiency with and without the dependency on dialysis as well as underlying or related kidney diseases such as renal hypoperfusion, hypotension during dialysis, obstructive uropathy, glomerulopathies, glomerular and tubular proteinuria, renal edema, hematuria, primary, secondary as well as chronic glomerulonephritis, membraneous and membraneous-proliferative glomerulonephritis, Alport-syndrome, glomerulosclerosis, tubulointerstitial diseases, nephropathic diseases such as primary and hereditary kidney disease(s), renal inflammation, immunologic kidney diseases such as transplant rejection, immuncomplex-induced kidney diseases, diabetic and non-diabetic nephropathy, pyelonephritis, renal cysts, nephrosclerosis, hypertensive nephrosderosis and nephrotic syndrome, which are diagnostically characterized by i.e. abnormally reduced creatinine- and/or water-excretion, abnormally increased blood-concentrations of urea, nitrogen, potassium and/or creatinine, altered activity of kidney enzymes, such as, e.g., glutamylsynthase, altered urinary osmolarity or volume, increased microalbuminuria, macroalbuminuria, lesions associated with glomeruli and arterioles, tubular dilatation, hyperphosphatemia and/or the need for dialysis, likewise included are renal cell carcinomas, conditions after partial kidney-resection, dehydration attributed to force diuresis, uncontrolled increase in blood pressure with malignant hypertension, urinary tract obstruction and urinary tract infection and amyloidosis as well as systemic diseases with glomerular participation such as rheumatologic-immunologic systemic diseases, such as lupus erythematodes, as well as renal artery stenosis, renal artery thrombosis, renal vein thrombosis, analgesics-induced nephropathy and renal-tubular acidosis. Furthermore, included are radio-opaque substance- or drug-induced chronic interstitial kidney diseases, metabolic syndrome and dyslipidemia. The current invention also includes the use of the drugs of the current invention for the treatment and/or prophylaxis of after-effects of renal insufficiency such as lung edema, heart failure, uremia, anemia, disturbances in electrolytes (e.g., hyperkalemia, hyponatremia) and disturbances in bone- and carbohydrate-metabolism.

Additionally, compounds of the current invention are suited for the treatment and/or prophylaxis of lung diseases (partially also seen as vascular diseases), such as, e.g., pulmonary arterial hypertension (PAH) and other forms of pulmonary hypertension (PH), chronic-obstructive pulmonary disease (COPD), acute respiratory distress syndrome (ARDS), acute lung injury (ALI), lung fibrosis, lung emphysema (e.g., lung emphysema induced by cigarette smoke), cystic fibrosis (CF) as well as for the treatment and/or prophylaxis of alpha-1-antitrypsin deficiency (AATD), acute coronary syndrome (ACS), inflammation of the heart muscle (myocarditis) and other autoimmune diseases of the heart (pericarditis, endocarditis, valvolitis, aortitis, cardiomyopathies), cardiogenicshock, aneurysms, sepsis (SIRS), multiple organ failure (MODS, MOF), inflammatory kidney diseases, chronic bowel diseases (IBD, Crohn's Disease, UC), pancreatitis, peritonitis, rheumatoid diseases, inflammatory skin diseases as well as inflammatory eye diseases.

Furthermore, compounds of the current invention can be used for the treatment and/or prophylaxis of asthmatic diseases of different severity with intermittent or persistent courses (refractive asthma, bronchial asthma, allergic asthma, intrinsic asthma, extrinsic asthma, asthma induced by drugs or dust), of different kinds of bronchitis (chronic bronchitis, infectious bronchitis, eosinophilic bronchitis), of bronchiolitis obliterans, bronchiectasia, pneumonia, idiopathic interstitial pneumonia, farmer's lung and related diseases, coughing and common cold diseases (chronic inflammatory cough, iatrogenic cough), inflammations of the nasal mucosa (including drug-induced rhinitis, vasomotor rhinitis and season-dependent allergic rhinitis, e.g., allergic coryza) as well as of polyps.

The compounds described in the current invention also represent active compounds for the treatment of diseases of the central nervous system, characterized by disturbances of the NO/cGMP-system. They are especially suited for improvement of perception, concentration-performance, learning-behaviour or memory-performance after cognitive disturbances as they occur with conditions/illnesses/syndromes such as "mild cognitive impairment", age-associated learning- and memory-disturbances, age-associated memory-loss, vascular dementia, craniocerebral injury, stroke, dementia occurring after stroke ("post stroke dementia"), post-traumatic craniocerebral injury, general concentration-disturbances, concentration-disturbances affecting children with learning- and memory-problems, Alzheimer's disease, dementia with Lewy-bodies, dementia with degeneration of the frontal lobe including Pick's syndrome, Parkinson's Disease, dementia with corticobasal degeneration, amyotrophic lateral sclerosis (ALS), Huntington's Disease, demyelination, multiple sclerosis, thalamic degeneration, Creutzfeld-Jacob-dementia, HIV-dementia, schizophrenia with dementia or Korsakoff-psychosis. They are also suited for the treatment and or prevention of diseases/disease states of the central nervous system such as conditions of anxiety, tension/pressure and depressions, bipolar disorder, sexual dysfunction due to disturbances in the central nervous system as well as sleep abnormalities and for regulation of pathological disturbances of food-, luxury food- and 'dependence causing substance'-intake.

Furthermore, the compounds of the current invention are also suited for the treatment and/or prophylaxis of urologic diseases/disease states such as, e.g., urinary incontinence, stress-induced incontinence, urge incontinence, reflex incontinence and overflow incontinence, detrusor hyperactivity, neurogenic detrusor hyperactivity, idiopathic detrusor hyperactivity, benign prostate hyperplasia (BPH-syndrome), lower urinary tract symptoms.

The compounds of the current invention are further suited for the treatment and/or prevention of conditions of pain, such as, e.g., menstrual disorders, dysmenorrhea, endometriosis, preterm delivery, tocolysis.

The compounds of the current invention are likewise suited for the treatment and/or prevention of erythematosis, onychomycosis, rheumatic diseases as well as for facilitation of wound healing.

The compounds of the current invention are also suited for the treatment and/or prevention of gastrointestinal diseases such as, e.g., diseases/disease states affecting the oesophagus, vomiting, achalasia, gastrooesophageal reflux disease, diseases of the stomach, such as, e.g., gastritis, diseases of the bowel, such as, e.g., diarrhea, constipation, malassimilation syndromes, syndromes of bile acid-loss, Crohn's Disease, Colitis ulcerosa, microscopic colitis, irritable bowel syndrome.

Furthermore, compounds of the current invention are suited for the treatment and/or prophylactic treatment of fibrotic diseases of inner organs such as lung, heart, kidney, bone marrow, and especially liver as well as dermatological fibrosis and fibrotic eye diseases. In the context of the current invention the term fibrotic diseases includes liver fibrosis, liver cirrhosis, lung fibrosis, endomyocardial fibrosis, cardiomyopathy, nephropathy, glomerulonephritis, interstitial kidney fibrosis, fibrotic damage as a consequence of diabetes, bone marrow fibrosis and similar fibrotic diseases, scleroderma, morphaea, keloids, hypertrophic scarring (also after surgical intervention), naevus, diabetic retinopathy and proliferative vitroretinopathy.

In addition, the compounds of the current invention can be used to treat and/or prophylactically treat dyslipidemias (hypercholesterolemia, hypertriglyceridemia, increased concentrations of post-prandial plasma triglycerides, hypo-alphalipoproteinemia, combined hyperlipidemias), metabolic diseases (type I and type II diabetes, metabolic syndrome, overweight, adipositas), nepropathy and neuropathy, cancer (skin cancer, brain tumors, breast cancer, tumors of the bone marrow, leukemias, liposarcoma, carcinoma of the gastrointestinal tract, liver, pancreas, lung, kidney, ureter, prostate and gential tract as well as carcinoma of the lymphoproliferative system such as, e.g., Hodgkin's and Non-Hodgkin's lymphoma), of gastrointestinal and abdominal diseases (glossitis, gingivitis, periodontitis, esophagitis, eosinophilic gastroenteritis, mastocytosis, Crohn's disease, colitis, proctitis, anal pruritis, diarrhea, celiac disease, hepatitis, chronic hepatitis, liver fibrosis, liver zirrhosis, pancreatitis and cholecystitis), skin diseases (allergicskin diseases, psoriasis, acne, eczema, neurodermatitis, multiple kinds of dermatitis, as well as keratitis, bullosis, vasculitis, cellulitis, panniculitis, lupus erythematodes, erythema, lymphoma, skin cancer, Sweet-syndrome, Weber-Christian-syndrome, scarring, wart formation, chilblains), of diseases of the sceletal bones and the joints as well as of sceletal muscle (multiple kinds of arthritis, multiple kinds of arthropathies, scleroderma as well as of further diseases with inflammatory or immunologic components, such as, e.g., paraneoplastic syndrome, rejection reactions after organ transplantations and for wound healing and angiogenesis, especially with chronic wounds.

The compounds of the current invention are suited for the treatment and/or prophylactic treatment of ophthalmologic diseases such as, e.g., glaucoma, normotensive glaucoma, increased/high ocular pressure and their combination, of age-related macula degeneration (AMD), dry (non-exudative) AMD, wet (exudative, neovascular) AMD, choroidal neovascularization (CNV), retinal detachment, diabetic retinopathy, atrophic changes of the retinal pigmented epithelium (RPE), hypertrophic changes of the retinal pigmented epithelium, diabetic macula edema, diabetic retinopathy, retinal vein occlusion, choroidal retinal vein occlusion, macula edema, diabetic macula edema, macula edema as a consequence of retinal vein occlusion, angiogenesis at the front-side of the eye such as corneal angiogenesis i.e. after keratitis, cornea transplantation or keratoplasty, corneal angiogenesis due to hypoxia (extensive wearing of contact lenses), Pterygium conjunctivae, sub-retinal edema and intra-retinal edema.

Furthermore, compounds of the current invention are suited for the treatment and/or prophylactic treatment of increased and high inner ocular pressure as a result of traumatic hyphema, periorbital edema, post-operative viscoelastic retention, intra-ocular inflammation, corticosteroid-use, pupil-block or idiopathic causes such as increased inner ocular pressure after trabeculectomy and due to pre-operative additives.

Furthermore, compounds of the current invention are suited for the treatment and/or prophylaxis of hepatitis, neoplasms, osteoporosis, glaucoma and gastroparesis.

Likewise, compounds of the current invention are suited for the regulation of cerebral blood circulation and represent useful agents for the treatment and or prophylaxis of migraine. They are also suited for the treatment and prophylaxis of cerebral infarcts such as stroke, cerebral ischemias and traumatic brain injury. Likewise, compounds of the current invention can be used for the treatment and/or prophylactic treatment of pain, neuralgias and tinnitus.

The aforementioned, well characterized human diseases may occur in other mammalians with a comparable etiology as well can be treated with the compounds of the current invention.

In the context of the current invention the term "treatment" or "treat" or "treated" includes inhibition, retardation, stopping, relief, reduction, attenuation, restriction, minimizing, suppression, repression or healing of a disease, a suffering, an illness, an injury or a health disorder, or the development, course and progression of such states/conditions and/or symptoms of these states/conditions.

The terms "prevention" and "prophylaxis" are used synonymously in the context of the present invention and refer to avoiding or reducing the risk to get, receive, experience, suffer from a disease, a suffering, an illness, an injury or a health disorder, the development, course and progression of such states/conditions and/or symptoms of these states/conditions.

Treatment or prevention of a disease, a suffering, an illness, an injury or a health disorder can be pursued in part or completely.

Other embodiments of the current invention therefore relate to the use of the compounds of the current invention for the treatment and/or prevention of diseases, especially of the aforementioned diseases/disease states.

Other embodiments of the current invention therefore relate to the use of the compounds of the current invention for the production/manufacturing of a compound/of compounds for the treatment and/or prevention of diseases, especially of the aforementioned diseases/disease states.

Other embodiments of the current invention therefore relate to is a drug containing at least one of the compounds of the present invention for the treatment and/or prevention of diseases, especially of the aforementioned diseases/disease states.

Other embodiments of the current invention therefore relate to the use of the compounds of the current invention in a process for the treatment and/or prevention of diseases, especially of the aforementioned diseases/disease states.

Other embodiments of the current invention therefore relate to a process for the treatment and/or prevention of diseases, especially of the aforementioned diseases, by use of an effective dose/amount of at least one of the compounds of the current invention.

Other embodiments of the current invention therefore relate to drugs and pharmaceutical formulations which contain at least one compound of the current invention, typically together with one or more inert, non- toxic, pharmaceutically suited additives, as well as their use for the aforementioned purposes.

Further embodiments of the current invention include the use of compound of formula (I) in a method for the treatment and/or prevention of heart diseases, vascular diseases, cardiovascular diseases, lung diseases, inflammatory diseases, fibrotic diseases, metabolic diseases and/or cardiometabolic diseases.

Further embodiments of the current invention include the use of compound of formula (I) in a method for the treatment and/or prevention of Atherosclerosis, atherosclerosis-related diseases such as coronary artery disease or peripheral vascular disease/arterial occlusive disease as well as post-surgery complications of these diseases such as restenosis after angioplasty.

Further embodiments include the use of a compound according to formula (I) for the manufacture of a pharmaceutical composition for the treatment and/or preventing atherosclerosis, athersclerosis-related diseases such as coronary artery disease or peripheral vascular disease/arterial occlusive disease as well as post-surgery complications of these diseases such as restenosis after angioplasty.

Further embodiments include the use of a compound according to the current invention for the manufacture of a pharmaceutical composition for the treatment and/or prevention atherosclerosis, atherosclerosis-related diseases such as coronary artery disease or peripheral vascular disease/arterial occlusive disease as well as post-surgery complications of these diseases such as restenosis after angioplasty.

Further embodiments include a pharmaceutical composition comprising a compound according to the current invention and one or more pharmaceutically acceptable excipients.

Other embodiments include a pharmaceutical composition comprising one or more first active ingredients, in particular compounds according to the current invention and one or more further active ingredients, in particular one or more additional therapeutic agents selected from the group consisting of angiotensin-converting enzyme inhibitors, angiotensin-receptor blockers, mineralocorticoid-receptor antagonists, endothelin antagonists, renin inhibitors, calcium blockers, beta-receptor blockers, vasopeptidase inhibitors, Sodium-Glucose-Transport-Antagonists, Metformin, Pioglitazones and Dipeptidyl-peptidase-IV inhibitors.

Further embodiments of the current invention include the pharmaceutical composition as defined above for the treatment and/or prevention of atherosclerosis, athersclerosis-related diseases such as coronary artery disease or peripheral vascular disease/arterial occlusive disease as well as post-surgery complications of these diseases such as restenosis after angioplasty Further embodiments of the invention include a method for the treatment and/or prevention atherosclerosis, athersclerosis-related diseases such as coronary artery disease or peripheral vascular disease/arterial occlusive disease as well as post-surgery complications of these diseases such as restenosis after angioplasty in a human or other mammal, comprising administering to a human or other mammal in need thereof a therapeutically effective amount of one or more compounds according to the current invention or of a pharmaceutical composition as defined above.

The compounds according to the invention can be used alone or in combination with one or more other pharmacologically active compounds if necessary as long as these combinations do not lead to unacceptable side effects. The present invention further relates to drugs containing at least one of the compounds according to the invention and one or more further active compounds/active components, in particular for the treatment and/or prophylaxis of the aforementioned diseases. As suitable active compounds/active components for combination, the following ones are mentioned exemplarily and preferably:

- Positive inotropic compounds, such as, e.g., cardiac glycosides (digoxin), beta-adrenergic and dopaminergic agonists, such as isoprenaline, adrenaline, noradrenaline, dopamine or dobutamine and serelaxine;
- Vasopressin-receptor antagonists, for example and preferably Conivaptan, Tolvaptan, Lixivaptan, Mozavaptan, Satavaptan, SR-121463, RWJ 676070 or BAY 86-8050, as well as the compounds described in WO 2010/105770, WO 2011/104322 and WO 2016/071212;
- Natriuretic peptides, for example and preferably atrial natriuretic peptide (ANP), natriuretic peptide type B (BNP, Nesiritide), natriuretic peptide type C (CNP) or urodilatin;
- Activators of cardiac myosin, for example and preferably e.g., Omecamtiv mecarbil (CK-1827452);
- Calcium-sensitizers, for example and preferably Levosimendan;
- Compounds affecting mitochondrial function and/or production of reactive oxygen species (ROS), for example Bendavia/Elamipritide;
- Compounds influencing cardiac energy-metabolism, for example and preferably etomoxir, dichloroacetate, ranolazine, trimetazidine, full or partial adenosine A1 receptor agonists such as GS-9667 (formerly known as CVT-3619), capadenosone and neladenosone;
- Compounds with an effect on heart rate, e.g., ivabradine
- Organic nitrates and NO-donors, such as sodium nitroprusside, nitroglycerin, isosorbide mononitrate, isosorbide dinitrate, molsidomine or SIN-1, and inhalational NO;
- Compounds that inhibit the degradation of cyclic guanosine monophosphate (cGMP) and/or cyclic adenosine monophosphate (cAMP), such as inhibitors of phosphodiesterases (PDE) 1, 2, 3, 4 and/or 5, in particular PDE 4 inhibitors such as roflumilast or revamilast and PDE 5 inhibitors such as sildenafil, vardenafil, tadalafil, udenafil, dasantafil, avanafil, mirodenafil, Iodenafil or PF-00489791;
- Compounds increasing cGMP synthesis, such as, e.g., sGC modulators in particular riociguat, nelociguat, vericiguat, cinaciguat and the compounds described in WO 00/06568, WO 00/06569, WO 02/42301, WO 03/095451, WO 2011/147809, WO 2012/004258, WO 2012/028647, WO 2012/059549, WO 2014/068099 and WO 2014/131760 as well as the compounds described in WO 01/19355, WO 01/19780, WO 2012/139888 and WO 2014/012934;
- Compounds which inhibit the soluble epoxid-hydrolase (sEH), such as, e.g., N,N'-dicyclohexylurea, 12-(3-Adamantan-1-yl-ureido)-dodecanoic acid or 1-Adamantan-1-yl-3-{5-[2-(2-ethoxyethoxy)ethoxy]pentyl}-urea;
- Compounds modulating neurotransmitters, such as, e.g., tricyclic antidepressants such as, e.g., amitryptiline and imaprimine, monoaminooxidase (MAO) inhibitors such as moclobemide, serotonin-noradrenaline-reuptake inhibitors such as venlaflaxine, selective serotonin-reuptake inhibitors such as sertraline or noradrenergic and specific serotonergic antidepressants such as mirtazapine.
- Compounds with anxiolytic, sedative and hypnotic properties, so-called tranquilizers such as, e.g., short- as well as mid-long acting benzodiazepines.
- Prostacyclin analogs and IP receptor agonists, for example and preferably iloprost, bera-prost, treprostinil, epoprostenol, NS-304, selexipag, or ralinepag;
- Compounds which inhibit the signal transduction cascade, in particular from the group of the tyrosine kinase inhibitors and/or from the group of serine/threoninekinase-inhibitors, for example and preferably dasatinib, nilotinib, bosutinib, regorafenib, sorafenib, sunitinib, cediranib, axitinib, telatinib, imatinib, brivanib, pazopanib, vatalanib, gefitinib, erlotinib, lapatinib, canertinib, lestaurtinib, pelitinib, semaxanib, masitinib or tandutinib, Rho kinase inhibitors, such as fasudil, Y-27632, SLx-2119, BF-66851, BF-66852, BF-66853, KI-23095 or BA-1049;
- Anti-obstructive agents as used, for example, for the therapy of chronic-obstructive pulmonary disease (COPD) or bronchial asthma, for example and preferably inhalatively or systemically administered beta-receptor mimetics (e.g., bedoradrine) or inhalatively administered anti-muscarinergic substances;
- Compounds with a bronchodilatory effect, for example and preferably from the group of β-adrenergic receptor-agonists, such as particularly albuterol, isoproterenol, metaproterenol, terbutaline, formoterol or salmeterol or from the group of anti-cholinergics, such as particularly ipratropiumbromide;
- Anti-inflammatory and/or immunosuppressive agents as used, for example for the therapy of chronic-obstructive pulmonary disease (COPD), of bronchial asthma or pulmonary fibrosis, for example and preferably from the group of corticosteroids, such as particularly prednisone, prednisolone, methylprednisolone, triamcinolone, dexamethasone, beclometasone, betamethasone, flunisolide, budesonide or fluticasone as well as from the group of non-steroidal anti-inflammatory drugs (NSAIDs), such as particularly acetylsalicylic acid (Aspirin), ibuprofen and naproxen, 5-aminosalicylic acid derivatives, leukotriene/leukotriene receptor antagonists, TNF-α inhibitors and chemokine receptor antagonists, such as, e.g., CCR-1, -2 and/or -5 inhibitors. Furthermore, drugs such as pirfenidone, acetylcysteine, azathioprine or BIBF-1120;

Chemotherapeutics as used, for example, for the therapy of neoplasias of the lung or other organs;

Active compounds used for the systemic and/or inhalative treatment of pulmonary disorders, for example for cystic fibrosis (alpha-1-antitrypsin, aztreonam, ivacaftor, lumacaftor, ataluren, amikacin, levofloxacin), chronic obstructive pulmonary diseases (COPD) (LAS40464, PT003, SUN-101), acute respiratory distress syndrome (ARDS) and acute lung injury (ALI) (interferon-beta-1a, traumakines), obstructive sleep apnea (VI-0521), bronchiectasis (mannitol, ciprofloxacin), Bronchiolitis obliterans (cyclosporine, aztreonam) and sepsis (pagibaximab, Voluven, ART-123);

Active compounds used for treating muscular dystrophy, for example idebenone;

Antithrombotic agents, for example and preferably from the group of platelet aggregation inhibiting drugs (platelet aggregation inhibitors, thrombocyte aggregation inhibitors), anticoagulants or compounds with anticoagulant properties or profibrinolytic substances;

Active compounds for lowering blood pressure, for example and preferably from the group of calcium antagonists, angiotensin AII antagonists, ACE inhibitors, NEP inhibitors, vasopeptidase inhibitors, and combinations thereof, such as, e.g., sacubitril/valsartan (Entresto®), furthermore nicorandil, endothelin antagonists/endothelin receptor antagonists, such as bosentan, darusentan, ambrisentan, macicentan or sitaxentan, thromboxane A2 (TXA2) antagonists/thromboxane A2 (TBX2) receptor antagonists, renin inhibitors, alpha-receptor blockers, beta-receptor blockers, mineralocorticoid-receptor antagonists, Rho-kinase inhibitors, diuretics as well as further vasoactive compounds/active components such as i.e. adenosine and adenosine receptor agonists.

Compounds which inhibit degradation and remodelling of the extracellular matrix, for example and preferably inhibitors of matrix metalloproteases (MMPs), in particular chymase-inhibitors, stromelysin-inhibitors, collagenase-inhibitors, gelatinase-inhibitors and aggrecanase-inhibitors (in these terms especially MMP-1, MMP-3, MMP-8, MMP-9, MMP-10, MMP-11 and MMP13) as well as inhibitors of the metallo-elastase MMP-12 as well as neutrophil elastase (HNE) inhibitors, for example and preferably sivelestat or DX-890 (Reltran);

Compounds which inhibit the binding of serotonin to its receptor, for example and preferably antagonists of the $5\text{-HT}_1$-, $5\text{-HT}_{2a}$-, $5\text{-HT}_{2b}$-, $5\text{-HT}_2\text{e}$-, $5\text{-HT}_3$- and $5\text{-HT}_4$-receptors;

Anti-arrhythmic compounds/active components, for example and preferably sodium channel inhibitors, beta-receptor blockers, potassium channel blockers, calcium antagonists, $I_f$-channel blockers, *digitalis*, parasympatholytics (vagolytics), sympathomimetics and other anti-arrhythmic drugs such as, e.g., adenosine, adenosine-receptor agonists as well as vernakalant.

Active compounds that alter fat metabolism, for example and preferably from the group of thyroid receptor agonists, cholesterol synthesis inhibitors, for example and preferably HMG-CoA-reductase or squalene synthesis inhibitors, ACAT inhibitors, CETP inhibitors, MTP inhibitors, PPAR-alpha-, PPAR-gamma- and/or PPAR-delta-agonists, cholesterol absorption inhibitors, lipase inhibitors, polymericbile acid adsorbers, bile acid reabsorption inhibitors and lipoprotein (a) antagonists.

Active ingredients which inhibit neoangiogenesis, for example and preferably inhibitors of the VEGF and/or PDGF signalling pathways, inhibitors of the integrin signalling pathways, inhibitors of the angiopoietin-Tie signalling pathways, inhibitors of the PI3K-Akt-mTor signalling pathways, inhibitors of the Ras-Raf-Mek-Erk signalling pathway, inhibitors of the MAPK signalling pathways, inhibitors of the FGF signalling pathways, inhibitors of the sphingosine-1-phosphate signalling pathways, inhibitors of endothelial cell proliferation or apoptosis-inducing active ingredients;

Active ingredients which reduce vascular wall permeability (edema formation), for example and preferably corticosteroids, inhibitors of the ALK1-Smad1/5 signalling pathway, inhibitors of the VEGF and/or PDGF signalling pathways, cyclooxygenase inhibitors, inhibitors of the kallikrein-kinin system or inhibitors of the sphingosine-1-phosphate signalling pathways;

Active ingredients which reduce damage to the retina under oxidative stress, for example and preferably addressing the complement system, especially antagonists of the complement C5a receptor, or agonists of the 5-HT1A receptor;

Antioxidants and free-radical scavengers;

Active hypotensive ingredients, for example and preferably from the group of the calcium antagonists, angiotensin AII antagonists, ACE inhibitors, beta-receptor blockers, alpha-receptorblockers, diuretics, phosphodiesterase inhibitors, sGC stimulators, cGMP elevators, aldosterone antagonists, mineralocorticoid-receptor antagonists, ECE inhibitors and vasopeptidase inhibitors;

Antidiabetics and accordingly compounds/active components changing glucose metabolism, for example and preferably from the group of the insulins and/or insulin derivatives, biguanides, sulfonylureas, acarbose, DPP4-inhibitors, meglitinide derivatives, glucosidase inhibitors, GLP 1 receptor agonists/GLP1 analogues, SGLT-2 inhibitors, glucagon antagonists, PPAR-gamma agonists/insulin sensitizers, such as, e.g., thiazolidinediones, CCK1 receptor agonists, leptin receptor agonists, potassium channel antagonists and the inhibitors of hepatic enzymes that are involved in the stimulation of gluconeogenesis and/or glycogenolysis;

Antiinfectives, for example and in particular from the group of the antibacterial, antifungal and/or antiviral substances;

Substances for treatment of glaucoma, for example and in particular from the group of the adrenergics, beta-receptor blockers, carbonic anhydrase inhibitors, parasympathomimetics and prostaglandins;

Pain-reducing compounds such as opiates.

Antithrombotic agents are for example and preferably to be understood as compounds from the group of platelet aggregation inhibiting drugs (platelet aggregation inhibitors, thrombocyte aggregation inhibitors), anticoagulants or compounds with anticoagulant properties or profibrinolytic substances.

In preferred embodiments of the invention, the compounds according to the invention are administered in combination with compounds from the group of platelet aggregation inhibiting drugs (platelet aggregation inhibitors, thrombocyte aggregation inhibitors), for example and preferably aspirin, clopidogrel, prasugrel, ticlopidine, ticagrelor, cangrelor, elinogrel, tirofiban, PAR1-antagonists such as, e.g., vorapaxar, PAR4-antagonists, EP3-antagonists, such as, e.g., DG041 or inhibitors of adenosine-transport, such as dipyridamole;

In preferred embodiments of the invention, the compounds according to the invention are administered in combination with a thrombin inhibitor, for example and preferably ximelagatran, melagatran, dabigatran, bivalirudin or Clexane.

In preferred embodiments of the invention, the compounds according to the invention are administered in combination with a GPIIb/IIIa antagonist, for example and preferably tirofiban or abciximab.

In preferred embodiments of the invention, the compounds according to the invention are administered in combination with a factor Xa inhibitor, for example and preferably rivaroxaban, apixaban, edoxaban (DU-176b), darexaban, betrixaban, otamixaban, letaxaban, fidexaban, razaxaban, fondaparinux, idraparinux, as well as thrombin-inhibitors, for example and preferably dabigatran, dual thrombin/factor Xa-inhibitors, such as for example and preferably tanogitran or with factor XI- or factor XIa-inhibitors.

In preferred embodiments of the invention, the compounds according to the invention are administered in combination with heparin or a low molecular weight (LMW) heparin derivatives, such as i.e. tinzaparin, certoparin, parnaparin, nadroparin, ardeparin, enoxaparin, reviparin, dalteparin, danaparoid, semuloparin (AVE 5026), adomiparin (M118) and EP-42675/ORG42675.

In preferred embodiments of the invention, the compounds according to the invention are administered in combination with a vitamin K antagonist, for example and preferably coumarines, such as marcumar/phenprocoumon.

In preferred embodiments of the invention, the compounds according to the invention are administered in combination with pro-fibrinolytic substances, for example and preferably streptokinase, urokinase or plasminogen-activator.

The agents for lowering blood pressure are preferably to be understood as compounds from the group of calcium antagonists, angiotensin All antagonists, ACE inhibitors, endothelin antagonists/endothelin receptor antagonists, thromboxane A2 (TBX2)-antagonists/thromboxane A2 (TBX2) receptor antagonists, renin inhibitors, alpha-receptor blockers, beta-receptor blockers, mineralocorticoid-receptor antagonists, Rho-kinase inhibitors as well as diuretics.

In preferred embodiments of the invention, the compounds according to the invention are administered in combination with a calcium antagonist, for example and preferably nifedipine, amlodipine, verapamil or diltiazem.

In preferred embodiments of the invention, the compounds according to the invention are administered in combination with an alpha-1-receptor blocker, for example and preferably prazosin.

In preferred embodiments of the invention, the compounds according to the invention are administered in combination with a beta-receptor blocker, for example and preferably propranolol, atenolol, timolol, pindolol, alprenolol, oxprenolol, penbutolol, bupranolol, metipranolol, nadolol, mepindolol, carazolol, sotalol, metoprolol, betaxolol, celiprolol, bisoprolol, carteolol, esmolol, labetalol, carvedilol, adaprolol, landiolol, nebivolol, epanolol or bucindolol.

In preferred embodiments of the invention, the compounds according to the invention are administered in combination with an angiotensin All antagonist, for example and preferably losartan, candesartan, valsartan, telmisartan or embursatan, irbesartan, olmesartan, eprosartan or azilsartan or a dual angiotensin All-antagonist/NEP-inhibitor, for example and preferably Entresto (LCZ696, Valsartan/Sacubitril).

In preferred embodiments of the invention, the compounds according to the invention are administered in combination with an ACE-inhibitor, for example and preferably enalapril, captopril, lisinopril, ramipril, delapril, fosinopril, quinopril, perindopril or trandopril.

In preferred embodiments of the invention, the compounds according to the invention are administered in combination with an endothelin antagonist/endothelin receptor antagonist, for example and preferably bosentan, darusentan, ambrisentan, avosentan, macicentan, atrasentan or sitaxsentan.

In preferred embodiments of the invention, the compounds according to the invention are administered in combination with a renin inhibitor, for example and preferably aliskiren, SPP-600 or SPP-800.

In preferred embodiments of the invention, the compounds according to the invention are administered in combination with a thromboxane A2 (TBX2)-antagonist, for example and preferably seratrodast or KP-496.

In preferred embodiments of the invention, the compounds according to the invention are administered in combination with a mineralocorticoid-receptor antagonist, for example and preferably spironolactone, eplerenone or finerenone.

In preferred embodiments of the invention, the compounds according to the invention are administered in combination with a diuretic, for example and preferably furosemide, torasemide bumetanide and piretanide, with potassium-saving diuretics, such as, e.g., amiloride or triamterene as well as with thiazide diuretics, such as, e.g., hydrochlorthiazide, chlorthalidone, xipamide and indapamide. Likewise, the combination with further diuretics is applicable, for example and preferably with bendroflumethiazide, chlorthiazide, hydroflumethiazide, methyclothiazide, polythiazide, trichlormethiazide, metolazone, quinethazone, acetazolamide, dichlorphenamide, methazolamide, glycerol, isosorbide or mannitol.

In preferred embodiments of the invention, the compounds according to the invention are administered in combination with a Rho-kinase inhibitor, for example and preferably fasudil, Y 27632, SLx-2119, BF-66851, BF-66852, BF-66853, KI-23095, SB-772077, GSK-269962A or BA-1049.

In preferred embodiments of the invention, the compounds according to the invention are administered in combination with natriuretic peptides, such as, for example "atrial natriuretic peptide" (ANP, Anaritide), "B-type natriuretic peptide", "brain natriuretic peptide" (BNP, Nesiritide), "C-type natriuretic peptide" (CNP) or Urodilatin;

In preferred embodiments of the invention, the compounds according to the invention are administered in combination with inhibitors of the endopeptidase (NEP-inhibitors), for example Sacubitril, Omapatrilat or AVE-7688, or as dual combinations ('ARNIs') with Angiotensin receptor antagonists (for example Valsartan), such as, for example Entresto/LCZ696.

In preferred embodiments of the invention, the compounds according to the invention are administered in combination with type II antidiabetic drugs, such as inhibitors of the sodium-glucose co-transporter 2 (SGLT2 inhibitors), for example Empagliflozin, Canagliflozin, Dapagliflozin, Ipragliflozin, Tofogliflozin and inhibitors of the dipeptidyl peptidase 4 (DPP-4 inhibitors), for example sitagliptin, saxagliptin, linagliptin, alogliptin.

Substances altering fat metabolism are preferably to be understood as compounds from the group of CETP inhibitors, thyroid receptor agonists, cholesterol synthesis inhibitors such as HMG-CoA-reductase or squalene synthesis inhibitors, the ACAT inhibitors, MTP inhibitors, PPAR-alpha, PPAR-gamma and/or PPAR-delta agonists, cholesterol-absorption inhibitors, polymeric bile acid adsorbers, bile acid reabsorption inhibitors, lipase inhibitors as well as the lipoprotein (a) antagonists.

In preferred embodiments of the invention, the compounds according to the invention are administered in combination with a CETP inhibitor, for example and preferably torcetrapib (CP-529414), anacetrapib, JJT-705 or CETP-vaccine (Avant).

In preferred embodiments of the invention, the compounds according to the invention are administered in combination with a thyroid receptor agonist, for example and preferably D-thyroxin, 3,5,3'-triiodothyronin (T3), CGS 23425 or axitirome (CGS 26214).

In preferred embodiments of the invention, the compounds according to the invention are administered in combination with a HMG-CoA-reductase inhibitor from the class of statins, for example and preferably lovastatin, simvastatin, pravastatin, fluvastatin, atorvastatin, rosuvastatin or pitavastatin.

In preferred embodiments of the invention, the compounds according to the invention are administered in combination with a squalene synthesis inhibitor, for example and preferably BMS-188494 or TAK-475.

In preferred embodiments of the invention, the compounds according to the invention are administered in combination with an ACAT inhibitor, for example and preferably avasimibe, melinamide, pactimibe, eflucimibe or SMP-797.

In preferred embodiments of the invention, the compounds according to the invention are administered in combination with an MTP inhibitor, for example and preferably implitapide, BMS-201038, R-103757 or JTT-130.

In preferred embodiments of the invention, the compounds according to the invention are administered in combination with a PPAR-gamma agonist, for example and preferably pioglitazone or rosiglitazone.

In preferred embodiments of the invention, the compounds according to the invention are administered in combination with a PPAR-delta agonist, for example and preferably GW 501516 or BAY 68-5042.

In preferred embodiments of the invention, the compounds according to the invention are administered in combination with a cholesterol-absorption inhibitor, for example and preferably ezetimibe, tiqueside or pamaqueside.

In preferred embodiments of the invention, the compounds according to the invention are administered in combination with a lipase inhibitor, for example and preferably orlistat.

In preferred embodiments of the invention, the compounds according to the invention are administered in combination with a polymeric bile acid adsorber, for example and preferably cholestyramine, colestipol, colesolvam, CholestaGel or colestimide.

In preferred embodiments of the invention, the compounds according to the invention are administered in combination with a bile acid reabsorption inhibitor, for example and preferably ASBT (=IBAT) inhibitors, such as i.e. AZD-7806, S-8921, AK-105, BARI-1741, SC-435 or SC-635.

In preferred embodiments of the invention, the compounds according to the invention are administered in combination with a lipoprotein (a) antagonist, for example and preferably gemcabene calcium (CI-1027) or nicotinic acid.

Substances inhibiting signal transduction are preferably to be understood as compounds from the group of the tyrosine-kinase inhibitors and/or serine/threonine-kinase-inhibitors.

In preferred embodiments of the invention, the compounds according to the invention are administered in combination with a kinase-inhibitor, for example and preferably canertinib, erlotinib, gefitinib, dasatinib, imatinib, lapatinib, lestaurtinib, lonafarnib, nintedanib, nilotinib, bosutinib, axitinib, telatinib, brivanib, pazo-panib, pegaptinib, peli-tinib, semaxa-nib, regora-fenib, sora-fenib, sunitinib, tandutinib, tipifarnib, vatalanib, cediranib, masitinib, fasudil, lonidamine, leflunomide, BMS-3354825 or Y-27632.

Substances modulating glucose metabolism are preferably to be understood as compounds from the group of insulins, sulfonylureas, acarbose, DPP4-inhibitors, GLP-1 analogues or SGLT-2 inhibitors.

Substances modulating neurotransmitters are preferably to be understood as compounds from the group of tricyclic antidepressants, monoaminooxidase (MAO)-inhibitors, serotonin-noradrenaline-reuptake inhibitors (SNRI) and noradrenergic and specific serotonergic antidepressants (NaSSa).

In preferred embodiments of the invention, the compounds according to the invention are administered in combination with a tricyclic antidepressant, for example and preferably amitryptilin or imipramin.

In preferred embodiments of the invention, the compounds according to the invention are administered in combination with a monoaminooxidase (MAO)-inhibitor, for example and preferably moclobemide.

In preferred embodiments of the invention, the compounds according to the invention are administered in combination with a selective serotonine-noradrenaline reuptake inhibitor (SNRI), for example and preferably venlafaxine.

In preferred embodiments of the invention, the compounds according to the invention are administered in combination with a selective serotonine reuptake inhibitor (SSRI), such as i.e. sertraline.

In preferred embodiments of the invention, the compounds according to the invention are administered in combination with a noradrenergic and specific serotonergic antidepressants (NaSSa), for example and preferably mirtazapine.

Substances with pain-reducing, anxiolytic or sedative properties are preferably to be understood as compounds from the group of opiates and benzodiazepines.

In preferred embodiments of the invention, the compounds according to the invention are administered in combination with an opiate, for example and preferably morphine or sulfentanyl or fentanyl.

In preferred embodiments of the invention, the compounds according to the invention are administered in combination with a benzodiazepine, for example and preferably midazolam or diazepam.

Substances modulating cGMP-synthesis, such as, e.g., sGC-modulators, are preferably to be understood as compounds that stimulate or activate the soluble guanylate cyclase.

In preferred embodiments of the invention, the compounds according to the invention are administered in combination with sGC modulators, for example and preferably in riociguat, nelociguat, vericiguat, cinciguat and the compounds described in WO 00/06568, WO 00/06569, WO 02/42301, WO 03/095451, WO 2011/147809, WO 2012/004258, WO 2012/028647, WO 2012/059549, WO 2014/068099 and WO 2014/131760 as well as the compounds described in WO 01/19355, WO 01/19780, WO 2012/139888 and WO 2014/012934;

In preferred embodiments of the invention, the compounds according to the invention are administered in combination with full or partial adenosine A1 receptor agonists, such as, e.g., GS-9667 (formerly known as CVT-3619), capadenosone and neladenosone or compounds affecting mitochondrial function/ROS-production such as i.e. Bendavia/elamipritide.

In preferred embodiments of the invention, the compounds according to the invention are administered in combination with a TGF-beta antagonist, for example and preferably pirfenidone or fresolimumab.

In preferred embodiments of the invention, the compounds according to the invention are administered in combination with a TNF-alpha antagonist, for example and preferably adalimumab.

In preferred embodiments of the invention, the compounds according to the invention are administered in combination with HIF-PH-inhibitors, for example and preferably molidustat or roxadustat.

In preferred embodiments of the invention, the compounds according to the invention are administered in combination with a serotonin-receptor antagonist, for example and preferably PRX-08066.

It is possible for the compounds according to the invention to have systemic and/or local activity. For this purpose, they can be administered in a suitable manner, such as, for example, via the oral, parenteral, pulmonary, nasal, sublingual, lingual, buccal, rectal, vaginal, dermal, transdermal, conjunctival, otic route or as an implant or stent.

For these administration routes, it is possible for the compounds according to the invention to be administered in suitable administration forms.

For oral administration, it is possible to formulate the compounds according to the invention to dosage forms known in the art that deliver the compounds of the invention rapidly and/or in a modified manner, such as, for example, tablets (uncoated or coated tablets, for example with enteric or controlled release coatings that dissolve with a delay or are insoluble), orally-disintegrating tablets, films/wafers, films/lyophylisates, capsules (for example hard or soft gelatine capsules), sugar-coated tablets, granules, pellets, powders, emulsions, suspensions, aerosols or solutions. It is possible to incorporate the compounds according to the invention in crystalline and/or amorphised and/or dissolved form into said dosage forms.

Parenteral administration can be effected with avoidance of an absorption step (for example intravenous, intraarterial, intracardial, intraspinal or intralumbal) or with inclusion of absorption (for example intramuscular, subcutaneous, intracutaneous, percutaneous or intraperitoneal). Administration forms which are suitable for parenteral administration are, inter alia, preparations for injection and infusion in the form of solutions, suspensions, emulsions, lyophylisates or sterile powders.

Examples which are suitable for other administration routes are pharmaceutical forms for inhalation [inter alia powder inhalers, nebulizers], nasal drops, nasal solutions, nasal sprays; tablets/films/wafers/capsules for lingual, sublingual or buccal administration; suppositories; eye drops, eye ointments, eye baths, ocular inserts, ear drops, ear sprays, ear powders, ear-rinses, ear tampons; vaginal capsules, aqueous suspensions (lotions, mixturae agitandae), lipophilic suspensions, emulsions, ointments, creams, transdermal therapeutic systems (such as, for example, patches), milk, pastes, foams, dusting powders, implants or stents.

The compounds according to the invention can be incorporated into the stated administration forms. This can be effected in a manner known per se by mixing with pharmaceutically suitable excipients. Pharmaceutically suitable excipients include, interalia, fillers and carriers (for example cellulose, microcrystalline cellulose (such as, for example, Avicel®), lactose, mannitol, starch, calcium phosphate (such as, for example, Di-Cafos®)), ointment bases (for example petroleum jelly, paraffins, triglycerides, waxes, wool wax, wool wax alcohols, lanolin, hydrophilic ointment, polyethylene glycols), bases for suppositories (for example polyethylene glycols, cacao butter, hard fat), solvents (for example water, ethanol, isopropanol, glycerol, propylene glycol, medium chain-length triglycerides fatty oils, liquid polyethylene glycols, paraffins), surfactants, emulsifiers, dispersants or wetters (for example sodium dodecyl sulfate), lecithin, phospholipids, fatty alcohols (such as, for example, Lanette®), sorbitan fatty acid esters (such as, for example, Span®), polyoxyethylene sorbitan fatty acid esters (such as, for example, Tween®), polyoxyethylene fatty acid glycerides (such as, for example, Cremophor®), polyoxethylene fatty acid esters, polyoxyethylene fatty alcohol ethers, glycerol fatty acid esters, poloxamers (such as, for example, Pluronic®), buffers, acids and bases (for example phosphates, carbonates, citric acid, acetic acid, hydrochloric acid, sodium hydroxide solution, ammonium carbonate, trometamol, triethanolamine), isotonicity agents (for example glucose, sodium chloride), adsorbents (for example highly-disperse silicas), viscosity-increasing agents, gel formers, thickeners and/or binders (for example polyvinylpyrrolidone, methylcellulose, hydroxypropylmethylcellulose, hydroxypropylcellulose, carboxymethylcellulose-sodium, starch, carbomers, polyacrylic acids (such as, for example, Carbopol®); alginates, gelatine), disintegrants (for example modified starch, carboxymethylcellulose-sodium, sodium starch glycolate (such as, for example, Explotab®), cross-linked polyvinylpyrrolidone, croscarmellose-sodium (such as, for example, AcDiSol®)), flow regulators, lubricants, glidants and mould release agents (for example magnesium stearate, stearic acid, talc, highly-disperse silicas (such as, for example, Aerosil®)), coating materials (for example sugar, shellac) and film formers for films or diffusion membranes which dissolve rapidly or in a modified manner (for example polyvinylpyrrolidones (such as, for example, Kollidon®), polyvinyl alcohol, hydroxypropylmethylcellulose, hydroxypropylcellulose, ethylcellulose, hydroxypropylmethylcellulose phthalate, cellulose acetate, cellulose acetate phthalate, polyacrylates, polymethacrylates such as, for example, Eudragit®)), capsule materials (for example gelatine, hydroxypropylmethylcellulose), synthetic polymers (for example polylactides, polyglycolides, polyacrylates, polymethacrylates (such as, for example, Eudragit®), polyvinylpyrrolidones (such as, for example, Kollidon®), polyvinyl alcohols, polyvinyl acetates, polyethylene oxides, polyethylene glycols and their copolymers and block copolymers), plasticizers (for example polyethylene glycols, propylene glycol, glycerol, triacetine, triacetyl citrate, dibutyl phthalate), penetration enhancers, stabilisers (for example antioxidants such as, for example, ascorbic acid, ascorbyl palmitate, sodium ascorbate, butylhydroxyanisole, butylhydroxytoluene, propyl gallate), preservatives (for example parabens, sorbic acid, thiomersal, benzalkonium chloride, chlorhexidine acetate, sodium benzoate), colourants (for example inorganic pigments such as, for example, iron oxides, titanium dioxide), flavourings, sweeteners, flavour- and/or odour-masking agents.

Biological Definitions

Unless otherwise defined, all scientific and technical terms used in the description, figures and claims have their ordinary meaning as commonly understood by one of ordinary skill in the art. All publications, patent applications, patents, and other references mentioned herein are incorporated by reference in their entirety. In case of conflict, the present specification, including definitions, will prevail. If two or more documents incorporated by reference include conflicting and/or inconsistent disclosure with respect to each other, then the document having the later effective date shall control. The materials, methods, and examples are illustrative only and not intended to be limiting. Unless stated otherwise, the following terms used in this document, including the description and claims, have the definitions given below.

The terms "comprising", "including", "containing", "having" etc. shall be read expansively or open-ended and without limitation.

Singular forms such as "a", "an" or "the" include plural references unless the context clearly indicates otherwise.

Unless otherwise indicated, the term "at least" preceding a series of elements is to be understood to refer to every element in the series. The terms "at least one" and "at least one of" include for example, one, two, three, four, or five or more elements.

Mutation numbering follows the species based positions for each construct, i.e. rat ADAMTS7 SP-Pro (1-217) followed by human ADAMTS7 CD (237-537).

The term "ADAMTS-7" (also ADAMTS7, ADAM-TS 7, ADAM-TS7) refers to the protein A disintegrin and metalloproteinase with thrombospondin motifs 7. The ADAMTS-7 protein is encoded by the gene ADAMTS-7. The ADAMTS-7 protein comprises human, murine, rat and further mammalian and non-mamalian homologues. Sequence(s) for human ADAMTS-7 are accessible via UniProt Identifier Q9UKP4 (ATS7_HUMAN), for instance human isoform Q9UKP4-1. Sequence(s) for murine ADAMTS-7 are accessible via UniProt Identifier Q68SA9 (ATS7_MOUSE). Different isoforms, variants and SNPs may exist for the different species and are all comprised by the term ADAMTS-7. Also comprised are ADAMTS-7 molecules before and after maturation, i.e., independent of cleavage of one or more pro-domains. In addition, synthetic variants of the ADAMTS-7 protein may be generated and are comprised by the term ADAMTS-7. The protein ADAMTS-7 may furthermore be subject to various modifications, e.g, synthetic or naturally occurring modifications. Recombinant functional human ADAMTS-7 (e.g. according to SEQ ID No. 01 and 02) can be manufactured as described in the examples.

The term "ADAMTS-12" (also ADAMTS12, ADAM-TS 12, ADAM-TS12) refers to the protein A disintegrin and metalloproteinase with thrombospondin motifs 12. Such proteins preferably include a ADAMTS-12 catalytic domain. The ADAMTS-12 protein is encoded by the gene ADAMTS-12. The ADAMTS-12 protein comprises human, murine, rat and further mammalian and non-mamalian homologues. Sequence(s) for human ADAMTS-12 including the catalytic domains are accessible via UniProt Identifier P58397 (ATS12_HUMAN), for instance human isoform P58397-1. Sequence(s) for murine ADAMTS-12 are accessible via UniProt Identifier Q811B3 (ATS12_MOUSE). Different isoforms and variants may exist for the different species and are all comprised by the term ADAMTS-12. Also comprised are ADAMTS-12 molecules before and after maturation, i.e., independent of cleavage of one or more pro-domains. In addition, synthetic variants of the ADAMTS-12 protein may be generated and are comprised by the term ADAMTS-12. The protein ADAMTS-12 may furthermore be subject to various modifications, e.g., synthetic or naturally occurring modifications. Recombinant functional human ADAMTS-12 (e.g., according to SEQ ID NO: 15) can be manufactured as described in the examples.

The terms "ADAMTS-4" and "ADAMTS-5" refer to the protein A disintegrin and metalloproteinase with thrombospondin motifs 4 and 5, respectively. The ADAMTS-4 and -5 proteins are encoded by the genes ADAMTS4 and ADAMTS-5, respectively. These proteins comprises human, murine, rat and further mammalian and non-mamalian homologues. Sequence(s) for human ADAMTS-4/-5 are accessible via UniProt Identifier O75173 (ATS4_HUMAN)/ Q9UNA0 (ATS5_HUMAN), respectively. Different isoforms and variants may exist. Recombinant active human ADAMTS-4 and ADAMTS-5 can be manufactured as known in the art.

The terms "MMP2", "MMP12", and "MMP15" refer to the 72 kDa type IV collagenase, Macrophage metalloelastase 2 and 12 and Matrix metalloproteinase-15, respectively. The MMP2, MMP12, and MMP15 proteins are encoded by the genes MMP2, MMP12, and MMP15, respectively. The proteins comprises human, murine, rat and further mammalian and non-mamalian homologues. Sequence(s) for human ADAMTS-4/-5 are accessible via UniProt Identifier P08253 (MMP2_HUMAN), P39900 (MMP12_HUMAN) and P51511 (MMP15_HUMAN), respectively. Different isoforms and variants may exist. Recombinant active human ADAMTS-4 and ADAMTS-5 can be manufactured as known in the art.

The term "ADAM17" refers to Disintegrin and metalloproteinase domain-containing protein 17, encoded by the gene ADAM17. The protein comprises human, murine, rat and further mammalian and non-mamalian homologues. Sequence(s) for human ADAM17 are accessible via UniProt Identifier P78536 (ADA17_HUMAN). Different isoforms and variants may exist. Recombinant active human ADAM17 can be manufactured as known in the art.

The term "prodomain" includes parts of ADAMTS-7 or ADAMTS-12 that are relatively N-terminal to the respective protein's functional chain (e.g., parts having metalloprotease function and disintergrin motifs). For example, a prodomain of ADAMTS-7 as provided in SEQ ID NO: 1 can include its signal peptide (residues 1-20) and its propeptide (residues 21-217), both of which are N-terminal to its peptidase domain, although not necessarily immediately N-terminal to it. In some embodiments, prodomain of ADAMTS-7 or ADAMTS-12 includes 75%, 80%, 85%, 90%, 95%, or 100% of the N-terminal part of the respective protein with its signal peptide plus its propeptide. The term "prodomain" also encompasses the parts of the encoded polypeptide that are processed (e.g., cleaved off) before generation of the functional enzymatic chain in the natural environment of the enzyme.

A "furin cleavage site" or furin consensus site is R-x-K/R-R↓D/S, cf. Shiryaev 2013 PLoS One. The ADAMTS7 prodomain contains multiple Furin protease cleavage sites, the last of which is thought to fully process the zymogen into the active form. Mutational analysis was described by Sommerville 2004 JBC for rat ADAMTS7 with R60A and R217A (referred to as mouse R220A in publication). R60A changes rat ADAMTS7 from LRKR↓D to LRKA↓D and R217A changes rat ADAMTS7 RQQR↓S to RQQA↓S.

The term "catalytic domain" includes parts of ADAMTS-7 or ADAMTS-12 that have ADAMTS-7 or ADAMTS-12 functionality, respectively, and that are C-terminal to the respective protein's prodomain. In some embodiments, the term "catalytic domain" refers to the peptidase plus disintegrin part of the respective protein (e.g., as characterized by UniProt), potentially also including any residues C-terminal to the respective protein's prodomain and N-terminal to the respective protein's peptidase domain. In some embodiments, the catalytic domain includes 75%, 80%, 85%, 90%, 95%, or 100% of the part of the respective enzyme having its disintegrin domain, its peptidase domain, and any residues it might have between its prodomain and its peptidase domain.

The term "functional protein" refers to a protein which has biological activity. For example, functional ADAMTS-7 refers to ADAMTS-7 which is able to catalyze the proteolytic cleavage of its (natural) substrate(s), e.g. TSP1 and/or COMP.

The term "metalloproteinase" refers to a protease enzyme whose catalytic mechanism involves a metal. Therefore a functional metalloproteinase is a functional protein, wherein the protein is a protease and wherein the protease is a metalloproteinase according to the foregoing definitions.

The expression "a cleavage site for a protease" refers to any peptide or protein sequence which is recognized and cleaved by the functional protease. A cleavage site for ADAMTS-7 thus refers to any peptide or protein sequence which is recognized and cleaved by functional ADAMTS-7. For example, being natural substrates of ADAMTS-7, the sequences of proteins COMP and TSP1 both comprise cleavage sites for ADAMTS-7. In particular the subsequence DELSSMVLELRGLRT (derived from TSP1, residues 275-289) constitutes or comprises a cleavage site for ADAMTS-7 and ADAMTS-12.

A "substrate" is a molecule upon which an enzyme acts. For example, the substrate of a proteinase can be a peptide or protein or derivative thereof, which is cleaved by the proteinase. Metalloproteinase paralogs ADAMTS-7/-12 on the one hand and their common peptide substrate on the other hand are interrelated in the sense of a plug and socket relationship.

The term "COMP", TSP-5 or TSP5 refers to the protein Cartilage oligomeric matrix protein. The COMP protein is encoded by the gene COMP. The COMP protein comprises human, murine, rat and further mammalian and homologues. Sequence(s) for human COMP are accessible via UniProt Identifier P49747 (COMP_HUMAN), for instance human isoform P49747-1. Sequence(s) for murine COMP are accessible via UniProt Identifier Q9ROG6 (COMP_MOUSE). Different isoforms and variants may exist for the different species and are all comprised by the term COMP. Also comprised are COMP molecules before and after maturation, i.e., independent of cleavage of one or more pro-domains. In addition, synthetic variants of the COMP protein may be generated and are comprised by the term COMP. The protein COMP may furthermore be subject to various modifications, e.g, synthetic or naturally occurring modifications. Recombinant human COMP or derivatives thereof can be manufactured as described in the examples.

The term "TSP1" (also THBS1 or TSP) refers to the protein Thrombospondin-1. The TSP1 protein is encoded by the gene THBS1. The TSP1 protein comprises human, murine, rat and further mammalian and non-mammalian homologues. Sequence(s) for human TSP1 are accessible via UniProt Identifier P07996 (TSP1_HUMAN), for instance human isoform P07996-1. Sequence(s) for murine TSP1 are accessible via UniProt Identifier P35441 (TSP1_MOUSE). Different isoforms and variants may exist for the different species and are all comprised by the term TSP1. Also comprised are TSP1 molecules before and after maturation, i.e., independent of cleavage of one or more pro-domains. In addition, synthetic variants of the TSP1 protein may be generated and are comprised by the term TSP1. The protein TSP1 may furthermore be subject to various modifications, e.g, synthetic or naturally occurring modifications. Recombinant human TSP1 or derivatives thereof can be manufactured as described in the examples.

The term "fluorophore" according to the current invention refers to a molecule or chemical group which has the ability to absorb energy from light, transfer this energy internally, and emit this energy as light of a characteristic wavelength. Without being bound by theory, since some energy is lost during this process, the energy of the emitted fluorescence light is lower than the energy of the absorbed light, and therefore emission occurs at a longer wavelength than absorption. A variety of fluorophores and quenchers has been described in the art and can be used according to the current invention, see for example Bajar et al, Sensors 2016, A Guide to Fluorescent Protein FRET Pairs.

The term "quencher" according to the current invention refers to a molecule or chemical group which has the ability to decrease the fluorescence intensity of a given fluorophore. Without being bound by theory a variety of processes can result in quenching, such as excited state reactions, energy transfer, complex-formation and collisional quenching. Dark quenchers are dyes with no native fluorescence. Quencher fluorescence can increase background noise due to overlap between the quencher and reporter fluorescence spectra. A variety of fluorophores and quenchers has been described in the art and can be used according to the current invention, see for example Bajar et al, Sensors 2016, A Guide to Fluorescent Protein FRET Pairs. Suitable quenchers according to the current invention include DDQ-I A (430 nm), Dabcyl (475 nm), Eclipse B (530 nm), Iowa Black FQ C (532 nm), BHQ-1 D (534 nm), QSY-7 E (571 nm), BHQ-2 D (580 nm), DDQ-11 A (630 nm), Iowa Black RQ C (645 nm), QSY-21 E (660 nm) or BHQ-3 D (670 nm). Preferred examples of quenchers according to the current invention include Dabsyl(dimethylaminoazobenzenesulfonic acid), which absorbs in the green spectrum and is often used with fluorescein, black hole quenchers which are capable of quenching across the entire visible spectrum, Qxl quenchers which span the full visible spectrum, Iowa black FQ (absorbs in the green-yellow part of the spectrum), Iowa black RQ (blocks in the orange-red part of the spectrum) and IRDye QC-1 (quenches dyes from the visible to the near-infrared range (500-900 nm)).

Suitable internally quenched fluorescent (IQF)/FRET pairs include ABz-Tyr(NO2), ABz-EDDNP, Trp-Dansyl, and 7-methoxy-coumarin-4-yl acetic acid-2,4-dinitrophenyl-lysine (MCA-Lys(DNP)) (Poreba, Marcin et al., Highly sensitive and adaptable fluorescence-quenched pair discloses the substrate specificity profiles in diverse protease families. Scientific reports 7, 43135. (2017), doi:10.1038/srep43135). Further suitable examples are listed in: Poreba M. & Drag M. Current strategies for probing substrate specificity of proteases. Curr Med Chem 17, 3968-3995 (2010).

The term "construct" refers to nucleic acids (e.g., double stranded DNA, which can be in the form of a plasmid).

The term "align" in the context of two sequences (e.g., amino acid sequences), includes arranging the two sequences with respect to each other (e.g., the first sequence along a first row, and the second sequence along a second row, potentially with gap(s) in one or both sequences) to obtain a measure of their relationship to each other (e.g., % identity, % similarity, alignment score). A particular alignment of two sequences can be optimal (i.e., there are no alignments of the two sequences that result in a higher alignment score, if alignment score is the metric of concern for optimality) or non-optimal. In addition, a particular alignment can be global or local with respect to either sequence. For example, if the alignment is global with respect to both sequences (i.e., a global-global alignment), then all residues of both of the sequences are factored in to the calculation of the measure of their relationship, including any internal or external gaps in either sequence. In contrast, in a global-local alignment, while all residues and gaps in the first sequence are considered, no external gaps in the second sequence are considered, thereby allowing fitting the first sequence into a part of the second sequence.

The term "Needleman-Wunsch score" implies that either a global-global or a global-local (or local-global) alignment has been used to generate the alignment score. When partiality modifiers are used for both the first sequence (e.g., "portion") and the second sequence (e.g., "segment"), this implies that the alignment is global-global. A "Needleman-Wunsch score" includes scores calculated by the originally published method (S. B. Needleman & C. D. Wunsch, A general method applicable to the search for similarities in the amino acid sequence of two proteins, J. Mol. Biol. 48(3):443-53 (1970)) as well as by subsequent refinements of the method. Although Needleman-Wunsch algorithm is able to, and is designed to, find an optimal alignment, and thereby a maximum alignment score, the term "Needleman-Wunsch score" as used here is not restricted to the optimal/maximum score; it can be the alignment score of any alignment of the two sequences as long as at least one of the sequences (e.g., as defined, for example as a residue range) is considered globally.

Alignment methods (e.g., Needleman-Wunsch) that generate an alignment score (e.g., Needleman-Wunsch score) can make use of a substitution matrix. A particular substitution matrix that can be used is BLOSUM62, which is reproduced below in Table B1.

TABLE B1

|   | A | R | N | D | C | Q | E | G | H | I | L | K | M | F | P | S | T | W | Y | V | B | Z | X | * |
|---|---|---|---|---|---|---|---|---|---|---|---|---|---|---|---|---|---|---|---|---|---|---|---|---|
| A | 4 | -1 | -2 | -2 | 0 | -1 | -1 | 0 | -2 | -1 | -1 | -1 | -1 | -2 | -1 | 1 | 0 | -3 | -2 | 0 | -2 | -1 | 0 | -4 |
| R | -1 | 5 | 0 | -2 | -3 | 1 | 0 | -2 | 0 | -3 | -2 | 2 | -1 | -3 | -2 | -1 | -1 | -3 | -2 | -3 | -1 | 0 | -1 | -4 |
| N | -2 | 0 | 6 | 1 | -3 | 0 | 0 | 0 | 1 | -3 | -3 | 0 | -2 | -3 | -2 | 1 | 0 | -4 | -2 | -3 | 3 | 0 | -1 | -4 |
| D | -2 | -2 | 1 | 6 | -3 | 0 | 2 | -1 | -1 | -3 | -4 | -1 | -3 | -3 | -1 | 0 | -1 | -4 | -3 | -3 | 4 | 1 | -1 | -4 |
| C | 0 | -3 | -3 | -3 | 9 | -3 | -4 | -3 | -3 | -1 | -1 | -3 | -1 | -2 | -3 | -1 | -1 | -2 | -2 | -1 | -3 | -3 | -2 | -4 |
| Q | -1 | 1 | 0 | 0 | -3 | 5 | 2 | -2 | 0 | -3 | -2 | 1 | 0 | -3 | -1 | 0 | -1 | -2 | -1 | -2 | 0 | 3 | -1 | -4 |
| E | -1 | 0 | 0 | 2 | -4 | 2 | 5 | -2 | 0 | -3 | -3 | 1 | -2 | -3 | -1 | 0 | -1 | -3 | -2 | -2 | 1 | 4 | -1 | -4 |
| G | 0 | -2 | 0 | -1 | -3 | -2 | -2 | 6 | -2 | -4 | -4 | -2 | -3 | -3 | -2 | 0 | -2 | -2 | -3 | -3 | -1 | -2 | -1 | -4 |
| H | -2 | 0 | 1 | -1 | -3 | 0 | 0 | -2 | 8 | -3 | -3 | -1 | -2 | -1 | -2 | -1 | -2 | -2 | 2 | -3 | 0 | 0 | -1 | -4 |
| I | -1 | -3 | -3 | -3 | -1 | -3 | -3 | -4 | -3 | 4 | 2 | -3 | 1 | 0 | -3 | -2 | -1 | -3 | -1 | 3 | -3 | -3 | -1 | -4 |
| L | -1 | -2 | -3 | -4 | -1 | -2 | -3 | -4 | -3 | 2 | 4 | -2 | 2 | 0 | -3 | -2 | -1 | -2 | -1 | 1 | -4 | -3 | -1 | -4 |
| K | -1 | 2 | 0 | -1 | -3 | 1 | 1 | -2 | -1 | -3 | -2 | 5 | -1 | -3 | -1 | 0 | -1 | -3 | -2 | -2 | 0 | 1 | -1 | -4 |
| M | -1 | -1 | -2 | -3 | -1 | 0 | -2 | -3 | -2 | 1 | 2 | -1 | 5 | 0 | -2 | -1 | -1 | -1 | -1 | 1 | -3 | -1 | -1 | -4 |
| F | -2 | -3 | -3 | -3 | -2 | -3 | -3 | -3 | -1 | 0 | 0 | -3 | 0 | 6 | -4 | -2 | -2 | 1 | 3 | -1 | -3 | -3 | -1 | -4 |
| P | -1 | -2 | -2 | -1 | -3 | -1 | -1 | -2 | -2 | -3 | -3 | -1 | -2 | -4 | 7 | -1 | -1 | -4 | -3 | -2 | -2 | -1 | -2 | -4 |
| S | 1 | -1 | 1 | 0 | -1 | 0 | 0 | 0 | -1 | -2 | -2 | 0 | -1 | -2 | -1 | 4 | 1 | -3 | -2 | -2 | 0 | 0 | 0 | -4 |
| T | 0 | -1 | 0 | -1 | -1 | -1 | -1 | -2 | -2 | -1 | -1 | -1 | -1 | -2 | -1 | 1 | 5 | -2 | -2 | 0 | -1 | -1 | 0 | -4 |
| W | -3 | -3 | -4 | -4 | -2 | -2 | -3 | -2 | -2 | -3 | -2 | -3 | -1 | 1 | -4 | -3 | -2 | 11 | 2 | -3 | -4 | -3 | -2 | -4 |
| Y | -2 | -2 | -2 | -3 | -2 | -1 | -2 | -3 | 2 | -1 | -1 | -2 | -1 | 3 | -3 | -2 | -2 | 2 | 7 | -1 | -3 | -2 | -1 | -4 |
| V | 0 | -3 | -3 | -3 | -1 | -2 | -2 | -3 | -3 | 3 | 1 | -2 | 1 | -1 | -2 | -2 | 0 | -3 | -1 | 4 | -3 | -2 | -1 | -4 |
| B | -2 | -1 | 3 | 4 | -3 | 0 | 1 | -1 | 0 | -3 | -4 | 0 | -3 | -3 | -2 | 0 | -1 | -4 | -3 | -3 | 4 | 1 | -1 | -4 |
| Z | -1 | 0 | 0 | 1 | -3 | 3 | 4 | -2 | 0 | -3 | -3 | 1 | -1 | -3 | -1 | 0 | -1 | -3 | -2 | -2 | 1 | 4 | -1 | -4 |
| X | 0 | -1 | -1 | -1 | -2 | -1 | -1 | -1 | -1 | -1 | -1 | -1 | -1 | -1 | -2 | 0 | 0 | -2 | -1 | -1 | -1 | -1 | -1 | -4 |
| * | -4 | -4 | -4 | -4 | -4 | -4 | -4 | -4 | -4 | -4 | -4 | -4 | -4 | -4 | -4 | -4 | -4 | -4 | -4 | -4 | -4 | -4 | -4 | 1 |

In this table, the first 20 columns (and the first 20 rows) labelled with single-letter amino acid codes represent the standard amino acids. The remaining columns/rows represent additional residue types (e.g., "B" for Asx (Asn/Asp), "Z" for Glx (Gln/Glu), "X" for any amino acid, and "*" for a translation stop encoded by a termination codon). If the sequences of interest have only a subset of these residues, then a corresponding sub-matrix of BLOSUM62 can also be alternatively sufficient for aligning them (e.g., the scores from the upper-left 20×20 part of the scores if only standard amino acids that are singly-identified are of concern).

As a demonstration of using BLOSUM62 in calculating an alignment score, if residues 1-8 of SEQ ID NO: 14 ("EEVKAKVQ") were aligned with themselves, the alignment score would be the sum of scores for each of those amino acids pairing with itself (e.g., when residue "A" in the first sequence pairs with itself, an "A," in the second sequence, it contributes a score of 4, as seen in the cell at row 2, column 2 of the BLOSUM62 matrix). Therefore, the alignment score in this hypothetical example would be 37 (5+5+4+5+4+5+4+5). If the "A" in the second sequence, in this hypothetical, is changed into a "W," the alignment score would be 30 (5+5+4+5-3+5+4+5). If the "E" at residue one, or the "K" at residue four, or the "Q" at residue eight is deleted in the second sequence instead, in this hypothetical, the alignment score in each case would be 20 (the original total score of 37 is lessened by 5 due to the deleted residue, and there is an additional total gap penalty of 12 in this case, as explained further next). The total gap penalty is calculated by summing a gap extension penalty as multiplied by the number of residues in the gap with a gap-opening penalty. As an example, a gap-opening penalty of 11 and a gap extension penalty of 1 can be used. In that case, a single gap as in the last hypothetical example would result in a total gap penalty of 12 (11+1*1), regardless of whether the gap is internal or external, which can be the case for global-global alignments. If the gap were three amino acids long in the middle of a sequence, the total gap penalty would be 14 (11+1*3), which would be subtracted from of the scores of the aligning residues (identical as well as non-identical) to arrive at the alignment score.

Using a substitution matrix such as BLOSUM62 is superior to cruder methods such as percent identity calculations, at least because different aligned identical residues can give different contributions to the overall score depending on how rare or common themselves or their mutations are (e.g., a W:W alignment contributes 11, as seen in Table B1, while an A:A alignment contributes only 4). In addition, mutations into different residues can also be treated differently with a substitution matrix (e.g., a D:E change has a positive score, 2, as seen in Table B1, while a D:L change has a negative score, –4, whereas each of these changes would be clumped as the same non-identical change in a percent-identity approach). Overall, using a substitution matrix like BLOSUM62 provides a dramatically more sensitive measure for inferring sequence relatedness than percent identity methods, since the matrix allows calibrating the score of changing each of the amino acids (e.g., 20) into each of the amino acids (e.g., 20) individually, while with percent identity the changes are limited to merely identical and non-identical ones. As a result, a polypeptide sequence defined with respect to its alignment to a reference sequence in terms of a Needleman-Wunsch score obtained by using BLOSUM62 matrix is significantly more likely to have structural features, physical properties, and functional features in common with the polypeptide of the reference sequence.

For percent sequence identity values, the same alignment method (e.g., Needleman-Wunsch algorithm for global-global alignment, using BLOSUM62 matrix, with gap opening penalty of 11 and a gap extension penalty of 1) can be used to obtain the alignment, after which the pairs of aligned identical residues can be counted and then divided by the total length of the alignment (including gaps, internal as well as external) to arrive at the percent identity value. For percent similarity values, the same approach as for percent identity values can be used, except that what is counted, instead of pairs of identical residues, would be the aligned residue pairs with BLOSUM62 values that are not negative (i.e., >0).

Numerous programs as well as websites exist for calculation of alignment scores. For example, executables for local use can be downloaded from the UVa FASTA Server (available from World Wide Web at fasta.bioch.virginia.edu/fasta_www2/fasta_list2.shtml). Among the programs available at the UVa FASTA server, ggsearch can perform global-global alignments (e.g., using Needleman-Wunsch algorithm, and BLOSUM62 matrix with gap opening penalty of 11 and a gap extension penalty of 1) and glsearch can perform global-local alignments. Similar functionality is also available through an online submission form at the same server (e.g., World Wide Web at fasta.bioch.virginia.edu/fasta_www2/fasta_www.cgi?rm=select&pgm=gnw, after selecting "Align two sequences" to align two sequences rather than one sequence against a database). Additional online sources for similar functionality include the National Center for Biotechnology Information (available through the World Wide Web at https://blast.ncbi.nlm.nih.gov/Blast.cgi) and the European Bioinformatics Institute of the European Molecular Biology Laboratory (available through the World Wide Web at https://www.ebi.ac.uk/Tools/sss/fasta/).

Biological Embodiments

According to a first biological aspect of the current invention, there is provided a recombinant nucleic acid sequence for the improved expression and purification of functional ADAMTS-7.

According to some first embodiments according to the first biological aspect, there is provided a recombinant nucleic acid for expression of an ADAMTS-7 polypeptide that comprises a rodent prodomain of ADAMTS-7 as a first portion and a functional human ADAMTS-7 as a second portion.

Figure 3A:
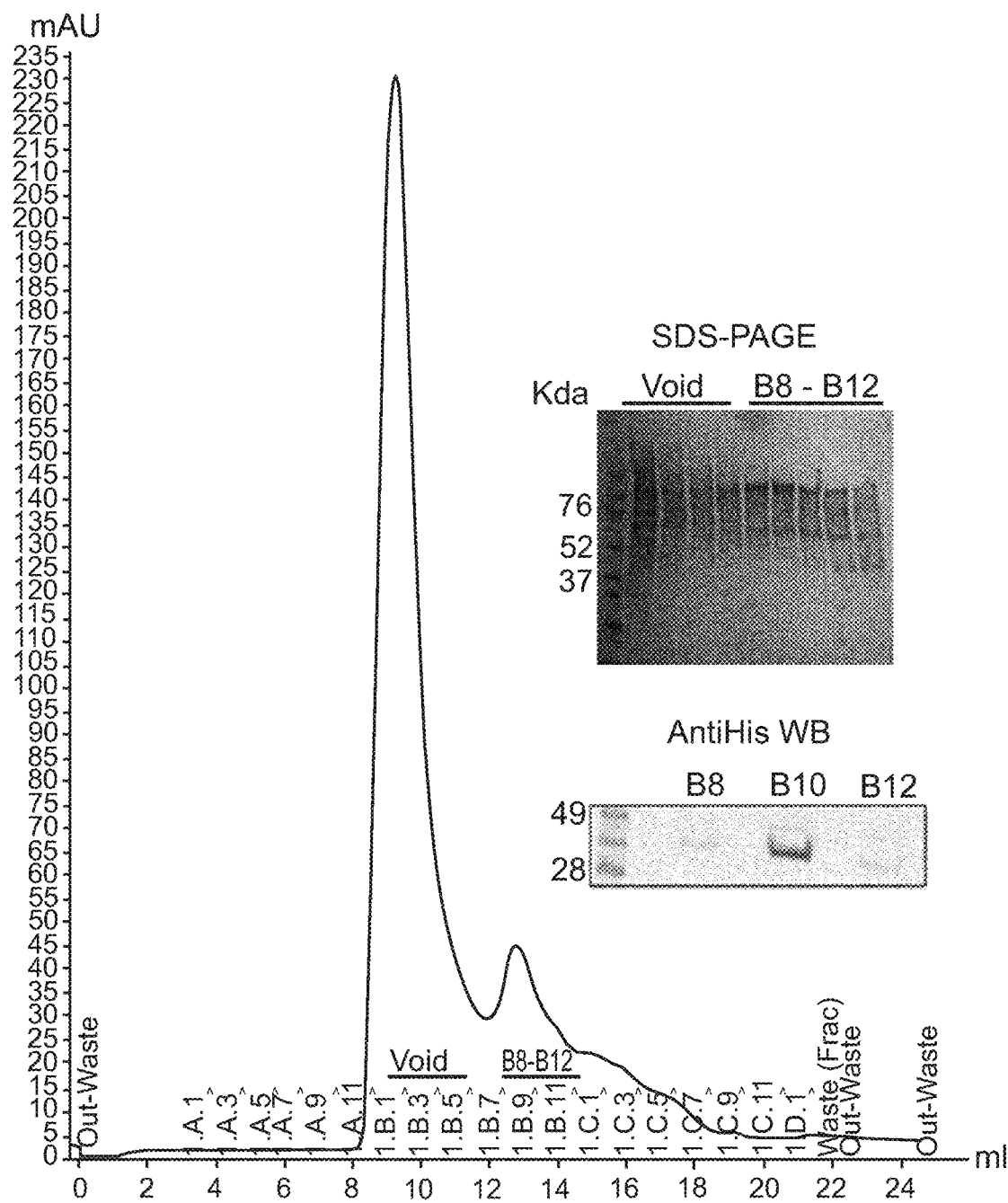
FIGS. 3A and 3B (consisting of panels A and B) shows two WT constructs for mammalian expression of ADAMTS-7 proteins.
Figure 3B:
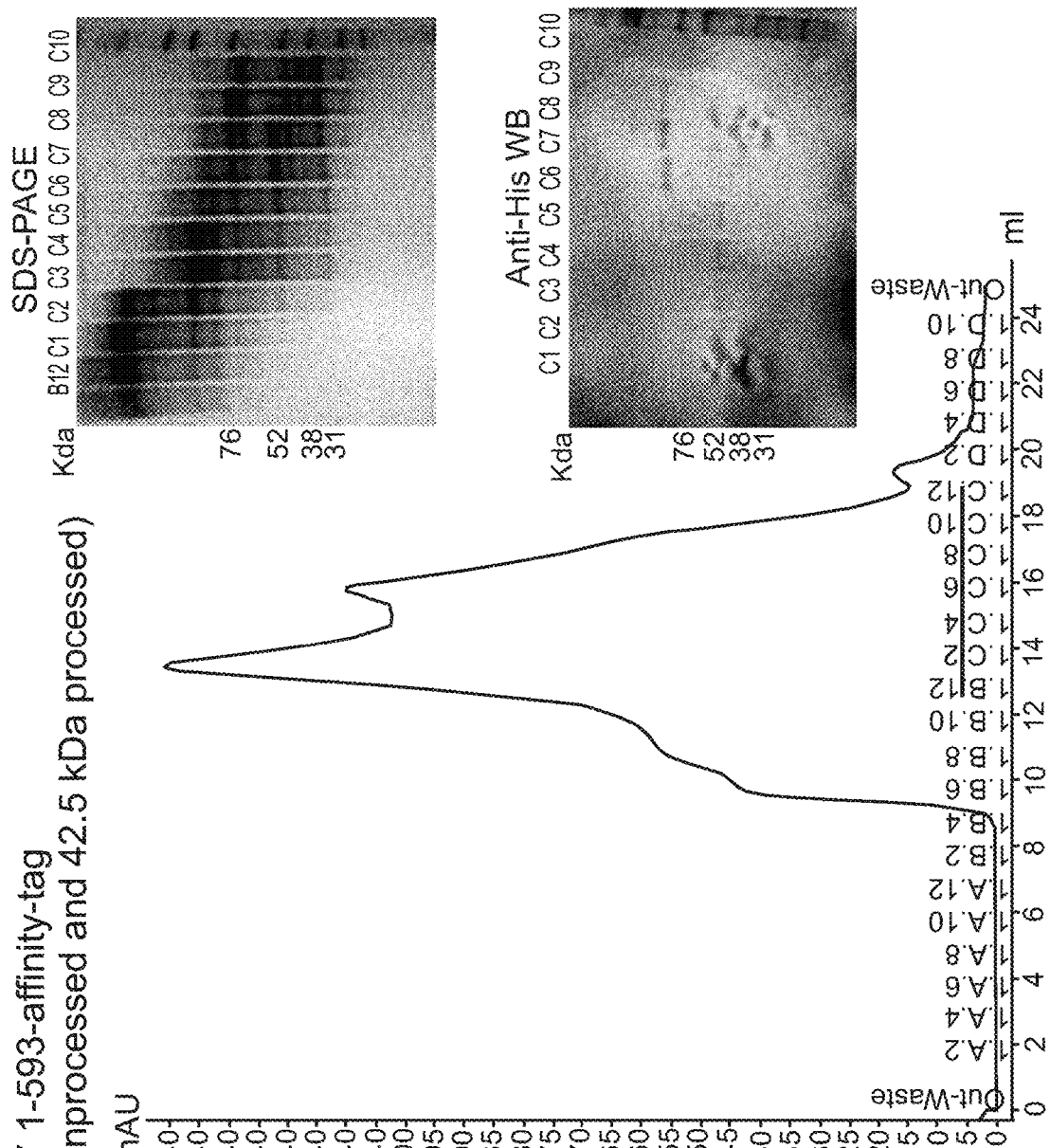

Commercial expression and purification of recombinant functional ADAMTS-7 has so far been a challenge (cf. FIG. 3), rendering the development of an assay for the identification and characterization of modulators of ADAMTS-7 extremely difficult. For example, as shown in FIG. 3, expression of hADAMTS-7 (residues 237-537) or hADAMTS-7 Pro-CD-TSR1 (residues 1-593) yielded little soluble proteins. The nucleic acids according to the first biological aspect solved the problem of protein solubility as well as expression yield, both of which were lower for fully human ADAMTS-7 constructs compared to hybrid constructs (cf. example B2).

The constructs according to the first biological aspect are suited for the production of sufficient amounts of ADAMTS-7 with reproducible activity and purity. The resulting recombinant functional ADAMTS-7 can therefore be used in an assay for the identification and characterization of modulators of ADAMTS-7.

In order to obtain a suitable construct for the expression of functional ADAMTS-7, more than 50 *E. coli* constructs, 20 constructs from Baculovirus and 30 HEK293 constructs were designed and evaluated to achieve the efficient expression of functional ADAMTS-7. The recombinant nucleic acid according to the first biological aspect surprisingly solved these problems and enabled the efficient expression and purification of functional ADAMTS-7 protein: In particular it was surprisingly found that a rodent prodomain is more effective in driving folding of the catalytic domain of human ADAMTS-7, thereby improving the yield of the soluble ADAMTS-7 proteins ~10 fold (see example B2).

In some embodiments according to the first biological aspect, the recombinant nucleic acid sequence encodes for a recombinant polypeptide that comprises a first portion and a second portion, wherein the first portion has a sequence identity of >80% with the sequence of residues 1-217 of SEQ ID NO: 1 or with the sequence of residues 1-217 of SEQ ID NO: 2, and the second portion has a sequence identity of >80% with the sequence of residues 218-518 of SEQ ID NO: 1.

In some embodiments according to the first biological aspect, the recombinant nucleic acid sequence encodes for a recombinant polypeptide that comprises a first portion and a second portion, wherein the first portion has a sequence identity of >90% with the sequence of residues 1-217 of SEQ ID NO: 1 or with the sequence of residues 1-217 of SEQ ID NO: 2, and the second portion has a sequence identity of >90% with the sequence of residues 218-518 of SEQ ID NO: 1.

In some embodiments according to the first biological aspect, the recombinant nucleic acid sequence encodes for a recombinant polypeptide that comprises a first portion and a second portion, wherein the first portion has a sequence identity of >95% with the sequence of residues 1-217 of SEQ ID NO: 1 or with the sequence of residues 1-217 of SEQ ID NO: 2, and the second portion has a sequence identity of >95% with the sequence of residues 218-518 of SEQ ID NO: 1.

In some embodiments according to the first biological aspect, the recombinant nucleic acid sequence encodes for a recombinant polypeptide that comprises a first portion and a second portion, wherein the first portion has a sequence identity of >98% with the sequence of residues 1-217 of SEQ ID NO: 1 or with the sequence of residues 1-217 of SEQ ID NO: 2, and the second portion has a sequence identity of >98% with the sequence of residues 218-518 of SEQ ID NO: 1.

In some embodiments according to the first biological aspect, the recombinant nucleic acid sequence encodes for a recombinant polypeptide that comprises a first portion and a second portion, wherein the first portion comprises residues 1-217 of SEQ ID NO: 1 or residues 1-217 of SEQ ID NO: 2, and/or the second portion comprises residues 218-518 of SEQ ID NO: 1 (cf. example B1). In some embodiments the second portion is C-terminal to the first portion.

In some embodiments according to the first biological aspect, the recombinant nucleic acid sequence encodes for a polypeptide that has a first portion and a second portion. The first portion of the polypeptide, in some embodiments, has an amino acid sequence that when aligned with an amino acid sequence of a ADAMTS-7 prodomain or a fragment thereof from a first species generates a Needleman-Wunsch score greater than 700, if BLOSUM62 matrix, a gap opening penalty of 11, and a gap extension penalty of 1 are used. In some embodiments, this generated Needleman-Wunsch score is greater than 750, 800, 850, 900, 950, 1000, 1050, or 1100. In some embodiments, the first portion and the ADAMTS-7 prodomain share a sequence identity that is at least 70%, 75%, 80%, 85%, 90%, 95%, 97% or 98%. The second portion of the polypeptide, in some embodiments, has an amino acid sequence that when aligned with an amino acid sequence of a ADAMTS-7 catalytic domain or a fragment thereof from a second species generates a Needleman-Wunsch score greater than 1000 if BLOSUM62 matrix, a gap opening penalty of 11, and a gap extension penalty of 1 are used. In some embodiments, this generated Needleman-Wunsch score is greater than 1050, 1100, 1150, 1200, 1250, 1300, 1350, 1400, 1450, 1500, 1550, 1600, or 1650. In some embodiments, the second portion and the ADAMTS-7 catalytic domain share a sequence identity that is at least 70%, 75%, 80%, 85%, 90%, 95%, 97% or 98%.

In some embodiments according to the first biological aspect, the recombinant nucleic acid sequence encodes for a recombinant polypeptide that comprises a first portion having an amino acid sequence that aligns with an amino acid sequence of an ADAMTS-7 prodomain or a fragment thereof from a first species with a Needleman-Wunsch score greater than 700, when BLOSUM62 matrix, a gap opening penalty of 11, and a gap extension penalty of 1 are used; and a second portion having an amino acid sequence that aligns with an amino acid sequence of a ADAMTS-7 catalytic domain or a fragment thereof from a second species with a Needleman-Wunsch score greater than 1000 when BLOSUM62 matrix, a gap opening penalty of 11, and a gap extension penalty of 1 are used.

In some embodiments, the first species is a non-human species, such as a rodent species, such as rat. In some different or the same embodiments the second species is human, e.g. the catalytic domain is derived from human ADAMTS-7. In some embodiments the first species is a rodent species and the second species is human.

In some embodiments according to the first biological aspect the first portion of the polypeptide comprises a mutation within the furin cleavage site. FIG. 4 shows that furin cleavage site mutants of ADAMTS-7 improved the yield of processed or unprocessed ADAMTS-7. For example, in some of these embodiments the motif RQQR is mutated to RQKR (Q216K). In some embodiments, the motif RQQR within the first portion of the polypeptide is altered, preferably into RQKR. Thus, in some embodiments the first portion comprises a mutation, e.g. at position 216, such as the mutation Q216K. This mutation was found to improve cleavage by Furin between the prodomain and the catalytic domain of ADAMTS-7, thereby leading to improved yields of processed ADAMTS-7 compared to the wild type (WT). (cf. example B1, cf. FIG. 4). Q216K mutation changes rat ADAMTS7 motif RQQR↓S to RQKR↓S, i.e. to a more optimized consensus to increase Furin processing of the zymogen into the active catalytic form.

In some embodiments the first portion comprises triple mutant R58A/R61A/R217A (rPro-hCD-3RA). FIG. 4 panel B shows that these mutations abolished the processing to generate unprocessed protein only. For example, R58A/R60A/R217A prevents all furin cleavage resulting in a zymogen form.

According to some embodiments of the first biological aspect the recombinant nucleic acid sequence encodes at least for a rat pro-domain of ADAMTS-7 (SEQ ID No. 1, residues 1-217) and a catalytic domain of human ADAMTS-7, wherein optionally within the rat pro-domain of ADAMTS-7 the motif RQQR is mutated to RQKR (SEQ ID No. 2, cf. residues 1-217). In some of these embodiments said rat pro-domain of ADAMTS-7 comprises or consists of a sequence according to SEQ ID No. 1, residues 1-217 or SEQ ID No. 2, residues 1-217 and/or said catalytic domain of human ADAMTS-7 comprises or consists of a sequence according to SEQ ID No. 1, residues 218-518 or SEQ ID No. 2, residues 218-518.

In some embodiments the polypeptide or a fragment thereof encoded by the recombinant nucleic acid is suited to cleave a peptide comprising standard residues 1-15 of the amino acid sequence of SEQ ID NO: 4. For example, the polypeptide is suited to cleave a peptide comprising standard residues 1-15 of the amino acid sequence of SEQ ID NO: 4 and/or SEQ ID No. 11 with a kcat/KM of at least 20% of a corresponding kcat/KM of human ADAMTS-7.

The produced polypeptide (e.g., having both the first portion and the second portion, or having only the second portion) can have a catalytic activity close to that of human ADAMTS-7 enzyme, e.g., in terms of kcat/KM, which can be even higher than the kcat/KM of the human enzyme, or can be within 50%, 45%, 40%, 35%, 30%, 25%, 20%, 15%, 10%, or 5% of the kcat/KM of the human enzyme, for example when a peptide having the sequence of SEQ ID No. 11 is used as the substrate.

Figure 8A:
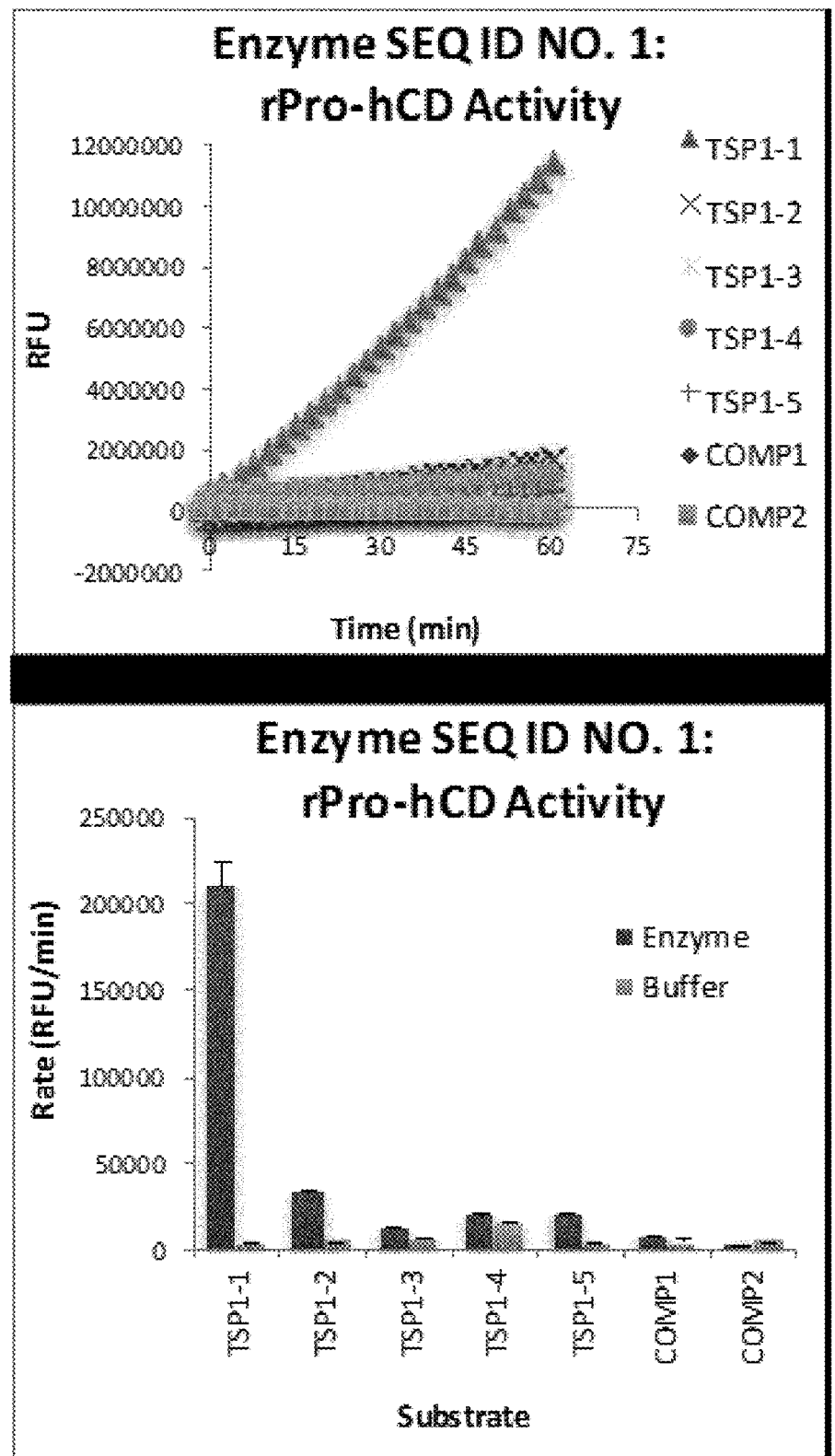

In some embodiments, for a given substrate, the produced polypeptide (e.g., having both the first portion and the second portion, or having only the second portion) has a catalytic activity in the same order of magnitude as rat ADAMTS-7, e.g., in terms of kcat, cf. FIGS. 8, 9. In some embodiments, for a substrate of SEQ ID No. 4, the produced polypeptide has a kcat (min$^{-1}$) in the order of magnitude of 10$^{-2}$. In some embodiments, for a substrate of SEQ ID No. 5, the produced polypeptide has a kcat (min$^{-1}$) in the order of magnitude of 10$^{-3}$.

Sequential cleavage or processing of ADAMTS-7 at furin cleavage sites by cellular enzyme furin leading to a complete removal of the Pro domain from the rest of the protein is likely a necessary step to a fully active or mature ADAMTS-7.

In some embodiments the recombinant nucleic acid sequence furthermore encodes for additional residues, such as a purification tag, such as a FLAG tag, a His tag, a Strep tag or any combination or repetition thereof. In some embodiments of the first biological aspect, the encoded polypeptide can have additional residues (e.g., purification tags such as His tag, Strep tag, 2×Strep tag, FLAG tag, 3×FLAG tag, and cleavage sequences such as TEV cleavage site). The presence of these additional residues is compatible with each of the described embodiments of the biological aspect. Purification of a polypeptide obtained from a nucleic acid according to the current invention can occur as described in example B3.

The recombinant nucleic acid according to the first biological aspect can be used for the expression of functional ADAMTS7 as described in example B3. For example, the construct can be inserted into a plasmid which is compatible with a certain expression system. In certain preferred embodiments the construct can be cloned into a plasmid, preferably into a mammalian expression vector, such as pcDNA6mycHis. Expression can be performed in a compatible expression system, such as in a mammalian expression system, such as in HEK cells or Expi293 cells as known in the art. The Gibco Expi293 Expression System is a commercially available high-yield transient expression system based on suspension-adapted Human Embryonic Kidney (HEK) cells.

According to a second biological aspect of the current invention, there is provided a recombinant nucleic acid for the expression of functional ADAMTS-12. It was surprisingly found that human ADAMTS-12 expression is improved when a non human prodomain is used (cf. example B9, cf. FIG. 6). In particular it was found that human ADAMTS-12 with a rodent prodomain demonstrated a better expression profile compared to human ADAMTS-12 with a human prodomain. The recombinant nucleic acids according to the second biological aspect are therefore suited for the improved production of sufficient amounts of ADAMTS-12 with reproducible activity and purity. The resulting recombinant functional ADAMTS-12 can be used in an assay for the characterization of modulators of ADAMTS-7, i.e. where the selectivity for ADAMTS-7 is assessed.

According to some first embodiments according to the second biological aspect, there is provided a recombinant nucleic acid for expression of an ADAMTS-12 polypeptide that comprises a rodent prodomain of ADAMTS-12 as a first portion and a functional human ADAMTS-12 as a second portion.

In some embodiments according to the second biological aspect, the recombinant nucleic acid sequence encodes for a recombinant polypeptide that comprises a first portion and a second portion, wherein the first portion has a sequence identity of >80% with the sequence of residues 1-244 of SEQ ID NO: 15, and the second portion has a sequence identity of >80% with the sequence of residues 245-547 of SEQ ID NO: 15 (cf. 241-544 of ADAMTS12).

For example, ADAMTS12 rat/human hybrid can be made by fusing respective rat ADAMTS12 SP-Pro (1-244) followed by human ADAMTS12 CD (241-544).

In some embodiments according to the second biological aspect, the recombinant nucleic acid sequence encodes for a recombinant polypeptide that comprises a first portion and a second portion, wherein the first portion has a sequence identity of >90% with the sequence of residues 1-244 of SEQ ID NO: 15, and the second portion has a sequence identity of >90% with the sequence of residues 245-547 of SEQ ID NO: 15.

In some embodiments according to the second biological aspect, the recombinant nucleic acid sequence encodes for a recombinant polypeptide that comprises a first portion and a second portion, wherein the first portion has a sequence identity of >95% with the sequence of residues 1-244 of SEQ ID NO: 15, and the second portion has a sequence identity of >95% with the sequence of residues 245-547 of SEQ ID NO: 15.

In some embodiments according to the second biological aspect, the recombinant nucleic acid sequence encodes for a recombinant polypeptide that comprises a first portion and a second portion, wherein the first portion has a sequence identity of >98% with the sequence of residues 1-244 of SEQ ID NO: 15, and the second portion has a sequence identity of >98% with the sequence of residues 245-547 of SEQ ID NO: 15.

In some embodiments, according to the second biological aspect, the recombinant nucleic acid sequence encodes for a recombinant polypeptide that comprises a first portion and a second portion, wherein the first portion comprises residues 1-244 of SEQ ID NO: 15, and/or the second portion comprises residues 245-547 of SEQ ID NO: 15. In some different or the same embodiments the second portion is immediately C-terminal to the first portion.

In some embodiments according to the second biological aspect, the recombinant nucleic acid encodes a polypeptide that has a first portion and a second portion. The first portion of the polypeptide, in some embodiments, has an amino acid sequence that when aligned with an amino acid sequence of an ADAMTS-12 prodomain (or a fragment thereof) from a first species generates a Needleman-Wunsch score greater than 800 if BLOSUM62 matrix, a gap opening penalty of 11, and a gap extension penalty of 1 are used. In some embodiments, this generated Needleman-Wunsch score is greater than 850, 900, 950, 1000, 1050, 1100, 1150, 1200, 1250, or 1300. In some embodiments, the first portion and the ADAMTS-12 prodomain share a sequence identity that is at least 70%, 75%, 80%, 85%, 90%, 95%, 97% or 98%. The second portion of the polypeptide, in some embodiments, has an amino acid sequence that when aligned with an amino acid sequence of a human ADAMTS-12 catalytic domain (or a fragment thereof) generates a Needleman-Wunsch score greater than 1000 if BLOSUM62 matrix, a gap opening penalty of 11, and a gap extension penalty of 1 are used. In some embodiments, this generated Needleman-Wunsch score is greater than 1050, 1100, 1150, 1200, 1250, 1300, 1350, 1400, 1450, 1500, 1550, 1600, or 1650. In some embodiments, the second portion and the ADAMTS-12 catalytic domain share a sequence identity that is at least 70%, 75%, 80%, 85%, 90%, 95%, 97% or 98%.

In some embodiments according to the second biological aspect, the recombinant nucleic acid for expression of an ADAMTS-12 polypeptide encodes for a recombinant polypeptide that comprises a first portion having an amino acid sequence that aligns with an amino acid sequence of a ADAMTS-12 prodomain or a fragment thereof from anonhuman species with a Needleman-Wunsch score greater than 800 when BLOSUM62 matrix, a gap opening penalty of 11, and a gap extension penalty of 1 are used; and a second portion having an amino acid sequence that aligns with an amino acid sequence of a ADAMTS-12 catalytic domain or a fragment thereof from a second species with a Needleman-Wunsch score greater than 1000 when BLOSUM62 matrix, a gap opening penalty of 11, and a gap extension penalty of 1 are used.

In some embodiments, the first species is a non-human species, such as a rodent species, such as rat. In some different or the same embodiments the second species is human, e.g. the catalytic domain is derived from human ADAMTS-12. In some embodiments the first species is a rodent species and the second species is human.

In some embodiments the second portion comprises a mutation at position E393, such as E393Q (EQ). This mutation results in increased protein yield similar to ADAMTS-7 catalytic mutations. Mutation numbering E393Q follows the species based positions for the human ADAMTS12 region of the construct, i.e. rat ADAMTS12 SP-Pro (1-244) followed by human ADAMTS12 CD (241-544).

In some embodiments the polypeptide or a fragment thereof encoded by the recombinant nucleic acid is suited to cleave a peptide comprising standard residues 1-15 of the amino acid sequence of SEQ ID NO: 4. For example, in some embodiments the polypeptide is suited to cleave a peptide comprising standard residues 1-15 of the amino acid sequence of SEQ ID NO: 4 and/or SEQ ID No. 11 with a kcat/KM of at least 20% of a corresponding kcat/KM of human ADAMTS-12.

The produced polypeptide (e.g., having both the first portion and the second portion, or having only the second portion) can have a catalytic activity close to that of human ADAMTS-12 enzyme (e.g., in terms of kcat/KM, which can be even higher than the kcat/KM of the human enzyme, or can be within 50%, 45%, 40%, 35%, 30%, 25%, 20%, 15%, 10%, or 5% of the kcat/KM of the human enzyme, for example when a peptide having the sequence of SEQ ID No. 4 or 11 is used as the substrate.

In some embodiments the recombinant nucleic acid sequence furthermore encodes for additional residues such as a purification tag, such as a FLAG tag, a His tag, a Strep tag or any combination or repetition thereof. In some embodiments of the second biological aspect, the encoded polypeptide can have additional residues (e.g., purification tags such as His tag, Strep tag, 2×Strep tag, FLAG tag, 3×FLAG tag, and cleavage sequences such as TEV cleavage site). The presence of these additional residues is compatible with each of the described embodiments of the biological aspect. Purification of the functional ADAMTS-12 obtained from a recombinant nucleic acid according to the current invention can occur as described in example B4.

According to some embodiments of the second biological aspect the recombinant nucleic acid sequence encodes at least for a rat pro-domain of ADAMTS-12, such as amino acids 1-244 of rat sequence UniProt D3ZTJ3 and/or encodes for a catalytic domain of human ADAMTS-12, such as amino acids 241-543 of human sequence UniProt P58397, cf. example B1. In certain preferred embodiments said recombinant nucleic acid encodes for a sequence according to SEQ ID No. 15.

The recombinant nucleic acid according to the second biological aspect can be used for the expression of functional ADAMTS-12 as described in example B4. For example, the recombinant nucleic acid can be inserted into a plasmid which is compatible with a certain expression system.

In certain preferred embodiments the construct can be inserted into a plasmid, preferably into a mammalian expression vector, such as pcDNA3.4. Expression can be performed in a compatible expression system, such as in a mammalian expression system, such as in HEK cells or Expi293 cells as known in the art. The Gibco Expi293 Expression System is a commercially available high-yield transient expression system based on suspension-adapted Human Embryonic Kidney (HEK) cells.

According to a third biological aspect of the current invention, there is provided a recombinant polypeptide, wherein the recombinant polypeptide is the recombinant polypeptide encoded by a recombinant nucleic acid according to the first or second biological aspect, or a fragment thereof. In some embodiments the fragment is the processed polypeptide which results after Furin cleavage. In some embodiments, the Furin cleavage occurs at the site known in the art or described herein.

In some embodiments the recombinant polypeptide according to the third biological aspect or a fragment thereof is suited to cleave a peptide substrate comprising standard residues 1-15 of SEQ ID NO: 4. The recombinant polypeptide according to the third biological aspect or a fragment thereof can be used in an assay for the identification and characterization of modulators of ADAMTS-7 and/or ADAMTS-12, as shown within the examples.

In some embodiments, the recombinant polypeptide according to the third biological aspect or a fragment thereof is a functional ADAMTS-7 protein. In some embodiments the polypeptide comprises a rodent prodomain of ADAMTS-7 as a first portion and afunctional human ADAMTS-7 as a second portion.

In some embodiments the polypeptide comprises a first portion and a second portion, wherein the first portion has a sequence identity of >80% with the sequence of residues 1-217 of SEQ ID NO: 1 or with the sequence of residues 1-217 of SEQ ID NO: 2, and the second portion has a sequence identity of >80% with the sequence of residues 218-518 of SEQ ID NO: 1.

In some embodiments according to the third biological aspect, the recombinant polypeptide comprises a first portion having an amino acid sequence that aligns with an amino acid sequence of an ADAMTS-7 prodomain or a fragment thereof from a first species with a Needleman-Wunsch score greater than 700, when BLOSUM62 matrix, a gap opening penalty of 11, and a gap extension penalty of 1 are used; and a second portion having an amino acid sequence that aligns with an amino acid sequence of a ADAMTS-7 catalytic domain or a fragment thereof from a second species with a Needleman-Wunsch score greater than 1000 when BLOSUM62 matrix, a gap opening penalty of 11, and a gap extension penalty of 1 are used. In some embodiments the first species is a rodent species such as rat and the second species is human.

In some embodiments the first portion of the polypeptide comprises a mutation within the furin cleavage site. In some embodiments, the motif RQQR within the first portion of the polypeptide is altered, preferably into RQKR. Thus, in some embodiments the first portion comprises a mutation, e.g. at position 216, such as the mutation Q216K. This mutation was found to improve cleavage by Furin between the prodomain and the catalytic domain of ADAMTS-7, thereby leading to improved yields of processed ADAMTS-7 compared to the wild type (WT). (cf. example B1, cf. FIG. 4).

In some embodiments the polypeptide comprises a rodent prodomain of ADAMTS-12 as a first portion and a functional human ADAMTS-12 as a second portion.

In some embodiments the polypeptide comprises a first portion and a second portion, wherein the first portion has a sequence identity of >80% with the sequence of residues 1-244 of SEQ ID NO: 15, and the second portion has a sequence identity of >80% with the sequence of residues 245-547 of SEQ ID NO: 15.

In some embodiments according to the current biological aspect, the polypeptide comprises a first portion having an amino acid sequence that aligns with an amino acid sequence of a ADAMTS-12 prodomain or a fragment thereof from a first species with a Needleman-Wunsch score greater than 800 when BLOSUM62 matrix, a gap opening penalty of 11, and a gap extension penalty of 1 are used; and a second portion having an amino acid sequence that aligns with an amino acid sequence of a ADAMTS-12 catalytic domain or a fragment thereof from a second species with a Needleman-Wunsch score greater than 1000 when BLOSUM62 matrix, a gap opening penalty of 11, and a gap extension penalty of 1 are used. In some embodiments, the first species is a non-human species, such as a rodent species, such as rat. In some different or the same embodiments the second species is human, e.g. the catalytic domain is derived from human ADAMTS-12. In some embodiments the first species is a rodent species and the second species is human.

In some embodiments the second portion comprises a mutation at position E393, such as E393Q (EQ). This mutation results in increased protein yield.

In some embodiments the polypeptide (e.g., having both the first portion and the second portion, or having only the second portion) has a catalytic activity close to that of human ADAMTS-7 or ADAMTS-12 enzyme (e.g., in terms of kcat/KM, which can be even higher than the kcat/KM of the human enzyme, or can be within 50%, 45%, 40%, 35%, 30%, 25%, 20%, 15%, 10%, or 5% of the kcat/KM of the human enzyme, for example when a peptide having the sequence of of SEQ ID No. 4 or 11 is used as the substrate.

In some embodiments the polypeptide or a fragment thereof is suited to cleave a peptide comprising standard residues 1-15 of the amino acid sequence of SEQ ID NO: 4. In some embodiments, the polypeptide is suited to cleave a peptide comprising standard residues 1-15 of the amino acid sequence of SEQ ID NO: 4 and/or SEQ ID No. 11 with a kcat/KM of at least 20% of a corresponding kcat/KM of human ADAMTS-7 or human ADAMTS-12.

In some embodiments the polypeptide comprises a purification tag, such as a FLAG tag, a His tag, a Strep tag or any combination or repetition thereof. In some embodiments of the first biological aspect, the encoded polypeptide can have additional residues (e.g., purification tags such as His tag, Strep tag, 2×Strep tag, FLAG tag, 3×FLAG tag, and cleavage sequences such as TEV cleavage site). The presence of these additional residues is compatible with each of the described embodiments of the biological aspect.

Surprisingly, the recombinant polypeptide according to the current biological aspect was found to fold into a functional ADAMTS, e.g. ADAMTS-7 or ADAMTS-12. Expression and purification of recombinant functional ADAMTS protein according to the third biological aspect can occur as described in example B3.

According to a fourth biological aspect of the current invention there is provided a recombinant peptide substrate for ADAMTS-7 and/or ADAMTS-12. The peptide substrate according to the current invention can be used as an artificial substrate for ADAMTS-7 and/or ADAMTS-12. The peptide substrate can furthermore be used in order to determine the proteolytic activity of ADAMTS-7 and/or ADAMTS-12, identify modulators of ADAMTS-7 and/or ADAMTS-12, and/or to determine the degree of modulation induced by an agonist or antagonist.

In some embodiments the peptide substrate comprises a subsequence of a natural ADAMTS-7 and/or ADAMTS-12 substrate, such as a subsequence of TSP1 or COMP. In some embodiments, the peptide substrate according to the fourth biological aspect comprises at least a sequence according to any of SEQ ID No. 4, 5, 8, 11, 12 or 13, or a fragment thereof comprising the amino acids EL. It was surprisingly found that theses sequences can be used as cleavage site for ADAMTS-7 and ADAMTS-12: For example, the sequence DELSSMVLELRGLRT, derived from TSP1, residues 275-289 has been surprisingly identified as a suitable substrate for ADAMTS-7 and ADAMTS-12. Without being bound by theory, cleavage occurs between Glu283 and Leu284 (EL).

In some embodiments the peptide substrate comprises (a) residues 1-15 of the amino acid sequence of SEQ ID NO: 4, or (b) residues 1-15 of the amino acid sequence of SEQ ID NO: 5, or (c) residues 1-13 of the amino acid sequence of SEQ ID NO: 8, or (d) a fragment of any of the sequences according to a), b) or c), the fragment comprising the amino acid sequence EL.

In some embodiments, the peptide substrate according to the fourth biological aspect comprises at least the amino acids EL. In some embodiments, the peptide substrate according to the fourth biological aspect comprise at least the SEQ ID No. 4, or a fragment thereof comprising the amino acids EL. In some embodiments, the peptide substrate according to the fourth biological aspect comprises at least the SEQ ID No. 5, or a fragment thereof comprising the amino acids EL. In some embodiments, the peptide substrate according to the fourth biological aspect comprises at least the SEQ ID No. 8, or a fragment thereof comprising the amino acids EL.

In some embodiments, the peptide substrate according to the fourth biological aspect comprises at least the SEQ ID No. 11, 12 or 13 or a fragment thereof comprising the amino acids EL. It was surprisingly found that the solubility of the described peptide substrate according to the fourth biological aspect could be improved by including an additional hydrophilic moiety without affecting the activity profile (cf. SEQ ID No. 11, 12, 13).

In some embodiments the peptide substrate according to the fourth biological aspect comprises a first moiety conjugated to a residue that is N-terminal to sequence fragment EL as comprised within SEQ ID No. 4, 5, or 8 or the fragment thereof, and a second moiety conjugated to a residue that is C-terminal to said sequence fragment EL. In some embodiments the first moiety comprises a fluorophore and the second moiety comprises a quencher, or the first moiety comprises a quencher and the second moiety comprises a fluorophore.

Without being bound by theory, the fluorophore of the peptide substrate can be excited at a suitable wavelength, e.g. by exposing it to light. The suitability of a wavelength depends on the specific fluorophore and can be determined as known in the art. Without being bound by theory, the excited fluorophore transfers the energy to the closely located quencher, which has the ability to decrease the fluorescence intensity of the fluorophore, such that no fluorescence or only background fluorescence is detected at the emission wavelength of the fluorophore. If the peptide substrate according to the current invention is however exposed to or contacted with a functional ADAMTS-7 or ADAMTS-12, the enzyme cleaves the peptide, thereby separating fluorophore and quencher. In the absence of the quencher, the excited fluorophore emits light in returning to the ground state and an increase in fluorescence can be detected.

Using a combination of functional ADAMTS-7 and the peptide substrate comprising a fluorophore and a quencher according to the fourth biological aspect as a substrate thus allows for the robust and reproducible identification and characterization of ADAMTS-7 modulators and/or ADAMTS-12 modulators.

The skilled person understands that according to the various biological aspects and embodiments of the current invention, multiple sites can be used to attach the fluorophore and the quencher to the peptide as long as a) the distance between fluorophore and quencher allows for the transfer of energy between fluorophore and quencher and b) the ADAMTS-7 cleavage site is arranged in such a way that fluorophore and quencher are separated upon ADAMTS-7 cleavage of the peptide. The latter effect can be obtained by interposing the ADAMTS-7 cleavage site between the fluorophore and the quencher.

A variety of suitable pairs of fluorophores and quenchers have been described in the literature. The skilled person is well aware which pairs of fluorophore and quencher can be combined. To obtain a peptide according to the biological aspect at hand, the distance between fluorophore and quencher has to be adjusted to allow for the necessary transfer of energy as described herein. The specific distance depends on the specific selection of fluorophore and quencher and can be adjusted as known in the art. For example in some embodiments according to the biological aspect at hand, EDANS as a fluorophore can be paired with DABCYL or DABSYL as a quencher. When EDANS and DABCYL are in a close proximity (10-100 Å), the energy emitted from EDANS will be quenched by Dabcyl, resulting in low or no fluorescence. However, if the compounds are separated EDANS will fluoresce. The optimal absorbance and emission wavelengths of EDANS are $\lambda_{abs}$=336 nm and $\lambda_{em}$=490 nm respectively, and for Dabcyl, the maximum absorbance wavelength is $\lambda_{abs}$=472 nm, which, to a large extent, overlap with the emission spectra of EDANS.

Another pair of fluorophore and quencher where the compounds can be used alone or in combination is 7-methoxy-coumarin-4-yl acetic acid (MCA) as the fluorophore with Lys(DNP) as a quencher. In some preferred embodiments according to the biological aspect at hand the fluorophore is MCA and the quencher is Lys(DNP). A further pair which can be used according to the current invention comprises 7-amino-4-carbamoylmethylcoumarin (ACC) as the fluorophore and 2,4-dinitrophenyl-lysine (Lys (DNP)) as the quencher. In some preferred embodiments according to the biological aspect at hand the fluorophore is ACC and the quencher is Lys(DNP). Another pair of fluorophore and quencher that can be used alone or in combination is HiLyteFluor, e.g. HiLyteFluor-488 as the fluorophore with QXL, e.g. QXL520 as a quencher. HiLyte Fluor fluorophores are commercially available for various wavelengths and can be prepared as known in the art (Jungbauer, L M et al. "Preparation of fluorescently-labeled amyloid-beta peptide assemblies: the effect of fluorophore conjugation on structure and function" Journal of molecular recognition: JMR vol. 22.5 (2009): 403-13.). QXL quenchers are commercially available for various wavelengths and can be prepared as known in the art. QXL 570 dyes are optimized quenchers for rhodamines (such as TAMRA, sulforhodamine B, ROX) and Cy3 fluorophores. Their absorption spectra overlap with the fluorescence spectra of TAMRA, sulforhodamine B, ROX and Cy3.

According to some embodiments according to the fourth biological aspect said fluorophore is HiLyteFluor, such as HiLyteFluor-488 and the quencher is a matching QXL quencher, such as QXL520.

According to some embodiments according to the fourth biological aspect said peptide substrate comprises or consists of a subsequence of a natural ADAMTS-7 and/or ADAMTS-12 substrate, such as a subsequence of TSP1 or COMP, such as (a) residues 1-15 of the amino acid sequence of SEQ ID NO: 4, or (b) residues 1-15 of the amino acid sequence of SEQ ID NO: 5, or (c) residues 1-13 of the amino acid sequence of SEQ ID NO: 8, or (d) a fragment of any of the sequences according to a), b) or c), the fragment comprising the amino acid sequence EL, said fluorophore is HiLyteFluor, such as HiLyteFluor-488 and the quencher is a matching QXL quencher such as QXL520.

According to some embodiments according to the fourth biological aspect said peptide substrate comprises or consists of a subsequence of a natural ADAMTS-7 and/or ADAMTS-12 substrate, such as a subsequence of TSP1 or COMP, such as (a) residues 1-15 of the amino acid sequence of SEQ ID NO: 4, or (b) residues 1-15 of the amino acid sequence of SEQ ID NO: 5, or (c) residues 1-13 of the amino acid sequence of SEQ ID NO: 8, or (d) a fragment of any of the sequences according to a), b) or c), the fragment comprising the amino acid sequence EL, said fluorophore is MCA and said quencher is Lys(DNP).

According to some embodiments according to the fourth biological aspect said peptide substrate comprises or consists of a subsequence of a natural ADAMTS-7 and/or ADAMTS-12 substrate, such as a subsequence of TSP1 or COMP, such as (a) residues 1-15 of the amino acid sequence of SEQ ID NO: 4, or (b) residues 1-15 of the amino acid sequence of SEQ ID NO: 5, or (c) residues 1-13 of the amino acid sequence of SEQ ID NO: 8, or (d) a fragment of any of the sequences according to a), b) or c), the fragment comprising the amino acid sequence EL, said fluorophore is ACC and said quencher is Lys(DNP).

In some embodiments, the fluorophore, such as HiLyte fluor488 is attached to the N-terminus of the peptide and the quencher, such as QXL520, is attached to the C-terminus or vice versa.

In certain preferred embodiments according to the biological aspect at hand, an additional negative residue, such as carboxyl position glutamic acid is attached C-terminal of the quencher, e.g. after the QXL520 quencher. The addition of the residue improved the solubility behavior of the peptide substrate and thereby lead to an improved reproducibility of the assay.

According to some embodiments according to the biological aspect at hand said peptide substrate for ADAMTS-7 and/or ADAMTS-12 comprises or consists of a subsequence of a natural ADAMTS-7 substrate, such as a subsequence of TSP1 or COMP, such as (a) residues 1-15 of the amino acid sequence of SEQ ID NO: 4, or (b) residues 1-15 of the amino acid sequence of SEQ ID NO: 5, or (c) residues 1-13 of the amino acid sequence of SEQ ID NO: 8, or (d) a fragment of any of the sequences according to a), b) or c), the fragment comprising the amino acid sequence EL, and the peptide substrate is further characterized in comprising an additional negatively charged residue such as a carboxyl position glutamic acid, e.g. C-terminal of the quencher.

According to some embodiments according to the biological aspect at hand said peptide substrate for ADAMTS-7 and/or ADAMTS-12 comprises or consists of a subsequence of a natural ADAMTS-7 substrate, such as a subsequence of TSP1 or COMP, such as (a) residues 1-15 of the amino acid sequence of SEQ ID NO: 4, or (b) residues 1-15 of the amino acid sequence of SEQ ID NO: 5, or (c) residues 1-13 of the amino acid sequence of SEQ ID NO: 8, or (d) a fragment of any of the sequences according to a), b) or c), the fragment comprising the amino acid sequence EL, said fluorophore is HiLyteFluor, such as HiLyteFluor-488, said quencher is a matching QXL quencher such as QXL520 and the peptide substrate is further characterized in comprising an additional negatively charged residue such as a carboxyl position glutamic acid, e.g. C-terminal of the quencher.

According to a fifth biological aspect of the current invention there is provided a method for the identification or characterization of an ADAMTS-7 and/or ADAMTS-12 modulator comprising the steps of
  a) contacting a recombinant polypeptide or a fragment thereof according to the third biological aspect, and
  b) contacting said recombinant polypeptide or fragment thereof with a peptide substrate according to the fourth biological aspect, wherein the peptide substrate comprises a fluorophore and a quencher, and
  c) detecting fluorescence as a measure for the activity of said recombinant polypeptide or a fragment thereof.

In some embodiments, the recombinant polypeptide is suited to cleave a peptide comprising standard residues 1-15 of the amino acid sequence of SEQ ID NO: 4.

In some embodiments, the recombinant polypeptide comprises a first portion and a second portion, the first portion having a sequence identity of at least 80% with the sequence of residues 1-217 of SEQ ID NO: 1 and/or having a sequence identity of at least 80% with the sequence of residues 1-217 of SEQ ID NO: 2, and the second portion having a sequence identity of >80% with the sequence of residues 218-518 of SEQ ID NO: 1 and the peptide substrate comprises (a) residues 1-15 of the amino acid sequence of SEQ ID NO: 4, or (b) residues 1-15 of the amino acid sequence of SEQ ID NO: 5, or (c) residues 1-13 of the amino acid sequence of SEQ ID NO: 8, or (d) a fragment of any of the sequences according to a), b) or c), the fragment comprising the amino acid sequence EL.

In some embodiments, the recombinant polypeptide comprises a first portion and a second portion, the first portion having a sequence identity of >80% with the sequence of residues 1-244 of SEQ ID NO: 15, and the second portion having a sequence identity of >80% with the sequence of residues 245-547 of SEQ ID NO: 15 and the peptide substrate comprises (a) residues 1-15 of the amino acid sequence of SEQ ID NO: 4, or (b) residues 1-15 of the amino acid sequence of SEQ ID NO: 5, or (c) residues 1-13 of the amino acid sequence of SEQ ID NO: 8, or (d) a fragment of any of the sequences according to a), b) or c), the fragment comprising the amino acid sequence EL.

In some embodiments, the recombinant polypeptide comprises a sequence according to SEQ ID No. 01, SEQ ID No. 02 or SEQ ID No. 15 and/or the peptide substrate comprises (a) residues 1-15 of the amino acid sequence of SEQ ID NO: 4, or (b) residues 1-15 of the amino acid sequence of SEQ ID NO: 5, or (c) residues 1-13 of the amino acid sequence of SEQ ID NO: 8, or (d) a fragment of any of the sequences according to a), b) or c), the fragment comprising the amino acid sequence EL, and optionally comprises a further carboxy group.

Contacting of different compounds can be performed by preparing a solution comprising the respective compounds, e.g. in an appropriate concentration, e.g. as described in the examples. The test compound can be any molecule, such as any small molecule provided for throughout this application.

There is no specific order with regard to the steps of the method, except for the obvious restrictions resulting from the mode of action. In some embodiments the method according to the biological aspect at hand is further characterized in that step c) is performed for a solution comprising said recombinant polypeptide, said test compound, and said peptide substrate.

In some embodiments, the method according to the biological aspect at hand can be used to determine the half maximal inhibitory concentration (IC50) or the half maximal effective concentration (EC50) of an ADAMTS-7 and/or ADAMTS-12 modulator. According to the FDA, IC50 represents the concentration of a drug that is required for 50% inhibition in vitro. The determined IC50 as described herein is a measure of the potency of the test compound in inhibiting ADAMTS-7 and/or ADAMTS-12 induced cleavage of a natural or artificial substrate. Half maximal effective concentration (EC50) refers to the concentration of a test compound which induces a response halfway between the baseline and maximum after a specified exposure time and can be used as a measure of agonistic potency of a compound. IC50 and EC50 can be determined as known in the art. In brief, the IC50 of a drug can be determined by constructing a dose-response curve and analyzing the resulting fluorescence for different concentrations of the test compound.

In some embodiments according to the fifth biological aspect a test compound can be or is selected as a modulator (e.g. agonist or inhibitor) if after contacting the recombinant polypeptide with the at least one test compound according to step a) and after contacting said recombinant polypeptide with a peptide substrate according to step b) no significant increase of fluorescence is detected or if an increase of fluorescence is detected which is significantly lower than the increase of fluorescence which is detectable for a control in the absence of the test compound. In some embodiments according to the fifth biological aspect a test compound is selected as an ADAMTS-7 and/or ADAMTS-12 agonist if after contacting the recombinant polypeptide with the at least one test compound according to step a) and after contacting said recombinant polypeptide with a peptide substrate according to step b) an increase of fluorescence is detected which is significantly higher than the increase of fluorescence which is detectable for a control in the absence of the test compound. An exemplary way how the method can be performed is described in example B5.

According to some embodiments according to the current biological aspect there is provided a method for evaluating the selectivity of an ADAMTS-7 and/or ADAMTS-12 modulator comprising the method according to the fifth biological aspect further characterized in comprising the steps of
  a) contacting a functional recombinant metalloproteinase different from ADAMTS-7 and ADAMTS-12 with the at least one test compound, and
  b) contacting said functional recombinant metalloproteinase with a peptide substrate comprising a fluorophore and a quencher, wherein said peptide substrate comprises a cleavage site for said functional recombinant metalloproteinase different from ADAMTS-7 and/or ADAMTS-12; and
  c) detecting the fluorescence as a measure for the activity of functional recombinant metalloproteinase different from ADAMTS-7 and ADAMTS-12.

In certain preferred embodiments, the functional recombinant metalloproteinase different from ADAMTS-7 and ADAMTS-12 is ADAMTS4, ADAMTS5, MMP12, MMP15, MMP2 or ADAM17 or any other enzyme listed in table 2. In some preferred embodiments, the peptide comprising a fluorophore and a quencher is the peptide as specified in table 2 and/or comprises a cleavage site of said functional recombinant metalloproteinase different from ADAMTS-7 and/or ADAMTS-12 as disclosed in table 2.

For characterization of the inhibition, based on the fluorescence IC50 values can be calculated from percentage of inhibition of enzyme activity as a function of test compound concentration.

According to a sixth biological aspect there is provided a modulator of ADAMTS-7 and/or ADAMTS-12 identified by a method according to the fifth biological aspect for use in the treatment of heart disease, vascular disease, and/or cardiovascular disease, including atherosclerosis, coronary artery disease (CAD), myocardial infarction (MI), peripheral vascular disease (PAD)/arterial occlusive disease and/or restenosis after angioplasty (including the use of drug-coated or non drug-coated balloons and/or stent-implantation) and/or for the treatment and/or prophylaxis of lung disease, inflammatory disease, fibrotic disease, metabolic disease, cardiometabolic disease and/or diseases/disease states affecting the kidneys and/or the central nervous and/or neurological system as well as gastrointestinal and/or urologic and/or ophthalmologic disease/disease states.

For these diseases or disease states, alterations or aberrant expression with regard to ADAMTS-7 and/or ADAMTS-12 have been described earlier. In some embodiments the modulator of ADAMTS-7 and/or ADAMTS-12 is a modulator for use in the treatment of coronary artery disease (CAD), peripheral vascular disease (PAD) and myocardial infarction (MI). In some embodiments, the modulator according to the sixth biological aspect is a small molecule. In some embodiments, the modulator according to the seventh biological aspect is an antagonist of human ADAMTS-7. In some different or the same embodiments, the modulator according to the sixth biological aspect is an antagonist of human ADAMTS-12. In some different or the same embodiments, the modulator according to the sixth biological aspect is an antagonist of human ADAMTS4. In some embodiments the modulator according to the sixth biological aspect is a small molecule, e.g. as provided in the examples. While the identification of selective ADAMTS-7 and ADAMTS-12 modulators has been extremely challenging in the past, the provided assay now offers all means to obtain these moulators according to the current biological aspect.

According to a seventh biological aspect there is provided a method of producing a recombinant polypeptide according to any of the previous biological aspects, the method comprising cultivating a recombinant host cell comprising a recombinant nucleic acid according to any biological aspect described herein and recovering the recombinant polypeptide of a fragment thereof.

According to an eighth biological aspect there is provided a kit of parts comprising a recombinant nucleic acid according to the first and/or second biological aspect and/or a polypeptide according to the third biological aspect and a peptide substrate according to the fourth biological aspect. In some embodiments the kit of parts can be used to perform a method according to the fifth biological aspect in a convenient and reproducible way. In some embodiments the provided kit of parts can be used to evaluate whether a test molecule is a modulator of ADAMTS-7. In some different or the same embodiments the provided kit of parts can be used to evaluate whether a test molecule is a modulator of ADAMTS-12. In some embodiments the provided kit of parts can be used to evaluate whether a test molecule is a modulator of ADAMTS-7 and a modulator of ADAMTS-12.

Experimental Section—Starting Materials and Intermediates

NMR Analytical Method:

Where indicated, intermediates and examples were characterized by $^1$H NMR with a 300 MHz spectrometer. Spectra were recorded on a Bruker Ultrashield AV300 MHz spectrometer, with a Bruker 5 mm BBI 1H/D-BB Z-GRD probe, using a BACS-60 sample changer, and registered with Bruker Topspin 2.1 software. For the $^1$H spectra, all chemical shifts are reported in part per million (δ) units, and are relative to the residual signal at 7.26 and 2.50 ppm for CDCl$_3$ and DMSO, respectively, at 25° C.

NMR peak forms are stated as they appear in the spectra, possible higher order effects have not been considered.

The $^1$H NMR data of selected synthesis intermediates and working examples are stated in the form of $^1$H NMR peak lists. For each signal peak, first the δ [ppm]=value in ppm and then the signal intensity in round brackets are listed. The δ [ppm]=value/signal intensity number pairs for different signal peaks are listed with separation from one another by commas. The peak list for an example therefore takes the following form: δ [ppm]=1 (intensity$_1$), δ [ppm]=2 (intensity$_2$), ..., δ [ppm]=$_i$(intensity$_i$), ..., δ [ppm]=$_n$(intensity$_n$).

The intensity of sharp signals correlates with the height of the signals in a printed example of an NMR spectrum in cm and shows the true ratios of the signal intensities in comparison with other signals. In the case of broad signals, several peaks or the middle of the signal and the relative intensity thereof may be shown in comparison to the most intense signal in the spectrum. The lists of the $^1$H NMR peaks are similar to the conventional $^1$H NMR printouts and thus usually contain all peaks listed in a conventional NMR interpretation. In addition, like conventional $^1$H NMR printouts, they may show solvent signals, signals of stereoisomers of the target compounds which are likewise provided by the invention, and/or peaks of impurities. The peaks of stereoisomers of the target compounds and/or peaks of impurities usually have a lower intensity on average than the peaks of the target compounds (for example with a purity of >90%). Such stereoisomers and/or impurities may be typical of the particular preparation process. Their peaks can thus help in identifying reproduction of our preparation process with reference to "by-product fingerprints". An expert calculating the peaks of the target compounds by known methods (MestreC, ACD simulation, or using empirically evaluated expected values) can, if required, isolate the peaks of the target compounds, optionally using additional intensity filters. This isolation would be similar to the peak picking in question in conventional $^1$H NMR interpretation. A detailed description of the presentation of NMR data in the form of peak lists can be found in the publication "Citation of NMR Peaklist Data within patent applications" (cf. Research Disclosure Database Number 605005, 2014, 1 Aug. 2014 or http://www.researchdisclosure.com/searching-disclosures). In the peak picking routine described in Research Disclosure Database Number 605005, the parameter "MinimumHeight" can be set between 1% and 4%. Depending on the type of chemical structure and/or depending on the concentration of the compound to be analysed, it may be advisable to set the parameters "MinimumHeight" to values of <1%.

Chemical names were generated using the ACD/Name software from ACD/Labs. In some cases generally accepted names of commercially available reagents were used in place of ACD/Name generated names.

The following table 1 lists the abbreviations used in this paragraph and in the Examples section as far as they are not explained within the text body. Other abbreviations have their meanings customary per se to the skilled person.

TABLE 1

Abbreviations

| Abbreviation | Meaning |
|---|---|
| Ac | acetate |
| acac | acetylacetonate |
| ACN | acetonitrile |
| aq. | aqueous |
| bp | broad peak |
| br | broad ($^1$H-NMR signal) |
| Bu | Butyl |
| BuLi | butyllithium |
| CDI | carbonyldiimidazole |
| CI | chemical ionisation |
| conc. | concentrated |
| d | doublet ($^1$H-NMR signal) |
| DBU | 1,8-Diazabicyclo[5.4.0]undec-7-ene |
| DCM | dichloromethane |
| dd | double-doublet ($^1$H-NMR signal) |
| ddd | doublet of doublets of doublets |
| diamix | mixture of diastereoisomers |
| DIPEA | diisopropylethylamine |
| DMA | dimethylacetamide |
| DMAP | N,N-dimethylpyridin-4-amine |
| DME | 1,2-dimethoxyethane |
| DMF | N,N-Dimethylformamide |
| DMSO | dimethylsulfoxide |
| EDC | 1-ethyl-3-(3-dimethylaminopropyl)carbodiimide hydrochloride |
| ent | enantiomerically pure compound |
| eq. | equivalents |
| ESI | electrospray (ES) ionisation |
| Et | ethyl |
| EtOH | ethanol |
| h | hour(s) |
| HATU | (1-[bis(dimethylamino)methylene)-1H-1,2,3-triazolo[4,5-b]pyridinium-3-oxide hexafluorophosphate |
| HOBt | 1-hydroxybenzotriazole hydrate |
| HPLC | high performance liquid chromatography |
| iPr | isopropyl |
| LC-MS | liquid chromatography mass spectrometry |
| LiHMDS | Lithium bis(trimethylsilyl)amide |
| M | molar (concentration) |
| Me | CH$_3$ |
| MeOH | methanol |

TABLE 1-continued

Abbreviations

| Abbreviation | Meaning |
|---|---|
| min | minute(s) |
| MS | mass spectrometry |
| N | normal (concentration) |
| NBS | N-bromosuccinimide |
| NCS | N-chlorosuccinimide |
| NMR | nuclear magnetic resonance spectroscopy: chemical shifts (δ) are given in ppm. The chemical shifts were corrected by setting the DMSO signal to 2.50 ppm unless otherwise stated. |
| PCC | Pyridinium chlorochromate |
| PdCl$_2$(PPh$_3$)$_2$ | dichloropalladium-triphenylphosphane (1:2) |
| Pd(PPh$_3$)$_4$ | palladium-triphenylphosphane (1:4) |
| Ph$_3$P | triphenylphosphane |
| q | quartet |
| rac | racemic mixture |
| RF | reflux |
| RP | Reversed-Phase chromatography |
| Rt | retention time (as measured either with HPLC or UPLC) in minutes |
| RT | Room Temperature |
| s | singlet ($^1$H-NMR signal) |
| sat. | saturated |
| SQD | Single-Quadrupole-Detector |
| t | triplet ($^1$H-NMR signal) |
| TBAF | tetrabutylammoniumfluoride |
| TBDMSCI | tert.-butyldimethylsilylchlorid |
| td | triple-doublet ($^1$H-NMR signal) |
| TEA | triethylamine |
| TFA | trifluoroacetic acid |
| TFE | 2,2,2-trifluoroethanol |
| THF | tetrahydrofuran |
| TLC | Thin Layer Chromatography |
| UPLC | ultra performance liquid chromatography |
| X-Phos | dicyclohexyl[2',4',6'-tri(propan-2-yl)biphenyl-2-yl]phosphane |

The following table lists the abbreviations used herein.

The various aspects of the invention described in this application are illustrated by the following examples which are not meant to limit the invention in any way.

The example testing experiments described herein serve to illustrate the present invention and the invention is not limited to the examples given.

Experimental Section—General Part

All reagents, for which the synthesis is not described in the experimental part, are either commercially available, or are known compounds or may be formed from known compounds by known methods by a person skilled in the art.

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example prepacked silica gel cartridges, e.g. Biotage SNAP cartridges KP-Sil® or KP-NH® in combination with a Biotage autopurifier system (SP4® or Isolera Four®) and eluents such as gradients of hexane/ethyl acetate or DCM/methanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia.

In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc.) of a compound of the present invention as isolated and as described herein is not necessarily the only form in which said compound can be applied to a biological assay in order to quantify the specific biological activity.

LC-MS Procedures

General Remarks:

Method 1-6 were performed using an Agilent G1956A LC/MSD quadrupole coupled to an Agilent 1100 series liquid chromatography (LC) system consisting of a binary pump with degasser, autosampler, thermostated column compartment and diode array detector. The mass spectrometer (MS) was operated with an atmospheric pressure electro-spray ionization (API-ES) source in positive ion mode (Mass method 1). The capillary voltage was set to 3000 V, the fragmentor voltage to 70 V and the quadrupole temperature was maintained at 100° C. The drying gas flow and temperature values were 12.0 L/min and 350° C., respectively. Nitrogen was used as the nebuliser gas, at a pressure of 35 psi. Data acquisition was performed with Agilent Chemstation software.

Method 1:

Analyses were carried out on a YMC pack ODS-AQ C18 column (50 mm long×4.6 mm I.D.; 3 μm particle size) at 35° C., with a flow rate of 2.6 mL/min. A gradient elution was performed from 95% (Water+0.1% Formic acid)/5% Acetonitrile to 5% (Water+0.1% Formic acid)/95% Acetonitrile in 4.8 min; the resulting composition was held for 1.0 min; from 5% (Water+0.1% formic acid)/95% Acetonitrile to 95% (Water+0.1% formic acid)/5% Acetonitrile in 0.2 min. The standard injection volume was 2 μL. Acquisition ranges were set to 190-400 nm for the UV-PDA detector and 100-1400 m/z for the MS detector.

Method 2:

Analyses were carried out on a Phenomenex Kinetex 00B-4475-AN C18 column (50 mm long×2.1 mm I.D.; 1.7 μm particles) at 60° C., with a flow rate of 1.5 mL/min. A gradient elution was performed from 90% (Water+0.1% Formic acid)/10% Acetonitrile to 10% (Water+0.1% Formic acid)/90% Acetonitrile in 1.50 minutes; the resulting composition was held for 0.40 min; then the final mobile phase composition; from 10% (Water+0.1% Formic acid)/90% Acetonitrile to 90% (Water+0.1% Formic acid)/10% Acetonitrile in 0.10 minutes. The injection volume was 2 μL with Agilent autosampler injector or 5 μL with Gerstel MPS injector. MS acquisition range and DAD detector were set to 100-800 m/z and 190-400 nm respectively.

Method 3:

Analyses were carried out on a Thermo Scientific Accucore C18 (50 mm long×2.1 mm I.D., 2.6 μm) at 35° C., with a flow rate of 1.50 mL/min. A gradient elution was performed from 95% (Water+0.1% Formic acid)/5% Acetonitrile to 5% (Water+0.1% Formic acid)/95% Acetonitrile in 1.30 minutes; the resulting composition was held for 0.5 min; then the final mobile phase composition; from 5% (Water+0.1% Formic acid)/95% Acetonitrile to 90% (Water+0.1% Formic acid)/10% Acetonitrile in 0.10 minutes. The injection volume was 1 μL. MS acquisition range and UV detector were set to 100-1000 m/z and 190-400 nm respectively.

Method 4:

Analyses were carried out on a Thermo Scientific Accucore C18 column PN17126-054630 (50 mm long×4.6 mm I.D.; 2.6 μm particles) at 30° C., with a flow rate of 3 mL/min. A gradient elution was performed from 90% (Water+0.1% Formic acid)/10% Acetonitrile to 5% (Water+0.1% Formic acid)/95% Acetonitrile in 1.50 minutes; the resulting composition was held for 0.90 min; then the final mobile phase composition; from 10% (Water+0.1% Formic acid)/90% Acetonitrile to 90% (Water+0.1% Formic acid)/10% Acetonitrile in 0.10 minutes. The injection volume was 2 μL. MS acquisition range and DAD detector were set to 100-1000 m/z and 200-400 nm respectively.

Method 5:

Analyses were carried out on a Thermo Scientific Accucore AQ C18 (50 mm long×2.1 mm I.D., 2.6 μm) at 35° C., with a flow rate of 1.50 mL/min. A gradient elution was performed from 95% (Water+0.1% Formic acid)/5% Acetonitrile to 5% (Water+0.1% Formic acid)/95% Acetonitrile in 1.50 minutes; the resulting composition was held for 0.3 min; then the final mobile phase composition; from 5% (Water+0.1% Formic acid)/95% Acetonitrile to 95% (Water+0.1% Formic acid)/5% Acetonitrile in 0.10 minutes. The injection volume was 1 μL. MS acquisition range and UV detector were set to 100-1000 m/z and 190-400 nm respectively.

Method 6:

Analyses were carried out on a YMC pack ODS-AQ C18 column (50 mm long×4.6 mm I.D.; 3 μm particle size) at 35° C., with a flow rate of 2.6 mL/min. A gradient elution was performed using ISET 2V1.0 Emulated Agilent Pump G1312A V1.0 from 94.51% (Water+0.1% Formic acid)/5.49% Acetonitrile to 5% (Water+0.1% Formic acid)/95% Acetonitrile in 4.8 min; the resulting composition was held for 1.0 min; from 5% (Water+0.1% formic acid)/95% Acetonitrile to 95% (Water+0.1% formic acid)/5% Acetonitrile in 0.2 min. The standard injection volume was 2 μL. Acquisition ranges were set to 190-400 nm for the UV-PDA detector and 100-1000 m/z for the TOF-MS detector.

Method 7:

Instrument MS: Thermo Scientific FT-MS; Instrument type UHPLC+: Thermo Scientific UltiMate 3000; Column: Waters, HSST3, 2.1×75 mm, C18 1.8 μm; eluent A: 1 L water+0.01% formic acid; eluent B: 1 L acetonitrile+0.01% formic acid; gradient: 0.0 min 10% B→2.5 min 95% B→3.5 min 95% B; oven: 50° C.; flow rate: 0.90 ml/min; UV detection: 210 nm/optimum integration path 210-300 nm.

Method 8:

Instrument: Waters ACQUITY SQD UPLC System; Column: Waters Acquity UPLC HSS T3 1.8μ 50×1 mm; eluent A: 1 L water+0.25 ml 99% formic acid, eluent B: 1 L acetonitrile+0.25 ml 99% formic acid; gradient: 0.0 min 90% A→1.2 min 5% A→2.0 min 5% A; oven: 50° C.; flow rate: 0.40 ml/min; UV detection: 210 nm.

Method 9

Instrument: Waters Single Quad MS System; Instrument Waters UPLC Acquity; Column: Waters BEH C18 1.7μ50× 2.1 mm; eluent A: 1 L water+1.0 mL (25% ammonia)/L, eluent B: 1 L acetonitrile; gradient: 0.0 min 92% A→0.1 min 92% A→1.8 min 5% A→3.5 min 5% A; oven: 50° C.; flow rate: 0.45 mL/min; UV-detection: 210 nm.

Method 10
Instrument: Agilent MS Quad 6150; HPLC: Agilent 1290; column: Waters Acquity UPLC HSS T3 1.8 µm 50×2.1 mm; eluent A: 1 L water+0.25 ml 99% formic acid, eluent B: 1 L acetonitrile+0.25 ml 99% formic acid; gradient: 0.0 min 90% A→0.3 min 90% A→1.7 min 5% A→3.0 min 5% A; ofen: 50° C.; flow rate: 1.20 mL/min; UV-detection: 205-305 nm.

Method 11
Instrument: Agilent MS Quad 6150; HPLC: Agilent 1290; column: Waters Acquity UPLC HSS T3 1.8 µm 50×2.1 mm; eluent A: 1 L water+0.25 ml 99% formic acid, eluent B: 1 L acetonitrile+0.25 ml 99% formic acid; gradient: 0.0 min 90% A→0.3 min 90% A→1.7 min 5% A→3.0 min 5% A; oven: 50° C.; flow rate: 1.20 ml/min; UV-detection: 205-305 nm.

Method 12
Instrument: Waters ACQUITY SQD UPLC System; column: Waters Acquity UPLC HSS T3 1.8 µm 50×1 mm; eluent A: 1 l water+0.25 ml 99% formic acid, Eluent B: 1 l Acetonitril+0.25 ml 99% formic acid; gradient: 0.0 min 95% A→6.0 min 5% A→7.5 min 5% A; oven: 50° C.; flow rate: 0.35 ml/min; UV-detection: 210 nm.

Method 13:
Instrument MS: Waters SQD; Instrument type HPLC: Waters Alliance 2795; Column: Waters, Cortecs, 3.0×30 mm, C18 2.7 µm; eluent A: 1 L water+0.01% formic acid; eluent B: 1 L acetonitrile+0.01% formic acid; gradient: 0.0 min 5% B→1.75 min 95% B→2.35 min 95% B; oven 45° C.: flow rate: 1.75 mL/min; UV detection: 210 nm.

Method 14:
Instrument MS: Waters SQD; Instrument HPLC: Waters UPLC; column: Zorbax SB-Aq (Agilent), 50 mm×2.1 mm, 1.8 µm; eluent A: water+0.025% formic acid, eluent B: acetonitrile (ULC)+0.025% formic acid; gradient: 0.0 min 98% A→0.9 min 25% A→1.0 min 5% A→1.4 min 5% A→1.41 min 98% A→1.5 min 98% A; oven: 40° C.; flow: 0.600 ml/min; UV-detection: DAD; 210 nm.

GC-MS Procedures

Method A:
Instrument: Thermo Scientific DSQII, Thermo Scientific Trace GC Ultra; column: Restek RTX-35MS, 15 m×200 µm×0.33 µm; constant flow with helium: 1.20 ml/min; oven: 60° C.; Inlet: 220° C.; gradient: 60° C., 30° C./min→300° C. (3.33 min hold).

Enantiomeric Separation, Preparative Scale:
Method 1 D: Phase: Daicel Chiralpak IF, 5 µm 250 mm×20 mm, eluent: n-heptane/ethanol 50:50; flow: 20 ml/min, temperature: 40° C.; UV-Detection: 220 nm.

Method 2D: Phase: Daicel Chiralpak IE, 5 µm 250 mm×20 mm, eluent: n-heptane/2-propanol 60:40; flow: 15 ml/min, temperature: 50° C.; UV-Detection: 220 nm.

Method 3D: Phase: Daicel Chiralpak IG, 5 µm 250 mm×20 mm, eluent: ethanol 100%; flow: 15 ml/min, temperature: 50° C.; UV-Detection: 220 nm.

Method 4D: Phase: Daicel Chiralpak AD-H, 5 µm 250 mm×20 mm, eluent: n-heptane:ethanol 40:60; flow: 25 ml/min, temperature: 35° C.; UV-Detection: 220 nm.

Method 5D: Phase: Daicel Chiralpak AD-H, 5 µm 250 mm×20 mm, eluent: n-heptane:ethanol 50:50; flow: 25 ml/min, temperature: 30° C.; UV-Detection: 220 nm.

Method 6D: Phase: Daicel Chiralpak IF, 5 µm 250 mm×20 mm, eluent: n-heptane:ethanol 50:50; flow: 15 ml/min, temperature: 40° C.; UV-Detection: 210 nm.

Method 7D: Phase: Daicel Chiralpak IF, 5 µm 250 mm×20 mm, Eluent: n-heptane:ethanol 50:50; flow: 15 ml/min, temperature: 40° C.; UV-Detection: 220 nm.

Method 8D: Phase: Daicel Chiralpak AD-H, 5 µm 250 mm×20 mm, Eluent: i-hexand:ethanol 50:50; flow: 20 ml/min, temperature: 40° C.; UV-Detection: 210 nm.

Method 9D: Phase: Daicel Chiralpak IF, 5 µm 250 mm×20 mm, eluent: n-heptane:ethanol 40:60; flow: 15 ml/min, temperature: 40° C.; UV-Detection: 210 nm.

Method 10D: Phase: Daicel Chiralpak IG, 5 µm 250 mm×20 mm, eluent: n-heptane:ethanol 30:70; flow: 15 ml/min, temperature: 30° C.; UV-Detection: 220 nm.

Method 11 D: Phase: Daicel Chiralpak IG, 5 µm 250 mm×20 mm, eluent: ethanol 100%; flow: 15 ml/min, temperature: 50° C.; UV-Detection: 220 nm.

Method 12D: Phase: Daicel Chiralpak IG, 5 µm 250 mm×20 mm, eluent: n-heptane:ethanol 10:90; flow: 15 ml/min, temperature: 50° C.; UV-Detection: 220 nm.

Method 13D: Phase: Daicel Chiralpak IG, 5 µm 250 mm×20 mm, Eluent: ethanol 100%; flow: 15 ml/min, temperature: 50° C.; UV-Detection: 220 nm.

Method 14D: Phase: Daicel Chiralpak IF, 5 µm 250 mm×20 mm, Eluent: ethanol 100%; flow: 15 ml/min, temperature: 50° C.; UV-Detection: 220 nm.

Method 15D: Phase: Daicel Chiralpak IG, 5 µm 250 mm×20 mm, eluent: n-heptane:ethanol 60:40; flow: 15 ml/min, temperature: 50° C.; UV-Detection: 235 nm.

Method 16D: Phase: Daicel Chiralpak IG, 5 µm 250 mm×20 mm, eluent: n-heptane:ethanol 10:90; flow: 15 ml/min, temperature: 30° C.; UV-Detection: 235 nm.

Method 17D: Phase: Daicel Chiralpak IF, 5 µm 250 mm×20 mm, eluent: ethanol 100%; flow: 15 ml/min, temperature: 70° C.; UV-Detection: 220 nm.

Enantiomeric Separation, Analytical Scale:
Method 1E: Phase: Chiratek IF-3; eluent: i-hexane/ethanol 50:50; flow: 1 ml/min; UV-Detection: 220 nm.

Method 2E: Phase: Daicel Chiralpak IF, 5 µm 250 mm×4.6 mm; eluent: hexane/2-propanol 30:70; flow: 1.0 ml/min, temperature: 60° C.; UV-Detection: 270 nm.

Method 3E: Phase: Daicel Chiralpak IG, 5 µm 250 mm×4.6 mm; eluent: ethanol 100%; flow: 1.0 ml/min, temperature: 50° C.; UV-Detection: 220 nm.

Method 4E: Phase: Daicel AD, 5 µm 250 mm×4.60 mm; eluent: ethanol 100%; flow: 1.0 ml/min; UV-Detection: 220 nm.

Method 5E: Phase: Daicel Chiralpak AD-H, 5 µm 250 mm×4.6 mm; eluent: ethanol 100%; flow: 1.0 ml/min, UV-Detection: 220 nm.

Method 6E: Phase: Daicel Chiralpak IF, 5 µm 50 mm×4.6 mm; eluent: n-heptane:ethanol 50:50; flow: 1.0 ml/min, Temperature: 25° C.; UV-Detection: 220 nm.

Method 7E: Phase: Daicel Chiralpak IF, 5 µm 50 mm×4.6 mm; eluent: n-heptane:ethanol 50:50; flow: 1.0 ml/min, UV-Detection: 220 nm.

Method 8E: Phase: Chiracel-H AD, 5 µm 250 mm×4.6 mm Eluent: n-heptane:ehanol 50:50; flow: 1.0 ml/min, UV-Detection: 220 nm.

Method 9E: Phase: Daicel Chiralpak IF-3, 5 µm 50 mm×4.6 mm; eluent: n-heptane:ehanol 50:50; flow: 1.0 ml/min, UV-Detection: 220 nm.

Method 10E: Phase: Daicel IG-3, 5 µm 50 mm×4.6 mm; flow: 1.0 ml/min, UV-Detection: 220 nm.

Method 11E: Phase: Daicel Chiralpak IG-3, 5 µm 250 mm×4.6 mm; eluent: ethanol 100%, flow: 1.0 ml/min, temperature: 50° C.; UV-Detection: 220 nm.

Method 12E: Phase: Daicel Chiralpak IG-3, 5 µm 250 mm×4.6 mm; eluent: ethanol 100%, flow: 1 ml/min, temperature: 50° C.; UV-Detection: 220 nm.

Method 13E: Phase: Daicel Chiralpak IG-3, 5 μm 250 mm×4.6 mm; eluent: ethanol 100%, flow: 1.0 ml/min, temperature:50° C.; UV-Detection: 220 nm.

Method 14E: Phase: Daicel Chiralpak IF, 5 μm 50 mm×4.60 mm; eluent: ethanol 100%, flow: 1.0 ml/min, UV-Detection: 220 nm.

Method 15E: Phase: Daicel Chiralpak IF, 5 μm 250 mm×4.60 mm; eluent: ethanol 100%, flow: 1.0 ml/min, temperature: 50° C.; UV-Detection: 220 nm.

Method 16E: Phase: Daicel IG-3 3 μm 50 mm×4.60 mm; eluent: ethanol 100%, flow 1.0 ml/min; UV-Detection: 220 nm.

Method 17E: Phase: Daicel Chiralpak IG 5 μm 50 mm×4.60 mm; eluent: ethanol 100%, flow 1.0 ml/min; temperature: 70° C., UV-Detection: 220 nm.

Preparative HPLC:

Method 1f

Column: Chromatorex C18 10 μm; 125×20 mm; Eluent A: water+0.05% trifluoroacetic acid, Eluent B: acetonitrile+ 0.05% trifluoroacetic acid; Gradient: 10% B→100% B; Flow: 20 ml/min UV-Detection 210 nm.

Method 2f

Column: Chromatorex C18 10 μm; 125×30 mm; Eluent A: water+0.05% trifluoroacetic acid, Eluent B: acetonitrile+ 0.05% trifluoroacetic acid; Gradient: 10% B→100% B; Flow: 50 till 100 ml/min UV-Detection 210 nm.

Method 3f

Instrument: Waters Prep LC/MS System, Colunmn: Phenomenex Kinetex C18 5 μm 100×30 mm; Eluent A: water, Eluent B: acetonitrile, Eluent C: 2% formic acid in Water, Eluent D: acetonitrile/water (80 Vol %/20 Vol %); Flow rate: 80 ml/min, room temperature, UV-detection 200-400 nm; Gradient: Eluent A 0→2 min 63 ml, Eluent B 0→2 min 7 ml, Eluent A 2→10 min from 63 ml till 39 ml and Eluent B from 7 ml till 31 ml, 10→12 min 0 ml Eluent A and 70 ml Eluent B. Eluent C and Eluent D constant flow of 5 ml/min during the complete HPLC run.

Method 4f

Instrument: Waters Prep LC/MS System, Colunmn: Phenomenex Kinetex C18 5 μm 100×30 mm; Eluent A: water, Eluent B: acetonitrile, Eluent C: 2% formic acid in Water, Eluent D: acetonitrile/water (80 Vol %/20 Vol %); Flow rate: 80 ml/min, room temperature, UV-detection 200-400 nm; Gradient: Eluent A 0→2 min 55 ml, Eluent B 0→2 min 15 ml, Eluent A 2→10 min from 55 ml till 31 ml and Eluent B from 15 ml till 39 ml, 10→12 min 0 ml Eluent A and 70 ml Eluent B. Eluent C and Eluent D constant flow of 5 ml/min during the complete HPLC run.

Method 5f

Instrument: Waters Prep LC/MS System; Column: XBridge C18 5 μm 100×30 mm; Eluent A: water, Eluent B: acetonitrile, Eluent C: 2% ammonia in water, Eluent D: acetonitrile/water (80 Vol. %/20 Vol %); Flow: 80 ml/min; Room temperature; Wavelength 200-400 nm; At-Column injection (complete injection); Gradient: eluent A 0 to 2 min 70 ml, eluent B 0 to 2 min 0 ml, eluent A 2 to 10 min from 70 ml to 55 ml and eluent B from 0 ml to 15 ml, 10 to 12 min 0 ml eluent A and 70 ml eluent B. Eluent C and Eluent D constant flow, each 5 ml/min during the complete HPLC run.

Method 6f

Instrument: Waters Prep LC/MS System; Column: Phenomenex Kinetex C18 5 μm 100×30 mm; Eluent A: water, Eluent B: acetonitrile, Eluent C: 2% formic acid in water, Eluent D: acetonitrile/water (80 Vol. %/20 Vol %); Flow: 80 ml/min; Room temperature; Wavelength 200-400 nm; At-Column injection (complete injection); Gradient: eluent A 0 to 2 min 70 ml, eluent B 0 bis 2 min 0 ml, eluent A 2 to 10 min from 70 ml to 55 ml and eluent B from 0 ml to 15 ml, 10 to 12 min 0 ml eluent A and 70 ml eluent B. Eluent C and eluent D constant flow, each 5 ml/min during the complete HPLC run.

Method 7f

Instrument: Waters Prep LC/MS System; Column: XBridge C18 5 μm 100×30 mm; Eluent A: water, Eluent B: Acetonitrile, Eluent C: 2% ammonia in water, Eluent D: Acetonitrile/water (80 Vol. %/20 Vol %) Flow: 80 ml/min; Room temperature; Wavelength 200-400 nm; At-Column injection (complete injection); Gradient: eluent A 0 to 2 min 63 ml, eluent B 0 to 2 min 7 ml, eluent A 2 to 10 min from 63 ml to 39 ml and eluent B from 7 ml to 31 ml, 10 to 12 min 0 ml eluent A and 70 ml eluent B. Eluent C and eluent D constant flow, each 5 ml/min during the complete HPLC run.

Method 8f

Instrument: Waters Prep LC/MS System; Column: Phenomenex Kinetex C18 5 μm 100×30 mm; Eluent A: water, Eluent B: acetonitrile, Eluent C: 2% formic acid in water, Eluent D acetonitrile/water (80 Vol. %/20 Vol %); Flow: 80 ml/min; Room temperature; Wavelength 200-400 nm; At-Column injection (complete injection); Gradient: eluent A 0 to 2 min 47 ml, eluent B 0 to 2 min 23 ml, eluent A 2 to 10 min from 47 ml to 23 ml and eluent B from 23 ml to 47 ml, 10 to 12 min 0 ml eluent A and 70 ml eluent B. Eluent C and eluent D constant flow, each 5 ml/min during the complete HPLC run.

Method 9f

Column: Chromatorex C18 10 μm; 125×40 mm; Eluent A: water+0.05% trifluoroacetic acid, Eluent B: acetonitrile+ 0.05% trifluoroacetic acid; Gradient: 10% B→100% B; Flow: 100 ml/min UV-Detection 210 nm.

Experimental Section—Starting Materials and Intermediates

Intermediate 1

1-(2-Cyclopropyl-2-Oxoethyl)-3,5,7-Triaza-1-Azoniatricyclo[3.3.1.1$^{3,7}$]Decane Bromide

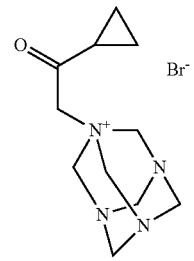 [SMILES: O=C(C[N+]12CN3CN(CN(C3)C1)C2)C1CC1 ; [Br-]]

100.00 g (0.61 mol) of 2-bromo-1-cyclopropylethanone was dissolved in 1.4 L of chloroform and 86.00 g (0.61 mol) of hexamethylenetetramine was added allowing the mixture to stir at room temperature for 12 hours. The solvent was partially removed and the resulting precipitate was filtered off, washed with cold chloroform and isolated. The remaining mother liquors were concentrated again, filtered and washed with cold chloroform several times until no more precipitate was appreciated. All the collected solids were dried in vacuo to give 185.67 g (100%) of the product as a white powder. The compound was used as such in the next synthetic step.

¹H-NMR (300 MHz, DMSO-d₆): δ [ppm]=0.98-1.10 (m, 4H), 2.02-2.17 (m, 1H), 4.31 (d, 2H), 4.51 (d, 3H), 4.65 (d, 3H), 5.32 (s, 6H).

LC-MS (Method 3): R$_t$=0.099 min. MS (Mass method 1): m/z=223 (M)⁺

Intermediate 2

Tert-Butyl (2-Cyclopropyl-2-Oxoethyl)Carbamate

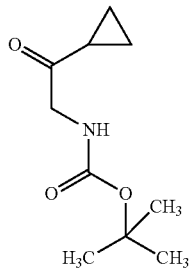

185.67 g (0.61 mol) of 1-(2-cyclopropyl-2-oxoethyl)-3,5,7-triaza-1-azoniatricyclo[3.3.1.1³,⁷]decane bromide was dissolved in 0.60 L of ethanol and 0.20 L of hydrochloric acid (conc). and the mixture was refluxed for 30 min. The resulting precipitate was filtered off, washed with ethanol and discarded. The filtrates were evaporated and dried to yield the corresponding crude ammonium salt as a thick oil. Next, 0.10 L (0.73 mol) of triethylamine and 0.14 L (0.61 mol) of di-tert-butyl dicarbonate were added to a solution of the aforementioned crude ammonium salt in 1.3 L of dichloromethane and the mixture was stirred at room temperature for 12 hours. Water was added to the reaction and the phases were separated. The organic layer was dried over magnesium sulfate, filtered and evaporated. The corresponding residue was purified by flash chromatography on silica gel eluting with n-heptane and ethyl acetate. 49.00 g (40%) of the product were isolated as a dark brown oil.

¹H-NMR (300 MHz, DMSO-d₆): δ [ppm]=0.78-0.85 (m, 1H), 0.86-0.94 (m, 2H), 1.38 (s, 9H), 1.99-2.11 (m, 1H), 3.88 (d, 2H), 7.03 (bp, 1H).

LC-MS (Method 3): R$_t$=0.630 min. MS (Mass method 1): m/z=222 (M+Na)+

Intermediate 3

Rac-Tert-Butyl [(4-Cyclopropyl-2,5-Dioxoimidazo-lidin-4-Yl)Methyl]Carbamate

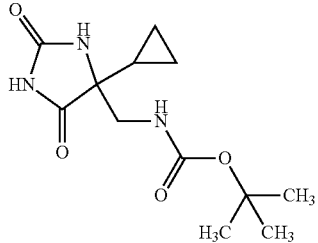 [SMILES: CC(C)(C)OC(=O)NCC1(C2CC2)NC(=O)NC1=O]

To a stirring solution of 50.63 g (526.97 mmol) of ammonium carbonate and 7.51 g (140.52 mmol) of ammonium chloride in 40 mL of water was added 7.00 g (35.13 mmol) of tert-butyl (2-cyclopropyl-2-oxoethyl)carbamate in 40 mL of ethanol. After 15 min, 10.29 g (158.09 mmol) of potassium cyanide were added and the mixture was heated up to 60° C. for 16 hours into a sealed pressure flask. The yellow solution was concentrated until only a small fraction of water remained (a white precipitate appeared). Then, more water was added and the suspension was allowed to stand at 0° C. for 1 hour. After that time, the resulting solid was filtered off and washed with water and diethyl ether to give 5.04 g (53%) of the product as a beige powder. The compound was used as such in the next step.

¹H-NMR (300 MHz, DMSO-d₆): δ [ppm]=0.01-0.14 (m, 1H), 0.23-0.34 (m, 1H), 0.35-0.46 (m, 2H), 0.97-1.10 (m, 1H), 1.36 (s, 9H), 3.25-3.32 (m, 2H), 6.78 (t, 1H), 7.36 (s, 1H), 10.46 (bp, 1H).

LC-MS (Method 3): R$_t$=0.388 min. MS (Mass method 1): m/z=214 (M–tBu+H)⁺

Intermediate 4

Tert-Butyl {[(4R)-4-Cyclopropyl-2,5-Dioxoimidazo-lidin-4-Yl]Methyl}Carbamate

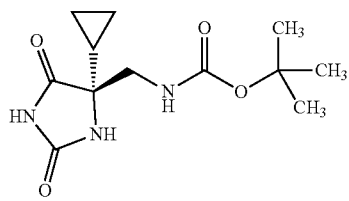 [SMILES: CC(C)(C)OC(=O)NC[C@@]1(C2CC2)NC(=O)NC1=O]

rac-tert-Butyl [(4-cyclopropyl-2,5-dioxoimidazolidin-4-yl)methyl]carbamate (26 g) was dissolved in 2600 ml of Methanol at 50° C., filtered and separated into it's enantiomers by chiral chromatography (Machine: SFC Prep Sepiatec 360; Column: Chiralpak AD 20μ, 450×50 mm; Eluent: CO₂/Methanol 70:30; Flow: 350 ml/min; UV Detection: 210 nm; Backpressure: 130 bar; Oven temperature: 35° C.). The enantiomer eluting at 1.52 minutes was collected. Enantiomeric purity was determined on an analytical scale (Column: Chiralpak AD-H 5μ, 250×4.6 mm; Eluent: CO₂/Methanol 80:20; Flow: 3 ml/min; UV Detection: 210 nm) as 99.9% ee. 8.6 g (33% yield).

LC-MS (Method 8): R$_t$=0.60 min; MS (ESIpos): m/z=270 [M+H]⁺

The absolute stereochemistry was deduced by deprotection (see next intermediate) and synthesis of example 3 from WO2014066151.

Intermediate 5

(5R)-5-(Aminomethyl)-5-Cyclopropylimidazolidine-2,4-Dione Hydrochloride

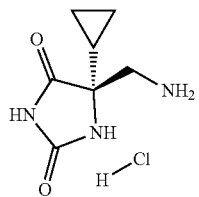

tert-butyl {[(4R)-4-cyclopropyl-2,5-dioxoimidazolidin-4-yl]methyl}carbamate (6 g, 22.28 mmol) was dissolved in 70 ml of dichloromethane and treated with 4N HCl in dioxane (27.85 ml, 111.4 mmol). The mixture was stirred at room temperature over night. The precipitate was filtered off, washed with dichloromethane and dried in vacuo. 4.29 g (94% yield, 100% purity) of the title compound were obtained.

LC-MS (Method 9): $R_t$=0.27 min; MS (ESIpos): m/z=170 [M−HCl+H]$^+$

Intermediate 6

Ethyl 5-(5-Methyl-1,3-Thiazol-4-Yl)-1,3-Oxazole-4-Carboxylate

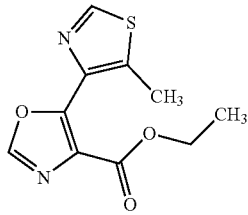 [SMILES: CCOC(=O)c1ncoc1-c1ncsc1C]

5-methyl-1,3-thiazole-4-carboxylic acid (940 mg, 6.57 mmol) dissolved in 10 ml of THF was treated with 1,1,-carbonyl-diimidazole (1.28 g, 7.88 mmol) and stirred at room temperature. After 2 h ethyl isocyanoacetate (790 µl, 7.2 mmol), dissolved in 10 ml of THF, and a solution of lithium bis(trimethylsilyl)amide in THF (6.6 ml, 1.0 M, 6.6 mmol) were added at 0° C. The mixture was allowed to warm to room temperature and stirred over night. The solvent was removed on a rotary evaporator. The residue was taken up with ethyl acetate and washed with water and saturated aqueous sodium chloride solution. The organic layer was dried over sodium sulfate, filtered, Isolute® was added and the solvent was evaporated on a rotary evaporator. The crude product was purified by column chromatography (Machine: Biotage® Isolera One; column: Biotage® SNAP Ultra 50 g; gradient: Cy/EE-gradient, 16% EE-100% EE; flow: 100 ml/min). Product containing samples were united and the solvents were removed on a rotary evaporator. 1.13 g (100% purity, 72% yield) of the title compound were obtained.

LC-MS (Method 7): $R_t$=1.15 min; MS (ESIpos): m/z=239 [M+H]$^+$

Intermediate 7

2-Amino-1-(5-Methyl-1,3-Thiazol-4-Yl)Ethan-1-One-Hydrogen Chloride

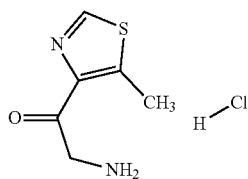

Ethyl 5-(5-methyl-1,3-thiazol-4-yl)-1,3-oxazole-4-carboxylate (1.13 g, 4.74 mmol) was taken up in 25 ml of 6 N hydrochloric acid and stirred at 100° C. After 2 h the solvent was removed on a rotary evaporator and the residue was treated with DCM/MeOH 20:1. The precipitate was filtered off, washed with DCM/MeOH 20:1 and dried in vacuo. 730 mg (98% purity, 79% yield) of the title compound were obtained.

LC-MS (Method 9): $R_t$=0.80 min; MS (ESIpos): m/z=157 [M−HCl+H]$^+$

Intermediate 8

Tert-Butyl [2-(5-Methyl-1,3-Thiazol-4-Yl)-2-Oxo-ethyl]Carbamate

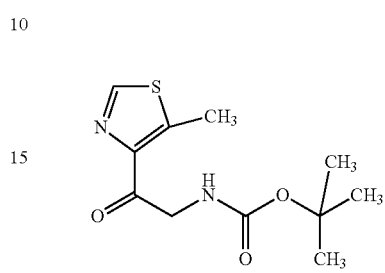

2-amino-1-(5-methyl-1,3-thiazol-4-yl)ethan-1-one-hydrogen chloride (730 mg, 3.79 mmol) dissolved in 15 ml of dichloromethane was treated with di-tert-butyl dicarbonate (960 µl, 4.2 mmol) and triethylamine (1.6 ml, 11 mmol). The mixture was stirred at room temperature. After 2 h the solvent was removed on a rotary evaporator. The residue was taken up with ethyl acetate and washed with water and saturated aqueous sodium chloride solution. The organic layer was dried over sodium sulfate, filtered and evaporated on a rotary evaporator. 980 mg (100% purity, 101% yield) of the title compound were obtained.

LC-MS (Method 7): $R_t$=1.57 min; MS (ESIpos): m/z=257 [M+H]$^+$

Intermediate 9

Rac-Tert-Butyl {[4-(5-Methyl-1,3-Thiazol-4-Yl)-2,5-Dioxoimidazolidin-4-Yl]Methyl}Carbamate

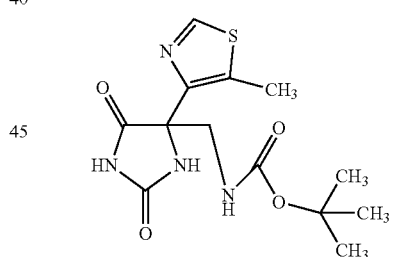

In a microwave vial tert-butyl [2-(5-methyl-1,3-thiazol-4-yl)-2-oxoethyl]carbamate (980 mg, 3.82 mmol) was dissolved in 7 ml of methanol. Potassium cyanide (996 mg, 15.3 mmol) and ammonium carbonate (1.47 g, 15.3 mmol) were added. The vial was sealed and the mixture was stirred at 40° C. for 48 h. Further potassium cyanide (996 mg, 15.3 mmol) and ammonium carbonate (1.47 g, 15.3 mmol) were added and the mixture was stirred for 72 h. Isolute® was added and the solvent was evaporated on a rotary evaporator. The crude product was purified by column chromatography (Machine: Biotage® Isolera One; column: Biotage® SNAP Ultra 50 g; gradient: DCM/MeOH-gradient, 2% MeOH-20% MeOH; flow: 100 ml/min). Product containing samples were united and the solvents were removed on a rotary evaporator. 766 mg (100% purity, 61% yield) of the title compound were obtained.

LC-MS (Method 7): $R_t$=1.09 min; MS (ESIneg): m/z=325 [M−H]⁻

Intermediate 10

Rac-5-(Aminomethyl)-5-(5-Methyl-1,3-Thiazol-4-Yl)Imidazolidine-2,4-Dione Hydrochloride

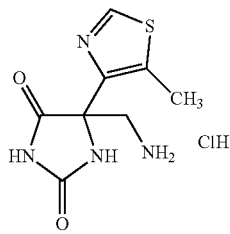

rac-tert-butyl {[4-(5-methyl-1,3-thiazol-4-yl)-2,5-dioxoimidazolidin-4-yl]methyl}carbamate (766 mg, 2.35 mmol) was dissolved in 9 ml of dichloromethane. 4 M hydrochloride acid in 1,4-dioxane (2.9 ml, 4.0 M, 12 mmol) was added and the mixture was stirred for 30 min. The precipitate was filtered off, washed with dichloromethane and dried in vacuo. 640 mg (86% purity, 89% yield) of the title compound were obtained.

LC-MS (Method 9): $R_t$=0.25 min; MS (ESIpos): m/z=227 [M−HCl+H]⁺

Intermediate 11

Ethyl 5-(1-Ethyl-1H-Pyrazol-5-Yl)-1,3-Oxazole-4-Carboxylate

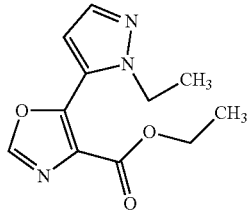 [SMILES: CCOC(=O)c1ncoc1-c1ccnn1CC]

A solution of 1-ethyl-1H-pyrazole-5-carboxylic acid (1.00 g, 7.14 mmol) and 1,1'-carbonyldiimidazole (1.39 g, 8.56 mmol) in 10 ml of THF was stirred for 2 h at room temperature. After that time, a solution of ethyl isocyanoacetate (860 µl, 7.8 mmol) in 10 ml of THE and a solution of lithium bis(trimethylsilyl)amide in THF (7.1 ml, 1.0 M, 7.1 mmol) were added dropwise at 0° C. When the addition was complete the resulting mixture was stirred at room temperature for 2 h. The reaction was concentrated in vacuo and extracted with ethyl acetate. The combined organic layers were dried over sodium sulfate, filtered and concentrated. The crude product was purified by column chromatography (Machine: Biotage® Isolera One; column: Biotage® SNAP Ultra 50 g; gradient: Cy/EE-gradient, 16% EE-100% EE; flow: 100 ml/min). Product containing samples were united and the solvents were removed on a rotary evaporator. 1.30 g (95% purity, 74% yield) of the title compound were obtained.

LC-MS (Method 7): $R_t$=1.23 min; MS (ESIpos): m/z=236 [M+H]⁺

Intermediate 12

2-Amino-1-(1-Ethyl-1H-Pyrazol-5-Yl)Ethan-1-One-Hydrogen Chloride (1/1)

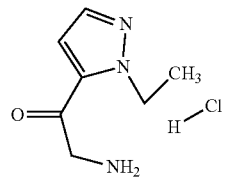

Ethyl 5-(1-ethyl-1H-pyrazol-5-yl)-1,3-oxazole-4-carboxylate (1.30 g, 5.53 mmol) were taken up in 29 ml of 6 N hydrochloric acid and stirred at 100° C. for 2 h. The solvent was removed on a rotary evaporator and the residue was taken up in DCM/MeOH 20:1. The solvent was removed an the residue was dried in vacuo. 1.19 g (114% yield) of the title compound were obtained.

Intermediate 13

Tert-Butyl [2-(1-Ethyl-1H-Pyrazol-5-Yl)-2-Oxoethyl]Carbamate

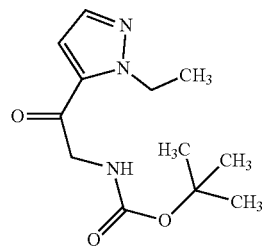 [SMILES: CCn1nccc1C(=O)CNC(=O)OC(C)(C)C]

2-amino-1-(1-ethyl-1H-pyrazol-5-yl)ethan-1-one-hydrogen chloride (1/1) (1.10 g, 5.80 mmol) dissolved in 23 ml of dichloromethane were treated with di-tert-butyl dicarbonate (1.5 ml, 6.4 mmol) and triethylamine (2.4 ml, 17 mmol). The mixture was stirred at room temperature for 2 h. The solvent was removed on a rotary evaporator. The residue was taken up with ethyl acetate and washed with water and saturated aqueous sodium chloride solution. The organic layer was dried over sodium sulfate, filtered and evaporated on a rotary evaporator. The crude product was purified by column chromatography (Machine: Biotage® Isolera One; column: Biotage® SNAP Ultra 25 g; gradient: Cy/EE-gradient, 12% EE-100% EE; flow: 75 ml/min). Product containing samples were united and the solvents were removed on a rotary evaporator. 1.07 g (100% purity, 73% yield) of the title compound were obtained.

LC-MS (Method 9): $R_t$=1.40 min; MS (ESIpos): m/z=254 [M+H]⁺

Intermediate 14

Rac-Tert-Butyl {[4-(1-Ethyl-1H-Pyrazol-5-Yl)-2,5-Dioxoimidazolidin-4-Yl]Methyl}Carbamate

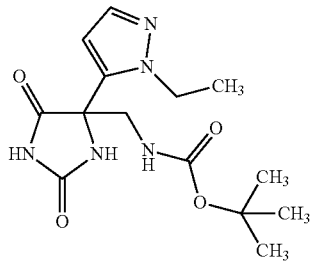

In a microwave vial tert-butyl [2-(1-ethyl-1H-pyrazol-5-yl)-2-oxoethyl]carbamate (1.00 g, 3.95 mmol) was dissolved in 8 ml of methanol. Potassium cyanide (1.03 g, 15.8 mmol) and ammonium carbonate (1.52 g, 15.8 mmol) were added. The vial was sealed and the mixture was stirred at 50° C. for 48 h. The mixture was filtered and the filtrate was purified by preparative HPLC (Column: Chromatorex C18 10 µm 250×30 mm; eluent A=water, B=acetonitrile; gradient: 0.0 min 30% B; 4.5 min 50% B; 11.5 min 70% B; 12 min 100% B; 14.75 min 30% B; flow: 50 ml/min; 0.1% formic acid). Product containing samples were united and the solvents were removed on a rotary evaporator. 137 mg (100% purity, 11% yield) of the title compound were obtained.

LC-MS (Method 7): $R_t$=1.02 min; MS (ESIpos): m/z=324 [M+H]$^+$

Intermediate 15

Rac-5-(Aminomethyl)-5-(1-Ethyl-1H-Pyrazol-5-Yl) Imidazolidine-2,4-Dione-Hydrogen Chloride

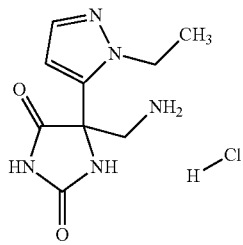

rac-tert-butyl {[4-(1-ethyl-1H-pyrazol-5-yl)-2,5-dioxo-imidazolidin-4-yl]methyl}carbamate (137 mg, 424 µmol) was dissolved in 2 ml of dichloromethane. 4 M hydrochloric acid in 1,4-dioxane (530 µl, 4.0 M, 2.1 mmol) was added and the mixture was stirred over night. The solvent was removed on a rotary evaporator and the residue was dried in vacuo. 142 mg (90% purity, 116% yield) of the title compound were obtained.

LC-MS (Method 9): $R_t$=0.22 min; MS (ESIpos): m/z=224 [M−HCl+H]$^+$

Intermediate 16

Ethyl 5-(4-Methyl-1,3-Thiazol-5-Yl)-1,3-Oxazole-4-Carboxylate

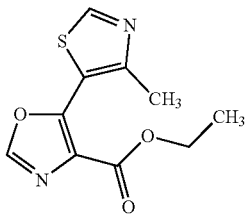 [SMILES: CCOC(=O)c1ncoc1-c1scnc1C]

A solution of 4-methyl-1,3-thiazole-5-carboxylic acid (5.00 g, 34.9 mmol) and 1,1'-carbonyldiimidazole (6.80 g, 41.9 mmol) in 50 ml of THF was stirred for 2 h at room temperature. After that time, a solution of ethyl isocyano-acetate (4.2 ml, 38 mmol) in 50 ml of THE and a solution of lithium bis(trimethylsilyl)amide in THF (35 ml, 1.0 M, 35 mmol) were added dropwise at 0° C. When the addition was complete the resulting mixture was stirred at room temperature over night. The reaction was concentrated in vacuo and extracted with ethyl acetate. The combined organic layers were dried over sodium sulfate, filtered and concentrated. The crude product was purified by column chromatography (Machine: Biotage® Isolera One; column: Biotage® SNAP Ultra 100 g; gradient: Cy/EE-gradient, 12% EE-100% EE; flow: 100 ml/min). Product containing samples were united and the solvents were removed on a rotary evaporator. 5.76 g (100% purity, 69% yield) of the title compound were obtained.

LC-MS (Method 7): $R_t$=1.15 min; MS (ESIpos): m/z=239 [M+H]$^+$

Intermediate 17

2-Amino-1-(4-Methyl-1,3-Thiazol-5-Yl)Ethan-1-One-Hydrogen Chloride

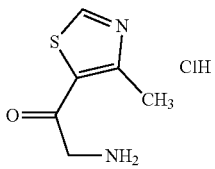

Ethyl 5-(4-methyl-1,3-thiazol-5-yl)-1,3-oxazole-4-carboxylate (5.76 g, 24.2 mmol) were taken up in 130 ml of 6 N hydrochloric acid and stirred at 100° C. for 1 h. The solvent was removed on a rotary evaporator and the residue was taken up in DCM/MeOH 20:1. The precipitate was filtered off, washed with dichloromethane and dried in vacuo. 4.79 g (97% purity, 100% yield) of the title compound were obtained.

LC-MS (Method 9): $R_t$=0.62 min; MS (ESIpos): m/z=157 [M−HCl+H]$^+$

Intermediate 18

Tert-Butyl [2-(4-Methyl-1,3-Thiazol-5-Yl)-2-Oxo-ethyl]Carbamate

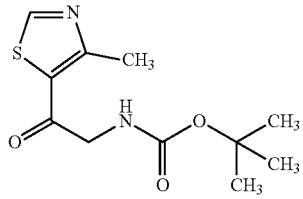

2-amino-1-(4-methyl-1,3-thiazol-5-yl)ethan-1-one-hydrogen chloride (4.79 g, 24.9 mmol) dissolved in 100 ml of dichloromethane were treated with di-tert-butyl dicarbonate (6.3 ml, 27 mmol) and triethylamine (10 ml, 75 mmol). The mixture was stirred at room temperature for 4 h. The solvent was removed on a rotary evaporator. The residue was taken up with ethyl acetate and washed with water and saturated aqueous sodium chloride solution. The organic layer was dried over sodium sulfate, filtered and evaporated on a rotary evaporator. 4.98 g (100% purity, 78% yield) of the title compound were obtained.

LC-MS (Method 7): $R_t$=1.50 min; MS (ESIpos): m/z=257 [M+H]$^+$

Intermediate 19

Rac-Tert-Butyl {[4-(4-Methyl-1,3-Thiazol-5-Yl)-2,5-Dioxoimidazolidin-4-Yl]Methyl}Carbamate

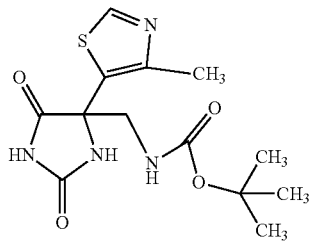

In a microwave vial tert-butyl [2-(4-methyl-1,3-thiazol-5-yl)-2-oxoethyl]carbamate (4.98 g, 19.4 mmol) was dissolved in 30 ml of methanol. Potassium cyanide (5.06 g, 77.7 mmol) and ammonium carbonate (7.47 g, 77.7 mmol) were added. The vial was sealed and the mixture was stirred at 60° C. for 3 d. The crude product was purified by column chromatography (Machine: Biotage® Isolera One; column: Biotage® SNAP Ultra 100 g; gradient: DCM/MeOH-gradient, 2% MeOH-20% MeOH; flow: 100 ml/min). Product containing samples were united and the solvents were removed on a rotary evaporator. 3.00 g (100% purity, 47% yield) of the title compound were obtained.

LC-MS (Method 7): $R_t$=1.11 min; MS (ESIpos): m/z=327 [M+H]$^+$

Intermediate 20

Rac-5-(Aminomethyl)-5-(4-Methyl-1,3-Thiazol-5-Yl)Imidazolidine-2,4-Dione-Hydrogen Chloride

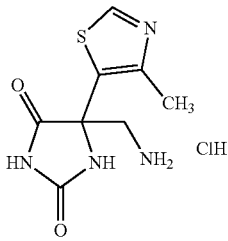

rac-tert-butyl {[4-(4-methyl-1,3-thiazol-5-yl)-2,5-dioxoimidazolidin-4-yl]methyl}carbamate (200 mg, 613 µmol) was dissolved in 3 ml of dichloromethane. 4 M hydrochloric acid in 1,4-dioxane (766 µl, 4.0 M, 3.1 mmol) was added and the mixture was stirred for 2 h. The precipitate was filtered off, washed with dichloromethane and dried in vacuo. 225 mg (95% purity, 133% yield) of the title compound were obtained.

LC-MS (Method 9): $R_t$=0.23 min; MS (ESIpos): m/z=227 [M−HCl+H]$^+$

Intermediate 21

Ethyl 5-[1-(2,2,2-Trifluoroethyl)-1H-Pyrazol-5-Yl]-1,3-Oxazole-4-Carboxylate

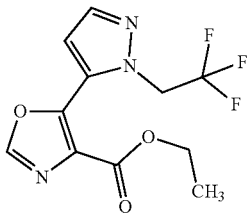 [SMILES: CCOC(=O)c1ncoc1-c1ccnn1CC(F)(F)F]

A solution of 1-(2,2,2-trifluoroethyl)-1H-pyrazole-5-carboxylic acid (1.00 g, 5.15 mmol) and 1,1'-carbonyldiimidazole (1.00 g, 6.18 mmol) in 11 ml of THF was stirred for 2 h at room temperature. After that time, a solution of ethyl isocyanoacetate (620 µl, 5.7 mmol) in 11 ml of THF and a solution of lithium bis(trimethylsilyl)amide in THF (5.2 ml, 1.0 M, 5.2 mmol) were added dropwise at 0° C. When the addition was complete the resulting mixture was stirred at room temperature for 1 h. The reaction was concentrated in vacuo and extracted with ethyl acetate. The combined organic layers were dried over sodium sulfate, filtered and concentrated. The crude product was purified by column chromatography (Machine: Biotage® Isolera One; column: Biotage® SNAP Ultra 25 g; gradient: Cy/EE-gradient, 12% EE-100% EE; flow: 75 ml/min). Product containing samples were united and the solvents were removed on a rotary evaporator. 1.16 g (100% purity, 78% yield) of the title compound were obtained.

LC-MS (Method 7): $R_t$=1.43 min; MS (ESIpos): m/z=290 [M+H]$^+$

Intermediate 22

2-Amino-1-[1-(2,2,2-Trifluoroethyl)-1H-Pyrazol-5-Yl]Ethan-1-One-Hydrogen Chloride

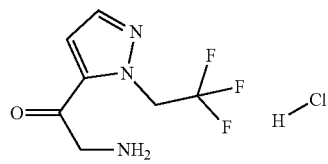

Ethyl 5-[1-(2,2,2-trifluoroethyl)-1H-pyrazol-5-yl]-1,3-oxazole-4-carboxylate (1.16 g, 4.01 mmol) were taken up in 20 ml of 6 N hydrochloric acid and stirred at 100° C. for 1 h. The solvent was removed on a rotary evaporator and the residue was taken up in DCM/MeOH 20:1. The solvent was removed and the residue was dried in vacuo. 1.07 g (100% purity, 110% yield of the title compound were obtained.

LC-MS (Method 9): $R_t$=0.95 min; MS (ESIpos): m/z=208 [M−HCl+H]$^+$

Intermediate 23

Tert-Butyl {2-Oxo-2-[1-(2,2,2-Trifluoroethyl)-1H-Pyrazol-5-Yl]Ethyl}Carbamate

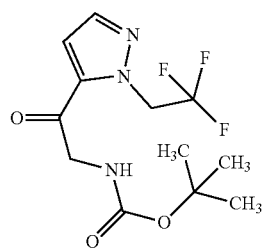 [SMILES: CC(C)(C)OC(=O)NCC(=O)c1ccnn1CC(F)(F)F]

2-amino-1-[1-(2,2,2-trifluoroethyl)-1H-pyrazol-5-yl]ethan-1-one-hydrogen chloride (1.07 g, 4.39 mmol) dissolved in 17 ml of dichloromethane were treated with di-tert-butyl dicarbonate (1.1 ml, 4.8 mmol) and triethylamine (1.8 ml, 13 mmol). The mixture was stirred at room temperature for 3 h. The solvent was removed on a rotary evaporator. The residue was taken up with ethyl acetate and washed with water and saturated aqueous sodium chloride solution. The organic layer was dried over sodium sulfate, filtered and evaporated on a rotary evaporator. 1.37 g (71% purity, 72% yield) of the title compound were obtained.

LC-MS (Method 9): $R_t$=1.52 min, MS (ESIpos): m/z=308 [M+H]$^+$

Intermediate 24

Rac-Tert-Butyl({2,5-Dioxo-4-[1-(2,2,2-Trifluoroethyl)-1H-Pyrazol-5-Yl]Imidazolidin-4-Yl}Methyl)Carbamate

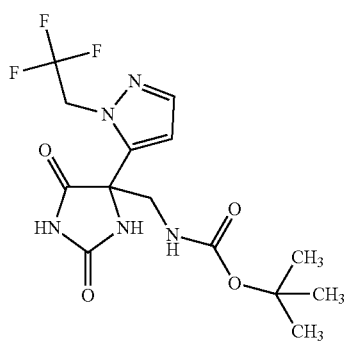 [SMILES: CC(C)(C)OC(=O)NCC1(c2ccnn2CC(F)(F)F)NC(=O)NC1=O]

In a microwave vial tert-butyl {2-oxo-2-[1-(2,2,2-trifluoroethyl)-1H-pyrazol-5-yl]ethyl}carbamate (689 mg, 2.24 mmol) was dissolved in 5 ml of methanol. Potassium cyanide (730 mg, 11.2 mmol) and ammonium carbonate (1.08 g, 11.2 mmol) were added. The vial was sealed and the mixture was stirred at 50° C. for 48 h. The mixture was filtered and the filtrate was purified by preparative HPLC (Column: Chromatorex C18 10 µm 250×30 mm; eluent A=water, B=acetonitrile; gradient: 0.0 min 30% B; 4.5 min 50% B; 11.5 min 70% B; 12 min 100% B; 14.75 min 30% B; flow: 50 ml/min; 0.1% formic acid). Product containing samples were united and the solvents were removed on a rotary evaporator. 195 mg (100% purity, 23% yield) of the title compound were obtained.

LC-MS (Method 7): $R_t$=1.21 min; MS (ESIpos): m/z=378 [M+H]$^+$

Intermediate 25

Rac-5-(Aminomethyl)-5-[1-(2,2,2-Trifluoroethyl)-1H-Pyrazol-5-Yl]Imidazolidine-2,4-Dione Hydrochloride

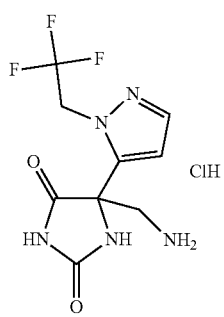 [SMILES: NCC1(c2ccnn2CC(F)(F)F)NC(=O)NC1=O ; Cl]

rac-tert-butyl({2,5-dioxo-4-[1-(2,2,2-trifluoroethyl)-1H-pyrazol-5-yl]imidazolidin-4-yl}methyl)carbamate (195 mg, 517 µmol) was dissolved in 2 ml of dichloromethane. 4 M hydrochloric acid in 1,4-dioxane (650 µl, 4.0 M, 2.6 mmol) was added and the mixture was stirred for 3 h. The solvent was removed on a rotary evaporator. The residue was taken up in dichloromethane, the solvent was removed and the residue was dried in vacuo. 155 mg (96% purity, 92% yield) of the title compound were obtained.

LC-MS (Method 9): $R_t$=0.23 min; MS (ESIpos): m/z=278 [M−HCl+H]$^+$

Intermediate 26

Ent-Tert-Butyl {[4-(4-Methyl-1,3-Thiazol-5-Yl)-2,5-Dioxoimidazolidin-4-Yl]Methyl}Carbamate

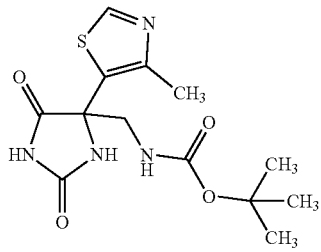 [SMILES: Cc1ncsc1C1(CNC(=O)OC(C)(C)C)NC(=O)NC1=O]

Enantiomeric separation of rac-tert-butyl {[4-(4-methyl-1,3-thiazol-5-yl)-2,5-dioxoimidazolidin-4-yl]methyl}carbamate (2.80 g, 8.58 mmol) was done using the following method:

Column: Daicel Chiralpak AD 20 μm 500×50 mm
Solvent: 60% CO$_2$: 40% methanol
Flow: 400 ml/min
Backpressure: 130 bar
Oven temperature: 35° C.
UV: 210 nm Product containing samples were united, the solvents were evaporated and the residue was lyophilized.

Enantiomer 1:
1.33 g (100% purity, 48% yield)
LC-MS (Method 8): $R_t$=0.55 min; MS (ESIpos): m/z=327 [M+H]$^+$
Chiral HPLC (Column: Chiralpack AD; solvent: 20% methanol: 80% CO$_2$; flow: 3 ml/min; UV: 210 nm): $R_t$=0.938 min, >99.0% ee Enantiomer 2:
1.17 g (100% purity, 42% yield)
LC-MS (Method 8): $R_t$=0.55 min; MS (ESIpos): m/z=327 [M+H]$^+$
HPLC (Column: ChiralpackAD; solvent: 20% methanol: 80% CO$_2$; flow: 3 ml/min; UV: 210 nm): $R_t$=2.074 min, >99.0% ee Intermediate 27

Ent-5-(Aminomethyl)-5-(4-Methyl-1,3-Thiazol-5-Yl)Imidazolidine-2,4-Dione Hydrochloride (Enantiomer 2)

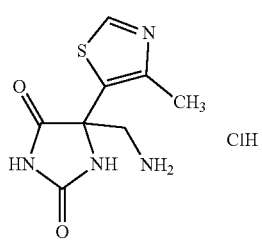

ent-tert-butyl {[4-(4-methyl-1,3-thiazol-5-yl)-2,5-dioxoimidazolidin-4-yl]methyl}carbamate (Enantiomer 2) (1.17 g, 3.58 mmol) was dissolved in 18 ml of dichloromethane and treated with 4 N HCl in dioxane (4.5 ml, 4.0 M, 18 mmol). The mixture was stirred at room temperature for 2 h. The precipitate was filtered, washed with dichloromethane and dried in vacuo. 1.01 g (100% purity, 107% yield) of the title compound were obtained.

LC-MS (Method 9): $R_t$=0.22 min; MS (ESIpos): m/z=227 [M−HCl+H]$^+$

Intermediate 28

Rac-Ethyl 5-(2-Methylcyclobutyl)-1,3-Oxazole-4-Carboxylate

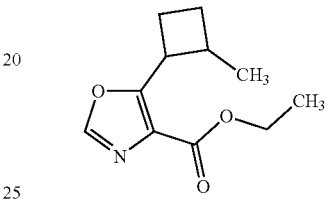

A solution of 2-methylcyclobutane-1-carboxylic acid (2.30 g, 20.1 mmol) and 1,1'-carbonyldiimidazole (3.92 g, 24.2 mmol) in 30 ml of THF was stirred for 2 h at room temperature. After that time, a solution of ethyl isocyanoacetate (2.4 ml, 22 mmol) in 30 ml of THF and a solution of lithium bis(trimethylsilyl)amide in THF (20 ml, 1.0 M, 20 mmol) were added dropwise at 0° C. When the addition was complete the resulting mixture was stirred at room temperature for 1 h. The solvent was removed on a rotary evaporator. The residue was taken up with ethyl acetate and washed with water and saturated aqueous sodium chloride solution. The organic layer was dried over sodium sulfate, filtered and evaporated on a rotary evaporator. The crude product was purified by column chromatography (Machine: Biotage® Isolera One; column: Biotage® SNAP Ultra 100 g; gradient: Cy/EE-gradient, 12% EE-100% EE; flow: 100 ml/min). Product containing samples were united and the solvents were removed on a rotary evaporator. 1.72 g (91% purity, 37% yield) of the title compound were obtained.

LC-MS (Method 7): $R_t$=1.79 min; MS (ESIpos): m/z=210 [M+H]$^+$

Intermediate 29

Rac-2-Amino-1-(2-Methylcyclobutyl)Ethanone Hydrochloride

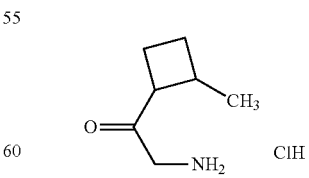

rac-ethyl 5-(2-methylcyclobutyl)-1,3-oxazole-4-carboxylate (1.09 g, 65% purity, 3.39 mmol) were taken up in 20 ml of 6 N hydrochloric acid and stirred at 100° C. for 2 h. The solvent was removed on a rotary evaporator and the residue was taken up in dichloromethane. The solvent was removed and the residue was dried in vacuo. 675 mg (88% purity, 107% yield) of the title compound were obtained.

LC-MS (Method 9): $R_t$=1.00 min; MS (ESIpos): m/z=128 [M−HCl+H]$^+$

Intermediate 30

Rac-Tert-Butyl [2-(2-Methylcyclobutyl)-2-Oxoethyl]Carbamate

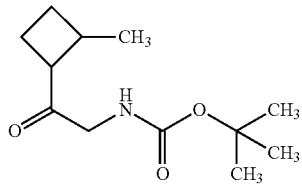

rac-2-amino-1-(2-methylcyclobutyl)ethanone hydrochloride (675 mg, 4.12 mmol) dissolved in 15 ml of dichloromethane was treated with di-tert-butyl dicarbonate (1.0 ml, 4.5 mmol) and triethylamine (1.7 ml, 12 mmol). The mixture was stirred at room temperature for 4 h. The solvent was removed on a rotary evaporator. The residue was taken up with ethyl acetate and washed with water and saturated aqueous sodium chloride solution. The organic layer was dried over sodium sulfate, filtered and evaporated on a rotary evaporator. 871 g (97% purity, 90% yield) of the title compound were obtained.

GC-MS (Method A): $R_t$=4.97 min; MS (EI-MS-POS): m/z=171 [M−C$_4$H$_8$]$^+$

Intermediate 31

Diamix-Tert-Butyl {[4-(2-Methylcyclobutyl)-2,5-Dioxoimidazolidin-4-Yl]Methyl}Carbamate

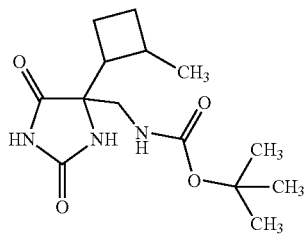

In a microwave vial rac-tert-butyl [2-(2-methylcyclobutyl)-2-oxoethyl]carbamate (870 mg, 3.83 mmol) was dissolved in 5 ml of methanol. Potassium cyanide (997 mg, 15.3 mmol) and ammonium carbonate (1.47 g, 15.3 mmol) were added. The vial was sealed and the mixture was stirred at 60° C. over night. The mixture was filtered and the filtrate was purified by preparative HPLC (Column: Chromatorex C18 10 µm 250×30 mm; eluent A=water with 0.1% formic acid, B=acetonitrile; gradient: 0.0 min 30% B; 4.5 min 50% B; 11.5 min 70% B; 12 min 100% B; 14.75 min 30% B; flow: 50 ml/min). Product containing samples were united and the solvents were removed on a rotary evaporator. 361 mg (100% purity, 32% yield) of the title compound were obtained.

LC-MS (Method 7): $R_t$=1.40 min; MS (ESIneg): m/z=296 [M−H]$^-$ $^1$H-NMR (600 MHz, DMSO-d6) δ [ppm]: 0.871 (1.58), 0.882 (1.60), 1.009 (1.88), 1.020 (1.90), 1.363 (16.00), 1.595 (0.45), 2.113 (0.46), 2.128 (0.60), 2.143 (0.49), 3.086 (0.41), 3.124 (0.51), 3.134 (0.49), 7.708 (0.41), 7.736 (0.55).

Intermediate 32

Diamix-5-(Aminomethyl)-5-(2-Methylcyclobutyl)Imidazolidine-2,4-Dione Hydrochloride

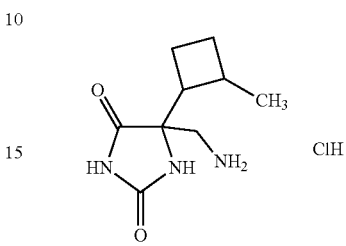

diamix-tert-butyl {[4-(2-methylcyclobutyl)-2,5-dioxoimidazolidin-4-yl]methyl}carbamate (360 mg, 1.21 mmol) was dissolved in 6 ml of dichloromethane and treated with 4 N HCl in dioxane (1.5 ml, 4.0 M, 6.1 mmol). The mixture was stirred at room temperature for 2 h. The solvent was removed on a rotary evaporator. The residue was taken up with dichloromethane, the solvent was removed and the residue was dried in vacuo. 294 mg (100% purity, 104% yield) of the title compound were obtained.

LC-MS (Method 9): $R_t$=0.52 min; MS (ESIpos): m/z=198 [M−HCl+H]$^+$

Intermediate 33

Ethyl 5-(1,5-Dimethyl-1H-Pyrazol-4-Yl)-1,3-Oxazole-4-Carboxylate

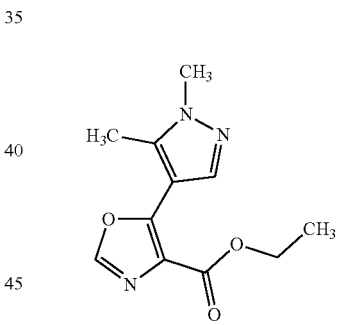

A solution of 1,5-dimethyl-1H-pyrazole-4-carboxylic acid (1.00 g, 7.14 mmol) and 1,1'-carbonyldiimidazole (1.39 g, 8.56 mmol) in 11 ml of THF was stirred for 2 h at room temperature. After that time, a solution of ethyl isocyanoacetate (860 µl, 7.8 mmol) in 11 ml of THF and a solution of lithium bis(trimethylsilyl)amide in THF (7.1 ml, 1.0 M, 7.1 mmol) were added dropwise at 0° C. When the addition was complete the resulting mixture was stirred at room temperature for 1 h. The solvent was removed on a rotary evaporator. The residue was taken up with ethyl acetate and washed with water and saturated aqueous sodium chloride solution. The organic layer was dried over sodium sulfate, filtered and evaporated on a rotary evaporator. The crude product was purified by column chromatography (Machine: Biotage® Isolera One; column: Biotage® SNAP Ultra 50 g; gradient: DCM/MeOH-gradient, 2% MeOH-20% MeOH; flow: 100 ml/min). Product containing samples were united and the solvents were removed on a rotary evaporator. 1.53 g (75% purity, 69% yield) of the title compound were obtained.

LC-MS (Method 9): $R_t$=1.05 min; MS (ESIpos): m/z=236 [M+H]$^+$

Intermediate 34

2-Amino-1-(1,5-Dimethyl-1H-Pyrazol-4-Yl)Ethan-1-One-Hydrogen Chloride

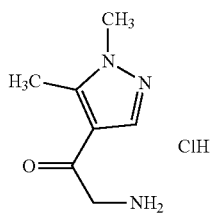

Ethyl 5-(1,5-dimethyl-1H-pyrazol-4-yl)-1,3-oxazole-4-carboxylate (1.53 g, 75% purity, 4.89 mmol) was taken up in 22 ml of 6 N hydrochloric acid and stirred at 100° C. for 1 h. The solvent was removed on a rotary evaporator and the residue was taken up in DCM/MeOH 20:1. The precipitate was filtered, washed with dichloromethane and dried in vacuo. 762 mg (97% purity, 80% yield) of the title compound were obtained.

LC-MS (Method 9): $R_t$=0.64 min; MS (ESIpos): m/z=154 [M−HCl+H]$^+$

Intermediate 35

Tert-Butyl [2-(1,5-Dimethyl-1H-Pyrazol-4-Yl)-2-Oxoethyl]Carbamate

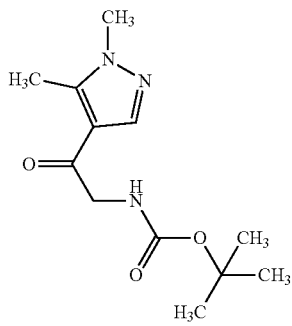 [SMILES: Cc1c(C(=O)CNC(=O)OC(C)(C)C)cnn1C]

2-amino-1-(1,5-dimethyl-1H-pyrazol-4-yl)ethan-1-one-hydrogen chloride (762 mg, 4.02 mmol) dissolved in 15 ml of dichloromethane was treated with di-tert-butyl dicarbonate (1.0 ml, 4.4 mmol) and triethylamine (1.7 ml, 12 mmol). The mixture was stirred at room temperature over night. The solvent was removed on a rotary evaporator. The residue was taken up with ethyl acetate and washed with water and saturated aqueous sodium chloride solution. The organic layer was dried over sodium sulfate, filtered and evaporated on a rotary evaporator. 980 mg (100% purity, 96% yield) of the title compound were obtained.

LC-MS (Method 9): $R_t$=1.22 min; MS (ESIpos): m/z=254 [M+H]$^+$

Intermediate 36

Rac-Tert-Butyl {[4-(1,5-Dimethyl-1H-Pyrazol-4-Yl)-2,5-Dioxoimidazolidin-4-Yl]Methyl}Carbamate

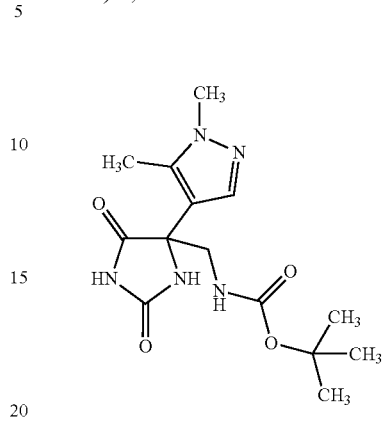

In a microwave vial tert-butyl [2-(1,5-dimethyl-1H-pyrazol-4-yl)-2-oxoethyl]carbamate (980 mg, 3.87 mmol) was dissolved in 10 ml of methanol. Potassium cyanide (1.26 g, 19.3 mmol) and ammonium carbonate (1.86 g, 19.3 mmol) were added. The vial was sealed and the mixture was stirred at 60° C. for 4 d. Isolute® was added and the solvent was evaporated on a rotary evaporator. The crude product was purified by column chromatography (Machine: Biotage® Isolera One; column: Biotage® SNAP Ultra 50 g; gradient: DCM/MeOH-gradient, 2% MeOH-20% MeOH; flow: 100 ml/min). Product containing samples were united and the solvents were removed on a rotary evaporator. 281 mg (100% purity, 22% yield) of the title compound were obtained.

LC-MS (Method 8): $R_t$=0.54 min; MS (ESIpos): m/z=324 [M+H]$^+$

Intermediate 37

Rac-5-(Aminomethyl)-5-(1,5-Dimethyl-1H-Pyrazol-4-Yl)Imidazolidine-2,4-Dione Hydrochloride

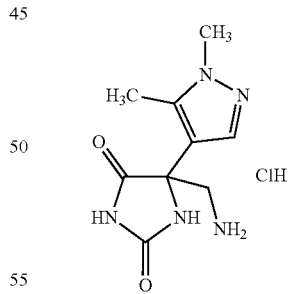

rac-tert-butyl {[4-(1,5-dimethyl-1H-pyrazol-4-yl)-2,5-dioxoimidazolidin-4-yl]methyl}carbamate (281 mg, 869 μmol) was dissolved in 4.5 ml of dichloromethane and treated with 4 N HCl in dioxane (1.1 ml, 4.0 M, 4.3 mmol). The mixture was stirred at room temperature for 4 h. The precipitate was filtered, washed with dichloromethane and dried in vacuo. 237 mg (97% purity, 102% yield) of the title compound were obtained.

LC-MS (Method 9): $R_t$=0.24 min; MS (ESIpos): m/z=224 [M−HCl+H]$^+$

Intermediate 38

Ethyl 5-(2,4-Dimethyl-1,3-Thiazol-5-Yl)-1,3-Oxazole-4-Carboxylate

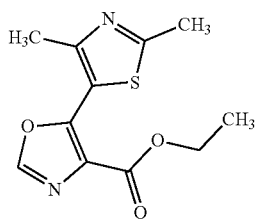 [SMILES: CCOC(=O)c1ncoc1-c1sc(C)nc1C]

2,4-dimethyl-1,3-thiazole-5-carboxylic acid (950 mg, 6.04 mmol) and 1,1'-carbonyldiimidazole (1.18 g, 7.25 mmol) in 10 ml of THF was stirred for 2 h at room temperature. After that time, a solution of ethyl isocyanoacetate (730 µl, 6.6 mmol) in 10 ml of THF and a solution of lithium bis(trimethylsilyl)amide in THF (6.0 ml, 1.0 M, 6.0 mmol) were added dropwise at 0° C. When the addition was complete the resulting mixture was stirred at room temperature for 1 h. The reaction was concentrated in vacuo and extracted between water and ethyl acetate. The combined organic layers were dried over sodium sulfate, filtered and concentrated. The crude product was purified by column chromatography (Machine: Biotage® Isolera One; column: Biotage® SNAP Ultra 25 g; gradient: Cy/EE-gradient, 12% EE-100% EE; flow: 75 ml/min). Product containing samples were united and the solvents were removed on a rotary evaporator. 1.06 g (100% purity, 70% yield) of the title compound were obtained.

LC-MS (Method 7): $R_t$=1.30 min; MS (ESIpos): m/z=253 [M+H]$^+$

Intermediate 39

2-Amino-1-(2,4-Dimethyl-1,3-Thiazol-5-Yl)Ethan-1-One-Hydrogen Chloride

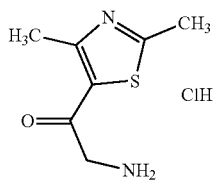

Ethyl 5-(2,4-dimethyl-1,3-thiazol-5-yl)-1,3-oxazole-4-carboxylate (1.06 g, 4.20 mmol) were taken up in 20 ml of 6 N hydrochloric acid and stirred 1 h at 100° C. The solvent was removed on a rotary evaporator and the residue was taken up in dichloromethane/methanol 20:1. The solvent was removed and the residue was dried in vacuo. 1.07 g (100% purity, 123% yield) of the title compound were obtained.

LC-MS (Method 9): $R_t$=0.78 min; MS (ESIpos): m/z=171 [M–HCl+H]$^+$

Intermediate 40

Tert-Butyl [2-(2,4-Dimethyl-1,3-Thiazol-5-Yl)-2-Oxoethyl]Carbamate

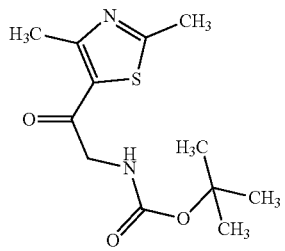 [SMILES: Cc1nc(C)c(C(=O)CNC(=O)OC(C)(C)C)s1]

2-amino-1-(2,4-dimethyl-1,3-thiazol-5-yl)ethan-1-one-hydrogen chloride (1.07 g, 5.18 mmol) dissolved in 20 ml of dichloromethane were treated with di-tert-butyl dicarbonate (1.3 ml, 5.7 mmol) and triethylamine (2.2 ml, 16 mmol). The mixture was stirred at room temperature for 3 h. The solvent was removed on a rotary evaporator. The residue was taken up with ethyl acetate and washed with water and saturated aqueous sodium chloride solution. The organic layer was dried over sodium sulfate, filtered and evaporated on a rotary evaporator. 1.30 g (100% purity, 93% yield) of the title compound were obtained.

LC-MS (Method 9): $R_t$=1.37 min; MS (ESIpos): m/z=271 [M+H]$^+$

Intermediate 41

Rac-Tert-Butyl {[4-(2,4-Dimethyl-1,3-Thiazol-5-Yl)-2,5-Dioxoimidazolidin-4-Yl]Methyl}Carbamate

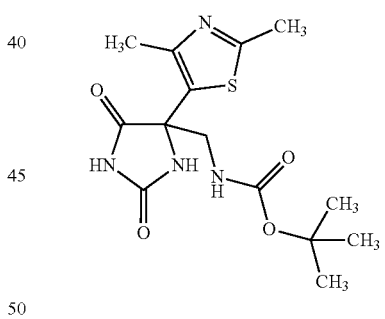

In a microwave vial tert-butyl [2-(2,4-dimethyl-1,3-thiazol-5-yl)-2-oxoethyl]carbamate (1.30 g, 4.82 mmol) was dissolved in 10 ml of methanol. Potassium cyanide (1.57 g, 24.1 mmol) and ammonium carbonate (2.31 g, 24.1 mmol) were added. The vial was sealed and the mixture was stirred at 60° C. over night. Isolute® was added and the solvent was evaporated on a rotary evaporator. The crude product was purified by column chromatography (Machine: Biotage® Isolera One; column: Biotage® SNAP Ultra 50 g; gradient: DCM/MeOH-gradient, 2% MeOH-20% MeOH; flow: 100 ml/min). Product containing samples were united and the solvents were removed on a rotary evaporator. 459 mg (100% purity, 28% yield) of the title compound were obtained.

LC-MS (Method 7): $R_t$=1.08 min; MS (ESIpos): m/z=341 [M+H]$^+$

Intermediate 42

Rac-5-(Aminomethyl)-5-(2,4-Dimethyl-1,3-Thiazol-5-Yl)Imidazolidine-2,4-Dione Hydrochloride

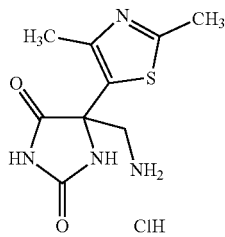 [SMILES: Cc1nc(C)c(C2(CN)NC(=O)NC2=O)s1 ; Cl]

rac-tert-butyl {[4-(2,4-dimethyl-1,3-thiazol-5-yl)-2,5-di-oxoimidazolidin-4-yl]methyl}carbamate (459 mg, 1.35 mmol) was dissolved in 7 ml of dichloromethane. 4 M hydrochloride acid in 1,4-dioxane (1.7 ml, 4.0 M, 6.7 mmol) was added and the mixture was stirred f or 2 h. The precipitate was filtered off, washed with dichloromethane and dried in vacuo. 404 mg (100% purity, 108% yield) of the title compound were obtained.

LC-MS (Method 9): $R_t$=0.26 min; MS (ESIpos): m/z=241 [M–HCl+H]$^+$

Intermediate 43

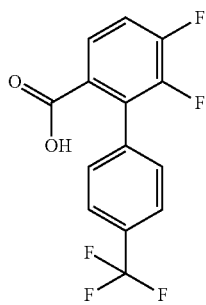 [SMILES: O=C(O)c1ccc(F)c(F)c1-c1ccc(C(F)(F)F)cc1]

To a suspension of [4-(trifluoromethyl)phenyl]boronic acid (601 mg, 3.16 mmol) and 2-bromo-3,4-difluorobenzoic acid (500 mg, 2.11 mmol) in 1,4-dioxane (13 ml) was added, under argon, a solution of K3PO4 in water (4.2 ml, 1.5 M, 6.3 mmol), dichlorobis(triphenylphosphin)palladium (II) (148 mg, 211 µmol, CAS 13965-03-2) and XPhos (101 mg, 211 µmol, CAS 564483-18-7). The reaction mixture was first stirred for 3 h at 80° C., then overnight at RT. The resulting mixture was filtered through celite and the filtrate was concentrated in vacuo. The residue was purified by preparative HPLC (Method 2f). 404 mg (100% purity, 63% yield) of the desired product was obtained LC-MS (Method 7): $R_t$=1.98 min; MS (ESIneg): m/z=301 [M–H]$^-$ $^1$H-NMR (600 MHz, DMSO-d6) δ [ppm]: 0.005 (0.65), 2.070 (0.85), 2.516 (0.59), 2.519 (0.56), 2.523 (0.49), 2.572 (0.46), 7.561 (12.82), 7.574 (14.36), 7.589 (0.47), 7.600 (2.15), 7.615 (4.15), 7.629 (4.31), 7.644 (2.94), 7.659 (0.51), 7.775 (3.26), 7.777 (3.45), 7.784 (3.80), 7.786 (3.66), 7.790 (3.27), 7.792 (3.21), 7.798 (3.48), 7.801 (3.94), 7.806 (16.00), 7.820 (14.36), 13.054 (0.73).

Intermediate 44

Tert-Butyl (2-Oxopentyl)Carbamate

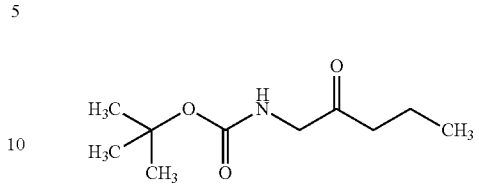

6.90 mL (14.00 mmol) of propylmagnesium chloride (2M in diethyl ether) was slowly added drop wise at 0° C. to a solution of 1.50 g (6.87 mmol) of tert-butyl {2-[methoxy (methyl)amino]-2-oxoethyl}carbamate in 10 mL of anhydrous tetrahydrofuran under nitrogen atmosphere and the mixture was stirred at room temperature for 10 hours. The reaction was quenched with saturated ammonium chloride (aq.) and the resulting slurry was extracted with ethyl acetate. The combined organic extracts were dried over magnesium sulfate, filtered, concentrated and chromatographed in heptane/ethyl acetate mixtures (potassium permanganate stain required) to afford 0.55 g (40%) of the expected compound as a colourless oil.

$^1$H-NMR (300 MHz, DMSO-d$_6$): δ [ppm]=0.84 (t, 3H), 1.38 (s, 9H), 1.47 (q, 2H), 2.35 (t, 2H), 3.71 (d, 2H), 7.01 (t, 1H).

LC-MS (Method 3): $R_t$=0.682 min. MS (Mass method 1): m/z=224 (M+Na)+

Intermediate 45

Rac-Tert-Butyl {[2,5-Dioxo-4-Propylimidazolidin-4-Yl]Methyl}Carbamate

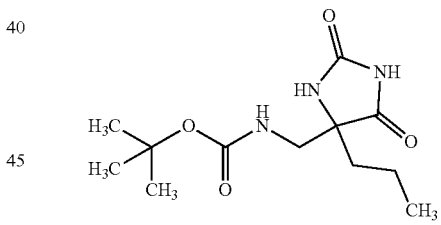

To a stirring solution of 3.94 g (41.00 mmol) of ammonium carbonate and 0.73 g (13.70 mmol) of ammonium chloride in 10 mL of water placed into a sealed flask, was added 0.55 g (2.73 mmol) of tert-butyl (2-oxopentyl)carbamate in 10 mL of ethanol. After 15 min, 0.80 g (12.30 mmol) of potassium cyanide was added and the mixture was heated at 60° C. for 16 hours. The organic solvent was removed and the resulting aqueous phase was allowed to stand at 0° C. for 12 hours. A white precipitate appeared after that time, which was collected by filtration giving 0.60 g (81%) of the product as a white crystalline solid. The compound was used as such in the next step.

$^1$H-NMR (300 MHz, DMSO-d$_6$): δ [ppm]=0.84 (t, 3H), 0.99-1.10 (m, 1H), 1.23-1.33 (m, 1H), 1.36 (s, 9H), 1.40-1.55 (m, 2H), 3.12 (d, 2H), 6.78 (bp, 1H), 7.55 (s, 1H), 10.55 (bp, 1H).

LC-MS (Method 3): $R_t$=0.513 min. MS (Mass method 1): m/z=272 (M+H)$^+$

Intermediate 46

Rac-5-(Aminomethyl)-5-Propylimidazolidine-2,4-Dione Hydrochloride

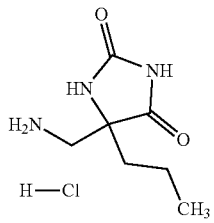

2.80 mL (11.00 mmol) of 4M hydrochloric acid in dioxane were added to a solution of 0.60 g (2.21 mmol) of rac-tert-Butyl {[2,5-dioxo-4-propylimidazolidin-4-yl]methyl}carbamate in 20 mL of dichloromethane and the mixture was stirred at room temperature for 72 hours. The resulting precipitate was filtered off and washed with dichloromethane, ethyl acetate and diethyl ether to afford 0.45 g (98%) of the product as a white powder. The compound was used in the next step without further purification.

$^1$H-NMR (300 MHz, DMSO-d$_6$): δ [ppm]=0.89 (t, 3H), 1.00-1.16 (m, 1H), 1.20-1.37 (m, 1H), 1.50-1.68 (m, 2H), 2.90 (d, 1H), 3.08 (d, 1H), 7.94 (s, 1H), 8.09 (bp, 3H), 10.99 (bp, 1H).

LC-MS (Method 3): R$_t$=0.122 min. MS (Mass method 1): m/z=172 (M−HCl+H)$^+$

Intermediate 47

1-Azido-3,3-Dimethylbutan-2-One

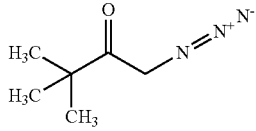

0.78 g (11.98 mmol) of sodium azide were suspended in 30 mL of acetone and 1.65 g (9.21 mmol) of 1-bromopinacolone were added. The resulting mixture was stirred at room temperature for 4 hours. The precipitate was filtered off and discarded and the filtrates were concentrated in vacuo to give 1.15 g (88%) of the product as a pale yellow oil. The compound was used as such in the next step.

$^1$H-NMR (300 MHz, DMSO-d$_6$): δ [ppm]=1.10 (s, 9H), 4.38 (s, 2H).

LC-MS (Method 3): R$_t$=0.138 min. MS (Mass method 1): m/z=no ionisation

Intermediate 48

Rac-5-(Azidomethyl)-5-Tert-Butylimidazolidine-2,4-Dione

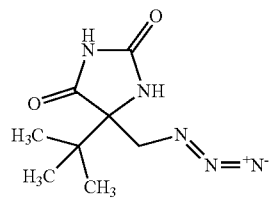

To a stirring solution of 25.52 g (0.26 mol) of ammonium carbonate and 3.79 g (0.07 mol) of ammonium chloride in 30 mL of water previously placed in a sealed tube was added a solution of 2.50 g (0.02 mol) of 1-azido-3,3-dimethylbutan-2-one in 30 mL of ethanol. After 15 min of stirring at room temperature, 5.19 g (0.08 mol) of potassium cyanide were added and the flask was sealed and stirred at 60° C. for 16 hours. After that time, the organic solvent was removed and the resulting precipitate was filtered off and washed with water to give 2.40 g (64%) of the product as a light brown solid. The compound was used as such in the next step.

$^1$H-NMR (300 MHz, DMSO-d$_6$): δ [ppm]=0.93 (s, 9H), 3.65 (dd, 2H), 8.13 (s, 1H), 10.72 (s, 1H).

LC-MS (Method 3): R$_t$=0.398 min. MS (Mass method 1): m/z=212 (M+H)$^+$

Intermediate 49

Rac-5-(Aminomethyl)-5-Tert-Butylimidazolidine-2,4-Dione

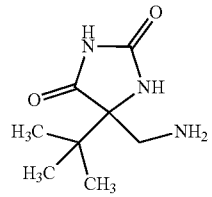

2.40 g (11.40 mmol) of rac-5-(azidomethyl)-5-tert-butyl-imidazolidine-2,4-dione and 2.98 g (11.40 mmol) of triphenylphosphine were dissolved in 40 mL of tetrahydrofuran and 8 mL of water and the mixture was stirred at 65° C. for 4 h. The solvent was removed and the pure compound was precipitated with dichloromethane/methanol 9:1 to give 1.30 g (61%) of the product as a white powder. The compound was used in the next step without further purification.

$^1$H-NMR (300 MHz, DMSO-d$_6$): δ [ppm]=0.91 (s, 9H), 1.22 (bp, 2H), 2.73 (d, 1H), 2.93 (d, 1H), 7.59 (s, 1H), 10.39 (bp, 1H).

LC-MS (Method 3): R$_t$=0.239 min. MS (Mass method 1): m/z=186 (M+H)$^+$

Intermediate 50

Ethyl 5-(Oxan-4-Yl)-1,3-Oxazole-4-Carboxylate

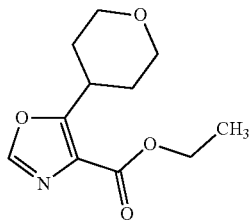 [SMILES: CCOC(=O)c1ncoc1C1CCOCC1]

Oxane-4-carboxylic acid (500 mg, 3.84 mmol) and 1,1'-carbonyldiimidazole (748 mg, 4.61 mmol) in 10 ml of THF was stirred for 2 h at room temperature. After that time, a solution of ethyl isocyanoacetate (460 µl, 4.2 mmol) in 10 ml of THF and a solution of lithium bis(trimethylsilyl)amide in THF (3.8 ml, 1.0 M, 3.8 mmol) were added dropwise at 0° C. When the addition was complete the resulting mixture was stirred at room temperature over night. The reaction was concentrated in vacuo and extracted between water and ethyl acetate. The combined organic layers were dried over sodium sulfate, filtered and concentrated. The crude product was purified by column chromatography (Machine: Biotage® Isolera One; column: Biotage® SNAP Ultra 25 g; gradient: Cy/EE-gradient, 12% EE-100% EE; flow: 75 ml/min). Product containing samples were united and the solvents were removed on a rotary evaporator. 680 mg (100% purity, 79% yield) of the title compound were obtained.

LC-MS (Method 7): $R_t$=1.15 min; MS (ESIpos): m/z=226 [M+H]$^+$

Intermediate 51

2-Amino-1-(Oxan-4-Yl)Ethan-1-One-Hydrogen Chloride

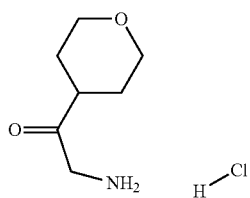

Ethyl 5-(oxan-4-yl)-1,3-oxazole-4-carboxylate (680 mg, 3.02 mmol) were taken up in 10 ml of 6 N hydrochloric acid and stirred 1 h at 100° C. The solvent was removed on a rotary evaporator and the residue was dried in vacuo. 590 mg (109% yield) of the title compound were obtained.

Intermediate 52

Tert-Butyl [2-(Oxan-4-Yl)-2-Oxoethyl]Carbamate

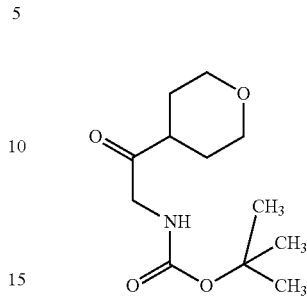

2-amino-1-(oxan-4-yl)ethan-1-one-hydrogen chloride (590 mg, 3.28 mmol) dissolved in 11 ml of dichloromethane were treated with di-tert-butyl dicarbonate (910 µl, 3.9 mmol) and triethylamine (1.4 ml, 9.9 mmol). The mixture was stirred at room temperature over night. The solvent was removed on a rotary evaporator. The residue was taken up with ethyl acetate and washed with water and saturated aqueous sodium chloride solution. The organic layer was dried over sodium sulfate, filtered and evaporated on a rotary evaporator. 780 mg (98% yield) of the title compound were obtained.

Intermediate 53

Rac-Tert-Butyl {[2,5-Dioxo-4-(Tetrahydro-2H-Pyran-4-Yl)Imidazolidin-4-Yl]Methyl}Carbamate

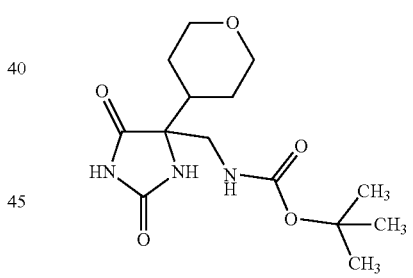

In a microwave vial tert-butyl [2-(oxan-4-yl)-2-oxoethyl]carbamate (785 mg, 3.23 mmol) was dissolved in 9 ml of methanol. Potassium cyanide (1.05 g, 16.1 mmol) and ammonium carbonate (1.55 g, 16.1 mmol) were added. The vial was sealed and the mixture was stirred at 60° C. over night. Isolute® was added and the solvent was evaporated on a rotary evaporator. The crude product was purified by preparative HPLC (Column: Chromatorex C18, 250×30 mm 10 µm; eluent: A=water, B=acetonitrile; gradient: 0 min 5% B, 9 min 5% B, 24 min 95% B, 27 min 95% B, 29 min 10% B; +0.1% formic acid; flow: 50 ml/min). Product containing samples were united and the solvents were removed on a rotary evaporator. 340 mg (100% purity, 34% yield) of the title compound were obtained.

LC-MS (Method 9): $R_t$=0.70 min; MS (ESIneg): m/z=312 [M−H]$^-$

Intermediate 54

Rac-5-(Aminomethyl)-5-(Tetrahydro-2H-Pyran-4-Yl)Imidazolidine-2,4-Dione Hydrochloride

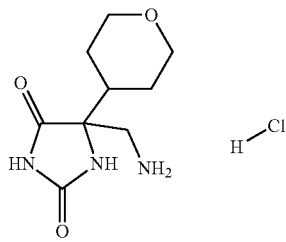 [SMILES: NCC1(C2CCOCC2)NC(=O)NC1=O ; Cl]

rac-tert-butyl {[2,5-dioxo-4-(tetrahydro-2H-pyran-4-yl)imidazolidin-4-yl]methyl}carbamate (340 mg, 1.09 mmol) was dissolved in 9 ml of dichloromethane. 4 M Hydrochloride acid in 1,4-dioxane (1.4 ml, 4.0 M, 5.4 mmol) was added and the mixture was stirred for 2 h. The precipitate was filtered off, washed with dichloromethane and dried in vacuo. The residue was taken up in 7 ml of dichloromethane again, 4 M hydrochloride acid in 1,4-dioxane (1.4 ml, 4.0 M, 5.4 mmol) was added and the mixture was stirred for 2 h. The precipitate was filtered off, washed with dichloromethane and dried in vacuo. 238 mg (77% purity, 68% yield) of the title compound were obtained.

LC-MS (Method 9): $R_t$=0.26 min; MS (ESIpos): m/z=214 [M–HCl+H]$^+$

Intermediate 55

Ethyl 5-(Pyrazin-2-Yl)-1,3-Oxazole-4-Carboxylate

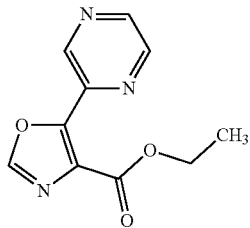 [SMILES: CCOC(=O)c1ncoc1-c1cnccn1]

Pyrazine-2-carboxylic acid (1.00 g, 8.06 mmol) and 1,1'-carbonyldiimidazole (1.57 g, 9.67 mmol) in 10 ml of THF was stirred for 2 h at room temperature. After that time, a solution of ethyl isocyanoacetate (970 µl, 8.9 mmol) in 15 ml of THF and a solution of lithium bis(trimethylsilyl)amide in THF (8.1 ml, 1.0 M, 8.1 mmol) were added dropwise at 0° C. When the addition was complete the resulting mixture was stirred at room temperature overnight. The reaction was concentrated in vacuo and extracted between water and ethyl acetate. The combined organic layers were dried over sodium sulfate, filtered and concentrated. The crude product was purified by column chromatography (Machine: Biotage® Isolera One; column: Biotage® SNAP Ultra 50 g; gradient: Cy/EE-gradient, 12% EE-100% EE; flow: 100 ml/min). Product containing samples were united and the solvents were removed on a rotary evaporator. 750 mg (100% purity, 42% yield) of the title compound were obtained.

LC-MS (Method 7): $R_t$=0.91 min; MS (ESIpos): m/z=220 [M+H]$^+$

Intermediate 56

2-Amino-1-(Pyrazin-2-Yl)Ethan-1-One-Hydrogen Chloride

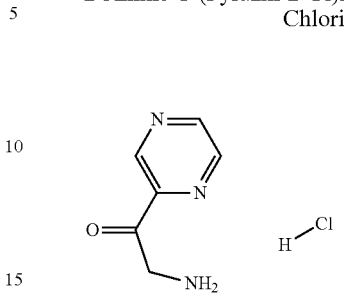

Ethyl 5-(pyrazin-2-yl)-1,3-oxazole-4-carboxylate (750 mg, 3.42 mmol) were taken up in 18 ml of 6 N hydrochloric acid and stirred 2 h at 100° C. The solvent was removed on a rotary evaporator and the residue was taken up in dichloromethane/methanol 20:1. The solvent was removed and the residue was dried in vacuo. 700 mg (118% yield) of the title compound were obtained.

Intermediate 57

Tert-Butyl [2-Oxo-2-(Pyrazin-2-Yl)Ethyl]Carbamate

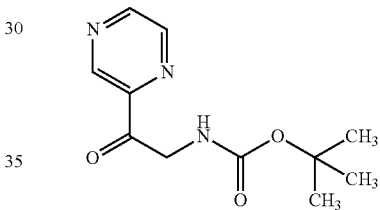

2-amino-1-(pyrazin-2-yl)ethan-1-one-hydrogen chloride (700 mg, 4.03 mmol) dissolved in 16 ml of dichloromethane were treated with di-tert-butyl dicarbonate (1.0 ml, 4.4 mmol) and triethylamine (1.7 ml, 12 mmol). The mixture was stirred at room temperature for 2 h. The solvent was removed on a rotary evaporator. The residue was taken up with ethyl acetate and washed with water and saturated aqueous sodium chloride solution. The organic layer was dried over sodium sulfate, filtered and evaporated on a rotary evaporator. 530 mg (55% yield) of the title compound were obtained.

Intermediate 58

Rac-Tert-Butyl {[2,5-Dioxo-4-(Pyrazin-2-Yl)Imidazolidin-4-Yl]Methyl}Carbamate

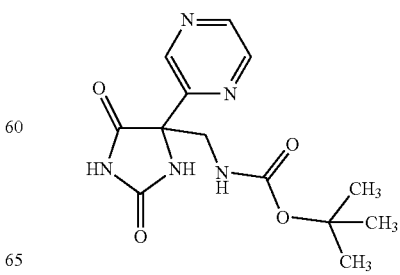

In a microwave vial tert-butyl [2-oxo-2-(pyrazin-2-yl)ethyl]carbamate (530 mg, 2.23 mmol) was dissolved in 6 ml of methanol. Potassium cyanide (727 mg, 11.2 mmol) and ammonium carbonate (1.07 g, 11.2 mmol) were added. The vial was sealed and the mixture was stirred at 60° C. overnight. Isolute® was added and the solvent was evaporated on a rotary evaporator. The crude product was purified by column chromatography (Machine: Biotage® Isolera One; column: Biotage® SNAP Ultra 25 g; gradient: Cy/EE-gradient, 12% EE-100% EE; then DCM/MeOH 10:1; flow: 100 ml/min). Product containing samples were united and the solvents were removed on a rotary evaporator. 120 mg (86% purity, 15% yield) of the title compound were obtained.

LC-MS (Method 8): $R_t$=0.52 min; MS (ESIneg): m/z=306 [M−H]⁻

Intermediate 59

Rac-5-(Aminomethyl)-5-(Pyrazin-2-Yl)Imidazolidine-2,4-Dione Hydrochloride

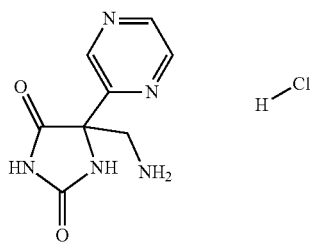 [SMILES: NCC1(c2cnccn2)NC(=O)NC1=O ; Cl]

rac-tert-butyl {[2,5-dioxo-4-(pyrazin-2-yl)imidazolidin-4-yl]methyl}carbamate (120 mg, 390 μmol) was dissolved in 3 ml of dichloromethane. 4 M Hydrochloride acid in 1,4-dioxane (490 μl, 4.0 M, 2.0 mmol) was added and the mixture was stirred for 2 h. The solvent was removed on a rotary evaporator and the residue was taken up in dichloromethane. The solvent was removed and the residue was dried in vacuo. 98.0 mg (95% purity, 98% yield) of the title compound were obtained.

LC-MS (Method 9): $R_t$=0.26 min; MS (ESIneg): m/z=206 [M−HCl+H]⁺

Intermediate 60

Ent-Tert-Butyl {[4-(5-Methyl-1,3-Thiazol-4-Yl)-2,5-Dioxoimidazolidin-4-Yl]Methyl}Carbamate

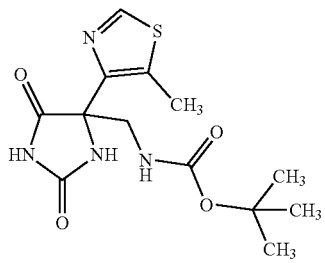 [SMILES: Cc1scnc1C1(CNC(=O)OC(C)(C)C)NC(=O)NC1=O]

Enantiomeric separation of rac-tert-butyl {[4-(5-methyl-1,3-thiazol-4-yl)-2,5-dioxoimidazolidin-4 yl]methyl}carbamate (3.00 g, 9.19 mmol) was done using the following method:

Column: Chiralpak AD 20 μm 450×50 mm
Solvent: 60% $CO_2$: 40% methanol
Flow: 400 ml/min
Backpressure: 130 bar
Oven temperature: 35° C.
UV: 210 nm Product containing samples were united, the solvents were evaporated and the residue was lyophilized.

1.27 g (100% purity, 42% yield)

LC-MS (Method 9): $R_t$=0.66 min; MS (ESIneg): m/z=325 [M−H]⁻

HPLC (Column: Chriralpack AD-3; solvent: 40% methanol: 60% $CO_2$; flow: 3 ml/min; UV: 210 nm): $R_t$=1.037 min, 100.0% ee Intermediate 61

Ent-5-(Aminomethyl)-5-(5-Methyl-1,3-Thiazol-4-Yl)Imidazolidine-2,4-Dione Hydrochloride

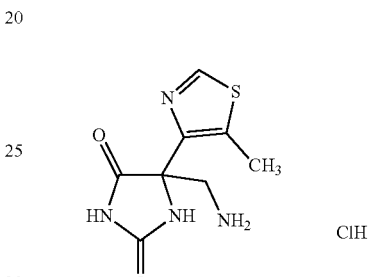

ent-tert-butyl {[4-(5-methyl-1,3-thiazol-4-yl)-2,5-dioxoimidazolidin-4-yl]methyl}carbamate (1.27 g, 3.89 mmol) was dissolved in 20 ml of dichloromethane and treated with 4 N HCl in dioxane (4.9 ml, 4.0 M, 19 mmol). The mixture was stirred at room temperature for 2 h. The precipitate was filtered, washed with dichloromethane and dried in vacuo. 1.30 g (100% purity, 128% yield) of the title compound were obtained.

LC-MS (Method 9): $R_t$=0.23 min; MS (ESIpos): m/z=227 [M−HCl+H]⁺

Intermediate 62

Ethyl 5-(4-Methyl-1,2,5-Oxadiazol-3-Yl)-1,3-Oxazole-4-Carboxylate

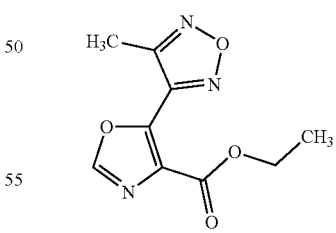

4-methyl-1,2,5-oxadiazole-3-carboxylic acid (1.00 g, 7.81 mmol) and 1,1'-carbonyldiimidazole (1.52 g, 9.37 mmol) in 10 ml of THF was stirred for 2 h at room temperature. After that time, a solution of ethyl isocyanoacetate (940 μl, 8.6 mmol) in 10 ml of THF and a solution of lithium bis(trimethylsilyl)amide in THF (7.8 ml, 1.0 M, 7.8 mmol) were added dropwise at 0° C. When the addition was complete the resulting mixture was stirred at room temperature for 1 h. The reaction was concentrated in vacuo and extracted between water and ethyl acetate. The combined organic layers were dried over sodium sulfate, filtered and concentrated. The crude product was purified by column chromatography (Machine: Biotage® Isolera One; column: Biotage® SNAP Ultra 50 g; gradient: Cy/EE-gradient, 12% EE-100% EE; flow: 100 ml/min). Product containing samples were united and the solvents were removed on a rotary evaporator. 822 mg (100% purity, 47% yield) of the title compound were obtained.

LC-MS (Method 7): $R_t$=1.40 min; MS (ESIpos): m/z=224 [M+H]$^+$

Intermediate 63

2-Amino-1-(4-Methyl-1,2,5-Oxadiazol-3-Yl)Ethan-1-One Hydrogen Chloride

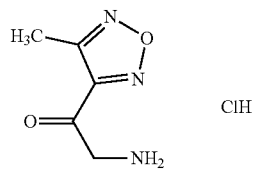

Ethyl 5-(4-methyl-1,2,5-oxadiazol-3-yl)-1,3-oxazole-4-carboxylate (822 mg, 3.68 mmol) were taken up in 20 ml of 6 N hydrochloric acid and stirred 2 h at 100° C. The solvent was removed on a rotary evaporator and the residue was dried in vacuo. 689 mg (100% purity, 105% yield) of the title compound were obtained.

LC-MS (Method 9): $R_t$=0.78 min; MS (ESIpos): m/z=142 [M+H−HCl]$^+$

Intermediate 64

Tert-Butyl [2-(4-Methyl-1,2,5-Oxadiazol-3-Yl)-2-Oxoethyl]Carbamate

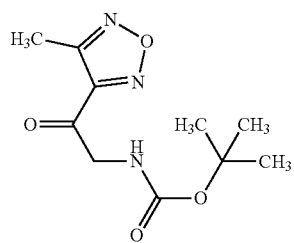 [SMILES: Cc1nonc1C(=O)CNC(=O)OC(C)(C)C]

2-amino-1-(4-methyl-1,2,5-oxadiazol-3-yl)ethan-1-one hydrogen chloride (689 mg, 3.88 mmol) dissolved in 15 ml of dichloromethane were treated with di-tert-butyl dicarbonate (980 µl, 4.3 mmol) and triethylamine (1.6 ml, 12 mmol). The mixture was stirred at room temperature for 2 h. The solvent was removed on a rotary evaporator. The residue was taken up with ethyl acetate and washed with water and saturated aqueous sodium chloride solution. The organic layer was dried over sodium sulfate, filtered and evaporated on a rotary evaporator. 1.01 g (108% yield) of the title compound were obtained.

Intermediate 65

Rac-Tert-Butyl {[4-(4-Methyl-1,2,5-Oxadiazol-3-Yl)-2,5-Dioxoimidazolidin-4-Yl]Methyl}Carbamate

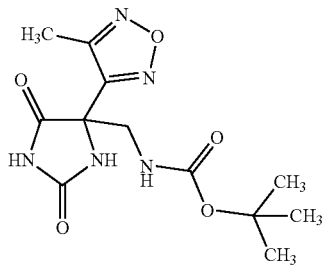 [SMILES: Cc1nonc1C1(CNC(=O)OC(C)(C)C)NC(=O)NC1=O]

In a microwave vial tert-butyl [2-(4-methyl-1,2,5-oxadiazol-3-yl)-2-oxoethyl]carbamate (1.01 g, 4.19 mmol) was dissolved in 20 ml of methanol. Potassium cyanide (1.36 g, 20.9 mmol) and ammonium carbonate (2.01 g, 20.9 mmol) were added. The vial was sealed and the mixture was stirred at 60° C. over night. Isolute® was added and the solvent was evaporated on a rotary evaporator. The crude product was purified by preparative HPLC (column: Chromatorex C18 10 µm 250×30 mm; eluent A=water with 0.1% formic acid, B=acetonitrile; gradient: 0.0 min 30% B; 4.5 min 50% B; 11.5 min 70% B; 12 min 100% B; 14.75 min 30% B; flow: 50 ml/min). Product containing samples were united and the solvents were removed on a rotary evaporator. 97.0 mg (82% purity, 6% yield) of the title compound were obtained.

LC-MS (Method 7): $R_t$=1.21 min; MS (ESIneg): m/z=310 [M−H]$^-$

Intermediate 66

Rac-5-(Aminomethyl)-5-(4-Methyl-1,2,5-Oxadiazol-3-Yl)Imidazolidine-2,4-Dione Hydrochloride

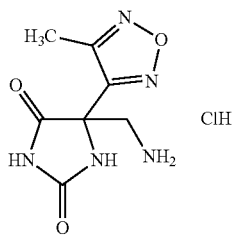

rac-tert-butyl {[4-(4-methyl-1,2,5-oxadiazol-3-yl)-2,5-dioxoimidazolidin-4-yl]methyl}carbamate (97.0 mg, 82% purity, 256 µmol) was dissolved in 2 ml of dichloromethane. 4 M hydrochloric acid in 1,4-dioxane (320 µl, 4.0 M, 1.3 mmol) was added and the mixture was stirred over night. The precipitate was filtered off, washed with dichloromethane and dried in vacuo. 80.0 mg (94% purity, 119% yield) of the title compound were obtained.

LC-MS (Method 9): $R_t$=0.23 min; MS (ESIpos): m/z=212 [M+H−HCl]$^+$

Intermediate 67

Ethyl 5-(1,4-Dimethyl-1H-Pyrazol-3-Yl)-1,3-Oxazole-4-Carboxylate

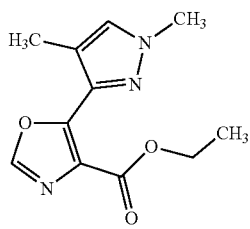 [SMILES: CCOC(=O)c1ncoc1-c1nn(C)cc1C]

1,4-dimethyl-1H-pyrazole-3-carboxylic acid (1.00 g, 7.14 mmol) and 1,1'-carbonyldiimidazole (1.39 g, 8.56 mmol) in 10 ml of THE was stirred for 2 h at room temperature. After that time, a solution of ethyl isocyanoacetate (970 µl, 8.9 mmol) in 10 ml of THE and a solution of lithium bis(trimethylsilyl)amide in THF (7.1 ml, 1.0 M, 7.1 mmol) were added dropwise at 0° C. When the addition was complete the resulting mixture was stirred at room temperature for 1 h. The reaction was concentrated in vacuo and extracted between water and ethyl acetate. The combined organic layers were dried over sodium sulfate, filtered and concentrated. The crude product was purified by column chromatography (Machine: Biotage® Isolera One; column: Biotage® SNAP Ultra 50 g; gradient: Cy/EE-gradient, 12% EE-100% EE; flow: 100 ml/min). Product containing samples were united and the solvents were removed on a rotary evaporator. 1.31 g (98% purity, 76% yield) of the title compound were obtained.

LC-MS (Method 7): $R_t$=1.12 min; MS (ESIpos): m/z=236 [M+H]$^+$

Intermediate 68

2-Amino-1-(1,4-Dimethyl-1H-Pyrazol-3-Yl)Ethan-1-One Hydrogen Chloride

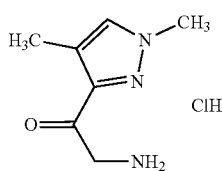

Ethyl 5-(1,4-dimethyl-1H-pyrazol-3-yl)-1,3-oxazole-4-carboxylate (1.31 g, 5.56 mmol) was taken up in 30 ml of 6 N hydrochloric acid and stirred 2 h at 100° C. The solvent was removed on a rotary evaporator and the residue was taken up in dichloromethane/methanol 20:1. The solvent was removed and the residue was dried in vacuo. 1.07 g (90% purity, 91% yield) of the title compound were obtained.

LC-MS (Method 9): $R_t$=0.81 min; MS (ESIpos): m/z=154 [M+H−HCl]$^+$

Intermediate 69

Tert-Butyl [2-(1,4-Dimethyl-1H-Pyrazol-3-Yl)-2-Oxoethyl]Carbamate

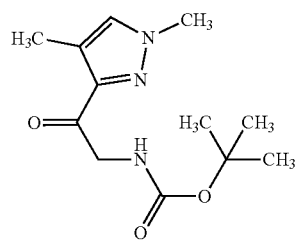 [SMILES: Cc1cn(C)nc1C(=O)CNC(=O)OC(C)(C)C]

2-amino-1-(1,4-dimethyl-1H-pyrazol-3-yl)ethan-1-one-hydrogen chloride (1.07 g, 5.66 mmol) dissolved in 20 ml of dichloromethane was treated with di-tert-butyl dicarbonate (1.4 ml, 6.2 mmol) and triethylamine (2.4 ml, 17 mmol). The mixture was stirred at room temperature for 2 h. The solvent was removed on a rotary evaporator. The residue was taken up with ethyl acetate and washed with water and saturated aqueous sodium chloride solution. The organic layer was dried over sodium sulfate, filtered and evaporated on a rotary evaporator. 1.53 g (92% purity, 98% yield) of the title compound were obtained.

LC-MS (Method 7): $R_t$=1.52 min; MS (ESIpos): m/z=198 [M+H−C$_4$H$_8$]$^+$

Intermediate 70

Rac-Tert-Butyl {[4-(1,4-Dimethyl-1H-Pyrazol-3-Yl)-2,5-Dioxoimidazolidin-4-Yl]Methyl}Carbamate

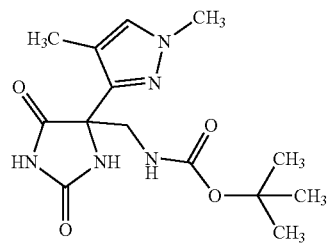 [SMILES: Cc1cn(C)nc1C1(CNC(=O)OC(C)(C)C)NC(=O)NC1=O]

In a microwave vial tert-butyl [2-(1,4-dimethyl-1H-pyrazol-3-yl)-2-oxoethyl]carbamate (1.53 g, 92% purity, 5.54 mmol) was dissolved in 30 ml of methanol. Potassium cyanide (1.80 g, 27.7 mmol) and ammonium carbonate (2.66 g, 27.7 mmol) were added. The vial was sealed and the mixture was stirred at 60° C. over night. Isolute® was added and the solvent was evaporated on a rotary evaporator. The crude product was purified by column chromatography (Machine: Biotage® Isolera One; column: Biotage® SNAP Ultra 50 g; gradient: DCM/MeOH-gradient, 2% MeOH-20% MeOH; flow: 100 ml/min). Product containing samples were united and the solvents were removed on a rotary evaporator. 747 mg (100% purity, 42% yield) of the title compound were obtained.

LC-MS (Method 7): $R_t$=1.02 min; MS (ESIneg): m/z=322 [M−H]$^−$

Intermediate 71

Rac-5-(Aminomethyl)-5-(1,4-Dimethyl-1H-Pyrazol-3-Yl)Imidazolidine-2,4-Dione Hydrochloride

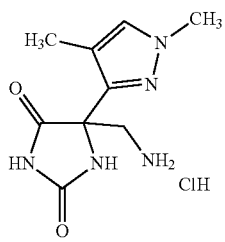

rac-tert-butyl {[4-(1,4-dimethyl-1H-pyrazol-3-yl)-2,5-dioxoimidazolidin-4-yl]methyl}carbamate (747 mg, 2.31 mmol) was dissolved in 12 ml of dichloromethane. 4 M hydrochloric acid in 1,4-dioxane (2.9 ml, 4.0 M, 12 mmol) was added and the mixture was stirred for 2 h. The precipitate was filtered off, washed with dichloromethane and dried in vacuo. 552 mg (99% purity, 91% yield) of the title compound were obtained.

LC-MS (Method 9): $R_t$=0.24 min; MS (ESIpos): m/z=224 [M+H−HCl]$^+$

Intermediate 72

Ethyl 5-(1-Cyclopropyl-1H-Pyrazol-5-Yl)-1,3-Oxazole-4-Carboxylate

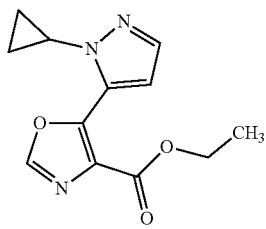 [SMILES: CCOC(=O)c1ncoc1-c1ccnn1C1CC1]

1-cyclopropyl-1H-pyrazole-5-carboxylic acid (1.00 g, 6.57 mmol) and 1,1'-carbonyldiimidazole (1.28 g, 7.89 mmol) in 11 ml of THF were stirred for 2 h at room temperature. After that time, a solution of ethyl isocyanoacetate (790 µl, 7.2 mmol) in 11 ml of THF and a solution of lithium bis(trimethylsilyl)amide in THF (6.6 ml, 1.0 M, 6.6 mmol) were added dropwise at 0° C. When the addition was complete the resulting mixture was stirred at room temperature for 1 h. The reaction was concentrated in vacuo and extracted between water and ethyl acetate. The combined organic layers were dried over sodium sulfate, filtered and concentrated. The crude product was purified by column chromatography (Machine: Biotage® Isolera One; column: Biotage® SNAP Ultra 25 g; gradient: Cy/EE-gradient, 12% EE-100% EE; flow: 75 ml/min). Product containing samples were united and the solvents were removed on a rotary evaporator. 929 mg (100% purity, 57% yield) of the title compound were obtained.

LC-MS (Method 7): $R_t$=1.29 min; MS (ESIpos): m/z=248 [M+H]$^+$

Intermediate 73

2-Amino-1-(1-Cyclopropyl-1H-Pyrazol-5-Yl)Ethan-1-One Hydrogen Chloride

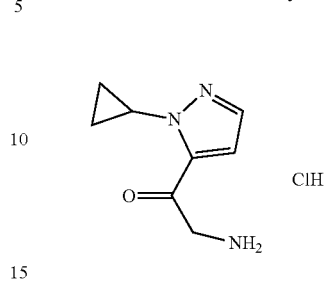

Ethyl 5-(1-cyclopropyl-1H-pyrazol-5-yl)-1,3-oxazole-4-carboxylate (929 mg, 3.76 mmol) was taken up in 18 ml of 6 N hydrochloric acid and stirred 1 h at 100° C. The solvent was removed on a rotary evaporator and the residue was taken up in dichloromethane/methanol 20:1. The solvent was removed and the residue was dried in vacuo. 886 mg (79% purity, 93% yield) of the title compound were obtained.

LC-MS (Method 9): $R_t$=0.85 min; MS (ESIneg): m/z=164 [M−H−HCl]$^-$

Intermediate 74

Tert-Butyl [2-(1-Cyclopropyl-1H-Pyrazol-5-Yl)-2-Oxoethyl]Carbamate

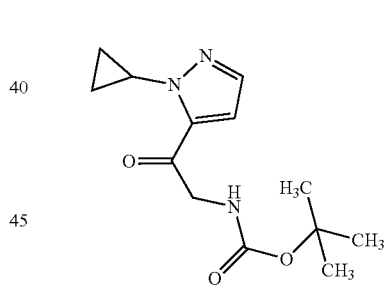

2-amino-1-(1-cyclopropyl-1H-pyrazol-5-yl)ethan-1-one hydrogen chloride (886 mg, 79% purity, 3.47 mmol) dissolved in 15 ml of dichloromethane was treated with di-tert-butyl dicarbonate (880 µl, 3.8 mmol) and triethylamine (1.5 ml, 10 mmol). The mixture was stirred at room temperature for 3 h. The solvent was removed on a rotary evaporator. The residue was taken up with ethyl acetate and washed with water and saturated aqueous sodium chloride solution. The organic layer was dried over sodium sulfate, filtered and evaporated on a rotary evaporator. 770 mg (78% purity, 65% yield) of the title compound were obtained.

LC-MS (Method 9): $R_t$=1.46 min; MS (ESIpos): m/z=266 [M+H]$^+$

Intermediate 75

Rac-Tert-Butyl {[4-(1-Cyclopropyl-1H-Pyrazol-5-Yl)-2,5-Dioxoimidazolidin-4-Yl]Methyl}Carbamate

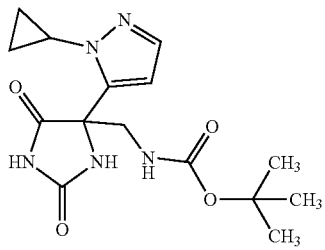 [SMILES: CC(C)(C)OC(=O)NCC1(c2ccnn2C2CC2)NC(=O)NC1=O]

In a microwave vial tert-butyl [2-(1-cyclopropyl-1H-pyrazol-5-yl)-2-oxoethyl]carbamate (770 mg, 2.90 mmol) was dissolved in 6 ml of methanol. Potassium cyanide (945 mg, 14.5 mmol) and ammonium carbonate (1.39 g, 14.5 mmol) were added. The vial was sealed and the mixture was stirred at 60° C. over night. Isolute® was added and the solvent was evaporated on a rotary evaporator. The crude product was purified by column chromatography (Machine: Biotage® Isolera One; column: Biotage® SNAP Ultra 50 g; gradient: Cy/EE-gradient, 12% EE-100% EE; then DCM/MeOH 20:1; flow: 100 ml/min). Product containing samples were united and the solvents were removed on a rotary evaporator. 236 mg (86% purity, 21% yield) of the title compound were obtained.

LC-MS (Method 7): $R_t$=1.03 min; MS (ESIpos): m/z=336 $[M+H]^+$

Intermediate 76

Rac-5-(Aminomethyl)-5-(1-Cyclopropyl-1H-Pyrazol-5-Yl)Imidazolidine-2,4-Dione Hydrochloride

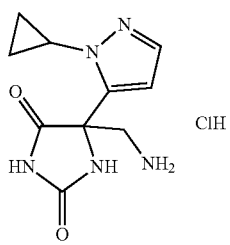 [SMILES: NCC1(c2ccnn2C2CC2)NC(=O)NC1=O ; Cl]

rac-tert-butyl {[4-(1-cyclopropyl-1H-pyrazol-5-yl)-2,5-dioxoimidazolidin-4-yl]methyl}carbamate (236 mg, 704 µmol) was dissolved in 4 ml of dichloromethane. 4 M hydrochloric acid in 1,4-dioxane (880 µl, 4.0 M, 3.5 mmol) was added and the mixture was stirred for 2 h. The solvent was removed on a rotary evaporator and the residue was taken up in dichloromethane. The solvent was removed and the residue was dried in vacuo. 208 mg (86% purity, 93% yield) of the title compound were obtained.

LC-MS (Method 9): $R_t$=0.26 min; MS (ESIpos): m/z=236 $[M+H-HCl]^+$

Intermediate 77

Ethyl 5-(3-Methyl-1,2-Oxazol-4-Yl)-1,3-Oxazole-4-Carboxylate

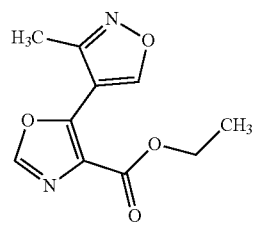 [SMILES: CCOC(=O)c1ncoc1-c1conc1C]

3-methyl-1,2-oxazole-4-carboxylic acid (1.10 g, 8.65 mmol) and 1,1'-carbonyldiimidazole (1.68 g, 10.4 mmol) in 11 ml of THF were stirred for 2 h at room temperature. After that time, a solution of ethyl isocyanoacetate (1.0 ml, 9.5 mmol) in 11 ml of THE and a solution of lithium bis(trimethylsilyl)amide in THF (8.7 ml, 1.0 M, 8.7 mmol) were added dropwise at 0° C. When the addition was complete the resulting mixture was stirred at room temperature for 1 h. The reaction was concentrated in vacuo and extracted between water and ethyl acetate. The combined organic layers were dried over sodium sulfate, filtered and concentrated. The crude product was purified by column chromatography (Machine: Biotage® Isolera One; column: Biotage® SNAP Ultra 50 g; gradient: DCM/MeOH-gradient, 2% MeOH-20% MeOH; flow: 100 ml/min). Product containing samples were united and the solvents were removed on a rotary evaporator. 813 mg (100% purity, 42% yield) of the title compound were obtained.

LC-MS (Method 9): $R_t$=1.24 min; MS (ESIpos): m/z=223 $[M+H]^+$

Intermediate 78

2-Amino-1-(3-Methyl-1,2-Oxazol-4-Yl)Ethan-1-One Hydrogen Chloride

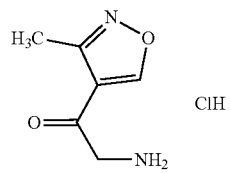

Ethyl 5-(3-methyl-1,2-oxazol-4-yl)-1,3-oxazole-4-carboxylate (813 mg, 3.66 mmol) was taken up in 17 ml of 6 N hydrochloric acid and stirred 1 h at 100° C. The solvent was removed on a rotary evaporator and the residue was taken up in dichloromethane/methanol 20:1. The solvent was removed and the residue was dried in vacuo. 653 mg (97% purity, 98% yield) of the title compound were obtained.

LC-MS (Method 9): $R_t$=0.63 min; MS (ESIpos): m/z=141 $[M+H-HCl]^+$

Intermediate 79

Tert-Butyl [2-(3-Methyl-1,2-Oxazol-4-Yl)-2-Oxo-ethyl]Carbamate

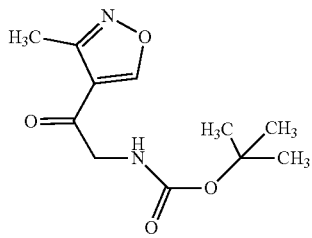 [SMILES: Cc1nocc1C(=O)CNC(=O)OC(C)(C)C]

2-amino-1-(3-methyl-1,2-oxazol-4-yl)ethan-1-one hydrogen chloride (653 mg, 3.70 mmol) dissolved in 14 ml of dichloromethane was treated with di-tert-butyl dicarbonate (930 µl, 4.1 mmol) and triethylamine (1.5 ml, 11 mmol). The mixture was stirred at room temperature over night. The solvent was removed on a rotary evaporator. The residue was taken up with ethyl acetate and washed with water and saturated aqueous sodium chloride solution. The organic layer was dried over sodium sulfate, filtered and evaporated on a rotary evaporator. 807 mg (100% purity, 91% yield) of the title compound were obtained.

LC-MS (Method 7): $R_t$=140.00 min; MS (ESIneg): m/z=285 [M−H+CHOOH]−

$^1$H-NMR (600 MHz, DMSO-d6) δ [ppm]: 1.280 (0.67), 1.367 (0.73), 1.390 (16.00), 1.469 (13.29), 2.391 (6.59), 3.266 (0.44), 4.207 (1.75), 4.216 (1.73), 5.746 (1.30), 7.122 (0.57), 9.763 (2.49).

Intermediate 80

Rac-Tert-Butyl {[4-(3-Methyl-1,2-Oxazol-4-Yl)-2,5-Dioxoimidazolidin-4-Yl]Methyl}Carbamate

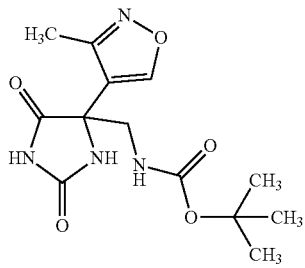 [SMILES: Cc1nocc1C1(CNC(=O)OC(C)(C)C)NC(=O)NC1=O]

In a microwave vial tert-butyl [2-(3-methyl-1,2-oxazol-4-yl)-2-oxoethyl]carbamate (807 mg, 3.36 mmol) was dissolved in 10 ml of methanol. Potassium cyanide (1.09 g, 16.8 mmol) and ammonium carbonate (1.61 g, 16.8 mmol) were added. The vial was sealed and the mixture was stirred at 60° C. over night. The solvent was removed on a rotary evaporator. The residue was treated with dichloromethane and the precipitate formed was filtered off. The filtrate was concentrated and the crude product was purified by preparative HPLC (column: Chromatorex C18 10 µm, 250×30 mm, eluent A=water with 0.1% formic acid, B=acetonitrile; gradient: 0.0 min 5% B; 3 min 5% B; 20 min 50% B; 23 min 100% B; 26 min 5% B; flow: 50 ml/min). Product containing samples were united and the solvents were removed on a rotary evaporator. 358 mg (100% purity, 34% yield) of the title compound were obtained.

LC-MS (Method 7): $R_t$=1.02 min; MS (ESIneg): m/z=309 [M−H]−

Intermediate 81

Rac-5-(Aminomethyl)-5-(3-Methyl-1,2-Oxazol-4-Yl)Imidazolidine-2,4-Dione Hydrochloride

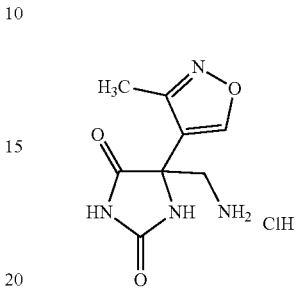

rac-tert-butyl {[4-(3-methyl-1,2-oxazol-4-yl)-2,5-dioxo-imidazolidin-4-yl]methyl}carbamate (358 mg, 1.15 mmol) was dissolved in 6 ml of dichloromethane. 4 M hydrochloric acid in 1,4-dioxane (1.4 ml, 4.0 M, 5.8 mmol) was added and the mixture was stirred over night. The precipitate was filtered off, washed with dichloromethane and dried in vacuo. 274 mg (100% purity, 96% yield) of the title compound were obtained.

LC-MS (Method 9): $R_t$=0.22 min; MS (ESIpos): m/z=211 [M+H−HCl]+

Intermediate 82

Ethyl 5-(Pyridazin-3-Yl)-1,3-Oxazole-4-Carboxylate

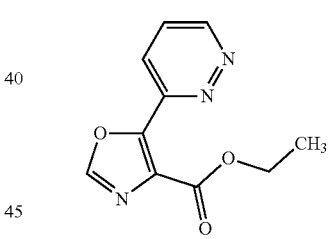

Pyridazine-3-carboxylic acid (1.00 g, 8.06 mmol) and 1,1'-carbonyldiimidazole (1.57 g, 9.67 mmol) in 10 ml of THF were stirred for 2 h at room temperature. After that time, a solution of ethyl isocyanoacetate (970 µl, 8.9 mmol) in 15 ml of THF and a solution of lithium bis(trimethylsilyl)amide in THF (8.1 ml, 1.0 M, 8.1 mmol) were added dropwise at 0° C. When the addition was complete the resulting mixture was stirred at room temperature over night. The reaction was concentrated in vacuo and extracted between water and ethyl acetate. The combined organic layers were dried over sodium sulfate, filtered and concentrated. The crude product was purified by column chromatography (Machine: Biotage® Isolera One; column: Biotage® SNAP Ultra 50 g; gradient: Cy/EE-gradient, 12% EE-100% EE; flow: 100 ml/min). Product containing samples were united and the solvents were removed on a rotary evaporator. 940 mg (70% purity, 37% yield) of the title compound were obtained.

LC-MS (Method 12): $R_t$=1.05 min; MS (ESIpos): m/z=220 [M+H]+

Intermediate 83

2-Amino-1-(Pyridazin-3-Yl)Ethan-1-One Hydrogen Chloride

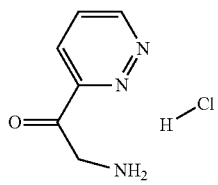

Ethyl 5-(pyridazin-3-yl)-1,3-oxazole-4-carboxylate (940 mg, 4.29 mmol) was taken up in 23 ml of 6 N hydrochloric acid and stirred 2 h at 100° C. The solvent was removed on a rotary evaporator and the residue was dried in vacuo. 800 mg (107% yield) of the title compound were obtained.

Intermediate 84

Tert-Butyl [2-Oxo-2-(Pyridazin-3-Yl)Ethyl]Carbamate

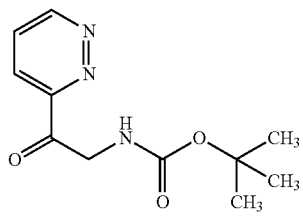

2-amino-1-(pyridazin-3-yl)ethan-1-one hydrogen chloride (800 mg, 4.61 mmol) dissolved in 18 ml of dichloromethane was treated with di-tert-butyl dicarbonate (1.2 ml, 5.1 mmol) and triethylamine (1.9 ml, 14 mmol). The mixture was stirred at room temperature for 2 h. The solvent was removed on a rotary evaporator. The residue was taken up with ethyl acetate and washed with water and saturated aqueous sodium chloride solution. The organic layer was dried over sodium sulfate, filtered and evaporated on a rotary evaporator. 612 mg (56% yield) of the title compound were obtained.

Intermediate 85

Rac-Tert-Butyl {[2,5-Dioxo-4-(Pyridazin-3-Yl)Imidazolidin-4-Yl]Methyl}Carbamate

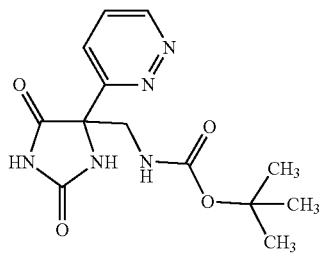 [SMILES: CC(C)(C)OC(=O)NCC1(c2cccnn2)NC(=O)NC1=O]

In a microwave vial tert-butyl [2-oxo-2-(pyridazin-3-yl)ethyl]carbamate (612 mg, 2.58 mmol) was dissolved in 7 ml of methanol. Potassium cyanide (840 mg, 12.9 mmol) and ammonium carbonate (1.24 g, 12.9 mmol) were added. The vial was sealed and the mixture was stirred at 60° C. for 48 h. Isolute® was added and the solvent was evaporated on a rotary evaporator. The crude product was purified by column chromatography (Machine: Biotage® IsoleraOne; column: Biotage® SNAP Ultra 25 g; gradient: DCM/MeOH-gradient, 10% MeOH-40% MeOH; flow: 75 ml/min). Product containing samples were united and the solvents were removed on a rotary evaporator. 57.0 mg (60% purity, 4% yield) of the title compound were obtained.

LC-MS (Method 9): $R_t$=0.29 min, MS (ESIpos): m/z=308 [M+H]$^+$

Intermediate 86

Rac-5-(Aminomethyl)-5-(Pyridazin-3-Yl)Imidazolidine-2,4-Dione Hydrochloride

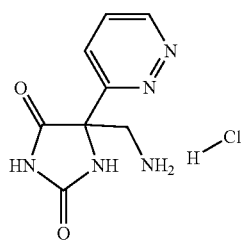

rac-tert-butyl {[2,5-dioxo-4-(pyridazin-3-yl)imidazolidin-4-yl]methyl}carbamate (58.0 mg, 189 µmol) was dissolved in 2 ml of dichloromethane. 4 M hydrochloric acid in 1,4-dioxane (240 µl, 4.0 M, 940 µmol) was added and the mixture was stirred over night. The solvent was removed on a rotary evaporator and the residue was taken up in dichloromethane. The solvent was removed and the residue was dried in vacuo. 57 mg (124% yield) of the title compound were obtained.

Intermediate 87

Ethyl 4'-Methyl[5,5'-Bi-1,3-Oxazole]-4-Carboxylate

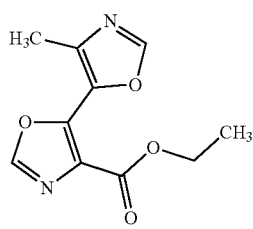 [SMILES: CCOC(=O)c1ncoc1-c1ocnc1C]

4-methyl-1,3-oxazole-5-carboxylic acid (1.00 g, 7.87 mmol) and 1,1'-carbonyldiimidazole (1.53 g, 9.44 mmol) in 10 ml of THF were stirred for 2 h at room temperature. After that time, a solution of ethyl isocyanoacetate (950 µl, 8.7 mmol) in 10 ml of THF and a solution of lithium bis (trimethylsilyl)amide in THF (7.9 ml, 1.0 M, 7.9 mmol) were added dropwise at 0° C. When the addition was complete the resulting mixture was stirred at room temperature for 1 h. The reaction was concentrated in vacuo and extracted between water and ethyl acetate. The combined organic layers were dried over sodium sulfate, filtered and concentrated. The crude product was purified by column chromatography (Machine: Biotage® Isolera One; column:

Biotage® SNAP Ultra 50 g; gradient: Cy/EE-gradient, 12% EE-100% EE; flow: 100 ml/min). Product containing samples were united and the solvents were removed on a rotary evaporator. 1.26 g (100% purity, 72% yield) of the title compound were obtained.

LC-MS (Method 7): $R_t$=1.05 min; MS (ESIpos): m/z=223 [M+H]$^+$

Intermediate 88

2-Amino-1-(4-Methyl-1,3-Oxazol-5-Yl)Ethan-1-One Hydrogen Chloride

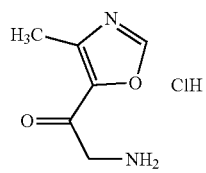

Ethyl 4'-methyl[5,5'-bi-1,3-oxazole]-4-carboxylate (1.26 g, 5.69 mmol) was taken up in 30 ml of 6 N hydrochloric acid and stirred 2 h at 100° C. The solvent was removed on a rotary evaporator and the residue was dried in vacuo. 1.14 g (113% yield) of the title compound were obtained.

Intermediate 89

Tert-Butyl [2-(4-Methyl-1,3-Oxazol-5-Yl)-2-Oxo-ethyl]Carbamate

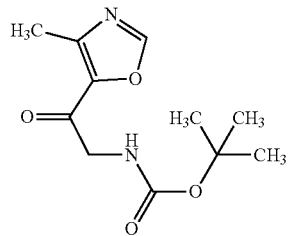 [SMILES: Cc1ncoc1C(=O)CNC(=O)OC(C)(C)C]

2-amino-1-(4-methyl-1,3-oxazol-5-yl)ethan-1-one hydrogen chloride (1.14 g, 6.46 mmol) dissolved in 30 ml of dichloromethane was treated with di-tert-butyl dicarbonate (1.6 ml, 7.1 mmol) and triethylamine (2.7 ml, 19 mmol). The mixture was stirred at room temperature over night. The solvent was removed on a rotary evaporator. The residue was taken up with ethyl acetate and washed with water and saturated aqueous sodium chloride solution. The organic layer was dried over sodium sulfate, filtered and evaporated on a rotary evaporator. 684 mg (44% yield) of the title compound were obtained.

Intermediate 90

Rac-Tert-Butyl {[4-(4-Methyl-1,3-Oxazol-5-Yl)-2,5-Dioxoimidazolidin-4-Yl]Methyl}Carbamate

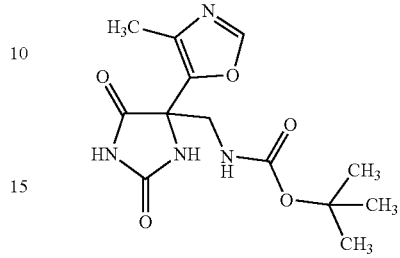

In a microwave vial tert-butyl [2-(4-methyl-1,3-oxazol-5-yl)-2-oxoethyl]carbamate (383 mg, 1.59 mmol) was dissolved in 10 ml of methanol. Potassium cyanide (519 mg, 7.97 mmol) and ammonium carbonate (766 mg, 7.97 mmol) were added. The vial was sealed and the mixture was stirred at 60° C. over night. The solvent was removed on a rotary evaporator. The crude product was purified by preparative HPLC (column: Chromatorex C18 10 µm, 250×30 mm, eluent A=water with 0.1% formic acid, B=acetonitrile; gradient: 0.0 min 5% B; 3 min 5% B; 20 min 50% B; 23 min 100% B; 26 min 5% B; flow: 50 ml/min). Product containing samples were united and the solvents were removed on a rotary evaporator. 8.00 mg (100% purity, 2% yield) of the title compound were obtained.

LC-MS (Method 7): $R_t$=0.92 min; MS (ESIpos): m/z=311 [M+H]$^+$

Intermediate 91

Rac-5-(Aminomethyl)-5-(4-Methyl-1,3-Oxazol-5-Yl)Imidazolidine-2,4-Dione Hydrochloride

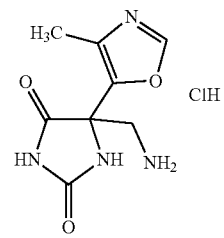

rac-tert-butyl {[4-(4-methyl-1,3-oxazol-5-yl)-2,5-dioxoimidazolidin-4-yl]methyl}carbamate (8.00 mg, 25.8 µmol) was dissolved in 0.5 ml of dichloromethane. 4 M hydrochloric acid in 1,4-dioxane (32 µl, 4.0 M, 130 µmol) was added and the mixture was stirred over night. The solvent was removed on a rotary evaporator and the residue was dried in vacuo. 8.00 mg (81% purity, 102% yield) of the title compound were obtained.

LC-MS (Method 9): $R_t$=0.23 min; MS (ESIpos): m/z=211 [M+H−HCl]$^+$

Intermediate 92

Ethyl 5-(4-Methyl-1,2-Oxazol-3-Yl)-1,3-Oxazole-4-Carboxylate

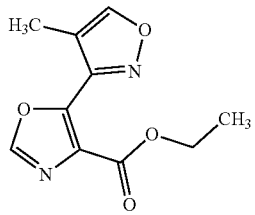 [SMILES: CCOC(=O)c1ncoc1-c1nocc1C]

4-methyl-1,2-oxazole-3-carboxylic acid (1.00 g, 7.87 mmol) and 1,1'-carbonyldiimidazole (1.53 g, 9.44 mmol) in 10 ml of THF were stirred for 2 h at room temperature. After that time, a solution of ethyl isocyanoacetate (950 µl, 8.7 mmol) in 10 ml of THF and a solution of lithium bis(trimethylsilyl)amide in THF (7.9 ml, 1.0 M, 7.9 mmol) were added dropwise at 0° C. When the addition was complete the resulting mixture was stirred at room temperature for 1 h. The reaction was concentrated in vacuo and extracted between water and ethyl acetate. The combined organic layers were dried over sodium sulfate, filtered and concentrated. The crude product was purified by column chromatography (Machine: Biotage® Isolera One; column: Biotage® SNAP Ultra 50 g; gradient: Cy/EE-gradient, 12% EE-100% EE; flow: 100 ml/min). Product containing samples were united and the solvents were removed on a rotary evaporator. 1.21 g (100% purity, 69% yield) of the title compound were obtained.

LC-MS (Method 7): $R_t$=1.22 min; MS (ESIpos): m/z=223 [M+H]$^+$

Intermediate 93

2-Amino-1-(4-Methyl-1,2-Oxazol-3-Yl)Ethan-1-One Hydrogen Chloride

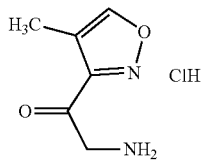

Ethyl 5-(4-methyl-1,2-oxazol-3-yl)-1,3-oxazole-4-carboxylate (1.21 g, 5.45 mmol) were taken up in 32 ml of 6 N hydrochloric acid and stirred 2 h at 100° C. The solvent was removed on a rotary evaporator and the residue was dried in vacuo. 1.08 g (62% purity, 70% yield) of the title compound were obtained.

LC-MS (Method 9): $R_t$=0.77 min; MS (ESIpos): m/z=141 [M+H−HCl]$^+$

Intermediate 94

Tert-Butyl [2-(4-Methyl-1,2-Oxazol-3-Yl)-2-Oxo-ethyl]Carbamate

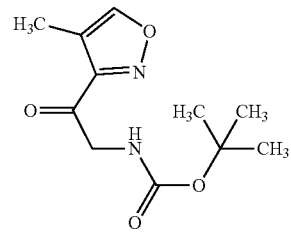 [SMILES: Cc1conc1C(=O)CNC(=O)OC(C)(C)C]

2-amino-1-(4-methyl-1,2-oxazol-3-yl)ethan-1-one hydrogen chloride (1.08 g, 62% purity, 3.80 mmol) dissolved in 20 ml of dichloromethane was treated with di-tert-butyl dicarbonate (960 µl, 4.2 mmol) and triethylamine (1.6 ml, 11 mmol). The mixture was stirred at room temperature for 4 h. The solvent was removed on a rotary evaporator. The residue was taken up with ethyl acetate and washed with water and saturated aqueous sodium chloride solution. The organic layer was dried over sodium sulfate, filtered and evaporated on a rotary evaporator. 1.49 g (42% purity, 69% yield) of the title compound were obtained.

LC-MS (Method 7): $R_t$=1.60 min; MS (ESIpos): m/z=263 [M+Na]$^+$

Intermediate 95

Rac-Tert-Butyl {[4-(4-Methyl-1,2-Oxazol-3-Yl)-2,5-Dioxoimidazolidin-4-Yl]Methyl}Carbamate

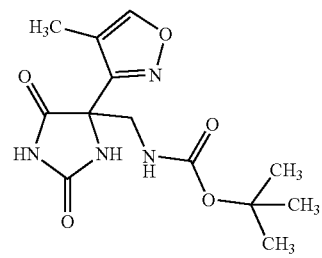 [SMILES: Cc1conc1C1(CNC(=O)OC(C)(C)C)NC(=O)NC1=O]

In a microwave vial tert-butyl [2-(4-methyl-1,2-oxazol-3-yl)-2-oxoethyl]carbamate (1.49 g, 42% purity, 2.60 mmol) was dissolved in 15 ml of methanol. Potassium cyanide (848 mg, 13.0 mmol) and ammonium carbonate (1.25 g, 13.0 mmol) were added. The vial was sealed and the mixture was stirred at 60° C. for 48 h. Isolute® was added and the solvent was evaporated on a rotary evaporator. The crude product was purified by column chromatography (Machine: Biotage® Isolera One; column: Biotage® SNAP Ultra 50 g; gradient: DCM/MeOH-gradient, 20% MeOH-20% MeOH; flow: 10 ml/min). Product containing samples were united and the solvents were removed on a rotary evaporator. 184 mg (100% purity, 23% yield) of the title compound were obtained.

LC-MS (Method 7): $R_t$=1.10 min; MS (ESIneg): m/z=309 [M−H]$^-$

Intermediate 96

Rac-5-(Aminomethyl)-5-(4-Methyl-1,2-Oxazol-3-Yl)Imidazolidine-2,4-Dione Hydrochloride

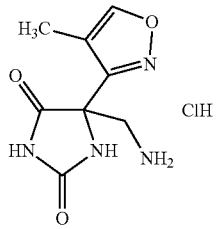

rac-tert-butyl {[4-(4-methyl-1,2-oxazol-3-yl)-2,5-dioxo-imidazolidin-4-yl]methyl}carbamate (184 mg, 593 µmol) was dissolved in 3 ml of dichloromethane. 4 M hydrochloric acid in 1,4-dioxane (740 µl, 4.0 M, 3.0 mmol) was added and the mixture was stirred for 6 h. The precipitate was filtered off, washed with dichloromethane and dried in vacuo. 86.0 mg (98% purity, 58% yield) of the title compound were obtained.

LC-MS (Method 9): $R_t$=0.22 min; MS (ESIpos): m/z=211 [M+H−HCl]$^+$

Intermediate 97

Ethyl 5-(3-Methyl-1,2-Thiazol-4-Yl)-1,3-Oxazole-4-Carboxylate

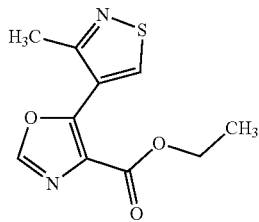 [SMILES: CCOC(=O)c1ncoc1-c1csnc1C]

3-methyl-1,2-thiazole-4-carboxylic acid (1.00 g, 6.98 mmol) dissolved in 10 ml of THF was treated with 1,1,-carbonyl-diimidazole (1.36 g, 8.38 mmol) and stirred at room temperature. After 2 h ethyl isocyanoacetate (840 µl, 7.7 mmol), dissolved in 10 ml of THF, and a solution of lithium bis(trimethylsilyl)amide in THF (7.0 ml, 1.0 M, 7.0 mmol) were added at 0° C. The mixture was allowed to warm to room temperature and stirred for 1 h. The solvent was removed on a rotary evaporator. The residue was taken up with ethyl acetate and washed with water and saturated aqueous sodium chloride solution. The organic layer was dried over sodium sulfate, filtered, Isolute® was added and the solvent was evaporated on a rotary evaporator. The crude product was purified by column chromatography (Machine: Biotage® Isolera One; column: Biotage® SNAP Ultra 50 g; gradient: Cy/EE-gradient, 12% EE-100% EE; flow: 100 ml/min). Product containing samples were united and the solvents were removed on a rotary evaporator. 1.28 g (99% purity, 76% yield) of the title compound were obtained.

LC-MS (Method 7): $R_t$=1.32 min; MS (ESIpos): m/z=239 [M+H]$^+$

Intermediate 98

2-Amino-1-(3-Methyl-1,2-Thiazol-4-Yl)Ethan-1-One-Hydrogen Chloride

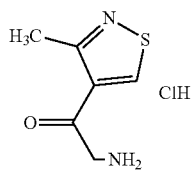

Ethyl 5-(3-methyl-1,2-thiazol-4-yl)-1,3-oxazole-4-carboxylate (1.28 g, 5.36 mmol) was taken up in 30 ml of 6 N hydrochloric acid and stirred at 100° C. After 2 h the solvent was removed on a rotary evaporator and the residue was treated with DCM. The solvent was removed and the residue was dried in vacuo. 1.27 g (85% purity, 105% yield) of the title compound were obtained.

LC-MS (Method 9): $R_t$=0.74 min; MS (ESIpos): m/z=157 [M+H−HCl]$^+$

Intermediate 99

Tert-Butyl [2-(3-Methyl-1,2-Thiazol-4-Yl)-2-Oxo-ethyl]Carbamate

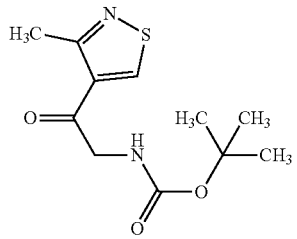 [SMILES: Cc1nscc1C(=O)CNC(=O)OC(C)(C)C]

2-amino-1-(3-methyl-1,2-thiazol-4-yl)ethan-1-one-hydrogen chloride (1.27 g, 6.59 mmol) dissolved in 30 ml of dichloromethane was treated with di-tert-butyl dicarbonate (1.7 ml, 7.3 mmol) and triethylamine (2.8 ml, 20 mmol). The mixture was stirred at room temperature. After 2 h the solvent was removed on a rotary evaporator. The residue was taken up with ethyl acetate and washed with water and saturated aqueous sodium chloride solution. The organic layer was dried over sodium sulfate, filtered and evaporated on a rotary evaporator. 1.86 g (79% purity, 87% yield) of the title compound were obtained.

LC-MS (Method 8): $R_t$=0.79 min; MS (ESIpos): m/z=257 [M+H]$^+$

Intermediate 100

Rac-Tert-Butyl {[4-(3-Methyl-1,2-Thiazol-4-Yl)-2,5-Dioxoimidazolidin-4-Yl]Methyl}Carbamate

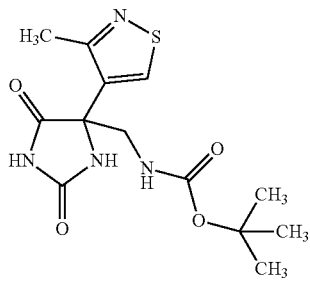 [SMILES: Cc1nscc1C1(CNC(=O)OC(C)(C)C)NC(=O)NC1=O]

In a microwave vial tert-butyl [2-(3-methyl-1,2-thiazol-4-yl)-2-oxoethyl]carbamate (1.86 g, 78% purity, 5.67 mmol) was dissolved in 20 ml of methanol. Potassium cyanide (1.85 g, 28.4 mmol) and ammonium carbonate (2.73 g, 28.4 mmol) were added. The vial was sealed and the mixture was stirred at 60° C. over night. Isolute® was added and the solvent was evaporated on a rotary evaporator. The crude product was purified by column chromatography (Machine: Biotage® Isolera One; column: Biotage® SNAP Ultra 50 g; gradient: DCM/MeOH-gradient, 2% MeOH-20% MeOH; flow: 100 ml/min). Product containing samples were united and the solvents were removed on a rotary evaporator. 739 mg (100% purity, 40% yield) of the title compound were obtained.

LC-MS (Method 7): $R_t$=1.06 min; MS (ESIpos): m/z=327 [M+H]$^+$

Intermediate 101

Rac-5-(Aminomethyl)-5-(3-Methyl-1,2-Thiazol-4-Yl)Imidazolidine-2,4-Dione Hydrochloride

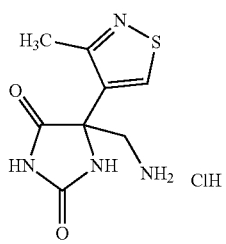

rac-tert-butyl {[4-(3-methyl-1,2-thiazol-4-yl)-2,5-dioxoimidazolidin-4-yl]methyl}carbamate (739 mg, 2.26 mmol) was dissolved in 20 ml of dichloromethane. 4 M hydrochloric acid in 1,4-dioxane (2.8 ml, 4.0 M, 11 mmol) was added and the mixture was stirred for 5 h. The precipitate was filtered off, washed with dichloromethane and dried in vacuo. 670 mg (100% purity, 113% yield) of the title compound were obtained.

LC-MS (Method 9): $R_t$=0.24 min; MS (ESIpos): m/z=227 [M+H−HCl]$^+$

Intermediate 102

Ethyl 5-(4-Methyl-1,2,5-Thiadiazol-3-Yl)-1,3-Oxazole-4-Carboxylate

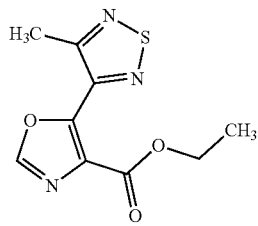 [SMILES: CCOC(=O)c1ncoc1-c1nsnc1C]

4-methyl-1,2,5-thiadiazole-3-carboxylic acid (1.00 g, 6.94 mmol) dissolved in 10 ml of THF was treated with 1,1,-carbonyl-diimidazole (1.35 g, 8.32 mmol) and stirred at room temperature. After 2 h ethyl isocyanoacetate (830 μl, 7.6 mmol), dissolved in 10 ml of THF, and a solution of lithium bis(trimethylsilyl)amide in THF (6.9 ml, 1.0 M, 6.9 mmol) were added at 0° C. The mixture was allowed to warm to room temperature and stirred for 1 h. The solvent was removed on a rotary evaporator. The residue was taken up with ethyl acetate and washed with water and saturated aqueous sodium chloride solution. The organic layer was dried over sodium sulfate, filtered, Isolute® was added and the solvent was evaporated on a rotary evaporator. The crude product was purified by column chromatography (Machine: Biotage® Isolera One; column: Biotage® SNAP Ultra 50 g; gradient: Cy/EE-gradient, 12% EE-100% EE; flow: 100 ml/min). Product containing samples were united and the solvents were removed on a rotary evaporator. 1.31 g (100% purity, 79% yield) of the title compound were obtained.

LC-MS (Method 7): $R_t$=1.39 min; MS (ESIpos): m/z=240 [M+H]$^+$

Intermediate 103

2-Amino-1-(4-Methyl-1,2,5-Thiadiazol-3-Yl)Ethan-1-One-Hydrogen Chloride

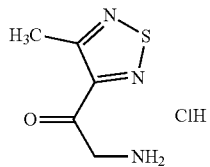

Ethyl 5-(4-methyl-1,2,5-thiadiazol-3-yl)-1,3-oxazole-4-carboxylate (1.31 g, 5.46 mmol) was taken up in 30 ml of 6 N hydrochloric acid and stirred at 100° C. After 2 h the solvent was removed on a rotary evaporator and the residue was treated with DCM. The solvent was removed and the residue was dried in vacuo. 1.03 g (100% purity, 98% yield) of the title compound were obtained.

LC-MS (Method 9): $R_t$=0.83 min; MS (ESIpos): m/z=158 [M+H−HCl]$^+$

Intermediate 104

Tert-Butyl [2-(4-Methyl-1,2,5-Thiadiazol-3-Yl)-2-Oxoethyl]Carbamate

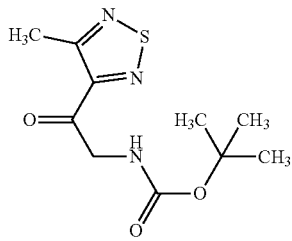 [SMILES: Cc1nsnc1C(=O)CNC(=O)OC(C)(C)C]

2-amino-1-(4-methyl-1,2,5-thiadiazol-3-yl)ethan-1-one-hydrogen chloride (1.04 g, 5.37 mmol) dissolved in 25 ml of dichloromethane was treated with di-tert-butyl dicarbonate (1.4 ml, 5.9 mmol) and triethylamine (2.2 ml, 16 mmol). The mixture was stirred at room temperature. After 2 h the solvent was removed on a rotary evaporator. The residue was taken up with ethyl acetate and washed with water and saturated aqueous sodium chloride solution. The organic layer was dried over sodium sulfate, filtered and evaporated on a rotary evaporator. 1.59 g (100% purity, 115% yield) of the title compound were obtained.

LC-MS (Method 7): $R_t$=1.71 min; MS (ESIpos): m/z=202 [M+H−C4H8]$^+$

Intermediate 105

Rac-Tert-Butyl {[4-(4-Methyl-1,2,5-Thiadiazol-3-Yl)-2,5-Dioxoimidazolidin-4-Yl]Methyl}Carbamate

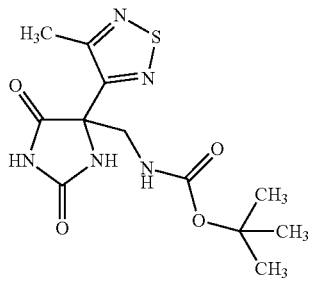 [SMILES: Cc1nsnc1C1(CNC(=O)OC(C)(C)C)NC(=O)NC1=O]

In a microwave vial tert-butyl [2-(4-methyl-1,2,5-thiadiazol-3-yl)-2-oxoethyl]carbamate (1.59 g, 6.19 mmol) was dissolved in 20 ml of methanol. Potassium cyanide (2.01 g, 30.9 mmol) and ammonium carbonate (2.97 g, 30.9 mmol) were added. The vial was sealed and the mixture was stirred at 60° C. over night. Isolute® was added and the solvent was evaporated on a rotary evaporator. The crude product was purified by column chromatography (Machine: Biotage® Isolera One; column: Biotage® SNAP Ultra 50 g; gradient: DCM/MeOH-gradient, 2% MeOH-20% MeOH; flow: 100 ml/min). Product containing samples were united and the solvents were removed on a rotary evaporator. 1.12 g (100% purity, 55% yield) of the title compound were obtained.

LC-MS (Method 7): $R_t$=1.17 min; MS (ESIneg): m/z=326 [M−H]$^-$

Intermediate 106

Rac-5-(Aminomethyl)-5-(4-Methyl-1,2,5-Thiadiazol-3-Yl)Imidazolidine-2,4-Dione Hydrochloride

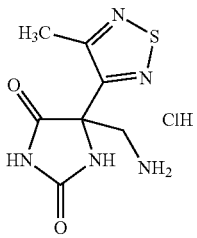

rac-tert-butyl {[4-(4-methyl-1,2,5-thiadiazol-3-yl)-2,5-dioxoimidazolidin-4-yl]methyl}carbamate (1.12 g, 3.42 mmol) was dissolved in 30 ml of dichloromethane. 4 M hydrochloric acid in 1,4-dioxane (4.3 ml, 4.0 M, 17 mmol) was added and the mixture was stirred over night. The precipitate was filtered off, washed with dichloromethane and dried in vacuo. 928 mg (100% purity, 103% yield) of the title compound were obtained.

LC-MS (Method 9): $R_t$=0.64 min; MS (ESIpos): m/z=228 [M+H−HCl]$^+$

Intermediate 107

Ethyl 5-(1,4-Dimethyl-1H-Pyrazol-5-Yl)-1,3-Oxazole-4-Carboxylate

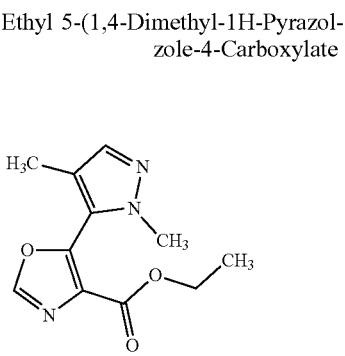

1,4-dimethyl-1H-pyrazole-5-carboxylic acid (1.00 g, 7.14 mmol) dissolved in 10 ml of THF was treated with 1,1,-carbonyl-diimidazole (1.39 g, 8.56 mmol) and stirred at room temperature. After 2 h ethyl isocyanoacetate (860 µl, 7.8 mmol), dissolved in 10 ml of THF, and a solution of lithium bis(trimethylsilyl)amide in THF (7.1 ml, 1.0 M, 7.1 mmol) were added at 0° C. The mixture was allowed to warm to room temperature and stirred for 1 h. The solvent was removed on a rotary evaporator. The residue was taken up with ethyl acetate and washed with water and saturated aqueous sodium chloride solution. The organic layer was dried over sodium sulfate, filtered, Isolute® was added and the solvent was evaporated on a rotary evaporator. The crude product was purified by column chromatography (Machine: Biotage® Isolera One; column: Biotage® SNAP Ultra 50 g; gradient: Cy/EE-gradient, 12% EE-100% EE; flow: 100 ml/min). Product containing samples were united and the solvents were removed on a rotary evaporator. 1.14 g (100% purity, 68% yield) of the title compound were obtained.

LC-MS (Method 7): $R_t$=1.19 min; MS (ESIpos): m/z=236 [M+H]$^+$

Intermediate 108

2-Amino-1-(1,4-Dimethyl-1H-Pyrazol-5-Yl)Ethan-1-One-Hydrogen Chloride

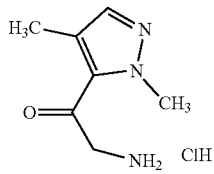

Ethyl 5-(1,4-dimethyl-1H-pyrazol-5-yl)-1,3-oxazole-4-carboxylate (1.14 g, 4.85 mmol) was taken up in 25 ml of 6 N hydrochloric acid and stirred at 100° C. After 2 h the solvent was removed on a rotary evaporator and the residue was treated with DCM. The solvent was removed an the residue was dried in vacuo. 1.14 g (57% purity, 71% yield) of the title compound were obtained.

LC-MS (Method 9): $R_t$=0.75 min; MS (ESIpos): m/z=154 [M+H−HCl]$^+$

Intermediate 109

Tert-Butyl [2-(1,4-Dimethyl-1H-Pyrazol-5-Yl)-2-Oxoethyl]Carbamate

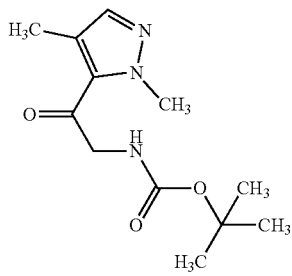 [SMILES: Cc1cnn(C)c1C(=O)CNC(=O)OC(C)(C)C]

2-amino-1-(1,4-dimethyl-1H-pyrazol-5-yl)ethan-1-one hydrogen chloride (1.14 g, 57% purity, 3.43 mmol) dissolved in 20 ml of dichloromethane was treated with di-tert-butyl dicarbonate (870 µl, 3.8 mmol) and triethylamine (1.4 ml, 10 mmol). The mixture was stirred at room temperature. After 2 h the solvent was removed on a rotary evaporator. The residue was taken up with ethyl acetate and washed with water and saturated aqueous sodium chloride solution. The organic layer was dried over sodium sulfate, filtered and evaporated on a rotary evaporator. 1.06 g (71% purity, 86% yield) of the title compound were obtained.

LC-MS (Method 7): $R_t$=1.50 min; MS (ESIpos): m/z=254 [M+H]$^+$

Intermediate 110

Rac-Tert-Butyl {[4-(1,4-Dimethyl-1H-Pyrazol-5-Yl)-2,5-Dioxoimidazolidin-4-Yl]Methyl}Carbamate

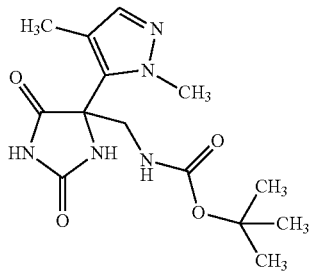 [SMILES: Cc1cnn(C)c1C1(CNC(=O)OC(C)(C)C)NC(=O)NC1=O]

In a microwave vial tert-butyl [2-(1,4-dimethyl-1H-pyrazol-5-yl)-2-oxoethyl]carbamate (1.06 g, 70% purity, 2.92 mmol) was dissolved in 15 ml of methanol. Potassium cyanide (950 mg, 14.6 mmol) and ammonium carbonate (1.40 g, 14.6 mmol) were added. The vial was sealed and the mixture was stirred at 60° C. for 3 d. Isolute® was added and the solvent was evaporated on a rotary evaporator. The crude product was purified by column chromatography (Machine: Biotage® Isolera One; column: Biotage® SNAP Ultra 50 g; gradient: DCM/MeOH-gradient, 2% MeOH-20% MeOH; flow: 100 ml/min). Product containing samples were united and the solvents were removed on a rotary evaporator. 465 mg (73% purity, 36% yield) of the title compound were obtained.

LC-MS (Method 7): $R_t$=1.05 min; MS (ESIpos): m/z=324 [M+H]$^+$

Intermediate 111

Rac-5-(Aminomethyl)-5-(1,4-Dimethyl-1H-Pyrazol-5-Yl)Imidazolidine-2,4-Dione Hydrochloride

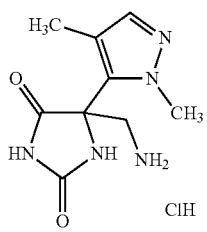

rac-tert-butyl {[4-(1,4-dimethyl-1H-pyrazol-5-yl)-2,5-dioxoimidazolidin-4-yl]methyl}carbamate (465 mg, 72% purity, 1.04 mmol) was dissolved in 10 ml of dichloromethane. 4 M hydrochloric acid in 1,4-dioxane (1.3 ml, 4.0 M, 5.2 mmol) was added and the mixture was stirred for 2 h. The precipitate was filtered off, washed with dichloromethane and dried in vacuo. 223 mg (86% purity, 71% yield) of the title compound were obtained.

LC-MS (Method 9): $R_t$=0.24 min; MS (ESIpos): m/z=224 [M+H−HCl]$^+$

Intermediate 112

Ethyl 5-(1,3-Dimethyl-1H-Pyrazol-4-Yl)-1,3-Oxazole-4-Carboxylate

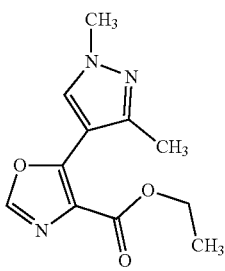 [SMILES: CCOC(=O)c1ncoc1-c1cn(C)nc1C]

1,3-dimethyl-1H-pyrazole-4-carboxylic acid (1.00 g, 7.14 mmol) dissolved in 10 ml of THE was treated with 1,1,-carbonyl-diimidazole (1.39 g, 8.56 mmol) and stirred at room temperature. After 2 h ethyl isocyanoacetate (860 µl, 7.8 mmol), dissolved in 10 ml of THF, and a solution of lithium bis(trimethylsilyl)amide in THF (7.1 ml, 1.0 M, 7.1 mmol) were added at 0° C. The mixture was allowed to warm to room temperature and stirred for 1 h. The solvent was removed on a rotary evaporator. The residue was taken up with ethyl acetate and washed with water and saturated aqueous sodium chloride solution. The organic layer was dried over sodium sulfate, filtered, Isolute® was added and the solvent was evaporated on a rotary evaporator. The crude product was purified by column chromatography (Machine: Biotage® Isolera One; column: Biotage® SNAP Ultra 50 g; gradient: Cy/EE-gradient, 12% EE-100% EE; flow: 100 ml/min). Product containing samples were united and the solvents were removed on a rotary evaporator. 1.30 g (100% purity, 77% yield) of the title compound were obtained.

LC-MS (Method 7): $R_t$=1.16 min; MS (ESIpos): m/z=236 [M+H]$^+$

Intermediate 113

2-Amino-1-(1,3-Dimethyl-1H-Pyrazol-4-Yl)Ethan-1-One Hydrogen Chloride

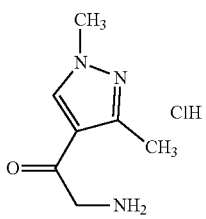

Ethyl 5-(1,3-dimethyl-1H-pyrazol-4-yl)-1,3-oxazole-4-carboxylate (1.30 g, 5.51 mmol) was taken up in 30 ml of 6 N hydrochloric acid and stirred at 100° C. After 2 h the solvent was removed on a rotary evaporator and the residue was treated with DCM. The solvent was removed and the residue was dried in vacuo. 1.44 g (100% purity, 138% yield) of the title compound were obtained.

LC-MS (Method 9): $R_t$=0.63 min; MS (ESIpos): m/z=154 [M+H−HCl]$^+$

Intermediate 114

Tert-Butyl [2-(1,3-Dimethyl-1H-Pyrazol-4-Yl)-2-Oxoethyl]Carbamate

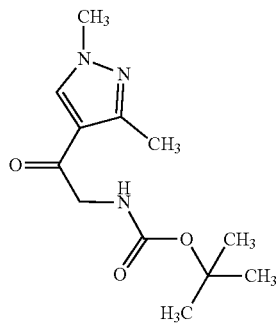 [SMILES: Cc1nn(C)cc1C(=O)CNC(=O)OC(C)(C)C]

2-amino-1-(1,3-dimethyl-1H-pyrazol-4-yl)ethan-1-one-hydrogen chloride (1.44 g, 7.59 mmol) dissolved in 35 ml of dichloromethane was treated with di-tert-butyl dicarbonate (1.9 ml, 8.4 mmol) and triethylamine (3.2 ml, 23 mmol). The mixture was stirred at room temperature. After 2 h the solvent was removed on a rotary evaporator. The residue was taken up with ethyl acetate and washed with water and saturated aqueous sodium chloride solution. The organic layer was dried over sodium sulfate, filtered and evaporated on a rotary evaporator. 1.75 g (100% purity, 91% yield) of the title compound were obtained.

LC-MS (Method 7): $R_t$=1.28 min; MS (ESIpos): m/z=254 [M+H]$^+$

Intermediate 115

Rac-Tert-Butyl {[4-(1,3-Dimethyl-1H-Pyrazol-4-Yl)-2,5-Dioxoimidazolidin-4-Yl]Methyl}Carbamate

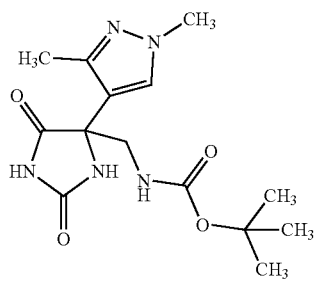 [SMILES: Cc1nn(C)cc1C1(CNC(=O)OC(C)(C)C)NC(=O)NC1=O]

In a microwave vial tert-butyl [2-(1,3-dimethyl-1H-pyrazol-4-yl)-2-oxoethyl]carbamate (1.75 g, 6.91 mmol) was dissolved in 20 ml of methanol. Potassium cyanide (2.25 g, 34.6 mmol) and ammonium carbonate (3.32 g, 34.6 mmol) were added. The vial was sealed and the mixture was stirred at 60° C. for 48 h. Isolute® was added and the solvent was evaporated on a rotary evaporator. The crude product was purified by column chromatography (Machine: Biotage® Isolera One; column: Biotage® SNAP Ultra 50 g; gradient: DCM/MeOH-gradient, 2% MeOH-20% MeOH; flow: 100 ml/min). Product containing samples were united and the solvents were removed on a rotary evaporator. 667 mg (100% purity, 30% yield) of the title compound were obtained.

LC-MS (Method 7): $R_t$=0.93 min; MS (ESIpos): m/z=324 [M+H]$^+$

Intermediate 116

Rac-5-(Aminomethyl)-5-(1,3-Dimethyl-1H-Pyrazol-4-Yl)Imidazolidine-2,4-Dione Hydrochloride

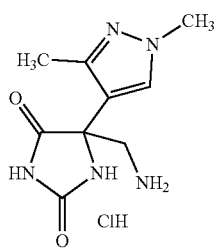

rac-tert-butyl {[4-(1,3-dimethyl-1H-pyrazol-4-yl)-2,5-dioxoimidazolidin-4-yl]methyl}carbamate (667 mg, 2.06 mmol) was dissolved in 20 ml of dichloromethane. 4 M hydrochloric acid in 1,4-dioxane (2.6 ml, 4.0 M, 10 mmol) was added and the mixture was stirred over night. The precipitate was filtered off, washed with dichloromethane and dried in vacuo. 660 mg (98% purity, 121% yield) of the title compound were obtained.

LC-MS (Method 9): $R_t$=0.24 min; MS (ESIpos): m/z=224 [M+H−HCl]$^+$

Intermediate 117

Ethyl 5-(4-Methyl-1,2-Oxazol-5-Yl)-1,3-Oxazole-4-Carboxylate

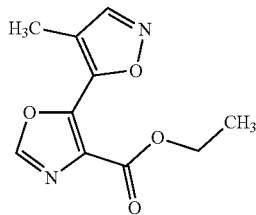 [SMILES: CCOC(=O)c1ncoc1-c1oncc1C]

4-methyl-1,2-oxazole-5-carboxylic acid (1.00 g, 7.87 mmol) dissolved in 10 ml of THF was treated with 1,1,-carbonyl-diimidazole (1.53 g, 9.44 mmol) and stirred at room temperature. After 2 h ethyl isocyanoacetate (950 μl, 8.7 mmol), dissolved in 10 ml of THF, and a solution of lithium bis(trimethylsilyl)amide in THF (7.9 ml, 1.0 M, 7.9 mmol) were added at 0° C. The mixture was allowed to warm to room temperature and stirred for 1 h. The solvent was removed on a rotary evaporator. The residue was taken up with ethyl acetate and washed with water and saturated aqueous sodium chloride solution. The organic layer was dried over sodium sulfate, filtered, Isolute® was added and the solvent was evaporated on a rotary evaporator. The crude product was purified by column chromatography (Machine: Biotage® Isolera One; column: Biotage® SNAP Ultra 50 g; gradient: Cy/EE-gradient, 12% EE-100% EE; flow: 100 ml/min). Product containing samples were united and the solvents were removed on a rotary evaporator. 1.28 g (100% purity, 73% yield) of the title compound were obtained.

LC-MS (Method 7): $R_t$=1.25 min; MS (ESIpos): m/z=223 [M+H]$^+$

Intermediate 118

2-Amino-1-(4-Methyl-1,2-Oxazol-5-Yl)Ethan-1-One Hydrogen Chloride

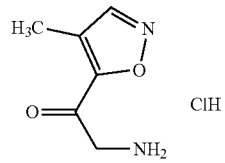

Ethyl 5-(4-methyl-1,2-oxazol-5-yl)-1,3-oxazole-4-carboxylate (1.28 g, 5.75 mmol) was taken up in 30 ml of 6 N hydrochloric acid and stirred at 100° C. After 2 h the solvent was removed on a rotary evaporator and the residue was treated with DCM. The solvent was removed and the residue was dried in vacuo. 1.11 g (100% purity, 109% yield) of the title compound were obtained.

LC-MS (Method 9): $R_t$=0.68 min, MS (ESIpos): m/z=141 [M+H−HCl]$^+$

Intermediate 119

Tert-Butyl [2-(4-Methyl-1,2-Oxazol-5-Yl)-2-Oxoethyl]Carbamate

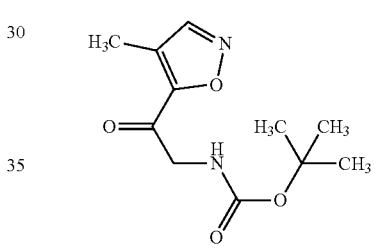

2-amino-1-(4-methyl-1,2-oxazol-5-yl)ethan-1-one-hydrogen chloride (1.11 g, 6.26 mmol) dissolved in 30 ml of dichloromethane was treated with di-tert-butyl dicarbonate (1.6 ml, 6.9 mmol) and triethylamine (2.6 ml, 19 mmol). The mixture was stirred at room temperature. After 2 h the solvent was removed on a rotary evaporator. The residue was taken up with ethyl acetate and washed with water and saturated aqueous sodium chloride solution. The organic layer was dried over sodium sulfate, filtered and evaporated on a rotary evaporator. 1.45 g (96% yield) of the title compound were obtained.

Intermediate 120

Rac-Tert-Butyl {[4-(4-Methyl-1,2-Oxazol-5-Yl)-2,5-Dioxoimidazolidin-4-Yl]Methyl}Carbamate

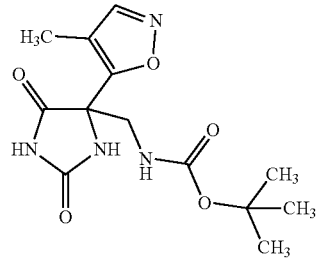 [SMILES: Cc1cnoc1C1(CNC(=O)OC(C)(C)C)NC(=O)NC1=O]

In a microwave vial tert-butyl [2-(4-methyl-1,2-oxazol-5-yl)-2-oxoethyl]carbamate (1.45 g, 6.03 mmol) was dissolved in 20 ml of methanol. Potassium cyanide (1.96 g, 30.2 mmol) and ammonium carbonate (2.90 g, 30.2 mmol) were added. The vial was sealed and the mixture was stirred at 60° C. over night. Isolute® was added and the solvent was evaporated on a rotary evaporator. The crude product was purified by column chromatography (Machine: Biotage® Isolera One; column: Biotage® SNAP Ultra 50 g; gradient: DCM/MeOH-gradient, 2% MeOH-20% MeOH; flow: 100 ml/min). Product containing samples were united and the solvents were removed on a rotary evaporator. 612 mg (100% purity, 33% yield) of the title compound were obtained.

LC-MS (Method 7): $R_t$=1.06 min; MS (ESIneg): m/z=309 [M−H]⁻

Intermediate 121

Rac-5-(Aminomethyl)-5-(4-Methyl-1,2-Oxazol-5-Yl)Imidazolidine-2,4-Dione Hydrochloride

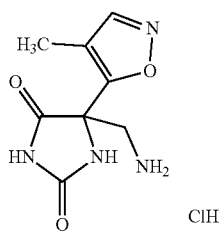

rac-tert-butyl {[4-(4-methyl-1,2-oxazol-5-yl)-2,5-dioxo-imidazolidin-4-yl]methyl}carbamate (612 mg, 1.97 mmol) was dissolved in 17 ml of dichloromethane. 4 M hydrochloric acid in 1,4-dioxane (2.5 ml, 4.0 M, 9.9 mmol) was added and the mixture was stirred over night. The precipitate was filtered off, washed with dichloromethane and dried in vacuo. 447 mg (95% purity, 87% yield) of the title compound were obtained.

LC-MS (Method 9): $R_t$=0.22 min; MS (ESIpos): m/z=211 [M+H−HCl]⁺

Intermediate 122

Ethyl 5-(3-Methylbutyl)-1,3-Oxazole-4-Carboxylate

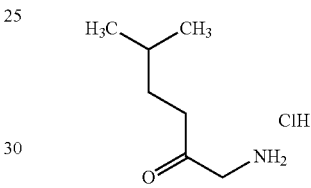

4-methylpentanoic acid (1.00 g, 8.61 mmol) dissolved in 10 ml of THF was treated with 1,1,-carbonyl-diimidazole (1.68 g, 10.3 mmol) and stirred at room temperature. After 2 h ethyl isocyanoacetate (1.0 ml, 9.5 mmol), dissolved in 10 ml of THF, and a solution of lithium bis(trimethylsilyl) amide in THF (8.6 ml, 1.0 M, 8.6 mmol) were added at 0° C. The mixture was allowed to warm to room temperature and stirred over night. The solvent was removed on a rotary evaporator. The residue was taken up with ethyl acetate and washed with water and saturated aqueous sodium chloride solution. The organic layer was dried over sodium sulfate, filtered, Isolute® was added and the solvent was evaporated on a rotary evaporator. The crude product was purified by column chromatography (Machine: Biotage® Isolera One; column: Biotage® SNAP Ultra 50 g; gradient: Cy/EE-gradient, 6% EE-50% EE; flow: 100 ml/min). Product containing samples were united and the solvents were removed on a rotary evaporator. 970 mg (100% purity, 53% yield) of the title compound were obtained.

LC-MS (Method 8): $R_t$=0.99 min; MS (ESIpos): m/z=212 [M+H]⁺

Intermediate 123

1-Amino-5-Methylhexan-2-One-Hydrogen Chloride

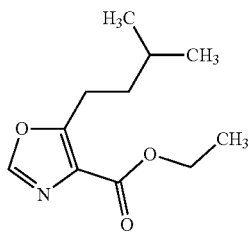

Ethyl 5-(3-methylbutyl)-1,3-oxazole-4-carboxylate (970 mg, 4.59 mmol) was taken up in 16 ml of 6 N hydrochloric acid and stirred at 100° C. After 2 h the solvent was removed on a rotary evaporator and the residue was dried in vacuo. 570 mg (75% yield) of the title compound were obtained.

Intermediate 124

Tert-Butyl (5-Methyl-2-Oxohexyl)Carbamate

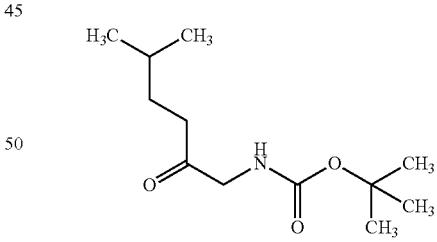

1-amino-5-methylhexan-2-one-hydrogen chloride (700 mg, 4.23 mmol) dissolved in 15 ml of dichloromethane was treated with di-tert-butyl dicarbonate (1.2 ml, 5.1 mmol) and triethylamine (1.8 ml, 13 mmol). The mixture was stirred at room temperature over night. After that time the solvent was removed on a rotary evaporator. The residue was taken up with ethyl acetate and washed with water and saturated aqueous sodium chloride solution. The organic layer was dried over sodium sulfate, filtered and evaporated on a rotary evaporator. 863 mg (89% yield) of the title compound were obtained.

Intermediate 125

Rac-Tert-Butyl {[4-(3-Methylbutyl)-2,5-Dioxoimidazolidin-4-Yl]Methyl}Carbamate

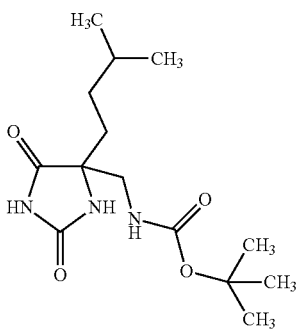 [SMILES: CC(C)CCC1(CNC(=O)OC(C)(C)C)NC(=O)NC1=O]

In a microwave vial ammonium carbonate (3.62 g, 37.6 mmol) and ammonium chloride (805 mg, 15.1 mmol) were dissolved in 6.5 ml of water. tert-butyl (5-methyl-2-oxohexyl)carbamate (863 mg, 3.76 mmol) dissolved in 6.5 ml of ethanol was added and the mixture was stirred at room temperature for 15 min. After that time potassium cyanide (1.10 g, 16.9 mmol) was added and the vial was sealed. The mixture was stirred at 60° C. over night. The solvent was removed on a rotary evaporator. The residue was taken up with water and extracted three times with ethyl acetate. The organic layer was washed with saturated aqueous sodium chloride solution, dried over sodium sulfate, filtered and the solvent was evaporated on a rotary evaporator. 790 mg (76% purity, 53% yield) of the title compound were obtained.

LC-MS (Method 7): $R_t$=1.46 min; MS (ESIneg): m/z=298 [M−H]⁻

Intermediate 126

Rac-5-(Aminomethyl)-5-(3-Methylbutyl)Imidazolidine-2,4-Dione Hydrochloride

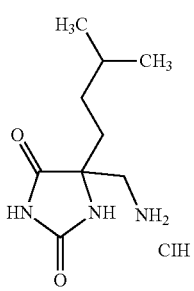

rac-tert-butyl {[4-(3-methylbutyl)-2,5-dioxoimidazolidin-4-yl]methyl}carbamate (790 mg, 78% purity, 2.06 mmol) was dissolved in 40 ml of dichloromethane. 4 M hydrochloric acid in 1,4-dioxane (2.6 ml, 4.0 M, 10 mmol) was added and the mixture was stirred over night. The solvent was removed on a rotary evaporator and the residue was dried in vacuo. 663 mg (90% purity, 123% yield) of the title compound were obtained.

LC-MS (Method 9): $R_t$=0.76 min; MS (ESIpos): m/z=200 [M+H−HCl]⁺

Intermediate 127

Rac-Ethyl 5-Sec-Butyl-1,3-Oxazole-4-Carboxylate

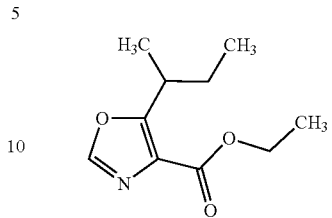

A solution of rac-2-methylbutanoic acid (1.1 ml, 9.8 mmol) and 1,1'-carbonyldiimidazole (1.91 g, 11.7 mmol) in 10 ml of THE was stirred for 3 h at room temperature. After that time, a solution of ethyl isocyanoacetate (1.2 ml, 11 mmol) in 10 ml of THE and a solution of lithium bis (trimethylsilyl)amide in THF (9.8 ml, 1.0 M, 9.8 mmol) were added dropwise at 0° C. When the addition was complete the resulting mixture was stirred at room temperature for 3 h. The reaction was concentrated in vacuo and extracted with ethyl acetate. The combined organic layers were dried over sodium sulfate, filtered and concentrated. The crude product was purified by column chromatography (Machine: Biotage® Isolera One; column: Biotage® SNAP Ultra 50 g; gradient: Cy/EE-gradient, 8% EE-66% EE; flow: 100 ml/min). Product containing samples were united and the solvents were removed on a rotary evaporator. 446 mg (97% purity, 22% yield) of the title compound were obtained.

LC-MS (Method 7): $R_t$=1.70 min; MS (ESIpos): m/z=198 [M+H]⁺

Intermediate 128

Rac-1-Amino-3-Methylpentan-2-One Hydrochloride

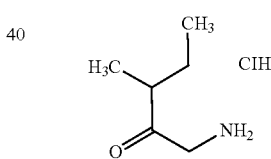

rac-ethyl 5-sec-butyl-1,3-oxazole-4-carboxylate (446 mg, 2.26 mmol) were taken up in 7.5 ml of 6 N hydrochloric acid and stirred at 100° C. over night. The solvent was removed on a rotary evaporator and the residue was dried in vacuo. 372 mg (108% yield) of the title compound were obtained.

Intermediate 129

Rac-Tert-Butyl (3-Methyl-2-Oxopentyl)Carbamate

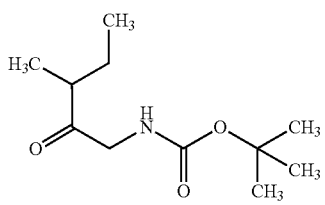

rac-1-amino-3-methylpentan-2-one hydrochloride (372 mg, 2.45 mmol) dissolved in 15 ml of dichloromethane were treated with di-tert-butyl dicarbonate (620 µl, 2.7 mmol) and triethylamine (1.0 ml, 7.4 mmol). The mixture was stirred at room temperature overnight. The solvent was removed on a rotary evaporator. The residue was taken up with ethyl acetate and washed with water and saturated aqueous sodium chloride solution. The organic layer was dried over sodium sulfate, filtered and evaporated on a rotary evaporator. 480 mg (100% purity, 91% yield) of the title compound were obtained.

$^1$H-NMR (400 MHz, DMSO-d6) δ [ppm]: 0.786 (2.10), 0.804 (4.90), 0.823 (2.39), 0.958 (3.46), 0.975 (3.56), 1.290 (0.48), 1.308 (0.75), 1.324 (1.46), 1.343 (0.69), 1.366 (2.11), 1.377 (16.00), 1.468 (1.14), 1.532 (0.41), 1.550 (0.50), 1.567 (0.50), 1.584 (0.41), 2.519 (0.94), 3.778 (0.94), 3.789 (1.12), 3.793 (1.06), 3.804 (0.89), 6.977 (0.42).

Intermediate 130

Diamix-Tert-Butyl [(4-Sec-Butyl-2,5-Dioxoimidazolidin-4-Yl)Methyl]Carbamate

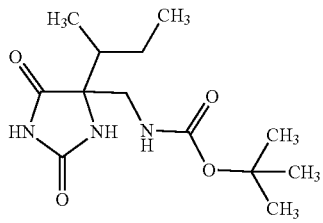 [SMILES: CCC(C)C1(CNC(=O)OC(C)(C)C)NC(=O)NC1=O]

In a microwave vial rac-tert-butyl (3-methyl-2-oxopentyl) carbamate (480 mg, 2.23 mmol) was dissolved in 4 ml of methanol. Potassium cyanide (581 mg, 8.92 mmol) and ammonium carbonate (857 mg, 8.92 mmol) were added. The vial was sealed and the mixture was stirred at 40° C. over night. The mixture was filtered an the filtrate was purified by preparative HPLC (Column: Chromatorex C18 10 µm 250× 30 mm; eluent A=water, B=acetonitrile; gradient: 0.0 min 30% B; 4.5 min 50% B; 11.5 min 70% B; 12 min 100% B; 14.75 min 30% B; flow: 50 ml/min; 0.1% formic acid). Product containing samples were united and the solvents were removed on a rotary evaporator. 237 mg (100% purity, 37% yield) of the title compound were obtained.

LC-MS (Method 7): $R_t$=1.27 min; MS (ESIneg): m/z=284 [M−H]$^−$

LC-MS (Method 8): $R_t$=0.74 min; MS (ESIneg): m/z=284 [M−H]$^−$

Intermediate 131

Diamix-5-(Aminomethyl)-5-Sec-Butylimidazolidine-2,4-Dione Hydrochloride

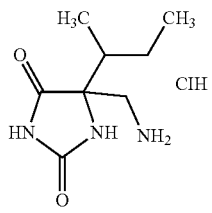

diamix-tert-butyl [(4-sec-butyl-2,5-dioxoimidazolidin-4-yl)methyl]carbamate (235 mg, 824 µmol) was dissolved in 3 ml of dichloromethane. 4 M hydrochloric acid in 1,4-dioxane (1.0 ml, 4.0 M, 4.1 mmol) was added and the mixture was stirred for 4 h. The solvent was removed on a rotary evaporator. The residue was taken up in dichloromethane, the precipitate was filtered off, washed with dichloromethane and dried in vacuo. 155 mg (100% purity, 85% yield) of the title compound were obtained.

LC-MS (Method 9): $R_t$=0.36 min; MS (ESIpos): m/z=186 [M−HCl+H]$^+$

Intermediate 132

Tert-Butyl {2-[Methoxy(Methyl)Amino]-2-Oxoethyl}Carbamate

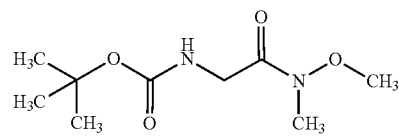

7.30 mL (56.00 mmol) of isobutyl chloroformate was added to a solution of 6.53 g (37.30 mmol) of N-BOC-glycine and 8.20 mL (75.00 mmol) of 4-methylmorpholine in 100 mL of dichloromethane at −15° C. and the mixture was stirred for 1 hour. Then 4.00 g (41.00 mmol) of N,O-dimethylhydroxiamine hydrochloride in 20 mL of dichloromethane was added to the solution at −15° C. and the reaction was further stirred at room temperature for 2 hours. The mixture was quenched with water and extracted with dichloromethane. The combined organic layers were dried over magnesium sulfate, filtered and concentrated. The corresponding residue was purified by flash chromatography on silica gel eluting with dichloromethane/methanol mixtures to afford 4.62 g (57%) of the product as a white powder.

$^1$H-NMR (300 MHz, DMSO-d$_6$): δ [ppm]=137 (s, 9H), 3.08 (s, 3H), 3.67 (s, 3H), 3.82 (d, 2H), 6.82 (bp, 1H).

LC-MS (Method 3): $R_t$=0.499 min. MS (Mass method 1): m/z=163 (M−tBu+H)$^+$

Intermediate 133

Tert-Butyl (2-Cyclopentyl-2-Oxoethyl)Carbamate

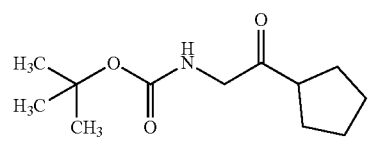 [SMILES: CC(C)(C)OC(=O)NCC(=O)C1CCCC1]

To a solution of 2.20 g (10.10 mmol) of tert-butyl {2-[methoxy(methyl)amino]-2-oxoethyl}carbamate in 10 mL of anhydrous tetrahydrofuran under inert atmosphere at 0° C. was added dropwise 13.00 mL (25.00 mmol) of cyclopentylmagnesium chloride solution (2M in tetrahydrofuran) and the reaction was stirred at room temperature for 12 hours. The solvent was partially removed and the mixture was diluted with ethyl acetate and quenched with saturated ammonium chloride (aq.). The organic layer was isolated, dried over magnesium sulfate, filtered and concentrated to afford a residue, which was purified by flash column chromatography on silica gel eluting with heptane/ethyl acetate to give 0.58 g (25%) of the product as a yellowish oil.

¹H-NMR (300 MHz, DMSO-d₆): δ [ppm]=1.37 (s, 9H), 1.49-1.67 (m, 6H), 1.68-1.84 (m, 2H), 2.85-3.00 (m, 1H), 3.80 (d, 2H), 6.98 (t, 1H).

LC-MS (Method 3): R_t=0.795 min. MS (Mass method 1): m/z=172 (M−tBu+H)⁺

Intermediate 134

Rac-Tert-Butyl {[4-Cyclopentyl-2,5-Dioxoimidazolidin-4-Yl]Methyl}Carbamate

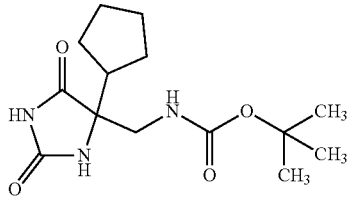 [SMILES: CC(C)(C)OC(=O)NCC1(C2CCCC2)NC(=O)NC1=O]

A solution of 0.58 g (2.56 mmol) of tert-butyl (2-cyclopentyl-2-oxoethyl)carbamate in 5 mL of ethanol was added to another solution of 0.33 g (5.12 mmol) of potassium cyanide and 2.46 g (25.60 mmol) of ammonium carbonate in 5 mL of water into a pressure flask, the container was sealed and the mixture was stirred at 60° C. for 12 hours. The ethanol was removed under reduced pressure and the resulting precipitate was collected by filtration, washed with water and dried in vacuo to give 0.46 g (60%) of the product as white solid.

¹H-NMR (300 MHz, DMSO-d₆): δ [ppm]=1.09-1.31 (m, 2H), 1.36 (s, 9H), 1.40-1.60 (m, 5H), 1.61-1.75 (m, 1H), 2.01-2.16 (m, 1H), 3.20-3.25 (m, 2H), 6.74 (t, 1H), 7.61 (s, 1H), 10.53 (bp, 1H).

LC-MS (Method 3): R_t=0.601 min. MS (Mass method 1): m/z=320 (M+Na)+

Intermediate 135

Rac-5-(Aminomethyl)-5-Cyclopentylimidazolidine-2,4-Dione Hydrochloride

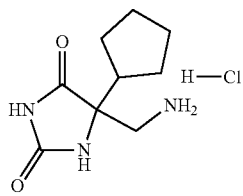

1.90 mL (7.70 mmol) of 4N hydrochloric acid in dioxane were added to a solution of 0.46 g (1.55 mmol) of rac-tert-Butyl {[4-cyclopentyl-2,5-dioxoimidazolidin-4-yl]methyl}carbamate in 10 mL of dichloromethane and the mixture was allowed to stir at room temperature for 16 hours. The resulting precipitate was collected by filtration and washed with dichloromethane, ethyl acetate and diethyl ether to give 0.32 g (88%) of the product as a yellow sticky solid. The compound was used as such in the next step.

¹H-NMR (300 MHz, DMSO-d₆): δ [ppm]=1.13-1.38 (m, 2H), 1.40-1.63 (m, 5H), 1.65-1.77 (m, 1H), 2.10-2.25 (m, 1H), 2.95 (d, 1H), 3.12 (d, 1H), 8.09 (s, 1H), 8.20 (bp, 3H), 10.99 (bp, 1H).

LC-MS (Method 1): R_t=0.801 min. MS (Mass method 1): m/z=198 (M+H)⁺

Intermediate 136

4-Chloro-2-[6-(Trifluoromethyl)Pyridin-3-Yl]Benzoic Acid

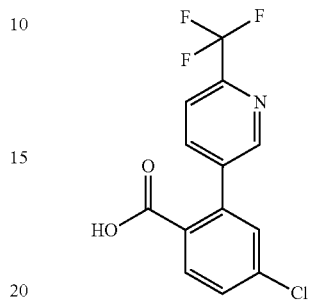

2-borono-4-chlorobenzoic acid (250 mg, 1.25 mmol) and 5-bromo-2-(trifluoromethyl)pyridine (352 mg, 1.56 mmol) dissolved in 7 ml 1,2-dimethoxethane were treated with sodium carbonate in water (3.1 ml, 2.0 M, 6.2 mmol). The mixture was degassed with argon. Then tetrakis(triphenylphosphine)palladium(0) (72.1 mg, 62.4 µmol) was added and the mixture was stirred at 80° C. over night. Purification was done by preparative HPLC (Column: Chromatorex C18 10 µm 250×30 mm; eluent A=water+0.1% formic acid, B=acetonitrile; gradient: 0.0 min 30% B; 4.5 min 50% B; 11.5 min 70% B; 12 min 100% B; 14.75 min 30% B; flow: 50 ml/min). Product containing samples were united and the solvents were removed on a rotary evaporator. 47.0 mg (100% purity, 12% yield) of the title compound were obtained.

LC-MS (Method 7): R_t=1.87 min; MS (ESIpos): m/z=302 [M+H]⁺

Intermediate 137

3,4-Difluoro-2-[6-(Trifluoromethyl)Pyridin-3-Yl]Benzoic Acid

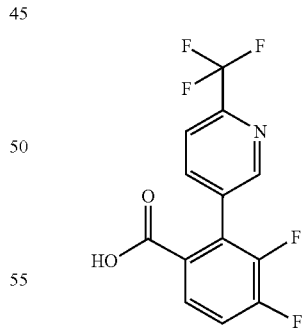

3,4-difluoro-2-(4,4,5,5-tetramethyl-1,3,2-dioxaborolan-2-yl)benzoic acid (250 mg, 880 µmol) and 5-bromo-2-(trifluoromethyl)pyridine (249 mg, 1.10 mmol) dissolved in 5 ml 1,2-dimethoxethane were treated with sodium carbonate in water (2.2 ml, 2.0 M, 4.4 mmol). The mixture was degassed with argon. Then tetrakis(triphenylphosphine)palladium(0) (50.8 mg, 44.0 µmol) was added and the mixture was stirred at 80° C. over night. Purification was done by preparative HPLC (Column: Chromatorex C18 10 µm 250×

Intermediate 138

Ethyl 5-Ethyl-1,3-Oxazole-4-Carboxylate

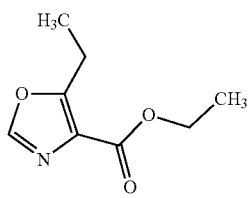

Propanoic acid (1.00 g, 13.5 mmol) dissolved in 15 ml of THF was treated with 1,1,-carbonyl-diimidazole (2.63 g, 16.2 mmol) and stirred at room temperature. After 2 h ethyl isocyanoacetate (1.6 ml, 15 mmol), dissolved in 10 ml of THF, and a solution of lithium bis(trimethylsilyl)amide in THF (13 ml, 1.0 M, 13 mmol) were added at 0° C. The mixture was allowed to warm to room temperature and stirred over night. The solvent was removed on a rotary evaporator. The residue was taken up with ethyl acetate and washed with water and saturated aqueous sodium chloride solution. The organic layer was dried over sodium sulfate, filtered, Isolute® was added and the solvent was evaporated on a rotary evaporator. The crude product was purified by column chromatography (Machine: Biotage® Isolera One; column: Biotage® SNAP Ultra 50 g; gradient: Cy/EE-gradient, 8% EE-80% EE; flow: 100 ml/min). Product containing samples were united and the solvents were removed on a rotary evaporator. 1.40 g (97% purity, 59% yield) of the title compound were obtained.

LC-MS (Method 7): $R_t$=1.30 min; MS (ESIpos): m/z=170 [M+H]$^+$

Intermediate 139

1-Aminobutan-2-One Hydrogen Chloride

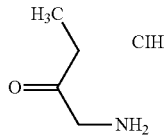

Ethyl 5-ethyl-1,3-oxazole-4-carboxylate (1.40 g, 8.28 mmol) was taken up in 28 ml of 6 N hydrochloric acid and stirred at 100° C. After 4 h the solvent was removed on a rotary evaporator and the residue was dried in vacuo. 0.99 g (97% yield) of the title compound were obtained.

Intermediate 140

Tert-Butyl (2-Oxobutyl)Carbamate

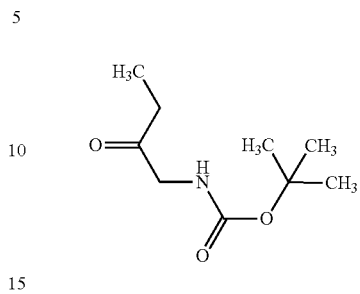

1-aminobutan-2-one-hydrogen chloride (990 mg, 8.01 mmol) dissolved in 30 ml of dichloromethane was treated with di-tert-butyl dicarbonate (2.0 ml, 8.8 mmol) and tri-ethylamine (3.3 ml, 24 mmol). The mixture was stirred at room temperature over night. The solvent was removed on a rotary evaporator. The residue was taken up with ethyl acetate and washed with water and saturated aqueous sodium chloride solution. The organic layer was dried over sodium sulfate, filtered and evaporated on a rotary evaporator. 1.2 g (80% yield) of the title compound were obtained.

Intermediate 141

Rac-Tert-Butyl [(4-Ethyl-2,5-Dioxoimidazolidin-4-Yl)Methyl]Carbamate

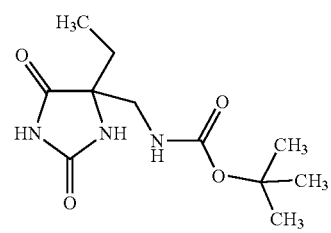 [SMILES: CCC1(CNC(=O)OC(C)(C)C)NC(=O)NC1=O]

Ammonium carbonate (6.16 g, 64.1 mmol) and ammonium chloride (1.37 g, 25.6 mmol) were dissolved in 10 ml of water. Tert-butyl (2-oxobutyl)carbamate (1.20 g, 6.41 mmol), dissolved in 10 ml of ethanol was added and the mixture was stirred for 15 min at room temperature. Then potassium cyanide (1.88 g, 28.8 mmol) was added, the vial was sealed and the mixture was stirred at 80° C. over night. The solvent was removed on a rotary evaporator. The residue was taken up with ethyl acetate and washed with water and saturated aqueous sodium chloride solution. The organic layer was dried over sodium sulfate, filtered and concentrated on a rotary evaporator. 1.17 g (100% purity, 71% yield) of the title compound were obtained.

LC-MS (Method 7): $R_t$=0.96 min; MS (ESIneg): m/z=256 [M−H]$^−$

Intermediate 142

Rac-5-(Aminomethyl)-5-Ethylimidazolidine-2,4-Dione Hydrochloride

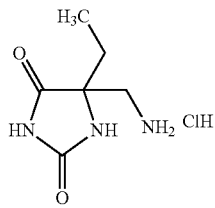

rac-tert-butyl [(4-ethyl-2,5-dioxoimidazolidin-4-yl)methyl]carbamate (1.17 g, 4.55 mmol) was dissolved in 26 ml of dichloromethane. 4 M hydrochloric acid in 1,4-dioxane (5.7 ml, 4.0 M, 23 mmol) was added and the mixture was stirred for 2 h. The solvent was removed on a rotary evaporator and the residue was taken up in dichloromethane. The solvent was removed and the residue was dried in vacuo. 1.00 g (95% purity, 108% yield) of the title compound were obtained.

LC-MS (Method 9): $R_t$=0.25 min; MS (ESIpos): m/z=158 [M+H−HCl]$^+$

Intermediate 143

2-[4-(Trifluoromethyl)Phenyl]Pyridine-3-Carboxylic Acid

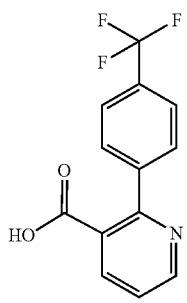 [SMILES: O=C(O)c1cccnc1-c1ccc(C(F)(F)F)cc1]

[4-(trifluoromethyl)phenyl]boronic acid (250 mg, 1.32 mmol) and 2-bromopyridine-3-carboxylic acid (332 mg, 1.65 mmol) dissolved in 7.5 ml 1,2-dimethoxethane were treated with sodium carbonate in water (3.3 ml, 2.0 M, 6.6 mmol). The mixture was degassed with argon. Then tetrakis(triphenylphosphine)palladium(0) (76.1 mg, 65.8 µmol) was added and the mixture was stirred at 80° C. over night. Purification was done by preparative HPLC (Column: Chromatorex C18 10 µm 250×30 mm; eluent A=water+0.1% formic acid, B=acetonitrile; gradient: 0.0 min 30% B; 4.5 min 50% B; 11.5 min 70% B; 12 min 100% B; 14.75 min 30% B; flow: 50 ml/min). Product containing samples were united and the solvents were removed on a rotary evaporator. 20.0 mg (70% purity, 4% yield) of the title compound were obtained.

LC-MS (Method 7): $R_t$=1.34 min; MS (ESIpos): m/z=268 [M+H]$^+$

Intermediate 144

3-[4-(Trifluoromethyl)Phenyl]Pyridine-4-Carboxylic Acid

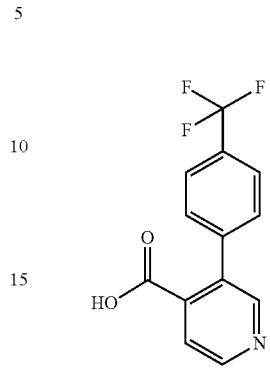

[4-(trifluoromethyl)phenyl]boronic acid (250 mg, 1.32 mmol) and 3-bromopyridine-4-carboxylic acid (332 mg, 1.65 mmol) dissolved in 7.5 ml 1,2-dimethoxethane were treated with sodium carbonate in water (3.3 ml, 2.0 M, 6.6 mmol). The mixture was degassed with argon. Then tetrakis(triphenylphosphine)palladium(0) (76.1 mg, 65.8 µmol) was added and the mixture was stirred at 80° C. over night. Purification was done by preparative HPLC (Column: Chromatorex C18 10 µm 250×30 mm; eluent A=water+0.1% formic acid, B=acetonitrile; gradient: 0.0 min 5% B; 3 min 5% B; 20 min 50% B; 23 min 100% B; 26 min 5% B; flow: 50 ml/min). Product containing samples were united and the solvents were removed on a rotary evaporator. 47.0 mg (100% purity, 13% yield) of the title compound were obtained.

LC-MS (Method 7): $R_t$=1.00 min; MS (ESIpos): m/z=268 [M+H]$^+$

Intermediate 145

2-[5-(Trifluoromethyl)Pyridin-2-Yl]Benzoic Acid

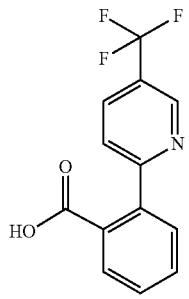 [SMILES: O=C(O)c1ccccc1-c1ccc(C(F)(F)F)cn1]

2-boronobenzoic acid (250 mg, 1.51 mmol) and 2-bromo-5-(trifluoromethyl)pyridine (426 mg, 1.88 mmol) dissolved in 7.5 ml 1,2-dimethoxethane were treated with sodium carbonate in water (3.8 ml, 2.0 M, 7.5 mmol). The mixture was degassed with argon. Then tetrakis(triphenylphosphine)palladium(0) (87.0 mg, 75.3 µmol) was added and the mixture was stirred at 80° C. over night. Purification was done by preparative HPLC (Column: Chromatorex C18 10 µm 250×30 mm; eluent A=water+0.1% formic acid, B=acetonitrile; gradient: 0.0 min 30% B; 4.5 min 50% B; 11.5 min 70% B; 12 min 100% B; 14.75 min 30% B; flow: 50 ml/min). Product containing samples were united and the solvents were removed on a rotary evaporator. 27.0 mg (75% purity, 5% yield) of the title compound were obtained.

LC-MS (Method 7): $R_t$=1.52 min; MS (ESIpos): m/z=268 [M+H]$^+$

Intermediate 146

4'-Chloro-5-(Trifluoromethyl)[1,1'-Biphenyl]-2-Carboxylic Acid

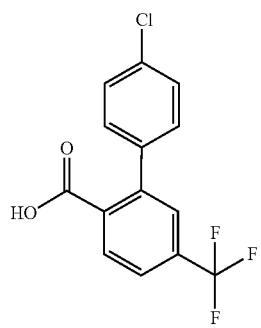 [SMILES: O=C(O)c1ccc(C(F)(F)F)cc1-c1ccc(Cl)cc1]

2-borono-4-(trifluoromethyl)benzoic acid (250 mg, 1.07 mmol) and 1-bromo-4-chlorobenzene (256 mg, 1.34 mmol) dissolved in 6 ml 1,2-dimethoxethane were treated with sodium carbonate in water (2.7 ml, 2.0 M, 5.3 mmol). The mixture was degassed with argon. Then tetrakis(triphenylphosphine)palladium(0) (61.7 mg, 53.4 µmol) was added and the mixture was stirred at 80° C. over night. Purification was done by preparative HPLC (Column: Chromatorex C18 10 µm 250×30 mm; eluent A=water+0.1% formic acid, B=acetonitrile; gradient: 0.0 min 30% B; 4.5 min 50% B; 11.5 min 70% B; 12 min 100% B; 14.75 min 30% B; flow: 50 ml/min). Product containing samples were united and the solvents were removed on a rotary evaporator. 129 mg (100% purity, 40% yield) of the title compound were obtained.

LC-MS (Method 7): $R_t$=2.03 min; MS (ESIneg): m/z=299 [M−H]$^-$

Intermediate 147

2-(4-Chlorophenyl)Pyridine-3-Carboxylic Acid

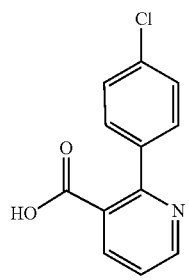 [SMILES: O=C(O)c1cccnc1-c1ccc(Cl)cc1]

(4-chlorophenyl)boronic acid (250 mg, 1.60 mmol) and 2-bromopyridine-3-carboxylic acid (404 mg, 2.00 mmol) dissolved in 9.1 ml 1,2-dimethoxethane were treated with sodium carbonate in water (4.0 ml, 2.0 M, 8.0 mmol). The mixture was degassed with argon. Then tetrakis(triphenylphosphine)palladium(0) (61.7 mg, 53.4 µmol) was added and the mixture was stirred at 80° C. over night. Purification was done by preparative HPLC (Column: Chromatorex C18 10 µm 250×30 mm; eluent A=water+0.1% formic acid, B=acetonitrile; gradient: 0.0 min 30% B; 4.5 min 50% B; 11.5 min 70% B; 12 min 100% B; 14.75 min 30% B; flow: 50 ml/min). Product containing samples were united and the solvents were removed on a rotary evaporator. 500 mg (70% purity, 94% yield) of the title compound were obtained.

LC-MS (Method 7): $R_t$=1.03 min; MS (ESIpos): m/z=234 [M+H]$^+$

Intermediate 148

Ethyl 5-[1-(2,2,2-Trifluoroethyl)-1H-Imidazol-5-Yl]-1,3-Oxazole-4-Carboxylate

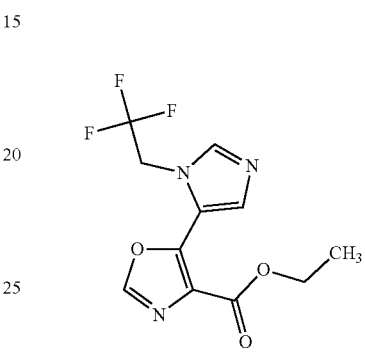

1-(2,2,2-trifluoroethyl)-1H-imidazole-5-carboxylic acid (1.00 g, 5.15 mmol) and 1,1'-carbonyldiimidazole (1.00 g, 6.18 mmol) in 11 ml of THF was stirred for 2 h at room temperature. After that time, a solution of ethyl isocyanoacetate (620 µl, 5.7 mmol) in 11 ml of THF and a solution of lithium bis(trimethylsilyl)amide in THF (5.2 ml, 1.0 M, 5.2 mmol) were added dropwise at 0° C. When the addition was complete the resulting mixture was stirred at room temperature for 1 h. The reaction was concentrated in vacuo and extracted between water and ethyl acetate. The combined organic layers were dried over sodium sulfate, filtered and concentrated. The crude product was purified by column chromatography (Machine: Biotage® Isolera One; column: Biotage® SNAP Ultra 50 g; gradient: Cy/EE-gradient, 16% EE-100% EE; flow: 100 ml/min). Product containing samples were united and the solvents were removed on a rotary evaporator. 724 mg (100% purity, 49% yield) of the title compound were obtained.

LC-MS (Method 7): $R_t$=1.10 min; MS (ESIpos): m/z=290 [M+H]$^+$

Intermediate 149

2-Amino-1-[1-(2,2,2-Trifluoroethyl)-1H-Imidazol-5-Yl]Ethan-1-One Hydrogen Chloride

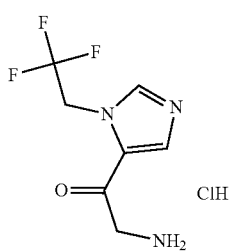 [SMILES: NCC(=O)c1cncn1CC(F)(F)F ; Cl]

Ethyl 5-[1-(2,2,2-trifluoroethyl)-1H-imidazol-5-yl]-1,3-oxazole-4-carboxylate (724 mg, 2.50 mmol) was treated with 12 ml of 6 N hydrochloric acid and stirred for 2 h at 100° C. The solvent was removed on a rotary evaporator and the residue was dried in vacuo. 670 mg (100% purity, 110% yield) of the title compound were obtained.

LC-MS (Method 9): $R_t$=0.82 min; MS (ESIpos): m/z=208 [M+H−HCl]$^+$

Intermediate 150

N-{2-Oxo-2-[1-(2,2,2-Trifluoroethyl)-1H-Imidazol-5-Yl]Ethyl}-4'-(Trifluoromethyl)[1,1'-Biphenyl]-2-Carboxamide

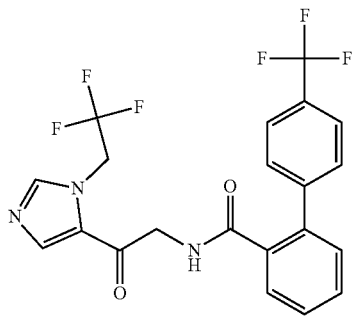 [SMILES: O=C(NCC(=O)c1cncn1CC(F)(F)F)c1ccccc1-c1ccc(C(F)(F)F)cc1]

4'-(trifluoromethyl)[1,1'-biphenyl]-2-carboxylic acid (109 mg, 410 µmol) dissolved in 2 ml of DMF was treated with N-ethyl-N-isopropylpropan-2-amine (210 µl, 1.2 mmol), 3-{[(ethylimino)methylene]amino}-N,N-dimethylpropan-1-amine hydrochloride (102 mg, 534 µmol), 1H-benzotriazol-1-ol hydrate (81.7 mg, 534 µmol) and 2-amino-1-[1-(2,2,2-trifluoroethyl)-1H-imidazol-5-yl]ethan-1-one hydrogen chloride (100 mg, 410 µmol). The mixture was stirred over night at room temperature. The product was purified by preparative HPLC (column: Chromatorex C18 10 µm 250×30 mm; eluent A=water+0.1% formic acid, B=acetonitrile; gradient: 0.0 min 30% B; 4.5 min 50% B; 11.5 min 70% B; 12 min 100% B; 14.75 min 30% B; flow: 50 ml/min). After lyophilization, 249 mg (100% purity, 133% yield) of the title compound were obtained.

LC-MS (Method 8): $R_t$=0.99 min; MS (ESIpos): m/z=456 [M+H]$^+$

Intermediate 151

5-Chloro-6-Fluoro-4'-(Trifluoromethyl)[1,1'-Biphenyl]-2-Carboxylic Acid

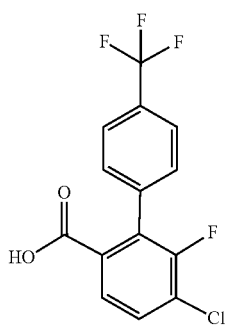 [SMILES: O=C(O)c1ccc(Cl)c(F)c1-c1ccc(C(F)(F)F)cc1]

[4-(trifluoromethyl)phenyl]boronic acid (250 mg, 1.32 mmol) and 2-bromo-4-chloro-3-fluorobenzoic acid (417 mg, 1.65 mmol) dissolved in 7.5 ml 1,2-dimethoxethane were treated with sodium carbonate in water (3.3 ml, 2.0 M, 6.6 mmol). The mixture was degassed with argon. Then tetrakis(triphenylphosphine)palladium(0) (76.1 mg, 65.8 µmol) was added and the mixture was stirred at 80° C. over night. Purification was done by preparative HPLC (Column: Chromatorex C18 10 µm 250×30 mm; eluent A=water+0.1% formic acid, B=acetonitrile: gradient: 0.0 min 30% B; 4.5 min 50% B; 11.5 min 70% B; 12 min 100% B; 14.75 min 30% B; flow: 50 ml/min). Product containing samples were united and the solvents were removed on a rotary evaporator. 598 mg (68% purity, 97% yield) of the title compound were obtained.

LC-MS (Method 7): $R_t$=2.06 min; MS (ESIneg): m/z=317 [M−H]$^−$

Intermediate 152

Methyl 5-(Trifluoromethoxy)-4'-(Trifluoromethyl) [1,1'-Biphenyl]-2-Carboxylate

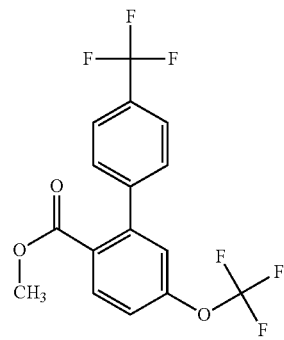 [SMILES: COC(=O)c1ccc(OC(F)(F)F)cc1-c1ccc(C(F)(F)F)cc1]

[2-(methoxycarbonyl)-5-(trifluoromethoxy)phenyl]boronic acid (250 mg, 947 µmol) and 1-bromo-4-(trifluoromethyl)benzene (170 µl, 1.2 mmol) dissolved in 5 ml 1,2-dimethoxethane were treated with sodium carbonate in water (2.4 ml, 2.0 M, 4.7 mmol). The mixture was degassed with argon. Then tetrakis(triphenylphosphine)palladium(0) (54.7 mg, 47.4 µmol) was added and the mixture was stirred at 80° C. over night. Water was added at room temperature and the reaction mixture was extracted with ethyl acetate. The combined organic layers were washed with brine, dried over sodium sulfate, filtered and evaporated on a rotary evaporator. 273 mg of a mixture which contains the title compound and the corresponding acid were obtained. The mixture was used as such in the following reaction.

Intermediate 153

5-(Trifluoromethoxy)-4'-(Trifluoromethyl)[1,1'-Biphenyl]-2-Carboxylic Acid

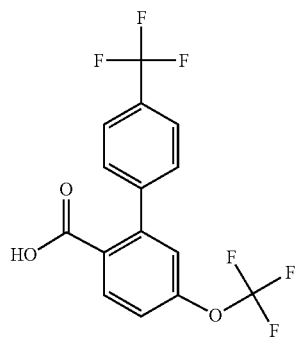 [SMILES: O=C(O)c1ccc(OC(F)(F)F)cc1-c1ccc(C(F)(F)F)cc1]

A mixture of methyl 5-(trifluoromethoxy)-4'-(trifluoromethyl)[1,1'-biphenyl]-2-carboxylate and 5-(trifluoromethoxy)-4'-(trifluoromethyl)[1,1'-biphenyl]-2-carboxylicacid (273 mg) was dissolved in 5 ml THF, treated with lithium hydroxide solution (750 µl, 1.0 M, 750 µmol), and the mixture was stirred at room temperature overnight. The solvent was removed on a rotary evaporator and the residue was acidified with 2N aqueous hydrochloric acid. The precipitate was filtered off, washed with water and dried in vacuo. 159 mg (82% purity) of the title compound were obtained.

LC-MS (Method 7): $R_t$=2.15 min, MS (ESIneg): m/z=349 [M−H]⁻

Intermediate 154

Rac-Tert-Butyl [(4-Methyl-2,5-Dioxoimidazolidin-4-Yl)Methyl]Carbamate

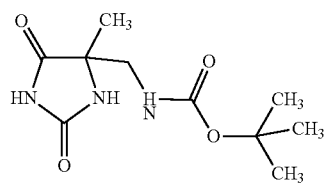

The reaction was performed in 2 Microwave Vials. To a solution of 1.85 g (34.6 mmol) of ammonium chloride and 12.5 g (130 mmol) of ammonium carbonate in 7.5 mL of water was added a solution of 1.50 g (8.66 mmol) of tert-butyl (2-oxopropyl)carbamate in 7.5 ml ethanol. The reaction mixture was stirred 15 minutes at room temperature and then 2.54 g (39.0 mmol) of potassium cyanide were added into the mixture and the vials were sealed. The mixture was stirred at 65° C. for 24 hours. After that time, the solvent was partially removed and the mixture was solved in water and extracted with ethyl acetate. The resulting organic phase was washed with Brine, filtered over an hydrophobic filter and evaporated under vacuo to give 1.69 g (79%) of the product which was used as such in the next step.

¹H-NMR (400 MHz, DMSO-d6) δ [ppm]: −0.008 (0.42), 0.008 (0.40), 1.186 (4.35), 1.371 (16.00), 3.129 (0.51), 3.145 (0.48), 7.626 (0.69).

LC-MS (Method 7): $R_t$=0.85 min; MS (ESIneg): m/z=242 [M−H]⁻

Intermediate 155

Rac-5-(Aminomethyl)-5-Methylimidazolidine-2,4-Dione-Hydrogen Chloride

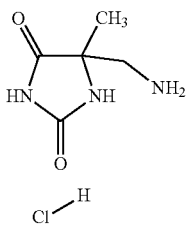

1.70 g (6.95 mmol) of rac-tert-butyl [(4-methyl-2,5-dioxoimidazolidin-4-yl)methyl]carbamate was dissolved in 25 mL of dioxane and 26.05 mL (104.21 mmol) of 4M hydrochloric acid in dioxane were added and the resulting suspension was stirred at room temperature for 16 hours. After that time, the solvent was evaporated and dried under vacuo to give 1.18 g (100%) of the product. The compound was used as such in the next step.

¹H-NMR (400 MHz, DMSO-d6) δ [ppm]: 1.343 (16.00), 2.908 (0.74), 2.942 (1.07), 3.074 (1.08), 3.107 (0.75), 8.012 (1.56), 8.215 (1.60), 10.948 (1.58).

LC-MS (Method 9): $R_t$=0.25 min; MS (ESIpos): m/z=144 [M+H−HCl]⁺

Intermediate 156

Ethyl 5-(4-Methyl-1,2-Thiazol-5-Yl)-1,3-Oxazole-4-Carboxylate

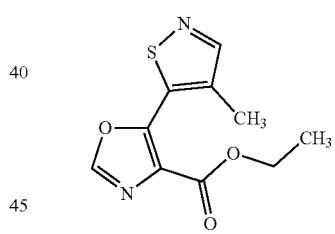

A solution of 4-methyl-1,2-thiazole-5-carboxylic acid (1.00 g, 6.98 mmol) and 1,1'-carbonyldiimidazole (1.36 g, 8.38 mmol) in 11 ml of THF was stirred for 2 h at room temperature. After that time, a solution of ethyl isocyanoacetate (840 µl, 7.7 mmol) in 11 ml of THE and a solution of lithium bis(trimethylsilyl)amide in THF (7.0 ml, 1.0 M, 7.0 mmol) were added dropwise at 0° C. When the addition was complete the resulting mixture was stirred at room temperature for 1 h. The reaction was concentrated in vacuo and extracted with ethyl acetate. The combined organic layers were dried over sodium sulfate, filtered and concentrated. The crude product was purified by column chromatography (Machine: Biotage® Isolera One; column: Biotage® SNAP Ultra 50 g; gradient: Cy/EE-gradient, 12% EE-100% EE; flow: 100 ml/min). Product containing samples were united and the solvents were removed on a rotary evaporator. 975 mg (100% purity, 59% yield) of the title compound were obtained.

LC-MS (Method 7): $R_t$=1.44 min; MS (ESIpos): m/z=239 [M+H]⁺

Intermediate 157

2-Amino-1-(4-Methyl-1,2-Thiazol-5-Yl)Ethan-1-One Hydrogen Chloride

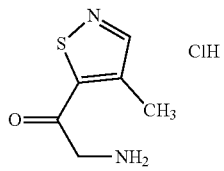

Ethyl 5-(4-methyl-1,2-thiazol-5-yl)-1,3-oxazole-4-carboxylate (975 mg, 4.09 mmol) was taken up in 20 ml of 6 N hydrochloric acid and stirred at 100° C. for 1 h. The solvent was removed on a rotary evaporator and the residue was dried in vacuo. 897 mg (100% purity, 114% yield) of the title compound were obtained.

LC-MS (Method 9): $R_t$=0.80 min; MS (ESIpos): m/z=157 [M−HCl+H]$^+$

Intermediate 158

N-[2-(4-Methyl-1,2-Thiazol-5-Yl)-2-Oxoethyl]-4'-(Trifluoromethyl)[1,1'-Biphenyl]-2-Carboxamide

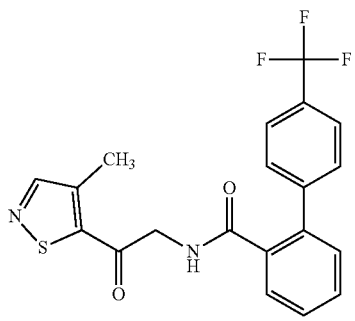 [SMILES: Cc1cnsc1C(=O)CNC(=O)c1ccccc1-c1ccc(C(F)(F)F)cc1]

4'-(trifluoromethyl)[1,1'-biphenyl]-2-carboxylic acid (207 mg, 779 μmol) dissolved in 2 ml of DMF was treated with N-ethyl-N-isopropylpropan-2-amine (380 μl, 2.2 mmol), 3-{[(ethylimino)methylene]amino}-N,N-dimethylpropan-1-amine hydrochloride (194 mg, 1.01 mmol), 1H-benzotriazol-1-ol hydrate (155 mg, 1.01 mmol) and 2-amino-1-(4-methyl-1,2-thiazol-5-yl)ethan-1-one-hydrogenchloride (150 mg, 779 μmol). The mixture was stirred over night at room temperature. The product was purified by preparative HPLC (column: Chromatorex C18 10 μm 250×30 mm; eluent A=water+0.1% formic acid, B=acetonitrile; gradient: 0.0 min 30% B; 4.5 min 50% B; 11.5 min 70% B; 12 min 100% B; 14.75 min 30% B; flow: 50 ml/min). After lyophilization, 18.0 mg (96% purity, 5% yield) of the title compound were obtained.

LC-MS (Method 7): $R_t$=2.01 min; MS (ESIpos): m/z=405 [M+H]$^+$

Intermediate 159

Ethyl 5-[5-Methyl-1-(2,2,2-Trifluoroethyl)-1H-Pyrazol-4-Yl]-1,3-Oxazole-4-Carboxylate

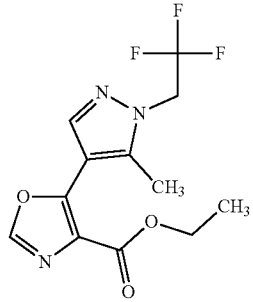 [SMILES: CCOC(=O)c1ncoc1-c1cnn(CC(F)(F)F)c1C]

A solution of 5-methyl-1-(2,2,2-trifluoroethyl)-1H-pyrazole-4-carboxylic acid (600 mg, 2.88 mmol) and 1,1'-carbonyldiimidazole (561 mg, 3.46 mmol) in 11 ml of THF was stirred for 2 h at room temperature. After that time, a solution of ethyl isocyanoacetate (350 μl, 3.2 mmol) in 11 ml of THF and a solution of lithium bis(trimethylsilyl)amide in THF (2.9 ml, 1.0 M, 2.9 mmol) were added dropwise at 0° C. When the addition was complete the resulting mixture was stirred at room temperature for 1 h. The reaction was concentrated in vacuo and extracted with ethyl acetate. The combined organic layers were dried over sodium sulfate, filtered and concentrated. The crude product was purified by column chromatography (Machine: Biotage® Isolera One; column: Biotage® SNAP Ultra 50 g; gradient: Cy/EE-gradient, 12% EE-100% EE; flow: 100 ml/min). Product containing samples were united and the solvents were removed on a rotary evaporator. 600 mg (100% purity, 69% yield) of the title compound were obtained.

LC-MS (Method 7): $R_t$=1.44 min; MS (ESIpos): m/z=304 [M+H]$^+$

Intermediate 160

2-Amino-1-[5-Methyl-1-(2,2,2-Trifluoroethyl)-1H-Pyrazol-4-Yl]Ethan-1-One Hydrochloride

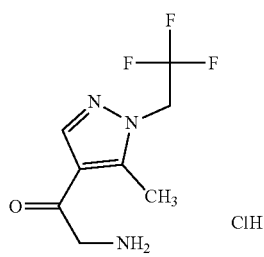

Ethyl 5-[5-methyl-1-(2,2,2-trifluoroethyl)-1H-pyrazol-4-yl]-1,3-oxazole-4-carboxylate (600 mg, 1.98 mmol) was taken up in 10 ml of 6 N hydrochloric acid and stirred at 100° C. for 1 h. The solvent was removed on a rotary evaporator and the residue was dried in vacuo. 507 mg (88% purity, 87% yield) of the title compound were obtained.

LC-MS (Method 9): $R_t$=0.93 min, MS (ESIpos): m/z=222 [M−HCl+H]$^+$

Intermediate 161

Tert-Butyl {2-[5-Methyl-1-(2,2,2-Trifluoroethyl)-1H-Pyrazol-4-Yl]-2-Oxoethyl}Carbamate

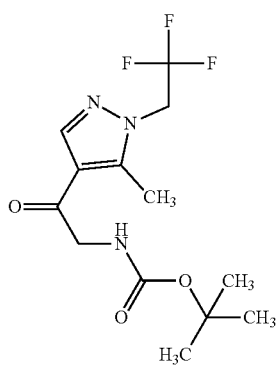 [SMILES: Cc1c(C(=O)CNC(=O)OC(C)(C)C)cnn1CC(F)(F)F]

2-amino-1-[5-methyl-1-(2,2,2-trifluoroethyl)-1H-pyrazol-4-yl]ethan-1-one hydrogenchloride (350 mg, 1.36 mmol) dissolved in 5 ml of dichloromethane was treated with di-tert-butyl dicarbonate (340 µl, 1.5 mmol) and triethylamine (570 µl, 4.1 mmol). The mixture was stirred at room temperature over night. The solvent was removed on a rotary evaporator. The residue was taken up with ethyl acetate and washed with water and saturated aqueous sodium chloride solution. The organic layer was dried over sodium sulfate, filtered and evaporated on a rotary evaporator. 367 mg (100% purity, 84% yield) of the title compound were obtained.

LC-MS (Method 7): $R_t$=1.62 min; MS (ESIpos): m/z=322 [M+H]$^+$

Intermediate 162

Rac-Tert-Butyl({4-[5-Methyl-1-(2,2,2-Trifluoroethyl)-1H-Pyrazol-4-Yl]-2,5-Dioxoimidazolidin-4-Yl}Methyl)Carbamate

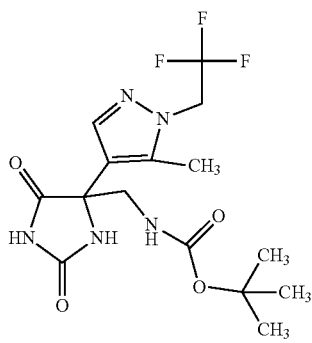 [SMILES: Cc1c(C2(CNC(=O)OC(C)(C)C)NC(=O)NC2=O)cnn1CC(F)(F)F]

tert-butyl {2-[5-methyl-1-(2,2,2-trifluoroethyl)-1H-pyrazol-4-yl]-2-oxoethyl}carbamate (367 mg, 1.14 mmol) was dissolved in 10 ml of methanol. Potassium cyanide (372 mg, 5.71 mmol) and ammonium carbonate (549 mg, 5.71 mmol) were added. The vial was sealed and the mixture was stirred at 60° C. for 2 d. Isolute® was added and the solvent was evaporated on a rotary evaporator. The crude product was purified by column chromatography (Machine: Biotage® Isolera One; column: Biotage® SNAP Ultra 25 g; gradient: DCM/MeOH-gradient, 2% MeOH-20% MeOH; flow: 50 ml/min). Product containing samples were united and the solvents were removed on a rotary evaporator. 70.0 mg (100% purity, 16% yield) of the title compound were obtained.

LC-MS (Method 7): $R_t$=1.20 min; MS (ESIpos): m/z=392 [M+H]$^+$

Intermediate 163

Rac-5-(Aminomethyl)-5-[5-Methyl-1-(2,2,2-Trifluoroethyl)-1H-Pyrazol-4-Yl]Imidazolidine-2,4-Dione Hydrochloride

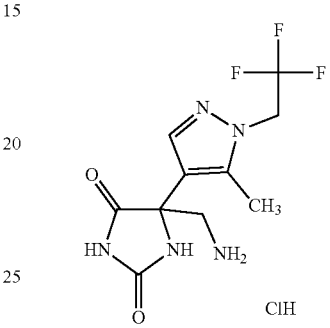

rac-tert-butyl({4-[5-methyl-1-(2,2,2-trifluoroethyl)-1H-pyrazol-4-yl]-2,5-dioxoimidazolidin-4-yl}methyl)carbamate (70.0 mg, 179 µmol) was dissolved in 2.5 ml of dichloromethane. 4 M hydrochloric acid in 1,4-dioxane (220 µl, 4.0 M, 890 µmol) was added and the mixture was stirred over night. The precipitate was filtered off, washed with dichloromethane and dried in vacuo. 52.0 mg (94% purity, 83% yield) of the title compound were obtained.

LC-MS (Method 9): $R_t$=0.26 min; MS (ESIpos): m/z=292 [M−HCl+H]$^+$

Intermediate 164

4'-Methyl-5-(Trifluoromethyl)[1,1'-Biphenyl]-2-Carboxylicacid

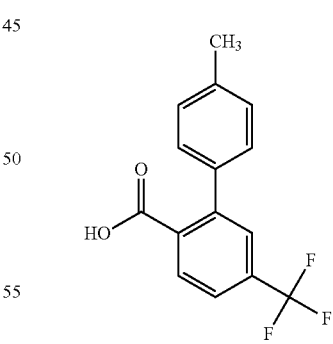

To a suspension of [2-(methoxycarbonyl)-5-(trifluoromethyl)phenyl]boronic acid (200 mg, 807 µmol) and 1-bromo-4-methylbenzene (172 mg, 1.01 mmol) in 1,2-dimethoxyethane (3.6 ml) was added under argon a 2 M solution sodium carbonate in water (2.0 ml, 2.0 M, 4.0 mmol) and tetrakis(triphenylphosphine)palladium(0) [Pd(PPh$_3$)$_4$] (46.8 mg, 40.3 µmol). The mixture was stirred over night at 90° C. Water (5 ml) was added at room temperature and the reaction was extracted with ethyl acetate (three times). The combined organic layers were dried, filtered and evaporated. Purification was done by preparative HPLC (column: Reprosil C18 10 μm, 250×30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated and the residue was lyophylized. 52 mg of the title compound were obtained.

LC-MS (Method 7): $R_t$=2.03 min; MS (ESIpos): m/z=279 [M−H]$^-$

Intermediate 165

Methyl 4',6-Dimethyl[1,1'-Biphenyl]-2-Carboxylate

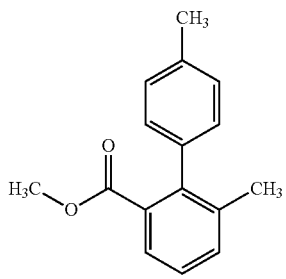

To a suspension of (4-methylphenyl)boronic acid (100 mg, 736 μmol) and methyl 2-bromo-3-methylbenzoate (150 μl, 920 μmol) in 1,2-dimethoxyethane (3.0 ml) was added under argon a 2 M solution sodium carbonate in water (1.8 ml, 2.0 M, 3.7 mmol) and tetrakis(triphenylphosphine)palladium(0) [Pd(PPh$_3$)$_4$] (42.7 mg, 36.8 μmol). The mixture was stirred overnight at 90° C. Water was added at room temperature and the reaction was extracted with ethyl acetate (three times). The combined organic layers were washed with brine and then dried, filtered and evaporated Purification was done by preparative HPLC (column: Reprosil C18 10 μm, 250×30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated and the residue was lyophylized. 129 mg (100% purity, 73% yield) of the title compound were obtained.

LC-MS (Method 7): $R_t$=2.29 min; MS (ESIpos): m/z=241 [M+H]$^+$ $^1$H-NMR (400 MHz, DMSO-d6) δ [ppm]: 2.056 (16.00), 2.349 (14.64), 3.327 (5.89), 6.998 (4.23), 7.019 (5.30), 7.197 (4.12), 7.216 (3.44), 7.336 (1.37), 7.355 (3.39), 7.374 (2.30), 7.459 (2.09), 7.477 (1.50), 7.523 (1.92), 7.542 (1.60).

Intermediate 166

4',6-Dimethyl[1,1'-Biphenyl]-2-Carboxylic Acid

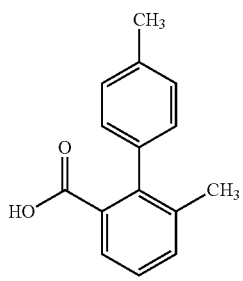 [SMILES: Cc1ccc(-c2c(C)cccc2C(=O)O)cc1]

To a solution of methyl 4',6-dimethyl[1,1'-biphenyl]-2-carboxylate (126 mg, 525 μmol) in THF (2 ml) and methanol (400 μl) an aqueous lithium hydroxide solution was added (1.3 ml, 2.0 M, 2.6 mmol) and the mixture was stirred at room temperature over night. The mixture was then heated to 60° C. and stirred over night. The reaction was cooled to room temperature and was acidified with excess 2N aqueous hydrochloric acid. The THF was removed on a rotary evaporator and the resulting precipitate was filtered off, washed with water and dried in vacuo. 127 mg (100% purity, 106% yield) of the title compound were obtained.

LC-MS (Method 7): $R_t$=1.86 min, MS (ESIpos): m/z=227 [M+H]$^+$ $^1$H-NMR (400 MHz, DMSO-d6) δ [ppm]: 1.236 (0.47), 2.034 (16.00), 2.341 (15.60), 7.021 (4.49), 7.040 (5.64), 7.183 (5.37), 7.202 (4.58), 7.302 (1.30), 7.321 (3.03), 7.340 (2.19), 7.407 (2.98), 7.425 (2.13), 7.501 (2.60), 7.520 (2.22), 12.379 (3.58).

Intermediate 167

Methyl 4'-(1,1-Difluoropropyl)[1,1'-Biphenyl]-2-Carboxylate

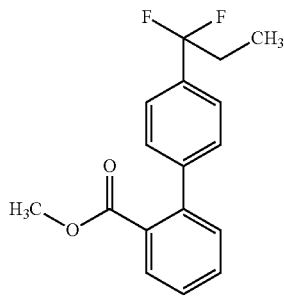 [SMILES: CCC(F)(F)c1ccc(-c2ccccc2C(=O)OC)cc1]

To a suspension of methyl 2-(4,4,5,5-tetramethyl-1,3,2-dioxaborolan-2-yl)benzoate (200 mg, 763 μmol) and 1-bromo-4-(1,1-difluoropropyl)benzene (224 mg, 954 μmol) in 1,2-dimethoxyethane (4.0 ml) was added under argon a 2 M solution sodium carbonate in water (1.9 ml, 2.0 M, 3.8 mmol) and tetrakis(triphenylphosphine)palladium(0) [Pd(PPh$_3$)$_4$] (44.3 mg, 38.2 μmol). The mixture was stirred over night at 90° C. Water was added at room temperature and the reaction was extracted with ethyl acetate. The combined organic layers were washed with brine dried, filtered and evaporated Purification was done by flash chromatography. Product containing samples were united, the solvents were evaporated and the residue was lyophylized. 138 mg (100% purity, 62% yield) of the title compound were obtained.

LC-MS (Method 8): $R_t$=1.18 min; MS (ESIpos): m/z=291 [M+H]$^+$ $^1$H-NMR (600 MHz, DMSO-d6) δ [ppm]: 0.928 (3.20), 0.941 (7.12), 0.953 (3.28), 2.221 (0.58), 2.233 (0.67), 2.249 (1.23), 2.261 (1.23), 2.276 (0.60), 2.289 (0.51), 3.323 (16.00), 7.392 (2.52), 7.406 (2.92), 7.456 (1.32), 7.457 (1.36), 7.469 (1.54), 7.470 (1.52), 7.516 (0.70), 7.518 (0.69), 7.529 (1.56), 7.531 (1.46), 7.541 (0.99), 7.543 (0.93), 7.552 (3.06), 7.565 (2.55), 7.639 (0.89), 7.641 (0.92), 7.651 (1.45), 7.654 (1.46), 7.664 (0.65), 7.666 (0.64), 7.786 (1.46), 7.788 (1.40), 7.799 (1.35), 7.801 (1.24).

Intermediate 168

4'-(1,1-Difluoropropyl)[1,1'-Biphenyl]-2-Carboxylic Acid

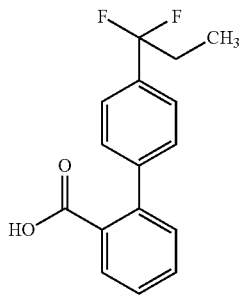 [SMILES: CCC(F)(F)c1ccc(-c2ccccc2C(=O)O)cc1]

To a solution of methyl 4'-(1,1-difluoropropyl)[1,1'-biphenyl]-2-carboxylate (135 mg, 463 µmol) in THF (2.5 ml) and methanol (500 µl) an aqueous lithium hydroxide solution was added (1.2 ml, 2.0 M, 2.3 mmol) and the mixture was stirred over night at 60° C. The reaction was cooled to room temperature and was acidified with excess 2N aqueous hydrochloric acid and the mixture was concentrated. Purification was done by preparative HPLC (column: Reprosil C18 10 µm, 250×30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated and the residue was lyophylized. 116 mg (100% purity, 91% yield) of the title compound were obtained.

LC-MS (Method 7): $R_t$=2.00 min; MS (ESIneg): m/z=275 [M−H]⁻

$^1$H-NMR (400 MHz, DMSO-d6) δ [ppm]: −0.008 (0.86), 0.008 (0.97), 0.929 (6.82), 0.948 (16.00), 0.967 (7.26), 2.182 (0.45), 2.200 (1.42), 2.219 (1.56), 2.242 (2.94), 2.260 (2.90), 2.284 (1.45), 2.303 (1.27), 2.321 (0.43), 7.396 (2.70), 7.398 (2.94), 7.415 (3.77), 7.418 (4.31), 7.423 (5.12), 7.444 (6.87), 7.471 (1.51), 7.474 (1.55), 7.490 (3.51), 7.493 (3.31), 7.509 (2.45), 7.512 (2.23), 7.537 (7.08), 7.558 (5.00), 7.579 (2.30), 7.582 (2.47), 7.598 (3.31), 7.601 (3.44), 7.616 (1.42), 7.620 (1.37), 7.759 (3.26), 7.762 (3.28), 7.778 (2.94), 7.781 (2.77), 12.794 (2.70).

Intermediate 169

Tert-Butyl 4'-Cyclopropyl-5-Methoxy[1,1'-Biphenyl]-2-Carboxylate

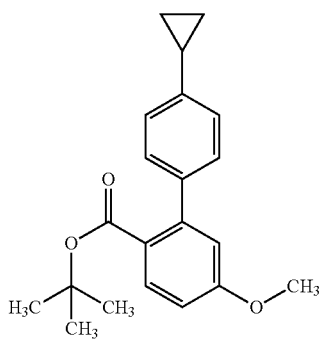 [SMILES: COc1ccc(C(=O)OC(C)(C)C)c(-c2ccc(C3CC3)cc2)c1]

To a suspension of [2-(tert-butoxycarbonyl)-5-methoxyphenyl]boronic acid (125 mg, 496 µmol) and 1-bromo-4-cyclopropylbenzene (122 mg, 620 µmol) in 1,2-dimethoxyethane (2.2 ml) was added under argon a 2 M solution sodium carbonate in water (1.2 ml, 2.0 M, 2.5 mmol) and tetrakis(triphenylphosphine)palladium(0) [Pd(PPh₃)₄] (28.8 mg, 24.8 µmol). The mixture was stirred over night at 80° C. Water was added at room temperature and the reaction was extracted with ethyl acetate (three times). The combined organic layers were dried, filtered and evaporated Purification was done by preparative HPLC (column: Reprosil C18 10 µm, 250×30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated and the residue was lyophylized. 72.0 mg (99% purity, 44% yield) of the title compound were obtained.

$^1$H-NMR (400 MHz, DMSO-d6) δ [ppm]: 0.670 (0.78), 0.675 (0.71), 0.682 (0.77), 0.687 (0.75), 0.960 (0.68), 0.965 (0.71), 0.980 (0.71), 0.986 (0.69), 1.175 (0.44), 1.188 (16.00), 1.988 (0.49), 3.822 (5.74), 6.804 (0.92), 6.811 (0.99), 6.961 (0.56), 6.968 (0.50), 6.983 (0.58), 6.989 (0.55), 7.098 (0.44), 7.120 (2.13), 7.132 (2.23), 7.153 (0.45), 7.655 (1.05), 7.677 (0.99).

Intermediate 170

4'-Cyclopropyl-5-Methoxy[1,1'-Biphenyl]-2-Carboxylic Acid

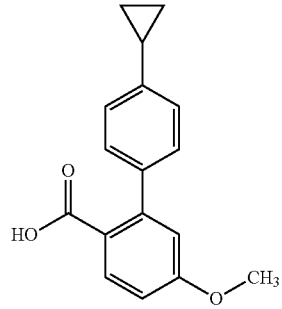 [SMILES: COc1ccc(C(=O)O)c(-c2ccc(C3CC3)cc2)c1]

To a solution of tert-butyl 4'-cyclopropyl-5-methoxy[1,1'-biphenyl]-2-carboxylate (70.0 mg, 216 µmol) in trifluoroethanol (2.5 ml) was added zinc chloride (176 mg, 1.29 mmol) and the reaction was stirred at 50° C. for 1 hour. EDTA (378 mg, 1.29 mmol) was added and the mixture was stirred for a few minutes. Water+0.1% TFA (1 ml) was added. Purification was done by preparative HPLC (column: Reprosil C18 10 µm, 250×30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated and the residue was lyophylized. 41.3 mg (100% purity, 71% yield) of the title compound were obtained.

LC-MS (Method 7): $R_t$=1.87 min; MS (ESIpos): m/z=269 [M+H]⁺

$^1$H-NMR (600 MHz, DMSO-d6) δ [ppm]: 0.680 (0.70), 0.687 (2.41), 0.691 (2.25), 0.696 (2.32), 0.699 (2.38), 0.706 (0.79), 0.954 (0.76), 0.961 (2.10), 0.965 (2.12), 0.968 (1.05), 0.972 (1.00), 0.975 (2.18), 0.978 (2.11), 0.986 (0.72), 1.925 (0.58), 1.931 (0.64), 1.939 (1.12), 1.947 (0.62), 1.953 (0.56), 3.825 (16.00), 6.803 (2.74), 6.807 (2.90), 6.961 (1.54), 6.965 (1.48), 6.975 (1.59), 6.980 (1.55), 7.071 (3.30), 7.085 (4.30), 7.176 (4.48), 7.189 (3.41), 7.731 (2.97), 7.745 (2.82).

Intermediate 171

Methyl 4'-Cyclopropyl-5-Fluoro[1,1'-Biphenyl]-2-Carboxylate

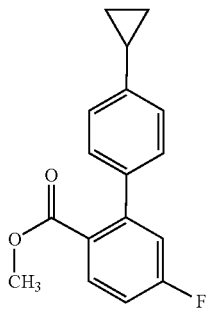 [SMILES: COC(=O)c1ccc(F)cc1-c1ccc(C2CC2)cc1]

To a suspension of methyl 4-fluoro-2-(4,4,5,5-tetramethyl-1,3,2-dioxaborolan-2-yl)benzoate (200 mg, 714 µmol) and 1-bromo-4-cyclopropylbenzene (176 mg, 893 µmol) in 1,2-dimethoxyethane (3.1 ml) was added under argon a 2 M solution sodium carbonate in water (1.8 ml, 2.0 M, 3.6 mmol) and tetrakis(triphenylphosphine)palladium(0) [Pd(PPh$_3$)$_4$] (41.4 mg, 35.7 µmol). The mixture was stirred over night at 90° C. Water was added at room temperature and the reaction was extracted with ethyl acetate (three times). The combined organic layers were dried, filtered and evaporated. Purification was done by flash chromatography (n-heptane 100-4 n-heptane:ethyl acetate (70:30)). Product containing samples were united, the solvents were evaporated and the residue was lyophylized. 55.0 mg (97% purity, 28% yield) of the title compound were obtained.

LC-MS (Method 8): R$_t$=1.23 min; MS (ESIpos): m/z=271 [M+H]$^+$ $^1$H-NMR (600 MHz, DMSO-d6) δ [ppm]: 0.698 (0.76), 0.706 (2.44), 0.709 (2.21), 0.714 (2.24), 0.717 (2.29), 0.725 (0.73), 0.970 (0.81), 0.977 (2.06), 0.980 (2.05), 0.984 (1.01), 0.988 (1.01), 0.991 (2.08), 0.994 (1.98), 1.002 (0.67), 1.942 (0.60), 1.948 (0.64), 1.957 (1.10), 1.965 (0.60), 1.970 (0.53), 3.594 (16.00), 7.117 (2.90), 7.131 (4.48), 7.178 (4.68), 7.192 (2.86), 7.244 (1.13), 7.248 (1.39), 7.260 (1.13), 7.265 (1.32), 7.286 (0.70), 7.291 (0.63), 7.300 (1.33), 7.305 (1.22), 7.314 (0.71), 7.319 (0.65), 7.779 (1.18), 7.789 (1.23), 7.794 (1.19), 7.803 (1.12).

Intermediate 172

4'-Cyclopropyl-5-Fluoro[1,1'-Biphenyl]-2-Carboxylic Acid

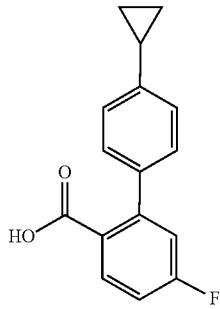 [SMILES: O=C(O)c1ccc(F)cc1-c1ccc(C2CC2)cc1]

To a solution of methyl 4'-cyclopropyl-5-fluoro[1,1'-biphenyl]-2-carboxylate (50.0 mg, 185 µmol) in THF (640 µl) and methanol (130 µl) an aqueous lithium hydroxide solution was added (460 µl, 2.0 M, 920 µmol) and the mixture was stirred at 60° C. over night. The THF was removed on a rotary evaporator and the residue was acidified with excess 2N aqueous hydrochloric acid. The mixture was extracted with ethyl acetate and the organic layers were dried, filtered and evaporated to give 48.0 mg (92% purity, 93% yield) of the title compound without further purification.

LC-MS (Method 8): R$_t$=1.04 min; MS (ESIpos): m/z=257 [M+H]$^+$

Intermediate 173

Methyl 4'-Cyclopropyl[1,1'-Biphenyl]-2-Carboxylate

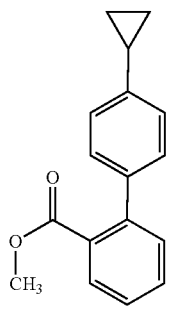 [SMILES: COC(=O)c1ccccc1-c1ccc(C2CC2)cc1]

To a suspension of methyl 2-(4,4,5,5-tetramethyl-1,3,2-dioxaborolan-2-yl)benzoate (200 mg, 763 µmol) and 1-bromo-4-cyclopropylbenzene (188 mg, 954 µmol) in 1,2-dimethoxyethane (3.4 ml) was added under argon a2 M solution sodium carbonate in water (1.9 ml, 2.0 M, 3.8 mmol) and tetrakis(triphenylphosphine)palladium(0) [Pd(PPh$_3$)$_4$] (44.3 mg, 38.2 µmol). The mixture was stirred over night at 80° C. Water was added at room temperature and the reaction was extracted with ethyl acetate (three times). The combined organic layers were dried, filtered and evaporated. Purification was done by preparative HPLC (column: Reprosil C18 10 µm, 250×30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated and the residue was lyophylized. 120 mg (95% purity, 59% yield) of the title compound were obtained.

$^1$H-NMR (500 MHz, DMSO-d6) δ [ppm]: −0.006 (1.18), 0.006 (0.97), 0.691 (2.22), 0.700 (7.36), 0.704 (6.88), 0.710 (7.06), 0.714 (7.11), 0.723 (2.48), 0.833 (0.52), 0.837 (0.48), 0.842 (0.50), 0.847 (0.53), 0.960 (2.51), 0.968 (6.28), 0.973 (6.54), 0.977 (3.29), 0.982 (3.17), 0.985 (6.62), 0.989 (6.33), 0.998 (2.23), 1.125 (0.44), 1.129 (0.46), 1.141 (0.65), 1.146 (0.46), 1.922 (0.90), 1.932 (1.81), 1.939 (1.98), 1.949 (3.42), 1.959 (1.89), 1.966 (1.70), 1.976 (0.80), 2.086 (0.41), 3.741 (1.44), 3.776 (1.60), 7.107 (7.45), 7.124 (15.33), 7.155 (16.00), 7.172 (7.54), 7.401 (4.76), 7.417 (5.54), 7.439 (2.46), 7.441 (2.46), 7.454 (5.62), 7.456 (5.40), 7.469 (3.78), 7.472 (3.66), 7.497 (0.74), 7.514 (0.42), 7.522 (0.65), 7.539 (0.55), 7.579 (3.13), 7.582 (3.42), 7.595 (5.03), 7.597 (5.31), 7.610 (2.32), 7.612 (2.42), 7.686 (4.89), 7.689 (4.93), 7.702 (4.39), 7.704 (4.27).

Intermediate 174

4'-Cyclopropyl[1,1'-Biphenyl]-2-Carboxylic Acid

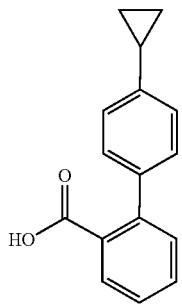 [SMILES: O=C(O)c1ccccc1-c1ccc(C2CC2)cc1]

To a solution of methyl 4'-cyclopropyl[1,1'-biphenyl]-2-carboxylate (120 mg, 476 µmol) in THF (1.6 ml) and methanol (330 µl) an aqueous lithium hydroxide solution was added (1.2 ml, 2.0 M, 2.4 mmol) and the mixture was stirred at 60° C. over night. The reaction was cooled to room temperature and was acidified with excess 2N aqueous hydrochloric acid. The mixture was extracted with ethyl acetate and the combined organic layers were dried, filtered and evaporated. Purification was done by flash chromatography (n-heptane→n-heptane:ethyl acetate (50:50)). Product containing samples were united, the solvents were evaporated and the residue was lyophylized. 73.0 mg (99% purity, 64% yield) of the title compound were obtained.

LC-MS (Method 7): $R_t$=1.87 min, MS (ESIneg): m/z=237 [M−H]−

$^1$H-NMR (500 MHz, DMSO-d6) δ [ppm]: 0.684 (2.57), 0.692 (8.57), 0.696 (7.92), 0.702 (8.17), 0.706 (8.30), 0.715 (2.78), 0.955 (2.86), 0.963 (7.34), 0.967 (7.41), 0.971 (3.71), 0.976 (3.66), 0.980 (7.67), 0.984 (7.21), 0.993 (2.47), 1.174 (0.70), 1.234 (0.46), 1.916 (1.08), 1.926 (2.13), 1.933 (2.31), 1.943 (3.96), 1.953 (2.18), 1.960 (1.96), 1.970 (0.93), 1.989 (1.32), 7.094 (11.30), 7.110 (15.30), 7.197 (16.00), 7.214 (11.49), 7.346 (5.66), 7.362 (6.47), 7.405 (2.63), 7.407 (2.77), 7.420 (5.97), 7.422 (5.91), 7.435 (3.74), 7.437 (3.60), 7.528 (3.50), 7.531 (3.81), 7.543 (5.52), 7.546 (5.74), 7.558 (2.42), 7.561 (2.43), 7.671 (5.78), 7.673 (5.87), 7.686 (5.25), 7.688 (5.08), 12.724 (2.04).

Intermediate 175

Methyl 4'-Ethyl[1,1'-Biphenyl]-2-Carboxylate

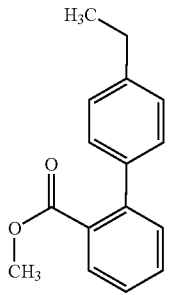

To a suspension of methyl 2-(4,4,5,5-tetramethyl-1,3,2-dioxaborolan-2-yl)benzoate (200 mg, 763 µmol) and 1-bromo-4-ethylbenzene (177 mg, 954 µmol) in 1,2-dimethoxyethane (3.4 ml) was added under argon a 2 M solution sodium carbonate in water (1.9 ml, 2.0 M, 3.8 mmol) and tetrakis(triphenylphosphine)palladium(0) [Pd(PPh$_3$)$_4$] (44.3 mg, 38.2 µmol). The mixture was stirred over night at 90° C. Water (5 ml) was added at room temperature and the reaction was extracted with ethyl acetate (three times). The combined organic layers were washed with brine, dried, filtered and evaporated. Purification was done by preparative HPLC (column: Reprosil C18 10 µm, 250×30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated and the residue was lyophylized. 113 mg (98% purity, 60% yield) of the title compound were obtained.

$^1$H-NMR (500 MHz, DMSO-d6) δ [ppm]: −0.007 (0.89), 0.006 (0.61), 1.188 (0.41), 1.201 (7.50), 1.216 (16.00), 1.231 (7.60), 1.236 (1.09), 1.252 (0.40), 2.625 (1.83), 2.640 (5.34), 2.655 (5.15), 2.670 (1.68), 7.194 (4.99), 7.207 (2.71), 7.211 (8.78), 7.252 (7.56), 7.268 (4.17), 7.418 (2.78), 7.433 (3.23), 7.448 (1.44), 7.450 (1.39), 7.463 (3.19), 7.465 (2.89), 7.478 (2.02), 7.481 (1.81), 7.587 (1.86), 7.590 (1.99), 7.603 (2.93), 7.605 (3.00), 7.613 (0.51), 7.618 (1.41), 7.621 (1.44), 7.638 (0.54), 7.696 (2.86), 7.698 (2.86), 7.711 (2.55), 7.713 (2.45).

Intermediate 176

4'-Ethyl[1,1'-Biphenyl]-2-Carboxylic Acid

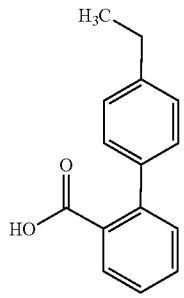

To a solution of methyl 4'-ethyl[1,1'-biphenyl]-2-carboxylate (110 mg, 458 µmol) in THF (1.6 ml) and methanol (320 µl) an aqueous lithium hydroxide solution (1.1 ml, 2.0 M, 2.3 mmol) was added and the mixture was stirred at 60° C. over night. The reaction was cooled to room temperature and was acidified with excess 2N aqueous hydrochloric acid and the mixture was extracted with ethyl acetate. The combined organic layers were dried, filtered and evaporated. Purification was done by flash chromatography (n-heptane→n-heptane:ethyl acetate (50:50)). Product containing samples were united, the solvents were evaporated. 92.0 mg (99% purity, 88% yield) of the title compound were obtained.

LC-MS (Method 7): $R_t$=1.87 min, MS (ESIneg): m/z=225 [M−H]−

$^1$H-NMR (500 MHz, DMSO-d6) δ [ppm]: 1.202 (2.92), 1.217 (6.22), 1.232 (3.03), 2.620 (0.90), 2.635 (2.68), 2.651 (2.58), 2.666 (0.81), 7.247 (16.00), 7.362 (1.05), 7.376 (1.25), 7.413 (0.56), 7.415 (0.52), 7.428 (1.25), 7.430 (1.10), 7.443 (0.79), 7.445 (0.67), 7.534 (0.74), 7.537 (0.75), 7.550 (1.15), 7.552 (1.12), 7.565 (0.50), 7.567 (0.47), 7.678 (1.17), 7.681 (1.10), 7.694 (1.06), 7.696 (0.94), 12.725 (0.76).

Intermediate 177

Tert-Butyl 5-Methoxy-4'-(Trifluoromethyl)[1,1'-Biphenyl]-2-Carboxylate

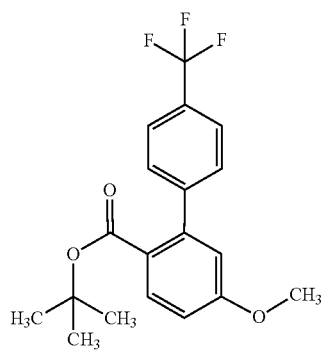 [SMILES: COc1ccc(C(=O)OC(C)(C)C)c(-c2ccc(C(F)(F)F)cc2)c1]

To a suspension of [2-(tert-butoxycarbonyl)-5-methoxyphenyl]boronic acid (125 mg, 496 µmol) and 1-bromo-4-(trifluoromethyl)benzene (139 mg, 620 µmol) in 1,2-dimethoxyethane (2.2 ml) was added under argon a 2 M solution sodium carbonate in water (1.2 ml, 2.0 M, 2.5 mmol) and tetrakis(triphenylphosphine)palladium(0) [Pd(PPh$_3$)$_4$] (28.8 mg, 24.8 µmol). The mixture was stirred overnight at 90° C. Water was added at room temperature and the reaction was extracted with ethyl acetate (three times). The combined organic layers were dried, filtered and evaporated Purification was done by flash chromatography (n-heptane→n-heptane:ethyl acetate (70:30)). Product containing samples were united, the solvents were evaporated and the residue was lyophylized. 133 mg (99% purity, 75% yield) of the title compound were obtained.

$^1$H-NMR (400 MHz, DMSO-d6) δ [ppm]: 1.164 (16.00), 3.846 (5.62), 6.881 (0.93), 6.888 (0.98), 7.059 (0.55), 7.066 (0.51), 7.081 (0.58), 7.088 (0.55), 7.490 (0.81), 7.510 (0.93), 7.770 (0.98), 7.785 (1.35), 7.790 (0.89), 7.807 (1.00).

Intermediate 178

5-Methoxy-4'-(Trifluoromethyl)[1,1'-Biphenyl]-2-Carboxylic Acid

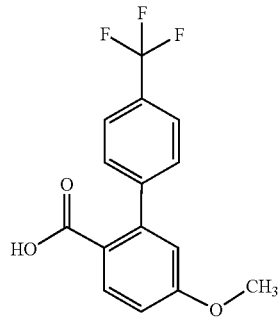 [SMILES: COc1ccc(C(=O)O)c(-c2ccc(C(F)(F)F)cc2)c1]

To a solution of tert-butyl 5-methoxy-4'-(trifluoromethyl)[1,1'-biphenyl]-2-carboxylate (130 mg, 369 µmol) in trifluoroethanol (6.5 ml) was added zinc chloride (302 mg, 2.21 mmol) and the reaction was stirred at 50° C. for 2 hours. EDTA (647 mg, 2.21 mmol) was added and the mixture was stirred for a few minutes. The mixture was filtered and the residue was washed with Acetonitrile. The filtrate was concentrated and purification was done by flash chromatography (n-heptane→n-heptane:ethyl acetate (50:50)). Product containing samples were united, the solvents were evaporated and the residue was lyophylized. 104 mg (98% purity, 93% yield) of the title compound were obtained.

LC-MS (Method 7): R$_t$=1.91 min, MS (ESIpos): m/z=297 [M+H]$^+$ $^1$H-NMR (400 MHz, DMSO-d6) δ [ppm]: 1.175 (0.74), 1.235 (0.40), 1.988 (1.27), 2.524 (0.57), 3.313 (16.00), 3.824 (0.94), 3.867 (0.69), 6.871 (9.40), 6.878 (10.14), 7.052 (5.60), 7.058 (5.22), 7.074 (5.88), 7.080 (5.68), 7.512 (8.24), 7.532 (9.92), 7.731 (10.21), 7.751 (8.56), 7.859 (10.47), 7.869 (0.42), 7.881 (10.09), 12.477 (8.54).

Intermediate 179

Methyl 4'-Cyclopropyl-5-(Trifluoromethyl)[1,1'-Biphenyl]-2-Carboxylate

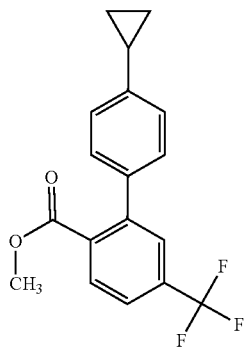 [SMILES: COC(=O)c1ccc(C(F)(F)F)cc1-c1ccc(C2CC2)cc1]

To a suspension of [2-(methoxycarbonyl)-5-(trifluoromethyl)phenyl]boronic acid (200 mg, 807 µmol) and 1-bromo-4-cyclopropylbenzene (199 mg, 1.01 mmol) in 1,2-dimethoxyethane (3.6 ml) was added under argon a 2 M solution sodium carbonate in water (2.0 ml, 2.0 M, 4.0 mmol) and tetrakis(triphenylphosphine)palladium(0) [Pd(PPh$_3$)$_4$] (46.8 mg, 40.3 µmol). The mixture was stirred overnight at 90° C. Water was added at room temperature and the reaction was extracted with ethyl acetate (three times). The combined organic layers were dried, filtered and evaporated Purification was done by flash chromatography (n-heptane→n-heptane:ethyl acetate (70:30)).

Product containing samples were united, the solvents were evaporated and the residue was lyophylized. 93.0 mg (70% purity, 25% yield) of the title compound were obtained.

Intermediate 180

4'-Cyclopropyl-5-(Trifluoromethyl)[1,1'-Biphenyl]-2-Carboxylic Acid

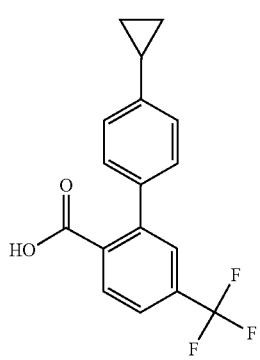 [SMILES: O=C(O)c1ccc(C(F)(F)F)cc1-c1ccc(C2CC2)cc1]

To a solution of methyl 4'-cyclopropyl-5-(trifluoromethyl)[1,1'-biphenyl]-2-carboxylate (90.0 mg, 281 μmol) in THF (970 μl) and methanol (190 μl) an aqueous lithium hydroxide solution (700 μl, 2.0 M, 1.4 mmol) q was added and the mixture was stirred at 60° C. over night. The reaction was cooled to room temperature and was acidified with excess 2N aqueous hydrochloric acid. The mixture was extracted with ethyl acetate. The combined organic layers were dried, filtered and evaporated. Purification was done by flash chromatography (n-heptane→n-heptane:ethyl acetate (50:50)). Product containing samples were united, the solvents were evaporated. 48.0 mg (99% purity, 55% yield) of the title compound were obtained.

LC-MS (Method 11): R$_t$=1.42 min, MS (ESIneg): m/z=305 [M−H]$^-$ $^1$H-NMR (600 MHz, DMSO-d6) δ [ppm]: 0.702 (2.66), 0.709 (8.96), 0.712 (8.21), 0.718 (8.42), 0.721 (8.80), 0.728 (2.85), 0.977 (2.84), 0.984 (7.60), 0.987 (7.67), 0.991 (3.80), 0.995 (3.73), 0.998 (7.94), 1.002 (7.51), 1.009 (2.57), 1.164 (0.58), 1.176 (1.20), 1.188 (0.59), 1.943 (1.11), 1.952 (2.20), 1.958 (2.39), 1.966 (4.13), 1.974 (2.26), 1.980 (2.05), 1.990 (2.84), 2.522 (0.47), 4.025 (0.55), 4.036 (0.52), 7.140 (12.42), 7.154 (15.22), 7.279 (16.00), 7.293 (12.83), 7.670 (8.88), 7.789 (3.78), 7.803 (5.29), 7.804 (5.27), 7.869 (7.56), 7.882 (5.36), 13.233 (0.57).

Intermediate 181

Methyl 6-Methyl-4'-(Trifluoromethyl)[1,1'-Biphenyl]-2-Carboxylate

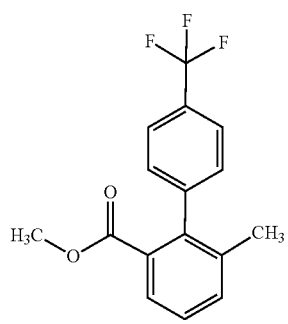

To a suspension of [4-(trifluoromethyl)phenyl]boronic acid (100 mg, 527 μmol) and methyl 2-bromo-3-methylbenzoate (110 μl, 660 μmol) in 1,2-dimethoxyethane (3.0 ml) was added under argon a 2 M solution sodium carbonate in water (1.3 ml, 2.0 M, 2.6 mmol) and tetrakis(triphenylphosphine)palladium(0) [Pd(PPh$_3$)$_4$] (30.5 mg, 26.3 μmol). The mixture was stirred over night at 90° C. Water (5 ml) was added at room temperature and the reaction was extracted with ethyl acetate (three times). The combined organic layers were washed with brine, dried, filtered and evaporated Purification was done by preparative HPLC (column: Reprosil C18 10 μm, 250×30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated and the residue was lyophylized. 92.0 mg (100% purity, 59% yield) of the title compound were obtained.

$^1$H-NMR (400 MHz, DMSO-d6) δ [ppm]: 2.035 (10.68), 3.311 (16.00), 7.365 (2.17), 7.385 (2.41), 7.427 (0.93), 7.446 (2.29), 7.465 (1.53), 7.544 (1.42), 7.562 (1.02), 7.682 (1.19), 7.700 (1.03), 7.757 (2.51), 7.777 (2.30).

Intermediate 182

6-Methyl-4'-(Trifluoromethyl)[1,1'-Biphenyl]-2-Carboxylic Acid

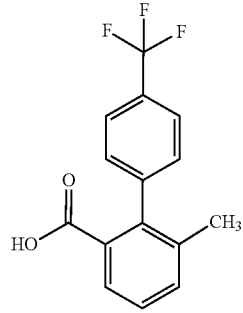 [SMILES: Cc1cccc(C(=O)O)c1-c1ccc(C(F)(F)F)cc1]

To a solution of methyl 6-methyl-4'-(trifluoromethyl)[1,1'-biphenyl]-2-carboxylate (90.0 mg, 306 μmol) in THF (2.0 ml) and methanol (400 μl) an aqueous lithium hydroxide solution (760 μl, 2.0 M, 1.5 mmol) was added and the mixture was stirred at room temperature over night. Aqueous lithium hydroxide solution (760 μl, 2.0 M, 1.5 mmol) was added and the mixture was then heated to 60° C. and stirred over night. The reaction was cooled to room temperature and was acidified with excess 2N aqueous hydrochloric acid. The THF was removed on a rotary evaporator and the resulting precipitate was filtered off, washed with water and dried in vacuo. 132 mg (97% purity, 150% yield) of the title compound were obtained.

LC-MS (Method 7): R$_t$=1.98 min, MS (ESIpos): m/z=281 [M+H]$^+$ $^1$H-NMR (600 MHz, DMSO-d6) δ [ppm]: 1.234 (0.99), 2.015 (16.00), 3.491 (0.48), 7.379 (5.58), 7.392 (6.54), 7.409 (3.71), 7.421 (2.36), 7.491 (3.22), 7.503 (2.65), 7.652 (2.98), 7.664 (2.79), 7.748 (5.68), 7.760 (5.62), 12.566 (2.37).

Intermediate 183

Methyl 4'-Ethyl-5-Fluoro[1,1'-Biphenyl]-2-Carboxylate

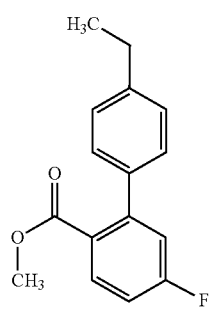 [SMILES: CCc1ccc(-c2cc(F)ccc2C(=O)OC)cc1]

To a suspension of methyl 4-fluoro-2-(4,4,5,5-tetramethyl-1,3,2-dioxaborolan-2-yl)benzoate (200 mg, 714 μmol) and 1-bromo-4-ethylbenzene (165 mg, 893 μmol) in 1,2-dimethoxyethane (3.1 ml) was added under argon a 2 M solution sodium carbonate in water (1.8 ml, 2.0 M, 3.6 mmol) and tetrakis(triphenylphosphine)palladium(0) [Pd(PPh$_3$)$_4$] (41.4 mg, 35.7 μmol). The mixture was stirred over night at 90° C. Water was added at room temperature and the reaction was extracted with ethyl acetate (three times). The combined organic layers were dried, filtered and evaporated Purification was done by flash chromatography (n-heptane→n-heptane:ethyl acetate (70:30)). Product containing samples were united, the solvents were evaporated. 92.0 mg (80% purity, 45% yield) of the title compound were obtained.

$^1$H-NMR (400 MHz, DMSO-d6) δ [ppm]: 1.196 (3.69), 1.206 (0.91), 1.215 (8.15), 1.225 (0.57), 1.234 (3.89), 2.624 (1.09), 2.643 (2.80), 2.662 (2.63), 2.681 (0.83), 3.592 (16.00), 7.213 (1.82), 7.217 (0.81), 7.228 (1.24), 7.233 (4.86), 7.260 (4.63), 7.280 (2.56), 7.287 (2.34), 7.293 (0.79), 7.308 (1.51), 7.315 (1.16), 7.329 (0.77), 7.336 (0.65), 7.782 (1.13), 7.797 (1.17), 7.804 (1.13), 7.819 (1.06).

Intermediate 184

4'-Ethyl-5-Fluoro[1,1'-Biphenyl]-2-Carboxylic Acid

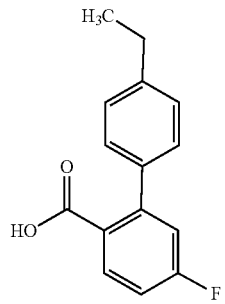 [SMILES: CCc1ccc(-c2cc(F)ccc2C(=O)O)cc1]

To a solution of methyl 4'-ethyl-5-fluoro[1,1'-biphenyl]-2-carboxylate (90.0 mg, 348 µmol) in THF (1.2 ml) and methanol (240 µl) an aqueous lithium hydroxide solution (870 µl, 2.0 M, 1.7 mmol) was added and the mixture was stirred at 60° C. for 3 hours. The reaction was cooled to room temperature and was acidified with excess 2N aqueous hydrochloric acid. The resulting precipitate was filtered off to give 74.0 mg (90% purity, 84% yield) of the title compound without further purification.

LC-MS (Method 8): $R_t$=1.04 min; MS (ESIneg): m/z=243 [M–H]$^-$

Intermediate 185

4'-(2,2-Difluorocyclopropyl)[1,1'-Biphenyl]-2-Carboxylic Acid (Racemic Mixture)

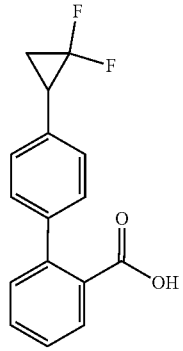 [SMILES: O=C(O)c1ccccc1-c1ccc(C2CC2(F)F)cc1]

To a suspension of [2-(methoxycarbonyl)phenyl]boronic acid (150 mg, 833 µmol) and 1-bromo-4-(2,2-difluorocyclopropyl)benzene (243 mg, 1.04 mmol) in 1,2-dimethoxyethane (3.7 ml) was added under argon a 2 M solution sodium carbonate in water (2.1 ml, 2.0 M, 4.2 mmol) and tetrakis(triphenylphosphine)palladium(0) [Pd(PPh$_3$)$_4$] (48.3 mg, 41.7 µmol). The mixture was stirred overnight at 90° C. Water was added at room temperature and the reaction was extracted with ethyl acetate (three times). The combined organic layers were dried, filtered and evaporated. Purification was done by preparative HPLC (column: Reprosil C18 10 µm, 250×30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated and the residue was lyophylized. 45.0 mg (95% purity, 20% yield) of the title compound were obtained.

LC-MS (Method 7): $R_t$=1.84 min; MS (ESIpos): m/z=275 [M+H]$^+$

Intermediate 186

Methyl 4'-Cyclobutyl[1,1'-Biphenyl]-2-Carboxylate

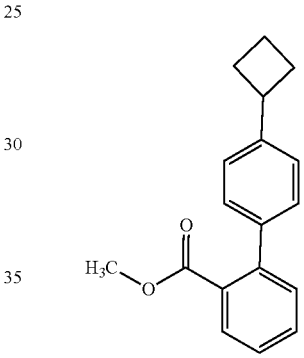

To a suspension of (4-cyclobutylphenyl)boronic acid (100 mg, 568 µmol) and methyl 2-bromobenzoate (110 µl, 710 µmol) in 1,2-dimethoxyethane (3.0 ml) was added under argon a 2 M solution sodium carbonate in water (1.4 ml, 2.0 M, 2.8 mmol) and tetrakis(triphenylphosphine)palladium(0) [Pd(PPh$_3$)$_4$] (32.9 mg, 28.4 µmol). The mixture was stirred overnight at 90° C. Water was added at room temperature and the reaction was extracted with ethyl acetate (three times). The combined organic layers were washed with brine, dried, filtered and evaporated Purification was done by flash chromatography (n-n-heptane/ethyl acetate gradient). Product containing samples were united, the solvents were evaporated. 97.2 mg (100% purity, 64% yield) of the title compound were obtained.

LC-MS (Method 7): $R_t$=2.48 min; MS (ESIpos): m/z=267 [M+H]$^+$ $^1$H-NMR (600 MHz, DMSO-d6) δ [ppm]: 1.822 (0.72), 1.839 (0.82), 1.966 (0.44), 1.982 (0.97), 1.998 (1.00), 2.012 (0.50), 2.015 (0.50), 2.088 (0.41), 2.103 (1.23), 2.107 (1.13), 2.119 (1.57), 2.123 (1.62), 2.135 (0.93), 2.138 (1.08), 2.288 (0.63), 2.292 (0.75), 2.302 (1.33), 2.306 (1.77), 2.310 (1.04), 2.316 (1.09), 2.320 (1.61), 2.324 (0.99), 2.334 (0.55), 3.328 (0.44), 3.333 (0.76), 3.542 (0.81), 3.557 (1.18), 3.571 (0.82), 3.586 (0.48), 3.601 (16.00), 7.210 (3.15), 7.223 (4.78), 7.269 (4.51), 7.283 (2.84), 7.413 (1.81), 7.425 (2.03), 7.451 (0.89), 7.463 (1.90), 7.476 (1.12), 7.589 (1.07), 7.590 (1.08), 7.602 (1.73), 7.603 (1.72), 7.614 (0.76), 7.701 (1.82), 7.714 (1.62).

Intermediate 187

4'-Cyclobutyl[1,1'-Biphenyl]-2-Carboxylic Acid

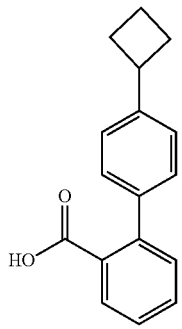 [SMILES: O=C(O)c1ccccc1-c1ccc(C2CCC2)cc1]

To a solution of methyl 4'-cyclobutyl[1,1'-biphenyl]-2-carboxylate (93.1 mg, 350 µmol) in THF (2.0 ml) and methanol (400 µl) an aqueous solution of lithium hydroxide (870 µl, 2.0 M, 1.7 mmol) was added and the mixture was stirred at 60° C. over night. The reaction was cooled to room temperature and was acidified with excess 2N aqueous hydrochloric acid and the mixture was evaporated. Purification was done by preparative HPLC (column: Reprosil C18 10 µm, 250×30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated. 76.9 mg (99% purity, 87% yield) of the title compound were obtained.

LC-MS (Method 8): $R_t$=1.07 min; MS (ESIneg): m/z=251 [M−H]⁻

¹H-NMR (400 MHz, DMSO-d6) δ [ppm]: 1.816 (0.42), 1.842 (0.53), 1.976 (0.61), 2.000 (0.64), 2.025 (0.40), 2.095 (0.82), 2.101 (0.74), 2.119 (0.92), 2.124 (1.07), 2.147 (0.71), 2.274 (0.44), 2.280 (0.47), 2.294 (0.86), 2.301 (1.13), 2.307 (0.62), 2.314 (0.69), 2.321 (1.12), 2.328 (0.70), 3.529 (0.54), 3.550 (0.78), 3.573 (0.51), 7.262 (16.00), 7.354 (1.07), 7.356 (1.06), 7.374 (1.33), 7.409 (0.56), 7.412 (0.50), 7.428 (1.31), 7.430 (1.12), 7.446 (0.90), 7.449 (0.73), 7.530 (0.79), 7.534 (0.78), 7.549 (1.20), 7.553 (1.13), 7.568 (0.52), 7.572 (0.46), 7.677 (1.25), 7.680 (1.23), 7.696 (1.12), 7.699 (1.04), 12.696 (1.78).

Intermediate 188

Methyl 4'-Tert-Butyl[1,1'-Biphenyl]-2-Carboxylate

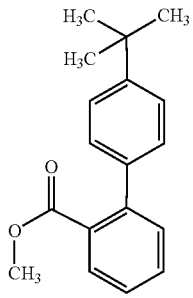 [SMILES: COC(=O)c1ccccc1-c1ccc(C(C)(C)C)cc1]

To a suspension of methyl 2-(4,4,5,5-tetramethyl-1,3,2-dioxaborolan-2-yl)benzoate (200 mg, 763 µmol) and 1-bromo-4-tert-butylbenzene (203 mg, 954 µmol) in 1,2-dimethoxyethane (3.4 ml) was added under argon a 2 M solution sodium carbonate in water (1.9 ml, 2.0 M, 3.8 mmol) and tetrakis(triphenylphosphine)palladium(0) [Pd (PPh₃)₄] (44.3 mg, 38.2 µmol). The mixture was stirred over night at 80° C. Water (5 ml) was added at room temperature and the reaction was extracted with ethyl acetate (three times). The combined organic layers were dried, filtered and evaporated. Purification was done by preparative HPLC (column: Reprosil C18 10 µm, 250×30 mm, eluent A=water+0.1% TFA, B=acetonitrile; gradient: 3 min 10% B; 21 min 95% B; 30 min 95% B; 32 min 10% B; flow: 50 ml/min) following flash chromatography (n-heptane:ethyl acetate). Product containing samples were united, the solvents were evaporated and the residue was lyophylized. 104 mg (99% purity, 66% yield) of the title compound were obtained.

LC-MS (Method 7): $R_t$=2.47 min; MS (ESIpos): m/z=269 [M+H]⁺

¹H-NMR (600 MHz, DMSO-d6) δ [ppm]: 1.296 (0.70), 1.318 (16.00), 3.319 (2.05), 7.217 (1.42), 7.230 (1.59), 7.425 (1.02), 7.430 (1.81), 7.436 (1.24), 7.444 (1.54), 7.463 (0.81), 7.476 (0.49), 7.590 (0.45), 7.603 (0.72), 7.703 (0.74), 7.716 (0.66).

Intermediate 189

4'-Tert-Butyl[1,1'-Biphenyl]-2-Carboxylic Acid

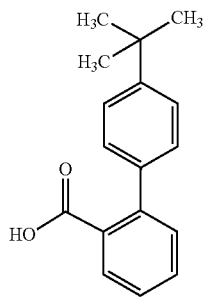 [SMILES: CC(C)(C)c1ccc(-c2ccccc2C(=O)O)cc1]

To a solution of methyl 4'-tert-butyl[1,1'-biphenyl]-2-carboxylate (100 mg, 373 µmol) in THF (1.3 ml) and methanol (260 µl) an aqueous solution of lithium hydroxide (930 µl, 2.0 M, 1.9 mmol) was added and the mixture was stirred at 60° C. for 5 hours. An aqueous solution of lithium hydroxide (930 µl, 2.0 M, 1.9 mmol) was added and the mixture was stirred over night at 60° C.

The reaction was cooled to room temperature and was acidified with excess 2N aqueous hydrochloric acid. The THF was removed on a rotary evaporator and the resulting precipitate was filtered off and dried in vacuo. 75.0 mg (95% purity, 75% yield) of the title compound were obtained.

LC-MS (Method 7): $R_t$=2.08 min; MS (ESIneg): m/z=253 [M−H]⁻

¹H-NMR (600 MHz, DMSO-d6) δ [ppm]: 1.315 (16.00), 3.330 (0.71), 7.267 (1.42), 7.281 (1.61), 7.372 (0.74), 7.384 (0.82), 7.423 (1.88), 7.427 (1.45), 7.437 (1.54), 7.536 (0.46), 7.547 (0.70), 7.674 (0.75), 7.686 (0.66), 12.717 (0.56).

Intermediate 190

Methyl 4'-(Trifluoromethyl)[1,1'-Biphenyl]-2-Carboxylate

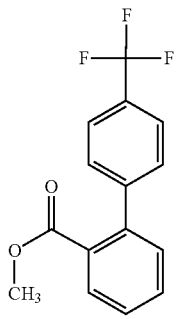 [SMILES: COC(=O)c1ccccc1-c1ccc(C(F)(F)F)cc1]

To a suspension of methyl 2-(4,4,5,5-tetramethyl-1,3,2-dioxaborolan-2-yl)benzoate (200 mg, 763 µmol) and 1-bromo-4-(trifluoromethyl)benzene (215 mg, 954 µmol) in 1,2-dimethoxyethane (3.4 ml) was added under argon a 2 M solution sodium carbonate in water (1.9 ml, 2.0 M, 3.8 mmol) and tetrakis(triphenylphosphine)palladium(0) [Pd (PPh$_3$)$_4$] (44.3 mg, 38.2 µmol). The mixture was stirred over night at 80° C. Water was added at room temperature and the reaction was extracted with ethyl acetate (three times). The combined organic layers were washed with brine, dried, filtered and evaporated. Purification was done by preparative HPLC (column: Reprosil C18 10 µm, 250×30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated and the residue was lyophilized. 123 mg (99% purity, 57% yield) of the title compound were obtained.

$^1$H-NMR (600 MHz, DMSO-d6) δ [ppm]: 1.144 (0.72), 2.087 (0.52), 2.518 (0.58), 2.521 (0.63), 2.524 (0.58), 3.487 (0.54), 3.591 (1.05), 3.733 (0.59), 7.452 (0.56), 7.463 (8.11), 7.465 (8.07), 7.476 (9.24), 7.477 (8.88), 7.509 (14.13), 7.523 (15.11), 7.551 (4.41), 7.554 (4.34), 7.564 (9.48), 7.566 (8.73), 7.577 (5.81), 7.579 (5.30), 7.666 (5.60), 7.668 (5.62), 7.679 (8.99), 7.681 (8.91), 7.692 (4.07), 7.694 (3.85), 7.773 (16.00), 7.786 (14.17), 7.836 (8.75), 7.838 (8.30), 7.849 (8.05), 7.851 (7.29).

Intermediate 191

4'-(Trifluoromethyl)[1,1'-Biphenyl]-2-Carboxylic Acid

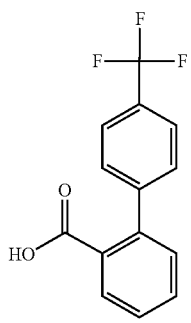

To a solution of methyl 4'-(trifluoromethyl)[1,1'-biphenyl]-2-carboxylate (120 mg, 428 µmol) in THF (1.5 ml) and methanol (300 µl) was added an aqueous lithium hydroxide solution (1.1 ml, 2.0 M, 2.1 mmol) and the mixture was stirred at 60° C. for 5 hours. An aqueous solution of lithium hydroxide (1.1 ml, 2.0 M, 2.1 mmol) was added and the reaction was stirred at 60° C. over night. The mixture was acidified with excess 2N aqueous hydrochloric acid and was extracted with ethyl acetate and the organic layers were dried, filtered and evaporated. Purification was done by flash chromatography (n-heptane→n-heptane:ethyl acetate (50:50)). Product containing samples were united, the solvents were evaporated. 97.0 mg (99% purity, 84% yield) of the title compound were obtained.

LC-MS (Method 7): R$_t$=1.87 min, MS (ESIneg): m/z=265 [M−H]$^−$ $^1$H-NMR (500 MHz, DMSO-d6) δ [ppm]: 0.006 (0.47), 1.234 (0.49), 2.731 (0.57), 2.890 (0.71), 7.408 (7.62), 7.410 (7.81), 7.423 (8.91), 7.425 (8.64), 7.514 (4.14), 7.516 (4.14), 7.529 (11.51), 7.532 (14.91), 7.535 (14.57), 7.545 (8.62), 7.547 (11.70), 7.551 (15.41), 7.614 (5.63), 7.617 (5.78), 7.630 (8.61), 7.632 (8.40), 7.645 (3.72), 7.647 (3.45), 7.762 (16.00), 7.778 (13.68), 7.819 (8.50), 7.822 (8.25), 7.835 (7.76), 7.837 (7.12), 12.881 (1.65).

Intermediate 192

Methyl 4'-[1-(Trifluoromethyl)Cyclopropyl][1,1'-Biphenyl]-2-Carboxylate

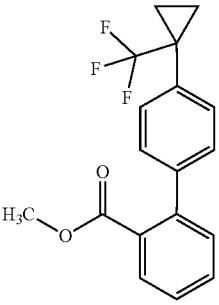 [SMILES: COC(=O)c1ccccc1-c1ccc(C2(C(F)(F)F)CC2)cc1]

To a suspension of [2-(methoxycarbonyl)phenyl]boronic acid (150 mg, 833 µmol) and 1-bromo-4-[1-(trifluoromethyl)cyclopropyl]benzene (276 mg, 1.04 mmol) in 1,2-dimethoxyethane (4.0 ml) was added under argon a2 M solution sodium carbonate in water (2.1 ml, 2.0 M, 4.2 mmol) and tetrakis(triphenylphosphine)palladium(0) [Pd (PPh$_3$)$_4$] (48.3 mg, 41.7 µmol). The mixture was stirred overnight at 90° C. Water was added at room temperature and the reaction was extracted with ethyl acetate (three times). The combined organic layers were washed with brine, dried, filtered and evaporated. Purification was done by flash chromatography. Product containing samples were united, the solvents were evaporated and the residue was lyophilized. 69.4 mg (100% purity, 26% yield) of the title compound were obtained.

$^1$H-NMR (600 MHz, DMSO-d6) δ [ppm]: 1.168 (4.47), 1.360 (1.56), 1.368 (5.76), 1.379 (1.20), 3.297 (0.48), 3.575 (0.66), 3.590 (16.00), 7.298 (4.45), 7.309 (4.62), 7.311 (4.53), 7.434 (2.21), 7.447 (2.54), 7.496 (4.84), 7.503 (3.35), 7.508 (4.29), 7.617 (1.42), 7.629 (2.38), 7.642 (1.06), 7.756 (2.65), 7.769 (2.41).

Intermediate 193

4'-[1-(Trifluoromethyl)Cyclopropyl][1,1'-Biphenyl]-2-Carboxylic Acid

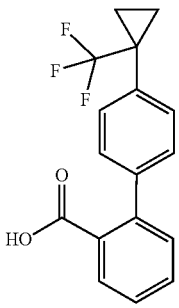

To a solution of methyl 4'-[1-(trifluoromethyl)cyclopropyl][1,1'-biphenyl]-2-carboxylate (65.2 mg, 204 µmol) in THF (1.5 ml) and methanol (300 µl) was added aqueous lithium hydroxide (510 µl, 2.0 M, 1.0 mmol) and the mixture was stirred at 60° C. over night. The reaction was cooled to room temperature and was acidified with excess 2N aqueous hydrochloric acid and evaporated. Purification was done by preparative HPLC (column: Reprosil C18 10 µm, 250×30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated. 58.9 mg (98% purity, 93% yield) of the title compound were obtained.

LC-MS (Method 12): $R_t$=3.47 min; MS (ESIneg): m/z=305 [M−H]⁻

¹H-NMR (400 MHz, DMSO-d6) δ [ppm]: −0.008 (1.47), 0.008 (1.56), 1.073 (1.45), 1.091 (2.97), 1.108 (1.56), 1.157 (8.75), 1.314 (0.42), 1.354 (4.62), 1.366 (10.76), 1.370 (10.60), 1.383 (3.53), 2.524 (0.87), 3.374 (3.21), 3.392 (2.17), 3.409 (0.85), 7.339 (11.78), 7.343 (4.36), 7.355 (5.03), 7.359 (16.00), 7.374 (4.77), 7.377 (5.07), 7.393 (5.78), 7.396 (5.91), 7.445 (2.69), 7.448 (2.67), 7.464 (5.94), 7.467 (5.62), 7.485 (15.34), 7.506 (9.17), 7.554 (3.69), 7.558 (4.01), 7.573 (5.48), 7.577 (5.61), 7.592 (2.38), 7.595 (2.25), 7.717 (5.22), 7.720 (5.16), 7.736 (4.66), 7.739 (4.33), 12.778 (0.64).

Intermediate 194

Methyl 5-Fluoro-4'-(Trifluoromethyl)[1,1'-Biphenyl]-2-Carboxylate

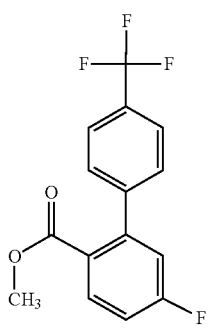 [SMILES: COC(=O)c1ccc(F)cc1-c1ccc(C(F)(F)F)cc1]

To a suspension of methyl 4-fluoro-2-(4,4,5,5-tetramethyl-1,3,2-dioxaborolan-2-yl)benzoate (200 mg, 714 µmol) and 1-bromo-4-(trifluoromethyl)benzene (201 mg, 893 µmol) in 1,2-dimethoxyethane (3.1 ml) was added under argon a 2 M solution sodium carbonate in water (1.8 ml, 2.0 M, 3.6 mmol) and tetrakis(triphenylphosphine)palladium(0) [Pd(PPh₃)₄] (41.4 mg, 35.7 µmol). The mixture was stirred over night at 90° C. Water was added at room temperature and the reaction was extracted with ethyl acetate (three times). The combined organic layers were dried, filtered and evaporated. Purification was done by preparative HPLC (column: Reprosil C18 10 µm, 250×30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated and the residue was lyophylized. 74.0 mg (97% purity, 34% yield) of the title compound were obtained.

¹H-NMR (400 MHz, DMSO-d6) δ [ppm]: 2.519 (0.53), 2.524 (0.41), 3.606 (16.00), 7.347 (0.95), 7.354 (1.24), 7.371 (0.96), 7.378 (1.25), 7.392 (0.69), 7.398 (0.58), 7.413 (1.30), 7.420 (1.12), 7.434 (0.76), 7.441 (0.70), 7.532 (2.02), 7.551 (2.37), 7.778 (2.43), 7.798 (2.09), 7.921 (1.10), 7.935 (1.14), 7.942 (1.11), 7.957 (1.04).

Intermediate 195

5-Fluoro-4'-(Trifluoromethyl)[1,1'-Biphenyl]-2-Carboxylic Acid

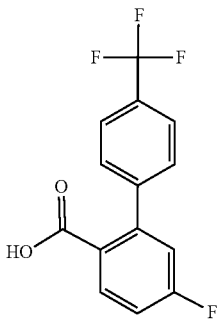 [SMILES: O=C(O)c1ccc(F)cc1-c1ccc(C(F)(F)F)cc1]

To a solution of methyl 5-fluoro-4'-(trifluoromethyl)[1,1'-biphenyl]-2-carboxylate (70.0 mg, 235 µmol) in THF (810 µl) and methanol (160 µl) was added aqueous lithium hydroxide (590 µl, 2.0 M, 1.2 mmol) and the mixture was stirred for 2 hours at 60° C. The reaction was cooled to room temperature and was acidified with excess 2N aqueous hydrochloric acid. The THF was removed on a rotary evaporator and the resulting precipitate was filtered off, washed with water and dried in vacuo. 64.0 mg (97% purity, 93% yield) of the title compound were obtained.

LC-MS (Method 7): $R_t$=1.93 min; MS (ESIneg): m/z=283 [M−H]⁻

Intermediate 196

Methyl 4',5-Bis(Trifluoromethyl)[1,1'-Biphenyl]-2-Carboxylic Acid

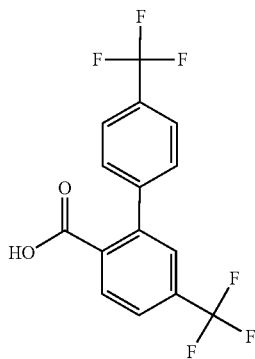 [SMILES: O=C(O)c1ccc(C(F)(F)F)cc1-c1ccc(C(F)(F)F)cc1]

To a suspension of [2-(methoxycarbonyl)-5-(trifluoromethyl)phenyl]boronic acid (200 mg, 807 µmol) and 1-bromo-4-(trifluoromethyl)benzene (227 mg, 1.01 mmol) in 1,2-dimethoxyethane (3.6 ml) was added under argon a 2 M solution sodium carbonate in water (2.0 ml, 2.0 M, 4.0 mmol) and tetrakis(triphenylphosphine)palladium(0) [Pd(PPh$_3$)$_4$] (46.8 mg, 40.3 µmol). The mixture was stirred over night at 90° C. Water was added at room temperature and the reaction was extracted with ethyl acetate (three times). The combined organic layers were dried, filtered and evaporated Purification was done by preparative HPLC (column: Reprosil C18 10 µm, 250×30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated and the residue was lyophylized. 99.0 mg (97% purity, 36% yield) of the title compound were obtained.

LC-MS (Method 8): R$_t$=1.12 min; MS (ESIneg): m/z=332 [M−H]⁻

$^1$H NMR (400 MHz, DMSO-d$_6$) δ ppm 7.63 (d, J=8.19 Hz, 2H) 7.76-7.84 (m, 3H) 7.88-7.94 (m, 1H) 8.02 (d, J=8.07 Hz, 1H) 13.37 (s, 1H).

Intermediate 197

Methyl 4'-(Propan-2-Yl)[1,1'-Biphenyl]-2-Carboxylate

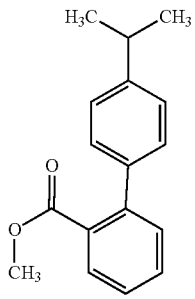 [SMILES: COC(=O)c1ccccc1-c1ccc(C(C)C)cc1]

To a suspension of methyl 2-(4,4,5,5-tetramethyl-1,3,2-dioxaborolan-2-yl)benzoate (200 mg, 763 µmol) and 1-bromo-4-(propan-2-yl)benzene (190 mg, 954 µmol) in 1,2-dimethoxyethane (3.4 ml) was added under argon a 2 M solution sodium carbonate in water (1.9 ml, 2.0 M, 3.8 mmol) and tetrakis(triphenylphosphine)palladium(0) [Pd(PPh$_3$)$_4$] (44.3 mg, 38.2 µmol). The mixture was stirred over night at 80° C. Water was added at room temperature and the reaction was extracted with ethyl acetate (three times). The combined organic layers were dried, filtered and evaporated. Purification was done by preparative HPLC (column: Reprosil C18 10 µm, 250×30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated and the residue was lyophilized. 262 mg (94% purity, 128% yield) of the title compound were obtained.

LC-MS (method 7): R$_t$=2.40 min; MS (ESIpos): m/z=255 [M+H]⁺

$^1$H-NMR (500 MHz, DMSO-d6) δ [ppm]: 1.231 (15.94), 1.245 (16.00), 2.916 (0.88), 2.930 (1.14), 2.944 (0.83), 3.717 (1.74), 7.203 (3.12), 7.216 (1.49), 7.220 (4.72), 7.284 (4.35), 7.300 (2.89), 7.423 (1.56), 7.438 (1.86), 7.447 (0.85), 7.450 (0.81), 7.462 (1.80), 7.465 (1.63), 7.478 (1.15), 7.480 (1.02), 7.587 (1.02), 7.590 (1.10), 7.602 (1.63), 7.605 (1.69), 7.617 (0.77), 7.620 (0.76), 7.699 (1.63), 7.701 (1.63), 7.714 (1.45), 7.716 (1.41).

Intermediate 198

4'-(Propan-2-Yl)[1,1'-Biphenyl]-2-Carboxylic Acid

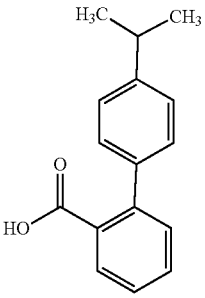 [SMILES: CC(C)c1ccc(-c2ccccc2C(=O)O)cc1]

To a solution of methyl 4'-(propan-2-yl)[1,1'-biphenyl]-2-carboxylate (260 mg, 1.02 mmol) in THF (3.5 ml) and methanol (710 µl) an aqueous solution of lithium hydroxide (2.6 ml, 2.0 M, 5.1 mmol) was added and the mixture was stirred at 60° C. over night. The reaction was cooled to room temperature and was acidified with excess 2N aqueous hydrochloric acid and the mixture was extracted with ethyl acetate. The combined organic layers were dried, filtered and evaporated. Purification was done by flash chromatography (n-heptane→n-heptane:ethyl acetate (50:50)). Product containing samples were united, the solvents were evaporated. 63.0 mg (99% purity, 25% yield) of the title compound were obtained.

LC-MS (Method 7): R$_t$=1.99 min; MS (ESIpos): m/z=241 [M+H]⁺

$^1$H-NMR (500 MHz, DMSO-d6) δ [ppm]: 1.229 (15.85), 1.243 (16.00), 1.250 (0.72), 2.911 (0.96), 2.925 (1.26), 2.939 (0.92), 7.249 (1.51), 7.253 (0.76), 7.261 (1.48), 7.266 (7.00), 7.275 (6.65), 7.292 (1.34), 7.367 (1.57), 7.381 (1.80), 7.383 (1.81), 7.411 (0.79), 7.414 (0.75), 7.427 (1.80), 7.429 (1.62), 7.442 (1.15), 7.444 (0.99), 7.532 (1.03), 7.535 (1.07), 7.547 (1.62), 7.550 (1.61), 7.562 (0.72), 7.565 (0.69), 7.672 (1.67), 7.674 (1.63), 7.687 (1.51), 7.690 (1.40), 12.728 (0.48).

Intermediate 199

Methyl 4'-(2,2,2-Trifluoroethyl)[1,1'-Biphenyl]-2-Carboxylate

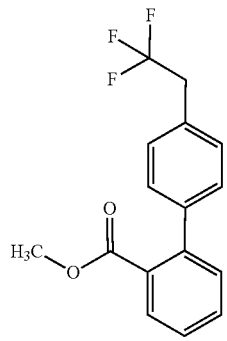 [SMILES: COC(=O)c1ccccc1-c1ccc(CC(F)(F)F)cc1]

To a suspension of methyl 2-(4,4,5,5-tetramethyl-1,3,2-dioxaborolan-2-yl)benzoate (200 mg, 763 µmol) and 1-bromo-4-(2,2,2-trifluoroethyl)benzene (228 mg, 954 µmol) in 1,2-dimethoxyethane (4.0 ml) was added under argon a 2 M solution sodium carbonate in water (1.9 ml, 2.0 M, 3.8 mmol) and tetrakis(triphenylphosphine)palladium(0) [Pd(PPh$_3$)$_4$] (44.3 mg, 38.2 µmol). The mixture was stirred over night at 90° C. Water was added at room temperature and the reaction was extracted with ethyl acetate (three times). The combined organic layers were washed with brine, dried, filtered and evaporated. Purification was done by flash chromatography (n-heptane:ethyl acetate gradient). Product containing samples were united, the solvents were evaporated and the residue was lyophylized. 122 mg (100% purity, 54% yield) of the title compound were obtained.

LC-MS (Method 8): R$_t$=1.13 min, MS (ESIpos): m/z=295 [M+H]$^+$ $^1$H-NMR (600 MHz, DMSO-d6) δ [ppm]: 3.324 (16.00), 3.670 (0.73), 3.689 (2.10), 3.709 (2.01), 3.728 (0.63), 7.294 (3.27), 7.307 (4.30), 7.399 (3.13), 7.413 (2.45), 7.444 (1.47), 7.445 (1.56), 7.456 (1.72), 7.458 (1.75), 7.486 (0.77), 7.488 (0.77), 7.499 (1.72), 7.501 (1.63), 7.511 (1.07), 7.513 (0.98), 7.616 (0.96), 7.618 (1.03), 7.628 (1.61), 7.630 (1.64), 7.641 (0.73), 7.643 (0.71), 7.747 (1.57), 7.748 (1.55), 7.759 (1.45), 7.761 (1.39).

Intermediate 200

4'-(2,2,2-Trifluoroethyl)[1,1'-Biphenyl]-2-Carboxylic Acid

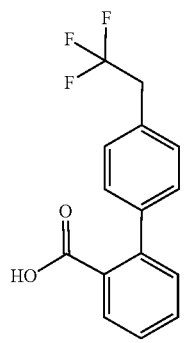 [SMILES: O=C(O)c1ccccc1-c1ccc(CC(F)(F)F)cc1]

To a solution of methyl 4'-(2,2,2-trifluoroethyl)[1,1'-biphenyl]-2-carboxylate (119 mg, 405 µmol) in THF (2.5 ml) and methanol (500 µl) an aqueous solution of lithium hydroxide (1.0 ml, 2.0 M, 2.0 mmol) was added and the mixture was stirred at 60° C. over night. The reaction was cooled to room temperature and was acidified with excess 2N aqueous hydrochloric acid and the mixture and evaporated. Purification was done by flash chromatography (n-heptane:ethyl acetate gradient). Product containing samples were united, the solvents were evaporated and the residue was lyophilized. 101 mg (100% purity, 89% yield) of the title compound were obtained.

LC-MS (Method 7): R$_t$=1.90 min; MS (ESIpos): m/z=281 [M+H]$^+$ $^1$H-NMR (400 MHz, DMSO-d6) δ [ppm]: −0.008 (0.98), 0.008 (1.01), 3.644 (2.35), 3.674 (6.85), 3.703 (6.56), 3.732 (2.07), 7.328 (7.03), 7.333 (3.01), 7.344 (4.33), 7.349 (16.00), 7.383 (14.81), 7.402 (9.91), 7.442 (2.12), 7.445 (2.13), 7.461 (5.06), 7.464 (4.59), 7.480 (3.47), 7.483 (2.99), 7.555 (3.14), 7.559 (3.35), 7.574 (4.68), 7.578 (4.73), 7.593 (2.02), 7.597 (1.89), 7.720 (4.70), 7.723 (4.64), 7.739 (4.19), 7.742 (3.88), 12.757 (4.01).

Intermediate 201

Methyl 4'-(1,1,1-Trifluoro-2-Methylpropan-2-Yl)[1,1'-Biphenyl]-2-Carboxylate

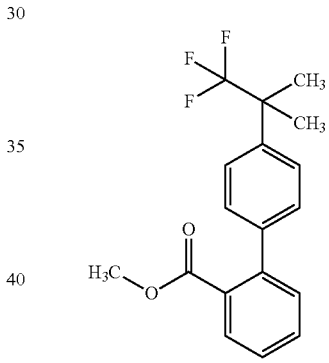

To a suspension of methyl 2-(4,4,5,5-tetramethyl-1,3,2-dioxaborolan-2-yl)benzoate (200 mg, 763 µmol) and 1-bromo-4-(1,1,1-trifluoro-2-methylpropan-2-yl)benzene (255 mg, 954 µmol, CAS 1225380-05-1) in 1,2-dimethoxyethane (4.0 ml) was added under argon a 2 M solution sodium carbonate in water (1.9 ml, 2.0 M, 3.8 mmol) and tetrakis(triphenylphosphine)palladium(0) [Pd(PPh$_3$)$_4$] (44.3 mg, 38.2 µmol). The mixture was stirred over night at 90° C. Water (5 ml) was added at room temperature and the reaction was extracted with ethyl acetate (three times). The combined organic layers were washed with brine dried, filtered and evaporated. Purification was done by preparative HPLC (column: Reprosil C18 10 µm, 250×30 mm, eluent A=water+0.1% TFA, B=acetonitrile; gradient: 3 min 10% B; 21 min 95% B; 30 min 95% B; 32 min 10% B: flow: 50 ml/min). Product containing samples were united, the solvents were evaporated and the residue was lyophylized. 123 mg (92% purity, 46% yield) of the title compound were obtained.

$^1$H-NMR (400 MHz, DMSO-d6) δ [ppm]: 1.591 (16.00), 3.383 (0.81), 3.586 (9.92), 3.588 (9.52), 3.614 (0.96), 3.616 (0.94), 7.307 (2.41), 7.326 (2.90), 7.444 (1.31), 7.463 (1.64), 7.480 (0.70), 7.499 (1.59), 7.518 (1.12), 7.572 (2.69), 7.592 (2.19), 7.610 (1.05), 7.629 (1.59), 7.648 (0.77), 7.746 (1.40), 7.766 (1.22).

Intermediate 202

4'-(1,1,1-Trifluoro-2-Methylpropan-2-Yl)[1,1'-Biphenyl]-2-Carboxylic Acid

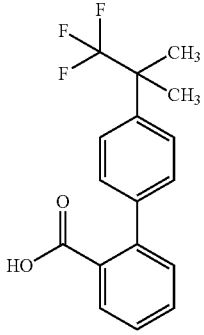

To a solution of methyl 4'-(1,1,1-trifluoro-2-methylpropan-2-yl)[1,1'-biphenyl]-2-carboxylate (118 mg, 366 µmol) in THF (2.5 ml) and methanol (500 µl) was added aqueous lithium hydroxide (920 µl, 2.0 M, 1.8 mmol) and the mixture was stirred at 60° C. over night. The reaction was cooled to room temperature and was acidified with excess 2N aqueous hydrochloric acid and the mixture was evaporated. Purification was done by preparative HPLC (column: Reprosil C18 10 µm, 250×30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated and the residue was lyophylized. 99.4 mg (94% purity, 83% yield) of the title compound were obtained.

LC-MS (Method 7): $R_t$=2.10 min; MS (ESIpos): m/z=309 [M+H]$^+$ $^1$H-NMR (400 MHz, DMSO-d6) δ [ppm]: 0.008 (0.43), 1.588 (16.00), 7.349 (0.41), 7.355 (3.10), 7.359 (1.08), 7.371 (1.23), 7.376 (3.82), 7.382 (0.61), 7.389 (1.20), 7.391 (1.28), 7.408 (1.51), 7.410 (1.56), 7.443 (0.66), 7.446 (0.66), 7.462 (1.56), 7.465 (1.43), 7.481 (1.09), 7.484 (0.96), 7.555 (1.09), 7.558 (1.38), 7.566 (2.64), 7.573 (2.07), 7.577 (1.80), 7.587 (2.10), 7.592 (1.15), 7.596 (0.86), 7.711 (1.35), 7.714 (1.34), 7.730 (1.20), 7.733 (1.11), 12.769 (0.88).

Intermediate 203

Methyl 4'-(Difluoromethyl)[1,1'-Biphenyl]-2-Carboxylate

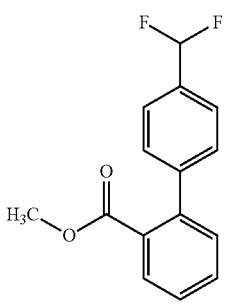 [SMILES: COC(=O)c1ccccc1-c1ccc(C(F)F)cc1]

To a suspension of [2-(methoxycarbonyl)phenyl]boronic acid (150 mg, 833 µmol) and 1-bromo-4-(difluoromethyl)benzene (130 µl, 1.0 mmol) in 1,2-dimethoxyethane (4.0 ml) was added under argon a 2 M solution sodium carbonate in water (2.1 ml, 2.0 M, 4.2 mmol) and tetrakis(triphenylphosphine)palladium(0) [Pd(PPh$_3$)$_4$] (48.3 mg, 41.7 µmol). The mixture was stirred over night at 90° C. Water (5 ml) was added at room temperature and the reaction was extracted with ethyl acetate (three times). The combined organic layers were washed with brine, dried, filtered and evaporated. Purification was done by flash chromatography (cyclohexane: ethyl acetate gradient). Product containing samples were united, the solvents were evaporated and the residue was lyophylized. 96.7 mg (100% purity, 44% yield) of the title compound were obtained.

LC-MS (Method 7): $R_t$=2.04 min, MS (ESIpos): m/z=263 [M+H]$^+$ $^1$H-NMR (600 MHz, DMSO-d6) δ [ppm]: 3.604 (16.00), 7.000 (1.00), 7.093 (2.00), 7.186 (0.92), 7.424 (2.57), 7.437 (2.94), 7.450 (1.52), 7.463 (1.69), 7.522 (0.69), 7.524 (0.73), 7.535 (1.56), 7.537 (1.59), 7.548 (0.95), 7.549 (0.95), 7.612 (2.63), 7.625 (2.30), 7.644 (0.90), 7.646 (0.95), 7.657 (1.48), 7.659 (1.54), 7.669 (0.67), 7.671 (0.67), 7.794 (1.51), 7.795 (1.50), 7.807 (1.39), 7.808 (1.35).

Intermediate 204

4'-(Difluoromethyl)[1,1'-Biphenyl]-2-Carboxylic Acid

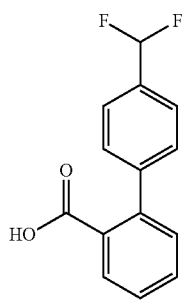 [SMILES: O=C(O)c1ccccc1-c1ccc(C(F)F)cc1]

To a solution of methyl 4'-(difluoromethyl)[1,1'-biphenyl]-2-carboxylate (90.6 mg, 345 µmol) in THF (2.0 ml) and methanol (400 µl) was added aqueous lithium hydroxide (860 µl, 2.0 M, 1.7 mmol) and the mixture was stirred at 60° C. over night. The reaction was cooled to room temperature and was acidified with excess 2N aqueous hydrochloric acid and the mixture was evaporated. Purification was done by preparative HPLC (column: Reprosil C18 10 µm, 250×30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated. 82.2 mg (100% purity, 96% yield) of the title compound were obtained.

LC-MS (Method 12): $R_t$=2.79 min; MS (ESIneg): m/z=247 [M−H]$^-$ $^1$H-NMR (400 MHz, DMSO-d6) δ [ppm]: −0.008 (1.20), 0.008 (1.58), 6.944 (5.73), 7.084 (11.35), 7.223 (5.28), 7.390 (6.81), 7.392 (7.25), 7.409 (8.53), 7.411 (8.60), 7.451 (12.04), 7.471 (16.00), 7.480 (4.63), 7.483 (4.07), 7.499 (8.48), 7.502 (8.03), 7.517 (5.81), 7.520 (5.24), 7.587 (6.90), 7.591 (12.93), 7.594 (14.78), 7.606 (9.78), 7.609 (12.63), 7.614 (11.61), 7.624 (4.19), 7.628 (3.61), 7.776 (7.75), 7.779 (7.81), 7.795 (7.04), 7.798 (6.70), 12.806 (4.91).

Intermediate 205

Methyl 4'-(2-Cyanopropan-2-Yl)[1,1'-Biphenyl]-2-Carboxylate

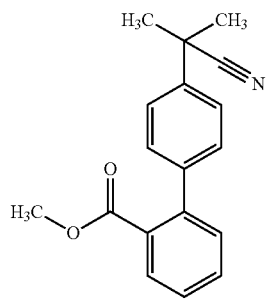 [SMILES: COC(=O)c1ccccc1-c1ccc(C(C)(C)C#N)cc1]

To a suspension of methyl 2-(4,4,5,5-tetramethyl-1,3,2-dioxaborolan-2-yl)benzoate (200 mg, 763 µmol) and 2-(4-bromophenyl)-2-methylpropanenitrile (160 µl, 950 µmol) in 1,2-dimethoxyethane (4.0 ml) was added under argon a 2 M solution sodium carbonate in water (1.9 ml, 2.0 M, 3.8 mmol) and tetrakis(triphenylphosphine)palladium(0) [Pd(PPh₃)₄] (44.3 mg, 38.2 µmol). The mixture was stirred over night at 90° C. Water (5 ml) was added at room temperature and the reaction was extracted with ethyl acetate (three times). The combined organic layers were washed with brine dried, filtered and evaporated Purification was done by flash chromatography (n-heptane:ethyl acetate gradient). Product containing samples were united, the solvents were evaporated and the residue was lyophylized. 126 mg (100% purity, 59% yield) of the title compound were obtained.

LC-MS (Method 8): $R_t$=1.06 min; MS (ESIpos): m/z=280 [M+H]⁺

¹H-NMR (600 MHz, DMSO-d6) δ [ppm]: 1.728 (16.00), 3.322 (9.42), 7.346 (2.11), 7.349 (0.71), 7.356 (0.78), 7.359 (2.45), 7.438 (0.80), 7.440 (0.84), 7.451 (0.93), 7.452 (0.93), 7.493 (0.44), 7.495 (0.43), 7.505 (0.94), 7.507 (0.88), 7.518 (0.58), 7.520 (0.53), 7.559 (2.43), 7.562 (0.75), 7.570 (0.74), 7.573 (2.10), 7.621 (0.54), 7.624 (0.57), 7.634 (0.89), 7.636 (0.91), 7.646 (0.41), 7.761 (0.89), 7.763 (0.86), 7.774 (0.82), 7.776 (0.76).

Intermediate 206

4'-(2-Cyanopropan-2-Yl)[1,1'-Biphenyl]-2-Carboxylic Acid

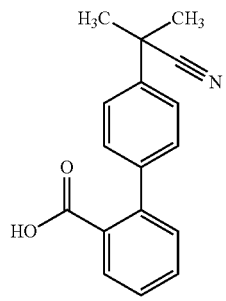 [SMILES: CC(C)(C#N)c1ccc(-c2ccccc2C(=O)O)cc1]

To a solution of methyl 4'-(2-cyanopropan-2-yl)[1,1'-biphenyl]-2-carboxylate (123 mg, 440 µmol) in THF (2.5 ml) and methanol (500 µl) an aqueous solution of lithium hydroxide (1.1 ml, 2.0 M, 2.2 mmol) was added and the mixture was stirred at 60° C. over night. The reaction was cooled to room temperature and was acidified with excess 2N aqueous hydrochloric acid. The mixture was evaporated and purification was done by preparative HPLC (column: Reprosil C18 10 µm, 250×30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated. 102 mg (100% purity, 87% yield) of the title compound were obtained.

LC-MS (Method 7): $R_t$=1.78 min; MS (ESIneg): m/z=264 [M−H]⁻

¹H-NMR (400 MHz, DMSO-d6) δ [ppm]: 1.726 (16.00), 7.381 (2.64), 7.402 (3.40), 7.407 (0.45), 7.450 (0.40), 7.453 (0.41), 7.469 (0.95), 7.472 (0.88), 7.488 (0.66), 7.491 (0.59), 7.547 (2.57), 7.553 (0.80), 7.561 (0.84), 7.565 (1.26), 7.569 (2.01), 7.580 (0.96), 7.584 (0.95), 7.728 (0.86), 7.731 (0.87), 7.748 (0.77), 7.751 (0.72), 12.769 (0.58).

Intermediate 207

Methyl 4'-(1,1-Difluoroethyl)[1,1'-Biphenyl]-2-Carboxylate

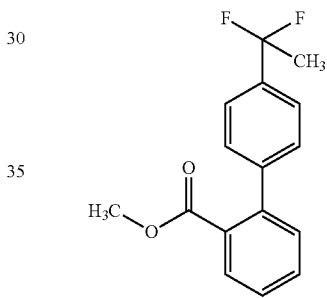

To a suspension of [2-(methoxycarbonyl)phenyl]boronic acid (150 mg, 833 µmol) and 1-bromo-4-(1,1-difluoroethyl)benzene (150 µl, 1.0 mmol) in 1,2-dimethoxyethane (4.0 ml) was added under argon a 2 M solution sodium carbonate in water (2.1 ml, 2.0 M, 4.2 mmol) and tetrakis(triphenylphosphine)palladium(0) [Pd(PPh₃)₄] (48.3 mg, 41.7 µmol). The mixture was stirred overnight at 90° C. Water was added at room temperature and the reaction was extracted with ethyl acetate (three times). The combined organic layers were washed with brine dried, filtered and evaporated. Purification was done by flash chromatography (cyclohexane: ethyl acetate gradient). Product containing samples were united, the solvents were evaporated and the residue was lyophylized. 61.1 mg (100% purity, 27% yield) of the title compound were obtained.

LC-MS (Method 7): $R_t$=2.14 min, MS (ESIpos): m/z=277 [M+H]⁺

¹H-NMR (600 MHz, DMSO-d6) δ [ppm]: 1.981 (3.05), 2.012 (6.24), 2.044 (2.73), 3.611 (16.00), 7.394 (2.57), 7.407 (2.83), 7.446 (1.39), 7.459 (1.60), 7.516 (0.73), 7.518 (0.67), 7.528 (1.61), 7.530 (1.43), 7.541 (1.01), 7.543 (0.86), 7.602 (2.87), 7.616 (2.48), 7.639 (0.91), 7.641 (0.91), 7.651 (1.52), 7.654 (1.45), 7.664 (0.70), 7.666 (0.63), 7.787 (1.44), 7.789 (1.41), 7.800 (1.33), 7.802 (1.25).

Intermediate 208

4'-(1,1-Difluoroethyl)[1,1'-Biphenyl]-2-Carboxylic Acid

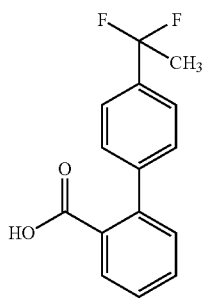

To a solution of methyl 4'-(1,1-difluoroethyl)[1,1'-biphenyl]-2-carboxylate (55.3 mg, 200 μmol) in THF (1.5 ml) and methanol (300 μl) was added aqueous lithium hydroxide (500 μl, 2.0 M, 1.0 mmol) and the mixture was stirred at 60° C. over night. The reaction was cooled to room temperature and was acidified with excess 2N aqueous hydrochloric acid. The mixture was evaporated and purification was done by preparative HPLC (column: Reprosil C18 10 μm, 250×30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated. 47.1 mg (97% purity, 90% yield) of the title compound were obtained.

LC-MS (Method 12): $R_t$=3.02 min; MS (ESIneg): m/z=261 [M−H]⁻

¹H-NMR (400 MHz, DMSO-d6) δ [ppm]: −0.008 (0.48), 0.008 (0.56), 1.964 (8.05), 2.011 (16.00), 2.058 (7.20), 7.387 (2.86), 7.390 (3.16), 7.406 (3.60), 7.409 (3.80), 7.424 (5.45), 7.445 (6.91), 7.473 (1.47), 7.476 (1.56), 7.492 (3.53), 7.495 (3.48), 7.511 (2.42), 7.514 (2.31), 7.580 (2.62), 7.584 (3.83), 7.589 (7.01), 7.599 (4.06), 7.603 (4.67), 7.610 (5.63), 7.618 (1.99), 7.621 (1.63), 7.763 (3.24), 7.766 (3.34), 7.782 (2.91), 7.785 (2.85), 12.797 (1.97).

Intermediate 209

Methyl 4'-(Difluoromethoxy)[1,1'-Biphenyl]-2-Carboxylate

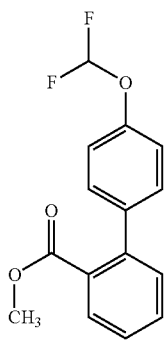 [SMILES: COC(=O)c1ccccc1-c1ccc(OC(F)F)cc1]

To a suspension of methyl 2-(4,4,5,5-tetramethyl-1,3,2-dioxaborolan-2-yl)benzoate (200 mg, 763 μmol) and 1-bromo-4-(difluoromethoxy)benzene (213 mg, 954 μmol) in 1,2-dimethoxyethane (3.4 ml) was added under argon a 2 M solution sodium carbonate in water (1.9 ml, 2.0 M, 3.8 mmol) and tetrakis(triphenylphosphine)palladium(0) [Pd(PPh₃)₄] (44.3 mg, 38.2 μmol). The mixture was stirred over night at 80° C. Water was added at room temperature and the reaction was extracted with ethyl acetate (three times). The combined organic layers were washed with brine, dried, filtered and evaporated. Purification was done by preparative HPLC (column: Reprosil C18 10 μm, 250×30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated and the residue was lyophilized. 122 mg (93% purity, 53% yield) of the title compound were obtained.

LC-MS (Method 12): $R_t$=3.39 min; MS (ESIpos): m/z=279 [M+H]⁺

¹H-NMR (600 MHz, DMSO-d6) δ [ppm]: 1.142 (0.63), 2.523 (0.74), 3.732 (0.62), 7.177 (4.49), 7.215 (11.45), 7.229 (13.82), 7.300 (8.90), 7.334 (16.00), 7.348 (12.22), 7.423 (10.05), 7.435 (6.67), 7.488 (3.31), 7.501 (6.98), 7.513 (4.21), 7.563 (0.46), 7.616 (3.69), 7.618 (3.59), 7.629 (6.23), 7.641 (3.16), 7.657 (0.46), 7.756 (6.12), 7.769 (5.53).

Intermediate 210

4'-(Difluoromethoxy)[1,1'-Biphenyl]-2-Carboxylic Acid

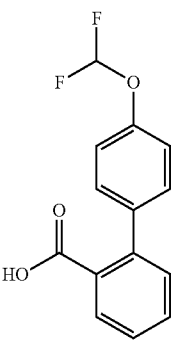 [SMILES: O=C(O)c1ccccc1-c1ccc(OC(F)F)cc1]

To a solution of methyl 4'-(difluoromethoxy)[1,1'-biphenyl]-2-carboxylate (120 mg, 431 μmol) in THF (1.5 ml) and methanol (300 μl) was added an aqueous solution of lithium hydroxide (1.1 ml, 2.0 M, 2.2 mmol) and the mixture was stirred at 60° C. overnight. The reaction was cooled to room temperature and was acidified with excess 2N aqueous hydrochloric acid and the mixture was extracted with ethyl acetate. The combined organic layers were dried, filtered and evaporated. Purification was done by flash chromatography (n-heptane→n-heptane:ethyl acetate (50:50)). Product containing samples were united, the solvents were evaporated. 90.0 mg (99% purity, 78% yield) of the title compound were obtained.

LC-MS (Method 8): $R_t$=0.94 min, MS (ESIneg): m/z=263 [M−H]⁻

¹H-NMR (500 MHz, DMSO-d6) δ [ppm]: −0.007 (0.41), 1.989 (0.54), 7.151 (3.91), 7.205 (8.62), 7.222 (10.43), 7.227 (1.24), 7.299 (7.92), 7.361 (1.89), 7.367 (16.00), 7.370 (7.15), 7.380 (4.43), 7.384 (14.37), 7.390 (1.36), 7.448 (3.97), 7.451 (2.37), 7.454 (2.18), 7.466 (4.73), 7.469 (4.40), 7.482 (3.06), 7.484 (2.74), 7.563 (2.88), 7.566 (2.99), 7.579 (4.47), 7.581 (4.43), 7.594 (1.99), 7.596 (1.87), 7.739 (4.37), 7.742 (4.33), 7.755 (3.98), 7.757 (3.72), 12.814 (2.80).

Intermediate 211

Methyl 4',5-Difluoro[1,1'-Biphenyl]-2-Carboxylate

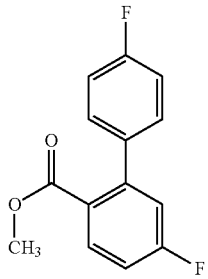 [SMILES: COC(=O)c1ccc(F)cc1-c1ccc(F)cc1]

To a suspension of methyl 4-fluoro-2-(4,4,5,5-tetramethyl-1,3,2-dioxaborolan-2-yl)benzoate (200 mg, 714 µmol) and 1-bromo-4-fluorobenzene (156 mg, 893 µmol) in 1,2-dimethoxyethane (3.1 ml) was added under argon a 2 M solution sodium carbonate in water (1.8 ml, 2.0 M, 3.6 mmol) and tetrakis(triphenylphosphine)palladium(0) [Pd(PPh$_3$)$_4$] (41.4 mg, 35.7 µmol). The mixture was stirred for 3.5 hours at 90° C. Water was added at room temperature and the reaction was extracted with ethyl acetate (three times). The combined organic layers were washed with brine dried, filtered and evaporated. Purification was done by flash chromatography (n-heptane:ethyl acetate (80:20)→ethyl acetate). Product containing samples were united, the solvents were evaporated and the residue was lyophylized. 102 mg (58% yield) of the title compound were obtained.

$^1$H NMR (400 MHz, DMSO-d$_6$) δ ppm 3.60 (s, 3H) 7.22-7.32 (m, 3H) 7.32-7.39 (m, 3H) 7.86 (dd, J=8.62, 5.93 Hz, 1H)

Intermediate 212

4',5-Difluoro[1,1'-Biphenyl]-2-Carboxylic Acid

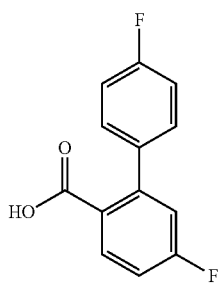

To a solution of methyl 4',5-difluoro[1,1'-biphenyl]-2-carboxylate (100 mg, 403 µmol) in THF (1.4 ml) and methanol (280 µl) an aqueous solution of lithium hydroxide (1.0 ml, 2.0 M, 2.0 mmol) was added and the mixture was stirred 60° C. for 3.5 hours. The reaction was cooled to room temperature and was acidified with excess 2N aqueous hydrochloric acid. The THF was removed on a rotary evaporator and the resulting precipitate was filtered off, washed with water and dried in vacuo. 76.0 mg (95% purity, 77% yield) of the title compound were obtained.

LC-MS (Method 7): R$_t$=1.70 min: MS (ESIneg): m/z=233 [M−H]$^-$ $^1$H-NMR (400 MHz, DMSO-d6) δ [ppm]: 1.235 (1.44), 7.212 (5.03), 7.219 (10.94), 7.241 (16.00), 7.263 (8.34), 7.270 (1.38), 7.278 (2.86), 7.285 (2.46), 7.299 (5.47), 7.306 (4.74), 7.321 (2.98), 7.327 (2.59), 7.363 (8.12), 7.368 (3.71), 7.377 (9.06), 7.385 (7.19), 7.393 (3.17), 7.398 (6.13), 7.549 (0.69), 7.557 (0.61), 7.566 (0.79), 7.574 (0.68), 7.598 (0.94), 7.615 (0.81), 7.627 (1.17), 7.645 (0.66), 7.815 (4.80), 7.830 (5.15), 7.837 (4.91), 7.852 (4.55), 12.871 (0.46).

Intermediate 213

Methyl 4'-Fluoro[1,1'-Biphenyl]-2-Carboxylate

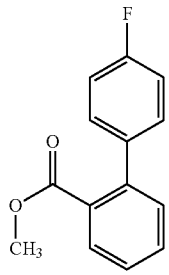

To a suspension of methyl 2-(4,4,5,5-tetramethyl-1,3,2-dioxaborolan-2-yl)benzoate (200 mg, 763 µmol) and 1-bromo-4-fluorobenzene (167 mg, 954 µmol) in 1,2-dimethoxyethane (3.4 ml) was added under argon a 2 M solution sodium carbonate in water (1.9 ml, 2.0 M, 3.8 mmol) and tetrakis(triphenylphosphine)palladium(0) [Pd(PPh$_3$)$_4$] (44.3 mg, 38.2 µmol). The mixture was stirred over night at 80° C. Water was added at room temperature and the reaction was extracted with ethyl acetate (three times). The combined organic layers were washed with brine, dried, filtered and evaporated. Purification was done by preparative HPLC (column: Reprosil C18 10 µm, 250×30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated and the residue was lyophylized. 80.0 mg (96% purity, 44% yield) of the title compound were obtained.

LC-MS (Method 7): R$_t$=2.00 min; MS (ESIpos): m/z=231 [M+H]$^+$ $^1$H-NMR (500 MHz, DMSO-d6) δ [ppm]: 3.600 (16.00), 7.232 (1.36), 7.236 (0.53), 7.245 (0.75), 7.249 (3.40), 7.254 (0.68), 7.263 (0.65), 7.267 (2.20), 7.310 (2.14), 7.315 (0.87), 7.321 (2.31), 7.328 (1.55), 7.334 (0.61), 7.339 (1.32), 7.420 (1.19), 7.422 (1.25), 7.435 (1.39), 7.437 (1.43), 7.484 (0.66), 7.486 (0.66), 7.499 (1.46), 7.501 (1.38), 7.514 (0.94), 7.516 (0.85), 7.611 (0.89), 7.613 (0.95), 7.626 (1.40), 7.629 (1.43), 7.641 (0.63), 7.644 (0.61), 7.751 (1.32), 7.753 (1.29), 7.767 (1.19), 7.769 (1.11).

Intermediate 214

4'-Fluoro[1,1'-Biphenyl]-2-Carboxylic Acid

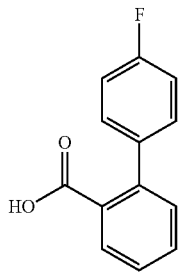 [SMILES: O=C(O)c1ccccc1-c1ccc(F)cc1]

To a solution of methyl 4'-fluoro[1,1'-biphenyl]-2-carboxylate (80.0 mg, 347 µmol) in THF (1.2 ml) and methanol (240 µl) was added aqueous lithium hydroxide (870 µl, 2.0 M, 1.7 mmol) and the mixture was stirred at 60° C. for 3.5 hours. An aqueous solution of lithium hydroxide (870 µl, 2.0 M, 1.7 mmol) was added and the mixture was stirred at 60° C. for 2 hours. The reaction was cooled to room temperature and was acidified with excess 2N aqueous hydrochloric acid. The THF was removed on a rotary evaporator and the resulting precipitate was filtered off, washed with water and dried in vacuo. 69.0 mg (99% purity, 91% yield) of the title compound were obtained.

LC-MS (Method 7): $R_t$=1.61 min, MS (ESIpos): m/z=217 [M+H]$^+$ $^1$H-NMR (600 MHz, DMSO-d6) δ [ppm]: 1.236 (0.41), 3.600 (0.78), 7.220 (7.61), 7.234 (16.00), 7.249 (9.30), 7.343 (10.00), 7.352 (12.11), 7.356 (10.48), 7.366 (14.14), 7.380 (9.31), 7.452 (4.05), 7.464 (8.71), 7.477 (5.23), 7.562 (5.14), 7.575 (8.21), 7.587 (3.62), 7.739 (8.56), 7.752 (7.79), 12.792 (5.90).

Intermediate 215

Methyl 6-Methyl-4'-(Trifluoromethyl)[1,1'-Biphenyl]-2-Carboxylate

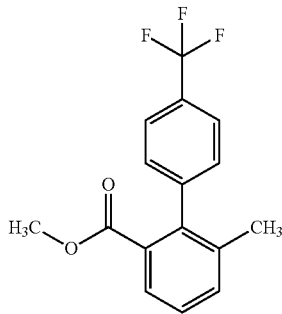

To a suspension of [4-(trifluoromethyl)phenyl]boronic acid (100 mg, 527 µmol) and methyl 2-bromo-3-methylbenzoate (110 µl, 660 µmol) in 1,2-dimethoxyethane (3.0 ml) was added under argon a 2 M solution sodiumcarbonat in water (1.3 ml, 2.0 M, 2.6 mmol) and tetrakis(triphenylphosphine)palladium(0) [Pd(PPh$_3$)$_4$] (30.5 mg, 26.3 µmol). The mixture was stirred over night at 90° C. Water (5 ml) was added at room temperature and the reaction was extracted with ethyl acetate (three times). The combined organic layers were washed with brine, dried, filtered and evaporated Purification was done by preparative HPLC (column: Reprosil C18 10 µm, 250×30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated and the residue was lyophylized. 92.0 mg (100% purity, 59% yield) of the title compound were obtained.

LC-MS (Method 7): $R_t$=2.35 min; MS (ESIpos): m/z=295 [M+H]$^+$ $^1$H-NMR (400 MHz, DMSO-d6) δ [ppm]: 2.035 (10.68), 3.311 (16.00), 7.365 (2.17), 7.385 (2.41), 7.427 (0.93), 7.446 (2.29), 7.465 (1.53), 7.544 (1.42), 7.562 (1.02), 7.682 (1.19), 7.700 (1.03), 7.757 (2.51), 7.777 (2.30).

Intermediate 216

6-Methyl-4'-(Trifluoromethyl)[1,1'-Biphenyl]-2-Carboxylic Acid

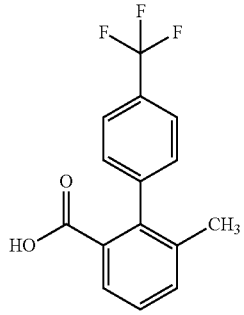 [SMILES: Cc1cccc(C(=O)O)c1-c1ccc(C(F)(F)F)cc1]

To a solution of methyl 6-methyl-4'-(trifluoromethyl)[1,1'-biphenyl]-2-carboxylate (90.0 mg, 306 µmol) in THF (2.0 ml) and methanol (400 µl) was added Lithiumhydroxide (760 µl, 2.0 M, 1.5 mmol) and the mixture was stirred at room temperature for over night. Lithiumhydroxide (760 µl, 2.0 M, 1.5 mmol) was added to the mixture and the reaction was stirred 60° C. over night. The reaction was cooled to room temperature and was acidified with excess 2N aqueous hydrochloric acid. The THF was removed on a rotary evaporator and the resulting precipitate was filtered off, washed with water and dried in vacuo. 132 mg (97% purity, 150% yield, contains salts) of the title compound were obtained.

LC-MS (Method 7): $R_t$=1.98 min; MS (ESIpos): m/z=281 [M+H]$^+$ $^1$H-NMR (600 MHz, DMSO-d6) δ [ppm]: 1.234 (0.99), 2.015 (16.00), 3.491 (0.48), 7.379 (5.58), 7.392 (6.54), 7.409 (3.71), 7.421 (2.36), 7.491 (3.22), 7.503 (2.65), 7.652 (2.98), 7.664 (2.79), 7.748 (5.68), 7.760 (5.62), 12.566 (2.37).

Intermediate 217

Methyl 4',6-Dimethyl[1,1'-Biphenyl]-2-Carboxylate

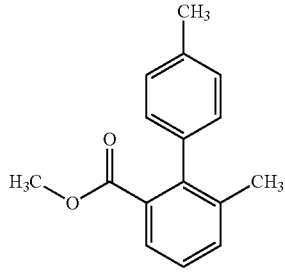

To a suspension of (4-methylphenyl)boronic acid (100 mg, 736 µmol) and methyl 2-bromo-3-methylbenzoate (150 µl, 920 µmol) in 1,2-dimethoxyethane (3.0 ml) was added under argon a2 M solution sodiumcarbonat in water (1.8 ml, 2.0 M, 3.7 mmol) and tetrakis(triphenylphosphine)palladium(0) [Pd(PPh$_3$)$_4$] (42.7 mg, 36.8 µmol). The mixture was stirred over night at 90° C. Water (5 ml) was added at room temperature and the reaction was extracted with ethyl acetate (three times). The combined organic layers were washed with brine, dried, filtered and evaporated Purification was done by preparative HPLC (column: Reprosil C18 10 µm, 250×30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated and the residue was lyophylized. 129 mg (100% purity, 73% yield) of the title compound were obtained.

LC-MS (Method 7): R$_t$=2.29 min; MS (ESIpos): m/z=241 [M+H]$^+$ $^1$H-NMR (400 MHz, DMSO-d6) δ [ppm]: 2.056 (16.00), 2.349 (14.64), 3.327 (5.89), 6.998 (4.23), 7.019 (5.30), 7.197 (4.12), 7.216 (3.44), 7.336 (1.37), 7.355 (3.39), 7.374 (2.30), 7.459 (2.09), 7.477 (1.50), 7.523 (1.92), 7.542 (1.60).

Intermediate 218

4',6-Dimethyl[1,1'-Biphenyl]-2-Carboxylic Acid

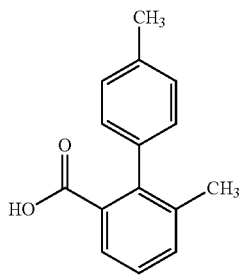 [SMILES: Cc1ccc(-c2c(C)cccc2C(=O)O)cc1]

To a solution of methyl 4',6-dimethyl[1,1'-biphenyl]-2-carboxylate (126 mg, 525 µmol) in THE (2.0 ml) and methanol (400 µl) was added Lithiumhydroxide (1.3 ml, 2.0 M, 2.6 mmol) and the mixture was stirred at room temperature for over night. Lithiumhydroxide (1.3 ml, 2.0 M, 2.6 mmol) was added to the mixture and the reaction was stirred over night at 60° C. The reaction was cooled to room temperature and was acidified with excess 2N aqueous hydrochloric acid. The THF was removed on a rotary evaporator and the resulting precipitate was filtered off, washed with water and dried in vacuo. 127 mg (98% purity, 106% yield) of the title compound were obtained.

LC-MS (Method 7): R$_t$=1.86 min, MS (ESIpos): m/z=227 [M+H]$^+$ $^1$H-NMR (400 MHz, DMSO-d6) δ [ppm]: 1.236 (0.47), 2.034 (16.00), 2.341 (15.60), 7.021 (4.49), 7.040 (5.64), 7.183 (5.37), 7.202 (4.58), 7.302 (1.30), 7.321 (3.03), 7.340 (2.19), 7.407 (2.98), 7.425 (2.13), 7.501 (2.60), 7.520 (2.22), 12.379 (3.58).

Intermediate 219

Tert-Butyl 4'-(2,2-Difluorocyclopropyl)-5-Methyl[1,1'-Biphenyl]-2-Carboxylate (Racemic Mixture)

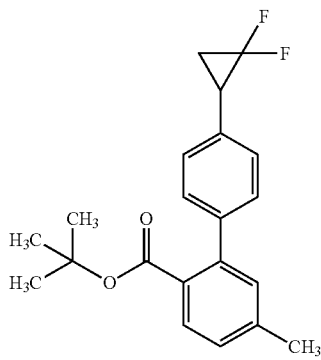 [SMILES: Cc1ccc(C(=O)OC(C)(C)C)c(-c2ccc(C3CC3(F)F)cc2)c1]

To a suspension of tert-butyl 4-methyl-2-(4,4,5,5-tetramethyl-1,3,2-dioxaborolan-2-yl)benzoate (197 mg, 618 µmol) and 1-bromo-4-(2,2-difluorocyclopropyl)benzene (180 mg, 772 µmol) in 1,2-dimethoxyethane (3.0 ml) was added under argon a 2 M solution sodium carbonate in water (1.5 ml, 2.0 M, 3.1 mmol) and tetrakis(triphenylphosphine)palladium(0) [Pd(PPh$_3$)$_4$] (35.8 mg, 30.9 µmol). The mixture was stirred over night at 90° C. Water (5 ml) was added at room temperature and the reaction was extracted with ethyl acetate (three times). The combined organic layers were washed with brine, dried, filtered and evaporated. Purification was done by flash chromatography (heptane:ethyl acetate gradient). Product containing samples were united, the solvents were evaporated and the residue was lyophylized. 175 mg (98% purity, 81% yield) of the title compound were obtained.

LC-MS (Method 7): R$_t$=2.59 min; MS (ESIpos): m/z=367 [M+Na]$^+$

Intermediate 220

4'-(2,2-Difluorocyclopropyl)-5-Methyl[1,1'-Biphenyl]-2-Carboxylicacid (Racemic Mixture)

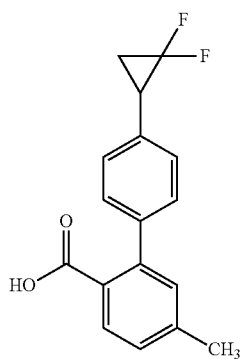 [SMILES: Cc1ccc(C(=O)O)c(-c2ccc(C3CC3(F)F)cc2)c1]

To a solution of tert-butyl 4'-(2,2-difluorocyclopropyl)-5-methyl[1,1'-biphenyl]-2-carboxylate (172 mg, 500 µmol) in trifluoroethanol (3.0 ml) was added zinc chloride (409 mg, 3.00 mmol) and the reaction was stirred at 50° C. for 1 hour. EDTA (877 mg, 3.00 mmol) was added and the mixture was stirred for a few minutes. Water+0.1% TFA (1 ml) was added. Purification was done by preparative HPLC (column:

Chromatorex C18 10 µm, 250×30 mm, eluent A=water+ 0.1% TFA, B=acetonitrile; gradient: 3 min 10% B; 21 min 95% B; 30 min 95% B; 32 min 10% B; flow: 50 ml/min). Product containing samples were united, the solvents were evaporated and the residue was lyophilized. 114 mg (100% purity, 79% yield) of the title compound were obtained.

LC-MS (Method 7): $R_t$=1.95 min; MS (ESIneg): m/z=287 [M−H]⁻

¹H-NMR (600 MHz, DMSO-d6) δ [ppm]: 1.930 (0.75), 1.936 (0.82), 1.943 (0.67), 1.951 (0.94), 1.958 (0.69), 1.966 (0.73), 1.972 (0.49), 1.976 (0.50), 1.988 (0.71), 1.997 (0.73), 2.009 (0.63), 2.018 (0.44), 2.375 (16.00), 3.004 (0.64), 3.018 (0.66), 3.026 (0.86), 3.040 (0.86), 3.046 (0.69), 3.060 (0.58), 3.274 (0.45), 7.174 (3.29), 7.247 (1.76), 7.248 (1.70), 7.260 (1.92), 7.264 (2.20), 7.268 (0.83), 7.274 (1.22), 7.278 (12.12), 7.283 (10.40), 7.293 (0.63), 7.297 (1.21), 7.643 (3.85), 7.656 (3.57).

Intermediate 221

Methyl 4'-(2,2-Difluorocyclopropyl)-4-Fluoro[1,1'-Biphenyl]-2-Carboxylate (Racemic Mixture)

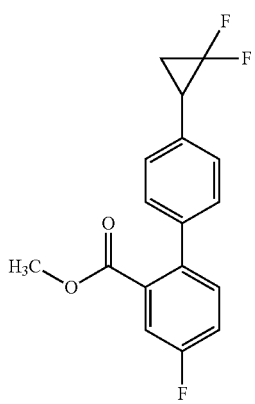 [SMILES: COC(=O)c1cc(F)ccc1-c1ccc(C2CC2(F)F)cc1]

To a suspension of [4-fluoro-2-(methoxycarbonyl)phenyl]boronic acid (122 mg, 618 µmol) and 1-bromo-4-(2,2-difluorocyclopropyl)benzene (180 mg, 772 µmol) in 1,2-dimethoxyethane (3.0 ml) was added under argon a 2 M solution sodium carbonate in water (1.5 ml, 2.0 M, 3.1 mmol) and tetrakis(triphenylphosphine)palladium(0) [Pd (PPh₃)₄] (35.8 mg, 30.9 µmol). The mixture was stirred over night at 90° C. Water (5 ml) was added at room temperature and the reaction was extracted with ethyl acetate (three times). The combined organic layers were washed with 1 N sodium hydroxide solution, dried, filtered and evaporated. Purification was done by flash chromatography (heptane:ethyl acetate gradient). Product containing samples were united, the solvents were evaporated and the residue was lyophilized. 36.1 mg (100% purity, 19% yield) of the title compound were obtained.

The aqueous phase was acidified (pH 1-2) with hydrochloric acid and extracted with dichloromethane. The combined organic layers were washed with brine, dried, filtered and evaporated. The crude material 83 mg (saponified product of this step) was purified together with the material described in the next step.

LC-MS (Method 7): $R_t$=2.22 min, MS (ESIpos): m/z=329 [M+Na]⁺

¹H-NMR (400 MHz, DMSO-d6) δ [ppm]: −0.008 (0.50), 0.008 (0.63), 1.951 (0.53), 1.963 (0.75), 1.972 (0.54), 1.982 (1.12), 1.995 (1.05), 2.004 (0.60), 2.010 (0.87), 2.016 (0.65), 2.024 (0.42), 3.038 (0.53), 3.043 (0.43), 3.063 (0.48), 3.072 (0.41), 3.610 (16.00), 7.239 (2.33), 7.244 (0.97), 7.255 (1.23), 7.260 (4.47), 7.311 (3.59), 7.331 (2.01), 7.474 (2.43), 7.478 (3.07), 7.491 (2.68), 7.495 (2.30), 7.553 (0.71), 7.557 (1.23), 7.561 (0.67), 7.576 (0.75), 7.580 (1.00), 7.584 (0.67).

Intermediate 222

4'-(2,2-Difluorocyclopropyl)-4-Fluoro[1,1'-Biphenyl]-2-Carboxylicacid (Racemic Mixture)

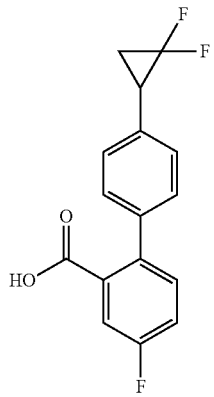 [SMILES: O=C(O)c1cc(F)ccc1-c1ccc(C2CC2(F)F)cc1]

To a solution of methyl 4'-(2,2-difluorocyclopropyl)-4-fluoro[1,1'-biphenyl]-2-carboxylate (33.6 mg, 110 µmol) in THF (4 ml) and methanol (200 µl) was added lithium hydroxide (270 µl, 2.0 M, 550 µmol) and the mixture was stirred at 60° C. over night. Lithium hydroxide (270 µl, 2.0 M, 550 µmol) was added 3 times and the mixture was stirred for additional 6.6 hours. The reaction was cooled to room temperature and acidified with excess 2N aqueous hydrochloric acid and evaporated. Purification was done (together with the saponified product from the previous step) by preparative HPLC (column: Chromatorex C18 10 µm, 250×30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated. 98.2 mg (97% purity) of the title compound were obtained.

LC-MS (Method 7): $R_t$=1.87 min; MS (ESIneg): m/z=291 [M−H]⁻

Intermediate 223

Methyl 4'-(2,2-Difluorocyclopropyl)-5-Fluoro[1,1'-Biphenyl]-2-Carboxylate (Racemic Mixture)

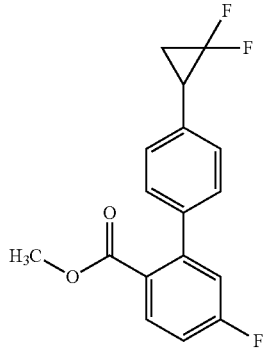

To a suspension of methyl 4-fluoro-2-(4,4,5,5-tetramethyl-1,3,2-dioxaborolan-2-yl)benzoate (173 mg, 618 μmol) and 1-bromo-4-(2,2-difluorocyclopropyl)benzene (180 mg, 772 μmol) in 1,2-dimethoxyethane (3.0 ml) was added under argon a 2 M solution sodium carbonate in water (1.5 ml, 2.0 M, 3.1 mmol) and tetrakis(triphenylphosphine)palladium(0) [Pd(PPh$_3$)$_4$] (35.8 mg, 30.9 μmol). The mixture was stirred over night at 90° C. Water (5 ml) was added at room temperature and the reaction was extracted with ethyl acetate (three times). The combined organic layers were washed with 1 N sodium hydroxide solution, dried, filtered and evaporated. Purification was done by flash chromatography (heptane:ethyl acetate gradient). Product containing samples were united, the solvents were evaporated and the residue was lyophylized. 72.9 mg (100% purity, 39% yield) of the title compound were obtained.

The aqueous phase was acidified (pH 1-2) with hydrochloric acid and extracted with dichloromethane. The combined organic layers were washed with brine, dried, filtered and evaporated. The crude material 47 mg (saponified product of this step) was purified together with the material described in the next step.

$^1$H-NMR (400 MHz, DMSO-d6) δ [ppm]: −0.008 (0.61), 0.008 (0.66), 1.962 (0.54), 1.974 (0.65), 1.984 (0.59), 1.990 (1.13), 1.995 (0.64), 2.000 (0.75), 2.006 (0.62), 2.016 (1.13), 2.030 (0.53), 3.046 (0.59), 3.052 (0.43), 3.073 (0.47), 3.082 (0.42), 3.589 (16.00), 7.273 (1.90), 7.278 (0.95), 7.282 (1.15), 7.289 (2.50), 7.294 (5.08), 7.307 (1.10), 7.313 (1.80), 7.323 (4.14), 7.332 (1.76), 7.339 (1.84), 7.344 (1.79), 7.353 (0.86), 7.360 (0.65), 7.814 (1.11), 7.829 (1.14), 7.836 (1.11), 7.850 (1.04).

Intermediate 224

4'-(2,2-Difluorocyclopropyl)-5-Fluoro[1,1'-Biphenyl]-2-Carboxylic Acid (Racemic Mixture)

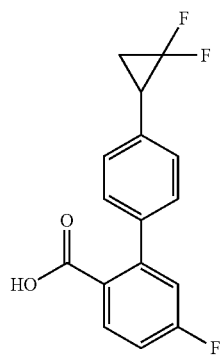

To a solution of methyl 4'-(2,2-difluorocyclopropyl)-5-fluoro[1,1'-biphenyl]-2-carboxylate (70.4 mg, 230 μmol) in THF (2.0 ml) and methanol (400 μl) was added lithium hydroxide (570 μl, 2.0 M, 1.1 mmol) and the mixture was stirred at 60° C. over night. Lithium hydroxide (570 μl, 2.0 M, 1.1 mmol) was added and the mixture was stirred for 5.5 hours at 60° C. The reaction was cooled to room temperature and was acidified with excess 2N aqueous hydrochloric acid and the mixture evaporated. Purification was done (together with the saponified product from the previous step) by preparative HPLC (column: Chromatorex C18 10 μm, 250× 30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated. 85.5 mg (100% purity) of the title compound were obtained.

LC-MS (Method 7): R$_t$=1.88 min; MS (ESIneg): m/z=291 [M−H]$^−$ $^1$H-NMR (400 MHz, DMSO-d6) δ [ppm]: 1.960 (0.44), 1.971 (0.43), 1.981 (0.71), 1.995 (0.60), 2.002 (0.44), 2.012 (0.65), 3.039 (0.49), 7.215 (0.80), 7.222 (1.06), 7.240 (0.82), 7.246 (1.03), 7.269 (0.55), 7.275 (0.50), 7.290 (1.08), 7.297 (1.04), 7.311 (1.02), 7.319 (16.00), 7.795 (0.92), 7.810 (0.96), 7.817 (0.95), 7.832 (0.88), 12.814 (1.32).

Intermediate 225

Methyl 4'-(2,2-Difluorocyclopropyl)-4,5-Difluoro[1,1'-Biphenyl]-2-Carboxylate (Racemic Mixture)

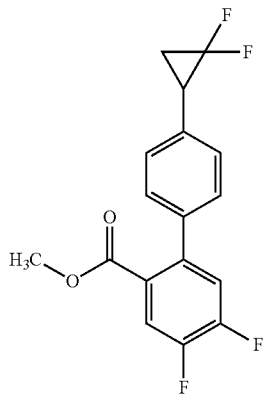

To a suspension of methyl 4,5-difluoro-2-(4,4,5,5-tetramethyl-1,3,2-dioxaborolan-2-yl)benzoate (184 mg, 618 μmol) and 1-bromo-4-(2,2-difluorocyclopropyl)benzene (180 mg, 772 μmol) in 1,2-dimethoxyethane (3.0 ml) was added under argon a 2 M solution sodium carbonate in water (1.5 ml, 2.0 M, 3.1 mmol) and tetrakis(triphenylphosphine)palladium(0) [Pd(PPh$_3$)$_4$] (35.8 mg, 30.9 μmol). The mixture was stirred over night at 90° C. Water (5 ml) was added at room temperature and the reaction was extracted with ethyl acetate (three times). The combined organic layers were washed with 1 N sodium hydroxide solution, dried, filtered and evaporated. Purification was done by flash chromatography (heptane:ethyl acetate gradient). Product containing samples were united, the solvents were evaporated and the residue was lyophylized. 50.1 mg (100% purity, 25% yield) of the title compound were obtained.

The aqueous phase was acidified (pH 1-2) with hydrochloric acid and extracted with dichloromethane. The combined organic layers were washed with brine, dried, filtered and evaporated. The crude material 71 mg (saponified product of this step) was purified together with the material described in the next step.

$^1$H-NMR (400 MHz, DMSO-d6) δ [ppm]: −0.008 (0.52), 0.008 (0.59), 1.962 (0.58), 1.970 (0.60), 1.974 (0.68), 1.984 (0.67), 1.990 (1.24), 1.995 (0.73), 1.999 (0.89), 2.006 (0.67), 2.016 (1.35), 2.029 (0.70), 2.045 (0.45), 3.018 (0.41), 3.044 (0.67), 3.051 (0.48), 3.071 (0.53), 3.080 (0.47), 3.604 (16.00), 7.262 (2.27), 7.283 (4.96), 7.321 (4.24), 7.341 (2.07), 7.548 (0.94), 7.568 (1.03), 7.577 (1.02), 7.596 (0.98), 7.824 (0.84), 7.844 (0.91), 7.851 (0.93), 7.871 (0.88).

Intermediate 226

4'-(2,2-Difluorocyclopropyl)-4,5-Difluoro[1,1'-Biphenyl]-2-Carboxylicacid (Racemic Mixture)

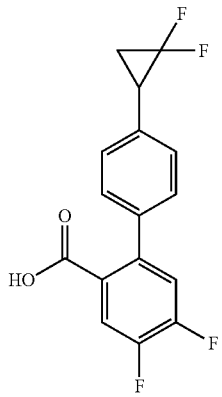

To a solution of methyl 4'-(2,2-difluorocyclopropyl)-4,5-difluoro[1,1'-biphenyl]-2-carboxylate (47.6 mg, 147 µmol) in THF (1.5 ml) and methanol (300 µl) was added lithium hydroxide (370 µl, 2.0 M, 730 µmol) and the mixture was stirred at 60° C. over night. Lithium hydroxide (370 µl, 2.0 M, 730 µmol) was added and the mixture was stirred for 5.5 hours at 60° C. The reaction was cooled to room temperature and was acidified with excess 2N aqueous hydrochloric acid and the mixture was evaporated. Purification was done (together with the saponified product from the previous step) by preparative HPLC (column: Chromatorex C18 10 µm, 250×30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated. 84.4 mg (98% purity) of the title compound were obtained.

LC-MS (Method 7): $R_t$=1.95 min; MS (ESIneg): m/z=309 [M–H]⁻

¹H-NMR (400 MHz, DMSO-d6) δ [ppm]: 0.008 (0.45), 1.091 (0.56), 1.950 (0.49), 1.961 (0.57), 1.965 (0.52), 1.971 (0.52), 1.982 (1.06), 1.994 (0.96), 2.003 (0.56), 2.011 (0.81), 2.014 (0.70), 3.037 (0.57), 3.042 (0.48), 3.063 (0.50), 3.071 (0.46), 7.312 (16.00), 7.478 (0.80), 7.498 (0.90), 7.507 (0.89), 7.526 (0.86), 7.776 (0.76), 7.796 (0.85), 7.803 (0.86), 7.823 (0.81), 13.110 (1.15).

Intermediate 227

Methyl 5,6-Dimethyl-4'-(Trifluoromethyl)[1,1'-Biphenyl]-2-Carboxylate

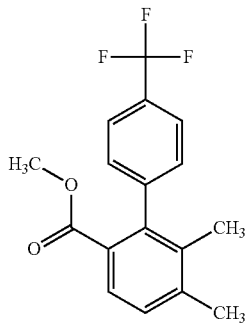 [SMILES: COC(=O)c1ccc(C)c(C)c1-c1ccc(C(F)(F)F)cc1]

To a suspension of [4-(trifluoromethyl)phenyl]boronic acid (300 mg, 1.58 mmol) and methyl 2-bromo-3,4-dimethylbenzoate (480 mg, 1.97 mmol) in DMF (7.7 ml) was added under argon a 2 M solution sodiumcarbonat in water (3.9 ml, 2.0 M, 7.9 mmol) and tetrakis(triphenylphosphine)palladium(0) [Pd(PPh₃)₄] (91.6 mg, 79.0 µmol). The mixture was stirred over night at 90° C. Ethylacetate was added at room temperature and the mixture was washed with water, 1 M Sodiumhydroxid solution and brine. The organic layer were dried, filtered and evaporated Purification was done by flash chromatography (n-hexane: ethyl acetate gradient). Product containing samples were united, the solvents were evaporated. 338 mg (81% purity, 56% yield) of the title compound were obtained.

¹H-NMR (600 MHz, DMSO-d6) δ [ppm]: 1.906 (9.66), 2.279 (0.47), 2.287 (0.48), 2.347 (9.43), 2.358 (5.55), 2.370 (5.72), 3.268 (0.40), 3.471 (16.00), 3.822 (0.99), 3.829 (9.56), 7.262 (0.69), 7.275 (0.91), 7.324 (2.12), 7.337 (2.25), 7.345 (1.45), 7.358 (1.57), 7.364 (1.03), 7.377 (0.76), 7.614 (1.71), 7.627 (1.54), 7.748 (2.33), 7.762 (2.19).

Intermediate 228

5,6-Dimethyl-4'-(Trifluoromethyl)[1,1'-Biphenyl]-2-Carboxylic Acid

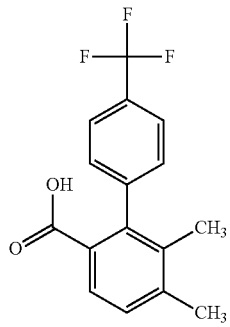 [SMILES: Cc1ccc(C(=O)O)c(-c2ccc(C(F)(F)F)cc2)c1C]

To a solution of methyl 5,6-dimethyl-4'-(trifluoromethyl)[1,1'-biphenyl]-2-carboxylate (218 mg, 81% purity, 573 µmol) in THF (5.2 ml) and [X³] was added Lithiumhydroxide (1.4 ml, 2.0 M, 2.9 mmol) and the mixture was stirred at room temperature over night. Lithiumhydroxide (1.4 ml, 2.0 M, 2.9 mmol) was added and the mixture was stirred at 60° C. over night. The mixture was diluted with water and was acidified with excess 2N aqueous hydrochloric acid. The mixture was extracted with ethyl acetate and the combined organic layers were washed with brine, dried, filtered and evaporated. The crude product was suspended in water and filtered. The residue was dired to give 171 mg (90% purity, 92% yield) of the title compound without further purification.

LC-MS (Method 7): $R_t$=2.15 min, MS (ESIneg): m/z=293 [M–H]⁻

¹H-NMR (600 MHz, DMSO-d6) δ [ppm]: 1.171 (1.25), 1.888 (16.00), 1.905 (1.58), 2.332 (15.44), 2.346 (1.77), 3.470 (2.13), 7.308 (2.46), 7.321 (2.91), 7.334 (4.04), 7.347 (4.11), 7.584 (2.93), 7.597 (2.68), 7.734 (4.16), 7.748 (4.30), 7.761 (0.43), 12.365 (0.57).

Intermediate 229

Ethyl 5-Isopropyl-1,3-Oxazole-4-Carboxylate

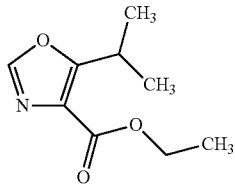

A solution of 2.47 mL (26.67 mmol) of 2-methylpropanoic acid and 5.19 g (32.00 mmol) of 1,1'-carbonyldiimidazole in 30 mL of tetrahydrofuran was stirred for 3 hours at room temperature. After that time, a solution of 3.21 mL (29.34 mmol) of ethyl isocyanoacetate in 35 mL of tetrahydrofuran and a solution of 26.67 mL (26.67 mmol) of 1 M lithium bis(trimethylsilyl)amide in tetrahydrofuran were added dropwise at 0° C. When the addition was complete the resulting mixture was stirred at room temperature for 16 hours. The reaction was concentrated in vacuo and extracted with ethyl acetate, the combined organic layers were filtered over magnesium sulfate and concentrated. The resulting residue was purified by flash chromatography on silica gel eluting with heptane/dichloromethane mixtures to give 2.26 g (46%) of the product as a brown oil.

$^1$H-NMR (300 MHz, DMSO-d$_6$): δ [ppm]=1.23 (d, 6H), 3.62-3.75 (m, 1H), 4.26 (q, 2H), 8.34 (s, 1H).

LC-MS (Method 3): R$_t$=0.708 min. MS (Mass method 1): m/z=184 (M+H)$^+$

Intermediate 230

Tert-Butyl (3-Methyl-2-Oxobutyl)Carbamate

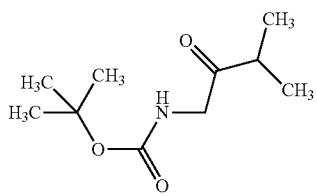

2.26 g (12.39 mmol) of ethyl 5-isopropyl-1,3-oxazole-4-carboxylate was suspended in 40 mL of 6N hydrochloric acid (aq.) and the mixture was refluxed for 12 hours. Concentration of the reaction under reduced pressure gave 1.69 g (99%) of the intermediate amino ketone hydrochloride as a brown oil. A solution of 1.69 g (12.28 mmol) of the latter compound and 3.10 mL (13.51 mmol) of di-tert-butyl dicarbonate were dissolved in 30 mL of dichloromethane and 4.28 mL (30.70 mmol) of triethylamine was added, allowing the mixture to stir at room temperature for 12 hours. The crude was diluted with ethyl acetate, washed with water, dried over magnesium sulfate, filtered and concentrated under vacuum. The resulting residue was purified by flash chromatography on silica gel eluting with heptane/ethyl acetate mixtures to provide 1.96 g (79%) of the product as an oil.

$^1$H-NMR (300 MHz, DMSO-d$_6$): δ [ppm]=0.99 (d, 6H), 1.37 (s, 9H), 2.59-2.73 (m, 1H), 3.82 (d, 2H), 6.96 (t, 1H).

LC-MS (Method 3): R$_t$=0.739 min. MS (Mass method 1): m/z=224 (M+Na)+

Intermediate 231

Tert-Butyl [(Rac-4-Isopropyl-2,5-Dioxoimidazolidin-4-Yl)Methyl]Carbamate

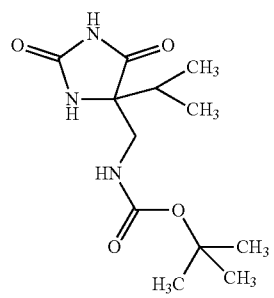 [SMILES: CC(C)C1(CNC(=O)OC(C)(C)C)NC(=O)NC1=O]

A solution of 1.93 g (9.59 mmol) of tert-butyl (3-methyl-2-oxobutyl)carbamate in 15 mL of ethanol was added to a solution of 1.25 g (19.18 mmol) of potassium cyanide and 9.21 g (95.89 mmol) of ammonium carbonate in 15 mL of water into a pressure flask, the container was sealed and the mixture was stirred at 60° C. for 24 hours. After that time, the solvent was partially removed and the resulting precipitate was filtered off to give 1.74 g (67%) of the product as a withe solid.

The compound was used as such in the next step.

$^1$H-NMR (300 MHz, DMSO-d$_6$): δ [ppm]=0.79 (d, 3H), 0.87 (d, 3H), 1.36 (s, 9H), 1.82-1.95 (m, 1H), 3.12-3.30 (m, 2H), 6.70 (bp, 1H), 7.38 (s, 1H), 10.53 (s, 1H).

LC-MS (Method 3): R$_t$=0.489 min. MS (Mass method 1): m/z=216 (M−t-Bu+H)$^+$

Intermediate 232

Ent-Tert-Butyl [(4-Isopropyl-2,5-Dioxoimidazolidin-4-Yl)Methyl]Carbamate

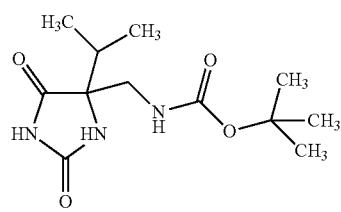 [SMILES: CC(C)C1(CNC(=O)OC(C)(C)C)NC(=O)NC1=O]

The reaction was performed in 2 batches.
A) To a solution of tert-Butyl (3-methyl-2-oxobutyl) carbamate (4.63 g, 23.0 mmol) in methanol (30 ml) was added potassium cyanide (5.99 g, 92.0 mmol) and ammonium carbonate (8.84 g, 92.0 mmol) at RT. The reaction mixture was heated up to 80° C. overnight into a sealed pressure flask. After filtration at RT, the filtrate was concentrated in vacuo (Batch 1)
B) To a solution of tert-Butyl (3-methyl-2-oxobutyl)carbamate (1.52 g, 7.55 mmol) in methanol (10 ml) was added potassium cyanide (1.97 g, 30.21 mmol) and ammonium carbonate (2.90 g, 30.21 mmol) at RT. The reaction mixture was heated up to 80° C. overnight into a sealed pressure flask. After filtration at RT, the filtrate was concentrated in vacuo (Batch 2)

The combined crude product (batch1+2) was purified by preparative chiral SFC [sample preparation: 13.36 g dissolved in 250 ml MeOH; column: Chiralpak AD SFC 20 µm 360×50 mm; eluent: 70% carbon dioxide/30% methanol; injection volume: 5 ml; flow rate: 400 ml/min; temperature: 35° C.; UV detection: 210 nm] afforded 3.03 g (100% purity) of the desired product.

Analytical chiral SFC: Analytical chiral SFC: $R_f$=2.27 min, e.e.=>99% [column: Chiralpak AD-3; eluent: carbon dioxide/methanol (5%→50% MeOH); flow rate: 3 ml/min; UV detection: 210 nm]

LC-MS (Method 7): $R_t$=1.10 min; MS (ESIneg): m/z=270 [M−H]⁻

¹H NMR (600 MHz, DMSO-d₆) δ ppm 10.52 (bs, 1H), 7.57 (s, 1H), 6.66 (brs, 1H), 3.13-3.32 (m, 2H), 1.82-1.95 (m, 1H), 1.36 (s, 9H), 0.73-0.91 (m, 6H)

Intermediate 233

Rac-5-(Aminomethyl)-5-Isopropylimidazolidine-2, 4-Dione Hydrochloride

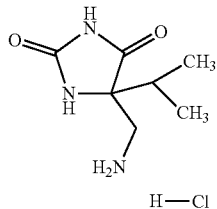

1.74 g (6.41 mmol) of tert-butyl [(rac-4-isopropyl-2,5-dioxoimidazolidin-4-yl)methyl] carbamate was dissolved in 20 mL of dichloromethane and 8.02 mL (32.06 mmol) of 4M hydrochloric acid in dioxane were added and the resulting suspension was stirred at room temperature for 12 hours. After that time, the solvent was in vacuo to give 1.10 g (83%) of the product a solid. The compound was used as such in the next step.

LC-MS (Method 3): $R_t$=0.125 min. MS (Mass method 1): m/z=172 (M+H)⁺

Intermediate 234

Ent-5-(Aminomethyl)-5-Isopropylimidazolidine-2,4-Dione Hydrochloride

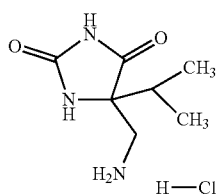

To a solution of ent-tert-butyl [(4-isopropyl-2,5-dioxoimidazolidin-4-yl)methyl]carbamate (3.03 g, 11.2 mmol) in dichloromethane (60 ml) were added 14 ml of 4M hydrochloric acid (56 mmol) in dioxane. The reaction mixture was stirred overnight at room temperature. The precipitate was filtered off, washed with dichloromethane, and then dissolved in water. After lyophilisation, 2.94 g of the title compound was obtained and used without further purification.

LC-MS (Method 9): $R_t$=0.28 min; MS (ESIpos): m/z=172 [M−HCl+H]⁺

¹H-NMR (600 MHz, DMSO-d6) δ [ppm]: 0.844 (4.80), 0.855 (4.96), 0.895 (4.80), 0.907 (4.97), 1.998 (0.72), 2.009 (0.96), 2.020 (0.71), 3.026 (0.61), 3.092 (0.61), 3.114 (0.40), 3.568 (16.00), 8.046 (1.80), 8.279 (1.55), 10.945 (1.34).

Intermediate 235

2-Bromo-1-Cyclobutylethan-1-One

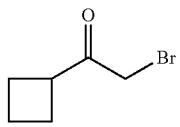

1.31 mL (25.47 mmol) of bromine were added drop wise to a solution of 2.50 g (25.47 mmol) of cyclobutyl methyl ketone in 25 mL of methanol at 0° C. and the solution was then stirred for 1 hour under the same conditions. The solvent was removed under vacuum and the mixture was partitioned between ethyl acetate and water. The organic layer was isolated, dried over magnesium sulfate, filtered and concentrated to afford 3.80 g (84%) of the product as a dark oil.

The compound was used as such in the next step.

¹H-NMR (300 MHz, DMSO-d₆): δ [ppm] 1.62-1.81 (m, 1H), 1.84-2.02 (m, 1H), 2.05-2.20 (m, 4H), 3.42-3.58 (m, 1H), 4.51 (s, 2H).

LC-MS (Method 1): $R_t$=2.665 min. MS (Mass method 1): m/z=no ionisation.

Intermediate 236

2-Azido-1-Cyclobutylethan-1-One

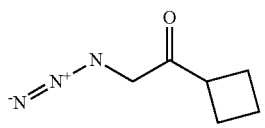

0.75 g (4.24 mmol) of 2-bromo-1-cyclobutylethan-1-one were added to a suspension of 0.36 g (5.51 mmol) of sodium azide in 20 mL of acetone and the mixture was stirred at room temperature for 16 hours. The resulting precipitate was filtered and the filtrate concentrated to give 0.43 g (73%) of the product as a pale orange oil. The compound was used as such in the next step.

¹H-NMR (300 MHz, DMSO-d₆): δ [ppm]=01.68-1.83 (m, 1H), 1.84-2.01 (m, 1H), 2.02-2.22 (m, 4H), 3.22-3.32 (m, 1H), 4.17 (, 1H).

LC-MS (Method 3): $R_t$=0.570 min. MS (Mass method 1): m/z=no ionisation.

Intermediate 237

Rac-5-(Azidomethyl)-5-Cyclobutylimidazolidine-2, 4-Dione

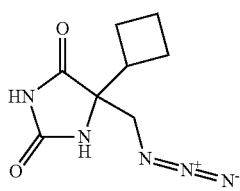 [SMILES: [N-]=[N+]=NCC1(C2CCC2)NC(=O)NC1=O]

A solution of 0.43 g (3.10 mmol) of 2-azido-1-cyclobutylethan-1-one in 5 mL of ethanol was added to a solution of 0.41 g (6.21 mmol) of potassium cyanide and 2.98 g (31.00 mmol) of ammonium carbonate in 5 mL water into a pressure flask. The container was sealed and the mixture was stirred at 60° C. for 12 hours. The ethanolic fraction was removed under reduced pressure and the mixture was extracted with ethyl acetate. The combined organic extracts were dried over magnesium sulfate, filtered and concentrated and the resulting precipitate was filtered off, washed with dichloromethane and dried in vacuo to give 0.23 g (35%) of the product as an orange solid.

$^1$H-NMR (300 MHz, DMSO-$d_6$): δ [ppm]=1.58-1.95 (m, 6H), 2.52-2.65 (m, 1H), 3.39 (s, 2H), 8.26 (s, 1H), 10.76 (bp, 1H).

Intermediate 238

Rac-5-(Aminomethyl)-5-Cyclobutylimidazolidine-2,4-Dione

230 mg (1.10 mmol) of rac-5-(azidomethyl)-5-cyclobutylimidazolidine-2,4-dione were dissolved in 15 mL of methanol in a round-bottom flask with a stirrer then the system was purged with nitrogen. 23 mg (0.22 mmol) of palladium on carbon (Degussa type, 10% loading, wet basis) was added the mixture was stirred at room temperature under hydrogen atmosphere for 12 hours. The black suspension was filtered through a pad of celite and the filtrates were concentrated to afford a pale-orange solid, which was washed with dichloromethane/methanol (9:1) give 180 mg (90%) of the product as white crystals.

$^1$H-NMR (300 MHz, DMSO-$d_6$): δ [ppm]=1.59-1.91 (m, 6H), 2.53-2.59 (m, 1H), 2.64 (d, 2H), 7.82 (s, 1H), 10.51 (bp, 1H).

LC-MS (Method 3): $R_t$=0.119 min. MS (Mass method 1): m/z=184 (M+H)$^+$

Intermediate 239

Rac-Tert-Butyl [(4-Cyclobutyl-2,5-Dioxoimidazolidin-4-Yl)Methyl]Carbamate

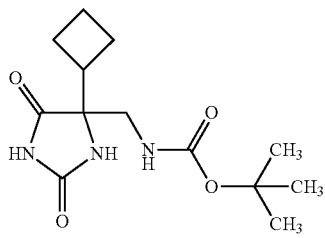

rac-5-(aminomethyl)-5-cyclobutylimidazolidine-2,4-dione-hydrogen chloride (1.00 g, 4.55 mmol) was dissolved in 10 ml of THF and cooled at 0° C. At this temperature triethylamine (1.9 ml, 14 mmol), 4-(dimethylamino)pyridine (83.4 mg, 683 μmol) and di-tert-butyl dicarbonate (1.04 g, 4.78 mmol) were added and the mixture was stirred over night at room temperature. The reaction was then diluted in ethyl acetate and washed twice with water and once with brine. The organic layer was dried over sodium sulfate, filtered and evaporated. The residue was put on Isolute® and purified by chromatography on silica gel (25 g Ultra Snap Cartridge Biotage®; Biotage-Isolera-One®; DCM/MeOH-gradient: 2% MeOH-20% MeOH; flow: 75 ml/min). Samples containing the desired product were united, the solvents were evaporated and the residue was dried in vacuum. 247 mg (100% purity, 19% yield) of the title compound were obtained.

LC-MS (Method 9): $R_t$=0.91 min; MS (ESIneg): m/z=282 [M–H]$^−$

Intermediate 240

Ent-Tert-Butyl [(4-Cyclobutyl-2,5-Dioxoimidazolidin-4-Yl)Methyl]Carbamate

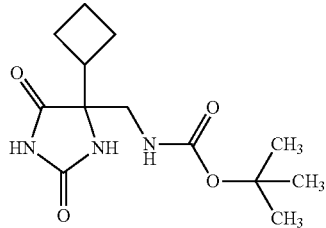 [SMILES: CC(C)(C)OC(=O)NCC1(C2CCC2)NC(=O)NC1=O]

Enantiomeric separation of rac-tert-butyl [(4-cyclobutyl-2,5-dioxoimidazolidin-4 yl)methyl]carbamate (245 mg, 865 μmol) using the following method Column: Maisch Diacel AD-H 5 μm 250*25 mm
Eluent A: 80% $CO_2$, eluent B: 20% methanol
Flow: 80 ml/min
UV-detection: 210 nm
Temperature: 40° C.

afforded 92.9 mg (100% purity, 38% yield) of the desired product.

Chiral-HPLC (Method Info: AD-15 MeOH, 3.0 ml/min, 210 nm, 10 min, 5 μl): $R_t$=1.87 min; 98% ee LC-MS (Method 7): $R_t$=1.25 min; MS (ESIneg): m/z=282 [M–H]$^−$ $^1$H-NMR (400 MHz, DMSO-d6) δ [ppm]: −0.008 (0.60), 0.008 (0.54), 1.364 (16.00), 1.867 (0.41), 3.085 (0.49), 7.724 (0.80), 10.536 (0.51).

Intermediate 241

Ent-5-(Aminomethyl)-5-Cyclobutylimidazolidine-2,4-Dione Hydrochloride

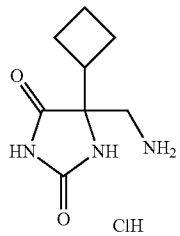 [SMILES: NCC1(C2CCC2)NC(=O)NC1=O ; Cl]

ent-tert-butyl [(4-cyclobutyl-2,5-dioxoimidazolidin-4-yl)methyl]carbamate (92.0 mg, 325 µmol) was dissolved in 1.5 ml of dichloromethane. 4 M hydrochloric acid in 1,4-dioxane (410 µl, 4.0 M, 1.6 mmol) was added and the mixture was stirred over night at room temperature. The solvent was removed on a rotary evaporator and the residue was dried in vacuo. 73.0 mg (100% purity, 102% yield) of the title compound were obtained.

LC-MS (Method 9): $R_t$=0.36 min; MS (ESIpos): m/z=184 [M−HCl+H]$^+$

Intermediate 242

Tert-Butyl [2-(1-Methyl-1H-Imidazol-2-Yl)-2-Oxo-ethyl]Carbamate

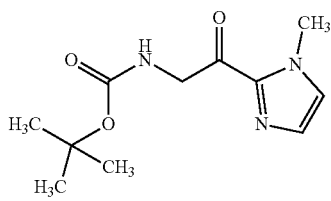 [SMILES: Cn1ccnc1C(=O)CNC(=O)OC(C)(C)C]

A solution of 2.70 mL (6.70 mmol) of 2.5M n-butyllithium in hexanes was added to a solution of 0.49 mL (6.10 mmol) of 1-methyl-1H-imidazole in 10 mL of anhydrous tetrahydrofuran under nitrogen atmosphere at 0° C. over 5 min and the resulting yellow solution was stirred under these conditions for 10 min. After that, the lithiated imidazole solution was transferred to a solution of 1.46 g (6.70 mmol) of tert-butyl {2-[methoxy(methyl)amino]-2-oxoethyl} carbamate at −78° C. over 15 min and the corresponding solution was further stirred for 1 hour under the same conditions. After that time, the solution was taken out of the cooling bath and it was stirred for 15 min while warming up to room temperature. The mixture was quenched with 5 mL of a 1 M solution of hydrochloric acid (aq.), stirred for 5 min, and 5 mL of brine and 5 mL of saturated hydrogencarbonate (aq.) were added. The resulting mixture was transferred to a separatory funnel and extracted with ethyl acetate. The organic layer was dried over magnesium sulfate, filtered and evaporated to dryness to give 0.70 g (48%) of the product as a pale orange oil. The compound was pure enough to be used as such without further purification.

$^1$H-NMR (300 MHz, DMSO-d$_6$): δ [ppm]=1.39 (s, 9H), 3.91 (s, 3H), 4.40 (d, 2H), 6.99 (t, 1H), 7.11 (s, 1H), 7.52 (s, 1H).

LC-MS (Method 3): $R_t$=0.546 min. MS (Mass method 1): m/z=240 (M+H)$^+$

Intermediate 243

Rac-Tert-Butyl {[4-(1-Methyl-1H-Imidazol-2-Yl)-2,5-Dioxoimidazolidin-4-Yl]Methyl}Carbamate

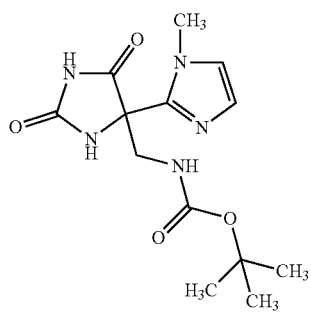 [SMILES: Cn1ccnc1C1(CNC(=O)OC(C)(C)C)NC(=O)NC1=O]

To a stirring solution of 4.22 g (43.90 mmol) of ammonium carbonate and 0.63 g (11.70 mmol) of ammonium chloride in 10 mL of water was added 0.70 g (2.93 mmol) of tert-butyl [2-(1-methyl-1H-imidazol-2-yl)-2-oxoethyl] carbamate in 10 mL of ethanol. After 15 min, 0.86 g (13.20 mmol) of potassium cyanide were added and the mixture was heated up to 60° C. for 16 hours into a sealed pressure flask. The yellow solution was concentrated until only a small fraction of water remained (a white precipitate appeared). Then, more water was added and the suspension was allowed to stand at 0° C. for 2 hour. After that time, the resulting solid was filtered off and washed with cold water and diethyl ether to give 0.90 g (98%) of the product as an off-white powder. The compound was used as such in the next step.

LC-MS (Method 3): $R_t$=0.253 min. MS (Mass method 1): m/z=310 (M+H)$^+$

Intermediate 244

Rac-5-(Aminomethyl)-5-(1-Methyl-1H-Imidazol-2-Yl)Imidazolidine-2,4-Dione Hydrochloride

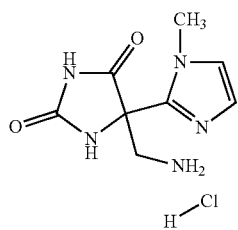

3.60 mL (15.00 mmol) of 4N hydrochloric acid in dioxane were added to a solution of 0.90 g (2.91 mmol) of rac-tert-Butyl {[4-(1-methyl-1H-imidazol-2-yl)-2,5-dioxoimidazolidin-4 yl]methyl}carbamate in 20 mL of dichloromethane and the mixture was allowed to stir at room temperature for 16 hours. The resulting precipitate was collected by filtration and washed with dichloromethane, ethyl acetate and diethyl ether to give 0.71 g (99%) of the product as a white solid. The compound was used as such in the next step.

LC-MS (Method 3): $R_t$=0.089 min. MS (Mass method 1): m/z=157 (M+H)$^+$

Intermediate 245

Ent-Tert-Butyl {[4-(1-Methyl-1H-Imidazol-2-Yl)-2,5-Dioxoimidazolidin-4-Yl]Methyl}Carbamate

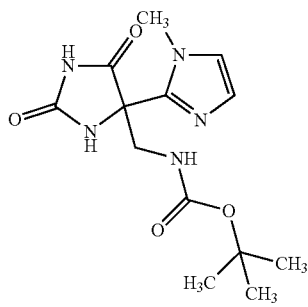 [SMILES: Cn1ccnc1C1(CNC(=O)OC(C)(C)C)NC(=O)NC1=O]

To a solution of tert-butyl [2-(1-methyl-1H-imidazol-2-yl)-2-oxoethyl]carbamate (4.96 g, 20.7 mmol, Example 3d in J: Med. Chem. 2014, 57, 10476-10485) in a mixture of Ethanol (30 ml) and water (12 ml) was added potassium cyanide (5.40 g, 82.9 mmol) and ammonium carbonate (7.97 g, 82.9 mmol) at RT. The reaction mixture was heated up to 80° C. for 2 days into a sealed pressure flask. The resulting mixture was diluted with water, partially concentrated in vacuo and filtered. The resulting filtrate was concentrated in vacuo and 10.78 g of the crude product were isolated. 9.3 g of this crude product were suspended in ethanol and the residue was filtered off and washed 3 times with ethanol. The combined filtrate was concentrated in vacuo and the resulting product was purified by preparative chiral SFC (sample preparation: 7.3 g dissolved in a mixture of methanol and acetonitrile; column: ChirapakAD-H (SFC) 5 µm, 250×30 mm; eluent: carbon dioxide/methanol 78:22; flow rate: 125 ml/min; temperature: 40° C.; UV detection: 210 nm). 2 g (6.47 mmol) of the desired product was obtained Analytical chiral SFC: $R_t$=1.70 min, e.e. =99%[column: AD 3 µm, 100×4.6 mm; eluent: carbon dioxide/methanol 80:20; flow rate: 3 ml/min; temperature: 40° C.; UV detection: 210 nm]

$^1$H NMR (600 MHz, DMSO-d$_6$) δ ppm 11.09 (bs, 1H), 8.16 (s, 1H), 7.20 (s, 1H), 6.67-6.95 (m, 2H), 3.73-3.91 (m, 2H), 3.49 (s, 3H), 1.37 (s, 9H)

The title compound can also be synthesized via the procedure described in J: Med. Chem. 2014, 57, 10476-10485

Intermediate 246

Ent-5-(Aminomethyl)-5-(1-Methyl-1H-Imidazol-2-Yl)Imidazolidine-2,4-Dione Hydrochloride

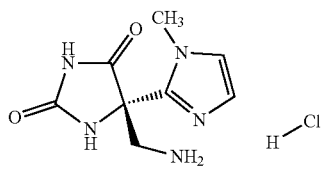

To a solution of ent-tert-butyl {[4-(1-methyl-1H-imidazol-2-yl)-2,5-dioxoimidazolidin-4 yl]methyl}carbamate (2.00 g, 6.46 mmol) in methanol (46 ml) were added 16 ml (65 mmol) of 4M hydrochloric acid in dioxane at 0° C. The resulting suspension was stirred overnight at room temperature. After filtration, the filtrate was concentrated in vacuo (1.23 g of the title compound) and the remaining residue was washed twice with methanol and dried under vacuum (0.41 g of of the title compound). Both fractions were used in the next step without further purification.

LC-MS (Method 9): $R_t$=0.23 min; MS (ESIpos): m/z=210 [M−HCl+H]$^+$ $^1$H-NMR (600 MHz, DMSO-d6) δ [ppm]: 2.389 (0.48), 2.428 (0.49), 3.061 (1.66), 3.166 (1.50), 3.296 (0.55), 3.388 (1.15), 3.494 (0.46), 3.510 (0.45), 3.666 (0.48), 3.677 (0.51), 3.702 (0.83), 3.738 (6.54), 3.782 (16.00), 3.846 (2.02), 3.895 (1.13), 3.910 (1.64), 3.924 (0.90), 3.929 (0.64), 3.988 (0.48), 4.021 (0.52), 4.050 (0.72), 4.080 (0.42), 4.119 (0.80), 4.129 (0.89), 4.160 (0.45), 4.259 (0.45), 4.697 (0.54), 7.250 (1.55), 7.322 (2.88), 7.335 (2.41), 7.419 (1.52), 7.545 (5.13), 7.729 (0.53), 7.776 (0.43), 8.699 (4.41), 9.125 (3.30), 11.735 (5.00).

Intermediate 247

Tert-Butyl [2-(1-Methyl-1H-Pyrazol-5-Yl)-2-Oxo-ethyl]Carbamate

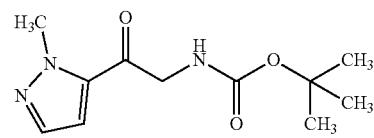 [SMILES: Cn1nccc1C(=O)CNC(=O)OC(C)(C)C]

To a solution of 2-amino-1-(2-methylpyrazol-3-yl)ethanone hydrochloride (3.00 g, 17.1 mmol) in dichloromethane (77 ml) was added di-tert-butyl dicarbonate (4.10 g, 18.8 mmol) and triethylamine (7.1 ml, 51 mmol). After 2 h of stirring at RT, the reaction mixture was diluted with dichloromethane and washed with water. The organic phase was dried, concentrated in vacuo and 4.40 g of the title compound was used without further purification.

LC-MS (Method 7): $R_t$=1.47 min; MS (ESIpos): m/z=240 [M+H]$^+$ $^1$H-NMR (400 MHz, DMSO-d6) δ [ppm]: 0.943 (0.60), 1.111 (3.12), 1.280 (0.80), 1.366 (0.51), 1.372 (0.47), 1.394 (16.00), 4.046 (6.83), 4.256 (1.81), 4.271 (1.81), 7.143 (0.56), 7.202 (1.19), 7.207 (1.20), 7.553 (1.30), 7.558 (1.32).

Intermediate 248

Rac-Tert-Butyl {[4-(1-Methyl-1H-Pyrazol-5-Yl)-2,5-Dioxoimidazolidin-4-Yl]Methyl}Carbamate

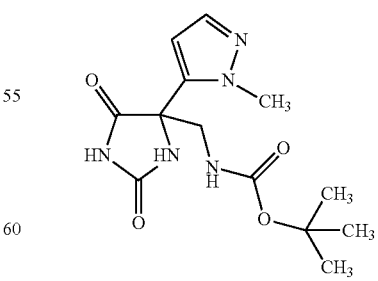

The reaction was performed in 2 batches.

A) To a solution of tert-butyl [2-(1-methyl-1H-pyrazol-5-yl)-2-oxoethyl]carbamate (2.00 g, 8.36 mmol) in methanol (15.3 ml) was added potassium cyanide (2.18 g, 33.4 mmol)

and ammonium carbonate (3.21 g, 33.4 mmol) at RT. The reaction mixture was heated up to 80° C. overnight into a sealed pressure flask. After filtration at RT, the filtrate was concentrated in vacuo and the crude was suspended in methanol. The suspension was filtered off and the resulting filtrate was concentrated in vacuo. (Batch 1)

B) To a solution of tert-butyl [2-(1-methyl-1H-pyrazol-5-yl)-2-oxoethyl]carbamate (2.00 g, 8.36 mmol) in a mixture of Ethanol (15 ml) and water (6 ml) was added potassium cyanide (2.18 g, 33.4 mmol) and ammonium carbonate (3.21 g, 33.4 mmol) at RT. The reaction mixture was heated up to 40° C. overnight into a sealed pressure flask. After filtration at RT, the resulting filtrate was concentrated in vacuo. (Batch 2)

The combined crude product (batch1+2) was purified by preparative HPLC (sample preparation: 15 g dissolved in a mixture of acetonitrile, methanol and water; column: XBridge C18 5 μm, 100×30 mm; eluent: water→acetonitrile/water 80:20+1% ammonia solution→acetonitrile; flow rate: 80 ml/min; temperature: 40° C.; UV detection: 220 nm). After lyophilisation, 1.8 g of the desired product was obtained and used without further purification.

LC-MS (Method 9): R$_t$=0.36 min; MS (ESIpos): m/z=310 [M+H]$^+$ $^1$H-NMR (400 MHz, DMSO-d6) δ [ppm]: −0.008 (0.43), 0.008 (0.54), 1.359 (16.00), 1.754 (0.51), 3.524 (0.41), 3.540 (0.41), 3.693 (4.71), 6.230 (0.96), 7.250 (0.96).

The title compound can also be synthesized via the procedure described in J: Med. Chem. 2014, 57, 10476-10485

Intermediate 249

Ent-Tert-Butyl {[4-(1-Methyl-1H-Pyrazol-5-Yl)-2,5-Dioxoimidazolidin-4-Yl]Methyl}Carbamate

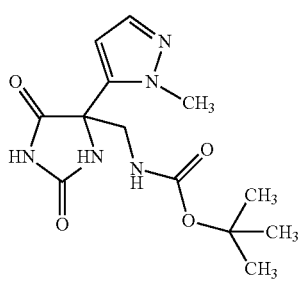 [SMILES: Cn1nccc1C1(CNC(=O)OC(C)(C)C)NC(=O)NC1=O]

To a solution of tert-butyl [2-(1-methyl-1H-pyrazol-5-yl)-2-oxoethyl]carbamate (5.26 g, 22.0 mmol) in methanol (30 ml) was added potassium cyanide (5.73 g, 87.9 mmol) and ammonium carbonate (8.45 g, 87.9 mmol) at RT. The reaction mixture was stirred overnight at 80° C. into a sealed pressure flask. After filtration and washing of the suspension with methanol at RT, the resulting filtrate was concentrated in vacuo. The residue was purified by preparative chiral SFC (sample preparation: 11.9 g dissolved in methanol; column: Daicel Chiralpak AD-H 5 μm, 250×30 mm; eluent: carbon dioxide/methanol 80:20; flow rate: 140 ml/min; temperature: 40° C.; UV detection: 210 nm]. 2.22 g (95% purity, 6.77 mmol) of the desired product was obtained.

Analytical chiral SFC: R$_t$=1.12 min, e.e. =99.1% [column: AD 3 μm, 100×4.6 mm; eluent: carbon dioxide/methanol 80:20; flow rate: 3 ml/min; UV detection: 210 nm]

LC-MS (Method 7): R$_t$=0.95 min; MS (ESIpos): m/z=310 [M+H]$^+$ $^1$H NMR (600 MHz, DMSO-d$_6$) δ ppm 10.84-11.40 (m, 1H), 8.13 (brs, 1H), 7.36 (d, 1H), 6.98-7.12 (m, 1H), 6.43 (d, 1H), 3.77 (s, 3H), 3.63-3.71 (m, 2H), 1.37 (s, 9H)

Intermediate 250

Rac-5-(Aminomethyl)-5-(1-Methyl-1H-Pyrazol-5-Yl)Imidazolidine-2,4-Dione Hydrochloride

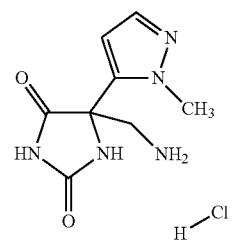

To a solution of rac-tert-butyl {[4-(1-methyl-1H-pyrazol-5-yl)-2,5-dioxoimidazolidin-4 yl]methyl}carbamate (520 mg, 1.68 mmol) in dichloromethane (14.5 ml) were added 2.1 ml (8.4 mmol) of 4M hydrochloric acid in dioxane at RT. The reaction mixture was stirred overnight and concentrated in vacuo. 400 mg of the title compound was used without further purification.

LC-MS (Method 9): R$_t$=0.22 min; MS (ESIneg): m/z=208 [M−HCl−H]$^-$ $^1$H-NMR (600 MHz, DMSO-d6) δ [ppm]: 1.767 (3.19), 2.119 (1.47), 2.390 (0.50), 3.166 (0.76), 3.463 (1.91), 3.473 (2.29), 3.485 (2.90), 3.494 (2.58), 3.590 (2.66), 3.598 (2.94), 3.612 (2.25), 3.620 (1.90), 3.725 (0.42), 4.091 (0.50), 5.692 (1.73), 6.501 (15.58), 6.504 (16.00), 7.358 (0.46), 7.425 (15.98), 7.428 (15.92), 8.608 (10.32), 8.873 (12.22), 11.515 (9.95).

The title compound can also be synthesized via the procedure described in J: Med. Chem. 2014, 57, 10476-10485

Intermediate 251

Ent-5-(Aminomethyl)-5-(1-Methyl-1H-Pyrazol-5-Yl)Imidazolidine-2,4-Dione Hydrochloride

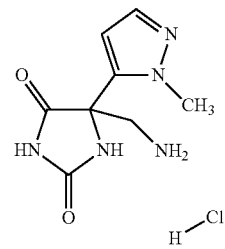

To a solution of ent-tert-butyl {[4-(1-methyl-1H-pyrazol-5-yl)-2,5-dioxoimidazolidin-4 yl]methyl}carbamate (2.20 g, 95% purity, 6.77 mmol) in dichloromethane (50 ml) were added 8.5 ml of 4M hydrochloric acid (34 mmol) in dioxane. The reaction mixture was stirred overnight at room temperature. The precipitate was filtered off, washed with dichloromethane, and then dissolved in water. After lyophilisation, 2.08 g of the title compound was obtained and used without further purification.

LC-MS (Method 9): R$_t$=0.23 min, MS (ESIpos): m/z=210 [M−HCl+H]$^+$ $^1$H-NMR (600 MHz, DMSO-d6) δ [ppm]: 0.005 (0.46), 1.596 (2.01), 2.427 (0.43), 2.522 (1.00), 2.525 (0.92), 2.576 (0.48), 3.468 (1.65), 3.483 (2.12), 3.568 (5.57), 3.603 (2.18), 3.619 (1.70), 3.725 (0.46), 3.868 (0.53), 3.877 (0.57), 3.959 (0.52), 4.186 (2.08), 4.295 (12.82), 6.494 (15.83), 6.497 (16.00), 7.424 (15.71), 7.427 (15.45), 8.554 (7.39), 8.823 (9.72), 11.497 (7.28).

Intermediate 252

Ethyl 5-[1-(Difluoromethyl)-1H-Pyrazol-5-Yl]-1,3-Oxazole-4-Carboxylate

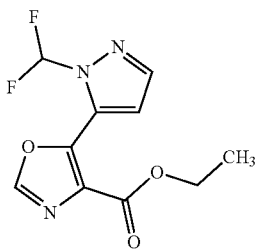 [SMILES: CCOC(=O)c1ncoc1-c1ccnn1C(F)F]

1-(difluoromethyl)-1H-pyrazole-5-carboxylic acid (2.60 g, 16.0 mmol) dissolved in 25 ml of THF was treated with 1,1,-carbonyl-diimidazole (3.12 g, 19.2 mmol) and stirred at room temperature. After 2 h ethyl isocyanoacetate (1.9 ml, 18 mmol), dissolved in 25 ml of THF, and a solution of lithium bis(trimethylsilyl)amide in THF (16 ml, 1.0 M, 16 mmol) were added at 0° C. The mixture was allowed to warm to room temperature, stirred overnight and then concentrated in vacuo. The residue was taken up with ethyl acetate and washed with water. The organic layer was dried over sodium sulfate, filtered, Isolute® was added and the solvent was evaporated on a rotary evaporator. The crude product was purified by column chromatography (100 g Ultra Snap Cartridge Biotage; eluent ethyl acetate/cyclohexane, elution gradient 10%→65%). Samples containing the desired product were united, the solvents were evaporated and the residue was dried in vacuum. 1.60 g (100% purity, 39% yield) of the title compound was obtained.

LC-MS (Method 7): R$_t$=1.43 min; MS (ESIpos): m/z=258 [M+H]$^+$ $^1$H-NMR (400 MHz, DMSO-d6) δ [ppm]: 1.173 (7.68), 1.191 (16.00), 1.209 (7.93), 4.212 (2.57), 4.230 (7.90), 4.247 (7.83), 4.265 (2.52), 7.086 (4.50), 7.090 (4.56), 7.709 (2.14), 7.851 (4.21), 7.994 (2.25), 8.000 (4.40), 8.004 (4.29), 8.759 (6.93).

Intermediate 253

2-Amino-1-[1-(Difluoromethyl)-1H-Pyrazol-5-Yl]Ethanone Hydrochloride

ethyl 5-[1-(difluoromethyl)-1H-pyrazol-5-yl]-1,3-oxazole-4-carboxylate (1.60 g, 6.22 mmol) was taken up in 35 ml of 6 N hydrochloric acid and stirred at 100° C. After 2 h the resulting mixture was concentrated in vacuo and the residue was treated with DCM and a small amount of methanol. The precipitate was filtered off and dried in vacuo. 1.10 g (84% yield) of the title compound was obtained.

LC-MS (Method 9): R$_t$=0.74 min; MS (ESIpos): m/z=176 [M−HCl+H]$^+$ $^1$H-NMR (400 MHz, DMSO-d6) δ [ppm]: 1.091 (0.50), 1.109 (1.11), 1.127 (0.59), 2.328 (0.75), 2.367 (1.14), 2.670 (0.78), 2.711 (1.17), 4.421 (0.53), 4.492 (13.60), 7.583 (16.00), 7.587 (15.25), 7.957 (6.86), 8.047 (13.41), 8.102 (13.69), 8.248 (6.77), 8.418 (8.00).

Intermediate 254

Tert-Butyl {2-[1-(Difluoromethyl)-1H-Pyrazol-5-Yl]-2-Oxoethyl}Carbamate

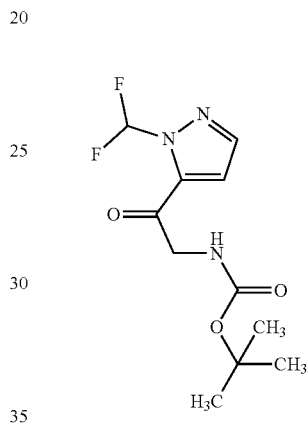

To a solution of 2-amino-1-[1-(difluoromethyl)-1H-pyrazol-5-yl]ethanone hydrochloride (1.10 g, 5.20 mmol) in dichloromethane (23 ml) was added di-tert-butyl dicarbonate (1.25 g, 5.72 mmol) and triethylamine (3.6 ml, 26 mmol). After 2 h of stirring at RT, the reaction mixture was diluted with dichloromethane and washed with water. The organic phase was dried, concentrated in vacuo and 1.44 g of the title compound was used without further purification.

LC-MS (Method 7): R$_t$=1.58 min; MS (ESIpos): m/z=276 [M+H]$^+$

Intermediate 255

Rac-Tert-Butyl({4-[1-(Difluoromethyl)-1H-Pyrazol-5-Yl]-2,5-Dioxoimidazolidin-4-Yl}Methyl)Carbamate

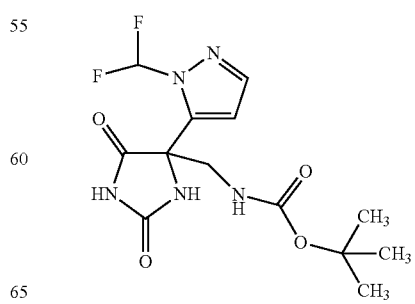

To a solution of tert-butyl {2-[1-(difluoromethyl)-1H-pyrazol-5-yl]-2-oxoethyl}carbamate (1.44 g, 5.23 mmol) in methanol (9.6 ml) was added potassium cyanide (1.36 g, 20.9 mmol) and ammonium carbonate (2.01 g, 20.9 mmol) at RT. The reaction mixture was stirred for 2 days at 60° C. into a sealed pressure flask. After filtration at RT, the resulting filtrate was concentrated in vacuo. The residue was purified by preparative HPLC (sample preparation: 3.9 g dissolved in a mixture of methanol, water, acetonitrile and ammonia; column: XBridge C18 5 µm, 100×30 mm; eluent: water→acetonitrile/water 80:20+1% ammonia solution→acetonitrile; flow rate: 80 ml/min; temperature: 40° C.; UV detection: 220 nm). 699 mg of the desired product was obtained and used without further purification.

LC-MS (Method 7): $R_t$=1.08 min; MS (ESIneg): m/z=344 [M−H]⁻

Intermediate 256

Rac-5-(Aminomethyl)-5-[1-(Difluoromethyl)-1H-Pyrazol-5-Yl]Imidazolidine-2,4-Dione Hydrochloride

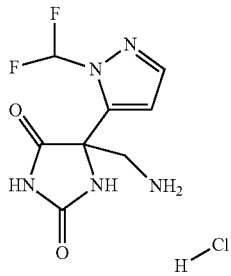 [SMILES: NCC1(c2ccnn2C(F)F)NC(=O)NC1=O ; Cl]

To a solution of rac-tert-butyl({4-[1-(difluoromethyl)-1H-pyrazol-5-yl]-2,5-dioxoimidazolidin-4 yl}methyl)carbamate (340 mg, 985 µmol) in dichloromethane (8.5 ml) were added 1.2 ml (4.9 mmol) of 4M hydrochloric acid in dioxane at RT. The reaction mixture was stirred for 2 h and concentrated in vacuo. 280 mg (99% purity, 100% yield) of the title compound was used without further purification.

LC-MS (Method 9): $R_t$=0.22 min; MS (ESIpos): m/z=246 [M−HCl+H]⁺

¹H-NMR (400 MHz, DMSO-d6) δ [ppm]: −0.149 (0.44), −0.008 (3.88), 0.008 (3.67), 0.146 (0.44), 1.110 (0.42), 1.596 (0.84), 1.754 (5.24), 2.111 (2.45), 2.324 (0.50), 2.329 (0.71), 2.333 (0.50), 2.367 (0.75), 2.524 (2.73), 2.666 (0.52), 2.671 (0.71), 2.675 (0.52), 2.711 (0.73), 3.457 (5.03), 3.491 (6.16), 3.568 (2.20), 3.689 (5.72), 3.723 (4.42), 5.756 (1.11), 6.811 (15.81), 6.816 (16.00), 7.820 (4.47), 7.835 (12.96), 7.839 (12.85), 7.960 (4.43), 7.969 (4.22), 8.109 (3.69), 8.504 (6.88), 8.825 (4.30), 11.497 (3.56).

Intermediate 257

Ethyl 5-[5-(Trifluoromethyl)-1,3-Thiazol-4-Yl]-1,3-Oxazole-4-Carboxylate

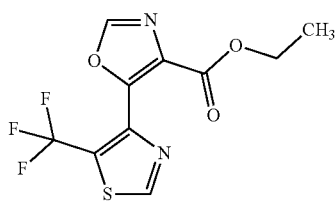 [SMILES: CCOC(=O)c1ncoc1-c1ncsc1C(F)(F)F]

5-(trifluoromethyl)-1,3-thiazole-4-carboxylic acid (2.00 g, 10.1 mmol) dissolved in 15 ml of THF was treated with 1,1,-carbonyl-diimidazole (1.97 g, 12.2 mmol) and stirred at room temperature. After 1 h ethyl isocyanoacetate (1.2 ml, 11 mmol), dissolved in 15 ml of THF, and a solution of lithium bis(trimethylsilyl)amide in THF (10 ml, 1.0 M, 10 mmol) were added at 0° C. The mixture was allowed to warm to room temperature, stirred over 2 days and then concentrated in vacuo. The residue was taken up with ethyl acetate and washed with water. The organic layer was dried and concentrated in vacuo. The crude product was purified by column chromatography (100 g Ultra Snap Cartridge Biotage; eluent ethyl acetate/cyclohexane, elution gradient 8%→85%). Samples containing the desired product were united, the solvents were evaporated and the residue was dried in vacuum. 1.43 g (48% yield) of the title compound was obtained.

LC-MS (Method 7): $R_t$=1.62 min; MS (ESIpos): m/z=293 [M+H]⁺

¹H-NMR (400 MHz, DMSO-d6) δ [ppm]: 1.086 (7.76), 1.104 (16.00), 1.122 (8.00), 4.148 (2.68), 4.166 (8.12), 4.184 (8.05), 4.201 (2.61), 8.780 (5.87), 9.570 (4.98).

Intermediate 258

2-Amino-1-[5-(Trifluoromethyl)-1,3-Thiazol-4-Yl]Ethanone Hydrochloride

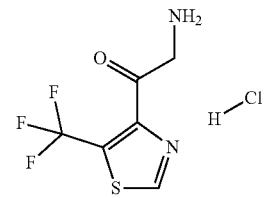

ethyl 5-[5-(trifluoromethyl)-1,3-thiazol-4-yl]-1,3-oxazole-4-carboxylate (1.43 g, 4.89 mmol) was taken up in 200 ml of 6 N hydrochloric acid and stirred for 2 h at 100° C. After further stirring overnight at room temperature, the resulting mixture was concentrated in vacuo. 1.25 g (95% purity, 98% yield) of the title compound was obtained.

LC-MS (Method 9): $R_t$=1.00 min; MS (ESIpos): m/z=211 [M−HCl+H]⁺

¹H-NMR (400 MHz, DMSO-d6) δ [ppm]: −0.008 (1.13), 0.008 (1.18), 4.571 (16.00), 8.411 (4.83), 9.517 (12.18).

Intermediate 259

Tert-Butyl {2-Oxo-2-[5-(Trifluoromethyl)-1,3-Thiazol-4-Yl]Ethyl}Carbamate

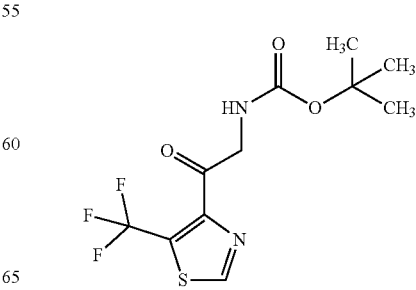

To a solution of 2-amino-1-[5-(trifluoromethyl)-1,3-thiazol-4-yl]ethanone hydrochloride (1.25 g, 5.07 mmol) in dichloromethane (23 ml) was added di-tert-butyl dicarbonate (1.22 g, 5.57 mmol) and triethylamine (3.5 ml, 25 mmol). After 2 h of stirring at RT, the reaction mixture was diluted with dichloromethane and washed with water. The organic phase was dried, concentrated in vacuo and 1.66 g of the title compound was used without further purification.

LC-MS (Method 9): $R_t$=1.58 min; MS (ESIpos): m/z=310 $[M-H]^+$

Intermediate 260

Rac-Tert-Butyl({2,5-Dioxo-4-[5-(Trifluoromethyl)-1,3-Thiazol-4-Yl]Imidazolidin-4-Yl}Methyl)Carbamate

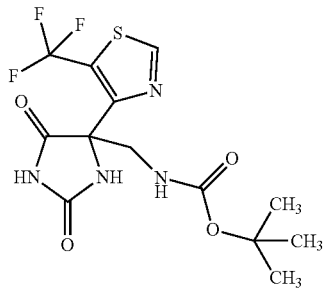 [SMILES: CC(C)(C)OC(=O)NCC1(c2ncsc2C(F)(F)F)NC(=O)NC1=O]

To a solution of tert-butyl {2-oxo-2-[5-(trifluoromethyl)-1,3-thiazol-4-yl]ethyl}carbamate (800 mg, 2.58 mmol) in methanol (4.6 ml) was added potassium cyanide (672 mg, 10.3 mmol) and ammonium carbonate (991 mg, 10.3 mmol) at RT. The reaction mixture was stirred overnight at 60° C. into a sealed pressure flask. After filtration at RT, the resulting filtrate was concentrated in vacuo. The residue was purified by preparative HPLC (sample preparation: 473 mg dissolved in a mixture of methanol, water, acetonitrile and ammonia; column: XBridge C18 5 µm, 100×30 mm; eluent: water→acetonitrile/water 80:20+1% ammonia solution→acetonitrile; flow rate: 80 ml/min; temperature: 40° C.; UV detection: 220 nm). 227 mg (100% purity, 23% yield) of the desired product was obtained and used without further purification.

LC-MS (Method 9): $R_t$=0.76 min; MS (ESIneg): m/z=379 $[M-H]^-$

Intermediate 261

Rac-5-(Aminomethyl)-5-[5-(Trifluoromethyl)-1,3-Thiazol-4-Yl]Imidazolidine-2,4-Dione Hydrochloride

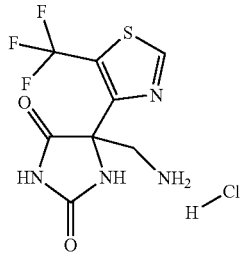

To a solution of rac-tert-butyl({2,5-dioxo-4-[5-(trifluoromethyl)-1,3-thiazol-4-yl]imidazolidin-4-yl}methyl)carbamate (485 mg, 1.28 mmol) in dichloromethane (20 ml) were added 1.2 ml (1.6 ml, 4.0 M, 6.4 mmol) of 4M hydrochloric acid in dioxane at RT. The reaction mixture was stirred overnight and concentrated in vacuo. 413 mg (95% purity, 97% yield) of the title compound was used without further purification.

LC-MS (Method 9): $R_t$=0.29 min; MS (ESIpos): m/z=281 $[M-HCl+H]^+$ $^1$H-NMR (400 MHz, DMSO-d6) δ [ppm]: −0.008 (0.97), 0.008 (0.91), 1.754 (10.12), 2.108 (3.70), 2.367 (0.43), 2.519 (1.81), 2.524 (1.46), 2.558 (0.54), 2.560 (0.45), 2.710 (0.41), 3.167 (16.00), 3.708 (3.29), 3.741 (2.54), 8.321 (2.94), 8.628 (1.96), 9.440 (7.56), 11.450 (3.19).

Intermediate 262

Tert-Butyl [2-Oxo-2-(1,3-Thiazol-2-Yl)Ethyl]Carbamate

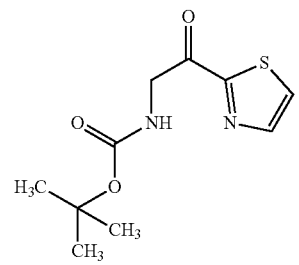 [SMILES: CC(C)(C)OC(=O)NCC(=O)c1nccs1]

Under argon, thiazole (3.6 ml, 51 mmol) was dissolved in THF (20 ml) and cooled in an acetonitrile/dry ice bath to −40° C. The solution was treated dropwise with n-butyllithium in hexane (20.3 ml, 2.5 M, 51 mmol). After 45 minutes at −35° C., a solution of tert-butyl {2-[methoxy (methyl)amino]-2-oxoethyl}carbamate (5.00 g, 22.9 mmol) in 30 ml of THF was added dropwise, while keeping the temperature below −40° C. After 2 h at −40 to −45° C., the reaction was quenched with 1 N citric acid (25 ml) and diluted with ethyl acetate. The layers were separated. The aqueous layer was extracted with ethyl acetate and the organic phases were combined, washed with brine, dried and concentrated under reduced pressure. The crude product was purified by column chromatography (100 g Ultra Snap Cartridge Biotage; eluent ethyl acetate/cyclohexane, elution gradient: 25%→60%) to give. 3.04 g (98% purity, 24% yield) of the title compound.

LC-MS (Method 8): $R_t$=0.78 min; MS (ESIpos): m/z=243 $[M+H]^+$ $^1$H-NMR (500 MHz, DMSO-d6) δ [ppm]: 1.263 (0.77), 1.398 (16.00), 4.515 (1.84), 4.527 (1.80), 7.182 (0.52), 8.167 (1.36), 8.173 (1.47), 8.257 (1.73), 8.263 (1.52).

Intermediate 263

Rac-Tert-Butyl {[2,5-Dioxo-4-(1,3-Thiazol-2-Yl)Imidazolidin-4-Yl]Methyl}Carbamate

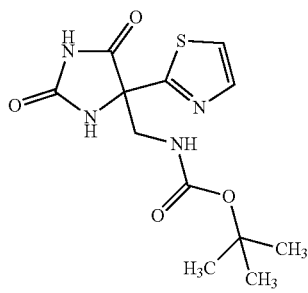 [SMILES: CC(C)(C)OC(=O)NCC1(c2nccs2)NC(=O)NC1=O]

To a solution of tert-butyl [2-oxo-2-(1,3-thiazol-2-yl)ethyl]carbamate (3.04 g, 12.5 mmol) in methanol (20 ml) was added potassium cyanide (3.27 g, 50.2 mmol) and ammonium carbonate (4.82 g, 50.2 mmol) at RT. The reaction mixture was stirred overnight at 40° C. into a sealed pressure flask and then diluted with water. The resulting suspension was extracted with dichloromethane. After phase separation; the aqueous phase was concentrated under reduced pressure and the crude product was suspended in a mixture of 30 ml acetonitrile and 20 ml methanol. After filtration of the residue, the filtrate was concentrated in vacuo and 1.4 g of the desired product was obtained and used without further purification.

LC-MS (Method 7): $R_t$=0.99 min; MS (ESIneg): m/z=311 [M−H]−

The title compound can also be synthesized via the procedure described in J. Med. Chem. 2014, 57, 10476-10485.

Intermediate 264

Rac-5-(Aminomethyl)-5-(1,3-Thiazol-2-Yl)Imidazolidine-2,4-Dione Hydrochloride

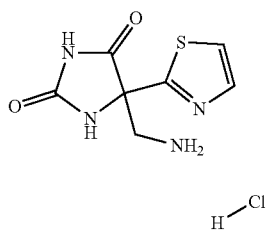 [SMILES: NCC1(c2nccs2)NC(=O)NC1=O ; Cl]

To a solution of rac-tert-butyl {[2,5-dioxo-4-(1,3-thiazol-2-yl)imidazolidin-4-yl]methyl}carbamate (1.40 g, 4.48 mmol) in methanol (28 ml) were added 22.4 ml (90 mmol) of 4M hydrochloric acid in dioxane at 0° C. After 1 h at 0° C., the reaction mixture was stirred overnight at RT and concentrated in vacuo. 1.30 g of the title compound was used without further purification.

LC-MS (Method 9): $R_t$=0.26 min; MS (ESIneg): m/z=211 [M−HCl−H]−

1H-NMR (600 MHz, DMSO-d6) δ [ppm]: 0.005 (1.86), 1.234 (0.56), 1.246 (0.80), 1.596 (0.54), 1.759 (0.78), 2.387 (0.62), 2.426 (1.00), 2.655 (0.64), 2.887 (0.46), 3.167 (0.62), 3.462 (0.48), 3.472 (0.58), 3.492 (0.52), 3.502 (0.56), 3.527 (1.42), 3.537 (1.68), 3.550 (1.90), 3.559 (1.52), 3.667 (0.54), 3.676 (0.42), 3.704 (0.58), 3.713 (0.54), 3.722 (1.86), 3.754 (1.74), 3.763 (1.94), 3.776 (1.62), 3.785 (1.34), 3.917 (0.52), 5.084 (1.26), 7.183 (2.00), 7.268 (2.21), 7.352 (2.00), 7.774 (0.52), 7.780 (0.46), 7.881 (10.95), 7.886 (15.10), 7.909 (16.00), 7.914 (10.55), 8.484 (5.59), 9.120 (5.57), 11.420 (5.69).

The title compound can also be synthesized via the procedure described in J. Med. Chem. 2014, 57, 10476-10485.

Intermediate 265

Ethyl 5-(1,3-Thiazol-4-Yl)-1,3-Oxazole-4-Carboxylate

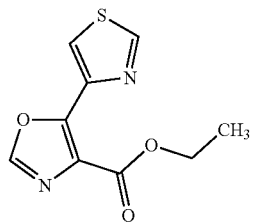

1,3-thiazole-4-carboxylic acid (1.00 g, 7.74 mmol) dissolved in 12 ml of THF was treated with 1,1,-carbonyldiimidazole (1.51 g, 9.29 mmol) and stirred at room temperature. After 2 h, ethyl isocyanoacetate (930 μl, 8.5 mmol), dissolved in 12 ml of THF, and a solution of lithium bis(trimethylsilyl)amide in THF (7.7 ml, 1.0 M, 7.7 mmol) were added at 0° C. The mixture was allowed to warm to room temperature, stirred overnight and then concentrated in vacuo. The residue was taken up with ethyl acetate and washed with water. The organic layer was dried and concentrated in vacuo. The crude product was purified by column chromatography (100 g Ultra Snap Cartridge Biotage; eluent ethyl acetate/cyclohexane, elution gradient 15%→100%). Samples containing the desired product were united, the solvents were evaporated and the residue was dried in vacuum. 783 mg (44% yield) of the title compound was used without further purification.

LC-MS (Method 8): $R_t$=0.65 min; MS (ESIpos): m/z=225 [M+H]+

1H-NMR (600 MHz, DMSO-d6) δ [ppm]: 1.291 (7.74), 1.302 (16.00), 1.314 (7.70), 4.313 (2.51), 4.325 (7.74), 4.337 (7.62), 4.349 (2.39), 8.580 (9.32), 8.744 (5.07), 8.747 (5.10), 9.273 (4.82), 9.276 (4.76).

Intermediate 266

2-Amino-1-(1,3-Thiazol-4-Yl)Ethanone Hydrochloride

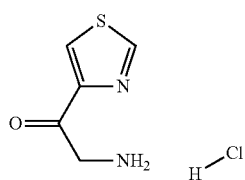

ethyl 5-(1,3-thiazol-4-yl)-1,3-oxazole-4-carboxylate (782 mg, 3.49 mmol) was taken up in 19 ml of 6 N hydrochloric acid. After 2 h the resulting mixture was concentrated in vacuo and the residue was treated with DCM and a small amount of methanol. The precipitate was filtered off and dried in vacuo. 613 mg (98% yield) of the title compound was obtained and used without further purification LC-MS (Method 9): $R_t$=0.48 min; MS (ESIpos): m/z=143 [M−HCl+H]$^+$ $^1$H-NMR (600 MHz, DMSO-d6) δ [ppm]: 1.067 (4.56), 1.079 (9.66), 1.091 (4.71), 2.525 (0.47), 4.145 (1.10), 4.156 (3.13), 4.168 (3.10), 4.180 (1.18), 4.437 (4.70), 4.479 (5.69), 4.488 (11.43), 4.497 (11.15), 5.938 (1.13), 8.478 (5.26), 8.827 (15.55), 8.830 (16.00), 8.982 (3.87), 8.985 (4.11), 9.202 (1.56), 9.303 (15.03), 9.307 (15.02), 9.322 (4.08), 9.325 (4.09).

Intermediate 267

Tert-Butyl [2-Oxo-2-(1,3-Thiazol-4-Yl)Ethyl]Carbamate

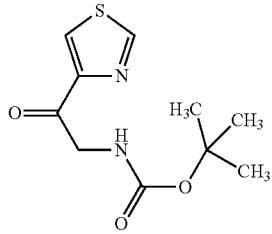 [SMILES: CC(C)(C)OC(=O)NCC(=O)c1cscn1]

To a solution of 2-amino-1-(1,3-thiazol-4-yl)ethanone hydrochloride (610 mg, 3.41 mmol) in dichloromethane (14 ml) was added di-tert-butyl dicarbonate (860 µl, 3.8 mmol) and triethylamine (1.4 ml, 10 mmol). After 1.5 h of stirring at RT, the reaction mixture was concentrated under reduced pressure, diluted with ethylacetate and washed with water and brine. After phase separation, the organic phase was dried; concentrated in vacuo and 781 mg of the title compound was used without further purification.

LC-MS (Method 7): $R_t$=1.33 min; MS (ESIpos): m/z=143 [M−Boc+H]

$^1$H-NMR (400 MHz, DMSO-d6) δ [ppm]: −0.008 (0.42), 0.008 (0.42), 1.093 (0.66), 1.110 (0.45), 1.282 (0.71), 1.306 (0.40), 1.366 (0.48), 1.387 (2.15), 1.398 (14.02), 1.468 (16.00), 4.430 (1.68), 4.445 (1.65), 7.061 (0.46), 8.635 (0.72), 8.640 (0.78), 9.236 (0.92), 9.240 (0.90).

Intermediate 268

Rac-Tert-Butyl {[2,5-Dioxo-4-(1,3-Thiazol-4-Yl)Imidazolidin-4-Yl]Methyl}Carbamate

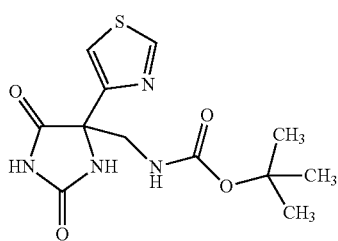 [SMILES: CC(C)(C)OC(=O)NCC1(c2cscn2)NC(=O)NC1=O]

To a solution of tert-butyl [2-oxo-2-(1,3-thiazol-4-yl)ethyl]carbamate (781 mg, 3.22 mmol) in methanol (5.9 ml) was added potassium cyanide (840 mg, 12.9 mmol) and ammonium carbonate (1.24 g, 12.9 mmol) at RT. The reaction mixture was stirred for 2 days at 40° C. into a sealed pressure flask. After filtration at RT, the resulting filtrate was concentrated in vacuo. The residue was purified by preparative HPLC (Method 2f). 283 mg of the desired product was obtained and used without further purification LC-MS (Method 8): $R_t$=0.63 min, MS (ESIneg): m/z=311 [M−H]$^−$ $^1$H-NMR (400 MHz, DMSO-d6) δ [ppm]: 1.366 (16.00), 1.434 (0.81), 7.733 (1.28), 7.738 (1.32), 8.136 (0.77), 9.107 (0.96), 9.111 (0.97), 10.776 (0.53).

Intermediate 269

Rac-5-(Aminomethyl)-5-(1,3-Thiazol-4-Yl)Imidazolidine-2,4-Dione Hydrochloride

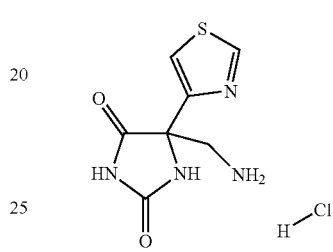

To a solution of rac-tert-butyl {[2,5-dioxo-4-(1,3-thiazol-4-yl)imidazolidin-4-yl]methyl}carbamate (283 mg, 906 µmol) in dichloromethane (7.8 ml) were added 1.1 ml of 4M hydrochloric acid in dioxane at RT. The reaction mixture was stirred for 4 h and concentrated in vacuo. 200 mg (84% yield) of the title compound was used without further purification.

LC-MS (Method 9): $R_t$=0.24 min; MS (ESIpos): m/z=213 [M−HCl+H]$^+$ $^1$H-NMR (400 MHz, DMSO-d6) δ [ppm]: −0.008 (2.08), 0.008 (2.39), 1.366 (1.42), 1.596 (1.40), 2.525 (0.83), 3.433 (0.84), 3.446 (1.03), 3.466 (1.26), 3.479 (1.11), 3.568 (16.00), 3.637 (0.42), 3.660 (1.41), 3.676 (1.25), 3.695 (1.03), 3.709 (0.84), 3.872 (0.44), 4.304 (1.61), 5.755 (1.98), 7.647 (0.43), 7.652 (0.46), 7.895 (8.71), 7.900 (8.69), 8.343 (3.74), 8.524 (4.89), 9.180 (4.89), 9.185 (4.86), 11.201 (4.04).

Intermediate 270

Ent-Tert-Butyl {[2,5-Dioxo-4-(1,3-Thiazol-4-Yl)Imidazolidin-4-Yl]Methyl}Carbamate

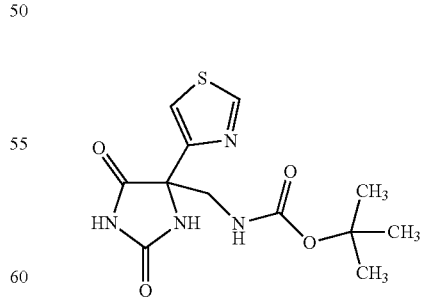

To a solution of tert-butyl [2-oxo-2-(1,3-thiazol-4-yl)ethyl]carbamate (6.95 g, 90% purity, 25.9 mmol) in methanol (40 ml) was added potassium cyanide (6.74 g, 104 mmol) and ammonium carbonate (9.94 g, 104 mmol) at RT. The reaction mixture was stirred overnight at 80° C. into a sealed pressure flask. After filtration and washing of the suspension with methanol at RT, the resulting filtrate was concentrated in vacuo. The residue was purified by preparative chiral SFC [sample preparation: 12 g dissolved in MeOH; column: Maisch chiralpak AD-H 5 μm 250×25 mm; eluent: 70% carbon dioxide/30% isopropanol; injection volume: 1.5 ml; flow rate: 100 ml/min; temperature: 38° C.; UV detection: 210 nm] afforded 2.63 g (100% purity) of the desired product that were used without further purification.

Analytical chiral SFC: Analytical chiral SFC: $R_f$=3.14 min, e.e. =>99% [column: Chiralpak AD-H 3 μm 100×4.6 mm; eluent: 80% carbon dioxide/20% isopropanol; flow rate: 3 ml/min; temperature: 40° C.; UV detection: 210 nm]

LC-MS (Method 7): $R_t$=0.96 min; MS (ESIneg): m/z=311 [M−H]⁻

Intermediate 271

Ent-5-(Aminomethyl)-5-(1,3-Thiazol-4-Yl)Imidazolidine-2,4-Dione Hydrochloride

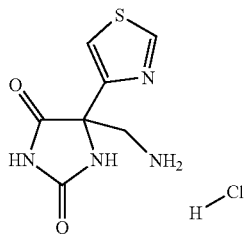 [SMILES: NCC1(c2cscn2)NC(=O)NC1=O ; Cl]

To a solution of ent-tert-butyl {[2,5-dioxo-4-(1,3-thiazol-4-yl)imidazolidin-4-yl]methyl}carbamate (2.63 g, 8.42 mmol) in dichloromethane (50 ml) were added 10.5 ml of 4M hydrochloric acid (42 mmol) in dioxane at RT. The reaction mixture was stirred overnight at RT and concentrated in vacuo. After lyophilisation, 2.43 g of the title compound was used without further purification.

LC-MS (Method 9): $R_t$=0.24 min; MS (ESIpos): m/z=213 [M−HCl+H]⁺

¹H-NMR (600 MHz, DMSO-d6) δ [ppm]: 1.596 (0.73), 2.521 (0.78), 2.524 (0.72), 3.467 (1.63), 3.477 (1.96), 3.490 (2.34), 3.499 (2.02), 3.638 (2.03), 3.648 (2.28), 3.660 (1.93), 3.670 (1.57), 4.683 (5.74), 7.898 (15.46), 7.901 (16.00), 8.491 (6.40), 8.588 (8.09), 9.175 (14.29), 9.177 (14.14), 11.172 (6.99).

Intermediate 272

Tert-Butyl {2-Oxo-2-[3-(Trifluoromethyl)Pyridin-2-Yl]Ethyl}Carbamate

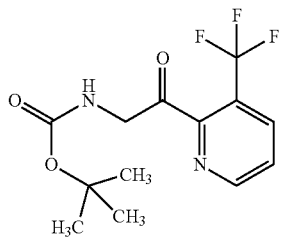 [SMILES: CC(C)(C)OC(=O)NCC(=O)c1ncccc1C(F)(F)F]

To a solution of 2-amino-1-[3-(trifluoromethyl)pyridin-2-yl]ethanone hydrochloride (2.00 g, 8.31 mmol, FCH1366623 HCl salt) in dichloromethane (37 ml) was added di-tert-butyl dicarbonate (2.00 g, 9.14 mmol) and triethylamine (3.5 ml, 25 mmol). After 2 h of stirring at RT, the reaction mixture was diluted with dichloromethane and extracted with water. After phase separation, the organic phase was dried; concentrated in vacuo and 2.30 g (91% yield) of the title compound was obtained.

LC-MS (Method 9): $R_t$=1.58 min; MS (ESIpos): m/z=205 [M−Boc+H]⁺

¹H-NMR (400 MHz, DMSO-d6) δ [ppm]: 1.284 (0.44), 1.322 (1.44), 1.371 (0.52), 1.394 (16.00), 4.481 (1.92), 4.496 (1.89), 7.197 (0.61), 7.842 (0.57), 7.853 (0.62), 7.862 (0.65), 7.874 (0.65), 8.378 (0.80), 8.399 (0.76), 8.939 (0.88), 8.950 (0.89).

Intermediate 273

Rac-Tert-Butyl({2,5-Dioxo-4-[3-(Trifluoromethyl)Pyridin-2-Yl]Imidazolidin-4-Yl}Methyl)Carbamate

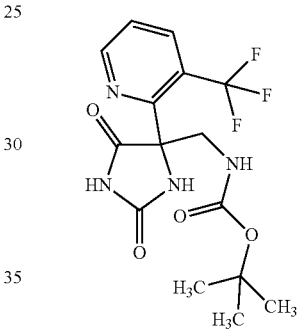

To a solution of tert-butyl {2-oxo-2-[3-(trifluoromethyl)pyridin-2-yl]ethyl}carbamate (2.30 g, 7.56 mmol) in methanol (13.6 ml) was added potassium cyanide (1.97 g, 30.2 mmol) and ammonium carbonate (2.91 g, 30.2 mmol) at RT. The reaction mixture was first stirred overnight at 60° C. into a sealed pressure flask. After additional 24 h stirring at 80° C., extra portion of potassium cyanide (738 mg, 11.3 mmol) and ammonium carbonate (1.09 g, 11.3 mmol) were added due to incomplete conversion. The reaction mixture was additionally stirred overnight at 80° C. After filtration at RT, the resulting filtrate was concentrated in vacuo. The residue was purified by preparative HPLC (sample preparation: 7.7 g dissolved in a mixture of methanol, water, acetonitrile; column: XBridge C18 5 μm, 100×30 mm; eluent: water-→acetonitrile/water 80:20+1% ammonia solution→acetonitrile; flow rate: 80 ml/min; temperature: 40° C.; UV detection: 210 nm). 730 mg of the desired product was obtained and used without further purification.

LC-MS (Method 9): $R_t$=0.87 min; MS (ESIneg): m/z=373 [M−H]⁻

¹H-NMR (600 MHz, DMSO-d6) δ [ppm]: 1.368 (16.00), 1.378 (2.03), 1.755 (0.91), 7.624 (0.46), 7.632 (0.55), 7.644 (0.48), 8.240 (0.67), 8.253 (0.66), 8.855 (0.75), 8.862 (0.75).

Intermediate 274 rac-5-(aminomethyl)-5-[3-(trifluoromethyl)pyridin-2-yl]imidazolidine-2,4-dione hydrochloride

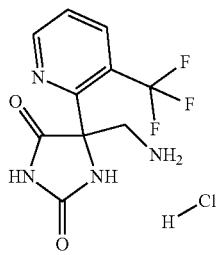 [SMILES: NCC1(c2ncccc2C(F)(F)F)NC(=O)NC1=O ; Cl]

To a solution of rac-tert-butyl({2,5-dioxo-4-[3-(trifluoromethyl)pyridin-2-yl]imidazolidin-4 yl}methyl)carbamate (725 mg, 1.94 mmol) in dichloromethane (7.6 ml) were added 2.42 ml of 4M hydrochloric acid (9.7 mmol) in dioxane at 0° C. The reaction mixture was stirred for 1 h at 0° C. then for 2 h at room temperature. The precipitate was filtered off, washed with dichloromethane and dried in vacuo. 610 mg of the title compound were obtained and used without further purification.

LC-MS (Method 9): $R_t$=0.28 min; MS (ESIneg): m/z=273 [M−HCl−H]⁻

$^1$H-NMR (600 MHz, DMSO-d6) δ [ppm]: 1.596 (0.55), 1.757 (2.53), 2.501 (16.00), 3.168 (2.76), 3.483 (0.75), 3.493 (0.85), 3.795 (0.96), 3.807 (0.84), 7.745 (1.54), 7.754 (1.68), 7.759 (1.72), 7.767 (1.66), 8.362 (5.66), 8.375 (3.57), 8.708 (3.61), 8.898 (2.56), 8.905 (2.54), 11.399 (3.00).

Intermediate 275

Ethyl 5-(3,3-Difluorocyclobutyl)-1,3-Oxazole-4-Carboxylate

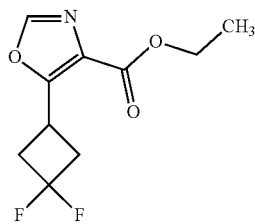 [SMILES: CCOC(=O)c1ncoc1C1CC(F)(F)C1]

3,3-difluorocyclobutane-1-carboxylic acid (3.00 g, 22.0 mmol) dissolved in 30 ml of THF was treated with 1,1,-carbonyl-diimidazole (4.29 g, 26.5 mmol) and stirred at room temperature. After 1 h, ethylisocyanoacetate (2.7 ml, 24 mmol), dissolved in 30 ml of THF, and a solution of lithium bis(trimethylsilyl)amide in THF (22 ml, 1.0 M, 22 mmol) were added at 0° C. The mixture was allowed to warm to room temperature, stirred overnight and then concentrated in vacuo. The residue was taken up with ethyl acetate and washed with water. The organic layer was dried and concentrated in vacuo. The crude product was purified by column chromatography (340 g Ultra Snap Cartridge Biotage; eluent ethyl acetate/cyclohexane, elution gradient 8%→58%). Samples containing the desired product were united, the solvents were evaporated and the residue was dried in vacuum. 2.50 g (100% purity, 49% yield) of the title compound was used without further purification.

LC-MS (Method 9): $R_t$=1.39 min; MS (ESIpos): m/z=232 [M+H]⁺

$^1$H-NMR (400 MHz, DMSO-d6) δ [ppm]: 1.272 (7.71), 1.290 (16.00), 1.308 (7.89), 2.831 (0.57), 2.852 (0.60), 2.864 (0.99), 2.868 (1.15), 2.873 (0.96), 2.884 (1.04), 2.889 (1.24), 2.893 (1.23), 2.901 (1.49), 2.906 (1.08), 2.910 (1.36), 2.921 (1.29), 2.926 (1.03), 2.930 (1.27), 2.943 (0.91), 2.963 (0.87), 3.004 (0.83), 3.013 (0.41), 3.022 (0.97), 3.027 (1.24), 3.031 (0.94), 3.038 (1.36), 3.045 (1.30), 3.061 (1.74), 3.075 (1.07), 3.080 (1.33), 3.088 (0.76), 3.093 (0.89), 3.098 (0.67), 3.116 (0.57), 4.005 (0.79), 4.026 (1.16), 4.032 (1.16), 4.047 (0.74), 4.249 (2.55), 4.267 (7.82), 4.285 (7.74), 4.303 (2.49), 8.450 (6.13).

Intermediate 276

2-Amino-1-(3,3-Difluorocyclobutyl)Ethanone Hydrochloride

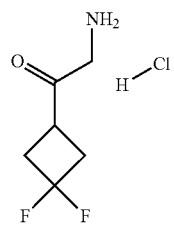

Ethyl 5-(3,3-difluorocyclobutyl)-1,3-oxazole-4-carboxylate (2.50 g, 10.8 mmol) was taken up in 70 ml of 6 N hydrochloric acid and stirred for 2 h at 100° C., then overnight at room temperature.

The resulting mixture was concentrated in vacuo. Due to incomplete conversion, the crude was taken up in 70 ml of 6 N hydrochloric acid, stirred for 2 h at 100° C. and concentrated in vacuo. 1.77 g of the title compound was obtained and used without further purification.

LC-MS (Method 9): $R_t$=0.82 min; MS (ESIpos): m/z=150 [M−HCl+H]⁺

$^1$H-NMR (400 MHz, DMSO-d6) δ [ppm]: −0.008 (1.34), 0.008 (1.24), 1.267 (0.48), 2.329 (0.48), 2.368 (0.73), 2.524 (2.03), 2.671 (0.48), 2.712 (1.34), 2.728 (0.98), 2.744 (4.36), 2.750 (2.01), 2.763 (5.03), 2.768 (5.47), 2.771 (5.05), 2.774 (5.44), 2.782 (7.33), 2.791 (9.26), 2.803 (9.07), 2.812 (7.08), 2.819 (5.74), 2.826 (8.00), 2.834 (4.36), 2.841 (3.64), 2.847 (3.75), 2.858 (1.51), 2.881 (0.78), 3.167 (1.28), 3.295 (0.80), 3.301 (0.82), 3.316 (2.32), 3.323 (2.55), 3.338 (3.25), 3.343 (3.54), 3.361 (2.01), 3.366 (2.03), 3.380 (0.63), 3.386 (0.54), 3.961 (6.24), 3.975 (16.00), 3.989 (15.43), 4.003 (4.82), 8.212 (5.51).

Intermediate 277

Tert-Butyl [2-(3,3-Difluorocyclobutyl)-2-Oxoethyl] Carbamate

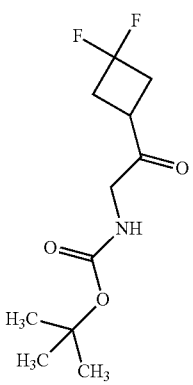 [SMILES: CC(C)(C)OC(=O)NCC(=O)C1CC(F)(F)C1]

To a solution of 2-amino-1-(3,3-difluorocyclobutyl)etha-none hydrochloride (1.77 g, 9.54 mmol) in dichloromethane (43 ml) was added di-tert-butyl dicarbonate (2.29 g, 10.5 mmol) and triethylamine (4.0 ml, 29 mmol). After 2 h of stirring at RT, the reaction mixture was diluted with dichloromethane and extracted with water. After phase separation, the organic phase was dried, concentrated in vacuo and 2.50 g (88% purity) of the title compound was obtained and used without further purification.

$^1$H-NMR (400 MHz, DMSO-d6) δ [ppm]: 1.382 (5.06), 1.468 (16.00), 2.517 (0.48), 3.324 (0.46), 3.789 (0.73), 3.804 (0.73).

Intermediate 278

Rac-Tert-Butyl {[4-(3,3-Difluorocyclobutyl)-2,5-Dioxoimidazolidin-4-Yl]Methyl}Carbamate

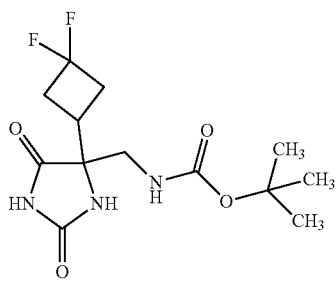 [SMILES: CC(C)(C)OC(=O)NCC1(C2CC(F)(F)C2)NC(=O)NC1=O]

To a solution of tert-butyl [2-(3,3-difluorocyclobutyl)-2-oxoethyl]carbamate (2.50 g, 88% purity, 8.83 mmol) in methanol (16 ml) was added potassium cyanide (2.30 g, 35.3 mmol) and ammonium carbonate (3.39 g, 35.3 mmol) at RT. The reaction mixture was first stirred overnight at 80° C. into a sealed pressure flask. Extra portion of potassium cyanide (1.15 g, 17.7 mmol) and ammonium carbonate (1.70 g, 17.7 mmol) were added due to incomplete conversion. The reaction mixture was additionally stirred overnight at 80° C.

After filtration and washing of the suspension with methanol at RT, the resulting filtrate was concentrated in vacuo. The residue was purified by preparative HPLC (sample preparation: 6.4 g dissolved in a mixture of methanol, water, acetonitrile; column: XBridge C18 5 µm, 100×30 mm; eluent: water→acetonitrile/water 80:20+1% ammonia solution→acetonitrile; flow rate: 80 ml/min; temperature: 40° C.; UV detection: 210 nm). 1.68 g of the desired product was obtained and used without further purification.

LC-MS (Method 9): $R_t$=0.92 min; MS (ESIneg): m/z=318 [M−H]$^-$

Intermediate 279

Rac-5-(Aminomethyl)-5-(3,3-Difluorocyclobutyl) Imidazolidine-2,4-Dione Hydrochloride

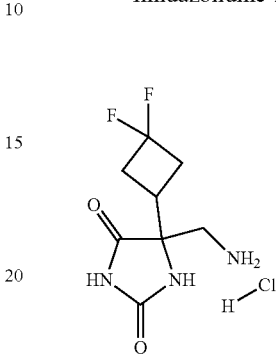

To a solution of rac-tert-butyl {[4-(3,3-difluorocyclobutyl)-2,5-dioxoimidazolidin-4 yl]methyl}carbamate (1.68 g, 5.26 mmol) in dichloromethane (21 ml) were added 6.6 ml of 4M hydrochloric acid (26 mmol) in dioxane at 0° C. The reaction mixture was stirred for 1 h at 0° C. then for 2 h at room temperature. The precipitate was filtered off, washed with dichloromethane and dried in vacuo. 1.46 g of the title compound was obtained and used without further purification.

LC-MS (Method 9): $R_t$=0.29 min; MS (ESIpos): m/z=220 [M−HCl+H]$^+$ $^1$H-NMR (600 MHz, DMSO-d6) δ [ppm]: 2.316 (0.52), 2.333 (0.53), 2.347 (0.45), 2.518 (1.08), 2.575 (0.84), 2.587 (1.27), 2.597 (1.19), 2.619 (0.73), 2.641 (0.62), 2.659 (0.75), 2.666 (0.72), 2.674 (0.61), 2.682 (0.51), 2.689 (0.41), 2.910 (1.65), 2.932 (2.01), 3.114 (2.03), 3.137 (1.66), 3.568 (16.00), 8.324 (2.83), 8.366 (3.74), 11.128 (1.25).

Intermediate 280

Ethyl 5-(1-Fluorocyclopropyl)-1,3-Oxazole-4-Carboxylate

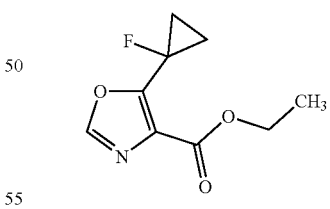

1-fluorocyclopropane-1-carboxylic acid (3.00 g, 28.8 mmol) dissolved in 45 ml of THF was treated with 1,1,-carbonyl-diimidazole (5.61 g, 34.6 mmol) and stirred at room temperature. After 2 h, ethyl isocyanoacetate (3.5 ml, 32 mmol), dissolved in 45 ml of THF, and a solution of lithium bis(trimethylsilyl)amide in THF (29 ml, 1.0 M, 29 mmol) were added at 0° C. The mixture was allowed to warm to room temperature, stirred overnight and then concentrated in vacuo. The residue was taken up with ethyl acetate and washed with water. The organic layer was dried and concentrated in vacuo. The crude product was purified by column chromatography (340 g Ultra Snap Cartridge Biotage; eluent ethyl acetate/cyclohexane, elution gradient 10%→65%).

Samples containing the desired product were united, the solvents were evaporated and the residue was dried in vacuum. 2.84 g (100% purity, 49% yield) of the title compound was used without further purification.

LC-MS (Method 7): $R_t$=1.37 min; MS (ESIpos): m/z=200 [M+H]$^+$ $^1$H-NMR (500 MHz, DMSO-d6) δ [ppm]: 1.205 (0.54), 1.226 (7.72), 1.240 (16.00), 1.254 (7.77), 1.264 (0.41), 1.308 (0.68), 1.421 (0.81), 1.428 (0.83), 1.439 (1.20), 1.445 (1.15), 1.452 (0.62), 1.456 (1.04), 1.461 (0.66), 1.467 (1.15), 1.475 (1.00), 1.480 (0.83), 1.483 (0.77), 1.490 (0.81), 1.493 (0.80), 1.528 (0.66), 1.531 (0.78), 1.538 (0.85), 1.543 (1.22), 1.548 (0.95), 1.554 (1.08), 1.559 (0.97), 1.563 (0.70), 1.570 (0.53), 1.577 (0.58), 1.579 (0.54), 1.585 (0.51), 1.596 (0.75), 1.603 (0.81), 1.621 (0.40), 1.632 (0.73), 1.639 (0.74), 1.652 (0.71), 1.676 (2.04), 1.679 (2.23), 1.689 (2.12), 1.712 (2.11), 1.715 (2.23), 1.722 (1.82), 1.725 (1.63), 4.220 (1.69), 4.234 (0.92), 4.242 (1.04), 4.249 (0.96), 4.256 (3.51), 4.263 (0.62), 4.269 (5.01), 4.276 (0.59), 4.283 (3.52), 4.290 (0.91), 4.297 (0.97), 4.305 (0.81), 4.307 (0.45), 5.551 (4.54), 5.554 (4.40), 9.124 (1.25).

Intermediate 281

2-Amino-1-(1-Fluorocyclopropyl)Ethanone Hydrochloride

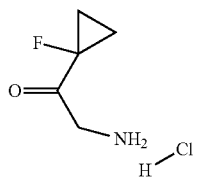

ethyl 5-(1-fluorocyclopropyl)-1,3-oxazole-4-carboxylate (2.84 g, 14.3 mmol) was taken up in 70 ml of 6 N hydrochloric acid and stirred for 2 h at 100° C. The resulting mixture was concentrated in vacuo. 1.88 g (100% purity, 86% yield) of the title compound was obtained and used without further purification.

$^1$H-NMR (400 MHz, DMSO-d6) δ [ppm]: 1.241 (0.49), 1.402 (2.22), 1.418 (6.53), 1.426 (7.45), 1.439 (9.53), 1.447 (7.17), 1.461 (3.46), 1.485 (0.57), 1.506 (0.48), 1.537 (0.47), 1.582 (3.31), 1.596 (6.52), 1.604 (6.02), 1.620 (2.26), 1.627 (3.14), 1.641 (6.56), 1.650 (6.39), 1.665 (2.14), 4.235 (16.00), 8.356 (5.64).

Intermediate 282

Tert-Butyl [2-(1-Fluorocyclopropyl)-2-Oxoethyl] Carbamate

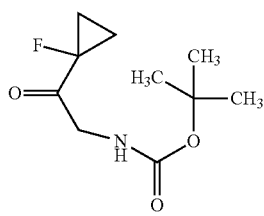

To a solution of 2-amino-1-(1-fluorocyclopropyl)ethanone hydrochloride (1.88 g, 12.2 mmol) in dichloromethane (55 ml) was added di-tert-butyl dicarbonate (2.94 g, 13.5 mmol) and triethylamine (5.1 ml, 37 mmol). After 1.5 h of stirring at RT, the reaction mixture was washed with water. After phase separation, the organic phase was dried; concentrated in vacuo and 2.48 g of the title compound was obtained and used without further purification.

LC-MS (Method 9): $R_t$=1.39 min; MS (ESIpos): m/z=218 [M+H]$^+$

Intermediate 283

Rac-Tert-Butyl {[4-(1-Fluorocyclopropyl)-2,5-Dioxoimidazolidin-4-Yl]Methyl}Carbamate

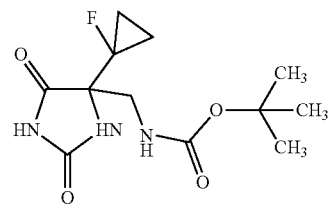 [SMILES: CC(C)(C)OC(=O)NCC1(C2(F)CC2)NC(=O)NC1=O]

To a solution of tert-butyl [2-(1-fluorocyclopropyl)-2-oxoethyl]carbamate (2.46 g, 11.3 mmol) in methanol (20 ml) was added potassium cyanide (2.95 g, 45.3 mmol) and ammonium carbonate (4.35 g, 45.3 mmol) at RT. The reaction mixture was stirred overnight at 80° C. into a sealed pressure flask. After filtration at RT, the resulting filtrate was concentrated in vacuo. The residue was purified by preparative HPLC (sample preparation: 7.4 g dissolved in a mixture of methanol, water, acetonitrile; column: XBridge C18 5 μm, 100×30 mm; eluent: water→acetonitrile/water 80:20+ 1% ammonia solution→acetonitrile; flow rate: 80 ml/min; temperature: 40° C.; UV detection: 220 nm). 2.31 g of the desired product was obtained and used without further purification LC-MS (Method 9): $R_t$=0.65 min; MS (ESIneg): m/z=286 [M−H]$^-$ Intermediate 284

Rac-5-(Aminomethyl)-5-(1-Fluorocyclopropyl)Imidazolidine-2,4-Dione Hydrochloride

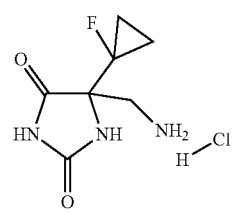

To a solution of rac-tert-butyl {[4-(1-fluorocyclopropyl)-2,5-dioxoimidazolidin-4 yl]methyl}carbamate (1.20 g, 4.18 mmol) in dichloromethane (36 ml) were added 5.2 ml (21 mmol) of 4M hydrochloric acid in dioxane at RT. The reaction mixture was stirred for 3 days and then concentrated in vacuo. 1.04 g of the title compound was used without further purification.

LC-MS (Method 9): $R_t$=0.25 min; MS (ESIpos): m/z=188 [M−HCl+H]$^+$

¹H-NMR (600 MHz, DMSO-d6) δ [ppm]: 0.814 (0.66), 0.833 (2.66), 0.842 (2.91), 0.847 (3.07), 0.851 (3.10), 0.859 (2.45), 0.869 (2.25), 0.892 (0.51), 0.965 (0.55), 0.999 (0.64), 1.020 (2.80), 1.039 (5.31), 1.043 (5.25), 1.048 (3.48), 1.060 (9.17), 1.076 (2.31), 1.081 (3.58), 1.091 (5.77), 1.109 (1.82), 1.120 (0.63), 1.182 (1.41), 1.194 (2.97), 1.206 (1.66), 1.368 (11.79), 1.757 (5.46), 2.117 (2.39), 3.109 (7.54), 3.132 (9.02), 3.347 (8.25), 3.568 (4.33), 3.864 (1.61), 3.874 (1.62), 4.084 (0.44), 4.096 (1.31), 4.108 (1.33), 4.120 (0.50), 7.902 (0.50), 8.098 (0.91), 8.444 (16.00), 8.474 (9.62), 11.159 (4.19).

Intermediate 285

Methyl 5-(2,5-Dimethyl-1,3-Thiazol-4-Yl)-1,3-Oxazole-4-Carboxylate

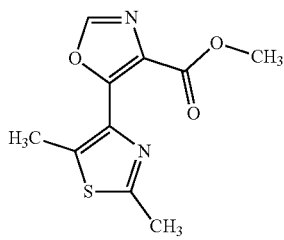

2,5-dimethyl-1,3-thiazole-4-carboxylicacid (3.00 g, 19.1 mmol) dissolved in 30 ml of THF was treated with 1,1,-carbonyl-diimidazole (3.71 g, 22.9 mmol) and stirred at room temperature. After 1 h, ethyl isocyanoacetate (2.3 ml, 21 mmol), dissolved in 30 ml of THF, and a solution of lithium bis(trimethylsilyl)amide in THF (19 ml, 1.0 M, 19 mmol) were added at 0° C. The mixture was allowed to warm to room temperature, stirred for 2 days and then concentrated in vacuo. The residue was taken up with ethyl acetate and washed with water. The organic layer was dried and concentrated in vacuo. The crude product (ethyl ester derivative) was diluted in 50 ml of methanol; Isolute® was added, and the solvent was evaporated on a rotary evaporator at higher temperature. The crude was then purified by column chromatography (340 g Ultra Snap Cartridge Biotage; eluent ethyl acetate/cyclohexane, elution gradient 15%→100%). Samples containing the desired product were united, the solvents were evaporated and the residue was dried in vacuum. 2.67 g (100% purity, 59% yield) of the title compound was used without further purification.

LC-MS (Method 7): $R_t$=1.11 min; MS (ESIpos): m/z=238 [M+H]⁺

¹H-NMR (400 MHz, DMSO-d6) δ [ppm]: 2.401 (13.72), 2.673 (12.80), 3.805 (16.00), 8.602 (2.93).

Intermediate 286

2-Amino-1-(2,5-Dimethyl-1,3-Thiazol-4-Yl)Ethanone Hydrochloride

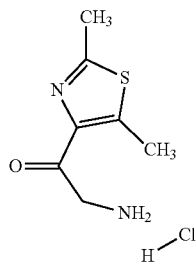

methyl 5-(2,5-dimethyl-1,3-thiazol-4-yl)-1,3-oxazole-4-carboxylate (2.67 g, 11.2 mmol) was taken up in 60 ml of 6 N hydrochloric acid and stirred for 2 h at 100° C. The resulting mixture was concentrated in vacuo. 2.90 g of the title compound was obtained and used without further purification.

LC-MS (Method 9): $R_t$=0.77 min; MS (ESIpos): m/z=171 [M−HCl+H]⁺

Intermediate 287

Tert-Butyl [2-(2,5-Dimethyl-1,3-Thiazol-4-Yl)-2-Oxoethyl]Carbamate

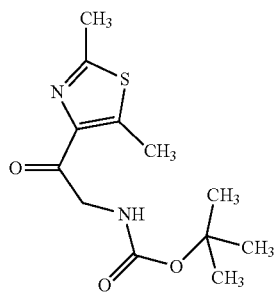 [SMILES: Cc1nc(C(=O)CNC(=O)OC(C)(C)C)c(C)s1]

To a solution of 2-amino-1-(2,5-dimethyl-1,3-thiazol-4-yl)ethanone hydrochloride (2.90 g, 14.0 mmol) in dichloromethane (80 ml) was added di-tert-butyl dicarbonate (2.86 g, 13.1 mmol) and triethylamine (13 ml, 95 mmol). After 2 h of stirring at RT, the reaction mixture was washed with water. After phase separation, the organic phase was dried; concentrated in vacuo and 3.17 g of the title compound was obtained and used without further purification.

LC-MS (Method 9): $R_t$=1.38 min; MS (ESIpos): m/z=271 [M+H]⁺

¹H-NMR (600 MHz, DMSO-d6) δ [ppm]: 1.111 (2.20), 1.275 (0.74), 1.367 (0.75), 1.394 (16.00), 1.412 (0.44), 2.500 (4.08), 2.607 (9.87), 2.663 (9.51), 4.143 (1.81), 4.153 (1.78), 7.156 (0.63).

Intermediate 288

Rac-Tert-Butyl {[4-(2,5-Dimethyl-1,3-Thiazol-4-Yl)-2,5-Dioxoimidazolidin-4-Yl]Methyl}Carbamate

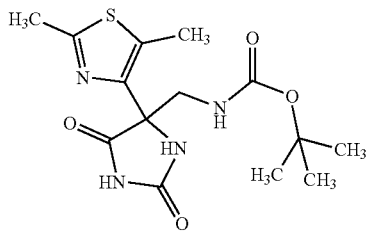 [SMILES: Cc1nc(C2(CNC(=O)OC(C)(C)C)NC(=O)NC2=O)c(C)s1]

To a solution of tert-butyl [2-(2,5-dimethyl-1,3-thiazol-4-yl)-2-oxoethyl]carbamate (3.17 g, 11.7 mmol) in methanol (21 ml) was added potassium cyanide (3.05 g, 46.9 mmol) and ammonium carbonate (4.51 g, 46.9 mmol) at RT. The reaction mixture was first stirred overnight at 60° C. into a sealed pressure flask. Extra portion of potassium cyanide (1.07 g, 16.4 mmol) and ammonium carbonate (1.58 g, 16.4 mmol) were added due to incomplete conversion. The reaction mixture was first stirred for 7 h at 60° C., then for 48 h at RT.

After filtration and washing of the suspension with methanol at RT, the resulting filtrate was concentrated in vacuo. The residue was purified by preparative HPLC (sample preparation: 5.4 g dissolved in acetonitrile; column: XBridge C18 5 μm, 100×30 mm; eluent: water→acetonitrile/water 80:20+1% ammonia solution→acetonitrile; flowrate: 80 ml/min; temperature: 45° C.; UV detection: 210 nm). 1.22 g of the desired product was obtained and used without further purification.

LC-MS (Method 7): $R_t$=1.09 min; MS (ESIpos): m/z=341 [M+H]$^+$

Intermediate 289

Rac-5-(Aminomethyl)-5-(2,5-Dimethyl-1,3-Thiazol-4-Yl)Imidazolidine-2,4-Dione Hydrochloride

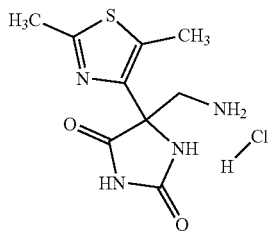

To a solution rac-tert-butyl {[4-(2,5-dimethyl-1,3-thiazol-4-yl)-2,5-dioxoimidazolidin-4 yl]methyl}carbamate (300 mg, 881 μmol) in dichloromethane (3.5 ml) were added 1.1 ml of 4M hydrochloric acid (4.4 mmol) in dioxane at RT. After stirring for 1 at RT, the precipitate was filtered off, washed with dichloromethane and dried in vacuo. 243 mg of the title compound was obtained and used without further purification.

LC-MS (Method 9): $R_t$=0.24 min; MS (ESIpos): m/z=241 [M−HCl+H]$^+$ $^1$H-NMR (400 MHz, DMSO-d6) δ [ppm]: −0.008 (2.30), 0.008 (2.40), 1.110 (0.56), 1.596 (1.42), 1.757 (2.42), 2.074 (2.42), 2.273 (0.40), 2.368 (0.52), 2.418 (12.62), 2.525 (1.42), 2.567 (16.00), 2.712 (0.47), 3.168 (8.55), 3.403 (0.64), 3.568 (1.07), 3.579 (0.83), 3.600 (0.74), 8.432 (1.64), 8.931 (0.84), 11.379 (2.14).

Intermediate 290

Ethyl 5-(5-Cyclopropyl-1,3-Thiazol-4-Yl)-1,3-Oxazole-4-Carboxylate

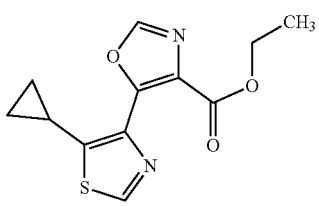 [SMILES: CCOC(=O)c1ncoc1-c1ncsc1C1CC1]

5-cyclopropyl-1,3-thiazole-4-carboxylic acid (2.00 g, 11.8 mmol) dissolved in 30 ml of THF was treated with 1,1,-carbonyl-diimidazole (2.30 g, 14.2 mmol) and stirred at room temperature. After 1 h, ethyl isocyanoacetate (1.4 ml, 13 mmol), dissolved in 20 ml of THF, and a solution of lithium bis(trimethylsilyl)amide in THF (12 ml, 1.0 M, 12 mmol) were added at 0° C. The mixture was allowed to warm to room temperature, stirred overnight and then concentrated in vacuo. The residue was taken up with ethyl acetate and washed with water. The organic layer was dried and concentrated in vacuo. The crude product was purified by column chromatography (50 g Ultra Snap Cartridge Biotage; eluent ethyl acetate/cyclohexane, elution gradient 10%→100%). Samples containing the desired product were united, the solvents were evaporated and the residue was dried in vacuum. 2.30 g (100% purity, 74% yield) of the title compound was used without further purification.

LC-MS (Method 7): $R_t$=1.37 min; MS (ESIpos): m/z=265 [M+H]$^+$ $^1$H-NMR (600 MHz, DMSO-d6) δ [ppm]: 0.614 (1.40), 0.622 (5.17), 0.625 (4.35), 0.630 (4.44), 0.633 (5.10), 0.641 (1.42), 1.077 (1.50), 1.084 (4.03), 1.088 (4.16), 1.098 (4.20), 1.101 (4.01), 1.109 (1.32), 1.162 (7.86), 1.174 (16.00), 1.186 (7.91), 1.989 (2.00), 2.046 (0.62), 2.054 (1.27), 2.060 (1.37), 2.068 (2.39), 2.076 (1.30), 2.082 (1.16), 2.090 (0.56), 4.026 (0.49), 4.038 (0.48), 4.198 (2.59), 4.209 (7.79), 4.221 (7.66), 4.233 (2.49), 8.623 (9.20), 8.975 (8.85).

Intermediate 291

2-Amino-1-(5-Cyclopropyl-1,3-Thiazol-4-Yl)Ethanone Hydrochloride

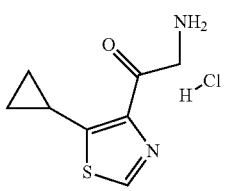

ethyl 5-(5-cyclopropyl-1,3-thiazol-4-yl)-1,3-oxazole-4-carboxylate (2.30 g, 8.70 mmol) was taken up in 43 ml of 6 N hydrochloric acid and stirred for 2 h at 100° C. The resulting mixture was concentrated in vacuo. 1.99 g (100% purity) of the title compound was obtained and used without further purification.

LC-MS (Method 9): $R_t$=1.15 min; MS (ESIpos): m/z=183 [M−HCl+H]$^+$

Intermediate 292

Tert-Butyl [2-(5-Cyclopropyl-1,3-Thiazol-4-Yl)-2-Oxoethyl]Carbamate

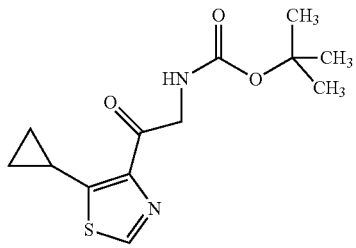 [SMILES: CC(C)(C)OC(=O)NCC(=O)c1ncsc1C1CC1]

To a solution of 2-amino-1-(5-cyclopropyl-1,3-thiazol-4-yl)ethanone hydrochloride (1.99 g, 9.10 mmol) in dichloromethane (41 ml) was added di-tert-butyl dicarbonate (2.18 g, 10.0 mmol) and triethylamine (7.6 ml, 55 mmol). After 2 h of stirring at RT, the reaction mixture was washed with water. After phase separation, the organic phase was dried; concentrated in vacuo and 2.44 g of the title compound was obtained and used without further purification.

LC-MS (Method 9): $R_t$=1.58 min; MS (ESIpos): m/z=283 [M+H]$^+$ $^1$H-NMR (400 MHz, DMSO-d6) δ [ppm]: 0.724 (1.35), 0.729 (1.19), 0.741 (1.36), 0.752 (0.43), 1.109 (0.60), 1.268 (0.47), 1.279 (1.24), 1.285 (1.29), 1.300 (1.80), 1.306 (2.06), 1.316 (0.84), 1.364 (0.70), 1.388 (1.53), 1.402 (16.00), 1.467 (8.35), 3.129 (0.61), 4.394 (1.90), 4.409 (1.87), 6.976 (0.58), 8.892 (1.62).

Intermediate 293

Rac-Tert-Butyl {[4-(5-Cyclopropyl-1,3-Thiazol-4-Yl)-2,5-Dioxoimidazolidin-4-Yl]Methyl}Carbamate

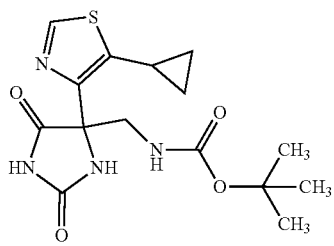 [SMILES: CC(C)(C)OC(=O)NCC1(c2ncsc2C2CC2)NC(=O)NC1=O]

To a solution of tert-butyl [2-(5-cyclopropyl-1,3-thiazol-4-yl)-2-oxoethyl]carbamate (2.44 g, 8.64 mmol) in methanol (20 ml) was added potassium cyanide (2.25 g, 34.6 mmol) and ammonium carbonate (3.32 g, 34.6 mmol) at RT. The reaction mixture was stirred for 5 hours at 60° C., followed by 48 h at RT. into a sealed pressure flask. After additional 24 h stirring at 80° C., the reaction mixture was filtered at RT and the resulting filtrate was concentrated in vacuo.

The residue was purified by preparative HPLC (sample preparation: 5.6 g dissolved in acetonitrile; column: XBridge C18 5 µm, 100×30 mm; eluent: water→acetonitrile/water 80:20+1% ammonia solution→acetonitrile; flow rate: 80 ml/min; temperature: 40° C.; UV detection: 210 nm). 1.98 g of the desired product was obtained and used without further purification.

LC-MS (Method 7): $R_t$=1.22 min; MS (ESIpos): m/z=353 [M+H]$^+$

Intermediate 294

Ent-Tert-Butyl {[4-(5-Cyclopropyl-1,3-Thiazol-4-Yl)-2,5-Dioxoimidazolidin-4-Yl]Methyl}Carbamate

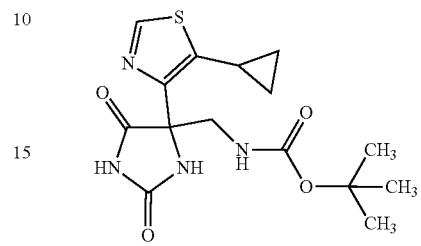

Enantiomeric separation of rac-tert-butyl {[4-(5-cyclopropyl-1,3-thiazol-4-yl)-2,5-dioxoimidazolidin-4-yl]methyl}carbamate by preparative chiral SFC [sample preparation: 1.48 g dissolved in 50 ml acetonitrile/50 ml MeOH; column: Chiralpak AD SFC 20 µm 360×50 mm; eluent: 80% carbon dioxide/20% isopropanol; injection volume: 5 ml; flow rate: 400 ml/min; temperature: 40° C.; UV detection: 210 nm] afforded 0.63 g (100% purity) of the desired product.

Analytical chiral SFC: Analytical chiral SFC: $R_t$=1.95 min, e.e. =98.4% [column: Chiralpak AD-3; eluent: 80% carbon dioxide/20% isopropanol; flow rate: 3 ml/min; temperature: 40° C.; UV detection: 210 nm]

LC-MS (Method 7): $R_t$=1.24 min; MS (ESIpos): m/z=353 [M+H]$^+$ $^1$H NMR (600 MHz, DMSO-d$_6$) δ ppm 10.72-11.07 (m, 1H), 8.78 (s, 1H), 7.97-8.17 (m, 1H), 6.63-6.80 (m, 1H), 3.70-4.05 (m, 2H), 1.89-2.05 (m, 1H), 1.38 (s, 9H), 0.93-1.10 (m, 2 H), 0.63-0.75 (m, 1H), 0.47-0.60 (m, 1H)

Intermediate 295

Rac-5-(Aminomethyl)-5-(5-Cyclopropyl-1,3-Thiazol-4-Yl)Imidazolidine-2,4-Dione Hydrochloride

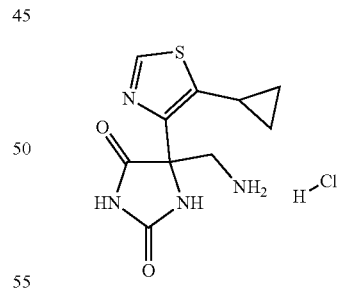

To a solution of rac-tert-butyl {[4-(5-cyclopropyl-1,3-thiazol-4-yl)-2,5-dioxoimidazolidin-4 yl]methyl}carbamate (500 mg, 1.42 mmol) in dichloromethane (12 ml) were added 1.8 ml of 4M hydrochloric acid (7.1 mmol) in dioxane at RT. The reaction mixture was stirred for 1 h at room temperature, after which extra portion of 4M hydrochloric acid (180 µl, 710 µmol) was added due to incomplete conversion. After stirring for 1 at RT, the precipitate was filtered off, washed with dichloromethane and dried in vacuo. 435 mg of the title compound was obtained and used without further purification.

LC-MS (Method 9): R$_t$=0.32 min, MS (ESIpos): m/z=253 [M–HCl+H]$^+$ $^1$H-NMR (600 MHz, DMSO-d6) δ [ppm]: 0.005 (0.77), 0.553 (0.63), 0.562 (1.05), 0.570 (1.98), 0.576 (1.14), 0.578 (2.43), 0.584 (1.74), 0.587 (1.07), 0.593 (0.85), 0.719 (0.75), 0.725 (1.02), 0.728 (1.68), 0.734 (2.45), 0.742 (2.06), 0.751 (1.31), 0.759 (0.76), 1.014 (0.53), 1.021 (0.52), 1.024 (0.48), 1.029 (1.40), 1.036 (1.57), 1.039 (1.34), 1.045 (1.89), 1.049 (1.86), 1.054 (2.04), 1.058 (2.06), 1.063 (1.84), 1.068 (1.52), 1.071 (1.57), 1.078 (1.43), 1.083 (0.58), 1.086 (0.55), 1.093 (0.53), 1.596 (0.75), 1.910 (0.78), 1.919 (1.58), 1.924 (1.69), 1.927 (0.97), 1.932 (3.13), 1.938 (1.02), 1.941 (1.62), 1.946 (1.54), 1.955 (0.75), 2.523 (0.42), 2.573 (0.85), 3.058 (0.68), 3.168 (12.10), 3.568 (0.84), 3.615 (0.43), 3.626 (0.72), 3.637 (1.65), 3.647 (1.89), 3.653 (1.97), 3.662 (1.71), 3.684 (0.47), 8.368 (3.59), 8.628 (4.46), 8.862 (16.00), 11.327 (3.71).

Intermediate 296

Ent-5-(Aminomethyl)-5-(5-Cyclopropyl-1,3-Thiazol-4-Yl)Imidazolidine-2,4-Dione Hydrochloride

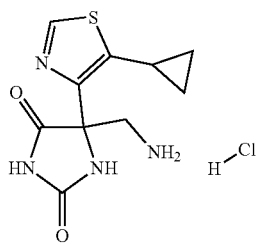 [SMILES: NCC1(c2ncsc2C2CC2)NC(=O)NC1=O ; Cl]

To a solution of ent-tert-butyl {[4-(5-cyclopropyl-1,3-thiazol-4-yl)-2,5-dioxoimidazolidin-4-yl]methyl}carbamate (630 mg, 1.79 mmol) in dichloromethane (9.6 ml) were added 2.7 ml of 4M hydrochloric acid (11 mmol) in dioxane at RT. After stirring overnight at RT, the precipitate was filtered off, washed with dichloromethane and dried in vacuo. 629 mg of the title compound was obtained and used without further purification.

LC-MS (Method 9): R$_t$=0.28 min, MS (ESIpos): m/z=253 [M–HCl+H]$^+$ $^1$H-NMR (400 MHz, DMSO-d6) δ [ppm]: –0.008 (0.98), 0.008 (0.97), 0.546 (0.72), 0.560 (1.47), 0.569 (1.66), 0.573 (1.79), 0.583 (1.98), 0.588 (1.89), 0.597 (1.28), 0.601 (1.04), 0.713 (1.00), 0.718 (1.31), 0.722 (1.47), 0.726 (1.98), 0.731 (1.99), 0.740 (1.67), 0.745 (1.72), 0.754 (1.66), 0.768 (0.83), 1.003 (0.62), 1.013 (0.56), 1.026 (1.67), 1.036 (2.17), 1.040 (2.13), 1.045 (4.49), 1.056 (2.75), 1.061 (2.48), 1.065 (4.72), 1.071 (2.24), 1.075 (2.04), 1.085 (1.58), 1.094 (0.52), 1.098 (0.47), 1.108 (0.51), 1.375 (0.77), 1.596 (1.47), 1.887 (0.79), 1.900 (1.60), 1.908 (1.73), 1.921 (3.04), 1.929 (1.13), 1.934 (1.66), 1.942 (1.50), 1.954 (0.71), 2.329 (0.56), 2.670 (0.55), 3.568 (16.00), 3.588 (0.86), 3.603 (1.13), 3.620 (1.81), 3.635 (1.66), 3.673 (1.54), 3.687 (1.68), 3.705 (1.06), 3.720 (0.75), 4.363 (2.00), 5.755 (12.12), 8.277 (3.98), 8.576 (3.11), 8.868 (12.20), 11.359 (4.74).

Intermediate 297

6-Fluoro-4'-(Trifluoromethyl)[1,1'-Biphenyl]-2-Carboxylic Acid

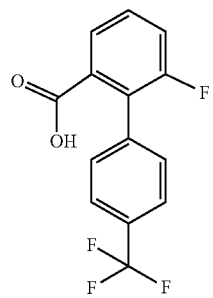 [SMILES: O=C(O)c1cccc(F)c1-c1ccc(C(F)(F)F)cc1]

To a suspension of [4-(trifluoromethyl)phenyl]boronic acid (2.47 g, 13.0 mmol) and 2-bromo-3-fluorobenzoic acid (1.90 g, 8.68 mmol) in 1,4-dioxane (53 ml) was added, under argon, a solution of K$_3$PO$_4$ in water (17 ml, 1.5 M, 26 mmol), dichlorobis(triphenylphosphin)palladium (II) (609 mg, 868 µmol, CAS 13965-03-2) and XPhos (414 mg, 868 µmol, CAS 564483-18-7). The reaction mixture was first stirred for 7.5 h at 80° C., then overnight at RT. The resulting mixture was filtered through celite, dried and concentrated in vacuo. 3.35 g (46% purity, 63% yield) of the title compound were obtained and used without further purification.

LC-MS (Method 7): R$_t$=1.86 min; MS (ESIneg): m/z=283 [M–H]$^-$

Intermediate 298

Methyl 5-(1,3-Dimethyl-1H-Pyrazol-5-Yl)-1,3-Oxazole-4-Carboxylate

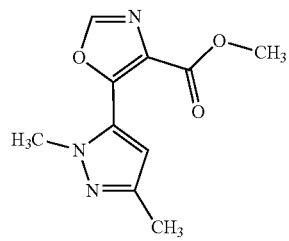

1,3-dimethyl-1H-pyrazole-5-carboxylic acid (4.00 g, 28.5 mmol) dissolved in 30 ml of THF was treated with 1,1,-carbonyl-diimidazole (5.55 g, 34.3 mmol) and stirred at room temperature. After 1 h, ethyl isocyanoacetate (3.4 ml, 31 mmol), dissolved in 30 ml of THF, and a solution of lithium bis(trimethylsilyl)amide in THF (28.5 ml, 1.0 M, 28.5 mmol) were added at 0° C. The mixture was allowed to warm to room temperature, stirred for 3 days and concentrated in vacuo. The crude product (ethyl ester derivative) was diluted in methanol; Isolute® was added, and the solvent was evaporated on a rotary evaporator at higher temperature. The crude was then purified by column chromatography (340 g Ultra Snap Cartridge Biotage; eluent ethyl acetate/cyclohexane, elution gradient 20%→100%). Samples containing the desired product were united, the solvents were evaporated and the residue was dried in vacuum. 2.17 g (100% purity, 34% yield) of the title compound was used without further purification.

LC-MS (Method 9): $R_t$=1.05 min; MS (ESIpos): m/z=222 [M+H]$^+$ $^1$H-NMR (400 MHz, DMSO-d6) δ [ppm]: 2.204 (6.75), 3.800 (16.00), 6.664 (1.56), 8.661 (1.60).

Intermediate 299

2-Amino-1-(1,3-Dimethyl-1H-Pyrazol-5-Yl)Ethanone Hydrochloride

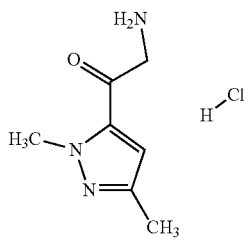

methyl 5-(1,3-dimethyl-1H-pyrazol-5-yl)-1,3-oxazole-4-carboxylate (2.17 g, 9.81 mmol) was taken up in 49 ml of 6 N hydrochloric acid and stirred for 2 h at 100° C. The resulting mixture was concentrated in vacuo. 2.28 g of the title compound was obtained and used without further purification.

LC-MS (Method 9): $R_t$=0.75 min; MS (ESIpos): m/z=154 [M–HCl+H]$^+$ $^1$H-NMR (400 MHz, DMSO-d6) δ [ppm]: 2.074 (0.56), 2.213 (13.73), 3.981 (0.52), 4.013 (16.00), 4.028 (0.44), 4.322 (0.88), 4.336 (2.45), 4.350 (2.49), 4.364 (0.98), 4.539 (0.66), 4.681 (0.72), 7.049 (4.23), 8.397 (1.22).

Intermediate 300

Tert-Butyl [2-(1,3-Dimethyl-1H-Pyrazol-5-Yl)-2-Oxoethyl]Carbamate

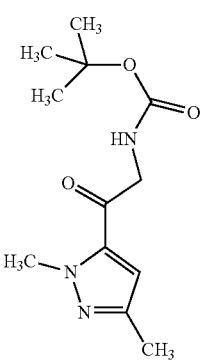

To a solution of 2-amino-1-(1,3-dimethyl-1H-pyrazol-5-yl)ethanone hydrochloride (2.28 g, 12.0 mmol) in dichloromethane (54 ml) was added di-tert-butyl dicarbonate (2.89 g, 13.2 mmol) and triethylamine (10 ml, 72 mmol). After 2 h of stirring at RT, the reaction mixture was diluted with dichlorometane and washed with water. After phase separation, the organic phase was dried; concentrated in vacuo and 2.77 g of the title compound was obtained and used without further purification.

LC-MS (Method 9): $R_t$=1.37 min; MS (ESIpos): m/z=254 [M+H]$^+$ $^1$H-NMR (600 MHz, DMSO-d6) δ [ppm]: 0.939 (0.43), 1.113 (1.13), 1.287 (0.64), 1.368 (1.90), 1.394 (12.03), 1.469 (16.00), 2.190 (6.38), 3.965 (5.13), 4.207 (1.38), 4.217 (1.35), 6.949 (1.37), 7.088 (0.49).

Intermediate 301

Rac-Tert-Butyl {[4-(1,3-Dimethyl-1H-Pyrazol-5-Yl)-2,5-Dioxoimidazolidin-4-Yl]Methyl}Carbamate

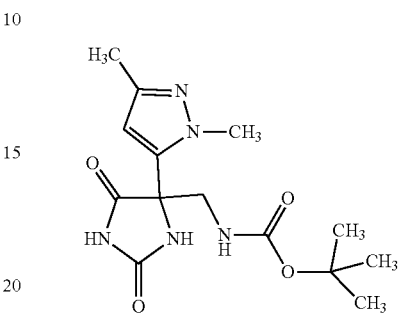

To a solution of tert-butyl [2-(1,3-dimethyl-1H-pyrazol-5-yl)-2-oxoethyl]carbamate (2.77 g, 10.9 mmol) in methanol (12 ml) was added potassium cyanide (2.85 g, 43.7 mmol) and ammonium carbonate (4.20 g, 43.7 mmol) at RT. The reaction mixture was stirred for 6 hours at 80° C., followed by 48 h at 40° C. into a sealed pressure flask. After filtration and washing of the suspension with methanol at RT, the resulting filtrate was concentrated in vacuo. The residue was purified by preparative HPLC (sample preparation: 3.25 g dissolved in a mixture of methanol/water; column: XBridge C18 5 μm, 100×30 mm; eluent: acetonitrile/water+1% ammonia solution; temperature: 40° C.; UV detection: 210 nm). 204 mg of the desired product was obtained and used without further purification.

LC-MS (Method 9): $R_t$=0.35 min; MS (ESIpos): m/z=324 [M+H]$^+$

Intermediate 302

Rac-5-(Aminomethyl)-5-(1,3-Dimethyl-1H-Pyrazol-5-Yl)Imidazolidine-2,4-Dione Hydrochloride

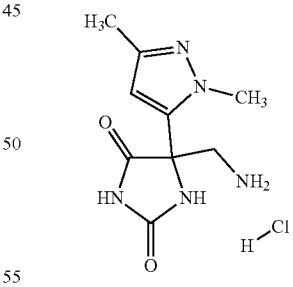

To a solution of rac-tert-butyl {[4-(1,3-dimethyl-1H-pyrazol-5-yl)-2,5-dioxoimidazolidin-4 yl]methyl}carbamate (200 mg, 619 μmol) in dichloromethane (5 ml) were added 770 μl of 4M hydrochloric acid (3.1 mmol) in dioxane at RT. The reaction mixture was stirred for 2 h and concentrated in vacuo. Due to incomplete conversion, the crude was diluted again in 5 ml DCM and 770 μl of 4M hydrochloric acid (3.1 mmol) in dioxane were added. The reaction mixture was stirred overnight at RT and concentrated in vacuo. 197 mg of the title compound was obtained and used without further purification.

LC-MS (Method 9): $R_t$=0.23 min; MS (ESIneg): m/z=222 [M−HCl−H]⁻

Intermediate 303

Ethyl 5-(1-Chlorocyclopropyl)-1,3-Oxazole-4-Carboxylate

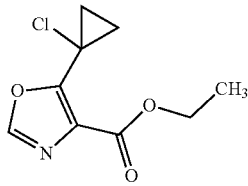

1-chlorocyclopropane-1-carboxylic acid (4.12 g, 34.2 mmol) dissolved in 50 ml of THF was treated with 1,1,-carbonyl-diimidazole (6.65 g, 41.0 mmol) and stirred at room temperature. After 2 h, ethyl isocyanoacetate (4.1 ml, 38 mmol), dissolved in 50 ml of TH F, and a solution of lithium bis(trimethylsilyl)amide in THF (34 ml, 1.0 M, 34 mmol) were added at 0° C. The mixture was allowed to warm to room temperature, stirred overnight and then concentrated in vacuo. The residue was taken up with ethyl acetate and washed with water. The organic layer was dried and concentrated in vacuo. The crude product was purified by column chromatography (340 g Ultra Snap Cartridge Biotage; eluent ethyl acetate/cyclohexane, elution gradient 10%→100%). Samples containing the desired product were united, the solvents were evaporated and the residue was dried in vacuum. 3.38 g of the title compound was used without further purification.

LC-MS (Method 7): $R_t$=1.50 min; MS (ESIpos): m/z=216 [M+H]⁺

¹H-NMR (400 MHz, DMSO-d6) δ [ppm]: −0.008 (0.64), 0.008 (0.67), 1.314 (7.63), 1.332 (16.00), 1.350 (7.76), 1.533 (3.46), 1.540 (13.18), 1.543 (13.20), 1.550 (3.34), 2.524 (0.43), 4.298 (2.49), 4.315 (7.69), 4.333 (7.55), 4.351 (2.42), 8.489 (5.44).

Intermediate 304

2-Amino-1-(1-Chlorocyclopropyl)Ethanone Hydrochloride

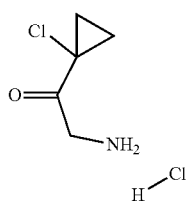

ethyl 5-(1-chlorocyclopropyl)-1,3-oxazole-4-carboxylate (3.38 g, 15.7 mmol) was taken up in 77 ml of 6 N hydrochloric acid and stirred for 2 h at 100° C. The resulting mixture was concentrated in vacuo. 2.56 g of the title compound was obtained and used without further purification.

LC-MS (Method 9): $R_t$=0.82 min; MS (ESIpos): m/z=134 [M−HCl+H]⁺

¹H-NMR (600 MHz, DMSO-d6) δ [ppm]: 1.253 (0.53), 1.574 (4.17), 1.583 (12.73), 1.589 (12.55), 1.597 (5.57), 1.625 (0.64), 1.721 (0.61), 1.749 (5.48), 1.758 (12.77), 1.763 (12.59), 1.773 (4.38), 3.652 (0.41), 4.187 (16.00), 7.297 (1.22), 7.381 (1.40), 7.466 (1.22), 8.403 (5.29).

Intermediate 305

Tert-Butyl [2-(1-Chlorocyclopropyl)-2-Oxoethyl] Carbamate

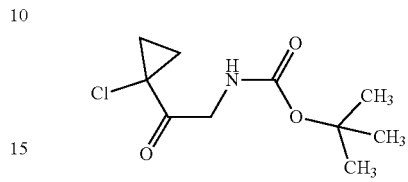

To a solution of 2-amino-1-(1-chlorocyclopropyl)ethanone hydrochloride (2.56 g, 15.1 mmol) in dichloromethane (100 ml) was added di-tert-butyl dicarbonate (3.61 g, 16.6 mmol) and triethylamine (17 ml, 120 mmol). After 2 h of stirring at RT, the reaction mixture was washed with water. After phase separation, the organic phase was dried; concentrated in vacuo and 3.22 g of the title compound was obtained and used without further purification.

¹H-NMR (600 MHz, DMSO-d6) δ [ppm]: 1.015 (0.44), 1.113 (1.18), 1.327 (0.64), 1.340 (0.71), 1.368 (4.07), 1.377 (9.45), 1.390 (0.93), 1.425 (0.51), 1.449 (0.50), 1.458 (1.39), 1.463 (1.83), 1.470 (16.00), 1.631 (0.53), 1.639 (1.01), 1.644 (0.90), 2.501 (1.09), 4.091 (1.08), 4.101 (1.07).

Intermediate 306

Rac-Tert-Butyl {[4-(1-Chlorocyclopropyl)-2,5-Dioxoimidazolidin-4-Yl]Methyl}Carbamate

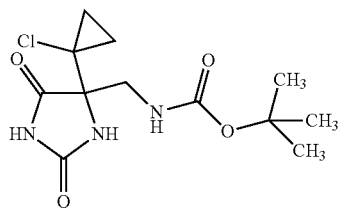 [SMILES: CC(C)(C)OC(=O)NCC1(C2(Cl)CC2)NC(=O)NC1=O]

To a solution of tert-butyl [2-(1-chlorocyclopropyl)-2-oxoethyl]carbamate (3.20 g, 13.7 mmol) in methanol (12 ml) was added potassium cyanide (3.57 g, 54.8 mmol) and ammonium carbonate (5.26 g, 54.8 mmol) at RT. The reaction mixture was stirred for 6 hours at 80° C., followed by 48 h at 40° C. into a sealed pressure flask. After filtration and washing of the suspension with methanol at RT, the resulting filtrate was concentrated in vacuo. The residue was purified by preparative HPLC (sample preparation: 5.14 g dissolved in acetonitrile; column: XBridge C18 5 μm, 100× 30 mm; eluent: water→acetonitrile/water 80:20+1% ammonia solution→acetonitrile; flow rate: 80 ml/min; temperature: 40° C.; UV detection: 210 nm). 342 mg of the desired product was obtained and used without further purification.

LC-MS (Method 9): $R_t$=0.72 min; MS (ESIneg): m/z=302 [M−H]⁻

¹H-NMR (400 MHz, DMSO-d6) δ [ppm]: 1.007 (0.66), 1.025 (0.99), 1.153 (0.56), 1.165 (1.09), 1.362 (16.00), 1.409 (0.62), 7.833 (0.77).

Intermediate 307

Rac-5-(Aminomethyl)-5-(1-Chlorocyclopropyl)Imidazolidine-2,4-Dione Hydrochloride

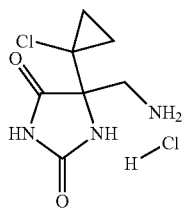

To a solution of rac-tert-butyl {[4-(1-chlorocyclopropyl)-2,5-dioxoimidazolidin-4 yl]methyl}carbamate (340 mg, 1.12 mmol) in dichloromethane (10 ml) were added 1.4 ml of 4M hydrochloric acid (5.6 mmol) in dioxane at RT. The reaction mixture was stirred for 2 h at room temperature and concentrated in vacuo. The crude was again diluted in 10 ml DCM after which extra portion of 4M hydrochloric acid (1.4 ml, 4.0 M, 5.6 mmol) was added due to incomplete conversion. After stirring overnight at RT, the precipitate was filtered off, washed with dichloromethane and dried in vacuo. 256 mg of the title compound was obtained and used without further purification.

LC-MS (Method 9): $R_t$=0.27 min; MS (ESIpos): m/z=204 [M−HCl+H]$^+$

Intermediate 308

Ethyl 5-(1-Methyl-1H-Imidazol-5-Yl)-1,3-Oxazole-4-Carboxylate

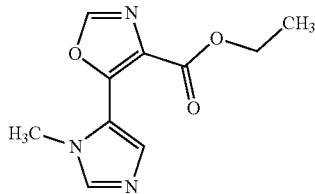 [SMILES: CCOC(=O)c1ncoc1-c1cncn1C]

1-methyl-1H-imidazole-5-carboxylic acid (1.00 g, 7.93 mmol) dissolved in 10 ml of THF was treated with 1,1,-carbonyl-diimidazole (1.54 g, 9.52 mmol) and stirred at room temperature. After 1 h, ethyl isocyanoacetate (950 µl, 8.7 mmol), dissolved in 10 ml of THF, and a solution of lithium bis(trimethylsilyl)amide in THF (7.9 ml, 1.0 M, 7.9 mmol) were added at 0° C. The mixture was allowed to warm to room temperature, stirred for 2 days and concentrated in vacuo. The residue was taken up with ethyl acetate and washed with water. The organic layer was dried and concentrated in vacuo. The crude product divided in 2 batches of 700 mg was purified by column chromatography (1$^{st}$ batch: Snap NH 110 g Cartridge Biotage; eluent ethyl acetate/cyclohexane, elution gradient 20%→100%; 2$^{nd}$ batch: Snap ultra 25 g Cartridge Biotage; eluent ethyl acetate/cyclohexane, elution gradient 20%→100%). Samples containing the desired product were united, the solvents were evaporated and the residue was dried in vacuum. 911 mg of the title compound was used without further purification.

LC-MS (Method 9): $R_t$=0.89 min; MS (ESIpos): m/z=222 [M+H]$^+$ $^1$H-NMR (400 MHz, DMSO-d6) δ [ppm]: −0.008 (0.50), 0.008 (0.48), 1.239 (4.81), 1.257 (10.07), 1.275 (4.86), 3.740 (16.00), 4.249 (1.57), 4.267 (4.86), 4.285 (4.79), 4.303 (1.52), 7.684 (2.40), 7.687 (2.59), 7.886 (2.53), 8.589 (3.64).

Intermediate 309

2-Amino-1-(1-Methyl-1H-Imidazol-5-Yl)Ethanone Hydrochloride

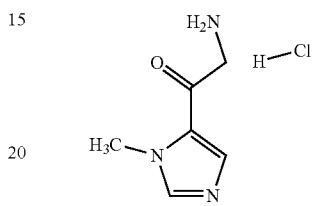

ethyl 5-(1-methyl-1H-imidazol-5-yl)-1,3-oxazole-4-carboxylate (911 mg, 4.12 mmol) was taken up in 20 ml of 6 N hydrochloric acid and stirred for 2 h at 100° C. The resulting mixture was concentrated in vacuo. 934 mg (84% purity) of the title compound was obtained and used without further purification.

LC-MS (Method 9): $R_t$=0.43 min; MS (ESIpos): m/z=140 [M−HCl+H]$^+$

Intermediate 310

Tert-Butyl [2-(1-Methyl-1H-Imidazol-5-Yl)-2-Oxoethyl]Carbamate

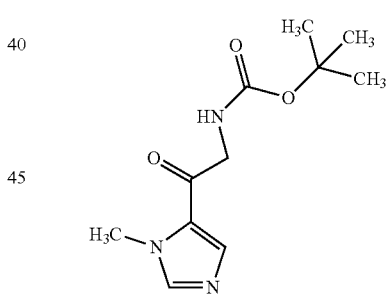

To a solution of 2-amino-1-(1-methyl-1H-imidazol-5-yl) ethanone hydrochloride (934 mg, 84% purity, 4.48 mmol) in dichloromethane (20 ml) was added di-tert-butyl dicarbonate (1.08 g, 4.93 mmol) and triethylamine (3.7 ml, 27 mmol). After 2 h of stirring at RT, the reaction mixture was diluted with dichloromethane and washed with water. After phase separation, the organic phase was dried; concentrated in vacuo and 883 mg (86% purity, 71% yield) of the title compound was obtained and used without further purification.

LC-MS (Method 9): $R_t$=1.09 min; MS (ESIpos): m/z=240 [M+H]$^+$ $^1$H-NMR (400 MHz, DMSO-d6) δ [ppm]: 0.909 (0.64), 0.927 (1.33), 0.945 (0.68), 1.110 (2.98), 1.277 (0.69), 1.366 (1.28), 1.390 (16.00), 1.409 (0.88), 1.422 (1.01), 1.438 (0.58), 1.449 (1.00), 1.473 (0.76), 1.481 (0.48), 1.574 (4.41), 2.411 (0.45), 2.429 (0.43), 3.311 (10.27), 4.192 (1.72), 4.207 (1.71), 7.088 (0.54), 7.932 (1.94), 7.987 (1.68).

Intermediate 311

Rac-Tert-Butyl {[4-(1-Methyl-1H-Imidazol-5-Yl)-2,5-Dioxoimidazolidin-4-Yl]Methyl}Carbamate

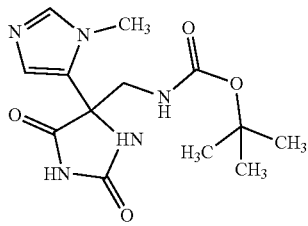 [SMILES: Cn1cncc1C1(CNC(=O)OC(C)(C)C)NC(=O)NC1=O]

To a solution of tert-butyl [2-(1-methyl-1H-imidazol-5-yl)-2-oxoethyl]carbamate (883 mg, 86% purity, 3.17 mmol) in methanol (12 ml) was added potassium cyanide (826 mg, 12.7 mmol) and ammonium carbonate (1.22 g, 12.7 mmol) at RT. The reaction mixture was stirred overnight at 80° C. into a sealed pressure flask. After filtration and washing of the suspension with methanol at RT, the resulting filtrate was concentrated in vacuo. The residue was purified by preparative HPLC (sample preparation: 2.74 g dissolved in water/methanol; column: XBridge C18 5 µm, 100×30 mm; eluent: water→acetonitrile/water 80:20+1% ammonia solution-→acetonitrile; flow rate: 80 ml/min; temperature: 40° C.; UV detection: 210 nm). 220 mg of the desired product was obtained and used without further purification.

LC-MS (Method 9): $R_t$=0.26 min; MS (ESIpos): m/z=310 [M+H]$^+$ $^1$H-NMR (400 MHz, DMSO-d6) δ [ppm]: 1.359 (16.00), 1.754 (0.40), 3.276 (0.68), 3.289 (0.98), 3.441 (0.68), 3.465 (6.39), 3.489 (0.54), 6.419 (0.50), 6.739 (1.49), 7.418 (1.44).

Intermediate 312

Rac-5-(Aminomethyl)-5-(1-Methyl-1H-Imidazol-5-Yl)Imidazolidine-2,4-Dione Hydrochloride

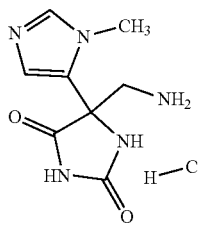

To a solution of rac-tert-butyl {[4-(1-methyl-1H-imidazol-5-yl)-2,5-dioxoimidazolidin-4 yl]methyl}carbamate in dichloromethane (6 ml) were added 890 µl (3.6 mmol) of 4M hydrochloric acid in dioxane at RT. The reaction mixture was stirred for 2 h and then concentrated in vacuo. 204 mg of the title compound was used without further purification.

LC-MS (Method 9): $R_t$=0.22 min; MS (ESIpos): m/z=210 [M–HCl+H]$^+$

Intermediate 313

Ethyl 5-(1,4-Dimethyl-1H-Imidazol-5-Yl)-1,3-Oxazole-4-Carboxylate

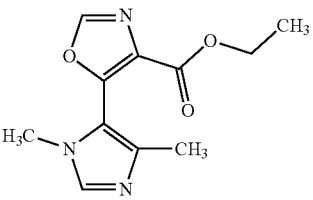 [SMILES: CCOC(=O)c1ncoc1-c1c(C)ncn1C]

1,4-dimethyl-1H-imidazole-5-carboxylic acid (2.00 g, 14.3 mmol) dissolved in 20.5 ml of THF was treated with 1,1,-carbonyl-diimidazole (2.78 g, 17.1 mmol) and stirred at room temperature. After 2 h, ethyl isocyanoacetate (1.7 ml, 16 mmol), dissolved in 20.5 ml of THF, and a solution of lithium bis(trimethylsilyl)amide in THF (14.3 ml, 1.0 M, 14.3 mmol) were added at 0° C. The mixture was allowed to warm to room temperature, stirred overnight and then concentrated in vacuo. The residue was taken up with ethyl acetate and washed with water. The organic layer was dried and concentrated in vacuo. The crude product was purified by column chromatography (110 g Snap NH Cartridge Biotage; eluent ethyl acetate/cyclohexane, elution gradient 20%→100%). Samples containing the desired product were united, the solvents were evaporated and the residue was dried in vacuum. 1.07 g (96% purity, 30% yield) of the title compound was used without further purification.

LC-MS (Method 9): $R_t$=0.93 min; MS (ESIpos): m/z=236 [M+H]$^+$ $^1$H-NMR (600 MHz, DMSO-d6) δ [ppm]: 1.191 (4.57), 1.203 (9.62), 1.215 (4.51), 1.700 (0.50), 2.024 (16.00), 3.518 (14.03), 3.559 (0.45), 4.213 (1.46), 4.224 (4.53), 4.236 (4.37), 4.248 (1.39), 7.752 (3.50), 8.630 (6.11).

Intermediate 314

2-Amino-1-(1,4-Dimethyl-1H-Imidazol-5-Yl)Ethanone Hydrochloride

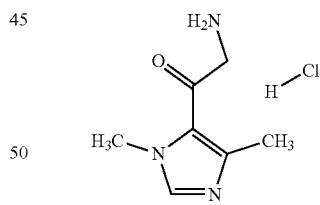

ethyl 5-(1,4-dimethyl-1H-imidazol-5-yl)-1,3-oxazole-4-carboxylate (1.07 g, 96% purity, 4.35 mmol) was taken up in 14.5 ml (87 mmol) of 6 N hydrochloric acid and stirred for 2 h at 100° C. The resulting mixture was concentrated in vacuo. 1.12 g (82% purity) of the title compound was obtained and used without further purification.

LC-MS (Method 9): $R_t$=0.52 min; MS (ESIpos): m/z=154 [M–HCl+H]$^+$ $^1$H-NMR (400 MHz, DMSO-d6) δ [ppm]: 0.980 (0.41), 0.997 (0.86), 1.015 (0.43), 1.125 (0.53), 1.143 (1.10), 1.161 (0.55), 2.174 (1.46), 2.197 (0.51), 2.647 (11.73), 2.703 (0.95), 3.622 (0.44), 3.693 (1.27), 3.886 (1.23), 3.951 (16.00), 3.977 (0.40), 4.378 (2.85), 4.390 (2.84), 5.570 (0.44), 8.592 (2.36), 9.036 (0.84).

Intermediate 315

Tert-Butyl [2-(1,4-Dimethyl-1H-Imidazol-5-Yl)-2-Oxoethyl]Carbamate

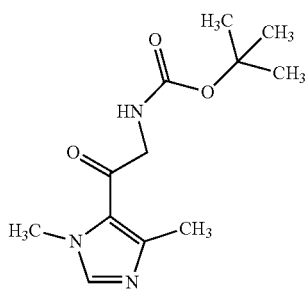

To a solution of 2-amino-1-(1,4-dimethyl-1H-imidazol-5-yl)ethanone hydrochloride (1.12 g, 82% purity, 4.84 mmol) in dichloromethane (20 ml) was added di-tert-butyl dicarbonate (1.16 g, 5.32 mmol) and triethylamine (5.4 ml, 39 mmol). After 20 h of stirring at RT, the reaction mixture was diluted with dichloromethane and washed with water. After phase separation, the organic phase was dried; concentrated in vacuo and 1.10 g of the title compound was obtained and used without further purification.

LC-MS (Method 9): $R_t$=1.17 min; MS (ESIpos): m/z=254 [M+H]$^+$

Intermediate 316

Rac-Tert-Butyl {[4-(1,4-Dimethyl-1H-Imidazol-5-Yl)-2,5-Dioxoimidazolidin-4-Yl]Methyl}Carbamate

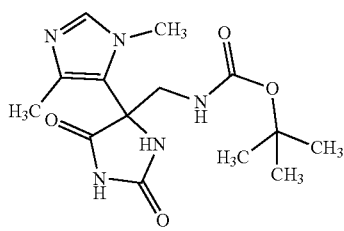 [SMILES: Cc1ncn(C)c1C1(CNC(=O)OC(C)(C)C)NC(=O)NC1=O]

To a solution of tert-butyl [2-(1,4-dimethyl-1H-imidazol-5-yl)-2-oxoethyl]carbamate (1.10 g, 4.34 mmol) in methanol (16 ml) was added potassium cyanide (1.13 g, 17.4 mmol) and ammonium carbonate (1.67 g, 17.4 mmol) at RT. The reaction mixture was first stirred overnight at 80° C. into a sealed pressure flask. Extra portion of potassium cyanide (566 mg, 8.69 mmol) and ammonium carbonate (835 mg, 8.69 mmol) were added due to incomplete conversion. The reaction mixture was then stirred for 2 days at 80° C.

After filtration and washing of the suspension with methanol at RT, the resulting filtrate was concentrated in vacuo, and then taken up in a mixture of dichloromethane and methanol (1/1). The resulting suspension was filtered through a pad of celite and the filtrates were concentrated in vacuo. The residue was purified by preparative HPLC (sample preparation: 2.4 g dissolved in acetonitrile, methanol and water; column: XBridge C18 5 µm, 100×30 mm; eluent: acetonitrile/water+0.07% ammonia solution; elution gradient 7.5%→92%; flow rate: 80 ml/min; UV detection: 210 nm). 134 mg (89% purity, 8% yield) of the desired product was obtained and used without further purification.

LC-MS (Method 9): $R_t$=0.41 min; MS (ESIpos): m/z=324 [M+H]$^+$

Intermediate 317

Rac-5-(Aminomethyl)-5-(1,4-Dimethyl-1H-Imidazol-5-Yl)Imidazolidine-2,4-Dione Hydrochloride

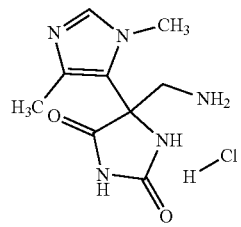

To a solution of rac-tert-butyl {[4-(1,4-dimethyl-1H-imidazol-5-yl)-2,5-dioxoimidazolidin-4 yl]methyl}carbamate (134 mg, 89% purity, 368 µmol) in dichloromethane (3 ml) were added 460 µl of 4M hydrochloric acid (1.8 mmol mmol) in dioxane at RT. After stirring overnight at RT, the precipitate was filtered off, washed with dichloromethane and dried in vacuo. The filtrate was then taken up in water, concentrated and dried in vacuo. 120 mg (93% purity) of the title compound was obtained and used without further purification.

LC-MS (Method 9): $R_t$=0.23 min; MS (ESIpos): m/z=224 [M−HCl+H]$^+$ $^1$H-NMR (600 MHz, DMSO-d6) δ [ppm]: 1.760 (1.93), 2.048 (0.62), 2.347 (1.96), 2.419 (0.54), 2.446 (0.42), 2.488 (16.00), 3.691 (0.49), 3.713 (0.85), 3.758 (0.88), 3.782 (0.54), 3.855 (1.74), 3.885 (0.62), 3.906 (0.43), 3.924 (0.62), 3.946 (0.54), 3.954 (0.57), 3.991 (0.56), 4.067 (12.91), 4.102 (0.46), 8.801 (1.30), 9.108 (3.51), 9.405 (1.53), 11.534 (1.99).

Intermediate 318

Rac-2-Nitro-1-(Pyridin-2-Yl)Ethan-1-Ol

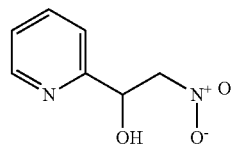

0.40 g (2.33 mmol) of barium hydroxide were added to a solution of 5.00 g (46.70 mmol) of pyridine-2-carbaldehyde and 25.00 mL (470.00 mmol) of nitromethane in 140 mL of water and the mixture was stirred at room temperature for 15 min. The reaction was the n extracted three times with ethyl acetate. The combined organic layers were dried over magnesium sulfate, filtered, and concentrated in vacuo to give 7.70 g (98%) of the crude product as a colourless oil.

The compound was used as such in the next step.

LC-MS (Method 3): $R_t$=0.163 min. MS (Mass method 1): m/z=169 (M+H)$^+$

Intermediate 319

Rac-2-[1-{[Tert-Butyl(Dimethyl)Silyl]Oxy}-2-Nitro-ethyl]Pyridine

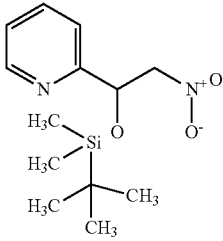

24.20 g (160.00 mmol) of tert-butyldimethylsilyl chloride were added to a solution of 7.70 (45.80 mmol) of rac-2-nitro-1-(pyridin-2-yl)ethan-1-ol and 15.60 g (229.00 mmol) of imidazole in 240 mL of N,N-dimethylformamide at 0° C. and the mixture was allowed to stir at room temperature for 14 hours. The solution was diluted with ethyl acetate and washed with water and brine. The organic layer was dried over magnesium sulfate, filtered and evaporated to dryness to yield a residue, which was purified by flash chromatography on silica gel eluting with heptane/ethyl acetate mixtures to afford 11.85 g (92%) of the product as a colourless oil.

$^1$H-NMR (300 MHz, DMSO-d$_6$): δ [ppm]=−0.10 (s, 3H), 0.01 (s, 3H), 0.82 (s, 9H), 4.75 (dd, 1H), 4.95 (dd, 1H), 5.43 (dd, 1H), 7.36 (dd, 1H), 7.54 (d, 1H), 7.88 (t, 1H), 8.56 (d, 1H).

LC-MS (Method 3): R$_t$=1.078 min. MS (Mass method 1): m/z=283 (M+H)$^+$

Intermediate 320

Rac-2-{[Tert-Butyl(Dimethyl)Silyl]Oxy}-2-(Pyridin-2-Yl)Ethan-1-Amine

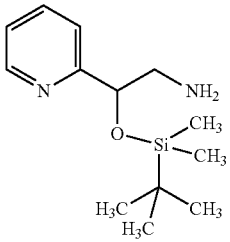 [SMILES: CC(C)(C)[Si](C)(C)OC(CN)c1ccccn1]

A mixture of 11.80 g (41.90 mmol) of rac-2-[1-{[tert-butyl(dimethyl)silyl]oxy}-2-nitroethyl]pyridine and 0.04 g (0.42 mmol) of palladium on carbon (10% loading, Degussa type, wet basis) in 50 mL of methanol was stirred under hydrogen atmosphere at room temperature for 12 hours. After that time, the catalyst was removed by filtration through a pad of celite and the cake was thoroughly washed with methanol. Evaporation of the solvent furnished a residue which was purified by flash chromatography on silica gel eluting with dichloromethane/methanol mixtures to afford 4.52 g (43%) of the product as a colourless oil.

$^1$H-NMR (300 MHz, DMSO-d$_6$): δ [ppm]=−0.08 (s, 3H), 0.06 (s, 3H), 0.87 (s, 9H), 2.74 (ddd, 2H), 4.66 (dd, 1H), 7.25 (dd, 1H), 7.41 (d, 1H), 7.78 (t, 1H), 8.48 (d, 1H).

LC-MS (Method 3): R$_t$=0.642 min. MS (Mass method 1): m/z=253 (M+H)$^+$

Intermediate 321

Rac-Tert-Butyl [2-{[Tert-Butyl(Dimethyl)Silyl]Oxy}-2-(Pyridin-2-Yl)Ethyl]Carbamate

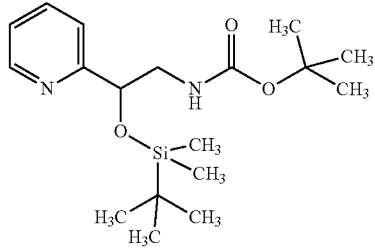 [SMILES: CC(C)(C)OC(=O)NCC(O[Si](C)(C)C(C)(C)C)c1ccccn1]

4.30 mL (19.00 mmol) of di-tert-butyl dicarbonate were added to a solution of 4.51 g (17.90 mmol) of rac-2-{[tert-butyl(dimethyl)silyl]oxy}-2-(pyridin-2-yl)ethanamine in 20 mL of dichloromethane and the mixture was stirred at room temperature for 12 hours. The reaction was washed with water and brine and the organic layer was dried over magnesium sulfate, filtered and evaporated to dryness to afford 6.31 g (99%) of the crude product as a light yellow oil. The compound was used as such in the next synthetic step.

LC-MS (Method 3): R$_t$=1.084 min. MS (Mass method 1): m/z=353 (M+H)$^+$

Intermediate 322

Rac-Tert-Butyl [2-Hydroxy-2-(Pyridin-2-Yl)Ethyl]Carbamate

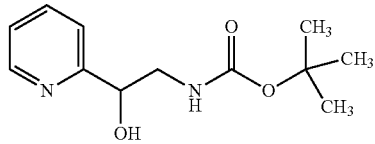 [SMILES: CC(C)(C)OC(=O)NCC(O)c1ccccn1]

27.00 mL (27.00 mmol) of 1 N tetra-n-butylammonium fluoride in tetrahydrofuran was added dropwise to a stirred solution of 6.31 g (17.90 mmol) of rac-tert-Butyl [2-{[tert-butyl(dimethyl)silyl]oxy}-2-(pyridin-2-yl)ethyl]carbamate in 100 mL of tetrahydrofuran and the mixture was stirred at room temperature for 14 hours. After that time, the solution was poured onto 50 mL of water, and extracted with ethyl acetate. The combined organic extracts were washed successively with water and brine, dried over magnesium sulfate, and concentrated in vacuo to furnish 4.26 g (99%) of the crude product as a colourless thick oil. The compound was used as such in the next step.

LC-MS (Method 3): R$_t$=0.201 min. MS (Mass method 1): m/z=239 (M+H)$^+$

Intermediate 323

Tert-Butyl [2-Oxo-2-(Pyridin-2-Yl)Ethyl]Carbamate

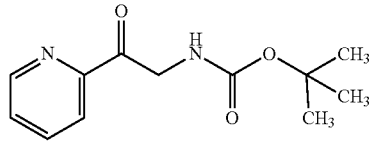 [SMILES: CC(C)(C)OC(=O)NCC(=O)c1ccccn1]

1.19 mL (16.90 mmol) of dimethyl sulfoxide were added drop wise to a solution of 0.73 mL (8.39 mmol) of oxalyl chloride in 20 mL of anhydrous dichloromethane at −78° C. and the mixture was stirred under nitrogen atmosphere under these conditions for 30 min. 1.00 g (4.20 mmol) of rac-tert-Butyl [2-hydroxy-2-(pyridin-2-yl)ethyl]carbamate was added to the cold solution and the resulting mixture was stirred for 15 additional min. After that, 2.92 mL (20.98 mmol) of triethylamine were added and the reaction was allowed to stir at 0° C. for 30 min. Finally, the mixture was diluted with ethyl acetate and the organic layer was washed once with water and brine, dried over magnesium sulfate, filtered and concentrated in vacuo. Flash chromatography of the resulting residue using heptane/ethyl acetate mixtures as eluent gave 0.41 g (41%) of the product as a light brown solid.

$^1$H-NMR (300 MHz, DMSO-$d_6$): δ [ppm]=1.39 (s, 9H), 4.58 (d, 2H), 7.00 (t, 1H), 7.70 (dd, 1H), 7.93-8.08 (m, 2H), 8.73 (d, 1H).

LC-MS (Method 3): $R_t$=0.661 min. MS (Mass method 1): m/z=181 (M−tBu+H)$^+$

Intermediate 324

Rac-Tert-Butyl {[2,5-Dioxo-4-(Pyridin-2-Yl)Imidazolidin-4-Yl]Methyl}Carbamate

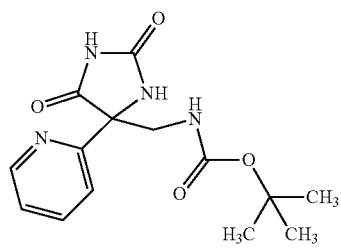 [SMILES: CC(C)(C)OC(=O)NCC1(c2ccccn2)NC(=O)NC1=O]

To a stirring solution of 3.29 g (34.30 mmol) of ammonium carbonate and 0.49 g (9.14 mmol) of ammonium chloride in 6 mL of water was added 0.54 g (2.29 mmol) of tert-butyl [2-oxo-2-(pyridin-2-yl)ethyl]carbamate in 6 mL of ethanol. After 15 min, 0.67 g (10.30 mmol) of potassium cyanide were added and the mixture was heated up to 60° C. for 16 hours into a sealed pressure flask. The yellow solution was concentrated until only a small fraction of water remained (a white precipitate appeared). Then, more water was added and the suspension was allowed to stand at 0° C. for 2 hour. After that time, the resulting solid was filtered off and washed with cold water and diethyl ether to give 0.70 g (98%) of the product as an off-white powder. The compound was used as such in the next step.

LC-MS (Method 3): $R_t$=0.466 min. MS (Mass method 1): m/z=307 (M+H)$^+$

Intermediate 325

Rac-5-(Aminomethyl)-5-(Pyridin-2-Yl)Imidazolidine-2,4-Dione Hydrochloride

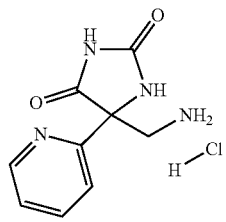

2.90 mL (11.00 mmol) of 4N hydrochloric acid in dioxane were added to a solution of 0.70 g (2.29 mmol) of rac-tert-Butyl {[2,5-dioxo-4-(pyridin-2-yl)imidazolidin-4-yl]methyl}carbamate in 10 mL of dichloromethane and the mixture was allowed to stir at room temperature for 16 hours.

The resulting precipitate was collected by filtration and washed with dichloromethane, ethyl acetate and diethyl ether to give 0.55 g (99%) of the product as a white solid. The compound was used as such in the next step.

LC-MS (Method 3): $R_t$=0.091 min. MS (Mass method 1): m/z=207 (M+H)$^+$

Intermediate 326

Ethyl 5-(2-Methyl-2H-Indazol-3-Yl)-1,3-Oxazole-4-Carboxylate

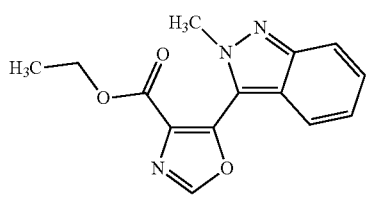 [SMILES: CCOC(=O)c1ncoc1-c1c2ccccc2nn1C]

2-methyl-2H-indazole-3-carboxylic acid (5.00 g, 28.4 mmol) dissolved in 41 ml of THF was treated with 1,1,-carbonyl-diimidazole (5.52 g, 34.1 mmol) and stirred at room temperature. After 2 h, ethyl isocyanoacetate (3.4 ml, 31 mmol), dissolved in 41 ml of THF, and a solution of lithium bis(trimethylsilyl)amide in THF (28.4 ml, 1.0 M, 28.4 mmol) were added at 0° C. The mixture was allowed to warm to room temperature, stirred overnight and then concentrated in vacuo. The residue was taken up with ethyl acetate and washed with water. The organic layer was dried and concentrated in vacuo. The crude product was purified by column chromatography (340 g Ultra Snap Cartridge Biotage; eluent ethyl acetate/cyclohexane, elution gradient 16%→100%). Samples containing the desired product were united, the solvents were evaporated and the residue was dried in vacuum. 5.12 g (97% purity, 65% yield) of the title compound was used without further purification.

LC-MS (Method 9): $R_t$=1.32 min; MS (ESIpos): m/z=272 [M+H]$^+$ $^1$H-NMR (600 MHz, DMSO-d6) δ [ppm]: 1.058 (4.12), 1.070 (8.63), 1.081 (4.09), 1.176 (0.56), 1.988 (1.02), 4.136 (16.00), 4.171 (1.29), 4.183 (4.05), 4.195 (4.05), 4.207 (1.24), 7.165 (0.80), 7.166 (0.79), 7.177 (0.98), 7.178 (1.02), 7.179 (0.98), 7.181 (0.89), 7.191 (0.99), 7.334 (0.84), 7.336 (0.87), 7.345 (0.80), 7.347 (0.86), 7.349 (0.99), 7.350 (0.93), 7.360 (0.82), 7.361 (0.77), 7.522 (1.70), 7.536 (1.56), 7.718 (1.72), 7.733 (1.62), 8.812 (5.48).

Intermediate 327

2-Amino-1-(2-Methyl-2H-Indazol-3-Yl)Ethanone Hydrochloride

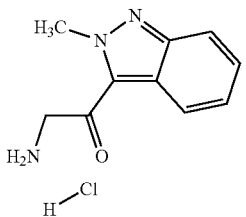

ethyl 5-(2-methyl-2H-indazol-3-yl)-1,3-oxazole-4-carboxylate (5.12 g, 97% purity, 18.3 mmol) was taken up in 61 ml (370 mmol) of 6 N hydrochloric acid and stirred for 2 h at 100° C. The resulting mixture was concentrated in vacuo. 5.19 g (38% purity, 48% yield) of the title compound was obtained and used without further purification.

LC-MS (Method 9): $R_t$=0.99 min; MS (ESIpos): m/z=190 $[M+H]^+$

Intermediate 328

Tert-Butyl [2-(2-Methyl-2H-Indazol-3-Yl)-2-Oxo-ethyl]Carbamate

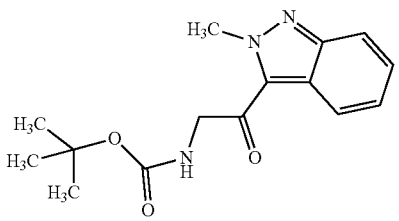 [SMILES: Cn1nc2ccccc2c1C(=O)CNC(=O)OC(C)(C)C]

To a solution of 2-amino-1-(2-methyl-2H-indazol-3-yl)ethanone hydrochloride (5.19 g, 38% purity, 8.77 mmol) in dichloromethane (40 ml) was added di-tert-butyl dicarbonate (2.11 g, 9.65 mmol) and triethylamine (9.8 ml, 70 mmol). After overnight stirring at RT, the reaction mixture was diluted with dichloromethane and washed with water. After phase separation, the organic phase was dried; concentrated in vacuo and 5.06 g (28% purity, 56% yield) of the title compound was obtained and used without further purification.

LC-MS (Method 9): $R_t$=1.56 min; MS (ESIpos): m/z=290 $[M+H]^+$

Intermediate 329

Rac-Tert-Butyl {[4-(2-Methyl-2H-Indazol-3-Yl)-2,5-Dioxoimidazolidin-4-Yl]Methyl}Carbamate

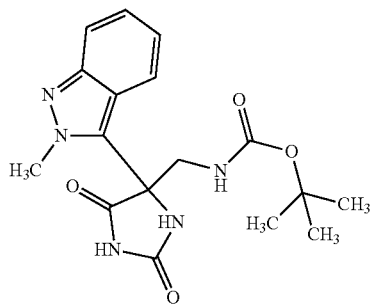 [SMILES: Cn1nc2ccccc2c1C1(CNC(=O)OC(C)(C)C)NC(=O)NC1=O]

To a solution of tert-butyl [2-(2-methyl-2H-indazol-3-yl)-2-oxoethyl]carbamate (5.06 g, 28% purity, 4.88 mmol) in methanol (18 ml) was added potassium cyanide (1.27 g, 19.5 mmol) and ammonium carbonate (1.87 g, 19.5 mmol) at RT. The reaction mixture was first stirred overnight at 80° C. into a sealed pressure flask. Extra portion of potassium cyanide (635 mg, 9.75 mmol) and ammonium carbonate (937 mg, 9.75 mmol) were added due to incomplete conversion. The reaction mixture was then stirred for 2 days at 80° C.

After filtration and washing of the suspension with methanol at RT, the resulting filtrate was concentrated in vacuo, and then taken up in a mixture of dichloromethane and methanol (1/1). The resulting suspension was filtered through a pad of celite and the filtrates were concentrated in vacuo. The residue was purified by preparative HPLC (sample preparation: 1.23 g dissolved in acetonitrile, methanol and water; column: XBridge C18 5 μm, 100×30 mm; eluent: acetonitrile/water+0.07% ammonia solution; elution gradient 7.5%→92%; flow rate: 80 ml/min; UV detection: 210 nm). 164 mg (98% purity, 9% yield) of the desired product was obtained and used without further purification.

LC-MS (Method 7): $R_t$=1.27 min; MS (ESIpos): m/z=360 $[M+H]^+$ $^1$H-NMR (600 MHz, DMSO-d6) δ [ppm]: 1.355 (16.00), 1.379 (2.50), 1.756 (0.41), 2.101 (0.81), 4.037 (0.51), 4.049 (0.74), 4.256 (15.15), 7.037 (0.79), 7.049 (1.00), 7.051 (0.93), 7.062 (0.90), 7.123 (0.48), 7.212 (0.96), 7.225 (0.95), 7.227 (1.09), 7.238 (0.92), 7.562 (1.80), 7.577 (1.65), 7.822 (0.96), 7.836 (0.92).

Intermediate 330

Rac-5-(Aminomethyl)-5-(2-Methyl-2H-Indazol-3-Yl)Imidazolidine-2,4-Dione Hydrochloride

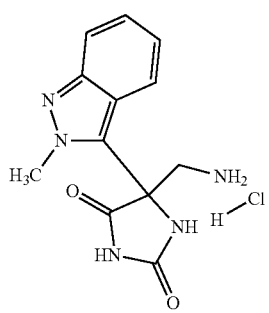

To a solution of rac-tert-butyl {[4-(2-methyl-2H-indazol-3-yl)-2,5-dioxoimidazolidin-4 yl]methyl}carbamate (164 mg, 98% purity, 447 µmol) in dichloromethane (2.4 ml) were added 560 µl of 4M hydrochloric acid (2.2 mmol) in dioxane at RT. The reaction mixture was stirred for 2 h at room temperature. Extra portion of 4M hydrochloric acid (340 µl, 4.0 M, 1.3 mmol) was added due to incomplete conversion. After stirring overnight at RT, the precipitate was filtered off, washed with dichloromethane. The filtrate was then taken up in water, concentrated and dried in vacuo. 133 mg (96% purity, 97% yield) of the title compound was obtained and used without further purification.

LC-MS (Method 9): $R_t$=0.25 min; MS (ESIneg): m/z=258 [M−HClH]⁻

¹H-NMR (600 MHz, DMSO-d6) δ [ppm]: 1.771 (0.77), 2.119 (1.16), 3.482 (0.44), 3.492 (0.43), 3.914 (1.49), 4.368 (16.00), 4.875 (1.13), 7.083 (1.03), 7.095 (1.35), 7.097 (1.26), 7.108 (1.18), 7.245 (1.17), 7.259 (1.40), 7.270 (1.10), 7.601 (2.21), 7.615 (2.01), 7.809 (2.12), 7.823 (2.04), 8.672 (2.17), 9.331 (2.38), 11.489 (2.08).

Intermediate 331

Methyl 4-Chloro-2-[6-(Trifluoromethyl)Pyridin-3-Yl]Benzoate

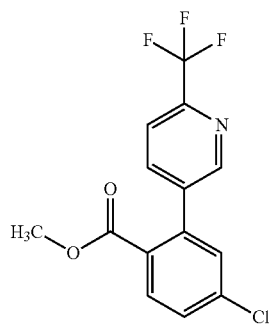 [SMILES: COC(=O)c1ccc(Cl)cc1-c1ccc(C(F)(F)F)nc1]

To a suspension of [6-(trifluoromethyl)pyridin-3-yl]boronic acid (750 mg, 3.93 mmol) and methyl 2-bromo-4-chlorobenzoate (1.23 g, 4.91 mmol) in 1,2-dimethoxyethane (22 ml) was added, under argon, a solution of sodium carbonate in water (9.8 ml, 2.0 M, 20 mmol) and Tetrakis(triphenylphosphine)palladium(0) (228 mg, 196 µmol). The reaction mixture was first stirred for 8 h at 90° C., then for 2 days at RT. The reaction mixture was diluted with ethyl acetate and washed with water. After phase separation, the combined organic phases were washed with brine, dried and concentrated under reduced pressure. The crude product was purified by preparative HPLC (Method 8f). After lyophilization, 814 mg (100% purity, 66% yield) of the desired product were obtained.

LC-MS (Method 7): $R_t$=2.15 min; MS (ESIpos): m/z=316 [M+H]⁺

¹H-NMR (600 MHz, DMSO-d6) δ [ppm]: 3.655 (16.00), 7.648 (2.33), 7.651 (2.60), 7.701 (1.53), 7.705 (1.30), 7.715 (1.64), 7.719 (1.45), 7.954 (1.37), 7.967 (1.77), 7.992 (2.61), 8.006 (2.37), 8.058 (0.93), 8.061 (0.91), 8.072 (0.71), 8.075 (0.71), 8.724 (1.44), 8.727 (1.41).

Intermediate 332

4-Chloro-2-[6-(Trifluoromethyl)Pyridin-3-Yl]Benzoic Acid

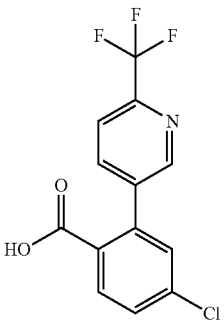 [SMILES: O=C(O)c1ccc(Cl)cc1-c1ccc(C(F)(F)F)nc1]

To a solution of methyl 4-chloro-2-[6-(trifluoromethyl)pyridin-3-yl]benzoate (774 mg, 2.45 mmol)

In THF (33 ml) was added a solution of lithium hydroxide in water (12.3 ml, 1.0 M, 12.3 mmol). The reaction mixture was stirred for 3 days at RT then diluted with a small amount of water and acidified with 1 N aqueous HCl. The resulting mixture was washed 3 times with ethyl acetate, dried and concentrated in vacuo. 720 mg (100% purity, 97% yield) of the desired product were obtained, LC-MS (Method 8): $R_t$=0.94 min; MS (ESIpos): m/z=302 [M+H]⁺

¹H-NMR (500 MHz, DMSO-d6) δ [ppm]: −0.007 (0.60), 0.006 (0.44), 1.161 (0.51), 1.170 (1.18), 1.175 (1.02), 1.182 (0.83), 1.189 (0.49), 1.760 (0.44), 1.988 (1.70), 3.601 (0.42), 7.594 (12.81), 7.598 (14.13), 7.658 (7.93), 7.663 (6.76), 7.675 (8.53), 7.679 (7.62), 7.948 (7.61), 7.962 (16.00), 7.979 (11.50), 8.063 (5.29), 8.067 (5.11), 8.079 (3.94), 8.083 (3.88), 8.725 (8.48), 8.729 (8.11).

Intermediate 333

Methyl 4-Fluoro-2-[6-(Trifluoromethyl)Pyridin-3-Yl]Benzoate

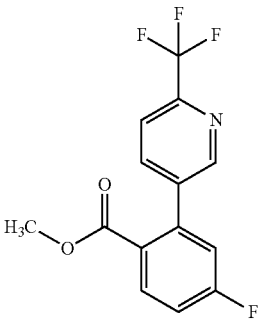

To a suspension of [6-(trifluoromethyl)pyridin-3-yl]boronic acid (750 mg, 3.93 mmol) and methyl 2-bromo-4-fluorobenzoate (1.14 g, 4.91 mmol) in 1,2-dimethoxyethane (22 ml) was added, under argon, a solution of sodium carbonate in water (9.8 ml, 2.0 M, 20 mmol) and Tetrakis(triphenylphosphine)palladium(0) (228 mg, 196 µmol). The reaction mixture was stirred for 8 h at 90° C., then diluted with ethyl acetate and washed with water. After phase separation, the combined organic phases were washed with brine, dried and concentrated under reduced pressure. The crude product was purified by preparative HPLC (Method 2f). After lyophilization, 986 mg (100% purity, 84% yield) of the desired product were obtained.

LC-MS Method 7): $R_t$=2.02 min, MS (ESIpos): m/z=300 $[M+H]^+$ $^1$H-NMR (600 MHz, DMSO-d6) δ [ppm]: 3.552 (0.46), 3.650 (16.00), 7.445 (0.84), 7.449 (1.26), 7.465 (1.47), 7.477 (1.30), 7.481 (0.98), 7.491 (0.68), 7.496 (0.55), 7.957 (1.64), 7.970 (2.17), 8.049 (1.13), 8.053 (1.76), 8.064 (1.79), 8.068 (1.31), 8.078 (1.05), 8.721 (1.69), 8.724 (1.69).

Intermediate 334

4-Fluoro-2-[6-(Trifluoromethyl)Pyridin-3-Yl]Benzoic Acid

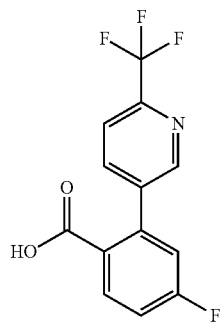

To a solution of methyl 4-fluoro-2-[6-(trifluoromethyl)pyridin-3-yl]benzoate (937 mg, 3.13 mmol) in THF (42 ml) was added a solution of lithium hydroxide in water (15.6 ml, 1.0 M, 15.6 mmol). The reaction mixture was stirred for 3 days at RT then diluted with a small amount of water and acidified with 1 N aqueous HCl. The resulting mixture was washed 3 times with ethyl acetate, dried and concentrated in vacuo. 832 mg (100% purity, 93% yield) of the desired product were obtained, LC-MS (Method 7): $R_t$=1.65 min; MS (ESIpos): m/z=286 $[M+H]^+$ $^1$H-NMR (500 MHz, DMSO-d6) δ [ppm]: −0.007 (0.80), 0.006 (0.71), 1.170 (3.83), 1.271 (0.62), 6.580 (0.55), 7.392 (8.00), 7.398 (11.16), 7.411 (8.11), 7.417 (10.86), 7.424 (6.03), 7.430 (4.92), 7.441 (10.47), 7.447 (8.72), 7.458 (5.87), 7.464 (5.01), 7.550 (0.74), 7.556 (0.70), 7.564 (0.79), 7.571 (0.69), 7.603 (0.95), 7.616 (0.89), 7.623 (1.01), 7.626 (1.17), 7.642 (0.76), 7.953 (11.78), 7.969 (16.00), 8.035 (9.28), 8.047 (9.92), 8.053 (14.07), 8.058 (9.07), 8.064 (9.77), 8.071 (6.26), 8.074 (6.18), 8.723 (13.16), 8.727 (12.86), 13.054 (1.84).

Intermediate 335

Methyl 5-Fluoro-2-[6-(Trifluoromethyl)Pyridin-3-Yl]Benzoate

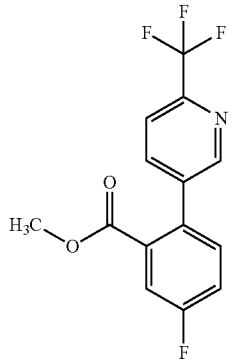 [SMILES: COC(=O)c1cc(F)ccc1-c1ccc(C(F)(F)F)nc1]

To a suspension of [6-(trifluoromethyl)pyridin-3-yl]boronic acid (750 mg, 3.93 mmol) and methyl 2-bromo-5-fluorobenzoate (1.14 g, 4.91 mmol) in 1,2-dimethoxyethane (22 ml) was added, under argon, a solution of sodium carbonate in water (9.8 ml, 2.0 M, 20 mmol) and Tetrakis(triphenylphosphine)palladium(0) (228 mg, 196 μmol). The reaction mixture was first stirred for 8 h at 90° C., then for 2 days at RT. The reaction mixture was diluted with ethyl acetate and washed with water. After phase separation, the combined organic phases were washed with brine, dried and concentrated under reduced pressure. The crude product was purified by preparative HPLC (Method 4f). After lyophilization, 841 mg (100% purity, 72% yield) of the desired product were obtained.

LC-MS (Method 7): $R_t$=2.00 min; MS (ESIpos): m/z=300 $[M+H]^+$ $^1$H-NMR (600 MHz, DMSO-d6) δ [ppm]: 3.672 (16.00), 7.579 (0.54), 7.589 (0.65), 7.594 (1.50), 7.603 (1.47), 7.607 (0.93), 7.612 (0.96), 7.621 (1.06), 7.626 (1.15), 7.640 (0.41), 7.764 (1.00), 7.768 (0.99), 7.779 (1.04), 7.784 (1.00), 7.945 (1.31), 7.958 (1.86), 8.018 (0.97), 8.022 (0.95), 8.032 (0.68), 8.035 (0.68), 8.695 (1.42), 8.698 (1.41).

Intermediate 336

5-Fluoro-2-[6-(Trifluoromethyl)Pyridin-3-Yl]Benzoic Acid

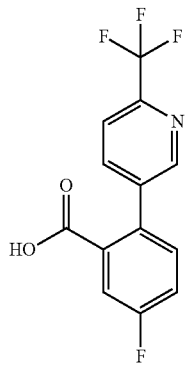 [SMILES: O=C(O)c1cc(F)ccc1-c1ccc(C(F)(F)F)nc1]

To a solution of methyl 5-fluoro-2-[6-(trifluoromethyl)pyridin-3-yl]benzoate (785 mg, 2.62 mmol) in THF (35 ml) was added a solution of lithium hydroxide in water (13.1 ml, 1.0 M, 13.1 mmol).

The reaction mixture was stirred for 3 days at RT then diluted with a small amount of water and acidified with 1 N aqueous HCl. The resulting mixture was washed 3 times with ethyl acetate, dried and concentrated in vacuo. 742 mg (100% purity, 99% yield) of the desired product were obtained.

LC-MS (Method 8): $R_t$=0.85 min, MS (ESIpos): m/z=286 [M+H]$^+$ $^1$H-NMR (500 MHz, DMSO-d6) δ [ppm]: −0.007 (0.42), 1.161 (0.45), 1.175 (0.92), 1.189 (0.47), 1.760 (0.65), 1.988 (1.59), 3.602 (0.56), 7.530 (2.49), 7.541 (3.71), 7.546 (10.63), 7.553 (8.00), 7.558 (16.00), 7.569 (7.10), 7.575 (7.56), 7.587 (1.77), 7.592 (2.30), 7.722 (6.44), 7.727 (6.19), 7.741 (6.79), 7.746 (6.37), 7.941 (8.95), 7.942 (9.22), 7.957 (12.91), 7.959 (12.92), 8.026 (6.97), 8.030 (6.63), 8.043 (4.67), 8.046 (4.59), 8.699 (10.47), 8.704 (10.03).

Intermediate 337

Ethyl 5-(3-Fluorobicyclo[1.1.1]Pentan-1-Yl)-1,3-Oxazole-4-Carboxylate

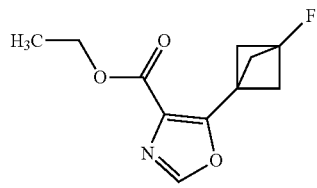 [SMILES: CCOC(=O)c1ncoc1C12CC(F)(C1)C2]

3-fluorobicyclo[1.1.1]pentane-1-carboxylic acid (5.00 g, 38.4 mmol) dissolved in 55 ml of THF was treated with 1,1,-carbonyl-diimidazole (7.48 g, 46.1 mmol) and stirred at room temperature. After 2 h, ethyl isocyanoacetate (4.6 ml, 42 mmol), dissolved in 55 ml of THF, and a solution of lithium bis(trimethylsilyl)amide in THF (38.4 ml, 1.0 M, 38.4 mmol) were added at 0° C. The mixture was allowed to warm to room temperature, stirred for 5 days and then concentrated in vacuo. The residue was taken up with ethyl acetate and washed with water. The organic layer was dried and concentrated in vacuo. The crude product was purified by column chromatography (340 g Ultra Snap Cartridge Biotage; eluent ethyl acetate/cyclohexane, elution gradient 16%→100%). Samples containing the desired product were united, the solvents were evaporated and the residue was dried in vacuum. 5.60 g (71% purity, 46% yield) of the title compound was used without further purification.

LC-MS (Method 9): $R_t$=1.44 min; MS (ESIpos): m/z=226 [M+H]$^+$ $^1$H-NMR (400 MHz, DMSO-d6) δ [ppm]: 1.285 (7.64), 1.303 (16.00), 1.321 (7.74), 2.322 (1.14), 2.595 (5.82), 2.602 (5.79), 4.266 (2.49), 4.284 (7.72), 4.301 (7.60), 4.319 (2.39), 8.430 (7.28), 8.590 (1.67).

Intermediate 338

2-Amino-1-(3-Fluorobicyclo[1.1.1]Pentan-1-Yl)Ethanone Hydrochloride

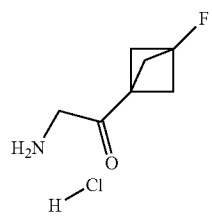

ethyl 5-(3-fluorobicyclo[1.1.1]pentan-1-yl)-1,3-oxazole-4-carboxylate (5.73 g, 71% purity, 18.0 mmol) was taken up in 60 ml (360 mmol) of 6 N hydrochloric acid and stirred for 2 h at 100° C. The resulting mixture was concentrated in vacuo. 4.30 g of the title compound was obtained and used without further purification.

LC-MS (Method 9): $R_t$=0.82 min; MS (ESIpos): m/z=144 [M−HCl+H]$^+$ $^1$H-NMR (400 MHz, DMSO-d6) δ [ppm]: −0.008 (0.64), −0.007 (0.51), 0.008 (0.77), 1.242 (0.78), 1.260 (1.63), 1.278 (0.80), 1.909 (4.05), 2.292 (0.48), 2.299 (0.49), 2.408 (15.91), 2.415 (16.00), 2.484 (2.16), 4.039 (1.63), 4.251 (0.51), 4.269 (0.49), 5.436 (0.42), 8.264 (0.65).

Intermediate 339

Tert-Butyl [2-(3-Fluorobicyclo[1.1.1]Pentan-1-Yl)-2-Oxoethyl]Carbamate

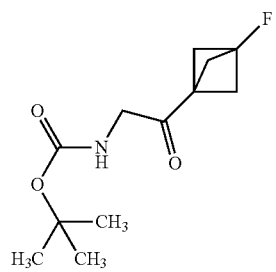 [SMILES: CC(C)(C)OC(=O)NCC(=O)C12CC(F)(C1)C2]

To a solution of 2-amino-1-(3-fluorobicyclo[1.1.1]pentan-1-yl)ethanone hydrochloride (4.30 g, 23.9 mmol) in dichloromethane (110 ml) was added di-tert-butyl dicarbonate (5.75 g, 26.3 mmol) and triethylamine (27 ml, 190 mmol). After overnight stirring at RT, the reaction mixture was diluted with dichloromethane and washed with water. After phase separation, the organic phase was dried, concentrated in vacuo and 3.96 g of the unpurified compound was obtained and used without further purification.

Intermediate 340

Rac-Tert-Butyl {[4-(3-Fluorobicyclo[1.1.1]Pentan-1-Yl)-2,5-Dioxoimidazolidin-4-Yl]Methyl}Carbamate

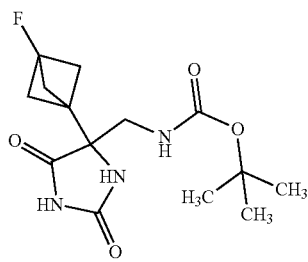 [SMILES: CC(C)(C)OC(=O)NCC1(C23CC(F)(C2)C3)NC(=O)NC1=O]

To a solution of tert-butyl [2-(3-fluorobicyclo[1.1.1]pentan-1-yl)-2-oxoethyl]carbamate (3.96 g, 16.3 mmol) in methanol (62 ml) was added potassium cyanide (4.24 g, 65.1 mmol) and ammonium carbonate (6.26 g, 65.1 mmol) at RT. The reaction mixture was stirred overnight at 80° C. into a sealed pressure flask. After filtration through celite and washing of the suspension with methanol at RT, the resulting filtrate was concentrated in vacuo. The residue was purified by preparative HPLC (sample preparation: 7.4 g dissolved in DMSO/water/methanol; column: XBridge C18 5 μm, 100× 30 mm; eluent: acetonitrile/water 7.5:92.5→acetonitrile/water 35:65+1% ammonia solution→acetonitrile; flow rate: 80 ml/min; temperature: 30° C.; UV detection: 210 nm). 786 mg (100% purity, 15% yield) of the desired product was obtained and used without further purification.

LC-MS (Method 7): $R_t$=1.25 min; MS (ESIneg): m/z=312 [M–H]⁻

¹H NMR (400 MHz, DMSO-d₆) δ ppm 10.63 (bs, 1H), 7.69 (bs, 1H), 6.70-6.94 (m, 1H), 3.17-3.26 (m, 2H), 1.93-2.08 (m, 6H), 1.37 (s, 9H).

Intermediate 341

Rac-5-(Aminomethyl)-5-(3-Fluorobicyclo[1.1.1]Pentan-1-Yl)Imidazolidine-2,4-Dione Hydrochloride

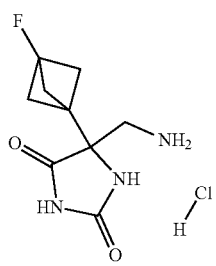 [SMILES: NCC1(C23CC(F)(C2)C3)NC(=O)NC1=O ; Cl]

To a solution of rac-tert-butyl {[4-(3-fluorobicyclo[1.1.1]pentan-1-yl)-2,5-dioxoimidazolidin-4 yl]methyl}carbamate (786 mg, 2.51 mmol) in dichloromethane (19 ml) were added 3.1 ml of 4M hydrochloric acid (12.5 mmol) in dioxane at RT. The reaction mixture was stirred for 6 h at room temperature. Extra portion of 4M hydrochloric acid (310 μl, 4.0 M, 1.3 mmol) was added due to incomplete conversion. After stirring overnight at RT, the precipitate was filtered off, washed with dichloromethane and dried in vacuo. 626 mg (100% purity, 99.9% yield) of the title compound was obtained and used without further purification.

LC-MS (Method 9): $R_t$=0.26 min; MS (ESIpos): m/z=214 [M–HCl+H]⁺

¹H-NMR (500 MHz, DMSO-d6) δ [ppm]: 2.061 (16.00), 2.066 (15.48), 2.918 (0.88), 2.945 (1.09), 3.124 (1.16), 3.151 (0.90), 5.756 (5.27), 8.227 (3.01), 8.406 (2.45), 11.074 (1.71).

Intermediate 342

Ethyl 5-[5-Methyl-2-(Trifluoromethyl)-1,3-Thiazol-4-Yl]-1,3-Oxazole-4-Carboxylate

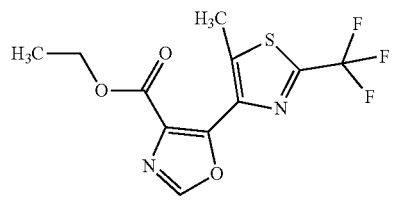 [SMILES: CCOC(=O)c1ncoc1-c1nc(C(F)(F)F)sc1C]

5-methyl-2-(trifluoromethyl)-1,3-thiazole-4-carboxylicacid (2.00 g, 9.47 mmol) dissolved in 15 ml of THF was treated with 1,1,-carbonyl-diimidazole (1.84 g, 11.4 mmol) and stirred at room temperature. After 2 h, ethyl isocyanoacetate (1.1 ml, 10 mmol), dissolved in 15 ml of THF, and a solution of lithium bis(trimethylsilyl)amide in THF (9.47 ml, 1.0 M, 9.47 mmol) were added at 0° C. The mixture was allowed to warm to room temperature, stirred for 2 h at room temperature, then stored overnight at –20° C. and finally concentrated in vacuo. The residue was taken up with ethyl acetate and washed with water. The organic layer was dried and concentrated in vacuo. 2.63 g (84% purity, 76% yield) of the title compound was used without further purification.

LC-MS (Method 7): $R_t$=1.76 min; MS (ESIpos): m/z=307 [M+H]⁺

Intermediate 343

2-Amino-1-[5-Methyl-2-(Trifluoromethyl)-1,3-Thiazol-4-Yl]Ethanone Hydrochloride

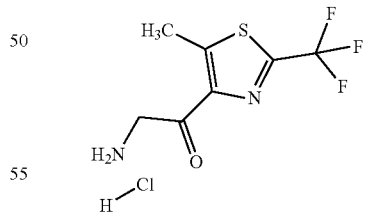

ethyl 5-[5-methyl-2-(trifluoromethyl)-1,3-thiazol-4-yl]-1,3-oxazole-4-carboxylate (2.63 g, 84% purity, 7.21 mmol) was taken up in 52 ml (310 mmol) of 6 N hydrochloric acid and stirred for 3 h at 100° C. The resulting mixture was concentrated in vacuo and 2.80 g (65% purity) of the title compound was obtained and used without further purification.

LC-MS (Method 9): $R_t$=1.26 min; MS (ESIpos): m/z=225 [M–HCl+H]⁺

Intermediate 344

Tert-Butyl {2-[5-Methyl-2-(Trifluoromethyl)-1,3-Thiazol-4-Yl]-2-Oxoethyl}Carbamate

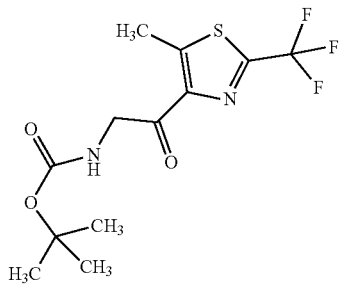 [SMILES: Cc1sc(C(F)(F)F)nc1C(=O)CNC(=O)OC(C)(C)C]

To a solution of 2-amino-1-[5-methyl-2-(trifluoromethyl)-1,3-thiazol-4-yl]ethanone hydrochloride (1.22 g, 65% purity, 3.01 mmol) in dichloromethane (15 ml) was added di-tert-butyl dicarbonate (723 mg, 3.31 mmol) and triethylamine (2.5 ml, 18 mmol). The reaction mixture was stirred for 3 h at RT, diluted with dichloromethane and washed with water. After phase separation, the organic phase was dried; concentrated in vacuo and 1.09 g of the title compound was obtained and used without further purification.

LC-MS (Method 9): $R_t$=1.78 min; MS (ESIneg): m/z=323 [M−H]⁻

Intermediate 345

Rac-Tert-Butyl({4-[5-Methyl-2-(Trifluoromethyl)-1,3-Thiazol-4-Yl]-2,5-Dioxoimidazolidin-4-Yl}Methyl)Carbamate

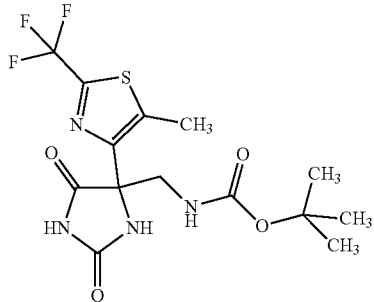 [SMILES: Cc1sc(C(F)(F)F)nc1C1(CNC(=O)OC(C)(C)C)NC(=O)NC1=O]

To a solution of tert-butyl {2-[5-methyl-2-(trifluoromethyl)-1,3-thiazol-4-yl]-2-oxoethyl}carbamate (1.09 g, 3.36 mmol) in methanol (20 ml) was added potassium cyanide (875 mg, 13.4 mmol) and ammonium carbonate (1.29 g, 13.4 mmol) at RT. The reaction mixture was stirred for 5 h at 60° C. into a sealed pressure flask. After filtration through celite and washing of the suspension with methanol at RT, the resulting filtrate was concentrated in vacuo. The residue was purified by preparative HPLC (sample preparation: 1.2 g dissolved in water/acetonitrile; column: XBridge C18 5 µm, 100×30 mm; eluent: acetonitrile/water/1% ammonia solution 1:94:5→acetonitrile/water 52:43+1% ammonia solution→acetonitrile+1% ammonia solution; flow rate: 80 ml/min; temperature: 40° C.; UV detection: 210 nm). 330 mg (100% purity, 25% yield) of the desired product was obtained and used without further purification.

LC-MS (Method 7): $R_t$=1.58 min; MS (ESIneg): m/z=393 [M−H]⁻

Intermediate 346

Rac-5-(Aminomethyl)-5-[5-Methyl-2-(Trifluoromethyl)-1,3-Thiazol-4-Yl]Imidazolidine-2,4-Dione Hydrochloride

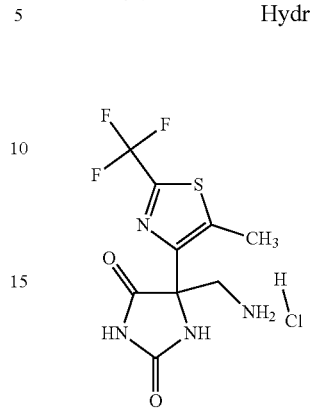

To a solution of rac-tert-butyl({4-[5-methyl-2-(trifluoromethyl)-1,3-thiazol-4-yl]-2,5-dioxoimidazolidin-4-yl}methyl)carbamate (330 mg, 837 µmol) in dichloromethane (7.2 ml) were added 1.05 ml of 4M hydrochloric acid (4.2 mmol) in dioxane at RT. The reaction mixture was stirred overnight at room temperature. Extra portion of 4M hydrochloric acid (1.05 ml, 4.0 M, 4.2 mmol) was added due to incomplete conversion. After stirring at RT then for 30 min at 40° C., the resulting mixture was concentrated in vacuo. 276 mg (90% purity, 90% yield) of the title compound was obtained and used without further purification.

LC-MS (Method 11): $R_t$=0.41 min; MS (ESIneg): m/z=293 [M−HCl−H]⁻

¹H-NMR (600 MHz, DMSO-d6) δ [ppm]: 1.367 (0.88), 1.755 (2.19), 2.113 (5.64), 2.516 (16.00), 3.568 (0.51), 3.581 (0.92), 3.604 (1.29), 3.690 (1.35), 3.711 (0.91), 8.439 (3.07), 8.590 (0.58), 8.808 (4.23), 9.005 (0.55), 11.524 (2.03).

Intermediate 347

Ethyl 5-(1,5-Dimethyl-1H-Imidazol-4-Yl)-1,3-Oxazole-4-Carboxylate

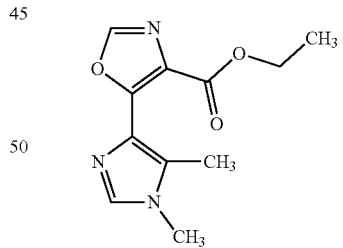

1,5-dimethyl-1H-imidazole-4-carboxylic acid (2.50 g, 17.8 mmol) dissolved in 26 ml of THF was treated with 1,1,-carbonyl-diimidazole (3.47 g, 21.4 mmol) and stirred at room temperature. After 2 h, ethyl isocyanoacetate (2.1 ml, 20 mmol), dissolved in 26 ml of THF, and a solution of lithium bis(trimethylsilyl)amide in THF (17.8 ml, 1.0 M, 17.8 mmol) were added at 0° C. The mixture was allowed to warm to room temperature, stirred overnight and then concentrated in vacuo. The residue was taken up with ethyl acetate and washed with water. The organic layer was dried and concentrated in vacuo. The crude product was purified by column chromatography (50 g Ultra Snap Cartridge Biotage; eluent ethyl acetate/cyclohexane, elution gradient 20%→100%). Samples containing the desired product were united, the solvents were evaporated and the residue was dried in vacuum. 3.19 g of the non pure compound was used without further purification.

Intermediate 348

2-Amino-1-(1,5-Dimethyl-1H-Imidazol-4-Yl)Ethanone Hydrochloride

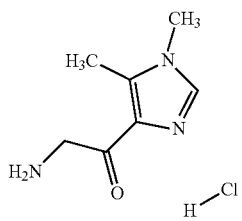

ethyl 5-(1,5-dimethyl-1H-imidazol-4-yl)-1,3-oxazole-4-carboxylate (3.19 g) was taken up in 45 ml, (6.0 M, 270 mmol) of 6 N hydrochloric acid and stirred for 2 h at 100° C. The resulting mixture was concentrated in vacuo and 2.55 g of the title compound was obtained and used without further purification.

LC-MS (Method 9): $R_t$=0.64 min; MS (ESIpos): m/z=153 [M–HCl+H]$^+$

Intermediate 349

Tert-Butyl [2-(1,5-Dimethyl-1H-Imidazol-4-Yl)-2-Oxoethyl]Carbamate

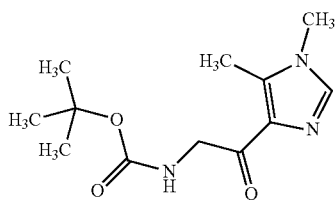 [SMILES: Cc1c(C(=O)CNC(=O)OC(C)(C)C)ncn1C]

To a solution of 2-amino-1-(1,5-dimethyl-1H-imidazol-4-yl)ethanone hydrochloride (2.50 g, 13.2 mmol) in dichloromethane (88 ml) was added di-tert-butyl dicarbonate (2.88 g, 13.2 mmol) and triethylamine (15 ml, 110 mmol). The reaction mixture was stirred overnight at RT, diluted with dichloromethane and washed with water. After phase separation, the organic phase was dried; concentrated in vacuo and 2.06 g of the crude compound was obtained and used without further purification.

Intermediate 350

Rac-Tert-Butyl {[4-(1,5-Dimethyl-1H-Imidazol-4-Yl)-2,5-Dioxoimidazolidin-4-Yl]Methyl}Carbamate

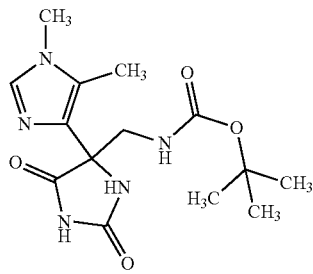 [SMILES: Cc1c(C2(CNC(=O)OC(C)(C)C)NC(=O)NC2=O)ncn1C]

To a solution of tert-butyl [2-(1,5-dimethyl-1H-imidazol-4-yl)-2-oxoethyl]carbamate (2.06 g, 8.12 mmol) in methanol (31 ml) was added potassium cyanide (2.11 g, 32.5 mmol) and ammonium carbonate (3.12 g, 32.5 mmol) at RT. The reaction mixture was first stirred for 8 h at 80° C., then for 2 days at RT, into a sealed pressure flask. Due to incomplete conversion, the reaction mixture was further stirred at 80° C. for 24 h. After filtration through celite and washing of the suspension with methanol at RT, the resulting filtrate was concentrated in vacuo. The residue was purified by preparative HPLC (sample preparation: 4.27 g dissolved in water/acetonitrile; column: XBridge C18 5 µm, 100×30 mm; eluent: acetonitrile/water/1% ammonia solution 1:94:5→acetonitrile/water 36:59+1% ammonia solution→acetonitrile+1% ammonia solution; flow rate: 80 ml/min; temperature: 40° C.; UV detection: 210 nm). 810 mg (100% purity, 31% yield) of the desired product was obtained and used without further purification.

LC-MS (Method 9): $R_t$=0.45 min; MS (ESIpos): m/z=324 [M+H]$^+$ $^1$H NMR (600 MHz, DMSO-d$_6$) δ ppm 10.6 (bs, 1H), 7.88 (s, 1H), 7.48 (s, 1H), 6.44-6.59 (m, 1H), 3.61-3.84 (m, 2H), 3.49 (s, 3H), 2.05 (s, 3H), 1.36 (s, 9H).

Intermediate 351

Rac-5-(Aminomethyl)-5-(1,5-Dimethyl-1H-Imidazol-4-Yl)Imidazolidine-2,4-Dione Hydrochloride

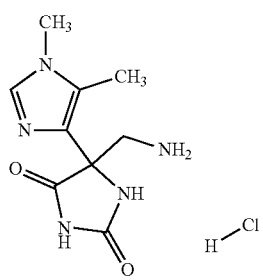 [SMILES: Cc1c(C2(CN)NC(=O)NC2=O)ncn1C ; Cl]

To a solution of rac-tert-butyl {[4-(1,5-dimethyl-1H-imidazol-4-yl)-2,5-dioxoimidazolidin-4 yl]methyl}carbamate (810 mg, 2.50 mmol) in dichloromethane (22 ml) were added 3.1 ml of 4M hydrochloric acid (12.5 mmol) in dioxane at RT. The reaction mixture was stirred overnight at room temperature, concentrated in vacuo and dried. 919 mg of the title compound was obtained and used without further purification.

LC-MS (Method 9): $R_t$=0.22 min, MS (ESIpos): m/z=224 [M+H]$^+$ $^1$H NMR (600 MHz, DMSO-d$_6$) δ ppm 11.46 (s, 1H), 9.20 (s, 1H), 9.02 (s, 1H), 8.76 (bs, 3H), 3.59-3.75 (m, 5H), 2.35 (s, 3H).

Intermediate 352

Ethyl 5-(1,5-Dimethyl-1H-Pyrazol-3-Yl)-1,3-Oxazole-4-Carboxylate

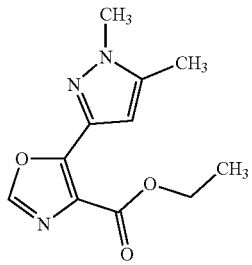 [SMILES: CCOC(=O)c1ncoc1-c1cc(C)n(C)n1]

1,5-dimethyl-1H-pyrazole-3-carboxylic acid (1.00 g, 7.14 mmol) and 1,1'-carbonyldiimidazole (1.39 g, 8.56 mmol) in 11 ml of THF were stirred for 2 h at room temperature. After that time, a solution of ethyl isocyanoacetate (860 µl, 7.8 mmol) in 11 ml of THF and a solution of lithium bis(trimethylsilyl)amide in THF (7.1 ml, 1.0 M, 7.1 mmol) were added dropwise at 0° C. When the addition was complete the resulting mixture was stirred at room temperature for 1 h. The reaction was concentrated in vacuo and extracted between water and ethyl acetate. The combined organic layers were dried over sodium sulfate, filtered and concentrated. The crude product was purified by column chromatography (Machine: Biotage® Isolera One; column: Biotage® SNAP Ultra 50 g; gradient: DCM/MeOH-gradient, 2% MeOH-20% MeOH; flow: 100 ml/min). Product containing samples were united, the solvents were removed on a rotary evaporator and the residue was dried in vacuo. 1.01 g (100% purity, 60% yield) of the title compound were obtained.

LC-MS (Method 7): $R_t$=1.16 min; MS (ESIpos): m/z=236 [M+H]$^+$

Intermediate 353

2-Amino-1-(1,5-Dimethyl-1H-Pyrazol-3-Yl)Ethan-1-One-Hydrogenchloride

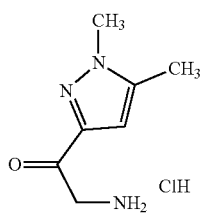

Ethyl 5-(1,5-dimethyl-1H-pyrazol-3-yl)-1,3-oxazole-4-carboxylate (1.01 g, 4.29 mmol) were taken up in 20 ml of 6 N hydrochloric acid and stirred 1 h at 100° C. The solvent was removed on a rotary evaporator and the residue was dried in vacuo. 903 mg (85% purity, 95% yield) of the title compound were obtained.

LC-MS (Method 9): $R_t$=0.73 min; MS (ESIpos): m/z=154 [M−HCl+H]$^+$

Intermediate 354

N-[2-(1,5-Dimethyl-1H-Pyrazol-3-Yl)-2-Oxoethyl]-5,6-Difluoro-4'-(Trifluoromethyl)[1,1'-Biphenyl]-2-Carboxamide

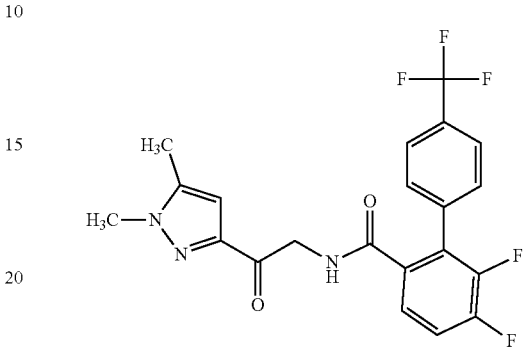

5,6-difluoro-4'-(trifluoromethyl)[1,1'-biphenyl]-2-carboxylic acid (226 mg, 747 µmol) dissolved in 7.5 ml of acetonitrile was treated with N-ethyl-N-isopropylpropan-2-amine (520 µl, 3.0 mmol) and 2,4,6-tripropyl-1,3,5,2,4,6-trioxatriphosphinane-2,4,6-trioxide in ethyl acetate (580 µl, 50% purity, 970 µmol) and the mixture was stirred at room temperature for 15 min. After that time, 2-amino-1-(1,5-dimethyl-1H-pyrazol-3-yl)ethan-1-one-hydrogenchloride (250 mg, 85% purity, 1.12 mmol) was added and the resulting mixture was stirred at room temperature for 30 min. Purification was done by preparative HPLC (column: Chromatorex C18 10 µm, 250×30 mm; eluent A=water with 0.1% formic acid, B=acetonitrile; gradient: 0.0 min 30% B, 4.5 min 50% B, 11.5 min 70% B, 12 min 100% B, 14.75 min 30% B; flow: 50 ml/min). Product containing samples were united, the solvents were evaporated and the residue was lyophilized. 140 mg (100% purity, 43% yield) of the title compound were obtained.

LC-MS (Method 7): $R_t$=1.93 min; MS (ESIpos): m/z=438 [M+H]$^+$

Intermediate 355

Ethyl 5-(1-Methyl-1H-Pyrazol-3-Yl)-1,3-Oxazole-4-Carboxylate

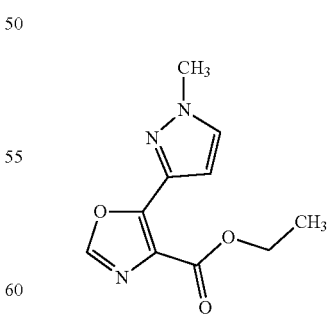

1-methyl-1H-pyrazole-3-carboxylic acid (1.00 g, 7.93 mmol) and 1,1'-carbonyldiimidazole (1.54 g, 9.52 mmol) in 11 ml of THF were stirred for 2 h at room temperature. After that time, a solution of ethyl isocyanoacetate (950 µl, 8.7 mmol) in 11 ml of THF and a solution of lithium bis (trimethylsilyl)amide in THF (7.9 ml, 1.0 M, 7.9 mmol) were added dropwise at 0° C. When the addition was complete the resulting mixture was stirred at room temperature for 1 h. The reaction was concentrated in vacuo and extracted between water and ethyl acetate. The combined organic layers were dried over sodium sulfate, filtered and concentrated. The crude product was purified by column chromatography (Machine: Biotage® Isolera One; column: Biotage® SNAP Ultra 50 g; gradient: Cy/EE-gradient, 16% EE-100% EE; flow: 100 ml/min). Product containing samples were united, the solvents were removed on a rotary evaporator and the residue was dried in vacuo. 1.09 g (100% purity, 62% yield) of the title compound were obtained.

LC-MS (Method 7): $R_t$=1.03 min; MS (ESIpos): m/z=222 [M+H]$^+$

Intermediate 356

2-Amino-1-(1-Methyl-1H-Pyrazol-3-Yl)Ethan-1-One-Hydrogenchloride

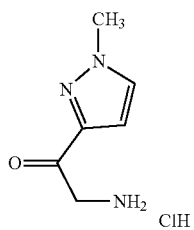

Ethyl 5-(1-methyl-1H-pyrazol-3-yl)-1,3-oxazole-4-carboxylate (1.09 g, 4.93 mmol) was taken up in 20 ml of 6 N hydrochloric acid and stirred 2 h at 100° C. The solvent was removed on a rotary evaporator and the residue was dried in vacuo. 826 mg (100% purity, 95% yield) of the title compound were obtained.

LC-MS (Method 9): $R_t$=0.52 min; MS (ESIpos): m/z=140 [M−HCl+H]$^+$

Intermediate 357

5,6-Difluoro-N-[2-(1-Methyl-1H-Pyrazol-3-Yl)-2-Oxoethyl]-4'-(Trifluoromethyl)[Biphenyl]-2-Carboxamide

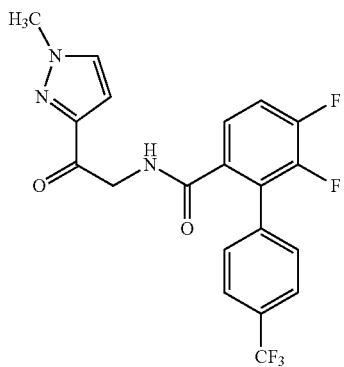 [SMILES: Cn1ccc(C(=O)CNC(=O)c2ccc(F)c(F)c2-c2ccc(C(F)(F)F)cc2)n1]

5,6-difluoro-4'-(trifluoromethyl)[1,1'-biphenyl]-2-carboxylicacid (430 mg, 1.42 mmol) dissolved in 7.5 ml DMF was treated with N,N-diisopropylethylamine (740 µl, 4.3 mmol), 1-ethyl-3-(3-dimethylaminopropyl)carbodiimide hydrochloride (355 mg, 1.85 mmol) and 1-hydroxybenzotriazole hydrate (283 mg, 1.85 mmol) and stirred for 5 min at room temperature before 2-amino-1-(1-methyl-1H-pyrazol-3-yl)ethan-1-one-hydrogenchloride (250 mg, 1.42 mmol) was added. The mixture was stirred at room temperature over night. The reaction mixture was diluted with water and extracted with ethyl acetate. The combined organic layers were dried over sodium sulfate, filtered and concentrated. The crude product was purified by column chromatography (Machine: Biotage® Isolera One; column: Biotage® SNAP Ultra 50 g; gradient: Cy/EE-gradient, 12% EE-100% EE; flow: 100 ml/min). Product containing samples were united, the solvents were removed on a rotary evaporator and the residue was dried in vacuo. 382 mg (93% purity, 59% yield) of the title compound were obtained.

LC-MS (Method 7): $R_t$=1.88 min; MS (ESIpos): m/z=424 [M+H]$^+$

Intermediate 358

5-(Difluoromethyl)-4'-(Trifluoromethyl)[1,1'-Biphenyl]-2-Carboxylic Acid

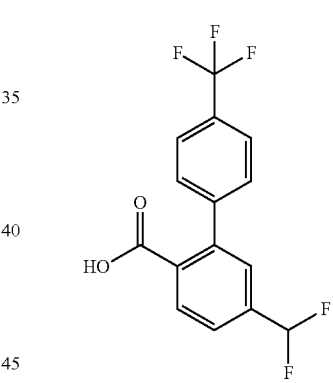

[4-(trifluoromethyl)phenyl]boronic acid (200 mg, 1.05 mmol) and 2-bromo-4 (difluoromethyl)benzoic acid (176 mg, 702 µmol) dissolved in 5 ml 1,2-dimethoxethane were treated with potassium phosphate in water (1.4 ml, 1.5 M, 2.1 mmol). The mixture was degassed with argon. Then dichlorobis(triphenylphosphine)palladium(II) (49.3 mg, 70.2 µmol) and XPhos (33.5 mg, 70.2 µmol) were added and the mixture was stirred at 80° C. over night. The reaction mixture was filtered over Celite® and the filtrate was concentrated in vacuo. The crude product was purified by column chromatography (Machine: Biotage® Isolera One; column: Biotage® SNAP Ultra 25 g; gradient: DCM/MeOH-gradient, 5% MeOH-20% MeOH; flow: 75 ml/min). Product containing samples were united and the solvents were removed on a rotary evaporator. 53.0 mg (100% purity, 16% yield) of the title compound were obtained.

LC-MS (Method 8): $R_t$=0.97 min; MS (ESIneg): m/z=315 [M−H]$^-$

Intermediate 359

6-Chloro-4'-(Trifluoromethyl)[1,1'-Biphenyl]-2-Carboxylic Acid

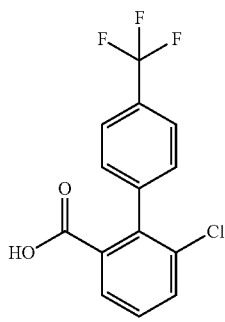 [SMILES: O=C(O)c1cccc(Cl)c1-c1ccc(C(F)(F)F)cc1]

[4-(trifluoromethyl)phenyl]boronic acid (200 mg, 1.05 mmol) and 2-bromo-3-chlorobenzoic acid (165 mg, 702 µmol) dissolved in 5 ml 1,2-dimethoxethane were treated with potassium phosphate in water (1.4 ml, 1.5 M, 2.1 mmol). The mixture was degassed with argon. Then dichlorobis(triphenylphosphine)palladium(II) (49.3 mg, 70.2 µmol) and XPhos (33.5 mg, 70.2 µmol) were added and the mixture was stirred at 80° C. over night. Purification was done by preparative HPLC (Column: Chromatorex C18 10 µm 250×30 mm; eluent A=water+0.1% formic acid, B=acetonitrile; gradient: 0.0 min 30% B; 4.5 min 50% B; 11.5 min 70% B; 12 min 100% B; 14.75 min 30% B; flow: 50 ml/min). Product containing samples were united and the solvents were removed on a rotary evaporator. 51.0 mg (63% purity, 10% yield) of the title compound were obtained.

LC-MS (Method 7): $R_t$=1.97 min; MS (ESIpos): m/z=301 [M+H]$^+$

Intermediate 360

Ethyl 5-(1-Phenyl-1H-Pyrazol-5-Yl)-1,3-Oxazole-4-Carboxylate

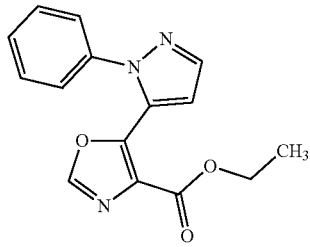 [SMILES: CCOC(=O)c1ncoc1-c1ccnn1-c1ccccc1]

1-phenyl-1H-pyrazole-5-carboxylic acid (1.00 g, 5.31 mmol) and 1,1'-carbonyldiimidazole (1.03 g, 6.38 mmol) in 11 ml of THF was stirred for 2 h at room temperature. After that time, a solution of ethyl isocyanoacetate (640 µl, 5.8 mmol) in 11 ml of THF and a solution of lithium bis(trimethylsilyl)amide in THF (5.3 ml, 1.0 M, 5.3 mmol) were added dropwise at 0° C. When the addition was complete the resulting mixture was stirred at room temperature for 1 h. The reaction was concentrated in vacuo and extracted between water and ethyl acetate. The combined organic layers were dried over sodium sulfate, filtered and concentrated. The crude product was purified by column chromatography (Machine: Biotage® Isolera One; column: Biotage® SNAP Ultra 50 g; gradient: Cy/EE-gradient, 12% EE-100% EE; flow: 100 ml/min). Product containing samples were united and the solvents were removed on a rotary evaporator. 1.03 g (100% purity, 68% yield) of the title compound were obtained.

LC-MS (Method 7): $R_t$=1.53 min; MS (ESIpos): m/z=284 [M+H]$^+$

Intermediate 361

2-Amino-1-(1-Phenyl-1H-Pyrazol-5-Yl)Ethan-1-One Hydrogen Chloride

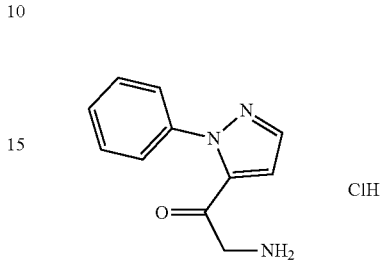

Ethyl 5-(1-phenyl-1H-pyrazol-5-yl)-1,3-oxazole-4-carboxylate (1.03 g, 3.64 mmol) was treated with 15 ml of 6 N hydrochloric acid and stirred for 2 h at 100° C. The solvent was removed on a rotary evaporator and the residue was dried in vacuo. 816 mg (63% purity, 59% yield) of the title compound were obtained.

LC-MS (Method 9): $R_t$=0.97 min; MS (ESIpos): m/z=202 [M+H−HCl]$^+$

Intermediate 362

5,6-Difluoro-N-[2-Oxo-2-(1-Phenyl-1H-Pyrazol-5-Yl)Ethyl]-4'-(Trifluoromethyl)[1,1'-Biphenyl]-3-Carboxamide 5,6-difluoro-N-[2-oxo-2-(1-phenyl-1H-pyrazol-5-yl)ethyl]-4'-(trifluoromethyl)[biphenyl]-2-carboxamide

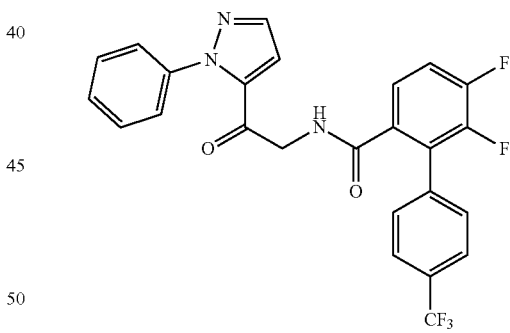

5,6-difluoro-4'-(trifluoromethyl)[1,1'-biphenyl]-2-carboxylic acid (315 mg, 1.04 mmol) dissolved in 5.5 ml of DMF was treated with N-ethyl-N-isopropylpropan-2-amine (550 µl, 3.1 mmo), 3-{[(ethylimino)methylene]amino}-N,N-dimethylpropan-1-amine hydrochloride (260 mg, 1.36 mmol), 1H-benzotriazol-1-ol hydrate (208 mg, 1.36 mmol) and 2-amino-1-(1-phenyl-1H-pyrazol-5-yl)ethan-1-one hydrogen chloride (400 mg, 62% purity, 1.04 mmol). The mixture was stirred over night at room temperature. The reaction mixture was diluted with water an extracted with ethyl acetate. The combined organic layers were dried over sodium sulfate, filtered and concentrated. The crude product was purified by column chromatography (Machine: Biotage® Isolera One; column: Biotage® SNAP Ultra 25 g; gradient: Cy/EE-gradient, 12% EE-100% EE: flow: 75 ml/min). Product containing samples were united and the solvents were removed on a rotary evaporator. 444 mg (66% purity, 58% yield) of the title compound were obtained.

LC-MS (Method 7): $R_t$=2.11 min; MS (ESIpos): m/z=486 [M+H]$^+$

Intermediate 363

N-[2-(1,5-Dimethyl-1H-Pyrazol-4-Yl)-2-Oxoethyl]-5,6-Difluoro-4'-(Trifluoromethyl)[Biphenyl]-2-Carboxamide

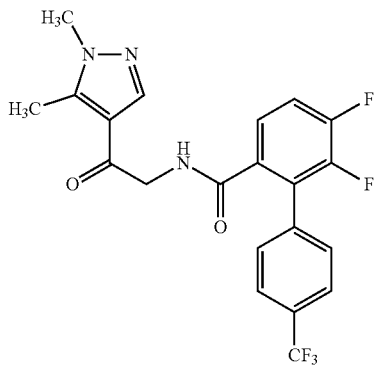 [SMILES: Cc1c(C(=O)CNC(=O)c2ccc(F)c(F)c2-c2ccc(C(F)(F)F)cc2)cnn1C]

5,6-difluoro-4'-(trifluoromethyl)[1,1'-biphenyl]-2-carboxylic acid (637 mg, 2.11 mmol) dissolved in 10 ml of DMF was treated with N-ethyl-N-isopropylpropan-2-amine (1.1 ml, 6.3 mmol), 3-{[(ethylimino)methylene]amino}-N,N-dimethylpropan-1-amine hydrochloride (526 mg, 2.74 mmol), 1H-benzotriazol-1-ol hydrate (420 mg, 2.74 mmol) and 2-amino-1-(1,5-dimethyl-1H-pyrazol-4-yl)ethan-1-one hydrogen chloride (400 mg, 2.11 mmol). The mixture was stirred 1.5 h at room temperature. The reaction mixture was diluted with water and extracted with ethyl acetate. The combined organic layers were dried over sodium sulfate, filtered and concentrated. The crude product was purified by column chromatography (Machine: Biotage® Isolera One; column: Biotage® SNAP NH 55 g; gradient: Cy/EE-gradient, 12% EE-100% EE; flow: 50 ml/min). Product containing samples were united and the solvents were removed on a rotary evaporator. 253 mg (100% purity, 27% yield) of the title compound were obtained.

LC-MS (Method 7): $R_t$=1.85 min; MS (ESIpos): m/z=438 [M+H]$^+$

EXPERIMENTAL SECTION—EXAMPLES

Example 1

Rac-N-{[4-(5-Methyl-1,3-Thiazol-4-Yl)-2,5-Dioxoimidazolidin-4-Yl]Methyl}-4'-(Trifluoromethyl)[Biphenyl]-2-Carboxamide

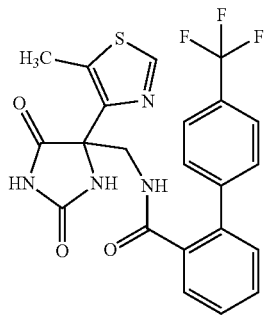 [SMILES: Cc1scnc1C1(CNC(=O)c2ccccc2-c2ccc(C(F)(F)F)cc2)NC(=O)NC1=O]

4'-(trifluoromethyl)[1,1'-biphenyl]-2-carboxylic acid (129 mg, 485 µmol) dissolved in 10 ml dichloromethane was treated with N,N-diisopropylethylamine (240 µl, 1.4 mmol), 1-ethyl-3-(3-dimethylaminopropyl)carbodiimide hydrochloride (121 mg, 631 µmol) and 1-hydroxybenzotriazole hydrate (96.6 mg, 631 µmol) and stirred for 5 min at room temperature before rac-5-(aminomethyl)-5-(5-methyl-1,3-thiazol-4-yl)imidazolidine-2,4-dione hydrochloride (150 mg, 85% purity, 485 µmol) was added. The mixture was stirred at room temperature over night. Purification was done by preparative HPLC (column: Chromatorex C18 10 µm, 250×30 mm; eluent A=water with 0.1% formic acid, B=acetonitrile; gradient: 0.0 min 30% B, 4.5 min 50% B, 11.5 min 70% B, 12 min 100% B, 14.75 min 30% B; flow: 50 ml/min). Further purification was needed and done by preparative HPLC (Instrument: Waters Prep LC/MS System; column: Phenomenex Kinetex C18 5 µm 100×30 mm; eluent A: water, eluent B: acetonitrile, eluent C: 2% formic acid in water, eluent D: acetonitrile/water (80 Vol. %/20 Vol %); flow: 80 ml/min; room temperature; UV 200-400 nm, At-Column Injektion. Gradient: eluent A0 to 2 min 55 ml, eluent B 0 to 2 min 15 ml, eluent A 2 to 10 min from 55 ml to 31 ml and eluent B from 15 ml to 39 ml, 10 to 12 min 0 ml eluent A and 70 ml eluent B. Eluent C and eluent D constant flow each 5 ml/min over the whole time). Product containing samples were united, the solvents were evaporated and the residue was lyophilized. 56.0 mg (100% purity, 24% yield) of the title compound were obtained.

LC-MS (Method 7): $R_t$=1.63 min; MS (ESIpos): m/z=475 [M+H]$^+$ $^1$H-NMR (400 MHz, DMSO-d6) δ [ppm]: −0.008 (0.69), 0.008 (0.74), 2.364 (16.00), 2.524 (0.51), 4.071 (1.72), 4.077 (1.76), 4.087 (1.77), 4.092 (1.82), 7.420 (0.77), 7.424 (0.92), 7.439 (4.10), 7.442 (2.14), 7.457 (3.03), 7.472 (1.92), 7.475 (1.37), 7.491 (0.82), 7.494 (0.64), 7.535 (1.27), 7.539 (1.22), 7.553 (1.58), 7.557 (1.45), 7.571 (3.05), 7.591 (3.05), 7.762 (3.18), 7.783 (2.60), 8.263 (3.37), 8.602 (0.68), 8.618 (1.47), 8.633 (0.67), 8.846 (5.58), 11.038 (1.22).

Example 2

Ent-N-{[4-(5-Methyl-1,3-Thiazol-4-Yl)-2,5-Dioxoimidazolidin-4-Yl]Methyl}-4'-(Trifluoromethyl)[Biphenyl]-2-Carboxamide

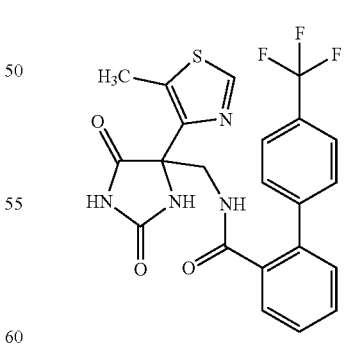

Enantiomeric separation of rac-N-{[4-(5-methyl-1,3-thiazol-4-yl)-2,5-dioxoimidazolidin-4 yl]methyl}-4'-(trifluoromethyl)[biphenyl]-2-carboxamide (52.0 mg, 110 µmol) was done using the following method:

Column: Daicel Chiralpak ID 5 µm 250×20 mm
Solvent: 70% iso-propanole/30% n-heptane Flow: 20 ml/min
Column temperature: 40° C.
UV-detection: 210 nm Further purification was needed and done by preparative HPLC (column: Chromatorex C18 10 μm, 250×30 mm; eluent A=water with 0.1% formic acid, B=acetonitrile; gradient: 0.0 min 30% B; 4.5 min 50% B; 11.5 min 70% B; 12 min 100% B; 14.75 min 30% B; flow: 50 ml/min). Product containing samples were united, the solvents were evaporated and the residue was lyophilized. 16.0 mg (100% purity, 31% yield) of the title compound were obtained.

LC-MS (Method 7): $R_t$=1.63 min; MS (ESIpos): m/z=475 [M+H]$^+$

Chiral HPLC (Column: Daicel ID-3 3 μm 50×4.6 mm; solvent: 50% n-heptane-50% iso-propanole; flow: 1 ml/min; UV-detection: 220 nm): $R_t$=1.812 min, >99.0% ee $^1$H-NMR (400 MHz, DMSO-d6) δ [ppm]: 2.364 (16.00), 4.072 (2.17), 4.077 (2.25), 4.091 (2.37), 7.424 (1.11), 7.439 (4.37), 7.456 (3.82), 7.472 (2.10), 7.491 (0.89), 7.535 (1.32), 7.538 (1.30), 7.553 (1.72), 7.557 (1.67), 7.571 (3.83), 7.591 (3.86), 7.763 (3.95), 7.783 (3.27), 8.262 (3.71), 8.602 (0.86), 8.618 (1.81), 8.634 (0.86), 8.846 (5.00), 11.040 (1.80).

Example 3

Ent-N-{[4-(5-Methyl-1,3-Thiazol-4-Yl)-2,5-Dioxo-imidazolidin-4-Yl]Methyl}-4'-(Trifluoromethyl)[Biphenyl]-2-Carboxamide

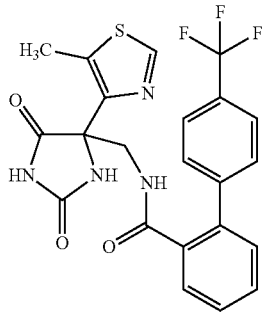 [SMILES: Cc1scnc1C1(CNC(=O)c2ccccc2-c2ccc(C(F)(F)F)cc2)NC(=O)NC1=O]

Enantiomeric separation of rac-N-{[4-(5-methyl-1,3-thiazol-4-yl)-2,5-dioxoimidazolidin-4 yl]methyl}-4'-(trifluoromethyl)[biphenyl]-2-carboxamide (52.0 mg, 110 μmol) was done using the following method:

Column: Daicel Chiralpak ID 5 μm 250×20 mm
Solvent: 70% iso-propnanole/30% n-heptane
Flow: 20 ml/min
Column temperature: 40° C.
UV-detection: 210 nm Further purification was needed and done by preparative HPLC (column: Chromatorex C18 10 μm, 250×30 mm; eluent A=water with 0.1% formic acid, B=acetonitrile; gradient: 0.0 min 30% B, 4.5 min 50% B, 11.5 min 70% B, 12 min 100% B, 14.75 min 30% B; flow: 50 ml/min). Product containing samples were united, the solvents were evaporated and the residue was lyophylized. 16.0 mg (100% purity, 31% yield) of the title compound were obtained.

LC-MS (Method 7): $R_t$=1.63 min; MS (ESIpos): m/z=475 [M+H]$^+$

Chiral HPLC (Column: Daicel ID-3 3 μm 50×4.6 mm; solvent: 50% n-heptane-50% iso-propanole; flow: 1 ml/min; UV detection: 220 nm): $R_t$=5.126 min, >99.0% ee $^1$H-NMR (400 MHz, DMSO-d6) δ [ppm]: 0.008 (0.43), 2.364 (16.00), 2.523 (0.77), 4.071 (1.85), 4.077 (1.91), 4.087 (1.95), 4.092 (1.99), 7.420 (0.84), 7.423 (0.97), 7.439 (4.13), 7.457 (3.21), 7.472 (1.98), 7.491 (0.83), 7.534 (1.28), 7.539 (1.22), 7.553 (1.63), 7.557 (1.49), 7.571 (3.27), 7.591 (3.27), 7.762 (3.41), 7.783 (2.81), 8.262 (2.49), 8.602 (0.74), 8.618 (1.61), 8.633 (0.72), 8.847 (5.22), 11.039 (2.15).

Example 4

Rac-N-{[4-(1-Ethyl-1H-Pyrazol-5-Yl)-2,5-Dioxo-imidazolidin-4-Yl]Methyl}-4'-(Trifluoromethyl)[Biphenyl]-2-Carboxamide

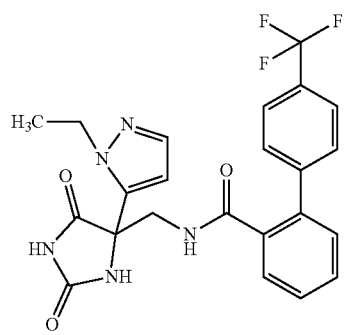 [SMILES: CCn1nccc1C1(CNC(=O)c2ccccc2-c2ccc(C(F)(F)F)cc2)NC(=O)NC1=O]

4'-(trifluoromethyl)[1,1'-biphenyl]-2-carboxylic acid (101 mg, 381 μmol) dissolved in 10 ml dichloromethane was treated with N,N-diisopropylethylamine (190 μl, 1.1 mmol), 1-ethyl-3-(3-dimethylaminopropyl)carbodiimide hydrochloride (95.0 mg, 496 μmol) and 1-hydroxybenzotriazole hydrate (75.9 mg, 496 μmol) and stirred for 5 min at room temperature before rac-5-(aminomethyl)-5-(1-ethyl-1H-pyrazol-5-yl)imidazolidine-2,4-dione hydrochloride (110 mg, 90% purity, 381 μmol) was added. The mixture was stirred at room temperature for 3 h. Purification was done by preparative HPLC (column: Chromatorex C18 10 μm, 250×30 mm, eluent A=water with 0.1% formic acid, B=acetonitrile; gradient: 0.0 min 30% B, 4.5 min 50% B, 11.5 min 70% B, 12 min 100% B, 14.75 min 30% B; flow: 50 ml/min) for two times. Further purification was needed by preparative HPLC (Instrument: Waters Prep LC/MS System; column: Phenomenex Kinetex C18 5 μm 100×30 mm; eluent A: water, eluent B: acetonitrile, eluent C: 2% formic acid in water, eluent D: acetonitrile/water (80 Vol. %/20 Vol %); flow: 80 ml/min; room temperature; UV 200-400 nm, At-Column Injektion; gradient: eluent A 0 to 2 min 63 ml, eluent B 0 to 2 min 7 ml, eluent A 2 to 10 min from 63 ml to 39 ml and eluent B from 7 ml to 31 ml, 10 to 12 min 0 ml eluent A and 70 ml eluent B. Eluent C and eluent D constant flow each 5 ml/min over the whole time). Product containing samples were united, the solvents were evaporated and the residue was lyophylized. 9.00 mg (100% purity, 5% yield) of the title compound were obtained.

LC-MS (Method 7): $R_t$=1.57 min; MS (ESIpos): m/z=472 [M+H]$^+$ $^1$H-NMR (400 MHz, DMSO-d6) δ [ppm]: −0.149 (0.61), −0.015 (0.73), −0.008 (5.14), −0.006 (3.55), 0.008 (5.14), 0.021 (0.42), 0.146 (0.61), 1.286 (6.92), 1.304 (16.00), 1.322 (7.02), 2.323 (0.54), 2.327 (0.76), 2.332 (0.56), 2.366 (0.64), 2.523 (2.91), 2.526 (2.18), 2.557 (0.81), 2.560 (0.64), 2.565 (0.44), 2.665 (0.56), 2.669 (0.78), 2.674 (0.54), 2.709 (0.66), 3.854 (0.86), 3.869 (1.00), 3.888 (2.37), 3.903 (2.20), 3.916 (2.30), 3.933 (2.32), 3.950 (0.93), 3.967 (0.91), 4.010 (1.35), 4.028 (3.52), 4.032 (3.40), 4.045 (3.38), 4.050 (3.45), 4.063 (1.13), 4.068 (1.30), 6.453 (6.48), 6.457 (6.58), 7.433 (10.15), 7.438 (7.73), 7.447 (4.43), 7.451 (6.87), 7.468 (2.18), 7.471 (2.18), 7.486 (3.50), 7.489 (2.81), 7.505 (1.57), 7.508 (1.44), 7.531 (5.04), 7.551 (7.95), 7.565 (3.16), 7.569 (2.74), 7.584 (1.10), 7.588 (1.15), 7.748 (6.12), 7.768 (5.09), 8.436 (4.82), 8.759 (1.30), 8.774 (2.64), 8.790 (1.27), 11.259 (3.13).

Example 5

Rac-N-{[4-(4-Methyl-1,3-Thiazol-5-Yl)-2,5-Dioxo-imidazolidin-4-Yl]Methyl}-4'-(Trifluoromethyl)[Biphenyl]-2-Carboxamide

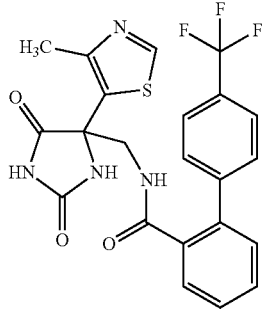 [SMILES: Cc1ncsc1C1(CNC(=O)c2ccccc2-c2ccc(C(F)(F)F)cc2)NC(=O)NC1=O]

4'-(trifluoromethyl)[1,1'-biphenyl]-2-carboxylic acid (101 mg, 381 µmol) dissolved in 10 ml dichloromethane was treated with N,N-diisopropylethylamine (190 µl, 1.1 mmol), 1-ethyl-3-(3-dimethylaminopropyl)carbodiimide hydrochloride (94.9 mg, 495 µmol) and 1-hydroxybenzotriazole hydrate (75.8 mg, 495 µmol) and stirred for 5 min at room temperature before rac-5-(aminomethyl)-5-(4-methyl-1,3-thiazol-5-yl)imidazolidine-2,4-dione hydrochloride (100 mg, 381 µmol) was added. The mixture was stirred at room temperature over night. Purification was done by preparative HPLC (column: Chromatorex C18 10 µm, 250×30 mm; eluent A=water with 0.1% formic acid, B=acetonitrile; gradient: 0.0 min 30% B, 4.5 min 50% B, 11.5 min 70% B, 12 min 100% B, 14.75 min 30% B; flow: 50 ml/min). Product containing samples were united, the solvents were evaporated and the residue was lyophylized. 135 mg (100% purity, 75% yield) of the title compound were obtained.

LC-MS (Method 7): $R_t$=1.54 min; MS (ESIpos): m/z=475 [M+H]$^+$ $^1$H-NMR (400 MHz, DMSO-d6) δ [ppm]: 2.456 (16.00), 3.895 (2.35), 3.912 (2.18), 7.403 (1.39), 7.422 (2.25), 7.437 (1.72), 7.456 (2.35), 7.469 (1.12), 7.486 (5.09), 7.506 (4.53), 7.546 (1.33), 7.550 (1.38), 7.565 (1.72), 7.568 (1.73), 7.587 (0.67), 7.746 (3.72), 7.767 (3.21), 8.530 (2.93), 8.747 (0.83), 8.763 (1.70), 8.778 (0.81), 8.939 (4.22), 11.198 (2.44).

Example 6

Rac-N-({2,5-Dioxo-4-[1-(2,2,2-Trifluoroethyl)-1H-Pyrazol-5-Yl]Imidazolidin-4-Yl}Methyl)-4'-(Trifluoromethyl)[Biphenyl]-2-Carboxamide

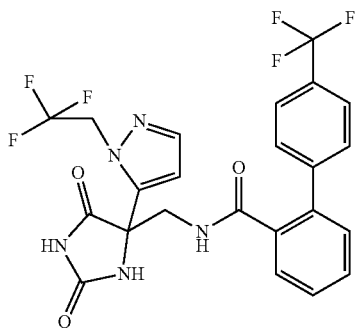 [SMILES: O=C1NC(=O)C(CNC(=O)c2ccccc2-c2ccc(C(F)(F)F)cc2)(c2ccnn2CC(F)(F)F)N1]

4'-(trifluoromethyl)[1,1'-biphenyl]-2-carboxylic acid (102 mg, 383 µmol) dissolved in 10 ml dichloromethane was treated with N,N-diisopropylethylamine (190 µl, 1.1 mmol), 1-ethyl-3-(3-dimethylaminopropyl)carbodiimide hydrochloride (95.3 mg, 497 µmol) and 1-hydroxybenzotriazole hydrate (76.2 mg, 497 µmol) and stirred for 5 min at room temperature before rac-5-(aminomethyl)-5-[1-(2,2,2-trifluoroethyl)-1H-pyrazol-5-yl]imidazolidine-2,4-dione hydrochloride (120 mg, 383 µmol) was added. The mixture was stirred at room temperature over night. Purification was done by preparative HPLC (column: Chromatorex C18 10 µm, 250×30 mm; eluent A=water with 0.1% formic acid, B=acetonitrile; gradient: 0.0 min 30% B, 4.5 min 50% B, 11.5 min 70% B, 12 min 100% B, 14.75 min 30% B; flow: 50 ml/min). Product containing samples were united, the solvents were evaporated and the residue was lyophylized. 39.0 mg (100% purity, 19% yield) of the title compound were obtained.

LC-MS (Method 7): $R_t$=1.71 min; MS (ESIpos): m/z=526 [M+H]$^+$ $^1$H-NMR (400 MHz, DMSO-d6) δ [ppm]: 2.328 (0.58), 2.366 (0.95), 2.669 (0.64), 2.710 (0.92), 3.767 (2.93), 3.784 (3.21), 3.801 (5.01), 3.818 (4.76), 3.882 (4.76), 3.897 (5.28), 3.917 (3.18), 3.932 (2.87), 5.125 (3.27), 5.147 (9.40), 5.169 (9.31), 5.191 (3.08), 6.589 (14.29), 6.593 (14.81), 7.412 (6.02), 7.432 (10.81), 7.456 (9.92), 7.473 (4.89), 7.489 (8.27), 7.511 (5.74), 7.518 (13.53), 7.539 (15.60), 7.550 (6.69), 7.553 (6.35), 7.569 (7.30), 7.572 (7.51), 7.591 (3.05), 7.604 (13.92), 7.609 (14.14), 7.745 (16.00), 7.765 (13.37), 8.465 (12.76), 8.808 (3.42), 8.823 (6.96), 8.839 (3.39), 11.302 (10.50).

Example 7

Ent-5-Chloro-N-{[4-(4-Methyl-1,3-Thiazol-5-Yl)-2,5-Dioxoimidazolidin-4-Yl]Methyl}-4'-(Trifluoromethyl)[Biphenyl]-2-Carboxamide

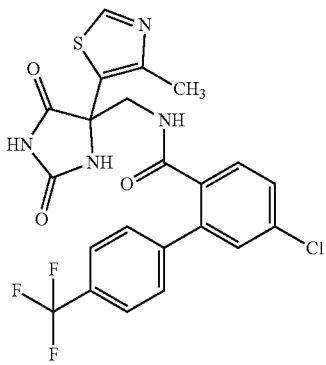 [SMILES: Cc1ncsc1C1(CNC(=O)c2ccc(Cl)cc2-c2ccc(C(F)(F)F)cc2)NC(=O)NC1=O]

5-chloro-4'-(trifluoromethyl)[1,1'-biphenyl]-2-carboxylic acid (85.8 mg, 285 µmol) dissolved in 2 ml DMF was treated with N,N-diisopropylethylamine (150 µl, 860 µmol), 1-ethyl-3-(3-dimethylaminopropyl)carbodiimide hydrochloride (71.1 mg, 371 µmol) and 1-hydroxybenzotriazole hydrate (56.8 mg, 371 µmol) and stirred for 5 min at room temperature before ent-5-(aminomethyl)-5-(4-methyl-1,3-thiazol-5-yl)imidazolidine-2,4-dione hydrochloride (Enantiomer 2) (75.0 mg, 285 µmol) was added. The mixture was stirred at room temperature overnight. Purification was done by preparative HPLC (Instrument: Waters Prep LC/MS System; column: Phenomenex Kinetex C18 5 µm 100×30 mm; eluent A: water, eluent B: acetonitrile, eluent C: 2% formic acid in water, eluent D: acetonitrile/water (80 Vol. %/20 Vol %); flow: 80 ml/min; room temperature; UV 200-400 nm; At-Column Injektion; Gradient: eluent A0 to 2 min 55 ml, eluent B 0 to 2 min 15 ml, eluent A 2 to 10 min from 55 ml to 31 ml and eluent B from 15 ml to 39 ml, 10 to 12 min 0 ml eluent A and 70 ml eluent B. Eluent C and eluent D constant flow each 5 ml/min over the whole time). Product containing samples were united, the solvents were evaporated and the residue was lyophylized. 75.0 mg (100% purity, 52% yield) of the title compound were obtained.

LC-MS (Method 7): $R_t$=1.72 min; MS (ESIpos): m/z=509 [M+H]$^+$ $^1$H-NMR (400 MHz, DMSO-d6) δ [ppm]: 2.073 (0.58), 2.449 (16.00), 2.523 (0.64), 3.881 (2.75), 3.896 (2.89), 7.416 (2.81), 7.436 (3.48), 7.516 (2.86), 7.528 (3.64), 7.533 (5.78), 7.577 (2.32), 7.583 (1.86), 7.598 (1.74), 7.603 (1.51), 7.760 (3.33), 7.781 (2.83), 8.565 (3.09), 8.826 (0.73), 8.841 (1.58), 8.857 (0.72), 8.937 (4.68).

Example 8

Ent-5-Methyl-N-{[4-(4-Methyl-1,3-Thiazol-5-Yl)-2,5-Dioxoimidazolidin-4-Yl]Methyl}-4'-(Trifluoromethyl)[Biphenyl]-2-Carboxamide

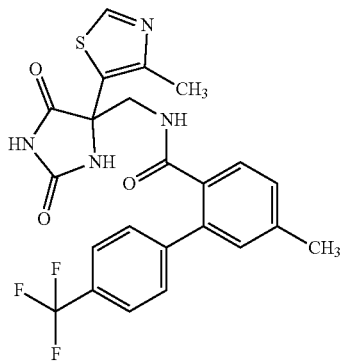 [SMILES: Cc1ccc(C(=O)NCC2(c3scnc3C)NC(=O)NC2=O)c(-c2ccc(C(F)(F)F)cc2)c1]

5-methyl-4'-(trifluoromethyl)[1,1'-biphenyl]-2-carboxylic acid (80.0 mg, 285 µmol) dissolved in 2 ml DMF was treated with N,N-diisopropylethylamine (150 µl, 860 µmol), 1-ethyl-3-(3-dimethylaminopropyl)carbodiimide hydrochloride (71.1 mg, 371 µmol) and 1-hydroxybenzotriazole hydrate (56.8 mg, 371 µmol) and stirred for 5 min at room temperature before ent-5-(aminomethyl)-5-(4-methyl-1,3-thiazol-5-yl)imidazolidine-2,4-dione hydrochloride (Enantiomer 2) (75.0 mg, 285 µmol) was added. The mixture was stirred at room temperature overnight. Purification was done by preparative HPLC (Instrument: Waters Prep LC/MS System; column: Phenomenex Kinetex C18 5 µm 100×30 mm; eluent A: water, eluent B: acetonitrile, eluent C: 2% formic acid in water, eluent D: acetonitrile/water (80 Vol. %/20 Vol %); flow: 80 ml/min; room temperature; UV 200-400 nm; At-Column Injektion; Gradient: eluent A0 to 2 min 55 ml, eluent B 0 to 2 min 15 ml, eluent A 2 to 10 min from 55 ml to 31 ml and eluent B from 15 ml to 39 ml, 10 to 12 min 0 ml eluent A and 70 ml eluent B. Eluent C and eluent D constant flow each 5 ml/min over the whole time). Product containing samples were united, the solvents were evaporated and the residue was lyophylized. 75.0 mg (100% purity, 54% yield) of the title compound were obtained.

LC-MS (Method 7): $R_t$=1.67 min; MS (ESIpos): m/z=489 [M+H]$^+$ $^1$H-NMR (400 MHz, DMSO-d6) δ [ppm]: 2.386 (10.99), 2.452 (16.00), 3.836 (0.50), 3.850 (0.59), 3.870 (1.41), 3.884 (1.27), 3.899 (1.31), 3.915 (1.37), 3.932 (0.54), 3.949 (0.51), 7.254 (2.90), 7.274 (0.93), 7.294 (2.16), 7.317 (3.78), 7.337 (1.45), 7.453 (2.91), 7.473 (3.26), 7.729 (3.42), 7.750 (2.98), 8.509 (2.24), 8.641 (0.75), 8.656 (1.42), 8.671 (0.74), 8.934 (4.86).

Example 9

Ent-4'-Chloro-N-{[4-(4-Methyl-1,3-Thiazol-5-Yl)-2,5-Dioxoimidazolidin-4-Yl]Methyl}[Biphenyl]-2-Carboxamide

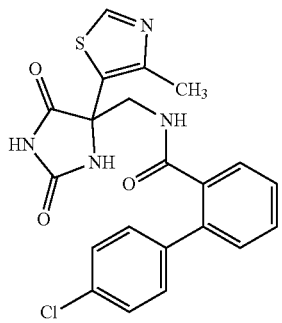 [SMILES: Cc1ncsc1C1(CNC(=O)c2ccccc2-c2ccc(Cl)cc2)NC(=O)NC1=O]

4'-chloro[1,1'-biphenyl]-2-carboxylic acid (66.4 mg, 285 µmol) dissolved in 2 ml DMF was treated with N,N-diisopropylethylamine (150 µl, 860 µmol), 1-ethyl-3-(3-dimethylaminopropyl)carbodiimide hydrochloride (71.1 mg, 371 µmol) and 1-hydroxybenzotriazole hydrate (56.8 mg, 371 µmol) and stirred for 5 min at room temperature before ent-5-(aminomethyl)-5-(4-methyl-1,3-thiazol-5-yl)imidazolidine-2,4-dione hydrochloride (Enantiomer 2) (75.0 mg, 285 µmol) was added. The mixture was stirred at room temperature overnight. Purification was done by preparative HPLC (Instrument: Waters Prep LC/MS System; column: Phenomenex Kinetex C18 5 µm 100×30 mm; eluent A: water, eluent B: acetonitrile, eluent C: 2% formic acid in water, eluent D: acetonitrile/water (80 Vol. %/20 Vol %); flow: 80 ml/min; room temperature; UV 200-400 nm; At-Column Injektion; Gradient: eluent A0 to 2 min 55 ml, eluent B 0 to 2 min 15 ml, eluent A 2 to 10 min from 55 ml to 31 ml and eluent B from 15 ml to 39 ml, 10 to 12 min 0 ml eluent A and 70 ml eluent B. Eluent C and eluent D constant flow each 5 ml/min over the whole time). Product containing samples were united, the solvents were evaporated and the residue was lyophylized. 65.0 mg (100% purity, 52% yield) of the title compound were obtained.

LC-MS (Method 7): $R_t$=1.44 min; MS (ESIpos): m/z=441 [M+H]$^+$ $^1$H-NMR (400 MHz, DMSO-d6) δ [ppm]: −0.008 (0.57), 0.008 (0.54), 2.461 (16.00), 2.523 (0.86), 2.526 (0.65), 3.878 (1.93), 3.883 (1.95), 3.893 (1.82), 3.899 (1.83), 7.285 (0.50), 7.292 (4.18), 7.297 (1.49), 7.308 (1.69), 7.313 (5.64), 7.320 (0.77), 7.344 (1.23), 7.347 (1.31), 7.363 (1.98), 7.366 (1.91), 7.383 (1.43), 7.385 (1.57), 7.402 (1.89), 7.404 (2.05), 7.416 (1.06), 7.419 (1.09), 7.438 (7.21), 7.443 (1.79), 7.454 (2.40), 7.459 (4.36), 7.466 (0.51), 7.505 (1.32), 7.509 (1.31), 7.524 (1.71), 7.527 (1.66), 7.543 (0.69), 7.546 (0.65), 8.504 (2.56), 8.660 (0.72), 8.676 (1.51), 8.691 (0.71), 8.939 (4.30).

Example 10

Ent-5-Fluoro-N-{[4-(4-Methyl-1,3-Thiazol-5-Yl)-2,5-Dioxoimidazolidin-4-Yl]Methyl}-4'-(Trifluoromethyl)[Biphenyl]-2-Carboxamide

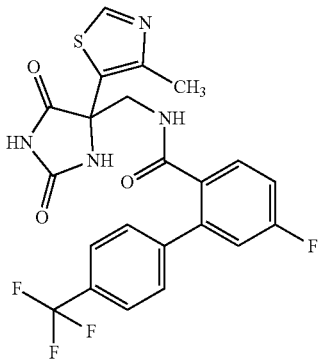 [SMILES: Cc1ncsc1C1(CNC(=O)c2ccc(F)cc2-c2ccc(C(F)(F)F)cc2)NC(=O)NC1=O]

5-fluoro-4'-(trifluoromethyl)[1,1'-biphenyl]-2-carboxylic acid (81.1 mg, 285 µmol) dissolved in 2 ml DMF was treated with N,N-diisopropylethylamine (150 µl, 860 µmol), 1-ethyl-3-(3-dimethylaminopropyl)carbodiimide hydrochloride (71.1 mg, 371 µmol) and 1-hydroxybenzotriazole hydrate (56.8 mg, 371 µmol) and stirred for 5 min at room temperature before ent-5-(aminomethyl)-5-(4-methyl-1,3-thiazol-5-yl)imidazolidine-2,4-dione hydrochloride (Enantiomer 2) (75.0 mg, 285 µmol) was added. The mixture was stirred at room temperature overnight. Purification was done by preparative HPLC (Instrument: Waters Prep LC/MS System; column: Phenomenex Kinetex C18 5 µm 100×30 mm; eluent A: water, eluent B: acetonitrile, eluent C: 2% formic acid in water, eluent D: acetonitrile/water (80 Vol. %/20 Vol %); flow: 80 ml/min; room temperature; UV 200-400 nm; At-Column Injektion; Gradient: eluent A0 to 2 min 55 ml, eluent B 0 to 2 min 15 ml, eluent A 2 to 10 min from 55 ml to 31 ml and eluent B from 15 ml to 39 ml, 10 to 12 min 0 ml eluent A and 70 ml eluent B. Eluent C and eluent D constant flow each 5 ml/min over the whole time). Product containing samples were united, the solvents were evaporated and the residue was lyophylized. 78.0 mg (100% purity, 55% yield) of the title compound were obtained.

LC-MS (Method 7): $R_t$=1.60 min; MS (ESIpos): m/z=493 [M+H]$^+$ $^1$H-NMR (400 MHz, DMSO-d6) δ [ppm]: −0.008 (0.41), 0.008 (0.41), 2.451 (16.00), 2.523 (0.75), 3.885 (2.70), 3.902 (2.55), 7.320 (1.04), 7.326 (1.80), 7.337 (0.94), 7.344 (1.28), 7.351 (1.88), 7.358 (1.88), 7.364 (1.18), 7.379 (1.00), 7.385 (0.79), 7.449 (1.47), 7.464 (1.52), 7.470 (1.20), 7.485 (1.05), 7.508 (2.90), 7.529 (3.29), 7.760 (3.44), 7.781 (2.96), 8.551 (2.84), 8.782 (0.76), 8.798 (1.64), 8.813 (0.76), 8.938 (4.18).

Example 11

Ent-4-Fluoro-N-{[4-(4-Methyl-1,3-Thiazol-5-Yl)-2,5-Dioxoimidazolidin-4-Yl]Methyl}-4'-(Trifluoromethyl)[Biphenyl]-2-Carboxamide

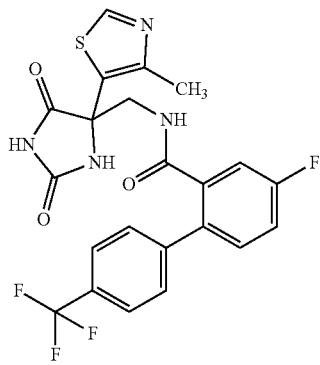 [SMILES: Cc1ncsc1C1(CNC(=O)c2cc(F)ccc2-c2ccc(C(F)(F)F)cc2)NC(=O)NC1=O]

4-fluoro-4'-(trifluoromethyl)[1,1'-biphenyl]-2-carboxylic acid (81.1 mg, 285 µmol) dissolved in 2 ml DMF was treated with N,N-diisopropylethylamine (150 µl, 860 µmol), 1-ethyl-3-(3-dimethylaminopropyl)carbodiimide hydrochloride (71.1 mg, 371 µmol) and 1-hydroxybenzotriazole hydrate (56.8 mg, 371 µmol) and stirred for 5 min at room temperature before ent-5-(aminomethyl)-5-(4-methyl-1,3-thiazol-5-yl)imidazolidine-2,4-dione hydrochloride (Enantiomer 2) (75.0 mg, 285 µmol) was added. The mixture was stirred at room temperature overnight. Purification was done by preparative HPLC (Instrument: Waters Prep LC/MS System; column: Phenomenex Kinetex C18 5 µm 100×30 mm; eluent A: water, eluent B: acetonitrile, eluent C: 2% formic acid in water, eluent D: acetonitrile/water (80 Vol. %/20 Vol %); flow: 80 ml/min; room temperature; UV 200-400 nm; At-Column Injektion: Gradient: eluent A 0 to 2 min 55 ml, eluent B 0 to 2 min 15 ml, eluent A 2 to 10 min from 55 ml to 31 ml and eluent B from 15 ml to 39 ml, 10 to 12 min 0 ml eluent A and 70 ml eluent B. Eluent C and eluent D constant flow each 5 ml/min over the whole time). Product containing samples were united, the solvents were evaporated and the residue was lyophylized. 88.0 mg (100% purity, 63% yield) of the title compound were obtained.

LC-MS (Method 7): $R_t$=1.59 min; MS (ESIpos): m/z=493 [M+H]$^+$ $^1$H-NMR (400 MHz, DMSO-d6) δ [ppm]: 2.073 (0.57), 2.455 (16.00), 3.890 (2.90), 3.906 (3.04), 7.222 (1.32), 7.229 (1.54), 7.245 (1.33), 7.251 (1.46), 7.403 (0.55), 7.410 (0.56), 7.424 (1.38), 7.431 (1.43), 7.446 (0.94), 7.452 (0.96), 7.476 (3.00), 7.485 (2.03), 7.498 (3.98), 7.507 (1.28), 7.521 (0.97), 7.746 (3.46), 7.767 (2.98), 8.590 (2.54), 8.891 (0.76), 8.906 (1.62), 8.922 (0.76), 8.943 (5.15).

Example 12

Rac-N-[(2,5-Dioxo-4-Phenylimidazolidin-4-Yl)Methyl]-4'-(Trifluoromethyl)[Biphenyl]-2-Carboxamide

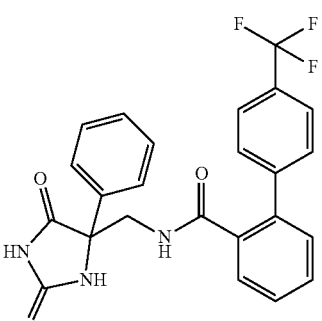

4'-(trifluoromethyl)[1,1'-biphenyl]-2-carboxylic acid (55.1 mg, 207 µmol) dissolved in 2 ml DMF was treated with N,N-diisopropylethylamine (100 µl, 580 µmol), 1-ethyl-3-(3-dimethylaminopropyl)carbodiimide hydrochloride (51.6 mg, 269 µmol) and 1-hydroxybenzotriazole hydrate (41.2 mg, 269 µmol) and stirred for 5 min at room temperature before rac-5-(aminomethyl)-5-phenylimidazolidine-2,4-dione hydrochloride (50.0 mg, 207 µmol) was added. The mixture was stirred at room temperature for 2 h. Purification was done by preparative HPLC (Instrument: Waters Prep LC/MS System; column: Phenomenex Kinetex C18 5 µm 100×30 mm; eluent A: water, eluent B: acetonitrile, eluent C: 2% formic acid in water, eluent D: acetonitrile/water (80 Vol. %/20 Vol %); flow: 80 ml/min; room temperature; UV 200-400 nm; At-Column Injektion; Gradient: eluent A 0 to 2 min 55 ml, eluent B 0 to 2 min 15 ml, eluent A 2 to 10 min from 55 ml to 31 ml and eluent B from 15 ml to 39 ml, 10 to 12 min 0 ml eluent A and 70 ml eluent B. Eluent C and eluent D constant flow each 5 ml/min over the whole time). Product containing samples were united, the solvents were evaporated and the residue was lyophylized. 69.0 mg (98% purity, 72% yield) of the title compound were obtained.

LC-MS (Method 7): $R_t$=1.76 min; MS (ESIpos): m/z=454 [M+H]$^+$ $^1$H-NMR (600 MHz, DMSO-d6) δ [ppm]: 2.422 (0.83), 2.511 (3.30), 2.573 (0.73), 2.651 (0.79), 2.783 (2.20), 3.330 (0.83), 3.725 (2.99), 3.737 (3.19), 3.748 (5.38), 3.759 (5.08), 3.799 (5.10), 3.808 (5.49), 3.821 (3.19), 3.831 (2.86), 7.347 (2.50), 7.355 (7.69), 7.359 (7.93), 7.367 (9.10), 7.396 (9.39), 7.410 (14.22), 7.423 (11.71), 7.436 (8.64), 7.449 (3.94), 7.461 (7.63), 7.473 (4.04), 7.502 (12.35), 7.516 (13.58), 7.534 (4.81), 7.546 (7.17), 7.561 (16.00), 7.574 (12.00), 7.719 (13.96), 7.733 (12.33), 7.790 (0.50), 7.805 (0.44), 8.437 (13.85), 8.630 (3.25), 8.640 (5.65), 8.650 (3.14), 10.835 (0.75).

Example 13

Diamix-N-{[4-(2-Methylcyclobutyl)-2,5-Dioxoimidazolidin-4-Yl]Methyl}-4'-(Trifluoromethyl)[Biphenyl]-2-Carboxamide

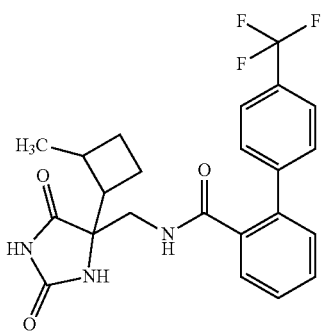 [SMILES: CC1CCC1C1(CNC(=O)c2ccccc2-c2ccc(C(F)(F)F)cc2)NC(=O)NC1=O]

4'-(trifluoromethyl)[1,1'-biphenyl]-2-carboxylic acid (171 mg, 642 µmol) dissolved in 15 ml dichloromethane was treated with N,N-diisopropylethylamine (310 µl, 1.8 mmol), 1-ethyl-3-(3-dimethylaminopropyl)carbodiimide hydrochloride (160 mg, 834 µmol) and 1-hydroxybenzotriazole hydrate (128 mg, 834 µmol) and stirred for 5 min at room temperature before diamix-5-(aminomethyl)-5-(2-methylcyclobutyl)imidazolidine-2,4-dione hydrochloride (150 mg, 642 µmol) was added. The mixture was stirred at room temperature for 5 h. Purification was done by preparative HPLC (column: Chromatorex C18 10 µm, 250×30 mm; eluent A=water with 0.1% formic acid, B=acetonitrile; gradient: 0.0 min 30% B; 4.5 min 50% B; 11.5 min 70% B; 12 min 100% B; 14.75 min 30% B; flow: 50 ml/min). Product containing samples were united, the solvents were evaporated and the residue was lyophylized. 162 mg (96% purity, 55% yield) of the title compound were obtained.

LC-MS (Method 8): $R_t$=0.95 min; MS (ESIpos): m/z=446 [M+H]$^+$ $^1$H-NMR (400 MHz, DMSO-d6) δ [ppm]: −0.008 (3.07), 0.008 (3.37), 0.883 (11.77), 0.899 (11.66), 1.007 (12.84), 1.024 (13.35), 1.050 (1.32), 1.069 (1.23), 1.324 (1.44), 1.347 (2.95), 1.369 (3.13), 1.391 (1.95), 1.415 (0.51), 1.581 (1.39), 1.602 (1.65), 1.607 (1.60), 1.634 (1.72), 1.658 (2.02), 1.683 (1.32), 1.708 (0.53), 1.732 (0.88), 1.751 (2.18), 1.771 (3.13), 1.792 (1.72), 1.828 (2.21), 1.850 (2.60), 1.870 (1.35), 2.108 (1.23), 2.113 (1.25), 2.130 (3.34), 2.150 (4.64), 2.170 (3.79), 2.191 (2.07), 2.214 (0.91), 2.238 (1.32), 2.255 (1.44), 2.276 (1.02), 2.323 (0.51), 2.327 (0.70), 2.332 (0.49), 2.366 (0.56), 2.523 (2.76), 2.587 (0.42), 2.665 (0.56), 2.669 (0.74), 2.674 (0.56), 2.710 (0.58), 3.295 (7.64), 3.328 (4.34), 3.343 (3.16), 3.375 (2.62), 3.391 (2.74), 3.409 (1.28), 3.425 (1.21), 7.402 (4.04), 7.406 (4.62), 7.424 (16.00), 7.443 (10.96), 7.465 (7.87), 7.484 (3.53), 7.524 (5.64), 7.528 (5.78), 7.543 (9.24), 7.547 (14.05), 7.570 (12.47), 7.760 (10.68), 7.778 (9.15), 7.853 (4.88), 7.904 (4.95), 8.474 (1.70), 8.490 (3.39), 8.505 (2.95), 8.520 (3.18), 8.535 (1.53), 10.639 (4.18), 10.673 (4.30), 10.735 (0.49).

Example 14

Rac-N-{[4-(1,5-Dimethyl-1H-Pyrazol-4-Yl)-2,5-Dioxoimidazolidin-4-Yl]Methyl}-4'-(Trifluoromethyl)[Biphenyl]-2-Carboxamide

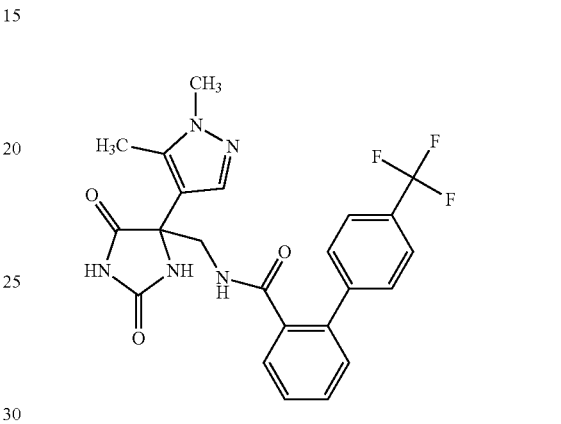

4'-(trifluoromethyl)[1,1'-biphenyl]-2-carboxylic acid (103 mg, 385 µmol) dissolved in 2.5 ml DMF was treated with N,N-diisopropylethylamine (200 µl, 1.2 mmol), 1-ethyl-3-(3-dimethylaminopropyl)carbodiimide hydrochloride (96.0 mg, 501 µmol) and 1-hydroxybenzotriazole hydrate (76.7 mg, 501 µmol) and stirred for 5 min at room temperature before rac-5-(aminomethyl)-5-(1,5-dimethyl-1H-pyrazol-4-yl)imidazolidine-2,4-dione hydrochloride (150 mg, 642 µmol) was added. The mixture was stirred at room temperature over night. Purification was done by preparative HPLC (column: Chromatorex C18 10 µm, 250×30 mm; eluent A=water with 0.1% formic acid, B=acetonitrile; gradient: 0.0 min 30% B; 4.5 min 50% B; 11.5 min 70% B; 12 min 100% B; 14.75 min 30% B; flow: 50 ml/min). Product containing samples were united, the solvents were evaporated and the residue was lyophylized. 91.0 mg (100% purity, 50% yield) of the title compound were obtained.

LC-MS (Method 7): $R_t$=1.48 min; MS (ESIpos): m/z=472 [M+H]$^+$ $^1$H-NMR (400 MHz, DMSO-d6) δ [ppm]: −0.008 (1.27), 0.008 (1.41), 2.252 (15.96), 2.523 (0.83), 3.703 (16.00), 3.769 (2.31), 3.784 (2.70), 7.374 (5.99), 7.398 (1.24), 7.401 (1.34), 7.417 (2.38), 7.420 (2.37), 7.429 (1.84), 7.448 (2.66), 7.454 (1.41), 7.469 (2.15), 7.472 (1.79), 7.488 (1.10), 7.491 (0.91), 7.533 (4.50), 7.552 (5.22), 7.570 (0.84), 7.573 (0.74), 7.741 (3.77), 7.762 (3.15), 8.159 (2.66), 8.162 (2.68), 8.621 (0.81), 8.637 (1.69), 8.652 (0.80), 10.878 (2.42).

Example 15

Rac-N-{[4-(2,4-Dimethyl-1,3-Thiazol-5-Yl)-2,5-Dioxoimidazolidin-4-Yl]Methyl}-4'-(Trifluoromethyl)[Biphenyl]-2-Carboxamide

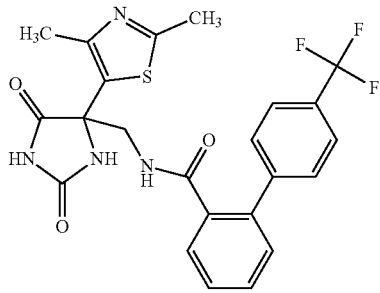 [SMILES: Cc1nc(C)c(C2(CNC(=O)c3ccccc3-c3ccc(C(F)(F)F)cc3)NC(=O)NC2=O)s1]

4'-(trifluoromethyl)[1,1'-biphenyl]-2-carboxylic acid (96.2 mg, 361 µmol) dissolved in 1.5 ml of DMF was treated with N-ethyl-N-isopropylpropan-2-amine (190 µl, 1.1 mmol), 3-{[(ethylimino)methylene]amino}-N,N-dimethylpropan-1-amine hydrochloride (90.1 mg, 470 µmol), 1H-benzotriazol-1-ol hydrate (71.9 mg, 470 µmol) and rac-5-(aminomethyl)-5-(2,4-dimethyl-1,3-thiazol-5-yl)imidazolidine-2,4-dione hydrochloride (100 mg, 361 µmol). The mixture was stirred over night at room temperature. The product was purified by preparative HPLC (column: Chromatorex C18 10 µm 250×30 mm; eluent A=water, B=acetonitrile; gradient: 0.0 min 30% B; 4.5 min 50% B; 11.5 min 70% B; 12 min 100% B; 14.75 min 30% B; flow: 50 ml/min; 0.1% formic acid). After lyophilization, 67.0 mg (90% purity, 34% yield) of the title compound were obtained.

LC-MS (Method 7): $R_t$=1.57 min; MS (ESIpos): m/z=489 [M+H]$^+$ $^1$H-NMR (400 MHz, DMSO-d6) δ [ppm]: –0.008 (0.64), 0.008 (0.73), 2.351 (16.00), 3.837 (2.13), 3.840 (2.13), 3.851 (2.00), 3.857 (2.00), 7.410 (1.21), 7.412 (1.32), 7.429 (2.37), 7.432 (2.93), 7.455 (2.23), 7.467 (1.14), 7.469 (1.14), 7.485 (2.27), 7.488 (2.40), 7.495 (3.27), 7.504 (1.56), 7.514 (3.54), 7.545 (1.39), 7.548 (1.36), 7.563 (1.73), 7.567 (1.68), 7.582 (0.69), 7.585 (0.65), 7.744 (3.60), 7.765 (3.11), 8.483 (2.65), 8.723 (0.79), 8.738 (1.64), 8.754 (0.78), 11.154 (2.33).

Example 16

Ent-5-Chloro-N-{[4-(5-Methyl-1,3-Thiazol-4-Yl)-2,5-Dioxoimidazolidin-4-Yl]Methyl}-4'-(Trifluoromethyl)[Biphenyl]-2-Carboxamide

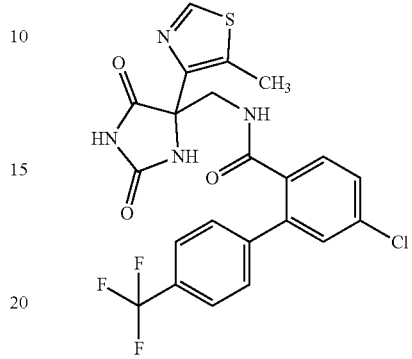

5-chloro-4'-(trifluoromethyl)[1,1'-biphenyl]-2-carboxylicacid (85.8 mg, 285 µmol) dissolved in 1.5 ml of DMF was treated with N-ethyl-N-isopropylpropan-2-amine (150 µl, 860 µmol), 3-{[(ethylimino)methylene]amino}-N,N-dimethylpropan-1-amine hydrochloride (71.1 mg, 371 µmol), 1H-benzotriazol-1-ol hydrate (56.8 mg, 371 µmol) and ent-5-(aminomethyl)-5-(5-methyl-1,3-thiazol-4-yl)imidazolidine-2,4-dione hydrochloride (75.0 mg, 285 µmol). The mixture was stirred over night at room temperature. The product was purified by preparative HPLC (Instrument: Waters Prep LC/MS System, Column: Phenomenex Kinetex C18 5 µm 100×30 mm; eluent A: water, eluent B: acetonitrile, eluent C: 2% formic acid in water, eluent D: acetonitrile/water (80 Vol. %/20 Vol %); flow: 80 ml/min, room temperature, UV-detection: 200-400 nm, At-Column Injektion; gradient: eluent A 0 bis 2 min 47 ml, eluent B 0 bis 2 min 23 ml, eluent A 2 bis 10 min from 47 ml to 23 ml and eluent B from 23 ml to 47 ml, 10 to 12 min 0 ml eluent A and 70 ml eluent B. Eluent C and Eluent D constant flow 5 ml/min over the whole runtime). After lyophilization, 65.0 mg (100% purity, 45% yield) of the title compound were obtained.

LC-MS (Method 7): $R_t$=1.80 min; MS (ESIpos): m/z=509 [M+H]$^+$ $^1$H-NMR (400 MHz, DMSO-d6) δ [ppm]: –0.008 (0.44), 0.008 (0.40), 2.359 (16.00), 2.522 (0.74), 4.063 (1.70), 4.070 (1.77), 4.079 (1.77), 4.085 (1.78), 7.428 (2.57), 7.448 (3.36), 7.526 (2.77), 7.531 (3.54), 7.557 (2.32), 7.562 (1.75), 7.577 (1.73), 7.583 (1.63), 7.592 (2.75), 7.612 (3.27), 7.777 (3.34), 7.797 (2.75), 8.299 (3.58), 8.686 (0.74), 8.702 (1.56), 8.718 (0.72), 8.844 (5.70).

Example 17

Ent-4,5-Difluoro-N-{[4-(5-Methyl-1,3-Thiazol-4-Yl)-2,5-Dioxoimidazolidin-4-Yl]Methyl}-4'-(Trifluoromethyl)[Biphenyl]-2-Carboxamide

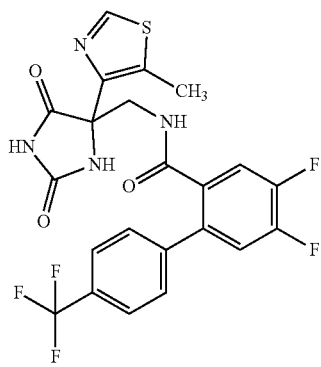 [SMILES: Cc1scnc1C1(CNC(=O)c2cc(F)c(F)cc2-c2ccc(C(F)(F)F)cc2)NC(=O)NC1=O]

4,5-difluoro-4'-(trifluoromethyl)[1,1'-biphenyl]-2-carboxylic acid (86.3 mg, 285 µmol) dissolved in 2 ml of DMF was treated with N-ethyl-N-isopropylpropan-2-amine (150 µl, 860 µmol), 3-{[(ethylimino)methylene]amino}-N,N-dimethylpropan-1-amine hydrochloride (71.1 mg, 371 µmol), 1H-benzotriazol-1-ol hydrate (56.8 mg, 371 µmol) and ent-5-(aminomethyl)-5-(5-methyl-1,3-thiazol-4-yl)imidazolidine-2,4-dione hydrochloride (75.0 mg, 285 µmol). The mixture was stirred over night at room temperature. The product was purified by preparative HPLC (Instrument: Waters Prep LC/MS System, Column: Phenomenex Kinetex C18 5 µm 100×30 mm; eluent A: water, eluent B: acetonitrile, eluent C: 2% formic acid in water, eluent D: acetonitrile/water (80 Vol. %/20 Vol %); flow: 80 ml/min, room temperature, UV-detection: 200-400 nm, At-Column Injektion; gradient: eluent A 0 bis 2 min 55 ml, eluent B 0 bis 2 min 15 ml, eluent A 2 bis 10 min from 55 ml to 31 ml and eluent B from 15 ml to 39 ml, 10 to 12 min 0 ml eluent A and 70 ml eluent B. Eluent C and Eluent D constant flow 5 ml/min over the whole runtime). After lyophilization, 70.0 mg (100% purity, 48% yield) of the title compound were obtained.

LC-MS (Method 7): $R_t$=1.74 min; MS (ESIpos): m/z=511 [M+H]$^+$ $^1$H-NMR (400 MHz, DMSO-d6) δ [ppm]: 2.364 (16.00), 2.523 (0.67), 4.079 (2.40), 4.094 (2.56), 7.456 (0.92), 7.476 (1.09), 7.483 (1.07), 7.503 (1.01), 7.568 (2.58), 7.588 (3.90), 7.608 (1.14), 7.617 (1.10), 7.637 (1.03), 7.775 (3.18), 7.796 (2.62), 8.346 (3.43), 8.760 (0.67), 8.776 (1.46), 8.791 (0.67), 8.851 (6.97).

Example 18

Ent-4-Chloro-N-{[4-(5-Methyl-1,3-Thiazol-4-Yl)-2,5-Dioxoimidazolidin-4-Yl]Methyl}-4'-(Trifluoromethyl)[Biphenyl]-2-Carboxamide

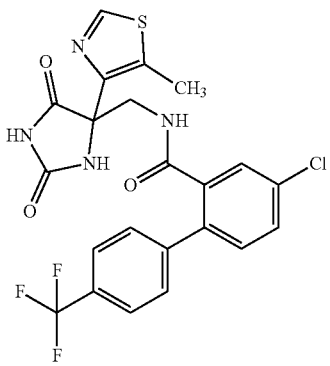 [SMILES: Cc1scnc1C1(CNC(=O)c2cc(Cl)ccc2-c2ccc(C(F)(F)F)cc2)NC(=O)NC1=O]

4-chloro-4'-(trifluoromethyl)[1,1'-biphenyl]-2-carboxylic acid (85.8 mg, 285 µmol) dissolved in 2 ml of DMF was treated with N-ethyl-N-isopropylpropan-2-amine (150 µl, 860 µmol), 3-{[(ethylimino)methylene]amino}-N,N-dimethylpropan-1-amine hydrochloride (71.1 mg, 371 µmol), 1H-benzotriazol-1-ol hydrate (56.8 mg, 371 µmol) and ent-5-(aminomethyl)-5-(5-methyl-1,3-thiazol-4-yl)imidazolidine-2,4-dione hydrochloride (75.0 mg, 285 µmol). The mixture was stirred over night at room temperature. The product was purified by preparative HPLC (Instrument: Waters Prep LC/MS System, Column: Phenomenex Kinetex C18 5 µm 100×30 mm; eluent A: water, eluent B: acetonitrile, eluent C: 2% formic acid in water, eluent D: acetonitrile/water (80 Vol. %/20 Vol %); flow: 80 ml/min, room temperature, UV-detection: 200-400 nm, At-Column Injektion; gradient: eluent A 0 bis 2 min 47 ml, eluent B 0 bis 2 min 23 ml, eluent A 2 bis 10 min from 47 ml to 23 ml and eluent B from 23 ml to 47 ml, 10 to 12 min 0 ml eluent A and 70 ml eluent B. Eluent C and Eluent D constant flow 5 ml/min over the whole runtime). After lyophilization, 57.0 mg (100% purity, 39% yield) of the title compound were obtained.

LC-MS (Method 7): $R_t$=1.78 min; MS (ESIpos): m/z=509 [M+H]$^+$ $^1$H-NMR (400 MHz, DMSO-d6) δ [ppm]: −0.008 (0.52), 0.008 (0.50), 2.367 (16.00), 2.518 (1.13), 2.523 (0.83), 2.525 (0.61), 4.080 (1.92), 4.083 (1.89), 4.098 (2.08), 7.463 (3.11), 7.469 (4.71), 7.491 (3.43), 7.559 (2.58), 7.579 (3.07), 7.612 (2.18), 7.617 (1.94), 7.632 (1.55), 7.638 (1.47), 7.773 (3.19), 7.793 (2.63), 8.329 (3.52), 8.806 (0.69), 8.822 (1.50), 8.837 (0.70), 8.852 (5.70).

Example 19

N-{[(4R)-4-Cyclopropyl-2,5-Dioxoimidazolidin-4-Yl]Methyl}-3-(4-Methylphenyl)Isonicotinamide

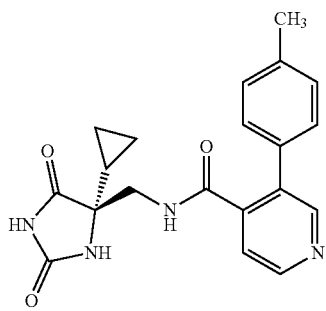 [SMILES: Cc1ccc(-c2cnccc2C(=O)NC[C@@]2(C3CC3)NC(=O)NC2=O)cc1]

3-(4-methylphenyl)pyridine-4-carboxylic acid (51.8 mg, 243 µmol) dissolved in 1.5 ml of DMF was treated with N-ethyl-N-isopropylpropan-2-amine (130 µl, 730 µmol), 3-{[(ethylimino)methylene]amino}-N,N-dimethylpropan-1-amine hydrochloride (60.6 mg, 316 µmol), 1H-benzotriazol-1-ol hydrate (48.4 mg, 316 µmol) and (5R)-5-(aminomethyl)-5-cyclopropylimidazolidine-2,4-dione hydrochloride (50.0 mg, 243 µmol). The mixture was stirred over night at room temperature. The product was purified by preparative HPLC (Instrument: Waters Prep LC/MS System, Column: Phenomenex Kinetex C18 5 µm 100×30 mm; eluent A: water, eluent B: acetonitrile, eluent C: 2% formic acid in water, eluent D: acetonitrile/water (80 Vol. %/20 Vol %); flow: 80 ml/min, room temperature, UV-detection: 200-400 nm, At-Column Injektion; gradient: eluent A 0 bis 2 min 63 ml, eluent B 0 bis 2 min 7 ml, eluent A 2 bis 10 min from 63 ml to 39 ml and eluent B from 7 ml to 31 ml, 10 to 12 min 0 ml eluent A an d 70 ml eluent B. Eluent C and Eluent D constant flow 5 ml/min over the whole runtime). After lyophilization, 46.0 mg (100% purity, 52% yield) of the title compound were obtained.

LC-MS (Method 7): $R_t$=1.10 min; MS (ESIpos): m/z=365 [M+H]$^+$ $^1$H-NMR (600 MHz, DMSO-d6) δ [ppm]: 0.128 (0.77), 0.136 (1.25), 0.144 (1.29), 0.152 (0.94), 0.161 (0.43), 0.317 (0.83), 0.325 (1.06), 0.332 (0.93), 0.340 (0.68), 0.347 (0.47), 0.389 (0.73), 0.397 (0.83), 0.404 (1.19), 0.412 (0.91), 0.418 (0.56), 0.436 (0.45), 0.444 (1.00), 0.453 (1.24), 0.461 (1.21), 0.469 (0.84), 1.059 (0.80), 1.064 (0.89), 1.073 (1.49), 1.081 (0.83), 1.086 (0.77), 2.338 (16.00), 3.266 (0.45), 3.332 (0.86), 3.497 (2.49), 3.502 (2.73), 3.507 (2.73), 3.512 (2.72), 3.524 (0.40), 7.241 (3.74), 7.254 (5.31), 7.284 (3.34), 7.292 (3.34), 7.316 (6.09), 7.329 (4.29), 7.538 (3.66), 8.598 (6.65), 8.601 (4.43), 8.610 (3.81), 8.619 (1.15), 8.629 (2.18), 8.639 (1.06), 10.624 (2.54).

Example 20

N-{[(4R)-4-Cyclopropyl-2,5-Dioxoimidazolidin-4-Yl]Methyl}-4,5-Difluoro-4'-(Trifluoromethyl)[Biphenyl]-2-Carboxamide

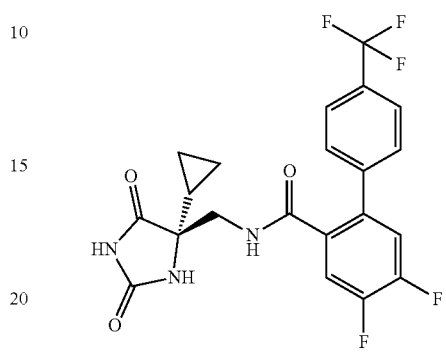

4,5-difluoro-4'-(trifluoromethyl)[1,1'-biphenyl]-2-carboxylic acid (73.5 mg, 243 µmol) dissolved in 2 ml of DMF was treated with N-ethyl-N-isopropylpropan-2-amine (120 µl, 680 µmol), 3-{[(ethylimino)methylene]amino}-N,N-dimethylpropan-1-amine hydrochloride (60.6 mg, 316 µmol), 1H-benzotriazol-1-ol hydrate (48.4 mg, 316 µmol) and (5R)-5-(aminomethyl)-5-cyclopropylimidazolidine-2,4-dione hydrochloride (50.0 mg, 243 µmol). The mixture was stirred at room temperature for 2 h. The product was purified by preparative HPLC (Instrument: Waters Prep LC/MS System, Column: Phenomenex Kinetex C18 5 µm 100×30 mm; eluent A: water, eluent B: acetonitrile, eluent C: 2% formic acid in water, eluent D: acetonitrile/water (80 Vol. %/20 Vol %); flow: 80 ml/min, room temperature, UV-detection: 200-400 nm, At-Column Injektion; gradient: eluent A 0 bis 2 min 55 ml, eluent B 0 bis 2 min 15 ml, eluent A 2 bis 10 min from 55 ml to 31 ml and eluent B from 15 ml to 39 ml, 10 to 12 min 0 ml eluent A and 70 ml eluent B.

Eluent C and Eluent D constant flow 5 ml/min over the whole runtime). After lyophilization, 25.0 mg (100% purity, 23% yield) of the title compound were obtained.

LC-MS (Method 9): $R_t$=1.44 min; MS (ESIpos): m/z=454 [M+H]$^+$ $^1$H-NMR (400 MHz, DMSO-d6) δ [ppm]: −0.008 (1.95), 0.008 (1.91), 0.131 (2.17), 0.142 (3.86), 0.155 (4.12), 0.166 (2.89), 0.178 (1.26), 0.295 (0.76), 0.318 (2.49), 0.331 (3.07), 0.339 (2.93), 0.352 (2.31), 0.363 (1.88), 0.370 (1.66), 0.381 (2.42), 0.395 (2.71), 0.404 (3.50), 0.417 (2.67), 0.426 (1.59), 0.439 (0.98), 0.449 (1.44), 0.462 (2.96), 0.474 (3.94), 0.486 (3.68), 0.498 (2.35), 0.512 (0.90), 1.050 (1.23), 1.064 (2.60), 1.071 (2.71), 1.084 (4.73), 1.098 (2.53), 1.105 (2.35), 1.118 (1.01), 2.072 (0.51), 2.327 (1.44), 2.366 (1.34), 2.665 (1.08), 2.670 (1.37), 2.710 (1.37), 3.461 (1.16), 3.476 (1.55), 3.495 (7.15), 3.506 (8.52), 3.509 (8.42), 3.521 (6.93), 3.540 (1.41), 3.555 (1.30), 7.493 (4.48), 7.513 (5.31), 7.520 (5.27), 7.543 (13.72), 7.564 (14.48), 7.580 (4.80), 7.599 (5.63), 7.613 (16.00), 7.628 (5.42), 7.765 (15.24), 7.785 (12.57), 8.689 (3.11), 8.705 (6.43), 8.720 (3.03), 10.602 (0.79).

Example 21

N-{[(4R)-4-Cyclopropyl-2,5-Dioxoimidazolidin-4-Yl]Methyl}-4'-(Trifluoromethoxy)[Biphenyl]-2-Carboxamide

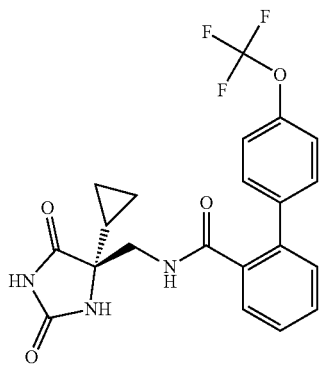 [SMILES: O=C1NC(=O)[C@](CNC(=O)c2ccccc2-c2ccc(OC(F)(F)F)cc2)(C2CC2)N1]

4'-(trifluoromethoxy)[1,1'-biphenyl]-2-carboxylic acid (68.6 mg, 243 µmol) dissolved in 1.5 ml of DMF was treated with N-ethyl-N-isopropylpropan-2-amine (130 µl, 730 µmol), 3-{[(ethylimino)methylene]amino}-N,N-dimethylpropan-1-amine hydrochloride (60.6 mg, 316 µmol), 1H-benzotriazol-1-ol hydrate (48.4 mg, 316 µmol) and (5R)-5-(aminomethyl)-5-cyclopropylimidazolidine-2,4-dione hydrochloride (50.0 mg, 243 µmol). The mixture was stirred over night at room temperature. The product was purified by preparative HPLC (Instrument: Waters Prep LC/MS System, Column: Phenomenex Kinetex C18 5 µm 100×30 mm; eluent A: water, eluent B: acetonitrile, eluent C: 2% formic acid in water, eluent D: acetonitrile/water (80 Vol. %/20 Vol %); flow: 80 ml/min, room temperature, UV-detection: 200-400 nm, At-Column Injektion; gradient: eluent A 0 bis 2 min 55 ml, eluent B 0 bis 2 min 15 ml, eluent A 2 bis 10 min from 55 ml to 31 ml and eluent B from 15 ml to 39 ml, 10 to 12 min 0 ml eluent A and 70 ml eluent B. Eluent C and Eluent D constant flow 5 ml/min over the whole runtime). After lyophilization, 90.0 mg (100% purity, 85% yield) of the title compound were obtained.

LC-MS (Method 7): $R_t$=1.63 min; MS (ESIpos): m/z=434 [M+H]$^+$ $^1$H-NMR (400 MHz, DMSO-d6) δ [ppm]: 0.103 (0.51), 0.117 (1.25), 0.128 (2.21), 0.141 (2.35), 0.151 (1.66), 0.165 (0.76), 0.285 (0.43), 0.299 (0.76), 0.307 (1.40), 0.319 (1.72), 0.329 (1.65), 0.342 (1.30), 0.352 (1.02), 0.362 (0.85), 0.373 (1.40), 0.387 (1.55), 0.395 (2.06), 0.409 (1.61), 0.417 (0.93), 0.430 (1.23), 0.443 (1.76), 0.454 (2.19), 0.467 (2.10), 0.478 (1.29), 0.492 (0.45), 1.044 (0.72), 1.057 (1.48), 1.065 (1.57), 1.070 (1.13), 1.078 (2.72), 1.086 (1.12), 1.091 (1.44), 1.098 (1.32), 1.112 (0.57), 2.072 (0.43), 2.522 (0.98), 2.525 (0.93), 2.557 (0.47), 3.477 (0.55), 3.497 (5.11), 3.501 (5.14), 3.512 (4.90), 3.516 (4.97), 3.535 (0.53), 3.551 (0.43), 7.375 (5.05), 7.396 (10.55), 7.410 (6.15), 7.414 (6.20), 7.421 (8.76), 7.439 (4.99), 7.442 (3.76), 7.452 (2.38), 7.458 (16.00), 7.464 (4.50), 7.475 (3.42), 7.480 (8.83), 7.488 (1.29), 7.500 (3.71), 7.505 (3.99), 7.514 (7.26), 7.518 (6.85), 7.523 (4.29), 7.537 (1.63), 7.541 (1.59), 8.475 (1.74), 8.491 (3.73), 8.506 (1.74), 10.643 (5.31).

Example 22

N-{[(4R)-4-Cyclopropyl-2,5-Dioxoimidazolidin-4-Yl]Methyl}-4',5-Dimethyl[Biphenyl]-2-Carboxamide

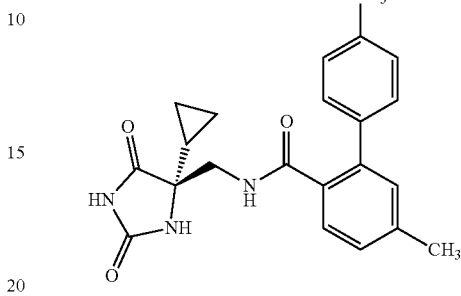

4',5-dimethyl[1,1'-biphenyl]-2-carboxylic acid (55.0 mg, 243 µmol) dissolved in 7 ml of DMF was treated with N-ethyl-N-isopropylpropan-2-amine (120 µl, 680 µmol), 3-{[(ethylimino)methylene]amino}-N,N-dimethylpropan-1-amine hydrochloride (60.6 mg, 316 µmol), 1H-benzotriazol-1-ol hydrate (48.4 mg, 316 µmol) and (5R)-5-(aminomethyl)-5-cyclopropylimidazolidine-2,4-dione hydrochloride (50.0 mg, 243 µmol). The mixture was stirred at room temperature for 2 h. The product was purified by preparative HPLC (Instrument: Waters Prep LC/MS System, Column: Phenomenex Kinetex C18 5 µm 100×30 mm; eluent A: water, eluent B: acetonitrile, eluent C: 2% formic acid in water, eluent D: acetonitrile/water (80 Vol. %/20 Vol %); flow: 80 ml/min, room temperature, UV-detection: 200-400 nm, At-Column Injektion; gradient: eluent A 0 bis 2 min 55 ml, eluent B 0 bis 2 min 15 ml, eluent A 2 bis 10 min from 55 ml to 31 ml and eluent B from 15 ml to 39 ml, 10 to 12 min 0 ml eluent A and 70 ml eluent B. Eluent C and Eluent D constant flow 5 ml/min over the whole runtime). After lyophilization, 5.00 mg (100% purity, 5% yield) of the title compound were obtained.

LC-MS (Method 9): $R_t$=1.33 min; MS (ESIpos): m/z=378 [M+H]$^+$ $^1$H-NMR (400 MHz, DMSO-d6) δ [ppm]: −0.008 (1.48), 0.008 (1.37), 0.096 (0.68), 0.107 (1.23), 0.120 (1.28), 0.131 (0.91), 0.145 (0.48), 0.290 (0.77), 0.303 (0.97), 0.314 (0.94), 0.325 (0.71), 0.335 (0.57), 0.353 (0.43), 0.364 (0.80), 0.378 (0.86), 0.386 (1.23), 0.399 (1.20), 0.410 (1.37), 0.421 (1.45), 0.434 (1.11), 0.446 (0.68), 1.005 (0.43), 1.018 (0.88), 1.026 (0.88), 1.039 (1.54), 1.052 (0.83), 1.059 (0.74), 2.315 (16.00), 2.327 (1.54), 2.332 (1.08), 2.359 (15.60), 2.523 (3.39), 2.526 (2.60), 2.557 (1.14), 2.560 (0.83), 2.562 (0.63), 2.565 (0.60), 2.567 (0.51), 2.569 (0.43), 2.665 (0.71), 2.669 (0.94), 2.674 (0.68), 2.709 (0.97), 3.413 (0.68), 3.428 (0.80), 3.447 (2.11), 3.462 (2.00), 3.473 (2.00), 3.489 (2.08), 3.507 (0.74), 3.523 (0.71), 7.168 (8.64), 7.189 (8.24), 7.228 (7.99), 7.248 (4.16), 7.256 (4.45), 7.274 (2.68), 7.435 (4.56), 8.150 (1.00), 8.166 (2.08), 8.181 (1.00), 10.608 (1.34).

Example 23

N-{[(4R)-4-Cyclopropyl-2,5-Dioxoimidazolidin-4-Yl]Methyl}-5,6-Difluoro-4'-(Trifluoromethyl)[Biphenyl]-2-Carboxamide

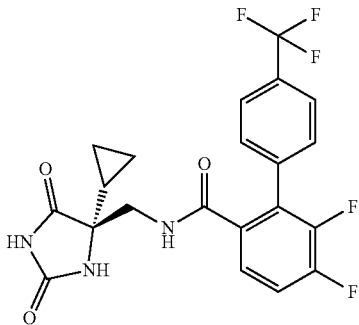 [SMILES: O=C1NC(=O)[C@](CNC(=O)c2ccc(F)c(F)c2-c2ccc(C(F)(F)F)cc2)(C2CC2)N1]

5,6-difluoro-4'-(trifluoromethyl)[1,1'-biphenyl]-2-carboxylicacid (28.0 mg, 92.7 µmol) dissolved in 2 ml of DMF was treated with N-ethyl-N-isopropylpropan-2-amine (45 µl, 260 µmol), 3-{[(ethylimino)methylene]amino}-N,N-dimethylpropan-1-amine hydrochloride (23.1 mg, 120 µmol), 1H-benzotriazol-1-ol hydrate (18.4 mg, 120 µmol) and (5R)-5-(aminomethyl)-5-cyclopropylimidazolidine-2,4-dione hydrochloride (19.1 mg, 92.7 µmol). The mixture was stirred at room temperature for 2 h. The product was purified by preparative HPLC (Instrument: Waters Prep LC/MS System, Column: Phenomenex Kinetex C18 5 µm 100×30 mm; eluent A: water, eluent B: acetonitrile, eluent C: 2% formic acid in water, eluent D: acetonitrile/water (80 Vol. %/20 Vol %); flow: 80 ml/min, room temperature, UV-detection: 200-400 nm, At-Column Injektion; gradient: eluent A 0 bis 2 min 55 ml, eluent B 0 bis 2 min 15 ml, eluent A 2 bis 10 min from 55 ml to 31 ml and eluent B from 15 ml to 39 ml, 10 to 12 min 0 ml eluent A and 70 ml eluent B. Eluent C and Eluent D constant flow 5 ml/min over the whole runtime). After lyophilization, 29.0 mg (100% purity, 69% yield) of the title compound were obtained.

LC-MS (Method 9): $R_t$=1.41 min; MS (ESIpos): m/z=454 [M+H]$^+$ $^1$H-NMR (400 MHz, DMSO-d6) δ [ppm]: −0.008 (0.98), 0.008 (1.02), 0.095 (0.54), 0.109 (1.35), 0.120 (2.45), 0.133 (2.61), 0.144 (1.84), 0.156 (0.84), 0.270 (0.46), 0.293 (1.56), 0.305 (1.91), 0.316 (1.86), 0.328 (1.49), 0.338 (1.33), 0.354 (1.56), 0.367 (1.77), 0.376 (2.26), 0.389 (1.77), 0.397 (0.96), 0.415 (1.07), 0.429 (1.91), 0.440 (2.49), 0.453 (2.37), 0.464 (1.44), 0.478 (0.51), 1.005 (0.77), 1.018 (1.61), 1.025 (1.75), 1.031 (1.24), 1.039 (3.00), 1.046 (1.23), 1.052 (1.58), 1.059 (1.44), 1.072 (0.61), 2.323 (0.47), 2.327 (0.67), 2.332 (0.47), 2.366 (0.65), 2.524 (2.63), 2.665 (0.51), 2.670 (0.68), 2.674 (0.51), 2.710 (0.65), 3.432 (8.50), 3.448 (8.48), 7.297 (1.84), 7.306 (2.00), 7.310 (1.98), 7.315 (2.38), 7.318 (2.28), 7.327 (2.28), 7.331 (2.09), 7.544 (16.00), 7.563 (7.94), 7.577 (1.79), 7.598 (2.51), 7.603 (2.21), 7.623 (2.54), 7.643 (1.47), 7.800 (9.17), 7.820 (7.92), 8.578 (1.91), 8.594 (4.15), 8.609 (1.91).

Example 24

Rac-N-[(2,5-Dioxo-4-Propylimidazolidin-4-Yl)Methyl]-4'-(Trifluoromethyl)[Biphenyl]-2-Carboxamide

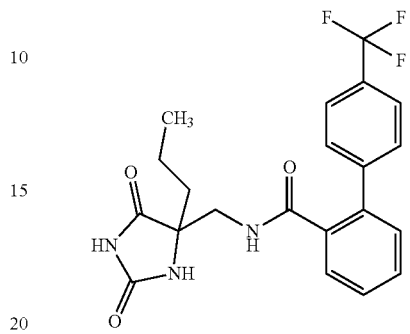

4'-(trifluoromethyl)[1,1'-biphenyl]-2-carboxylicacid (51.3 mg, 193 µmol) dissolved in 2 ml of DMF was treated with N-ethyl-N-isopropylpropan-2-amine (94 µl, 540 µmol), 3-{[(ethylimino)methylene]amino}-N,N-dimethylpropan-1-amine hydrochloride (48.0 mg, 250 µmol), 1H-benzotriazol-1-ol hydrate (38.3 mg, 250 µmol) and rac-5-(aminomethyl)-5-propylimidazolidine-2,4-dione hydrochloride (40.0 mg, 193 µmol). The mixture was stirred at room temperature for 2 h. The product was purified by preparative HPLC (Instrument: Waters Prep LC/MS System, Column: Phenomenex Kinetex C18 5 µm 100×30 mm; eluent A: water, eluent B: acetonitrile, eluent C: 2% formic acid in water, eluent D: acetonitrile/water (80 Vol. %/20 Vol %); flow: 80 ml/min, room temperature, UV-detection: 200-400 nm, At-Column Injektion; gradient: eluent A 0 bis 2 min 55 ml, eluent B 0 bis 2 min 15 ml, eluent A 2 bis 10 min from 55 ml to 31 ml and eluent B from 15 ml to 39 ml, 10 to 12 min 0 ml eluent A and 70 ml eluent B. Eluent C and Eluent D constant flow 5 ml/min over the whole runtime). After lyophilization, 63.0 mg (100% purity, 78% yield) of the title compound were obtained.

LC-MS (Method 7): $R_t$=1.64 min; MS (ESIpos): m/z=420 [M+H]$^+$ $^1$H-NMR (400 MHz, DMSO-d6) δ [ppm]: −0.008 (3.02), 0.008 (3.25), 0.815 (6.05), 0.833 (16.00), 0.851 (7.76), 1.040 (0.74), 1.058 (1.14), 1.073 (1.11), 1.088 (1.20), 1.105 (0.77), 1.120 (0.54), 1.236 (0.46), 1.248 (0.77), 1.266 (1.20), 1.279 (1.03), 1.297 (1.23), 1.315 (0.68), 1.327 (0.48), 1.424 (0.71), 1.434 (0.83), 1.457 (1.77), 1.469 (1.48), 1.486 (1.65), 1.503 (1.88), 1.516 (1.74), 1.532 (1.48), 1.544 (1.40), 1.566 (0.74), 1.579 (0.54), 2.328 (0.51), 2.366 (0.97), 2.523 (2.62), 2.670 (0.57), 2.710 (1.00), 3.298 (2.77), 3.331 (3.85), 3.346 (3.05), 3.387 (2.80), 3.403 (2.97), 3.421 (1.60), 3.437 (1.48), 7.424 (4.31), 7.443 (5.36), 7.452 (1.25), 7.463 (8.96), 7.470 (6.53), 7.474 (6.47), 7.494 (0.94), 7.519 (0.63), 7.529 (3.17), 7.538 (2.80), 7.543 (2.20), 7.548 (2.62), 7.551 (2.37), 7.556 (2.99), 7.563 (7.87), 7.583 (7.96), 7.675 (5.79), 7.746 (8.24), 7.767 (6.73), 8.512 (1.63), 8.527 (3.28), 8.543 (1.65), 10.685 (4.85).

Example 25

Rac-N-[(4-Tert-Butyl-2,5-Dioxoimidazolidin-4-Yl)Methyl]-4'-(Trifluoromethyl)[Biphenyl]-2-Carboxamide

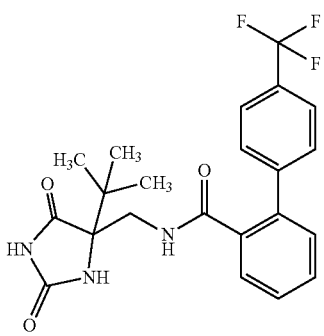 [SMILES: CC(C)(C)C1(CNC(=O)c2ccccc2-c2ccc(C(F)(F)F)cc2)NC(=O)NC1=O]

4'-(trifluoromethyl)[1,1'-biphenyl]-2-carboxylicacid (43.1 mg, 162 µmol) dissolved in 2 ml of DMF was treated with N-ethyl-N-isopropylpropan-2-amine (79 µl, 450 µmol), 3-{[(ethylimino)methylene]amino}-N,N-dimethylpropan-1-amine hydrochloride (40.4 mg, 211 µmol), 1H-benzotriazol-1-ol hydrate (32.2 mg, 211 µmol) and rac-5-(aminomethyl)-5-tert-butylimidazolidine-2,4-dione (30.0 mg, 162 µmol). The mixture was stirred at room temperature for 2 h. The product was purified by preparative HPLC (Instrument: Waters Prep LC/MS System, Column: Phenomenex Kinetex C18 5 µm 100×30 mm; eluent A: water, eluent B: acetonitrile, eluent C: 2% formic acid in water, eluent D: acetonitrile/water (80 Vol. %/20 Vol %); flow: 80 ml/min, room temperature, UV-detection: 200-400 nm, At-Column Injektion; gradient: eluent A0 bis 2 min 55 ml, eluent B 0 bis 2 min 15 ml, eluent A 2 bis 10 min from 55 ml to 31 ml and eluent B from 15 ml to 39 ml, 10 to 12 min 0 ml eluent A and 70 ml eluent B. Eluent C and Eluent D constant flow 5 ml/min over the whole runtime). After lyophilization, 56.0 mg (100% purity, 80% yield) of the title compound were obtained.

LC-MS (Method 7): $R_t$=1.72 min; MS (ESIpos): m/z=434 [M+H]$^+$ $^1$H-NMR (400 MHz, DMSO-d6) δ [ppm]: −0.008 (0.66), 0.008 (0.75), 0.982 (16.00), 3.537 (0.59), 3.552 (0.57), 3.580 (0.59), 3.595 (0.64), 7.361 (0.65), 7.364 (0.69), 7.380 (1.03), 7.421 (0.79), 7.440 (1.52), 7.456 (1.03), 7.459 (0.83), 7.475 (0.53), 7.522 (0.69), 7.525 (0.72), 7.544 (2.15), 7.563 (2.32), 7.757 (1.78), 7.778 (1.46), 8.480 (0.74), 10.664 (0.99).

Example 26

Ent-N-{[4-(2-Methylcyclobutyl)-2,5-Dioxoimidazolidin-4-Yl]Methyl}-4'-(Trifluoromethyl)[Biphenyl]-2-Carboxamide

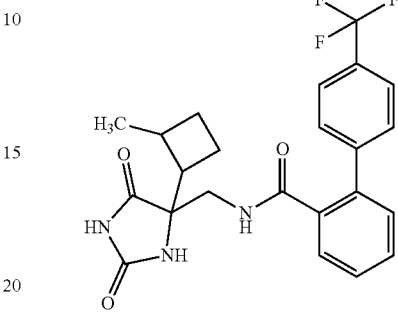

Enantiomeric separation of diamix-N-{[4-(2-methylcyclobutyl)-2,5-dioxoimidazolidin-4 yl]methyl}-4'-(trifluoromethyl)[biphenyl]-2-carboxamide (150 mg, 337 µmol) using the following two methods. At first Diacel Chiralpak IA 5 µm 250*20 mm Eluent A: 80% n-heptane, eluent B: 20% ethanol Flow: 15 ml/min UV-detection: 220 nm Temperature: 35° C.

then

Chiralcel OZ-H 5 µm 250*20 mm

Eluent A: 80% n-heptane, eluent B: 20% ethanol

Flow: 15 ml/min

UV-detection: 220 nm

Temperature: 35° C.

34.0 mg (100% purity, 23% yield) of the title compound were obtained.

Chiral-HPLC (Column: Diacel Chiralcel OZ-H 5 µm 250*4.6 mm, eluent A: 80% iso-hexane, eluent B: 20% ethanol, flow: 1 ml/min, temperature: 30° C., UV-detection: 220 nm): $R_t$=5.529 min; 99.64% ee LC-MS (Method 7): $R_t$=1.78 min; MS (ESIpos): m/z=446 [M+H]$^+$ $^1$H-NMR (600 MHz, DMSO-d6) δ [ppm]: 0.887 (16.00), 0.897 (15.47), 1.352 (1.87), 1.368 (2.93), 1.383 (2.13), 1.400 (0.67), 1.739 (1.20), 1.754 (3.47), 1.768 (4.60), 1.783 (2.40), 1.845 (1.93), 1.857 (1.80), 2.085 (1.33), 2.123 (1.47), 2.137 (1.80), 2.148 (1.73), 2.157 (2.40), 2.171 (3.73), 2.185 (2.73), 2.200 (0.80), 2.383 (0.93), 2.423 (1.00), 2.467 (1.80), 2.611 (1.00), 2.652 (1.00), 3.266 (5.07), 3.340 (0.60), 3.363 (0.47), 7.408 (3.33), 7.422 (9.00), 7.436 (5.53), 7.452 (2.60), 7.465 (4.80), 7.477 (2.33), 7.529 (2.93), 7.543 (4.47), 7.552 (8.40), 7.565 (8.67), 7.756 (8.87), 7.769 (7.87), 7.875 (8.73), 8.447 (1.93), 8.457 (4.13), 8.467 (2.07), 10.650 (1.47).

Example 27

Ent-N-{[4-(4-Methyl-1,3-Thiazol-5-Yl)-2,5-Dioxo-imidazolidin-4-Yl]Methyl}-4'-(Trifluoromethyl)[Biphenyl]-2-Carboxamide

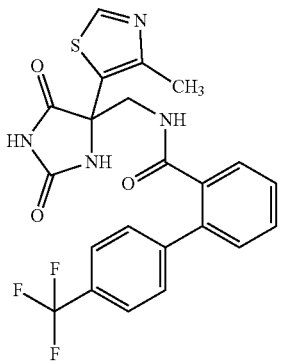 [SMILES: Cc1ncsc1C1(CNC(=O)c2ccccc2-c2ccc(C(F)(F)F)cc2)NC(=O)NC1=O]

Enantiomeric separation of rac-N-{[4-(4-methyl-1,3-thiazol-5-yl)-2,5-dioxoimidazolidin-4-yl]methyl}-4'-(trifluoromethyl)[biphenyl]-2-carboxamide (130 mg, 274 µmol) using the following method
Chiralcel OZ-H 5 µm 250*20 mm
Eluent A: 80% n-heptane, eluent B: 20% iso-propanol
Flow: 20 ml/min
UV-detection: 220 nm
Temperature: 40° C.
22.0 mg (100% purity, 17% yield) of the title compound were obtained.
Chiral-HPLC (Column: Diacel Chrialpak OZ-3 3 µm 250*4.6 mm, eluent A: 80% n-heptane, eluent B: 20% iso-propanol, flow: 1 ml/min, UV-detection: 220 nm): $R_t$=2.785 min; 100% ee
LC-MS (Method 7): $R_t$=1.53 min; MS (ESIpos): m/z=475 [M+H]$^+$
$^1$H-NMR (600 MHz, DMSO-d6) δ [ppm]: 1.109 (0.46), 1.119 (0.46), 2.458 (16.00), 3.879 (0.41), 3.892 (1.84), 3.901 (2.93), 3.911 (1.78), 7.406 (1.59), 7.419 (2.20), 7.437 (1.87), 7.449 (2.25), 7.472 (1.06), 7.485 (2.42), 7.490 (3.43), 7.503 (3.59), 7.552 (1.25), 7.564 (1.83), 7.576 (0.76), 7.746 (3.64), 7.759 (3.32), 8.505 (2.84), 8.723 (0.86), 8.734 (1.69), 8.744 (0.85), 8.935 (5.65), 11.179 (2.43).

Example 28

Ent-N-({2,5-Dioxo-4-[1-(2,2,2-Trifluoroethyl)-1H-Pyrazol-5-Yl]Imidazolidin-4-Yl}Methyl)-4'-(Trifluoromethyl)[Biphenyl]-2-Carboxamide

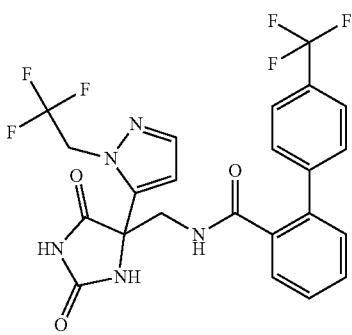 [SMILES: O=C1NC(=O)C(CNC(=O)c2ccccc2-c2ccc(C(F)(F)F)cc2)(c2ccnn2CC(F)(F)F)N1]

Enantiomeric separation of rac-N-({2,5-dioxo-4-[1-(2,2,2-trifluoroethyl)-1H-pyrazol-5-yl]imidazolidin-4-yl}methyl)-4'-(trifluoromethyl)[biphenyl]-2-carboxamide (35.0 mg, 66.6 µmol) using the following method
Diacel Chiralcel OX-H 5 µm 250*20 mm
Eluent A: 50% n-heptane, eluent B: 50% iso-propanol
Flow: 20 ml/min
UV-detection: 220 nm
Temperature: 40° C.
12.0 mg (100% purity, 34% yield) of the title compound were obtained.
Chiral-HPLC (Column: Diacel OX-3 3 µm 50*4.6 mm, eluent A: 50% n-heptane, eluent B: 50% iso-propanol, flow: 1 ml/min, UV-detection: 220 nm): $R_t$=2.483 min; 99.54% ee
LC-MS (Method 7): $R_t$=1.71 min; MS (ESIpos): m/z=526 [M+H]$^+$
$^1$H-NMR (600 MHz, DMSO-d6) δ [ppm]: 1.107 (0.49), 1.118 (0.52), 1.159 (0.72), 1.171 (0.40), 2.084 (16.00), 2.422 (0.52), 2.465 (0.64), 2.651 (0.46), 3.777 (0.61), 3.788 (0.64), 3.799 (0.87), 3.811 (0.84), 3.883 (0.86), 3.893 (0.94), 3.907 (0.65), 3.916 (0.59), 5.134 (0.43), 5.148 (1.06), 5.162 (1.02), 5.175 (0.44), 6.583 (2.31), 6.586 (2.33), 7.414 (1.11), 7.426 (1.59), 7.436 (1.34), 7.449 (1.60), 7.475 (0.77), 7.487 (1.45), 7.499 (0.75), 7.521 (2.31), 7.534 (2.56), 7.554 (0.85), 7.566 (1.30), 7.579 (0.53), 7.601 (2.34), 7.604 (2.30), 7.743 (2.59), 7.757 (2.33), 8.438 (2.04), 8.781 (0.60), 8.791 (1.20), 8.802 (0.61), 11.282 (1.78).

Example 29

Rac-N-{[2,5-Dioxo-4-(Tetrahydro-2H-Pyran-4-Yl)Imidazolidin-4-Yl]Methyl}-4'-(Trifluoromethyl)[Biphenyl]-2-Carboxamide

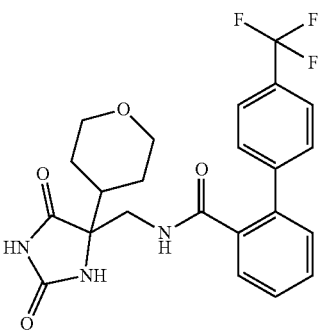 [SMILES: O=C1NC(=O)C(CNC(=O)c2ccccc2-c2ccc(C(F)(F)F)cc2)(C2CCOCC2)N1]

4'-(trifluoromethyl)[1,1'-biphenyl]-2-carboxylicacid (53.3 mg, 200 µmol) dissolved in 2 ml of DMF was treated with N-ethyl-N-isopropylpropan-2-amine (98 µl, 560 µmol), 3-{[(ethylimino)methylene]amino}-N,N-dimethylpropan-1-amine hydrochloride (49.9 mg, 260 µmol), 1H-benzotriazol-1-ol hydrate (39.9 mg, 260 µmol) and rac-5-(aminomethyl)-5-(tetrahydro-2H-pyran-4-yl)imidazolidine-2,4-dione hydrochloride (50.0 mg, 200 µmol). The mixture was stirred at room temperature for 2 h. The product was purified by preparative HPLC (Instrument: Waters Prep LC/MS System, Column: Phenomenex Kinetex C18 5 µm 100×30 mm; eluent A: water, eluent B: acetonitrile, eluent C: 2% formic acid in water, eluent D: acetonitrile/water (80 Vol. %/20 Vol %); flow: 80 ml/min, room temperature, UV-detection: 200-400 nm, At-Column Injektion; gradient: eluent A 0 bis 2 min 55 ml, eluent B 0 bis 2 min 15 ml, eluent A 2 bis 10 min from 55 ml to 31 ml and eluent B from 15 ml to 39 ml, 10 to 12 min 0 ml eluent A and 70 ml eluent B. Eluent C and Eluent D constant flow 5 ml/min over the whole runtime). After lyophilization, 26.0 mg (100% purity, 28% yield) of the title compound were obtained.

LC-MS (Method 7): $R_t$=1.51 min; MS (ESIpos): m/z=462 [M+H]$^+$ $^1$H-NMR (600 MHz, DMSO-d6) δ [ppm]: 1.280 (2.51), 1.299 (4.09), 1.320 (2.60), 1.328 (2.79), 1.341 (2.88), 1.348 (2.70), 1.362 (1.12), 1.369 (1.02), 1.385 (1.12), 1.393 (1.21), 1.405 (2.79), 1.413 (2.88), 1.426 (2.70), 1.434 (2.51), 1.447 (0.93), 1.454 (0.84), 1.560 (3.07), 1.580 (2.60), 1.861 (1.21), 1.867 (2.14), 1.873 (1.30), 1.881 (2.23), 1.887 (3.72), 1.893 (2.05), 1.901 (1.12), 1.907 (1.77), 2.084 (1.02), 2.384 (0.56), 2.422 (1.12), 2.477 (0.84), 2.515 (1.30), 2.517 (1.21), 2.521 (1.12), 2.612 (0.56), 2.652 (1.02), 3.191 (3.44), 3.197 (3.07), 3.212 (6.70), 3.227 (3.16), 3.232 (3.72), 3.273 (0.65), 3.276 (2.70), 3.279 (1.77), 3.284 (1.77), 3.288 (2.14), 3.331 (0.56), 3.338 (1.02), 3.342 (1.12), 3.345 (0.65), 3.362 (0.56), 3.366 (0.84), 3.390 (3.72), 3.400 (4.09), 3.413 (5.40), 3.423 (4.84), 3.515 (4.93), 3.526 (5.30), 3.538 (4.00), 3.549 (3.63), 3.817 (2.88), 3.824 (3.07), 3.835 (2.79), 3.842 (2.79), 3.854 (2.98), 3.861 (3.07), 3.873 (2.79), 3.879 (2.60), 7.422 (7.53), 7.434 (15.16), 7.444 (9.95), 7.447 (10.05), 7.458 (5.95), 7.459 (5.95), 7.470 (8.74), 7.472 (7.81), 7.482 (3.72), 7.484 (3.53), 7.532 (5.95), 7.535 (5.58), 7.545 (7.91), 7.548 (7.72), 7.560 (15.53), 7.574 (14.51), 7.748 (15.35), 7.762 (13.30), 7.796 (16.00), 8.480 (3.35), 8.490 (6.88), 8.500 (3.35), 10.707 (4.37).

Example 30

Rac-N-{[2,5-Dioxo-4-(Pyrazin-2-Yl)Imidazolidin-4-Yl]Methyl}-4'-(Trifluoromethyl)[Biphenyl]-2-Carboxamide

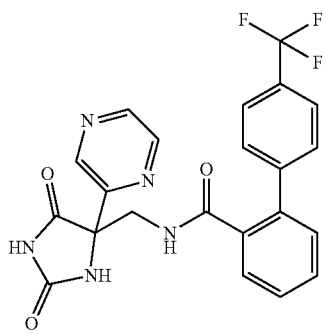 [SMILES: O=C1NC(=O)C(CNC(=O)c2ccccc2-c2ccc(C(F)(F)F)cc2)(c2cnccn2)N1]

4'-(trifluoromethyl)[1,1'-biphenyl]-2-carboxylicacid (53.5 mg, 201 μmol) dissolved in 2 ml of DMF was treated with N-ethyl-N-isopropylpropan-2-amine (98 μl, 560 μmol), 3-{[(ethylimino)methylene]amino}-N,N-dimethylpropan-1-amine hydrochloride (50.1 mg, 261 μmol), 1H-benzotriazol-1-ol hydrate (40.0 mg, 261 μmol) and rac-5-(aminomethyl)-5-(pyrazin-2-yl)imidazolidine-2,4-dione hydrochloride (53.5 mg, 201 μmol). The mixture was stirred at room temperature for 2 h. The product was purified by preparative HPLC (Instrument: Waters Prep LC/MS System, Column: Phenomenex Kinetex C18 5 μm 100×30 mm; eluent A: water, eluent B: acetonitrile, eluent C: 2% formic acid in water, eluent D: acetonitrile/water (80 Vol. %/20 Vol %); flow: 80 ml/min, room temperature, UV-detection: 200-400 nm, At-Column Injektion; gradient: eluent A 0 bis 2 min 55 ml, eluent B 0 bis 2 min 15 ml, eluent A 2 bis 10 min from 55 ml to 31 ml and eluent B from 15 ml to 39 ml, 10 to 12 min 0 ml eluent A and 70 ml eluent B. Eluent C and Eluent D constant flow 5 ml/min over the whole runtime). After lyophilization, 16.0 mg (96% purity, 17% yield) of the title compound were obtained.

LC-MS (Method 7): $R_t$=1.49 min; MS (ESIpos): m/z=456 [M+H]$^+$ $^1$H-NMR (600 MHz, DMSO-d6) δ [ppm]: 2.085 (0.88), 2.384 (0.53), 2.423 (0.80), 2.515 (1.06), 2.518 (1.06), 2.521 (0.97), 2.572 (3.09), 2.612 (0.53), 2.652 (0.80), 2.732 (0.44), 2.890 (0.53), 3.275 (2.56), 3.280 (2.65), 3.286 (2.48), 3.289 (3.36), 3.318 (2.56), 3.337 (0.53), 3.340 (12.55), 3.343 (1.59), 3.950 (3.01), 3.960 (3.18), 3.973 (4.42), 3.983 (4.15), 4.056 (4.15), 4.066 (4.60), 4.079 (3.27), 4.089 (2.92), 5.798 (0.44), 5.806 (0.44), 7.415 (4.33), 7.418 (4.42), 7.429 (13.70), 7.441 (6.63), 7.458 (3.89), 7.461 (3.62), 7.471 (6.54), 7.473 (6.01), 7.483 (3.09), 7.485 (2.74), 7.527 (9.64), 7.540 (14.41), 7.551 (6.28), 7.553 (5.75), 7.563 (2.83), 7.565 (2.65), 7.576 (0.62), 7.714 (0.53), 7.734 (10.96), 7.748 (9.46), 8.380 (11.58), 8.545 (0.53), 8.662 (3.09), 8.665 (11.40), 8.669 (16.00), 8.682 (2.74), 8.689 (8.49), 8.692 (9.02), 8.693 (6.90), 8.696 (6.36), 8.709 (0.53), 8.809 (12.46), 8.811 (11.85), 11.050 (2.74).

Example 31

Ent-N-{[4-(1,5-Dimethyl-1H-Pyrazol-4-Yl)-2,5-Dioxoimidazolidin-4-Yl]Methyl}-4'-(Trifluoromethyl)[Biphenyl]-2-Carboxamide

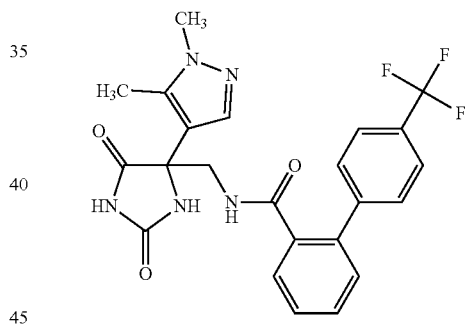

Enantiomeric separation of rac-N-{[4-(1,5-dimethyl-1H-pyrazol-4-yl)-2,5-dioxoimidazolidin-4 yl]methyl}-4'-(trifluoromethyl)[biphenyl]-2-carboxamide (85.0 mg, 180 μmol) using the following method:

Diacel Chiralpak IA 5 μm 250*20 mm
Eluent A: 40% n-heptane, eluent B: 60% iso-propanol
Flow: 15 ml/min
UV-detection: 220 nm
Temperature: 40° C.

Further purification was needed bei preparative HPLC (Column: Chromatorex C18 10 μm 250×30 mm; eluent A=water, B=acetonitrile; gradient: 0.0 min 30% B; 4.5 min 50% B; 11.5 min 70% B; 12 min 100% B; 14.75 min 30% B; flow: 50 ml/min; 0.1% formic acid). After lyophilisation 16.0 mg (97% purity, 18% yield) of the title compound were obtained.

Chiral-HPLC (Column: DiacellC-3 3 μm 50*4.6 mm, eluent A: 50% n-heptane, eluent B: 50% iso-propanol, flow: 1 ml/min, UV-detection: 220 nm): $R_t$=1.787 min; 100% ee LC-MS (Method 7): $R_t$=1.48 min; MS (ESIpos): m/z=472 [M+H]$^+$ ¹H-NMR (600 MHz, DMSO-d6) δ [ppm]: 2.253 (15.10), 2.470 (0.44), 3.266 (1.35), 3.333 (0.66), 3.702 (16.00), 3.767 (2.04), 3.770 (1.98), 3.780 (2.23), 7.371 (5.13), 7.402 (1.19), 7.404 (1.27), 7.415 (1.94), 7.417 (1.87), 7.429 (1.58), 7.442 (1.91), 7.455 (1.08), 7.457 (1.05), 7.467 (1.90), 7.469 (1.63), 7.480 (0.92), 7.482 (0.79), 7.536 (3.61), 7.549 (4.69), 7.561 (0.69), 7.564 (0.63), 7.740 (3.18), 7.754 (2.76), 8.132 (3.14), 8.592 (0.76), 8.602 (1.51), 8.612 (0.71), 10.858 (1.72).

Example 32

Rac-N-{[4-(4-Methyl-1,2,5-Oxadiazol-3-Yl)-2,5-Dioxoimidazolidin-4-Yl]Methyl}-4'-(Trifluoromethyl)[Biphenyl]-2-Carboxamide

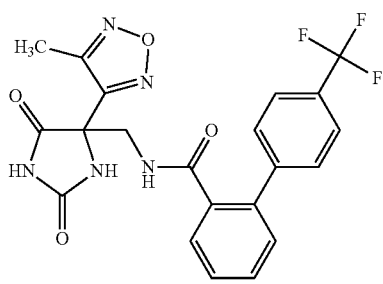 [SMILES: Cc1nonc1C1(CNC(=O)c2ccccc2-c2ccc(C(F)(F)F)cc2)NC(=O)NC1=O]

4'-(trifluoromethyl)[1,1'-biphenyl]-2-carboxylic acid (80.0 mg, 300 µmol) dissolved in 2.5 ml of DMF was treated with N-ethyl-N-isopropylpropan-2-amine (80.0 mg, 300 µmol), 3-{[(ethylimino)methylene]amino}-N,N-dimethylpropan-1-amine hydrochloride (74.9 mg, 391 µmol), 1H-benzotriazol-1-ol hydrate (59.8 mg, 391 µmol) and rac-5-(aminomethyl)-5-(4-methyl-1,2,5-oxadiazol-3-yl)imidazolidine-2,4-dione hydrochloride (80.0 mg, 93% purity, 300 µmol). The mixture was stirred at room temperature for 3 h. The product was purified by preparative HPLC (Instrument: Waters Prep LC/MS System, Column: Phenomenex Kinetex C18 5 µm 100×30 mm; eluent A: water, eluent B: acetonitrile, eluent C: 2% formic acid in water, eluent D: acetonitrile/water (80 Vol. %/20 Vol %); flow: 80 ml/min, room temperature, UV-detection: 200-400 nm, At-Column Injektion; gradient: eluent A 0 bis 2 min 55 ml, eluent B 0 bis 2 min 15 ml, eluent A 2 bis 10 min from 55 ml to 31 ml and eluent B from 15 ml to 39 ml, 10 to 12 min 0 ml eluent A and 70 ml eluent B. Eluent C and eluent D constant flow 5 ml/min over the whole runtime). After lyophilization, 42.0 mg (98% purity, 30% yield) of the title compound were obtained.

LC-MS (Method 7): $R_t$=1.73 min; MS (ESIpos): m/z=460 [M+H]⁺

¹H-NMR (400 MHz, DMSO-d6) δ [ppm]: −0.008 (0.51), 0.008 (0.57), 2.363 (16.00), 2.525 (0.43), 4.015 (1.81), 4.022 (1.86), 4.030 (1.82), 4.038 (1.76), 7.443 (2.33), 7.462 (4.14), 7.474 (1.21), 7.477 (1.22), 7.492 (1.96), 7.496 (1.42), 7.511 (0.79), 7.514 (0.96), 7.524 (2.78), 7.544 (3.25), 7.552 (1.68), 7.556 (1.35), 7.571 (1.61), 7.575 (1.35), 7.590 (0.53), 7.593 (0.59), 7.749 (3.32), 7.770 (2.75), 8.550 (2.71), 8.868 (0.72), 8.883 (1.52), 8.899 (0.71).

Example 33

Rac-5-Chloro-N-{[4-(1,5-Dimethyl-1H-Pyrazol-4-Yl)-2,5-Dioxoimidazolidin-4-Yl]Methyl}-4'-(Trifluoromethyl)[Biphenyl]-2-Carboxamide

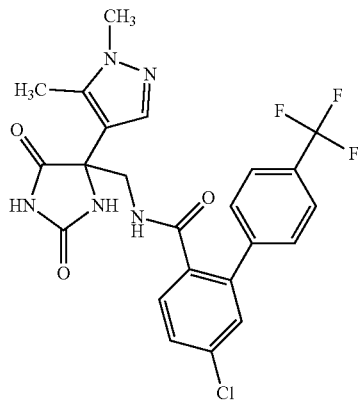 [SMILES: Cc1c(C2(CNC(=O)c3ccc(Cl)cc3-c3ccc(C(F)(F)F)cc3)NC(=O)NC2=O)cnn1C]

5-chloro-4'-(trifluoromethyl)[1,1'-biphenyl]-2-carboxylic acid (139 mg, 462 µmol) dissolved in 2 ml of DMF was treated with N-ethyl-N-isopropylpropan-2-amine (240 µl, 1.4 mmol), 3-{[(ethylimino)methylene]amino}-N,N-dimethylpropan-1-amine hydrochloride (115 mg, 601 µmol), 1H-benzotriazol-1-ol hydrate (92.0 mg, 601 µmol) and rac-5-(aminomethyl)-5-(1,5-dimethyl-1H-pyrazol-4-yl)imidazolidine-2,4-dione hydrochloride (120 mg, 462 µmol). The mixture was stirred at room temperature over night. The product was purified by preparative HPLC (Instrument: Waters Prep LC/MS System, Column: Phenomenex Kinetex C18 5 µm 100×30 mm; eluent A: water, eluent B: acetonitrile, eluent C: 2% formic acid in water, eluent D: acetonitrile/water (80 Vol. %/20 Vol %); flow: 80 ml/min, room temperature, UV-detection: 200-400 nm, At-Column Injektion; gradient: eluent A 0 bis 2 min 55 ml, eluent B 0 bis 2 min 15 ml, eluent A 2 bis 10 min from 55 ml to 31 ml and eluent B from 15 ml to 39 ml, 10 to 12 min 0 ml eluent A and 70 ml eluent B. Eluent C and eluent D constant flow 5 ml/min over the whole runtime). After lyophilization, 130 mg (100% purity, 56% yield) of the title compound were obtained.

LC-MS (Method 7): $R_t$=1.67 min; MS (ESIpos): m/z=506 [M+H]⁺

¹H-NMR (600 MHz, DMSO-d6) δ [ppm]: 2.068 (1.02), 2.250 (15.24), 3.699 (16.00), 3.742 (0.44), 3.754 (1.51), 3.766 (2.69), 3.776 (1.59), 3.788 (0.44), 7.369 (5.50), 7.413 (2.83), 7.427 (3.31), 7.514 (3.10), 7.517 (3.48), 7.558 (3.48), 7.561 (4.09), 7.572 (3.57), 7.575 (3.99), 7.756 (3.19), 7.770 (2.77), 8.168 (2.91), 8.678 (0.76), 8.688 (1.51), 8.698 (0.74), 10.865 (1.79).

Example 34

Rac-N-{[4-(2,4-Dimethyl-1,3-Thiazol-5-Yl)-2,5-Dioxoimidazolidin-4-Yl]Methyl}-2-[6-(Trifluoromethyl)Pyridin-3-Yl]Benzamide

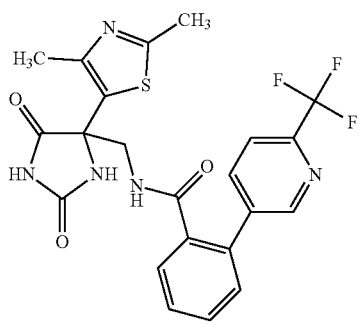 [SMILES: Cc1nc(C)c(C2(CNC(=O)c3ccccc3-c3ccc(C(F)(F)F)nc3)NC(=O)NC2=O)s1]

2-[6-(trifluoromethyl)pyridin-3-yl]benzoic acid (96.6 mg, 361 µmol) dissolved in 2 ml of DMF was treated with N-ethyl-N-isopropylpropan-2-amine (190 µl, 1.1 mmol), 3-{[(ethylimino)methylene]amino}-N,N-dimethylpropan-1-amine hydrochloride (90.1 mg, 470 µmol), 1H-benzotriazol-1-ol hydrate (71.9 mg, 470 µmol) and rac-5-(aminomethyl)-5-(2,4-dimethyl-1,3-thiazol-5-yl)imidazolidine-2,4-dione hydrochloride (100 mg, 361 µmol). The mixture was stirred at room temperature over night. The product was purified by preparative HPLC (Instrument: Waters Prep LC/MS System, Column: Phenomenex Kinetex C18 5 µm 100×30 mm; eluent A: water, eluent B: acetonitrile, eluent C: 2% formic acid in water, eluent D: acetonitrile/water (80 Vol. %/20 Vol. %); flow: 80 ml/min, room temperature, UV-detection: 200-400 nm, At-Column Injektion; gradient: eluent A 0 bis 2 min 63 ml, eluent B 0 bis 2 min 7 ml, eluent A 2 bis 10 min from 63 ml to 39 ml and eluent B from 7 ml to 31 ml, 10 to 12 min 0 ml eluent A and 70 ml eluent B. Eluent C and eluent D constant flow 5 ml/min over the whole runtime). After lyophilization, 110 mg (100% purity, 62% yield) of the title compound were obtained.

LC-MS (Method 7): $R_t$=1.37 min; MS (ESIpos): m/z=490 [M+H]$^+$ $^1$H-NMR (600 MHz, DMSO-d6) δ [ppm]: 2.346 (16.00), 3.832 (2.05), 3.835 (2.00), 3.842 (1.84), 3.845 (1.93), 7.480 (1.27), 7.481 (1.32), 7.492 (1.81), 7.494 (1.77), 7.520 (1.35), 7.521 (1.46), 7.534 (1.93), 7.542 (0.93), 7.544 (0.91), 7.555 (1.83), 7.557 (1.60), 7.567 (0.96), 7.569 (0.83), 7.603 (1.25), 7.606 (1.22), 7.616 (1.68), 7.618 (1.60), 7.628 (0.65), 7.631 (0.60), 7.911 (2.89), 7.913 (5.90), 8.469 (3.34), 8.721 (2.45), 8.767 (0.76), 8.777 (1.53), 8.787 (0.73), 11.139 (1.13).

Example 35

Rac-N-{[4-(1,4-Dimethyl-1H-Pyrazol-3-Yl)-2,5-Dioxoimidazolidin-4-Yl]Methyl}-2-[6-(Trifluoromethyl)Pyridin-3-Yl]Benzamide

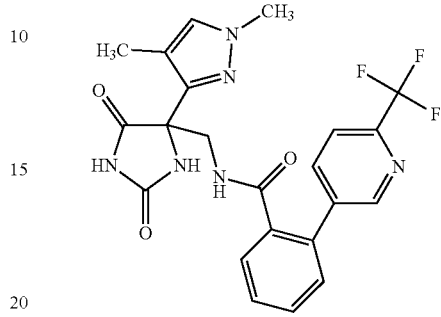

2-[6-(trifluoromethyl)pyridin-3-yl]benzoic acid (170 mg, 635 µmol) dissolved in 2.5 ml of DMF was treated with N-ethyl-N-isopropylpropan-2-amine (330 µl, 1.9 mmol), 3-{[(ethylimino)methylene]amino}-N,N-dimethylpropan-1-amine hydrochloride (158 mg, 826 µmol), 1H-benzotriazol-1-ol hydrate (126 mg, 826 µmol) and rac-5-(aminomethyl)-5-(1,4-dimethyl-1H-pyrazol-3-yl)imidazolidine-2,4-dione hydrochloride (165 mg, 635 µmol). The mixture was stirred at room temperature over night. The product was purified by preparative HPLC (Instrument: Waters Prep LC/MS System, Column: Phenomenex Kinetex C18 5 µm 100×30 mm; eluent A: water, eluent B: acetonitrile, eluent C: 2% formic acid in water, eluent D: acetonitrile/water (80 Vol. %/20 Vol. %); flow: 80 ml/min, room temperature, UV-detection: 200-400 nm, At-Column Injektion; gradient: eluent A 0 bis 2 min 63 ml, eluent B 0 bis 2 min 7 ml, eluent A 2 bis 10 min from 63 ml to 39 ml and eluent B from 7 ml to 31 ml, 10 to 12 min 0 ml eluent A and 70 ml eluent B. Eluent C and eluent D constant flow 5 ml/min over the whole runtime). After lyophilization, 200 mg (100% purity, 67% yield) of the title compound were obtained.

LC-MS (Method 7): $R_t$=1.35 min; MS (ESIpos): m/z=473 [M+H]$^+$ $^1$H-NMR (600 MHz, DMSO-d6) δ [ppm]: 1.883 (11.89), 2.068 (0.53), 3.269 (0.49), 3.742 (16.00), 3.943 (0.44), 3.955 (1.60), 3.966 (2.89), 3.976 (1.64), 3.988 (0.41), 7.458 (3.53), 7.471 (1.21), 7.484 (1.97), 7.523 (2.44), 7.536 (3.79), 7.548 (1.02), 7.551 (0.70), 7.587 (1.32), 7.589 (1.24), 7.600 (1.28), 7.602 (1.61), 7.612 (0.64), 7.614 (0.59), 7.932 (1.65), 7.945 (2.62), 7.986 (1.41), 7.990 (1.37), 8.000 (0.85), 8.003 (0.83), 8.106 (3.26), 8.558 (0.73), 8.568 (1.52), 8.579 (0.71), 8.744 (2.06), 8.747 (2.03), 10.898 (1.36).

Example 36

Rac-N-{[2,5-Dioxo-4-(Tetrahydro-2H-Pyran-4-Yl)Imidazolidin-4-Yl]Methyl}-2-[6-(Trifluoromethyl)Pyridin-3-Yl]Benzamide

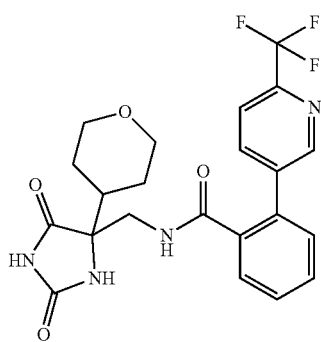 [SMILES: O=C1NC(=O)C(CNC(=O)c2ccccc2-c2ccc(C(F)(F)F)nc2)(C2CCOCC2)N1]

2-[6-(trifluoromethyl)pyridin-3-yl]benzoic acid (53.5 mg, 200 μmol) dissolved in 2 ml of DMF was treated with N-ethyl-N-isopropylpropan-2-amine (98 μl, 560 μmol), 3-{[(ethylimino)methylene]amino}-N,N-dimethylpropan-1-amine hydrochloride (49.9 mg, 260 μmol), 1H-benzotriazol-1-ol hydrate (39.9 mg, 260 μmol) and rac-5-(aminomethyl)-5-(tetrahydro-2H-pyran-4-yl)imidazolidine-2,4-dione hydrochloride (50.0 mg, 200 μmol). The mixture was stirred at room temperature for 2 h. The product was purified by preparative HPLC (Instrument: Waters Prep LC/MS System, Column: Phenomenex Kinetex C18 5 μm 100×30 mm; eluent A: water, eluent B: acetonitrile, eluent C: 2% formic acid in water, eluent D: acetonitrile/water (80 Vol. %/20 Vol. %); flow: 80 ml/min, room temperature, UV-detection: 200-400 nm, At-Column Injektion; gradient: eluent A 0 bis 2 min 63 ml, eluent B 0 bis 2 min 7 ml, eluent A 2 bis 10 min from 63 ml to 39 ml and eluent B from 7 ml to 31 ml, 10 to 12 min 0 ml eluent A and 70 ml eluent B. Eluent C and eluent D constant flow 5 ml/min over the whole runtime). After lyophilization, 43.0 mg (99% purity, 46% yield) of the title compound were obtained.

LC-MS (Method 7): $R_t$=1.28 min; MS (ESIpos): m/z=463 [M+H]$^+$ $^1$H-NMR (600 MHz, DMSO-d6) δ [ppm]: 0.005 (0.77), 1.281 (3.18), 1.300 (5.21), 1.312 (4.06), 1.320 (3.56), 1.333 (3.75), 1.340 (3.52), 1.353 (1.53), 1.361 (1.34), 1.378 (1.38), 1.386 (1.61), 1.399 (3.52), 1.406 (3.75), 1.419 (3.33), 1.426 (3.29), 1.440 (1.30), 1.447 (1.11), 1.570 (3.98), 1.591 (3.37), 1.868 (1.45), 1.873 (2.60), 1.879 (1.61), 1.887 (2.79), 1.893 (4.71), 1.899 (2.68), 1.908 (1.45), 1.913 (2.22), 2.069 (4.13), 2.383 (0.50), 2.422 (0.80), 2.514 (1.11), 2.517 (1.11), 2.520 (1.03), 2.571 (1.99), 2.611 (0.46), 2.651 (0.73), 3.201 (5.74), 3.221 (10.60), 3.241 (5.74), 3.261 (0.57), 3.325 (0.88), 3.329 (3.87), 3.385 (4.48), 3.395 (5.09), 3.407 (6.55), 3.418 (6.01), 3.516 (5.93), 3.527 (6.28), 3.539 (4.71), 3.550 (4.40), 3.812 (3.67), 3.819 (3.94), 3.831 (3.64), 3.837 (3.48), 3.853 (3.83), 3.859 (4.02), 3.871 (3.64), 3.878 (3.41), 7.500 (6.24), 7.502 (7.08), 7.508 (9.68), 7.512 (12.78), 7.515 (12.52), 7.520 (12.40), 7.529 (6.55), 7.531 (6.39), 7.542 (10.91), 7.544 (9.19), 7.554 (5.01), 7.556 (4.17), 7.588 (7.46), 7.591 (7.16), 7.600 (9.68), 7.603 (8.88), 7.613 (3.56), 7.615 (3.52), 7.827 (13.59), 7.926 (10.26), 7.939 (16.00), 7.982 (8.73), 7.985 (8.34), 7.995 (5.24), 7.998 (5.09), 8.547 (4.33), 8.557 (8.61), 8.568 (4.13), 8.735 (13.01), 8.738 (12.52), 10.711 (11.79).

Example 37

Ent-N-{[4-(4-Methyl-1,3-Thiazol-5-Yl)-2,5-Dioxo-imidazolidin-4-Yl]Methyl}-2-[6-(Trifluoromethyl)Pyridin-3-Yl]Benzamide

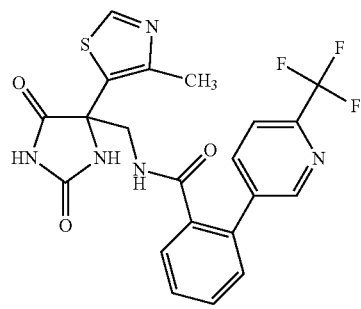 [SMILES: Cc1ncsc1C1(CNC(=O)c2ccccc2-c2ccc(C(F)(F)F)nc2)NC(=O)NC1=O]

2-[6-(trifluoromethyl)pyridin-3-yl]benzoic acid (50.9 mg, 190 μmol) dissolved in 1.5 ml of DMF was treated with N-ethyl-N-isopropylpropan-2-amine (99 μl, 570 μmol), 3-{[(ethylimino)methylene]amino}-N,N-dimethylpropan-1-amine hydrochloride (47.4 mg, 247 μmol), 1H-benzotriazol-1-ol hydrate (37.9 mg, 247 μmol) and ent-5-(aminomethyl)-5-(4-methyl-1,3-thiazol-5-yl)imidazolidine-2,4-dione hydrochloride (Enantiomer 2) (50.0 mg, 190 μmol). The mixture was stirred at room temperature for 2 h. The product was purified by preparative HPLC (Instrument: Waters Prep LC/MS System, Column: Phenomenex Kinetex C18 5 μm 100×30 mm; eluent A: water, eluent B: acetonitrile, eluent C: 2% formic acid in water, eluent D: acetonitrile/water (80 Vol. %/20 Vol. %); flow: 80 ml/min, room temperature, UV-detection: 200-400 nm, At-Column Injektion; gradient: eluent A 0 bis 2 min 63 ml, eluent B 0 bis 2 min 7 ml, eluent A 2 bis 10 min from 63 ml to 39 ml and eluent B from 7 ml to 31 ml, 10 to 12 min 0 ml eluent A and 70 ml eluent B. Eluent C and eluent D constant flow 5 ml/min over the whole runtime). After lyophilization, 65.0 mg (100% purity, 72% yield) of the title compound were obtained.

LC-MS (Method 7): $R_t$=1.31 min; MS (ESIpos): m/z=476 [M+H]$^+$ $^1$H-NMR (600 MHz, DMSO-d6) δ [ppm]: 2.069 (0.41), 2.451 (16.00), 3.886 (3.09), 3.897 (3.18), 7.467 (1.28), 7.469 (1.36), 7.480 (1.78), 7.482 (1.76), 7.521 (1.32), 7.522 (1.48), 7.535 (1.96), 7.541 (0.96), 7.543 (0.92), 7.553 (1.87), 7.555 (1.62), 7.566 (0.99), 7.568 (0.85), 7.604 (1.25), 7.606 (1.25), 7.617 (1.68), 7.619 (1.65), 7.629 (0.65), 7.631 (0.62), 7.886 (0.58), 7.890 (0.56), 7.900 (1.75), 7.903 (1.83), 7.912 (3.02), 7.913 (3.16), 7.926 (0.95), 7.927 (0.92), 8.517 (2.61), 8.723 (1.99), 8.726 (2.07), 8.798 (0.73), 8.808 (1.52), 8.818 (0.72), 8.927 (5.41), 11.179 (1.75).

Example 38

Diamix-N-[(4-Sec-Butyl-2,5-Dioxoimidazolidin-4-Yl)Methyl]-4'-(Trifluoromethyl)[Biphenyl]-2-Carboxamide

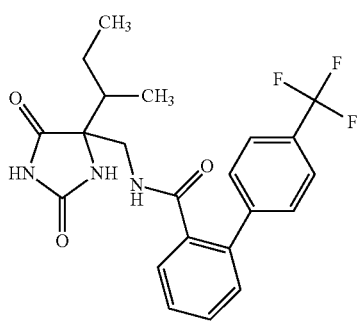 [SMILES: CCC(C)C1(CNC(=O)c2ccccc2-c2ccc(C(F)(F)F)cc2)NC(=O)NC1=O]

4'-(trifluoromethyl)[1,1'-biphenyl]-2-carboxylic acid (60.0 mg, 226 µmol) dissolved in 2.2 ml of DMF was treated with N-ethyl-N-isopropylpropan-2-amine (110 µl, 630 µmol), 3-{[(ethylimino)methylene]amino}-N,N-dimethylpropan-1-amine hydrochloride (56.2 mg, 293 µmol), 1H-benzotriazol-1-ol hydrate (44.9 mg, 293 µmol) and diamix-5-(aminomethyl)-5-sec-butylimidazolidine-2,4-dione hydrochloride (50.0 mg, 226 µmol). The mixture was stirred at room temperature for 2 h. The product was purified by preparative HPLC (Instrument: Waters Prep LC/MS System, Column: Phenomenex Kinetex C18 5 µm 100×30 mm; eluent A: water, eluent B: acetonitrile, eluent C: 2% formic acid in water, eluent D: acetonitrile/water (80 Vol. %/20 Vol. %); flow: 80 ml/min, room temperature, UV-detection: 200-400 nm, At-Column Injektion; gradient: eluent A 0 bis 2 min 55 ml, eluent B 0 bis 2 min 15 ml, eluent A 2 bis 10 min from 55 ml to 31 ml and eluent B from 15 ml to 39 ml, 10 to 12 min 0 ml eluent A and 70 ml eluent B. Eluent C and eluent D constant flow 5 ml/min over the whole runtime). After lyophilization, 46.0 mg (100% purity, 47% yield) and 16.0 mg (97% purity, 16% yield) of the title compound were obtained.

LC-MS (Method 7): $R_t$=1.77 min; MS (ESIpos): m/z=434 [M+H]$^+$ $^1$H-NMR (600 MHz, DMSO-d6) δ [ppm]: 0.802 (9.99), 0.813 (12.49), 0.823 (13.69), 0.836 (7.92), 0.839 (11.43), 0.851 (5.56), 0.880 (11.36), 0.891 (11.71), 0.950 (0.62), 0.962 (0.64), 0.968 (0.76), 0.972 (0.86), 0.980 (0.76), 0.990 (0.75), 1.002 (0.53), 1.038 (0.70), 1.050 (0.75), 1.055 (0.84), 1.060 (0.97), 1.068 (0.84), 1.072 (0.81), 1.078 (0.96), 1.090 (0.75), 1.274 (0.76), 1.279 (0.86), 1.287 (0.89), 1.291 (0.96), 1.296 (0.84), 1.301 (0.81), 1.309 (0.67), 1.314 (0.62), 1.532 (0.64), 1.536 (0.72), 1.548 (0.86), 1.558 (0.88), 1.566 (0.75), 1.572 (1.31), 1.578 (0.88), 1.584 (1.21), 1.590 (1.10), 1.595 (0.89), 1.601 (0.83), 1.606 (0.69), 1.621 (0.86), 1.627 (1.02), 1.633 (1.00), 1.638 (1.47), 1.644 (0.97), 1.650 (0.92), 1.655 (0.76), 2.383 (0.48), 2.422 (0.46), 2.466 (0.61), 2.514 (1.04), 2.517 (0.96), 2.520 (0.81), 2.611 (0.41), 3.260 (1.31), 3.324 (0.56), 3.381 (1.61), 3.391 (1.80), 3.399 (1.72), 3.404 (2.49), 3.409 (1.93), 3.414 (2.22), 3.422 (2.09), 3.432 (1.82), 3.520 (2.17), 3.530 (2.23), 3.544 (2.60), 3.555 (2.52), 3.567 (1.53), 3.578 (1.39), 7.411 (2.29), 7.413 (2.68), 7.419 (7.94), 7.423 (4.94), 7.426 (4.56), 7.432 (10.41), 7.449 (2.33), 7.451 (2.28), 7.453 (2.23), 7.455 (2.10), 7.461 (3.79), 7.463 (3.62), 7.466 (3.63), 7.474 (1.83), 7.476 (1.75), 7.480 (1.51), 7.528 (2.69), 7.530 (4.08), 7.542 (5.83), 7.559 (10.44), 7.572 (11.33), 7.632 (5.66), 7.746 (16.00), 7.759 (8.51), 8.402 (2.04), 8.413 (3.98), 8.421 (1.93), 10.654 (3.35).

Example 39

Rac-N-{[4-(1,4-Dimethyl-1H-Pyrazol-3-Yl)-2,5-Dioxoimidazolidin-4-Yl]Methyl}-4'-(Trifluoromethyl)[Biphenyl]-2-Carboxamide

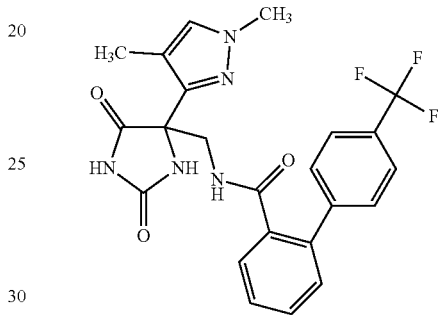

4'-(trifluoromethyl)[1,1'-biphenyl]-2-carboxylic acid (103 mg, 385 µmol) dissolved in 3 ml of DMF was treated with N-ethyl-N-isopropylpropan-2-amine (200 µl, 1.2 mmol), 3-{[(ethylimino)methylene]amino}-N,N-dimethylpropan-1-amine hydrochloride (96.0 mg, 501 µmol), 1H-benzotriazol-1-ol hydrate (76.7 mg, 501 µmol) and rac-5-(aminomethyl)-5-(1,4-dimethyl-1H-pyrazol-3-yl)imidazolidine-2,4-dione hydrochloride (100 mg, 385 µmol). The mixture was stirred at room temperature for 3 h. The product was purified by preparative HPLC (Instrument: Waters Prep LC/MS System, Column: Phenomenex Kinetex C185 µm 100×30 mm; eluent A: water, eluent B: acetonitrile, eluent C: 2% formic acid in water, eluent D: acetonitrile/water (80 Vol. %/20 Vol. %); flow: 80 ml/min, room temperature, UV-detection: 200-400 nm, At-Column Injektion; gradient: eluent A 0 bis 2 min 55 ml, eluent B 0 bis 2 min 15 ml, eluent A 2 bis 10 min from 55 ml to 31 ml and eluent B from 15 ml to 39 ml, 10 to 12 min 0 ml eluent A and 70 ml eluent B. Eluent C and eluent D constant flow 5 ml/min over the whole runtime). After lyophilization, 125 mg (100% purity, 69% yield) of the title compound were obtained.

LC-MS (Method 7): $R_t$=1.60 min; MS (ESIpos): m/z=472 [M+H]$^+$ $^1$H-NMR (400 MHz, DMSO-d6) δ [ppm]: 1.886 (14.96), 2.071 (0.73), 2.499 (3.55), 3.739 (16.00), 3.912 (0.76), 3.928 (0.74), 3.947 (1.73), 3.962 (1.62), 3.981 (1.65), 3.997 (1.80), 4.016 (0.81), 4.032 (0.71), 7.407 (1.20), 7.410 (1.35), 7.426 (2.80), 7.428 (2.83), 7.435 (2.18), 7.454 (3.44), 7.465 (5.58), 7.486 (1.11), 7.529 (1.46), 7.532 (1.51), 7.548 (1.84), 7.551 (1.86), 7.570 (4.08), 7.591 (4.20), 7.762 (4.30), 7.783 (3.58), 8.119 (4.76), 8.512 (1.00), 8.528 (2.02), 8.543 (0.94), 10.902 (0.42).

Example 40

Rac-N-{[4-(1-Cyclopropyl-1H-Pyrazol-5-Yl)-2,5-Dioxoimidazolidin-4-Yl]Methyl}-2-[6-(Trifluoromethyl)Pyridin-3-Yl]Benzamide

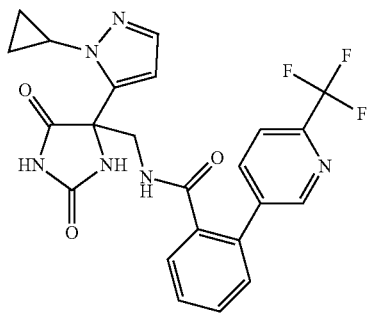 [SMILES: O=C1NC(=O)C(CNC(=O)c2ccccc2-c2ccc(C(F)(F)F)nc2)(c2ccnn2C2CC2)N1]

2-[6-(trifluoromethyl)pyridin-3-yl]benzoic acid (98.3 mg, 368 µmol) dissolved in 2 ml of DMF was treated with N-ethyl-N-isopropylpropan-2-amine (190 µl, 1.1 mmol), 3-{[(ethylimino)methylene]amino}-N,N-dimethylpropan-1-amine hydrochloride (91.7 mg, 478 µmol), 1H-benzotriazol-1-ol hydrate (73.3 mg, 478 µmol) and rac-5-(aminomethyl)-5-(1-cyclopropyl-1H-pyrazol-5-yl)imidazolidine-2,4-dione hydrochloride (100 mg, 368 µmol). The mixture was stirred at room temperature for 3 h. The product was purified by preparative HPLC (Instrument: Waters Prep LC/MS System, Column: Phenomenex Kinetex C18 5 µm 100×30 mm; eluent A: water, eluent B: acetonitrile, eluent C: 2% formic acid in water, eluent D: acetonitrile/water (80 Vol. %/20 Vol. %); flow: 80 ml/min, room temperature, UV-detection: 200-400 nm, At-Column Injektion; gradient: eluent A 0 bis 2 min 63 ml, eluent B 0 bis 2 min 7 ml, eluent A 2 bis 10 min from 63 ml to 39 ml and eluent B from 7 ml to 31 ml, 10 to 12 min 0 ml eluent A and 70 ml eluent B. Eluent C and eluent D constant flow 5 ml/min over the whole runtime). After lyophilization, 65.0 mg (100% purity, 36% yield) of the title compound were obtained.

LC-MS (Method 7): $R_t$=1.36 min; MS (ESIpos): m/z=485 [M+H]$^+$ $^1$H-NMR (600 MHz, DMSO-d6) δ [ppm]: 0.831 (0.97), 0.839 (2.04), 0.846 (2.04), 0.849 (2.81), 0.851 (2.52), 0.857 (3.39), 0.860 (2.13), 0.863 (2.04), 0.867 (2.23), 0.875 (1.75), 0.881 (1.26), 0.893 (2.72), 0.897 (2.23), 0.901 (2.23), 0.905 (3.01), 0.909 (4.17), 0.917 (3.39), 0.921 (2.42), 0.929 (1.65), 0.950 (1.94), 0.959 (2.52), 0.963 (3.39), 0.967 (1.65), 0.971 (3.98), 0.975 (3.30), 0.979 (2.42), 0.984 (2.04), 0.987 (2.52), 1.000 (1.07), 1.260 (1.55), 1.268 (2.23), 1.272 (1.94), 1.275 (2.23), 1.278 (3.10), 1.286 (3.20), 1.292 (1.75), 1.295 (1.75), 1.304 (1.16), 2.383 (0.68), 2.422 (1.07), 2.517 (1.45), 2.571 (2.33), 2.611 (0.58), 2.651 (1.07), 3.264 (1.94), 3.312 (2.62), 3.322 (1.55), 3.331 (8.63), 3.443 (1.65), 3.449 (3.01), 3.455 (4.07), 3.461 (5.72), 3.467 (4.17), 3.473 (3.10), 3.479 (1.45), 3.892 (2.91), 3.902 (3.39), 3.914 (5.53), 3.924 (4.85), 3.962 (5.04), 3.973 (5.33), 3.984 (3.10), 3.996 (2.91), 6.526 (14.45), 6.529 (14.64), 7.339 (16.00), 7.342 (15.42), 7.513 (4.27), 7.515 (4.85), 7.525 (14.84), 7.527 (8.92), 7.536 (8.82), 7.544 (4.95), 7.546 (4.56), 7.556 (7.95), 7.558 (6.79), 7.569 (3.78), 7.571 (3.10), 7.606 (5.43), 7.609 (5.14), 7.619 (7.18), 7.621 (6.40), 7.632 (2.42), 7.634 (2.81), 7.918 (7.56), 7.931 (11.44), 7.979 (6.11), 7.982 (6.01), 7.992 (3.88), 7.995 (3.98), 8.324 (10.18), 8.738 (9.12), 8.741 (9.12), 8.827 (3.20), 8.837 (6.30), 8.848 (3.20), 11.186 (8.63).

Example 41

Rac-N-{[4-(3-Methyl-1,2-Oxazol-4-Yl)-2,5-Dioxoimidazolidin-4-Yl]Methyl}-2-[6-(Trifluoromethyl)Pyridin-3-Yl]Benzamide

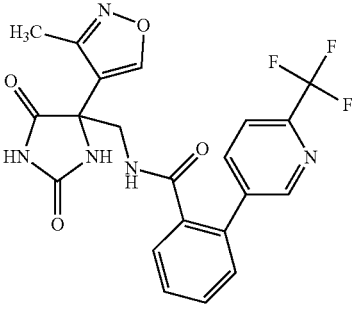 [SMILES: Cc1nocc1C1(CNC(=O)c2ccccc2-c2ccc(C(F)(F)F)nc2)NC(=O)NC1=O]

2-[6-(trifluoromethyl)pyridin-3-yl]benzoic acid (179 mg, 669 µmol) dissolved in 2.5 ml of DMF was treated with N-ethyl-N-isopropylpropan-2-amine (350 µl, 2.0 mmol), 3-{[(ethylimino)methylene]amino}-N,N-dimethylpropan-1-amine hydrochloride (167, 870 µmol), 1H-benzotriazol-1-ol hydrate (133 mg, 870 µmol) and rac-5-(aminomethyl)-5-(3-methyl-1,2-oxazol-4-yl)imidazolidine-2,4-dione hydrochloride (165 mg, 669 µmol). The mixture was stirred at room temperature for 3 h. The product was purified by preparative HPLC (Instrument: Waters Prep LC/MS System, Column: Phenomenex Kinetex C18 5 µm 100×30 mm; eluent A: water, eluent B: acetonitrile, eluent C: 2% formic acid in water, eluent D: acetonitrile/water (80 Vol. %/20 Vol. %); flow: 80 ml/min, room temperature, UV-detection: 200-400 nm, At-Column Injektion; gradient: eluent A 0 bis 2 min 63 ml, eluent B 0 bis 2 min 7 ml, eluent A 2 bis 10 min from 63 ml to 39 ml and eluent B from 7 ml to 31 ml, 10 to 12 min 0 ml eluent A and 70 ml eluent B. Eluent C and eluent D constant flow 5 ml/min over the whole runtime). After lyophilization, 180 mg (100% purity, 59% yield) of the title compound were obtained.

LC-MS (Method 7): $R_t$=1.36 min; MS (ESIpos): m/z=460 [M+H]$^+$ $^1$H-NMR (600 MHz, DMSO-d6) δ [ppm]: 2.069 (5.93), 2.230 (16.00), 3.777 (0.74), 3.786 (0.82), 3.799 (1.54), 3.809 (1.38), 3.833 (1.42), 3.844 (1.49), 3.856 (0.75), 3.867 (0.70), 7.485 (1.40), 7.487 (1.46), 7.497 (2.10), 7.499 (2.03), 7.517 (1.52), 7.518 (1.65), 7.530 (1.98), 7.531 (2.14), 7.541 (1.08), 7.543 (1.05), 7.554 (2.13), 7.556 (1.79), 7.566 (1.12), 7.568 (0.92), 7.602 (1.46), 7.605 (1.40), 7.615 (1.96), 7.617 (1.84), 7.628 (0.75), 7.630 (0.69), 7.895 (1.50), 7.907 (3.24), 7.928 (1.83), 7.931 (1.74), 7.942 (0.80), 7.945 (0.82), 8.273 (2.63), 8.726 (2.33), 8.729 (2.27), 8.804 (0.83), 8.815 (1.54), 8.825 (0.80), 8.959 (5.13), 11.141 (2.11).

Example 42

Rac-N-{[2,5-Dioxo-4-(Pyridazin-3-Yl)Imidazolidin-4-Yl]Methyl}-4'-(Trifluoromethyl)[Biphenyl]-2-Carboxamide

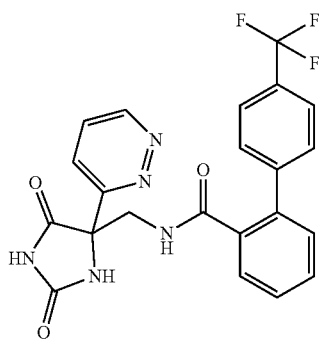 [SMILES: O=C1NC(=O)C(CNC(=O)c2ccccc2-c2ccc(C(F)(F)F)cc2)(c2cccnn2)N1]

4'-(trifluoromethyl)[1,1'-biphenyl]-2-carboxylicacid (62.3 mg, 234 µmol) dissolved in 2 ml of DMF was treated with N-ethyl-N-isopropylpropan-2-amine (110 µl, 660 µmol), 3-{[(ethylimino)methylene]amino}-N,N-dimethylpropan-1-amine hydrochloride (58.3 mg, 304 µmol), 1H-benzotriazol-1-ol hydrate (46.6 mg, 304 µmol) and rac-5-(aminomethyl)-5-(pyridazin-3-yl)imidazolidine-2,4-dione hydrochloride (57.0 mg, 234 µmol). The mixture was stirred at room temperature for 2 h. The product was purified by preparative HPLC (Instrument: Waters Prep LC/MS System, Column: Phenomenex Kinetex C18 5 µm 100×30 mm; eluent A: water, eluent B: acetonitrile, eluent C: 2% formic acid in water, eluent D: acetonitrile/water (80 Vol. %/20 Vol. %); flow: 80 ml/min, room temperature, UV-detection: 200-400 nm, At-Column Injektion; gradient: eluent A 0 bis 2 min 55 ml, eluent B 0 bis 2 min 15 ml, eluent A 2 bis 10 min from 55 ml to 31 ml and eluent B from 15 ml to 39 ml, 10 to 12 min 0 ml eluent A and 70 ml eluent B. Eluent C and eluent D constant flow 5 ml/min over the whole runtime). After lyophilization, 2.50 mg (87% purity, 2% yield) of the title compound were obtained.

LC-MS (Method 7): $R_t$=1.47 min; MS (ESIpos): m/z=456 [M+H]$^+$ $^1$H-NMR (400 MHz, DMSO-d6) δ [ppm]: −0.150 (1.56), −0.008 (14.63), 0.008 (16.00), 0.146 (1.95), 0.960 (1.76), 2.327 (2.73), 2.366 (2.73), 2.524 (9.76), 2.669 (2.73), 2.710 (2.54), 2.821 (1.17), 2.934 (2.15), 3.776 (3.71), 3.790 (2.73), 3.941 (0.98), 4.000 (1.37), 4.017 (1.37), 4.035 (1.95), 4.051 (1.95), 4.122 (1.76), 4.137 (2.15), 4.157 (1.56), 4.171 (1.17), 7.412 (1.95), 7.428 (6.24), 7.448 (5.27), 7.472 (4.49), 7.494 (3.12), 7.528 (5.27), 7.538 (3.71), 7.549 (7.22), 7.572 (2.93), 7.634 (2.54), 7.654 (4.29), 7.705 (3.51), 7.739 (8.39), 7.751 (3.71), 7.761 (8.59), 7.773 (5.07), 7.817 (4.68), 7.821 (4.88), 7.838 (2.54), 7.842 (2.34), 8.490 (4.88), 8.720 (2.73), 9.245 (3.51), 9.249 (3.71), 9.257 (3.51), 9.261 (3.12), 11.105 (2.34).

Example 43

Rac-N-{[4-(4-Methyl-1,3-Oxazol-5-Yl)-2,5-Dioxo-imidazolidin-4-Yl]Methyl}-4'-(Trifluoromethyl)[Biphenyl]-2-Carboxamide

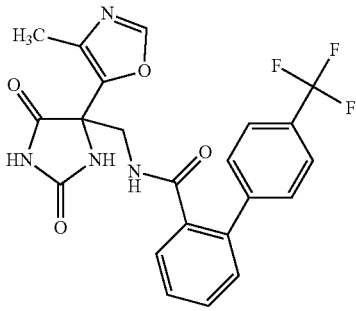 [SMILES: Cc1ncoc1C1(CNC(=O)c2ccccc2-c2ccc(C(F)(F)F)cc2)NC(=O)NC1=O]

4'-(trifluoromethyl)[1,1'-biphenyl]-2-carboxylic acid (6.99 mg, 26.3 µmol) dissolved in 0.5 ml of DMF was treated with N-ethyl-N-isopropylpropan-2-amine (14 µl, 79 µmol), 3-{[(ethylimino)methylene]amino}-N,N-dimethyl-propan-1-amine hydrochloride (6.55 mg, 34.2 µmol), 1H-benzotriazol-1-ol hydrate (5.23 mg, 34.2 µmol) and rac-5-(aminomethyl)-5-(4-methyl-1,3-oxazol-5-yl)imidazo-lidine-2,4-dione hydrochloride (8.00 mg, 81% purity, 26.3 µmol). The mixture was stirred at room temperature for 3 h. The product was purified by preparative HPLC (Instrument: Waters Prep LC/MS System, Column: Phenomenex Kinetex C18 5 µm 100×30 mm; eluent A: water, eluent B: acetonitrile, eluent C: 2% formic acid in water, eluent D: acetonitrile/water (80 Vol. %/20 Vol. %); flow: 80 ml/min, room temperature, UV-detection: 200-400 nm, At-Column Injektion; gradient: eluent A 0 bis 2 min 63 ml, eluent B 0 bis 2 min 7 ml, eluent A 2 bis 10 min from 63 ml to 39 ml and eluent B from 7 ml to 31 ml, 10 to 12 min 0 ml eluent A and 70 ml eluent B. Eluent C and eluent D constant flow 5 ml/min over the whole runtime). After lyophilization, 5.00 mg (100% purity, 42% yield) of the title compound were obtained.

LC-MS (Method 8): $R_t$=0.82 min; MS (ESIpos): m/z=459 [M+H]$^+$ $^1$H-NMR (400 MHz, DMSO-d6) δ [ppm]: −0.008 (0.46), 0.008 (0.56), 2.121 (16.00), 2.328 (0.64), 2.366 (0.51), 2.670 (0.59), 2.710 (0.48), 3.893 (3.05), 3.909 (3.05), 7.415 (1.17), 7.435 (3.15), 7.458 (2.54), 7.478 (1.98), 7.496 (0.97), 7.529 (2.85), 7.541 (1.81), 7.549 (3.43), 7.559 (1.88), 7.563 (1.68), 7.578 (0.71), 7.581 (0.64), 7.750 (3.51), 7.770 (2.85), 8.292 (4.58), 8.466 (3.15), 8.737 (0.71), 8.752 (1.58), 8.768 (0.74), 11.143 (1.04).

Example 44

Rac-N-{[4-(4-Methyl-1,2-Oxazol-3-Yl)-2,5-Dioxo-imidazolidin-4-Yl]Methyl}-4'-(Trifluoromethyl)[Biphenyl]-2-Carboxamide

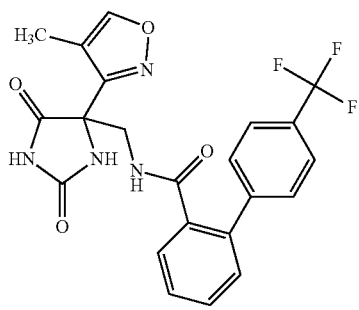 [SMILES: Cc1conc1C1(CNC(=O)c2ccccc2-c2ccc(C(F)(F)F)cc2)NC(=O)NC1=O]

4'-(trifluoromethyl)[1,1'-biphenyl]-2-carboxylicacid (92.8 mg, 349 µmol) dissolved in 3 ml of DMF was treated with N-ethyl-N-isopropylpropan-2-amine (180 µl, 1.0 mmol), 3-{[(ethylimino)methylene]amino}-N,N-dimethylpropan-1-amine hydrochloride (86.9 mg, 453 µmol), 1H-benzotriazol-1-ol hydrate (69.4 mg, 453 µmol) and rac-5-(aminomethyl)-5-(4-methyl-1,2-oxazol-3-yl)imidazolidine-2,4-dione hydrochloride (86.0 mg, 349 µmol). The mixture was stirred at room temperature for 3 h. The product was purified by preparative HPLC (Instrument: Waters Prep LC/MS System, Column: Phenomenex Kinetex C18 5 µm 100×30 mm; eluent A: water, eluent B: acetonitrile, eluent C: 2% formic acid in water, eluent D: acetonitrile/water (80 Vol. %/20 Vol. %); flow: 80 ml/min, room temperature, UV-detection: 200-400 nm, At-Column Injektion; gradient: eluent A 0 bis 2 min 55 ml, eluent B 0 bis 2 min 15 ml, eluent A 2 bis 10 min from 55 ml to 31 ml and eluent B from 15 ml to 39 ml, 10 to 12 min 0 ml eluent A and 70 ml eluent B. Eluent C and eluent D constant flow 5 ml/min over the whole runtime). After lyophilization, 80.0 mg (100% purity, 50% yield) of the title compound were obtained.

LC-MS (Method 7): $R_t$=1.66 min; MS (ESIpos): m/z=459 $[M+H]^+$ $^1$H-NMR (400 MHz, DMSO-d6) δ [ppm]: −0.008 (0.55), 0.008 (0.66), 1.927 (16.00), 2.072 (1.37), 3.994 (4.56), 4.010 (4.58), 7.423 (1.39), 7.427 (1.59), 7.442 (5.88), 7.462 (4.78), 7.480 (2.73), 7.499 (1.23), 7.502 (1.07), 7.543 (2.18), 7.551 (4.42), 7.561 (3.00), 7.565 (3.51), 7.572 (4.99), 7.583 (1.07), 7.759 (5.07), 7.780 (4.14), 8.454 (4.98), 8.745 (4.22), 8.747 (4.89), 8.765 (2.43), 8.780 (1.09).

Example 45

Rac-N-{[4-(1-Cyclopropyl-1H-Pyrazol-5-Yl)-2,5-Dioxoimidazolidin-4-Yl]Methyl}-4'-(Trifluoromethyl)[Biphenyl]-2-Carboxamide

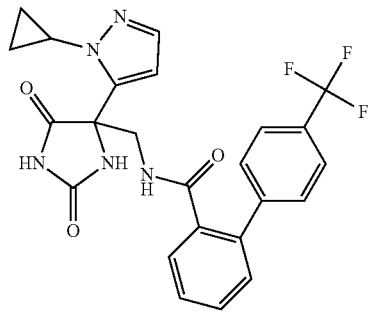

4'-(trifluoromethyl)[1,1'-biphenyl]-2-carboxylic acid (98.0 mg, 368 µmol) dissolved in 1.5 ml of DMF was treated with N-ethyl-N-isopropylpropan-2-amine (190 µl, 1.1 mmol), 3-{[(ethylimino)methylene]amino}-N,N-dimethylpropan-1-amine hydrochloride (91.7 mg, 478 µmol), 1H-benzotriazol-1-ol hydrate (73.3 mg, 478 µmol) and rac-5-(aminomethyl)-5-(1-cyclopropyl-1H-pyrazol-5-yl)imidazolidine-2,4-dione hydrochloride (100 mg, 368 µmol). The mixture was stirred at room temperature for 2 h. The product was purified by preparative HPLC (Column: Chromatorex C18 10 µm 250×30 mm; eluent A=water with 0.1% formic acid, B=acetonitrile; gradient: 0.0 min 30% B; 4.5 min 50% B; 11.5 min 70% B; 12 min 100% B; 14.75 min 30% B; flow: 50 ml/min). After lyophilisation 69.0 mg (100% purity, 39% yield) of the title compound were obtained.

LC-MS (Method 7): $R_t$=1.58 min; MS (ESIpos): m/z=484 $[M+H]^+$ $^1$H-NMR (400 MHz, DMSO-d6) δ [ppm]: −0.008 (2.14), 0.008 (2.72), 0.815 (0.91), 0.828 (2.07), 0.837 (2.15), 0.843 (2.92), 0.846 (3.04), 0.855 (3.63), 0.860 (2.47), 0.863 (2.41), 0.871 (3.98), 0.881 (2.39), 0.890 (2.83), 0.896 (2.67), 0.902 (1.91), 0.908 (3.43), 0.913 (4.69), 0.925 (3.72), 0.931 (2.90), 0.945 (3.12), 0.957 (2.83), 0.964 (3.79), 0.976 (4.26), 0.981 (3.43), 0.987 (2.20), 0.994 (2.26), 0.999 (2.47), 1.005 (1.29), 1.018 (1.07), 1.059 (1.27), 1.076 (2.22), 1.133 (0.54), 1.256 (1.61), 1.268 (2.67), 1.273 (2.20), 1.277 (2.43), 1.282 (3.60), 1.294 (3.55), 1.299 (2.15), 1.304 (1.97), 1.309 (2.00), 1.321 (1.21), 1.757 (0.49), 2.370 (1.73), 2.572 (1.69), 2.710 (0.49), 2.890 (0.43), 3.449 (1.54), 3.458 (3.04), 3.467 (4.13), 3.476 (5.63), 3.485 (4.22), 3.494 (3.02), 3.503 (1.46), 3.890 (2.22), 3.905 (2.52), 3.924 (5.71), 3.939 (5.24), 3.958 (5.29), 3.974 (5.49), 3.991 (2.33), 4.008 (2.15), 4.376 (0.97), 4.390 (0.96), 5.364 (1.03), 5.387 (1.03), 6.517 (14.19), 6.522 (14.53), 7.061 (0.44), 7.188 (0.47), 7.317 (0.52), 7.342 (14.22), 7.347 (14.32), 7.438 (7.21), 7.448 (2.94), 7.458 (9.93), 7.466 (11.09), 7.471 (16.00), 7.488 (8.42), 7.507 (3.20), 7.509 (3.01), 7.529 (0.50), 7.547 (6.34), 7.558 (13.35), 7.565 (8.49), 7.571 (9.55), 7.578 (15.21), 7.588 (3.48), 7.753 (15.00), 7.773 (12.33), 8.350 (11.33), 8.353 (11.33), 8.792 (3.29), 8.807 (6.74), 8.823 (3.26), 11.205 (9.93).

Example 46

Ent-N-{[4-(1-Cyclopropyl-1H-Pyrazol-5-Yl)-2,5-Dioxoimidazolidin-4-Yl]Methyl}-4'-(Trifluoromethyl)[Biphenyl]-2-Carboxamide

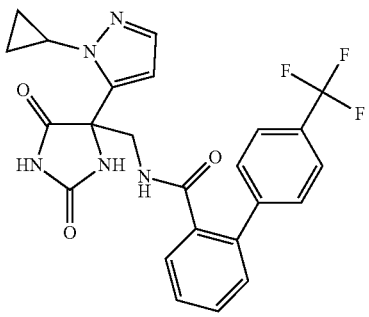 [SMILES: O=C1NC(=O)C(CNC(=O)c2ccccc2-c2ccc(C(F)(F)F)cc2)(c2ccnn2C2CC2)N1]

Enantiomeric separation of rac-N-{[4-(1-cyclopropyl-1H-pyrazol-5-yl)-2,5-dioxoimidazolidin-4 yl]methyl}-4'-(trifluoromethyl)[biphenyl]-2-carboxamide (65.0 mg, 134 µmol) using the following method:

Diacel Chiralcel OX-H 5 µm 250×20 mm
Eluent A: 70% n-heptane, eluent B: 30% ethanol
Flow: 25 ml/min
UV-detection: 220 nm
Temperature: 40° C.

Further purification was necessary and done by preparative HPLC (Column: Chromatorex C18 10 µm 250×30 mm; eluent A=water with 0.1% formic acid, B=acetonitrile; gradient: 0.0 min 30% B; 4.5 min 50% B; 11.5 min 70% B; 12 min 100% B; 14.75 min 30% B; flow: 50 ml/min). After lyophilisation 21.0 mg (100% purity, 32% yield) of the title compound were obtained.

Chiral-HPLC: (Column: Diacel Chiralpak OX-3 3 µm 50*4.6 mm, eluent A: 70% i-hexane, eluent B: 30% ethanol, flow: 1 ml/min, UV-detection: 220 nm): $R_t$=1.600 min; 99.05% ee LC-MS (Method 7): $R_t$=1.59 min; MS (ESIpos): m/z=484 [M+H]$^+$ $^1$H-NMR (600 MHz, DMSO-d6) δ [ppm]: 0.833 (1.19), 0.841 (2.29), 0.847 (2.39), 0.851 (3.15), 0.859 (3.87), 0.865 (2.29), 0.869 (2.53), 0.877 (1.91), 0.885 (1.43), 0.897 (2.91), 0.901 (2.48), 0.905 (2.39), 0.909 (3.30), 0.913 (4.54), 0.921 (3.68), 0.925 (2.58), 0.933 (1.81), 0.954 (2.01), 0.962 (2.72), 0.966 (3.73), 0.970 (1.81), 0.974 (4.30), 0.978 (3.53), 0.982 (2.63), 0.987 (2.10), 0.991 (2.58), 1.003 (1.05), 1.266 (1.72), 1.274 (2.48), 1.278 (2.10), 1.284 (3.49), 1.292 (3.53), 1.298 (1.96), 1.302 (2.01), 1.310 (1.34), 2.352 (1.10), 2.383 (0.57), 2.422 (1.15), 2.570 (1.29), 2.611 (0.57), 2.651 (1.05), 3.261 (0.81), 3.272 (2.24), 3.333 (3.15), 3.366 (0.43), 3.459 (1.72), 3.466 (3.20), 3.472 (4.44), 3.478 (5.92), 3.484 (4.39), 3.490 (3.15), 3.496 (1.53), 3.900 (3.10), 3.909 (3.49), 3.922 (6.16), 3.932 (5.59), 3.961 (5.54), 3.972 (5.87), 3.983 (3.15), 3.994 (2.96), 6.510 (14.85), 6.513 (14.95), 7.339 (16.00), 7.342 (16.00), 7.439 (7.74), 7.452 (12.32), 7.465 (10.03), 7.467 (10.13), 7.473 (6.45), 7.475 (6.21), 7.485 (8.21), 7.498 (3.49), 7.551 (5.68), 7.554 (5.87), 7.561 (14.19), 7.563 (12.90), 7.566 (8.64), 7.574 (15.62), 7.751 (15.28), 7.765 (13.37), 8.313 (11.22), 8.315 (11.22), 8.756 (3.58), 8.766 (6.97), 8.777 (3.49), 11.182 (9.79).

Example 47

Ent-N-{[4-(2,4-Dimethyl-1,3-Thiazol-5-Yl)-2,5-Dioxoimidazolidin-4-Yl]Methyl}-4'-(Trifluoromethyl)[Biphenyl]-2-Carboxamide

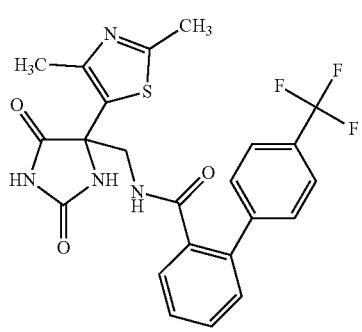 [SMILES: Cc1nc(C)c(C2(CNC(=O)c3ccccc3-c3ccc(C(F)(F)F)cc3)NC(=O)NC2=O)s1]

Enantiomeric separation of rac-N-{[4-(2,4-dimethyl-1,3-thiazol-5-yl)-2,5-dioxoimidazolidin-4 yl]methyl}-4'-(trifluoromethyl)[biphenyl]-2-carboxamide (60.0 mg, 123 µmol) using the following method:

Diacel Chiralpak IC 5 µm 250×20 mm
Eluent A: 50% n-heptane, eluent B: 50% iso-propanol
Flow: 30 ml/min
UV-detection: 220 nm
Temperature: 40° C.

Further purification was necessary and done by preparative HPLC (Column: Chromatorex C18 10 µm 250×30 mm; eluent A=water with 0.1% formic acid, B=acetonitrile; gradient: 0.0 min 30% B; 4.5 min 50% B; 11.5 min 70% B; 12 min 100% B; 14.75 min 30% B; flow: 50 ml/min). After lyophilisation 21.0 mg (100% purity, 35% yield) of the title compound were obtained.

Chiral-HPLC: (Column: Diacel Chiralpak IC-3 3 µm 50*4.6 mm, eluent A: 50% n-heptane, eluent B: 50% iso-propanol, flow: 1 ml/min, UV-detection: 220 nm): $R_t$=1.078 min; 96.21% ee LC-MS (Method 7): $R_t$=1.60 min; MS (ESIpos): m/z=489 [M+H]$^+$ $^1$H-NMR (600 MHz, DMSO-d6) δ [ppm]: 2.352 (16.00), 3.333 (0.47), 3.835 (1.65), 3.844 (2.49), 3.854 (1.60), 7.413 (1.25), 7.415 (1.31), 7.426 (1.90), 7.428 (1.85), 7.436 (1.57), 7.449 (1.86), 7.471 (0.97), 7.473 (0.94), 7.483 (1.82), 7.485 (1.66), 7.498 (3.55), 7.511 (2.96), 7.549 (1.17), 7.551 (1.12), 7.561 (1.66), 7.563 (1.58), 7.574 (0.68), 7.576 (0.65), 7.743 (3.13), 7.757 (2.79), 8.453 (2.97), 8.696 (0.75), 8.707 (1.45), 8.717 (0.72), 11.135 (0.46).

Example 48

Rac-N-[(4-Cyclopentyl-2,5-Dioxoimidazolidin-4-Yl)Methyl]-4'-(Trifluoromethyl)[Biphenyl]-2-Carboxamide

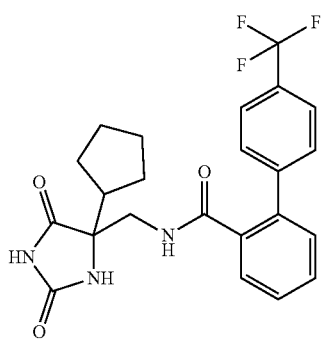 [SMILES: O=C1NC(=O)C(CNC(=O)c2ccccc2-c2ccc(C(F)(F)F)cc2)(C2CCCC2)N1]

4'-(trifluoromethyl)[1,1'-biphenyl]-2-carboxylic acid (57.0 mg, 214 μmol) dissolved in 2 ml DMF was treated with N,N-diisopropylethylamine (110 μl, 640 μmol), 1-ethyl-3-(3-dimethylaminopropyl)carbodiimide hydrochloride (53.3 mg, 278 μmol) and 1-hydroxybenzotriazole hydrate (42.6 mg, 278 μmol) and stirred for 5 min at room temperature before rac-5-(aminomethyl)-5-cyclopentylimidazolidine-2,4-dione hydrochloride (50.0 mg, 214 μmol) was added. The mixture was stirred at room temperature for 2 h. Purification was done by preparative HPLC (Instrument: Waters Prep LC/MS System; column: Phenomenex Kinetex C18 5 μm 100×30 mm; eluent A: water, eluent B: acetonitrile, eluent C: 2% formic acid in water, eluent D: acetonitrile/water (80 Vol. %/20 Vol. %); flow: 80 ml/min; room temperature; UV 200-400 nm; At-Column Injektion; Gradient: eluent A 0 to 2 min 47 ml, eluent B 0 to 2 min 23 ml, eluent A 2 to 10 min from 47 ml to 23 ml and eluent B from 23 ml to 47 ml, 10 to 12 min 0 ml eluent A and 70 ml eluent B. Eluent C and eluent D constant flow each 5 ml/min over the whole time). Product containing samples were united, the solvents were evaporated and the residue was lyophylized. 62.0 mg (100% purity, 65% yield) and 8.00 mg (95% purity, 8% yield) of the title compound were obtained.

LC-MS (Method 7): $R_t$=1.78 min; MS (ESIpos): m/z=446 [M+H]$^+$ $^1$H-NMR (400 MHz, DMSO-d6) δ [ppm]: −0.008 (0.87), 0.008 (0.90), 1.187 (1.27), 1.217 (2.48), 1.241 (1.44), 1.312 (2.17), 1.328 (1.82), 1.355 (1.04), 1.456 (7.68), 1.484 (4.53), 1.531 (4.62), 1.544 (3.90), 1.679 (2.43), 1.698 (2.02), 2.072 (1.27), 2.093 (2.14), 2.112 (2.97), 2.132 (1.96), 2.156 (0.61), 2.327 (0.78), 2.332 (0.55), 2.366 (0.61), 2.523 (3.06), 2.665 (0.55), 2.670 (0.78), 2.710 (0.61), 3.376 (2.60), 3.392 (2.92), 3.411 (5.69), 3.426 (5.23), 3.458 (5.17), 3.474 (5.46), 3.492 (2.66), 3.508 (2.51), 7.410 (4.39), 7.413 (5.52), 7.421 (7.65), 7.428 (10.57), 7.432 (10.95), 7.439 (10.86), 7.447 (5.92), 7.449 (5.78), 7.465 (8.69), 7.468 (7.16), 7.483 (3.96), 7.487 (3.32), 7.524 (6.06), 7.528 (5.98), 7.542 (7.91), 7.546 (8.17), 7.555 (13.72), 7.565 (4.71), 7.575 (15.34), 7.750 (16.00), 7.770 (14.38), 7.779 (12.27), 8.500 (3.23), 8.516 (6.82), 8.531 (3.21), 10.667 (9.99).

Example 49

Rac-N-{[4-(3-Methyl-1,2-Thiazol-4-Yl)-2,5-Dioxoimidazolidin-4-Yl]Methyl}-2-[6-(Trifluoromethyl)Pyridin-3-Yl]Benzamide

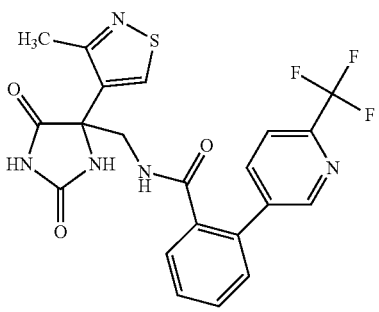 [SMILES: Cc1nscc1C1(CNC(=O)c2ccccc2-c2ccc(C(F)(F)F)nc2)NC(=O)NC1=O]

2-[6-(trifluoromethyl)pyridin-3-yl]benzoic acid (102 mg, 381 μmol) dissolved in 2 ml DMF was treated with N,N-diisopropylethylamine (200 μl, 1.1 mmol), 1-ethyl-3-(3-dimethylaminopropyl)carbodiimide hydrochloride (94.9 mg, 495 μmol) and 1-hydroxybenzotriazole hydrate (75.8 mg, 495 μmol) and stirred for 5 min at room temperature before rac-5-(aminomethyl)-5-(3-methyl-1,2-thiazol-4-yl)imidazolidine-2,4-dione hydrochloride (100 mg, 381 μmol) was added. The mixture was stirred at room temperature over night. Purification was done by preparative HPLC (Instrument: Waters Prep LC/MS System; column: Phenomenex Kinetex C18 5 μm 100×30 mm; eluent A: water, eluent B: acetonitrile, eluent C: 2% formic acid in water, eluent D: acetonitrile/water (80 Vol. %/20 Vol. %); flow: 80 ml/min; room temperature; UV 200-400 nm; At-Column Injektion; Gradient: eluent A0 to 2 min 63 ml, eluent B 0 to 2 min 7 ml, eluent A 2 to 10 min from 63 ml to 39 ml and eluent B from 7 ml to 31 ml, 10 to 12 min 0 ml eluent A and 70 ml eluent B. Eluent C and eluent D constant flow each 5 ml/min over the whole time). Product containing samples were united, the solvents were evaporated and the residue was lyophylized. 73.0 mg (100% purity, 40% yield) of the title compound were obtained.

LC-MS (Method 7): $R_t$=1.37 min; MS (ESIpos): m/z=476 [M+H]$^+$ $^1$H-NMR (400 MHz, DMSO-d6) δ [ppm]: 2.406 (16.00), 3.891 (0.50), 3.906 (0.59), 3.925 (1.57), 3.940 (1.51), 3.950 (1.53), 3.966 (1.51), 3.984 (0.55), 4.000 (0.51), 7.483 (1.24), 7.486 (1.34), 7.502 (2.36), 7.505 (2.28), 7.521 (1.64), 7.539 (3.55), 7.554 (2.30), 7.558 (1.70), 7.573 (1.19), 7.576 (0.90), 7.599 (1.61), 7.603 (1.57), 7.618 (1.79), 7.622 (1.72), 7.637 (0.65), 7.640 (0.60), 7.905 (1.32), 7.925 (3.64), 7.945 (2.15), 7.949 (2.06), 7.965 (0.76), 7.970 (0.78), 8.286 (2.87), 8.732 (2.43), 8.736 (2.37), 8.827 (0.83), 8.843 (1.72), 8.858 (0.83), 9.117 (5.62), 11.175 (2.50).

Example 50

Rac-N-[(2,5-Dioxo-4-Phenylimidazolidin-4-Yl)Methyl]-2-[6-(Trifluoromethyl)Pyridin-3-Yl]Benzamide

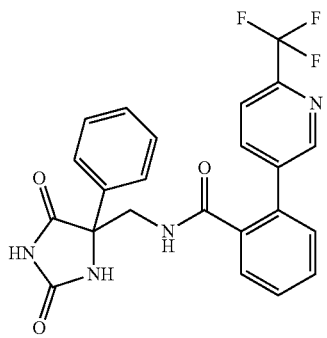 [SMILES: O=C1NC(=O)C(CNC(=O)c2ccccc2-c2ccc(C(F)(F)F)nc2)(c2ccccc2)N1]

2-[6-(trifluoromethyl)pyridin-3-yl]benzoic acid (55.3 mg, 207 µmol) dissolved in 2 ml DMF was treated with N,N-diisopropylethylamine (100 µl, 580 µmol), 1-ethyl-3-(3-dimethylaminopropyl)carbodiimide hydrochloride (51.6 mg, 269 µmol) and 1-hydroxybenzotriazole hydrate (41.2 mg, 269 µmol) and stirred for 5 min at room temperature before rac-5-(aminomethyl)-5-phenylimidazolidine-2,4-dione hydrochloride (50.0 mg, 207 µmol) was added. The mixture was stirred at room temperature for 2 h. Purification was done by preparative HPLC (Instrument: Waters Prep LC/MS System; column: Phenomenex Kinetex C18 5 µm 100×30 mm; eluent A: water, eluent B: acetonitrile, eluent C: 2% formic acid in water, eluent D: acetonitrile/water (80 Vol. %/20 Vol. %); flow: 80 ml/min; room temperature; UV 200-400 nm; At-Column Injektion; Gradient: eluent A 0 to 2 min 55 ml, eluent B 0 to 2 min 15 ml, eluent A 2 to 10 min from 55 ml to 31 ml and eluent B from 15 ml to 39 ml, 10 to 12 min 0 ml eluent A and 70 ml eluent B. Eluent C and eluent D constant flow each 5 ml/min over the whole time). Product containing samples were united, the solvents were evaporated and the residue was lyophylized. 71.0 mg (99% purity, 75% yield) of the title compound were obtained.

LC-MS (Method 7): $R_t$=1.55 min; MS (ESIpos): m/z=455 [M+H]$^+$ $^1$H-NMR (600 MHz, DMSO-d6) δ [ppm]: 0.005 (0.76), 2.383 (0.61), 2.422 (0.76), 2.463 (0.58), 2.466 (0.47), 2.514 (1.34), 2.517 (1.30), 2.520 (1.16), 2.570 (0.72), 2.611 (0.47), 2.651 (0.65), 3.253 (0.94), 3.258 (0.72), 3.261 (2.17), 3.326 (1.55), 3.334 (0.47), 3.729 (3.25), 3.741 (3.47), 3.752 (6.07), 3.764 (5.74), 3.795 (5.71), 3.804 (6.32), 3.817 (3.47), 3.827 (3.07), 7.340 (2.60), 7.349 (1.91), 7.352 (8.49), 7.356 (2.56), 7.365 (6.43), 7.392 (10.22), 7.405 (16.00), 7.414 (2.85), 7.417 (7.26), 7.424 (6.47), 7.426 (6.57), 7.436 (8.13), 7.438 (7.87), 7.507 (6.83), 7.519 (13.18), 7.532 (8.78), 7.534 (7.44), 7.545 (5.74), 7.547 (5.74), 7.551 (15.10), 7.563 (14.05), 7.566 (9.90), 7.586 (5.71), 7.588 (5.74), 7.598 (7.77), 7.601 (7.73), 7.611 (3.14), 7.613 (3.07), 7.885 (3.25), 7.897 (15.31), 7.898 (15.42), 7.903 (10.62), 7.906 (9.61), 7.917 (1.91), 7.920 (2.17), 8.452 (14.59), 8.701 (12.89), 8.713 (3.47), 10.872 (7.15).

Example 51

Diamix-N-[(4-Sec-Butyl-2,5-Dioxoimidazolidin-4-Yl)Methyl]-2-[6-(Trifluoromethyl)Pyridin-3-Yl]Benzamide

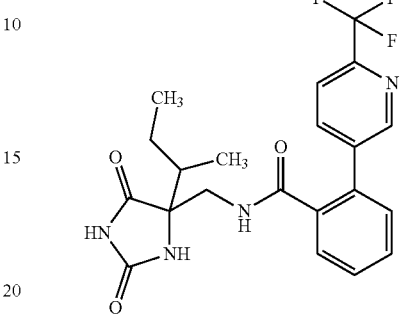

2-[6-(trifluoromethyl)pyridin-3-yl]benzoic acid (60.3 mg, 226 µmol) dissolved in 2 ml DMF was treated with N,N-diisopropylethylamine (110 µl, 630 µmol), 1-ethyl-3-(3-dimethylaminopropyl)carbodiimide hydrochloride (56.2 mg, 293 µmol) and 1-hydroxybenzotriazole hydrate (44.9 mg, 293 µmol) and stirred for 5 min at room temperature before diamix-5-(aminomethyl)-5-sec-butylimidazolidine-2,4-dione hydrochloride (50.0 mg, 226 µmol) was added. The mixture was stirred at room temperature for 2 h. Purification was done by preparative HPLC (Instrument: Waters Prep LC/MS System; column: Phenomenex Kinetex C18 5 µm 100×30 mm; eluent A: water, eluent B: acetonitrile, eluent C: 2% formic acid in water, eluent D: acetonitrile/water (80 Vol. %/20 Vol. %); flow: 80 ml/min; room temperature; UV 200-400 nm; At-Column Injektion; Gradient: eluent A0 to 2 min 63 ml, eluent B 0 to 2 min 7 ml, eluent A 2 to 10 min from 63 ml to 39 ml and eluent B from 7 ml to 31 ml, 10 to 12 min 0 ml eluent A and 70 ml eluent B. Eluent C and eluent D constant flow each 5 ml/min over the whole time). Product containing samples were united, the solvents were evaporated and the residue was lyophylized. 78.0 mg (100% purity, 80% yield) of the title compound were obtained.

LC-MS (Method 7): $R_t$=1.52 min; MS (ESIpos): m/z=435 [M+H]$^+$ $^1$H-NMR (600 MHz, DMSO-d6) δ [ppm]: 0.800 (12.82), 0.812 (16.00), 0.825 (14.31), 0.829 (7.30), 0.838 (8.74), 0.841 (14.62), 0.853 (7.22), 0.882 (11.63), 0.893 (11.98), 0.950 (0.77), 0.962 (0.79), 0.968 (0.98), 0.972 (1.09), 0.980 (0.98), 0.984 (0.96), 0.990 (1.00), 1.002 (0.69), 1.035 (0.71), 1.047 (0.79), 1.053 (0.86), 1.057 (0.98), 1.065 (0.92), 1.069 (0.82), 1.074 (0.96), 1.087 (0.77), 1.272 (0.79), 1.277 (0.86), 1.285 (0.94), 1.290 (1.00), 1.294 (0.88), 1.299 (0.84), 1.307 (0.67), 1.312 (0.63), 1.537 (0.79), 1.542 (0.94), 1.554 (1.13), 1.559 (0.92), 1.564 (1.11), 1.572 (1.07), 1.576 (1.05), 1.581 (1.28), 1.586 (1.17), 1.592 (1.36), 1.599 (1.42), 1.604 (1.11), 1.610 (1.05), 1.615 (0.82), 1.622 (0.54), 1.634 (0.86), 1.639 (1.05), 1.645 (1.07), 1.651 (1.48), 1.656 (1.00), 1.663 (0.96), 1.668 (0.77), 2.422 (0.42), 2.517 (0.59), 2.520 (0.54), 2.570 (0.63), 3.262 (0.50), 3.283 (0.90), 3.327 (1.30), 3.370 (1.72), 3.380 (1.84), 3.392 (2.45), 3.397 (2.24), 3.403 (2.38), 3.407 (2.26), 3.420 (2.59), 3.430 (2.34), 3.528 (2.07), 3.538 (2.38), 3.543 (2.57), 3.551 (2.18), 3.554 (2.78), 3.561 (1.88), 3.566 (1.99), 3.577 (1.76), 7.472 (2.45), 7.474 (2.57), 7.481 (3.01), 7.484 (5.04), 7.486 (4.08), 7.493 (4.58), 7.495 (4.45), 7.505

(6.13), 7.517 (8.39), 7.522 (3.05), 7.524 (3.07), 7.526 (2.66), 7.532 (4.31), 7.536 (5.31), 7.538 (3.91), 7.545 (2.28), 7.548 (2.66), 7.551 (1.92), 7.584 (5.04), 7.586 (3.49), 7.596 (6.71), 7.609 (2.55), 7.661 (4.94), 7.768 (4.39), 7.923 (6.30), 7.937 (10.21), 7.977 (5.61), 7.991 (3.45), 8.487 (1.69), 8.497 (4.06), 8.505 (3.97), 8.515 (1.53), 8.733 (8.97), 8.736 (8.93), 10.654 (4.41), 10.664 (4.02).

Example 52

Rac-N-{[4-(1,4-Dimethyl-1H-Pyrazol-5-Yl)-2,5-Dioxoimidazolidin-4-Yl]Methyl}-2-[6-(Trifluoromethyl)Pyridin-3-Yl]Benzamide

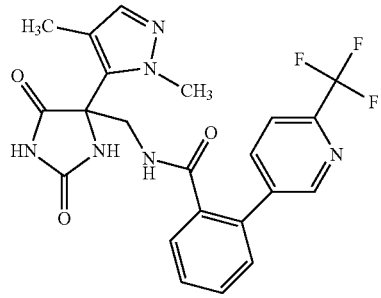 [SMILES: Cc1cnn(C)c1C1(CNC(=O)c2ccccc2-c2ccc(C(F)(F)F)nc2)NC(=O)NC1=O]

2-[6-(trifluoromethyl)pyridin-3-yl]benzoic acid (97.3 mg, 364 µmol) dissolved in 1.5 ml DMF was treated with N,N-diisopropylethylamine (190 µl, 1.1 mmol), 1-ethyl-3-(3-dimethylaminopropyl)carbodiimide hydrochloride (90.8 mg, 474 µmol) and 1-hydroxybenzotriazole hydrate (72.5 mg, 474 µmol) and stirred for 5 min at room temperature before rac-5-(aminomethyl)-5-(1,4-dimethyl-1H-pyrazol-5-yl)imidazolidine-2,4-dione hydrochloride (50.0 mg, 226 µmol) was added. The mixture was stirred at room temperature overnight. Purification was done by preparative HPLC (Instrument: Waters Prep LC/MS System; column: Phenomenex Kinetex C18 5 µm 100×30 mm; eluent A: water, eluent B: acetonitrile, eluent C: 2% formic acid in water, eluent D: acetonitrile/water (80 Vol. %/20 Vol. %); flow: 80 ml/min; room temperature; UV 200-400 nm; At-Column Injektion; Gradient: eluent A0 to 2 min 63 ml, eluent B 0 to 2 min 7 ml, eluent A 2 to 10 min from 63 ml to 39 ml and eluent B from 7 ml to 31 ml, 10 to 12 min 0 ml eluent A and 70 ml eluent B. Eluent C and eluent D constant flow each 5 ml/min over the whole time). Product containing samples were united, the solvents were evaporated and the residue was lyophylized. 17.0 mg (100% purity, 10% yield) of the title compound were obtained.

LC-MS (Method 7): $R_t$=1.34 min; MS (ESIpos): m/z=473 [M+H]$^+$ $^1$H-NMR (400 MHz, DMSO-d6) δ [ppm]: −0.008 (0.51), 0.008 (0.54), 2.102 (13.39), 2.523 (1.32), 3.836 (16.00), 3.966 (0.58), 3.981 (0.65), 4.000 (1.27), 4.014 (1.16), 4.043 (1.16), 4.060 (1.21), 4.077 (0.59), 4.094 (0.55), 7.198 (4.44), 7.482 (1.10), 7.485 (1.21), 7.501 (2.02), 7.503 (1.97), 7.519 (1.31), 7.522 (1.46), 7.538 (2.61), 7.540 (3.18), 7.556 (2.08), 7.559 (1.55), 7.574 (1.09), 7.578 (0.83), 7.603 (1.49), 7.606 (1.44), 7.621 (1.66), 7.625 (1.61), 7.640 (0.61), 7.643 (0.55), 7.891 (0.50), 7.896 (0.47), 7.911 (2.08), 7.916 (2.33), 7.923 (3.44), 7.925 (3.63), 7.943 (0.76), 7.945 (0.73), 8.373 (2.94), 8.738 (2.19), 8.797 (0.73), 8.812 (1.46), 8.828 (0.70), 11.201 (1.86).

Example 53

Rac-N-{[4-(4-Methyl-1,2,5-Thiadiazol-3-Yl)-2,5-Dioxoimidazolidin-4-Yl]Methyl}-2-[6-(Trifluoromethyl)Pyridin-3-Yl]Benzamide

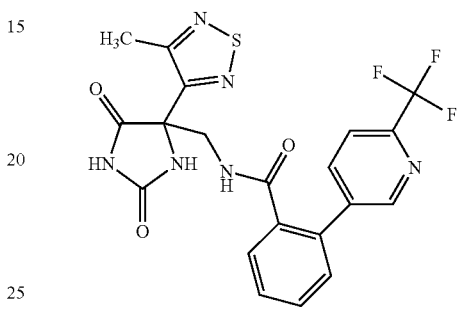

2-[6-(trifluoromethyl)pyridin-3-yl]benzoic acid (101 mg, 379 µmol) dissolved in 1.5 ml DMF was treated with N,N-diisopropylethylamine (200 µl, 1.1 mmol), 1-ethyl-3-(3-dimethylaminopropyl)carbodiimide hydrochloride (200 µl, 1.1 mmol) and 1-hydroxybenzotriazole hydrate (75.5 mg, 493 µmol) and stirred for 5 min at room temperature before rac-5-(aminomethyl)-5-(4-methyl-1,2,5-thiadiazol-3-yl)imidazolidine-2,4-dione hydrochloride (100 mg, 379 µmol) was added. The mixture was stirred at room temperature over night. Purification was done by preparative HPLC (Instrument: Waters Prep LC/MS System; column: Phenomenex Kinetex C18 5 µm 100×30 mm; eluent A: water, eluent B: acetonitrile, eluent C: 2% formic acid in water, eluent D: acetonitrile/water (80 Vol. %/20 Vol. %); flow: 80 ml/min; room temperature; UV 200-400 nm; At-Column Injektion; Gradient: eluent A0 to 2 min 63 ml, eluent B 0 to 2 min 7 ml, eluent A 2 to 10 min from 63 ml to 39 ml and eluent B from 7 ml to 31 ml, 10 to 12 min 0 ml eluent A and 70 ml eluent B. Eluent C and eluent D constant flow each 5 ml/min over the whole time). Product containing samples were united, the solvents were evaporated and the residue was lyophylized. 46.0 mg (100% purity, 25% yield) of the title compound were obtained.

LC-MS (Method 7): $R_t$=1.47 min; MS (ESIpos): m/z=477 [M+H]$^+$ $^1$H-NMR (600 MHz, DMSO-d6) δ [ppm]: 0.005 (0.48), 2.069 (3.00), 2.471 (16.00), 2.518 (0.48), 3.274 (2.00), 3.279 (1.24), 3.340 (0.97), 3.344 (0.79), 4.117 (2.14), 4.129 (2.07), 7.499 (1.03), 7.501 (1.07), 7.512 (1.83), 7.531 (1.34), 7.544 (2.59), 7.555 (1.79), 7.557 (1.38), 7.567 (0.86), 7.569 (0.69), 7.605 (1.17), 7.607 (1.10), 7.618 (1.52), 7.620 (1.45), 7.630 (0.59), 7.632 (0.55), 7.925 (1.41), 7.939 (2.55), 7.970 (1.38), 7.973 (1.38), 7.984 (0.76), 7.987 (0.76), 8.382 (2.93), 8.743 (1.93), 8.746 (1.90), 8.825 (0.69), 8.835 (1.41), 8.845 (0.66), 11.369 (1.21).

Example 54

4'-Chloro-N-{[(4R)-4-Cyclopropyl-2,5-Dioxoimidazolidin-4-Yl]Methyl}-2'-Fluoro[Biphenyl]-2-Carboxamide

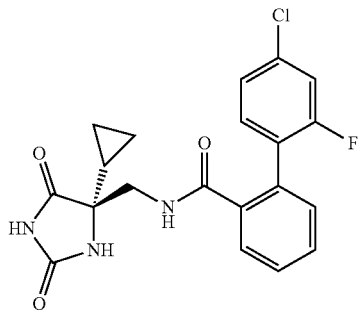 [SMILES: O=C1NC(=O)[C@](CNC(=O)c2ccccc2-c2ccc(Cl)cc2F)(C2CC2)N1]

4'-chloro-2'-fluoro[1,1'-biphenyl]-2-carboxylic acid (48.8 mg, 195 μmol) dissolved in 2 ml of DMF was treated with N,N-diisopropylethylamine (95 μl, 540 μmol), 1-ethyl-3-(3-dimethylaminopropyl)carbodiimide hydrochloride (48.5 mg, 253 μmol) and 1-hydroxybenzotriazole hydrate (38.7 mg, 253 μmol) and stirred for 5 min at room temperature before (5R)-5-(aminomethyl)-5-cyclopropylimidazolidine-2,4-dione hydrochloride (40.0 mg, 195 μmol) was added. The mixture was stirred at room temperature overnight. Purification was done by preparative HPLC (Instrument: Waters Prep LC/MS System; column: Phenomenex Kinetex C18 5 μm 100×30 mm; eluent A: water, eluent B: acetonitrile, eluent C: 2% formic acid in water, eluent D: acetonitrile/water (80 Vol. %/20 Vol. %); flow: 80 ml/min; room temperature; UV 200-400 nm; At-Column Injektion; Gradient: eluent A 0 to 2 min 63 ml, eluent B 0 to 2 min 7 ml, eluent A 2 to 10 min from 63 ml to 39 ml and eluent B from 7 ml to 31 ml, 10 to 12 min 0 ml eluent A and 70 ml eluent B. Eluent C and eluent D constant flow each 5 ml/min over the whole time). Product containing samples were united, the solvents were evaporated and the residue was lyophylized. 69.0 mg (100% purity, 88% yield) of the title compound were obtained.

LC-MS (Method 7): $R_t$=1.54 min; MS (ESIpos): m/z=402 [M+H]$^+$ $^1$H-NMR (400 MHz, DMSO-d6) δ [ppm]: 0.008 (0.88), 0.087 (0.94), 0.101 (2.35), 0.112 (4.05), 0.125 (4.27), 0.136 (3.08), 0.149 (1.40), 0.277 (0.79), 0.300 (2.59), 0.312 (3.23), 0.323 (3.08), 0.334 (2.38), 0.345 (1.74), 0.363 (1.43), 0.374 (2.50), 0.388 (2.80), 0.396 (3.87), 0.409 (2.99), 0.423 (2.16), 0.437 (3.44), 0.448 (3.99), 0.461 (3.84), 0.473 (2.41), 0.486 (0.82), 1.035 (1.31), 1.048 (2.68), 1.056 (2.90), 1.061 (2.13), 1.069 (4.97), 1.076 (2.07), 1.082 (2.65), 1.090 (2.44), 1.103 (1.07), 2.072 (0.67), 2.327 (0.79), 2.366 (0.58), 2.669 (0.85), 2.674 (0.64), 2.710 (0.58), 3.429 (2.38), 3.444 (2.68), 3.463 (6.28), 3.478 (5.88), 3.497 (5.88), 3.513 (6.10), 3.531 (2.53), 3.548 (2.41), 7.285 (0.91), 7.305 (15.54), 7.310 (12.04), 7.316 (16.00), 7.330 (1.34), 7.337 (1.04), 7.355 (6.77), 7.373 (7.89), 7.405 (6.06), 7.432 (6.13), 7.465 (12.04), 7.488 (5.73), 7.503 (8.53), 7.506 (8.50), 7.516 (12.89), 7.527 (8.26), 7.532 (7.38), 7.545 (6.74), 7.550 (5.52), 7.563 (2.86), 7.568 (2.41), 8.392 (3.20), 8.408 (6.64), 8.423 (3.23), 10.615 (9.30).

Example 55

Rac-N-{[4-(1,3-Dimethyl-1H-Pyrazol-4-Yl)-2,5-Dioxoimidazolidin-4-Yl]Methyl}-2-[6-(Trifluoromethyl)Pyridin-3-Yl]Benzamide

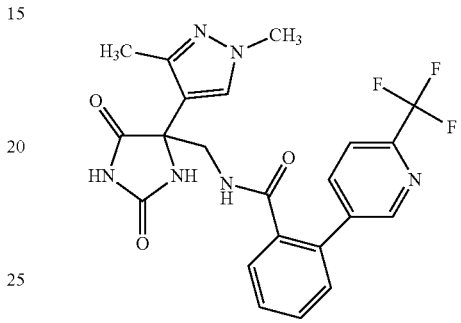

2-[6-(trifluoromethyl)pyridin-3-yl]benzoic acid (103 mg, 385 μmol) dissolved in 1.5 ml of DMF was treated with N,N-diisopropylethylamine (200 μl, 1.2 mmol), 1-ethyl-3-(3-dimethylaminopropyl)carbodiimide hydrochloride (96.0 mg, 501 μmol) and 1-hydroxybenzotriazole hydrate (76.7 mg, 501 μmol) and stirred for 5 min at room temperature before rac-5-(aminomethyl)-5-(1,3-dimethyl-1H-pyrazol-4-yl)imidazolidine-2,4-dione hydrochloride (100 mg, 385 μmol) was added. The mixture was stirred at room temperature over night. Purification was done by preparative HPLC (Instrument: Waters Prep LC/MS System; column: Phenomenex Kinetex C18 5 μm 100×30 mm; eluent A: water, eluent B: acetonitrile, eluent C: 2% formic acid in water, eluent D: acetonitrile/water (80 Vol. %/20 Vol. %); flow: 80 ml/min; room temperature; UV 200-400 nm; At-Column Injektion; Gradient: eluent A0 to 2 min 63 ml, eluent B 0 to 2 min 7 ml, eluent A 2 to 10 min from 63 ml to 39 ml and eluent B from 7 ml to 31 ml, 10 to 12 min 0 ml eluent A and 70 ml eluent B. Eluent C and eluent D constant flow each 5 ml/min over the whole time). Product containing samples were united, the solvents were evaporated and the residue was lyophylized. 63.0 mg (100% purity, 35% yield) of the title compound were obtained.

LC-MS (Method 7): $R_t$=1.25 min; MS (ESIpos): m/z=473 [M+H]$^+$ $^1$H-NMR (600 MHz, DMSO-d6) δ [ppm]: 2.101 (15.88), 3.341 (0.93), 3.345 (0.44), 3.703 (16.00), 3.759 (2.99), 3.769 (2.72), 7.474 (1.56), 7.487 (2.37), 7.515 (1.76), 7.529 (3.40), 7.542 (2.26), 7.554 (1.16), 7.592 (1.49), 7.605 (1.99), 7.618 (0.77), 7.685 (5.42), 7.907 (1.08), 7.921 (3.88), 7.930 (2.45), 7.933 (2.22), 7.943 (0.68), 7.946 (0.68), 8.065 (3.92), 8.669 (0.91), 8.679 (1.83), 8.689 (0.89), 8.726 (2.80), 10.872 (2.49).

Example 56

3-(4-Chlorophenyl)-N-{[(4R)-4-Cyclopropyl-2,5-Dioxoimidazolidin-4-Yl]Methyl}Isonicotinamide

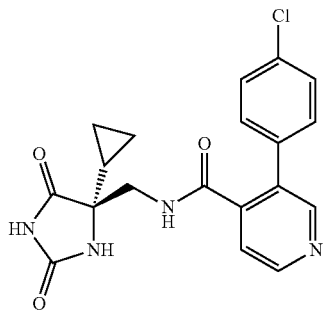

3-(4-chlorophenyl)pyridine-4-carboxylic acid (56.8 mg, 243 μmol) dissolved in 1.5 ml of DMF was treated with N,N-diisopropylethylamine (130 μl, 730 μmol), 1-ethyl-3-(3-dimethylaminopropyl)carbodiimide hydrochloride (60.6 mg, 316 μmol) and 1-hydroxybenzotriazole hydrate (48.4 mg, 316 μmol) and stirred for 5 min at room temperature before (5R)-5-(aminomethyl)-5-cyclopropylimidazolidine-2,4-dione hydrochloride (50.0 mg, 243 μmol) was added. The mixture was stirred at room temperature overnight. Purification was done by preparative HPLC (Instrument: Waters Prep LC/MS System; column: Phenomenex Kinetex C18 5 μm 100×30 mm; eluent A: water, eluent B: acetonitrile, eluent C: 2% formic acid in water, eluent D: acetonitrile/water (80 Vol. %/20 Vol. %); flow: 80 ml/min; room temperature; UV 200-400 nm; At-Column Injektion; Gradient: eluent A 0 to 2 min 63 ml, eluent B 0 to 2 min 7 ml, eluent A 2 to 10 min from 63 ml to 39 ml and eluent B from 7 ml to 31 ml, 10 to 12 min 0 ml eluent A and 70 ml eluent B. Eluent C and eluent D constant flow each 5 ml/min over the whole time). Product containing samples were united, the solvents were evaporated and the residue was lyophylized. 63.0 mg (100% purity, 67% yield) of the title compound were obtained.

LC-MS (Method 7): $R_t$=1.20 min; MS (ESIpos): m/z=385 $[M+H]^+$ $^1$H-NMR (400 MHz, DMSO-d6) δ [ppm]: 0.115 (0.53), 0.129 (1.34), 0.140 (2.36), 0.153 (2.55), 0.164 (1.80), 0.177 (0.84), 0.302 (0.45), 0.317 (0.79), 0.325 (1.49), 0.337 (1.89), 0.348 (1.79), 0.359 (1.43), 0.369 (1.11), 0.380 (0.94), 0.391 (1.47), 0.405 (1.71), 0.413 (2.24), 0.426 (1.72), 0.434 (1.02), 0.448 (1.42), 0.461 (1.94), 0.472 (2.40), 0.485 (2.31), 0.497 (1.44), 0.510 (0.53), 0.948 (0.47), 0.964 (3.30), 0.980 (3.04), 1.050 (0.78), 1.063 (1.59), 1.070 (1.71), 1.076 (1.27), 1.083 (2.96), 1.091 (1.26), 1.097 (1.61), 1.104 (1.48), 1.117 (0.69), 2.523 (1.47), 2.819 (0.48), 3.482 (0.44), 3.498 (0.53), 3.517 (5.65), 3.520 (5.78), 3.535 (6.53), 3.555 (0.62), 3.570 (0.43), 7.330 (6.79), 7.342 (7.01), 7.417 (1.11), 7.423 (9.10), 7.428 (3.61), 7.440 (4.37), 7.445 (16.00), 7.451 (2.53), 7.498 (2.22), 7.504 (15.23), 7.509 (4.34), 7.520 (3.22), 7.525 (8.93), 7.531 (1.21), 7.611 (7.96), 8.632 (13.06), 8.648 (9.08), 8.661 (8.71), 8.754 (1.92), 8.769 (4.04), 8.784 (1.89), 10.661 (3.43).

Example 57

Rac-N-[(2,5-Dioxo-4-Propylimidazolidin-4-Yl)Methyl]-2-[6-(Trifluoromethyl)Pyridin-3-Yl]Benzamide

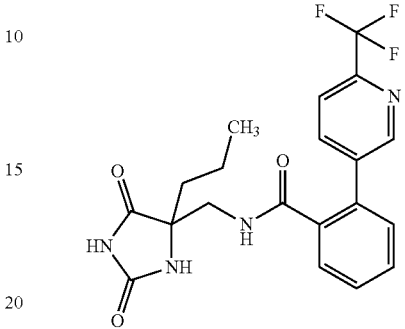

2-[6-(trifluoromethyl)pyridin-3-yl]benzoic acid (64.3 mg, 241 μmol) dissolved in 2 ml of DMF was treated with N,N-diisopropylethylamine (120 μl, 670 μmol), 1-ethyl-3-(3-dimethylaminopropyl)carbodiimide hydrochloride (60.0 mg, 313 μmol) and 1-hydroxybenzotriazole hydrate (47.9 mg, 313 μmol) and stirred for 5 min at room temperature before rac-5-(aminomethyl)-5-propylimidazolidine-2,4-dione hydrochloride (50.0 mg, 241 μmol) 10 was added. The mixture was stirred at room temperature over night. Purification was done by preparative HPLC (Instrument: Waters Prep LC/MS System; column: Phenomenex Kinetex C18 5 μm 100×30 mm; eluent A: water, eluent B: acetonitrile, eluent C: 2% formic acid in water, eluent D: acetonitrile/water (80 Vol. %/20 Vol. %); flow: 80 ml/min; room temperature; UV 200-400 nm; At-Column Injektion; Gradient: eluent A0 to 2 min 63 ml, eluent B 0 to 2 min 7 ml, eluent A 2 to 10 min from 63 ml to 39 ml and eluent B from 7 ml to 31 ml, 10 to 12 min 0 ml eluent A and 70 ml eluent B. Eluent C and eluent D constant flow each 5 ml/min over the whole time). Product containing samples were united, the solvents were evaporated and the residue was lyophylized. 85.0 mg (100% purity, 84% yield) of the title compound were obtained.

LC-MS (Method 7): $R_t$=1.43 min; MS (ESIpos): m/z=421 $[M+H]^+$ $^1$H-NMR (600 MHz, DMSO-d6) δ [ppm]: 0.826 (6.82), 0.838 (16.00), 0.850 (7.71), 1.046 (0.40), 1.055 (0.72), 1.067 (1.17), 1.076 (1.07), 1.087 (1.23), 1.099 (0.72), 1.108 (0.48), 1.253 (0.44), 1.261 (0.76), 1.266 (0.58), 1.273 (1.19), 1.282 (0.97), 1.285 (0.97), 1.294 (1.15), 1.302 (0.58), 1.306 (0.66), 1.314 (0.46), 1.448 (0.81), 1.455 (0.91), 1.471 (1.67), 1.478 (1.45), 1.491 (1.45), 1.498 (1.15), 1.524 (1.43), 1.532 (1.57), 1.544 (1.43), 1.547 (1.27), 1.552 (1.45), 1.566 (0.85), 1.575 (0.70), 2.517 (0.42), 2.570 (0.58), 2.605 (0.46), 3.264 (1.05), 3.313 (2.23), 3.326 (3.10), 3.328 (2.15), 3.335 (2.82), 3.396 (2.72), 3.407 (2.82), 3.418 (1.87), 3.429 (1.77), 7.508 (4.13), 7.521 (5.05), 7.528 (1.11), 7.534 (8.43), 7.540 (6.04), 7.543 (5.33), 7.556 (0.80), 7.581 (0.52), 7.588 (2.84), 7.593 (2.46), 7.597 (1.99), 7.600 (2.31), 7.602 (1.95), 7.606 (1.79), 7.610 (1.47), 7.615 (1.25), 7.690 (5.70), 7.918 (4.19), 7.932 (6.16), 7.985 (3.34), 7.988 (3.24), 7.998 (2.15), 8.001 (2.13), 8.564 (1.67), 8.575 (3.18), 8.585 (1.63), 8.738 (5.01), 8.741 (4.89), 10.665 (4.55).

Example 58

Rac-N-{[4-(3-Methylbutyl)-2,5-Dioxoimidazolidin-4-Yl]Methyl}-4'-(Trifluoromethyl)[Biphenyl]-2-Carboxamide

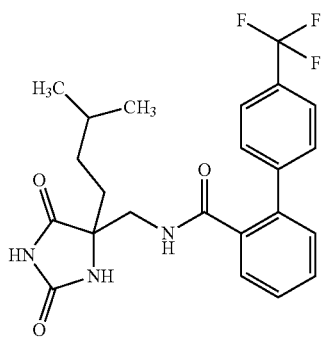 [SMILES: CC(C)CCC1(CNC(=O)c2ccccc2-c2ccc(C(F)(F)F)cc2)NC(=O)NC1=O]

4'-(trifluoromethyl)[1,1'-biphenyl]-2-carboxylic acid (56.5 mg, 212 µmol) dissolved in 1.9 ml of DMF was treated with N,N-diisopropylethylamine (100 µl, 590 µmol), 1-ethyl-3-(3-dimethylaminopropyl)carbodiimide hydrochloride (52.9 mg, 276 µmol) and 1-hydroxybenzotriazole hydrate (42.2 mg, 276 µmol) and stirred for 5 min at room temperature before rac-5-(aminomethyl)-5-(3-methylbutyl) imidazolidine-2,4-dione hydrochloride (50.0 mg, 212 µmol) was added. The mixture was stirred at room temperature for 2 h. Purification was done by preparative HPLC (Instrument: Waters Prep LC/MS System; column: Phenomenex Kinetex C18 5 µm 100×30 mm; eluent A: water, eluent B: acetonitrile, eluent C: 2% formic acid in water, eluent D: acetonitrile/water (80 Vol. %/20 Vol. %); flow: 80 ml/min; room temperature; UV 200-400 nm; At-Column Injektion; Gradient: eluent A0 to 2 min 47 ml, eluent B 0 to 2 min 23 ml, eluent A 2 to 10 min from 47 ml to 23 ml and eluent B from 23 ml to 47 ml, 10 to 12 min 0 ml eluent A and 70 ml eluent B. Eluent C and eluent D constant flow each 5 ml/min over the whole time). Product containing samples were united, the solvents were evaporated and the residue was lyophylized. 54.0 mg (98% purity, 56% yield) of the title compound were obtained.

LC-MS (Method 7): $R_t$=1.86 min; MS (ESIpos): m/z=448 [M+H]$^+$ $^1$H-NMR (400 MHz, DMSO-d6) δ [ppm]: 0.816 (13.73), 0.827 (15.07), 0.832 (16.00), 0.843 (14.36), 0.876 (0.43), 0.889 (0.67), 0.907 (1.01), 0.921 (1.06), 0.937 (1.21), 0.955 (0.65), 0.968 (0.50), 1.131 (0.57), 1.149 (1.08), 1.165 (1.07), 1.178 (1.04), 1.197 (0.61), 1.209 (0.42), 1.404 (0.80), 1.420 (1.51), 1.437 (1.79), 1.454 (1.40), 1.470 (0.91), 1.498 (1.26), 1.509 (1.19), 1.528 (1.19), 1.541 (1.07), 1.546 (1.21), 1.559 (1.21), 1.577 (1.16), 1.589 (1.11), 1.611 (0.58), 1.623 (0.41), 2.731 (0.97), 2.890 (1.27), 3.331 (2.19), 3.351 (2.50), 3.366 (2.16), 3.397 (2.11), 3.413 (2.21), 3.431 (1.08), 3.448 (1.02), 7.401 (0.69), 7.425 (3.30), 7.444 (4.05), 7.452 (1.02), 7.463 (6.80), 7.471 (5.03), 7.474 (4.93), 7.493 (0.69), 7.501 (0.43), 7.520 (1.20), 7.523 (1.03), 7.529 (2.79), 7.538 (2.95), 7.543 (2.21), 7.548 (2.55), 7.552 (3.12), 7.561 (6.08), 7.570 (1.84), 7.581 (6.07), 7.599 (0.53), 7.603 (0.56), 7.618 (0.66), 7.622 (0.70), 7.668 (5.28), 7.743 (6.30), 7.764 (5.25), 7.774 (1.48), 7.806 (0.60), 7.823 (0.52), 8.537 (1.28), 8.553 (2.62), 8.568 (1.26), 10.674 (2.63).

Example 59

Rac-N-{[4-(4-Methyl-1,2-Oxazol-5-Yl)-2,5-Dioxo-imidazolidin-4-Yl]Methyl}-4'-(Trifluoromethyl)[Biphenyl]-2-Carboxamide

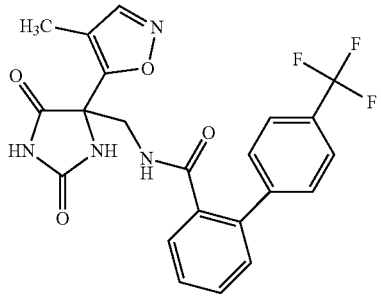 [SMILES: Cc1cnoc1C1(CNC(=O)c2ccccc2-c2ccc(C(F)(F)F)cc2)NC(=O)NC1=O]

4'-(trifluoromethyl)[1,1'-biphenyl]-2-carboxylic acid (103 mg, 385 µmol) dissolved in 1.5 ml of DMF was treated with N,N-diisopropylethylamine (200 µl, 1.2 mmol), 1-ethyl-3-(3-dimethylaminopropyl)carbodiimide hydrochloride (96.0 mg, 501 µmol) and 1-hydroxybenzotriazole hydrate (76.7 mg, 501 µmol) and stirred for 5 min at room temperature before rac-5-(aminomethyl)-5-(4-methyl-1,2-oxazol-5-yl) imidazolidine-2,4-dione hydrochloride (50.0 mg, 241 µmol) was added. The mixture was stirred at room temperature over night. Purification was done by preparative HPLC (Instrument: Waters Prep LC/MS System; column: Phenomenex Kinetex C18 5 µm 100×30 mm; eluent A: water, eluent B: acetonitrile, eluent C: 2% formic acid in water, eluent D: acetonitrile/water (80 Vol. %/20 Vol. %); flow: 80 ml/min; room temperature; UV 200-400 nm; At-Column Injektion; Gradient: eluent A0 to 2 min 63 ml, eluent B 0 to 2 min 7 ml, eluent A 2 to 10 min from 63 ml to 39 ml and eluent B from 7 ml to 31 ml, 10 to 12 min 0 ml eluent A and 70 ml eluent B. Eluent C and eluent D constant flow each 5 ml/min over the whole time). Product containing samples were united, the solvents were evaporated and the residue was lyophylized. 76.0 mg (100% purity, 43% yield) of the title compound were obtained.

LC-MS (Method 7): $R_t$=1.61 min; MS (ESIpos): m/z=459 [M+H]$^+$ $^1$H-NMR (400 MHz, DMSO-d6) δ [ppm]: 2.004 (16.00), 3.967 (2.77), 3.983 (3.00), 7.413 (1.09), 7.416 (1.21), 7.432 (2.25), 7.435 (2.29), 7.442 (1.75), 7.462 (2.74), 7.482 (1.92), 7.500 (0.94), 7.533 (2.94), 7.545 (1.84), 7.553 (3.58), 7.563 (1.85), 7.567 (1.67), 7.582 (0.63), 7.585 (0.60), 7.754 (3.53), 7.775 (2.94), 8.492 (5.06), 8.583 (2.66), 8.787 (0.77), 8.802 (1.63), 8.818 (0.76), 11.264 (2.16).

Example 60

Rac-N-{[4-(1,3-Dimethyl-1H-Pyrazol-4-Yl)-2,5-Dioxoimidazolidin-4-Yl]Methyl}-4'-(Trifluoromethyl)[Biphenyl]-2-Carboxamide

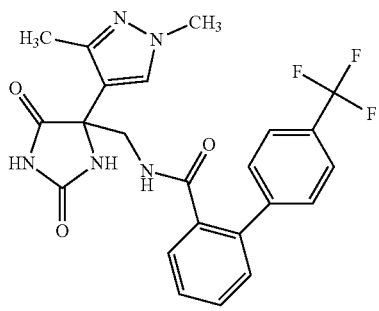 [SMILES: Cc1nn(C)cc1C1(CNC(=O)c2ccccc2-c2ccc(C(F)(F)F)cc2)NC(=O)NC1=O]

4'-(trifluoromethyl)[1,1'-biphenyl]-2-carboxylic acid (103 mg, 385 µmol) dissolved in 1.5 ml of DMF was treated with N,N-diisopropylethylamine (200 µl, 1.2 mmol), 1-ethyl-3-(3-dimethylaminopropyl)carbodiimide hydrochloride (96.0 mg, 501 µmol) and 1-hydroxybenzotriazole hydrate (76.7 mg, 501 µmol) and stirred for 5 min at room temperature before rac-5-(aminomethyl)-5-(1,3-dimethyl-1H-pyrazol-4-yl)imidazolidine-2,4-dione hydrochloride (100 mg, 385 µmol) was added. The mixture was stirred at room temperature over night. Purification was done by preparative HPLC (Instrument: Waters Prep LC/MS System; column: Phenomenex Kinetex C18 5 µm 100×30 mm; eluent A: water, eluent B: acetonitrile, eluent C: 2% formic acid in water, eluent D: acetonitrile/water (80 Vol. %/20 Vol. %); flow: 80 ml/min; room temperature; UV 200-400 nm; At-Column Injektion; Gradient: eluent A0 to 2 min 63 ml, eluent B 0 to 2 min 7 ml, eluent A 2 to 10 min from 63 ml to 39 ml and eluent B from 7 ml to 31 ml, 10 to 12 min 0 ml eluent A and 70 ml eluent B. Eluent C and eluent D constant flow each 5 ml/min over the whole time). Product containing samples were united, the solvents were evaporated and the residue was lyophylized. 93.0 mg (100% purity, 51% yield) of the title compound were obtained.

LC-MS (Method 7): $R_t$=1.49 min; MS (ESIpos): m/z=472 [M+H]$^+$ $^1$H-NMR (600 MHz, DMSO-d6) δ [ppm]: 0.005 (0.52), 2.111 (15.81), 2.514 (0.63), 2.518 (0.63), 2.521 (0.56), 2.572 (0.63), 3.272 (1.04), 3.277 (0.74), 3.290 (0.89), 3.319 (1.70), 3.326 (0.85), 3.330 (0.85), 3.339 (3.07), 3.702 (16.00), 3.761 (2.22), 3.764 (2.15), 3.771 (2.00), 3.775 (2.07), 7.410 (1.26), 7.412 (1.37), 7.423 (2.15), 7.425 (2.11), 7.430 (1.78), 7.443 (2.07), 7.458 (1.07), 7.460 (1.07), 7.470 (1.96), 7.472 (1.74), 7.483 (0.96), 7.485 (0.85), 7.523 (2.96), 7.537 (4.30), 7.550 (1.85), 7.552 (1.78), 7.563 (0.78), 7.565 (0.74), 7.679 (5.30), 7.741 (3.37), 7.755 (3.00), 8.046 (2.81), 8.592 (0.81), 8.602 (1.67), 8.612 (0.78), 10.867 (2.04).

Example 61

Rac-N-{[4-(1,4-Dimethyl-1H-Pyrazol-5-Yl)-2,5-Dioxoimidazolidin-4-Yl]Methyl}-4'-(Trifluoromethyl)[Biphenyl]-2-Carboxamide

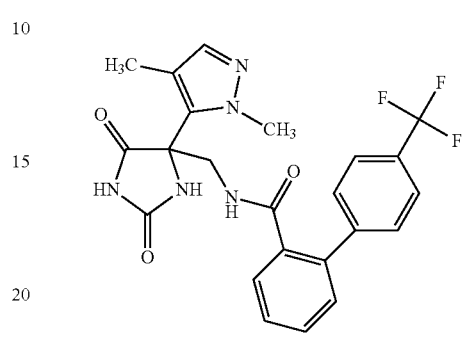

4'-(trifluoromethyl)[1,1'-biphenyl]-2-carboxylic acid (97.0 mg, 364 µmol) dissolved in 1.5 ml of DMF was treated with N,N-diisopropylethylamine (190 µl, 1.1 mmol), 1-ethyl-3-(3-dimethylaminopropyl)carbodiimide hydrochloride (90.8 mg, 474 µmol) and 1-hydroxybenzotriazole hydrate (72.5 mg, 474 µmol) and stirred for 5 min at room temperature before rac-5-(aminomethyl)-5-(1,4-dimethyl-1H-pyrazol-5-yl)imidazolidine-2,4-dione hydrochloride (110 mg, 86% purity, 364 µmol) was added. The mixture was stirred at room temperature over night. Purification was done by preparative HPLC (Instrument: Waters Prep LC/MS System; column: Phenomenex Kinetex C18 5 µm 100×30 mm; eluent A: water, eluent B: acetonitrile, eluent C: 2% formic acid in water, eluent D: acetonitrile/water (80 Vol. %/20 Vol. %); flow: 80 ml/min; room temperature; UV 200-400 nm; At-Column Injektion; Gradient: eluent A 0 to 2 min 63 ml, eluent B 0 to 2 min 7 ml, eluent A 2 to 10 min from 63 ml to 39 ml and eluent B from 7 ml to 31 ml, 10 to 12 min 0 ml eluent A and 70 ml eluent B. Eluent C and eluent D constant flow each 5 ml/min over the whole time). Product containing samples were united, the solvents were evaporated and the residue was lyophylized. 21.0 mg (100% purity, 12% yield) of the title compound were obtained.

LC-MS (Method 7): $R_t$=1.58 min; MS (ESIpos): m/z=472 [M+H]$^+$ $^1$H-NMR (400 MHz, DMSO-d6) δ [ppm]: −0.008 (0.71), 0.008 (0.76), 2.102 (13.54), 2.327 (0.50), 2.669 (0.53), 3.850 (16.00), 3.960 (0.65), 3.974 (0.74), 3.994 (1.20), 4.008 (1.09), 4.065 (1.09), 4.082 (1.18), 4.098 (0.70), 4.115 (0.65), 7.205 (4.78), 7.421 (1.07), 7.425 (1.23), 7.438 (2.75), 7.443 (2.25), 7.455 (2.17), 7.468 (1.15), 7.471 (1.12), 7.487 (2.17), 7.490 (2.45), 7.495 (3.19), 7.505 (1.36), 7.515 (3.35), 7.548 (1.33), 7.551 (1.33), 7.567 (1.67), 7.570 (1.54), 7.585 (0.62), 7.589 (0.65), 7.754 (3.45), 7.775 (2.96), 8.369 (3.01), 8.713 (0.73), 8.729 (1.39), 8.744 (0.71), 11.198 (1.64).

Example 62

Rac-N-{[4-(4-Methyl-1,2,5-Thiadiazol-3-Yl)-2,5-Dioxoimidazolidin-4-Yl]Methyl}-4'-(Trifluoromethyl)[Biphenyl]-2-Carboxamide

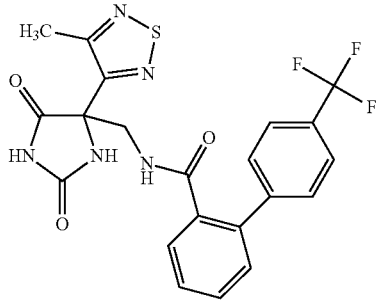 [SMILES: Cc1nsnc1C1(CNC(=O)c2ccccc2-c2ccc(C(F)(F)F)cc2)NC(=O)NC1=O]

4'-(trifluoromethyl)[1,1'-biphenyl]-2-carboxylic acid (101 mg, 379 µmol) dissolved in 1.5 ml of DMF was treated with N,N-diisopropylethylamine (200 µl, 1.1 mmol), 1-ethyl-3-(3-dimethylaminopropyl)carbodiimide hydrochloride (94.5 mg, 493 µmol) and 1-hydroxybenzotriazole hydrate (75.5 mg, 493 µmol) and stirred for 5 min at room temperature before rac-5-(aminomethyl)-5-(4-methyl-1,2,5-thiadiazol-3-yl)imidazolidine-2,4-dione hydrochloride (100 mg, 379 µmol) was added. The mixture was stirred at room temperature over night. Purification was done by preparative HPLC (Instrument: Waters Prep LC/MS System; column: Phenomenex Kinetex C18 5 µm 100×30 mm; eluent A: water, eluent B: acetonitrile, eluent C: 2% formic acid in water, eluent D: acetonitrile/water (80 Vol. %/20 Vol. %); flow: 80 ml/min; room temperature; UV 200-400 nm; At-Column Injektion; Gradient: eluent A0 to 2 min 55 ml, eluent B 0 to 2 min 15 ml, eluent A 2 to 10 min from 55 ml to 31 ml and eluent B from 15 ml to 39 ml, 10 to 12 min 0 ml eluent A and 70 ml eluent B. Eluent C and eluent D constant flow each 5 ml/min over the whole time). Product containing samples were united, the solvents were evaporated and the residue was lyophylized. 35.0 mg (100% purity, 19% yield) of the title compound were obtained.

LC-MS (Method 7): $R_t$=1.71 min; MS (ESIpos): m/z=476 [M+H]$^+$ $^1$H-NMR (600 MHz, DMSO-d6) δ [ppm]: 2.479 (16.00), 3.274 (0.56), 4.127 (3.06), 4.138 (3.08), 7.441 (1.04), 7.444 (1.96), 7.454 (2.04), 7.456 (2.89), 7.472 (1.11), 7.474 (1.02), 7.484 (1.68), 7.486 (1.42), 7.497 (0.73), 7.499 (0.65), 7.551 (1.24), 7.553 (1.50), 7.558 (2.63), 7.563 (1.90), 7.566 (1.85), 7.571 (2.89), 7.575 (1.03), 7.578 (0.76), 7.761 (2.92), 7.775 (2.58), 8.372 (0.95), 8.761 (0.67), 8.772 (1.43), 8.783 (0.68).

Example 63

Rac-N-{[4-(3-Methyl-1,2-Thiazol-4-Yl)-2,5-Dioxoimidazolidin-4-Yl]Methyl}-4'-(Trifluoromethyl)[Biphenyl]-2-Carboxamide

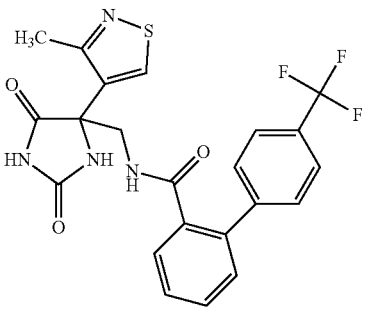 [SMILES: Cc1nscc1C1(CNC(=O)c2ccccc2-c2ccc(C(F)(F)F)cc2)NC(=O)NC1=O]

4'-(trifluoromethyl)[1,1'-biphenyl]-2-carboxylic acid (101 mg, 381 µmol) dissolved in 2 ml of DMF was treated with N,N-diisopropylethylamine (200 µl, 1.1 mmol), 1-ethyl-3-(3-dimethylaminopropyl)carbodiimide hydrochloride (94.9 mg, 495 µmol) and 1-hydroxybenzotriazole hydrate (75.8 mg, 495 µmol) and stirred for 5 min at room temperature before rac-5-(aminomethyl)-5-(3-methyl-1,2-thiazol-4-yl) imidazolidine-2,4-dione hydrochloride (110 mg, 86% purity, 364 µmol) was added. The mixture was stirred at room temperature over night. Purification was done by preparative HPLC (Instrument: Waters Prep LC/MS System; column: Phenomenex Kinetex C18 5 µm 100×30 mm; eluent A: water, eluent B: acetonitrile, eluent C: 2% formic acid in water, eluent D: acetonitrile/water (80 Vol. %/20 Vol. %); flow: 80 ml/min; room temperature; UV 200-400 nm; At-Column Injektion; Gradient: eluent A0 to 2 min 63 ml, eluent B 0 to 2 min 7 ml, eluent A 2 to 10 min from 63 ml to 39 ml and eluent B from 7 ml to 31 ml, 10 to 12 min 0 ml eluent A and 70 ml eluent B. Eluent C and eluent D constant flow each 5 ml/min over the whole time). Product containing samples were united, the solvents were evaporated and the residue was lyophylized. 86.0 mg (100% purity, 48% yield) of the title compound were obtained.

LC-MS (Method 7): $R_t$=1.62 min; MS (ESIpos): m/z=475 [M+H]$^+$ $^1$H-NMR (400 MHz, DMSO-d6) δ [ppm]: 2.418 (16.00), 2.522 (0.86), 3.887 (0.61), 3.902 (0.69), 3.921 (1.50), 3.936 (1.35), 3.959 (1.37), 3.976 (1.43), 3.993 (0.64), 4.010 (0.61), 7.422 (1.23), 7.425 (1.43), 7.435 (1.99), 7.440 (2.56), 7.444 (2.60), 7.453 (2.56), 7.466 (1.24), 7.468 (1.31), 7.484 (2.08), 7.487 (1.89), 7.502 (1.07), 7.506 (0.99), 7.524 (3.28), 7.544 (5.16), 7.563 (1.86), 7.566 (1.77), 7.582 (0.69), 7.585 (0.72), 7.740 (3.92), 7.761 (3.24), 8.272 (2.80), 8.275 (2.84), 8.747 (0.84), 8.763 (1.67), 8.778 (0.83), 9.099 (5.63), 11.170 (2.49).

Example 64

Ent-N-{[4-(3-Methyl-1,2-Thiazol-4-Yl)-2,5-Dioxo-imidazolidin-4-Yl]Methyl}-2-[6-(Trifluoromethyl)Pyridin-3-Yl]Benzamide

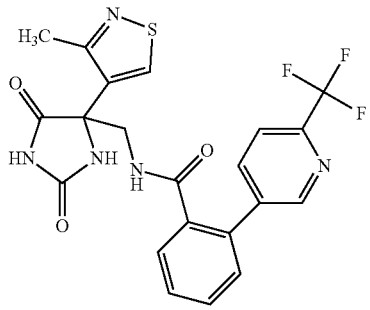 [SMILES: Cc1nscc1C1(CNC(=O)c2ccccc2-c2ccc(C(F)(F)F)nc2)NC(=O)NC1=O]

Enantiomeric separation of rac-N-{[4-(3-methyl-1,2-thiazol-4-yl)-2,5-dioxoimidazolidin-4 yl]methyl}-2-[6-(trifluoromethyl)pyridin-3-yl]benzamide (63.0 mg, 133 µmol) was done using the following method:
Column: Diacel Chiralpak IG 5 µm 250×20 mm
Solvent: 70% n-heptane: 30% ethanol
Flow: 20 ml/min
Oven temperature: 50° C.
UV: 220 nm
Product containing samples were united, the solvents were evaporated and the residue was dried in vacuo.
28.0 mg (100% purity, 44% yield)
LC-MS (Method 7): $R_t$=1.37 min; MS (ESIpos): m/z=476 [M+H]$^+$
Chiral HPLC (Column: Diacel Chiralpak IG 5 µm 250×4.6 mm; solvent: 70% n-heptane: 30% ethanol; flow: 1 ml/min; temperature: 50° C.): $R_t$=9.468 min, 100.0% ee $^1$H-NMR (600 MHz, DMSO-d6) δ [ppm]: 2.410 (16.00), 2.423 (0.41), 3.170 (0.41), 3.273 (0.84), 3.335 (1.28), 3.342 (0.58), 3.900 (0.71), 3.911 (0.78), 3.923 (1.63), 3.933 (1.48), 3.953 (1.53), 3.964 (1.58), 3.976 (0.74), 3.987 (0.70), 7.489 (1.63), 7.501 (2.46), 7.519 (1.94), 7.532 (2.56), 7.541 (1.23), 7.554 (2.18), 7.566 (1.11), 7.605 (1.46), 7.618 (1.99), 7.630 (0.79), 7.905 (1.89), 7.918 (3.49), 7.947 (1.94), 7.950 (1.89), 7.960 (1.04), 8.264 (3.05), 8.730 (2.77), 8.803 (0.94), 8.813 (1.83), 8.824 (0.94), 9.108 (5.51), 11.156 (2.68).

Example 65

Ent-N-{[4-(3-Methyl-1,2-Oxazol-4-Yl)-2,5-Dioxo-imidazolidin-4-Yl]Methyl}-2-[6-(Trifluoromethyl)Pyridin-3-Yl]Benzamide

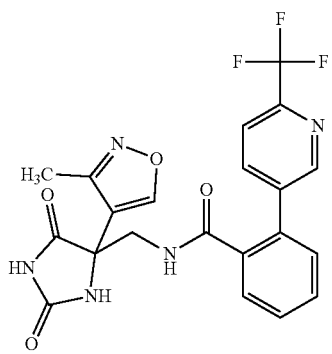 [SMILES: Cc1nocc1C1(CNC(=O)c2ccccc2-c2ccc(C(F)(F)F)nc2)NC(=O)NC1=O]

Enantiomeric separation of rac-N-{[4-(3-methyl-1,2-oxazol-4-yl)-2,5-dioxoimidazolidin-4 yl]methyl}-2-[6-(trifluoromethyl)pyridin-3-yl]benzamide (170 mg, 370 µmol) was done using the following method:
Column: Diacel Chiralpak IG 5 µm 250×20 mm
Solvent: 60% n-heptane: 40% ethanol
Flow: 20 ml/min
Oven temperature: 50° C.
UV: 220 nm
Product containing samples were united, the solvents were evaporated and the residue was dried in vacuo.
73.0 mg (100% purity, 43% yield)
LC-MS (Method 7): $R_t$=1.35 min; MS (ESIpos): m/z=460 [M+H]$^+$
Chiral HPLC (Column: Diacel Chiralpak IG 3 µm 50×4.6 mm; solvent: 60% iso-hexane: 40% ethanol): $R_t$=2.539 min, 100.0% ee $^1$H-NMR (400 MHz, DMSO-d6) δ [ppm]: −0.008 (2.32), 0.008 (2.61), 1.038 (0.81), 1.056 (1.67), 1.073 (0.85), 2.225 (16.00), 3.764 (0.54), 3.778 (0.62), 3.798 (1.57), 3.813 (1.47), 3.825 (1.50), 3.842 (1.52), 3.860 (0.57), 3.877 (0.53), 7.477 (1.29), 7.480 (1.40), 7.496 (2.29), 7.499 (2.21), 7.516 (1.48), 7.518 (1.62), 7.537 (3.23), 7.555 (2.35), 7.558 (1.79), 7.573 (1.27), 7.577 (0.95), 7.598 (1.67), 7.602 (1.66), 7.617 (1.87), 7.621 (1.81), 7.636 (0.68), 7.639 (0.61), 7.894 (1.07), 7.912 (3.87), 7.914 (3.85), 7.924 (2.48), 7.929 (2.31), 7.945 (0.63), 7.949 (0.65), 8.294 (2.77), 8.297 (2.75), 8.728 (2.55), 8.825 (0.83), 8.841 (1.65), 8.856 (0.81), 8.971 (5.39), 11.158 (2.39).

Example 66

Ent-N-{[4-(1-Cyclopropyl-1H-Pyrazol-5-Yl)-2,5-Dioxoimidazolidin-4-Yl]Methyl}-2-[6-(Trifluoromethyl)Pyridin-3-Yl]Benzamide

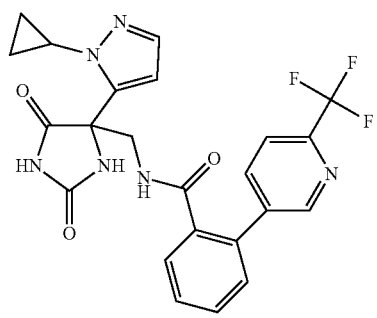 [SMILES: O=C1NC(=O)C(CNC(=O)c2ccccc2-c2ccc(C(F)(F)F)nc2)(c2ccnn2C2CC2)N1]

Enantiomeric separation of rac-N-{[4-(1-cyclopropyl-1H-pyrazol-5-yl)-2,5-dioxoimidazolidin-4 yl]methyl}-2-[6-(trifluoromethyl)pyridin-3-yl]benzamide (58.0 mg, 120 µmol) was done using the following method:
Column: Diacel Chiralpak OH-H 5 µm 250×20 mm
Solvent: 60% n-heptane: 40% ethanol
Flow: 20 ml/min
Oven temperature: 40° C.
UV: 210 nm
Product containing samples were united, the solvents were evaporated and the residue was lyophilized.
16.0 mg (100% purity, 28% yield)
LC-MS (Method 7): $R_t$=1.36 min; MS (ESIpos): m/z=485 [M+H]$^+$ Chiral HPLC (Column: Diacel OX-3 3 μm 50×4.6 mm; solvent: 50% n-heptane: 50% ethanol): $R_t$=1.716 min, 100.0% ee $^1$H-NMR (400 MHz, DMSO-d6) δ [ppm]: −0.149 (1.31), −0.008 (10.95), 0.008 (11.61), 0.146 (1.38), 0.826 (2.36), 0.844 (3.67), 0.853 (4.00), 0.868 (4.07), 0.880 (3.02), 0.885 (2.82), 0.892 (2.62), 0.897 (1.84), 0.904 (3.21), 0.909 (4.39), 0.921 (3.48), 0.926 (2.75), 0.942 (2.75), 0.954 (2.62), 0.960 (3.61), 0.972 (4.07), 0.978 (3.15), 0.983 (2.03), 0.990 (2.10), 0.996 (2.30), 1.015 (1.05), 1.117 (1.77), 1.133 (3.15), 1.151 (1.64), 1.235 (4.00), 1.249 (2.49), 1.260 (3.15), 1.275 (3.74), 1.287 (3.54), 1.314 (1.31), 2.327 (2.62), 2.332 (1.97), 2.366 (1.77), 2.523 (11.67), 2.665 (2.23), 2.670 (2.95), 2.674 (2.23), 2.710 (2.03), 2.859 (1.05), 2.878 (0.98), 3.429 (1.57), 3.438 (3.02), 3.447 (3.93), 3.456 (5.38), 3.465 (4.13), 3.474 (2.89), 3.484 (1.51), 3.880 (2.36), 3.895 (2.69), 3.914 (5.25), 3.929 (4.66), 3.958 (4.72), 3.975 (5.05), 3.992 (2.49), 4.009 (2.36), 6.533 (13.38), 6.538 (13.70), 7.342 (13.05), 7.346 (13.18), 7.511 (4.00), 7.525 (16.00), 7.544 (13.57), 7.559 (8.07), 7.577 (3.67), 7.603 (5.64), 7.607 (5.51), 7.622 (6.36), 7.626 (5.84), 7.640 (2.30), 7.644 (2.23), 7.919 (6.23), 7.939 (12.26), 7.976 (6.69), 7.981 (6.62), 7.996 (3.41), 8.001 (3.41), 8.348 (14.23), 8.741 (8.46), 8.745 (8.66), 8.852 (2.95), 8.868 (6.10), 8.884 (3.02).

Example 67

Rac-N-{[4-(3-Methyl-1,2-Oxazol-4-Yl)-2,5-Dioxo-imidazolidin-4-Yl]Methyl}-4'-(Trifluoromethyl)[Biphenyl]-2-Carboxamide

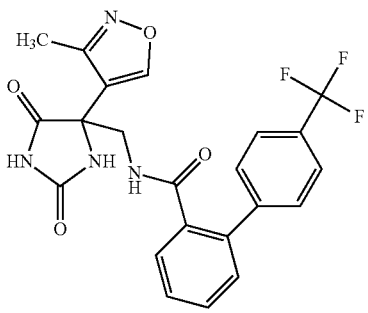 [SMILES: Cc1nocc1C1(CNC(=O)c2ccccc2-c2ccc(C(F)(F)F)cc2)NC(=O)NC1=O]

4'-(trifluoromethyl)[1,1'-biphenyl]-2-carboxylic acid (108 mg, 405 μmol) dissolved in 2.5 ml DMF was treated with N,N-diisopropylethylamine (210 μl, 1.2 mmol), 1-ethyl-3-(3-dimethylaminopropyl)carbodiimide hydrochloride (101 mg, 527 μmol) and 1-hydroxybenzotriazole hydrate (80.7 mg, 527 μmol) and stirred for 5 min at room temperature before rac-5-(aminomethyl)-5-(3-methyl-1,2-oxazol-4-yl)imidazolidine-2,4-dione hydrochloride (100 mg, 405 μmol) was added. The mixture was stirred at room temperature over night. Purification was done by preparative HPLC (Column: Chromatorex C18 10 μm 250×30 mm; eluent A=water+0.1% formic acid, B=acetonitrile; gradient: 0.0 min 30% B; 4.5 min 50% B; 11.5 min 70% B; 12 min 100% B; 14.75 min 30% B; flow: 50 ml/min). Product containing samples were united, the solvents were evaporated and the residue was lyophilized. 86.0 mg (100% purity, 46% yield) of the title compound were obtained.

LC-MS (Method 7): $R_t$=1.60 min; MS (ESIpos): m/z=459 [M+H]$^+$ $^1$H-NMR (400 MHz, DMSO-d6) δ [ppm]: −0.008 (1.96), 0.008 (2.17), 2.234 (16.00), 2.524 (1.08), 2.558 (0.47), 3.758 (0.68), 3.773 (0.78), 3.792 (1.46), 3.807 (1.32), 3.841 (1.34), 3.858 (1.44), 3.875 (0.71), 3.892 (0.68), 7.017 (1.77), 7.144 (1.84), 7.271 (1.77), 7.421 (1.23), 7.425 (1.48), 7.433 (1.86), 7.440 (2.52), 7.444 (2.59), 7.448 (2.38), 7.451 (2.50), 7.466 (1.25), 7.469 (1.27), 7.484 (2.17), 7.488 (1.86), 7.508 (3.42), 7.529 (3.70), 7.544 (1.60), 7.548 (1.53), 7.562 (1.91), 7.566 (1.77), 7.581 (0.73), 7.585 (0.73), 7.731 (3.82), 7.751 (3.16), 8.292 (2.97), 8.758 (0.80), 8.774 (1.56), 8.789 (0.82), 8.961 (5.28), 11.159 (1.91).

Example 68

Ent-N-{[4-(3-Methyl-1,2-Oxazol-4-Yl)-2,5-Dioxo-imidazolidin-4-Yl]Methyl}-4'-(Trifluoromethyl)[Biphenyl]-2-Carboxamide

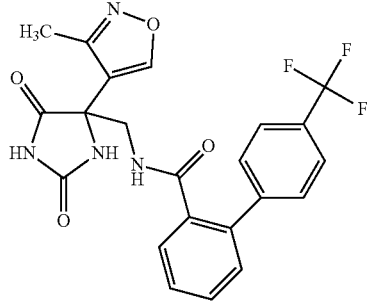 [SMILES: Cc1nocc1C1(CNC(=O)c2ccccc2-c2ccc(C(F)(F)F)cc2)NC(=O)NC1=O]

Enantiomeric separation of rac-N-{[4-(3-methyl-1,2-oxazol-4-yl)-2,5-dioxoimidazolidin-4 yl]methyl}-4'-(trifluoromethyl)[biphenyl]-2-carboxamide (85.0 mg, 185 μmol) was done using the following method:

Column: Daicel Chiralcel OZ-H 5 μm 250×20 mm

Solvent: 80% n-heptane: 20% iso-propanol

Flow: 20 ml/min

Oven temperature: 50° C.

UV: 220 nm

Further purification by preparative HPLC (Column: Chromatorex C18 10 μm250×30 mm; eluent A=water+0.1% formic acid, B=acetonitrile; gradient: 0.0 min 30% B; 4.5 min 50% B; 11.5 min 70% B; 12 min 100% B; 14.75 min 30% B; flow: 50 ml/min) was needed. Product containing samples were united, the solvents were evaporated and the residue was lyophilized. 24.0 mg (100% purity, 28% yield) of the title compound were obtained.

LC-MS (Method 7): $R_t$=1.60 min; MS (ESIpos): m/z=459 [M+H]$^+$

Chiral HPLC (Column: Chiraltek OZ-3 3 μm, 220 nm, solvent: 50% iso-hexane: 50% iso-propanol): $R_t$=2.938 min, 99.56% ee $^1$H-NMR (600 MHz, DMSO-d6) δ [ppm]: 2.236 (16.00), 2.514 (0.42), 3.279 (0.60), 3.346 (0.99), 3.349 (0.81), 3.768 (0.83), 3.777 (0.91), 3.790 (1.45), 3.800 (1.32), 3.846 (1.30), 3.858 (1.39), 3.868 (0.86), 3.880 (0.81), 7.426 (1.31), 7.428 (1.50), 7.433 (1.85), 7.438 (2.23), 7.441 (2.29), 7.445 (2.25), 7.471 (1.14), 7.472 (1.14), 7.483 (1.93), 7.485 (1.83), 7.496 (0.93), 7.498 (0.86), 7.514 (3.05), 7.527 (3.35), 7.548 (1.28), 7.550 (1.25), 7.561 (1.87), 7.563 (1.75), 7.574 (0.75), 7.575 (0.76), 7.731 (3.46), 7.745 (3.10), 8.255 (2.51), 8.257 (2.53), 8.726 (0.81), 8.737 (1.44), 8.747 (0.81), 8.947 (5.13), 11.139 (2.10).

Example 69

Ent-N-{[4-(4-Methyl-1,2-Oxazol-3-Yl)-2,5-Dioxo-imidazolidin-4-Yl]Methyl}-4'-(Trifluoromethyl)[Biphenyl]-2-Carboxamide

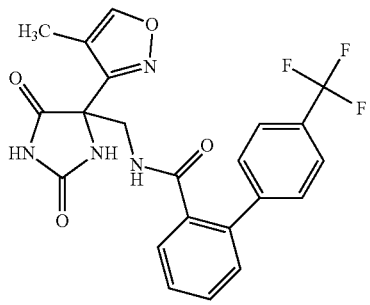 [SMILES: Cc1conc1C1(CNC(=O)c2ccccc2-c2ccc(C(F)(F)F)cc2)NC(=O)NC1=O]

Enantiomeric separation of rac-N-{[4-(4-methyl-1,2-oxazol-3-yl)-2,5-dioxoimidazolidin-4 yl]methyl}-4'-(trifluoromethyl)[biphenyl]-2-carboxamide (73.0 mg, 159 µmol) was done using the following method:

Column: Daicel Chiralpak ID 5 µm 250×20 mm

Solvent: 50% n-heptane: 50% iso-propanol

Flow: 20 ml/min

Oven temperature: 40° C.

UV: 210 nm

Further purification by preparative HPLC (Column: Chromatorex C18 10 µm250×30 mm; eluent A=water+0.1% formic acid, B=acetonitrile; gradient: 0.0 min 30% B; 4.5 min 50% B; 11.5 min 70% B; 12 min 100% B; 14.75 min 30% B; flow: 50 ml/min) was needed. Product containing samples were united, the solvents were evaporated and the residue was lyophilized. 15.0 mg (100% purity, 21% yield) of the title compound were obtained.

LC-MS (Method 7): $R_t$=1.68 min; MS (ESIpos): m/z=459 [M+H]$^+$

Chiral HPLC (Column: Daicel Chiralpak ID-3 3 µm, 50×4.6 mm, 1 ml/min, 220 nm, solvent: 50% n-heptane: 50% iso-propanol): $R_t$=3.572 min, 100% ee $^1$H-NMR (600 MHz, DMSO-d6) δ [ppm]: 1.927 (15.18), 1.929 (16.00), 2.514 (0.60), 2.517 (0.56), 2.520 (0.50), 3.269 (0.72), 3.328 (0.54), 3.335 (0.66), 3.994 (4.99), 4.005 (5.01), 7.427 (1.61), 7.430 (1.81), 7.441 (4.93), 7.442 (5.40), 7.455 (2.95), 7.465 (1.65), 7.467 (1.55), 7.478 (2.74), 7.480 (2.47), 7.490 (1.24), 7.492 (1.11), 7.546 (1.84), 7.549 (2.04), 7.554 (4.27), 7.559 (3.55), 7.561 (2.93), 7.568 (4.66), 7.758 (4.74), 7.772 (4.17), 8.420 (3.73), 8.716 (1.07), 8.727 (2.29), 8.736 (5.05), 8.737 (5.44), 11.256 (1.03).

Example 70

Ent-N-{[4-(1,4-Dimethyl-1H-Pyrazol-3-Yl)-2,5-Dioxoimidazolidin-4-Yl]Methyl}-4'-(Trifluoromethyl)[Biphenyl]-2-Carboxamide

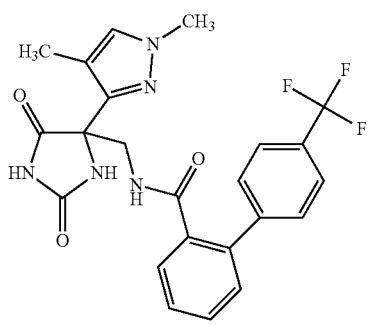 [SMILES: Cc1cn(C)nc1C1(CNC(=O)c2ccccc2-c2ccc(C(F)(F)F)cc2)NC(=O)NC1=O]

Enantiomeric separation of rac-N-{[4-(1,4-dimethyl-1H-pyrazol-3-yl)-2,5-dioxoimidazolidin-4 yl]methyl}-4'-(trifluoromethyl)[biphenyl]-2-carboxamide (116 mg, 246 µmol) was done using the following method:

Column: Maisch Diacel OJ-H 250×25 mm

Solvent: 85% $CO_2$: 15% methanol

Flow: 80 ml/min

Oven temperature: 40° C.

UV: 210 nm

Product containing samples were united, the solvents were evaporated and the residue was lyophilized. 44.0 mg (100% purity, 38% yield) of the title compound were obtained.

LC-MS (Method 7): $R_t$=1.62 min; MS (ESIpos): m/z=472 [M+H]$^+$

Chiral HPLC (Column: OJ-3, 3 ml/min, 210 nm, solvent: 90% $CO_2$: 10% methanol): $R_t$=0.968 min, 100% ee $^1$H-NMR (600 MHz, DMSO-d6) δ [ppm]: 1.887 (4.74), 3.292 (16.00), 3.294 (11.32), 3.296 (10.91), 3.942 (0.53), 3.953 (0.50), 3.980 (0.51), 3.990 (0.56), 7.411 (0.45), 7.413 (0.48), 7.423 (0.77), 7.425 (0.76), 7.436 (0.64), 7.449 (0.83), 7.452 (0.54), 7.454 (0.52), 7.459 (1.46), 7.465 (0.81), 7.467 (0.66), 7.533 (0.47), 7.535 (0.46), 7.545 (0.67), 7.547 (0.64), 7.573 (1.08), 7.586 (1.19), 7.761 (1.26), 7.774 (1.09), 8.084 (1.16), 8.486 (0.60), 10.890 (0.77).

Example 71

Ent-N-[(4-Tert-Butyl-2,5-Dioxoimidazolidin-4-Yl)Methyl]-4'-(Trifluoromethyl)[Biphenyl]-2-Carboxamide

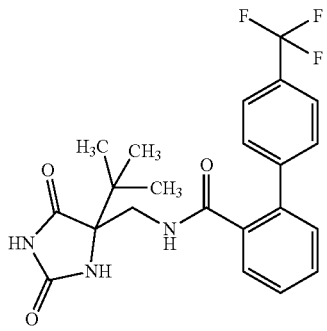 [SMILES: CC(C)(C)C1(CNC(=O)c2ccccc2-c2ccc(C(F)(F)F)cc2)NC(=O)NC1=O]

357

Enantiomeric separation of rac-N-[(4-tert-butyl-2,5-dioxoimidazolidin-4-yl)methyl]-4'-(trifluoromethyl)[biphenyl]-2-carboxamide (53.0 mg, 122 µmol) was done using the following method:

Column: Daicel Chiralpak IE 5 µm 250×20 mm
Solvent: 60% n-heptane: 40% iso-propanol
Flow: 20 ml/min
Oven temperature: 40° C.
UV: 210 nm Product containing samples were united, the solvents were evaporated and the residue was lyophilized. 17.5 mg (100% purity, 33% yield) of the title compound were obtained.

LC-MS (Method 7): $R_t$=1.77 min; MS (ESIpos): m/z=434 [M+H]$^+$

Chiral HPLC (Chiraltek IE-3 3 µm, 220 nm, 50% iso-hexane: 50% iso-propanol): $R_t$=2.492 min, 100% ee $^1$H-NMR (600 MHz, DMSO-d6) δ [ppm]: 0.005 (0.44), 0.982 (16.00), 3.327 (0.78), 3.533 (0.58), 3.544 (0.56), 3.587 (0.57), 3.598 (0.62), 7.370 (0.69), 7.382 (0.92), 7.421 (0.79), 7.434 (0.98), 7.442 (0.48), 7.455 (0.91), 7.457 (0.84), 7.468 (0.48), 7.527 (0.63), 7.529 (0.70), 7.535 (1.69), 7.539 (1.18), 7.542 (1.19), 7.546 (1.52), 7.560 (1.59), 7.757 (1.59), 7.771 (1.42), 8.447 (0.73).

Example 72

Ent-N-{[4-(1,4-Dimethyl-1H-Pyrazol-3-Yl)-2,5-Dioxoimidazolidin-4-Yl]Methyl}-2-[6-(Trifluoromethyl)Pyridin-3-Yl]Benzamide

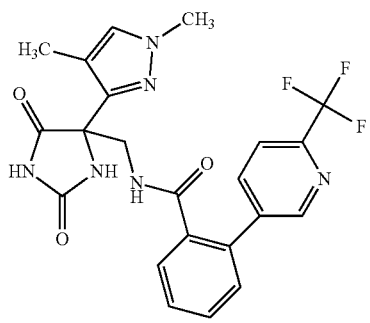 [SMILES: Cc1cn(C)nc1C1(CNC(=O)c2ccccc2-c2ccc(C(F)(F)F)nc2)NC(=O)NC1=O]

Enantiomeric separation of rac-N-{[4-(1,4-dimethyl-1H-pyrazol-3-yl)-2,5-dioxoimidazolidin-4 yl]methyl}-2-[6-(trifluoromethyl)pyridin-3-yl]benzamide (191 mg, 404 µmol) was done using the following method:

Column: Daicel Chiralpak IG 5 µm 250×20 mm
Solvent: 70% n-heptane: 30% ethanol
Flow: 20 ml/min
Oven temperature: 50° C.
UV: 210 nm Product containing samples were united, the solvents were evaporated and the residue was lyophilized. 88.0 mg (100% purity, 46% yield) of the title compound were obtained.

LC-MS (Method 7): $R_t$=1.35 min; MS (ESIpos): m/z=473 [M+H]$^+$

Chiral HPLC (Daicel IG-3 3 µm, 220 nm, 1 ml/min, 70% n-heptane: 30% ethanol): $R_t$=4.645 min, 100% ee

358

$^1$H-NMR (600 MHz, DMSO-d6) δ [ppm]: 1.886 (12.59), 2.067 (1.67), 3.743 (16.00), 3.948 (0.41), 3.961 (1.59), 3.972 (2.91), 3.982 (1.74), 3.995 (0.49), 4.005 (0.44), 7.457 (3.73), 7.475 (1.25), 7.477 (1.12), 7.488 (2.10), 7.524 (2.35), 7.537 (3.65), 7.550 (1.06), 7.551 (0.75), 7.587 (1.31), 7.590 (1.25), 7.600 (1.40), 7.602 (1.64), 7.612 (0.66), 7.615 (0.61), 7.933 (1.76), 7.947 (2.80), 7.989 (1.49), 7.993 (1.47), 8.003 (0.92), 8.006 (0.92), 8.109 (2.43), 8.111 (2.41), 8.562 (0.79), 8.573 (1.66), 8.583 (0.79), 8.746 (2.20), 8.750 (2.20), 10.904 (2.08).

Example 73

Ent-N-{[4-(4-Methyl-1,2,5-Oxadiazol-3-Yl)-2,5-Dioxoimidazolidin-4-Yl]Methyl}-4'-(Trifluoromethyl)[Biphenyl]-2-Carboxamide

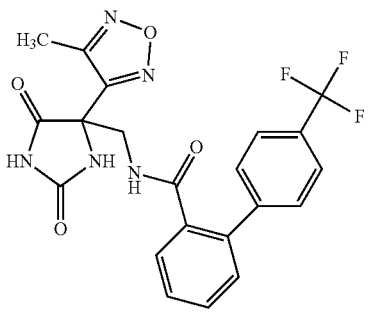 [SMILES: Cc1nonc1C1(CNC(=O)c2ccccc2-c2ccc(C(F)(F)F)cc2)NC(=O)NC1=O]

Enantiomeric separation of rac-N-{[4-(4-methyl-1,2,5-oxadiazol-3-yl)-2,5-dioxoimidazolidin-4 yl]methyl}-4'-(trifluoromethyl)[biphenyl]-2-carboxamide (36.0 mg, 78.4 µmol) was done using the following method:

Column: Daicel Chiralpak ID 5 µm 250×20 mm
Solvent: 50% n-heptane: 50% iso-propanol
Flow: 20 ml/min
Oven temperature: 40° C.
UV: 210 nm Product containing samples were united, the solvents were evaporated and the residue was lyophilized. 11.0 mg (100% purity, 31% yield) of the title compound were obtained.

LC-MS (Method 7): $R_t$=1.73 min; MS (ESIpos): m/z=460 [M+H]$^+$

Chiral HPLC (Daicel Chiralpak ID-3 3 µm, 50×4.6 mm, 220 nm, 1 ml/min, 220 nm, 50% n-heptane: 50% iso-propanol): $R_t$=4.645 min, 100% ee $^1$H-NMR (600 MHz, DMSO-d6) δ [ppm]: 2.362 (16.00), 2.385 (0.43), 2.423 (0.43), 2.572 (1.30), 2.574 (1.30), 2.612 (0.48), 2.652 (0.43), 3.278 (2.21), 3.343 (7.11), 4.000 (0.48), 4.013 (1.83), 4.023 (3.12), 4.034 (1.78), 4.046 (0.48), 4.057 (0.43), 7.442 (2.83), 7.456 (4.28), 7.478 (1.20), 7.490 (1.97), 7.503 (0.82), 7.526 (3.12), 7.540 (3.46), 7.558 (1.20), 7.569 (1.73), 7.583 (0.77), 7.748 (3.51), 7.761 (3.12), 8.517 (1.92), 8.838 (0.82), 8.848 (1.59), 8.858 (0.82).

Example 74

Ent-N-{[4-(2,4-Dimethyl-1,3-Thiazol-5-Yl)-2,5-Dioxoimidazolidin-4-Yl]Methyl}-2-[6-(Trifluoromethyl)Pyridin-3-Yl]Benzamide

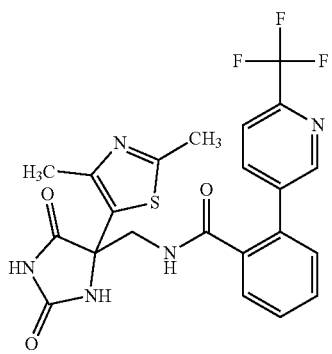 [SMILES: Cc1nc(C)c(C2(CNC(=O)c3ccccc3-c3ccc(C(F)(F)F)nc3)NC(=O)NC2=O)s1]

Enantiomeric separation of rac-N-{[4-(2,4-dimethyl-1,3-thiazol-5-yl)-2,5-dioxoimidazolidin-4 yl]methyl}-2-[6-(trifluoromethyl)pyridin-3-yl]benzamide (103 mg, 210 μmol) was done using the following method:

Column: Daicel Chiralpak IG 5 μm 250×20 mm

Solvent: 60% n-heptane: 40% ethanol

Flow: 20 ml/min

Oven temperature: 50° C.

UV: 220 nm

Product containing samples were united, the solvents were evaporated and the residue was lyophilized. 51.0 mg (100% purity, 50% yield) of the title compound were obtained.

LC-MS (Method 7): $R_t$=1.39 min; MS (ESIpos): m/z=490 [M+H]$^+$

Chiral HPLC (Daicel Chiralpak IG 5 μm, 250×4.6 mm, 1 ml/min, 50° C., 60% n-heptane: 40% ethanol): $R_t$=8.602 min, 100% ee $^1$H-NMR (400 MHz, DMSO-d6) δ [ppm]: −0.008 (3.11), 0.008 (3.45), 2.328 (0.90), 2.343 (16.00), 2.366 (0.62), 2.523 (2.72), 2.665 (0.50), 2.670 (0.73), 2.674 (0.50), 2.710 (0.60), 3.827 (2.69), 3.843 (2.60), 7.472 (1.16), 7.475 (1.24), 7.491 (1.94), 7.521 (1.38), 7.537 (2.54), 7.540 (3.04), 7.555 (1.99), 7.559 (1.53), 7.574 (1.09), 7.577 (0.85), 7.599 (1.43), 7.603 (1.40), 7.618 (1.56), 7.621 (1.56), 7.637 (0.59), 7.640 (0.52), 7.908 (2.51), 7.914 (5.53), 7.916 (4.23), 7.934 (0.49), 8.496 (2.41), 8.722 (2.46), 8.787 (0.70), 8.803 (1.56), 8.818 (0.73), 11.154 (2.15).

Example 75

4-Chloro-N-{[(4R)-4-Cyclopropyl-2,5-Dioxoimidazolidin-4-Yl]Methyl}-2-[6-(Trifluoromethyl)Pyridin-3-Yl]Benzamide

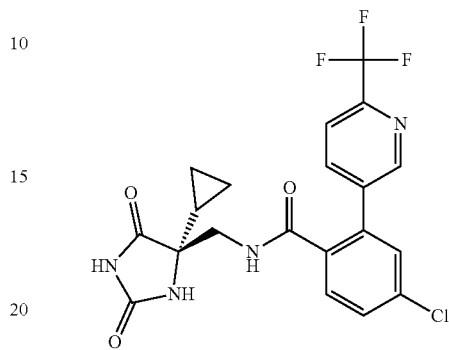

4-chloro-2-[6-(trifluoromethyl)pyridin-3-yl]benzoic acid (47.0 mg, 156 μmol) dissolved in 1.5 ml of DMF was treated with N-ethyl-N-isopropylpropan-2-amine (76 μl, 440 μmol), 3-{[(ethylimino)methylene]amino}-N,N-dimethylpropan-1-amine hydrochloride (38.8 mg, 203 μmol), 1H-benzotriazol-1-ol hydrate (31.0 mg, 203 μmol) and (5R)-5-(aminomethyl)-5-cyclopropylimidazolidine-2,4-dione hydrogen chloride (32.0 mg, 156 μmol). The mixture was stirred over night at room temperature. The product was purified by preparative HPLC (Instrument: Waters Prep LC/MS System, Column: Phenomenex Kinetex C18 5 μm 100×30 mm; eluent A: water, eluent B: acetonitrile, eluent C: 2% formic acid in water, eluent D: acetonitrile/water (80 Vol. %/20 Vol. %); flow: 80 ml/min, room temperature, UV-detection: 200-400 nm, At-Column Injektion; gradient: eluent A 0 bis 2 min 63 ml, eluent B 0 to 2 min 7 ml, eluent A 2 to 10 min from 63 ml to 39 ml and eluent B from 7 ml to 31 ml, 10 to 12 min 0 ml eluent A and 70 ml eluent B. Eluent C and eluent D constant flow 5 ml/min over the whole runtime). After lyophilization, 53.0 mg (100% purity, 75% yield) of the title compound were obtained.

LC-MS (Method 7): $R_t$=1.55 min; MS (ESIpos): m/z=453 [M+H]$^+$ $^1$H-NMR (400 MHz, DMSO-d6) δ [ppm]: 0.102 (0.57), 0.115 (1.27), 0.126 (2.35), 0.139 (2.48), 0.150 (1.78), 0.163 (0.83), 0.288 (0.44), 0.311 (1.46), 0.323 (1.84), 0.334 (1.71), 0.345 (1.40), 0.356 (1.08), 0.365 (0.95), 0.375 (1.52), 0.390 (1.65), 0.398 (2.16), 0.411 (1.71), 0.419 (1.02), 0.428 (1.08), 0.442 (1.90), 0.453 (2.35), 0.466 (2.22), 0.478 (1.40), 0.491 (0.51), 1.044 (0.76), 1.058 (1.52), 1.065 (1.65), 1.078 (2.92), 1.091 (1.52), 1.099 (1.40), 1.112 (0.63), 2.328 (0.51), 2.366 (0.38), 2.670 (0.57), 2.710 (0.38), 3.446 (1.02), 3.461 (1.21), 3.480 (4.00), 3.497 (6.10), 3.514 (3.94), 3.532 (1.14), 3.548 (1.14), 7.508 (6.79), 7.514 (1.65), 7.523 (2.16), 7.529 (9.14), 7.577 (8.95), 7.632 (4.38), 7.638 (7.68), 7.648 (9.02), 7.654 (16.00), 7.938 (3.05), 7.956 (8.83), 7.975 (5.21), 7.980 (4.95), 7.995 (1.71), 8.000 (1.78), 8.677 (1.90), 8.693 (4.00), 8.708 (1.90), 8.759 (6.03), 8.764 (5.78), 10.651 (4.13).

Example 76

N-{[(4R)-4-Cyclopropyl-2,5-Dioxoimidazolidin-4-Yl]Methyl}-3,4-Difluoro-2-[6-(Trifluoromethyl)Pyridin-3-Yl]Benzamide

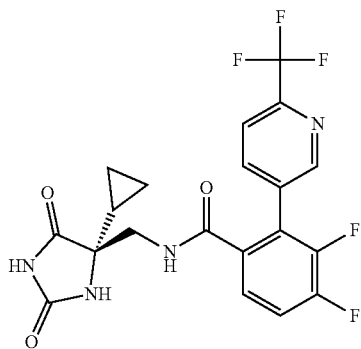 [SMILES: O=C1NC(=O)[C@](CNC(=O)c2ccc(F)c(F)c2-c2ccc(C(F)(F)F)nc2)(C2CC2)N1]

3,4-difluoro-2-[6-(trifluoromethyl)pyridin-3-yl]benzoic acid (21.0 mg, 69.3 μmol) dissolved in 1.5 ml of DMF was treated with N-ethyl-N-isopropylpropan-2-amine (34 μl, 190 μmol), 3-{[(ethylimino)methylene]amino}-N,N-dimethylpropan-1-amine hydrochloride (17.3 mg, 90.0 μmol), 1H-benzotriazol-1-ol hydrate (13.8 mg, 90.0 μmol) and (5R)-5-(aminomethyl)-5-cyclopropylimidazolidine-2,4-dione hydrogen chloride (14.2 mg, 69.3 μmol). The mixture was stirred over night at room temperature. The product was purified by preparative HPLC (Instrument: Waters Prep LC/MS System, Column: Phenomenex Kinetex C18 5 μm 100×30 mm; eluent A: water, eluent B: acetonitrile, eluent C: 2% formic acid in water, eluent D: acetonitrile/water (80 Vol. %/20 Vol. %); flow: 80 ml/min, room temperature, UV-detection: 200-400 nm, At-Column Injektion; gradient: eluent A 0 bis 2 min 63 ml, eluent B 0 to 2 min 7 ml, eluent A 2 to 10 min from 63 ml to 39 ml and eluent B from 7 ml to 31 ml, 10 to 12 min 0 ml eluent A and 70 ml eluent B. Eluent C and eluent D constant flow 5 ml/min over the whole runtime). After lyophilization, 18.0 mg (100% purity, 57% yield) of the title compound were obtained.

LC-MS (Method 8): $R_t$=0.79 min; MS (ESIpos): m/z=455 [M+H]$^+$ $^1$H-NMR (600 MHz, DMSO-d6) δ [ppm]: 0.107 (0.72), 0.116 (1.51), 0.123 (2.69), 0.132 (2.77), 0.139 (1.89), 0.149 (0.91), 0.287 (0.62), 0.294 (0.90), 0.296 (0.93), 0.302 (1.66), 0.309 (2.09), 0.317 (1.82), 0.323 (1.31), 0.325 (1.44), 0.332 (1.07), 0.356 (0.94), 0.364 (1.63), 0.371 (1.65), 0.373 (1.70), 0.379 (2.39), 0.388 (1.87), 0.393 (1.08), 0.402 (0.72), 0.419 (0.97), 0.428 (2.03), 0.436 (2.67), 0.444 (2.53), 0.452 (1.67), 0.461 (0.61), 1.030 (0.93), 1.038 (1.84), 1.043 (1.95), 1.047 (1.27), 1.052 (3.45), 1.057 (1.27), 1.061 (1.78), 1.066 (1.69), 1.074 (0.75), 2.516 (0.47), 2.519 (0.46), 3.267 (0.62), 3.414 (1.48), 3.424 (1.70), 3.436 (4.80), 3.447 (4.55), 3.452 (4.70), 3.463 (4.69), 3.475 (1.56), 3.486 (1.48), 7.390 (1.97), 7.397 (2.12), 7.404 (2.35), 7.411 (2.28), 7.542 (10.01), 7.664 (1.23), 7.678 (2.31), 7.694 (2.41), 7.708 (1.26), 7.993 (1.10), 7.995 (1.44), 8.007 (11.73), 8.009 (16.00), 8.013 (7.39), 8.023 (0.85), 8.026 (0.98), 8.638 (2.14), 8.649 (4.36), 8.659 (2.16), 8.747 (6.38), 10.571 (0.49).

Example 77

Rac-N-{[4-(4-Methyl-1,2-Oxazol-5-Yl)-2,5-Dioxoimidazolidin-4-Yl]Methyl}-2-[6-(Trifluoromethyl)Pyridin-3-Yl]Benzamide

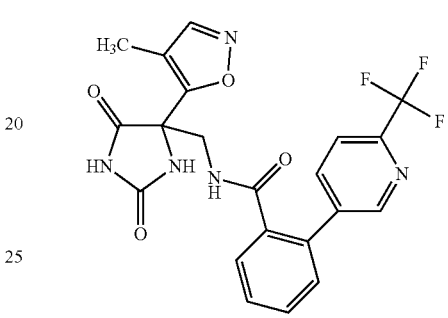

2-[6-(trifluoromethyl)pyridin-3-yl]benzoic acid (103 mg, 385 μmol) dissolved in 1.5 ml of DMF was treated with N-ethyl-N-isopropylpropan-2-amine (200 μl, 1.2 mmol), 3-{[(ethylimino)methylene]amino}-N,N-dimethylpropan-1-amine hydrochloride (96.0 mg, 501 μmol), 1H-benzotriazol-1-ol hydrate (76.7 mg, 501 μmol) and rac-5-(aminomethyl)-5-(4-methyl-1,2-oxazol-5-yl)imidazolidine-2,4-dione hydrochloride (100 mg, 95% purity, 385 μmol). The mixture was stirred over night at room temperature. The product was purified by preparative HPLC (Instrument: Waters Prep LC/MS System, Column: Phenomenex Kinetex C18 5 μm 100×30 mm; eluent A: water, eluent B: acetonitrile, eluent C: 2% formic acid in water, eluent D: acetonitrile/water (80 Vol. %/20 Vol. %); flow: 80 ml/min, room temperature, UV-detection: 200-400 nm, At-Column Injektion; gradient: eluent A 0 bis 2 min 63 ml, eluent B 0 to 2 min 7 ml, eluent A 2 to 10 min from 63 ml to 39 ml and eluent B from 7 ml to 31 ml, 10 to 12 min 0 ml eluent A and 70 ml eluent B. Eluent C and eluent D constant flow 5 ml/min over the whole runtime). After lyophilization, 72.0 mg (100% purity, 41% yield) of the title compound were obtained.

LC-MS (Method 7): $R_t$=1.37 min; MS (ESIpos): m/z=460 [M+H]$^+$ $^1$H-NMR (400 MHz, DMSO-d6) δ [ppm]: 0.008 (0.43), 1.999 (16.00), 2.073 (5.01), 3.959 (3.05), 3.974 (3.12), 7.475 (1.13), 7.478 (1.17), 7.494 (2.05), 7.526 (1.44), 7.533 (1.03), 7.537 (1.16), 7.544 (2.46), 7.552 (2.18), 7.571 (1.06), 7.599 (1.36), 7.603 (1.41), 7.618 (1.45), 7.621 (1.53), 7.636 (0.54), 7.640 (0.52), 7.914 (0.59), 7.934 (4.37), 7.942 (2.50), 7.962 (0.41), 8.484 (5.20), 8.594 (3.18), 8.726 (2.43), 8.841 (0.74), 8.856 (1.60), 8.872 (0.74), 11.262 (1.49).

Example 78

Ent-N-{[4-(4-Methyl-1,2-Oxazol-5-Yl)-2,5-Dioxo-imidazolidin-4-Yl]Methyl}-2-[6-(Trifluoromethyl)Pyridin-3-Yl]Benzamide

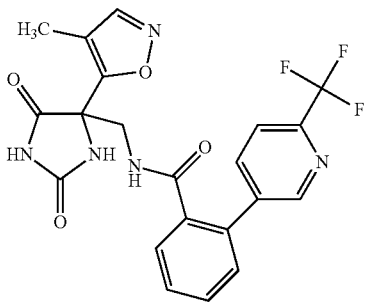

Enantiomeric separation of rac-N-{[4-(4-methyl-1,2-oxazol-5-yl)-2,5-dioxoimidazolidin-4 yl]methyl}-2-[6-(trifluoromethyl)pyridin-3-yl]benzamide (62.0 mg, 135 µmol) was done using the following method:
Column: Daicel Chiralpak IE 5 µm 250×20 mm
Solvent: 70% n-heptane: 30% ethanol
Flow: 20 ml/min
Oven temperature: 50° C.
UV: 220 nm
Product containing samples were united, the solvents were evaporated and the residue was lyophilized. 23.0 mg (100% purity, 37% yield) of the title compound were obtained.
LC-MS (Method 7): $R_t$=1.37 min; MS (ESIpos): m/z=460 [M+H]$^+$
Chiral HPLC (Column: Daicel IE-3 3 µm, 50×4.6 mm, 220 nm, solvent: 70% n-heptane: 30% ethanol): $R_t$=2.825 min, 97.78% ee
$^1$H-NMR (600 MHz, DMSO-d6) δ [ppm]: 2.000 (16.00), 2.514 (0.41), 3.960 (3.25), 3.970 (3.24), 7.479 (1.20), 7.481 (1.25), 7.491 (1.81), 7.493 (1.74), 7.525 (1.45), 7.538 (2.88), 7.550 (1.87), 7.552 (1.53), 7.563 (0.95), 7.565 (0.78), 7.602 (1.21), 7.605 (1.21), 7.615 (1.65), 7.617 (1.61), 7.627 (0.64), 7.629 (0.60), 7.915 (1.04), 7.928 (2.99), 7.939 (1.81), 7.942 (1.71), 7.953 (0.57), 7.956 (0.61), 8.475 (5.18), 8.567 (2.24), 8.569 (2.23), 8.722 (2.02), 8.725 (1.98), 8.816 (0.73), 8.826 (1.52), 8.837 (0.72), 11.242 (1.86).

Example 79

Ent-5-Chloro-N-{[4-(1,5-Dimethyl-1H-Pyrazol-4-Yl)-2,5-Dioxoimidazolidin-4-Yl]Methyl}-4'-(Trifluoromethyl)[Biphenyl]-2-Carboxamide

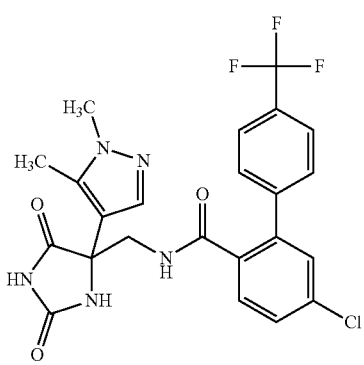 [SMILES: Cc1c(C2(CNC(=O)c3ccc(Cl)cc3-c3ccc(C(F)(F)F)cc3)NC(=O)NC2=O)cnn1C]

Enantiomeric separation of rac-5-chloro-N-{[4-(1,5-dimethyl-1H-pyrazol-4-yl)-2,5-dioxoimidazolidine-4-yl]methyl}-4'-(trifluoromethyl)[biphenyl]-2-carboxamide (123 mg, 243 µmol) was done using the following method:
Column: Daicel Chiralpak IE 5 µm 250×20 mm
Solvent: 70% n-heptane: 30% ethanol
Flow: 20 ml/min
Oven temperature: 50° C.
UV: 220 nm
Product containing samples were united, the solvents were evaporated and the residue was lyophilized. 53.0 mg (100% purity, 43% yield) of the title compound were obtained.
LC-MS (Method 7): $R_t$=1.66 min; MS (ESIpos): m/z=506 [M+H]$^+$
Chiral HPLC (Column: Daicel IE-3 3 µm, 50×4.6 mm, 220 nm, solvent: 70% n-heptane: 30% ethanol): $R_t$=3.474 min, 97.08% ee
$^1$H-NMR (600 MHz, DMSO-d6) δ [ppm]: 2.248 (15.56), 2.422 (0.45), 2.464 (0.65), 2.514 (1.01), 2.517 (0.87), 2.520 (0.78), 2.570 (0.45), 2.651 (0.44), 3.262 (1.02), 3.699 (16.00), 3.728 (0.45), 3.739 (0.47), 3.751 (1.54), 3.762 (2.79), 3.772 (1.66), 3.786 (0.46), 7.367 (5.40), 7.411 (2.84), 7.424 (3.34), 7.513 (3.10), 7.516 (3.56), 7.558 (4.31), 7.560 (3.50), 7.571 (4.31), 7.755 (3.25), 7.769 (2.89), 8.164 (2.42), 8.167 (2.37), 8.675 (0.76), 8.685 (1.54), 8.696 (0.76), 10.863 (2.08).

Example 80

Ent-N-{[4-(1-Ethyl-1H-Pyrazol-5-Yl)-2,5-Dioxoimidazolidin-4-Yl]Methyl}-4'-(Trifluoromethyl)[Biphenyl]-2-Carboxamide

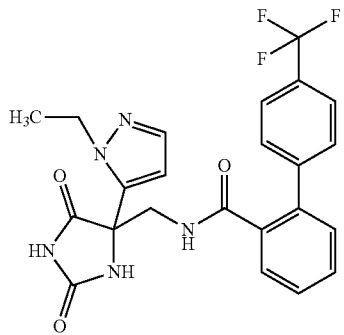 [SMILES: CCn1nccc1C1(CNC(=O)c2ccccc2-c2ccc(C(F)(F)F)cc2)NC(=O)NC1=O]

Enantiomeric separation of rac-5 N-{[4-(1-ethyl-1H-pyrazol-5-yl)-2,5-dioxoimidazolidin-4 yl]methyl}-4'-(trifluoromethyl)[biphenyl]-2-carboxamide (500 mg, 1.06 mmol) was done using the following method:
Column: Daicel Chiralpak IC 5 µm 250×20 mm
Solvent: 80% CO$_2$: 20% methanol
Flow: 140 ml/min
Backpressure: 100 bar
Oven temperature: 40° C.
UV: 210 nm
Product containing samples were united, the solvents were evaporated and the residue was lyophilized. 95.0 mg (100% purity, 19% yield) of the title compound were obtained.
LC-MS (Method 7): $R_t$=1.60 min; MS (ESIpos): m/z=472 [M+H]$^+$ Chiral HPLC (Column: IC, 250×4.6 mm, 210 nm, solvent: 70% CO$_2$: 30% methanol): R$_t$=2.903 min, 98.3% ee $^1$H-NMR (600 MHz, DMSO-d6) δ [ppm]: 1.294 (7.38), 1.306 (16.00), 1.318 (7.30), 2.517 (0.54), 2.520 (0.44), 3.865 (1.17), 3.874 (1.32), 3.887 (2.52), 3.897 (2.22), 3.921 (2.36), 3.932 (2.47), 3.943 (1.24), 3.955 (1.16), 4.012 (0.45), 4.023 (1.35), 4.029 (1.08), 4.035 (3.31), 4.041 (3.19), 4.047 (3.20), 4.053 (3.21), 4.059 (1.07), 4.064 (1.30), 4.076 (0.45), 6.447 (6.28), 6.451 (6.35), 7.431 (7.15), 7.434 (11.71), 7.447 (6.96), 7.449 (7.43), 7.471 (2.05), 7.473 (1.91), 7.484 (3.45), 7.498 (1.46), 7.535 (5.26), 7.549 (6.27), 7.562 (3.09), 7.565 (2.87), 7.575 (1.11), 7.577 (1.28), 7.747 (6.04), 7.761 (5.32), 8.413 (6.41), 8.733 (1.41), 8.744 (2.74), 8.755 (1.39), 11.238 (1.19).

Example 81

Rac-N-[(4-Ethyl-2,5-Dioxoimidazolidin-4-Yl)Methyl]-4'-(Trifluoromethyl)[Biphenyl]-2-Carboxamide

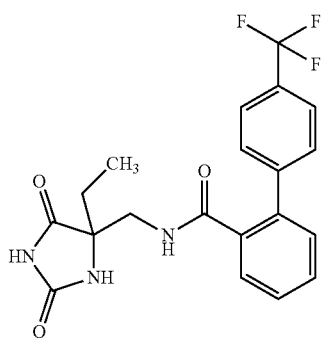 [SMILES: CCC1(CNC(=O)c2ccccc2-c2ccc(C(F)(F)F)cc2)NC(=O)NC1=O]

4'-(trifluoromethyl)[1,1'-biphenyl]-2-carboxylicacid (84.7 mg, 318 µmol) dissolved in 2 ml of DMF was treated with N-ethyl-N-isopropylpropan-2-amine (160 µl, 890 µmol), 3-{[(ethylimino)methylene]amino}-N,N-dimethylpropan-1-amine hydrochloride (79.3 mg, 414 µmol), 1H-benzotriazol-1-ol hydrate (63.3 mg, 414 µmol) and rac-5-(aminomethyl)-5-ethylimidazolidine-2,4-dione hydrochloride (50.0 mg, 258 µmol). The mixture was stirred for 2 h at room temperature. The product was purified by preparative HPLC (Instrument: Waters Prep LC/MS System, Column: Phenomenex Kinetex C18 5 µm 100×30 mm; eluent A: water, eluent B: acetonitrile, eluent C: 2% formic acid in water, eluent D: acetonitrile/water (80 Vol. %/20 Vol. %); flow: 80 ml/min, room temperature, UV-detection: 200-400 nm, At-Column Injektion; gradient: eluent A 0 bis 2 min 55 ml, eluent B 0 to 2 min 15 ml, eluent A 2 to 10 min from 55 ml to 31 ml and eluent B from 15 ml to 39 ml, 10 to 12 min 0 ml eluent A and 70 ml eluent B. Eluent C and eluent D constant flow 5 ml/min over the whole runtime). After lyophilization, 81.0 mg (99% purity, 62% yield) of the title compound were obtained.

LC-MS (Method 7): R$_t$=1.56 min; MS (ESIpos): m/z=406 [M+H]$^+$ $^1$H-NMR (400 MHz, DMSO-d6) δ [ppm]: −0.008 (0.44), 0.008 (0.50), 0.722 (6.54), 0.740 (16.00), 0.758 (7.30), 1.411 (0.41), 1.430 (1.37), 1.448 (1.89), 1.465 (2.69), 1.483 (2.20), 1.501 (0.57), 1.524 (0.64), 1.542 (2.32), 1.560 (2.69), 1.577 (1.94), 1.596 (1.33), 2.072 (1.04), 2.523 (1.23), 3.340 (3.60), 3.355 (3.14), 3.393 (3.10), 3.410 (3.26), 3.427 (1.69), 3.444 (1.60), 7.427 (4.58), 7.446 (5.73), 7.460 (8.96), 7.462 (9.82), 7.468 (6.79), 7.474 (6.06), 7.477 (4.70), 7.493 (1.22), 7.496 (1.09), 7.519 (0.55), 7.530 (3.43), 7.537 (3.04), 7.545 (2.43), 7.549 (3.14), 7.558 (7.86), 7.579 (8.51), 7.634 (8.67), 7.752 (8.93), 7.772 (7.29), 8.489 (1.76), 8.505 (3.49), 8.520 (1.76), 10.677 (1.38).

Example 82

N-{[(4R)-4-Cyclopropyl-2,5-Dioxoimidazolidin-4-Yl]Methyl}-2-[4-(Trifluoromethyl)Phenyl]Pyridine-3-Carboxamide

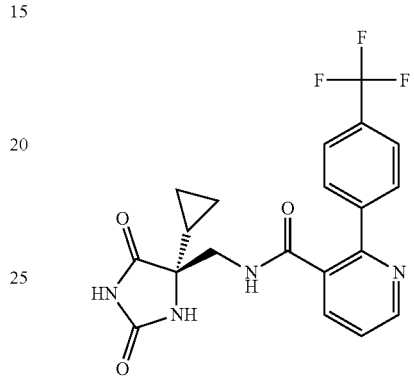

2-[4-(trifluoromethyl)phenyl]pyridine-3-carboxylic acid (20.0 mg, 70% purity, 52.4 µmol) dissolved in 1.5 ml of DMF was treated with N-ethyl-N-isopropylpropan-2-amine (26 µl, 150 µmol), 3-{[(ethylimino)methylene]amino}-N,N-dimethylpropan-1-amine hydrochloride (13.1 mg, 68.1 µmol), 1H-benzotriazol-1-ol hydrate (10.4 mg, 68.1 µmol) and (5R)-5-(aminomethyl)-5-cyclopropylimidazolidine-2,4-dione hydrogen chloride (10.8 mg, 52.4 µmol). The mixture was stirred over night at room temperature. The product was purified by preparative HPLC (Instrument: Waters Prep LC/MS System, Column: Phenomenex Kinetex C18 5 µm 100×30 mm; eluent A: water, eluent B: acetonitrile, eluent C: 2% formic acid in water, eluent D: acetonitrile/water (80 Vol. %/20 Vol. %); flow: 80 ml/min, room temperature, UV-detection: 200-400 nm, At-Column Injektion; gradient: eluent A 0 bis 2 min 63 ml, eluent B 0 to 2 min 7 ml, eluent A 2 to 10 min from 63 ml to 39 ml and eluent B from 7 ml to 31 ml, 10 to 12 min 0 ml eluent A and 70 ml eluent B. Eluent C and eluent D constant flow 5 ml/min over the whole runtime). After lyophilization, 9.00 mg (100% purity, 41% yield) of the title compound were obtained.

LC-MS (Method 7): R$_t$=1.32 min; MS (ESIpos): m/z=419 [M+H]$^+$ $^1$H-NMR (400 MHz, DMSO-d6) δ [ppm]: −0.008 (1.04), 0.008 (0.97), 0.151 (0.57), 0.164 (0.58), 0.175 (0.40), 0.344 (0.44), 0.353 (0.42), 0.421 (0.53), 0.475 (0.45), 0.486 (0.56), 0.499 (0.54), 1.097 (0.40), 1.110 (0.68), 2.327 (0.49), 2.366 (0.42), 2.523 (2.09), 2.669 (0.52), 2.710 (0.40), 3.565 (1.93), 3.580 (1.98), 7.493 (1.04), 7.505 (1.08), 7.512 (1.17), 7.524 (1.19), 7.632 (1.50), 7.797 (1.32), 7.801 (1.62), 7.809 (16.00), 7.816 (1.91), 7.820 (1.46), 8.736 (1.10), 8.741 (1.19), 8.748 (1.17), 8.752 (1.10), 8.808 (0.44), 8.824 (0.94), 8.840 (0.46), 10.670 (1.24).

Example 83

N-{[(4R)-4-Cyclopropyl-2,5-Dioxoimidazolidin-4-Yl]Methyl}-3-[4-(Trifluoromethyl)Phenyl]Pyridine-4-Carboxamide

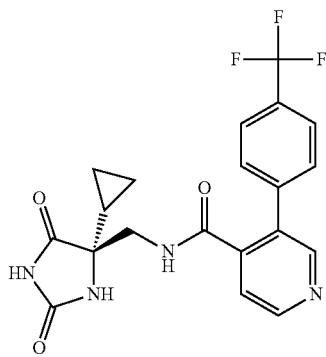 [SMILES: O=C1NC(=O)[C@](CNC(=O)c2ccncc2-c2ccc(C(F)(F)F)cc2)(C2CC2)N1]

3-[4-(trifluoromethyl)phenyl]pyridine-4-carboxylic acid (47.0 mg, 176 μmol) dissolved in 1.5 ml of DMF was treated with N-ethyl-N-isopropylpropan-2-amine (86 μl, 490 μmol), 3-{[(ethylimino)methylene]amino}-N,N-dimethylpropan-1-amine hydrochloride (43.8 mg, 229 μmol), 1H-benzotriazol-1-ol hydrate (35.0 mg, 229 μmol) and (5R)-5-(aminomethyl)-5-cyclopropylimidazolidine-2,4-dione hydrogen chloride (36.2 mg, 176 μmol). The mixture was stirred over night at room temperature. The product was purified by preparative HPLC (Instrument: Waters Prep LC/MS System, Column: Phenomenex Kinetex C18 5 μm 100×30 mm; eluent A: water, eluent B: acetonitrile, eluent C: 2% formic acid in water, eluent D: acetonitrile/water (80 Vol. %/20 Vol. %); flow: 80 ml/min, room temperature, UV-detection: 200-400 nm, At-Column Injektion; gradient: eluent A 0 bis 2 min 63 ml, eluent B 0 to 2 min 7 ml, eluent A 2 to 10 min from 63 ml to 39 ml and eluent B from 7 ml to 31 ml, 10 to 12 min 0 ml eluent A and 70 ml eluent B. Eluent C and eluent D constant flow 5 ml/min over the whole runtime). After lyophilization, 43.0 mg (100% purity, 58% yield) of the title compound were obtained.

LC-MS (Method 7): $R_t$=1.33 min; MS (ESIpos): m/z=419 [M+H]$^+$ $^1$H-NMR (400 MHz, DMSO-d6) δ [ppm]: −0.008 (1.56), 0.008 (1.71), 0.118 (0.61), 0.132 (1.51), 0.143 (2.66), 0.156 (2.83), 0.166 (1.97), 0.180 (0.88), 0.298 (0.52), 0.321 (1.68), 0.333 (2.09), 0.342 (1.97), 0.355 (1.58), 0.366 (1.27), 0.373 (1.10), 0.384 (1.62), 0.398 (1.88), 0.407 (2.44), 0.420 (1.86), 0.428 (1.04), 0.442 (0.78), 0.449 (1.02), 0.462 (2.07), 0.474 (2.64), 0.487 (2.55), 0.498 (1.58), 0.512 (0.56), 1.050 (0.86), 1.063 (1.75), 1.071 (1.92), 1.084 (3.32), 1.097 (1.77), 1.105 (1.58), 1.118 (0.69), 2.323 (0.60), 2.327 (0.84), 2.332 (0.63), 2.366 (0.61), 2.523 (3.02), 2.665 (0.61), 2.670 (0.84), 2.674 (0.61), 2.710 (0.54), 3.490 (0.50), 3.507 (0.56), 3.525 (5.81), 3.530 (5.96), 3.545 (6.52), 3.564 (0.65), 3.579 (0.47), 7.381 (7.77), 7.394 (7.93), 7.623 (16.00), 7.643 (10.26), 7.808 (10.52), 7.829 (8.64), 8.683 (15.61), 8.698 (11.59), 8.711 (10.95), 8.827 (2.12), 8.843 (4.53), 8.858 (2.10), 10.675 (6.37).

Example 84

N-{[(4R)-4-Cyclopropyl-2,5-Dioxoimidazolidin-4-Yl]Methyl}-2-[5-(Trifluoromethyl)Pyridin-2-Yl]Benzamide

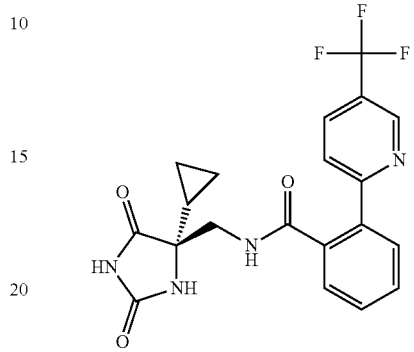

2-[5-(trifluoromethyl)pyridin-2-yl]benzoic acid (27.0 mg, 75% purity, 75.8 μmol) dissolved in 1.5 ml of DMF was treated with N-ethyl-N-isopropylpropan-2-amine (37 μl, 210 μmol), 3-{[(ethylimino)methylene]amino}-N,N-dimethylpropan-1-amine hydrochloride (18.9 mg, 98.5 μmol), 1H-benzotriazol-1-ol hydrate (15.1 mg, 98.5 μmol) and (5R)-5-(aminomethyl)-5-cyclopropylimidazolidine-2,4-dione hydrogen chloride (15.6 mg, 75.8 μmol). The mixture was stirred at room temperature for 3 h. The product was purified by preparative HPLC (Instrument: Waters Prep LC/MS System, Column: Phenomenex Kinetex C18 5 μm 100×30 mm; eluent A: water, eluent B: acetonitrile, eluent C: 2% formic acid in water, eluent D: acetonitrile/water (80 Vol. %/20 Vol. %); flow: 80 ml/min, room temperature, UV-detection: 200-400 nm, At-Column Injektion; gradient: eluent A 0 bis 2 min 63 ml, eluent B 0 to 2 min 7 ml, eluent A 2 to 10 min from 63 ml to 39 ml and eluent B from 7 ml to 31 ml, 10 to 12 min 0 ml eluent A and 70 ml eluent B. Eluent C and eluent D constant flow 5 ml/min over the whole runtime). After lyophilization, 18.0 mg (100% purity, 57% yield) of the title compound were obtained.

LC-MS (Method 7): $R_t$=1.35 min; MS (ESIpos): m/z=419 [M+H]$^+$ $^1$H-NMR (400 MHz, DMSO-d6) δ [ppm]: −0.008 (2.05), 0.008 (1.92), 0.115 (0.94), 0.129 (2.13), 0.140 (3.81), 0.153 (3.97), 0.163 (2.82), 0.177 (1.31), 0.303 (0.78), 0.325 (2.37), 0.338 (3.03), 0.349 (2.82), 0.360 (2.21), 0.371 (1.64), 0.391 (1.35), 0.402 (2.37), 0.416 (2.58), 0.424 (3.56), 0.438 (2.86), 0.449 (2.33), 0.464 (3.40), 0.475 (3.76), 0.488 (3.60), 0.499 (2.21), 0.513 (0.74), 1.087 (1.27), 1.101 (2.58), 1.108 (2.70), 1.121 (4.79), 1.134 (2.54), 1.142 (2.29), 1.155 (1.02), 2.327 (1.47), 2.332 (1.06), 2.366 (0.90), 2.523 (4.75), 2.665 (1.10), 2.669 (1.47), 2.674 (1.15), 2.710 (0.94), 3.504 (1.60), 3.519 (1.84), 3.539 (6.71), 3.554 (11.50), 3.571 (6.63), 3.589 (1.80), 3.605 (1.68), 7.488 (3.97), 7.492 (5.57), 7.502 (16.00), 7.510 (10.93), 7.520 (4.99), 7.524 (5.07), 7.538 (8.10), 7.542 (7.65), 7.557 (4.01), 7.560 (3.97), 7.568 (5.16), 7.573 (4.71), 7.587 (7.16), 7.591 (7.16), 7.605 (3.48), 7.609 (3.23), 7.683 (8.72), 7.686 (8.18), 7.694 (8.88), 7.702 (7.04), 7.705 (6.22), 7.715 (8.88), 8.208 (5.16), 8.214 (5.20), 8.229 (4.87), 8.235 (4.83), 8.584 (3.03), 8.599 (6.34), 8.615 (3.03), 8.989 (8.27), 10.631 (2.50).

Example 85

Ent-N-{[4-(4-Methyl-1,2,5-Thiadiazol-3-Yl)-2,5-Dioxoimidazolidin-4-Yl]Methyl}-4'-(Trifluoromethyl)[Biphenyl]-2-Carboxamide

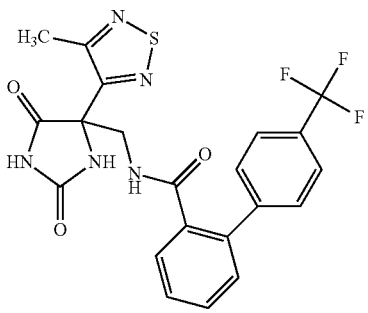 [SMILES: Cc1nsnc1C1(CNC(=O)c2ccccc2-c2ccc(C(F)(F)F)cc2)NC(=O)NC1=O]

Enantiomeric separation of rac-N-{[4-(4-methyl-1,2,5-thiadiazol-3-yl)-2,5-dioxoimidazolidin-4 yl]methyl}-4'-(trifluoromethyl)[biphenyl]-2-carboxamide (22.0 mg, 46.3 μmol) was done using the following chiral HPLC method:
Column: Daicel Chiralpak ID 5 μm 250×20 mm
Solvent: 50% n-heptane: 50% iso-propanol
Flow: 20 ml/min
Oven temperature: 40° C.
UV: 210 nm
Product containing samples were united, the solvents were evaporated and the residue was lyophilized. 7.00 mg (100% purity, 32% yield) of the title compound were obtained.
LC-MS (Method 7): $R_t$=1.70 min; MS (ESIpos): m/z=476 [M+H]$^+$
Chiral HPLC (Column: Daicel Chiralpak ID-3 3 μm, 50×4.6 mm, 220 nm, solvent: 50% n-heptane: 50% iso-propanol): $R_t$=1.862 min, 99% ee
$^1$H-NMR (600 MHz, DMSO-d6) δ [ppm]: 2.386 (0.72), 2.426 (0.86), 2.475 (16.00), 2.615 (0.86), 2.655 (0.86), 4.129 (4.02), 4.140 (3.95), 7.441 (1.58), 7.453 (4.52), 7.464 (2.65), 7.477 (1.43), 7.489 (2.22), 7.502 (1.00), 7.558 (4.88), 7.571 (5.52), 7.769 (4.09), 7.782 (3.66), 8.421 (3.37), 8.824 (1.00), 8.835 (1.94), 8.845 (1.08).

Example 86

Ent-N-{[4-(3-Methyl-1,2-Thiazol-4-Yl)-2,5-Dioxoimidazolidin-4-Yl]Methyl}-4'-(Trifluoromethyl)[Biphenyl]-2-Carboxamide

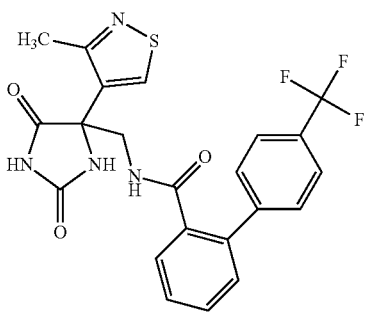 [SMILES: Cc1nscc1C1(CNC(=O)c2ccccc2-c2ccc(C(F)(F)F)cc2)NC(=O)NC1=O]

Enantiomeric separation of rac-N-{[4-(3-methyl-1,2-thiazol-4-yl)-2,5-dioxoimidazolidin-4 yl]methyl}-4'-(trifluoromethyl)[biphenyl]-2-carboxamide (76.0 mg, 160 μmol) was done using the following chiral HPLC method:
Column: Daicel Chiralpak IC-3 5 μm 250×20 mm
Solvent: 80% n-heptane: 20% iso-propanol
Flow: 25 ml/min
Oven temperature: 40° C.
UV: 220 nm
Product containing samples were united, the solvents were evaporated and the residue was lyophilized. 30.0 mg (100% purity, 39% yield) of the title compound were obtained.
LC-MS (Method 7): $R_t$=1.61 min; MS (ESIpos): m/z=475 [M+H]$^+$
Chiral HPLC (Column: Daicel IC-3 3 μm, 50×4.6 mm, 220 nm, solvent: 80% iso-hexane: 20% iso-propanol): $R_t$=1.948 min, >99.5% ee
$^1$H-NMR (600 MHz, DMSO-d6) δ [ppm]: 0.005 (0.99), 1.260 (0.41), 2.386 (0.58), 2.415 (16.00), 2.426 (0.91), 2.517 (1.15), 2.521 (1.24), 2.524 (0.99), 2.615 (0.49), 2.655 (0.74), 3.370 (0.66), 3.380 (0.66), 3.901 (0.74), 3.911 (0.82), 3.923 (1.40), 3.933 (1.24), 3.965 (1.32), 3.977 (1.40), 3.988 (0.82), 3.999 (0.74), 7.428 (1.48), 7.439 (4.04), 7.453 (2.06), 7.474 (1.15), 7.476 (1.07), 7.486 (2.06), 7.488 (1.81), 7.499 (0.99), 7.528 (3.13), 7.542 (3.38), 7.553 (1.32), 7.555 (1.32), 7.565 (1.98), 7.568 (1.81), 7.578 (0.74), 7.580 (0.74), 7.747 (3.55), 7.761 (3.22), 8.294 (3.05), 8.779 (0.82), 8.790 (1.57), 8.800 (0.82), 9.106 (5.20), 11.188 (0.82).

Example 87

Ent-N-{[4-(1,3-Dimethyl-1H-Pyrazol-4-Yl)-2,5-Dioxoimidazolidin-4-Yl]Methyl}-4'-(Trifluoromethyl)[Biphenyl]-2-Carboxamide

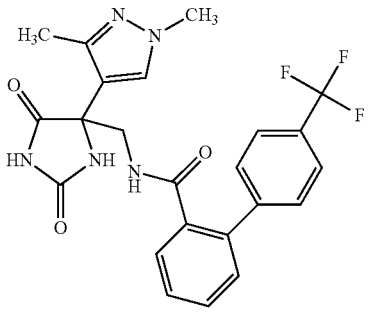 [SMILES: Cc1nn(C)cc1C1(CNC(=O)c2ccccc2-c2ccc(C(F)(F)F)cc2)NC(=O)NC1=O]

Enantiomeric separation of rac-N-{[4-(1,3-dimethyl-1H-pyrazol-4-yl)-2,5-dioxoimidazolidin-4 yl]methyl}-4'-(trifluoromethyl)[biphenyl]-2-carboxamide (83.0 mg, 176 μmol) was done using the following chiral HPLC method:
Column: Daicel Chiralpak ID 5 μm 250×20 mm
Solvent: 60% n-heptane: 40% iso-propanol
Flow: 20 ml/min
Oven temperature: 40° C.
UV: 210 nm
Product containing samples were united, the solvents were evaporated and the residue was lyophilized. 26.0 mg (100% purity, 31% yield) of the title compound were obtained.
LC-MS (Method 7): $R_t$=1.47 min; MS (ESIpos): m/z=472 [M+H]$^+$ Chiral HPLC (Column: Daicel ID-3 3 µm, 50×4.6 mm, 220 nm, solvent: 50% n-heptane: 50% iso-propanol): $R_t$=1.728 min, 99% ee $^1$H-NMR (600 MHz, DMSO-d6) δ [ppm]: 2.107 (15.78), 2.387 (0.41), 2.426 (0.63), 2.615 (0.48), 2.655 (0.56), 3.703 (16.00), 3.766 (3.48), 3.777 (3.41), 7.411 (1.48), 7.423 (2.30), 7.436 (1.89), 7.448 (2.30), 7.462 (1.11), 7.474 (2.07), 7.487 (1.00), 7.524 (3.37), 7.538 (3.78), 7.555 (1.93), 7.567 (0.78), 7.695 (5.37), 7.749 (3.81), 7.763 (3.37), 8.099 (4.22), 8.654 (0.93), 8.664 (1.89), 8.674 (0.93), 10.898 (0.63).

Example 88

Ent-N-{[4-(4-Methyl-1,2-Oxazol-5-Yl)-2,5-Dioxoimidazolidin-4-Yl]Methyl}-4'-(Trifluoromethyl)[Biphenyl]-2-Carboxamide

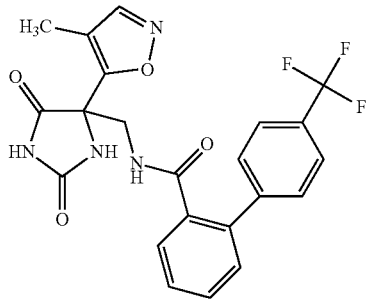 [SMILES: Cc1cnoc1C1(CNC(=O)c2ccccc2-c2ccc(C(F)(F)F)cc2)NC(=O)NC1=O]

Enantiomeric separation of rac-N-{[4-(4-methyl-1,2-oxazol-5-yl)-2,5-dioxoimidazolidin-4-yl]methyl}-4'-(trifluoromethyl)[biphenyl]-2-carboxamide (66.0 mg, 144 µmol) was done using the following chiral HPLC method:

Column: Daicel Chiralpak ID-3 5 µm 250×20 mm

Solvent: 50% n-heptane: 50% iso-propanol

Flow: 20 ml/min

Oven temperature: 40° C.

UV: 220 nm

Product containing samples were united, the solvents were evaporated and the residue was lyophilized. 24.0 mg (100% purity, 36% yield) of the title compound were obtained.

LC-MS (Method 7): $R_t$=1.61 min; MS (ESIpos): m/z=459 [M+H]$^+$

Chiral HPLC (Column: Daicel ID-3 3 µm, 50×4.6 mm, 220 nm, solvent: 50% n-heptane: 50% iso-propanol): $R_t$=2.666 min, 97.2% ee $^1$H-NMR (600 MHz, DMSO-d6) δ [ppm]: 0.005 (0.55), 1.282 (0.87), 2.002 (16.00), 2.426 (0.41), 2.517 (0.73), 2.521 (0.69), 3.309 (0.46), 3.968 (1.83), 3.973 (1.92), 3.978 (1.87), 3.983 (1.87), 7.419 (1.33), 7.429 (2.01), 7.448 (1.60), 7.461 (1.97), 7.471 (1.01), 7.484 (1.87), 7.497 (0.91), 7.537 (2.88), 7.550 (3.29), 7.566 (1.69), 7.568 (1.65), 7.578 (0.73), 7.580 (0.69), 7.761 (3.29), 7.774 (2.88), 8.498 (5.39), 8.603 (3.20), 8.818 (0.82), 8.828 (1.65), 8.839 (0.78).

Example 89

4'-Chloro-N-{[(4R)-4-Cyclopropyl-2,5-Dioxoimidazolidin-4-Yl]Methyl}-5-(Trifluoromethyl)[1,1'-Biphenyl]-2-Carboxamide

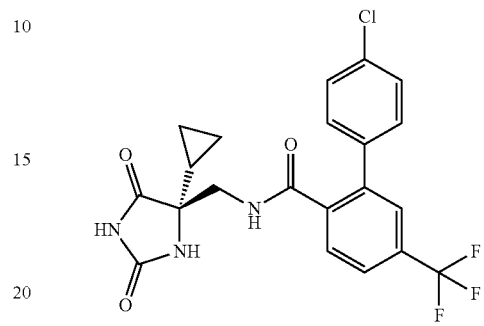

4'-chloro-5-(trifluoromethyl)[1,1'-biphenyl]-2-carboxylic acid (73.1 mg, 243 µmol) dissolved in 2 ml of DMF was treated with N-ethyl-N-isopropylpropan-2-amine (120 µl, 680 µmol), 3-{[(ethylimino)methylene]amino}-N,N-dimethylpropan-1-amine hydrochloride (60.6 mg, 316 µmol), 1H-benzotriazol-1-ol hydrate (48.4 mg, 316 µmol) and (5R)-5-(aminomethyl)-5-cyclopropylimidazolidine-2,4-dione hydrochloride (50.0 mg, 243 µmol). The mixture was stirred for 2.5 h at room temperature. The product was purified by preparative HPLC (Instrument: Waters Prep LC/MS System, Column: Phenomenex Kinetex C18 5 µm 100×30 mm; eluent A: water, eluent B: acetonitrile, eluent C: 2% formic acid in water, eluent D: acetonitrile/water (80 Vol. %/20 Vol %); flow: 80 ml/min, room temperature, UV-detection: 200-400 nm, At-Column Injektion; gradient: eluent A 0 bis 2 min 63 ml, eluent B 0 bis 2 min 7 ml, eluent A 2 bis 10 min from 63 ml to 39 ml and eluent B from 7 ml to 31 ml, 10 to 12 min 0 ml eluent A and 70 ml eluent B. Eluent C and Eluent D constant flow 5 ml/min over the whole runtime). After lyophilization, 45.0 mg (100% purity, 41% yield) of the title compound were obtained.

LC-MS (Method 8): $R_t$=0.93 min; MS (ESIpos): m/z=452 [M+H]$^+$ $^1$H-NMR (400 MHz, DMSO-d6) δ [ppm]: −0.008 (0.58), 0.008 (0.61), 0.115 (0.52), 0.128 (1.20), 0.139 (2.13), 0.152 (2.26), 0.163 (1.58), 0.176 (0.74), 0.301 (0.42), 0.323 (1.33), 0.335 (1.65), 0.346 (1.55), 0.358 (1.26), 0.368 (0.97), 0.379 (0.81), 0.390 (1.36), 0.404 (1.49), 0.412 (1.97), 0.426 (1.55), 0.434 (0.91), 0.445 (1.03), 0.458 (1.68), 0.469 (2.13), 0.482 (2.00), 0.494 (1.23), 0.507 (0.45), 1.047 (0.68), 1.061 (1.42), 1.068 (1.52), 1.073 (1.10), 1.081 (2.65), 1.089 (1.10), 1.094 (1.39), 1.102 (1.26), 1.115 (0.55), 2.323 (0.42), 2.327 (0.61), 2.332 (0.45), 2.524 (2.29), 2.558 (0.68), 2.665 (0.48), 2.670 (0.61), 2.674 (0.48), 3.471 (0.45), 3.486 (0.55), 3.505 (4.43), 3.511 (4.53), 3.521 (4.72), 3.526 (4.82), 3.545 (0.58), 3.560 (0.42), 7.426 (7.66), 7.431 (3.07), 7.442 (4.11), 7.448 (16.00), 7.453 (2.59), 7.483 (2.46), 7.489 (15.97), 7.494 (3.98), 7.505 (3.07), 7.510 (7.79), 7.516 (1.00), 7.571 (4.30), 7.592 (12.48), 7.712 (6.08), 7.815 (3.33), 7.818 (3.30), 7.835 (2.91), 7.838 (2.78), 8.672 (1.75), 8.687 (3.72), 8.702 (1.75), 10.649 (3.46).

Example 90

2-(4-Chlorophenyl)-N-{[(4R)-4-Cyclopropyl-2,5-Dioxoimidazolidin-4-Yl]Methyl}Pyridine-3-Carboxamide

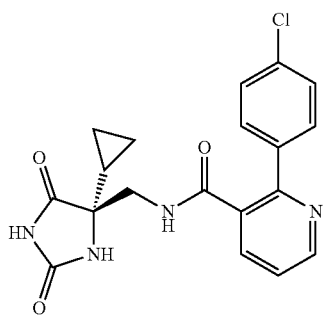 [SMILES: O=C1NC(=O)[C@](CNC(=O)c2cccnc2-c2ccc(Cl)cc2)(C2CC2)N1]

2-(4-chlorophenyl)pyridine-3-carboxylic acid (81.2 mg, 70% purity, 243 μmol) dissolved in 2 ml of DMF was treated with N-ethyl-N-isopropylpropan-2-amine (120 μl, 680 μmol), 3-{[(ethylimino)methylene]amino}-N,N-dimethylpropan-1-amine hydrochloride (60.6 mg, 316 μmol), 1H-benzotriazol-1-ol hydrate (48.4 mg, 316 μmol) and (5R)-5-(aminomethyl)-5-cyclopropylimidazolidine-2,4-dione hydrochloride (50.0 mg, 243 μmol). The mixture was stirred for 5 h at room temperature. The product was purified by preparative HPLC (Instrument: Waters Prep LC/MS System, Column: Phenomenex Kinetex C18 5 μm 100×30 mm; eluent A: water, eluent B: acetonitrile, eluent C: 2% formic acid in water, eluent D: acetonitrile/water (80 Vol. %/20 Vol %); flow: 80 ml/min, room temperature, UV-detection: 200-400 nm, At-Column Injektion; gradient: eluent A 0 bis 2 min 63 ml, eluent B 0 bis 2 min 7 ml, eluent A 2 bis 10 min from 63 ml to 39 ml and eluent B from 7 ml to 31 ml, 10 to 12 min 0 ml eluent A and 70 ml eluent B. Eluent C and Eluent D constant flow 5 ml/min over the whole runtime). After lyophilization, 12.0 mg (100% purity, 13% yield) of the title compound were obtained.

LC-MS (Method 8): $R_t$=0.63 min; MS (ESIpos): m/z=385 [M+H]$^+$ $^1$H-NMR (400 MHz, DMSO-d6) δ [ppm]: −0.008 (1.40), 0.008 (1.34), 0.122 (0.55), 0.135 (1.28), 0.146 (2.37), 0.159 (2.31), 0.170 (1.64), 0.183 (0.73), 0.312 (0.49), 0.334 (1.40), 0.346 (1.76), 0.358 (1.64), 0.369 (1.28), 0.380 (0.97), 0.392 (0.79), 0.403 (1.34), 0.417 (1.52), 0.426 (2.07), 0.439 (1.64), 0.447 (0.97), 0.459 (1.16), 0.472 (1.76), 0.483 (2.19), 0.496 (2.07), 0.508 (1.28), 0.521 (0.43), 1.076 (0.67), 1.089 (1.46), 1.097 (1.58), 1.110 (2.68), 1.123 (1.40), 1.131 (1.34), 1.144 (0.61), 2.323 (0.85), 2.327 (1.22), 2.332 (0.91), 2.366 (1.10), 2.523 (4.99), 2.665 (0.91), 2.669 (1.28), 2.674 (0.91), 2.710 (0.97), 3.556 (7.67), 3.571 (7.79), 7.437 (4.26), 7.449 (4.26), 7.456 (4.62), 7.468 (4.81), 7.490 (9.49), 7.495 (3.47), 7.506 (3.95), 7.511 (14.05), 7.517 (1.95), 7.609 (7.48), 7.615 (16.00), 7.620 (4.81), 7.632 (3.65), 7.637 (10.16), 7.643 (1.34), 7.739 (4.68), 7.743 (4.99), 7.758 (4.32), 7.763 (4.20), 8.693 (4.44), 8.697 (4.62), 8.704 (4.62), 8.709 (4.38), 8.732 (1.76), 8.747 (3.77), 8.762 (1.76), 10.654 (4.93).

Example 91

Ent-N-{[4-(4-Methyl-1,2,5-Thiadiazol-3-Yl)-2,5-Dioxoimidazolidin-4-Yl]Methyl}-2-[6-(Trifluoromethyl)Pyridin-3-Yl]Benzamide

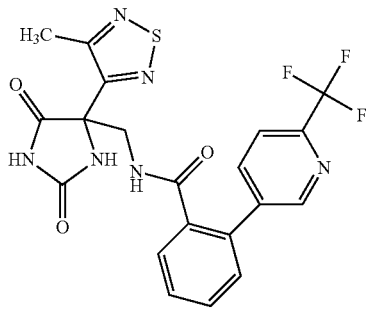 [SMILES: Cc1nsnc1C1(CNC(=O)c2ccccc2-c2ccc(C(F)(F)F)nc2)NC(=O)NC1=O]

Enantiomeric separation of rac-N-{[4-(4-methyl-1,2,5-thiadiazol-3-yl)-2,5-dioxoimidazolidin-4 yl]methyl}-2-[6-(trifluoromethyl)pyridin-3-yl]benzamide (36.0 mg, 75.6 μmol) was done using the following chiral HPLC method:
Daicel Chiralpak ID 5 μm 250*20 mm
Eluent A: 50% n-heptane, eluent B: 50% iso-propanol
Flow: 20 ml/min
UV-detection: 210 nm
Temperature: 40° C.
12.2 mg (100% purity, 34% yield) of the title compound were obtained.

Chiral-HPLC (Column: Diacel Chrialpak ID-3 3 μm 50*4.6 mm, eluent A: 50% n-heptane, eluent B: 50% iso-propanol, flow: 1 ml/min, UV-detection: 220 nm): $R_t$=2.852 min; 100% ee LC-MS (Method 8): $R_t$=0.77 min; MS (ESIpos): m/z=477 [M+H]$^+$ $^1$H-NMR (400 MHz, DMSO-d6) δ [ppm]: 2.072 (2.10), 2.327 (0.45), 2.469 (16.00), 2.670 (0.53), 4.115 (2.89), 4.131 (2.89), 7.498 (1.08), 7.513 (2.28), 7.532 (1.59), 7.538 (1.24), 7.541 (1.30), 7.550 (2.75), 7.557 (2.50), 7.575 (1.08), 7.601 (1.47), 7.605 (1.47), 7.620 (1.51), 7.624 (1.57), 7.639 (0.57), 7.642 (0.55), 7.925 (1.28), 7.945 (3.34), 7.967 (1.95), 7.972 (1.89), 7.987 (0.77), 7.992 (0.79), 8.400 (2.46), 8.747 (2.30), 8.849 (0.79), 8.865 (1.69), 8.880 (0.81).

Example 92

N-{[(4R)-4-Cyclopropyl-2,5-Dioxoimidazolidin-4-Yl]Methyl}-5-(Trifluoromethoxy)-4'-(Trifluoromethyl)[1,1'-Biphenyl]-2-Carboxamide

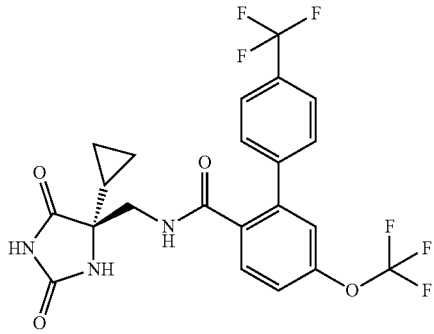 [SMILES: O=C1NC(=O)[C@](CNC(=O)c2ccc(OC(F)(F)F)cc2-c2ccc(C(F)(F)F)cc2)(C2CC2)N1]

5-(trifluoromethoxy)-4'-(trifluoromethyl)[1,1'-biphenyl]-2-carboxylic acid (104 mg, 82% purity, 243 µmol) dissolved in 1.5 ml of DMF was treated with N-ethyl-N-isopropylpropan-2-amine (120 µl, 680 µmol), 3-{[(ethylimino)methylene]amino}-N,N-dimethylpropan-1-amine hydrochloride (60.6 mg, 316 µmol), 1H-benzotriazol-1-ol hydrate (48.4 mg, 316 µmol) and (5R)-5-(aminomethyl)-5-cyclopropylimidazolidine-2,4-dione hydrochloride (50.0 mg, 243 µmol). The mixture was stirred over night at room temperature. The product was purified by preparative HPLC (Instrument: Waters Prep LC/MS System, Column: Phenomenex Kinetex C18 5 µm 100×30 mm; eluent A: water, eluent B: acetonitrile, eluent C: 2% formic acid in water, eluent D: acetonitrile/water (80 Vol. %/20 Vol %); flow: 80 ml/min, room temperature, UV-detection: 200-400 nm, At-Column Injektion; gradient: eluent A 0 to 2 min 55 ml, eluent B 0 to 2 min 15 ml, eluent A 2 to 10 min from 55 ml to 31 ml and eluent B from 15 ml to 39 ml, 10 to 12 min 0 ml eluent A and 70 ml eluent B. Eluent C and eluent D constant flow 5 ml/min over the whole runtime). After lyophilization, 85.0 mg (100% purity, 70% yield) of the title compound were obtained.

LC-MS (Method 9): $R_t$=1.45 min; MS (ESIpos): m/z=502 [M+H]$^+$ $^1$H-NMR (400 MHz, DMSO-d6) δ [ppm]: −0.149 (1.69), −0.008 (13.88), 0.008 (14.90), 0.126 (1.86), 0.137 (3.39), 0.151 (3.47), 0.161 (2.46), 0.314 (2.12), 0.327 (2.62), 0.336 (2.46), 0.349 (1.95), 0.359 (1.61), 0.369 (1.27), 0.380 (2.20), 0.394 (2.29), 0.402 (2.96), 0.416 (2.37), 0.443 (1.44), 0.457 (2.54), 0.468 (3.30), 0.480 (3.13), 0.492 (2.03), 1.045 (1.10), 1.058 (2.29), 1.066 (2.37), 1.079 (3.98), 1.092 (2.20), 1.099 (2.03), 2.072 (0.93), 2.327 (1.27), 2.366 (1.44), 2.670 (1.27), 2.710 (1.35), 3.506 (10.58), 3.522 (11.01), 7.452 (8.55), 7.503 (2.46), 7.524 (6.26), 7.547 (16.00), 7.568 (6.18), 7.580 (14.22), 7.587 (12.44), 7.607 (12.53), 7.783 (13.12), 7.803 (10.75), 8.686 (2.62), 8.701 (5.67), 8.717 (2.71), 10.647 (3.98).

Example 93

5-Chloro-N-{[(4R)-4-Cyclopropyl-2,5-Dioxoimidazolidin-4-Yl]Methyl}-6-Fluoro-4'-(Trifluoromethyl)[1,1'-Biphenyl]-2-Carboxamide

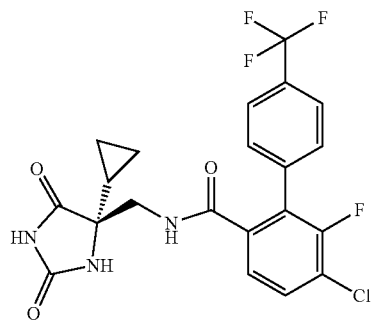 [SMILES: O=C1NC(=O)[C@](CNC(=O)c2ccc(Cl)c(F)c2-c2ccc(C(F)(F)F)cc2)(C2CC2)N1]

5-chloro-6-fluoro-4'-(trifluoromethyl)[1,1'-biphenyl]-2-carboxylic acid (77.5 mg, 243 µmol) dissolved in 2 ml of DMF was treated with N-ethyl-N-isopropylpropan-2-amine (120 µl, 680 µmol), 3-{[(ethylimino)methylene]amino}-N,N-dimethylpropan-1-amine hydrochloride (60.6 mg, 316 µmol), 1H-benzotriazol-1-ol hydrate (48.4 mg, 316 µmol) and (5R)-5-(aminomethyl)-5-cyclopropylimidazolidine-2,4-dione hydrochloride (50.0 mg, 243 µmol). The mixture was stirred over night at room temperature. The product was purified by preparative HPLC (Instrument: Waters Prep LC/MS System, Column: Phenomenex Kinetex C18 5 µm 100×30 mm; eluent A: water, eluent B: acetonitrile, eluent C: 2% formic acid in water, eluent D: acetonitrile/water (80 Vol. %/20 Vol %); flow: 80 ml/min, room temperature, UV-detection: 200-400 nm, At-Column Injektion; gradient: eluent A 0 to 2 min 63 ml, eluent B 0 to 2 min 7 ml, eluent A 2 to 10 min from 63 ml to 39 ml and eluent B from 7 ml to 31 ml, 10 to 12 min 0 ml eluent A and 70 ml eluent B. Eluent C and Eluent D constant flow 5 ml/min over the whole runtime). After lyophilization, 14.0 mg (100% purity, 12% yield) of the title compound were obtained.

LC-MS (Method 7): $R_t$=1.79 min; MS (ESIpos): m/z=470 [M+H]$^+$ $^1$H-NMR (400 MHz, DMSO-d6) δ [ppm]: −0.149 (0.73), −0.008 (6.16), 0.008 (6.95), 0.094 (0.69), 0.108 (1.70), 0.119 (3.05), 0.132 (3.23), 0.143 (2.40), 0.155 (1.07), 0.268 (0.57), 0.292 (1.88), 0.304 (2.46), 0.313 (2.42), 0.326 (1.86), 0.337 (1.82), 0.351 (1.96), 0.365 (2.26), 0.373 (2.87), 0.387 (2.20), 0.411 (1.47), 0.425 (2.40), 0.436 (3.07), 0.449 (2.91), 0.461 (1.82), 0.474 (0.69), 0.999 (0.97), 1.012 (1.98), 1.020 (2.16), 1.033 (3.64), 1.046 (1.98), 1.054 (1.78), 1.067 (0.75), 2.073 (0.57), 2.328 (0.65), 2.367 (0.69), 2.670 (0.61), 2.710 (0.63), 3.387 (0.55), 3.425 (7.37), 3.439 (8.28), 3.460 (0.71), 3.475 (0.46), 7.288 (6.12), 7.309 (6.63), 7.539 (9.21), 7.557 (16.00), 7.742 (4.67), 7.762 (5.84), 7.781 (4.69), 7.793 (11.76), 7.814 (10.02), 8.602 (2.48), 8.618 (5.23), 8.633 (2.48), 10.649 (7.37).

Example 94

Rac-N-({2,5-Dioxo-4-[1-(2,2,2-Trifluoroethyl)-1H-Imidazol-5-Yl]Imidazolidin-4-Yl}Methyl)-4'-(Trifluoromethyl)[Biphenyl]-2-Carboxamide

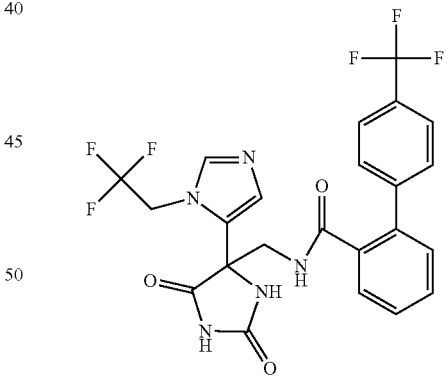

N-{2-oxo-2-[1-(2,2,2-trifluoroethyl)-1H-imidazol-5-yl]ethyl}-4'-(trifluoromethyl)[1,1'-biphenyl]-2-carboxamide (249 mg, 547 µmol) was dissolved in 3.5 ml of ethanol. Ammonium carbonate (525 mg, 5.47 mmol) and potassium cyanide (142 mg, 2.19 mmol), dissolved in 7 ml of water, were added, the vial was sealed and the mixture was stirred at 60° C. for 2 days. More potassium cyanide (142 mg, 2.19 mmol) was added and the mixture was stirred at 80° C. for 35 days. The product was purified by preparative HPLC (Instrument: Waters Prep LC/MS System, Column: Phenomenex Kinetex C18 5 µm 100×30 mm; eluent A: water, eluent B: acetonitrile, eluent C: 2% formic acid in water, eluent D: acetonitrile/water (80 Vol. %/20 Vol %); flow: 80 ml/min, room temperature, UV-detection: 200-400 nm, At-Column Injektion; gradient: eluent A 0 to 2 min 63 ml, eluent B 0 to 2 min 7 ml, eluent A 2 to 10 min from 63 ml to 39 ml and eluent B from 7 ml to 31 ml, 10 to 12 min 0 ml eluent A and 70 ml eluent B. Eluent C and Eluent D constant flow 5 ml/min over the whole runtime). After lyophilization, 7.00 mg (91% purity, 2% yield) of the title compound were obtained.

LC-MS (Method 7): $R_t$=1.53 min; MS (ESIpos): m/z=526 $[M+H]^+$ $^1$H-NMR (400 MHz, DMSO-d6) δ [ppm]: 2.327 (0.49), 2.366 (0.47), 2.670 (0.54), 2.709 (0.45), 3.765 (2.10), 3.782 (2.33), 3.799 (4.31), 3.816 (4.08), 3.853 (4.03), 3.867 (4.43), 3.887 (2.29), 3.902 (2.05), 5.008 (1.93), 5.027 (4.90), 5.054 (4.74), 5.072 (1.84), 5.698 (0.66), 5.721 (0.64), 7.174 (15.10), 7.420 (4.45), 7.436 (14.30), 7.455 (8.06), 7.466 (3.89), 7.469 (3.91), 7.485 (6.79), 7.488 (6.53), 7.504 (3.58), 7.532 (10.63), 7.551 (16.00), 7.565 (7.12), 7.569 (6.46), 7.584 (2.22), 7.587 (2.40), 7.637 (1.89), 7.658 (1.20), 7.710 (1.04), 7.750 (13.13), 7.771 (10.77), 7.789 (11.73), 8.020 (1.51), 8.335 (10.39), 8.784 (2.71), 8.799 (5.47), 8.815 (2.69), 11.208 (0.68).

Example 95

Rac-N-[(4-Methyl-2,5-Dioxoimidazolidin-4-Yl) Methyl]-4'-(Trifluoromethyl)[Biphenyl]-2-Carboxamide

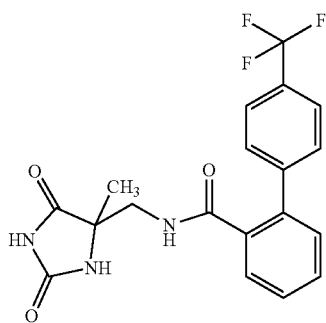 [SMILES: CC1(CNC(=O)c2ccccc2-c2ccc(C(F)(F)F)cc2)NC(=O)NC1=O]

4'-(trifluoromethyl)[1,1'-biphenyl]-2-carboxylic acid (148 mg, 557 µmol) dissolved in 4 ml of DMF was treated with N-ethyl-N-isopropylpropan-2-amine (270 µl, 1.6 mmol), 3-{[(ethylimino)methylene]amino}-N,N-dimethylpropan-1-amine hydrochloride (139 mg, 724 µmol), 1H-benzotriazol-1-ol hydrate (111 mg, 724 µmol) and rac-5-(aminomethyl)-5-methylimidazolidine-2,4-dione hydrochloride (100 mg, 557 µmol). The mixture was stirred over night at room temperature. The product was purified by preparative HPLC (Instrument: Waters Prep LC/MS System, Column: Phenomenex Kinetex C18 5 µm 100×30 mm; eluent A: water, eluent B: acetonitrile, eluent C: 2% formic acid in water, eluent D: acetonitrile/water (80 Vol. %/20 Vol. %); flow: 80 ml/min, room temperature, UV-detection: 200-400 nm, At-Column Injektion; gradient: eluent A 0 bis 2 min 63 ml, eluent B 0 to 2 min 7 ml, eluent A 2 to 10 min from 63 ml to 39 ml and eluent B from 7 ml to 31 ml, 10 to 12 min 0 ml eluent A and 70 ml eluent B. Eluent C and eluent D constant flow 5 ml/min over the whole runtime). After lyophilization, 153 mg (98% purity, 69% yield) of the title compound were obtained.

LC-MS (Method 7): $R_t$=1.48 min; MS (ESIpos): m/z=392 $[M+H]^+$

Example 96

Ent-N-[(4-Methyl-2,5-Dioxoimidazolidin-4-Yl) Methyl]-4'-(Trifluoromethyl)[Biphenyl]-2-Carboxamide

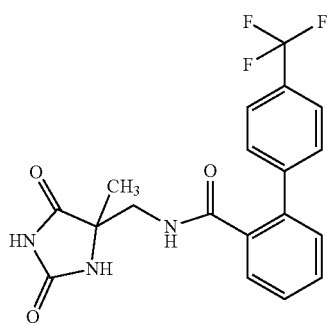 [SMILES: CC1(CNC(=O)c2ccccc2-c2ccc(C(F)(F)F)cc2)NC(=O)NC1=O]

Enantiomeric separation of rac-N-[(4-methyl-2,5-dioxoimidazolidin-4-yl)methyl]-4'-(trifluoromethyl)[biphenyl]-2-carboxamide (145 mg, 371 µmol) was done using the following chiral HPLC method:

Daicel Chiralpak AD-H 5 µm 250*20 mm
Eluent A: 60% n-heptane, eluent B: 40% ethanol
Flow: 15 ml/min
UV-detection: 210 nm
Temperature: 40° C.

48.4 mg (100% purity, 33% yield) of the title compound were obtained.

Chiral-HPLC (Column: Chiraltek AD-3 3 µm, eluent A: 50% iso-hexane, eluent B: 50% ethanol, flow: 1 ml/min, UV-detection: 220 nm): $R_t$=3.309 min; 100% ee LC-MS (Method 7): $R_t$=1.48 min; MS (ESIpos): m/z=392 $[M+H]^+$ $^1$H-NMR (600 MHz, DMSO-d6) δ [ppm]: 1.194 (16.00), 3.312 (1.45), 3.325 (1.99), 3.335 (1.57), 3.384 (1.65), 3.395 (1.67), 3.407 (1.04), 3.418 (0.97), 7.432 (2.22), 7.444 (2.86), 7.475 (3.16), 7.480 (6.03), 7.537 (1.27), 7.543 (1.20), 7.547 (1.20), 7.550 (1.40), 7.561 (4.01), 7.575 (4.18), 7.709 (4.08), 7.749 (4.32), 7.763 (3.76), 8.494 (0.96), 8.505 (1.85), 8.515 (1.00), 10.640 (0.73).

Example 97

Rac-N-{[4-(4-Methyl-1,2-Thiazol-5-Yl)-2,5-Dioxoimidazolidin-4-Yl]Methyl}-4'-(Trifluoromethyl) [Biphenyl]-2-Carboxamide

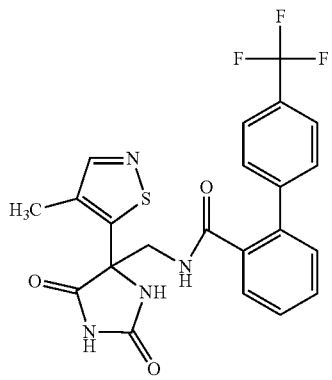 [SMILES: Cc1cnsc1C1(CNC(=O)c2ccccc2-c2ccc(C(F)(F)F)cc2)NC(=O)NC1=O]

N-[2-(4-methyl-1,2-thiazol-5-yl)-2-oxoethyl]-4'-(trifluoromethyl)[1,1'-biphenyl]-2-carboxamide (18.0 mg, 44.5 µmol) was dissolved in 290 µl of ethanol. Ammonium carbonate (42.8 mg, 445 µmol) and potassium cyanide (11.6 mg, 178 µmol), dissolved in 570 µl of water, were added, the vial was sealed and the mixture was stirred at 60° C. for 2 days. The product was purified by preparative HPLC (Instrument: Waters Prep LC/MS System, Column: Phenomenex Kinetex C18 5 µm 100×30 mm; eluent A: water, eluent B: acetonitrile, eluent C: 2% formic acid in water, eluent D: acetonitrile/water (80 Vol. %/20 Vol %); flow: 80 ml/min, room temperature, UV-detection: 200-400 nm, At-Column Injektion; gradient: eluent A 0 to 2 min 63 ml, eluent B 0 to 2 min 7 ml, eluent A 2 to 10 min from 63 ml to 39 ml and eluent B from 7 ml to 31 ml, 10 to 12 min 0 ml eluent A and 70 ml eluent B. Eluent C and Eluent D constant flow 5 ml/min over the whole runtime). After lyophilization, 3.00 mg (100% purity, 14% yield) of the title compound were obtained.

LC-MS (Method 7): $R_t$=1.68 min; MS (ESIpos): m/z=475 [M+H]$^+$ $^1$H-NMR (600 MHz, DMSO-d6) δ [ppm]: 2.157 (0.71), 2.312 (1.04), 2.365 (16.00), 2.383 (0.88), 2.422 (1.17), 2.612 (1.04), 2.651 (1.25), 3.924 (2.67), 3.936 (3.09), 6.930 (0.42), 7.386 (2.01), 7.399 (2.55), 7.433 (2.51), 7.445 (2.84), 7.473 (1.34), 7.486 (2.55), 7.496 (4.80), 7.510 (4.34), 7.551 (1.71), 7.564 (2.26), 7.576 (1.00), 7.729 (4.18), 7.742 (3.76), 8.353 (5.39), 8.602 (3.80), 8.719 (2.01), 8.729 (1.09), 11.258 (1.21).

Example 98

Rac-N-({4-[5-Methyl-1-(2,2,2-Trifluoroethyl)-1H-Pyrazol-4-Yl]-2,5-Dioxoimidazolidin-4-Yl}Methyl)-4'-(Trifluoromethyl)[Biphenyl]-2-Carboxamide

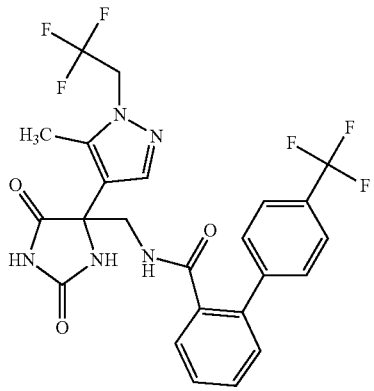 [SMILES: Cc1c(C2(CNC(=O)c3ccccc3-c3ccc(C(F)(F)F)cc3)NC(=O)NC2=O)cnn1CC(F)(F)F]

4'-(trifluoromethyl)[1,1'-biphenyl]-2-carboxylicacid (42.2 mg, 159 µmol) dissolved in 1 ml of DMF was treated with N-ethyl-N-isopropylpropan-2-amine (83 µl, 480 µmol), 3-{[(ethylimino)methylene]amino}-N,N-dimethylpropan-1-amine hydrochloride (39.5 mg, 206 µmol), 1H-benzotriazol-1-ol hydrate (31.6 mg, 206 µmol) and rac-5-(aminomethyl)-5-[5-methyl-1-(2,2,2-trifluoroethyl)-1H-pyrazol-4-yl]imidazolidine-2,4-dione hydrochloride (52.0 mg, 159 µmol). The mixture was stirred for 4 h at room temperature. The product was purified by preparative HPLC (Instrument: Waters Prep LC/MS System, Column: Phenomenex Kinetex C18 5 µm 100×30 mm; eluent A: water, eluent B: acetonitrile, eluent C: 2% formic acid in water, eluent D: acetonitrile/water (80 Vol. %/20 Vol. %); flow: 80 ml/min, room temperature, UV-detection: 200-400 nm, At-Column Injektion; gradient: eluent A 0 to 2 min 55 ml, eluent B 0 to 2 min 15 ml, eluent A 2 to 10 min from 55 ml to 31 ml and eluent B from 15 ml to 39 ml, 10 to 12 min 0 ml eluent A and 70 ml eluent B. Eluent C and eluent D constant flow 5 ml/min over the whole runtime). After lyophilization, 57.0 mg (100% purity, 67% yield) of the title compound were obtained.

LC-MS (Method 8): $R_t$=0.86 min; MS (ESIpos): m/z=540 [M+H]$^+$ $^1$H-NMR (400 MHz, DMSO-d6) δ [ppm]: −0.008 (0.66), 0.008 (0.78), 2.320 (16.00), 3.797 (3.56), 3.813 (3.77), 5.058 (1.08), 5.081 (3.06), 5.104 (2.91), 5.126 (0.91), 7.374 (1.67), 7.377 (1.75), 7.393 (2.73), 7.434 (2.16), 7.451 (3.51), 7.466 (2.72), 7.484 (1.36), 7.540 (5.09), 7.558 (5.29), 7.578 (7.93), 7.751 (4.72), 7.772 (3.90), 8.218 (4.76), 8.673 (0.96), 8.689 (2.03), 8.704 (0.96), 10.939 (1.15).

Example 99

N-{[(4R)-4-Cyclopropyl-2,5-Dioxoimidazolidin-4-Yl]Methyl}-4'-Methyl-5-(Trifluoromethyl)[Biphenyl]-2-Carboxamide

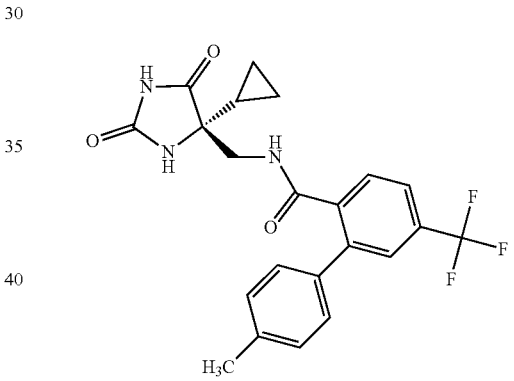

(5R)-5-(aminomethyl)-5-cyclopropylimidazolidine-2,4-dione hydrochloride (40.0 mg, 195 µmol) and 4'-methyl-5-(trifluoromethyl)[1,1'-biphenyl]-2-carboxylic acid (54.5 mg, 195 µmol) dissolved in DMF (1.7 ml) were treated with 1-ethyl-3-(3-dimethylaminopropyl)carbodiimide hydrochloride (48.5 mg, 253 µmol), 1-hydroxybenzotriazole hydrate (38.7 mg, 253 µmol) and N,N-diisopropylethylamine (95 µl, 540 µmol). The mixture was stirred 3 hours at room temperature. Water (5 ml) was added to the reaction and the resulting precipitate was filtered off. The residue was washed with water and dried to obtain 42.0 mg (96% purity, 48% yield) of the title compound.

LC-MS (Method 7): $R_t$=1.75 min; MS (ESIpos): m/z=432

$^1$H NMR (400 MHz, DMSO-d$_6$) δ ppm 0.10-0.17 (m, 1H)$_{0.29}$-0.49 (m, 1H) 0.32-0.37 (m, 1 H) 0.54-0.55 (m, 1H) 1.07 (ddd, J=8.22, 5.17, 3.00 Hz, 1H) 2.34 (s, 3H) 3.45-3.54 (m, 2H) 7.21-7.27 (m, 2H) 7.33 (m, J=8.07 Hz, 2H) 7.47-7.61 (m, 2H) 7.66 (s, 1H) 7.78 (d, J=7.95 Hz, 1H) 8.58 (t, J=5.99 Hz, 1H) 10.58-10.71 (m, 1H).

Example 100

N-{[(4R)-4-Cyclopropyl-2,5-Dioxoimidazolidin-4-Yl]Methyl}-5-Fluoro-4-Methyl[Biphenyl]-2-Carboxamide

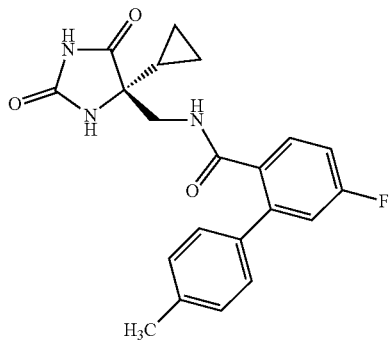 [SMILES: Cc1ccc(-c2cc(F)ccc2C(=O)NC[C@@]2(C3CC3)NC(=O)NC2=O)cc1]

(5R)-5-(aminomethyl)-5-cyclopropylimidazolidine-2,4-dione hydrochloride (40.0 mg, 195 µmol) and 5-fluoro-4'-methyl[1,1'-biphenyl]-2-carboxylic acid (44.8 mg, 195 µmol) dissolved in DMF (1.7 ml) were treated with 1-ethyl-3-(3-dimethylaminopropyl)carbodiimide hydrochloride (48.5 mg, 253 µmol), 1-hydroxybenzotriazole hydrate (38.7 mg, 253 µmol) and N,N-diisopropylethylamine (95 µl, 540 µmol). The mixture was stirred for 2.5 hours at room temperature. Water (4 ml) was added to the reaction and the resulting precipitate was filtered off. The residue was washed with water and dried to obtain 28.0 mg (99% purity, 37% yield) of the title compound.

LC-MS (Method 8): $R_t$=0.87 min, MS (ESIpos): m/z=382 [M+H]$^+$ $^1$H NMR (400 MHz, DMSO-d$_6$) δ ppm 0.09-0.16 (m, 1H) 0.28-0.47 (m, 3H) 0.98-1.10 (m, 1H) 2.32 (s, 4H) 3.48 (m, J=5.80, 5.80 Hz, 2H) 7.17-7.30 (m, 6H) 7.40 (dd, J=8.31, 5.99 Hz, 1H) 7.49 (s, 1H) 8.37 (t, J=5.99 Hz, 1H) 10.62 (s, 1H).

Example 101

N-{[(4R)-4-Cyclopropyl-2,5-Dioxoimidazolidin-4-Yl]Methyl}-4',6-Dimethyl[Biphenyl]-2-Carboxamide

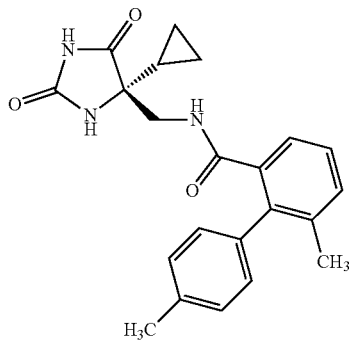 [SMILES: Cc1ccc(-c2c(C)cccc2C(=O)NC[C@@]2(C3CC3)NC(=O)NC2=O)cc1]

(5R)-5-(aminomethyl)-5-cyclopropylimidazolidine-2,4-dione hydrochloride (40.0 mg, 195 µmol) and 4',6-dimethyl[1,1'-biphenyl]-2-carboxylic acid (44.0 mg, 195 µmol) dissolved in DMF (1000 µl) were treated with 1-ethyl-3-(3-dimethylaminopropyl)carbodiimide hydrochloride (48.5 mg, 253 µmol), 1-hydroxybenzotriazole hydrate (38.7 mg, 253 µmol) and N,N-diisopropylethylamine (95 µl, 540 µmol). The mixture was stirred over night at room temperature. Water (2 ml) was added to the mixture and purification was done by preparative HPLC (column: Reprosil C18 10 µm, 250×30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated and the residue was lyophylized. 54.3 mg (100% purity, 74% yield) of the title compound were obtained.

LC-MS (Method 7): $R_t$=1.57 min; MS (ESIpos): m/z=378 [M+H]$^+$ $^1$H NMR (600 MHz, DMSO-d$_6$) δ ppm 0.07-0.12 (m, 1H) 0.24-0.32 (m, 1H) 0.32-0.41 (m, 2H) 0.95 (m, 1H) 2.04 (s, 3H) 2.32 (s, 3H) 3.32 (d, J=6.24 Hz, 2H) 7.07 (d, J=8.07 Hz, 2H) 7.13-7.18 (m, 3H) 7.28 (t, J=7.61 Hz, 1H) 7.33 (d, J=7.34 Hz, 1H) 7.39 (s, 1H) 8.02 (t, J=6.24 Hz, 1H) 10.60 (s, 1H).

Example 102

N-{[(4R)-4-Cyclopropyl-2,5-Dioxoimidazolidin-4-Yl]Methyl}-4'-(1,1-Difluoropropyl)[Biphenyl]-2-Carboxamide

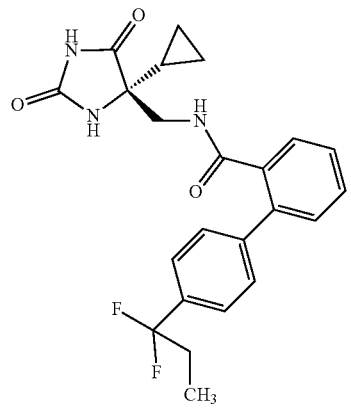 [SMILES: CCC(F)(F)c1ccc(-c2ccccc2C(=O)NC[C@@]2(C3CC3)NC(=O)NC2=O)cc1]

(5R)-5-(aminomethyl)-5-cyclopropylimidazolidine-2,4-dione hydrochloride (40.0 mg, 195 µmol) and 4'-(1,1-difluoropropyl)[1,1'-biphenyl]-2-carboxylic acid (53.7 mg, 195 µmol) dissolved in DMF (1000 µl) were treated with 1-ethyl-3-(3-dimethylaminopropyl)carbodiimide hydrochloride (48.5 mg, 253 µmol), 1-hydroxybenzotriazole hydrate (38.7 mg, 253 µmol) and N,N-diisopropylethylamine (95 µl, 540 µmol). The mixture was stirred overnight at room temperature. Water (2 ml) was added and the purification was done by preparative HPLC (column: Reprosil C18 10 µm, 250×30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated and the residue was lyophylized. 82.4 mg (100% purity, 99% yield) of the title compound were obtained.

LC-MS (Method 7) $R_t$=1.68 min; MS (ESIneg): m/z=426 [M−H]$^-$

¹H-NMR (400 MHz, DMSO-d6) δ [ppm]: −0.008 (1.72), 0.008 (1.57), 0.099 (0.43), 0.113 (1.01), 0.123 (1.80), 0.137 (1.90), 0.147 (1.48), 0.160 (0.61), 0.293 (0.63), 0.300 (1.15), 0.313 (1.42), 0.324 (1.35), 0.335 (1.06), 0.345 (0.82), 0.356 (0.70), 0.367 (1.15), 0.381 (1.28), 0.389 (1.68), 0.402 (1.30), 0.410 (0.79), 0.420 (0.86), 0.424 (0.77), 0.433 (1.45), 0.444 (1.77), 0.457 (1.67), 0.469 (1.02), 0.936 (7.03), 0.955 (16.00), 0.973 (7.33), 1.033 (0.58), 1.046 (1.19), 1.054 (1.28), 1.059 (0.93), 1.067 (2.18), 1.074 (0.89), 1.080 (1.16), 1.087 (1.05), 1.100 (0.46), 2.171 (0.47), 2.189 (1.47), 2.208 (1.65), 2.231 (3.01), 2.250 (2.95), 2.273 (1.51), 2.292 (1.26), 2.523 (0.54), 3.470 (0.53), 3.489 (3.92), 3.494 (3.94), 3.504 (3.82), 3.510 (3.75), 3.528 (0.48), 3.544 (0.42), 3.958 (0.45), 7.394 (1.46), 7.398 (1.84), 7.412 (8.80), 7.416 (4.80), 7.423 (3.47), 7.430 (5.13), 7.441 (4.33), 7.444 (2.91), 7.459 (6.09), 7.479 (8.66), 7.504 (6.13), 7.509 (3.47), 7.527 (11.47), 7.547 (5.36), 8.441 (1.45), 8.456 (3.10), 8.472 (1.44), 10.642 (4.18).

Example 103

4'-Cyclopropyl-N-{[(4R)-4-Cyclopropyl-2,5-Dioxo-imidazolidin-4-Yl]Methyl}-5-Methoxy[Biphenyl]-2-Carboxamide

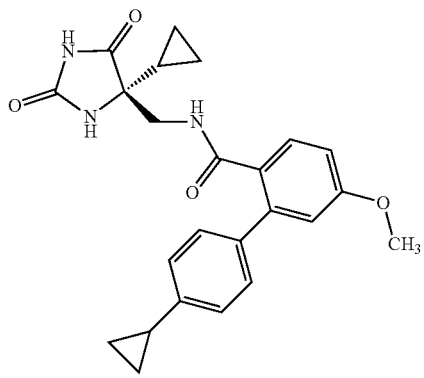 [SMILES: COc1ccc(C(=O)NC[C@@]2(C3CC3)NC(=O)NC2=O)c(-c2ccc(C3CC3)cc2)c1]

(5R)-5-(aminomethyl)-5-cyclopropylimidazolidine-2,4-dione hydrochloride (29.9 mg, 145 µmol) and 4'-cyclopropyl-5-methoxy[1,1'-biphenyl]-2-carboxylic acid (39.0 mg, 145 µmol) dissolved in DMF (1.0 ml) were treated with 1-ethyl-3-(3-dimethylaminopropyl)carbodiimide hydrochloride (36.2 mg, 189 µmol), 1-hydroxybenzotriazole hydrate (28.9 mg, 189 µmol) and N,N-diisopropylethylamine (71 µl, 410 µmol). The mixture was stirred overnight at room temperature. Purification was done by preparative HPLC (column: Chromatorex C18 10 µm, 250×30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated and the residue was lyophylized. 10.3 mg (100% purity, 17% yield) of the title compound were obtained.

LC-MS (Method 7): $R_t$=1.75 min; MS (ESIpos): m/z=420 [M+H]⁺

¹H-NMR (400 MHz, DMSO-d6) δ [ppm]: 0.083 (0.83), 0.096 (1.90), 0.107 (3.23), 0.120 (3.39), 0.130 (2.46), 0.144 (1.19), 0.268 (0.70), 0.291 (2.10), 0.304 (2.70), 0.315 (2.65), 0.325 (1.92), 0.336 (1.47), 0.350 (1.23), 0.361 (2.09), 0.375 (2.37), 0.383 (3.33), 0.396 (3.41), 0.407 (3.70), 0.419 (3.83), 0.432 (2.96), 0.444 (1.83), 0.457 (0.60), 0.650 (0.57), 0.667 (3.06), 0.674 (5.05), 0.679 (8.05), 0.685 (7.85), 0.691 (7.81), 0.702 (3.44), 0.719 (0.56), 0.945 (7.26), 0.951 (7.11), 0.966 (7.64), 0.972 (6.96), 1.001 (1.19), 1.014 (2.18), 1.021 (2.38), 1.035 (3.84), 1.047 (2.14), 1.055 (1.86), 1.068 (0.81), 1.885 (1.13), 1.898 (2.25), 1.906 (2.56), 1.919 (4.11), 1.931 (2.37), 1.939 (2.07), 1.952 (0.97), 2.072 (1.13), 2.366 (0.44), 3.407 (2.01), 3.422 (2.29), 3.441 (4.83), 3.456 (4.41), 3.481 (4.48), 3.497 (4.69), 3.515 (2.19), 3.531 (2.07), 3.626 (0.76), 3.987 (0.46), 6.843 (9.48), 6.849 (10.78), 6.913 (5.41), 6.920 (4.59), 6.935 (5.77), 6.941 (5.14), 7.065 (12.18), 7.086 (15.50), 7.223 (16.00), 7.244 (12.35), 7.319 (10.20), 7.340 (9.07), 7.435 (8.91), 8.097 (2.77), 8.112 (5.50), 8.127 (2.70), 10.618 (8.15).

Example 104

4'-Cyclopropyl-N-{[(4R)-4-Cyclopropyl-2,5-Dioxo-imidazolidin-4-Yl]Methyl}-5-Fluoro[Biphenyl]-2-Carboxamide

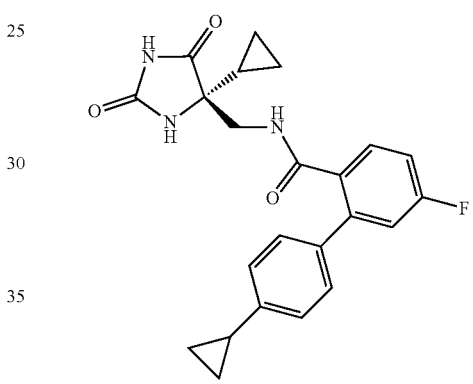

(5R)-5-(aminomethyl)-5-cyclopropylimidazolidine-2,4-dione hydrochloride (40.0 mg, 195 µmol) and 4'-cyclopropyl-5-fluoro[1,1'-biphenyl]-2-carboxylic acid (49.8 mg, 195 µmol) dissolved in DMF (1.7 ml) were treated with 1-ethyl-3-(3-dimethylaminopropyl)carbodiimide hydrochloride (48.5 mg, 253 µmol), 1-hydroxybenzotriazole hydrate (38.7 mg, 253 µmol) and N,N-diisopropylethylamine (95 µl, 540 µmol). The mixture was stirred for 2.5 hours at room temperature. Water (5 mL) was added to the reaction and the mixture was extracted with ethyl acetate three times. The combined organic layers were dried over sodium sulfate, filtered and evaporated Purification was done by flash-column chromatography (n-heptane:ethyl acetate (60:40)+ ethyl acetate+ethyl acetate:methanol (80:20)). Product containing samples were united, the solvents were evaporated. 52.0 mg (99% purity, 65% yield) of the title compound were obtained.

LC-MS (Method 7): $R_t$=1.67 min, MS (ESIpos): m/z=408 [M+H]⁺

¹H NMR (400 MHz, DMSO-d₆) δ ppm 0.05-0.18 (m, 1H) 0.28-0.50 (m, 3H) 0.64-0.74 (m, 2H) 0.92-1.00 (m, 2H) 1.01-1.10 (m, 1H) 1.89-1.96 (m, 1H) 3.48 (m, 2H) 7.10 (d, J=8.31 Hz, 2H) 7.16-7.29 (m, 4H) 7.39 (dd, J=8.44, 5.99 Hz, 1H) 7.49 (s, 1H) 8.38 (t, J=6.17 Hz, 1H) 10.63 (s, 1H).

Example 105

4'-Cyclopropyl-N-{[(4R)-4-Cyclopropyl-2,5-Dioxo-imidazolidin-4-Yl]Methyl}[Biphenyl]-2-Carboxamide

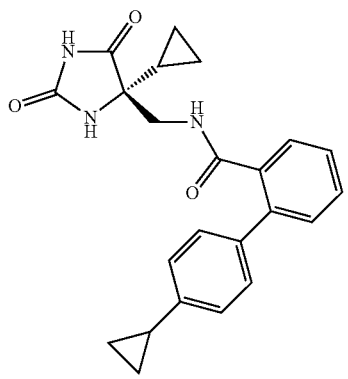 [SMILES: O=C1NC(=O)[C@](CNC(=O)c2ccccc2-c2ccc(C3CC3)cc2)(C2CC2)N1]

(5R)-5-(aminomethyl)-5-cyclopropylimidazolidine-2,4-dione hydrochloride (40.0 mg, 195 µmol) and 4'-cyclopropyl [1,1'-biphenyl]-2-carboxylic acid (46.3 mg, 195 µmol) dissolved in DMF (1.6 ml) were treated with 1-ethyl-3-(3-dimethylaminopropyl)carbodiimide hydrochloride (48.5 mg, 253 µmol), 1-hydroxybenzotriazole hydrate (38.7 mg, 253 µmol) and N,N-diisopropylethylamine (95 µl, 540 µmol). The mixture was stirred over night at room temperature. Water (4 ml) was added and the mixture was extracted with ethyl acetate. The combined organic layers were dried, filtered and evaporated and the residue was purified by flash-column chromatography (n-heptane:ethyl actetate (70:30)→ethyl acetate). Product containing samples were united, the solvents were evaporated and the residue was lyophylized. 60.0 mg (99% purity, 78% yield) of the title compound were obtained.

LC-MS (Method 7): $R_f$=1.61 min, MS (ESIpos): m/z=390 [M+H]$^+$ $^1$H-NMR (400 MHz, DMSO-d6) δ [ppm]: −0.008 (2.51), 0.008 (2.24), 0.092 (0.74), 0.105 (1.72), 0.116 (3.03), 0.129 (3.22), 0.140 (2.31), 0.153 (1.03), 0.275 (0.60), 0.297 (1.93), 0.310 (2.44), 0.321 (2.35), 0.332 (1.73), 0.342 (1.33), 0.357 (1.07), 0.368 (1.91), 0.382 (2.14), 0.390 (2.98), 0.404 (3.05), 0.420 (2.80), 0.430 (3.12), 0.443 (2.79), 0.455 (1.70), 0.469 (0.56), 0.654 (0.46), 0.671 (2.89), 0.678 (4.75), 0.684 (7.62), 0.690 (7.19), 0.695 (7.20), 0.707 (3.29), 0.724 (0.49), 0.937 (2.07), 0.946 (6.99), 0.952 (6.89), 0.960 (3.72), 0.967 (7.34), 0.973 (6.69), 0.980 (1.79), 0.983 (1.84), 1.012 (1.00), 1.026 (2.09), 1.033 (2.19), 1.039 (1.66), 1.047 (3.72), 1.054 (1.58), 1.059 (2.02), 1.067 (1.77), 1.080 (0.77), 1.886 (1.09), 1.899 (2.14), 1.907 (2.40), 1.920 (4.00), 1.932 (2.19), 1.941 (1.98), 1.953 (0.91), 3.436 (1.17), 3.451 (1.40), 3.470 (5.36), 3.485 (9.60), 3.501 (5.26), 3.519 (1.31), 3.535 (1.23), 7.074 (12.16), 7.094 (15.42), 7.238 (16.00), 7.259 (12.37), 7.343 (6.12), 7.352 (9.18), 7.357 (13.30), 7.362 (9.94), 7.372 (6.89), 7.391 (2.17), 7.453 (4.78), 7.459 (6.15), 7.464 (11.43), 7.471 (6.45), 7.490 (2.14), 7.494 (2.14), 8.304 (2.40), 8.319 (5.03), 8.334 (2.40), 10.623 (5.61).

Example 106

N-{[(4R)-4-Cyclopropyl-2,5-Dioxoimidazolidin-4-Yl]Methyl}-4'-Ethyl[Biphenyl]-2-Carboxamide

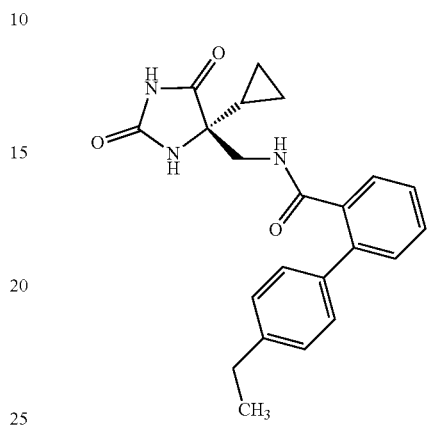

(5R)-5-(aminomethyl)-5-cyclopropylimidazolidine-2,4-dione hydrochloride (40.0 mg, 195 µmol) and 4'-ethyl[1,1'-biphenyl]-2-carboxylicacid (44.0 mg, 195 µmol) dissolved in DMF (1.6 ml) were treated with 1-ethyl-3-(3-dimethylaminopropyl)carbodiimide hydrochloride (48.5 mg, 253 µmol), 1-hydroxybenzotriazole hydrate (38.7 mg, 253 µmol) and N,N-diisopropylethylamine (95 µl, 540 µmol). The mixture was stirred over night at room temperature. Water (4 ml) was added and the mixture was extracted with ethyl acetate. The combined organic layers were dried, filtered and evaporated and the residue was purified by flash-column chromatography (n-heptane:ethyl actetate (70:30)→ethyl acetate). Product containing samples were united, the solvents were evaporated and the residue was lyophylized. 54.0 mg (99% purity, 73% yield) of the title compound were obtained.

LC-MS (Method 7): $R_f$=1.61 min, MS (ESIpos): m/z=378 [M+H]$^+$ $^1$H-NMR (400 MHz, DMSO-d6) δ [ppm]: 0.008 (0.63), 0.104 (0.92), 0.115 (1.58), 0.128 (1.67), 0.138 (1.22), 0.151 (0.54), 0.294 (1.01), 0.306 (1.29), 0.317 (1.24), 0.328 (0.93), 0.339 (0.71), 0.353 (0.57), 0.364 (1.00), 0.378 (1.12), 0.386 (1.56), 0.400 (1.38), 0.418 (1.51), 0.429 (1.58), 0.441 (1.46), 0.454 (0.91), 1.021 (0.52), 1.034 (1.08), 1.042 (1.17), 1.048 (0.96), 1.055 (1.93), 1.068 (1.11), 1.075 (0.94), 1.088 (0.41), 1.174 (0.41), 1.189 (7.29), 1.208 (16.00), 1.227 (7.59), 1.987 (0.47), 2.594 (1.85), 2.613 (5.41), 2.632 (5.29), 2.651 (1.70), 3.439 (0.54), 3.454 (0.66), 3.473 (2.84), 3.486 (4.56), 3.501 (2.79), 3.519 (0.63), 3.536 (0.58), 7.214 (4.61), 7.234 (8.29), 7.282 (9.40), 7.303 (5.06), 7.347 (1.26), 7.360 (8.40), 7.364 (6.66), 7.378 (5.59), 7.381 (5.50), 7.400 (1.26), 7.461 (7.37), 7.479 (2.75), 7.484 (2.28), 7.497 (1.05), 7.502 (1.04), 8.309 (1.27), 8.324 (2.60), 8.339 (1.25), 10.628 (4.04).

Example 107

N-{[(4R)-4-Cyclopropyl-2,5-Dioxoimidazolidin-4-Yl]Methyl}-5-Methoxy-4'-(Trifluoromethyl)[Biphenyl]-2-Carboxamide

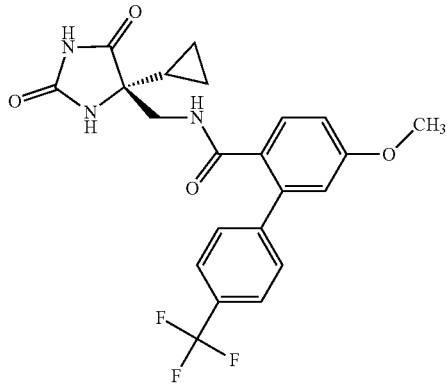 [SMILES: COc1ccc(C(=O)NC[C@@]2(C3CC3)NC(=O)NC2=O)c(-c2ccc(C(F)(F)F)cc2)c1]

(5R)-5-(aminomethyl)-5-cyclopropylimidazolidine-2,4-dione hydrochloride (40.0 mg, 195 µmol) and 5-methoxy-4'-(trifluoromethyl)[1,1'-biphenyl]-2-carboxylic acid (57.6 mg, 195 µmol) dissolved in DMF (1.7 ml) were treated with 1-ethyl-3-(3-dimethylaminopropyl)carbodiimide hydrochloride (48.5 mg, 253 µmol), 1-hydroxybenzotriazole hydrate (38.7 mg, 253 µmol) and N,N-diisopropylethylamine (95 µl, 540 µmol). The mixture was stirred for 3 hours at room temperature. Water was added and the mixture was extracted with ethyl acetate. The combined organic layers were dried, filtered and evaporated and the residue was purified by flash-column chromatography (n-heptane:ethyl acetate (60:40)+ethyl acetate+ethyl acetate:methanol (80:20)). Product containing samples were united, the solvents were evaporated and the residue was lyophylized. 52.0 mg (99% purity, 59% yield) of the title compound were obtained.

LC-MS (Method 7): $R_t$=1.64 min, MS (ESIpos): m/z=448 [M+H]$^+$ $^1$H NMR (600 MHz, DMSO-d$_6$) δ ppm 0.13 (m, 1H) 0.29-0.37 (m, 1H) 0.39 (m, 1H) 0.43-0.48 (m, 1H) 1.04-1.09 (m, 1H) 3.42-3.58 (m, 2H) 3.83 (s, 3H) 6.94 (d, J=2.38 Hz, 1H) 7.02 (dd, J=8.53, 2.48 Hz, 1H) 7.43 (d, J=8.44 Hz, 1H) 7.49 (s, 1H) 7.55 (d, J=8.07 Hz, 2H) 7.75 (d, J=8.25 Hz, 2H) 8.39 (t, J=6.14 Hz, 1H) 10.65 (br s, 1H).

Example 108

4'-Cyclopropyl-N-{[(4R)-4-Cyclopropyl-2,5-Dioxoimidazolidin-4-Yl]Methyl}-5-(Trifluoromethyl)[Biphenyl]-2-Carboxamide

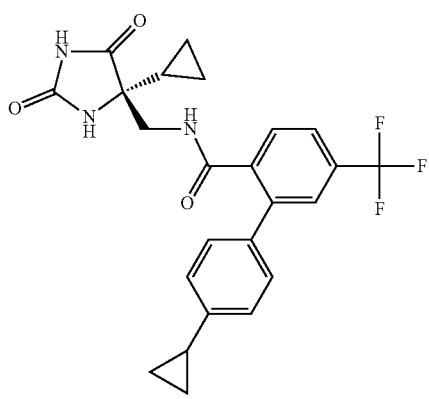 [SMILES: O=C1NC(=O)[C@](CNC(=O)c2ccc(C(F)(F)F)cc2-c2ccc(C3CC3)cc2)(C2CC2)N1]

(5R)-5-(aminomethyl)-5-cyclopropylimidazolidine-2,4-dione hydrochloride (32.2 mg, 157 µmol) and 4'-cyclopropyl-5-(trifluoromethyl)[1,1'-biphenyl]-2-carboxylic acid (48.0 mg, 157 µmol) dissolved in DMF (1.4 ml) were treated with 1-ethyl-3-(3-dimethylaminopropyl)carbodiimide hydrochloride (39.1 mg, 204 µmol), 1-hydroxybenzotriazole hydrate (31.2 mg, 204 µmol) and N,N-diisopropylethylamine (76 µl, 440 µmol). The mixture was stirred 3 hours at room temperature. Water (5 ml) was added to the reaction and the resulting precipitate was filtered off. The residue was washed with water and dried to obtain 43.0 mg (99% purity, 59% yield) of the title compound.

LC-MS (Method 7): $R_t$=1.91 min; MS (ESIpos): m/z=458 [M+H]$^+$ $^1$H NMR (400 MHz, DMSO-d$_6$) δ ppm 0.07-0.19 (m, 1H) 0.26-0.51 (m, 3H) 0.62-0.78 (m, 2H) 0.94-1.01 (m, 2H) 1.07 (m, 1H) 1.90-1.98 (m, 1H) 3.50 (d, J=6.11 Hz, 2H) 7.13 (d, J=8.31 Hz, 2H) 7.31 (d, J=8.19 Hz, 2H) 7.51-7.58 (m, 2H) 7.65 (s, 1H) 7.74-7.79 (m, 1H) 8.59 (t, J=6.11 Hz, 1H) 10.64 (s, 1H).

Example 109

N-{[(4R)-4-Cyclopropyl-2,5-Dioxoimidazolidin-4-Yl]Methyl}-6-Methyl-4'-(Trifluoromethyl)[Biphenyl]-2-Carboxamide

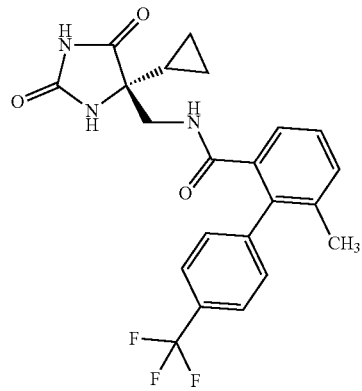 [SMILES: Cc1cccc(C(=O)NC[C@@]2(C3CC3)NC(=O)NC2=O)c1-c1ccc(C(F)(F)F)cc1]

(5R)-5-(aminomethyl)-5-cyclopropylimidazolidine-2,4-dione hydrochloride (40.0 mg, 195 µmol) and 6-methyl-4'-(trifluoromethyl)[1,1'-biphenyl]-2-carboxylic acid (54.5 mg, 195 µmol) dissolved in DMF (1000 µl) were treated with 1-ethyl-3-(3-dimethylaminopropyl)carbodiimide hydrochloride (48.5 mg, 253 µmol), 1-hydroxybenzotriazole hydrate (38.7 mg, 253 µmol) and N,N-diisopropylethylamine (95 µl, 540 µmol). The mixture was stirred overnight at room temperature. Purification was done by preparative HPLC (column: ReprosilC18 10 µm, 250×30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated and the residue was lyophylized. 50.2 mg (100% purity, 60% yield) of the title compound were obtained.

LC-MS (Method 7): $R_t$=1.68 min; MS (ESIpos): m/z=432 [M+H]$^+$ $^1$H-NMR (600 MHz, DMSO-d6) δ [ppm]: 0.092 (0.76), 0.100 (1.23), 0.108 (1.28), 0.116 (0.92), 0.124 (0.41), 0.256 (0.47), 0.262 (0.83), 0.270 (1.04), 0.277 (0.94), 0.284 (0.70), 0.292 (0.47), 0.322 (0.42), 0.330 (0.76), 0.340 (0.84), 0.345 (1.19), 0.354 (0.91), 0.359 (0.55), 0.383 (0.40), 0.392 (0.92), 0.400 (1.16), 0.408 (1.11), 0.416 (0.75), 0.958 (0.42), 0.966 (0.81), 0.971 (0.90), 0.980 (1.52), 0.985 (0.63), 0.989 (0.82), 0.994 (0.76), 2.045 (16.00), 3.339 (2.95), 3.341 (3.12), 3.351 (3.43), 3.364 (0.44), 7.231 (2.01), 7.243 (2.39), 7.346

(1.51), 7.358 (3.45), 7.371 (2.26), 7.393 (4.69), 7.406 (3.46), 7.448 (3.37), 7.717 (4.13), 7.731 (3.82), 8.269 (1.05), 8.279 (2.15), 8.290 (1.05), 10.621 (2.99).

Example 110

N-{[(4R)-4-Cyclopropyl-2,5-Dioxoimidazolidin-4-Yl]Methyl}-4'-Ethyl-5-Fluoro[Biphenyl]-2-Carboxamide

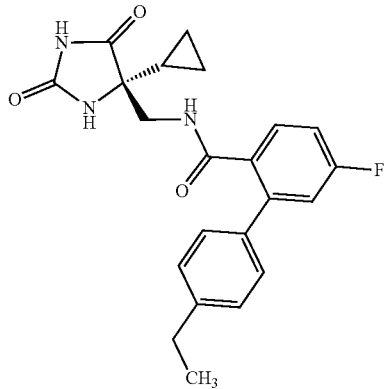 [SMILES: CCc1ccc(-c2cc(F)ccc2C(=O)NC[C@@]2(C3CC3)NC(=O)NC2=O)cc1]

(5R)-5-(aminomethyl)-5-cyclopropylimidazolidine-2,4-dione hydrochloride (40.0 mg, 195 µmol) and 4'-ethyl-5-fluoro[1,1'-biphenyl]-2-carboxylic acid (47.5 mg, 195 µmol) dissolved in DMF (1.7 ml) were treated with 1-ethyl-3-(3-dimethylaminopropyl)carbodiimide hydrochloride (48.5 mg, 253 µmol), 1-hydroxybenzotriazole hydrate (38.7 mg, 253 µmol) and N,N-diisopropylethylamine (95 µl, 540 µmol). The mixture was stirred for 2.5 hours at room temperature. Water was added and the mixture was extracted with ethyl acetate. The combined organic layers were dried, filtered and evaporated. The residue was purified twice by flash-column chromatography. Product containing samples were united, the solvents were evaporated. 46.0 mg (99% purity, 59% yield) of the title compound were obtained.

LC-MS (Method 7): $R_t$=1.67 min, MS (ESIpos): m/z=396 [M+H]$^+$ $^1$H NMR (600 MHz, DMSO-d$_6$) δ ppm 0.09-0.16 (m, 1H) 0.27-0.35 (m, 1H) 0.35-0.48 (m, 2H) 1.06 (ddd, J=8.21, 5.18, 2.93 Hz, 1H) 1.21 (t, J=7.61 Hz, 3H) 2.63 (q, J=7.70 Hz, 2H) 3.39-3.54 (m, 2H) 7.20-7.27 (m, 4H) 7.31 (d, J=8.07 Hz, 2H) 7.40 (dd, J=8.44, 6.05 Hz, 1H) 7.50 (s, 1H) 8.40 (t, J=6.14 Hz, 1H) 10.64 (s, 1H).

Example 111

N-{[(4R)-4-Cyclopropyl-2,5-Dioxoimidazolidin-4-Yl]Methyl}-4'-(2,2-Difluorocyclopropyl)[Biphenyl]-2-Carboxamide (Mixture of Diastereoisomers)

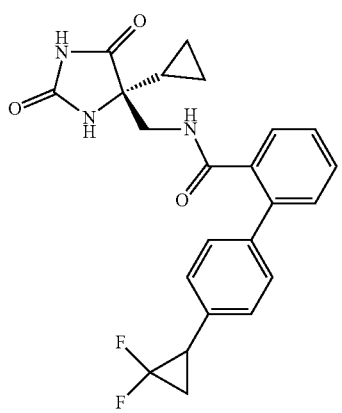 [SMILES: O=C1NC(=O)[C@](CNC(=O)c2ccccc2-c2ccc(C3CC3(F)F)cc2)(C2CC2)N1]

(5R)-5-(aminomethyl)-5-cyclopropylimidazolidine-2,4-dione hydrochloride (30.0 mg, 146 µmol) and 4'-(2,2-difluorocyclopropyl)[1,1'-biphenyl]-2-carboxylicacid (40.0 mg, 146 µmol) dissolved in DMF (1.3 ml) were treated with 1-ethyl-3-(3-dimethylaminopropyl)carbodiimide hydrochloride (36.3 mg, 190 µmol), 1-hydroxybenzotriazole hydrate (29.0 mg, 190 µmol) and N,N-diisopropylethylamine (71 µl, 410 µmol). The mixture was for 3 hours at room temperature. Water was added and the mixture was extracted with ethyl acetate. The combined organic layers were dried, filtered and evaporated and the residue was purified by flash-column chromatography (heptan:ethyl actetate (60:40)+ethyl acetate+ethyl acetate:methanol (80:20)). Product containing samples were united, the solvents were evaporated and the residue was lyophylized. 32.0 mg (99% purity, 51% yield) of the title compound were obtained.

LC-MS (Method 7): $R_t$=1.61 min, MS (ESIpos): m/z=426 [M+H]$^+$ $^1$H-NMR (400 MHz, DMSO-d6) δ [ppm]: −0.008 (1.62), 0.008 (1.60), 0.105 (1.26), 0.118 (1.93), 0.129 (2.08), 0.142 (1.57), 0.276 (0.46), 0.299 (1.50), 0.311 (1.90), 0.322 (1.80), 0.333 (1.41), 0.343 (1.08), 0.369 (1.30), 0.380 (1.57), 0.391 (1.89), 0.412 (1.59), 0.424 (2.16), 0.437 (2.06), 0.448 (1.96), 0.461 (1.28), 1.026 (0.78), 1.039 (1.62), 1.047 (1.72), 1.052 (1.28), 1.060 (2.94), 1.073 (1.60), 1.080 (1.44), 1.093 (0.61), 1.901 (0.45), 1.911 (0.59), 1.921 (1.60), 1.932 (1.83), 1.942 (1.53), 1.953 (3.29), 1.965 (1.90), 1.974 (1.88), 1.985 (2.52), 1.998 (1.93), 2.015 (1.31), 2.029 (1.07), 2.049 (0.48), 2.072 (1.63), 2.669 (0.40), 2.970 (1.30), 2.993 (1.36), 3.001 (1.86), 3.024 (1.83), 3.033 (1.44), 3.055 (1.20), 3.439 (0.61), 3.453 (0.74), 3.475 (3.46), 3.490 (5.19), 3.498 (3.04), 3.506 (2.44), 3.524 (0.68), 3.540 (0.61), 7.277 (6.33), 7.298 (12.84), 7.336 (16.00), 7.357 (8.97), 7.377 (11.38), 7.385 (5.34), 7.388 (4.18), 7.395 (7.24), 7.403 (6.13), 7.421 (2.14), 7.476 (10.59), 7.480 (6.22), 7.494 (4.63), 7.499 (3.97), 7.512 (1.73), 7.517 (1.75), 8.365 (2.01), 8.380 (4.17), 8.395 (1.96), 10.631 (4.52).

Example 112

4'-Cyclobutyl-N-{[(4R)-4-Cyclopropyl-2,5-Dioxoimidazolidin-4-Yl]Methyl}[Biphenyl]-2-Carboxamide

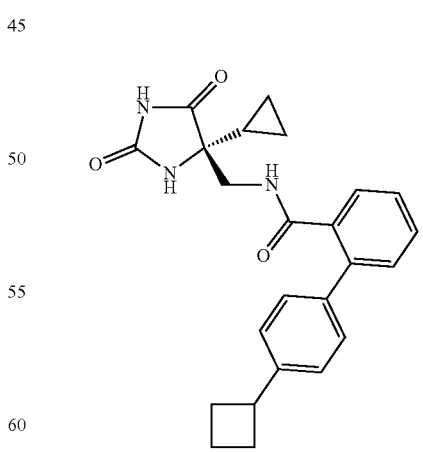

(5R)-5-(aminomethyl)-5-cyclopropylimidazolidine-2,4-dione hydrochloride (40.0 mg, 195 µmol) and 4'-cyclobutyl [1,1'-biphenyl]-2-carboxylic acid (49.1 mg, 195 µmol) dissolved in DMF (1000 µl) were treated with 1-ethyl-3-(3-dimethylaminopropyl)carbodiimide hydrochloride (48.5 mg, 253 µmol), 1-hydroxybenzotriazole hydrate (38.7 mg, 253 µmol) and N,N-diisopropylethylamine (95 µl, 540 µmol). The mixture was stirred overnight at room temperature. Purification was done by preparative HPLC (column: Reprosil C18 10 µm, 250×30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated and the residue was lyophylized. 76.1 mg (100% purity, 97% yield) of the title compound were obtained.

LC-MS (Method 7): $R_t$=1.80 min; MS (ESIpos): m/z=404 [M+H]$^+$ $^1$H-NMR (600 MHz, DMSO-d6) δ [ppm]: 0.102 (0.81), 0.111 (1.82), 0.118 (2.96), 0.127 (3.04), 0.134 (2.18), 0.143 (0.95), 0.282 (0.70), 0.297 (2.00), 0.304 (2.50), 0.312 (2.24), 0.320 (1.62), 0.327 (1.08), 0.360 (0.96), 0.368 (1.77), 0.377 (2.01), 0.383 (2.79), 0.392 (2.15), 0.397 (1.34), 0.407 (0.83), 0.416 (1.10), 0.425 (2.34), 0.432 (2.95), 0.441 (2.82), 0.449 (1.90), 0.458 (0.67), 1.029 (0.98), 1.038 (1.98), 1.042 (2.16), 1.051 (3.58), 1.056 (1.58), 1.060 (1.98), 1.065 (1.79), 1.074 (0.79), 1.801 (0.77), 1.816 (2.19), 1.833 (2.64), 1.847 (1.16), 1.945 (0.50), 1.959 (1.30), 1.962 (1.39), 1.975 (3.19), 1.992 (3.29), 2.006 (1.65), 2.009 (1.61), 2.023 (0.76), 2.084 (1.09), 2.098 (3.39), 2.100 (3.50), 2.116 (4.95), 2.133 (3.27), 2.147 (0.87), 2.150 (0.89), 2.272 (1.84), 2.276 (2.37), 2.286 (4.13), 2.290 (5.73), 2.294 (3.42), 2.300 (3.44), 2.304 (5.35), 2.308 (3.45), 2.318 (1.83), 2.322 (1.32), 3.456 (1.50), 3.466 (1.72), 3.478 (5.04), 3.488 (5.21), 3.493 (5.37), 3.504 (5.04), 3.513 (3.04), 3.527 (5.04), 3.542 (2.46), 3.557 (0.78), 3.835 (0.45), 7.240 (9.24), 7.254 (14.50), 7.298 (16.00), 7.311 (9.73), 7.351 (3.11), 7.361 (13.48), 7.370 (5.95), 7.374 (8.20), 7.381 (6.28), 7.394 (2.31), 7.471 (9.48), 7.480 (5.92), 7.483 (5.11), 7.492 (2.20), 7.495 (2.21), 8.339 (2.64), 8.349 (5.23), 8.360 (2.59), 10.639 (7.17).

Example 113

4'-Tert-Butyl-N-{[(4R)-4-Cyclopropyl-2,5-Dioxoimidazolidin-4-Yl]Methyl}[Biphenyl]-2-Carboxamide

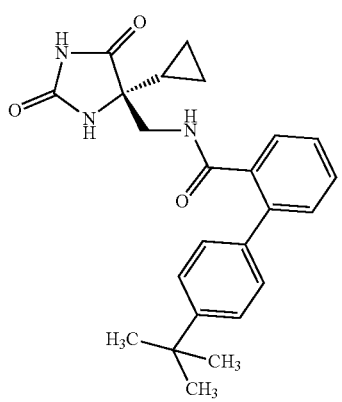 [SMILES: CC(C)(C)c1ccc(-c2ccccc2C(=O)NC[C@@]2(C3CC3)NC(=O)NC2=O)cc1]

(5R)-5-(aminomethyl)-5-cyclopropylimidazolidine-2,4-dione hydrochloride (40.0 mg, 195 µmol) and 4'-tert-butyl [1,1'-biphenyl]-2-carboxylic acid (49.5 mg, 195 µmol) dissolved in DMF (1.6 ml) were treated with 1-ethyl-3-(3-dimethylaminopropyl)carbodiimide hydrochloride (48.5 mg, 253 µmol), 1-hydroxybenzotriazole hydrate (38.7 mg, 253 µmol) and N,N-diisopropylethylamine (95 µl, 540 µmol). The mixture was stirred over night at room temperature. Water was added and the mixture was extracted with ethyl acetate. The combined organic layers were dried, filtered and evaporated and the residue was purified by flash-column chromatography (n-heptane:ethyl actetate (70:30)→ethyl acetate). Product containing samples were united, the solvents were evaporated and the residue was lyophylized. 52.0 mg (99% purity, 65% yield) of the title compound were obtained.

LC-MS (Method 7): $R_t$=1.82 min, MS (ESIpos): m/z=406 [M+H]$^+$ $^1$H-NMR (600 MHz, DMSO-d6) δ [ppm]: 1.065 (0.43), 1.285 (0.74), 1.304 (16.00), 3.324 (8.15), 3.328 (8.13), 3.486 (0.59), 3.496 (0.57), 3.504 (0.56), 3.515 (0.54), 7.313 (1.27), 7.327 (1.67), 7.349 (0.47), 7.359 (0.90), 7.362 (0.90), 7.372 (1.09), 7.384 (1.08), 7.386 (1.21), 7.402 (1.73), 7.416 (1.24), 7.469 (1.62), 7.484 (0.63), 8.373 (0.61), 10.640 (0.53).

Example 114

N-{[(4R)-4-Cyclopropyl-2,5-Dioxoimidazolidin-4-Yl]Methyl}-4'-(Trifluoromethyl)[Biphenyl]-2-Carboxamide

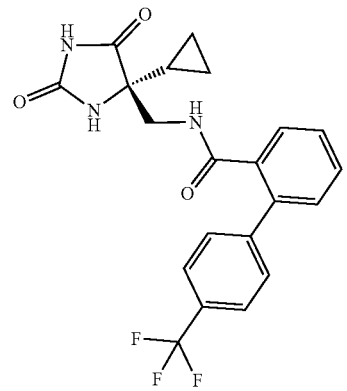 [SMILES: O=C1NC(=O)[C@](CNC(=O)c2ccccc2-c2ccc(C(F)(F)F)cc2)(C2CC2)N1]

(5R)-5-(aminomethyl)-5-cyclopropylimidazolidine-2,4-dione hydrochloride (40.0 mg, 195 µmol) and 4'-(trifluoromethyl)[1,1'-biphenyl]-2-carboxylicacid (51.8 mg, 195 µmol) dissolved in DMF (1.6 ml) were treated with 1-ethyl-3-(3-dimethylaminopropyl)carbodiimide hydrochloride (48.5 mg, 253 µmol), 1-hydroxybenzotriazole hydrate (38.7 mg, 253 µmol) and N,N-diisopropylethylamine (95 µl, 540 µmol). The mixture was stirred overnight at room temperature. Water was added and the mixture was extracted with ethylacetate. The combined organic layers were dried, filtered and evaporated and the residue was purified by flash-column chromatography (n-heptane:ethyl actetate (80:20) →n-heptane:ethyl acetate (20:80)). Product containing samples were united, the solvents were evaporated and the residue was lyophylized. 61.0 mg (99% purity, 74% yield) of the title compound were obtained.

LC-MS (Method 10): $R_t$=1.14 min, MS (ESIneg): m/z=416 [M−H]$^-$ $^1$H-NMR (400 MHz, DMSO-d6) δ [ppm]: −0.008 (2.24), 0.008 (1.85), 0.110 (0.81), 0.123 (1.98), 0.134 (3.47), 0.147 (3.83), 0.158 (2.57), 0.171 (1.14), 0.286 (0.69), 0.301 (1.21), 0.310 (2.23), 0.321 (2.80), 0.331 (2.62), 0.343 (2.04), 0.354 (1.52), 0.366 (1.33), 0.377 (2.16), 0.391 (2.47), 0.399 (3.23), 0.412 (2.47), 0.420 (1.42), 0.437 (1.69), 0.451 (2.74), 0.462 (3.45), 0.475 (3.28), 0.487 (2.04), 0.501 (0.69), 1.039 (1.10), 1.052 (2.31), 1.060 (2.49), 1.065 (1.86), 1.073 (4.19), 1.080 (1.76), 1.086 (2.26), 1.093 (2.00), 1.106 (0.86), 1.988 (0.67), 2.731 (3.71), 2.890 (4.90), 3.470 (0.74), 3.485 (1.00), 3.504 (7.35), 3.510 (7.51), 3.519 (7.25), 3.526 (6.94), 3.545 (0.90), 3.561 (0.78), 7.430 (7.99), 7.449 (16.00), 7.459 (6.02), 7.474 (7.51), 7.493 (2.73), 7.526 (13.32), 7.534 (5.95), 7.550 (14.84), 7.571 (14.71), 7.751 (13.08), 7.771 (10.63), 7.953 (0.54), 8.538 (2.73), 8.553 (5.64), 8.569 (2.64), 10.644 (6.47).

Example 115

N-{[(4R)-4-Cyclopropyl-2,5-Dioxoimidazolidin-4-Yl]Methyl}-4'-[1-(Trifluoromethyl)Cyclopropyl][Biphenyl]-2-Carboxamide

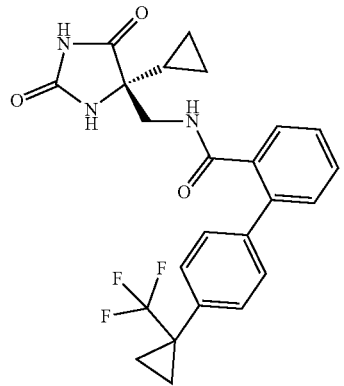 [SMILES: O=C1NC(=O)[C@](CNC(=O)c2ccccc2-c2ccc(C3(C(F)(F)F)CC3)cc2)(C2CC2)N1]

(5R)-5-(aminomethyl)-5-cyclopropylimidazolidine-2,4-dione hydrochloride (37.8 mg, 184 μmol) and 4'-[1-(trifluoromethyl)cyclopropyl][1,1'-biphenyl]-2-carboxylic acid (56.3 mg, 184 μmol) dissolved in DMF (1.0 ml) were treated with 1-ethyl-3-(3-dimethylaminopropyl)carbodiimide hydrochloride (45.8 mg, 239 μmol), 1-hydroxybenzotriazole hydrate (36.6 mg, 239 μmol) and N,N-diisopropylethylamine (90 μl, 510 μmol). The mixture was stirred over night at room temperature. Purification was done by preparative HPLC (column: Chromatorex C18 10 μm, 250×30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated and the residue was lyophylized. 48.8 mg (100% purity, 58% yield) of the title compound were obtained.

LC-MS (Method 7): $R_t$=1.87 min; MS (ESIpos): m/z=458 [M+H]$^+$ $^1$H-NMR (400 MHz, DMSO-d6) δ [ppm]: 0.008 (1.86), 0.094 (0.56), 0.107 (1.38), 0.118 (2.29), 0.131 (2.42), 0.142 (1.73), 0.155 (0.77), 0.275 (0.45), 0.298 (1.48), 0.310 (1.91), 0.320 (1.86), 0.332 (1.42), 0.343 (1.22), 0.358 (1.46), 0.372 (1.71), 0.380 (2.21), 0.394 (1.67), 0.402 (1.03), 0.411 (1.13), 0.424 (1.91), 0.435 (2.29), 0.448 (2.19), 0.461 (1.34), 0.473 (0.45), 1.044 (0.75), 1.058 (1.50), 1.065 (1.68), 1.078 (2.70), 1.091 (1.52), 1.098 (1.45), 1.112 (0.79), 1.157 (5.88), 1.343 (3.40), 1.354 (8.40), 1.369 (2.75), 3.454 (0.73), 3.469 (0.89), 3.489 (4.16), 3.502 (5.45), 3.515 (4.02), 3.533 (0.84), 3.549 (0.74), 3.924 (1.10), 7.374 (9.99), 7.388 (12.13), 7.395 (16.00), 7.406 (7.19), 7.416 (5.23), 7.435 (1.96), 7.469 (10.97), 7.484 (11.32), 7.488 (11.32), 7.503 (3.94), 7.507 (3.61), 7.521 (1.42), 7.525 (1.46), 8.432 (1.93), 8.447 (3.98), 8.462 (1.87), 10.640 (5.68).

Example 116

N-{[(4R)-4-Cyclopropyl-2,5-Dioxoimidazolidin-4-Yl]Methyl}-5-Fluoro-4'-(Trifluoromethyl)[Biphenyl]-2-Carboxamide

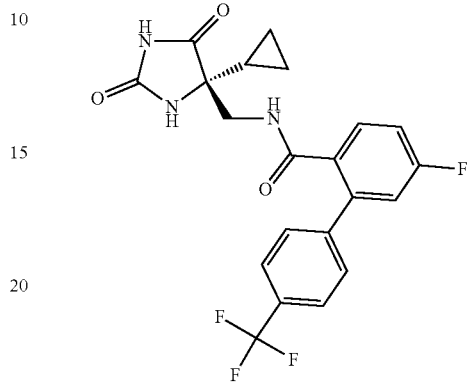

(5R)-5-(aminomethyl)-5-cyclopropylimidazolidine-2,4-dione hydrochloride (40.0 mg, 195 μmol) and 5-fluoro-4'-(trifluoromethyl)[1,1'-biphenyl]-2-carboxylic acid (55.3 mg, 195 μmol) dissolved in DMF (1.7 ml) were treated with 1-ethyl-3-(3-dimethylaminopropyl)carbodiimide hydrochloride (48.5 mg, 253 μmol), 1-hydroxybenzotriazole hydrate (38.7 mg, 253 μmol) and N,N-diisopropylethylamine (95 μl, 540 μmol). The mixture was stirred overnight at room temperature. Water was added and the mixture was extracted with ethyl acetate. The combined organic layers were dried, filtered and evaporated and the residue was purified by flash-column chromatography (n-heptane:ethyl acetetate (80:20)-ethyl acetate). Product containing samples were united, the solvents were evaporated and the residue was lyophylized. 68.0 mg (99% purity, 79% yield) of the title compound were obtained.

LC-MS (Method 7): $R_t$=1.66 min, MS (ESIpos): m/z=436 [M+H]$^+$ $^1$H-NMR (400 MHz, DMSO-d6) δ [ppm]: −0.008 (0.75), 0.008 (0.79), 0.110 (0.98), 0.123 (2.31), 0.134 (4.08), 0.148 (4.36), 0.158 (3.05), 0.171 (1.37), 0.289 (0.79), 0.303 (1.38), 0.311 (2.63), 0.323 (3.29), 0.333 (3.13), 0.346 (2.45), 0.356 (1.89), 0.366 (1.65), 0.377 (2.56), 0.391 (2.91), 0.399 (3.82), 0.413 (2.92), 0.420 (1.70), 0.439 (1.79), 0.453 (3.22), 0.464 (4.11), 0.477 (3.89), 0.489 (2.40), 0.502 (0.88), 1.042 (1.37), 1.055 (2.71), 1.063 (2.92), 1.069 (2.19), 1.076 (4.97), 1.083 (2.12), 1.089 (2.70), 1.097 (2.43), 1.110 (1.05), 2.731 (0.91), 2.890 (1.16), 3.461 (1.33), 3.476 (1.66), 3.495 (7.44), 3.507 (9.79), 3.522 (7.28), 3.540 (1.54), 3.556 (1.42), 7.311 (3.82), 7.317 (12.06), 7.339 (16.00), 7.359 (4.69), 7.365 (3.13), 7.479 (5.34), 7.492 (4.97), 7.499 (5.13), 7.514 (3.87), 7.547 (15.54), 7.568 (13.20), 7.588 (15.23), 7.765 (15.84), 7.786 (13.04), 8.579 (3.33), 8.595 (6.90), 8.610 (3.29), 10.647 (8.35).

Example 117

N-{[(4R)-4-Cyclopropyl-2,5-Dioxoimidazolidin-4-Yl]Methyl}-4',5-Bis(Trifluoromethyl)[Biphenyl]-2-Carboxamide

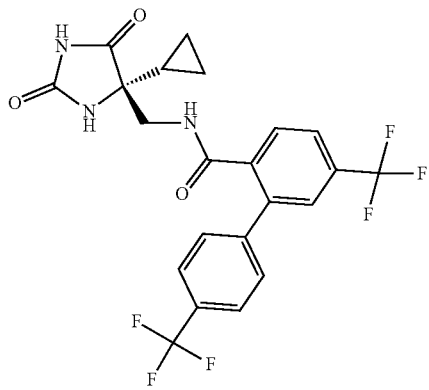 [SMILES: O=C1NC(=O)[C@](CNC(=O)c2ccc(C(F)(F)F)cc2-c2ccc(C(F)(F)F)cc2)(C2CC2)N1]

(5R)-5-(aminomethyl)-5-cyclopropylimidazolidine-2,4-dione hydrochloride (40.0 mg, 195 µmol) and 4',5-bis(trifluoromethyl)[1,1'-biphenyl]-2-carboxylic acid (65.0 mg, 195 µmol) dissolved in DMF (1.7 ml) were treated with 1-ethyl-3-(3-dimethylaminopropyl)carbodiimide hydrochloride (48.5 mg, 253 µmol), 1-hydroxybenzotriazole hydrate (38.7 mg, 253 µmol) and N,N-diisopropylethylamine (95 µl, 540 µmol). The mixture was stirred 3 hours at room temperature. Water (5 ml) was added to the reaction and the resulting precipitate was filtered off. The residue was washed with water and dried to obtain 76.0 mg (97% purity, 78% yield) of the title compound.

LC-MS (Method 7): $R_t$=1.85 min, MS (ESIpos): m/z=486 [M+H]$^+$ $^1$H-NMR (400 MHz, DMSO-d6) δ [ppm]: −0.008 (0.81), 0.008 (1.06), 0.118 (0.81), 0.132 (2.03), 0.143 (3.60), 0.156 (3.85), 0.166 (2.75), 0.179 (1.28), 0.296 (0.68), 0.319 (2.30), 0.331 (2.94), 0.341 (2.79), 0.353 (2.21), 0.364 (1.70), 0.372 (1.51), 0.383 (2.30), 0.397 (2.63), 0.405 (3.44), 0.419 (2.61), 0.427 (1.51), 0.446 (1.55), 0.460 (2.84), 0.471 (3.68), 0.483 (3.50), 0.495 (2.21), 0.509 (0.81), 0.960 (0.68), 0.978 (0.43), 1.048 (1.14), 1.062 (2.36), 1.069 (2.59), 1.074 (1.97), 1.082 (4.43), 1.090 (1.97), 1.095 (2.44), 1.103 (2.21), 1.116 (0.99), 2.075 (0.68), 2.366 (0.41), 2.710 (0.43), 3.478 (1.01), 3.494 (1.10), 3.512 (6.75), 3.521 (7.58), 3.528 (7.68), 3.536 (7.45), 3.555 (1.32), 3.570 (0.99), 7.609 (11.07), 7.624 (13.83), 7.646 (16.00), 7.692 (0.41), 7.713 (0.68), 7.774 (10.78), 7.793 (14.80), 7.813 (11.76), 7.867 (5.77), 7.887 (5.01), 8.752 (3.06), 8.767 (6.44), 8.782 (3.02), 10.665 (8.47).

Example 118

N-{[(4R)-4-Cyclopropyl-2,5-Dioxoimidazolidin-4-Yl]Methyl}-4'-Isopropyl[Biphenyl]-2-Carboxamide

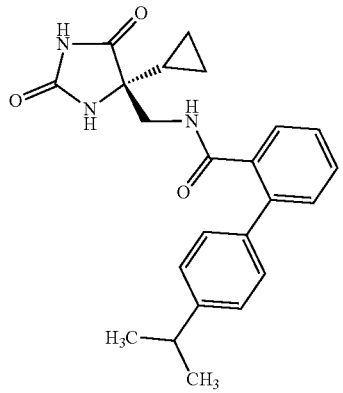 [SMILES: CC(C)c1ccc(-c2ccccc2C(=O)NC[C@@]2(C3CC3)NC(=O)NC2=O)cc1]

(5R)-5-(aminomethyl)-5-cyclopropylimidazolidine-2,4-dione hydrochloride (40.0 mg, 195 µmol) and 4'-(propan-2-yl)[1,1'-biphenyl]-2-carboxylic acid (46.7 mg, 195 µmol) dissolved in DMF (1.6 ml) were treated with 1-ethyl-3-(3-dimethylaminopropyl)carbodiimide hydrochloride (48.5 mg, 253 µmol), 1-hydroxybenzotriazole hydrate (38.7 mg, 253 µmol) and N,N-diisopropylethylamine (95 µl, 540 µmol). The mixture was stirred over night at room temperature. Water was added and the mixture was extracted with ethyl acetate. The combined organic layers were dried, filtered and evaporated and the residue was purified by flash-column chromatography (n-heptane:ethyl actetate (70:30)→ethyl acetate). Product containing samples were united, the solvents were evaporated and the residue was lyophylized. 56.0 mg (99% purity, 73% yield) of the title compound were obtained.

LC-MS (Method 7): $R_t$=1.73 min, MS (ESIpos): m/z=392 [M+H]$^+$ $^1$H-NMR (400 MHz, DMSO-d6) δ [ppm]: −0.008 (0.67), 0.008 (0.57), 0.102 (0.48), 0.113 (0.84), 0.126 (0.89), 0.136 (0.63), 0.291 (0.53), 0.303 (0.67), 0.313 (0.65), 0.325 (0.50), 0.335 (0.40), 0.354 (0.54), 0.369 (0.60), 0.376 (0.81), 0.391 (0.66), 0.398 (0.66), 0.412 (0.87), 0.423 (0.83), 0.436 (0.78), 0.448 (0.49), 1.039 (0.58), 1.047 (0.70), 1.060 (1.15), 1.073 (0.61), 1.080 (0.56), 1.218 (15.71), 1.235 (16.00), 2.885 (0.93), 2.903 (1.21), 2.920 (0.88), 3.478 (1.48), 3.492 (2.60), 3.508 (1.45), 7.246 (2.22), 7.267 (5.24), 7.296 (5.69), 7.317 (2.33), 7.343 (0.67), 7.359 (2.77), 7.364 (5.43), 7.383 (4.59), 7.400 (0.75), 7.458 (3.25), 7.466 (1.47), 7.484 (1.32), 7.498 (0.60), 7.502 (0.57), 8.327 (0.67), 8.342 (1.38), 8.357 (0.66), 10.629 (1.62).

Example 119

N-{[(4R)-4-Cyclopropyl-2,5-Dioxoimidazolidin-4-Yl]Methyl}-4'-(2,2,2-Trifluoroethyl)[Biphenyl]-2-Carboxamide

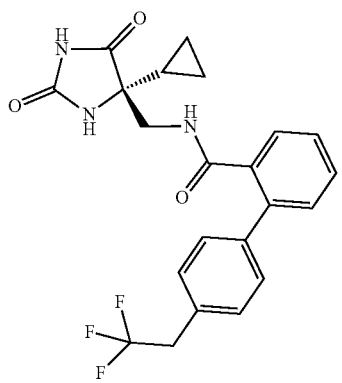 [SMILES: O=C1NC(=O)[C@](CNC(=O)c2ccccc2-c2ccc(CC(F)(F)F)cc2)(C2CC2)N1]

(5R)-5-(aminomethyl)-5-cyclopropylimidazolidine-2,4-dione hydrochloride (40.0 mg, 195 µmol) and 4'-(2,2,2-trifluoroethyl)[1,1'-biphenyl]-2-carboxylic acid (54.5 mg, 195 µmol) dissolved in DMF (1000 µl) were treated with 1-ethyl-3-(3-dimethylaminopropyl)carbodiimide hydrochloride (48.5 mg, 253 µmol), 1-hydroxybenzotriazole hydrate (38.7 mg, 253 µmol) and N,N-diisopropylethylamine (95 µl, 540 µmol). The mixture was stirred overnight at room temperature. Purification was done by preparative HPLC (column: ReprosilC18 10 µm, 250×30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated and the residue was lyophylized. 61.5 mg (100% purity, 73% yield) of the title compound were obtained.

LC-MS (Method 7): $R_t$=1.59 min; MS (ESIpos): m/z=432 [M+H]$^+$ $^1$H-NMR (400 MHz, DMSO-d6) δ [ppm]: −0.008 (0.87), 0.008 (0.92), 0.104 (0.48), 0.115 (0.85), 0.128 (0.90), 0.139 (0.64), 0.297 (0.53), 0.309 (0.67), 0.320 (0.64), 0.332 (0.50), 0.363 (0.54), 0.377 (0.59), 0.385 (0.81), 0.399 (0.63), 0.410 (0.56), 0.423 (0.79), 0.435 (0.84), 0.448 (0.79), 0.459 (0.48), 1.047 (0.57), 1.054 (0.61), 1.059 (0.44), 1.067 (1.04), 1.074 (0.43), 1.080 (0.56), 1.087 (0.50), 3.474 (1.69), 3.482 (1.80), 3.489 (1.77), 3.498 (1.64), 3.616 (0.78), 3.646 (2.25), 3.675 (2.14), 3.704 (0.68), 7.353 (0.45), 7.376 (16.00), 7.386 (2.86), 7.391 (3.13), 7.412 (2.94), 7.415 (3.17), 7.434 (0.83), 7.485 (3.38), 7.504 (1.47), 7.508 (1.41), 7.522 (0.61), 7.526 (0.56), 8.373 (0.69), 8.389 (1.47), 8.404 (0.69), 10.628 (1.99).

Example 120

N-{[(4R)-4-Cyclopropyl-2,5-Dioxoimidazolidin-4-Yl]Methyl}-4'-(1,1,1-Trifluoro-2-Methylpropan-2-Yl)[Biphenyl]-2-Carboxamide

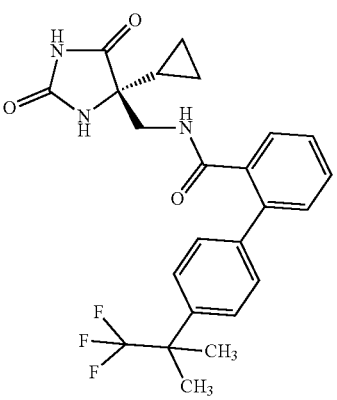 [SMILES: CC(C)(c1ccc(-c2ccccc2C(=O)NC[C@@]2(C3CC3)NC(=O)NC2=O)cc1)C(F)(F)F]

(5R)-5-(aminomethyl)-5-cyclopropylimidazolidine-2,4-dione hydrochloride (40.0 mg, 195 µmol) and 4'-(1,1,1-trifluoro-2-methylpropan-2-yl)[1,1'-biphenyl]-2-carboxylic acid (60.0 mg, 195 µmol) dissolved in DMF (1000 µl) were treated with 1-ethyl-3-(3-dimethylaminopropyl)carbodiimide hydrochloride (48.5 mg, 253 µmol), 1-hydroxybenzotriazole hydrate (38.7 mg, 253 µmol) and N,N-diisopropylethylamine (95 µl, 540 µmol). The mixture was stirred over night at room temperature. Purification was done by preparative HPLC (column: Reprosil C18 10 µm, 250×30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated and the residue was lyophylized. 65.3 mg (94% purity, 69% yield) of the title compound were obtained.

LC-MS (Method 7): $R_t$=1.79 min; MS (ESIpos): m/z=460 [M+H]$^+$ $^1$H-NMR (400 MHz, DMSO-d6) δ [ppm]: 0.008 (0.47), 0.118 (0.71), 0.131 (0.76), 0.141 (0.55), 0.295 (0.45), 0.308 (0.56), 0.317 (0.56), 0.330 (0.45), 0.355 (0.46), 0.369 (0.52), 0.377 (0.67), 0.391 (0.54), 0.423 (0.58), 0.434 (0.73), 0.447 (0.70), 0.459 (0.44), 1.057 (0.48), 1.065 (0.53), 1.078 (0.90), 1.091 (0.49), 1.098 (0.44), 1.577 (16.00), 3.490 (1.31), 3.500 (1.59), 3.504 (1.51), 3.515 (1.39), 7.367 (0.63), 7.370 (0.76), 7.386 (2.04), 7.391 (2.17), 7.397 (4.03), 7.399 (3.76), 7.418 (6.67), 7.434 (1.00), 7.486 (3.28), 7.490 (1.53), 7.503 (1.03), 7.508 (1.36), 7.523 (0.60), 7.527 (0.65), 7.547 (2.75), 7.568 (2.02), 8.424 (0.58), 8.440 (1.23), 8.455 (0.58), 10.649 (1.36).

Example 121

N-{[(4R)-4-Cyclopropyl-2,5-Dioxoimidazolidin-4-Yl]Methyl}-4-Fluoro-4'-(Trifluoromethyl)[Biphenyl]-2-Carboxamide

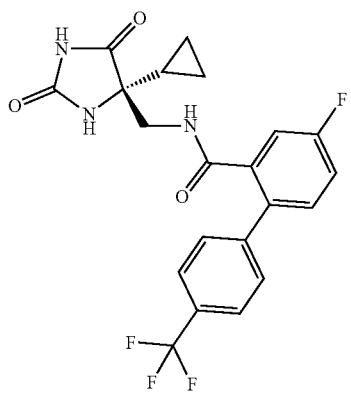 [SMILES: O=C1NC(=O)[C@](CNC(=O)c2cc(F)ccc2-c2ccc(C(F)(F)F)cc2)(C2CC2)N1]

(5R)-5-(aminomethyl)-5-cyclopropylimidazolidine-2,4-dione hydrochloride (40.0 mg, 195 µmol) and 4-fluoro-4'-(trifluoromethyl)[1,1'-biphenyl]-2-carboxylic acid (55.3 mg, 195 µmol, CAS 537713-35-2) dissolved in DMF (1000 µl) were treated with 1-ethyl-3-(3-dimethylaminopropyl)carbodiimide hydrochloride (48.5 mg, 253 µmol), 1-hydroxybenzotriazole hydrate (38.7 mg, 253 µmol) and N,N-diisopropylethylamine (95 µl, 540 µmol). The mixture was stirred over night at room temperature. Purification was done by preparative HPLC (column: Chromatorex C18 10 µm, 250×30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated and the residue was lyophylized. 73.7 mg (100% purity, 87% yield) of the title compound were obtained.

LC-MS (Method 7): $R_t$=1.65 min; MS (ESIpos): m/z=436 $[M+H]^+$ $^1$H-NMR (400 MHz, DMSO-d6) δ [ppm]: 0.008 (1.46), 0.118 (1.02), 0.131 (2.45), 0.142 (4.19), 0.155 (4.41), 0.166 (3.19), 0.179 (1.42), 0.294 (0.86), 0.317 (2.70), 0.329 (3.44), 0.339 (3.28), 0.351 (2.50), 0.362 (1.92), 0.371 (1.66), 0.382 (2.61), 0.396 (2.99), 0.405 (3.91), 0.418 (2.93), 0.426 (1.69), 0.440 (1.13), 0.449 (1.58), 0.463 (3.29), 0.474 (4.22), 0.486 (4.00), 0.499 (2.52), 0.512 (0.86), 1.050 (1.32), 1.064 (2.76), 1.071 (2.97), 1.084 (4.97), 1.098 (2.70), 1.105 (2.39), 1.118 (1.02), 2.366 (0.42), 3.469 (0.89), 3.484 (1.25), 3.504 (9.49), 3.508 (9.44), 3.519 (9.20), 3.524 (8.95), 3.542 (1.17), 3.559 (1.05), 3.726 (1.54), 7.253 (5.76), 7.259 (6.86), 7.275 (5.90), 7.282 (6.52), 7.383 (2.48), 7.389 (2.44), 7.404 (6.11), 7.411 (6.03), 7.425 (3.94), 7.432 (3.82), 7.477 (6.88), 7.491 (7.24), 7.499 (5.06), 7.512 (4.67), 7.527 (13.28), 7.547 (15.54), 7.592 (11.10), 7.749 (16.00), 7.770 (13.32), 8.684 (3.41), 8.700 (7.15), 8.715 (3.36), 10.678 (9.99).

Example 122

N-{[(4R)-4-Cyclopropyl-2,5-Dioxoimidazolidin-4-Yl]Methyl}-4'-(Difluoromethyl)[Biphenyl]-2-Carboxamide

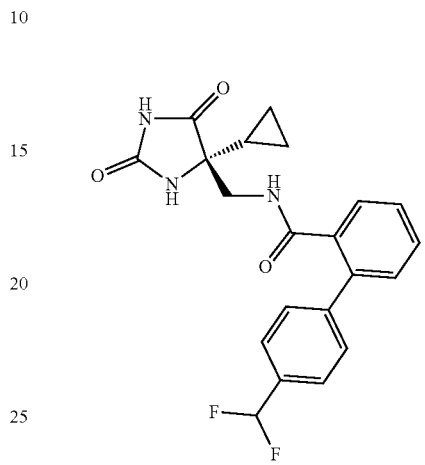

(5R)-5-(aminomethyl)-5-cyclopropylimidazolidine-2,4-dione hydrochloride (40.0 mg, 195 µmol) and 4'-(difluoromethyl)[1,1'-biphenyl]-2-carboxylic acid (48.3 mg, 195 µmol) dissolved in DMF (1000 µl) were treated with 1-ethyl-3-(3-dimethylaminopropyl)carbodiimide hydrochloride (48.5 mg, 253 µmol), 1-hydroxybenzotriazole hydrate (38.7 mg, 253 µmol) and N,N-diisopropylethylamine (95 µl, 540 µmol). The mixture was stirred overnight at room temperature. Purification was done by preparative HPLC (column: Chromatorex C18 10 µm, 250×30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated and the residue was lyophylized. 63.6 mg (100% purity, 82% yield) of the title compound were obtained.

LC-MS (Method 7): $R_t$=1.55 min; MS (ESIpos): m/z=400 $[M+H]^+$ $^1$H-NMR (600 MHz, DMSO-d6) δ [ppm]: −0.138 (0.54), −0.008 (0.64), 0.008 (0.46), 0.172 (0.41), 0.179 (0.52), 0.187 (0.46), 0.252 (0.41), 0.258 (0.58), 0.267 (0.45), 0.308 (0.50), 0.316 (0.64), 0.324 (0.61), 0.332 (0.40), 0.912 (0.42), 0.917 (0.46), 0.926 (0.78), 0.935 (0.42), 2.360 (3.47), 2.363 (4.87), 2.366 (3.63), 2.402 (16.00), 3.355 (1.28), 3.363 (1.50), 3.365 (1.50), 3.373 (1.25), 6.828 (0.77), 6.921 (1.58), 7.014 (0.68), 7.273 (1.71), 7.286 (2.65), 7.298 (0.82), 7.300 (0.86), 7.310 (1.25), 7.312 (1.15), 7.323 (0.51), 7.325 (0.54), 7.346 (2.01), 7.359 (2.56), 7.377 (1.84), 7.381 (1.07), 7.391 (1.14), 7.394 (1.06), 7.404 (0.46), 7.406 (0.50), 7.448 (2.24), 7.461 (1.76), 8.334 (0.55), 8.344 (1.12), 8.354 (0.55), 10.508 (1.49).

Example 123

4'-(2-Cyanopropan-2-Yl)-N-{[(4R)-4-Cyclopropyl-2,5-Dioxoimidazolidin-4-Yl]Methyl}[Biphenyl]-2-Carboxamide

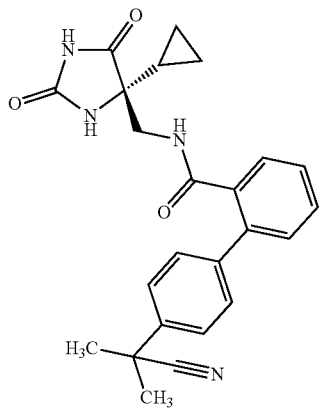 [SMILES: CC(C)(C#N)c1ccc(-c2ccccc2C(=O)NC[C@@]2(C3CC3)NC(=O)NC2=O)cc1]

(5R)-5-(aminomethyl)-5-cyclopropylimidazolidine-2,4-dione hydrochloride (40.0 mg, 195 µmol) and 4'-(2-cyanopropan-2-yl)[1,1'-biphenyl]-2-carboxylic acid (51.6 mg, 195 µmol) dissolved in DMF (1000 µl) were treated with 1-ethyl-3-(3-dimethylaminopropyl)carbodiimide hydrochloride (48.5 mg, 253 µmol), 1-hydroxybenzotriazole hydrate (38.7 mg, 253 µmol) and N,N-diisopropylethylamine (95 µl, 540 µmol). The mixture was stirred overnight at room temperature. Purification was done by preparative HPLC (column: Reprosil C18 10 µm, 250×30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated and the residue was lyophylized. 89.8 mg (100% purity, 111% yield) of the title compound were obtained.

LC-MS (Method 7): R$_t$=1.47 min; MS (ESIpos): m/z=417 [M+H]$^+$ $^1$H-NMR (400 MHz, DMSO-d6) δ [ppm]: −0.008 (0.87), 0.008 (0.81), 0.112 (0.42), 0.123 (0.77), 0.136 (0.81), 0.146 (0.66), 0.302 (0.48), 0.314 (0.60), 0.325 (0.57), 0.337 (0.45), 0.365 (0.49), 0.379 (0.54), 0.387 (0.71), 0.401 (0.55), 0.430 (0.61), 0.441 (0.75), 0.454 (0.71), 0.465 (0.42), 1.057 (0.51), 1.065 (0.55), 1.078 (0.94), 1.091 (0.49), 1.098 (0.44), 1.714 (16.00), 1.716 (15.64), 3.497 (1.57), 3.503 (1.60), 3.512 (1.56), 3.519 (1.51), 7.373 (0.62), 7.377 (0.78), 7.392 (3.87), 7.403 (1.52), 7.411 (2.40), 7.419 (3.86), 7.423 (2.31), 7.435 (1.55), 7.439 (5.27), 7.491 (2.66), 7.495 (3.07), 7.508 (1.53), 7.513 (1.35), 7.528 (5.04), 7.544 (1.24), 7.549 (3.11), 8.430 (0.63), 8.445 (1.36), 8.461 (0.63), 10.644 (1.79).

Example 124

4'-Tert-Butyl-N-{[(4R)-4-Cyclopropyl-2,5-Dioxoimidazolidin-4-Yl]Methyl}-5-Fluoro[Biphenyl]-2-Carboxamide

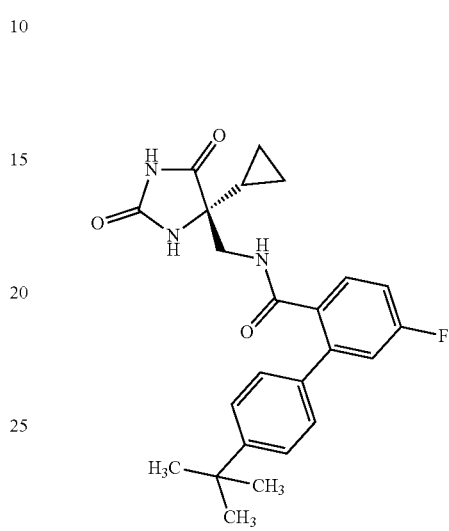

(5R)-5-(aminomethyl)-5-cyclopropylimidazolidine-2,4-dione hydrochloride (40.0 mg, 195 µmol) and 4'-tert-butyl-5-fluoro[1,1'-biphenyl]-2-carboxylic acid (53.0 mg, 195 µmol, CAS 926200-09-1) dissolved in DMF (1.7 ml) were treated with 1-ethyl-3-(3-dimethylaminopropyl)carbodiimide hydrochloride (48.5 mg, 253 µmol), 1-hydroxybenzotriazole hydrate (38.7 mg, 253 µmol) and N,N-diisopropylethylamine (95 µl, 540 µmol). The mixture was for 2.5 hours at room temperature. Water was added and the mixture was extracted with ethyl acetate. The combined organic layers were dried, filtered and evaporated and the residue was purified by flash-column chromatography (n-heptane:ethyl actetate (80:20)→n-heptane:ethyl acetate (20:80)). Product containing samples were united, the solvents were evaporated and the residue was lyophylized. 47.0 mg (99% purity, 56% yield) of the title compound were obtained.

LC-MS (Method 7): R$_t$=1.88 min, MS (ESIpos): m/z=424 [M+H]$^+$ $^1$H-NMR (600 MHz, DMSO-d6) δ [ppm]: 1.072 (0.40), 1.304 (16.00), 3.481 (0.55), 3.491 (0.52), 3.500 (0.52), 3.511 (0.52), 7.222 (0.62), 7.240 (0.81), 7.330 (1.24), 7.344 (1.61), 7.386 (0.48), 7.396 (0.51), 7.400 (0.48), 7.410 (0.51), 7.417 (1.68), 7.431 (1.17), 7.498 (1.11), 8.432 (0.59), 10.650 (0.55).

Example 125

N-{[(4R)-4-Cyclopropyl-2,5-Dioxoimidazolidin-4-Yl]Methyl}-4'-(1,1-Difluoroethyl)[Biphenyl]-2-Carboxamide

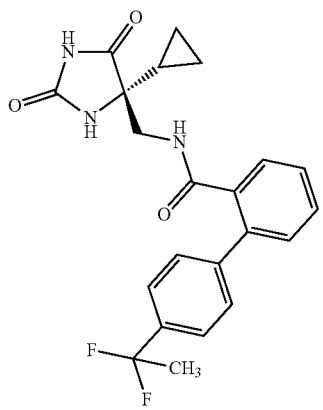 [SMILES: CC(F)(F)c1ccc(-c2ccccc2C(=O)NC[C@@]2(C3CC3)NC(=O)NC2=O)cc1]

(5R)-5-(aminomethyl)-5-cyclopropylimidazolidine-2,4-dione hydrochloride (34.5 mg, 168 μmol) and 4'-(1,1-difluoroethyl)[1,1'-biphenyl]-2-carboxylic acid (44.0 mg, 168 μmol) dissolved in DMF (1.0 ml) were treated with 1-ethyl-3-(3-dimethylaminopropyl)carbodiimide hydrochloride (41.8 mg, 218 μmol), 1-hydroxybenzotriazole hydrate (33.4 mg, 218 μmol) and N,N-diisopropylethylamine (82 μl, 470 μmol). The mixture was stirred overnight at room temperature. Purification was done by preparative HPLC (column: Chromatorex C18 10 μm, 250×30 mm, eluent A=water+ 0.1% TFA, B=acetonitrile; gradient: 3 min 10% B; 21 min 95% B; 30 min 95% B; 32 min 10% B; flow: 50 ml/min). Product containing samples were united, the solvents were evaporated and the residue was lyophilized. 45.1 mg (100% purity, 65% yield) of the title compound were obtained.

LC-MS (Method 7): $R_t$=1.66 min; MS (ESIneg): m/z=412 [M−H]⁻

¹H-NMR (400 MHz, DMSO-d6) δ [ppm]: 0.008 (1.70), 0.102 (0.44), 0.116 (1.13), 0.126 (1.95), 0.140 (2.08), 0.150 (1.51), 0.163 (0.67), 0.304 (1.26), 0.316 (1.61), 0.326 (1.53), 0.338 (1.16), 0.349 (0.87), 0.361 (0.72), 0.372 (1.21), 0.385 (1.40), 0.394 (1.85), 0.408 (1.42), 0.415 (0.90), 0.424 (0.93), 0.438 (1.63), 0.449 (1.95), 0.462 (1.86), 0.474 (1.17), 1.035 (0.61), 1.048 (1.26), 1.055 (1.40), 1.069 (2.34), 1.082 (1.28), 1.089 (1.14), 1.102 (0.51), 1.951 (8.14), 1.998 (16.00), 2.045 (7.18), 3.462 (0.41), 3.476 (0.56), 3.496 (4.23), 3.501 (4.32), 3.511 (4.21), 3.517 (4.06), 3.535 (0.53), 3.552 (0.43), 4.103 (0.65), 7.405 (3.81), 7.414 (5.34), 7.418 (5.91), 7.424 (7.90), 7.442 (4.13), 7.456 (6.60), 7.477 (8.48), 7.506 (7.79), 7.524 (3.37), 7.543 (1.25), 7.546 (1.22), 7.575 (8.29), 7.596 (5.96), 8.461 (1.62), 8.476 (3.42), 8.491 (1.60), 10.642 (4.76).

Example 126

4'-Chloro-N-{[(4R)-4-Cyclopropyl-2,5-Dioxoimidazolidin-4-Yl]Methyl}-5-Fluoro[Biphenyl]-2-Carboxamide

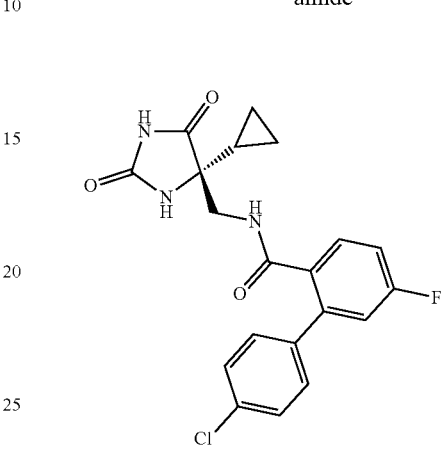

(5R)-5-(aminomethyl)-5-cyclopropylimidazolidine-2,4-dione hydrochloride (40.0 mg, 195 μmol) and 4'-chloro-5-fluoro[1,1'-biphenyl]-2-carboxylic acid (48.8 mg, 195 μmol, CAS 1179253-24-7) dissolved in DMF (1.7 ml) were treated with 1-ethyl-3-(3-dimethylaminopropyl)carbodiimide hydrochloride (48.5 mg, 253 μmol), 1-hydroxybenzotriazole hydrate (38.7 mg, 253 μmol) and N,N-diisopropylethylamine (95 μl, 540 μmol). The mixture was stirred 2.5 hours at room temperature. Water (4 ml) was added to the reaction and the resulting precipitate was filtered off. The residue was washed with water and dried to obtain 37.0 mg (97% purity, 46% yield) of the title compound.

LC-MS (Method 8): $R_t$=0.88 min, MS (ESIpos): m/z=402 [M+H]⁺

¹H-NMR (600 MHz, DMSO-d6) δ [ppm]: 0.117 (1.08), 0.125 (2.35), 0.133 (3.50), 0.142 (3.58), 0.149 (2.61), 0.158 (1.11), 0.306 (0.88), 0.321 (2.56), 0.329 (3.17), 0.336 (2.85), 0.351 (1.28), 0.384 (1.24), 0.392 (2.21), 0.400 (2.67), 0.406 (3.37), 0.415 (2.54), 0.430 (0.94), 0.449 (1.33), 0.457 (2.88), 0.465 (3.58), 0.474 (3.38), 0.482 (2.28), 1.053 (1.16), 1.062 (2.35), 1.067 (2.67), 1.075 (3.96), 1.084 (2.41), 1.089 (2.07), 1.098 (0.92), 2.731 (1.32), 2.890 (1.44), 3.465 (1.80), 3.475 (2.09), 3.488 (5.57), 3.498 (5.57), 3.505 (5.58), 3.515 (5.27), 3.528 (1.81), 3.538 (1.68), 7.253 (4.12), 7.257 (5.37), 7.273 (7.38), 7.287 (5.11), 7.292 (4.29), 7.302 (3.01), 7.306 (2.54), 7.377 (11.89), 7.391 (15.75), 7.431 (4.54), 7.441 (5.08), 7.445 (4.79), 7.455 (4.68), 7.464 (16.00), 7.478 (11.59), 7.542 (11.06), 8.509 (3.11), 8.520 (5.77), 8.530 (2.92), 10.649 (5.30).

Example 127

N-{[(4R)-4-Cyclopropyl-2,5-Dioxoimidazolidin-4-Yl]Methyl}-4'-(Difluoromethoxy)[Biphenyl]-2-Carboxamide

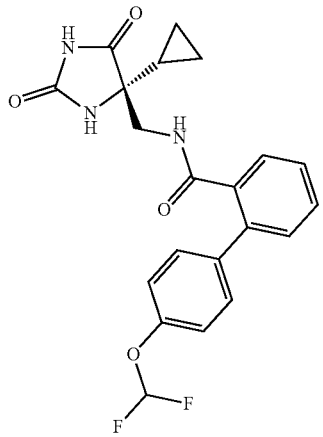 [SMILES: O=C1NC(=O)[C@](CNC(=O)c2ccccc2-c2ccc(OC(F)F)cc2)(C2CC2)N1]

(5R)-5-(aminomethyl)-5-cyclopropylimidazolidine-2,4-dione hydrochloride (40.0 mg, 195 µmol) and 4'-(difluoromethoxy)[1,1'-biphenyl]-2-carboxylic acid (51.4 mg, 195 µmol) dissolved in DMF (1.6 ml) were treated with 1-ethyl-3-(3-dimethylaminopropyl)carbodiimide hydrochloride (48.5 mg, 253 µmol), 1-hydroxybenzotriazole hydrate (38.7 mg, 253 µmol) and N,N-diisopropylethylamine (95 µl, 540 µmol). The mixture was stirred overnight at room temperature. Water (5 ml) was added to the reaction and the resulting precipitate was filtered off. The residue was washed with water and dried to obtain 69.0 mg (99% purity, 85% yield) of the title compound.

LC-MS (Method 7): $R_t$=1.48 min, MS (ESIpos): m/z=416 [M+H]$^+$ $^1$H-NMR (500 MHz, DMSO-d6) δ [ppm]: 0.104 (0.78), 0.114 (1.84), 0.123 (2.75), 0.134 (2.82), 0.142 (2.10), 0.153 (0.90), 0.294 (0.67), 0.312 (1.94), 0.322 (2.41), 0.330 (2.22), 0.349 (1.08), 0.376 (0.97), 0.385 (1.75), 0.396 (2.08), 0.403 (2.67), 0.413 (2.04), 0.432 (1.56), 0.444 (2.28), 0.453 (2.79), 0.463 (2.64), 0.472 (1.74), 1.049 (0.91), 1.060 (1.87), 1.066 (2.09), 1.076 (3.20), 1.086 (1.91), 1.092 (1.64), 1.102 (0.73), 2.074 (2.25), 3.462 (0.99), 3.474 (1.23), 3.490 (4.98), 3.501 (7.72), 3.512 (4.69), 3.527 (1.05), 3.540 (0.95), 7.121 (3.62), 7.189 (9.86), 7.207 (11.31), 7.269 (7.29), 7.375 (6.24), 7.390 (10.46), 7.396 (15.01), 7.413 (16.00), 7.429 (2.56), 7.487 (3.42), 7.489 (3.51), 7.504 (5.45), 7.514 (8.42), 8.441 (2.43), 8.454 (4.69), 8.466 (2.32), 10.648 (6.81).

Example 128

N-{[(4R)-4-Cyclopropyl-2,5-Dioxoimidazolidin-4-Yl]Methyl}-4',5-Difluoro[Biphenyl]-2-Carboxamide

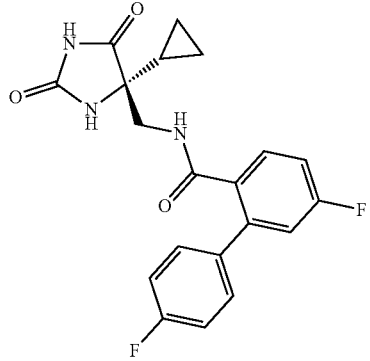 [SMILES: O=C1NC(=O)[C@](CNC(=O)c2ccc(F)cc2-c2ccc(F)cc2)(C2CC2)N1]

(5R)-5-(aminomethyl)-5-cyclopropylimidazolidine-2,4-dione hydrochloride (40.0 mg, 195 µmol) and 4',5-difluoro[1,1'-biphenyl]-2-carboxylic acid (45.6 mg, 195 µmol) dissolved in DMF (1.7 ml) were treated with 1-ethyl-3-(3-dimethylaminopropyl)carbodiimide hydrochloride (48.5 mg, 253 µmol), 1-hydroxybenzotriazole hydrate (38.7 mg, 253 µmol) and N,N-diisopropylethylamine (95 µl, 540 µmol). The mixture was for 2 hours at room temperature. Water was added and the mixture was extracted with ethyl acetate. The combined organic layers were dried, filtered and evaporated and the residue was purified by flash-column chromatography (n-heptane:ethyl actetate (70:30)→ethyl acetate). Product containing samples were united, the solvents were evaporated and the residue was lyophylized. 63.0 mg (99% purity, 83% yield) of the title compound were obtained.

LC-MS (Method 7): $R_t$=1.43 min, MS (ESIpos): m/z=386 [M+H]$^+$ $^1$H-NMR (400 MHz, DMSO-d6) δ [ppm]: −0.008 (2.68), 0.008 (2.50), 0.101 (0.57), 0.114 (1.37), 0.125 (2.41), 0.138 (2.59), 0.148 (1.83), 0.162 (0.83), 0.288 (0.49), 0.311 (1.52), 0.323 (1.92), 0.334 (1.80), 0.345 (1.40), 0.356 (1.09), 0.369 (0.89), 0.380 (1.50), 0.394 (1.68), 0.402 (2.29), 0.415 (1.80), 0.428 (1.31), 0.442 (2.09), 0.453 (2.40), 0.466 (2.26), 0.479 (1.40), 0.492 (0.51), 1.041 (0.79), 1.054 (1.64), 1.061 (1.74), 1.067 (1.33), 1.075 (3.01), 1.088 (1.59), 1.095 (1.43), 1.108 (0.63), 1.141 (2.01), 2.072 (0.74), 2.117 (0.82), 2.327 (0.63), 2.366 (0.49), 2.523 (2.56), 2.665 (0.52), 2.669 (0.67), 2.709 (0.46), 3.443 (0.64), 3.458 (0.83), 3.478 (4.78), 3.486 (5.11), 3.492 (4.99), 3.501 (4.56), 3.519 (0.76), 3.536 (0.69), 6.942 (0.97), 7.070 (1.04), 7.198 (1.12), 7.211 (5.65), 7.216 (2.18), 7.228 (5.62), 7.234 (16.00), 7.246 (3.64), 7.256 (9.09), 7.259 (6.21), 7.267 (5.48), 7.274 (3.40), 7.289 (2.79), 7.295 (2.13), 7.391 (7.02), 7.397 (3.29), 7.405 (11.40), 7.413 (6.91), 7.421 (6.23), 7.427 (8.83), 7.441 (3.26), 7.515 (6.15), 8.445 (1.91), 8.461 (4.01), 8.476 (1.88), 10.632 (5.38).

Example 129

N-{[(4R)-4-Cyclopropyl-2,5-Dioxoimidazolidin-4-Yl]Methyl}-4'-Fluoro[Biphenyl]-2-Carboxamide

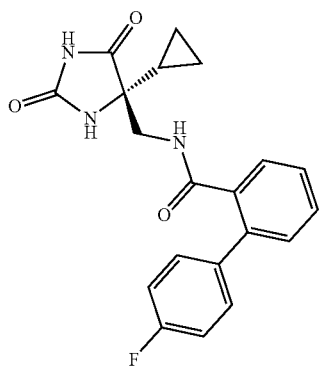 [SMILES: O=C1NC(=O)[C@](CNC(=O)c2ccccc2-c2ccc(F)cc2)(C2CC2)N1]

(5R)-5-(aminomethyl)-5-cyclopropylimidazolidine-2,4-dione hydrochloride (40.0 mg, 195 µmol) and 4'-fluoro[1,1'-biphenyl]-2-carboxylic acid (42.1 mg, 195 µmol) dissolved in DMF (1.6 ml) were treated with 1-ethyl-3-(3-dimethylaminopropyl)carbodiimide hydrochloride (48.5 mg, 253 µmol), 1-hydroxybenzotriazole hydrate (38.7 mg, 253 µmol) and N,N-diisopropylethylamine (95 µl, 540 µmol). The mixture was stirred over night at room temperature. Water was added and the mixture was extracted with ethyl acetate. The combined organic layers were dried, filtered and evaporated and the residue was purified by flash-column chromatography (n-heptane:ethyl actetate (80:20)→ethyl acetate). Product containing samples were united, the solvents were evaporated and the residue was lyophylized. 59.0 mg (99% purity, 82% yield) of the title compound were obtained.

LC-MS (Method 7): $R_t$=1.36 min, MS (ESIpos): m/z=368 [M+H]$^+$ $^1$H-NMR (400 MHz, DMSO-d6) δ [ppm]: 0.008 (2.25), 0.100 (0.60), 0.113 (1.44), 0.124 (2.45), 0.137 (2.58), 0.148 (2.03), 0.161 (0.80), 0.285 (0.50), 0.308 (1.60), 0.319 (2.02), 0.330 (1.90), 0.342 (1.41), 0.352 (1.05), 0.368 (0.90), 0.379 (1.57), 0.390 (1.72), 0.401 (2.38), 0.415 (1.83), 0.425 (1.71), 0.438 (2.45), 0.450 (2.43), 0.463 (2.29), 0.475 (1.43), 0.488 (0.45), 1.036 (0.80), 1.049 (1.65), 1.057 (1.78), 1.062 (1.38), 1.070 (2.89), 1.083 (1.60), 1.090 (1.39), 1.103 (0.60), 2.072 (0.62), 2.731 (2.45), 2.890 (3.07), 3.449 (0.43), 3.464 (0.64), 3.484 (5.84), 3.488 (5.74), 3.499 (5.58), 3.504 (5.36), 3.522 (0.58), 3.538 (0.50), 7.195 (4.55), 7.217 (9.95), 7.239 (5.81), 7.367 (11.95), 7.381 (14.34), 7.386 (16.00), 7.403 (5.64), 7.409 (5.80), 7.427 (1.93), 7.477 (3.48), 7.481 (3.64), 7.491 (9.80), 7.514 (1.67), 7.517 (1.59), 8.395 (1.92), 8.410 (3.99), 8.426 (1.91), 10.625 (4.72).

Example 130

N-{[(4R)-4-Cyclopropyl-2,5-Dioxoimidazolidin-4-Yl]Methyl}-4'-Methoxy[Biphenyl]-2-Carboxamide

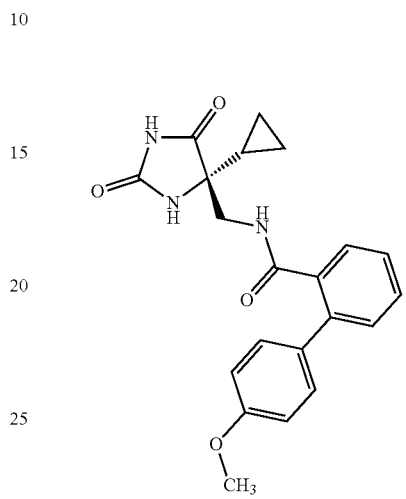

(5R)-5-(aminomethyl)-5-cyclopropylimidazolidine-2,4-dione hydrochloride (40.0 mg, 195 µmol) and 4'-methoxy [1,1'-biphenyl]-2-carboxylic acid (44.4 mg, 195 µmol, CAS 18110-71-9) dissolved in DMF (1.0 ml) were treated with 1-ethyl-3-(3-dimethylaminopropyl)carbodiimide hydrochloride (48.5 mg, 253 µmol), 1-hydroxybenzotriazole hydrate (38.7 mg, 253 µmol) and N,N-diisopropylethylamine (95 µl, 540 µmol). The mixture was stirred overnight at room temperature.

Water (5 ml) was added to the reaction and the resulting precipitate was filtered off. The residue was washed with water and dried to obtain 54.7 mg (100% purity, 74% yield) of the title compound.

LC-MS (Method 7): $R_t$=1.34 min, MS (ESIpos): m/z=380 [M+H]$^+$ $^1$H-NMR (400 MHz, DMSO-d6) δ [ppm]: 0.107 (0.59), 0.118 (0.97), 0.130 (0.98), 0.142 (0.77), 0.312 (0.82), 0.324 (0.81), 0.345 (0.42), 0.376 (0.63), 0.397 (0.98), 0.412 (1.03), 0.426 (0.98), 0.438 (1.02), 0.450 (0.89), 0.463 (0.59), 1.040 (0.64), 1.061 (1.08), 1.073 (0.69), 3.477 (1.64), 3.491 (2.69), 3.505 (1.62), 3.776 (16.00), 6.943 (3.73), 6.965 (4.23), 7.290 (4.30), 7.312 (3.83), 7.343 (6.24), 7.361 (4.21), 7.377 (0.75), 7.446 (1.15), 7.452 (1.20), 7.469 (3.92), 8.290 (0.75), 8.306 (1.53), 8.321 (0.76), 10.627 (2.30).

Example 131

N-{[(4R)-4-Cyclopropyl-2,5-Dioxoimidazolidin-4-Yl]Methyl}[Biphenyl]-2-Carboxamide

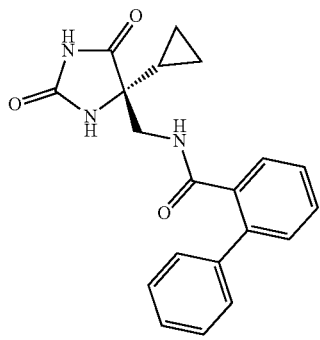 [SMILES: O=C1NC(=O)[C@](CNC(=O)c2ccccc2-c2ccccc2)(C2CC2)N1]

(5R)-5-(aminomethyl)-5-cyclopropylimidazolidine-2,4-dione hydrochloride (40.0 mg, 195 µmol) and [1,1'-biphenyl]-2-carboxylic acid (38.6 mg, 195 µmol, CAS 947-84-2) dissolved in DMF (1000 µl) were treated with 1-ethyl-3-(3-dimethylaminopropyl)carbodiimide hydrochloride (48.5 mg, 253 µmol), 1-hydroxybenzotriazole hydrate (38.7 mg, 253 µmol) and N,N-diisopropylethylamine (95 µl, 540 µmol). The mixture was stirred overnight at room temperature. Purification was done by preparative HPLC (column: Reprosil C18 10 µm, 250×30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated and the residue was lyophylized. 54.5 mg (100% purity, 80% yield) of the title compound were obtained.

LC-MS (Method 7): $R_t$=1.31 min; MS (ESIpos): m/z=350 [M+H]$^+$ $^1$H-NMR (600 MHz, DMSO-d6) δ [ppm]: 0.100 (0.44), 0.109 (0.92), 0.116 (1.47), 0.125 (1.47), 0.133 (1.03), 0.141 (0.48), 0.298 (0.59), 0.303 (0.99), 0.311 (1.21), 0.319 (1.07), 0.326 (0.77), 0.334 (0.51), 0.371 (0.51), 0.379 (0.92), 0.388 (0.99), 0.393 (1.40), 0.403 (1.10), 0.408 (0.70), 0.417 (0.96), 0.426 (1.21), 0.433 (1.43), 0.442 (1.36), 0.450 (0.92), 1.034 (0.51), 1.043 (1.03), 1.048 (1.07), 1.057 (1.80), 1.062 (0.74), 1.065 (0.96), 1.070 (0.85), 2.071 (0.63), 3.288 (0.44), 3.292 (0.48), 3.322 (1.69), 3.328 (2.46), 3.380 (0.51), 3.382 (0.81), 3.388 (0.51), 3.449 (0.59), 3.459 (0.74), 3.472 (2.91), 3.481 (4.08), 3.491 (2.72), 3.503 (0.55), 3.514 (0.51), 7.304 (0.59), 7.307 (1.03), 7.311 (0.77), 7.318 (2.43), 7.326 (0.96), 7.329 (1.62), 7.332 (1.18), 7.367 (3.46), 7.369 (3.20), 7.375 (9.86), 7.379 (16.00), 7.391 (7.50), 7.407 (3.16), 7.420 (1.29), 7.477 (5.15), 7.488 (1.91), 7.490 (1.80), 7.500 (2.65), 7.503 (2.43), 7.513 (1.10), 7.515 (1.07), 8.345 (1.29), 8.356 (2.46), 8.366 (1.18), 10.637 (2.28).

Example 132

N-{[(4R)-4-Cyclopropyl-2,5-Dioxoimidazolidin-4-Yl]Methyl}-2-(4-Methylphenyl)Nicotinamide

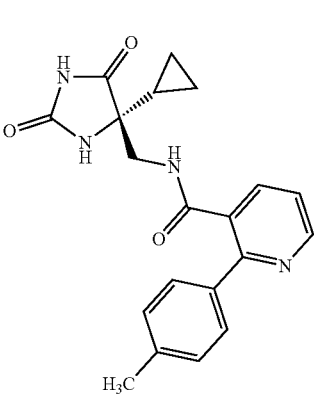 [SMILES: Cc1ccc(-c2ncccc2C(=O)NC[C@@]2(C3CC3)NC(=O)NC2=O)cc1]

(5R)-5-(aminomethyl)-5-cyclopropylimidazolidine-2,4-dione hydrochloride (40.0 mg, 195 µmol) and 2-(4-methylphenyl)pyridine-3-carboxylic acid (41.5 mg, 195 µmol, CAS 1226205-68-0) dissolved in DMF (1000 µl) were treated with 1-ethyl-3-(3-dimethylaminopropyl)carbodiimide hydrochloride (48.5 mg, 253 µmol), 1-hydroxybenzotriazole hydrate (38.7 mg, 253 µmol) and N,N-diisopropylethylamine (95 µl, 540 µmol). The mixture was stirred over night at room temperature. Water was added to the mixture an purification was done by preparative HPLC (column: Reprosil C18 10 µm, 250×30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated and the residue was lyophylized. 34.0 mg (100% purity, 48% yield) of the title compound were obtained.

LC-MS (Method 7): $R_t$=1.06 min; MS (ESIpos): m/z=365 [M+H]$^+$ $^1$H-NMR (400 MHz, DMSO-d6) δ [ppm]: 0.008 (0.43), 0.123 (0.71), 0.133 (1.24), 0.146 (1.36), 0.157 (0.92), 0.171 (0.43), 0.321 (0.77), 0.334 (0.99), 0.345 (0.92), 0.356 (0.72), 0.366 (0.54), 0.382 (0.45), 0.393 (0.79), 0.408 (0.86), 0.415 (1.19), 0.429 (0.92), 0.438 (0.89), 0.452 (1.25), 0.464 (1.22), 0.476 (1.15), 0.488 (0.72), 1.066 (0.41), 1.079 (0.85), 1.087 (0.90), 1.100 (1.53), 1.113 (0.82), 1.120 (0.74), 2.340 (16.00), 3.534 (4.41), 3.550 (4.48), 7.223 (4.41), 7.243 (5.00), 7.390 (2.35), 7.402 (2.39), 7.410 (2.58), 7.421 (2.65), 7.524 (6.45), 7.544 (5.59), 7.559 (3.29), 7.692 (2.77), 7.697 (2.91), 7.711 (2.51), 7.716 (2.39), 8.617 (1.02), 8.633 (2.15), 8.648 (1.03), 8.668 (2.74), 8.672 (2.81), 8.680 (2.75), 8.684 (2.50), 10.632 (2.86).

Example 133

Ent-6-Methyl-N-{[4-(1-Methyl-1H-Imidazol-2-Yl)-2,5-Dioxoimidazolidin-4-Yl]Methyl}-4'-(Trifluoromethyl)[1,1'-Biphenyl]-2-Carboxamide

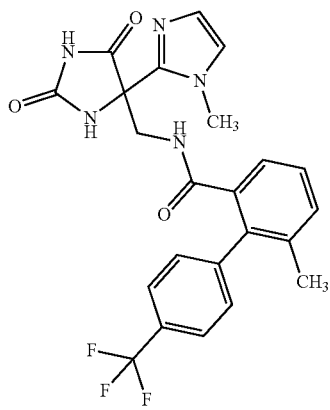 [SMILES: Cc1cccc(C(=O)NCC2(c3nccn3C)NC(=O)NC2=O)c1-c1ccc(C(F)(F)F)cc1]

ent-5-(aminomethyl)-5-(1-methyl-1H-imidazol-2-yl)imidazolidine-2,4-dione-hydrogen chloride (40.0 mg, 163 µmol) and 6-methyl-4'-(trifluoromethyl)[1,1'-biphenyl]-2-carboxylic acid (45.6 mg, 163 µmol) dissolved in DMF (1.0 ml) were treated with 1-ethyl-3-(3-dimethylaminopropyl)carbodiimide hydrochloride (40.6 mg, 212 µmol) 1-hydroxybenzotriazole hydrate (32.4 mg, 212 µmol) and N,N-diisopropylethylamine (79 µl, 460 µmol) The mixture was stirred over night at room temperature. Water was added and the mixture was evaporated. The residue was purified by preparative HPLC (column: Chromatorex C18 10 µm, 250×30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated and the residue was lyophylized. Product containing samples were united, the solvents were evaporated and the residue was lyophylized. 66.2 mg (100% purity, 86% yield) of the title compound were obtained.

LC-MS (Method 7): $R_t$=1.48 min; MS (ESIpos): m/z=472 [M+H]$^+$ $^1$H-NMR (600 MHz, DMSO-d6) δ [ppm]: 2.049 (16.00), 3.902 (4.80), 3.913 (4.73), 3.936 (0.52), 4.099 (0.68), 7.218 (3.23), 7.230 (3.46), 7.358 (1.50), 7.370 (3.36), 7.383 (3.95), 7.398 (2.76), 7.414 (3.20), 7.427 (1.92), 7.451 (2.80), 7.726 (3.47), 7.739 (3.19), 8.308 (3.63), 8.476 (0.91), 8.485 (1.70), 8.495 (0.89), 11.414 (2.38).

Example 134

Ent-4',6-Dimethyl-N-{[4-(1-Methyl-1H-Imidazol-2-Yl)-2,5-Dioxoimidazoidin-4-Yl]Methyl}[1,1'-Biphenyl]-2-Carboxamide

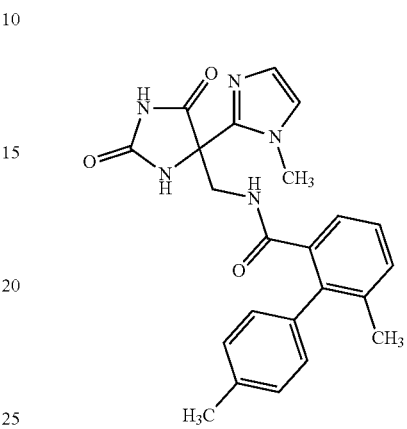

ent-5-(aminomethyl)-5-(1-methyl-1H-imidazol-2-yl)imidazolidine-2,4-dione-hydrogen chloride (40.0 mg, 163 µmol) and 4',6-dimethyl[1,1'-biphenyl]-2-carboxylic acid (36.8 mg, 163 µmol) dissolved in DMF (1.0 ml) were treated with 1-ethyl-3-(3-dimethylaminopropyl)carbodiimide hydrochloride (40.6 mg, 212 µmol) 1-hydroxybenzotriazole hydrate (32.4 mg, 212 µmol) and N,N-diisopropylethylamine (79 µl, 460 µmol) The mixture was stirred over night at room temperature. Water was added and the mixture was evaporated. The residue was purified by preparative HPLC (column: Chromatorex C18 10 µm, 250×30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated and the residue was lyophylized. 65.2 mg (100% purity, 96% yield) of the title compound were obtained.

LC-MS (Method 7): $R_t$=1.37 min; MS (ESIpos): m/z=418 [M+H]$^+$ $^1$H-NMR (600 MHz, DMSO-d6) δ [ppm]: 2.043 (16.00), 2.337 (15.94), 3.837 (0.82), 3.847 (0.91), 3.860 (2.05), 3.870 (1.85), 3.885 (1.87), 3.896 (1.95), 3.908 (0.86), 3.919 (0.83), 7.037 (2.10), 7.049 (2.38), 7.115 (2.22), 7.128 (2.54), 7.156 (4.92), 7.169 (3.97), 7.276 (1.76), 7.289 (4.68), 7.302 (2.27), 7.348 (2.75), 7.361 (1.89), 7.503 (2.50), 8.259 (3.14), 8.291 (0.85), 8.301 (1.48), 8.311 (0.80), 11.441 (2.16).

Example 135

4'-(2,2-Difluorocyclopropyl)-5-Methyl-N-{[4-(1-Methyl-1H-Imidazol-2-Yl)-2,5-Dioxoimidazolidin-4-Yl]Methyl}[1,1'-Biphenyl]-2-Carboxamide (Mixture of Diastereoisomers)

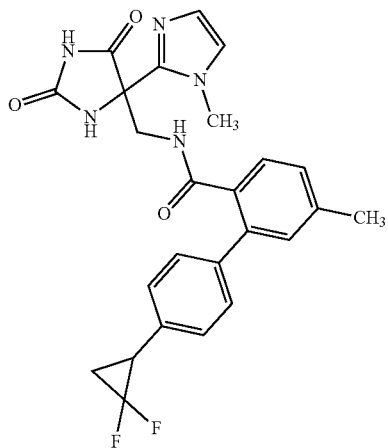 [SMILES: Cc1ccc(C(=O)NCC2(c3nccn3C)NC(=O)NC2=O)c(-c2ccc(C3CC3(F)F)cc2)c1]

ent-5-(aminomethyl)-5-(1-methyl-1H-imidazol-2-yl)imidazolidine-2,4-dione hydrochloride (40.0 mg, 163 µmol) and rac-4'-(2,2-difluorocyclopropyl)-5-methyl[1,1'-biphenyl]-2-carboxylic acid (46.9 mg, 163 µmol) dissolved in DMF (1.0 ml) were treated with 1-ethyl-3-(3-dimethylaminopropyl)carbodiimide hydrochloride (40.6 mg, 212 µmol) 1-hydroxybenzotriazole hydrate (32.4 mg, 212 µmol) and N,N-diisopropylethylamine (79 µl, 460 µmol) The mixture was stirred over night at room temperature. Water was added to the mixture and purification was done by preparative HPLC (column: Chromatorex C18 10 µm, 250×30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated and the residue was lyophylized. 69.8 mg (100% purity, 89% yield) of the title compound were obtained.

LC-MS (Method 7): $R_t$=1.52 min; MS (ESIpos): m/z=480 [M+H]$^+$ $^1$H-NMR (600 MHz, DMSO-d6) δ [ppm]: 1.930 (0.64), 1.937 (0.76), 1.944 (0.67), 1.951 (0.90), 1.957 (0.63), 1.966 (0.47), 1.972 (0.72), 1.982 (0.48), 1.985 (0.42), 1.993 (0.82), 2.002 (0.82), 2.014 (0.75), 2.022 (0.46), 2.369 (16.00), 2.994 (0.50), 3.014 (0.98), 3.028 (0.94), 3.048 (0.45), 3.759 (6.48), 3.762 (6.39), 3.972 (1.64), 3.977 (1.70), 3.981 (1.77), 3.987 (1.75), 3.995 (2.05), 4.000 (2.15), 4.005 (2.01), 4.010 (1.92), 4.061 (2.03), 4.070 (2.04), 4.072 (2.01), 4.082 (1.55), 4.084 (1.56), 4.093 (1.46), 4.095 (1.45), 7.203 (4.49), 7.221 (2.67), 7.255 (5.07), 7.268 (4.52), 7.282 (14.11), 7.288 (6.58), 7.297 (1.03), 7.302 (0.92), 7.488 (2.07), 8.362 (3.04), 8.452 (0.81), 8.462 (1.50), 8.472 (0.80), 11.438 (1.62).

Example 136

N-{[(4R)-4-Cyclopropyl-2,5-Dioxoimidazolidin-4-Yl]Methyl}-4'-(2,2-Difluorocyclopropyl)-5-Methyl[1,1'-Biphenyl]-2-Carboxamide (Mixture of Diastereoisomers)

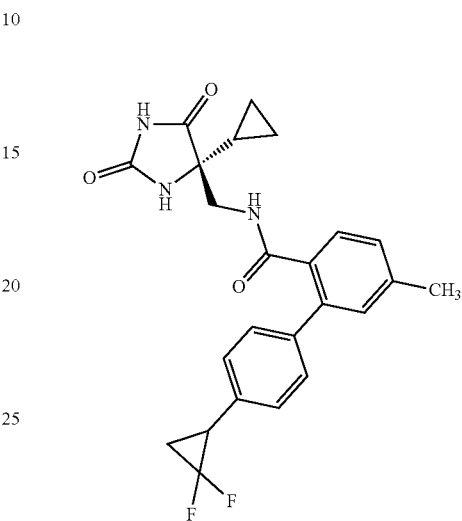

(5R)-5-(aminomethyl)-5-cyclopropylimidazolidine-2,4-dione-hydrogen chloride (33.5 mg, 163 µmol) and rac-4'-(2,2-difluorocyclopropyl)-5-methyl[1,1'-biphenyl]-2-carboxylic acid (47.0 mg, 163 µmol) dissolved in DMF (1.0 ml) were treated with 1-ethyl-3-(3-dimethylaminopropyl)carbodiimide hydrochloride (40.6 mg, 212 µmol) 1-hydroxybenzotriazole hydrate (32.5 mg, 212 µmol) and N,N-diisopropylethylamine (79 µl, 460 µmol) The mixture was stirred over night at room temperature. Water was added to the mixture and purification was done by preparative HPLC (column: Chromatorex C18 10 µm, 250×30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated and the residue was lyophylized. 69.3 mg (100% purity, 97% yield) of the title compound were obtained.

LC-MS (Method 7): $R_t$=1.71 min; MS (ESIpos): m/z=440 [M+H]$^+$ $^1$H-NMR (600 MHz, DMSO-d6) δ [ppm]: 0.924 (0.58), 2.238 (5.88), 2.368 (2.82), 2.371 (5.86), 2.374 (8.03), 2.377 (5.81), 2.380 (2.74), 2.413 (16.00), 3.358 (0.91), 3.368 (0.96), 3.378 (0.61), 3.391 (0.42), 7.068 (1.66), 7.084 (0.84), 7.141 (1.35), 7.155 (3.22), 7.166 (0.83), 7.190 (2.84), 7.203 (1.52), 7.307 (1.20), 8.078 (0.41), 8.088 (0.80), 10.484 (0.85).

Example 137

N-{[(4R)-4-Cyclopropyl-2,5-Dioxoimidazolidin-4-Yl]Methyl}-4'-(2,2-Difluorocyclopropyl)-5-Methyl [1,1'-Biphenyl]-2-Carboxamide (Enantiomer 1)

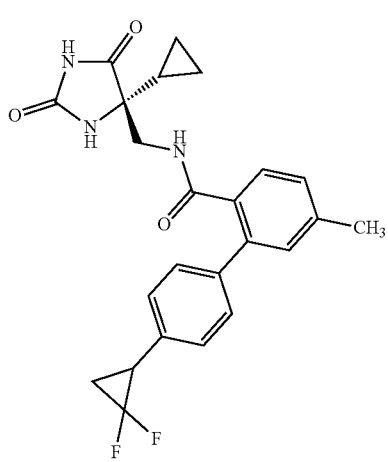 [SMILES: Cc1ccc(C(=O)NC[C@@]2(C3CC3)NC(=O)NC2=O)c(-c2ccc(C3CC3(F)F)cc2)c1]

Separation of diastereoisomers of N-{[(4R)-4-cyclopropyl-2,5-dioxoimidazolidin-4-yl]methyl}-4'-(2,2-difluorocyclopropyl)-5-methyl[1,1'-biphenyl]-2-carboxamide (mixture of diastereoisomers) was done using the following chiral HPLC method:

Column: Daicel Chiralpak OJ-H 250×25 mm

Solvent: 90% $CO_2$: 10% methanol

Flow: 80 ml/min

Column temperature: 40° C.

UV: 210 nm

Product containing samples were united, the solvents were evaporated and the residue was lyophilized. 22.80 mg (31% yield) of the title compound were obtained.

LC-MS (Method 7): $R_t$=1.69 min; MS (ESIpos): m/z=440 [M+H]$^+$

Chiral HPLC (Column: Daicel OJ-3-10, 220 nm, solvent: 90% $CO_2$: 10% methanol): $R_t$=1.249 min, 100% de $^1$H-NMR (600 MHz, DMSO-d6) δ [ppm]: 2.236 (1.50), 2.369 (1.91), 2.372 (2.57), 2.375 (1.89), 2.411 (4.35), 3.177 (16.00), 7.065 (0.42), 7.151 (0.71), 7.187 (0.69).

Example 138

N-{[(4R)-4-Cyclopropyl-2,5-Dioxoimidazolidin-4-Yl]Methyl}-4'-(2,2-Difluorocyclopropyl)-5-Methyl [1,1'-Biphenyl]-2-Carboxamide (Enantiomer 2)

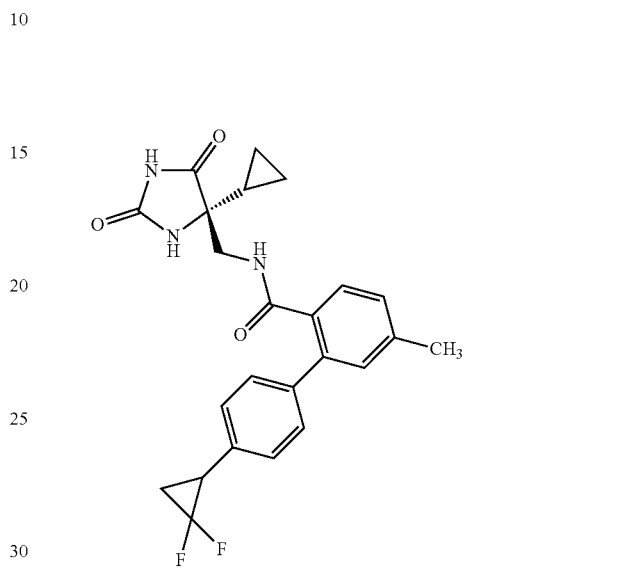

Separation of diastereoisomers of N-{[(4R)-4-cyclopropyl-2,5-dioxoimidazolidin-4-yl]methyl}-4'-(2,2-difluorocyclopropyl)-5-methyl[1,1'-biphenyl]-2-carboxamide (mixture of diastereoisomers) was done using the following chiral HPLC method:

Column: Daicel Chiralpak OJ-H 250×25 mm

Solvent: 90% $CO_2$: 10% methanol

Flow: 80 ml/min

Column temperature: 40° C.

UV: 210 nm

Product containing samples were united, the solvents were evaporated and the residue was lyophilized. 21.6 mg (30% yield) of the title compound were obtained.

LC-MS (method 7): $R_t$=1.69 min; MS (ESIpos): m/z=440 [M+H]$^+$

Chiral HPLC (Column: Daicel OJ-3-10, 220 nm, solvent: 90% $CO_2$: 10% methanol): $R_t$=1.604 min, 99.5% de $^1$H-NMR (600 MHz, DMSO-d6) δ [ppm]: 2.240 (2.07), 2.372 (3.02), 2.375 (3.99), 2.378 (2.95), 2.415 (5.53), 3.185 (16.00), 7.069 (0.64), 7.142 (0.48), 7.155 (1.24), 7.191 (0.93), 7.204 (0.51), 7.309 (0.46), 10.482 (0.40).

Example 139

4'-(2,2-Difluorocyclopropyl)-4-Fluoro-N-{[4-(1-Methyl-1H-Imidazol-2-Yl)-2,5-Dioxoimidazolidin-4-Yl]Methyl}[1,1'-Biphenyl]-2-Carboxamide (Mixture of Diastereoisomers)

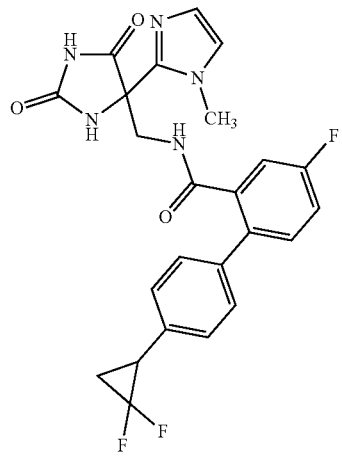 [SMILES: Cn1ccnc1C1(CNC(=O)c2cc(F)ccc2-c2ccc(C3CC3(F)F)cc2)NC(=O)NC1=O]

4'-(2,2-difluorocyclopropyl)-4-fluoro[1,1'-biphenyl]-2-carboxylic acid (46.5 mg, 159 µmol) dissolved in DMF (1.0 ml) were treated with ent-5-(aminomethyl)-5-(1-methyl-1H-imidazol-2-yl)imidazolidine-2,4-dione hydrochloride (39.1 mg, 159 µmol), 1-ethyl-3-(3-dimethylaminopropyl)carbodiimide hydrochloride (39.7 mg, 207 µmol) 1-hydroxybenzotriazole hydrate (31.7 mg, 207 µmol) and N,N-diisopropylethylamine (78 µl, 450 µmol) The mixture was stirred over night at room temperature. Water was added to the mixture and purification was done by preparative HPLC HPLC (column: Chromatorex C18 10 µm, 250×30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated and the residue was lyophylized. 74.8 mg (100% purity, 97% yield) of the title compound were obtained.

LC-MS (Method 7): $R_t$=1.48 min; MS (ESIpos): m/z=484 [M+H]$^+$ $^1$H-NMR (600 MHz, DMSO-d6) δ [ppm]: 1.933 (0.68), 1.940 (0.76), 1.947 (0.66), 1.955 (0.88), 1.962 (0.61), 1.969 (0.47), 1.974 (0.62), 1.983 (0.42), 1.995 (0.72), 2.004 (0.71), 2.016 (0.64), 2.996 (0.50), 3.010 (0.57), 3.017 (0.90), 3.031 (0.87), 3.037 (0.55), 3.052 (0.46), 3.997 (1.21), 4.001 (1.22), 4.007 (1.32), 4.012 (1.30), 4.020 (1.82), 4.024 (1.90), 4.030 (1.81), 4.035 (1.77), 4.054 (1.88), 4.058 (1.92), 4.065 (2.00), 4.069 (1.94), 4.077 (1.45), 4.081 (1.47), 4.088 (1.41), 4.092 (1.43), 7.149 (1.69), 7.153 (1.94), 7.164 (1.70), 7.168 (1.80), 7.257 (1.15), 7.281 (0.81), 7.295 (16.00), 7.298 (8.12), 7.308 (0.57), 7.313 (0.58), 7.354 (0.77), 7.358 (0.79), 7.368 (1.75), 7.372 (1.84), 7.382 (1.08), 7.386 (1.09), 7.430 (1.93), 7.439 (1.99), 7.444 (1.46), 7.453 (1.37), 7.481 (2.11), 8.446 (2.85), 8.730 (0.72), 8.740 (1.40), 8.749 (0.72), 11.464 (1.61).

Example 140

N-{[(4R)-4-Cyclopropyl-2,5-Dioxoimidazolidin-4-Yl]Methyl}-4'-(2,2-Difluorocyclopropyl)-4-Fluoro[1,1'-Biphenyl]-2-Carboxamide (Mixture of Diastereoisomers)

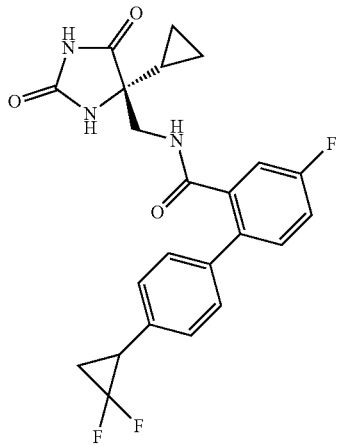 [SMILES: O=C1NC(=O)[C@](CNC(=O)c2cc(F)ccc2-c2ccc(C3CC3(F)F)cc2)(C2CC2)N1]

4'-(2,2-difluorocyclopropyl)-4-fluoro[1,1'-biphenyl]-2-carboxylic acid (46.5 mg, 159 µmol) dissolved in DMF (1.0 ml) were treated with (5R)-5-(aminomethyl)-5-cyclopropylimidazolidine-2,4-dione-hydrogen chloride (32.7 mg, 159 µmol), 1-ethyl-3-(3-dimethylaminopropyl)carbodiimide hydrochloride (39.7 mg, 207 µmol) 1-hydroxybenzotriazole hydrate (31.7 mg, 207 µmol) and N,N-diisopropylethylamine (78 µl, 450 µmol) The mixture was stirred over night at room temperature. Water was added to the mixture and purification was done by preparative HPLC HPLC (column: Chromatorex C18 10 µm, 250×30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated and the residue was lyophylized. 70.4 mg (100% purity, 100% yield) of the title compound were obtained.

LC-MS (Method 7): $R_t$=1.63 min; MS (ESIpos): m/z=444 [M+H]$^+$ $^1$H-NMR (600 MHz, DMSO-d6) δ [ppm]: −0.007 (0.52), 0.009 (0.40), 0.171 (0.44), 0.178 (0.55), 0.186 (0.48), 0.249 (0.42), 0.256 (0.48), 0.298 (0.42), 0.307 (0.53), 0.314 (0.49), 0.918 (0.47), 0.923 (0.51), 0.932 (0.87), 0.940 (0.46), 0.945 (0.42), 1.782 (0.42), 1.797 (0.48), 1.843 (0.42), 1.851 (0.40), 2.351 (3.02), 2.353 (6.25), 2.356 (8.64), 2.360 (6.23), 2.363 (2.94), 2.396 (16.00), 2.857 (0.52), 2.871 (0.51), 3.347 (3.11), 3.357 (1.34), 3.370 (0.56), 3.380 (0.41), 7.024 (0.55), 7.028 (0.85), 7.031 (0.65), 7.039 (0.59), 7.043 (0.82), 7.046 (0.59), 7.134 (1.72), 7.148 (3.72), 7.170 (4.44), 7.184 (2.35), 7.189 (0.63), 7.199 (1.02), 7.203 (1.05), 7.213 (0.60), 7.217 (0.61), 7.272 (1.10), 7.281 (1.15), 7.286 (0.89), 7.295 (0.81), 7.385 (1.76), 8.368 (0.60), 8.379 (1.22), 8.389 (0.58), 10.502 (1.23).

Example 141

4'-(2,2-Difluorocyclopropyl)-5-Fluoro-N-{[4-(1-Methyl-1H-Imidazol-2-Yl)-2,5-Dioxoimidazolidin-4-Yl]Methyl}[1,1'-Biphenyl]-2-Carboxamide (Mixture of Diastereoisomers)

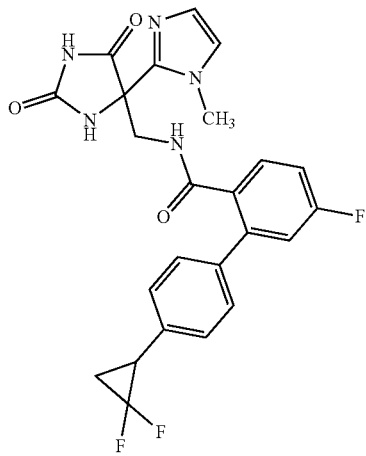 [SMILES: Cn1ccnc1C1(CNC(=O)c2ccc(F)cc2-c2ccc(C3CC3(F)F)cc2)NC(=O)NC1=O]

4'-(2,2-difluorocyclopropyl)-5-fluoro[1,1'-biphenyl]-2-carboxylic acid (41.0 mg, 140 µmol) dissolved in DMF (1.0 ml) were treated with ent-5-(aminomethyl)-5-(1-methyl-1H-imidazol-2-yl)imidazolidine-2,4-dione-hydrogen chloride (34.5 mg, 140 µmol), 1-ethyl-3-(3-dimethylaminopropyl)carbodiimide hydrochloride (35.0 mg, 182 µmol) 1-hydroxybenzotriazole hydrate (27.9 mg, 182 µmol) and N,N-diisopropylethylamine (68 µl, 390 µmol) The mixture was stirred over night at room temperature. Water was added to the mixture and purification was done by preparative HPLC HPLC (column: Chromatorex C18 10 µm, 250×30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated and the residue was lyophylized. 62.1 mg (98% purity, 92% yield) of the title compound were obtained.

LC-MS (Method 7): $R_t$=1.47 min; MS (ESIpos): m/z=484 [M+H]$^+$ $^1$H-NMR (600 MHz, DMSO-d6) δ [ppm]: 1.934 (0.55), 1.941 (0.63), 1.947 (1.57), 1.954 (1.81), 1.962 (1.64), 1.969 (2.25), 1.976 (1.69), 1.983 (1.76), 1.990 (1.85), 2.002 (1.83), 2.011 (1.90), 2.023 (1.64), 2.031 (1.13), 2.045 (0.62), 2.084 (0.46), 2.384 (0.42), 2.423 (0.60), 2.466 (0.42), 2.518 (2.94), 2.571 (1.13), 2.577 (0.53), 2.652 (0.56), 3.008 (1.16), 3.028 (2.20), 3.042 (2.11), 3.048 (1.51), 3.063 (1.21), 3.727 (15.67), 3.730 (16.00), 3.820 (4.22), 3.985 (2.89), 3.989 (2.90), 3.995 (3.01), 3.999 (2.90), 4.008 (3.78), 4.012 (3.96), 4.018 (3.66), 4.022 (3.56), 4.054 (3.29), 4.058 (3.41), 4.065 (3.54), 4.069 (3.47), 4.077 (2.38), 4.081 (2.45), 4.088 (2.20), 4.092 (2.25), 7.219 (2.39), 7.244 (3.70), 7.249 (5.65), 7.262 (4.89), 7.265 (6.48), 7.276 (4.63), 7.281 (3.75), 7.291 (2.71), 7.295 (2.66), 7.300 (6.92), 7.314 (14.52), 7.335 (10.42), 7.339 (11.23), 7.343 (3.87), 7.345 (3.06), 7.349 (5.25), 7.353 (5.21), 7.388 (4.52), 7.397 (4.72), 7.402 (4.31), 7.411 (3.91), 7.457 (4.29), 8.389 (6.76), 8.590 (1.58), 8.600 (3.03), 8.609 (1.78), 11.421 (3.50).

Example 142

N-{[(4R)-4-Cyclopropyl-2,5-Dioxoimidazolidin-4-Yl]Methyl}-4'-(2,2-Difluorocyclopropyl)-5-Fluoro[1,1'-Biphenyl]-2-Carboxamide (Mixture of Diastereoisomers)

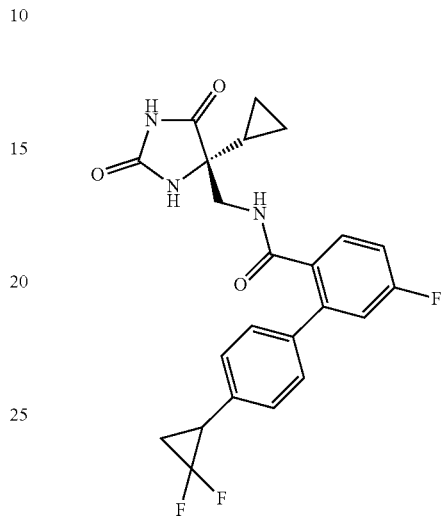

4'-(2,2-difluorocyclopropyl)-5-fluoro[1,1'-biphenyl]-2-carboxylic acid (41.0 mg, 140 µmol) dissolved in DMF (1.0 ml) were treated with (5R)-5-(aminomethyl)-5-cyclopropylimidazolidine-2,4-dione-hydrogen chloride (28.8 mg, 140 µmol), 1-ethyl-3-(3-dimethylaminopropyl)carbodiimide hydrochloride (35.0 mg, 182 µmol) 1-hydroxybenzotriazole hydrate (27.9 mg, 182 µmol) and N,N-diisopropylethylamine (68 µl, 390 µmol) The mixture was stirred over night at room temperature. Water was added to the mixture and purification was done by preparative HPLC HPLC (column: Chromatorex C18 10 µm, 250×30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated and the residue was lyophylized. 61.6 mg (100% purity, 99% yield) of the title compound were obtained.

LC-MS (Method 7): $R_t$=1.63 min; MS (ESIpos): m/z=444 [M+H]$^+$ $^1$H-NMR (600 MHz, DMSO-d6) δ [ppm]: 0.932 (0.60), 2.359 (2.72), 2.362 (5.77), 2.365 (8.01), 2.368 (5.81), 2.371 (2.69), 2.404 (16.00), 3.311 (0.65), 3.315 (0.52), 3.321 (0.49), 3.333 (0.61), 3.338 (0.65), 3.344 (0.60), 3.348 (0.93), 3.358 (0.74), 3.368 (0.46), 7.093 (0.53), 7.097 (0.86), 7.109 (0.74), 7.114 (0.97), 7.122 (0.63), 7.125 (0.46), 7.160 (1.46), 7.174 (2.22), 7.222 (2.72), 7.236 (1.67), 7.273 (0.45), 7.283 (0.54), 7.349 (1.20), 8.267 (0.72), 10.484 (0.86).

Example 143

4'-(2,2-Difluorocyclopropyl)-4,5-Difluoro-N-{[4-(1-Methyl-1H-Imidazol-2-Yl)-2,5-Dioxoimidazolidin-4-Yl]Methyl}[1,1'-Biphenyl]-2-Carboxamide (Mixture of Diastereoisomers)

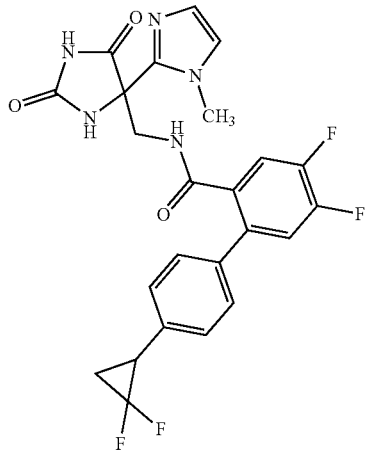 [SMILES: Cn1ccnc1C1(CNC(=O)c2cc(F)c(F)cc2-c2ccc(C3CC3(F)F)cc2)NC(=O)NC1=O]

4'-(2,2-difluorocyclopropyl)-4,5-difluoro[1,1'-biphenyl]-2-carboxylic acid (40.0 mg, 129 µmol) dissolved in DMF (1.0 ml) were treated with ent-5-(aminomethyl)-5-(1-methyl-1H-imidazol-2-yl)imidazolidine-2,4-dione-hydrogen chloride (31.7 mg, 129 µmol), 1-ethyl-3-(3-dimethylaminopropyl)carbodiimide hydrochloride (32.1 mg, 168 µmol) 1-hydroxybenzotriazole hydrate (25.7 mg, 168 µmol) and N,N-diisopropylethylamine (63 µl, 360 µmol) The mixture was stirred over night at room temperature. Water was added to the mixture and purification was done by preparative HPLC HPLC (column: Chromatorex C18 10 µm, 250× 30 mm, eluent A=water+0.1% TFA, B=acetonitrile; gradient: 3 min 10% B; 21 min 95% B; 30 min 95% B; 32 min 10% B; flow: 50 ml/min). Product containing samples were united, the solvents were evaporated and the residue was lyophylized. 58.3 mg (98% purity, 90% yield) of the title compound were obtained.

LC-MS (Method 7): $R_t$=1.56 min; MS (ESIpos): m/z=502 [M+H]$^+$ $^1$H-NMR (600 MHz, DMSO-d6) δ [ppm]: 1.929 (0.53), 1.936 (0.57), 1.943 (1.45), 1.950 (1.64), 1.957 (1.43), 1.965 (1.91), 1.972 (1.34), 1.979 (1.58), 1.986 (1.06), 2.001 (1.50), 2.010 (1.51), 2.022 (1.33), 2.030 (0.81), 2.044 (0.43), 2.423 (0.46), 2.518 (0.79), 2.570 (0.43), 2.652 (0.45), 3.004 (1.16), 3.018 (1.26), 3.025 (1.95), 3.039 (1.84), 3.045 (1.27), 3.059 (1.04), 3.721 (13.73), 3.867 (3.83), 3.990 (2.93), 3.995 (2.87), 4.000 (2.92), 4.005 (2.79), 4.013 (3.63), 4.018 (3.71), 4.024 (3.40), 4.028 (3.25), 4.050 (3.05), 4.055 (3.15), 4.061 (3.22), 4.066 (2.98), 4.073 (2.05), 4.078 (2.06), 4.084 (1.87), 4.089 (1.84), 4.361 (0.59), 7.218 (2.23), 7.297 (3.53), 7.311 (16.00), 7.317 (11.97), 7.321 (11.00), 7.331 (2.78), 7.335 (2.38), 7.371 (2.26), 7.385 (2.77), 7.389 (2.68), 7.402 (2.37), 7.454 (4.06), 7.509 (2.34), 7.522 (2.65), 7.528 (2.59), 7.541 (2.43), 8.459 (5.80), 8.727 (1.47), 8.737 (2.79), 8.747 (1.45), 11.443 (3.21).

Example 144

N-{[(4R)-4-Cyclopropyl-2,5-Dioxoimidazolidin-4-Yl]Methyl}-4'-(2,2-Difluorocyclopropyl)-4,5-Difluoro[1,1'-Biphenyl]-2-Carboxamide (Mixture of Diastereoisomers)

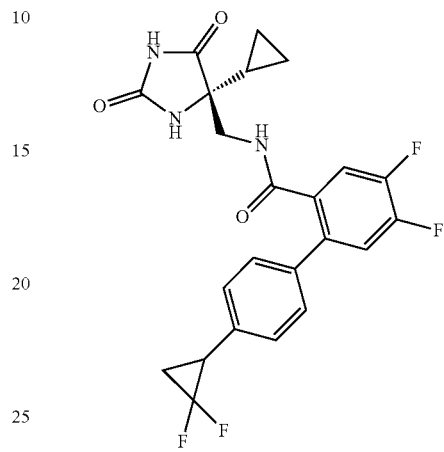

4'-(2,2-difluorocyclopropyl)-4,5-difluoro[1,1'-biphenyl]-2-carboxylic acid (40.0 mg, 129 µmol) dissolved in DMF (1.0 ml) were treated with (5R)-5-(aminomethyl)-5-cyclopropylimidazolidine-2,4-dione-hydrogen chloride (26.5 mg, 129 µmol), 1-ethyl-3-(3-dimethylaminopropyl)carbodiimide hydrochloride (32.1 mg, 168 µmol) 1-hydroxybenzotriazole hydrate (25.7 mg, 168 µmol) and N,N-diisopropylethylamine (63 µl, 360 µmol) The mixture was stirred over night at room temperature. Water was added to the mixture and purification was done by preparative HPLC HPLC (column: Chromatorex C18 10 µm, 250×30 mm, eluent A=water+ 0.1% TFA, B=acetonitrile; gradient: 3 min 10% B; 21 min 95% B; 30 min 95% B; 32 min 10% B; flow: 50 ml/min). Product containing samples were united, the solvents were evaporated and the residue was lyophylized. 57.2 mg (100% purity, 96% yield) of the title compound were obtained.

LC-MS (Method 7): $R_t$=1.72 min; MS (ESIpos): m/z=462 [M+H]$^+$ $^1$H-NMR (600 MHz, DMSO-d6) δ [ppm]: −0.144 (0.40), −0.016 (0.46), −0.007 (0.66), 0.009 (0.51), 0.172 (0.55), 0.179 (0.68), 0.187 (0.60), 0.195 (0.44), 0.242 (0.43), 0.248 (0.53), 0.256 (0.61), 0.263 (0.47), 0.266 (0.44), 0.298 (0.50), 0.307 (0.64), 0.313 (0.60), 0.919 (0.58), 0.924 (0.63), 0.928 (0.43), 0.933 (1.06), 0.938 (0.43), 0.941 (0.56), 0.947 (0.52), 1.784 (0.41), 1.791 (0.50), 1.798 (0.43), 1.805 (0.58), 1.827 (0.43), 1.848 (0.51), 1.857 (0.50), 1.869 (0.46), 2.349 (3.86), 2.353 (7.90), 2.356 (10.73), 2.359 (7.74), 2.361 (3.72), 2.395 (16.00), 2.843 (0.40), 2.857 (0.44), 2.864 (0.65), 2.879 (0.63), 2.885 (0.44), 3.376 (0.71), 7.148 (2.25), 7.161 (4.40), 7.188 (4.93), 7.202 (2.38), 7.251 (0.49), 7.254 (0.52), 7.264 (0.63), 7.268 (0.97), 7.272 (0.59), 7.282 (0.54), 7.286 (0.48), 7.343 (0.76), 7.357 (0.87), 7.363 (0.85), 7.376 (0.82), 7.407 (2.17), 8.380 (0.66), 8.390 (1.29), 8.401 (0.63), 10.503 (1.52).

Example 145

N-{[(4R)-4-Cyclopropyl-2,5-Dioxoimidazolidin-4-Yl]Methyl}-5,6-Dimethyl-4'-(Trifluoromethyl)[1,1'-Biphenyl]-2-Carboxamide

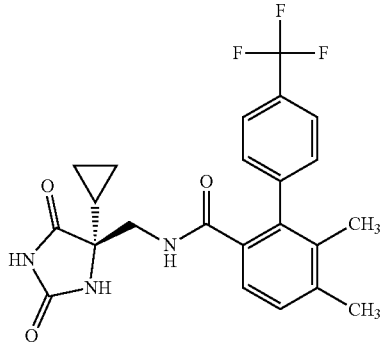 [SMILES: Cc1ccc(C(=O)NC[C@@]2(C3CC3)NC(=O)NC2=O)c(-c2ccc(C(F)(F)F)cc2)c1C]

5,6-dimethyl-4'-(trifluoromethyl)[1,1'-biphenyl]-2-carboxylic acid (50.0 mg, 170 µmol) dissolved in DMF (1.4 ml) was treated with HATU (129 mg, 340 µmol) and N,N-diisopropylethylamine (59 µl, 340 µmol). The mixture was stirred for 5 minutes then (5R)-5-(aminomethyl)-5-cyclopropylimidazolidine-2,4-dione (57.5 mg, 340 µmol) was added and the reaction was stirred over night at room temperature. Purification was done by preparative HPLC. Product containing samples were united, the solvents were evaporated and the residue was lyophylized. 42.6 mg (98% purity, 55% yield) of the title compound were obtained.

LC-MS (Method 7): $R_t$=1.78 min, MS (ESIpos): m/z=446 [M+H]$^+$ $^1$H-NMR (600 MHz, DMSO-d6) δ [ppm]: 0.005 (0.54), 0.090 (0.70), 0.097 (1.31), 0.106 (1.25), 0.113 (0.88), 0.122 (0.42), 0.247 (0.43), 0.250 (0.43), 0.255 (0.77), 0.263 (0.93), 0.271 (0.85), 0.278 (0.65), 0.285 (0.48), 0.314 (0.42), 0.321 (0.74), 0.329 (0.76), 0.331 (0.79), 0.336 (1.10), 0.346 (0.88), 0.351 (0.52), 0.367 (0.48), 0.376 (0.94), 0.383 (1.19), 0.392 (1.15), 0.399 (0.75), 0.947 (0.43), 0.956 (0.85), 0.961 (0.90), 0.965 (0.58), 0.970 (1.56), 0.975 (0.58), 0.978 (0.81), 0.984 (0.77), 1.917 (16.00), 2.313 (15.59), 2.514 (0.49), 2.517 (0.47), 2.520 (0.43), 3.321 (4.58), 3.332 (4.20), 7.147 (2.64), 7.160 (3.24), 7.251 (2.97), 7.264 (2.38), 7.341 (1.38), 7.355 (2.77), 7.368 (1.49), 7.389 (3.04), 7.391 (3.03), 7.703 (3.11), 7.717 (2.89), 8.100 (1.03), 8.111 (2.16), 8.121 (1.02), 10.587 (2.61).

Example 146

Ent-4'-Methyl-N-{[4-(1-Methyl-1H-Imidazol-2-Yl)-2,5-Dioxoimidazolidin-4-Yl]Methyl}[Biphenyl]-2-Carboxamide

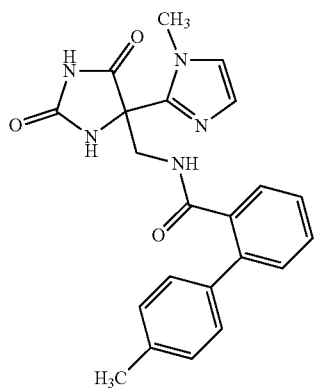 [SMILES: Cc1ccc(-c2ccccc2C(=O)NCC2(c3nccn3C)NC(=O)NC2=O)cc1]

To a solution of rac-5-(aminomethyl)-5-(1-methyl-1H-imidazol-2-yl)imidazolidine-2,4-dione hydrochloride (100 mg, 407 µmol) and 4'-methyl[1,1'-biphenyl]-2-carboxylic acid (86.4 mg, 407 µmol) in DMF (8.4 ml) was added 1-ethyl-3-(3-dimethylaminopropyl)carbodiimide hydrochloride (101 mg, 529 µmol), 1-hydroxybenzotriazole hydrate (81.0 mg, 529 µmol) and N,N-diisopropylethylamine (200 µl, 1.1 mmol). The reaction mixture was stirred overnight at 50° C. and concentrated under reduced pressure. The crude product was first purified by preparative HPLC (Method 9f). The combined organic phases were concentrated in vacuo and the remaining TFA was removed, using a Stratospheres PL-HCO3 MP SPE cartridge. After lyophilization, 20 mg of the racemate product were obtained. A second purification by preparative chiral HPLC [sample preparation: 20 mg; column: Daicel Chiralpack AD-H 5 µm 250*20 mm; eluent: 2-propanol; flow rate: 9 ml/min; temperature: 20° C.; UV detection: 240 nm] gave 2.55 mg (95% purity, 1% yield) of the desired product Analytical chiral HPLC: $R_t$=11.28 min, e.e. =>95% [column: Daicel Chiralpack AD-H 5 µm 250*4.6 mm; eluent: 2-propanol; flow rate: 0.5 ml/min; temperature: 20° C.; UV detection: 240 nm]

LC-MS (Method 8): $R_t$=0.73 min; MS (ESIpos): m/z=404 [M+H]$^+$ $^1$H-NMR (500 MHz, DMSO-d6) δ [ppm]: −0.007 (1.07), 0.006 (0.79), 1.236 (0.55), 2.075 (1.42), 2.333 (12.66), 3.510 (16.00), 3.577 (0.42), 3.948 (0.82), 3.961 (0.90), 3.976 (1.41), 3.989 (1.26), 4.046 (1.30), 4.059 (1.37), 4.074 (0.86), 4.087 (0.80), 6.844 (4.15), 6.846 (4.37), 7.206 (2.99), 7.213 (4.67), 7.215 (4.93), 7.222 (4.70), 7.267 (5.61), 7.283 (3.22), 7.336 (1.00), 7.339 (1.10), 7.351 (2.58), 7.354 (2.48), 7.360 (2.36), 7.365 (1.79), 7.368 (1.61), 7.375 (2.89), 7.380 (2.56), 7.395 (0.92), 7.471 (1.28), 7.474 (1.27), 7.486 (1.80), 7.489 (1.68), 7.500 (0.78), 7.504 (0.74), 8.267 (3.69), 8.383 (0.84), 8.396 (1.71), 8.409 (0.82), 11.222 (1.27).

Example 147

Ent-5-Fluoro-4'-Methyl-N-{[4-(1-Methyl-1H-Imidazol-2-Yl)-2,5-Dioxoimidazolidin-4-Yl]Methyl}[Biphenyl]-2-Carboxamide

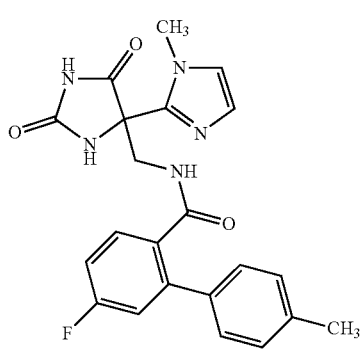 [SMILES: Cc1ccc(-c2cc(F)ccc2C(=O)NCC2(c3nccn3C)NC(=O)NC2=O)cc1]

To a solution of ent-5-(aminomethyl)-5-(1-methyl-1H-imidazol-2-yl)imidazolidine-2,4-dione hydrochloride (50.0 mg, 204 µmol) and 5-fluoro-4'-methyl[1,1'-biphenyl]-2-carboxylic acid (46.9 mg, 204 µmol) in DMF (4.2 ml) was added 1-ethyl-3-(3-dimethylaminopropyl)carbodiimide hydrochloride (50.7 mg, 265 µmol), 1-hydroxybenzotriazole hydrate (40.5 mg, 265 µmol) and N,N-diisopropylethylamine (99 µl, 570 µmol). The reaction mixture was stirred overnight at RT and concentrated under reduced pressure. The crude product was purified by preparative HPLC (Method 2f). The combined organic phases were concentrated in vacuo and the remaining TFA was removed, using a Stratospheres PL-HCO3 MP SPE cartridge. After lyophilization, 36.1 mg (97% purity, 41% yield) of the desired product were obtained.

LC-MS (Method 7): $R_t$=1.33 min, MS (ESIpos): m/z=421 [M+H]$^+$ $^1$H-NMR (600 MHz, DMSO-d6) δ [ppm]: 2.072 (2.18), 2.334 (13.01), 2.730 (0.66), 2.889 (0.75), 3.500 (16.00), 3.907 (0.82), 3.917 (0.89), 3.930 (1.18), 3.940 (1.04), 4.028 (1.27), 4.039 (1.32), 4.051 (0.95), 4.062 (0.87), 6.827 (4.24), 7.190 (4.50), 7.197 (1.89), 7.210 (1.59), 7.217 (3.48), 7.231 (4.71), 7.240 (1.50), 7.250 (0.97), 7.254 (0.81), 7.287 (5.32), 7.301 (3.50), 7.385 (1.45), 7.395 (1.56), 7.399 (1.38), 7.409 (1.20), 8.052 (0.47), 8.368 (0.79), 8.378 (1.45), 8.389 (0.72).

Example 148

Ent-N-{[4-(1-Methyl-1H-Imidazol-2-Yl)-2,5-Dioxoimidazolidin-4-Yl]Methyl}-4'-(Trifluoromethyl)[Biphenyl]-2-Carboxamide

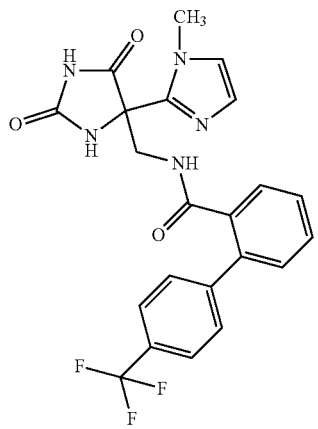 [SMILES: Cn1ccnc1C1(CNC(=O)c2ccccc2-c2ccc(C(F)(F)F)cc2)NC(=O)NC1=O]

To a solution of ent-5-(aminomethyl)-5-(1-methyl-1H-imidazol-2-yl)imidazolidine-2,4-dione hydrochloride (50.0 mg, 204 µmol) and 4'-(trifluoromethyl)[1,1'-biphenyl]-2-carboxylic acid (54.2 mg, 204 µmol) in DMF (4.2 ml) was added 1-ethyl-3-(3-dimethylaminopropyl)carbodiimide hydrochloride (50.7 mg, 265 µmol), 1-hydroxybenzotriazole hydrate (40.5 mg, 265 µmol) and N,N-diisopropylethylamine (99 µl, 570 µmol). The reaction mixture was stirred overnight at RT and concentrated under reduced pressure. The crude product was purified by preparative HPLC (Method 3f). After lyophilization, 51.5 mg (98% purity, 54% yield) of the desired product were obtained.

LC-MS (Method 7): $R_t$=1.41 min, MS (ESIpos): m/z=458 [M+H]$^+$ $^1$H-NMR (400 MHz, DMSO-d6) δ [ppm]: −0.008 (1.43), 0.008 (1.63), 2.523 (0.85), 3.518 (16.00), 3.989 (0.70), 4.004 (0.79), 4.024 (1.32), 4.039 (1.18), 4.092 (1.22), 4.108 (1.31), 4.126 (0.76), 4.143 (0.70), 6.849 (4.01), 6.852 (4.11), 7.212 (3.83), 7.214 (3.84), 7.440 (1.88), 7.445 (0.85), 7.460 (5.27), 7.464 (4.27), 7.478 (2.17), 7.497 (0.65), 7.499 (0.55), 7.540 (1.39), 7.545 (1.24), 7.558 (1.32), 7.564 (1.54), 7.571 (2.96), 7.580 (1.04), 7.591 (3.33), 7.763 (3.42), 7.784 (2.83), 8.330 (3.52), 8.575 (0.74), 8.592 (1.57), 8.607 (0.74), 11.230 (0.95).

Example 149

Ent-4-Fluoro-N-{[4-(1-Methyl-1H-Imidazol-2-Yl)-2,5-Dioxoimidazolidin-4-Yl]Methyl}-4'-(Trifluoromethyl)[Biphenyl]-2-Carboxamide

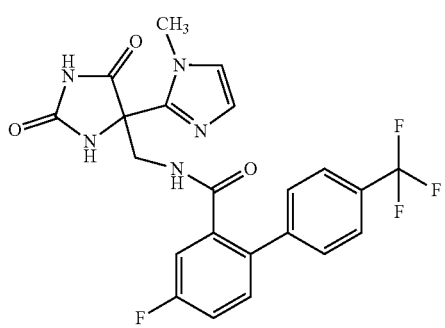 [SMILES: Cn1ccnc1C1(CNC(=O)c2cc(F)ccc2-c2ccc(C(F)(F)F)cc2)NC(=O)NC1=O]

To a solution of ent-5-(aminomethyl)-5-(1-methyl-1H-imidazol-2-yl)imidazolidine-2,4-dione hydrochloride (60.0 mg, 90% purity, 220 µmol) and 4-fluoro-4'-(trifluoromethyl)[1,1'-biphenyl]-2-carboxylic acid (62.5 mg, 220 µmol) in DMF (1.4 ml) was added 1-ethyl-3-(3-dimethylaminopropyl)carbodiimide hydrochloride (54.8 mg, 286 µmol), 1-hydroxybenzotriazole hydrate (43.8 mg, 286 µmol) and N,N-diisopropylethylamine (190 µl, 1.1 mmol). The reaction mixture was stirred overnight at RT and concentrated under reduced pressure. The crude product was purified by preparative HPLC (Method 2f) The combined organic phases were concentrated in vacuo and the remaining TFA was removed, using a Stratospheres PL-HCO3 MP SPE cartridge. After lyophilization, 79.7 mg (100% purity, 76% yield) of the desired product were obtained.

LC-MS (Method 7): $R_t$=1.56 min; MS (ESIpos): m/z=476 [M+H]$^+$ $^1$H-NMR (400 MHz, DMSO-d6) δ [ppm]: 3.512 (16.00), 3.961 (0.62), 3.976 (0.68), 3.995 (1.06), 4.011 (0.97), 4.085 (1.20), 4.102 (1.27), 4.120 (0.80), 4.137 (0.75), 6.842 (3.65), 6.844 (3.75), 7.201 (3.69), 7.204 (3.76), 7.247 (1.35), 7.253 (1.62), 7.269 (1.39), 7.276 (1.56), 7.389 (0.64), 7.396 (0.65), 7.411 (1.56), 7.418 (1.58), 7.432 (1.01), 7.439 (1.02), 7.485 (1.72), 7.499 (1.81), 7.506 (1.27), 7.520 (1.14), 7.555 (3.08), 7.575 (3.62), 7.760 (3.74), 7.781 (3.13), 8.698 (0.62), 8.714 (1.17), 8.730 (0.60).

Example 150

Ent-5-Fluoro-N-{[4-(1-Methyl-1H-Imidazol-2-Yl)-2,5-Dioxoimidazolidin-4-Yl]Methyl}-4'-(Trifluoromethyl)[Biphenyl]-2-Carboxamide

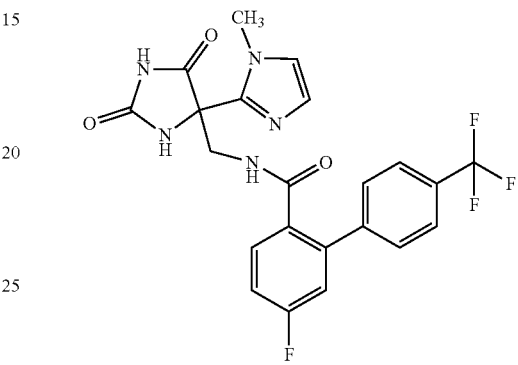

To a solution of ent-5-(aminomethyl)-5-(1-methyl-1H-imidazol-2-yl)imidazolidine-2,4-dione hydrochloride (60.0 mg, 90% purity, 220 µmol) and 5-fluoro-4'-(trifluoromethyl)[1,1'-biphenyl]-2-carboxylic acid (62.5 mg, 220 µmol) in DMF (1.4 ml) was added 1-ethyl-3-(3-dimethylaminopropyl)carbodiimide hydrochloride (54.8 mg, 286 µmol), 1-hydroxybenzotriazole hydrate (43.8 mg, 286 µmol) and N,N-diisopropylethylamine (190 µl, 1.1 mmol). The reaction mixture was stirred overnight at RT and concentrated under reduced pressure. The crude product was purified by preparative HPLC (Method 2f) The combined organic phases were concentrated in vacuo and the remaining TFA was removed, using a Stratospheres PL-HCO3 MP SPE cartridge. After lyophilization, 72.3 mg (100% purity, 69% yield) of the desired product were obtained.

LC-MS (Method 7): $R_t$=1.56 min, MS (ESIpos): m/z=476 [M+H]$^+$ $^1$H-NMR (400 MHz, DMSO-d6) δ [ppm]: 3.502 (16.00), 3.921 (0.61), 3.937 (0.65), 3.956 (1.00), 3.971 (0.90), 4.061 (1.12), 4.077 (1.19), 4.095 (0.79), 4.112 (0.74), 6.826 (3.86), 6.828 (3.85), 7.182 (3.80), 7.316 (3.25), 7.339 (3.60), 7.357 (1.11), 7.364 (0.67), 7.497 (1.08), 7.510 (1.16), 7.514 (1.29), 7.532 (0.89), 7.597 (3.12), 7.617 (3.76), 7.772 (3.95), 7.793 (3.16), 8.534 (0.59), 8.549 (1.07).

Example 151

Ent-5-Methyl-N-{[4-(1-Methyl-1H-Imidazol-2-Yl)-2,5-Dioxoimidazolidin-4-Yl]Methyl}-4'-(Trifluoromethyl)[Biphenyl]-2-Carboxamide

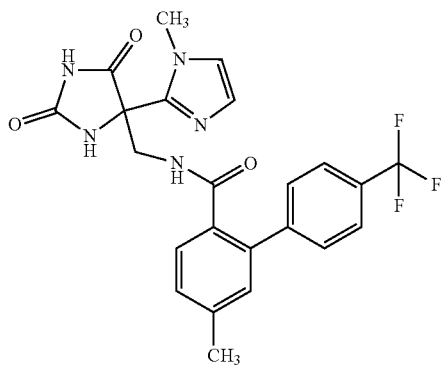 [SMILES: Cc1ccc(C(=O)NCC2(c3nccn3C)NC(=O)NC2=O)c(-c2ccc(C(F)(F)F)cc2)c1]

To a solution of ent-5-(aminomethyl)-5-(1-methyl-1H-imidazol-2-yl)imidazolidine-2,4-dione hydrochloride (60.0 mg, 90% purity, 220 µmol) and 5-methyl-4'-(trifluoromethyl)[1,1'-biphenyl]-2-carboxylic acid (61.6 mg, 220 µmol) in DMF (1.4 ml) was added 1-ethyl-3-(3-dimethylaminopropyl)carbodiimide hydrochloride (54.8 mg, 286 µmol), 1-hydroxybenzotriazole hydrate (43.8 mg, 286 µmol) and N,N-diisopropylethylamine (190 µl, 1.1 mmol). The reaction mixture was stirred overnight at RT and concentrated under reduced pressure. The crude product was purified by preparative HPLC (Method 3f). After lyophilization, 67.1 mg (100% purity, 65% yield) of the desired product were obtained.

LC-MS (Method 7): $R_t$=1.52 min, MS (ESIpos): m/z=472 [M+H]$^+$ $^1$H-NMR (400 MHz, DMSO-d6) δ [ppm]: −0.008 (0.71), 0.008 (0.72), 2.388 (11.22), 2.523 (0.81), 3.513 (16.00), 3.966 (0.76), 3.981 (0.85), 4.001 (1.31), 4.016 (1.14), 4.089 (1.18), 4.105 (1.27), 4.124 (0.80), 4.140 (0.74), 6.844 (3.99), 6.847 (4.08), 7.208 (3.87), 7.211 (3.91), 7.258 (3.08), 7.266 (1.53), 7.286 (1.81), 7.363 (3.21), 7.382 (2.15), 7.546 (2.90), 7.566 (3.40), 7.746 (3.55), 7.766 (2.93), 8.304 (3.44), 8.458 (0.78), 8.475 (1.63), 8.491 (0.76), 11.220 (1.46).

Example 152

Ent-4-Fluoro-4'-Methyl-N-{[4-(1-Methyl-1H-Imidazol-2-Yl)-2,5-Dioxoimidazolidin-4-Yl]Methyl}[Biphenyl]-2-Carboxamide

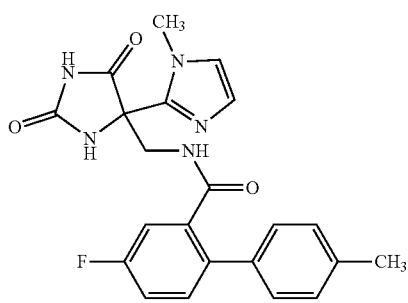 [SMILES: Cc1ccc(-c2ccc(F)cc2C(=O)NCC2(c3nccn3C)NC(=O)NC2=O)cc1]

To a solution of ent-5-(aminomethyl)-5-(1-methyl-1H-imidazol-2-yl)imidazolidine-2,4-dione hydrochloride (100 mg, 407 µmol) and 4-fluoro-4'-methyl[1,1'-biphenyl]-2-carboxylic acid (112 mg, 488 µmol) in DMF (2.5 ml) was added 1-ethyl-3-(3-dimethylaminopropyl)carbodiimide hydrochloride (101 mg, 529 µmol), 1-hydroxybenzotriazole hydrate (81.0 mg, 529 µmol) and N,N-diisopropylethylamine (350 µl, 2.0 mmol). The reaction mixture was stirred for 2 days at 40° C. and concentrated under reduced pressure. The crude product was purified by preparative HPLC (Method 3f). After lyophilization, 67.4 mg (96% purity, 38% yield) of the desired product were obtained.

LC-MS (Method 7): $R_t$=1.31 min, MS (ESIpos): m/z=422 [M+H]$^+$ $^1$H-NMR (600 MHz, DMSO-d6) δ [ppm]: 2.328 (13.26), 3.512 (16.00), 3.952 (0.93), 3.962 (1.00), 3.975 (1.42), 3.985 (1.28), 4.058 (1.34), 4.069 (1.40), 4.081 (0.96), 4.092 (0.90), 6.848 (4.51), 7.112 (1.35), 7.117 (1.53), 7.127 (1.36), 7.132 (1.42), 7.204 (2.69), 7.215 (7.36), 7.246 (5.76), 7.259 (3.01), 7.323 (0.60), 7.327 (0.63), 7.337 (1.43), 7.341 (1.46), 7.351 (0.87), 7.355 (0.89), 7.395 (1.56), 7.404 (1.64), 7.409 (1.20), 7.418 (1.07), 8.140 (0.45), 8.311 (3.94), 8.547 (0.92), 8.

Example 153

Ent-5-Chloro-4'-Methyl-N-{[4-(1-Methyl-1H-Imidazol-2-Yl)-2,5-Dioxoimidazolidin-4-Yl]Methyl}[Biphenyl]-2-Carboxamide

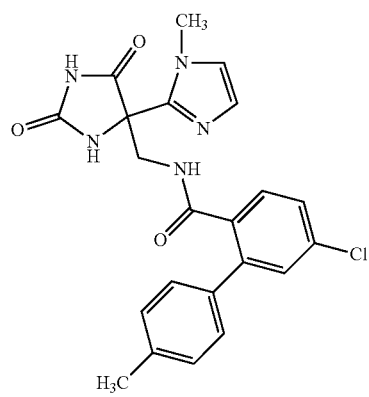 [SMILES: Cc1ccc(-c2cc(Cl)ccc2C(=O)NCC2(c3nccn3C)NC(=O)NC2=O)cc1]

To a solution of ent-5-(aminomethyl)-5-(1-methyl-1H-imidazol-2-yl)imidazolidine-2,4-dione hydrochloride (100 mg, 407 µmol) and 5-chloro-4'-methyl[1,1'-biphenyl]-2-carboxylic acid (100 mg, 407 µmol) in DMF (7.5 ml) was added 1-ethyl-3-(3-dimethylaminopropyl)carbodiimide hydrochloride (101 mg, 529 µmol), 1-hydroxybenzotriazole hydrate (81.0 mg, 529 µmol) and N,N-diisopropylethylamine (200 µl, 1.1 mmol). The reaction mixture was stirred overnight at room temperature and concentrated under reduced pressure. The crude product was purified by preparative HPLC (Method 4f). After lyophilization, 92.0 mg (98% purity, 51% yield) of the desired product were obtained.

LC-MS (Method 7): $R_t$=1.48 min; MS (ESIpos): m/z=438 [M+H]$^+$ $^1$H-NMR (600 MHz, DMSO-d6) δ [ppm]: 2.336 (13.22), 2.567 (0.48), 3.508 (16.00), 3.944 (0.92), 3.954 (1.01), 3.966 (1.49), 3.977 (1.38), 4.039 (1.39), 4.049 (1.48), 4.061 (1.00), 4.073 (0.92), 6.838 (4.35), 7.201 (4.48), 7.220 (3.18), 7.234 (4.67), 7.284 (5.29), 7.297 (3.57), 7.342 (2.75), 7.356 (3.43), 7.407 (3.15), 7.410 (3.59), 7.459 (2.01), 7.462 (1.85), 7.473 (1.66), 7.476 (1.56), 8.258 (4.13), 8.420 (0.95), 8.431 (1.91), 8.441 (0.98), 11.187 (0.51).

Example 154

Ent-4,5-Difluoro-N-{[4-(1-Methyl-1H-Imidazol-2-Yl)-2,5-Dioxoimidazolidin-4-Yl]Methyl}-4'-(Trifluoromethyl)[Biphenyl]-2-Carboxamide

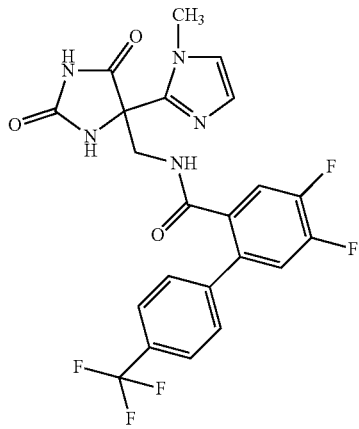 [SMILES: Cn1ccnc1C1(CNC(=O)c2cc(F)c(F)cc2-c2ccc(C(F)(F)F)cc2)NC(=O)NC1=O]

To a solution of ent-5-(aminomethyl)-5-(1-methyl-1H-imidazol-2-yl)imidazolidine-2,4-dione hydrochloride (100 mg, 407 µmol) and 4,5-difluoro-4'-(trifluoromethyl)[1,1'-biphenyl]-2-carboxylic acid (123 mg, 407 µmol) in DMF (2 ml) was added 1-ethyl-3-(3-dimethylaminopropyl)carbodiimide hydrochloride (101 mg, 529 µmol), 1-hydroxybenzotriazole hydrate (81.0 mg, 529 µmol) and N,N-diisopropylethylamine (350 µl, 2.0 mmol). After overnight stirring at room temperature, the reaction was additionally stirred for 2 h at 50° C. The resulting reaction mixture was concentrated under reduced pressure and the crude product was purified by preparative HPLC (Method 3f). After lyophilization, 82.0 mg (98% purity, 40% yield) of the desired product were obtained.

LC-MS (Method 7): $R_t$=1.54 min; MS (ESIpos): m/z=494 [M+H]$^+$ $^1$H-NMR (600 MHz, DMSO-d6) δ [ppm]: 2.571 (0.46), 3.262 (0.46), 3.333 (1.27), 3.520 (16.00), 3.997 (0.87), 4.007 (0.99), 4.020 (1.38), 4.031 (1.26), 4.104 (1.27), 4.115 (1.37), 4.127 (0.97), 4.139 (0.92), 6.852 (3.96), 6.854 (3.93), 7.212 (3.90), 7.213 (3.88), 7.473 (0.89), 7.487 (1.13), 7.491 (1.10), 7.505 (1.00), 7.574 (3.06), 7.587 (3.75), 7.603 (1.24), 7.609 (1.17), 7.622 (1.05), 7.775 (3.59), 7.789 (3.25), 8.390 (3.66), 8.718 (0.83), 8.729 (1.68), 8.740 (0.90), 11.249 (1.06).

Example 155

Ent-4'-Chloro-N-{[4-(1-Methyl-1H-Imidazol-2-Yl)-2,5-Dioxoimidazolidin-4-Yl]Methyl}[Biphenyl]-2-Carboxamide

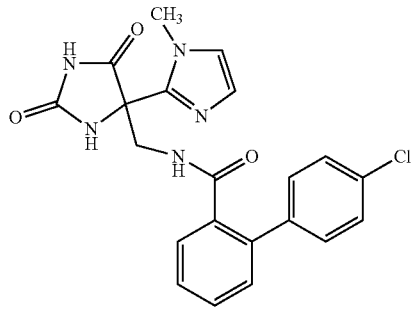 [SMILES: Cn1ccnc1C1(CNC(=O)c2ccccc2-c2ccc(Cl)cc2)NC(=O)NC1=O]

To a solution of ent-5-(aminomethyl)-5-(1-methyl-1H-imidazol-2-yl)imidazolidine-2,4-dione hydrochloride (60.0 mg, 244 µmol) and 4'-chloro[1,1'-biphenyl]-2-carboxylic acid (68.2 mg, 293 µmol) in DMF (1.5 ml) was added 1-ethyl-3-(3-dimethylaminopropyl)carbodiimide hydrochloride (60.9 mg, 317 µmol), 1-hydroxybenzotriazole hydrate (48.6 mg, 317 µmol) and N,N-diisopropylethylamine (210 µl, 1.2 mmol). The reaction mixture was stirred for 2 days at 40° C. and concentrated under reduced pressure. The crude product was first purified by preparative HPLC (Method 5f). A second purification by preparative thin-layer chromatography (silica gel, eluent: ethyl acetate/methanol: 10/1) gave 23.9 mg (100% purity, 23% yield) of the desired product LC-MS (Method 7): $R_t$=1.29 min, MS (ESIpos): m/z=424 [M+H]$^+$ $^1$H-NMR (400 MHz, DMSO-d6) δ [ppm]: 1.235 (0.49), 2.327 (0.65), 2.366 (0.54), 2.669 (0.75), 2.709 (0.61), 3.515 (16.00), 3.965 (0.70), 3.980 (0.82), 3.999 (1.41), 4.015 (1.28), 4.069 (1.37), 4.085 (1.44), 4.103 (0.83), 4.120 (0.77), 6.848 (4.02), 7.210 (4.24), 7.373 (3.84), 7.388 (3.73), 7.394 (7.05), 7.414 (4.79), 7.429 (2.40), 7.458 (6.13), 7.480 (3.81), 7.499 (1.46), 7.504 (1.31), 7.517 (1.62), 7.522 (1.52), 7.535 (0.75), 8.267 (0.92), 8.463 (0.83), 8.479 (1.62), 8.494 (0.83), 11.220 (0.64).

Example 156

Ent-4-Chloro-N-{[4-(1-Methyl-1H-Imidazol-2-Yl)-2,5-Dioxoimidazolidin-4-Yl]Methyl}-4'-(Trifluoromethyl)[Biphenyl]-2-Carboxamide

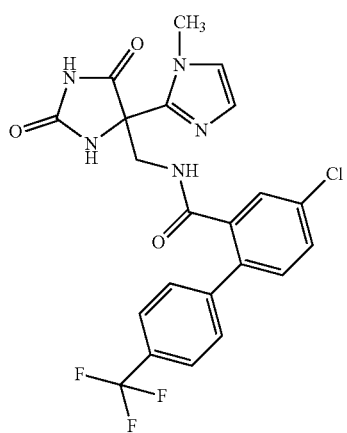 [SMILES: Cn1ccnc1C1(CNC(=O)c2cc(Cl)ccc2-c2ccc(C(F)(F)F)cc2)NC(=O)NC1=O]

To a solution of ent-5-(aminomethyl)-5-(1-methyl-1H-imidazol-2-yl)imidazolidine-2,4-dione hydrochloride (100 mg, 407 μmol) and 4-chloro-4'-(trifluoromethyl)[1,1'-biphenyl]-2-carboxylic acid (122 mg, 407 μmol) in DMF (2 ml) was added 1-ethyl-3-(3-dimethylaminopropyl)carbodiimide hydrochloride (101 mg, 529 μmol), 1-hydroxybenzotriazole hydrate (81.0 mg, 529 μmol) and N,N-diisopropylethylamine (350 μl, 2.0 mmol). After overnight stirring at room temperature, the reaction was additionally stirred for 2 h at 50° C. The resulting reaction mixture was concentrated under reduced pressure and the crude product was purified by preparative HPLC (Method 3f). After lyophilization, 70.8 mg (98% purity, 35% yield) of the desired product were obtained.

LC-MS (Method 7): $R_t$=1.57 min, MS (ESIpos): m/z=492 [M+H]$^+$ $^1$H-NMR (600 MHz, DMSO-d6) δ [ppm]: 3.267 (0.50), 3.272 (0.48), 3.523 (16.00), 4.001 (0.92), 4.011 (1.00), 4.024 (1.44), 4.034 (1.29), 4.108 (1.31), 4.119 (1.42), 4.131 (1.00), 4.142 (0.92), 6.853 (4.22), 7.213 (4.21), 7.473 (2.76), 7.484 (3.85), 7.487 (6.67), 7.564 (3.28), 7.577 (3.72), 7.617 (1.98), 7.621 (1.76), 7.631 (1.57), 7.635 (1.59), 7.774 (3.80), 7.787 (3.43), 8.374 (3.95), 8.760 (0.90), 8.771 (1.79), 8.782 (0.93), 11.257 (0.71).

Example 157

Ent-4'-Chloro-5-Fluoro-N-{[4-(1-Methyl-1H-Imidazol-2-Yl)-2,5-Dioxoimidazolidin-4-Yl]Methyl}[Biphenyl]-2-Carboxamide

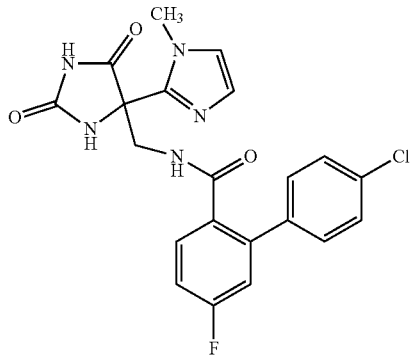 [SMILES: Cn1ccnc1C1(CNC(=O)c2ccc(F)cc2-c2ccc(Cl)cc2)NC(=O)NC1=O]

To a solution of ent-5-(aminomethyl)-5-(1-methyl-1H-imidazol-2-yl)imidazolidine-2,4-dione hydrochloride (100 mg, 407 μmol) and 4'-chloro-5-fluoro[1,1'-biphenyl]-2-carboxylic acid (122 mg, 488 μmol) in DMF (2.5 ml) was added 1-ethyl-3-(3-dimethylaminopropyl)carbodiimide hydrochloride (101 mg, 529 μmol), 1-hydroxybenzotriazole hydrate (81.0 mg, 529 μmol) and N,N-diisopropylethylamine (350 μl, 2.0 mmol). The reaction mixture was stirred for 2 days at 40° C. and concentrated under reduced pressure. The crude product was first purified by preparative HPLC (Method 5f). A second purification by preparative thin-layer chromatography (silica gel, eluent: ethyl acetate/methanol: 10/1) gave 17.4 mg (100% purity, 10% yield) of the desired product LC-MS (Method 7): $R_t$=1.36 min, MS (ESIpos): m/z=442 [M+H]$^+$ $^1$H-NMR (400 MHz, DMSO-d6) δ [ppm]: 2.327 (0.78), 2.366 (0.64), 2.669 (0.82), 2.709 (0.64), 3.168 (5.84), 3.343 (5.77), 3.967 (1.66), 3.983 (1.86), 4.002 (3.13), 4.017 (2.84), 4.073 (3.05), 4.089 (3.24), 4.107 (1.91), 4.124 (1.75), 6.913 (1.84), 7.256 (5.83), 7.262 (7.32), 7.274 (3.41), 7.281 (4.33), 7.287 (5.09), 7.296 (4.60), 7.302 (3.02), 7.317 (2.37), 7.323 (1.83), 7.387 (9.12), 7.392 (3.78), 7.409 (15.15), 7.428 (4.02), 7.443 (4.14), 7.449 (3.57), 7.465 (4.50), 7.472 (16.00), 7.477 (4.73), 7.489 (3.74), 7.493 (9.43), 8.349 (5.74), 8.554 (2.64), 11.261 (3.18).

Example 158

Ent-N-{[4-(1-Methyl-1H-Imidazol-2-Yl)-2,5-Dioxoimidazolidin-4-Yl]Methyl}-2-[6-(Trifluoromethyl)Pyridin-3-Yl]Benzamide

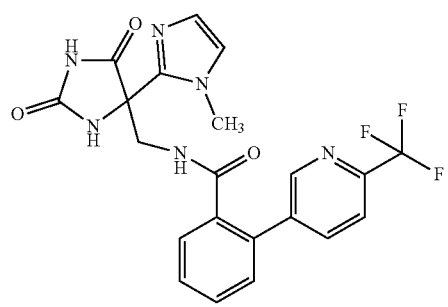 [SMILES: Cn1ccnc1C1(CNC(=O)c2ccccc2-c2ccc(C(F)(F)F)nc2)NC(=O)NC1=O]

To a solution of ent-5-(aminomethyl)-5-(1-methyl-1H-imidazol-2-yl)imidazolidine-2,4-dione hydrochloride (100 mg, 407 μmol) and 2-[6-(trifluoromethyl)pyridin-3-yl]benzoic acid (109 mg, 407 μmol) in DMF (2.3 ml) was added 1-ethyl-3-(3-dimethylaminopropyl)carbodiimide hydrochloride (101 mg, 529 μmol), 1-hydroxybenzotriazole hydrate (81.0 mg, 529 μmol) and N,N-diisopropylethylamine (350 μl, 2.0 mmol). The reaction mixture was stirred overnight at room temperature and concentrated under reduced pressure. The crude product was purified by preparative HPLC (Method 3f). After lyophilization, 92.8 mg (96% purity, 48% yield) of the desired product were obtained.

LC-MS (Method 7): $R_t$=1.15 min, MS (ESIpos): m/z=459 [M+H]$^+$ $^1$H-NMR (400 MHz, DMSO-d6) δ [ppm]: −0.008 (1.48), 0.008 (1.59), 2.731 (1.05), 2.889 (1.29), 3.315 (8.83), 3.978 (3.17), 3.994 (3.53), 4.013 (5.52), 4.028 (4.98), 4.098 (5.09), 4.114 (5.44), 4.132 (3.37), 4.149 (3.17), 6.854 (14.61), 6.856 (15.15), 7.215 (15.75), 7.503 (2.82), 7.507 (3.22), 7.525 (14.98), 7.544 (12.79), 7.547 (12.89), 7.566 (3.73), 7.594 (5.69), 7.599 (5.32), 7.612 (5.59), 7.617 (5.69), 7.631 (2.21), 7.635 (2.04), 7.928 (6.81), 7.949 (13.03), 7.989 (7.04), 7.994 (6.94), 8.010 (3.69), 8.015 (3.77), 8.141 (4.40), 8.347 (16.00), 8.652 (3.27), 8.668 (6.85), 8.684 (3.27), 8.749 (9.40), 8.754 (9.31), 11.238 (2.39).

Example 159

Ent-3-Fluoro-N-{[4-(1-Methyl-1H-Imidazol-2-Yl)-2,5-Dioxoimidazolidin-4-Yl]Methyl}-4'-(Trifluoromethyl)[Biphenyl]-2-Carboxamide

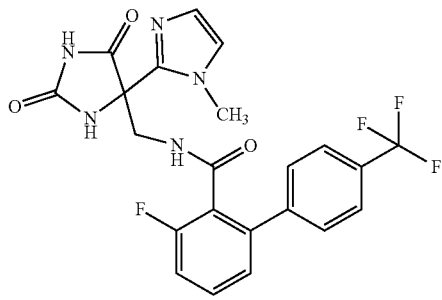 [SMILES: Cn1ccnc1C1(CNC(=O)c2c(F)cccc2-c2ccc(C(F)(F)F)cc2)NC(=O)NC1=O]

To a solution of ent-5-(aminomethyl)-5-(1-methyl-1H-imidazol-2-yl)imidazolidine-2,4-dione hydrochloride (100 mg, 407 µmol) and 3-fluoro-4'-(trifluoromethyl)[1,1'-biphenyl]-2-carboxylic acid (116 mg, 407 µmol) in DMF (2.3 ml) was added 1-ethyl-3-(3-dimethylaminopropyl)carbodiimide hydrochloride (101 mg, 529 µmol), 1-hydroxybenzotriazole hydrate (81.0 mg, 529 µmol) and N,N-diisopropylethylamine (350 µl, 2.0 mmol). The reaction mixture was stirred overnight at room temperature and concentrated under reduced pressure.

The crude product was purified by preparative HPLC (Method 3f). After lyophilization, 65.5 mg (99% purity, 34% yield) of the desired product were obtained.

LC-MS (Method 7): $R_t$=1.37 min; MS (ESIpos): m/z=476 [M+H]$^+$ $^1$H-NMR (400 MHz, DMSO-d6) δ [ppm]: −0.008 (0.41), 0.008 (0.47), 3.315 (16.00), 3.966 (1.02), 3.981 (1.08), 4.001 (1.53), 4.017 (1.42), 4.119 (1.51), 4.135 (1.65), 4.154 (1.14), 4.170 (1.02), 6.836 (5.12), 6.839 (5.39), 7.200 (5.19), 7.274 (2.69), 7.293 (3.05), 7.310 (1.27), 7.331 (2.49), 7.353 (1.47), 7.527 (1.04), 7.542 (1.19), 7.547 (1.65), 7.562 (1.59), 7.567 (0.97), 7.582 (0.82), 7.618 (3.89), 7.639 (4.58), 7.800 (4.85), 7.820 (3.92), 8.328 (3.76), 8.885 (1.03), 8.901 (2.12), 8.917 (1.00), 11.168 (2.74).

Example 160

Ent-4'-Chloro-4-Fluoro-N-{[4-(1-Methyl-1H-Imidazol-2-Yl)-2,5-Dioxoimidazolidin-4-Yl]Methyl}[Biphenyl]-2-Carboxamide

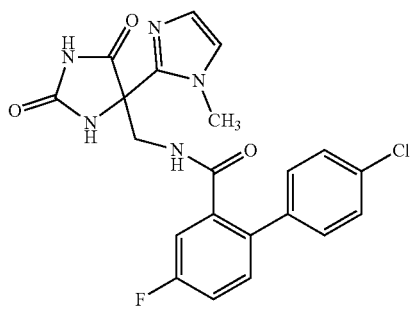 [SMILES: Cn1ccnc1C1(CNC(=O)c2cc(F)ccc2-c2ccc(Cl)cc2)NC(=O)NC1=O]

To a solution of ent-5-(aminomethyl)-5-(1-methyl-1H-imidazol-2-yl)imidazolidine-2,4-dione hydrochloride (100 mg, 407 µmol) and 4'-chloro-4-fluoro[1,1'-biphenyl]-2-carboxylic acid (102 mg, 407 µmol) in DMF (2.3 ml) was added 1-ethyl-3-(3-dimethylaminopropyl)carbodiimide hydrochloride (101 mg, 529 µmol), 1-hydroxybenzotriazole hydrate (81.0 mg, 529 µmol) and N,N-diisopropylethylamine (350 µl, 2.0 mmol). The reaction mixture was stirred overnight at room temperature and concentrated under reduced pressure. The crude product was purified by preparative HPLC (Method 3f). After lyophilization, 65.5 mg (97% purity, 35% yield) of the desired product were obtained.

LC-MS (Method 7): $R_t$=1.36 min; MS (ESIpos): m/z=442 [M+H]$^+$ $^1$H-NMR (400 MHz, DMSO-d6) δ [ppm]: −0.008 (1.31), 0.008 (1.50), 2.523 (0.75), 3.517 (16.00), 3.971 (0.76), 3.986 (0.85), 4.006 (1.38), 4.021 (1.23), 4.084 (1.26), 4.100 (1.33), 4.118 (0.81), 4.135 (0.77), 6.853 (3.89), 6.855 (4.19), 7.179 (1.41), 7.186 (1.68), 7.202 (1.49), 7.208 (1.74), 7.216 (3.98), 7.219 (4.14), 7.351 (4.48), 7.356 (2.08), 7.373 (7.25), 7.378 (2.42), 7.392 (1.11), 7.399 (1.08), 7.429 (1.80), 7.443 (1.95), 7.451 (1.99), 7.457 (6.08), 7.463 (2.30), 7.474 (1.48), 7.479 (4.02), 8.362 (3.78), 8.643 (0.78), 8.659 (1.62), 8.675 (0.78), 11.249 (0.80).

Example 161

Ent-5-Chloro-N-{[4-(1-Methyl-1H-Imidazol-2-Yl)-2,5-Dioxoimidazolidin-4-Yl]Methyl}-4'-(Trifluoromethyl)[Biphenyl]-2-Carboxamide

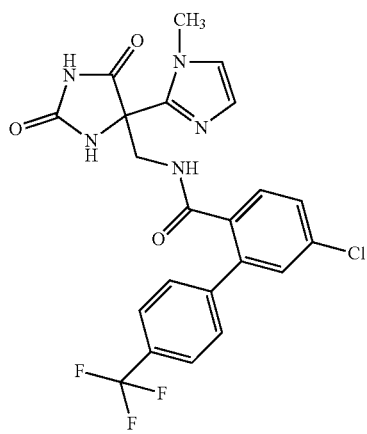 [SMILES: Cn1ccnc1C1(CNC(=O)c2ccc(Cl)cc2-c2ccc(C(F)(F)F)cc2)NC(=O)NC1=O]

To a solution of ent-5-(aminomethyl)-5-(1-methyl-1H-imidazol-2-yl)imidazolidine-2,4-dione hydrochloride (100 mg, 407 µmol) and 5-chloro-4'-(trifluoromethyl)[1,1'-biphenyl]-2-carboxylic acid (122 mg, 407 µmol) in DMF (7.5 ml) was added 1-ethyl-3-(3-dimethylaminopropyl)carbodiimide hydrochloride (101 mg, 529 µmol), 1-hydroxybenzotriazole hydrate (81.0 mg, 529 µmol) and N,N-diisopropylethylamine (200 µl, 1.1 mmol). The reaction mixture was stirred overnight at room temperature and concentrated under reduced pressure.

The crude product was purified by preparative HPLC (Method 3F). After lyophilization, 112 mg (97% purity, 54% yield) of the desired product were obtained.

LC-MS (Method 7): $R_t$=1.61 min, MS (ESIpos): m/z=492 [M+H]$^+$ $^1$H-NMR (600 MHz, DMSO-d6) δ [ppm]: 2.570 (0.40), 3.327 (0.67), 3.516 (16.00), 3.989 (0.87), 3.999 (0.99), 4.012 (1.42), 4.023 (1.30), 4.090 (1.30), 4.101 (1.41), 4.113 (0.97), 4.124 (0.92), 6.848 (4.12), 7.207 (4.15), 7.454 (2.70), 7.468 (3.40), 7.524 (3.01), 7.528 (3.52), 7.564 (2.06), 7.567 (1.77), 7.578 (1.61), 7.581 (1.46), 7.598 (3.21), 7.611 (3.67), 7.778 (3.74), 7.791 (3.30), 8.344 (3.91), 8.634 (0.86), 8.644 (1.79), 8.655 (0.92), 11.221 (0.93).

Example 162

Ent-4',5-Dichloro-N-{[4-(1-Methyl-1H-Imidazol-2-Yl)-2,5-Dioxoimidazolidin-4-Yl]Methyl}[Biphenyl]-2-Carboxamide

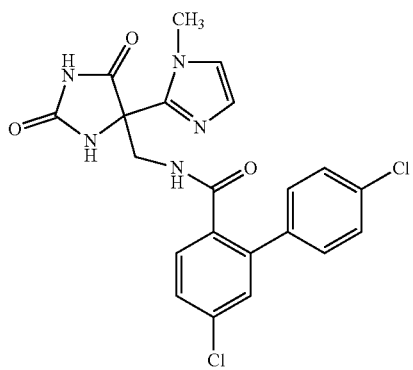 [SMILES: Cn1ccnc1C1(CNC(=O)c2ccc(Cl)cc2-c2ccc(Cl)cc2)NC(=O)NC1=O]

To a solution of ent-5-(aminomethyl)-5-(1-methyl-1H-imidazol-2-yl)imidazolidine-2,4-dione hydrochloride (100 mg, 407 µmol) and 4',5-dichloro[1,1'-biphenyl]-2-carboxylic acid (109 mg, 407 µmol) in DMF (2.3 ml) was added 1-ethyl-3-(3-dimethylaminopropyl)carbodiimide hydrochloride (101 mg, 529 µmol), 1-hydroxybenzotriazole hydrate (81.0 mg, 529 µmol) and N,N-diisopropylethylamine (350 µl, 2.0 mmol). The reaction mixture was stirred overnight at room temperature and concentrated under reduced pressure. The crude product was purified by preparative HPLC (Method 3f). After lyophilization, 132 mg (95% purity, 67% yield) of the desired product were obtained.

LC-MS (Method 7): $R_t$=1.52 min, MS (ESIpos): m/z=458 [M+H]$^+$ $^1$H-NMR (400 MHz, DMSO-d6) δ [ppm]: −0.008 (0.81), 0.008 (0.85), 2.523 (0.46), 3.469 (0.71), 3.512 (16.00), 3.963 (0.73), 3.979 (0.83), 3.998 (1.38), 4.013 (1.23), 4.070 (1.24), 4.086 (1.33), 4.104 (0.81), 4.121 (0.75), 6.847 (4.20), 6.850 (4.29), 7.211 (4.08), 7.214 (4.11), 7.395 (6.42), 7.399 (1.78), 7.411 (2.22), 7.416 (10.08), 7.422 (1.18), 7.467 (3.89), 7.474 (7.77), 7.479 (1.96), 7.486 (0.62), 7.491 (1.53), 7.496 (3.77), 7.502 (0.61), 7.512 (2.69), 7.518 (2.13), 7.533 (2.03), 7.538 (1.59), 8.161 (0.61), 8.346 (4.10), 8.567 (0.79), 8.583 (1.64), 8.599 (0.78).

Example 163

Ent-6-Fluoro-N-{[4-(1-Methyl-1H-Imidazol-2-Yl)-2,5-Dioxoimidazolidin-4-Yl]Methyl}-4'-(Trifluoromethyl)[Biphenyl]-2-Carboxamide

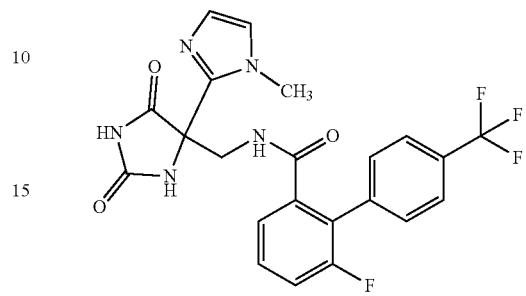

To a solution of ent-5-(aminomethyl)-5-(1-methyl-1H-imidazol-2-yl)imidazolidine-2,4-dione hydrochloride (100 mg, 407 µmol) and 6-fluoro-4'-(trifluoromethyl)[1,1'-biphenyl]-2-carboxylic acid (249 mg, 46% purity, 407 µmol) in DMF (3 ml) was added 1-ethyl-3-(3-dimethylaminopropyl)carbodiimide hydrochloride (101 mg, 529 µmol), 1-hydroxybenzotriazole hydrate (81.0 mg, 529 µmol) and N,N-diisopropylethylamine (350 µl, 2.0 mmol). The reaction mixture was stirred overnight at room temperature and concentrated under reduced pressure. The crude product was purified by preparative HPLC (Method 9f). After lyophilization, 81.8 mg (98% purity, 41% yield) of the desired product were obtained.

LC-MS (Method 7): $R_t$=1.43 min, MS (ESIpos): m/z=476 [M+H]$^+$ $^1$H-NMR (600 MHz, DMSO-d6) δ [ppm]: 0.005 (0.57), 1.169 (2.18), 1.182 (4.48), 1.194 (2.20), 2.385 (0.48), 2.424 (0.57), 2.467 (0.43), 2.519 (0.73), 2.522 (0.76), 3.089 (1.18), 3.097 (1.20), 3.101 (1.18), 3.109 (1.13), 3.813 (0.47), 3.911 (0.49), 3.973 (1.12), 3.984 (1.46), 3.997 (11.29), 4.010 (11.14), 4.022 (1.30), 4.033 (1.15), 4.356 (1.12), 7.187 (5.50), 7.277 (8.22), 7.279 (8.46), 7.290 (9.02), 7.291 (8.95), 7.432 (8.97), 7.440 (4.52), 7.456 (6.73), 7.471 (4.61), 7.519 (12.08), 7.533 (16.00), 7.543 (4.25), 7.547 (5.24), 7.556 (4.93), 7.560 (2.97), 7.569 (2.54), 7.778 (15.60), 7.792 (13.97), 8.408 (10.69), 8.729 (2.96), 8.740 (5.85), 8.750 (2.92), 11.415 (7.33).

Example 164

Rac-N-{[2,5-Dioxo-4-(Pyridin-2-Yl)Imidazolidin-4-Yl]Methyl}-4'-Methyl[Biphenyl]-2-Carboxamide

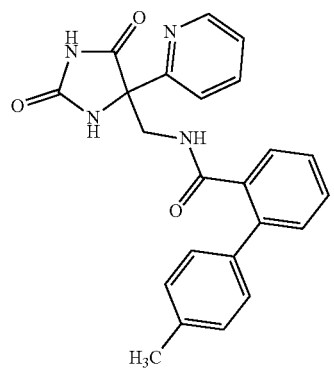 [SMILES: Cc1ccc(-c2ccccc2C(=O)NCC2(c3ccccn3)NC(=O)NC2=O)cc1]

To a solution of rac-5-(aminomethyl)-5-(pyridin-2-yl)imidazolidine-2,4-dione hydrochloride (100 mg, 412 μmol) and 4'-methyl[1,1'-biphenyl]-2-carboxylic acid (76.0 mg, 358 μmol) in DMF (7.4 ml) was added 1-ethyl-3-(3-dimethylaminopropyl)carbodiimide hydrochloride (89.3 mg, 466 μmol), 1-hydroxybenzotriazole hydrate (71.4 mg, 466 μmol) and N,N-diisopropylethylamine (500 μl, 2.9 mmol). After overnight stirring at room temperature, the reaction mixture was additionally stirred for 3 h at 50° C., then diluted with ethyl acetate and extracted with water. After phase separation, the water phase was concentrated under reduced pressure and the crude product was purified by preparative HPLC (Method 3f). After lyophilization, 3.30 mg (100% purity, 2% yield) of the desired product were obtained.

LC-MS (Method 7): $R_t$=1.47 min, MS (ESIpos): m/z=401 [M+H]$^+$ $^1$H-NMR (600 MHz, DMSO-d6) δ [ppm]: 2.324 (16.00), 2.423 (0.45), 3.280 (0.65), 3.292 (0.71), 3.317 (2.07), 3.326 (3.82), 3.383 (0.39), 3.392 (0.71), 3.888 (1.17), 3.898 (1.30), 3.911 (1.75), 3.921 (1.55), 4.002 (1.68), 4.011 (1.75), 4.025 (1.23), 4.034 (1.17), 7.174 (3.43), 7.187 (5.77), 7.222 (7.13), 7.235 (3.82), 7.280 (2.01), 7.293 (2.72), 7.344 (2.59), 7.350 (1.81), 7.356 (3.24), 7.362 (3.04), 7.375 (1.43), 7.385 (1.49), 7.393 (1.62), 7.398 (1.62), 7.406 (1.55), 7.459 (1.62), 7.461 (1.49), 7.472 (2.40), 7.474 (2.20), 7.484 (1.10), 7.486 (1.10), 7.494 (2.79), 7.507 (2.79), 7.838 (1.30), 7.841 (1.30), 7.851 (2.14), 7.854 (2.07), 7.864 (1.10), 7.867 (1.04), 8.190 (4.21), 8.345 (1.17), 8.355 (2.20), 8.365 (1.10), 8.588 (1.94), 8.594 (1.88), 10.902 (2.46).

Example 165

Rac-4-Fluoro-N-{[4-(5-Methyl-1,3-Thiazol-4-Yl)-2,5-Dioxoimidazolidin-4-Yl]Methyl}-4'-(Trifluoromethyl)[Biphenyl]-2-Carboxamide

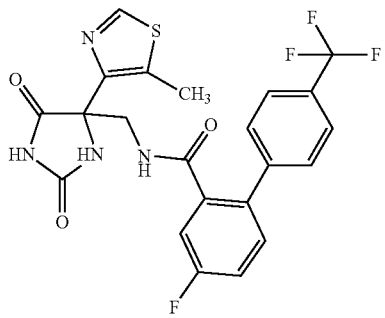 [SMILES: Cc1scnc1C1(CNC(=O)c2cc(F)ccc2-c2ccc(C(F)(F)F)cc2)NC(=O)NC1=O]

To a solution of rac-5-(aminomethyl)-5-(5-methyl-1,3-thiazol-4-yl)imidazolidine-2,4-dione hydrochloride (70.0 mg, 266 μmol) and 4-fluoro-4'-(trifluoromethyl)[1,1'-biphenyl]-2-carboxylic acid (75.7 mg, 266 μmol) in DMF (1.7 ml) was added 1-ethyl-3-(3-dimethylaminopropyl)carbodiimide hydrochloride (66.4 mg, 346 μmol), 1-hydroxybenzotriazole hydrate (53.0 mg, 346 μmol) and N,N-diisopropylethylamine (230 μl, 1.3 mmol). The reaction mixture was stirred overnight at room temperature, diluted with ethyl acetate and washed with water. After phase separation, the combined organic phases were dried and concentrated under reduced pressure. The crude product was purified by preparative HPLC (Method 6f). After lyophilization, 41.0 mg (98% purity, 31% yield) of the desired product were obtained.

LC-MS (Method 7): $R_t$=1.68 min; MS (ESIpos): m/z=493 [M+H]$^+$ $^1$H-NMR (600 MHz, DMSO-d6) δ [ppm]: 2.157 (0.51), 2.365 (16.00), 3.306 (0.47), 4.080 (2.06), 4.087 (2.49), 4.097 (2.18), 7.227 (1.35), 7.232 (1.50), 7.242 (1.39), 7.247 (1.41), 7.398 (0.67), 7.402 (0.66), 7.412 (1.47), 7.417 (1.46), 7.426 (0.88), 7.431 (0.83), 7.492 (1.47), 7.501 (1.61), 7.506 (1.26), 7.515 (1.09), 7.554 (3.52), 7.568 (3.98), 7.766 (4.11), 7.779 (3.57), 8.328 (3.90), 8.772 (0.95), 8.782 (1.93), 8.792 (0.94), 8.851 (5.65), 11.074 (0.78).

Example 166

Ent-4-Fluoro-N-{[4-(5-Methyl-1,3-Thiazol-4-Yl)-2,5-Dioxoimidazolidin-4-Yl]Methyl}-4'-(Trifluoromethyl)[Biphenyl]-2-Carboxamide

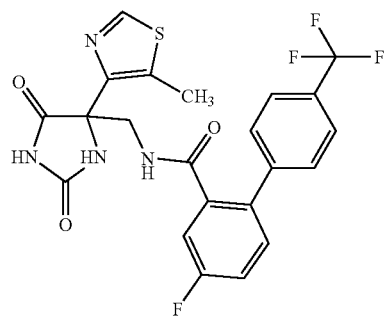 [SMILES: Cc1scnc1C1(CNC(=O)c2cc(F)ccc2-c2ccc(C(F)(F)F)cc2)NC(=O)NC1=O]

Enantiomeric separation of rac-4-fluoro-N-{[4-(5-methyl-1,3-thiazol-4-yl)-2,5-dioxoimidazolidin-4-yl]methyl}-4'-(trifluoromethyl)[biphenyl]-2-carboxamide (40 mg) by preparative chiral HPLC [column: Daicel Chiralpak AZ-H 5 μm, 250×20 mm; eluent: 50% n-heptane/50% ethanol; flow rate: 20 ml/min; temperature: 40° C.; UV detection: 220 nm] afforded 5.93 mg (98% purity) of the desired product.

Analytical chiral HPLC: $R_t$=2.43 min, e.e. =99% [column: Daicel AZ-3 3 μm, 50×4.6 mm; eluent: 50% n-heptane/50% ethanol; flow rate: 1 ml/min; UV detection: 220 nm]

LC-MS (Method 7): $R_t$=1.66 min; MS (ESIpos): m/z=493 [M+H]$^+$ $^1$H-NMR (400 MHz, DMSO-d6) δ [ppm]: −0.008 (2.71), 0.845 (0.53), 0.862 (0.57), 1.236 (1.74), 1.259 (0.89), 1.282 (0.59), 1.298 (0.60), 2.365 (16.00), 4.079 (2.64), 4.095 (2.86), 7.221 (1.31), 7.228 (1.56), 7.244 (1.36), 7.251 (1.51), 7.388 (0.59), 7.394 (0.63), 7.409 (1.44), 7.415 (1.49), 7.430 (0.94), 7.437 (0.94), 7.485 (1.56), 7.499 (1.68), 7.506 (1.23), 7.520 (1.06), 7.550 (3.04), 7.570 (3.59), 7.761 (3.68), 7.781 (3.11), 8.319 (4.00), 8.756 (0.81), 8.772 (1.75), 8.787 (0.85), 8.851 (4.97).

Example 167

Rac-5-Methyl-N-{[4-(5-Methyl-1,3-Thiazol-4-Yl)-2,5-Dioxoimidazolidin-4-Yl]Methyl}-4'-(Trifluoromethyl)[Biphenyl]-2-Carboxamide

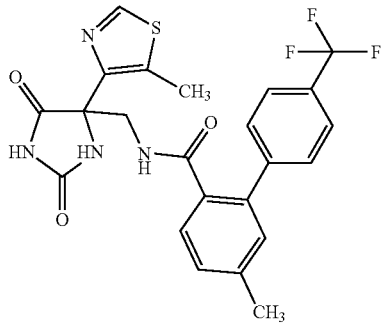 [SMILES: Cc1ccc(C(=O)NCC2(c3ncsc3C)NC(=O)NC2=O)c(-c2ccc(C(F)(F)F)cc2)c1]

To a solution of rac-5-(aminomethyl)-5-(5-methyl-1,3-thiazol-4-yl)imidazolidine-2,4-dione hydrochloride (70.0 mg, 266 µmol) and 5-methyl-4'-(trifluoromethyl)[1,1'-biphenyl]-2-carboxylic acid (74.7 mg, 266 µmol) in DMF (1.7 ml) was added 1-ethyl-3-(3-dimethylaminopropyl)carbodiimide hydrochloride (66.4 mg, 346 µmol), 1-hydroxybenzotriazole hydrate (53.0 mg, 346 µmol) and N,N-diisopropylethylamine (230 µl, 1.3 mmol). The reaction mixture was stirred overnight at room temperature, then for 1 h at 50° C. The reactions mixture was concentrated under reduced pressure and the crude product was purified by preparative HPLC (Method 4f). After lyophilization, 66.1 mg (99% purity, 50% yield) of the desired product were obtained.

LC-MS (Method 7): $R_t$=1.86 min, MS (ESIpos): m/z=489 [M+H]$^+$ $^1$H-NMR (600 MHz, DMSO-d6) δ [ppm]: 2.360 (16.00), 2.378 (0.57), 2.388 (10.54), 4.066 (2.95), 4.076 (2.95), 7.257 (2.66), 7.266 (1.27), 7.279 (1.58), 7.343 (2.79), 7.355 (1.96), 7.549 (2.69), 7.562 (2.97), 7.750 (3.14), 7.763 (2.73), 8.245 (3.50), 8.499 (0.75), 8.509 (1.58), 8.520 (0.73), 8.843 (6.69), 11.035 (1.07).

Example 168

Ent-5-Methyl-N-{[4-(5-Methyl-1,3-Thiazol-4-Yl)-2,5-Dioxoimidazolidin-4-Yl]Methyl}-4'-(Trifluoromethyl)[Biphenyl]-2-Carboxamide

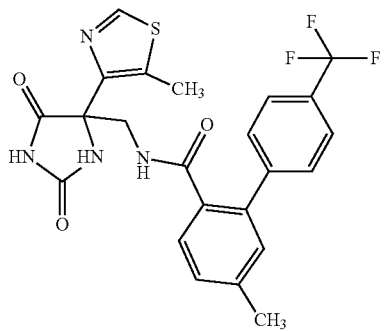 [SMILES: Cc1ccc(C(=O)NCC2(c3ncsc3C)NC(=O)NC2=O)c(-c2ccc(C(F)(F)F)cc2)c1]

Enantiomeric separation of rac-5-methyl-N-{[4-(5-methyl-1,3-thiazol-4-yl)-2,5-dioxoimidazolidin-4-yl]methyl}-4'-(trifluoromethyl)[biphenyl]-2-carboxamide (63 mg) by preparative chiral HPLC [column: Daicel Chiralpak ID 5 µm, 250×20 mm; eluent: 50% n-heptane/50% ethanol; flow rate: 15 ml/min; temperature: 30° C.; UV detection: 220 nm] afforded 25 mg (98% purity) of the desired product.

Analytical chiral HPLC: $R_t$=6.66 min, e.e. =97.9% [column: Daicel chiralcel ID 5 µm, 250×4.6 mm; eluent: 50% n-heptane/50% ethanol; flow rate: 1 ml/min; temperature: 40° C.; UV detection: 220 nm]

LC-MS (Method 7): $R_t$=1.74 min; MS (ESIpos): m/z=489 [M+H]$^+$ $^1$H-NMR (400 MHz, DMSO-d6) δ [ppm]: −0.149 (0.80), −0.022 (0.45), −0.020 (0.57), −0.017 (0.68), −0.015 (0.98), −0.012 (1.44), −0.008 (7.02), −0.006 (4.88), 0.006 (4.98), 0.008 (7.08), 0.012 (1.56), 0.015 (1.09), 0.017 (0.84), 0.020 (0.64), 0.022 (0.49), 0.025 (0.41), 0.146 (0.80), 2.322 (0.49), 2.327 (0.70), 2.332 (0.57), 2.359 (16.00), 2.388 (9.95), 2.518 (3.43), 2.523 (2.58), 2.526 (1.95), 2.557 (0.82), 2.560 (0.64), 2.562 (0.53), 2.565 (0.43), 2.665 (0.49), 2.669 (0.66), 2.674 (0.49), 2.709 (0.59), 4.061 (2.71), 4.077 (2.71), 7.256 (2.97), 7.281 (1.72), 7.339 (2.85), 7.358 (1.74), 7.544 (2.56), 7.564 (3.00), 7.745 (3.12), 7.765 (2.58), 8.236 (3.55), 8.482 (0.68), 8.498 (1.50), 8.513 (0.68), 8.842 (5.78).

Example 169

Rac-4'-Chloro-5-Fluoro-N-{[4-(5-Methyl-1,3-Thiazol-4-Yl)-2,5-Dioxoimidazolidin-4-Yl]Methyl}[Biphenyl]-2-Carboxamide

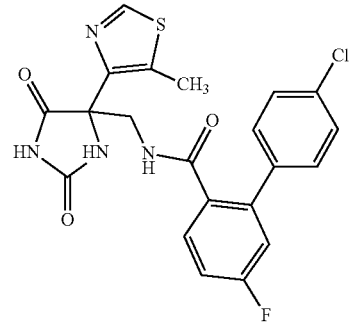 [SMILES: Cc1scnc1C1(CNC(=O)c2ccc(F)cc2-c2ccc(Cl)cc2)NC(=O)NC1=O]

To a solution of rac-5-(aminomethyl)-5-(5-methyl-1,3-thiazol-4-yl)imidazolidine-2,4-dione hydrochloride (120 mg, 457 µmol) and 4'-chloro-5-fluoro[1,1'-biphenyl]-2-carboxylic acid (114 mg, 457 µmol) in DMF (2.8 ml) was added 1-ethyl-3-(3-dimethylaminopropyl)carbodiimide hydrochloride (114 mg, 594 µmol), 1-hydroxybenzotriazole hydrate (90.9 mg, 594 µmol) and N,N-diisopropylethylamine (400 µl, 2.3 mmol). The reaction mixture was stirred overnight at room temperature, diluted with ethyl acetate and extracted with water. After phase separation, the combined organic phases were dried and concentrated under reduced pressure. The crude product was purified by preparative HPLC (Method 6f). After lyophilization, 92.0 mg (98% purity, 43% yield) of the desired product were obtained.

LC-MS (Method 7): $R_t$=1.60 min; MS (ESIpos): m/z=459 [M+H]$^+$

¹H-NMR (600 MHz, DMSO-d6) δ [ppm]: 2.361 (2.52), 3.333 (16.00), 3.341 (7.04), 4.057 (0.43), 4.068 (0.46), 7.398 (0.58), 7.412 (0.91), 7.475 (0.84), 7.489 (0.57), 8.273 (0.57), 8.845 (1.00).

Example 170

Ent-4'-Chloro-5-Fluoro-N-{[4-(5-Methyl-1,3-Thiazol-4-Yl)-2,5-Dioxoimidazolidin-4-Yl]Methyl}[Biphenyl]-2-Carboxamide

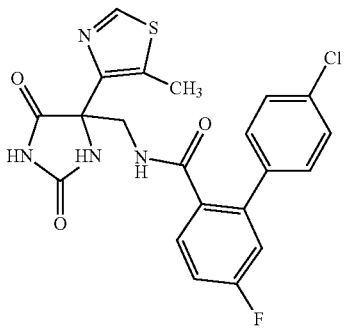 [SMILES: Cc1scnc1C1(CNC(=O)c2ccc(F)cc2-c2ccc(Cl)cc2)NC(=O)NC1=O]

Enantiomeric separation of rac-4'-chloro-5-fluoro-N-{[4-(5-methyl-1,3-thiazol-4-yl)-2,5-dioxoimidazolidin-4-yl]methyl}[biphenyl]-2-carboxamide (92 mg) by preparative chiral SFC [column: Maisch Daicel OJ-H 5 µm, 250×25 mm; eluent: carbon dioxide/methanol 75:25; flow rate: 80 ml/min; temperature: 40° C.; UV detection: 210 nm] afforded 17.9 mg (100% purity) of the desired product.

Analytical chiral SFC: $R_t$=0.907 min, e.e. =>99% [column: OJ 3 µm, 100×4.6 mm; eluent: carbon dioxide/methanol 80:20; flow rate: 3 ml/min; UV detection: 210 nm]

LC-MS (Method 7): $R_t$=1.60 min; MS (ESIpos): m/z=459 [M+H]⁺

¹H-NMR (600 MHz, DMSO-d6) δ [ppm]: 2.363 (16.00), 4.055 (3.74), 4.065 (3.78), 7.250 (1.22), 7.254 (1.66), 7.270 (2.11), 7.282 (1.66), 7.286 (1.24), 7.296 (0.89), 7.300 (0.71), 7.397 (3.74), 7.411 (5.42), 7.415 (2.18), 7.425 (1.56), 7.429 (1.37), 7.439 (1.17), 7.471 (5.33), 7.485 (3.59), 8.237 (3.86), 8.503 (0.95), 8.514 (1.87), 8.524 (0.91), 8.839 (5.53), 11.008 (1.08).

Example 171

Rac-4'-Chloro-N-{[4-(5-Methyl-1,3-Thiazol-4-Yl)-2,5-Dioxoimidazolidin-4-Yl]Methyl}[Biphenyl]-2-Carboxamide

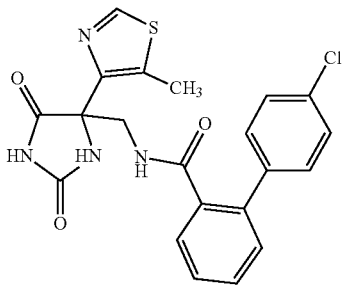 [SMILES: Cc1scnc1C1(CNC(=O)c2ccccc2-c2ccc(Cl)cc2)NC(=O)NC1=O]

To a solution of rac-5-(aminomethyl)-5-(5-methyl-1,3-thiazol-4-yl)imidazolidine-2,4-dione hydrochloride (120 mg, 457 µmol) and 4'-chloro[1,1'-biphenyl]-2-carboxylicacid (106 mg, 457 µmol) in DMF (2.8 ml) was added 1-ethyl-3-(3-dimethylaminopropyl)carbodiimide hydrochloride (114 mg, 594 µmol), 1-hydroxybenzotriazole hydrate (90.9 mg, 594 µmol) and N,N-diisopropylethylamine (400 µl, 2.3 mmol). The reaction mixture was stirred overnight at room temperature, diluted with ethyl acetate and extracted with water. After phase separation, the combined organic phases were dried and concentrated under reduced pressure. The crude product was purified by preparative HPLC (Method 6f). After lyophilization, 64.0 mg (99% purity, 31% yield) of the desired product were obtained.

LC-MS (Method 7): $R_t$=1.54 min; MS (ESIpos): m/z=441 [M+H]⁺

¹H-NMR (600 MHz, DMSO-d6) δ [ppm]: 2.363 (9.75), 2.501 (16.00), 3.300 (0.96), 4.056 (1.16), 4.064 (1.51), 4.074 (1.18), 7.377 (3.02), 7.390 (3.97), 7.400 (1.46), 7.412 (0.76), 7.425 (1.28), 7.437 (0.59), 7.460 (3.22), 7.474 (2.26), 7.502 (0.75), 7.514 (1.13), 7.526 (0.46), 8.250 (2.42), 8.508 (0.56), 8.519 (1.11), 8.529 (0.53), 8.846 (3.42), 11.032 (0.63).

Example 172

Ent-4'-Chloro-N-{[4-(5-Methyl-1,3-Thiazol-4-Yl)-2,5-Dioxoimidazolidin-4-Yl]Methyl}[Biphenyl]-2-Carboxamide

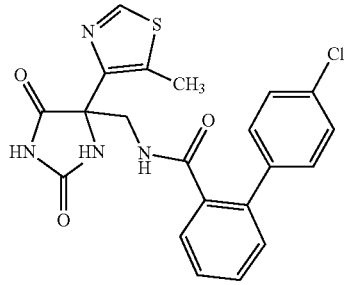 [SMILES: Cc1scnc1C1(CNC(=O)c2ccccc2-c2ccc(Cl)cc2)NC(=O)NC1=O]

Enantiomeric separation of rac-4'-chloro-N-{[4-(5-methyl-1,3-thiazol-4-yl)-2,5-dioxoimidazolidin-4-yl]methyl}[biphenyl]-2-carboxamide (64 mg) by preparative chiral SFC [column: Maisch Daicel OJ-H 5 µm, 250×25 mm; eluent: carbon dioxide/methanol 75:25; flow rate: 80 ml/min; temperature: 40° C.; UV detection: 210 nm] afforded 15.6 mg (100% purity) of the desired product.

Analytical chiral HPLC: $R_t$=0.95 min, e.e. =>99% [column: OJ 3 µm, 100×4.6 mm; eluent: carbon dioxide/methanol 80:20; flow rate: 3 ml/min; UV detection: 210 nm]

LC-MS (Method 7): $R_t$=1.54 min; MS (ESIpos): m/z=441 [M+H]⁺

¹H-NMR (600 MHz, DMSO-d6) δ [ppm]: 2.367 (16.00), 4.056 (2.04), 4.061 (2.12), 4.067 (2.14), 4.071 (2.14), 7.377 (4.86), 7.391 (7.56), 7.398 (2.56), 7.411 (1.26), 7.423 (1.95), 7.436 (0.88), 7.457 (5.17), 7.471 (3.62), 7.500 (1.15), 7.512 (1.76), 7.526 (0.73), 8.216 (3.53), 8.461 (0.85), 8.472 (1.72), 8.482 (0.83), 8.841 (5.66), 11.007 (2.04).

Example 173

Ent-N-{[4-(5-Methyl-1,3-Thiazol-4-Yl)-2,5-Dioxo-imidazolidin-4-Yl]Methyl}-2-[6-(Trifluoromethyl)Pyridin-3-Yl]Benzamide

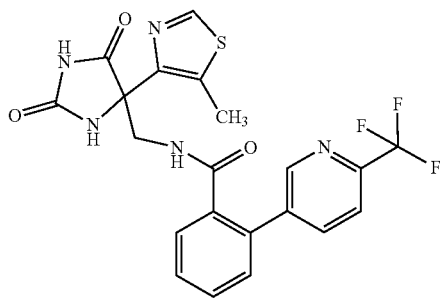 [SMILES: Cc1scnc1C1(CNC(=O)c2ccccc2-c2ccc(C(F)(F)F)nc2)NC(=O)NC1=O]

To a solution of ent-5-(aminomethyl)-5-(5-methyl-1,3-thiazol-4-yl)imidazolidine-2,4-dione hydrochloride (50.0 mg, 190 µmol) and 2-[6-(trifluoromethyl)pyridin-3-yl]benzoic acid (50.9 mg, 190 µmol) in DMF (1.1 ml) was added 1-ethyl-3-(3-dimethylaminopropyl)carbodiimide hydrochloride (47.4 mg, 247 µmol), 1-hydroxybenzotriazole hydrate (37.9 mg, 247 µmol) and N,N-diisopropylethylamine (170 µl, 950 µmol). The reaction mixture was stirred overnight at room temperature and then concentrated under reduced pressure. The crude product was purified by preparative HPLC (Method 3f). After lyophilization, 50.6 mg (100% purity, 56% yield) of the desired product were obtained.

LC-MS (Method 7): $R_t$=1.38 min, MS (ESIpos): m/z=476 [M+H]$^+$ $^1$H-NMR (400 MHz, DMSO-d6) δ [ppm]: −0.008 (0.92), 0.006 (0.67), 0.008 (1.01), 2.360 (16.00), 4.070 (2.69), 4.086 (2.70), 7.479 (0.99), 7.482 (0.81), 7.485 (0.58), 7.498 (2.17), 7.502 (1.40), 7.523 (2.06), 7.543 (4.08), 7.561 (1.06), 7.564 (0.64), 7.589 (1.42), 7.593 (1.39), 7.606 (0.77), 7.611 (1.64), 7.626 (0.53), 7.630 (0.49), 7.933 (1.31), 7.952 (2.70), 7.985 (1.52), 7.990 (1.47), 8.005 (0.71), 8.010 (0.72), 8.278 (3.08), 8.675 (0.66), 8.691 (1.45), 8.707 (0.66), 8.746 (1.92), 8.751 (1.89), 8.849 (5.53), 11.045 (1.80).

Example 174

Ent-4'-Chloro-4-Fluoro-N-{[4-(5-Methyl-1,3-Thiazol-4-Yl)-2,5-Dioxoimidazolidin-4-Yl]Methyl}[Biphenyl]-2-Carboxamide

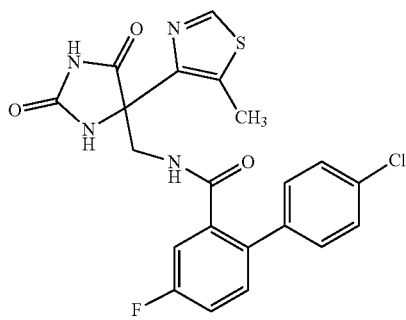 [SMILES: Cc1scnc1C1(CNC(=O)c2cc(F)ccc2-c2ccc(Cl)cc2)NC(=O)NC1=O]

To a solution of ent-5-(aminomethyl)-5-(5-methyl-1,3-thiazol-4-yl)imidazolidine-2,4-dione hydrochloride (50.0 mg, 190 µmol) and 4'-chloro-4-fluoro[1,1'-biphenyl]-2-carboxylic acid (47.7 mg, 190 µmol) in DMF (1.1 ml) was added 1-ethyl-3-(3-dimethylaminopropyl)carbodiimide hydrochloride (47.4 mg, 247 µmol), 1-hydroxybenzotriazole hydrate (37.9 mg, 247 µmol) and N,N-diisopropylethylamine (170 µl, 950 µmol). The reaction mixture was stirred overnight at room temperature and then concentrated under reduced pressure. The crude product was purified by preparative HPLC (Method 4f). After lyophilization, 39.5 mg (99% purity, 45% yield) of the desired product were obtained.

LC-MS (Method 7): $R_t$=1.60 min; MS (ESIpos): m/z=459 [M+H]$^+$ $^1$H-NMR (400 MHz, DMSO-d6) δ [ppm]: −0.008 (1.53), 0.008 (1.67), 2.363 (16.00), 2.523 (0.91), 4.061 (2.72), 4.076 (2.87), 7.162 (1.26), 7.169 (1.50), 7.185 (1.28), 7.191 (1.42), 7.344 (0.99), 7.351 (4.10), 7.355 (1.53), 7.366 (2.83), 7.372 (6.89), 7.387 (1.06), 7.394 (1.02), 7.425 (1.61), 7.439 (1.72), 7.447 (1.57), 7.454 (5.57), 7.459 (2.35), 7.471 (1.31), 7.476 (3.69), 8.298 (3.33), 8.658 (0.69), 8.673 (1.51), 8.689 (0.70), 8.850 (5.77), 11.059 (1.36).

Example 175

Ent-4'-(Methylsulfonyl)-N-{[4-(5-Methyl-1,3-Thiazol-4-Yl)-2,5-Dioxoimidazolidin-4-Yl]Methyl}[Biphenyl]-2-Carboxamide

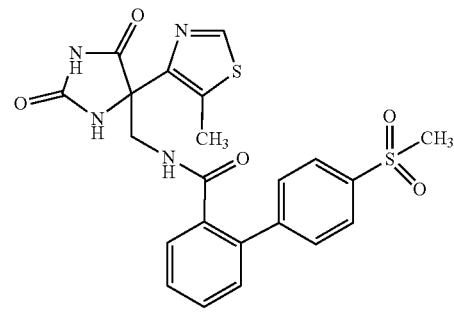 [SMILES: Cc1scnc1C1(CNC(=O)c2ccccc2-c2ccc(S(C)(=O)=O)cc2)NC(=O)NC1=O]

To a solution of ent-5-(aminomethyl)-5-(5-methyl-1,3-thiazol-4-yl)imidazolidine-2,4-dione hydrochloride (50.0 mg, 190 µmol) and 4'-(methanesulfonyl)[1,1'-biphenyl]-2-carboxylic acid (52.6 mg, 190 µmol) in DMF (1.1 ml) was added 1-ethyl-3-(3-dimethylaminopropyl)carbodiimide hydrochloride (47.4 mg, 247 µmol), 1-hydroxybenzotriazole hydrate (37.9 mg, 247 µmol) and N,N-diisopropylethylamine (170 µl, 950 µmol). The reaction mixture was stirred overnight at room temperature and then concentrated under reduced pressure. The crude product was purified by preparative HPLC (Method 3f). After lyophilization, 15.8 mg (100% purity, 17% yield) of the desired product were obtained.

LC-MS (Method 8): $R_t$=0.64 min; MS (ESIpos): m/z=485 [M+H]$^+$ $^1$H NMR (600 MHz, DMSO-d$_6$) δ ppm 10.85-11.20 (m, 1H), 8.84 (s, 1H), 8.60 (t, 1H), 8.23 (s, 1H), 7.96 (d, 2H), 7.38-7.72 (m, 6H), 4.09 (dd, 2H), 3.25 (s, 3H), 2.37 (s, 3H).

Example 176

Ent-5-Fluoro-N-{[4-(5-Methyl-1,3-Thiazol-4-Yl)-2, 5-Dioxoimidazolidin-4-Yl]Methyl}-4'-(Trifluoromethyl)[Biphenyl]-2-Carboxamide

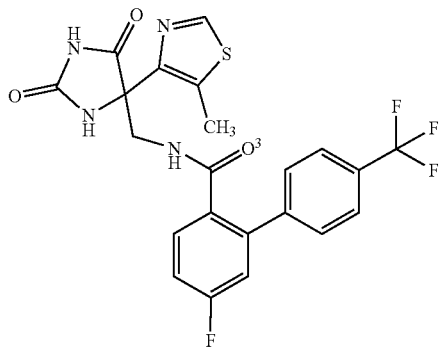

To a solution of ent-5-(aminomethyl)-5-(5-methyl-1,3-thiazol-4-yl)imidazolidine-2,4-dione hydrochloride (50.0 mg, 190 µmol) and 5-fluoro-4'-(trifluoromethyl)[1,1'-biphenyl]-2-carboxylic acid (54.1 mg, 190 µmol) in DMF (1.1 ml) was added 1-ethyl-3-(3-dimethylaminopropyl)carbodiimide hydrochloride (47.4 mg, 247 µmol), 1-hydroxybenzotriazole hydrate (37.9 mg, 247 µmol) and N,N-diisopropylethylamine (170 µl, 950 µmol). The reaction mixture was stirred overnight at room temperature and then concentrated under reduced pressure. The crude product was purified by preparative HPLC (Method 4f). After lyophilization, 50.6 mg (100% purity, 54% yield) of the desired product were obtained.

LC-MS (Method 7): $R_t$=1.69 min, MS (ESIpos): m/z=493 [M+H]$^+$ $^1$H-NMR (400 MHz, DMSO-d6) δ [ppm]: -0.008 (1.38), 0.008 (1.54), 2.361 (16.00), 4.069 (2.60), 4.085 (2.72), 7.319 (2.78), 7.324 (1.29), 7.338 (1.28), 7.343 (2.68), 7.349 (1.33), 7.359 (1.07), 7.365 (0.58), 7.461 (0.90), 7.466 (0.57), 7.476 (1.20), 7.484 (1.07), 7.499 (0.84), 7.589 (2.60), 7.610 (3.05), 7.776 (3.21), 7.797 (2.64), 8.285 (3.42), 8.640 (0.68), 8.655 (1.46), 8.671 (0.67), 8.845 (6.61), 11.043 (0.99).

Example 177

Rac-4-Fluoro-N-{[4-(1-Methyl-1H-Pyrazol-5-Yl)-2, 5-Dioxoimidazolidin-4-Yl]Methyl}-4'-(Trifluoromethyl)[Biphenyl]-2-Carboxamide

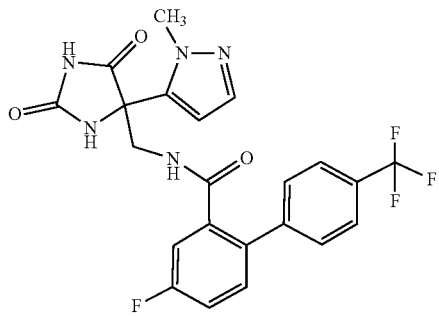 [SMILES: Cn1nccc1C1(CNC(=O)c2cc(F)ccc2-c2ccc(C(F)(F)F)cc2)NC(=O)NC1=O]

To a solution of rac-5-(aminomethyl)-5-(1-methyl-1H-pyrazol-5-yl)imidazolidine-2,4-dione hydrochloride (100 mg, 407 µmol) and 4-fluoro-4'-(trifluoromethyl)[1,1'-biphenyl]-2-carboxylic acid (139 mg, 488 µmol) in DMF (2.5 ml) was added 1-ethyl-3-(3-dimethylaminopropyl)carbodiimide hydrochloride (101 mg, 529 µmol), 1-hydroxybenzotriazole hydrate (81.0 mg, 529 µmol) and N,N-diisopropylethylamine (350 µl, 2.0 mmol). The reaction mixture was stirred overnight at room temperature and then concentrated under reduced pressure. The crude product was purified by preparative HPLC (Method 6f). After lyophilization, 66.0 mg (99% purity, 34% yield) of the desired product were obtained.

LC-MS (Method 7): $R_t$=1.56 min; MS (ESIpos): m/z=476 [M+H]$^+$ $^1$H-NMR (600 MHz, DMSO-d6) δ [ppm]: 3.302 (0.79), 3.369 (0.49), 3.373 (0.52), 3.790 (16.00), 3.864 (0.79), 3.873 (0.87), 3.886 (1.32), 3.896 (1.21), 3.947 (1.22), 3.959 (1.31), 3.970 (0.87), 3.981 (0.80), 6.483 (3.36), 6.486 (3.39), 7.236 (1.28), 7.240 (1.45), 7.251 (1.35), 7.255 (1.41), 7.389 (3.41), 7.392 (3.38), 7.413 (0.64), 7.418 (0.66), 7.428 (1.40), 7.432 (1.44), 7.442 (0.92), 7.446 (0.90), 7.489 (1.48), 7.499 (1.64), 7.508 (3.37), 7.521 (3.52), 7.752 (3.49), 7.766 (3.24), 8.463 (3.55), 8.908 (0.82), 8.919 (1.59), 8.929 (0.89), 11.294 (0.41).

Example 178

Ent-4-Fluoro-N-{[4-(1-Methyl-1H-Pyrazol-5-Yl)-2, 5-Dioxoimidazolidin-4-Yl]Methyl}-4'-(Trifluoromethyl)[Biphenyl]-2-Carboxamide

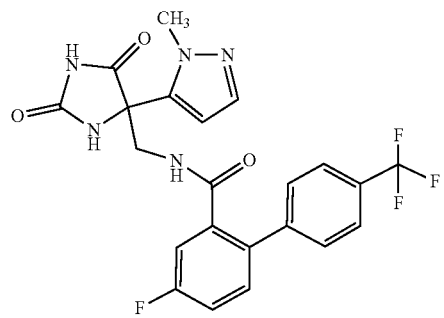 [SMILES: Cn1nccc1C1(CNC(=O)c2cc(F)ccc2-c2ccc(C(F)(F)F)cc2)NC(=O)NC1=O]

Enantiomeric separation of rac-4-fluoro-N-{[4-(1-methyl-1H-pyrazol-5-yl)-2,5-dioxoimidazolidin-4-yl]methyl}-4'-(trifluoromethyl)[biphenyl]-2-carboxamide (66 mg) by preparative chiral SFC [column: Daicel Chiralpak ID 5 µm, 250×20 mm; eluent: 82% carbon dioxide/18% methanol; flow rate: 80 ml/min; temperature: 40° C.; UV detection: 210 nm] afforded 14.8 mg (99% purity) of the desired product.

Analytical chiral SFC: $R_t$=1.68 min, e.e. =98.1% [column: OJ 3 µm, 100×4.6 mm; eluent: carbon dioxide/isopropanol 80:20; flow rate: 3 ml/min; UV detection: 210 nm]

LC-MS (Method 7): $R_t$=1.57 min; MS (ESIpos): m/z=476 [M+H]$^+$ $^1$H-NMR (600 MHz, DMSO-d6) δ [ppm]: 1.035 (1.88), 1.045 (1.89), 3.794 (16.00), 3.861 (0.96), 3.870 (1.03), 3.883 (1.59), 3.893 (1.47), 3.945 (1.49), 3.956 (1.53), 3.967 (0.98), 3.979 (0.91), 6.477 (3.88), 7.239 (1.71), 7.250 (1.59), 7.254 (1.61), 7.386 (3.80), 7.412 (0.79), 7.422 (1.64), 7.426 (1.66), 7.436 (1.05), 7.486 (1.70), 7.495 (1.97), 7.508 (4.98), 7.521 (4.43), 7.748 (4.46), 7.762 (4.02), 8.431 (4.21), 8.871 (1.13), 8.881 (2.04), 8.892 (1.09), 11.272 (2.21).

Example 179

Rac-4'-Chloro-5-Fluoro-N-{[4-(1-Methyl-1H-Pyrazol-5-Yl)-2,5-Dioxoimidazolidin-4-Yl]Methyl}[Biphenyl]-2-Carboxamide

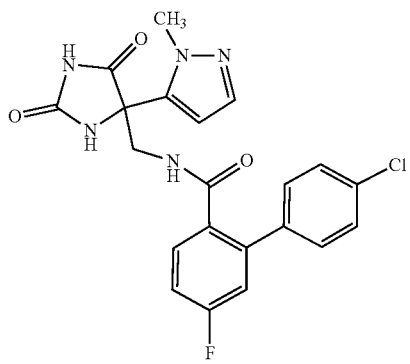 [SMILES: Cn1nccc1C1(CNC(=O)c2ccc(F)cc2-c2ccc(Cl)cc2)NC(=O)NC1=O]

To a solution of rac-5-(aminomethyl)-5-(1-methyl-1H-pyrazol-5-yl)imidazolidine-2,4-dione hydrochloride (100 mg, 407 μmol) and 4'-chloro-5-fluoro[1,1'-biphenyl]-2-carboxylic acid (122 mg, 488 μmol) in DMF (2.5 ml) was added 1-ethyl-3-(3-dimethylaminopropyl)carbodiimide hydrochloride (101 mg, 529 μmol), 1-hydroxybenzotriazole hydrate (81.0 mg, 529 μmol) and N,N-diisopropylethylamine (350 μl, 2.0 mmol). The reaction mixture was stirred overnight at room temperature and then concentrated under reduced pressure. The crude product was purified by preparative HPLC (Method 7f). After lyophilization, 75.0 mg (100% purity, 42% yield) of the desired product were obtained.

LC-MS (Method 7): $R_t$=1.47 min, MS (ESIpos): m/z=442 [M+H]$^+$ $^1$H-NMR (400 MHz, DMSO-d6) δ [ppm]: 0.998 (2.46), 1.014 (2.59), 1.026 (0.44), 2.523 (0.61), 2.526 (0.50), 3.790 (16.00), 3.818 (0.70), 3.833 (0.73), 3.852 (1.15), 3.866 (1.02), 3.924 (1.05), 3.941 (1.13), 3.958 (0.70), 3.976 (0.64), 6.458 (3.59), 6.463 (3.63), 7.252 (1.09), 7.258 (1.65), 7.277 (1.21), 7.283 (1.81), 7.301 (1.61), 7.308 (1.27), 7.322 (0.93), 7.329 (0.83), 7.336 (0.48), 7.342 (3.79), 7.347 (1.37), 7.359 (1.61), 7.364 (5.54), 7.370 (0.82), 7.382 (3.58), 7.387 (3.51), 7.408 (1.44), 7.423 (1.50), 7.429 (1.21), 7.444 (1.12), 7.451 (0.77), 7.458 (5.43), 7.462 (1.52), 7.474 (1.30), 7.479 (3.69), 7.485 (0.43), 8.353 (1.22), 8.693 (0.66), 8.709 (1.26), 8.725 (0.66).

Example 180

Ent-4'-Chloro-5-Fluoro-N-{[4-(1-Methyl-1H-Pyrazol-5-Yl)-2,5-Dioxoimidazolidin-4-Yl]Methyl}[Biphenyl]-2-Carboxamide

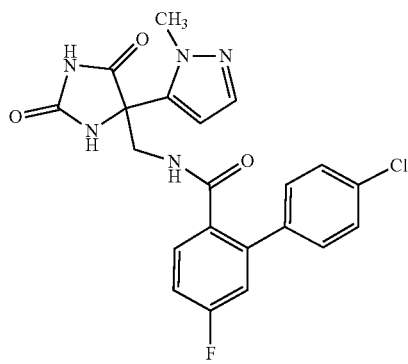 [SMILES: Cn1nccc1C1(CNC(=O)c2ccc(F)cc2-c2ccc(Cl)cc2)NC(=O)NC1=O]

Enantiomeric separation of rac-4'-chloro-5-fluoro-N-{[4-(1-methyl-1H-pyrazol-5-yl)-2,5-dioxoimidazolidin-4-yl]methyl}[biphenyl]-2-carboxamide (75 mg) by preparative chiral HPLC [column: Daicel Chiralpak ID 5 μm, 250×20 mm; eluent: 50% n-heptan/50% isopropanol; flow rate: 15 ml/min; temperature: 50° C.; UV detection: 220 nm] afforded 25.7 mg (100% purity) of the desired product.

Analytical chiral HPLC: $R_t$=7.43 min, e.e. =99% [column: 250×4.6 mm filled with Daicel Chiralpak ID 5 μm; eluent: 50% n-heptan/50% isopropanol; flow rate: 1 ml/min; temperature: 50° C.; UV detection: 220 nm]

LC-MS (Method 7): $R_t$=1.49 min; MS (ESIpos): m/z=442 [M+H]$^+$ $^1$H-NMR (400 MHz, DMSO-d6) δ [ppm]: 2.523 (0.97), 3.792 (16.00), 3.827 (0.67), 3.842 (0.73), 3.861 (1.20), 3.876 (1.06), 3.927 (1.09), 3.944 (1.16), 3.962 (0.68), 3.979 (0.62), 6.466 (3.56), 6.471 (3.60), 7.253 (1.11), 7.260 (1.67), 7.278 (1.23), 7.284 (1.89), 7.303 (1.63), 7.309 (1.29), 7.324 (0.96), 7.330 (0.86), 7.337 (0.51), 7.343 (3.87), 7.348 (1.38), 7.359 (1.63), 7.365 (5.63), 7.371 (0.81), 7.385 (3.51), 7.390 (3.46), 7.407 (1.48), 7.422 (1.54), 7.429 (1.24), 7.444 (1.14), 7.452 (0.75), 7.458 (5.51), 7.463 (1.54), 7.474 (1.30), 7.479 (3.76), 7.486 (0.43), 8.394 (3.39), 8.702 (0.70), 8.718 (1.35), 8.733 (0.70), 11.241 (0.72).

Example 181

Rac-4'-Chloro-N-{[4-(1-Methyl-1H-Pyrazol-5-Yl)-2,5-Dioxoimidazolidin-4-Yl]Methyl}[Biphenyl]-2-Carboxamide

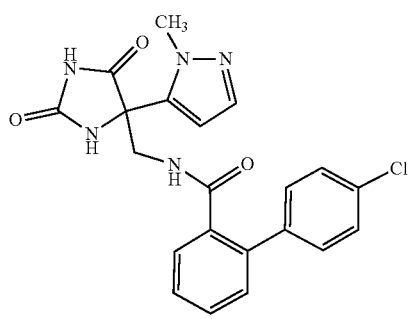 [SMILES: Cn1nccc1C1(CNC(=O)c2ccccc2-c2ccc(Cl)cc2)NC(=O)NC1=O]

To a solution of rac-5-(aminomethyl)-5-(1-methyl-1H-pyrazol-5-yl)imidazolidine-2,4-dione hydrochloride (100 mg, 407 µmol) and 4'-chloro[1,1'-biphenyl]-2-carboxylicacid (114 mg, 488 µmol) in DMF (2.5 ml) was added 1-ethyl-3-(3-dimethylaminopropyl)carbodiimide hydrochloride (101 mg, 529 µmol), 1-hydroxybenzotriazole hydrate (81.0 mg, 529 µmol) and N,N-diisopropylethylamine (350 µl, 2.0 mmol). The reaction mixture was stirred overnight at room temperature and then concentrated under reduced pressure. The crude product was purified by preparative HPLC (Method 7f). After lyophilization, 136 mg (100% purity, 79% yield) of the desired product were obtained.

LC-MS (Method 7): $R_t$=1.41 min, MS (ESIpos): m/z=424 [M+H]$^+$ $^1$H-NMR (400 MHz, DMSO-d6) δ [ppm]: 1.037 (1.09), 1.040 (1.08), 1.053 (1.32), 1.065 (0.49), 2.100 (0.73), 2.524 (0.46), 3.795 (16.00), 3.831 (0.66), 3.846 (0.71), 3.866 (1.19), 3.880 (1.07), 3.929 (1.09), 3.946 (1.17), 3.963 (0.68), 3.980 (0.63), 6.462 (3.60), 6.467 (3.66), 7.314 (0.47), 7.320 (3.85), 7.325 (1.37), 7.337 (1.61), 7.342 (5.47), 7.348 (0.76), 7.368 (1.07), 7.372 (1.23), 7.384 (5.17), 7.389 (5.21), 7.401 (2.10), 7.415 (1.10), 7.418 (1.10), 7.434 (2.01), 7.437 (2.22), 7.443 (5.49), 7.448 (1.65), 7.453 (1.16), 7.456 (1.03), 7.459 (1.42), 7.464 (3.76), 7.471 (0.43), 7.505 (1.21), 7.508 (1.20), 7.523 (1.58), 7.527 (1.46), 7.542 (0.61), 7.545 (0.61), 8.359 (1.74), 8.664 (0.68), 8.680 (1.29), 8.695 (0.66).

Example 182

Ent-4'-Chloro-N-{[4-(1-Methyl-1H-Pyrazol-5-Yl)-2,5-Dioxoimidazolidin-4-Yl]Methyl}[Biphenyl]-2-Carboxamide

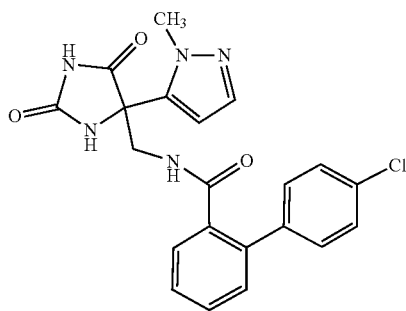 [SMILES: Cn1nccc1C1(CNC(=O)c2ccccc2-c2ccc(Cl)cc2)NC(=O)NC1=O]

Enantiomeric separation of rac-4'-chloro-N-{[4-(1-methyl-1H-pyrazol-5-yl)-2,5-dioxoimidazolidin-4-yl]methyl}[biphenyl]-2-carboxamide (136 mg) by preparative chiral HPLC [column: Daicel Chiralpak IC 5 µm, 250×20 mm; eluent: 70% n-heptane/30% ethanol; flow rate: 20 ml/min; temperature: 40° C.; UV detection: 220 nm] afforded 14.3 mg (100% purity) of the desired product.

Analytical chiral HPLC: $R_t$=1.63 min, e.e. =>99% [column: 50×4.6 mm filled with Daicel Chiralpak IC-3 3 µm; eluent: 70% n-heptane/30% ethanol; flow rate: 1 ml/min; temperature: 30° C.; UV detection: 220 nm]

LC-MS (Method 7): $R_t$=1.42 min; MS (ESIpos): m/z=424 [M+H]$^+$ $^1$H-NMR (600 MHz, DMSO-d6) δ [ppm]: 3.799 (16.00), 3.845 (0.84), 3.854 (0.92), 3.867 (1.37), 3.877 (1.26), 3.937 (1.25), 3.948 (1.32), 3.959 (0.86), 3.971 (0.82), 6.460 (3.25), 6.463 (3.26), 7.324 (3.96), 7.339 (4.92), 7.375 (1.60), 7.383 (5.75), 7.386 (5.86), 7.395 (2.45), 7.421 (1.24), 7.433 (2.15), 7.443 (5.26), 7.457 (3.96), 7.510 (1.23), 7.522 (1.90), 7.535 (0.80), 8.350 (2.91), 8.638 (0.86), 8.648 (1.62), 8.659 (0.86), 11.223 (2.49).

Example 183

Rac-5-Fluoro-N-{[4-(1-Methyl-1H-Pyrazol-5-Yl)-2,5-Dioxoimidazolidin-4-Yl]Methyl}-4'-(Trifluoromethyl)[Biphenyl]-2-Carboxamide

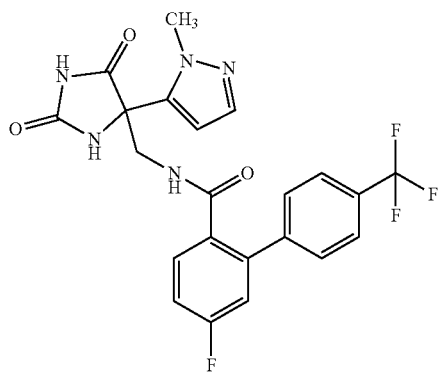 [SMILES: Cn1nccc1C1(CNC(=O)c2ccc(F)cc2-c2ccc(C(F)(F)F)cc2)NC(=O)NC1=O]

To a solution of rac-5-(aminomethyl)-5-(1-methyl-1H-pyrazol-5-yl)imidazolidine-2,4-dione hydrochloride (100 mg, 407 µmol) and 5-fluoro-4'-(trifluoromethyl)[1,1'-biphenyl]-2-carboxylic acid (139 mg, 488 µmol) in DMF (2.5 ml) was added 1-ethyl-3-(3-dimethylaminopropyl)carbodiimide hydrochloride (101 mg, 529 µmol), 1-hydroxybenzotriazole hydrate (81.0 mg, 529 µmol) and N,N-diisopropylethylamine (350 µl, 2.0 mmol). The reaction mixture was stirred overnight at room temperature and then concentrated under reduced pressure. The crude product was purified by preparative HPLC (Method 6f). After lyophilization, 60.0 mg (100% purity, 31% yield) of the desired product were obtained.

LC-MS (Method 7): $R_t$=1.57 min, MS (ESIpos): m/z=476 [M+H]$^+$ $^1$H-NMR (400 MHz, DMSO-d6) δ [ppm]: 2.523 (0.49), 3.788 (16.00), 3.842 (0.61), 3.857 (0.68), 3.877 (1.16), 3.891 (1.05), 3.938 (1.07), 3.955 (1.14), 3.973 (0.65), 3.990 (0.59), 6.471 (3.61), 6.476 (3.67), 7.318 (0.97), 7.324 (1.69), 7.335 (0.93), 7.342 (1.31), 7.348 (1.79), 7.356 (1.79), 7.363 (1.16), 7.377 (1.08), 7.382 (4.07), 7.387 (3.67), 7.467 (1.37), 7.481 (1.39), 7.488 (1.16), 7.502 (1.01), 7.537 (2.64), 7.557 (3.10), 7.762 (3.22), 7.783 (2.70), 8.420 (3.37), 8.784 (0.68), 8.800 (1.31), 8.816 (0.68), 11.262 (0.78).

Example 184

Ent-5-Fluoro-N-{[4-(1-Methyl-1H-Pyrazol-5-Yl)-2,5-Dioxoimidazolidin-4-Yl]Methyl}-4'-(Trifluoromethyl)[Biphenyl]-2-Carboxamide

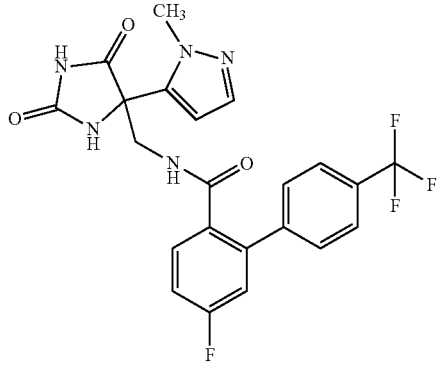 [SMILES: Cn1nccc1C1(CNC(=O)c2ccc(F)cc2-c2ccc(C(F)(F)F)cc2)NC(=O)NC1=O]

To a solution of ent-5-(aminomethyl)-5-(1-methyl-1H-pyrazol-5-yl)imidazolidine-2,4-dione hydrochloride (100 mg, 407 µmol) and 5-fluoro-4'-(trifluoromethyl)[1,1'-biphenyl]-2-carboxylic acid (121 mg, 425 µmol) in DMF (2.5 ml) was added 1-ethyl-3-(3-dimethylaminopropyl)carbodiimide hydrochloride (101 mg, 529 µmol), 1-hydroxybenzotriazole hydrate (81.0 mg, 529 µmol) and N,N-diisopropylethylamine (350 µl, 2.0 mmol). The reaction mixture was stirred overnight at room temperature and then concentrated under reduced pressure. The crude product was purified by preparative HPLC (Method 2f). After lyophilization, 52.1 mg (98% purity, 26% yield) of the desired product were obtained.

LC-MS (Method 7): $R_t$=1.57 min; MS (ESIpos): m/z=476 [M+H]$^+$ $^1$H-NMR (600 MHz, DMSO-d6) δ [ppm]: 3.791 (16.00), 3.799 (1.04), 3.851 (0.80), 3.861 (0.88), 3.874 (1.29), 3.884 (1.15), 3.943 (1.18), 3.955 (1.25), 3.966 (0.81), 3.977 (0.76), 6.465 (3.24), 6.468 (3.25), 7.316 (1.09), 7.320 (1.55), 7.332 (1.13), 7.337 (2.01), 7.342 (0.63), 7.352 (1.48), 7.356 (1.23), 7.366 (0.81), 7.370 (0.72), 7.380 (3.27), 7.383 (3.25), 7.472 (1.30), 7.482 (1.39), 7.486 (1.21), 7.496 (1.08), 7.540 (3.07), 7.554 (3.33), 7.762 (3.49), 7.775 (3.09), 8.397 (2.61), 8.761 (0.83), 8.772 (1.50), 8.782 (0.79), 11.243 (2.31).

Example 185

Ent-N-{[4-(1-Methyl-1H-Pyrazol-5-Yl)-2,5-Dioxoimidazolidin-4-Yl]Methyl}-4'-(Trifluoromethyl)[Biphenyl]-2-Carboxamide

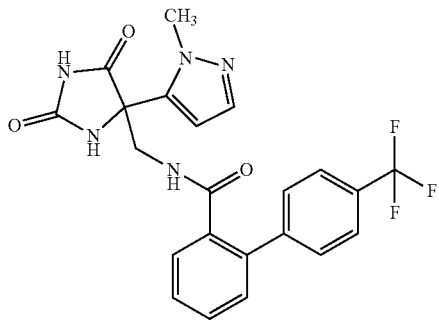 [SMILES: Cn1nccc1C1(CNC(=O)c2ccccc2-c2ccc(C(F)(F)F)cc2)NC(=O)NC1=O]

To a solution of ent-5-(aminomethyl)-5-(1-methyl-1H-pyrazol-5-yl)imidazolidine-2,4-dione hydrochloride (100 mg, 407 µmol) and 4'-(trifluoromethyl)[1,1'-biphenyl]-2-carboxylic acid (94.4 mg, 354 µmol) in DMF (2.0 ml) was added 1-ethyl-3-(3-dimethylaminopropyl)carbodiimide hydrochloride (88.3 mg, 461 µmol), 1-hydroxybenzotriazole hydrate (70.6 mg, 461 µmol) and N,N-diisopropylethylamine (190 µl, 1.1 mmol). The reaction mixture was stirred overnight at room temperature and then concentrated under reduced pressure. The crude product was purified by preparative HPLC (Method 2f). After lyophilization, 62.9 mg (100% purity, 34% yield) of the desired product were obtained.

LC-MS (Method 7): $R_t$=1.51 min; MS (ESIpos): m/z=458 [M+H]$^+$ $^1$H-NMR (400 MHz, DMSO-d6) δ [ppm]: 3.793 (16.00), 3.853 (0.64), 3.867 (0.70), 3.887 (1.23), 3.902 (1.12), 3.944 (1.12), 3.961 (1.21), 3.978 (0.65), 3.995 (0.62), 6.472 (3.55), 6.477 (3.60), 7.383 (3.51), 7.388 (3.48), 7.424 (1.07), 7.428 (1.30), 7.435 (1.69), 7.443 (2.29), 7.447 (2.35), 7.453 (2.30), 7.466 (1.14), 7.469 (1.17), 7.484 (1.87), 7.488 (1.62), 7.503 (0.96), 7.506 (0.97), 7.516 (2.89), 7.536 (3.32), 7.546 (1.51), 7.550 (1.35), 7.565 (1.64), 7.568 (1.54), 7.584 (0.62), 7.587 (0.61), 7.749 (3.44), 7.769 (2.89), 8.400 (2.48), 8.751 (0.73), 8.767 (1.42), 8.783 (0.71), 11.260 (2.19).

Example 186

Ent-3-Fluoro-N-{[4-(1-Methyl-1H-Pyrazol-5-Yl)-2,5-Dioxoimidazolidin-4-Yl]Methyl}-4'-(Trifluoromethyl)[Biphenyl]-2-Carboxamide

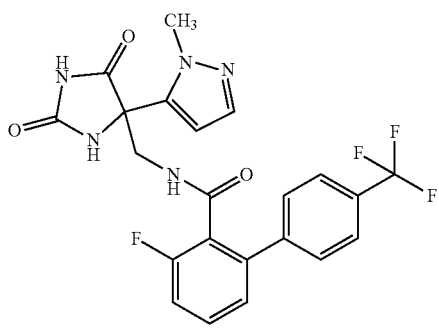 [SMILES: Cn1nccc1C1(CNC(=O)c2c(F)cccc2-c2ccc(C(F)(F)F)cc2)NC(=O)NC1=O]

To a solution of ent-5-(aminomethyl)-5-(1-methyl-1H-pyrazol-5-yl)imidazolidine-2,4-dione hydrochloride (100 mg, 407 µmol) and 3-fluoro-4'-(trifluoromethyl)[1,1'-biphenyl]-2-carboxylic acid (139 mg, 488 µmol) in DMF (3 ml) was added 1-ethyl-3-(3-dimethylaminopropyl)carbodiimide hydrochloride (101 mg, 529 µmol), 1-hydroxybenzotriazole hydrate (81.0 mg, 529 µmol) and N,N-diisopropylethylamine (350 µl, 2.0 mmol). The reaction mixture was stirred overnight at room temperature and then concentrated under reduced pressure. The crude product was purified by preparative HPLC (Method 3f). After lyophilization, 94.4 mg (98% purity, 48% yield) of the desired product were obtained.

LC-MS (Method 8): $R_t$=0.78 min, MS (ESIpos): m/z=476 [M+H]$^+$ $^1$H-NMR (600 MHz, DMSO-d6) δ [ppm]: 3.787 (16.00), 3.836 (0.73), 3.847 (0.77), 3.859 (1.00), 3.869 (0.94), 3.964 (0.98), 3.974 (1.06), 3.986 (0.80), 3.997 (0.71), 6.427 (3.33), 6.430 (3.35), 7.270 (1.64), 7.271 (1.69), 7.283 (1.78), 7.324 (0.72), 7.338 (1.49), 7.356 (3.56), 7.359 (3.37), 7.543 (0.61), 7.552 (0.69), 7.556 (0.97), 7.565 (0.93), 7.569 (0.61), 7.579 (0.56), 7.590 (2.40), 7.604 (2.67), 7.782 (2.78), 7.795 (2.43), 8.354 (0.55), 8.987 (0.65), 8.998 (1.35), 9.008 (0.63).

Example 187

Ent-4'-Chloro-4-Fluoro-N-{[4-(1-Methyl-1H-Pyrazol-5-Yl)-2,5-Dioxoimidazolidin-4-Yl]Methyl}[Biphenyl]-2-Carboxamide

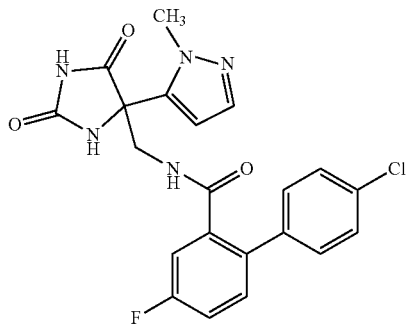 [SMILES: Cn1nccc1C1(CNC(=O)c2cc(F)ccc2-c2ccc(Cl)cc2)NC(=O)NC1=O]

To a solution of ent-5-(aminomethyl)-5-(1-methyl-1H-pyrazol-5-yl)imidazolidine-2,4-dione hydrochloride (100 mg, 407 µmol) and 4'-chloro-4-fluoro[1,1'-biphenyl]-2-carboxylic acid (94.4 mg, 376 µmol) in DMF (2.3 ml) was added 1-ethyl-3-(3-dimethylaminopropyl)carbodiimide hydrochloride (88.3 mg, 461 µmol), 1-hydroxybenzotriazole hydrate (70.6 mg, 461 µmol) and N,N-diisopropylethylamine (310 µl, 1.8 mmol). The reaction mixture was stirred overnight at room temperature and then concentrated under reduced pressure. The crude product was purified by preparative HPLC (Method 2f). After lyophilization, 42.5 mg (100% purity, 24% yield) of the desired product were obtained.

LC-MS (Method 7): $R_t$=1.46 min, MS (ESIpos): m/z=442 [M+H]$^+$ $^1$H-NMR (400 MHz, DMSO-d6) δ [ppm]: 2.072 (1.33), 3.791 (16.00), 3.833 (0.60), 3.848 (0.66), 3.867 (1.16), 3.882 (1.05), 3.925 (1.05), 3.942 (1.10), 3.959 (0.62), 3.976 (0.57), 6.475 (3.52), 6.480 (3.55), 7.167 (1.24), 7.174 (1.48), 7.190 (1.26), 7.197 (1.39), 7.299 (0.46), 7.306 (3.93), 7.311 (1.37), 7.322 (1.61), 7.327 (5.38), 7.333 (0.73), 7.359 (0.53), 7.366 (0.54), 7.381 (1.47), 7.389 (4.31), 7.394 (3.82), 7.402 (1.12), 7.408 (1.08), 7.425 (1.70), 7.441 (6.26), 7.447 (2.53), 7.458 (1.64), 7.463 (4.27), 7.469 (0.50), 8.428 (2.27), 8.431 (2.24), 8.815 (0.66), 8.831 (1.29), 8.846 (0.66), 11.276 (1.96).

Example 188

Ent-5-Chloro-N-{[4-(1-Methyl-1H-Pyrazol-5-Yl)-2,5-Dioxoimidazolidin-4-Yl]Methyl}-4'-(Trifluoromethyl)[Biphenyl]-2-Carboxamide

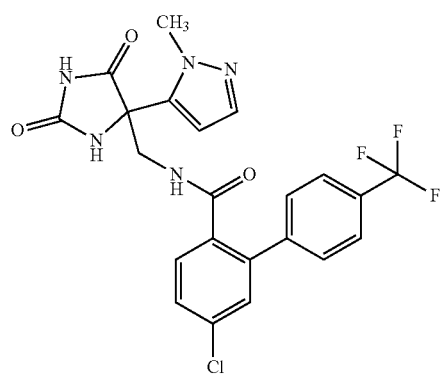 [SMILES: Cn1nccc1C1(CNC(=O)c2ccc(Cl)cc2-c2ccc(C(F)(F)F)cc2)NC(=O)NC1=O]

To a solution of ent-5-(aminomethyl)-5-(1-methyl-1H-pyrazol-5-yl)imidazolidine-2,4-dione hydrochloride (100 mg, 407 µmol) and 5-chloro-4'-(trifluoromethyl)[1,1'-biphenyl]-2-carboxylic acid (147 mg, 488 µmol) in DMF (3 ml) was added 1-ethyl-3-(3-dimethylaminopropyl)carbodiimide hydrochloride (101 mg, 529 µmol), 1-hydroxybenzotriazole hydrate (81.0 mg, 529 µmol) and N,N-diisopropylethylamine (350 µl, 2.0 mmol). The reaction mixture was stirred overnight at room temperature and then concentrated under reduced pressure. The crude product was purified by preparative HPLC (Method 4f). After lyophilization, 84.2 mg (98% purity, 41% yield) of the desired product were obtained.

LC-MS (Method 8): $R_t$=0.87 min, MS (ESIpos): m/z=492 [M+H]$^+$ $^1$H-NMR (600 MHz, DMSO-d6) δ [ppm]: 3.790 (16.00), 3.855 (0.74), 3.864 (0.81), 3.877 (1.25), 3.887 (1.10), 3.935 (1.17), 3.946 (1.23), 3.957 (0.77), 3.969 (0.72), 6.464 (3.39), 6.467 (3.39), 7.378 (3.58), 7.381 (3.49), 7.437 (2.64), 7.450 (3.09), 7.522 (3.01), 7.525 (3.34), 7.547 (2.82), 7.561 (3.08), 7.575 (2.03), 7.579 (1.77), 7.589 (1.61), 7.592 (1.45), 7.762 (3.21), 7.776 (2.83), 8.412 (2.28), 8.808 (0.77), 8.818 (1.41), 8.829 (0.75).

Example 189

Ent-3,4'-Dichloro-N-{[4-(1-Methyl-1H-Pyrazol-5-Yl)-2,5-Dioxoimidazolidin-4-Yl]Methyl}[Biphenyl]-2-Carboxamide

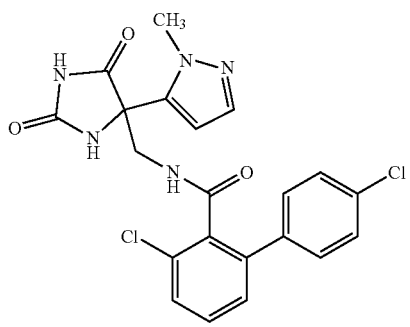 [SMILES: Cn1nccc1C1(CNC(=O)c2c(Cl)cccc2-c2ccc(Cl)cc2)NC(=O)NC1=O]

To a solution of ent-5-(aminomethyl)-5-(1-methyl-1H-pyrazol-5-yl)imidazolidine-2,4-dione hydrochloride (100 mg, 407 μmol) and 3,4'-dichloro[1,1'-biphenyl]-2-carboxylic acid (130 mg, 488 μmol) in DMF (3 ml) was added 1-ethyl-3-(3-dimethylaminopropyl)carbodiimide hydrochloride (101 mg, 529 μmol), 1-hydroxybenzotriazole hydrate (81.0 mg, 529 μmol) and N,N-diisopropylethylamine (350 μl, 2.0 mmol). The reaction mixture was stirred overnight at room temperature and then concentrated under reduced pressure. The crude product was purified by preparative HPLC (Method 3f). After lyophilization, 31.7 mg (98% purity, 17% yield) of the desired product were obtained.

LC-MS (Method 8): $R_t$=0.76 min; MS (ESIpos): m/z=458 [M+H]$^+$ $^1$H-NMR (600 MHz, DMSO-d6) δ [ppm]: 3.794 (16.00), 6.391 (3.07), 6.394 (3.06), 7.308 (1.60), 7.311 (1.61), 7.321 (1.86), 7.323 (1.79), 7.345 (3.39), 7.348 (3.30), 7.404 (3.33), 7.408 (1.17), 7.415 (1.51), 7.418 (5.34), 7.423 (0.75), 7.458 (0.77), 7.462 (5.62), 7.465 (2.52), 7.473 (1.25), 7.476 (3.66), 7.478 (2.85), 7.491 (2.26), 7.499 (2.47), 7.501 (2.58), 7.513 (1.05), 7.515 (0.82), 8.316 (1.77), 8.820 (0.71), 8.830 (1.48), 8.840 (0.70).

Example 190

Ent-N-{[4-(1-Methyl-1H-Pyrazol-5-Yl)-2,5-Dioxo-imidazolidin-4-Yl]Methyl}-2-[6-(Trifluoromethyl)Pyridin-3-Yl]Benzamide

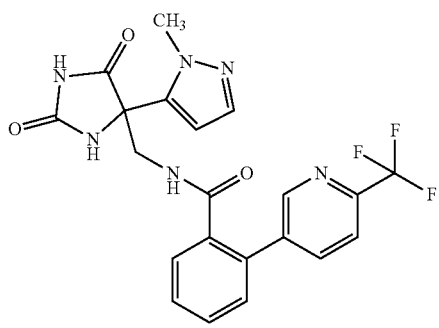 [SMILES: Cn1nccc1C1(CNC(=O)c2ccccc2-c2ccc(C(F)(F)F)nc2)NC(=O)NC1=O]

To a solution of ent-5-(aminomethyl)-5-(1-methyl-1H-pyrazol-5-yl)imidazolidine-2,4-dione hydrochloride (100 mg, 407 μmol) and 2-[6-(trifluoromethyl)pyridin-3-yl]benzoic acid (131 mg, 488 μmol) in DMF (3 ml) was added 1-ethyl-3-(3-dimethylaminopropyl)carbodiimide hydrochloride (101 mg, 529 μmol), 1-hydroxybenzotriazole hydrate (81.0 mg, 529 μmol) and N,N-diisopropylethylamine (350 μl, 2.0 mmol). The reaction mixture was stirred overnight at room temperature and then concentrated under reduced pressure. The crude product was purified by preparative HPLC (Method 3f). After lyophilization, 86.8 mg (100% purity, 47% yield) of the desired product were obtained.

LC-MS (Method 8): $R_t$=0.67 min; MS (ESIpos): m/z=459 [M+H]$^+$ $^1$H-NMR (600 MHz, DMSO-d6) δ [ppm]: 3.785 (16.00), 3.861 (0.68), 3.870 (0.75), 3.883 (1.15), 3.893 (1.02), 3.940 (1.07), 3.952 (1.13), 3.963 (0.70), 3.974 (0.66), 6.479 (3.34), 6.482 (3.36), 7.376 (3.42), 7.379 (3.36), 7.490 (1.07), 7.493 (1.16), 7.503 (1.70), 7.505 (1.69), 7.519 (1.36), 7.532 (1.80), 7.540 (0.92), 7.542 (0.90), 7.552 (1.74), 7.554 (1.48), 7.565 (0.86), 7.567 (0.75), 7.604 (1.15), 7.606 (1.14), 7.616 (1.55), 7.619 (1.51), 7.629 (0.60), 7.631 (0.58), 7.910 (0.69), 7.911 (0.78), 7.924 (2.92), 7.925 (2.95), 7.931 (1.91), 7.934 (1.77), 7.944 (0.41), 7.948 (0.45), 8.388 (3.11), 8.728 (1.89), 8.801 (0.66), 8.811 (1.23), 8.822 (0.64), 11.240 (0.74).

Example 191

Ent-5,6-Difluoro-N-{[4-(1-Methyl-1H-Pyrazol-5-Yl)-2,5-Dioxoimidazolidin-4-Yl]Methyl}-4'-(Trifluoromethyl)[Biphenyl]-2-Carboxamide

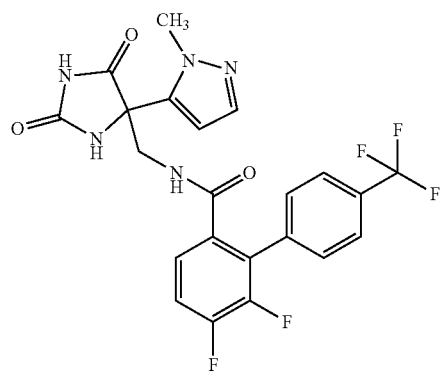 [SMILES: Cn1nccc1C1(CNC(=O)c2ccc(F)c(F)c2-c2ccc(C(F)(F)F)cc2)NC(=O)NC1=O]

To a solution of ent-5-(aminomethyl)-5-(1-methyl-1H-pyrazol-5-yl)imidazolidine-2,4-dione hydrochloride (100 mg, 407 μmol) and 5,6-difluoro-4'-(trifluoromethyl)[1,1'-biphenyl]-2-carboxylic acid (148 mg, 488 μmol) in DMF (3 ml) was added 1-ethyl-3-(3-dimethylaminopropyl)carbodiimide hydrochloride (101 mg, 529 μmol), 1-hydroxybenzotriazole hydrate (81.0 mg, 529 μmol) and N,N-diisopropylethylamine (350 μl, 2.0 mmol). The reaction mixture was stirred overnight at room temperature and then concentrated under reduced pressure. The crude product was purified by preparative HPLC (Method 4f). After lyophilization, 90.9 mg (97% purity, 44% yield) of the desired product were obtained.

LC-MS (Method 8): $R_t$=0.83 min, MS (ESIpos): m/z=494 [M+H]$^+$ $^1$H-NMR (600 MHz, DMSO-d6) δ [ppm]: 3.767 (16.00), 3.802 (0.67), 3.812 (0.75), 3.825 (1.30), 3.835 (1.17), 3.867

(1.21), 3.878 (1.28), 3.890 (0.71), 3.901 (0.67), 6.445 (3.35), 6.448 (3.31), 7.284 (0.66), 7.291 (0.71), 7.298 (0.77), 7.306 (0.75), 7.366 (3.46), 7.369 (3.36), 7.527 (2.47), 7.541 (2.72), 7.603 (0.50), 7.617 (0.81), 7.633 (0.83), 7.647 (0.41), 7.801 (3.10), 7.814 (2.91), 8.392 (0.57), 8.786 (0.72), 8.796 (1.38), 8.807 (0.72).

Example 192

Ent-4,5-Difluoro-N-{[4-(1-Methyl-1H-Pyrazol-5-Yl)-2,5-Dioxoimidazolidin-4-Yl]Methyl}-4'-(Trifluoromethyl)[Biphenyl]-2-Carboxamide

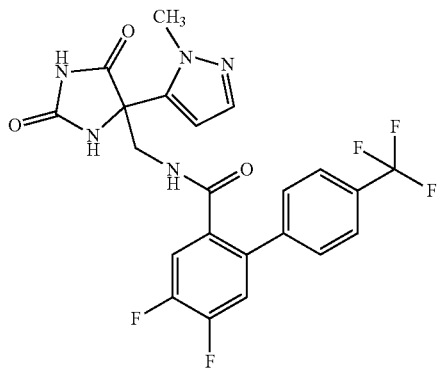 [SMILES: Cn1nccc1C1(CNC(=O)c2cc(F)c(F)cc2-c2ccc(C(F)(F)F)cc2)NC(=O)NC1=O]

To a solution of ent-5-(aminomethyl)-5-(1-methyl-1H-pyrazol-5-yl)imidazolidine-2,4-dione hydrochloride (100 mg, 407 µmol) and 4,5-difluoro-4'-(trifluoromethyl)[1,1'-biphenyl]-2-carboxylic acid (148 mg, 488 µmol) in DMF (3 ml) was added 1-ethyl-3-(3-dimethylaminopropyl)carbodiimide hydrochloride (101 mg, 529 µmol), 1-hydroxybenzotriazole hydrate (81.0 mg, 529 µmol) and N,N-diisopropylethylamine (350 µl, 2.0 mmol). The reaction mixture was stirred overnight at room temperature and then concentrated under reduced pressure. The crude product was purified by preparative HPLC (Method 4f). After lyophilization, 96.3 mg (98% purity, 47% yield) of the desired product were obtained.

LC-MS (Method 8): $R_t$=0.84 min, MS (ESIpos): m/z=494 [M+H]$^+$ $^1$H-NMR (600 MHz, DMSO-d6) δ [ppm]: 0.005 (0.65), 2.513 (0.66), 2.517 (0.69), 2.520 (0.61), 2.570 (0.45), 2.731 (0.41), 2.889 (0.53), 3.298 (5.55), 3.758 (0.48), 3.824 (0.41), 3.855 (3.18), 3.864 (3.56), 3.877 (5.24), 3.887 (4.59), 3.907 (0.41), 3.942 (4.81), 3.954 (5.10), 3.965 (3.35), 3.977 (3.10), 6.471 (15.31), 6.474 (15.49), 7.384 (16.00), 7.387 (15.73), 7.463 (3.31), 7.477 (3.99), 7.481 (3.87), 7.495 (3.58), 7.525 (11.28), 7.539 (12.44), 7.560 (0.54), 7.565 (0.48), 7.590 (3.31), 7.603 (4.18), 7.609 (3.95), 7.616 (1.21), 7.622 (4.29), 7.636 (0.60), 7.761 (12.81), 7.775 (11.53), 8.170 (0.99), 8.459 (5.50), 8.881 (2.99), 8.891 (5.53), 8.902 (2.97).

Example 193

Ent-4',5-Dichloro-N-{[4-(1-Methyl-1H-Pyrazol-5-Yl)-2,5-Dioxoimidazolidin-4-Yl]Methyl}[Biphenyl]-2-Carboxamide

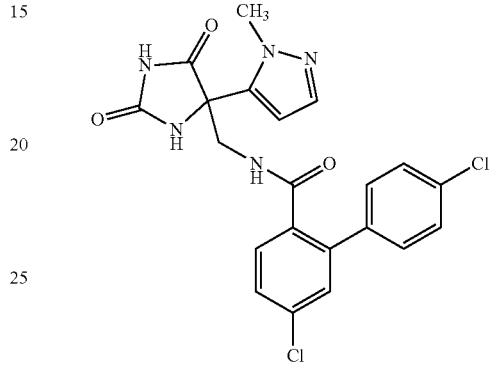

To a solution of ent-5-(aminomethyl)-5-(1-methyl-1H-pyrazol-5-yl)imidazolidine-2,4-dione hydrochloride (100 mg, 407 µmol) and 4',5-dichloro[1,1'-biphenyl]-2-carboxylic acid (130 mg, 488 µmol) in DMF (3 ml) was added 1-ethyl-3-(3-dimethylaminopropyl)carbodiimide hydrochloride (101 mg, 529 µmol), 1-hydroxybenzotriazole hydrate (81.0 mg, 529 µmol) and N,N-diisopropylethylamine (350 µl, 2.0 mmol). The reaction mixture was stirred overnight at room temperature and then concentrated under reduced pressure. The crude product was purified by preparative HPLC (method 4f). After lyophilization, 67.5 mg (100% purity, 36% yield) of the desired product were obtained.

LC-MS (Method 8): $R_t$=0.83 min, MS (ESIpos): m/z=458 [M+H]$^+$ $^1$H-NMR (600 MHz, DMSO-d6) δ [ppm]: 3.792 (16.00), 3.839 (0.67), 3.848 (0.75), 3.861 (1.14), 3.871 (0.99), 3.922 (1.05), 3.933 (1.11), 3.944 (0.72), 3.956 (0.67), 6.459 (3.28), 6.462 (3.32), 7.346 (0.40), 7.351 (3.77), 7.354 (1.25), 7.362 (1.42), 7.365 (4.80), 7.370 (0.63), 7.378 (2.76), 7.381 (3.67), 7.384 (3.48), 7.392 (3.09), 7.453 (0.62), 7.457 (5.08), 7.461 (4.03), 7.465 (3.41), 7.469 (1.38), 7.472 (3.76), 7.476 (0.40), 7.523 (1.92), 7.526 (1.68), 7.536 (1.54), 7.540 (1.43), 8.384 (3.09), 8.723 (0.66), 8.734 (1.21), 8.744 (0.65).

Example 194

Ent-N-{[4-(1-Methyl-1H-Pyrazol-5-Yl)-2,5-Dioxo-imidazolidin-4-Yl]Methyl}-4'-(Methylsulfonyl)[Biphenyl]-2-Carboxamide

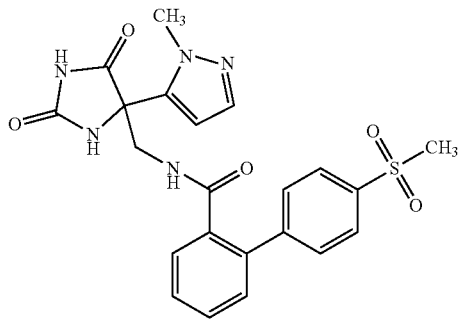 [SMILES: Cn1nccc1C1(CNC(=O)c2ccccc2-c2ccc(S(C)(=O)=O)cc2)NC(=O)NC1=O]

To a solution of ent-5-(aminomethyl)-5-(1-methyl-1H-pyrazol-5-yl)imidazolidine-2,4-dione hydrochloride (100 mg, 407 μmol) and 4'-(methanesulfonyl)[1,1'-biphenyl]-2-carboxylicacid (135 mg, 488 μmol) in DMF (3 ml) was added 1-ethyl-3-(3-dimethylaminopropyl)carbodiimide hydrochloride (101 mg, 529 μmol), 1-hydroxybenzotriazole hydrate (81.0 mg, 529 μmol) and N,N-diisopropylethylamine (350 μl, 2.0 mmol). The reaction mixture was stirred overnight at room temperature and then concentrated under reduced pressure. The crude product was purified by preparative HPLC (Method 6f). After lyophilization, 76.1 mg (100% purity, 40% yield) of the desired product were obtained.

LC-MS (Method 7): $R_t$=1.01 min, MS (ESIpos): m/z=468 [M+H]$^+$ $^1$H-NMR (500 MHz, DMSO-d6) δ [ppm]: 2.071 (0.61), 3.261 (16.00), 3.793 (15.82), 3.861 (0.61), 3.873 (0.69), 3.888 (1.05), 3.900 (0.91), 3.955 (0.96), 3.969 (1.01), 3.982 (0.65), 3.996 (0.60), 6.479 (3.53), 6.483 (3.47), 7.387 (3.90), 7.391 (3.72), 7.436 (2.26), 7.452 (3.34), 7.481 (0.98), 7.483 (0.94), 7.496 (1.72), 7.498 (1.38), 7.511 (0.76), 7.513 (0.77), 7.559 (4.82), 7.562 (1.48), 7.572 (2.97), 7.575 (4.95), 7.579 (0.73), 7.587 (0.61), 7.589 (0.62), 7.937 (0.73), 7.941 (4.51), 7.945 (1.35), 7.954 (1.40), 7.958 (3.97), 7.962 (0.53), 8.397 (3.16), 8.764 (0.65), 8.777 (1.19), 8.789 (0.62), 11.255 (0.46).

Example 195

Ent-6-Fluoro-N-{[4-(1-Methyl-1H-Pyrazol-5-Yl)-2,5-Dioxoimidazolidin-4-Yl]Methyl}-4'-(Trifluoromethyl)[Biphenyl]-2-Carboxamide

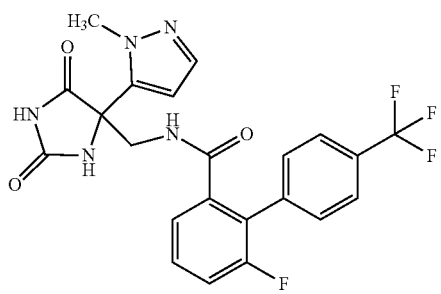 [SMILES: Cn1nccc1C1(CNC(=O)c2cccc(F)c2-c2ccc(C(F)(F)F)cc2)NC(=O)NC1=O]

To a solution of ent-5-(aminomethyl)-5-(1-methyl-1H-pyrazol-5-yl)imidazolidine-2,4-dione hydrochloride (100 mg, 407 μmol) and 6-fluoro-4'-(trifluoromethyl)[1,1'-biphenyl]-2-carboxylic acid (249 mg, 46% purity, 407 μmol) in DMF (2.3 ml) was added 1-ethyl-3-(3-dimethylaminopropyl)carbodiimide hydrochloride (101 mg, 529 μmol), 1-hydroxybenzotriazole hydrate (81.0 mg, 529 μmol) and N,N-diisopropylethylamine (350 μl, 2.0 mmol). The reaction mixture was stirred overnight at room temperature and then concentrated under reduced pressure. The crude product was purified by preparative HPLC (Method 3f). After lyophilization, 52.8 mg (93% purity, 25% yield) of the desired product were obtained.

LC-MS (Method 7): $R_t$=1.55 min; MS (ESIpos): m/z=476 [M+H]$^+$ $^1$H-NMR (500 MHz, DMSO-d6) δ [ppm]: 3.768 (16.00), 3.807 (0.49), 3.819 (0.56), 3.834 (1.15), 3.846 (1.01), 3.864 (1.06), 3.877 (1.12), 3.891 (0.51), 3.905 (0.50), 6.454 (3.48), 6.457 (3.44), 7.263 (1.50), 7.265 (1.49), 7.278 (1.64), 7.280 (1.55), 7.370 (3.87), 7.374 (3.70), 7.433 (0.62), 7.435 (0.63), 7.449 (0.97), 7.452 (1.16), 7.454 (0.72), 7.469 (0.87), 7.471 (0.80), 7.498 (2.04), 7.514 (2.22), 7.527 (0.75), 7.538 (0.90), 7.544 (0.99), 7.547 (0.47), 7.553 (1.11), 7.559 (0.71), 7.564 (0.43), 7.570 (0.78), 7.602 (0.44), 7.616 (0.41), 7.623 (0.45), 7.626 (0.57), 7.775 (2.74), 7.791 (2.41), 8.393 (1.42), 8.787 (0.61), 8.800 (1.18), 8.812 (0.59).

Example 196

Rac-N-{[2,5-Dioxo-4-(1,3-Thiazol-4-Yl)Imidazolidin-4-Yl]Methyl}-4'-(Trifluoromethyl)[Biphenyl]-2-Carboxamide

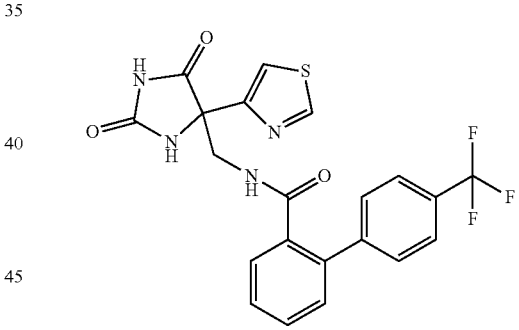

To a solution of rac-5-(aminomethyl)-5-(1,3-thiazol-4-yl)imidazolidine-2,4-dione hydrochloride (67.0 mg, 269 μmol) and 4'-(trifluoromethyl)[1,1'-biphenyl]-2-carboxylicacid (71.7 mg, 269 μmol) in DMF (1.7 ml) was added 1-ethyl-3-(3-dimethylaminopropyl)carbodiimide hydrochloride (67.1 mg, 350 μmol), 1-hydroxybenzotriazole hydrate (53.6 mg, 350 μmol) and N,N-diisopropylethylamine (230 μl, 1.3 mmol). The reaction mixture was stirred for 3 days at room temperature and then concentrated under reduced pressure. The crude product was purified by preparative HPLC (Method 4f). After lyophilization, 65.9 mg (99% purity, 52% yield) of the desired product were obtained.

LC-MS (Method 7): $R_t$=1.66 min; MS (ESIpos): m/z=461 [M+H]$^+$ $^1$H-NMR (600 MHz, DMSO-d6) δ [ppm]: 2.385 (0.46), 2.424 (0.50), 2.612 (0.41), 2.653 (0.46), 3.896 (2.61), 3.907 (2.77), 3.919 (4.57), 3.930 (4.25), 3.971 (4.38), 3.981 (4.74), 3.993 (2.80), 4.003 (2.50), 7.424 (4.54), 7.437 (12.20), 7.451 (7.39), 7.461 (3.81), 7.473 (6.39), 7.486 (2.91), 7.541

(4.09), 7.543 (4.25), 7.556 (16.00), 7.569 (13.69), 7.750 (12.04), 7.764 (10.71), 7.784 (11.71), 7.787 (12.25), 8.292 (12.53), 8.697 (2.88), 8.707 (5.72), 8.717 (2.83), 9.129 (10.40), 9.132 (10.86), 10.919 (5.43).

Example 197

Ent-N-{[2,5-Dioxo-4-(1,3-Thiazol-4-Yl)Imidazoli-din-4-Yl]Methyl}-4'-(Trifluoromethyl)[Biphenyl]-2-Carboxamide

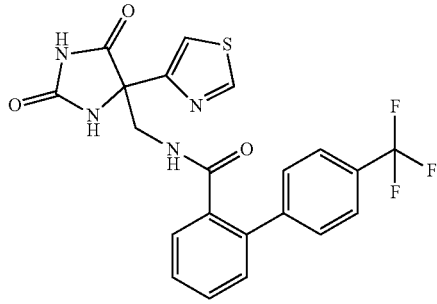 [SMILES: O=C1NC(=O)C(CNC(=O)c2ccccc2-c2ccc(C(F)(F)F)cc2)(c2cscn2)N1]

Enantiomeric separation of rac-N-{[2,5-dioxo-4-(1,3-thiazol-4-yl)imidazolidin-4-yl]methyl}-4'-(trifluoromethyl) [biphenyl]-2-carboxamide (63.3 mg) by preparative chiral HPLC [Daicel Chiralpak IA 5 μm, 250×20 mm; eluent: 40% n-heptane/60% ethanol; flow rate: 20 ml/min; temperature: 40° C.; UV detection: 220 nm] afforded 19.4 mg (95% purity) of the desired product.

Analytical chiral HPLC: $R_t$=3.22 min, e.e. =>99% [column: 50×4.6 mm filled with Daicel Chiralpak IA-3 3 μm; eluent: 50% n-heptane/50% ethanol; flow rate: 1 ml/min; UV detection: 220 nm]

LC-MS (Method 7): $R_t$=1.53 min; MS (ESIpos): m/z=461 [M+H]$^+$ $^1$H-NMR (600 MHz, DMSO-d6) δ [ppm]: 0.846 (1.06), 0.861 (1.32), 0.872 (1.09), 1.089 (0.81), 1.100 (0.84), 1.108 (0.76), 1.118 (0.71), 1.145 (0.46), 1.158 (0.84), 1.170 (0.51), 1.236 (1.09), 1.258 (0.94), 1.299 (0.81), 2.386 (0.41), 2.424 (0.66), 2.572 (1.01), 2.613 (0.43), 2.653 (0.76), 3.304 (1.70), 3.895 (2.35), 3.906 (2.53), 3.918 (4.20), 3.929 (3.97), 3.971 (4.03), 3.981 (4.41), 3.994 (2.56), 4.003 (2.41), 7.422 (4.51), 7.436 (11.04), 7.451 (7.32), 7.462 (3.90), 7.474 (6.35), 7.486 (3.01), 7.543 (4.10), 7.555 (16.00), 7.568 (13.77), 7.750 (11.77), 7.763 (10.35), 7.784 (10.28), 7.786 (10.35), 8.291 (9.47), 8.696 (2.81), 8.706 (5.52), 8.716 (2.78), 9.128 (9.72), 9.131 (9.70), 10.921 (8.28).

Example 198

Rac-N-{[2,5-Dioxo-4-(1,3-Thiazol-4-Yl)Imidazoli-din-4-Yl]Methyl}-5-Fluoro-4'-(Trifluoromethyl)[Biphenyl]-2-Carboxamide

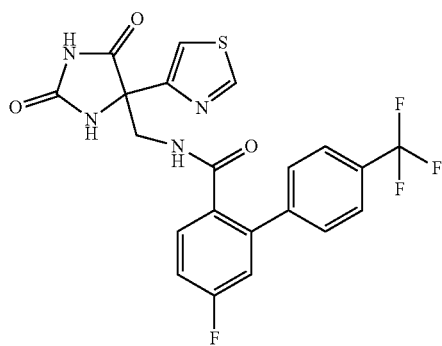 [SMILES: O=C1NC(=O)C(CNC(=O)c2ccc(F)cc2-c2ccc(C(F)(F)F)cc2)(c2cscn2)N1]

To a solution of rac-5-(aminomethyl)-5-(1,3-thiazol-4-yl) imidazolidine-2,4-dione hydrochloride (67.0 mg, 269 μmol) and 5-fluoro-4'-(trifluoromethyl)[1,1'-biphenyl]-2-carboxylic acid (76.6 mg, 269 μmol) in DMF (1.7 ml) was added 1-ethyl-3-(3-dimethylaminopropyl)carbodiimide hydrochloride (67.1 mg, 350 μmol), 1-hydroxybenzotriazole hydrate (53.6 mg, 350 μmol) and N,N-diisopropylethylamine (230 μl, 1.3 mmol). The reaction mixture was stirred for 3 days at room temperature and then concentrated under reduced pressure. The crude product was purified by preparative HPLC (Method 4f). After lyophilization, 71.5 mg (98% purity, 54% yield) of the desired product were obtained.

LC-MS (Method 7): $R_t$=1.72 min, MS (ESIpos): m/z=479 [M+H]$^+$ $^1$H-NMR (600 MHz, DMSO-d6) δ [ppm]: 2.385 (0.57), 2.424 (0.65), 2.519 (1.08), 2.522 (0.96), 2.613 (0.58), 2.653 (0.65), 2.890 (0.48), 3.891 (2.93), 3.902 (3.12), 3.914 (5.14), 3.924 (4.73), 3.965 (5.01), 3.974 (5.54), 3.988 (3.28), 3.997 (2.90), 7.322 (3.14), 7.327 (9.19), 7.342 (13.62), 7.355 (3.58), 7.359 (2.42), 7.471 (4.51), 7.481 (4.12), 7.485 (4.39), 7.495 (3.34), 7.575 (11.52), 7.588 (12.72), 7.765 (13.50), 7.778 (12.09), 7.786 (16.00), 7.789 (15.88), 8.316 (10.03), 8.318 (9.83), 8.734 (3.22), 8.745 (6.52), 8.755 (3.17), 9.128 (13.82), 9.132 (13.92), 10.921 (8.56).

Example 199

Ent-N-{[2,5-Dioxo-4-(1,3-Thiazol-4-Yl)Imidazolidin-4-Yl]Methyl}-5-Fluoro-4'-(Trifluoromethyl)[Biphenyl]-2-Carboxamide

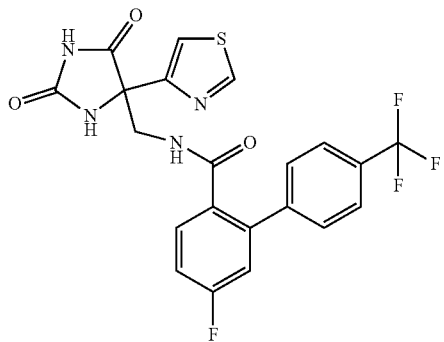 [SMILES: O=C1NC(=O)C(CNC(=O)c2ccc(F)cc2-c2ccc(C(F)(F)F)cc2)(c2cscn2)N1]

Enantiomeric separation of rac-N-{[2,5-dioxo-4-(1,3-thiazol-4-yl)imidazolidin-4-yl]methyl}-5-fluoro-4'-(trifluoromethyl)[biphenyl]-2-carboxamide (68.9 mg) by preparative chiral SFC [column: Chiralpak AD SFC, 250×20 mm; eluent: 65% carbon dioxide/35% ethanol; flow rate: 80 ml/min; temperature: 40° C.; UV detection: 210 nm] afforded 25.5 mg (100% purity) of the desired product.

Analytical chiral SFC: $R_t$=4.14 min, e.e. =>99% [column: OJ 3 μm, 100×4.6 mm; eluent: carbon dioxide/ethanol 70:30; flow rate: 3 ml/min; UV detection: 210 nm]

LC-MS (Method 7): $R_t$=1.60 min; MS (ESIpos): m/z=479 [M+H]$^+$ $^1$H-NMR (400 MHz, DMSO-d6) δ [ppm]: −0.149 (0.41), −0.008 (3.67), 0.008 (3.97), 0.146 (0.41), 2.327 (0.75), 2.366 (0.59), 2.669 (0.75), 2.710 (0.55), 3.879 (1.48), 3.895 (1.60), 3.913 (3.35), 3.929 (3.14), 3.956 (3.16), 3.971 (3.49), 3.991 (1.64), 4.005 (1.46), 7.318 (7.44), 7.341 (8.19), 7.359 (2.70), 7.366 (1.66), 7.465 (2.43), 7.479 (2.80), 7.484 (2.84), 7.501 (2.03), 7.570 (7.30), 7.590 (8.56), 7.760 (8.96), 7.782 (16.00), 7.787 (11.05), 8.307 (7.97), 8.719 (1.93), 8.734 (3.99), 8.750 (1.91), 9.126 (6.65), 9.131 (6.63), 10.915 (5.52).

Example 200

Rac-N-{[2,5-Dioxo-4-(1,3-Thiazol-2-Yl)Imidazolidin-4-Yl]Methyl}-4'-Methyl[Biphenyl]-2-Carboxamide

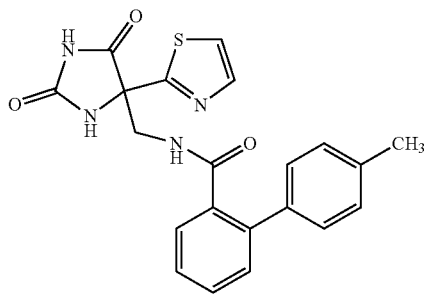 [SMILES: Cc1ccc(-c2ccccc2C(=O)NCC2(c3nccs3)NC(=O)NC2=O)cc1]

To a solution of rac-5-(aminomethyl)-5-(1,3-thiazol-2-yl)imidazolidine-2,4-dione hydrochloride (70.0 mg, 281 μmol) and 4'-methyl[1,1'-biphenyl]-2-carboxylic acid (59.7 mg, 281 μmol) in DMF (1.7 ml) was added 1-ethyl-3-(3-dimethylaminopropyl)carbodiimide hydrochloride (70.1 mg, 366 μmol), 1-hydroxybenzotriazole hydrate (56.0 mg, 366 μmol) and N,N-diisopropylethylamine (250 μl, 1.4 mmol). The reaction mixture was stirred overnight at room temperature, diluted with ethyl acetate and extracted with water. After phase separation, the organic phase was concentrated under reduced pressure, dried and purified by preparative HPLC. 24 mg of the desired product contaminated with impurities were obtained.

The aqueous phase was also concentrated under reduced pressure, dried and purified by preparative HPLC. 15 mg (98% purity) of the desired product were obtained.

LC-MS (Method 7): $R_t$=1.46 min; MS (ESIpos): m/z=407 [M+H]$^+$ $^1$H-NMR (600 MHz, DMSO-d6) δ [ppm]: 1.244 (1.42), 1.256 (1.64), 1.270 (1.05), 2.073 (2.45), 2.326 (16.00), 3.820 (1.33), 3.830 (1.39), 3.843 (1.58), 3.853 (1.45), 4.086 (1.55), 4.096 (1.61), 4.109 (1.39), 4.119 (1.25), 7.183 (3.45), 7.197 (6.18), 7.224 (6.97), 7.238 (3.52), 7.302 (2.14), 7.314 (2.95), 7.357 (2.66), 7.369 (3.59), 7.378 (2.77), 7.391 (1.31), 7.473 (1.63), 7.485 (2.42), 7.498 (1.03), 7.809 (3.51), 7.814 (4.01), 7.867 (4.12), 7.872 (3.33), 8.545 (1.25), 8.555 (2.32), 8.565 (1.12), 8.664 (3.85), 11.102 (3.30).

Example 201

Ent-N-{[2,5-Dioxo-4-(1,3-Thiazol-2-Yl)Imidazolidin-4-Yl]Methyl}-4'-Methyl[Biphenyl]-2-Carboxamide

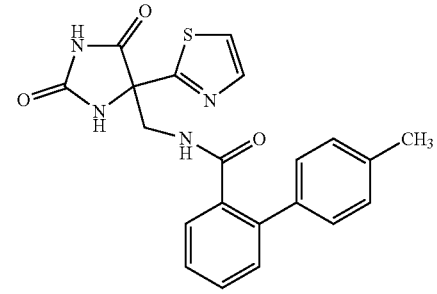 [SMILES: Cc1ccc(-c2ccccc2C(=O)NCC2(c3nccs3)NC(=O)NC2=O)cc1]

Enantiomeric separation of rac-N-{[2,5-dioxo-4-(1,3-thiazol-2-yl)imidazolidin-4-yl]methyl}-4'-methyl[biphenyl]-2-carboxamide (39 mg of impure material) by preparative chiral HPLC [column: Daicel Chiralpak AD-H 5 μm, 250×20 mm; eluent: 70% n-heptane/30% isopropanol; flow rate: 20 ml/min; temperature: 40° C.; UV detection: 220 nm] afforded 3.88 mg (98% purity) of the desired product.

Analytical chiral HPLC: $R_t$=13.36 min, e.e. =96.3% [column: Daicel Chiralpak AD-H 5 μm, 250×4.6 mm; eluent: 65% n-heptane/35% isopropanol; flow rate: 1 ml/min; temperature: 40° C.; UV detection: 220 nm]

LC-MS (Method 8): $R_t$=0.78 min; MS (ESIpos): m/z=407 [M+H]$^+$ $^1$H-NMR (400 MHz, DMSO-d6) δ [ppm]: −0.008 (1.94), 0.008 (2.20), 1.029 (0.50), 1.045 (0.65), 1.120 (0.42), 1.235 (0.42), 2.326 (16.00), 2.365 (0.48), 2.669 (0.69), 2.709 (0.44), 3.812 (1.16), 3.828 (1.25), 3.846 (1.45), 3.862 (1.37), 4.074 (1.38), 4.089 (1.57), 4.108 (1.22), 4.123 (1.15), 7.178

(2.49), 7.198 (6.67), 7.222 (8.20), 7.242 (2.90), 7.296 (1.56), 7.315 (2.81), 7.353 (2.35), 7.358 (1.81), 7.372 (3.45), 7.377 (3.45), 7.396 (1.36), 7.465 (1.66), 7.469 (1.69), 7.484 (2.23), 7.488 (2.13), 7.503 (0.91), 7.806 (4.83), 7.815 (6.32), 7.864 (6.31), 7.872 (4.77), 8.527 (0.97), 8.543 (2.03), 8.558 (0.93), 8.654 (3.41), 11.094 (2.44).

Example 202

Rac-N-[(4-Isopropyl-2,5-Dioxoimidazolidin-4-Yl) Methyl]-5-Methyl-4'-(Trifluoromethyl)[Biphenyl]-2-Carboxamide

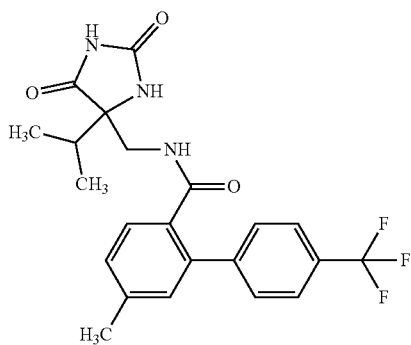 [SMILES: Cc1ccc(C(=O)NCC2(C(C)C)NC(=O)NC2=O)c(-c2ccc(C(F)(F)F)cc2)c1]

To a solution of rac-5-(aminomethyl)-5-isopropylimidazolidine-2,4-dione hydrochloride (150 mg, 722 μmol) and 5-methyl-4'-(trifluoromethyl)[1,1'-biphenyl]-2-carboxylic acid (202 mg, 722 μmol) in DMF (4.5 ml) was added 1-ethyl-3-(3-dimethylaminopropyl)carbodiimide hydrochloride (180 mg, 939 μmol), 1-hydroxybenzotriazole hydrate (144 mg, 939 μmol) and N,N-diisopropylethylamine (630 μl, 3.6 mmol). The reaction mixture was stirred for 3 days at room temperature and then concentrated under reduced pressure. The crude product was purified by preparative HPLC (Method 6f). After lyophilization, 211 mg (98% purity, 66% yield) of the desired product were obtained.

LC-MS (Method 7): $R_t$=1.74 min, MS (ESIpos): m/z=434 [M+H]$^+$ $^1$H-NMR (400 MHz, DMSO-d6) δ [ppm]: 0.788 (8.00), 0.805 (8.35), 0.872 (7.96), 0.889 (8.31), 1.813 (0.47), 1.830 (1.25), 1.847 (1.68), 1.864 (1.17), 1.881 (0.43), 2.367 (0.59), 2.382 (16.00), 2.519 (1.29), 2.524 (0.98), 2.558 (0.47), 3.292 (0.82), 3.350 (1.56), 3.365 (1.37), 3.385 (1.68), 3.400 (1.52), 3.499 (1.44), 3.515 (1.52), 3.534 (1.09), 3.549 (0.98), 7.240 (4.02), 7.256 (1.68), 7.276 (2.65), 7.326 (4.88), 7.345 (2.77), 7.526 (4.02), 7.547 (4.72), 7.692 (3.36), 7.737 (4.88), 7.757 (4.06), 8.291 (1.01), 8.306 (2.11), 8.322 (0.98), 10.662 (2.89).

Example 203

Ent-N-[(4-Isopropyl-2,5-Dioxoimidazolidin-4-Yl) Methyl]-5-Methyl-4'-(Trifluoromethyl)[Biphenyl]-2-Carboxamide

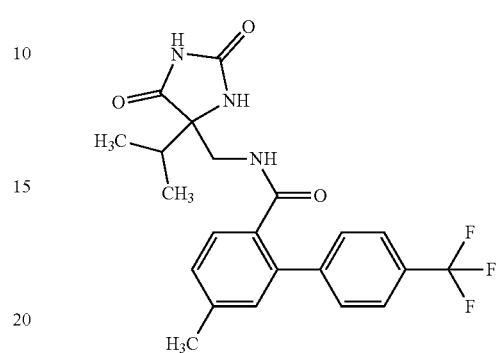

Enantiomeric separation of rac-N-[(4-isopropyl-2,5-dioxoimidazolidin-4-yl)methyl]-5-methyl-4'-(trifluoromethyl)[biphenyl]-2-carboxamide (211 mg) by preparative chiral SFC [column: Daicel Chiralpak AD-H 5 μm SFC, 250×30 mm; eluent: carbon dioxide/isopropanol 72:28; flow rate: 100 ml/min; temperature: 38° C.; UV detection: 210 nm] afforded 39.5 mg (95% purity) of the desired product.

Analytical chiral SFC: $R_t$=3.09 min, e.e. =97.5% [column: AD-3, 50×4.6 mm; eluent: carbon dioxide (95%→50%)/isopropanol (5%→50%); flow rate: 3 ml/min; UV detection: 220 nm]

LC-MS (Method 7): $R_t$=1.74 min; MS (ESIpos): m/z=434 [M+H]$^+$ $^1$H-NMR (400 MHz, DMSO-d6) δ [ppm]: –0.008 (0.77), 0.008 (0.80), 0.788 (8.20), 0.805 (8.51), 0.872 (8.16), 0.889 (8.45), 1.030 (4.46), 1.045 (4.53), 1.813 (0.46), 1.830 (1.26), 1.847 (1.68), 1.864 (1.19), 1.881 (0.42), 1.908 (0.41), 2.382 (16.00), 2.523 (0.80), 2.526 (0.66), 3.350 (1.15), 3.365 (1.21), 3.384 (1.64), 3.399 (1.49), 3.500 (1.48), 3.515 (1.57), 3.534 (1.09), 3.550 (1.02), 4.324 (0.62), 4.334 (0.61), 7.240 (4.07), 7.256 (1.70), 7.275 (2.67), 7.326 (4.87), 7.345 (2.80), 7.526 (4.07), 7.547 (4.75), 7.693 (3.85), 7.737 (4.97), 7.757 (4.10), 8.291 (1.04), 8.306 (2.17), 8.322 (1.03), 10.661 (3.00).

Example 204

Rac-N-[(4-Isopropyl-2,5-Dioxoimidazolidin-4-Yl) Methyl]-4'-Methyl[Biphenyl]-2-Carboxamide

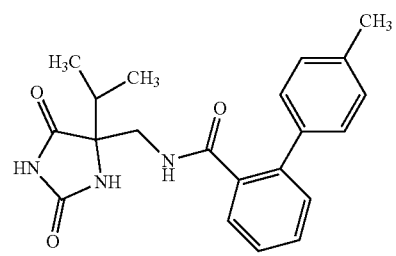 [SMILES: Cc1ccc(-c2ccccc2C(=O)NCC2(C(C)C)NC(=O)NC2=O)cc1]

To a solution of rac-5-(aminomethyl)-5-isopropylimidazolidine-2,4-dione hydrochloride (60.0 mg, 289 μmol) and 4'-methyl[1,1'-biphenyl]-2-carboxylic acid (61.3 mg, 289 µmol) in DMF (5.9 ml) was added 1-ethyl-3-(3-dimethylaminopropyl)carbodiimide hydrochloride (72.0 mg, 376 µmol), 1-hydroxybenzotriazole hydrate (57.5 mg, 376 µmol) and N,N-diisopropylethylamine (140 µl, 810 µmol). The reaction mixture was stirred overnight at room temperature and then concentrated under reduced pressure. The crude product was purified by preparative HPLC (Method 4f). After lyophilization, 99.4 mg (99% purity, 93% yield) of the desired product were obtained.

LC-MS (Method 8): $R_t$=0.80 min; MS (ESIpos): m/z=366 [M+H]$^+$ $^1$H-NMR (600 MHz, DMSO-d6) δ [ppm]: 0.794 (8.17), 0.805 (8.14), 0.873 (8.12), 0.884 (8.10), 1.822 (0.52), 1.833 (1.26), 1.844 (1.64), 1.856 (1.17), 1.867 (0.43), 2.322 (16.00), 3.355 (1.18), 3.365 (1.25), 3.377 (1.68), 3.388 (1.50), 3.473 (1.57), 3.483 (1.62), 3.495 (1.17), 3.506 (1.07), 7.186 (3.77), 7.199 (5.44), 7.249 (6.65), 7.263 (4.19), 7.325 (1.75), 7.339 (4.76), 7.353 (2.99), 7.360 (1.67), 7.372 (2.58), 7.384 (1.14), 7.461 (1.51), 7.463 (1.45), 7.473 (2.27), 7.475 (2.13), 7.486 (0.94), 7.488 (0.89), 7.663 (3.63), 8.199 (1.13), 8.209 (2.19), 8.219 (1.03), 10.648 (2.96).

Example 205

Ent-N-[(4-Isopropyl-2,5-Dioxoimidazolidin-4-Yl) Methyl]-4'-Methyl[Biphenyl]-2-Carboxamide

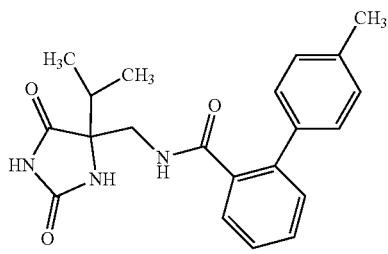 [SMILES: Cc1ccc(-c2ccccc2C(=O)NCC2(C(C)C)NC(=O)NC2=O)cc1]

Enantiomeric separation of rac-N-[(4-isopropyl-2,5-dioxoimidazolidin-4-yl)methyl]-4'-methyl[biphenyl]-2-carboxamide (99 mg) by preparative chiral SFC [column: Maisch Daicel AD-H 5 µm, 250×25 mm; eluent: carbon dioxide/methanol 75:25; flow rate: 80 ml/min; temperature: 40° C.; UV detection: 210 nm] afforded 35.6 mg (100% purity) of the desired product.

Analytical chiral SFC: $R_t$=2.26 min, e.e. =>99% [column: OJ 3 µm, 100×4.6 mm; eluent: carbon dioxide/methanol 80:20; flow rate: 3 ml/min; UV detection: 210 nm LC-MS (Method 7): $R_t$=1.60 min; MS (ESIpos): m/z=366 [M+H]$^+$ $^1$H-NMR (400 MHz, DMSO-d6) δ [ppm]: −0.008 (0.98), 0.008 (1.11), 0.791 (8.11), 0.808 (8.43), 0.869 (8.03), 0.886 (8.38), 1.809 (0.45), 1.826 (1.23), 1.843 (1.65), 1.860 (1.16), 1.877 (0.42), 2.322 (16.00), 2.523 (0.66), 3.345 (1.26), 3.361 (1.19), 3.379 (1.75), 3.395 (1.58), 3.464 (1.55), 3.479 (1.65), 3.498 (1.03), 3.514 (0.98), 7.182 (3.23), 7.201 (6.02), 7.246 (7.72), 7.251 (2.25), 7.267 (3.97), 7.319 (1.16), 7.322 (1.40), 7.337 (6.36), 7.341 (3.18), 7.354 (4.61), 7.356 (4.54), 7.372 (2.91), 7.375 (2.17), 7.391 (1.25), 7.394 (0.98), 7.455 (1.80), 7.459 (1.78), 7.473 (2.36), 7.478 (2.07), 7.492 (0.84), 7.496 (0.94), 7.653 (3.50), 8.181 (0.96), 8.196 (2.07), 8.211 (0.98), 10.641 (2.81).

Example 206

Rac-5-Fluoro-N-[(4-Isopropyl-2,5-Dioxoimidazolidin-4-Yl)Methyl]-4'-(Trifluoromethyl)[Biphenyl]-2-Carboxamide

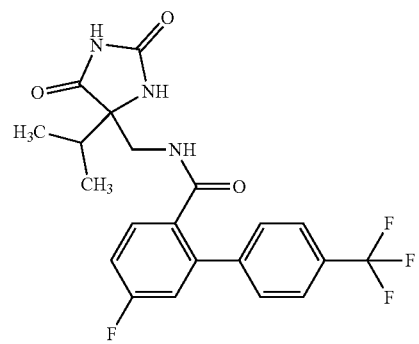 [SMILES: CC(C)C1(CNC(=O)c2ccc(F)cc2-c2ccc(C(F)(F)F)cc2)NC(=O)NC1=O]

To a solution of rac-5-(aminomethyl)-5-isopropylimidazolidine-2,4-dione hydrochloride (150 mg, 722 µmol) and 5-fluoro-4'-(trifluoromethyl)[1,1'-biphenyl]-2-carboxylic acid (205 mg, 722 µmol) in DMF (4.5 ml) was added 1-ethyl-3-(3-dimethylaminopropyl)carbodiimide hydrochloride (180 mg, 939 µmol), 1-hydroxybenzotriazole hydrate (144 mg, 939 µmol) and N,N-diisopropylethylamine (630 µl, 3.6 mmol). The reaction mixture was stirred for 3 days at room temperature and then concentrated under reduced pressure. The crude product was purified by preparative HPLC (Method 6f). After lyophilization, 198 mg (100% purity, 63% yield) of the desired product were obtained.

LC-MS (Method 7): $R_t$=1.68 min, MS (ESIpos): m/z=438 [M+H]$^+$ $^1$H-NMR (400 MHz, DMSO-d6) δ [ppm]: −0.008 (0.48), 0.008 (0.48), 0.793 (15.41), 0.810 (16.00), 0.879 (15.25), 0.896 (15.95), 1.834 (0.86), 1.851 (2.37), 1.868 (3.12), 1.885 (2.21), 1.902 (0.81), 2.367 (0.48), 2.524 (1.62), 2.558 (0.75), 2.710 (0.48), 3.356 (2.69), 3.371 (2.53), 3.390 (3.23), 3.405 (2.96), 3.505 (2.80), 3.521 (2.96), 3.539 (2.05), 3.555 (1.94), 7.301 (2.21), 7.307 (6.41), 7.315 (1.13), 7.330 (9.64), 7.350 (2.86), 7.357 (1.94), 7.452 (3.34), 7.466 (3.02), 7.472 (3.07), 7.487 (2.32), 7.569 (7.60), 7.589 (8.94), 7.746 (6.46), 7.768 (9.43), 7.788 (7.70), 8.464 (1.94), 8.480 (4.04), 8.495 (1.94), 10.674 (5.49).

Example 207

Ent-5-Fluoro-N-[(4-Isopropyl-2,5-Dioxoimidazolidin-4-Yl)Methyl]-4'-(Trifluoromethyl)[Biphenyl]-2-Carboxamide

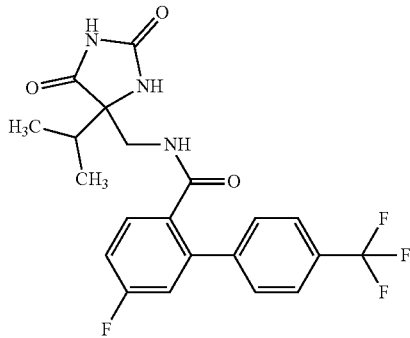 [SMILES: CC(C)C1(CNC(=O)c2ccc(F)cc2-c2ccc(C(F)(F)F)cc2)NC(=O)NC1=O]

Enantiomeric separation of rac-5-fluoro-N-[(4-isopropyl-2,5-dioxoimidazolidin-4-yl)methyl]-4'-(trifluoromethyl)[biphenyl]-2-carboxamide (198 mg) by preparative chiral SFC [column: Daicel Chiralpak ID 5 μm, 250×20 mm; eluent: carbon dioxide/isopropanol 82:18; flow rate: 80 ml/min; temperature: 40° C.; UV detection: 210 nm] afforded 63.6 mg (100% purity) of the desired product.

Analytical chiral SFC: $R_t$=1.74 min, e.e. =>99% [column: Daicel ID 3 μm, 100×4.6 mm; eluent: carbon dioxide/isopropanol 80:20; flow rate: 3 ml/min; UV detection: 210 nm]

LC-MS (Method 7): $R_t$=1.69 min; MS (ESIpos): m/z=438 [M+H]$^+$ $^1$H-NMR (600 MHz, DMSO-d6) δ [ppm]: 0.798 (15.81), 0.809 (16.00), 0.881 (15.68), 0.893 (15.98), 1.843 (1.00), 1.855 (2.49), 1.866 (3.25), 1.877 (2.38), 1.889 (0.89), 3.264 (1.71), 3.332 (0.64), 3.368 (2.36), 3.378 (2.41), 3.391 (3.16), 3.401 (2.92), 3.508 (3.00), 3.519 (3.09), 3.530 (2.30), 3.541 (2.17), 7.303 (4.29), 7.316 (4.08), 7.319 (4.79), 7.325 (4.39), 7.339 (2.23), 7.459 (3.27), 7.469 (3.59), 7.472 (3.32), 7.482 (2.74), 7.573 (8.42), 7.587 (9.51), 7.716 (7.80), 7.767 (9.75), 7.780 (8.52), 8.436 (2.23), 8.447 (4.40), 8.457 (2.23), 10.654 (6.46).

Example 208

Rac-N-[(4-Isopropyl-2,5-Dioxoimidazolidin-4-Yl)Methyl]-4'-(Trifluoromethyl)[Biphenyl]-2-Carboxamide

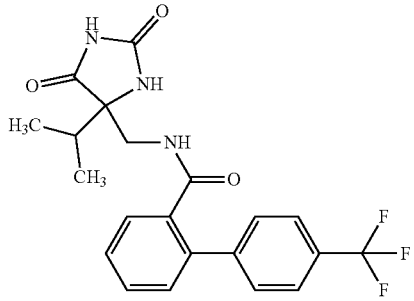 [SMILES: CC(C)C1(CNC(=O)c2ccccc2-c2ccc(C(F)(F)F)cc2)NC(=O)NC1=O]

To a solution of rac-5-(aminomethyl)-5-isopropylimidazolidine-2,4-dione hydrochloride (150 mg, 722 μmol) and 4'-(trifluoromethyl)[1,1'-biphenyl]-2-carboxylic acid (192 mg, 722 μmol) in DMF (4.5 ml) was added 1-ethyl-3-(3-dimethylaminopropyl)carbodiimide hydrochloride (180 mg, 939 μmol), 1-hydroxybenzotriazole hydrate (144 mg, 939 μmol) and N,N-diisopropylethylamine (630 μl, 3.6 mmol). The reaction mixture was stirred for 3 days at room temperature and then concentrated under reduced pressure. The crude product was purified by preparative HPLC (Method 6f). After lyophilization, 302 mg (100% purity, 99.6% yield) of the desired product were obtained.

LC-MS (Method 7): $R_t$=1.62 min; MS (ESIpos): m/z=420 [M+H]$^+$ $^1$H-NMR (400 MHz, DMSO-d6) δ [ppm]: 0.793 (15.36), 0.810 (16.00), 0.878 (15.18), 0.895 (15.90), 1.824 (0.87), 1.841 (2.35), 1.858 (3.13), 1.875 (2.22), 1.892 (0.80), 2.524 (0.58), 3.369 (2.14), 3.385 (2.24), 3.404 (3.19), 3.419 (2.90), 3.506 (2.84), 3.522 (3.01), 3.540 (2.00), 3.556 (1.89), 7.410 (2.61), 7.414 (3.25), 7.418 (4.08), 7.421 (4.39), 7.429 (6.12), 7.432 (6.36), 7.437 (5.81), 7.440 (6.26), 7.447 (3.50), 7.451 (3.36), 7.466 (5.29), 7.469 (4.24), 7.484 (2.43), 7.488 (1.98), 7.525 (3.67), 7.530 (3.62), 7.544 (5.56), 7.549 (8.22), 7.551 (8.26), 7.563 (3.09), 7.572 (9.00), 7.722 (6.24), 7.724 (6.26), 7.752 (9.22), 7.773 (7.60), 8.413 (1.91), 8.429 (4.00), 8.444 (1.91), 10.671 (5.35).

Example 209

Ent-N-[(4-Isopropyl-2,5-Dioxoimidazolidin-4-Yl)Methyl]-4'-(Trifluoromethyl)[Biphenyl]-2-Carboxamide

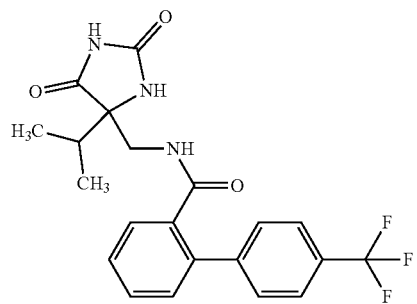 [SMILES: CC(C)C1(CNC(=O)c2ccccc2-c2ccc(C(F)(F)F)cc2)NC(=O)NC1=O]

Enantiomeric separation of rac-N-[(4-isopropyl-2,5-dioxoimidazolidin-4-yl)methyl]-4'-(trifluoromethyl)[biphenyl]-2-carboxamide (302 mg) by preparative chiral SFC [column: Daicel Chiralpak AD-H 5 μm SFC, 250×30 mm; eluent: carbon dioxide/isopropanol 72:28; flow rate: 90 ml/min; temperature: 38° C.; UV detection: 210 nm] afforded 138 mg (99% purity) of the desired product.

Analytical chiral SFC: $R_t$=2.76 min, e.e.=92.7% [column: AD-3, 50×4.6 mm; eluent: carbon dioxide (95%→50%)/isopropanol (5%→50%); flow rate: 3 ml/min; UV detection: 220 nm]

LC-MS (Method 8): $R_t$=0.88 min; MS (ESIpos): m/z=420 [M+H]$^+$ $^1$H-NMR (400 MHz, DMSO-d6) δ [ppm]: −0.007 (1.16), 0.008 (1.35), 0.793 (15.39), 0.810 (16.00), 0.878 (15.22), 0.896 (15.82), 0.988 (1.02), 1.003 (1.03), 1.030 (1.92), 1.046 (1.93), 1.236 (0.82), 1.824 (0.90), 1.841 (2.35), 1.858 (3.15), 1.875 (2.23), 1.892 (0.80), 3.369 (2.02), 3.384 (2.17), 3.403 (3.21), 3.419 (2.96), 3.506 (2.93), 3.522 (3.09), 3.541 (2.06), 3.556 (2.01), 7.414 (3.36), 7.421 (4.69), 7.429 (6.32), 7.432 (6.57), 7.439 (6.57), 7.450 (3.34), 7.466 (4.85), 7.485 (2.18), 7.526 (3.24), 7.529 (3.28), 7.551 (8.95), 7.572 (9.43), 7.724 (6.91), 7.752 (9.58), 7.773 (7.89), 8.414 (2.00), 8.429 (4.13), 8.444 (1.99), 10.671 (5.89).

Example 210

Ent-6-Fluoro-N-[(4-Isopropyl-2,5-Dioxoimidazolidin-4-Yl)Methyl]-4'-(Trifluoromethyl)[Biphenyl]-2-Carboxamide

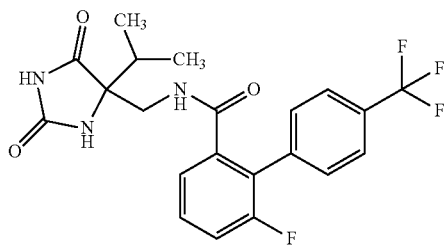 [SMILES: CC(C)C1(CNC(=O)c2cccc(F)c2-c2ccc(C(F)(F)F)cc2)NC(=O)NC1=O]

To a solution of ent-5-(aminomethyl)-5-isopropylimidazolidine-2,4-dione hydrochloride (100 mg, 482 μmol) and 6-fluoro-4'-(trifluoromethyl)[1,1'-biphenyl]-2-carboxylic acid (295 mg, 46% purity, 482 μmol) in DMF (2.7 ml) was added 1-ethyl-3-(3-dimethylaminopropyl)carbodiimide hydrochloride (120 mg, 626 μmol), 1-hydroxybenzotriazole hydrate (95.9 mg, 626 μmol) and N,N-diisopropylethylamine (420 μl, 2.4 mmol). The reaction mixture was stirred overnight at room temperature and concentrated under reduced pressure. The crude product was first purified by preparative HPLC (Method 2f). A second purification by preparative HPLC (Method 4f) gave, after lyophilization, 26.2 mg (100% purity, 12% yield) of the desired product were obtained.

LC-MS (Method 7): $R_t$=1.66 min; MS (ESIpos): m/z=438 [M+H]$^+$ $^1$H-NMR (500 MHz, DMSO-d6) δ [ppm]: 0.766 (15.65), 0.779 (16.00), 0.845 (15.49), 0.859 (15.92), 1.775 (0.89), 1.789 (2.35), 1.802 (3.13), 1.816 (2.21), 1.830 (0.78), 3.332 (2.68), 3.347 (3.35), 3.360 (2.97), 3.423 (3.00), 3.436 (3.17), 3.450 (2.05), 3.463 (1.91), 7.246 (4.84), 7.248 (4.81), 7.261 (5.34), 7.263 (5.02), 7.408 (2.01), 7.410 (2.05), 7.424 (3.14), 7.427 (3.69), 7.430 (2.29), 7.444 (2.79), 7.446 (2.54), 7.506 (2.42), 7.517 (3.40), 7.523 (8.92), 7.534 (4.12), 7.539 (7.98), 7.549 (1.92), 7.713 (7.73), 7.774 (8.86), 7.791 (7.71), 8.427 (1.90), 8.439 (3.87), 8.452 (1.81), 10.665 (3.64).

Example 211

Ent-N-[(4-Isopropyl-2,5-Dioxoimidazolidin-4-Yl)Methyl]-2-[6-(Trifluoromethyl)Pyridin-3-Yl]Benzamide

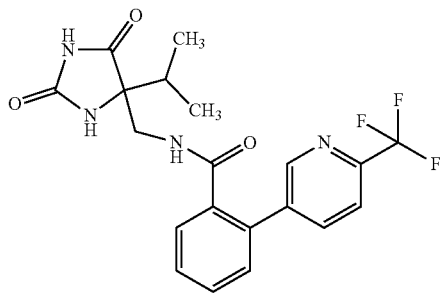 [SMILES: CC(C)C1(CNC(=O)c2ccccc2-c2ccc(C(F)(F)F)nc2)NC(=O)NC1=O]

To a solution of ent-5-(aminomethyl)-5-isopropylimidazolidine-2,4-dione hydrochloride (100 mg, 482 μmol) and 2-[6-(trifluoromethyl)pyridin-3-yl]benzoic acid (154 mg, 578 μmol) in DMF (4.0 ml) was added 1-ethyl-3-(3-dimethylaminopropyl)carbodiimide hydrochloride (120 mg, 626 μmol), 1-hydroxybenzotriazole hydrate (95.9 mg, 626 μmol) and N,N-diisopropylethylamine (420 μl, 2.4 mmol). The reaction mixture was stirred overnight at room temperature and then concentrated under reduced pressure. The crude product was purified by preparative HPLC (Method 3f). After lyophilization, 129 mg (100% purity, 64% yield) of the desired product were obtained.

LC-MS (Method 8): $R_t$=0.72 min, MS (ESIpos): m/z=421 [M+H]$^+$ $^1$H-NMR (600 MHz, DMSO-d6) δ [ppm]: 0.799 (15.92), 0.810 (16.00), 0.885 (15.79), 0.897 (15.98), 1.859 (0.92), 1.870 (2.40), 1.882 (3.16), 1.893 (2.22), 1.904 (0.80), 2.069 (0.78), 2.383 (0.41), 2.422 (0.49), 2.469 (0.70), 2.514 (0.70), 2.517 (0.70), 2.520 (0.60), 2.611 (0.41), 2.651 (0.43), 3.262 (1.17), 3.371 (2.26), 3.381 (2.42), 3.394 (3.14), 3.404 (2.79), 3.513 (2.86), 3.524 (2.94), 3.536 (2.24), 3.547 (2.10), 7.475 (3.16), 7.477 (3.31), 7.488 (5.20), 7.490 (4.99), 7.507 (3.92), 7.519 (5.59), 7.524 (2.85), 7.534 (5.24), 7.536 (4.21), 7.547 (2.61), 7.549 (2.05), 7.583 (3.51), 7.586 (3.37), 7.596 (4.58), 7.598 (4.38), 7.608 (1.77), 7.611 (1.68), 7.719 (5.75), 7.929 (4.00), 7.943 (7.44), 7.970 (4.15), 7.973 (3.94), 7.983 (2.09), 7.987 (2.10), 8.485 (1.85), 8.496 (3.74), 8.506 (1.79), 8.732 (5.57), 8.735 (5.46), 10.651 (4.87).

Example 212

Ent-4-Fluoro-N-[(4-Isopropyl-2,5-Dioxoimidazolidin-4-Yl)Methyl]-4'-(Trifluoromethyl)[Biphenyl]-2-Carboxamide

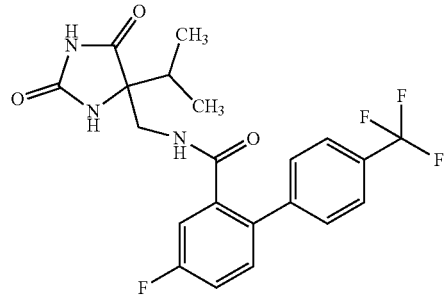 [SMILES: CC(C)C1(CNC(=O)c2cc(F)ccc2-c2ccc(C(F)(F)F)cc2)NC(=O)NC1=O]

To a solution of ent-5-(aminomethyl)-5-isopropylimidazolidine-2,4-dione hydrochloride (100 mg, 482 μmol) and 4-fluoro-4'-(trifluoromethyl)[1,1'-biphenyl]-2-carboxylicacid (164 mg, 578 μmol) in DMF (4.0 ml) was added 1-ethyl-3-(3-dimethylaminopropyl)carbodiimide hydrochloride (120 mg, 626 μmol), 1-hydroxybenzotriazole hydrate (95.9 mg, 626 μmol) and N,N-diisopropylethylamine (420 μl, 2.4 mmol). The reaction mixture was stirred overnight at room temperature and then concentrated under reduced pressure. The crude product was purified by preparative HPLC (Method 4f). After lyophilization, 111 mg (100% purity, 53% yield) of the desired product were obtained.

LC-MS (Method 8): $R_t$=0.86 min, MS (ESIpos): m/z=438 [M+H]$^+$ $^1$H-NMR (600 MHz, DMSO-d6) δ [ppm]: 0.804 (15.73), 0.815 (16.00), 0.887 (15.60), 0.898 (15.93), 1.855 (0.90), 1.866 (2.34), 1.877 (3.13), 1.888 (2.25), 1.900 (0.82), 2.731 (0.43), 3.329 (0.52), 3.372 (2.22), 3.382 (2.43), 3.395 (3.11), 3.405 (2.83), 3.516 (2.85), 3.527 (2.98), 3.539 (2.24), 3.549 (2.13), 7.219 (3.27), 7.223 (3.72), 7.234 (3.26), 7.238 (3.50), 7.381 (1.58), 7.386 (1.65), 7.395 (3.56), 7.400 (3.64), 7.410 (2.14), 7.414 (2.14), 7.469 (3.74), 7.478 (3.87), 7.483 (3.03), 7.492 (2.75), 7.533 (7.55), 7.547 (8.15), 7.750 (14.62), 7.764 (7.65), 8.554 (1.93), 8.565 (3.85), 8.575 (1.86), 10.681 (4.90).

Example 213

Ent-4,5-Difluoro-N-[(4-Isopropyl-2,5-Dioxoimidazolidin-4-Yl)Methyl]-4'-(Trifluoromethyl)[Biphenyl]-2-Carboxamide

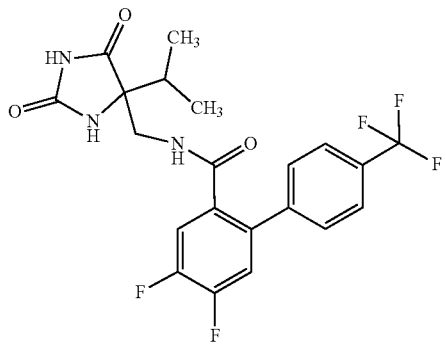 [SMILES: CC(C)C1(CNC(=O)c2cc(F)c(F)cc2-c2ccc(C(F)(F)F)cc2)NC(=O)NC1=O]

To a solution of ent-5-(aminomethyl)-5-isopropylimidazolidine-2,4-dione hydrochloride (100 mg, 482 µmol) and 4,5-difluoro-4'-(trifluoromethyl)[1,1'-biphenyl]-2-carboxylic acid (175 mg, 578 µmol) in DMF (4.0 ml) was added 1-ethyl-3-(3-dimethylaminopropyl)carbodiimide hydrochloride (120 mg, 626 µmol), 1-hydroxybenzotriazole hydrate (95.9 mg, 626 µmol) and N,N-diisopropylethylamine (420 µl, 2.4 mmol). The reaction mixture was stirred overnight at room temperature and then concentrated under reduced pressure. The crude product was purified by preparative HPLC (Method 4f). After lyophilization, 125 mg (100% purity, 57% yield) of the desired product were obtained.

LC-MS (Method 8): $R_t$=0.89 min, MS (ESIpos): m/z=456 [M+H]$^+$ $^1$H-NMR (600 MHz, DMSO-d6) δ [ppm]: 0.804 (15.62), 0.815 (16.00), 0.886 (15.54), 0.897 (15.92), 1.857 (0.89), 1.869 (2.32), 1.880 (3.13), 1.891 (2.20), 1.903 (0.82), 2.514 (0.61), 2.517 (0.61), 2.520 (0.46), 3.259 (0.44), 3.261 (0.51), 3.263 (0.52), 3.366 (2.26), 3.376 (2.40), 3.389 (3.08), 3.399 (2.73), 3.512 (2.76), 3.523 (2.89), 3.535 (2.20), 3.546 (2.07), 7.451 (2.18), 7.465 (2.61), 7.469 (2.50), 7.482 (2.33), 7.551 (7.26), 7.564 (8.10), 7.570 (2.71), 7.583 (2.48), 7.590 (2.45), 7.602 (2.36), 7.767 (12.01), 7.780 (7.55), 8.559 (1.86), 8.569 (3.73), 8.580 (1.83), 10.684 (4.81).

Example 214

Ent-5,6-Difluoro-N-[(4-Isopropyl-2,5-Dioxoimidazolidin-4-Yl)Methyl]-4'-(Trifluoromethyl)[Biphenyl]-2-Carboxamide

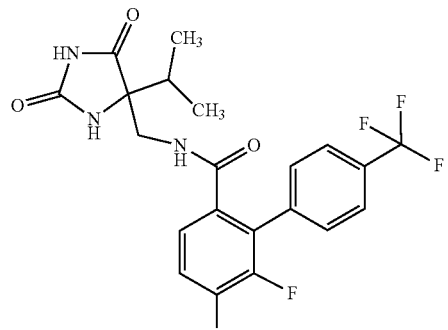

To a solution of ent-5-(aminomethyl)-5-isopropylimidazolidine-2,4-dione hydrochloride (100 mg, 482 µmol) and 5,6-difluoro-4'-(trifluoromethyl)[1,1'-biphenyl]-2-carboxylic acid (175 mg, 578 µmol) in DMF (3.0 ml) was added 1-ethyl-3-(3-dimethylaminopropyl)carbodiimide hydrochloride (120 mg, 626 µmol), 1-hydroxybenzotriazole hydrate (95.9 mg, 626 µmol) and N,N-diisopropylethylamine (420 µl, 2.4 mmol). The reaction mixture was stirred overnight at room temperature and then concentrated under reduced pressure. The crude product was purified by preparative HPLC (Method 9f). After lyophilization, 117 mg (100% purity, 53% yield) of the desired product were obtained.

LC-MS (Method 12): $R_t$=2.78 min; MS (ESIpos): m/z=456 [M+H]$^+$ $^1$H-NMR (600 MHz, DMSO-d6) δ [ppm]: 0.005 (1.38), 0.771 (15.62), 0.782 (16.00), 0.848 (15.50), 0.859 (15.94), 1.790 (0.91), 1.802 (2.36), 1.813 (3.14), 1.825 (2.27), 1.836 (0.86), 2.518 (0.69), 3.281 (0.53), 3.332 (5.54), 3.345 (4.29), 3.355 (3.36), 3.424 (2.96), 3.435 (3.12), 3.447 (2.14), 3.457 (2.02), 7.270 (1.85), 7.278 (2.01), 7.285 (2.21), 7.292 (2.10), 7.554 (6.89), 7.567 (7.71), 7.587 (2.30), 7.603 (2.40), 7.617 (1.25), 7.692 (0.85), 7.702 (6.12), 7.803 (8.66), 7.817 (7.99), 8.426 (1.96), 8.436 (3.99), 8.446 (1.98), 10.653 (5.32).

Example 215

5-Chloro-N-{[(4R)-4-Cyclopropyl-2,5-Dioxoimidazolidin-4-Yl]Methyl}-4'-Methyl[Biphenyl]-2-Carboxamide

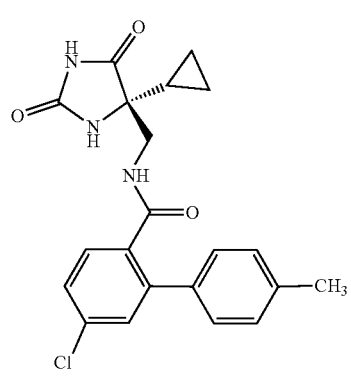 [SMILES: Cc1ccc(-c2cc(Cl)ccc2C(=O)NC[C@@]2(C3CC3)NC(=O)NC2=O)cc1]

To a solution of (5R)-5-(aminomethyl)-5-cyclopropylimidazolidine-2,4-dione hydrochloride (100 mg, 486 µmol) and 5-chloro-4'-methyl[1,1'-biphenyl]-2-carboxylic acid (175 mg, 709 µmol) in DMF (3.7 ml) was added 1-ethyl-3-(3-dimethylaminopropyl)carbodiimide hydrochloride (147 mg, 768 µmol), 1-hydroxybenzotriazole hydrate (118 mg, 768 µmol) and N,N-diisopropylethylamine (510 µl, 2.9 mmol). The reaction mixture was stirred overnight at room temperature and then concentrated under reduced pressure. The crude product was purified by preparative HPLC (Method 4f). After lyophilization, 124 mg (100% purity, 64% yield) of the desired product were obtained.

LC-MS (Method 7): $R_t$=1.66 min; MS (ESIpos): m/z=398 [M+H]$^+$ $^1$H-NMR (400 MHz, DMSO-d6) δ [ppm]: −0.008 (1.42), 0.008 (1.24), 0.106 (0.71), 0.117 (1.27), 0.130 (1.31), 0.140 (0.94), 0.154 (0.42), 0.293 (0.45), 0.301 (0.80), 0.313 (0.99), 0.324 (0.95), 0.335 (0.72), 0.346 (0.55), 0.360 (0.46), 0.371 (0.81), 0.386 (0.88), 0.393 (1.22), 0.407 (1.01), 0.414 (0.99), 0.427 (1.25), 0.438 (1.23), 0.451 (1.15), 0.463 (0.70), 1.024 (0.42), 1.037 (0.85), 1.044 (0.91), 1.050 (0.67), 1.058 (1.56), 1.065 (0.64), 1.071 (0.83), 1.078 (0.74), 2.325 (16.00), 2.523 (0.91), 2.526 (0.70), 3.463 (2.86), 3.468 (2.84), 3.478 (2.74), 3.483 (2.72), 7.198 (3.41), 7.218 (6.01), 7.268 (7.63), 7.288 (4.15), 7.348 (3.79), 7.369 (5.20), 7.403 (4.32), 7.409 (5.06), 7.458 (3.41), 7.464 (2.82), 7.479 (2.40), 7.484 (2.16), 7.501 (4.18), 8.407 (1.03), 8.422 (2.20), 8.438 (1.02), 10.623 (2.99).

Example 216

5-Chloro-N-{[(4R)-4-Cyclopropyl-2,5-Dioxoimidazolidin-4-Yl]Methyl}-4'-(Trifluoromethyl)[1,1'-Biphenyl]-2-Carboxamide

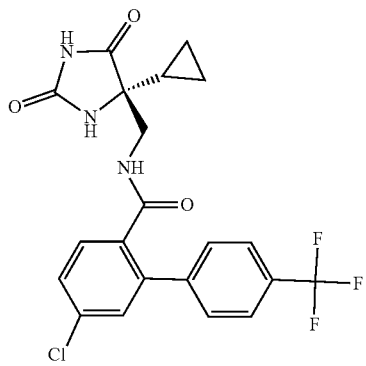 [SMILES: O=C1NC(=O)[C@](CNC(=O)c2ccc(Cl)cc2-c2ccc(C(F)(F)F)cc2)(C2CC2)N1]

To a solution of (5R)-5-(aminomethyl)-5-cyclopropylimidazolidine-2,4-dione hydrochloride (100 mg, 486 µmol) and 5-chloro-4'-(trifluoromethyl)[1,1'-biphenyl]-2-carboxylic acid (213 mg, 709 µmol) in DMF (3.7 ml) was added 1-ethyl-3-(3-dimethylaminopropyl)carbodiimide hydrochloride (147 mg, 768 µmol), 1-hydroxybenzotriazole hydrate (118 mg, 768 µmol) and N,N-diisopropylethylamine (510 µl, 2.9 mmol). The reaction mixture was stirred overnight at room temperature and then concentrated under reduced pressure. The crude product was purified by preparative HPLC (Method 4f). After lyophilization, 158 mg (99% purity, 71% yield) of the desired product were obtained.

LC-MS (Method 7): $R_t$=1.78 min, MS (ESIpos): m/z=452 [M+H]$^+$ $^1$H-NMR (600 MHz, DMSO-d6) δ [ppm]: −0.008 (0.45), 0.248 (0.43), 0.310 (0.46), 0.318 (0.43), 0.923 (0.52), 2.350 (5.08), 2.389 (11.86), 3.145 (16.00), 3.346 (0.90), 3.352 (1.02), 3.355 (0.96), 3.362 (0.83), 7.299 (1.07), 7.312 (1.33), 7.365 (1.37), 7.368 (1.39), 7.388 (1.35), 7.409 (0.88), 7.412 (0.72), 7.425 (1.94), 7.438 (1.63), 7.615 (1.66), 7.628 (1.44), 8.457 (0.76), 10.486 (1.11).

Example 217

N-{[(4R)-4-Cyclopropyl-2,5-Dioxoimidazolidin-4-Yl]Methyl}-4'-(Methanesulfonyl)[1,1'-Biphenyl]-2-Carboxamide

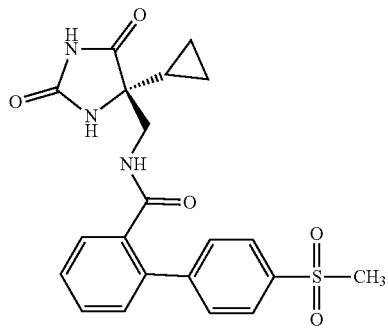 [SMILES: CS(=O)(=O)c1ccc(-c2ccccc2C(=O)NC[C@@]2(C3CC3)NC(=O)NC2=O)cc1]

To a solution of (5R)-5-(aminomethyl)-5-cyclopropylimidazolidine-2,4-dione hydrochloride (100 mg, 486 µmol) and 4'-(methanesulfonyl)[1,1'-biphenyl]-2-carboxylic acid (196 mg, 709 µmol) in DMF (3.7 ml) was added 1-ethyl-3-(3-dimethylaminopropyl)carbodiimide hydrochloride (147 mg, 768 µmol), 1-hydroxybenzotriazole hydrate (118 mg, 768 µmol) and N,N-diisopropylethylamine (510 µl, 2.9 mmol). The reaction mixture was stirred overnight at room temperature and then concentrated under reduced pressure. The crude product was purified by preparative HPLC (Method 3f). After lyophilization, 147 mg (100% purity, 71% yield) of the desired product were obtained.

LC-MS (Method 7): $R_t$=1.06 min, MS (ESIpos): m/z=428 [M+H]$^+$ $^1$H-NMR (400 MHz, DMSO-d6) δ [ppm]: 0.122 (0.44), 0.133 (0.80), 0.145 (0.88), 0.156 (0.59), 0.316 (0.50), 0.329 (0.63), 0.339 (0.59), 0.351 (0.48), 0.383 (0.50), 0.397 (0.55), 0.405 (0.75), 0.419 (0.59), 0.446 (0.67), 0.458 (0.79), 0.471 (0.75), 0.483 (0.46), 1.061 (0.54), 1.068 (0.57), 1.074 (0.41), 1.081 (0.99), 1.089 (0.41), 1.094 (0.53), 1.102 (0.48), 2.523 (0.84), 3.255 (16.00), 3.507 (1.86), 3.511 (1.86), 3.522 (1.78), 3.527 (1.78), 7.433 (1.39), 7.442 (0.99), 7.452 (2.09), 7.456 (2.18), 7.460 (2.14), 7.468 (1.20), 7.471 (1.16), 7.486 (1.73), 7.488 (1.42), 7.505 (0.82), 7.508 (0.76), 7.522 (2.45), 7.537 (1.30), 7.542 (1.20), 7.556 (1.39), 7.560 (1.34), 7.574 (0.62), 7.579 (0.68), 7.587 (3.90), 7.592 (1.39), 7.604 (1.48), 7.608 (4.35), 7.936 (4.35), 7.940 (1.39), 7.952 (1.37), 7.957 (3.81), 8.542 (0.67), 8.558 (1.43), 8.573 (0.66), 10.641 (1.83).

Example 218

N-{[(4R)-4-Cyclopropyl-2,5-Dioxoimidazolidin-4-Yl]Methyl}-5-Methyl-4'-(Trifluoromethyl)[Biphenyl]-2-Carboxamide

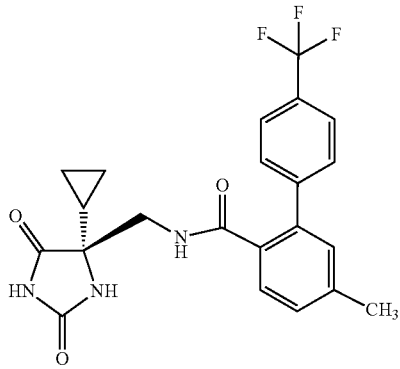 [SMILES: Cc1ccc(C(=O)NC[C@@]2(C3CC3)NC(=O)NC2=O)c(-c2ccc(C(F)(F)F)cc2)c1]

To a solution of (5R)-5-(aminomethyl)-5-cyclopropylimidazolidine-2,4-dione hydrochloride (50.0 mg, 243 µmol) and 5-methyl-4'-(trifluoromethyl)[1,1'-biphenyl]-2-carboxylic acid (68.1 mg, 243 µmol) in DMF (3.3 ml) was added 1-ethyl-3-(3-dimethylaminopropyl)carbodiimide hydrochloride (60.6 mg, 316 µmol), 1-hydroxybenzotriazole hydrate (48.4 mg, 316 µmol) and N,N-diisopropylethylamine (120 µl, 680 µmol). The reaction mixture was stirred overnight at room temperature and then concentrated under reduced pressure. The crude product was purified by preparative HPLC (Method 4f). After lyophilization, 83.5 mg (100% purity, 80% yield) of the desired product were obtained.

LC-MS (Method 7): $R_t$=1.75 min, MS (ESIpos): m/z=432 [M+H]$^+$ $^1$H-NMR (600 MHz, DMSO-d6) δ [ppm]: 0.122 (0.72), 0.130 (1.25), 0.138 (1.28), 0.146 (0.90), 0.155 (0.41), 0.303 (0.43), 0.309 (0.81), 0.316 (1.00), 0.323 (0.89), 0.332 (0.67), 0.339 (0.48), 0.370 (0.41), 0.377 (0.73), 0.384 (0.80), 0.386 (0.81), 0.392 (1.13), 0.401 (0.86), 0.406 (0.52), 0.441 (0.43), 0.449 (0.95), 0.457 (1.26), 0.466 (1.20), 0.474 (0.79), 1.042 (0.43), 1.051 (0.84), 1.056 (0.91), 1.060 (0.61), 1.065 (1.56), 1.070 (0.61), 1.074 (0.82), 1.079 (0.78), 2.383 (16.00), 3.462 (0.87), 3.472 (0.98), 3.485 (1.98), 3.495 (1.78), 3.516 (1.84), 3.527 (1.95), 3.538 (0.93), 3.550 (0.88), 7.250 (3.85), 7.268 (1.75), 7.281 (2.28), 7.351 (4.18), 7.364 (3.03), 7.507 (4.70), 7.529 (4.06), 7.543 (4.41), 7.739 (4.66), 7.753 (4.08), 8.442 (1.10), 8.453 (2.12), 8.463 (1.08), 10.648 (2.72).

Example 219

N-{[(4R)-4-Cyclopropyl-2,5-Dioxoimidazolidin-4-Yl]Methyl}-4-Fluoro-4-Methyl[Biphenyl]-2-Carboxamide

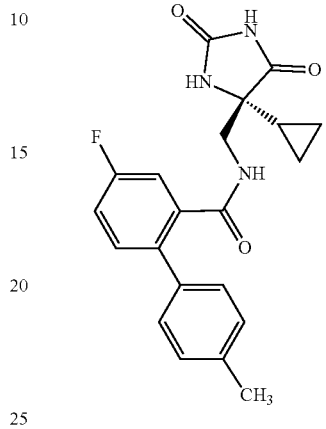

To a solution of (5R)-5-(aminomethyl)-5-cyclopropylimidazolidine-2,4-dione hydrochloride (100 mg, 486 µmol) and 4-fluoro-4'-methyl[1,1'-biphenyl]-2-carboxylic acid (134 mg, 584 µmol) in DMF (3.0 ml) was added 1-ethyl-3-(3-dimethylaminopropyl)carbodiimide hydrochloride (121 mg, 632 µmol), 1-hydroxybenzotriazole hydrate (96.8 mg, 632 µmol) and N,N-diisopropylethylamine (420 µl, 2.4 mmol). The reaction mixture was stirred for 2 days at 40° C. and then concentrated under reduced pressure. The crude product was purified by preparative HPLC (Method 4f). After lyophilization, 122.5 mg (99% purity, 65% yield) of the desired product were obtained.

LC-MS (Method 7): $R_t$=1.51 min, MS (ESIpos): m/z=382 [M+H]$^+$ $^1$H-NMR (600 MHz, DMSO-d6) δ [ppm]: 0.119 (0.78), 0.126 (1.26), 0.135 (1.27), 0.143 (0.90), 0.312 (0.85), 0.319 (1.06), 0.327 (0.92), 0.334 (0.65), 0.342 (0.44), 0.378 (0.41), 0.386 (0.74), 0.395 (0.83), 0.401 (1.19), 0.410 (0.88), 0.416 (0.55), 0.435 (0.46), 0.443 (1.01), 0.451 (1.24), 0.459 (1.19), 0.468 (0.81), 1.045 (0.42), 1.054 (0.83), 1.059 (0.88), 1.067 (1.50), 1.076 (0.81), 1.081 (0.74), 2.316 (16.00), 2.327 (1.31), 2.501 (15.88), 3.302 (0.44), 3.363 (0.90), 3.458 (0.48), 3.471 (2.41), 3.478 (2.96), 3.488 (2.35), 3.500 (0.41), 3.511 (0.41), 7.146 (1.61), 7.150 (1.82), 7.161 (1.63), 7.165 (1.73), 7.182 (3.36), 7.196 (5.95), 7.228 (6.88), 7.241 (3.70), 7.314 (0.80), 7.319 (0.80), 7.328 (1.75), 7.333 (1.79), 7.343 (1.10), 7.347 (1.10), 7.385 (1.93), 7.394 (2.00), 7.399 (1.43), 7.408 (1.26), 7.539 (3.98), 8.489 (1.08), 8.499 (2.14), 8.509 (1.04), 10.656 (2.55).

Example 220

4'-Chloro-N-{[(4R)-4-Cyclopropyl-2,5-Dioxoimidazolidin-4-Yl]Methyl}[1,1'-Biphenyl]-2-Carboxamide

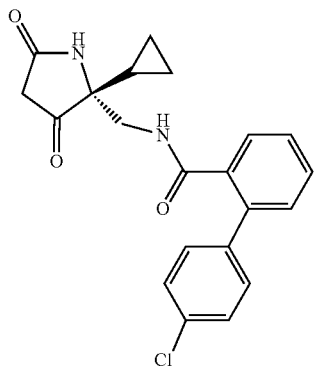 [SMILES: O=C1CC(=O)[C@](CNC(=O)c2ccccc2-c2ccc(Cl)cc2)(C2CC2)N1]

To a solution of (5R)-5-(aminomethyl)-5-cyclopropylimidazolidine-2,4-dione hydrochloride (70.0 mg, 340 µmol) and 4'-chloro[1,1'-biphenyl]-2-carboxylic acid (79.2 mg, 340 µmol) in DMF (7.0 ml) was added 1-ethyl-3-(3-dimethylaminopropyl)carbodiimide hydrochloride (84.8 mg, 443 µmol), 1-hydroxybenzotriazole hydrate (67.8 mg, 443 µmol) and N,N-diisopropylethylamine (170 µl, 950 µmol). The reaction mixture was stirred overnight at room temperature and then concentrated under reduced pressure. The crude product was purified by preparative HPLC (Method 3f). After lyophilization, 89.4 mg (100% purity, 68% yield)

LC-MS (Method 8): $R_t$=0.85 min, MS (ESIpos): m/z=384 [M+H]$^+$ $^1$H-NMR (400 MHz, DMSO-d6) δ [ppm]: 0.106 (0.55), 0.120 (1.40), 0.131 (2.37), 0.144 (2.53), 0.155 (1.82), 0.167 (0.82), 0.291 (0.46), 0.313 (1.50), 0.326 (1.94), 0.336 (1.84), 0.347 (1.39), 0.358 (1.03), 0.372 (0.83), 0.383 (1.45), 0.397 (1.66), 0.405 (2.29), 0.419 (1.75), 0.433 (1.21), 0.447 (2.05), 0.458 (2.36), 0.471 (2.27), 0.483 (1.40), 0.497 (0.50), 1.036 (0.73), 1.049 (1.54), 1.056 (1.68), 1.069 (2.84), 1.077 (1.21), 1.083 (1.57), 1.090 (1.41), 1.103 (0.63), 3.459 (0.59), 3.474 (0.76), 3.493 (4.70), 3.501 (5.12), 3.508 (5.03), 3.517 (4.65), 3.535 (0.75), 3.551 (0.67), 7.353 (8.99), 7.375 (16.00), 7.399 (11.34), 7.425 (4.97), 7.444 (15.56), 7.466 (8.80), 7.490 (3.26), 7.495 (3.32), 7.508 (12.54), 7.526 (1.69), 7.531 (1.64), 8.444 (1.91), 8.459 (3.99), 8.474 (1.90), 10.629 (1.65).

Example 221

N-{[(4R)-4-Cyclopropyl-2,5-Dioxoimidazolidin-4-Yl]Methyl}-3'-Fluoro-4'-Methyl[1,1'-Biphenyl]-2-Carboxamide

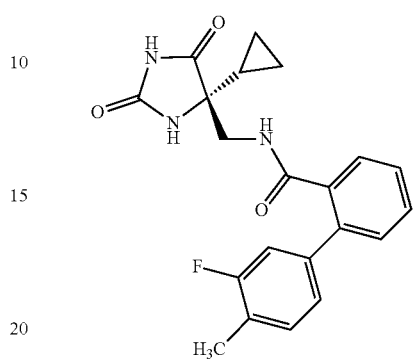

To a solution of (5R)-5-(aminomethyl)-5-cyclopropylimidazolidine-2,4-dione hydrochloride (50.0 mg, 243 µmol) and 3'-fluoro-4'-methyl[1,1'-biphenyl]-2-carboxylic acid (56.0 mg, 243 µmol) in DMF (2.1 ml) was added 1-ethyl-3-(3-dimethylaminopropyl)carbodiimide hydrochloride (60.6 mg, 316 µmol), 1-hydroxybenzotriazole hydrate (48.4 mg, 316 µmol) and N,N-diisopropylethylamine (120 µl, 680 µmol). The reaction mixture was stirred overnight at room temperature and then concentrated under reduced pressure. The crude product was purified by preparative HPLC (Method 4f). After lyophilization, 77.5 mg (100% purity, 84% yield) of the desired product were obtained.

LC-MS (Method 8): $R_t$=0.82 min, MS (ESIpos): m/z=382 [M+H]$^+$ $^1$H-NMR (400 MHz, DMSO-d6) δ [ppm]: −0.008 (2.13), −0.007 (1.26), 0.006 (1.56), 0.008 (2.36), 0.096 (0.52), 0.109 (1.15), 0.120 (2.08), 0.133 (2.18), 0.145 (1.64), 0.157 (0.73), 0.279 (0.45), 0.294 (0.75), 0.301 (1.28), 0.314 (1.61), 0.325 (1.53), 0.336 (1.18), 0.347 (0.88), 0.366 (0.73), 0.377 (1.31), 0.388 (1.30), 0.392 (1.38), 0.399 (1.99), 0.413 (1.79), 0.431 (1.88), 0.442 (2.03), 0.455 (1.88), 0.467 (1.16), 1.034 (0.68), 1.047 (1.41), 1.055 (1.48), 1.061 (1.05), 1.068 (2.61), 1.076 (1.01), 1.081 (1.36), 1.089 (1.25), 1.102 (0.53), 2.247 (16.00), 2.250 (15.85), 2.322 (0.45), 2.327 (0.63), 2.332 (0.45), 2.366 (0.53), 2.523 (2.34), 2.665 (0.45), 2.669 (0.61), 2.674 (0.47), 2.709 (0.52), 3.453 (0.55), 3.472 (4.74), 3.477 (4.75), 3.488 (4.59), 3.493 (4.64), 3.511 (0.52), 3.527 (0.43), 7.072 (3.09), 7.077 (3.61), 7.092 (3.51), 7.096 (4.45), 7.113 (3.57), 7.118 (2.79), 7.141 (3.32), 7.145 (2.99), 7.266 (2.28), 7.286 (4.10), 7.306 (1.96), 7.348 (2.46), 7.352 (2.66), 7.367 (5.02), 7.370 (4.74), 7.379 (3.34), 7.381 (3.71), 7.398 (6.58), 7.401 (7.54), 7.416 (5.13), 7.419 (3.77), 7.435 (2.48), 7.438 (1.89), 7.477 (3.56), 7.481 (3.64), 7.495 (10.72), 7.499 (5.65), 7.514 (1.78), 7.518 (1.60), 8.366 (1.63), 8.381 (3.52), 8.396 (1.63), 10.618 (2.53).

Example 222

3-Chloro-N-{[(4R)-4-Cyclopropyl-2,5-Dioxoimidazolidin-4-Yl]Methyl}-4'-Methyl[1,1'-Biphenyl]-2-Carboxamide

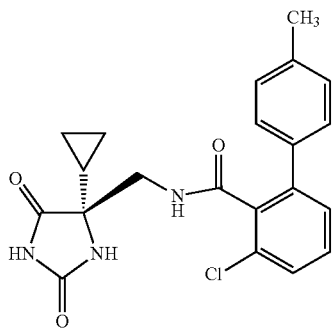 [SMILES: Cc1ccc(-c2cccc(Cl)c2C(=O)NC[C@@]2(C3CC3)NC(=O)NC2=O)cc1]

To a solution of (5R)-5-(aminomethyl)-5-cyclopropylimidazolidine-2,4-dione hydrochloride (50.0 mg, 243 µmol) and 3-chloro-4'-methyl[1,1'-biphenyl]-2-carboxylic acid (60.0 mg, 243 µmol) in DMF (3.3 ml) was added 1-ethyl-3-(3-dimethylaminopropyl)carbodiimide hydrochloride (60.6 mg, 316 µmol), 1-hydroxybenzotriazole hydrate (48.4 mg, 316 µmol) and N,N-diisopropylethylamine (120 µl, 680 µmol). The reaction mixture was stirred overnight at room temperature and then concentrated under reduced pressure. The crude product was purified by preparative HPLC (Method 3f). After lyophilization, 46.6 mg (100% purity, 48% yield) of the desired product were obtained.

LC-MS (Method 7): $R_t$=1.53 min, MS (ESIpos): m/z=398 [M+H]$^+$ $^1$H-NMR (600 MHz, DMSO-d6) δ [ppm]: 0.100 (0.73), 0.108 (1.26), 0.117 (1.26), 0.124 (0.90), 0.279 (0.81), 0.286 (1.02), 0.293 (0.92), 0.302 (0.67), 0.309 (0.49), 0.327 (0.43), 0.335 (0.73), 0.342 (0.81), 0.349 (1.11), 0.358 (0.82), 0.364 (0.47), 0.424 (0.90), 0.432 (1.20), 0.440 (1.13), 0.448 (0.76), 0.969 (0.42), 0.977 (0.83), 0.982 (0.91), 0.991 (1.52), 1.000 (0.81), 1.005 (0.74), 2.320 (16.00), 7.190 (3.95), 7.203 (5.07), 7.266 (2.10), 7.271 (2.02), 7.277 (2.34), 7.281 (2.46), 7.292 (6.35), 7.306 (4.71), 7.418 (1.13), 7.426 (4.13), 7.431 (4.47), 7.438 (4.32), 7.442 (8.05), 7.451 (0.79), 8.573 (1.07), 8.583 (2.17), 8.594 (1.04), 10.539 (2.67).

Example 223

4'-Cyano-N-{[(4R)-4-Cyclopropyl-2,5-Dioxoimidazolidin-4-Yl]Methyl}[1,1'-Biphenyl]-2-Carboxamide

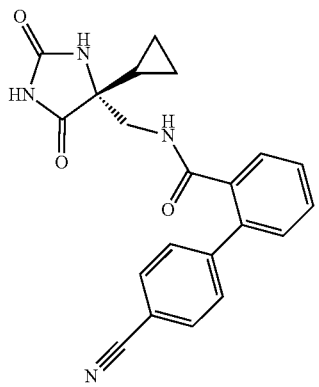 [SMILES: N#Cc1ccc(-c2ccccc2C(=O)NC[C@@]2(C3CC3)NC(=O)NC2=O)cc1]

To a solution of (5R)-5-(aminomethyl)-5-cyclopropylimidazolidine-2,4-dione hydrochloride (70.0 mg, 340 µmol) and 4'-cyano[1,1'-biphenyl]-2-carboxylic acid (76.0 mg, 340 µmol) in DMF (7 ml) was added 1-ethyl-3-(3-dimethylaminopropyl)carbodiimide hydrochloride (84.8 mg, 443 µmol), 1-hydroxybenzotriazole hydrate (67.8 mg, 443 µmol) and N,N-diisopropylethylamine (170 µl, 950 µmol). The reaction mixture was stirred overnight at room temperature and then concentrated under reduced pressure. The crude product was purified by preparative HPLC (Method 3f). After lyophilization, 101 mg (100% purity, 80% yield) of the desired product were obtained.

LC-MS (Method 8): $R_t$=0.75 min, MS (ESIpos): m/z=375 [M+H]$^+$ $^1$H-NMR (400 MHz, DMSO-d6) δ [ppm]: 0.109 (0.45), 0.123 (1.09), 0.133 (1.94), 0.147 (2.10), 0.157 (1.45), 0.170 (0.67), 0.311 (0.66), 0.319 (1.20), 0.332 (1.51), 0.343 (1.45), 0.354 (1.12), 0.364 (0.86), 0.377 (0.72), 0.388 (1.19), 0.402 (1.33), 0.410 (1.83), 0.424 (1.43), 0.438 (0.97), 0.452 (1.62), 0.463 (1.92), 0.476 (1.84), 0.488 (1.14), 1.046 (0.63), 1.060 (1.30), 1.067 (1.38), 1.073 (1.00), 1.080 (2.42), 1.088 (0.96), 1.093 (1.29), 1.101 (1.16), 1.114 (0.50), 2.073 (0.73), 3.462 (0.42), 3.477 (0.58), 3.497 (4.12), 3.502 (4.23), 3.512 (4.08), 3.518 (4.02), 3.536 (0.53), 3.552 (0.47), 7.423 (3.24), 7.432 (1.94), 7.440 (4.40), 7.442 (4.62), 7.450 (4.98), 7.454 (5.05), 7.462 (2.76), 7.465 (2.78), 7.480 (4.13), 7.483 (3.49), 7.499 (2.00), 7.502 (1.92), 7.517 (16.00), 7.538 (11.58), 7.549 (3.67), 7.554 (3.43), 7.568 (1.39), 7.572 (1.28), 7.848 (10.12), 7.853 (3.38), 7.865 (3.13), 7.869 (9.09), 8.537 (1.55), 8.553 (3.30), 8.568 (1.55), 10.627 (1.00).

Example 224

N-{[(4R)-4-Cyclopropyl-2,5-Dioxoimidazolidin-4-Yl]Methyl}-2-[6-(Trifluoromethyl)Pyridin-3-Yl]Benzamide

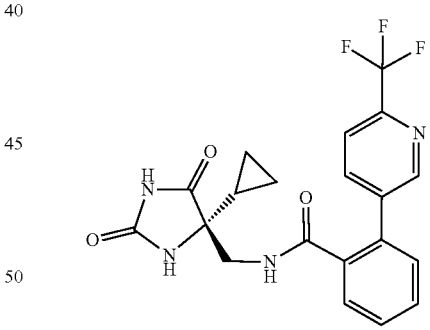

To a solution of (5R)-5-(aminomethyl)-5-cyclopropylimidazolidine-2,4-dione hydrochloride (100 mg, 486 µmol) and 2-[6-(trifluoromethyl)pyridin-3-yl]benzoic acid (130 mg, 486 µmol) in DMF (4.0 ml) was added 1-ethyl-3-(3-dimethylaminopropyl)carbodiimide hydrochloride (121 mg, 632 µmol), 1-hydroxybenzotriazole hydrate (96.8 mg, 632 µmol) and N,N-diisopropylethylamine (240 µl, 1.4 mmol). The reaction mixture was stirred overnight at room temperature and then concentrated under reduced pressure. The crude product was purified by preparative HPLC (Method 3f). After lyophilization, 157 mg (99% purity, 76% yield) of the desired product were obtained.

LC-MS (Method 7): $R_t$=1.34 min, MS (ESIpos): m/z=419 [M+H]$^+$

¹H-NMR (600 MHz, DMSO-d6) δ [ppm]: 0.116 (0.98), 0.125 (2.48), 0.133 (3.89), 0.141 (3.95), 0.149 (2.91), 0.157 (1.21), 0.303 (0.88), 0.318 (2.71), 0.325 (3.43), 0.332 (3.04), 0.339 (2.19), 0.348 (1.37), 0.381 (1.24), 0.389 (2.35), 0.396 (2.78), 0.403 (3.76), 0.412 (2.78), 0.427 (0.98), 0.445 (1.37), 0.453 (3.13), 0.462 (4.02), 0.470 (3.76), 0.478 (2.55), 0.487 (0.88), 1.061 (1.21), 1.070 (2.55), 1.075 (2.87), 1.084 (4.54), 1.092 (2.58), 1.097 (2.25), 1.106 (1.01), 2.574 (0.56), 2.731 (0.42), 2.890 (0.46), 3.305 (1.11), 3.367 (2.38), 3.397 (0.42), 3.473 (2.35), 3.483 (2.55), 3.496 (5.91), 3.506 (5.45), 3.521 (5.55), 3.532 (5.75), 3.544 (2.45), 3.555 (2.35), 7.507 (4.64), 7.520 (16.00), 7.534 (13.19), 7.547 (8.29), 7.559 (15.09), 7.592 (5.39), 7.605 (6.86), 7.617 (2.58), 7.931 (5.39), 7.945 (12.77), 7.962 (8.13), 7.976 (3.43), 8.628 (3.43), 8.639 (6.56), 8.649 (3.27), 8.739 (10.84), 10.661 (9.47).

Example 225

3'-Chloro-N-{[(4R)-4-Cyclopropyl-2,5-Dioxoimidazolidin-4-Yl]Methyl}-4'-Methyl[1,1'-Biphenyl]-2-Carboxamide

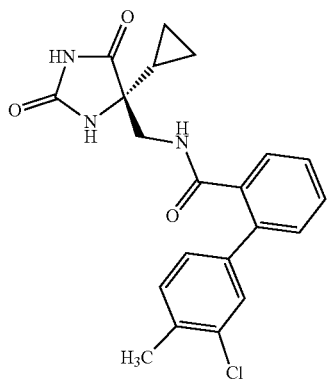 [SMILES: Cc1ccc(-c2ccccc2C(=O)NC[C@@]2(C3CC3)NC(=O)NC2=O)cc1Cl]

To a solution of (5R)-5-(aminomethyl)-5-cyclopropylimidazolidine-2,4-dione hydrochloride (50.0 mg, 243 µmol) and 3'-chloro-4'-methyl[1,1'-biphenyl]-2-carboxylic acid (60.0 mg, 243 µmol) in DMF (2.1 ml) was added 1-ethyl-3-(3-dimethylaminopropyl)carbodiimide hydrochloride (60.6 mg, 316 µmol), 1-hydroxybenzotriazole hydrate (48.4 mg, 316 µmol) and N,N-diisopropylethylamine (120 µl, 680 µmol). The reaction mixture was stirred overnight at room temperature and then concentrated under reduced pressure. The crude product was purified by preparative HPLC (Method 4f). After lyophilization, 56.5 mg (100% purity, 58% yield) of the desired product were obtained.

LC-MS (Method 7): $R_t$=1.65 min, MS (ESIpos): m/z=398 [M+H]⁺

¹H-NMR (400 MHz, DMSO-d6) δ [ppm]: 0.110 (0.66), 0.121 (1.17), 0.134 (1.19), 0.145 (0.89), 0.302 (0.72), 0.315 (0.90), 0.327 (0.86), 0.348 (0.51), 0.380 (0.73), 0.394 (0.80), 0.402 (1.15), 0.416 (1.22), 0.431 (1.06), 0.442 (1.18), 0.455 (1.07), 0.466 (0.67), 1.037 (0.41), 1.050 (0.79), 1.058 (0.86), 1.071 (1.47), 1.084 (0.77), 1.091 (0.73), 2.344 (16.00), 2.366 (0.46), 3.435 (0.41), 3.450 (0.46), 3.470 (2.13), 3.482 (3.04), 3.497 (2.13), 3.515 (0.46), 3.532 (0.41), 7.203 (1.80), 7.208 (1.88), 7.223 (2.27), 7.227 (2.38), 7.350 (3.20), 7.359 (1.80), 7.371 (2.95), 7.375 (3.33), 7.378 (3.04), 7.385 (2.34), 7.397 (4.59), 7.402 (6.54), 7.424 (2.82), 7.427 (2.18), 7.443 (1.39), 7.446 (1.08), 7.482 (1.90), 7.486 (1.96), 7.500 (6.09), 7.519 (0.95), 7.523 (0.88), 8.392 (0.94), 8.407 (1.94), 8.423 (0.95), 10.624 (0.82).

Example 226

3'-Chloro-N-{[(4R)-4-Cyclopropyl-2,5-Dioxoimidazolidin-4-Yl]Methyl}-4'-(Trifluoromethyl)[1,1'-Biphenyl]-2-Carboxamide

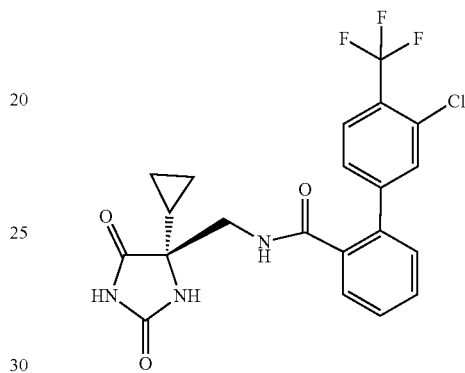

To a solution of (5R)-5-(aminomethyl)-5-cyclopropylimidazolidine-2,4-dione hydrochloride (60.0 mg, 292 µmol) and 3'-chloro-4'-(trifluoromethyl)[1,1'-biphenyl]-2-carboxylic acid (87.7 mg, 292 µmol) in DMF (4 ml) was added 1-ethyl-3-(3-dimethylaminopropyl)carbodiimide hydrochloride (72.7 mg, 379 µmol), 1-hydroxybenzotriazole hydrate (58.1 mg, 379 µmol) and N,N-diisopropylethylamine (140 µl, 820 µmol). The reaction mixture was stirred overnight at room temperature and then concentrated under reduced pressure. The crude product was purified by preparative HPLC (Method 4f). After lyophilization, 99.1 mg (100% purity, 75% yield) of the desired product were obtained.

LC-MS (Method 7): $R_t$=1.75 min, MS (ESIpos): m/z=452 [M+H]⁺

¹H-NMR (400 MHz, DMSO-d6) δ [ppm]: 0.111 (0.75), 0.124 (1.81), 0.135 (3.25), 0.148 (3.41), 0.159 (2.42), 0.172 (1.10), 0.291 (0.64), 0.305 (1.10), 0.313 (2.03), 0.325 (2.56), 0.336 (2.38), 0.347 (1.87), 0.358 (1.39), 0.372 (1.17), 0.383 (2.01), 0.398 (2.19), 0.406 (3.02), 0.419 (2.33), 0.427 (1.42), 0.438 (1.58), 0.451 (2.58), 0.462 (3.18), 0.475 (3.02), 0.487 (1.90), 0.500 (0.69), 1.052 (1.05), 1.065 (2.15), 1.073 (2.29), 1.078 (1.69), 1.086 (3.95), 1.094 (1.65), 1.099 (2.15), 1.107 (1.92), 1.120 (0.82), 2.890 (0.43), 3.464 (1.19), 3.479 (1.44), 3.499 (5.65), 3.513 (9.71), 3.528 (5.58), 3.546 (1.37), 3.563 (1.26), 7.449 (8.43), 7.468 (11.47), 7.472 (10.15), 7.491 (9.74), 7.494 (11.22), 7.509 (7.43), 7.512 (5.33), 7.527 (4.14), 7.531 (3.22), 7.546 (16.00), 7.564 (5.94), 7.568 (5.42), 7.583 (2.03), 7.587 (1.78), 7.689 (9.46), 7.877 (8.57), 7.898 (7.95), 8.571 (2.58), 8.587 (5.39), 8.602 (2.58), 10.651 (6.81).

Example 227

3',4'-Dichloro-N-{[(4R)-4-Cyclopropyl-2,5-Dioxoimidazolidin-4-Yl]Methyl}[1,1'-Biphenyl]-2-Carboxamide

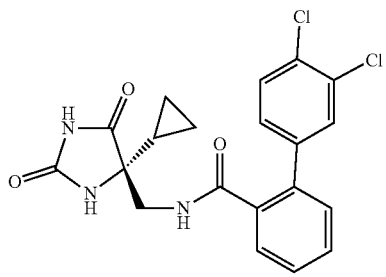 [SMILES: O=C1NC(=O)[C@](CNC(=O)c2ccccc2-c2ccc(Cl)c(Cl)c2)(C2CC2)N1]

To a solution of (5R)-5-(aminomethyl)-5-cyclopropylimidazolidine-2,4-dione hydrochloride (100 mg, 486 µmol) and 3',4'-dichloro[1,1'-biphenyl]-2-carboxylic acid (130 mg, 486 µmol) in DMF (4.0 ml) was added 1-ethyl-3-(3-dimethylaminopropyl)carbodiimide hydrochloride (121 mg, 632 µmol), 1-hydroxybenzotriazole hydrate (96.8 mg, 632 µmol) and N,N-diisopropylethylamine (240 µl, 1.4 mmol). The reaction mixture was stirred overnight at room temperature and then concentrated under reduced pressure. The crude product was purified by preparative HPLC (Method 6f). After lyophilization, 48.0 mg (100% purity, 24% yield) of the desired product were obtained.

LC-MS (Method 11): $R_t$=1.16 min, MS (ESIneg): m/z=416 [M−H]⁻

¹H-NMR (600 MHz, DMSO-d6) δ [ppm]: 0.117 (0.49), 0.125 (1.13), 0.133 (1.82), 0.141 (1.85), 0.149 (1.33), 0.158 (0.57), 0.304 (0.44), 0.319 (1.22), 0.327 (1.54), 0.334 (1.36), 0.341 (0.96), 0.349 (0.64), 0.386 (0.57), 0.394 (1.06), 0.402 (1.22), 0.409 (1.73), 0.418 (1.30), 0.423 (0.81), 0.433 (0.51), 0.442 (0.66), 0.451 (1.45), 0.459 (1.81), 0.467 (1.72), 0.475 (1.16), 1.058 (0.61), 1.066 (1.18), 1.071 (1.30), 1.080 (2.14), 1.089 (1.19), 1.094 (1.07), 1.103 (0.48), 1.756 (0.44), 3.468 (2.70), 3.478 (4.10), 3.491 (9.66), 3.502 (16.00), 3.512 (13.44), 7.288 (2.91), 7.291 (2.90), 7.302 (3.09), 7.305 (3.12), 7.401 (2.75), 7.413 (4.13), 7.428 (3.27), 7.441 (4.23), 7.452 (1.96), 7.465 (3.72), 7.477 (1.91), 7.515 (2.42), 7.529 (3.50), 7.539 (5.85), 7.603 (5.86), 7.606 (5.72), 7.647 (5.70), 7.661 (5.23), 8.500 (1.58), 8.510 (3.13), 8.520 (1.54), 10.650 (4.39).

Example 228

N-{[(4R)-4-Cyclopropyl-2,5-Dioxoimidazolidin-4-Yl]Methyl}-2-(6-Methylpyridin-3-Yl)Benzamide

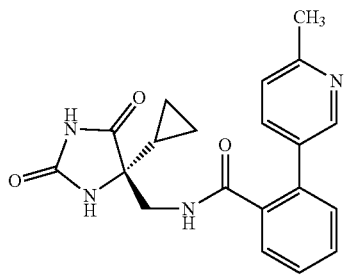 [SMILES: Cc1ccc(-c2ccccc2C(=O)NC[C@@]2(C3CC3)NC(=O)NC2=O)cn1]

To a solution of (5R)-5-(aminomethyl)-5-cyclopropylimidazolidine-2,4-dione hydrochloride (100 mg, 486 µmol) and 2-(6-methylpyridin-3-yl)benzoic acid (104 mg, 486 µmol) in DMF (4.0 ml) was added 1-ethyl-3-(3-dimethylaminopropyl)carbodiimide hydrochloride (121 mg, 632 µmol), 1-hydroxybenzotriazole hydrate (96.8 mg, 632 µmol) and N,N-diisopropylethylamine (240 µl, 1.4 mmol). The reaction mixture was stirred overnight at room temperature and then concentrated under reduced pressure. The crude product was purified by preparative HPLC (Method 5f). After lyophilization, 21.4 mg (100% purity, 12% yield) of the desired product were obtained.

LC-MS (Method 12): $R_t$=0.97 min, MS (ESIpos): m/z=365 [M+H]⁺

¹H-NMR (400 MHz, DMSO-d6) δ [ppm]: −0.008 (1.36), 0.008 (1.33), 0.103 (0.68), 0.115 (1.21), 0.128 (1.26), 0.139 (0.92), 0.152 (0.41), 0.301 (0.77), 0.315 (0.97), 0.325 (0.94), 0.336 (0.68), 0.346 (0.53), 0.380 (0.77), 0.394 (0.85), 0.401 (1.23), 0.415 (1.19), 0.424 (1.40), 0.436 (1.43), 0.449 (1.09), 0.461 (0.68), 1.051 (0.80), 1.059 (0.87), 1.072 (1.50), 1.085 (0.80), 1.092 (0.70), 2.328 (16.00), 2.366 (0.56), 2.669 (0.46), 2.710 (0.53), 3.449 (0.41), 3.468 (2.44), 3.476 (2.61), 3.483 (2.57), 3.491 (2.40), 7.411 (3.15), 7.430 (5.47), 7.453 (1.48), 7.469 (2.57), 7.490 (1.36), 7.501 (3.87), 7.521 (1.77), 7.525 (1.72), 7.540 (2.13), 7.544 (2.03), 7.562 (2.61), 7.567 (3.24), 8.341 (3.17), 8.346 (3.22), 8.361 (2.98), 8.365 (2.95), 8.414 (0.99), 8.429 (2.06), 8.445 (0.99), 10.625 (2.64).

Example 229

N-{[(4R)-4-Cyclopropyl-2,5-Dioxoimidazolidin-4-Yl]Methyl}-3-Fluoro-4'-Methyl[1,1'-Biphenyl]-2-Carboxamide

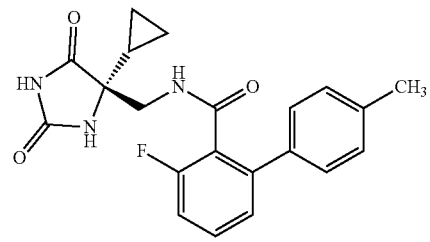 [SMILES: Cc1ccc(-c2cccc(F)c2C(=O)NC[C@@]2(C3CC3)NC(=O)NC2=O)cc1]

To a solution of (5R)-5-(aminomethyl)-5-cyclopropylimidazolidine-2,4-dione hydrochloride (100 mg, 486 µmol) and 3-fluoro-4'-methyl[1,1'-biphenyl]-2-carboxylic acid (112 mg, 486 µmol) in DMF (2.7 ml) was added 1-ethyl-3-(3-dimethylaminopropyl)carbodiimide hydrochloride (121 mg, 632 µmol), 1-hydroxybenzotriazole hydrate (96.8 mg, 632 µmol) and N,N-diisopropylethylamine (420 µl, 2.4 mmol). The reaction mixture was stirred overnight at room temperature and then concentrated under reduced pressure. The crude product was purified by preparative HPLC (Method 3f). After lyophilization, 118 mg (98% purity, 62% yield) of the desired product were obtained.

LC-MS (Method 7): $R_t$=1.46 min; MS (ESIpos): m/z=382 [M+H]⁺

¹H-NMR (400 MHz, DMSO-d6) δ [ppm]: −0.008 (0.41), 0.008 (0.42), 0.099 (0.75), 0.110 (1.30), 0.123 (1.38), 0.134 (0.99), 0.147 (0.49), 0.273 (0.43), 0.282 (0.83), 0.294 (1.04), 0.304 (1.03), 0.316 (0.81), 0.327 (1.03), 0.338 (0.85), 0.351 (0.95), 0.360 (1.23), 0.374 (0.91), 0.382 (0.51), 0.400 (0.56), 0.414 (1.03), 0.425 (1.30), 0.438 (1.25), 0.450 (0.77), 0.976

(0.41), 0.990 (0.85), 0.997 (0.91), 1.002 (0.68), 1.010 (1.54), 1.018 (0.66), 1.023 (0.84), 1.031 (0.75), 2.072 (0.53), 2.322 (16.00), 3.372 (1.16), 3.387 (1.21), 3.407 (1.67), 3.421 (1.57), 3.535 (1.58), 3.550 (1.70), 3.569 (1.19), 3.584 (1.11), 7.175 (2.91), 7.194 (4.63), 7.200 (4.24), 7.220 (6.00), 7.235 (1.67), 7.297 (6.93), 7.317 (4.54), 7.432 (4.86), 7.442 (1.45), 7.458 (1.30), 7.463 (1.80), 7.477 (1.73), 7.482 (1.08), 7.497 (0.87), 8.610 (1.05), 8.624 (2.17), 8.639 (1.03), 10.556 (0.60).

Example 230

N-{[(4R)-4-Cyclopropyl-2,5-Dioxoimidazolidin-4-Yl]Methyl}-3-Fluoro-4'-(Trifluoromethyl)[1,1'-Biphenyl]-2-Carboxamide

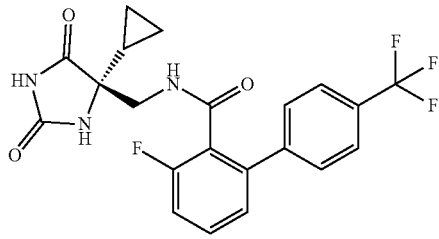 [SMILES: O=C1NC(=O)[C@](CNC(=O)c2c(F)cccc2-c2ccc(C(F)(F)F)cc2)(C2CC2)N1]

To a solution of (5R)-5-(aminomethyl)-5-cyclopropylimidazolidine-2,4-dione hydrochloride (100 mg, 486 μmol) and (3-fluoro-4'-(trifluoromethyl)[1,1'-biphenyl]-2-carboxylic acid (138 mg, 486 μmol) in DMF (2.7 ml) was added 1-ethyl-3-(3-dimethylaminopropyl)carbodiimide hydrochloride (121 mg, 632 μmol), 1-hydroxybenzotriazole hydrate (96.8 mg, 632 μmol) and N,N-diisopropylethylamine (420 μl, 2.4 mmol). The reaction mixture was stirred overnight at room temperature and then concentrated under reduced pressure. The crude product was purified by preparative HPLC (Method 4f). After lyophilization, 150 mg (100% purity, 71% yield) of the desired product were obtained.

LC-MS (Method 7): $R_t$=1.60 min; MS (ESIpos): m/z=436 [M+H]$^+$ $^1$H-NMR (400 MHz, DMSO-d6) δ [ppm]: −0.149 (0.48), −0.008 (3.94), 0.008 (3.80), 0.102 (0.99), 0.115 (2.32), 0.126 (4.19), 0.139 (4.47), 0.149 (3.16), 0.162 (1.42), 0.271 (0.80), 0.285 (1.31), 0.293 (2.66), 0.305 (3.23), 0.314 (3.26), 0.328 (2.64), 0.337 (3.44), 0.347 (2.78), 0.361 (3.05), 0.369 (3.81), 0.383 (2.93), 0.391 (1.56), 0.405 (0.98), 0.421 (1.51), 0.435 (3.25), 0.445 (4.29), 0.458 (4.06), 0.470 (2.45), 0.483 (0.85), 0.994 (1.37), 1.007 (2.75), 1.015 (2.94), 1.020 (2.15), 1.028 (5.06), 1.036 (2.09), 1.041 (2.68), 1.048 (2.41), 1.061 (1.05), 2.327 (0.46), 2.366 (0.66), 2.523 (1.90), 2.670 (0.46), 2.710 (0.64), 3.391 (3.57), 3.405 (3.78), 3.425 (5.02), 3.440 (4.74), 3.578 (4.93), 3.593 (5.37), 3.612 (4.01), 3.628 (3.65), 7.263 (9.22), 7.280 (9.74), 7.282 (10.36), 7.296 (4.10), 7.298 (4.19), 7.319 (8.39), 7.340 (4.93), 7.516 (4.59), 7.530 (15.11), 7.535 (8.14), 7.551 (5.75), 7.556 (3.80), 7.570 (3.19), 7.601 (12.86), 7.621 (15.38), 7.780 (16.00), 7.800 (12.91), 8.800 (3.37), 8.815 (7.01), 8.829 (3.33), 10.615 (9.81).

Example 231

3,4'-Dichloro-N-{[(4R)-4-Cyclopropyl-2,5-Dioxoimidazoidin-4-Yl]Methyl}[1,1'-Biphenyl]-2-Carboxamide

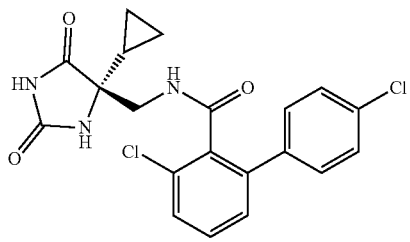 [SMILES: O=C1NC(=O)[C@](CNC(=O)c2c(Cl)cccc2-c2ccc(Cl)cc2)(C2CC2)N1]

To a solution of (5R)-5-(aminomethyl)-5-cyclopropylimidazolidine-2,4-dione hydrochloride (100 mg, 486 μmol) and 3,4'-dichloro[1,1'-biphenyl]-2-carboxylicacid (130 mg, 486 μmol) in DMF (2.7 ml) was added 1-ethyl-3-(3-dimethylaminopropyl)carbodiimide hydrochloride (121 mg, 632 μmol), 1-hydroxybenzotriazole hydrate (96.8 mg, 632 μmol) and N,N-diisopropylethylamine (420 μl, 2.4 mmol). The reaction mixture was stirred overnight at room temperature and then concentrated under reduced pressure. The crude product was purified by preparative HPLC (Method 4f). After lyophilization, 31.1 mg (99% purity, 15% yield) of the desired product were obtained.

LC-MS (Method 7): $R_t$=1.55 min, MS (ESIpos): m/z=418 [M+H]$^+$ $^1$H-NMR (400 MHz, DMSO-d6) δ [ppm]: −0.008 (2.13), 0.008 (2.17), 0.094 (0.45), 0.108 (1.10), 0.119 (1.96), 0.132 (2.08), 0.142 (1.47), 0.155 (0.67), 0.283 (0.63), 0.291 (1.27), 0.302 (1.57), 0.312 (1.57), 0.325 (1.26), 0.335 (1.61), 0.345 (1.30), 0.358 (1.49), 0.367 (1.80), 0.380 (1.37), 0.388 (0.73), 0.403 (0.45), 0.424 (0.68), 0.438 (1.49), 0.448 (2.01), 0.461 (1.90), 0.473 (1.17), 0.486 (0.41), 0.973 (0.64), 0.986 (1.30), 0.993 (1.39), 0.999 (1.03), 1.006 (2.33), 1.019 (1.26), 1.027 (1.13), 1.040 (0.49), 2.523 (1.05), 3.338 (1.52), 3.352 (1.35), 3.503 (1.09), 3.518 (1.17), 3.537 (0.90), 3.551 (0.80), 7.294 (3.49), 7.298 (3.65), 7.311 (4.45), 7.316 (4.37), 7.399 (6.48), 7.404 (2.62), 7.415 (3.62), 7.420 (14.08), 7.426 (2.41), 7.441 (2.59), 7.458 (16.00), 7.479 (12.83), 7.486 (8.80), 7.492 (7.63), 7.502 (2.68), 7.506 (1.59), 8.653 (1.59), 8.668 (3.33), 8.683 (1.57), 10.550 (1.27).

Example 232

4',5-Dichloro-N-{[(4R)-4-Cyclopropyl-2,5-Dioxoimidazolidin-4-Yl]Methyl}[1,1'-Biphenyl]-2-Carboxamide

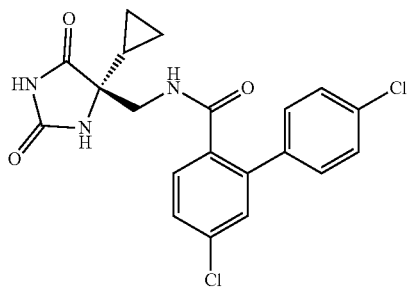 [SMILES: O=C1NC(=O)[C@](CNC(=O)c2ccc(Cl)cc2-c2ccc(Cl)cc2)(C2CC2)N1]

To a solution of (5R)-5-(aminomethyl)-5-cyclopropylimidazolidine-2,4-dione hydrochloride (100 mg, 486 µmol) and 4',5-dichloro[1,1'-biphenyl]-2-carboxylicacid (130 mg, 486 µmol) in DMF (2.7 ml) was added 1-ethyl-3-(3-dimethylaminopropyl)carbodiimide hydrochloride (121 mg, 632 µmol), 1-hydroxybenzotriazole hydrate (96.8 mg, 632 µmol) and N,N-diisopropylethylamine (420 µl, 2.4 mmol). The reaction mixture was stirred overnight at room temperature and then concentrated under reduced pressure. The crude product was purified by preparative HPLC (Method 4f). After lyophilization, 129 mg (98% purity, 62% yield) of the desired product were obtained.

LC-MS (Method 7): $R_t$=1.70 min, MS (ESIpos): m/z=418 [M+H]$^+$ $^1$H-NMR (400 MHz, DMSO-d6) δ [ppm]: −0.008 (2.05), 0.008 (1.98), 0.106 (0.45), 0.119 (1.07), 0.130 (1.92), 0.143 (2.05), 0.154 (1.42), 0.167 (0.66), 0.307 (0.65), 0.315 (1.20), 0.327 (1.49), 0.338 (1.43), 0.349 (1.13), 0.360 (0.88), 0.370 (0.75), 0.381 (1.22), 0.395 (1.34), 0.403 (1.78), 0.417 (1.39), 0.425 (0.84), 0.435 (0.91), 0.448 (1.53), 0.459 (1.90), 0.472 (1.80), 0.484 (1.11), 1.037 (0.62), 1.050 (1.26), 1.058 (1.36), 1.064 (0.99), 1.071 (2.34), 1.079 (0.95), 1.084 (1.26), 1.092 (1.12), 1.105 (0.51), 2.523 (1.01), 3.466 (0.53), 3.485 (4.14), 3.490 (4.17), 3.500 (4.01), 3.506 (4.01), 3.524 (0.51), 3.541 (0.45), 7.366 (0.92), 7.372 (7.96), 7.377 (3.08), 7.394 (15.10), 7.400 (2.24), 7.412 (8.12), 7.460 (16.00), 7.463 (10.79), 7.476 (2.96), 7.481 (7.95), 7.488 (1.07), 7.507 (5.34), 7.512 (4.38), 7.527 (3.78), 7.533 (3.52), 7.546 (6.92), 8.537 (1.51), 8.553 (3.24), 8.568 (1.52), 10.640 (3.59).

Example 233

4'-Chloro-N-{[(4R)-4-Cyclopropyl-2,5-Dioxoimidazolidin-4-Yl]Methyl}-4-Fluoro[1,1'-Biphenyl]-2-Carboxamide

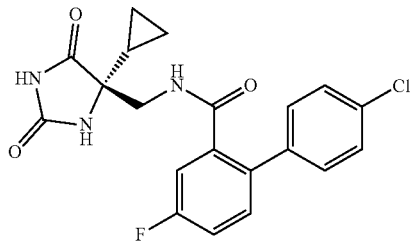 [SMILES: O=C1NC(=O)[C@](CNC(=O)c2cc(F)ccc2-c2ccc(Cl)cc2)(C2CC2)N1]

To a solution of (5R)-5-(aminomethyl)-5-cyclopropylimidazolidine-2,4-dione hydrochloride (100 mg, 486 µmol) and 4'-chloro-4-fluoro[1,1'-biphenyl]-2-carboxylic acid (122 mg, 486 µmol) in DMF (2.7 ml) was added 1-ethyl-3-(3-dimethylaminopropyl)carbodiimide hydrochloride (121 mg, 632 µmol), 1-hydroxybenzotriazole hydrate (96.8 mg, 632 µmol) and N,N-diisopropylethylamine (420 µl, 2.4 mmol). The reaction mixture was stirred overnight at room temperature and then concentrated under reduced pressure. The crude product was purified by preparative HPLC (Method 4f). After lyophilization, 126 mg (100% purity, 64% yield) of the desired product were obtained.

LC-MS (Method 7): $R_t$=1.56 min, MS (ESIpos): m/z=402 [M+H]$^+$ $^1$H-NMR (400 MHz, DMSO-d6) δ [ppm]: −0.008 (1.57), 0.008 (1.60), 0.113 (0.59), 0.126 (1.42), 0.137 (2.51), 0.150 (2.65), 0.161 (1.87), 0.174 (0.85), 0.297 (0.49), 0.312 (0.86), 0.320 (1.60), 0.332 (2.00), 0.342 (1.88), 0.354 (1.46), 0.365 (1.11), 0.376 (0.96), 0.387 (1.54), 0.401 (1.74), 0.409 (2.35), 0.423 (1.82), 0.431 (1.04), 0.445 (1.49), 0.459 (1.99), 0.470 (2.50), 0.483 (2.38), 0.495 (1.48), 0.508 (0.51), 1.046 (0.79), 1.060 (1.64), 1.067 (1.77), 1.072 (1.31), 1.080 (3.03), 1.088 (1.27), 1.093 (1.63), 1.101 (1.49), 1.114 (0.65), 2.366 (0.45), 2.523 (1.08), 2.709 (0.45), 3.456 (0.58), 3.471 (0.76), 3.491 (5.11), 3.497 (5.28), 3.506 (5.17), 3.513 (4.97), 3.531 (0.74), 3.548 (0.63), 7.197 (3.58), 7.203 (4.23), 7.219 (3.65), 7.226 (4.05), 7.322 (1.32), 7.328 (10.64), 7.333 (3.88), 7.340 (2.44), 7.349 (15.66), 7.355 (2.65), 7.361 (4.30), 7.367 (4.06), 7.382 (2.76), 7.389 (2.63), 7.418 (4.61), 7.432 (5.29), 7.442 (16.00), 7.447 (4.64), 7.454 (3.48), 7.458 (3.96), 7.463 (10.19), 7.575 (7.62), 8.598 (1.98), 8.614 (4.15), 8.629 (1.96), 10.664 (5.97).

Example 234

3',4'-Dichloro-N-{[(4R)-4-Cyclopropyl-2,5-Dioxoimidazolidin-4-Yl]Methyl}-4-Fluoro[1,1'-Biphenyl]-2-Carboxamide

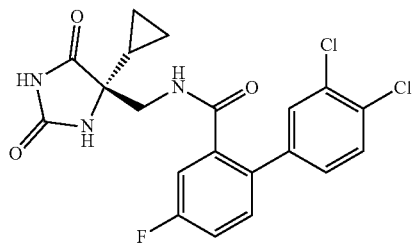 [SMILES: O=C1NC(=O)[C@](CNC(=O)c2cc(F)ccc2-c2ccc(Cl)c(Cl)c2)(C2CC2)N1]

To a solution of (5R)-5-(aminomethyl)-5-cyclopropylimidazolidine-2,4-dione hydrochloride (100 mg, 486 µmol) and 3',4'-dichloro-4-fluoro[1,1'-biphenyl]-2-carboxylic acid (139 mg, 486 µmol) in DMF (2.7 ml) was added 1-ethyl-3-(3-dimethylaminopropyl)carbodiimide hydrochloride (121 mg, 632 µmol), 1-hydroxybenzotriazole hydrate (96.8 mg, 632 µmol) and N,N-diisopropylethylamine (420 µl, 2.4 mmol). The reaction mixture was stirred overnight at room temperature and then concentrated under reduced pressure. The crude product was purified by preparative HPLC (Method 4f). After lyophilization, 129 mg (98% purity, 60% yield) of the desired product were obtained.

LC-MS (Method 7): $R_t$=1.71 min, MS (ESIpos): m/z=436 [M+H]$^+$ $^1$H-NMR (400 MHz, DMSO-d6) δ [ppm]: −0.149 (0.45), −0.008 (3.52), 0.008 (3.64), 0.112 (0.61), 0.125 (1.41), 0.136 (2.49), 0.149 (2.61), 0.160 (1.83), 0.173 (0.82), 0.296 (0.52), 0.310 (0.89), 0.319 (1.57), 0.331 (1.95), 0.342 (1.83), 0.353 (1.48), 0.364 (1.13), 0.377 (0.94), 0.388 (1.55), 0.402 (1.72), 0.410 (2.30), 0.424 (1.81), 0.432 (1.15), 0.440 (1.20), 0.454 (2.00), 0.465 (2.42), 0.478 (2.30), 0.490 (1.43), 0.503 (0.49), 1.053 (0.80), 1.066 (1.64), 1.074 (1.74), 1.079 (1.27), 1.087 (3.03), 1.094 (1.25), 1.100 (1.60), 1.107 (1.46), 1.120 (0.66), 2.327 (0.42), 2.366 (0.80), 2.518 (2.61), 2.523 (2.26), 2.526 (1.95), 2.557 (1.06), 2.561 (0.80), 2.669 (0.42), 2.710 (0.80), 3.451 (0.59), 3.466 (0.78), 3.485 (4.93), 3.492 (5.10), 3.500 (4.96), 3.508 (4.79), 3.526 (0.75), 3.542 (0.68), 7.210 (3.57), 7.216 (4.32), 7.232 (3.69), 7.239 (4.16), 7.254 (5.12), 7.260 (5.17), 7.275 (5.50), 7.281 (5.73), 7.363 (1.76), 7.370 (1.81), 7.384 (4.14), 7.391 (4.28), 7.405 (2.58), 7.412 (2.58), 7.476 (4.44), 7.490 (4.63), 7.497 (3.55), 7.511 (3.17), 7.592 (16.00), 7.598 (11.86), 7.639 (10.08), 7.660 (9.09), 8.628 (1.95), 8.644 (4.09), 8.659 (1.93), 10.670 (5.52).

Example 235

N-{[(4R)-4-Cyclopropyl-2,5-Dioxoimidazolidin-4-Yl]Methyl}-6-Fluoro-4'-(Trifluoromethyl)[1,1'-Biphenyl]-2-Carboxamide

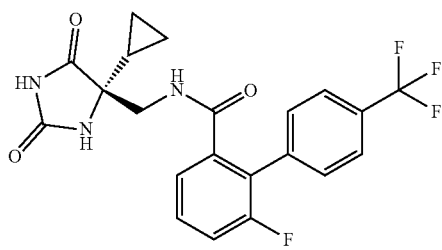 [SMILES: O=C1NC(=O)[C@](CNC(=O)c2cccc(F)c2-c2ccc(C(F)(F)F)cc2)(C2CC2)N1]

To a solution of (5R)-5-(aminomethyl)-5-cyclopropylimidazolidine-2,4-dione hydrochloride (100 mg, 486 µmol) and 6-fluoro-4'-(trifluoromethyl)[1,1'-biphenyl]-2-carboxylic acid (298 mg, 46% purity, 486 µmol) in DMF (2.7 ml) was added 1-ethyl-3-(3-dimethylaminopropyl)carbodiimide hydrochloride (121 mg, 632 µmol), 1-hydroxybenzotriazole hydrate (96.8 mg, 632 µmol) and N,N-diisopropylethylamine (420 µl, 2.4 mmol). The reaction mixture was stirred overnight at room temperature and then concentrated under reduced pressure. The crude product was purified by preparative HPLC (Method 3f). After lyophilization, 97.5 mg (96% purity, 44% yield) of the desired product were obtained.

LC-MS (Method 7): $R_t$=1.63 min; MS (ESIneg): m/z=434 [M−H]$^-$ $^1$H-NMR (500 MHz, DMSO-d6) δ [ppm]: −0.007 (0.60), 0.006 (0.46), 0.105 (0.82), 0.116 (1.84), 0.124 (3.22), 0.134 (3.32), 0.143 (2.30), 0.154 (1.06), 0.276 (0.72), 0.284 (1.08), 0.287 (1.14), 0.294 (2.06), 0.303 (2.48), 0.312 (2.22), 0.319 (1.58), 0.322 (1.76), 0.330 (1.32), 0.350 (1.16), 0.359 (2.02), 0.367 (2.06), 0.370 (2.14), 0.377 (2.88), 0.387 (2.26), 0.394 (1.28), 0.405 (0.84), 0.419 (1.18), 0.430 (2.44), 0.439 (3.20), 0.450 (3.00), 0.459 (1.94), 0.470 (0.72), 1.008 (1.14), 1.018 (2.24), 1.024 (2.38), 1.029 (1.62), 1.035 (4.15), 1.041 (1.58), 1.045 (2.14), 1.051 (1.96), 1.062 (0.86), 2.072 (1.10), 3.407 (0.44), 3.420 (0.58), 3.435 (9.45), 3.448 (10.39), 3.464 (0.54), 7.274 (6.57), 7.276 (6.55), 7.289 (7.31), 7.291 (6.91), 7.413 (2.74), 7.415 (2.78), 7.429 (4.29), 7.432 (4.99), 7.435 (3.16), 7.450 (3.80), 7.452 (3.50), 7.518 (10.49), 7.525 (16.00), 7.531 (11.09), 7.534 (11.35), 7.540 (5.73), 7.546 (2.86), 7.557 (2.52), 7.564 (0.58), 7.570 (0.46), 7.599 (0.46), 7.602 (0.70), 7.616 (0.60), 7.623 (0.68), 7.626 (0.76), 7.642 (0.42), 7.772 (12.12), 7.788 (10.59), 8.556 (2.64), 8.569 (5.45), 8.581 (2.50), 10.643 (5.19).

Example 236

Ent-N-[(4-Cyclobutyl-2,5-Dioxoimidazolidin-4-Yl)Methyl]-4'-Methyl[Biphenyl]-2-Carboxamide

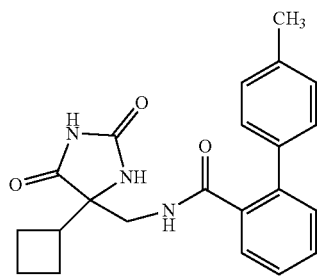 [SMILES: Cc1ccc(-c2ccccc2C(=O)NCC2(C3CCC3)NC(=O)NC2=O)cc1]

To a solution of ent-5-(aminomethyl)-5-cyclobutylimidazolidine-2,4-dione hydrochloride (50.0 mg, 228 µmol) and 4'-methyl[1,1'-biphenyl]-2-carboxylic acid (48.3 mg, 228 µmol) in DMF (2 ml) was added 1-ethyl-3-(3-dimethylaminopropyl)carbodiimide hydrochloride (56.7 mg, 296 µmol), 1-hydroxybenzotriazole hydrate (45.3 mg, 296 µmol) and N,N-diisopropylethylamine (110 µl, 640 µmol). The reaction mixture was stirred overnight at room temperature and then concentrated under reduced pressure. The crude product was purified by preparative HPLC (Method 4f). After lyophilization, 71.3 mg (99% purity, 82% yield) of the desired product were obtained.

LC-MS (Method 8): $R_t$=0.83 min, MS (ESIpos): m/z=378 [M+H]$^+$ $^1$H-NMR (600 MHz, DMSO-d6) δ [ppm]: 1.630 (1.11), 1.644 (1.55), 1.657 (1.45), 1.752 (0.79), 1.768 (1.61), 1.780 (2.37), 1.791 (2.00), 1.806 (0.87), 1.821 (0.67), 1.839 (0.98), 1.847 (1.11), 1.852 (1.09), 1.861 (0.97), 1.879 (1.16), 1.895 (1.30), 1.911 (0.71), 2.325 (16.00), 2.566 (1.08), 2.581 (1.46), 2.595 (0.89), 3.229 (0.89), 3.239 (0.98), 3.252 (2.08), 3.261 (1.92), 3.279 (2.02), 3.290 (2.09), 3.302 (1.22), 7.192 (3.95), 7.205 (5.88), 7.249 (5.88), 7.263 (4.13), 7.345 (3.24), 7.354 (4.29), 7.365 (2.01), 7.377 (2.56), 7.390 (1.02), 7.462 (1.54), 7.464 (1.61), 7.474 (2.34), 7.489 (0.98), 7.816 (3.99), 8.225 (1.29), 8.235 (2.33), 8.245 (1.14), 10.629 (3.45).

Example 237

Ent-N-[(4-Cyclobutyl-2,5-Dioxoimidazolidin-4-Yl)Methyl]-4'-(Trifluoromethyl)[Biphenyl]-2-Carboxamide

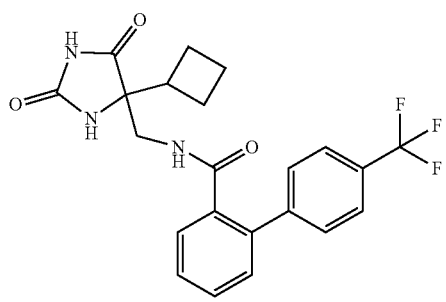 [SMILES: O=C1NC(=O)C(CNC(=O)c2ccccc2-c2ccc(C(F)(F)F)cc2)(C2CCC2)N1]

To a solution of ent-5-(aminomethyl)-5-cyclobutylimidazolidine-2,4-dione hydrochloride (100 mg, 455 µmol) and 4'-(trifluoromethyl)[1,1'-biphenyl]-2-carboxylic acid (145 mg, 546 µmol) in DMF (2.8 ml) was added 1-ethyl-3-(3-dimethylaminopropyl)carbodiimide hydrochloride (113 mg, 592 µmol), 1-hydroxybenzotriazole hydrate (90.6 mg, 592 µmol) and N,N-diisopropylethylamine (400 µl, 2.3 mmol). The reaction mixture was stirred for 3 days at room temperature and then concentrated under reduced pressure. The crude product was purified by preparative HPLC (Method 6f). After lyophilization, 82.0 mg (100% purity, 42% yield) of the desired product were obtained.

LC-MS (Method 7): $R_t$=1.69 min; MS (ESIpos): m/z=432 [M+H]$^+$ $^1$H-NMR (600 MHz, DMSO-d6) δ [ppm]: 1.635 (2.50), 1.649 (3.78), 1.665 (3.52), 1.680 (3.12), 1.741 (0.51), 1.755 (1.60), 1.770 (2.88), 1.788 (5.43), 1.802 (5.11), 1.817 (2.56), 1.840 (2.50), 1.853 (2.82), 1.887 (1.15), 1.902 (2.76), 1.918 (3.50), 1.935 (2.07), 1.951 (0.58), 2.572 (0.83), 2.587 (2.85), 2.601 (3.82), 2.615 (2.61), 3.264 (2.29), 3.274 (2.54), 3.286 (5.49), 3.296 (5.51), 3.304 (3.76), 3.315 (7.11), 7.427 (10.83), 7.440 (16.00), 7.459 (4.68), 7.471 (7.05), 7.484 (3.05), 7.533 (4.66), 7.546 (7.16), 7.557 (13.67), 7.570 (12.82), 7.762 (12.99), 7.775 (11.49), 7.895 (10.19), 8.477 (3.23), 8.487 (6.02), 8.497 (3.16), 10.661 (8.84).

Example 238

Ent-N-[(4-Cyclobutyl-2,5-Dioxoimidazolidin-4-Yl) Methyl]-5-Methyl-4'-(Trifluoromethyl)[Biphenyl]-2-Carboxamide

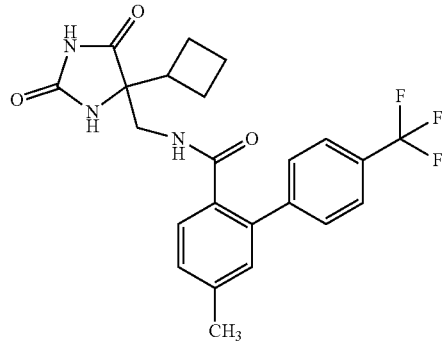 [SMILES: Cc1ccc(C(=O)NCC2(C3CCC3)NC(=O)NC2=O)c(-c2ccc(C(F)(F)F)cc2)c1]

To a solution of ent-5-(aminomethyl)-5-cyclobutylimidazolidine-2,4-dione hydrochloride (100 mg, 455 µmol) and 5-methyl-4'-(trifluoromethyl)[1,1'-biphenyl]-2-carboxylic acid (153 mg, 546 µmol) in DMF (2.8 ml) was added 1-ethyl-3-(3-dimethylaminopropyl)carbodiimide hydrochloride (113 mg, 592 µmol), 1-hydroxybenzotriazole hydrate (90.6 mg, 592 µmol) and N,N-diisopropylethylamine (400 µl, 2.3 mmol). The reaction mixture was stirred for 3 days at room temperature and then concentrated under reduced pressure. The crude product was purified by preparative chiral HPLC [Daicel Chiralcel OX-H 5 µm, 250×20 mm; eluent: 65% n-heptane/35% ethanol; flow rate: 25 ml/min; temperature: 50° C.; UV detection: 220 nm]. After lyophilization, 15.4 mg (96% purity, 7% yield) of the desired product were obtained.

LC-MS (Method 7): $R_t$=1.80 min; MS (ESIpos): m/z=446 [M+H]$^+$ $^1$H-NMR (600 MHz, DMSO-d6) δ [ppm]: 1.629 (0.94), 1.645 (1.39), 1.658 (1.31), 1.749 (0.58), 1.765 (1.03), 1.779 (2.22), 1.794 (1.95), 1.809 (0.91), 1.844 (1.05), 1.877 (0.42), 1.893 (1.05), 1.909 (1.36), 1.925 (0.78), 2.380 (16.00), 2.562 (0.50), 2.577 (1.08), 2.591 (1.50), 2.605 (0.98), 3.241 (0.94), 3.251 (1.05), 3.264 (1.81), 3.274 (1.72), 3.293 (0.56), 3.309 (2.26), 3.342 (1.69), 7.242 (4.43), 7.264 (1.95), 7.277 (2.67), 7.337 (3.84), 7.350 (2.70), 7.531 (4.43), 7.544 (4.89), 7.745 (5.00), 7.759 (4.53), 7.862 (4.07), 8.361 (1.19), 8.371 (2.29), 8.381 (1.17), 10.649 (3.53).

Example 239

Ent-N-[(4-Cyclobutyl-2,5-Dioxoimidazolidin-4-Yl) Methyl]-5-Fluoro-4'-(Trifluoromethyl)[Biphenyl]-2-Carboxamide

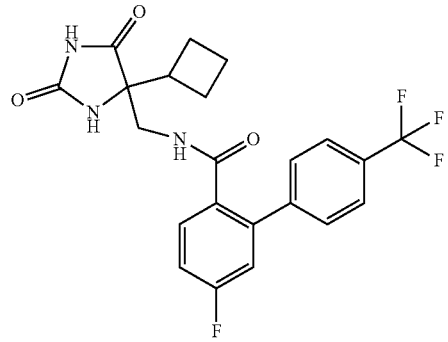 [SMILES: O=C1NC(=O)C(CNC(=O)c2ccc(F)cc2-c2ccc(C(F)(F)F)cc2)(C2CCC2)N1]

To a solution of ent-5-(aminomethyl)-5-cyclobutylimidazolidine-2,4-dione hydrochloride (100 mg, 455 µmol) and 5-fluoro-4'-(trifluoromethyl)[1,1'-biphenyl]-2-carboxylicacid (155 mg, 546 µmol) in DMF (2.8 ml) was added 1-ethyl-3-(3-dimethylaminopropyl)carbodiimide hydrochloride (113 mg, 592 µmol), 1-hydroxybenzotriazole hydrate (90.6 mg, 592 µmol) and N,N-diisopropylethylamine (400 µl, 2.3 mmol). The reaction mixture was stirred for 3 days at room temperature and then concentrated under reduced pressure. The crude product was purified by preparative chiral HPLC [Daicel Chiralcel OX-H 5 µm, 250×20 mm; eluent: 65% n-heptane/35% ethanol; flow rate: 25 ml/min; temperature: 50° C.; UV detection: 220 nm]. After lyophilization, 13.8 mg (93% purity, 6% yield) of the desired product were obtained.

LC-MS (Method 7): $R_t$=1.74 min; MS (ESIpos): m/z=450 [M+H]$^+$ $^1$H-NMR (600 MHz, DMSO-d6) δ [ppm]: 0.419 (0.79), 0.431 (0.79), 0.875 (0.92), 0.887 (1.21), 0.899 (1.05), 0.911 (0.52), 1.148 (0.52), 1.179 (0.68), 1.234 (0.63), 1.633 (2.68), 1.647 (3.86), 1.665 (3.38), 1.672 (3.23), 1.679 (3.23), 1.739 (0.50), 1.754 (1.78), 1.769 (3.12), 1.784 (6.37), 1.790 (5.27), 1.799 (5.77), 1.814 (2.68), 1.838 (2.70), 1.843 (2.54), 1.850 (2.99), 1.855 (2.75), 1.863 (2.10), 1.886 (1.15), 1.901 (3.10), 1.917 (4.14), 1.934 (2.41), 1.949 (0.71), 2.422 (0.45), 2.572 (1.02), 2.587 (3.33), 2.602 (4.59), 2.616 (2.89), 2.630 (0.73), 2.652 (0.55), 3.249 (2.81), 3.259 (3.07), 3.272 (6.06), 3.282 (5.53), 3.293 (1.65), 3.310 (7.00), 3.344 (5.01), 3.365 (0.89), 3.397 (0.42), 7.313 (6.92), 7.325 (6.30), 7.329 (7.63), 7.335 (7.21), 7.339 (4.75), 7.349 (3.70), 7.353 (2.89), 7.470 (5.43), 7.480 (5.82), 7.484 (5.35), 7.494 (4.51), 7.513 (0.68), 7.573 (13.95), 7.586 (15.50), 7.652 (0.58), 7.666 (0.58), 7.752 (0.55), 7.775 (16.00), 7.788 (14.58), 7.918 (14.24), 8.519 (3.67), 8.529 (7.27), 8.540 (3.67), 10.661 (9.47).

Example 240

Rac-N-({2,5-Dioxo-4-[3-(Trifluoromethyl)Pyridin-2-Yl]Imidazolidin-4-Yl}Methyl)-5-Fluoro-4'-(Trifluoromethyl)[Biphenyl]-2-Carboxamide

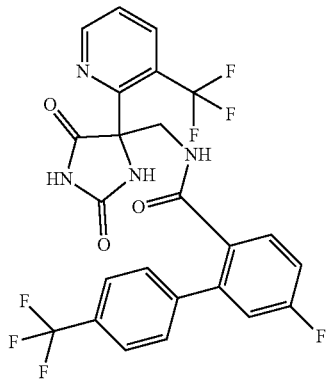 [SMILES: O=C1NC(=O)C(CNC(=O)c2ccc(F)cc2-c2ccc(C(F)(F)F)cc2)(c2ncccc2C(F)(F)F)N1]

To a solution of rac-5-(aminomethyl)-5-[3-(trifluoromethyl)pyridin-2-yl]imidazolidine-2,4-dione hydrochloride (100 mg, 322 µmol) and 5-fluoro-4'-(trifluoromethyl)[1,1'-biphenyl]-2-carboxylic acid (104 mg, 365 µmol) in DMF (1.8 ml) was added 1-ethyl-3-(3-dimethylaminopropyl)carbodiimide hydrochloride (90.9 mg, 474 µmol), 1-hydroxybenzotriazole hydrate (72.6 mg, 474 µmol) and N,N-diisopropylethylamine (320 µl, 1.8 mmol). The reaction mixture was stirred overnight at room temperature and then concentrated under reduced pressure. The crude product was purified by preparative HPLC (Method 8f). After lyophilization, 64.7 mg (96% purity, 36% yield) of the desired product were obtained.

LC-MS (Method 7): $R_t$=1.78 min, MS (ESIpos): m/z=541 [M+H]$^+$ $^1$H-NMR (600 MHz, DMSO-d6) δ [ppm]: 2.045 (0.46), 2.069 (8.29), 2.422 (0.41), 2.510 (3.07), 2.776 (2.26), 4.015 (4.00), 4.026 (4.28), 4.037 (4.93), 4.048 (4.59), 4.238 (4.74), 4.249 (5.09), 4.261 (4.25), 4.271 (3.84), 7.311 (4.33), 7.315 (6.72), 7.327 (6.92), 7.331 (8.33), 7.340 (6.59), 7.345 (4.69), 7.354 (3.62), 7.359 (2.77), 7.495 (5.38), 7.504 (5.63), 7.508 (5.12), 7.518 (4.58), 7.602 (12.83), 7.615 (14.73), 7.669 (4.44), 7.677 (4.63), 7.682 (4.62), 7.690 (4.52), 7.769 (15.14), 7.783 (12.89), 7.805 (0.57), 7.819 (0.50), 8.077 (16.00), 8.283 (6.86), 8.297 (6.45), 8.473 (3.51), 8.484 (7.10), 8.494 (3.39), 8.850 (6.76), 8.857 (6.59), 11.024 (1.48).

Example 241

Rac-4'-Chloro-N-({2,5-Dioxo-4-[3-(Trifluoromethyl)Pyridin-2-Yl]Imidazolidin-4-Yl}Methyl)-5-Fluoro[Biphenyl]-2-Carboxamide

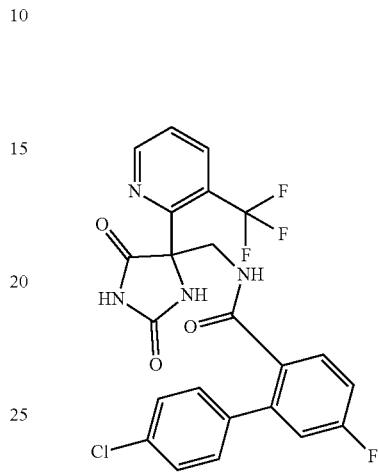

To a solution of rac-5-(aminomethyl)-5-[3-(trifluoromethyl)pyridin-2-yl]imidazolidine-2,4-dione hydrochloride (100 mg, 322 µmol) and 4'-chloro-5-fluoro[1,1'-biphenyl]-2-carboxylic acid (91.5 mg, 365 µmol) in DMF (1.8 ml) was added 1-ethyl-3-(3-dimethylaminopropyl)carbodiimide hydrochloride (90.9 mg, 474 µmol), 1-hydroxybenzotriazole hydrate (72.6 mg, 474 µmol) and N,N-diisopropylethylamine (320 µl, 1.8 mmol). The reaction mixture was stirred overnight at room temperature and then concentrated under reduced pressure. The crude product was purified by preparative HPLC (Method 4f). After lyophilization, 77.8 mg (97% purity, 46% yield) of the desired product were obtained.

LC-MS (Method 7): $R_t$=1.72 min, MS (ESIpos): m/z=507 [M+H]$^+$ $^1$H-NMR (600 MHz, DMSO-d6) δ [ppm]: 2.465 (2.26), 2.778 (2.15), 4.006 (2.58), 4.017 (2.77), 4.029 (3.23), 4.040 (2.98), 4.217 (3.08), 4.228 (3.34), 4.240 (2.73), 4.250 (2.49), 7.243 (3.22), 7.247 (4.36), 7.260 (3.23), 7.264 (4.16), 7.273 (1.99), 7.277 (1.66), 7.287 (3.97), 7.291 (3.49), 7.301 (2.26), 7.305 (2.04), 7.372 (0.72), 7.386 (1.20), 7.405 (9.12), 7.419 (15.28), 7.428 (1.94), 7.442 (0.75), 7.452 (3.95), 7.459 (16.00), 7.462 (8.39), 7.466 (4.32), 7.473 (9.56), 7.503 (0.70), 7.517 (0.48), 7.668 (2.81), 7.676 (2.96), 7.681 (2.95), 7.689 (2.91), 8.077 (7.74), 8.178 (0.55), 8.285 (4.36), 8.296 (4.07), 8.298 (4.11), 8.362 (2.18), 8.373 (4.47), 8.383 (2.19), 8.844 (4.27), 8.850 (4.19).

Example 242

Rac-4'-Chloro-N-({2,5-Dioxo-4-[3-(Trifluoromethyl)Pyridin-2-Yl]Imidazolidin-4-Yl}Methyl)[Biphenyl]-2-Carboxamide

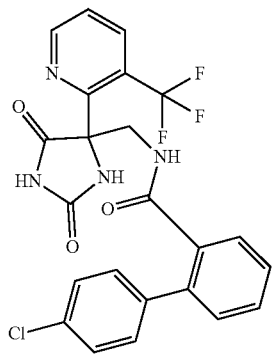 [SMILES: O=C1NC(=O)C(CNC(=O)c2ccccc2-c2ccc(Cl)cc2)(c2ncccc2C(F)(F)F)N1]

To a solution of rac-5-(aminomethyl)-5-[3-(trifluoromethyl)pyridin-2-yl]imidazolidine-2,4-dione hydrochloride (100 mg, 322 µmol) and 4'-chloro[1,1'-biphenyl]-2-carboxylic acid (84.9 mg, 365 µmol) in DMF (1.8 ml) was added 1-ethyl-3-(3-dimethylaminopropyl)carbodiimide hydrochloride (90.9 mg, 474 µmol), 1-hydroxybenzotriazole hydrate (72.6 mg, 474 µmol) and N,N-diisopropylethylamine (320 µl, 1.8 mmol). The reaction mixture was stirred overnight at room temperature and then concentrated under reduced pressure. The crude product was purified by preparative HPLC (Method 4f). After lyophilization, 45.9 mg (95% purity, 28% yield) of the desired product were obtained.

LC-MS (Method 7): $R_t$=1.67 min, MS (ESIpos): m/z=489 [M+H]$^+$ $^1$H-NMR (400 MHz, DMSO-d6) δ [ppm]: −0.008 (1.58), 0.008 (1.75), 1.175 (0.68), 1.988 (1.21), 2.366 (0.50), 2.466 (2.81), 2.523 (1.73), 2.710 (0.50), 2.782 (2.67), 3.987 (1.71), 4.003 (1.93), 4.021 (2.56), 4.037 (2.32), 4.220 (2.02), 4.236 (2.19), 4.254 (1.73), 4.270 (1.53), 7.345 (0.44), 7.377 (10.26), 7.398 (16.00), 7.404 (3.05), 7.418 (8.07), 7.426 (5.94), 7.429 (5.85), 7.438 (2.72), 7.444 (13.52), 7.449 (4.19), 7.460 (3.29), 7.466 (6.82), 7.488 (1.12), 7.494 (2.74), 7.503 (2.61), 7.508 (2.24), 7.513 (2.28), 7.516 (1.99), 7.521 (1.91), 7.527 (1.47), 7.535 (1.27), 7.666 (2.02), 7.678 (2.13), 7.685 (2.15), 7.698 (2.10), 8.045 (3.84), 8.283 (3.02), 8.286 (3.24), 8.303 (3.00), 8.306 (2.94), 8.327 (1.47), 8.343 (3.05), 8.358 (1.42), 8.848 (3.07), 8.856 (3.05), 11.036 (3.35).

Example 243

Rac-N-({2,5-Dioxo-4-[3-(Trifluoromethyl)Pyridin-2-Yl]Imidazolidin-4-Yl}Methyl)-4'-(Trifluoromethyl)[Biphenyl]-2-Carboxamide

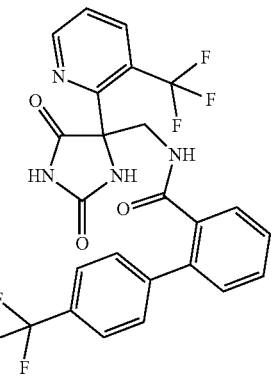

To a solution of rac-5-(aminomethyl)-5-[3-(trifluoromethyl)pyridin-2-yl]imidazolidine-2,4-dione hydrochloride (100 mg, 322 µmol) and 4'-(trifluoromethyl)[1,1'-biphenyl]-2-carboxylic acid (85.7 mg, 322 µmol) in DMF (2 ml) was added 1-ethyl-3-(3-dimethylaminopropyl)carbodiimide hydrochloride (80.2 mg, 418 µmol), 1-hydroxybenzotriazole hydrate (64.1 mg, 418 µmol) and N,N-diisopropylethylamine (280 µl, 1.6 mmol). The reaction mixture was stirred overnight at room temperature and then concentrated under reduced pressure. The crude product was purified by preparative HPLC (Method 4f). After lyophilization, 90.0 mg (99% purity, 53% yield) of the desired product were obtained.

LC-MS (Method 7): $R_t$=1.74 min, MS (ESIpos): m/z=523 [M+H]$^+$ $^1$H-NMR (600 MHz, DMSO-d6) δ [ppm]: 2.069 (3.51), 3.635 (0.49), 4.013 (3.68), 4.024 (3.91), 4.036 (4.45), 4.047 (4.15), 4.255 (4.30), 4.266 (4.63), 4.278 (3.88), 4.288 (3.54), 7.432 (7.35), 7.444 (8.81), 7.459 (1.81), 7.466 (16.00), 7.471 (10.24), 7.475 (8.86), 7.488 (1.39), 7.531 (0.62), 7.538 (3.83), 7.543 (3.58), 7.548 (3.10), 7.551 (3.96), 7.556 (3.01), 7.561 (2.62), 7.565 (2.30), 7.581 (11.67), 7.594 (13.26), 7.667 (4.00), 7.675 (4.20), 7.681 (4.16), 7.689 (4.09), 7.755 (13.64), 7.768 (11.77), 8.042 (14.40), 8.283 (6.22), 8.296 (5.86), 8.430 (3.18), 8.441 (6.46), 8.451 (3.14), 8.851 (6.14), 8.858 (6.00), 11.031 (4.23).

Example 244

Ent-N-({2,5-Dioxo-4-[3-(Trifluoromethyl)Pyridin-2-Yl]Imidazolidin-4-Yl}Methyl)-4'-(Trifluoromethyl)[Biphenyl]-2-Carboxamide

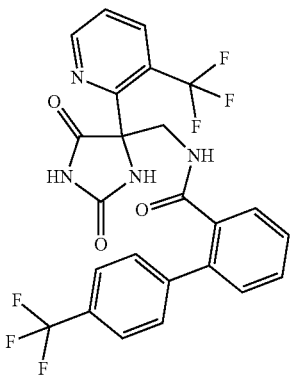 [SMILES: O=C1NC(=O)C(CNC(=O)c2ccccc2-c2ccc(C(F)(F)F)cc2)(c2ncccc2C(F)(F)F)N1]

Enantiomeric separation of rac-N-({2,5-dioxo-4-[3-(trifluoromethyl)pyridin-2-yl]imidazolidin-4 yl}methyl)-4'-(trifluoromethyl)[biphenyl]-2-carboxamide (89 mg) by preparative chiral HPLC [column: Daicel Chiralcel OD-H 5 μm, 250×20 mm; eluent: 80% n-heptane/20% ethanol; flow rate: 20 ml/min; temperature: 30° C.; UV detection: 220 nm] afforded 33.5 mg (100% purity) of the desired product.

Analytical chiral HPLC: $R_t$=1.46 min, e.e. =99% [column: 50×4.6 mm filled with Phen.

Cellulose-1 3 μm; eluent: 80% n-heptane/20% ethanol; flow rate: 1 ml/min; temperature: 30° C. UV detection: 220 nm]

LC-MS (Method 7): $R_t$=1.77 min; MS (ESIpos): m/z=523 [M+H]$^+$ $^1$H-NMR (400 MHz, DMSO-d6) δ [ppm]: 1.236 (0.81), 2.328 (0.99), 2.366 (0.99), 2.670 (1.11), 2.710 (1.05), 3.997 (3.49), 4.013 (3.72), 4.031 (4.54), 4.047 (4.25), 4.252 (4.31), 4.268 (4.71), 4.286 (3.72), 4.302 (3.37), 7.431 (6.87), 7.451 (10.71), 7.463 (16.00), 7.470 (10.71), 7.477 (8.67), 7.498 (1.80), 7.523 (0.76), 7.535 (4.65), 7.542 (4.19), 7.553 (4.13), 7.557 (3.84), 7.560 (3.78), 7.577 (13.21), 7.597 (13.73), 7.667 (4.01), 7.679 (4.36), 7.687 (4.25), 7.698 (4.25), 7.756 (14.14), 7.776 (11.40), 8.068 (14.84), 8.286 (6.40), 8.306 (5.82), 8.459 (3.08), 8.475 (6.52), 8.491 (3.03), 8.854 (5.99), 8.863 (5.70), 11.044 (3.84).

Example 245

Rac-4'-Chloro-N-{[4-(3,3-Difluorocyclobutyl)-2,5-Dioxoimidazoidin-4-Yl]Methyl}-5-Fluoro[Biphenyl]-2-Carboxamide

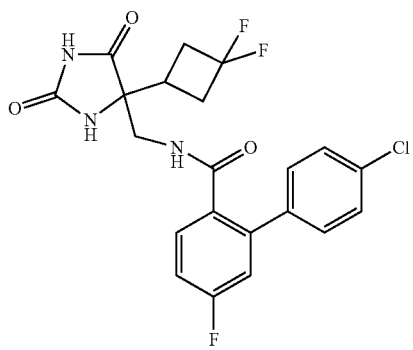 [SMILES: O=C1NC(=O)C(CNC(=O)c2ccc(F)cc2-c2ccc(Cl)cc2)(C2CC(F)(F)C2)N1]

To a solution of rac-5-(aminomethyl)-5-(3,3-difluorocyclobutyl)imidazolidine-2,4-dione hydrochloride (100 mg, 391 μmol) and 4'-chloro-5-fluoro[1,1'-biphenyl]-2-carboxylic acid (98.0 mg, 391 μmol) in DMF (1.9 ml) was added 1-ethyl-3-(3-dimethylaminopropyl)carbodiimide hydrochloride (97.5 mg, 509 μmol), 1-hydroxybenzotriazole hydrate (77.9 mg, 509 μmol) and N,N-diisopropylethylamine (340 μl, 2.0 mmol). The reaction mixture was stirred overnight at room temperature and then concentrated under reduced pressure. The crude product was purified by preparative HPLC (Method 4f). After lyophilization, 109 mg (100% purity, 62% yield) of the desired product were obtained.

LC-MS (Method 7): $R_t$=1.68 min, MS (ESIpos): m/z=452 [M+H]$^+$ $^1$H-NMR (400 MHz, DMSO-d6) δ [ppm]: −0.149 (0.54), −0.008 (4.47), 0.008 (4.85), 0.146 (0.54), 2.056 (0.57), 2.072 (0.52), 2.297 (0.71), 2.327 (1.28), 2.345 (1.04), 2.366 (1.54), 2.375 (1.04), 2.407 (1.16), 2.443 (1.92), 2.469 (2.15), 2.576 (2.11), 2.670 (0.62), 2.710 (0.88), 3.351 (6.60), 3.367 (6.49), 7.248 (2.89), 7.255 (4.31), 7.274 (3.10), 7.280 (5.99), 7.286 (1.78), 7.300 (4.14), 7.307 (3.29), 7.322 (2.37), 7.328 (1.92), 7.372 (8.88), 7.377 (3.31), 7.388 (4.14), 7.393 (15.01), 7.399 (2.18), 7.445 (3.98), 7.450 (2.77), 7.456 (16.00), 7.461 (7.53), 7.466 (4.02), 7.472 (3.64), 7.477 (9.49), 8.061 (7.24), 8.546 (1.73), 8.562 (3.69), 8.577 (1.70), 10.852 (5.23).

Example 246

Rac-4'-Chloro-N-{[4-(3,3-Difluorocyclobutyl)-2,5-Dioxoimidazolidin-4-Yl]Methyl}[Biphenyl]-2-Carboxamide

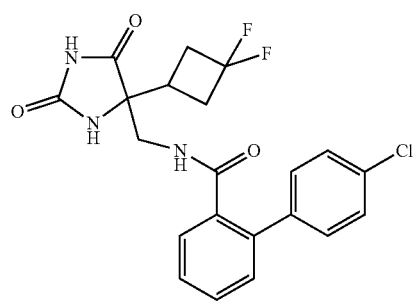 [SMILES: O=C1NC(=O)C(CNC(=O)c2ccccc2-c2ccc(Cl)cc2)(C2CC(F)(F)C2)N1]

To a solution of rac-5-(aminomethyl)-5-(3,3-difluorocyclobutyl)imidazolidine-2,4-dione hydrochloride (100 mg, 391 μmol) and 4'-chloro[1,1'-biphenyl]-2-carboxylic acid (91.0 mg, 391 μmol) in DMF (1.9 ml) was added 1-ethyl-3-(3-dimethylaminopropyl)carbodiimide hydrochloride (97.5 mg, 509 μmol), 1-hydroxybenzotriazole hydrate (77.9 mg, 509 μmol) and N,N-diisopropylethylamine (340 μl, 2.0 mmol). The reaction mixture was stirred overnight at room temperature and then concentrated under reduced pressure. The crude product was purified by preparative HPLC (Method 4f). After lyophilization, 96.1 mg (100% purity, 57% yield) of the desired product were obtained.

LC-MS (Method 7): $R_t$=1.62 min; MS (ESIpos): m/z=434 [M+H]$^+$ $^1$H-NMR (400 MHz, DMSO-d6) δ [ppm]: −0.149 (0.40), −0.008 (3.82), 0.008 (4.02), 0.146 (0.40), 2.298 (0.63), 2.318 (0.97), 2.327 (1.04), 2.348 (0.92), 2.366 (1.18), 2.376 (0.98), 2.394 (0.86), 2.407 (1.12), 2.442 (1.85), 2.467 (1.92), 2.523 (2.90), 2.574 (1.99), 2.669 (0.41), 2.709 (0.52), 3.356 (6.50), 3.372 (6.48), 7.352 (7.85), 7.356 (3.11), 7.368 (3.92), 7.373 (13.30), 7.379 (5.38), 7.398 (5.41), 7.417 (5.35), 7.421 (8.02), 7.440 (16.00), 7.457 (4.28), 7.461 (8.49), 7.498 (2.84), 7.503 (2.71), 7.517 (2.96), 7.522 (2.80), 7.534 (1.43), 7.539 (1.33), 8.038 (5.49), 8.504 (1.52), 8.519 (3.23), 8.535 (1.50), 10.848 (4.67).

Example 247

Ent-4'-Chloro-N-{[4-(3,3-Difluorocyclobutyl)-2,5-Dioxoimidazolidin-4-Yl]Methyl}[Biphenyl]-2-Carboxamide

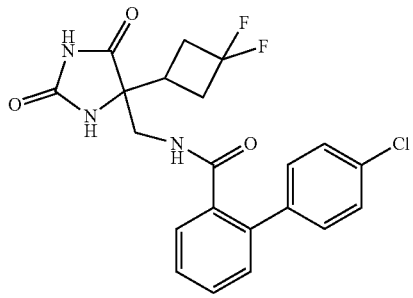 [SMILES: O=C1NC(=O)C(CNC(=O)c2ccccc2-c2ccc(Cl)cc2)(C2CC(F)(F)C2)N1]

Enantiomeric separation of rac-4'-chloro-N-{[4-(3,3-difluorocyclobutyl)-2,5-dioxoimidazolidin-4 yl]methyl}[biphenyl]-2-carboxamide (95 mg) by preparative chiral HPLC [column: Daicel Chiralpak OX-H 5 µm, 250×20 mm; eluent: 80% n-heptane/20% ethanol; flow rate: 20 ml/min; temperature: 30° C.; UV detection: 220 nm] afforded 41.2 mg (99% purity) of the desired product.

Analytical chiral HPLC: $R_t$=1.82 min, e.e. =>99% [column: Daicel OX-3 3 µm, 50×4.6 mm; eluent: 80% n-heptane/20% ethanol; flow rate: 1 ml/min; UV detection: 220 nm]

LC-MS (Method 7): $R_t$=1.65 min; MS (ESIpos): m/z=434 [M+H]$^+$ $^1$H-NMR (600 MHz, DMSO-d6) δ [ppm]: 2.316 (0.80), 2.331 (1.11), 2.351 (1.13), 2.364 (0.82), 2.383 (0.60), 2.412 (1.00), 2.422 (1.27), 2.434 (1.51), 2.454 (1.84), 2.464 (1.84), 2.481 (1.27), 2.520 (1.31), 2.565 (2.09), 3.262 (0.47), 3.266 (0.71), 3.270 (0.47), 3.329 (0.40), 3.360 (8.71), 3.370 (8.73), 7.356 (9.96), 7.367 (4.38), 7.370 (13.71), 7.374 (2.16), 7.379 (4.62), 7.393 (5.22), 7.405 (1.78), 7.408 (2.36), 7.418 (5.89), 7.420 (6.04), 7.425 (4.04), 7.426 (3.82), 7.440 (16.00), 7.451 (5.29), 7.454 (9.78), 7.502 (2.89), 7.505 (2.76), 7.515 (3.78), 7.517 (3.67), 7.527 (1.76), 7.530 (1.67), 8.010 (8.80), 8.475 (1.93), 8.486 (4.07), 8.496 (1.91), 10.823 (0.96).

Example 248

Ent-N-{[4-(3,3-Difluorocyclobutyl)-2,5-Dioxoimidazolidin-4-Yl]Methyl}-4'-(Trifluoromethyl)[Biphenyl]-2-Carboxamide

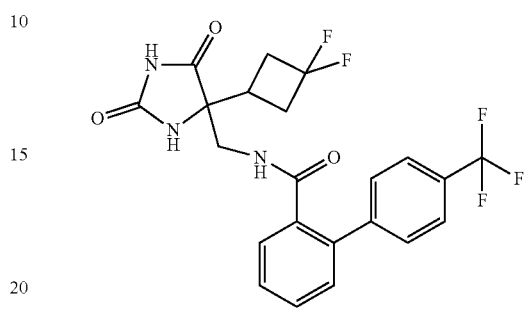

To a solution of rac-5-(aminomethyl)-5-(3,3-difluorocyclobutyl)imidazolidine-2,4-dione hydrochloride (100 mg, 391 µmol) and 4'-(trifluoromethyl)[1,1'-biphenyl]-2-carboxylicacid (104 mg, 391 µmol) in DMF (1.9 ml) was added 1-ethyl-3-(3-dimethylaminopropyl)carbodiimide hydrochloride (97.5 mg, 509 µmol), 1-hydroxybenzotriazole hydrate (77.9 mg, 509 µmol) and N,N-diisopropylethylamine (340 µl, 2.0 mmol). The reaction mixture was stirred overnight at room temperature and then concentrated under reduced pressure. The crude product was purified by preparative HPLC (Method 4f). After lyophilization, 123 mg (98.5% purity, 67% yield) of the racemic product were obtained.

Enantiomeric separation of rac-N-{[4-(3,3-difluorocyclobutyl)-2,5-dioxoimidazolidin-4-yl]methyl}-4'-(trifluoromethyl)[biphenyl]-2-carboxamide (112 mg) by preparative chiral HPLC [column: Daicel Chiralpak OX-H 5 µm, 250×20 mm; eluent: 80% n-heptane/20% ethanol; flow rate: 20 ml/min; temperature: 40° C.; UV detection: 220 nm] afforded 54.4 mg (99% purity) of the desired product.

Analytical chiral HPLC: $R_t$=1.15 min, e.e. =>99% [column: Daicel OX-3 3 µm, 50×4.6 mm; eluent: 80% n-heptane/20% ethanol; flow rate: 1 ml/min; temperature=30° C.; UV detection: 220 nm]

LC-MS (Method 7): $R_t$=1.73 min; MS (ESIpos): m/z=468 [M+H]$^+$ $^1$H-NMR (600 MHz, DMSO-d6) δ [ppm]: 1.237 (1.14), 1.361 (1.55), 2.297 (0.41), 2.319 (1.10), 2.333 (1.59), 2.340 (1.43), 2.353 (1.55), 2.366 (1.35), 2.387 (1.59), 2.403 (1.43), 2.409 (1.43), 2.422 (2.29), 2.453 (2.00), 2.466 (2.53), 2.484 (1.71), 2.517 (2.61), 2.561 (3.35), 2.573 (1.14), 2.576 (1.22), 2.652 (0.53), 3.264 (1.84), 3.267 (3.02), 3.327 (1.35), 3.330 (1.51), 3.358 (0.49), 3.371 (11.31), 3.382 (12.00), 7.431 (6.37), 7.444 (7.47), 7.455 (2.33), 7.458 (3.27), 7.467 (8.57), 7.470 (8.98), 7.473 (6.45), 7.475 (5.71), 7.485 (6.78), 7.497 (2.65), 7.542 (4.45), 7.545 (4.24), 7.558 (16.00), 7.571 (12.86), 7.745 (12.69), 7.759 (11.10), 8.029 (9.02), 8.566 (2.86), 8.576 (6.00), 8.587 (2.90), 10.844 (7.67).

Example 249

Rac-4'-Chloro-5-Fluoro-N-{[4-(1-Fluorocyclopropyl)-2,5-Dioxoimidazolidin-4-Yl]Methyl}[Biphenyl]-2-Carboxamide

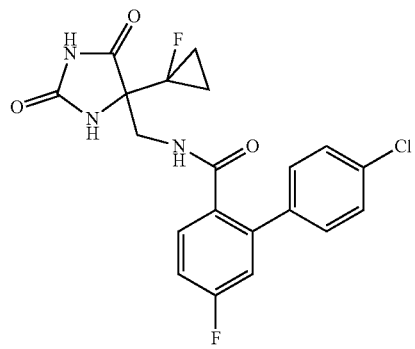 [SMILES: O=C1NC(=O)C(CNC(=O)c2ccc(F)cc2-c2ccc(Cl)cc2)(C2(F)CC2)N1]

To a solution of rac-5-(aminomethyl)-5-(1-fluorocyclopropyl)imidazolidine-2,4-dione hydrochloride (100 mg, 447 µmol) and 4'-chloro-5-fluoro[1,1'-biphenyl]-2-carboxylic acid (112 mg, 447 µmol) in DMF (2.2 ml) was added 1-ethyl-3-(3-dimethylaminopropyl)carbodiimide hydrochloride (111 mg, 581 µmol), 1-hydroxybenzotriazole hydrate (89.0 mg, 581 µmol) and N,N-diisopropylethylamine (390 µl, 2.2 mmol). The reaction mixture was stirred overnight at room temperature and then concentrated under reduced pressure. The crude product was purified by preparative HPLC (Method 4f). After lyophilization, 139 mg (100% purity, 74% yield) of the desired product were obtained.

LC-MS (Method 7): $R_t$=1.59 min, MS (ESIpos): m/z=420 [M+H]$^+$ $^1$H-NMR (400 MHz, DMSO-d$_6$) δ [ppm]: −0.149 (0.52), −0.008 (4.50), −0.007 (2.91), 0.006 (3.25), 0.008 (4.88), 0.146 (0.54), 0.821 (0.65), 0.848 (1.95), 0.875 (1.57), 0.912 (1.45), 0.943 (1.99), 0.962 (1.57), 0.974 (1.30), 0.984 (1.78), 0.993 (3.94), 1.007 (2.22), 1.034 (1.63), 1.043 (3.90), 1.050 (2.18), 2.072 (2.68), 2.366 (0.71), 2.518 (2.76), 2.523 (2.18), 2.526 (1.82), 2.560 (0.77), 2.709 (0.71), 3.491 (1.51), 3.507 (1.59), 3.525 (3.08), 3.541 (2.91), 3.575 (2.74), 3.590 (2.97), 3.609 (1.45), 3.624 (1.30), 7.250 (2.76), 7.257 (4.75), 7.269 (2.60), 7.275 (3.85), 7.282 (4.86), 7.290 (4.98), 7.296 (3.25), 7.311 (2.70), 7.317 (2.09), 7.356 (1.17), 7.363 (10.16), 7.368 (3.71), 7.379 (4.52), 7.385 (16.00), 7.391 (2.79), 7.395 (4.36), 7.410 (4.06), 7.416 (3.35), 7.431 (2.87), 7.455 (2.12), 7.462 (15.75), 7.467 (4.27), 7.478 (3.54), 7.483 (9.95), 7.490 (1.17), 8.106 (6.55), 8.613 (1.84), 8.628 (3.83), 8.643 (1.80), 10.876 (4.90).

Example 250

Rac-4'-Chloro-N-{[4-(1-Fluorocyclopropyl)-2,5-Dioxoimidazolidin-4-Yl]Methyl}[Biphenyl]-2-Carboxamide

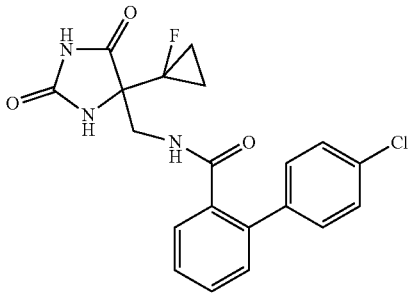 [SMILES: O=C1NC(=O)C(CNC(=O)c2ccccc2-c2ccc(Cl)cc2)(C2(F)CC2)N1]

To a solution of rac-5-(aminomethyl)-5-(1-fluorocyclopropyl)imidazolidine-2,4-dione hydrochloride (100 mg, 447 µmol) and 4'-chloro[1,1'-biphenyl]-2-carboxylicacid (104 mg, 447 µmol) in DMF (2.2 ml) was added 1-ethyl-3-(3-dimethylaminopropyl)carbodiimide hydrochloride (111 mg, 581 µmol), 1-hydroxybenzotriazole hydrate (89.0 mg, 581 µmol) and N,N-diisopropylethylamine (390 µl, 2.2 mmol). The reaction mixture was stirred overnight at room temperature and then concentrated under reduced pressure. The crude product was purified by preparative HPLC (Method 3f). After lyophilization, 95.4 mg (100% purity, 53% yield) of the desired product were obtained.

LC-MS (Method 7): $R_t$=1.53 min, MS (ESIpos): m/z=402 [M+H]$^+$ $^1$H-NMR (400 MHz, DMSO-d6) δ [ppm]: −0.149 (0.45), −0.008 (4.07), 0.008 (4.13), 0.146 (0.43), 0.818 (0.64), 0.837 (1.04), 0.849 (1.94), 0.875 (1.54), 0.914 (1.38), 0.944 (2.08), 0.961 (1.52), 0.982 (1.89), 0.992 (3.86), 1.006 (1.94), 1.032 (1.54), 1.042 (3.81), 1.056 (1.14), 2.072 (5.59), 2.366 (0.93), 2.518 (2.64), 2.521 (2.16), 2.522 (2.18), 2.524 (2.16), 2.558 (1.09), 2.561 (0.85), 2.563 (0.72), 2.565 (0.64), 2.568 (0.51), 2.570 (0.43), 2.709 (0.93), 3.489 (1.54), 3.504 (1.65), 3.523 (2.90), 3.539 (2.77), 3.586 (2.58), 3.601 (2.77), 3.620 (1.46), 3.635 (1.36), 7.337 (1.12), 7.344 (9.53), 7.349 (3.86), 7.353 (3.54), 7.357 (3.94), 7.360 (4.87), 7.365 (15.17), 7.372 (7.29), 7.375 (5.80), 7.381 (4.23), 7.383 (4.39), 7.402 (5.56), 7.407 (3.41), 7.410 (3.06), 7.425 (5.03), 7.429 (4.23), 7.439 (2.32), 7.446 (16.00), 7.451 (4.37), 7.462 (3.33), 7.467 (9.37), 7.473 (1.17), 7.495 (3.33), 7.499 (3.30), 7.513 (4.26), 7.517 (4.13), 7.532 (1.70), 7.536 (1.62), 8.078 (6.47), 8.575 (1.70), 8.591 (3.62), 8.606 (1.73), 10.871 (4.63).

Example 251

Ent-4'-Chloro-N-{[4-(1-Fluorocyclopropyl)-2,5-Dioxoimidazolidin-4-Yl]Methyl}[Biphenyl]-2-Carboxamide

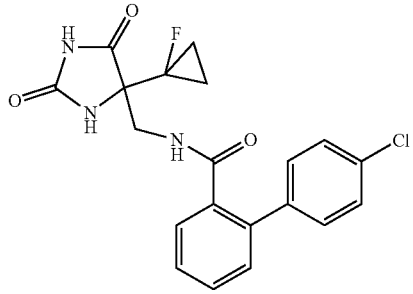 [SMILES: O=C1NC(=O)C(CNC(=O)c2ccccc2-c2ccc(Cl)cc2)(C2(F)CC2)N1]

Enantiomeric separation of rac-4'-chloro-N-{[4-(1-fluorocyclopropyl)-2,5-dioxoimidazolidin-4 yl]methyl}[biphenyl]-2-carboxamide (92.6 mg) by preparative chiral HPLC [column: Daicel Chiralpak ID 5 µm, 250×20 mm; eluent: 60% n-heptan/40% isopropanol; flow rate: 30 ml/min; temperature: 40° C.; UV detection: 220 nm] afforded 31.0 mg (98% purity) of the desired product.

Analytical chiral HPLC: $R_t$=1.86 min, e.e. =97.8% [column: 50×4.6 mm filled with Daicel Chiralpak ID-3 3 µm; eluent: 50% n-heptan/50% isopropanol; flow rate: 1 ml/min; UV detection: 220 nm]

LC-MS (Method 7): $R_t$=1.55 min; MS (ESIpos): m/z=402 [M+H]$^+$ $^1$H-NMR (600 MHz, DMSO-d6) δ [ppm]: 0.834 (0.71), 0.842 (1.04), 0.852 (2.29), 0.869 (1.77), 0.920 (1.63), 0.937 (2.17), 0.955 (0.83), 0.971 (0.68), 0.990 (1.25), 0.998 (3.85), 1.009 (1.27), 1.023 (1.42), 1.031 (4.08), 1.043 (1.53), 2.383 (0.54), 2.422 (0.73), 2.517 (1.30), 2.573 (1.56), 2.611 (0.57), 2.651 (0.71), 3.264 (1.77), 3.331 (2.67), 3.500 (1.96), 3.511 (2.05), 3.523 (3.04), 3.534 (2.83), 3.592 (2.55), 3.603 (2.71), 3.615 (1.72), 3.625 (1.60), 7.348 (9.70), 7.351 (3.68), 7.362 (16.00), 7.373 (5.12), 7.374 (4.91), 7.383 (4.22), 7.396 (5.05), 7.411 (2.50), 7.413 (2.53), 7.424 (4.60), 7.426 (4.18), 7.436 (2.50), 7.438 (2.50), 7.441 (2.17), 7.445 (13.12), 7.448 (3.99), 7.456 (3.49), 7.459 (9.63), 7.499 (2.93), 7.501 (2.88), 7.512 (4.18), 7.514 (4.06), 7.524 (1.82), 7.526 (1.75), 8.048 (7.62), 8.547 (1.84), 8.557 (3.66), 8.567 (1.77), 10.172 (2.01).

Example 252

Rac-5-Fluoro-N-{[4-(1-Fluorocyclopropyl)-2,5-Dioxoimidazolidin-4-Yl]Methyl}-4'-(Trifluoromethyl)[Biphenyl]-2-Carboxamide

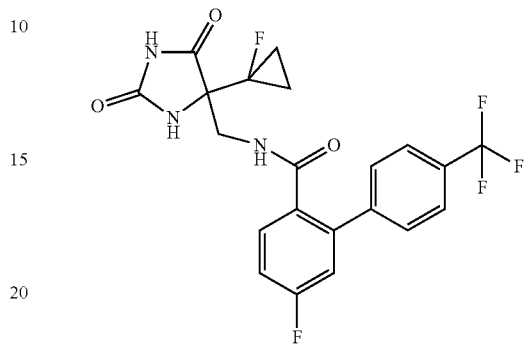

To a solution of rac-5-(aminomethyl)-5-(1-fluorocyclopropyl)imidazolidine-2,4-dione hydrochloride (100 mg, 447 µmol) and 5-fluoro-4'-(trifluoromethyl)[1,1'-biphenyl]-2-carboxylic acid (127 mg, 447 µmol) in DMF (2.2 ml) was added 1-ethyl-3-(3-dimethylaminopropyl)carbodiimide hydrochloride (111 mg, 581 µmol), 1-hydroxybenzotriazole hydrate (89.0 mg, 581 µmol) and N,N-diisopropylethylamine (390 µl, 2.2 mmol). The reaction mixture was stirred overnight at room temperature and then concentrated under reduced pressure. The crude product was purified by preparative HPLC (Method 4f). After lyophilization, 123 mg (100% purity, 61% yield) of the desired product were obtained.

LC-MS (Method 7): $R_t$=1.69 min, MS (ESIpos): m/z=454 [M+H]$^+$ $^1$H-NMR (400 MHz, DMSO-d6) δ [ppm]: −0.149 (0.47),-0.008 (3.88), 0.008 (4.16), 0.146 (0.45), 0.819 (1.20), 0.824 (1.16), 0.837 (1.94), 0.850 (3.41), 0.859 (1.41), 0.871 (2.51), 0.877 (2.76), 0.914 (2.49), 0.944 (3.63), 0.962 (2.82), 0.976 (2.55), 0.984 (3.53), 0.992 (6.94), 0.999 (3.06), 1.006 (3.82), 1.034 (3.02), 1.043 (6.88), 1.049 (3.82), 1.084 (0.43), 2.073 (2.00), 2.327 (0.41), 2.366 (0.69), 2.524 (1.98), 2.557 (1.04), 2.561 (0.76), 2.670 (0.43), 2.710 (0.69), 2.890 (0.43), 3.503 (2.63), 3.519 (2.84), 3.537 (5.53), 3.553 (5.27), 3.585 (4.88), 3.600 (5.29), 3.619 (2.49), 3.635 (2.29), 7.316 (3.69), 7.322 (12.39), 7.344 (16.00), 7.364 (5.02), 7.370 (3.37), 7.451 (5.29), 7.464 (4.96), 7.467 (4.67), 7.471 (4.88), 7.486 (3.65), 7.558 (12.73), 7.579 (14.96), 7.768 (15.61), 7.789 (13.00), 8.128 (14.06), 8.148 (0.84), 8.696 (3.24), 8.711 (6.84), 8.726 (3.24), 10.893 (7.33).

Example 253

Ent-5-Fluoro-N-{[4-(1-Fluorocyclopropyl)-2,5-Dioxoimidazolidin-4-Yl]Methyl}-4'-(Trifluoromethyl)[Biphenyl]-2-Carboxamide

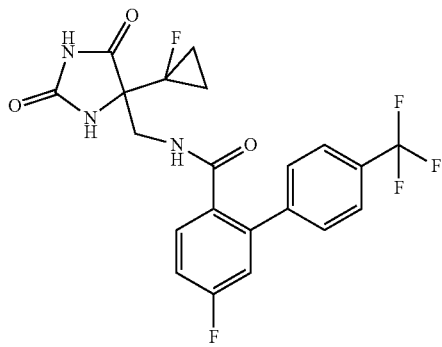 [SMILES: O=C1NC(=O)C(CNC(=O)c2ccc(F)cc2-c2ccc(C(F)(F)F)cc2)(C2(F)CC2)N1]

Enantiomeric separation of rac-5-fluoro-N-{[4-(1-fluorocyclopropyl)-2,5-dioxoimidazolidin-4 yl]methyl}-4'-(trifluoromethyl)[biphenyl]-2-carboxamide (120.1 mg) by preparative chiral HPLC [column: Daicel Chiralpak ID 5 µm, 250×20 mm; eluent: 60% n-heptan/40% isopropanol; flow rate: 20 ml/min; temperature: 40° C.; UV detection: 220 nm] afforded 39.3 mg (100% purity) of the desired product.

Analytical chiral HPLC: $R_t$=1.41 min, e.e. =>99% [column: 50×4.6 mm filled with Daicel Chiralpak ID-3 3 µm; eluent: 50% n-heptan/50% isopropanol; flow rate: 1 ml/min; UV detection: 220 nm]

LC-MS (Method 7): $R_t$=1.69 min; MS (ESIpos): m/z=454 [M+H]$^+$ $^1$H-NMR (600 MHz, DMSO-d6) δ [ppm]: 0.831 (1.62), 0.840 (2.12), 0.849 (4.63), 0.866 (3.75), 0.926 (3.37), 0.943 (4.37), 0.962 (1.62), 0.976 (1.62), 0.995 (2.50), 1.002 (7.75), 1.014 (2.63), 1.032 (7.12), 1.036 (8.12), 1.042 (6.25), 1.088 (0.37), 2.386 (1.12), 2.425 (1.37), 2.615 (1.00), 2.654 (1.25), 3.510 (3.50), 3.521 (3.63), 3.533 (5.63), 3.544 (5.25), 3.591 (5.12), 3.601 (5.37), 3.614 (3.37), 3.624 (3.00), 4.352 (0.63), 4.359 (0.63), 7.330 (8.25), 7.347 (13.63), 7.362 (4.00), 7.366 (2.75), 7.454 (5.50), 7.464 (6.00), 7.468 (5.12), 7.477 (4.37), 7.561 (13.88), 7.575 (15.25), 7.774 (16.00), 7.788 (14.00), 8.150 (15.87), 8.725 (3.75), 8.735 (7.50), 8.745 (3.75), 10.897 (1.75).

Example 254

Rac-N-{[4-(1-Fluorocyclopropyl)-2,5-Dioxoimidazolidin-4-Yl]Methyl}-4'-(Trifluoromethyl)[Biphenyl]-2-Carboxamide

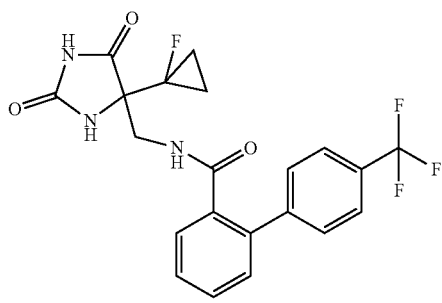

To a solution of rac-5-(aminomethyl)-5-(1-fluorocyclopropyl)imidazolidine-2,4-dione hydrochloride (100 mg, 447 µmol) and 4'-(trifluoromethyl)[1,1'-biphenyl]-2-carboxylic acid (119 mg, 447 µmol) in DMF (2.2 ml) was added 1-ethyl-3-(3-dimethylaminopropyl)carbodiimide hydrochloride (111 mg, 581 µmol), 1-hydroxybenzotriazole hydrate (89.0 mg, 581 µmol) and N,N-diisopropylethylamine (390 µl, 2.2 mmol). The reaction mixture was stirred overnight at room temperature and then concentrated under reduced pressure. The crude product was purified by preparative HPLC (Method 4f). After lyophilisation, 133 mg (100% purity, 68% yield) of the desired product were obtained.

LC-MS (Method 7): $R_t$=1.63 min; MS (ESIpos): m/z=436 [M+H]$^+$ $^1$H-NMR (600 MHz, DMSO-d6) δ [ppm]: 0.828 (0.87), 0.836 (1.31), 0.845 (1.91), 0.854 (4.29), 0.862 (1.54), 0.871 (3.45), 0.896 (0.60), 0.923 (2.98), 0.940 (4.06), 0.958 (1.71), 0.965 (1.49), 0.971 (1.74), 0.990 (2.47), 0.998 (7.47), 1.008 (2.69), 1.023 (2.70), 1.031 (7.69), 1.042 (2.16), 1.061 (0.61), 2.068 (0.43), 2.084 (1.73), 3.515 (3.44), 3.526 (3.66), 3.538 (5.56), 3.548 (5.37), 3.606 (4.82), 3.616 (5.23), 3.629 (3.40), 3.639 (3.25), 7.414 (6.07), 7.426 (9.79), 7.435 (8.21), 7.448 (9.87), 7.461 (5.11), 7.473 (8.67), 7.486 (4.35), 7.546 (14.05), 7.554 (10.30), 7.559 (16.00), 7.753 (15.24), 7.767 (13.91), 8.074 (15.47), 8.637 (3.46), 8.647 (7.11), 8.658 (3.70), 10.868 (2.80).

Example 255

Ent-N-{[4-(1-Fluorocyclopropyl)-2,5-Dioxoimidazolidin-4-Yl]Methyl}-4'-(Trifluoromethyl)[Biphenyl]-2-Carboxamide

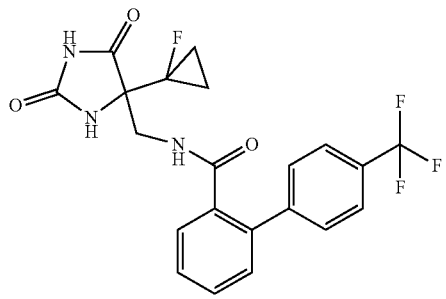 [SMILES: O=C1NC(=O)C(CNC(=O)c2ccccc2-c2ccc(C(F)(F)F)cc2)(C2(F)CC2)N1]

Enantiomeric separation of rac-N-{[4-(1-fluorocyclopropyl)-2,5-dioxoimidazolidin-4-yl]methyl}-4'-(trifluoromethyl)[biphenyl]-2-carboxamide by preparative chiral HPLC [sample preparation: 130.3 mg; column: Daicel Chiralpak ID 5 µm, 250×20 mm; eluent: 75% n-heptan/25% isopropanol; flow rate: 25 ml/min; temperature: 40° C.; UV detection: 220 nm] afforded 64.2 mg of the desired product. A second purification by chromatography on silica gel (10 g Ultra Snap Cartridge Biotage; eluent ethyl acetate/cyclohexane, elution gradient 16%→100%; flow: 36 ml/min) gave 30.4 mg (97% purity) of the desired product Analytical chiral HPLC: $R_t$=2.15 min, e.e. =96.8% [column: 50×4.6 mm filled with Daicel Chiralpak ID-3 3 µm; eluent: 70% n-heptan/30% isopropanol; flow rate: 1 ml/min; UV detection: 220 nm]

LC-MS (Method 7): $R_t$=1.65 min; MS (ESIpos): m/z=436 [M+H]$^+$

¹H-NMR (400 MHz, DMSO-d6) δ [ppm]: −0.008 (0.81), 0.008 (0.98), 0.820 (1.31), 0.825 (1.19), 0.838 (2.02), 0.851 (3.56), 0.878 (2.79), 0.915 (2.44), 0.945 (3.83), 0.961 (2.85), 0.982 (4.10), 0.991 (6.92), 1.006 (3.56), 1.032 (2.88), 1.041 (6.83), 1.082 (0.42), 1.157 (1.19), 1.175 (2.40), 1.192 (1.25), 1.236 (0.46), 1.988 (4.35), 2.072 (1.00), 2.327 (0.42), 2.366 (0.40), 2.669 (0.44), 2.709 (0.42), 3.502 (2.83), 3.518 (3.02), 3.536 (5.35), 3.552 (5.10), 3.598 (4.69), 3.613 (5.06), 3.632 (2.67), 3.647 (2.46), 4.021 (1.06), 4.038 (1.04), 7.406 (4.79), 7.409 (5.31), 7.425 (9.73), 7.428 (9.81), 7.436 (7.44), 7.455 (13.13), 7.474 (8.56), 7.477 (7.17), 7.493 (4.19), 7.496 (3.52), 7.540 (15.31), 7.558 (15.25), 7.561 (16.00), 7.572 (3.56), 7.576 (3.02), 7.754 (15.38), 7.774 (12.63), 8.100 (14.73), 8.662 (3.27), 8.678 (6.83), 8.693 (3.25), 10.889 (10.27).

Example 256

Rac-5,6-Difluoro-N-{[4-(1-Fluorocyclopropyl)-2,5-Dioxoimidazolidin-4-Yl]Methyl}-4'-(Trifluoromethyl)[Biphenyl]-2-Carboxamide

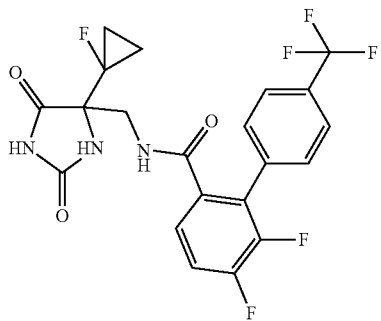 [SMILES: O=C1NC(=O)C(CNC(=O)c2ccc(F)c(F)c2-c2ccc(C(F)(F)F)cc2)(C2(F)CC2)N1]

To a solution of rac-5-(aminomethyl)-5-(1-fluorocyclopropyl)imidazolidine-2,4-dione hydrochloride (35.4 mg, 158 µmol) and 5,6-difluoro-4'-(trifluoromethyl)[1,1'-biphenyl]-2-carboxylic acid (47.8 mg, 158 µmol) in DMF (1 ml) was added 1-ethyl-3-(3-dimethylaminopropyl)carbodiimide hydrochloride (39.4 mg, 206 µmol), 1-hydroxybenzotriazole hydrate (31.5 mg, 206 µmol) and N,N-diisopropylethylamine (140 µl, 790 µmol). The reaction mixture was stirred overnight at room temperature and then concentrated under reduced pressure. The crude product was purified by preparative HPLC (Method 4f). After lyophilisation, 29.1 mg (100% purity, 39% yield) of the desired product were obtained.

LC-MS (Method 7): $R_t$=1.72 min, MS (ESIpos): m/z=472 [M+H]⁺

¹H-NMR (500 MHz, DMSO-d6) δ [ppm]: −0.007 (0.48), 0.803 (0.99), 0.813 (1.29), 0.823 (2.00), 0.834 (4.09), 0.843 (1.38), 0.855 (3.29), 0.875 (0.47), 0.884 (0.63), 0.902 (2.99), 0.922 (3.91), 0.930 (2.09), 0.945 (1.61), 0.953 (2.42), 0.959 (1.48), 0.974 (2.57), 0.983 (7.66), 0.997 (2.48), 1.014 (2.82), 1.023 (7.42), 1.037 (1.76), 2.072 (0.43), 2.731 (0.41), 2.890 (0.50), 3.434 (3.54), 3.446 (3.71), 3.461 (5.68), 3.474 (5.23), 3.531 (4.91), 3.543 (5.20), 3.558 (3.16), 3.570 (2.87), 7.268 (3.35), 7.276 (3.68), 7.284 (4.00), 7.293 (3.77), 7.539 (12.25), 7.555 (13.20), 7.591 (2.32), 7.607 (4.09), 7.627 (4.12), 7.644 (2.26), 7.806 (16.00), 7.823 (13.99), 8.125 (13.99), 8.699 (3.61), 8.711 (7.26), 8.724 (3.40), 10.823 (0.82).

Example 257

Rac-4'-Chloro-N-({4-[1-(Difluoromethyl)-1H-Pyrazol-5-Yl]-2,5-Dioxoimidazolidin-4-Yl}Methyl)-5-Fluoro[Biphenyl]-2-Carboxamide

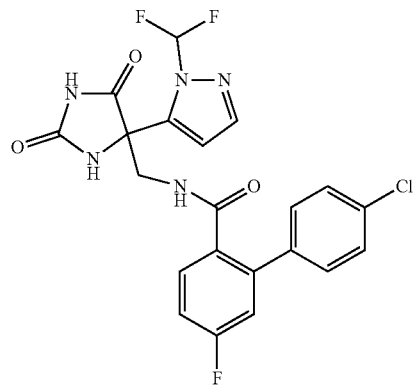 [SMILES: O=C1NC(=O)C(CNC(=O)c2ccc(F)cc2-c2ccc(Cl)cc2)(c2ccnn2C(F)F)N1]

To a solution of rac-5-(aminomethyl)-5-[1-(difluoromethyl)-1H-pyrazol-5-yl]imidazolidine-2,4-dione hydrochloride (57.0 mg, 202 µmol) and 4'-chloro-5-fluoro[1,1'-biphenyl]-2-carboxylic acid (50.7 mg, 202 µmol) in DMF (990 µl) was added 1-ethyl-3-(3-dimethylaminopropyl)carbodiimide hydrochloride (50.4 mg, 263 µmol), 1-hydroxybenzotriazole hydrate (40.3 mg, 263 µmol) and N,N-diisopropylethylamine (180 µl, 1.0 mmol). The reaction mixture was stirred overnight at room temperature and then concentrated under reduced pressure. The crude product was purified by preparative HPLC (Method 3f). After lyophilization, 57.5 mg (100% purity, 59% yield) of the desired product were obtained.

LC-MS (Method 7): $R_t$=1.61 min; MS (ESIpos): m/z=478 [M+H]⁺

¹H-NMR (600 MHz, DMSO-d6) δ [ppm]: 2.084 (2.10), 2.517 (0.58), 3.263 (0.42), 3.267 (0.54), 3.790 (2.44), 3.801 (2.59), 3.813 (4.11), 3.824 (3.86), 3.871 (3.91), 3.881 (4.18), 3.894 (2.54), 3.904 (2.32), 6.708 (9.77), 6.710 (10.16), 7.259 (3.71), 7.263 (4.83), 7.275 (3.79), 7.279 (4.69), 7.295 (2.10), 7.299 (1.91), 7.309 (4.52), 7.313 (4.11), 7.323 (2.59), 7.328 (2.30), 7.351 (12.09), 7.365 (15.90), 7.418 (4.30), 7.428 (4.55), 7.432 (4.05), 7.442 (3.91), 7.450 (16.00), 7.464 (12.02), 7.783 (9.48), 7.785 (9.77), 7.816 (2.68), 7.909 (2.73), 7.916 (2.57), 8.009 (2.29), 8.490 (10.48), 8.767 (2.69), 8.777 (5.32), 8.787 (2.61), 11.244 (2.23).

Example 258

Rac-4'-Chloro-N-({4-[1-(Difluoromethyl)-1H-Pyrazol-5-Yl]-2,5-Dioxoimidazolidin-4-Yl}Methyl)[Biphenyl]-2-Carboxamide

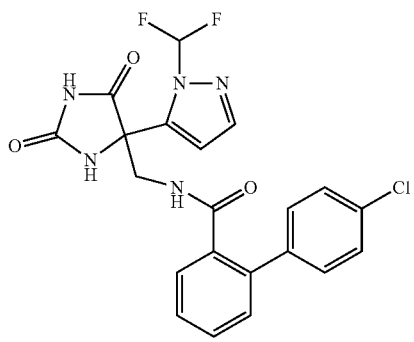 [SMILES: O=C1NC(=O)C(CNC(=O)c2ccccc2-c2ccc(Cl)cc2)(c2ccnn2C(F)F)N1]

To a solution of rac-5-(aminomethyl)-5-[1-(difluoromethyl)-1H-pyrazol-5-yl]imidazolidine-2,4-dione hydrochloride (57.0 mg, 202 µmol) and 4'-chloro[1,1'-biphenyl]-2-carboxylicacid (47.1 mg, 202 µmol) in DMF (990 µl) was added 1-ethyl-3-(3-dimethylaminopropyl)carbodiimide hydrochloride (50.4 mg, 263 µmol), 1-hydroxybenzotriazole hydrate (40.3 mg, 263 µmol) and N,N-diisopropylethylamine (180 µl, 1.0 mmol). The reaction mixture was stirred overnight at room temperature and then concentrated under reduced pressure. The crude product was purified by preparative HPLC (Method 4f). After lyophilization, 49.5 mg (100% purity, 53% yield) of the desired product were obtained.

LC-MS (Method 7): $R_t$=1.55 min; MS (ESIpos): m/z=460 [M+H]$^+$ $^1$H-NMR (600 MHz, DMSO-d6) δ [ppm]: 2.069 (1.66), 2.084 (2.94), 2.422 (0.58), 2.651 (0.50), 2.889 (0.47), 3.328 (0.87), 3.788 (2.47), 3.799 (2.65), 3.811 (4.06), 3.822 (3.80), 3.875 (3.80), 3.885 (4.09), 3.898 (2.54), 3.909 (2.40), 6.703 (9.65), 6.705 (9.83), 7.330 (12.05), 7.344 (15.48), 7.376 (4.83), 7.388 (12.71), 7.401 (6.92), 7.430 (5.38), 7.435 (16.00), 7.442 (7.11), 7.449 (12.22), 7.454 (3.98), 7.518 (3.64), 7.531 (5.48), 7.543 (2.24), 7.783 (9.40), 7.785 (9.48), 7.823 (2.66), 7.916 (2.66), 7.923 (2.55), 8.016 (2.25), 8.465 (3.67), 8.734 (2.64), 8.744 (5.15), 8.755 (2.54).

Example 259

Ent-4'-Chloro-N-({4-[1-(Difluoromethyl)-1H-Pyrazol-5-Yl]-2,5-Dioxoimidazolidin-4-Yl}Methyl)[Biphenyl]-2-Carboxamide

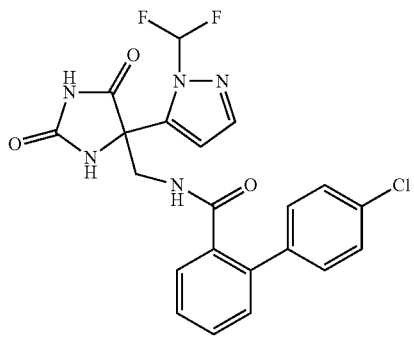 [SMILES: O=C1NC(=O)C(CNC(=O)c2ccccc2-c2ccc(Cl)cc2)(c2ccnn2C(F)F)N1]

Enantiomeric separation of rac-4'-chloro-N-({4-[1-(difluoromethyl)-1H-pyrazol-5-yl]-2,5-dioxoimidazolidin-4-yl}methyl)[biphenyl]-2-carboxamide (47.2 mg) by preparative chiral HPLC [column: Daicel Chiralpak ID 5 µm, 250×20 mm; eluent: 55% n-heptan/45% isopropanol; flow rate: 25 ml/min; temperature: 50° C.; UV detection: 220 nm] afforded 20.0 mg (98% purity) of the desired product.

Analytical chiral HPLC: $R_t$=1.86 min, e.e. =97.7% [column: 50×4.6 mm filled with Daicel Chiralpak ID-3 3 µm; eluent: 50% n-heptan/50% isopropanol; flow rate: 1 ml/min; UV detection: 220 nm]

LC-MS (Method 7): $R_t$=1.56 min; MS (ESIpos): m/z=460 [M+H]$^+$ $^1$H-NMR (600 MHz, DMSO-d6) δ [ppm]: 0.991 (0.41), 1.001 (0.41), 1.033 (1.75), 1.044 (1.69), 1.121 (0.80), 1.133 (1.63), 1.145 (0.80), 2.383 (0.92), 2.422 (1.15), 2.460 (0.61), 2.464 (1.08), 2.467 (1.27), 2.470 (1.08), 2.514 (1.43), 2.517 (1.53), 2.520 (1.40), 2.572 (2.93), 2.611 (1.02), 2.614 (0.64), 2.651 (1.08), 2.859 (0.64), 2.872 (0.61), 3.259 (1.50), 3.264 (1.82), 3.329 (2.45), 3.339 (0.45), 3.787 (2.17), 3.799 (2.33), 3.811 (3.54), 3.822 (3.28), 3.871 (3.22), 3.881 (3.47), 3.894 (2.20), 3.904 (1.94), 6.700 (8.48), 6.703 (8.51), 7.329 (11.86), 7.332 (3.86), 7.340 (4.53), 7.343 (15.36), 7.347 (1.75), 7.373 (3.67), 7.375 (3.76), 7.388 (9.53), 7.401 (5.42), 7.430 (4.59), 7.434 (16.00), 7.438 (4.69), 7.441 (5.96), 7.443 (5.71), 7.445 (4.59), 7.448 (11.89), 7.453 (3.44), 7.516 (3.35), 7.518 (3.35), 7.529 (4.81), 7.531 (4.62), 7.541 (2.01), 7.544 (1.98), 7.781 (8.19), 7.784 (8.03), 7.823 (2.20), 7.916 (2.10), 7.923 (2.04), 8.016 (1.75), 8.451 (1.59), 8.729 (2.07), 8.739 (3.98), 8.750 (1.91).

Example 260

Rac-N-({4-[1-(Difluoromethyl)-1H-Pyrazol-5-Yl]-2,5-Dioxoimidazolidin-4-Yl}Methyl)-4'-(Trifluoromethyl)[Biphenyl]-2-Carboxamide

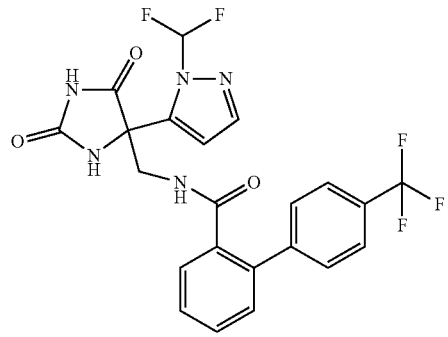 [SMILES: O=C1NC(=O)C(CNC(=O)c2ccccc2-c2ccc(C(F)(F)F)cc2)(c2ccnn2C(F)F)N1]

To a solution of rac-5-(aminomethyl)-5-[1-(difluoromethyl)-1H-pyrazol-5-yl]imidazolidine-2,4-dione hydrochloride (57.0 mg, 202 µmol) and 4'-(trifluoromethyl)[1, 1'-biphenyl]-2-carboxylic add (53.9 mg, 202 µmol) in DMF (990 µl) was added 1-ethyl-3-(3-dimethylaminopropyl)carbodiimide hydrochloride (50.4 mg, 263 µmol), 1-hydroxybenzotriazole hydrate (40.3 mg, 263 µmol) and N,N-diisopropylethylamine (180 µl, 1.0 mmol). The reaction mixture was stirred overnight at room temperature and then concentrated under reduced pressure. The crude product was purified by preparative HPLC (Method 4f). After lyophilization, 66.4 mg (100% purity, 66% yield) of the desired product were obtained.

LC-MS (Method 7): $R_t$=1.64 min; MS (ESIpos): m/z=494 [M+H]$^+$

¹H-NMR (600 MHz, DMSO-d6) δ [ppm]: 2.069 (0.81), 2.084 (3.39), 2.384 (0.47), 2.422 (0.76), 2.572 (0.50), 2.611 (0.39), 2.651 (0.68), 2.731 (0.42), 2.889 (0.42), 3.260 (0.42), 3.266 (1.12), 3.330 (0.99), 3.803 (3.39), 3.815 (3.52), 3.827 (5.52), 3.838 (5.19), 3.892 (5.34), 3.902 (5.65), 3.915 (3.52), 3.925 (3.34), 6.715 (14.07), 7.430 (6.75), 7.441 (14.12), 7.452 (10.06), 7.479 (4.93), 7.492 (8.78), 7.505 (4.33), 7.525 (14.07), 7.538 (15.61), 7.558 (5.45), 7.570 (8.13), 7.583 (3.34), 7.740 (16.00), 7.753 (14.23), 7.780 (13.79), 7.819 (3.70), 7.912 (3.80), 7.919 (3.67), 8.012 (3.15), 8.494 (14.38), 8.818 (3.70), 8.828 (7.40), 8.839 (3.70), 11.255 (2.50).

Example 261

Ent-N-({4-[1-(Difluoromethyl)-1H-Pyrazol-5-Yl]-2, 5-Dioxoimidazolidin-4-Yl}Methyl)-4'-(Trifluoromethyl)[Biphenyl]-2-Carboxamide

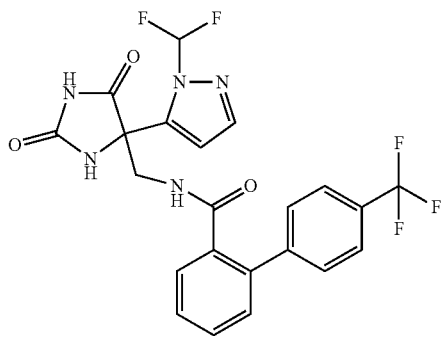 [SMILES: O=C1NC(=O)C(CNC(=O)c2ccccc2-c2ccc(C(F)(F)F)cc2)(c2ccnn2C(F)F)N1]

Enantiomeric separation of rac-N-({4-[1-(difluoromethyl)-1H-pyrazol-5-yl]-2,5-dioxoimidazolidin-4-yl}methyl)-4'-(trifluoromethyl)[biphenyl]-2-carboxamide (64.4 mg) by preparative chiral HPLC [column: Daicel Chiralpak ID 5 μm, 250×20 mm; eluent: 70% n-heptan/30% isopropanol; flow rate: 25 ml/min; temperature: 40° C.; UV detection: 220 nm] afforded 28.0 mg (100% purity) of the desired product.

Analytical chiral HPLC: $R_t$=1.43 min, e.e. =>99% [column: 50×4.6 mm filled with Daicel Chiralpak ID-3 3 μm; eluent: 70% n-heptan/30% isopropanol; flow rate: 1 ml/min; UV detection: 220 nm]

LC-MS (Method 7): $R_t$=1.65 min; MS (ESIpos): m/z=494 [M+H]⁺

¹H-NMR (400 MHz, DMSO-d6) δ [ppm]: −0.149 (0.96), −0.008 (7.84), 0.008 (8.56), 0.146 (0.90), 0.841 (0.93), 0.859 (2.31), 0.875 (0.80), 1.030 (4.89), 1.045 (4.94), 1.055 (0.66), 1.150 (0.61), 1.248 (1.73), 2.327 (0.74), 2.366 (1.04), 2.523 (3.48), 2.670 (0.74), 2.710 (1.01), 3.792 (2.92), 3.809 (3.08), 3.827 (5.45), 3.844 (5.08), 3.887 (5.05), 3.902 (5.50), 3.921 (2.95), 3.936 (2.68), 4.323 (0.90), 4.334 (0.85), 6.717 (14.11), 6.721 (14.35), 7.424 (5.08), 7.428 (5.74), 7.442 (11.69), 7.447 (10.18), 7.458 (9.91), 7.474 (4.84), 7.477 (4.94), 7.493 (8.40), 7.496 (7.65), 7.511 (5.05), 7.521 (13.29), 7.541 (15.34), 7.553 (6.54), 7.557 (6.22), 7.572 (7.55), 7.575 (7.18), 7.591 (2.76), 7.594 (2.82), 7.740 (16.00), 7.760 (13.34), 7.781 (14.03), 7.786 (13.50), 7.916 (4.07), 7.926 (3.83), 8.065 (3.51), 8.514 (11.64), 8.839 (3.30), 8.855 (6.91), 8.871 (3.30), 11.258 (1.65).

Example 262

Rac-N-({4-[1-(Difluoromethyl)-1H-Pyrazol-5-Yl]-2, 5-Dioxoimidazolidin-4-Yl}Methyl)-5-Fluoro-4'-(Trifluoromethyl)[Biphenyl]-2-Carboxamide

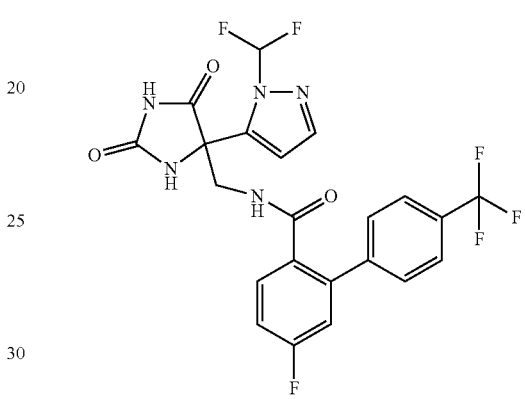

To a solution of rac-5-(aminomethyl)-5-[1-(difluoromethyl)-1H-pyrazol-5-yl]imidazolidine-2,4-dione hydrochloride (57.0 mg, 202 μmol) and 5-fluoro-4'-(trifluoromethyl)[1,1'-biphenyl]-2-carboxylic acid (57.5 mg, 202 μmol) in DMF (990 μl) was added 1-ethyl-3-(3-dimethylaminopropyl)carbodiimide hydrochloride (50.4 mg, 263 μmol), 1-hydroxybenzotriazole hydrate (40.3 mg, 263 μmol) and N,N-diisopropylethylamine (180 μl, 1.0 mmol). The reaction mixture was stirred overnight at room temperature and then concentrated under reduced pressure. The crude product was purified by preparative HPLC (Method 4f). After lyophilization, 66.4 mg (100% purity, 66% yield) of the desired product were obtained.

LC-MS (Method 7): $R_t$=1.70 min, MS (ESIpos): m/z=512 [M+H]⁺

¹H-NMR (600 MHz, DMSO-d6) δ [ppm]: 2.069 (0.82), 2.084 (4.72), 2.422 (0.97), 2.570 (1.31), 2.651 (0.94), 3.249 (0.41), 3.329 (3.00), 3.802 (3.30), 3.813 (3.56), 3.825 (5.66), 3.836 (5.32), 3.882 (5.40), 3.892 (5.73), 3.905 (3.52), 3.915 (3.22), 6.715 (13.86), 6.717 (13.83), 7.322 (4.95), 7.326 (6.71), 7.338 (5.06), 7.342 (6.63), 7.348 (3.26), 7.352 (2.55), 7.362 (6.33), 7.366 (5.43), 7.376 (3.52), 7.380 (3.07), 7.475 (5.81), 7.484 (6.15), 7.489 (5.36), 7.499 (4.72), 7.544 (13.94), 7.558 (15.44), 7.753 (16.00), 7.767 (14.31), 7.777 (13.68), 7.780 (13.45), 7.810 (3.93), 7.903 (3.86), 7.910 (3.52), 8.003 (3.19), 8.510 (13.60), 8.845 (3.67), 8.855 (7.34), 8.865 (3.60), 11.257 (2.32).

Example 263

Rac-N-({2,5-Dioxo-4-[5-(Trifluoromethyl)-1,3-Thiazol-4-Yl]Imidazolidin-4-Yl}Methyl)-4'-(Trifluoromethyl)[Biphenyl]-2-Carboxamide

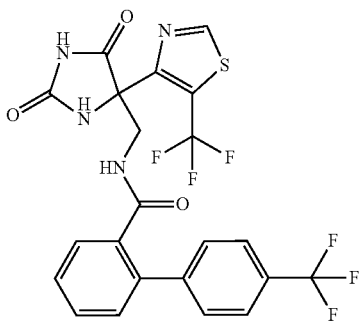 [SMILES: O=C1NC(=O)C(CNC(=O)c2ccccc2-c2ccc(C(F)(F)F)cc2)(c2ncsc2C(F)(F)F)N1]

To a solution of rac-5-(aminomethyl)-5-[5-(trifluoromethyl)-1,3-thiazol-4-yl]imidazolidine-2,4-dione hydrochloride (109 mg, 343 µmol) and 4'-(trifluoromethyl)[1,1'-biphenyl]-2-carboxylic acid (110 mg, 412 µmol) in DMF (2.1 ml) was added 1-ethyl-3-(3-dimethylaminopropyl)carbodiimide hydrochloride (85.5 mg, 446 µmol), 1-hydroxybenzotriazole hydrate (68.3 mg, 446 µmol) and N,N-diisopropylethylamine (300 µl, 1.7 mmol). The reaction mixture was stirred for 3 days at room temperature and then concentrated under reduced pressure. The crude product was purified by preparative HPLC (Method 4f). After lyophilization, 109 mg (85% purity, 51% yield) of the desired product were obtained.

LC-MS (Method 7): $R_t$=1.72 min; MS (ESIpos): m/z=529 [M+H]$^+$ $^1$H-NMR (600 MHz, DMSO-d6) δ [ppm]: 2.056 (2.52), 2.073 (16.00), 3.359 (0.54), 4.010 (2.01), 4.020 (2.15), 4.032 (2.51), 4.043 (2.34), 4.239 (2.41), 4.250 (2.61), 4.262 (2.19), 4.273 (2.01), 7.424 (3.16), 7.436 (5.10), 7.444 (4.14), 7.456 (4.91), 7.471 (2.51), 7.483 (4.32), 7.495 (2.10), 7.550 (2.76), 7.562 (10.78), 7.575 (9.18), 7.760 (7.86), 7.773 (6.95), 7.793 (0.72), 7.806 (0.60), 8.230 (7.11), 8.638 (1.88), 8.649 (3.85), 8.659 (1.90), 9.379 (10.42), 11.126 (4.37).

Example 264

Ent-N-({2,5-Dioxo-4-[5-(Trifluoromethyl)-1,3-Thiazol-4-Yl]Imidazolidin-4-Yl}Methyl)-4'-(Trifluoromethyl)[Biphenyl]-2-Carboxamide

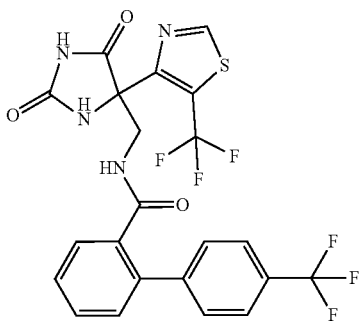 [SMILES: O=C1NC(=O)C(CNC(=O)c2ccccc2-c2ccc(C(F)(F)F)cc2)(c2ncsc2C(F)(F)F)N1]

Enantiomeric separation of rac-N-({2,5-dioxo-4-[5-(trifluoromethyl)-1,3-thiazol-4-yl]imidazolidin-4-yl}methyl)-4'-(trifluoromethyl)[biphenyl]-2-carboxamide (108 mg) by preparative chiral HPLC [column: Daicel Chiralpak ID 5 µm, 250×20 mm; eluent: 50% n-heptan/50% isopropanol; flow rate: 20 ml/min; temperature: 40° C.; UV detection: 220 nm] afforded 31.1 mg (100% purity) of the desired product.

Analytical chiral HPLC: $R_t$=1.63 min, e.e. =>99% [column: 50×4.6 mm filled with Daicel Chiralpak ID-3 3 µm; eluent: 50% n-heptan/50% isopropanol; flow rate: 1 ml/min; UV detection: 220 nm]

LC-MS (Method 7): $R_t$=1.73 min; MS (ESIpos): m/z=529 [M+H]$^+$ $^1$H-NMR (600 MHz, DMSO-d6) δ [ppm]: 0.067 (0.43), 1.034 (0.52), 1.043 (0.54), 2.069 (7.89), 2.422 (0.57), 2.572 (0.83), 2.651 (0.57), 3.269 (1.46), 3.331 (2.04), 4.012 (2.98), 4.022 (3.04), 4.034 (3.67), 4.045 (3.44), 4.226 (3.81), 4.236 (4.04), 4.249 (3.38), 4.259 (3.10), 7.422 (4.99), 7.437 (10.29), 7.451 (7.46), 7.466 (3.87), 7.479 (6.68), 7.492 (3.15), 7.546 (4.33), 7.559 (16.00), 7.573 (13.36), 7.754 (12.04), 7.767 (10.38), 8.188 (12.22), 8.593 (2.81), 8.603 (5.65), 8.614 (2.70), 9.373 (14.54), 11.087 (1.26).

Example 265

Rac-N-({2,5-Dioxo-4-[5-(Trifluoromethyl)-1,3-Thiazol-4-Yl]Imidazolidin-4-Yl}Methyl)-4-Fluoro-4'-(Trifluoromethyl)[Biphenyl]-2-Carboxamide

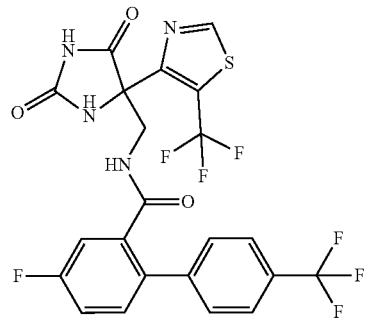 [SMILES: O=C1NC(=O)C(CNC(=O)c2cc(F)ccc2-c2ccc(C(F)(F)F)cc2)(c2ncsc2C(F)(F)F)N1]

To a solution of rac-5-(aminomethyl)-5-[5-(trifluoromethyl)-1,3-thiazol-4-yl]imidazolidine-2,4-dione hydrochloride (100 mg, 316 µmol) and 4-fluoro-4'-(trifluoromethyl)[1,1'-biphenyl]-2-carboxylic acid (108 mg, 379 µmol) in DMF (2.0 ml) was added 1-ethyl-3-(3-dimethylaminopropyl)carbodiimide hydrochloride (78.7 mg, 410 µmol), 1-hydroxybenzotriazole hydrate (62.9 mg, 410 µmol) and N,N-diisopropylethylamine (280 µl, 1.6 mmol). The reaction mixture was stirred for 3 days at room temperature and then concentrated under reduced pressure. The crude product was purified by preparative HPLC (Method 4f). After lyophilization, 85.6 mg (95% purity, 47% yield) of the desired product were obtained.

LC-MS (Method 7): $R_t$=1.76 min; MS (ESIpos): m/z=547 [M+H]$^+$ $^1$H-NMR (600 MHz, DMSO-d6) δ [ppm]: 2.057 (3.29), 2.073 (1.01), 2.425 (0.87), 2.654 (0.81), 3.290 (0.47), 3.299 (1.82), 3.361 (0.81), 3.368 (0.61), 4.016 (3.03), 4.027 (3.23), 4.039 (3.76), 4.049 (3.56), 4.236 (3.63), 4.246 (3.97), 4.259 (3.29), 4.269 (3.03), 7.231 (3.90), 7.236 (4.50), 7.246 (4.03), 7.251 (4.24), 7.405 (1.82), 7.410 (1.95), 7.419 (4.24), 7.424 (4.37), 7.434 (2.49), 7.438 (2.62), 7.494 (4.64), 7.503 (4.71), 7.508 (3.70), 7.517 (3.56), 7.542 (10.49), 7.556 (11.16), 7.759 (11.56), 7.773 (10.22), 7.790 (0.81), 7.803 (0.74), 8.312 (10.15), 8.790 (2.76), 8.800 (5.71), 8.811 (2.76), 9.381 (16.00), 11.091 (0.54), 11.153 (6.66).

Example 266

Ent-N-({2,5-Dioxo-4-[5-(Trifluoromethyl)-1,3-Thiazol-4-Yl]Imidazolidin-4-Yl}Methyl)-4-Fluoro-4'-(Trifluoromethyl)[Biphenyl]-2-Carboxamide

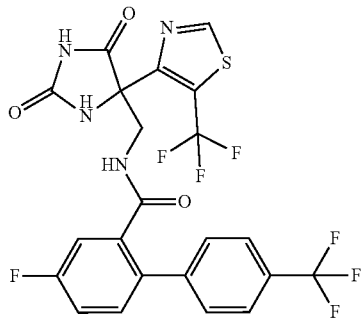 [SMILES: O=C1NC(=O)C(CNC(=O)c2cc(F)ccc2-c2ccc(C(F)(F)F)cc2)(c2ncsc2C(F)(F)F)N1]

Enantiomeric separation of rac-N-({2,5-dioxo-4-[5-(trifluoromethyl)-1,3-thiazol-4-yl]imidazolidin-4-yl}methyl)-4-fluoro-4'-(trifluoromethyl)[biphenyl]-2-carboxamide (85 mg) by preparative chiral HPLC [column: Daicel Chiralpak ID 5 µm, 250×20 mm; eluent: 70% n-heptan/30% isopropanol; flow rate: 20 ml/min; temperature: 40° C.; UV detection: 210 nm] afforded 28.8 mg (94% purity) of the desired product.

Analytical chiral HPLC: $R_t$=1.64 min, e.e. =99% [column: 50×4.6 mm filled with Daicel Chiralpak ID-3 3 µm; eluent: 50% n-heptan/50% isopropanol; flow rate: 1 ml/min; UV detection: 220 nm]

LC-MS (Method 7): $R_t$=1.76 min; MS (ESIpos): m/z=547 [M+H]$^+$ $^1$H-NMR (400 MHz, DMSO-d6) δ [ppm]: 1.157 (0.45), 2.073 (16.00), 4.008 (1.11), 4.024 (1.21), 4.043 (1.53), 4.058 (1.42), 4.224 (1.43), 4.240 (1.59), 4.258 (1.22), 4.274 (1.11), 7.226 (1.72), 7.233 (2.07), 7.248 (1.79), 7.255 (1.96), 7.395 (0.77), 7.402 (0.80), 7.417 (1.92), 7.423 (1.99), 7.438 (1.25), 7.444 (1.26), 7.488 (2.12), 7.502 (2.26), 7.509 (1.58), 7.523 (1.45), 7.538 (3.88), 7.558 (4.54), 7.754 (4.76), 7.775 (3.96), 8.303 (4.56), 8.776 (1.01), 8.791 (2.17), 8.807 (1.04), 9.381 (5.86), 11.144 (1.48).

Example 267

Rac-N-({2,5-Dioxo-4-[5-(Trifluoromethyl)-1,3-Thiazol-4-Yl]Imidazolidin-4-Yl}Methyl)-5-Fluoro-4'-(Trifluoromethyl)[Biphenyl]-2-Carboxamide

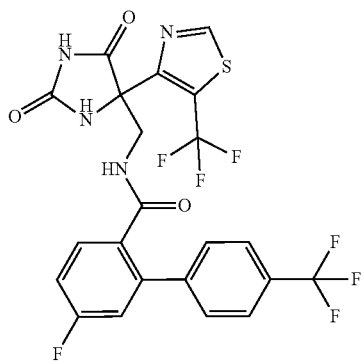 [SMILES: O=C1NC(=O)C(CNC(=O)c2ccc(F)cc2-c2ccc(C(F)(F)F)cc2)(c2ncsc2C(F)(F)F)N1]

To a solution of rac-5-(aminomethyl)-5-[5-(trifluoromethyl)-1,3-thiazol-4-yl]imidazolidine-2,4-dione hydrochloride (100 mg, 316 µmol) and 5-fluoro-4'-(trifluoromethyl)[1,1'-biphenyl]-2-carboxylic acid (108 mg, 379 µmol) in DMF (2.0 ml) was added 1-ethyl-3-(3-dimethylaminopropyl)carbodiimide hydrochloride (78.7 mg, 410 µmol), 1-hydroxybenzotriazole hydrate (62.9 mg, 410 µmol) and N,N-diisopropylethylamine (280 µl, 1.6 mmol). The reaction mixture was stirred for 3 days at room temperature and then concentrated under reduced pressure. The crude product was purified by preparative HPLC (Method 4f). After lyophilization, 84.9 mg (91% purity, 45% yield) of the desired product were obtained.

LC-MS (Method 7): $R_t$=1.78 min, MS (ESIpos): m/z=547 [M+H]$^+$ $^1$H-NMR (600 MHz, DMSO-d6) δ [ppm]: 2.047 (2.35), 2.073 (16.00), 2.425 (0.50), 2.653 (0.50), 3.296 (0.46), 3.300 (1.18), 3.365 (1.09), 3.372 (0.46), 4.009 (2.52), 4.020 (2.65), 4.032 (3.11), 4.043 (2.90), 4.224 (2.98), 4.234 (3.28), 4.247 (2.69), 4.257 (2.44), 7.328 (2.56), 7.332 (4.45), 7.339 (2.48), 7.344 (3.65), 7.348 (4.75), 7.353 (4.54), 7.357 (2.98), 7.367 (2.44), 7.372 (2.18), 7.386 (0.50), 7.465 (3.44), 7.474 (3.57), 7.478 (3.19), 7.488 (2.77), 7.580 (8.44), 7.594 (9.28), 7.773 (9.57), 7.787 (8.36), 7.806 (0.63), 7.820 (0.55), 8.260 (8.57), 8.669 (2.31), 8.680 (4.75), 8.690 (2.27), 9.376 (13.14), 11.127 (5.67).

Example 268

Ent-N-({2,5-Dioxo-4-[5-(Trifluoromethyl)-1,3-Thiazol-4-Yl]Imidazolidin-4-Yl}Methyl)-5-Fluoro-4'-(Trifluoromethyl)[Biphenyl]-2-Carboxamide

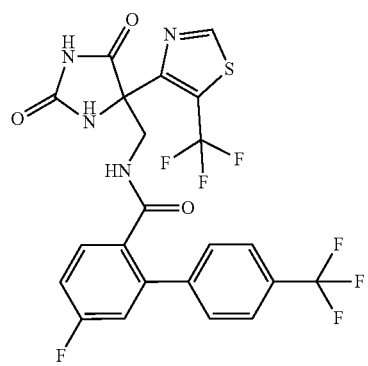 [SMILES: O=C1NC(=O)C(CNC(=O)c2ccc(F)cc2-c2ccc(C(F)(F)F)cc2)(c2ncsc2C(F)(F)F)N1]

Enantiomeric separation of rac-N-({2,5-dioxo-4-[5-(trifluoromethyl)-1,3-thiazol-4-yl]imidazolidin-4-yl}methyl)-5-fluoro-4'-(trifluoromethyl)[biphenyl]-2-carboxamide (85 mg) by preparative chiral HPLC [column: Daicel Chiralpak ID 5 µm, 250×20 mm; eluent: 50% n-heptan/50% isopropanol; flow rate: 15 ml/min; temperature: 50° C.; UV detection: 220 nm] afforded 26.9 mg (100% purity) of the desired product.

Analytical chiral HPLC: $R_t$=5.30 min, e.e. =99% [column: 250×4.6 mm filled with Daicel Chiralpak ID 5 µm; eluent: 50% n-heptan/50% isopropanol; flow rate: 1 ml/min; temperature: 50° C.; UV detection: 220 nm]

LC-MS (Method 7): $R_t$=1.78 min; MS (ESIpos): m/z=547 [M+H]$^+$ $^1$H-NMR (400 MHz, DMSO-d6) δ [ppm]: −0.008 (1.81), 0.008 (1.73), 0.987 (0.51), 1.003 (0.53), 1.261 (0.51), 2.323 (0.70), 2.327 (0.98), 2.332 (0.72), 2.366 (0.75), 2.523 (3.92), 2.665 (0.79), 2.669 (1.07), 2.674 (0.79), 2.710 (0.79), 4.002 (3.26), 4.017 (3.47), 4.036 (4.43), 4.052 (4.11), 4.211 (4.11), 4.226 (4.56), 4.245 (3.52), 4.260 (3.13), 7.321 (3.26), 7.327 (7.63), 7.336 (1.75), 7.351 (13.85), 7.357 (4.39), 7.372 (4.09), 7.378 (2.88), 7.458 (4.99), 7.473 (4.73), 7.479 (4.47), 7.494 (3.45), 7.576 (10.97), 7.596 (12.87), 7.768 (13.38), 7.789 (11.10), 8.248 (12.02), 8.654 (2.88), 8.669 (6.33), 8.685 (2.96), 9.376 (16.00), 11.116 (5.52).

Example 269

Rac-N-{[4-(2,5-Dimethyl-1,3-Thiazol-4-Yl)-2,5-Dioxoimidazolidin-4-Yl]Methyl}-5-Fluoro-4'-(Trifluoromethyl)[Biphenyl]-2-Carboxamide

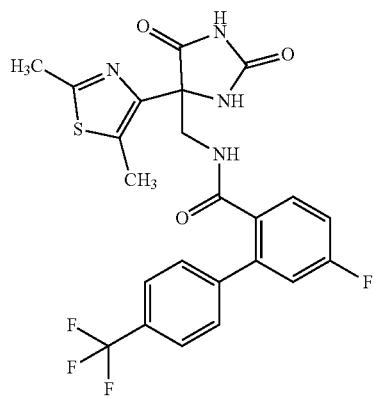 [SMILES: Cc1nc(C2(CNC(=O)c3ccc(F)cc3-c3ccc(C(F)(F)F)cc3)NC(=O)NC2=O)c(C)s1]

To a solution of rac-5-(aminomethyl)-5-(2,5-dimethyl-1,3-thiazol-4-yl)imidazolidine-2,4-dione hydrochloride (60.0 mg, 217 µmol) and 5-fluoro-4'-(trifluoromethyl)[1,1'-biphenyl]-2-carboxylic acid (61.6 mg, 217 µmol) in DMF (1.1 ml) was added 1-ethyl-3-(3-dimethylaminopropyl)carbodiimide hydrochloride (54.0 mg, 282 µmol), 1-hydroxybenzotriazole hydrate (43.2 mg, 282 µmol) and N,N-diisopropylethylamine (260 µl, 1.5 mmol). The reaction mixture was stirred overnight at room temperature and then concentrated under reduced pressure. The crude product was purified by preparative HPLC (Method 4f). After lyophilization, 30.9 mg (96% purity, 27% yield) of the desired product were obtained.

LC-MS (Method 8): $R_t$=0.88 min, MS (ESIpos): m/z=507 [M+H]$^+$ $^1$H-NMR (400 MHz, DMSO-d6) δ [ppm]: −0.008 (1.02), 0.008 (1.05), 2.347 (16.00), 2.524 (0.83), 3.828 (2.08), 3.843 (1.90), 3.847 (1.97), 7.319 (1.17), 7.325 (1.81), 7.336 (1.02), 7.343 (1.35), 7.350 (1.88), 7.357 (1.92), 7.363 (1.26), 7.378 (1.03), 7.385 (0.83), 7.456 (1.46), 7.471 (1.47), 7.477 (1.21), 7.491 (1.05), 7.517 (2.83), 7.537 (3.20), 7.758 (3.38), 7.779 (2.99), 8.503 (2.44), 8.506 (2.45), 8.755 (0.74), 8.770 (1.57), 8.785 (0.72), 11.157 (2.16).

Example 270

Rac-N-{[4-(5-Cyclopropyl-1,3-Thiazol-4-Yl)-2,5-Dioxoimidazolidin-4-Yl]Methyl}-4'-(Trifluoromethyl)[Biphenyl]-2-Carboxamide

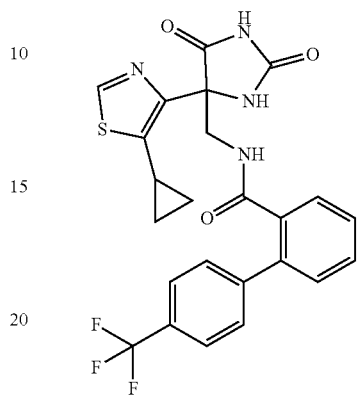

To a solution of rac-5-(aminomethyl)-5-(5-cyclopropyl-1,3-thiazol-4-yl)imidazolidine-2,4-dione hydrochloride (110 mg, 381 µmol) and 4'-(trifluoromethyl)[1,1'-biphenyl]-2-carboxylic acid (101 mg, 381 µmol) in DMF (2.0 ml) was added 1-ethyl-3-(3-dimethylaminopropyl)carbodiimide hydrochloride (94.9 mg, 495 µmol), 1-hydroxybenzotriazole hydrate (75.8 mg, 495 µmol) and N,N-diisopropylethylamine (460 µl, 2.7 mmol). The reaction mixture was stirred overnight at room temperature and then concentrated under reduced pressure. The crude product was purified by preparative HPLC (Method 4f). After lyophilization, 110 mg (98% purity, 57% yield) of the desired product were obtained.

LC-MS (Method 8): $R_t$=0.92 min, MS (ESIpos): m/z=501 [M+H]$^+$ $^1$H-NMR (400 MHz, DMSO-d6) δ [ppm]: −0.008 (0.96), 0.008 (0.97), 0.524 (0.76), 0.538 (1.56), 0.547 (1.80), 0.551 (2.00), 0.561 (2.22), 0.565 (2.00), 0.575 (1.41), 0.579 (1.13), 0.680 (1.03), 0.685 (1.39), 0.689 (1.56), 0.694 (2.08), 0.699 (2.17), 0.708 (1.87), 0.712 (1.82), 0.722 (1.75), 0.735 (0.87), 0.976 (0.62), 0.985 (0.55), 0.989 (0.50), 0.999 (1.78), 1.008 (2.29), 1.012 (2.25), 1.018 (4.69), 1.028 (3.04), 1.033 (2.64), 1.038 (5.04), 1.044 (2.37), 1.048 (2.20), 1.058 (1.63), 1.067 (0.55), 1.071 (0.50), 1.081 (0.52), 1.923 (0.92), 1.936 (1.88), 1.944 (2.00), 1.948 (1.26), 1.957 (3.58), 1.964 (1.24), 1.969 (1.88), 1.977 (1.75), 1.990 (0.79), 2.072 (9.88), 4.106 (8.05), 4.122 (8.07), 7.441 (5.80), 7.460 (16.00), 7.476 (5.48), 7.497 (1.63), 7.536 (3.28), 7.541 (3.01), 7.554 (3.70), 7.559 (3.23), 7.582 (7.71), 7.602 (8.87), 7.766 (9.26), 7.787 (7.56), 8.265 (7.04), 8.601 (2.05), 8.617 (4.39), 8.632 (2.00), 8.788 (12.35), 11.000 (5.93).

Example 271

Ent-N-{[4-(5-Cyclopropyl-1,3-Thiazol-4-Yl)-2,5-Dioxoimidazolidin-4-Yl]Methyl}-4'-(Trifluoromethyl)[Biphenyl]-2-Carboxamide

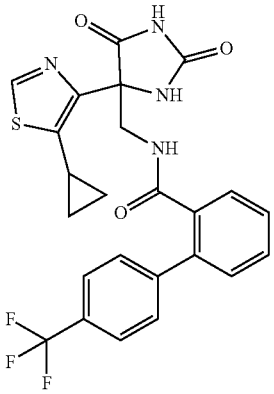 [SMILES: O=C1NC(=O)C(CNC(=O)c2ccccc2-c2ccc(C(F)(F)F)cc2)(c2ncsc2C2CC2)N1]

Enantiomeric separation of rac-N-{[4-(5-cyclopropyl-1,3-thiazol-4-yl)-2,5-dioxoimidazolidin-4 yl]methyl}-4'-(trifluoromethyl)[biphenyl]-2-carboxamide (110 mg) by preparative chiral HPLC [column: Daicel Chiralpak IA 5 µm, 250×20 mm; eluent: 50% n-heptane/50% isopropanol; flow rate: 20 ml/min; temperature: 50° C.; UV detection: 220 nm] afforded 40.9 mg (100% purity) of the desired product.

Analytical chiral HPLC: $R_t$=7.65 min, e.e. =>99% [column: 250×4.6 mm filled with Daicel Chiralpak IA 5 µm; eluent: 50% n-heptane/50% isopropanol; flow rate: 1 ml/min; temperature: 50° C.; UV detection: 220 nm]

LC-MS (Method 7): $R_t$=1.74 min; MS (ESIpos): m/z=501 [M+H]$^+$ $^1$H-NMR (400 MHz, DMSO-d6) δ [ppm]: −0.008 (0.65), 0.008 (0.68), 0.523 (0.62), 0.537 (1.29), 0.547 (1.48), 0.551 (1.66), 0.561 (1.79), 0.564 (1.57), 0.574 (1.20), 0.579 (0.96), 0.680 (0.86), 0.685 (1.20), 0.689 (1.29), 0.694 (1.70), 0.698 (1.79), 0.708 (1.57), 0.712 (1.51), 0.722 (1.48), 0.735 (0.71), 0.975 (0.52), 0.985 (0.49), 0.998 (1.48), 1.008 (1.91), 1.012 (1.76), 1.017 (3.98), 1.022 (2.22), 1.029 (3.27), 1.038 (4.35), 1.045 (3.02), 1.058 (1.42), 1.066 (0.43), 1.081 (0.46), 1.922 (0.86), 1.935 (1.70), 1.943 (1.82), 1.948 (1.05), 1.956 (3.33), 1.964 (1.11), 1.969 (1.66), 1.977 (1.60), 1.990 (0.74), 2.327 (0.68), 2.332 (0.52), 2.366 (0.40), 2.523 (2.34), 2.665 (0.52), 2.670 (0.71), 2.710 (0.40), 4.105 (6.57), 4.121 (6.60), 7.440 (4.78), 7.459 (12.92), 7.475 (4.90), 7.493 (1.20), 7.497 (1.39), 7.536 (2.96), 7.541 (2.74), 7.554 (3.14), 7.559 (2.71), 7.581 (6.35), 7.601 (7.34), 7.766 (7.77), 7.787 (6.29), 8.263 (6.72), 8.600 (1.60), 8.616 (3.51), 8.631 (1.57), 8.788 (16.00), 10.999 (5.21).

Example 272

Rac-N-{[4-(5-Cyclopropyl-1,3-Thiazol-4-Yl)-2,5-Dioxoimidazolidin-4-Yl]Methyl}-5-Fluoro-4'-(Trifluoromethyl)[Biphenyl]-2-Carboxamide

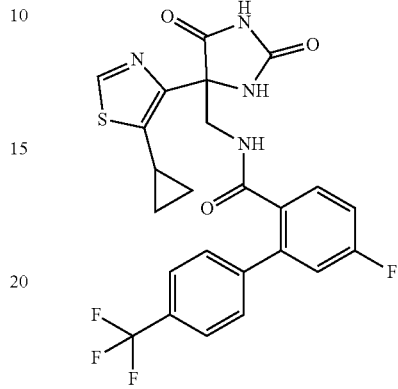

To a solution of rac-5-(aminomethyl)-5-(5-cyclopropyl-1,3-thiazol-4-yl)imidazolidine-2,4-dione hydrochloride (110 mg, 381 µmol) and 5-fluoro-4'-(trifluoromethyl)[1,1'-biphenyl]-2-carboxylic acid (108 mg, 381 µmol) in DMF (2.0 ml) was added 1-ethyl-3-(3-dimethylaminopropyl)carbodiimide hydrochloride (94.9 mg, 495 µmol), 1-hydroxybenzotriazole hydrate (75.8 mg, 495 µmol) and N,N-diisopropylethylamine (460 µl, 2.7 mmol). The reaction mixture was stirred overnight at room temperature and then concentrated under reduced pressure. The crude product was purified by preparative HPLC (Method 4f). After lyophilization, 78.1 mg (100% purity, 40% yield) of the desired product were obtained.

LC-MS (Method 8): $R_t$=0.94 min, MS (ESIpos): m/z=519 [M+H]$^+$ $^1$H-NMR (400 MHz, DMSO-d6) δ [ppm]: −0.008 (0.90), 0.008 (0.90), 0.523 (0.70), 0.537 (1.37), 0.547 (1.57), 0.551 (1.75), 0.560 (1.92), 0.564 (1.70), 0.574 (1.26), 0.578 (0.99), 0.680 (0.93), 0.685 (1.23), 0.689 (1.35), 0.694 (1.78), 0.698 (1.86), 0.707 (1.65), 0.712 (1.58), 0.722 (1.56), 0.735 (0.77), 0.975 (0.57), 0.984 (0.51), 0.989 (0.44), 0.998 (1.58), 1.008 (2.02), 1.012 (1.90), 1.017 (4.18), 1.022 (2.35), 1.028 (2.67), 1.032 (2.25), 1.038 (4.45), 1.043 (2.03), 1.048 (1.86), 1.058 (1.45), 1.066 (0.48), 1.071 (0.43), 1.080 (0.45), 1.918 (0.90), 1.931 (1.78), 1.939 (1.92), 1.944 (1.15), 1.952 (3.47), 1.960 (1.18), 1.964 (1.80), 1.972 (1.67), 1.985 (0.77), 4.081 (0.51), 4.100 (4.64), 4.104 (4.65), 4.116 (4.56), 4.120 (4.76), 4.139 (0.53), 4.155 (0.40), 7.322 (6.84), 7.325 (3.33), 7.340 (3.15), 7.345 (6.92), 7.350 (3.39), 7.361 (2.61), 7.367 (1.44), 7.478 (2.19), 7.483 (1.45), 7.493 (2.99), 7.500 (2.65), 7.508 (0.84), 7.516 (2.17), 7.600 (6.56), 7.621 (7.85), 7.780 (8.26), 7.801 (6.75), 8.286 (8.85), 8.639 (1.73), 8.654 (3.81), 8.670 (1.76), 8.787 (16.00), 11.003 (3.31).

Example 273

Ent-N-{[4-(5-Cyclopropyl-1,3-Thiazol-4-Yl)-2,5-Dioxoimidazolidin-4-Yl]Methyl}-5-Fluoro-4'-(Trifluoromethyl)[Biphenyl]-2-Carboxamide

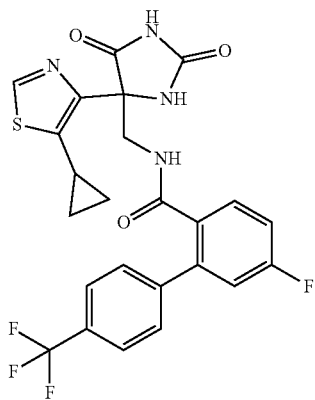 [SMILES: O=C1NC(=O)C(CNC(=O)c2ccc(F)cc2-c2ccc(C(F)(F)F)cc2)(c2ncsc2C2CC2)N1]

To a solution of ent-5-(aminomethyl)-5-(5-cyclopropyl-1,3-thiazol-4-yl)imidazolidine-2,4-dione hydrochloride (100 mg, 346 µmol) and 5-fluoro-4'-(trifluoromethyl)[1,1'-biphenyl]-2-carboxylic acid (98.4 mg, 346 µmol) in DMF (2.2 ml) was added 1-ethyl-3-(3-dimethylaminopropyl)carbodiimide hydrochloride (86.3 mg, 450 µmol), 1-hydroxybenzotriazole hydrate (68.9 mg, 450 µmol) and N,N-diisopropylethylamine (300 µl, 1.7 mmol). The reaction mixture was stirred overnight at room temperature and then concentrated under reduced pressure. The crude product was purified by preparative HPLC (Method 4f). After lyophilization, 73.8 mg (100% purity, 41% yield) of the desired product were obtained.

LC-MS (Method 7): $R_t$=1.78 min, MS (ESIpos): m/z=519 [M+H]$^+$ $^1$H-NMR (500 MHz, DMSO-d6) δ [ppm]: 0.530 (0.64), 0.538 (0.90), 0.540 (1.05), 0.551 (1.57), 0.556 (1.10), 0.560 (1.87), 0.566 (1.46), 0.570 (0.96), 0.576 (0.75), 0.683 (0.76), 0.689 (1.04), 0.692 (1.36), 0.699 (1.83), 0.702 (1.12), 0.708 (1.66), 0.718 (1.25), 0.729 (0.69), 0.983 (0.49), 0.991 (0.50), 0.995 (0.44), 1.001 (1.26), 1.010 (1.58), 1.013 (1.35), 1.018 (2.83), 1.026 (2.59), 1.030 (2.29), 1.037 (2.53), 1.043 (1.44), 1.046 (1.37), 1.055 (1.22), 1.061 (0.45), 1.065 (0.43), 1.073 (0.42), 1.925 (0.77), 1.936 (1.53), 1.942 (1.64), 1.946 (0.91), 1.952 (2.94), 1.959 (0.95), 1.963 (1.47), 1.969 (1.41), 1.979 (0.65), 4.074 (0.41), 4.086 (0.55), 4.102 (3.44), 4.107 (3.42), 4.114 (3.28), 4.119 (3.33), 4.134 (0.50), 4.147 (0.42), 7.324 (5.67), 7.343 (5.91), 7.357 (1.87), 7.362 (1.08), 7.482 (1.66), 7.485 (1.42), 7.494 (1.97), 7.498 (1.86), 7.500 (1.82), 7.508 (0.80), 7.512 (1.56), 7.603 (5.17), 7.619 (5.91), 7.782 (6.33), 7.799 (5.21), 8.285 (7.08), 8.640 (1.42), 8.652 (2.93), 8.665 (1.35), 8.786 (16.00), 10.999 (1.18).

Example 274

Ent-N-{[4-(5-Cyclopropyl-1,3-Thiazol-4-Yl)-2,5-Dioxoimidazolidin-4-Yl]Methyl}-2-[6-(Trifluoromethyl)Pyridin-3-Yl]Benzamide

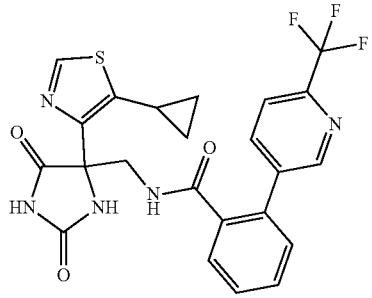 [SMILES: O=C1NC(=O)C(CNC(=O)c2ccccc2-c2ccc(C(F)(F)F)nc2)(c2ncsc2C2CC2)N1]

To a solution of ent-5-(aminomethyl)-5-(5-cyclopropyl-1,3-thiazol-4-yl)imidazolidine-2,4-dione hydrochloride (100 mg, 346 µmol) and 2-[6-(trifluoromethyl)pyridin-3-yl]benzoic acid (92.5 mg, 346 µmol) in DMF (2.2 ml) was added 1-ethyl-3-(3-dimethylaminopropyl)carbodiimide hydrochloride (86.3 mg, 450 µmol), 1-hydroxybenzotriazole hydrate (68.9 mg, 450 µmol) and N,N-diisopropylethylamine (300 µl, 1.7 mmol). The reaction mixture was stirred overnight at room temperature and then concentrated under reduced pressure. The crude product was purified by preparative HPLC (Method 3f). After lyophilization, 88.8 mg (96% purity, 49% yield) of the desired product were obtained.

LC-MS (Method 7): $R_t$=1.50 min, MS (ESIpos): m/z=502 [M+H]$^+$ $^1$H-NMR (500 MHz, DMSO-d6) δ [ppm]: −0.007 (0.44), 0.528 (0.64), 0.536 (0.87), 0.538 (0.98), 0.549 (1.48), 0.555 (1.02), 0.559 (1.88), 0.565 (1.44), 0.569 (0.87), 0.575 (0.70), 0.680 (0.75), 0.686 (0.98), 0.690 (1.38), 0.696 (1.88), 0.700 (1.04), 0.706 (1.53), 0.716 (1.13), 0.727 (0.66), 0.980 (0.47), 0.988 (0.50), 0.992 (0.44), 0.999 (1.21), 1.007 (1.48), 1.010 (1.25), 1.016 (2.33), 1.019 (1.65), 1.025 (2.03), 1.027 (1.82), 1.033 (1.70), 1.036 (2.03), 1.042 (1.30), 1.045 (1.25), 1.053 (1.16), 1.060 (0.41), 1.922 (0.75), 1.932 (1.45), 1.939 (1.54), 1.942 (0.84), 1.949 (2.78), 1.955 (0.87), 1.959 (1.38), 1.965 (1.30), 1.976 (0.61), 4.068 (0.67), 4.081 (0.80), 4.096 (2.77), 4.109 (4.80), 4.121 (2.68), 4.136 (0.73), 4.149 (0.63), 7.498 (1.70), 7.500 (1.50), 7.513 (3.93), 7.516 (2.77), 7.530 (4.48), 7.533 (2.11), 7.543 (5.71), 7.546 (7.08), 7.560 (1.84), 7.563 (1.19), 7.593 (2.74), 7.596 (2.54), 7.608 (2.16), 7.611 (2.88), 7.623 (1.12), 7.626 (1.02), 7.938 (2.97), 7.954 (4.89), 7.997 (2.68), 8.001 (2.54), 8.013 (1.51), 8.017 (1.50), 8.278 (5.43), 8.676 (1.32), 8.689 (2.75), 8.701 (1.42), 8.757 (3.90), 8.761 (3.75), 8.790 (16.00), 11.003 (2.92).

Example 275

Rac-N-{[4-(1,3-Dimethyl-1H-Pyrazol-5-Yl)-2,5-Dioxoimidazolidin-4-Yl]Methyl}-4'-(Trifluoromethyl)[Biphenyl]-2-Carboxamide

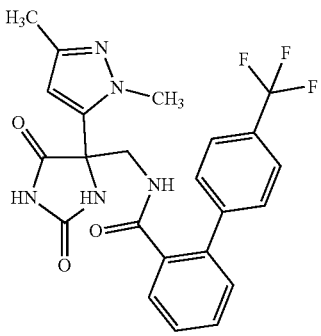 [SMILES: Cc1cc(C2(CNC(=O)c3ccccc3-c3ccc(C(F)(F)F)cc3)NC(=O)NC2=O)n(C)n1]

To a solution of rac-5-(aminomethyl)-5-(1,3-dimethyl-1H-pyrazol-5-yl)imidazolidine-2,4-dione hydrochloride (50.0 mg, 193 µmol) and 4'-(trifluoromethyl)[1,1'-biphenyl]-2-carboxylic acid (56.4 mg, 212 µmol) in DMF (2 ml) was added 1-ethyl-3-(3-dimethylaminopropyl)carbodiimide hydrochloride (48.0 mg, 250 µmol), 1-hydroxybenzotriazole hydrate (38.3 mg, 250 µmol) and N,N-diisopropylethylamine (200 µl, 1.2 mmol). The reaction mixture was stirred overnight at room temperature and then concentrated under reduced pressure. The crude product was purified by preparative HPLC (Method 3f). After lyophilization, 27.4 mg (100% purity, 30% yield) of the desired product were obtained.

LC-MS (Method 7): $R_t$=1.61 min, MS (ESIpos): m/z=472 [M+H]$^+$ $^1$H-NMR (600 MHz, DMSO-d6) δ [ppm]: 2.097 (14.29), 3.702 (16.00), 3.823 (0.79), 3.833 (0.86), 3.845 (1.31), 3.856 (1.15), 3.905 (1.21), 3.916 (1.27), 3.927 (0.81), 3.939 (0.76), 6.235 (5.17), 7.429 (1.26), 7.432 (1.47), 7.436 (1.72), 7.442 (2.17), 7.444 (2.25), 7.448 (2.15), 7.469 (1.09), 7.471 (1.05), 7.482 (1.85), 7.484 (1.66), 7.494 (0.92), 7.496 (0.83), 7.519 (2.91), 7.532 (3.18), 7.548 (1.22), 7.550 (1.15), 7.561 (1.73), 7.563 (1.59), 7.573 (0.71), 7.575 (0.72), 7.747 (3.31), 7.761 (2.96), 8.339 (3.31), 8.700 (0.78), 8.711 (1.45), 8.721 (0.78), 11.197 (1.58).

Example 276

Rac-N-{[4-(1,3-Dimethyl-1H-Pyrazol-5-Yl)-2,5-Dioxoimidazolidin-4-Yl]Methyl}-5-Fluoro-4'-(Trifluoromethyl)[Biphenyl]-2-Carboxamide

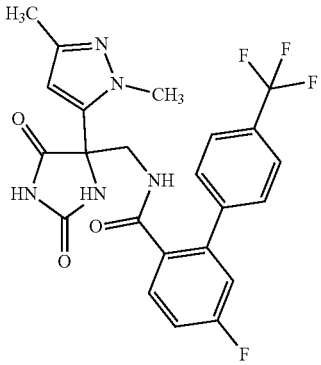 [SMILES: Cc1cc(C2(CNC(=O)c3ccc(F)cc3-c3ccc(C(F)(F)F)cc3)NC(=O)NC2=O)n(C)n1]

To a solution of rac-5-(aminomethyl)-5-(1,3-dimethyl-1H-pyrazol-5-yl)imidazolidine-2,4-dione hydrochloride (50.0 mg, 193 µmol) and 5-fluoro-4'-(trifluoromethyl)[1,1'-biphenyl]-2-carboxylic acid (60.2 mg, 212 µmol) in DMF (990µ) was added 1-ethyl-3-(3-dimethylaminopropyl)carbodiimide hydrochloride (48.0 mg, 250 µmol), 1-hydroxybenzotriazole hydrate (38.3 mg, 250 µmol) and N,N-diisopropylethylamine (200 µl, 1.2 mmol). The reaction mixture was stirred overnight at room temperature and then concentrated under reduced pressure. The crude product was purified by preparative HPLC (Method 3f). After lyophilization, 33.2 mg (90% purity, 32% yield) of the desired product were obtained.

LC-MS (Method 7): $R_t$=1.66 min; MS (ESIpos): m/z=490 [M+H]$^+$ $^1$H-NMR (600 MHz, DMSO-d6) δ [ppm]: 2.096 (13.73), 3.698 (16.00), 3.813 (0.80), 3.823 (0.84), 3.836 (1.23), 3.846 (1.07), 3.899 (1.15), 3.911 (1.21), 3.922 (0.79), 3.934 (0.72), 6.233 (5.02), 7.316 (1.09), 7.320 (1.59), 7.332 (1.11), 7.337 (2.21), 7.342 (0.71), 7.351 (1.54), 7.356 (1.23), 7.365 (0.79), 7.370 (0.66), 7.473 (1.30), 7.483 (1.34), 7.487 (1.18), 7.497 (1.09), 7.541 (2.72), 7.554 (2.93), 7.638 (0.46), 7.760 (3.27), 7.774 (3.08), 8.360 (3.36), 8.736 (0.75), 8.746 (1.34), 8.757 (0.72).

Example 277

Ent-N-{[2,5-Dioxo-4-(1,3-Thiazol-4-Yl)Imidazolidin-4-Yl]Methyl}-2-[6-(Trifluoromethyl)Pyridin-3-Yl]Benzamide

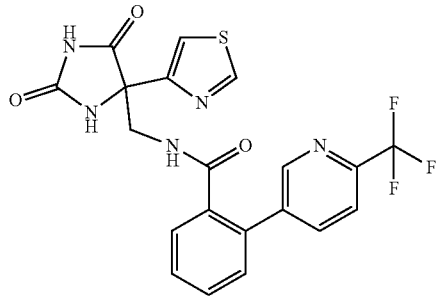 [SMILES: O=C1NC(=O)C(CNC(=O)c2ccccc2-c2ccc(C(F)(F)F)nc2)(c2cscn2)N1]

To a solution of ent-5-(aminomethyl)-5-(1,3-thiazol-4-yl)imidazolidine-2,4-dione hydrochloride (100 mg, 402 µmol) and 2-[6-(trifluoromethyl)pyridin-3-yl]benzoic acid (107 mg, 402 µmol) in DMF (2.5 ml) was added 1-ethyl-3-(3-dimethylaminopropyl)carbodiimide hydrochloride (100 mg, 523 µmol), 1-hydroxybenzotriazole hydrate (80.1 mg, 523 µmol) and N,N-diisopropylethylamine (350 µl, 2.0 mmol). The reaction mixture was stirred overnight at room temperature and then concentrated under reduced pressure. The crude product was purified by preparative HPLC (Method 3f). After lyophilization, 78.6 mg (100% purity, 42% yield) of the desired product were obtained.

LC-MS (Method 7): $R_t$=1.29 min; MS (ESIpos): m/z=462 [M+H]$^+$ $^1$H-NMR (600 MHz, DMSO-d6) δ [ppm]: 0.005 (0.56), 2.383 (0.54), 2.422 (0.59), 2.514 (1.10), 2.517 (1.00), 2.520 (0.91), 2.574 (1.01), 2.608 (0.46), 2.611 (0.54), 2.651 (0.52), 2.731 (0.49), 2.890 (0.63), 3.264 (0.49), 3.331 (0.96), 3.902 (2.62), 3.912 (2.79), 3.925 (5.59), 3.935 (5.14), 3.956 (5.22), 3.966 (5.74), 3.979 (2.79), 3.988 (2.45), 7.485 (4.43), 7.487 (4.54), 7.498 (7.54), 7.500 (7.03), 7.519 (5.76), 7.531 (10.63), 7.541 (7.99), 7.543 (5.90), 7.554 (3.85), 7.556 (2.96), 7.592 (5.15), 7.595 (5.03), 7.605 (6.83), 7.607 (6.45), 7.617 (2.64), 7.619 (2.43), 7.787 (16.00), 7.790 (15.93), 7.916 (6.27), 7.929 (10.24), 7.967 (5.63), 7.970 (5.46), 7.980 (3.24), 7.983 (3.19), 8.287 (14.26), 8.728 (9.11), 8.732 (9.66), 8.745 (2.77), 9.121 (14.61), 9.124 (14.70), 10.882 (0.78).

Example 278

Ent-N-{[2,5-Dioxo-4-(1,3-Thiazol-4-Yl)Imidazolidin-4-Yl]Methyl}-5,6-Difluoro-4'-(Trifluoromethyl)[Biphenyl]-2-Carboxamide

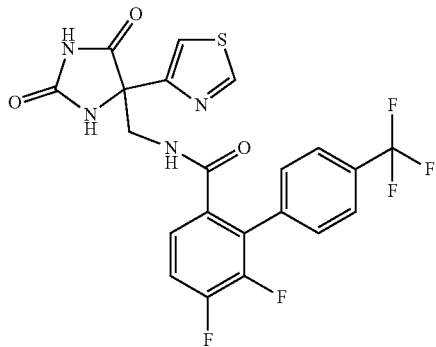 [SMILES: O=C1NC(=O)C(CNC(=O)c2ccc(F)c(F)c2-c2ccc(C(F)(F)F)cc2)(c2cscn2)N1]

To a solution of ent-5-(aminomethyl)-5-(1,3-thiazol-4-yl)imidazolidine-2,4-dione hydrochloride (100 mg, 402 µmol) and 5,6-difluoro-4'-(trifluoromethyl)[1,1'-biphenyl]-2-carboxylicacid (122 mg, 402 µmol) in DMF (2.5 ml) was added 1-ethyl-3-(3-dimethylaminopropyl)carbodiimide hydrochloride (100 mg, 523 µmol), 1-hydroxybenzotriazole hydrate (80.1 mg, 523 µmol) and N,N-diisopropylethylamine (350 µl, 2.0 mmol). The reaction mixture was stirred overnight at room temperature and then concentrated under reduced pressure. The crude product was purified by preparative HPLC (Method 4f). After lyophilization, 96.0 mg (96% purity, 46% yield) of the desired product were obtained.

LC-MS (Method 7): $R_t$=1.64 min, MS (ESIpos): m/z=497 [M+H]$^+$ $^1$H-NMR (400 MHz, DMSO-d6) δ [ppm]: −0.008 (0.82), 0.008 (0.93), 2.323 (0.51), 2.328 (0.68), 2.332 (0.54), 2.367 (0.56), 2.524 (2.59), 2.665 (0.54), 2.670 (0.70), 2.675 (0.54), 2.710 (0.51), 2.732 (0.54), 2.890 (0.70), 3.802 (2.62), 3.818 (2.85), 3.836 (4.73), 3.853 (4.37), 3.906 (4.39), 3.921 (4.87), 3.940 (2.87), 3.955 (2.51), 7.279 (2.51), 7.288 (2.76), 7.291 (2.70), 7.297 (3.21), 7.300 (3.04), 7.309 (3.07), 7.313 (2.76), 7.547 (9.24), 7.567 (10.85), 7.579 (2.73), 7.599 (3.61), 7.604 (3.44), 7.624 (3.61), 7.645 (2.11), 7.764 (15.63), 7.769 (16.00), 7.798 (12.82), 7.818 (11.15), 7.835 (0.68), 8.295 (13.41), 8.724 (2.76), 8.739 (5.86), 8.754 (2.73), 9.116 (10.48), 9.121 (10.48).

Example 279

Rac-N-{[4-(1-Chlorocyclopropyl)-2,5-Dioxoimidazolidin-4-Yl]Methyl}-4'-(Trifluoromethyl)[Biphenyl]-2-Carboxamide

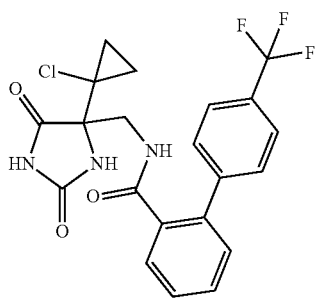 [SMILES: O=C1NC(=O)C(CNC(=O)c2ccccc2-c2ccc(C(F)(F)F)cc2)(C2(Cl)CC2)N1]

To a solution of rac-5-(aminomethyl)-5-(1-chlorocyclopropyl)imidazolidine-2,4-dione hydrochloride (50.0 mg, 208 µmol) and 4'-(trifluoromethyl)[1,1'-biphenyl]-2-carboxylic acid (61.0 mg, 229 µmol) in DMF (2 ml) was added 1-ethyl-3-(3-dimethylaminopropyl)carbodiimide hydrochloride (51.9 mg, 271 µmol), 1-hydroxybenzotriazole hydrate (41.5 mg, 271 µmol) and N,N-diisopropylethylamine (220 µl, 1.2 mmol). The reaction mixture was stirred overnight at room temperature and then concentrated under reduced pressure. The crude product was purified by preparative HPLC (Method 3f). After lyophilization, 50.0 mg (92% purity, 49% yield) of the desired product were obtained.

LC-MS (Method 7): $R_t$=1.74 min, MS (ESIpos): m/z=452 [M+H]$^+$ $^1$H-NMR (600 MHz, DMSO-d6) δ [ppm]: 0.005 (0.90), 1.004 (1.36), 1.013 (2.00), 1.024 (2.91), 1.032 (5.41), 1.037 (3.73), 1.050 (3.66), 1.055 (6.40), 1.062 (3.30), 1.073 (2.34), 1.082 (1.86), 1.182 (1.59), 1.190 (2.08), 1.202 (3.15), 1.209 (6.37), 1.215 (7.80), 1.220 (5.82), 1.228 (2.92), 1.239 (1.67), 1.248 (1.15), 2.053 (0.42), 2.511 (2.23), 2.517 (0.79), 2.520 (0.77), 2.783 (1.55), 3.326 (0.42), 3.471 (3.74), 3.481 (3.96), 3.494 (5.06), 3.504 (4.80), 3.597 (4.93), 3.608 (5.35), 3.620 (3.95), 3.630 (3.59), 7.386 (5.75), 7.388 (6.01), 7.399 (8.51), 7.401 (8.14), 7.410 (0.67), 7.429 (6.26), 7.430 (6.91), 7.443 (8.44), 7.454 (4.43), 7.456 (4.32), 7.466 (8.32), 7.469 (7.36), 7.479 (4.34), 7.481 (3.82), 7.505 (0.42), 7.516 (0.65), 7.538 (15.35), 7.548 (11.06), 7.550 (16.00), 7.552 (14.93), 7.560 (3.77), 7.563 (3.46), 7.601 (0.47), 7.613 (0.41), 7.752 (14.58), 7.766 (12.90), 7.803 (0.48), 8.031 (14.40), 8.603 (3.14), 8.614 (6.57), 8.624 (3.15), 10.877 (3.55).

Example 280

Ent-N-{[4-(1-Chlorocyclopropyl)-2,5-Dioxoimidazolidin-4-Yl]Methyl}-4'-(Trifluoromethyl)[Biphenyl]-2-Carboxamide

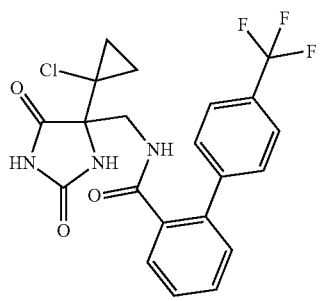 [SMILES: O=C1NC(=O)C(CNC(=O)c2ccccc2-c2ccc(C(F)(F)F)cc2)(C2(Cl)CC2)N1]

Enantiomeric separation of rac-N-{[4-(1-chlorocyclopropyl)-2,5-dioxoimidazolidin-4-yl]methyl}-4'-(trifluoromethyl)[biphenyl]-2-carboxamide (50 mg) by preparative chiral HPLC [column: Daicel Chiralpak IF 5 µm, 250×20 mm; eluent: 70% n-heptane/30% ethanol; flow rate: 20 ml/min; temperature: 50° C.; UV detection: 220 nm] afforded 23.9 mg (97% purity) of the desired product.

Analytical chiral HPLC: $R_t$=1.97 min, e.e. =>99% [Daicel Chiralpak IF-3 3 µm, 50×4.6 mm; eluent: 70% n-heptane/30% ethanol; flow rate: 1 ml/min; UV detection: 220 nm]

LC-MS (Method 7): $R_t$=1.71 min; MS (ESIpos): m/z=452 [M+H]$^+$ $^1$H-NMR (600 MHz, DMSO-d6) δ [ppm]: 0.005 (1.28), 0.847 (0.97), 0.858 (0.89), 0.874 (0.53), 1.004 (1.31), 1.013

(1.93), 1.024 (2.84), 1.032 (5.33), 1.036 (3.59), 1.050 (3.52), 1.054 (6.15), 1.062 (3.10), 1.073 (2.28), 1.082 (1.83), 1.090 (0.52), 1.100 (0.45), 1.114 (0.46), 1.125 (0.42), 1.181 (1.55), 1.189 (2.04), 1.201 (3.04), 1.208 (6.25), 1.214 (7.61), 1.219 (5.66), 1.228 (2.91), 1.238 (2.31), 1.248 (1.41), 2.383 (0.46), 2.422 (0.49), 2.514 (0.97), 2.517 (0.94), 2.520 (0.80), 2.573 (0.46), 2.611 (0.45), 2.651 (0.46), 3.328 (0.59), 3.470 (3.52), 3.480 (3.72), 3.493 (4.78), 3.503 (4.56), 3.596 (4.63), 3.607 (5.08), 3.619 (3.76), 3.629 (3.38), 3.733 (1.41), 3.895 (0.77), 7.385 (5.42), 7.387 (5.76), 7.398 (7.73), 7.400 (7.67), 7.430 (6.63), 7.443 (8.12), 7.454 (4.07), 7.456 (3.95), 7.466 (7.89), 7.468 (7.02), 7.479 (3.98), 7.481 (3.50), 7.538 (15.25), 7.548 (11.09), 7.550 (16.00), 7.560 (3.32), 7.562 (3.04), 7.752 (13.28), 7.766 (11.71), 8.029 (13.13), 8.602 (3.04), 8.612 (6.26), 8.622 (3.01), 10.877 (7.01).

Example 281

Rac-N-{[4-(1-Chlorocyclopropyl)-2,5-Dioxoimida-zolidin-4-Yl]Methyl}-2-[6-(Trifluoromethyl)Pyridin-3-Yl]Benzamide

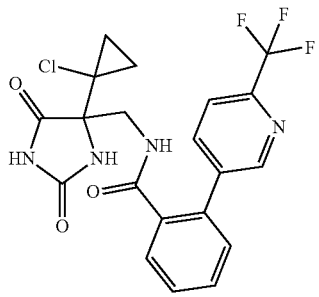 [SMILES: O=C1NC(=O)C(CNC(=O)c2ccccc2-c2ccc(C(F)(F)F)nc2)(C2(Cl)CC2)N1]

To a solution of rac-5-(aminomethyl)-5-(1-chlorocyclopropyl)imidazolidine-2,4-dione hydrochloride (50.0 mg, 208 µmol) and 2-[6-(trifluoromethyl)pyridin-3-yl]benzoic acid (61.2 mg, 229 µmol) in DMF (1.1 ml) was added 1-ethyl-3-(3-dimethylaminopropyl)carbodiimide hydrochloride (51.9 mg, 271 µmol), 1-hydroxybenzotriazole hydrate (41.5 mg, 271 µmol) and N,N-diisopropylethylamine (220 µl, 1.2 mmol). The reaction mixture was stirred overnight at room temperature and then concentrated under reduced pressure. The crude product was purified by preparative HPLC (Method 3f). After lyophilization, 52.9 mg (99% purity, 56% yield) of the desired product were obtained.

LC-MS (Method 7): $R_t$=1.47 min, MS (ESIpos): m/z=453 $[M+H]^+$ $^1$H-NMR (600 MHz, DMSO-d6) δ [ppm]: 0.005 (0.95), 1.004 (1.57), 1.013 (2.23), 1.026 (3.21), 1.032 (5.48), 1.035 (4.86), 1.053 (4.89), 1.056 (6.60), 1.062 (3.34), 1.074 (2.60), 1.083 (1.85), 1.183 (1.82), 1.191 (1.79), 1.202 (3.67), 1.210 (7.75), 1.214 (9.92), 1.218 (6.87), 1.227 (3.18), 1.236 (1.38), 1.247 (1.09), 2.383 (0.52), 2.422 (0.60), 2.467 (0.90), 2.470 (1.12), 2.473 (1.06), 2.514 (0.79), 2.517 (0.71), 2.520 (0.62), 2.572 (1.08), 2.605 (0.62), 2.611 (0.54), 2.651 (0.55), 2.816 (0.46), 3.261 (1.39), 3.264 (0.87), 3.328 (1.12), 3.477 (3.86), 3.488 (4.04), 3.500 (5.74), 3.510 (5.40), 3.572 (5.60), 3.582 (6.03), 3.594 (3.94), 3.605 (3.61), 7.446 (6.36), 7.448 (6.36), 7.458 (8.56), 7.460 (8.20), 7.515 (7.14), 7.526 (11.41), 7.528 (13.75), 7.538 (9.57), 7.540 (7.26), 7.551 (5.02), 7.553 (3.94), 7.590 (6.33), 7.592 (6.17), 7.603 (8.09), 7.605 (7.88), 7.615 (3.12), 7.617 (2.96), 7.926 (3.81), 7.939 (15.84), 7.940 (15.81), 7.945 (10.54), 7.948 (9.54), 7.959 (2.06), 7.962 (2.23), 8.059 (16.00), 8.668 (3.45), 8.679 (7.06), 8.689 (3.32), 8.727 (10.11), 10.874 (5.44).

Example 282

Rac-N-{[4-(1-Chlorocyclopropyl)-2,5-Dioxoimida-zolidin-4-Yl]Methyl}-5-Fluoro-4'-(Trifluoromethyl) [Biphenyl]-2-Carboxamide

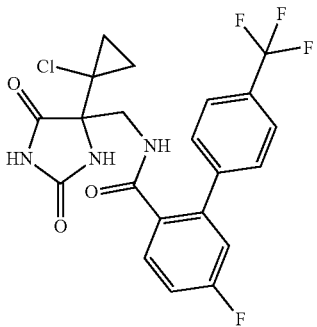 [SMILES: O=C1NC(=O)C(CNC(=O)c2ccc(F)cc2-c2ccc(C(F)(F)F)cc2)(C2(Cl)CC2)N1]

To a solution of rac-5-(aminomethyl)-5-(1-chlorocyclopropyl)imidazolidine-2,4-dione hydrochloride (50.0 mg, 208 µmol) and 5-fluoro-4'-(trifluoromethyl)[1,1'-biphenyl]-2-carboxylic acid (65.1 mg, 229 µmol) in DMF (1.1 ml) was added 1-ethyl-3-(3-dimethylaminopropyl)carbodiimide hydrochloride (51.9 mg, 271 µmol), 1-hydroxybenzotriazole hydrate (41.5 mg, 271 µmol) and N,N-diisopropylethylamine (220 µl, 1.2 mmol). The reaction mixture was stirred overnight at room temperature and then concentrated under reduced pressure. The crude product was purified by preparative HPLC (Method 4f). After lyophilization, 52.4 mg (99% purity, 53% yield) of the desired product were obtained.

LC-MS (Method 7): $R_t$=1.79 min, MS (ESIpos): m/z=470 $[M+H]^+$ $^1$H-NMR (600 MHz, DMSO-d6) δ [ppm]: 0.005 (2.10), 1.005 (1.58), 1.014 (2.26), 1.025 (3.23), 1.033 (6.19), 1.037 (4.08), 1.051 (4.05), 1.055 (7.13), 1.063 (3.66), 1.074 (2.62), 1.083 (2.10), 1.179 (1.80), 1.187 (2.44), 1.199 (3.54), 1.206 (7.16), 1.212 (8.59), 1.217 (6.37), 1.225 (3.11), 1.236 (1.80), 1.245 (1.34), 2.383 (0.98), 2.422 (1.10), 2.513 (1.55), 2.517 (1.58), 2.520 (1.37), 2.569 (1.13), 2.571 (1.40), 2.611 (0.85), 2.650 (0.88), 3.326 (1.98), 3.469 (4.02), 3.480 (4.27), 3.492 (5.82), 3.503 (5.39), 3.580 (5.58), 3.590 (6.00), 3.603 (4.27), 3.613 (3.84), 7.309 (4.57), 7.313 (8.11), 7.320 (4.42), 7.325 (5.55), 7.329 (8.38), 7.334 (8.47), 7.338 (5.09), 7.348 (4.24), 7.352 (3.26), 7.426 (6.34), 7.436 (6.37), 7.440 (5.49), 7.450 (4.91), 7.555 (13.41), 7.569 (14.63), 7.767 (15.54), 7.780 (13.53), 8.056 (16.00), 8.635 (3.60), 8.645 (7.44), 8.655 (3.44), 10.871 (2.35).

Example 283

Rac-N-{[4-(1-Methyl-1H-Imidazol-5-Yl)-2,5-Dioxoimidazolidin-4-Yl]Methyl}-4'-(Trifluoromethyl)[Biphenyl]-2-Carboxamide

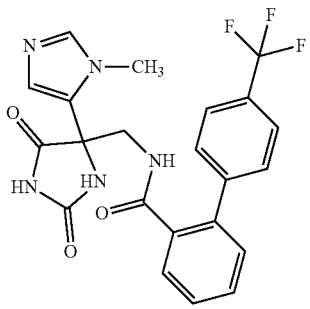 [SMILES: Cn1cncc1C1(CNC(=O)c2ccccc2-c2ccc(C(F)(F)F)cc2)NC(=O)NC1=O]

To a solution of rac-5-(aminomethyl)-5-(1-methyl-1H-imidazol-5-yl)imidazolidine-2,4-dione hydrochloride (50.0 mg, 204 µmol) and 4'-(trifluoromethyl)[1,1'-biphenyl]-2-carboxylic acid (59.6 mg, 224 µmol) in DMF (2 ml) was added 1-ethyl-3-(3-dimethylaminopropyl)carbodiimide hydrochloride (50.7 mg, 265 µmol), 1-hydroxybenzotriazole hydrate (40.5 mg, 265 µmol) and N,N-diisopropylethylamine (210 µl, 1.2 mmol). The reaction mixture was stirred overnight at room temperature and then concentrated under reduced pressure. The crude product was purified by preparative HPLC (Method 3f). After lyophilization, 32.2 mg (96% purity, 33% yield) of the desired product were obtained.

LC-MS (Method 7): $R_t$=1.14 min, MS (ESIpos): m/z=458 [M+H]$^+$ $^1$H-NMR (400 MHz, DMSO-d6) δ [ppm]: −0.008 (1.18), −0.007 (0.93), 0.008 (1.31), 2.523 (1.28), 2.526 (0.95), 2.557 (0.47), 3.574 (16.00), 3.838 (0.68), 3.852 (0.77), 3.872 (1.45), 3.887 (1.31), 3.921 (1.31), 3.938 (1.38), 3.955 (0.71), 3.972 (0.67), 7.090 (3.61), 7.426 (1.14), 7.430 (2.40), 7.445 (2.67), 7.449 (4.07), 7.462 (1.46), 7.464 (1.48), 7.480 (2.14), 7.483 (1.78), 7.498 (0.93), 7.502 (0.85), 7.535 (3.26), 7.543 (2.07), 7.547 (2.17), 7.555 (3.93), 7.561 (2.63), 7.566 (1.94), 7.580 (0.74), 7.584 (0.77), 7.665 (3.36), 7.750 (3.93), 7.770 (3.23), 8.286 (2.79), 8.289 (2.84), 8.726 (0.82), 8.742 (1.67), 8.758 (0.84), 11.175 (2.42).

Example 284

Rac-5-Fluoro-N-{[4-(1-Methyl-1H-Imidazol-5-Yl)-2,5-Dioxoimidazolidin-4-Yl]Methyl}-4'-(Trifluoromethyl)[Biphenyl]-2-Carboxamide

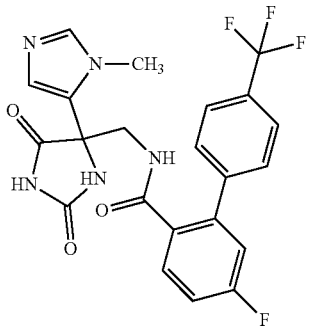 [SMILES: Cn1cncc1C1(CNC(=O)c2ccc(F)cc2-c2ccc(C(F)(F)F)cc2)NC(=O)NC1=O]

To a solution of rac-5-(aminomethyl)-5-(1-methyl-1H-imidazol-5-yl)imidazolidine-2,4-dione hydrochloride (50.0 mg, 204 µmol) and 5-fluoro-4'-(trifluoromethyl)[1,1'-biphenyl]-2-carboxylic acid (63.6 mg, 224 µmol) in DMF (1 ml) was added 1-ethyl-3-(3-dimethylaminopropyl)carbodiimide hydrochloride (50.7 mg, 265 µmol), 1-hydroxybenzotriazole hydrate (40.5 mg, 265 µmol) and N,N-diisopropylethylamine (210 µl, 1.2 mmol). The reaction mixture was stirred overnight at room temperature and then concentrated under reduced pressure. The crude product was purified by preparative HPLC (Method 3f). After lyophilization, 28.1 mg (99% purity, 29% yield) of the desired product were obtained.

LC-MS (Method 7): $R_t$=1.19 min; MS (ESIpos): m/z=476 [M+H]$^+$ $^1$H-NMR (600 MHz, DMSO-d6) δ [ppm]: 0.005 (0.48), 2.514 (0.44), 2.517 (0.43), 3.569 (16.00), 3.834 (0.84), 3.844 (0.94), 3.857 (1.40), 3.867 (1.26), 3.921 (1.29), 3.933 (1.36), 3.944 (0.87), 3.955 (0.81), 7.071 (3.75), 7.314 (1.15), 7.318 (1.73), 7.330 (1.31), 7.334 (2.01), 7.346 (1.65), 7.351 (1.30), 7.360 (0.87), 7.365 (0.74), 7.475 (1.41), 7.485 (1.48), 7.489 (1.32), 7.499 (1.20), 7.558 (3.13), 7.571 (3.43), 7.638 (3.71), 7.762 (3.62), 7.776 (3.18), 8.134 (0.74), 8.283 (3.56), 8.733 (0.86), 8.744 (1.58), 8.754 (0.83), 11.152 (1.31).

Example 285

Rac-N-{[4-(1-Methyl-1H-Imidazol-5-Yl)-2,5-Dioxoimidazolidin-4-Yl]Methyl}-2-[6-(Trifluoromethyl)Pyridin-3-Yl]Benzamide

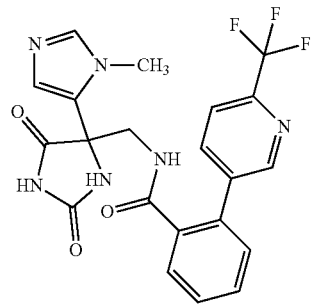 [SMILES: Cn1cncc1C1(CNC(=O)c2ccccc2-c2ccc(C(F)(F)F)nc2)NC(=O)NC1=O]

To a solution of rac-5-(aminomethyl)-5-(1-methyl-1H-imidazol-5-yl)imidazolidine-2,4-dione hydrochloride (50.0 mg, 204 µmol) and 2-[6-(trifluoromethyl)pyridin-3-yl]benzoic acid (59.8 mg, 224 µmol) in DMF (1 ml) was added 1-ethyl-3-(3-dimethylaminopropyl)carbodiimide hydrochloride (50.7 mg, 265 µmol), 1-hydroxybenzotriazole hydrate (40.5 mg, 265 µmol) and N,N-diisopropylethylamine (210 µl, 1.2 mmol). The reaction mixture was stirred overnight at room temperature and then concentrated under reduced pressure. The crude product was purified by preparative HPLC (Method 6f). After lyophilization, 25.6 mg (99% purity, 27% yield) of the desired product were obtained.

LC-MS (Method 7): $R_t$=0.92 min; MS (ESIpos): m/z=459 [M+H]$^+$ $^1$H-NMR (600 MHz, DMSO-d6) δ [ppm]: 2.514 (0.49), 2.517 (0.45), 2.572 (0.68), 2.731 (0.88), 2.890 (1.10), 3.330 (0.60), 3.566 (16.00), 3.843 (0.83), 3.853 (0.92), 3.866 (1.40), 3.876 (1.24), 3.924 (1.29), 3.936 (1.35), 3.947 (0.87), 3.958 (0.80), 7.079 (3.90), 7.080 (3.85), 7.491 (1.29), 7.493 (1.33), 7.503 (2.14), 7.505 (2.04), 7.517 (1.66), 7.530 (2.19), 7.535 (1.18), 7.537 (1.10), 7.547 (2.11), 7.550 (1.71), 7.560 (1.03), 7.562 (0.84), 7.601 (1.38), 7.603 (1.33), 7.613 (1.91), 7.615 (1.77), 7.626 (0.80), 7.628 (0.80), 7.636 (3.66), 7.912 (1.56), 7.925 (3.14), 7.949 (1.81), 7.952 (1.80), 7.962 (0.83), 7.966 (0.81), 8.134 (1.19), 8.277 (3.46), 8.718 (2.28), 8.721 (2.21), 8.770 (0.83), 8.781 (1.52), 8.791 (0.76), 11.150 (1.05).

Example 286

Rac-N-{[4-(1,4-Dimethyl-1H-Imidazol-5-Yl)-2,5-Dioxoimidazolidin-4-Yl]Methyl}-5-Fluoro-4'-(Trifluoromethyl)[Biphenyl]-2-Carboxamide

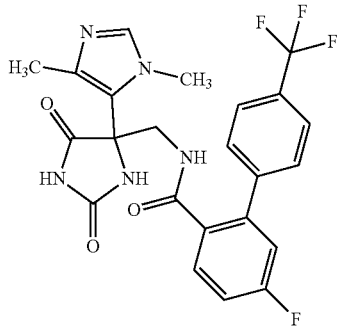 [SMILES: Cc1ncn(C)c1C1(CNC(=O)c2ccc(F)cc2-c2ccc(C(F)(F)F)cc2)NC(=O)NC1=O]

To a solution of rac-5-(aminomethyl)-5-(1,4-dimethyl-1H-imidazol-5-yl)imidazolidine-2,4-dione hydrochloride (60.0 mg, 93% purity, 214 µmol) and 5-fluoro-4'-(trifluoromethyl)[1,1'-biphenyl]-2-carboxylic acid (67.0 mg, 236 µmol) in DMF (1.1 ml) was added 1-ethyl-3-(3-dimethylaminopropyl)carbodiimide hydrochloride (53.4 mg, 278 µmol), 1-hydroxybenzotriazole hydrate (42.6 mg, 278 µmol) and N,N-diisopropylethylamine (220 µl, 1.3 mmol). The reaction mixture was stirred overnight at room temperature and then concentrated under reduced pressure. The crude product was purified by preparative HPLC (Method 3f). After lyophilization, 8.51 mg (100% purity, 8% yield) of the desired product were obtained.

LC-MS (Method 7): $R_t$=1.19 min, MS (ESIpos): m/z=490 [M+H]$^+$ $^1$H-NMR (500 MHz, DMSO-d6) δ [ppm]: 2.223 (16.00), 3.593 (14.59), 3.909 (0.76), 3.921 (0.85), 3.936 (1.25), 3.948 (1.08), 4.009 (1.14), 4.023 (1.21), 4.036 (0.80), 4.049 (0.73), 7.318 (1.13), 7.323 (1.86), 7.334 (1.11), 7.338 (1.40), 7.342 (1.92), 7.350 (1.87), 7.356 (1.28), 7.367 (0.96), 7.372 (0.77), 7.469 (1.56), 7.481 (6.09), 7.486 (1.71), 7.498 (1.19), 7.547 (3.03), 7.563 (3.34), 7.765 (3.56), 7.781 (3.05), 8.140 (1.38), 8.277 (3.55), 8.717 (0.78), 8.730 (1.51), 8.742 (0.75), 11.109 (0.76).

Example 287

Ent-5,6-Dimethyl-N-{[4-(1-Methyl-1H-Imidazol-2-Yl)-2,5-Dioxoimidazolidin-4-Yl]Methyl}-4'-(Trifluoromethyl)[Biphenyl]-2-Carboxamide

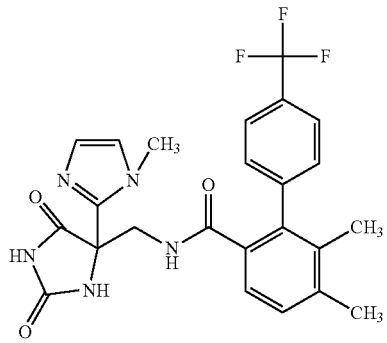 [SMILES: Cc1ccc(C(=O)NCC2(c3nccn3C)NC(=O)NC2=O)c(-c2ccc(C(F)(F)F)cc2)c1C]

5,6-dimethyl-4'-(trifluoromethyl)[1,1'-biphenyl]-2-carboxylic acid (30.0 mg, 102 µmol) dissolved in DMF (840 µl) was treated with N,N-diisopropylethylamine (36 µl, 200 µmol), and HATU (77.5 mg, 204 µmol). After stirring at room temperature for 5 min ent-5-(aminomethyl)-5-(1-methyl-1H-imidazol-2-yl)imidazolidine-2,4-dione hydrochloride (50.1 mg, 204 µmol) was added and the mixture was stirred over night at room temperature. The reaction was concentrated and the crude mixture was purified by preparative HPLC. Product containing samples were united, the solvents were evaporated and the residue was lyophilized. 23.8 mg (98% purity, 47% yield) of the title compound were obtained.

LC-MS (Method 8): $R_t$=0.79 min; MS (ESIpos): m/z=486 [M+H]$^+$ $^1$H-NMR (400 MHz, DMSO-d6) δ [ppm]: −0.008 (0.68), 0.008 (0.72), 1.928 (16.00), 2.317 (15.82), 2.366 (0.41), 2.670 (0.72), 3.497 (13.17), 3.803 (0.82), 3.819 (0.92), 3.838 (1.91), 3.853 (1.69), 3.878 (1.80), 3.895 (1.92), 3.913 (1.00), 3.929 (0.82), 6.858 (2.23), 7.141 (2.69), 7.160 (3.70), 7.208 (3.49), 7.249 (3.49), 7.269 (2.53), 7.359 (4.06), 7.380 (4.48), 7.722 (3.87), 7.743 (3.53), 8.187 (3.69), 8.209 (1.86), 8.224 (0.92), 11.199 (2.53).

Example 288

Rac-5-Fluoro-N-{[4-(2-Methyl-2H-Indazol-3-Yl)-2,5-Dioxoimidazolidin-4-Yl]Methyl}-4'-(Trifluoromethyl)[Biphenyl]-2-Carboxamide

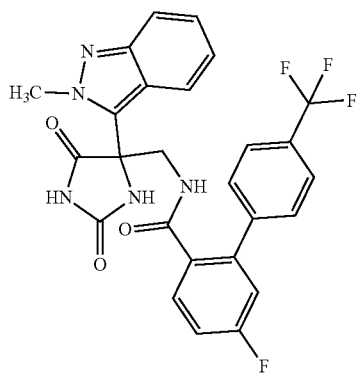 [SMILES: Cn1nc2ccccc2c1C1(CNC(=O)c2ccc(F)cc2-c2ccc(C(F)(F)F)cc2)NC(=O)NC1=O]

To a solution of rac-5-(aminomethyl)-5-(2-methyl-2H-indazol-3-yl)imidazolidine-2,4-dione hydrochloride (67.0 mg, 97% purity, 220 µmol) and 5-fluoro-4'-(trifluoromethyl)[1,1'-biphenyl]-2-carboxylic acid (68.7 mg, 242 µmol) in DMF (1.1 ml) was added 1-ethyl-3-(3-dimethylaminopropyl)carbodiimide hydrochloride (54.7 mg, 286 µmol), 1-hydroxybenzotriazole hydrate (43.7 mg, 286 µmol) and N,N-diisopropylethylamine (230 µl, 1.3 mmol). The reaction mixture was stirred overnight at room temperature and then concentrated under reduced pressure. The crude product was purified by preparative HPLC (Method 4f). After lyophilization, 30.1 mg (90% purity, 23% yield) of the desired product were obtained.

LC-MS (Method 7): $R_t$=1.77 min, MS (ESIpos): m/z=526 [M+H]$^+$ $^1$H-NMR (500 MHz, DMSO-d6) δ [ppm]: 2.047 (0.91), 4.256 (0.66), 4.268 (1.11), 4.276 (16.00), 4.283 (1.62), 4.295 (1.08), 4.320 (1.09), 4.333 (1.15), 4.347 (0.59), 4.360 (0.54), 7.066 (0.89), 7.067 (0.89), 7.079 (1.12), 7.081 (1.13), 7.083 (1.05), 7.085 (0.97), 7.096 (1.04), 7.098 (0.99), 7.233 (1.08), 7.234 (1.06), 7.246 (1.01), 7.248 (1.03), 7.250 (1.23), 7.252 (1.19), 7.263 (0.99), 7.265 (0.94), 7.319 (1.04), 7.324 (1.68), 7.336 (1.10), 7.339 (1.25), 7.344 (1.74), 7.353 (1.64), 7.358 (1.15), 7.369 (0.93), 7.375 (0.70), 7.472 (1.34), 7.484 (1.77), 7.489 (3.68), 7.501 (1.92), 7.506 (2.98), 7.593 (2.23), 7.611 (1.98), 7.734 (3.15), 7.750 (2.74), 7.832 (1.91), 7.850 (1.75), 8.712 (3.18), 8.868 (0.71), 8.881 (1.35), 8.893 (0.68), 11.357 (0.43).

Example 289

Ent-4-Chloro-N-{[4-(1-Methyl-1H-Pyrazol-5-Yl)-2,5-Dioxoimidazolidin-4-Yl]Methyl}-2-[6-(Trifluoromethyl)Pyridin-3-Yl]Benzamide

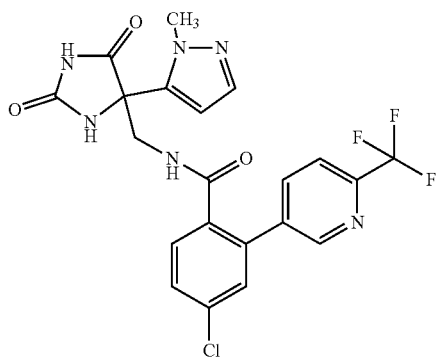 [SMILES: Cn1nccc1C1(CNC(=O)c2ccc(Cl)cc2-c2ccc(C(F)(F)F)nc2)NC(=O)NC1=O]

To a solution of ent-5-(aminomethyl)-5-(1-methyl-1H-pyrazol-5-yl)imidazolidine-2,4-dione hydrochloride (80.0 mg, 326 µmol) and 4-chloro-2-[6-(trifluoromethyl)pyridin-3-yl]benzoic acid (118 mg, 391 µmol) in DMF (2.4 ml) was added 1-ethyl-3-(3-dimethylaminopropyl)carbodiimide hydrochloride (81.2 mg, 423 µmol), 1-hydroxybenzotriazole hydrate (64.8 mg, 423 µmol) and N,N-diisopropylethylamine (280 µl, 1.6 mmol). The reaction mixture was stirred overnight at room temperature and then concentrated under reduced pressure. The crude product was purified by preparative HPLC (Method 3f). After lyophilization, 112.2 mg (95.8% purity, 67% yield) of the desired product were obtained.

LC-MS (Method 12): $R_t$=2.28 min, MS (ESIpos): m/z=493 [M+H]$^+$ $^1$H-NMR (400 MHz, DMSO-d6) δ [ppm]: −0.008 (0.57), 0.008 (0.62), 2.073 (6.00), 3.773 (16.00), 3.836 (0.60), 3.851 (0.68), 3.871 (1.30), 3.886 (1.15), 3.918 (1.18), 3.935 (1.24), 3.952 (0.63), 3.969 (0.58), 6.478 (3.55), 6.483 (3.62), 7.375 (3.39), 7.380 (3.41), 7.483 (2.57), 7.491 (0.55), 7.497 (0.59), 7.505 (3.19), 7.648 (0.96), 7.655 (4.82), 7.661 (3.13), 7.669 (2.11), 7.675 (1.07), 7.922 (0.97), 7.942 (3.49), 7.953 (2.18), 7.958 (2.05), 7.974 (0.56), 7.978 (0.60), 8.434 (2.55), 8.437 (2.57), 8.753 (2.22), 8.885 (0.75), 8.901 (1.49), 8.917 (0.74), 11.267 (2.28).

Example 290

N-{[(4R)-4-Cyclopropyl-2,5-Dioxoimidazolidin-4-Yl]Methyl}-4-Fluoro-2-[6-(Trifluoromethyl)Pyridin-3-Yl]Benzamide

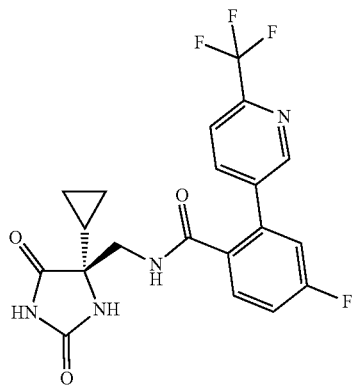 [SMILES: O=C1NC(=O)[C@](CNC(=O)c2ccc(F)cc2-c2ccc(C(F)(F)F)nc2)(C2CC2)N1]

To a solution of (5R)-5-(aminomethyl)-5-cyclopropylimidazolidine-2,4-dione hydrochloride (70.0 mg, 340 µmol) and 4-fluoro-2-[6-(trifluoromethyl)pyridin-3-yl]benzoic acid (194 mg, 681 µmol) in DMF (3 ml) was added 1-ethyl-3-(3-dimethylaminopropyl)carbodiimide hydrochloride (84.8 mg, 443 µmol), 1-hydroxybenzotriazole hydrate (67.8 mg, 443 µmol) and N,N-diisopropylethylamine (300 µl, 1.7 mmol). The reaction mixture was stirred overnight at room temperature and then concentrated under reduced pressure. The crude product was purified by preparative HPLC (Method 3f). After lyophilization, 129 mg (100% purity, 87% yield) of the desired product were obtained.

LC-MS (Method 7): $R_t$=1.43 min, MS (ESIpos): m/z=437 [M+H]$^+$ $^1$H-NMR (600 MHz, DMSO-d6) δ [ppm]: 0.119 (1.18), 0.128 (2.86), 0.136 (4.75), 0.144 (4.80), 0.152 (3.46), 0.161 (1.54), 0.302 (1.03), 0.317 (3.15), 0.325 (3.91), 0.332 (3.44), 0.340 (2.48), 0.347 (1.72), 0.378 (1.54), 0.385 (2.83), 0.393 (3.12), 0.400 (4.37), 0.409 (3.32), 0.415 (2.03), 0.424 (1.21), 0.439 (1.65), 0.447 (3.68), 0.455 (4.75), 0.464 (4.49), 0.472 (3.01), 0.481 (1.09), 1.059 (1.52), 1.068 (3.10), 1.073 (3.39), 1.082 (5.67), 1.091 (3.12), 1.096 (2.83), 1.105 (1.25), 2.069 (3.93), 2.422 (0.65), 2.612 (0.47), 2.651 (0.69), 3.458 (3.32), 3.467 (3.66), 3.480 (7.23), 3.490 (6.63), 3.514 (6.85), 3.524 (7.10), 3.536 (3.48), 3.547 (3.30), 7.397 (2.77), 7.401 (3.50), 7.411 (5.91), 7.415 (7.50), 7.426 (3.32), 7.430 (4.08), 7.444 (6.85), 7.448 (6.16), 7.460 (6.94), 7.464 (5.89), 7.544 (16.00), 7.556 (6.69), 7.565 (6.85), 7.570 (6.03), 7.580 (5.42), 7.938 (7.63), 7.952 (15.55), 7.976 (8.79), 7.979 (8.30), 7.989 (4.20), 7.992 (4.08), 8.145 (0.69), 8.618 (4.02), 8.629 (7.68), 8.639 (3.84), 8.756 (12.05), 10.633 (7.56).

Example 291

Ent-4-Fluoro-N-{[4-(1-Methyl-1H-Pyrazol-5-Yl)-2,5-Dioxoimidazolidin-4-Yl]Methyl}-2-[6-(Trifluoromethyl)Pyridin-3-Yl]Benzamide

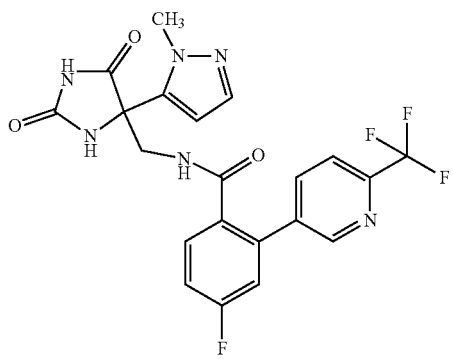 [SMILES: Cn1nccc1C1(CNC(=O)c2ccc(F)cc2-c2ccc(C(F)(F)F)nc2)NC(=O)NC1=O]

To a solution of ent-5-(aminomethyl)-5-(1-methyl-1H-pyrazol-5-yl)imidazolidine-2,4-dione hydrochloride (90.0 mg, 366 µmol) and 4-fluoro-2-[6-(trifluoromethyl)pyridin-3-yl]benzoic acid (125 mg, 440 µmol) in DMF (2.7 ml) was added 1-ethyl-3-(3-dimethylaminopropyl)carbodiimide hydrochloride (91.3 mg, 476 µmol), 1-hydroxybenzotriazole hydrate (72.9 mg, 476 µmol) and N,N-diisopropylethylamine (320 µl, 1.8 mmol). The reaction mixture was stirred overnight at room temperature and then concentrated under reduced pressure. The crude product was purified by preparative HPLC (Method 3f). After lyophilization, 106 mg (100% purity, 61% yield) of the desired product were obtained.

LC-MS (Method 7): $R_t$=1.35 min, MS (ESIpos): m/z=477 [M+H]$^+$ $^1$H-NMR (600 MHz, DMSO-d6) δ [ppm]: 3.780 (16.00), 3.848 (0.76), 3.858 (0.84), 3.871 (1.26), 3.881 (1.14), 3.934 (1.19), 3.945 (1.24), 3.957 (0.79), 3.968 (0.74), 6.475 (3.41), 6.479 (3.39), 7.375 (3.46), 7.378 (3.34), 7.414 (0.51), 7.418 (0.71), 7.428 (1.10), 7.432 (1.55), 7.442 (0.66), 7.446 (1.00), 7.450 (1.46), 7.455 (1.19), 7.467 (1.40), 7.471 (1.11), 7.533 (1.26), 7.543 (1.35), 7.547 (1.14), 7.557 (1.02), 7.923 (1.09), 7.936 (3.19), 7.948 (1.95), 7.951 (1.84), 7.962 (0.64), 7.965 (0.65), 8.404 (2.91), 8.748 (2.31), 8.827 (0.78), 8.838 (1.47), 8.848 (0.76).

Example 292

Ent-5-Fluoro-N-{[4-(1-Methyl-1H-Pyrazol-5-Yl)-2,5-Dioxoimidazolidin-4-Yl]Methyl}-2-[6-(Trifluoromethyl)Pyridin-3-Yl]Benzamide

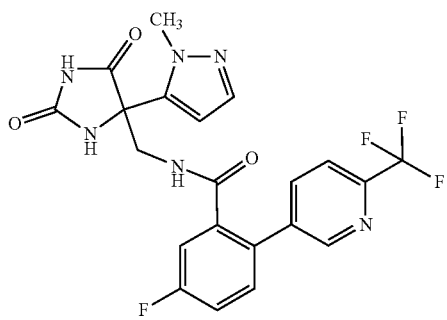 [SMILES: Cn1nccc1C1(CNC(=O)c2cc(F)ccc2-c2ccc(C(F)(F)F)nc2)NC(=O)NC1=O]

To a solution of ent-5-(aminomethyl)-5-(1-methyl-1H-pyrazol-5-yl)imidazolidine-2,4-dione hydrochloride (90.0 mg, 366 µmol) and 5-fluoro-2-[6-(trifluoromethyl)pyridin-3-yl]benzoic acid (125 mg, 440 µmol) in DMF (2.7 ml) was added 1-ethyl-3-(3-dimethylaminopropyl)carbodiimide hydrochloride (91.3 mg, 476 µmol), 1-hydroxybenzotriazole hydrate (72.9 mg, 476 µmol) and N,N-diisopropylethylamine (320 µl, 1.8 mmol). The reaction mixture was stirred overnight at room temperature and then concentrated under reduced pressure. The crude product was purified by preparative HPLC (Method 3f). After lyophilization, 99.2 mg (100% purity, 57% yield) of the desired product were obtained.

LC-MS (Method 7): $R_t$=1.33 min, MS (ESIpos): m/z=477 [M+H]$^+$ $^1$H-NMR (600 MHz, DMSO-d6) δ [ppm]: 0.005 (0.56), 3.782 (16.00), 3.856 (0.77), 3.866 (0.85), 3.879 (1.32), 3.888 (1.18), 3.937 (1.23), 3.948 (1.28), 3.959 (0.81), 3.971 (0.74), 6.483 (3.38), 6.487 (3.25), 7.293 (1.22), 7.298 (1.37), 7.308 (1.23), 7.313 (1.27), 7.379 (3.42), 7.382 (3.20), 7.473 (0.59), 7.478 (0.61), 7.488 (1.29), 7.492 (1.32), 7.502 (0.76), 7.506 (0.76), 7.583 (1.33), 7.592 (1.38), 7.597 (1.15), 7.606 (1.06), 7.908 (0.51), 7.922 (4.94), 7.926 (2.46), 8.438 (2.98), 8.714 (2.52), 8.936 (0.79), 8.946 (1.50), 8.957 (0.77).

Example 293

Rac-5-Fluoro-N-{[4-(3-Fluorobicyclo[1.1.1]Pentan-1-Yl)-2,5-Dioxoimidazolidin-4-Yl]Methyl}-4'-(Trifluoromethyl)[Biphenyl]-2-Carboxamide

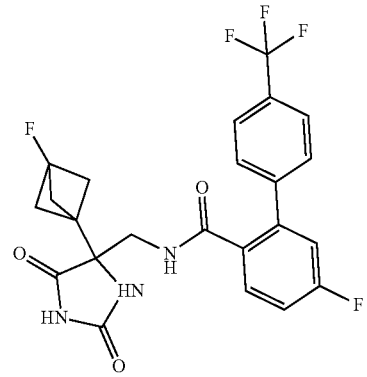 [SMILES: O=C1NC(=O)C(CNC(=O)c2ccc(F)cc2-c2ccc(C(F)(F)F)cc2)(C23CC(F)(C2)C3)N1]

To a solution of rac-5-(aminomethyl)-5-(3-fluorobicyclo[1.1.1]pentan-1-yl)imidazolidine-2,4-dione hydrochloride (100 mg, 401 µmol) and 5-fluoro-4'-(trifluoromethyl)[1,1'-biphenyl]-2-carboxylic acid (137 mg, 481 µmol) in DMF (3 ml) was added 1-ethyl-3-(3-dimethylaminopropyl)carbodiimide hydrochloride (99.8 mg, 521 µmol), 1-hydroxybenzotriazole hydrate (79.7 mg, 521 µmol) and N,N-diisopropylethylamine (350 µl, 2.0 mmol). The reaction mixture was stirred overnight at room temperature and then concentrated under reduced pressure. The crude product was purified by preparative HPLC (Method 3f). After lyophilization, 111 mg (90% purity, 52% yield) of the desired product were obtained.

LC-MS (Method 7): $R_t$=1.76 min; MS (ESIpos): m/z=480 [M+H]$^+$ $^1$H-NMR (400 MHz, DMSO-d6) δ [ppm]: 2.030 (15.12), 2.036 (16.00), 3.449 (3.32), 3.464 (3.33), 7.315 (3.04), 7.337 (3.71), 7.355 (1.23), 7.362 (0.82), 7.433 (1.26), 7.445

(1.26), 7.452 (1.34), 7.468 (0.86), 7.555 (3.76), 7.575 (4.43), 7.771 (4.27), 7.792 (3.56), 8.022 (3.18), 8.657 (0.86), 8.672 (1.81), 8.688 (0.86), 10.798 (2.64).

Example 294

Ent-5-Fluoro-N-{[4-(3-Fluorobicyclo[1.1.1]Pentan-1-Yl)-2,5-Dioxoimidazolidin-4-Yl]Methyl}-4'-(Trifluoromethyl)[Biphenyl]-2-Carboxamide

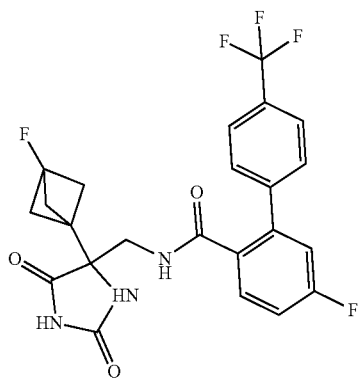 [SMILES: O=C1NC(=O)C(CNC(=O)c2ccc(F)cc2-c2ccc(C(F)(F)F)cc2)(C23CC(F)(C2)C3)N1]

Enantiomeric separation of rac-5-fluoro-N-{[4-(3-fluorobicyclo[1.1.1]pentan-1-yl)-2,5-dioxoimidazolidin-4-yl]methyl}-4'-(trifluoromethyl)[biphenyl]-2-carboxamide (109.4 mg) by preparative chiral HPLC [column: Daicel Chiralpak AD-H 5 µm, 250×20 mm; eluent: 80% n-heptane/20% ethanol; flow rate: 30 ml/min; temperature: 30° C.; UV detection: 220 nm] afforded 42.0 mg (100% purity) of the desired product.

Analytical chiral HPLC: $R_t$=4.23 min, e.e. =93.3% [column: Daicel Chiralpak AD-3 3 µm, 50×4.6 mm; eluent: 80% n-heptane/20% ethanol; flow rate: 1 ml/min; temperature: 30° C.; UV detection: 220 nm]

LC-MS (Method 7): $R_t$=1.76 min; MS (ESIpos): m/z=480 [M+H]$^+$ $^1$H-NMR (600 MHz, DMSO-d6) δ [ppm]: 2.029 (16.00), 2.033 (15.59), 3.448 (3.48), 3.459 (3.26), 7.308 (1.02), 7.312 (1.93), 7.316 (1.15), 7.324 (1.14), 7.329 (2.33), 7.330 (2.34), 7.335 (1.15), 7.344 (0.99), 7.349 (0.72), 7.437 (1.40), 7.447 (1.42), 7.451 (1.29), 7.461 (1.10), 7.558 (3.22), 7.571 (3.54), 7.769 (3.71), 7.783 (3.27), 7.991 (2.76), 7.993 (2.69), 8.629 (0.88), 8.640 (1.82), 8.650 (0.87), 10.776 (2.38).

Example 295

Rac-5,6-Difluoro-N-{[4-(3-Fluorobicyclo[1.1.1]Pentan-1-Yl)-2,5-Dioxoimidazolidin-4-Yl]Methyl}-4'-(Trifluoromethyl)[Biphenyl]-2-Carboxamide

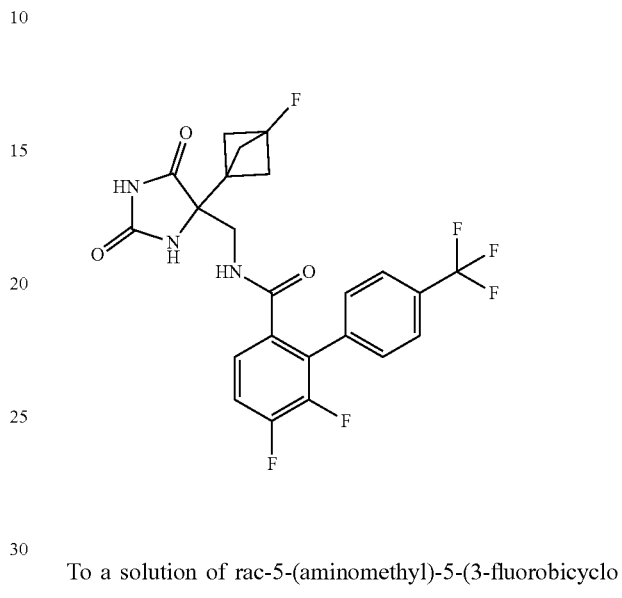

To a solution of rac-5-(aminomethyl)-5-(3-fluorobicyclo[1.1.1]pentan-1-yl)imidazolidine-2,4-dione hydrochloride (120 mg, 479 µmol) and 5,6-difluoro-4'-(trifluoromethyl)[1,1'-biphenyl]-2-carboxylic acid (174 mg, 575 µmol) in DMF (2.4 ml) was added 1-ethyl-3-(3-dimethylaminopropyl)carbodiimide hydrochloride (119 mg, 623 µmol), 1-hydroxybenzotriazole hydrate (95.4 mg, 623 µmol) and N,N-diisopropylethylamine (420 µl, 2.4 mmol). The reaction mixture was stirred overnight at room temperature, diluted with ethyl acetate and washed with water. The organic layer was dried and concentrated in vacuo. The crude product was purified by column chromatography (25 g Ultra Snap Cartridge Biotage; eluent ethyl acetate/cyclohexane, elution gradient 16%→100%). Samples containing the desired product were united, the solvents were evaporated and the residue was dried in vacuum. 143 mg (100% purity, 60% yield) of the title compound was obtained.

LC-MS (Method 7): $R_t$=1.78 min; MS (ESIpos): m/z=498 [M+H]$^+$ $^1$H-NMR (600 MHz, DMSO-d6) δ [ppm]: 2.014 (16.00), 2.017 (15.42), 2.069 (1.69), 3.386 (2.31), 3.389 (2.34), 3.396 (2.50), 3.399 (2.48), 7.249 (0.86), 7.256 (0.93), 7.263 (1.01), 7.270 (0.94), 7.536 (3.07), 7.549 (3.32), 7.580 (0.52), 7.593 (1.03), 7.609 (1.00), 7.623 (0.47), 7.805 (3.76), 7.819 (3.39), 7.978 (3.04), 8.627 (0.90), 8.637 (1.80), 8.648 (0.88), 10.776 (2.61).

Example 296

Ent-N-({4-[1-(Difluoromethyl)-1H-Pyrazol-5-Yl]-2,5-Dioxoimidazolidin-4-Yl}Methyl)-5-Fluoro-4'-(Trifluoromethyl)[Biphenyl]-2-Carboxamide

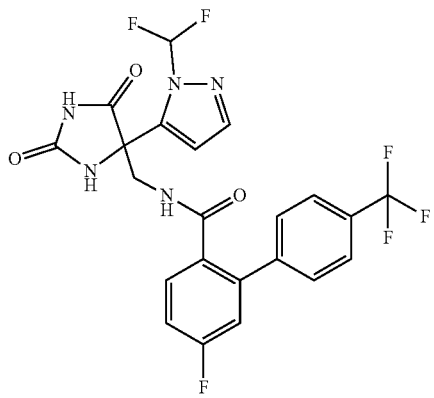 [SMILES: O=C1NC(=O)C(CNC(=O)c2ccc(F)cc2-c2ccc(C(F)(F)F)cc2)(c2ccnn2C(F)F)N1]

Enantiomeric separation of rac-N-({4-[1-(difluoromethyl)-1H-pyrazol-5-yl]-2,5-dioxoimidazolidin-4-yl}methyl)-5-fluoro-4'-(trifluoromethyl)[biphenyl]-2-carboxamide (38.1 mg) by preparative chiral HPLC [column: Daicel Chiralpak ID 5 μm, 250×20 mm; eluent: 60% n-heptan/40% isopropanol; flow rate: 20 ml/min; temperature: 40° C.; UV detection: 210 nm] afforded 14.3 mg (98% purity) of the desired product.

Analytical chiral HPLC: $R_t$=1.92 min, e.e. =>99% [column: 50×4.6 mm filled with Daicel Chiralpak ID-3 3 μm; eluent: 70% n-heptan/30% isopropanol; flow rate: 1 ml/min; temperature: 30° C.; UV detection: 220 nm]

LC-MS (Method 7): $R_t$=1.69 min; MS (ESIpos): m/z=512 [M+H]$^+$ $^1$H-NMR (600 MHz, DMSO-d6) δ [ppm]: 0.858 (1.26), 1.032 (3.78), 1.042 (3.78), 1.107 (0.90), 1.235 (0.90), 2.386 (2.34), 2.426 (2.88), 2.615 (2.16), 2.655 (2.34), 3.803 (3.42), 3.814 (3.60), 3.826 (5.57), 3.837 (5.21), 3.888 (5.21), 3.898 (5.75), 3.911 (3.60), 3.921 (3.24), 4.353 (0.72), 6.725 (14.02), 6.727 (13.48), 7.334 (5.03), 7.338 (6.83), 7.354 (7.37), 7.372 (6.47), 7.376 (5.57), 7.386 (3.78), 7.474 (5.75), 7.484 (6.47), 7.488 (5.39), 7.498 (4.67), 7.545 (13.84), 7.558 (15.46), 7.760 (16.00), 7.774 (14.38), 7.785 (14.02), 7.819 (3.78), 7.912 (3.78), 7.919 (3.60), 8.011 (3.06), 8.554 (8.45), 8.895 (3.78), 8.905 (7.55), 8.916 (3.96), 11.289 (0.90).

Example 297

Ent-N-{[4-(1-Methyl-1H-Imidazol-5-Yl)-2,5-Dioxoimidazolidin-4-Yl]Methyl}-4'-(Trifluoromethyl)[Biphenyl]-2-Carboxamide

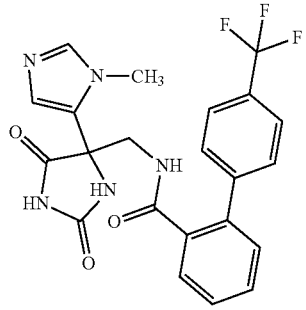 [SMILES: Cn1cncc1C1(CNC(=O)c2ccccc2-c2ccc(C(F)(F)F)cc2)NC(=O)NC1=O]

Enantiomeric separation of rac-N-{[4-(1-methyl-1H-imidazol-5-yl)-2,5-dioxoimidazolidin-4 yl]methyl}-4'-(trifluoromethyl)[biphenyl]-2-carboxamide (32.2 mg) by preparative chiral HPLC [column: Daicel Chiralpak OX-H 5 μm, 250×20 mm; eluent: 65% n-heptane/35% ethanol; flow rate: 20 ml/min; temperature: 40° C.; UV detection: 220 nm] afforded 5.20 mg (98% purity) of the desired product.

Analytical chiral HPLC: $R_t$=7.82 min, e.e. =>99% [column: Daicel OX-H 5 μm, 250×4.6 mm; eluent: 65% n-heptane/35% ethanol; flow rate: 1 ml/min; temperature: 40° C.; UV detection: 220 nm]

LC-MS (Method 7): $R_t$=1.06 min; MS (ESIpos): m/z=458 [M+H]$^+$ $^1$H-NMR (600 MHz, DMSO-d6) δ [ppm]: 1.158 (0.63), 1.236 (0.42), 3.574 (16.00), 3.847 (0.89), 3.857 (0.97), 3.869 (1.57), 3.880 (1.41), 3.925 (1.46), 3.936 (1.52), 3.948 (0.94), 3.959 (0.86), 7.073 (3.16), 7.433 (3.82), 7.445 (5.54), 7.466 (1.59), 7.478 (2.51), 7.491 (1.07), 7.538 (4.08), 7.551 (5.07), 7.560 (2.46), 7.573 (0.94), 7.640 (3.29), 7.749 (4.68), 7.763 (4.10), 8.261 (4.34), 8.699 (1.07), 8.709 (1.96), 8.720 (1.02), 11.151 (0.47).

Example 298

Ent-5,6-Difluoro-N-{[4-(1-Fluorocyclopropyl)-2,5-Dioxoimidazolidin-4-Yl]Methyl}-4'-(Trifluoromethyl)[Biphenyl]-2-Carboxamide

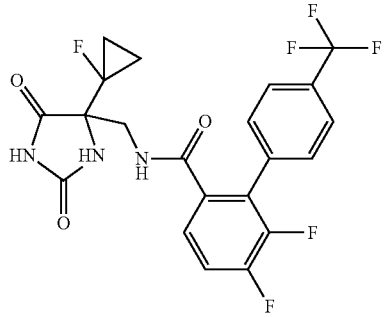 [SMILES: O=C1NC(=O)C(CNC(=O)c2ccc(F)c(F)c2-c2ccc(C(F)(F)F)cc2)(C2(F)CC2)N1]

Enantiomeric separation of rac-5,6-difluoro-N-{[4-(1-fluorocyclopropyl)-2,5-dioxoimidazolidin-4 yl]methyl}-4'-

(trifluoromethyl)[biphenyl]-2-carboxamide (28.1 mg) by preparative chiral HPLC [Daicel Chiralpak IA 5 µm, 250×20 mm; eluent: 90% n-heptane/9% ethanol+1% water; flow rate: 15 ml/min; temperature: 22.5° C.; UV detection: 220 nm] afforded 9.40 mg (98% purity) of the desired product.

Analytical chiral HPLC: $R_t$=22.04 min, e.e. =95% [column: 250×4.6 mm filled with Daicel Chiralpak IA 5 µm; eluent: 90% n-heptane/10% ethanol; flow rate: 1 ml/min; temperature: 20° C.; UV detection: 220 nm]

LC-MS (Method 7): $R_t$=1.72 min; MS (ESIpos): m/z=472 [M+H]$^+$ $^1$H-NMR (400 MHz, DMSO-d6) δ [ppm]: −0.149 (0.39), 0.008 (4.48), 0.147 (0.43), 0.806 (1.26), 0.832 (4.04), 0.858 (3.83), 0.894 (3.35), 0.923 (3.96), 0.945 (2.83), 0.955 (2.17), 0.977 (7.57), 0.991 (3.87), 1.018 (3.09), 1.028 (7.61), 1.088 (0.43), 1.103 (0.43), 1.236 (1.26), 2.328 (0.70), 2.366 (0.78), 2.670 (0.78), 2.710 (0.83), 3.425 (3.00), 3.441 (3.22), 3.460 (5.61), 3.476 (5.35), 3.523 (5.04), 3.538 (5.43), 3.557 (2.91), 3.573 (2.70), 3.733 (0.43), 7.263 (3.30), 7.276 (3.65), 7.282 (4.22), 7.294 (3.87), 7.536 (11.96), 7.555 (13.83), 7.585 (2.43), 7.606 (4.35), 7.630 (4.52), 7.651 (2.30), 7.804 (16.00), 7.824 (13.87), 8.116 (14.52), 8.692 (3.39), 8.707 (7.09), 8.723 (3.39), 10.865 (3.17).

Example 299

Rac-6-Fluoro-N-{[4-(1-Fluorocyclopropyl)-2,5-Dioxoimidazolidin-4-Yl]Methyl}-4'-(Trifluoromethyl)[Biphenyl]-2-Carboxamide

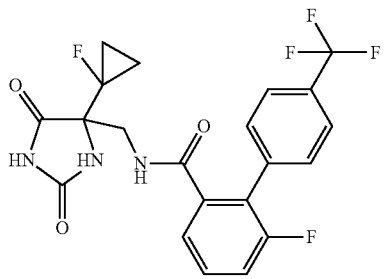 [SMILES: O=C1NC(=O)C(CNC(=O)c2cccc(F)c2-c2ccc(C(F)(F)F)cc2)(C2(F)CC2)N1]

To a solution of rac-5-(aminomethyl)-5-(1-fluorocyclopropyl)imidazolidine-2,4-dione hydrochloride (70.0 mg, 313 µmol) and 6-fluoro-4'-(trifluoromethyl)[1,1'-biphenyl]-2-carboxylic acid (89.0 mg, 313 µmol) in DMF (2 ml) was added 1-ethyl-3-(3-dimethylaminopropyl)carbodiimide hydrochloride (78.0 mg, 407 µmol), 1-hydroxybenzotriazole hydrate (62.3 mg, 407 µmol) and N,N-diisopropylethylamine (270 µl, 1.6 mmol). The reaction mixture was stirred overnight at room temperature and then concentrated under reduced pressure. The crude product was purified by preparative HPLC (Method 4f). After lyophilisation, 78.5 mg (98% purity, 54% yield) of the desired product were obtained.

LC-MS (Method 8): $R_t$=0.86 min; MS (ESIpos): m/z=454 [M+H]$^+$ $^1$H-NMR (600 MHz, DMSO-d6) δ [ppm]: 0.829 (1.43), 0.848 (4.11), 0.865 (3.17), 0.930 (3.17), 0.946 (4.07), 0.965 (1.70), 0.996 (2.37), 1.004 (7.11), 1.016 (2.37), 1.029 (2.55), 1.037 (7.28), 1.049 (1.65), 2.386 (0.76), 2.426 (1.34), 2.577 (0.76), 2.615 (0.80), 2.655 (1.21), 2.730 (1.21), 2.891 (1.52), 3.305 (0.67), 3.320 (1.65), 3.381 (1.30), 3.510 (3.26), 3.521 (3.49), 3.532 (5.36), 3.544 (5.09), 3.591 (4.83), 3.601 (5.05), 3.613 (3.08), 3.623 (2.86), 7.336 (8.94), 7.352 (15.20), 7.366 (3.98), 7.370 (2.77), 7.453 (5.32), 7.463 (5.23), 7.467 (5.01), 7.477 (3.93), 7.561 (13.27), 7.575 (14.53), 7.777 (15.20), 7.791 (13.45), 8.173 (16.00), 8.749 (3.58), 8.759 (7.33), 8.770 (3.44), 10.922 (3.98).

Example 300

Ent-6-Fluoro-N-{[4-(1-Fluorocyclopropyl)-2,5-Dioxoimidazolidin-4-Yl]Methyl}-4'-(Trifluoromethyl)[Biphenyl]-2-Carboxamide

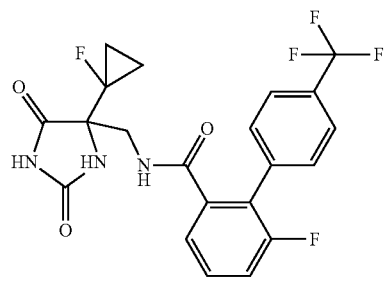 [SMILES: O=C1NC(=O)C(CNC(=O)c2cccc(F)c2-c2ccc(C(F)(F)F)cc2)(C2(F)CC2)N1]

Enantiomeric separation of rac-6-fluoro-N-{[4-(1-fluorocyclopropyl)-2,5-dioxoimidazolidin-4 yl]methyl}-4'-(trifluoromethyl)[biphenyl]-2-carboxamide (68.8 mg) by preparative chiral HPLC [column: Daicel Chiralpak ID 5 µm, 250×20 mm; eluent: 50% n-heptane/50% isopropanol; flow rate: 20 ml/min; temperature: 40° C.; UV detection: 220 nm] afforded 22.9 mg (99% purity) of the desired product.

Analytical chiral HPLC: $R_t$=1.39 min, e.e. =99% [column: Daicel chiralcel ID-3 3 µm, 50×4.6 mm; eluent: 50% n-heptane/50% isopropanol; flow rate: 1 ml/min; UV detection: 220 nm]

LC-MS (Method 7): $R_t$=1.69 min; MS (ESIpos): m/z=454 [M+H]$^+$ $^1$H-NMR (600 MHz, DMSO-d6) δ [ppm]: −0.063 (3.75), 0.828 (1.43), 0.838 (1.98), 0.848 (4.24), 0.856 (1.56), 0.865 (3.38), 0.889 (0.50), 0.930 (3.08), 0.947 (4.08), 0.965 (1.52), 0.977 (1.40), 0.996 (2.30), 1.004 (7.16), 1.016 (2.37), 1.029 (2.51), 1.037 (7.32), 1.049 (1.59), 2.387 (0.48), 2.426 (0.80), 2.655 (0.62), 3.318 (0.65), 3.511 (3.22), 3.521 (3.41), 3.533 (5.39), 3.544 (4.97), 3.591 (4.74), 3.601 (5.14), 3.614 (3.06), 3.624 (2.79), 7.337 (8.91), 7.352 (14.97), 7.366 (3.91), 7.371 (2.74), 7.454 (5.25), 7.464 (5.20), 7.467 (4.93), 7.477 (3.85), 7.562 (13.33), 7.575 (14.48), 7.777 (15.13), 7.791 (13.42), 8.173 (16.00), 8.749 (3.68), 8.759 (7.30), 8.770 (3.57), 10.923 (4.70).

Example 301

Ent-4'-Chloro-5-Fluoro-N-{[4-(1-Fluorocyclopropyl)-2,5-Dioxoimidazolidin-4-Yl]Methyl}[Biphenyl]-2-Carboxamide

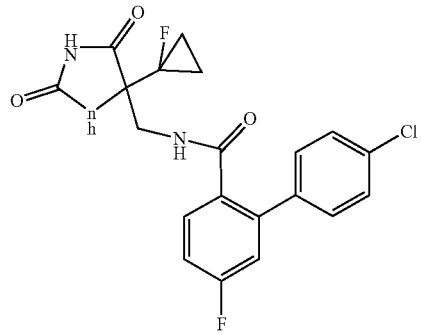

Enantiomeric separation of rac-4'-chloro-5-fluoro-N-{[4-(1-fluorocyclopropyl)-2,5-dioxoimidazolidin-4-yl]methyl}[biphenyl]-2-carboxamide (136.4 mg) by preparative chiral HPLC [column: Daicel Chiralpak ID-3 3 µm, 50×4.6 mm; eluent: 50% n-heptane/50% isopropanol; flow rate: 10 ml/min; temperature: 30° C.; UV detection: 220 nm] afforded 58.0 mg (95% purity) of the desired product.

Analytical chiral HPLC: $R_t$=3.00 min, e.e. =>99% [column: Daicel chiralcel AD-3 3 µm, 50×4.6 mm; eluent: 70% n-heptane/30% ethanol; flow rate: 1 ml/min; UV detection: 220 nm]

LC-MS (Method 7): $R_t$=1.59 min; MS (ESIpos): m/z=420 [M+H]$^+$ $^1$H-NMR (400 MHz, DMSO-d6) δ [ppm]: −0.149 (0.72), −0.008 (5.15), 0.008 (6.42), 0.146 (0.68), 0.822 (0.77), 0.847 (2.36), 0.874 (2.11), 0.914 (1.59), 0.944 (2.01), 0.962 (1.59), 0.993 (4.00), 1.007 (2.34), 1.030 (13.29), 1.045 (16.00), 1.086 (0.74), 1.102 (0.58), 1.157 (0.56), 1.261 (0.62), 2.328 (0.60), 2.366 (0.81), 2.670 (0.70), 2.710 (0.77), 3.491 (1.53), 3.507 (1.61), 3.526 (3.11), 3.541 (3.02), 3.576 (2.79), 3.590 (3.04), 3.610 (1.39), 3.625 (1.35), 3.752 (0.41), 3.762 (0.46), 3.766 (0.54), 3.777 (0.56), 3.782 (0.43), 3.793 (0.41), 4.323 (1.90), 4.333 (1.88), 7.251 (2.73), 7.257 (4.64), 7.269 (2.44), 7.275 (3.79), 7.282 (4.80), 7.290 (4.76), 7.296 (3.10), 7.311 (2.55), 7.318 (2.01), 7.363 (9.63), 7.368 (3.50), 7.380 (4.24), 7.385 (15.15), 7.395 (4.30), 7.410 (4.00), 7.416 (3.27), 7.431 (2.88), 7.462 (14.97), 7.467 (4.18), 7.478 (3.41), 7.483 (9.75), 8.106 (7.84), 8.612 (1.78), 8.628 (3.87), 8.643 (1.86), 10.875 (3.95).

Example 302

Ent-N-{[4-(1,3-Dimethyl-1H-Pyrazol-5-Yl)-2,5-Dioxoimidazolidin-4-Yl]Methyl}-4'-(Trifluoromethyl)[Biphenyl]-2-Carboxamide

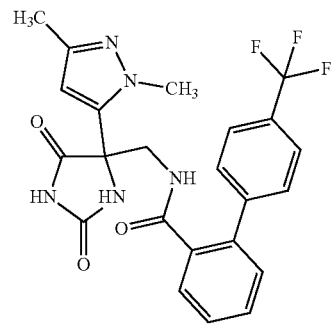 [SMILES: Cc1cc(C2(CNC(=O)c3ccccc3-c3ccc(C(F)(F)F)cc3)NC(=O)NC2=O)n(C)n1]

Enantiomeric separation of rac-N-{[4-(1,3-dimethyl-1H-pyrazol-5-yl)-2,5-dioxoimidazolidin-4 yl]methyl}-4'-(trifluoromethyl)[biphenyl]-2-carboxamide (27.4 mg) by preparative chiral HPLC [column: Daicel Chiralpak IC-3 3 µm, 50×4.6 mm; eluent: 50% n-heptane/50% isopropanol; flow rate: 25 ml/min; temperature: 40° C.; UV detection: 220 nm] afforded 11.4 mg (100% purity) of the desired product.

Analytical chiral HPLC: $R_t$=0.84 min, e.e. =>99% [column: 50×4.6 mm filled with Daicel Chiralpak IC-3 3 µm; eluent: 50% n-heptane/50% ethanol; flow rate: 1 ml/min; UV detection: 220 nm]

LC-MS (Method 7): $R_t$=1.57 min; MS (ESIpos): m/z=472 [M+H]$^+$ $^1$H-NMR (400 MHz, DMSO-d6) δ [ppm]: 1.283 (0.67), 2.097 (13.86), 2.523 (1.66), 3.699 (16.00), 3.814 (0.67), 3.829 (0.73), 3.848 (1.37), 3.863 (1.24), 3.899 (1.24), 3.916 (1.31), 3.933 (0.70), 3.950 (0.64), 6.240 (5.51), 7.424 (1.05), 7.428 (1.27), 7.436 (1.82), 7.443 (2.39), 7.446 (2.45), 7.455 (2.42), 7.466 (1.21), 7.468 (1.24), 7.484 (1.98), 7.487 (1.72), 7.502 (0.99), 7.506 (0.99), 7.515 (3.06), 7.536 (3.54), 7.545 (1.75), 7.549 (1.53), 7.563 (1.75), 7.567 (1.66), 7.582 (0.67), 7.586 (0.67), 7.747 (3.63), 7.768 (3.06), 8.365 (3.76), 8.726 (0.76), 8.742 (1.53), 8.758 (0.76), 11.216 (0.64).

Example 303

Rac-5-Fluoro-N-({4-[5-Methyl-2-(Trifluoromethyl)-1,3-Thiazol-4-Yl]-2,5-Dioxoimidazolidin-4-Yl}Methyl)-4'-(Trifluoromethyl)[Biphenyl]-2-Carboxamide

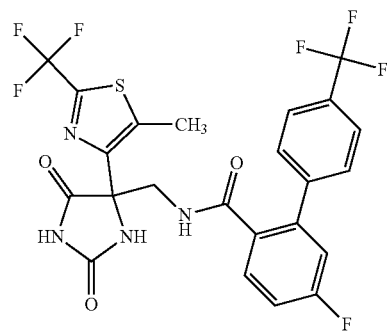 [SMILES: Cc1sc(C(F)(F)F)nc1C1(CNC(=O)c2ccc(F)cc2-c2ccc(C(F)(F)F)cc2)NC(=O)NC1=O]

To a solution of rac-5-(aminomethyl)-5-[5-methyl-2-(trifluoromethyl)-1,3-thiazol-4-yl]imidazolidine-2,4-dione hydrochloride (70.0 mg, 212 µmol) and 5-fluoro-4'-(trifluoromethyl)[1,1'-biphenyl]-2-carboxylicacid (72.2 mg, 254 µmol) in DMF (1.9 ml) was added 1-ethyl-3-(3-dimethylaminopropyl)carbodiimide hydrochloride (52.7 mg, 275 µmol), 1-hydroxybenzotriazole hydrate (42.1 mg, 275 µmol) and N,N-diisopropylethylamine (180 µl, 1.1 mmol). The reaction mixture was stirred for 3 days at room temperature and then concentrated under reduced pressure. The crude product was purified by preparative HPLC (Method 8f). After lyophilisation, 23.3 mg (98% purity, 19% yield) of the desired product were obtained.

LC-MS (Method 7): $R_t$=2.00 min, MS (ESIpos): m/z=561 [M+H]$^+$ $^1$H-NMR (400 MHz, DMSO-d6) δ [ppm]: 2.478 (16.00), 4.069 (4.24), 4.085 (4.56), 7.329 (4.21), 7.352 (4.87), 7.370 (1.58), 7.376 (1.02), 7.455 (1.60), 7.467 (1.77), 7.473 (1.77), 7.490 (1.18), 7.586 (4.63), 7.606 (5.45), 7.777 (5.58), 7.798 (4.65), 8.380 (4.83), 8.788 (1.24), 8.803 (2.63), 8.819 (1.23).

Example 304

Rac-N-{[4-(1,5-Dimethyl-1H-Imidazol-4-Yl)-2,5-Dioxoimidazolidin-4-Yl]Methyl}-5-Fluoro-4'-(Trifluoromethyl)[Biphenyl]-2-Carboxamide

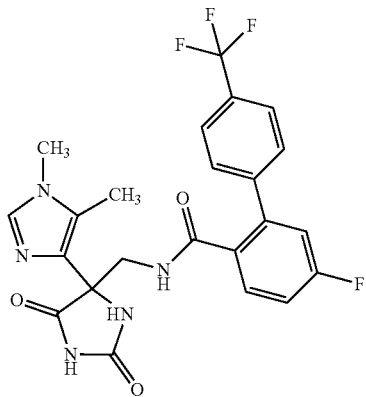 [SMILES: Cc1c(C2(CNC(=O)c3ccc(F)cc3-c3ccc(C(F)(F)F)cc3)NC(=O)NC2=O)ncn1C]

To a solution of rac-5-(aminomethyl)-5-(1,5-dimethyl-1H-imidazol-4-yl)imidazolidine-2,4-dione hydrochloride (50.0 mg, 193 µmol) and 5-fluoro-4'-(trifluoromethyl)[1,1'-biphenyl]-2-carboxylic acid (54.7 mg, 193 µmol) in DMF (1.2 ml) was added 1-ethyl-3-(3-dimethylaminopropyl)carbodiimide hydrochloride (48.0 mg, 250 µmol), 1-hydroxybenzotriazole hydrate (38.3 mg, 250 µmol) and N,N-diisopropylethylamine (170 µl, 960 µmol). The reaction mixture was first stirred overnight at room temperature, then for 2 h at 40° C. and finally concentrated under reduced pressure. The crude product was purified by preparative HPLC (Method 3f). After lyophilisation, 40.6 mg (99% purity, 43% yield) of the desired product were obtained.

LC-MS (Method 8): $R_t$=0.68 min; MS (ESIpos): m/z=490 [M+H]$^+$ $^1$H-NMR (600 MHz, DMSO-d6) δ [ppm]: 2.062 (16.00), 3.504 (13.56), 3.904 (0.50), 3.914 (0.55), 3.927 (1.37), 3.937 (1.26), 3.947 (1.32), 3.957 (1.44), 3.970 (0.55), 3.980 (0.49), 7.324 (1.71), 7.328 (1.43), 7.333 (1.36), 7.337 (1.46), 7.341 (1.44), 7.344 (1.59), 7.348 (1.18), 7.469 (1.05), 7.478 (1.32), 7.484 (1.11), 7.498 (5.10), 7.600 (2.83), 7.613 (3.14), 7.779 (3.35), 7.793 (2.86), 8.112 (2.56), 8.538 (0.80), 8.549 (1.67), 8.559 (0.78), 10.844 (2.22).

Example 305

Rac-N-{[4-(1,5-Dimethyl-1H-Pyrazol-3-Yl)-2,5-Dioxoimidazolidin-4-Yl]Methyl}-5,6-Difluoro-4'-(Trifluoromethyl)[Biphenyl]-2-Carboxamide

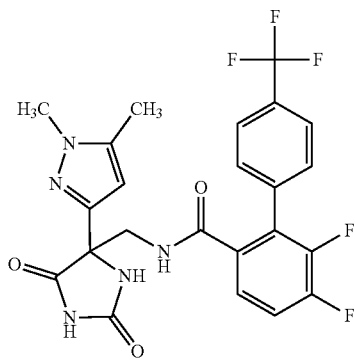 [SMILES: Cc1cc(C2(CNC(=O)c3ccc(F)c(F)c3-c3ccc(C(F)(F)F)cc3)NC(=O)NC2=O)nn1C]

N-[2-(1,5-dimethyl-1H-pyrazol-3-yl)-2-oxoethyl]-5,6-difluoro-4'-(trifluoromethyl)[1,1'-biphenyl]-2-carboxamide (140 mg, 320 µmol) was dissolved in 2 ml of ethanol. Ammonium carbonate (308 mg, 3.20 mmol) and potassium cyanide (83.4 mg, 1.28 mmol), dissolved in 4 ml of water, were added. The vial was sealed and the mixture was stirred at 80° C. over night. The product was purified by preparative HPLC (Instrument: Waters Prep LC/MS System, Column: XBridge C18 5 µm 100×30 mm; eluent A: water, eluent B: acetonitrile, eluent C: 2% ammonia in water, eluent D: acetonitrile/water (80 Vol. %/20 Vol %); flow: 80 ml/min, room temperature, UV-detection: 200-400 nm, At-Column Injektion; gradient: eluent A 0 to 2 min 63 ml, eluent B 0 to 2 min 7 ml, eluent A 2 to 10 min from 63 ml to 39 ml and eluent B from 7 ml to 31 ml, 10 to 12 min 0 ml eluent A and 70 ml eluent B. Eluent C and eluent D constant flow 5 ml/min over the whole runtime). After lyophilization, 35.0 mg (100% purity, 22% yield) of the title compound were obtained.

LC-MS (Method 7): $R_t$=1.65 min; MS (ESIpos): m/z=508 [M+H]$^+$ $^1$H-NMR (600 MHz, DMSO-d6) δ [ppm]: 2.207 (11.78), 3.625 (0.85), 3.635 (0.91), 3.648 (1.10), 3.658 (1.03), 3.679 (16.00), 3.812 (1.00), 3.822 (1.08), 3.834 (0.89), 3.845 (0.79), 5.980 (3.69), 7.256 (0.60), 7.264 (0.63), 7.270 (0.70), 7.278 (0.66), 7.550 (2.21), 7.563 (2.44), 7.581 (0.68), 7.597 (0.70), 7.797 (2.84), 7.811 (2.52), 8.084 (3.14), 8.540 (0.68), 8.550 (1.40), 8.561 (0.64), 10.694 (0.43).

Example 306

Rac-5,6-Difluoro-N-{[4-(3-Methyl-1,2-Thiazol-4-Yl)-2,5-Dioxoimidazolidin-4-Yl]Methyl}-4'-(Trifluoromethyl)[Biphenyl]-2-Carboxamide

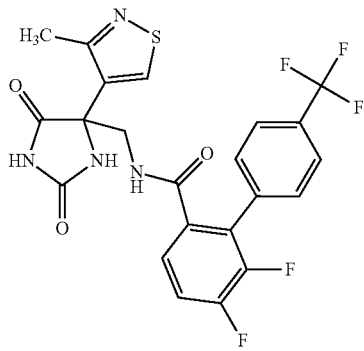 [SMILES: Cc1nscc1C1(CNC(=O)c2ccc(F)c(F)c2-c2ccc(C(F)(F)F)cc2)NC(=O)NC1=O]

5,6-difluoro-4'-(trifluoromethyl)[1,1'-biphenyl]-2-carboxylic acid (115 mg, 381 µmol) dissolved in 2 ml of DMF was treated with N-ethyl-N-isopropylpropan-2-amine (200 µl, 1.1 mmol), 3-{[(ethylimino)methylene]amino}-N,N-dimethylpropan-1-amine hydrochloride (94.9 mg, 495 µmol), 1H-benzotriazol-1-ol hydrate (75.8 mg, 495 µmol) and rac-5-(aminomethyl)-5-(3-methyl-1,2-thiazol-4-yl)imidazolidine-2,4-dione-hydrochloride (100 mg, 381 µmol). The mixture was stirred at room temperature for 3 h. The product was purified by preparative HPLC (Instrument: Waters Prep LC/MS System, Column: XBridge C18 5 µm 100×30 mm; eluent A: water, eluent B: acetonitrile, eluent C: 2% formic acid in water, eluent D: acetonitrile/water (80 Vol. %/20 Vol. %); flow: 80 ml/min, room temperature, UV-detection: 200-400 nm, At-Column Injektion; gradient: eluent A 0 to 2 min 55 ml, eluent B 0 to 2 min 15 ml, eluent A 2 to 10 min from 55 ml to 31 ml and eluent B from 15 ml to 39 ml, 10 to 12 min 0 ml eluent A and 70 ml eluent B. Eluent C and eluent D constant flow 5 ml/min over the whole runtime). After lyophilization, 77.0 mg (100% purity, 40% yield) of the title compound were obtained.

LC-MS (Method 7): $R_t$=1.69 min; MS (ESIpos): m/z=511 [M+H]$^+$ $^1$H-NMR (600 MHz, DMSO-d6) δ [ppm]: 2.068 (0.57), 2.396 (16.00), 3.842 (0.57), 3.852 (0.65), 3.865 (1.60), 3.874 (1.43), 3.884 (1.51), 3.896 (1.56), 3.907 (0.61), 3.918 (0.58), 7.285 (0.73), 7.291 (0.77), 7.298 (0.85), 7.306 (0.80), 7.535 (2.72), 7.549 (2.93), 7.600 (0.47), 7.614 (0.84), 7.630 (0.86), 7.644 (0.45), 7.793 (3.45), 7.807 (3.11), 8.251 (2.64), 8.771 (0.82), 8.781 (1.58), 8.792 (0.78), 9.069 (5.25).

Example 307

Rac-5,6-Difluoro-N-{[4-(1-Methyl-1H-Pyrazol-3-Yl)-2,5-Dioxoimidazolidin-4-Yl]Methyl}-4'-(Trifluoromethyl)[Biphenyl]-2-Carboxamide

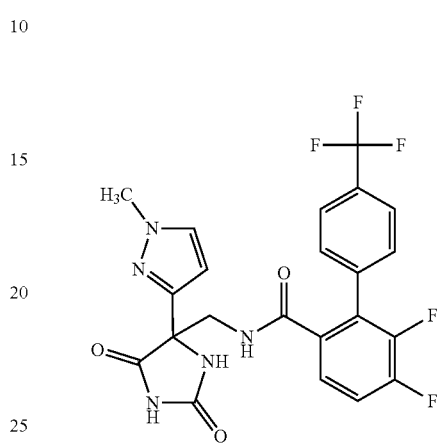

5,6-difluoro-N-[2-(1-methyl-1H-pyrazol-3-yl)-2-oxoethyl]-4'-(trifluoromethyl)[biphenyl]-2-carboxamide (382 mg, 902 µmol) was dissolved in 5.5 ml of ethanol. Ammonium carbonate (867 mg, 9.02 mmol) and potassium cyanide (235 mg, 3.61 mmol), dissolved in 11 ml of water, were added. The vial was sealed and the mixture was stirred at 80° C. over night. The reaction was concentrated in vacuo and extracted between water and ethyl acetate. The combined organic layers were dried over sodium sulfate, filtered and concentrated. The crude product was purified by column chromatography (Machine: Biotage® Isolera One; column: Biotage® SNAP Ultra 25 g; gradient: DCM/MeOH-gradient, 2% MeOH-20% MeOH; flow: 75 ml/min). Product containing samples were united, the solvents were removed on a rotary evaporator and the residue was dried in vacuo. 347 mg (100% purity, 78% yield) of the title compound were obtained.

LC-MS (Method 7): $R_t$=1.59 min; MS (ESIpos): m/z=494 [M+H]$^+$ $^1$H-NMR (400 MHz, DMSO-d6) δ [ppm]: 3.661 (0.70), 3.677 (0.75), 3.696 (1.01), 3.711 (0.94), 3.811 (16.00), 3.835 (1.01), 3.850 (1.07), 3.869 (0.77), 3.884 (0.69), 5.753 (0.46), 6.182 (3.47), 6.188 (3.42), 7.254 (0.61), 7.263 (0.68), 7.266 (0.66), 7.272 (0.79), 7.285 (0.75), 7.545 (2.28), 7.566 (2.74), 7.590 (0.85), 7.614 (0.86), 7.636 (0.47), 7.653 (2.89), 7.659 (2.80), 7.802 (3.09), 7.823 (2.66), 8.183 (2.89), 8.610 (0.67), 8.625 (1.42), 8.640 (0.65), 10.785 (2.18).

Example 308

Ent-5-Methyl-N-{[4-(1-Methyl-1H-Pyrazol-5-Yl)-2,5-Dioxoimidazolidin-4-Yl]Methyl}-4'-(Trifluoromethyl)[Biphenyl]-2-Carboxamide

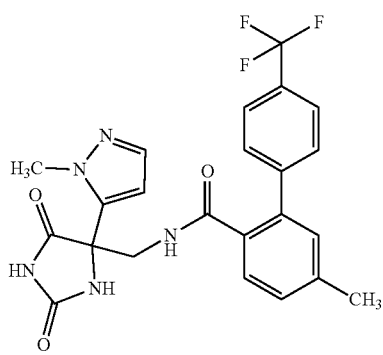 [SMILES: Cc1ccc(C(=O)NCC2(c3ccnn3C)NC(=O)NC2=O)c(-c2ccc(C(F)(F)F)cc2)c1]

5-methyl-4'-(trifluoromethyl)[1,1'-biphenyl]-2-carboxylic acid (114 mg, 407 µmol) dissolved in 2.5 ml DMF was treated with N,N-diisopropylethylamine (350 µl, 2.0 mmol), 1-ethyl-3-(3-dimethylaminopropyl)carbodiimide hydrochloride (101 mg, 529 µmol) and 1-hydroxybenzotriazole hydrate (81.0 mg, 529 µmol) and stirred for 5 min at room temperature before ent-5-(aminomethyl)-5-(1-methyl-1H-pyrazol-5-yl)imidazolidine-2,4-dione hydrochloride (100 mg, 407 µmol) was added. The mixture was stirred at room temperature for 4 h. Purification was done by preparative HPLC (Column: Chromatorex C18 10 µm, 250×30 mm; eluent A=water with 0.1% formic acid, B=acetonitrile; gradient: 0.0 min 30% B, 4.5 min 50% B, 11.5 min 70% B, 12 min 100% B, 14.75 min 30% B; flow: 50 ml/min). Further purification was needed and done by preparative HPLC (Instrument: Waters Prep LC/MS System; column: Phenomenex Kinetex C18 5 µm 100×30 mm; eluent A: water, eluent B: acetonitrile, eluent C: 2% formic acid in water, eluent D: acetonitrile/water (80 Vol. %/20 Vol %); flow: 80 ml/min; room temperature; UV 200-400 nm, At-Column Injektion. Gradient: eluent A 0 to 2 min 63 ml, eluent B 0 to 2 min 7 ml, eluent A 2 to 10 min from 63 ml to 39 ml and eluent B from 7 ml to 31 ml, 10 to 12 min 0 ml eluent A and 70 ml eluent B. Eluent C and eluent D constant flow each 5 ml/min over the whole time). Product containing samples were united, the solvents were evaporated and the residue was lyophylized. 45.0 mg (100% purity, 23% yield) of the title compound were obtained.

LC-MS (Method 7): $R_t$=1.63 min; MS (ESIpos): m/z=472 [M+H]$^+$ $^1$H-NMR (500 MHz, DMSO-d6) δ [ppm]: 2.388 (11.07), 3.790 (16.00), 3.835 (0.75), 3.846 (0.85), 3.862 (1.19), 3.874 (1.05), 3.952 (1.08), 3.966 (1.15), 3.979 (0.79), 3.993 (0.73), 6.464 (3.55), 6.468 (3.56), 7.252 (2.86), 7.276 (1.19), 7.292 (1.82), 7.344 (3.12), 7.360 (1.97), 7.380 (3.73), 7.384 (3.65), 7.488 (2.95), 7.504 (3.26), 7.734 (3.43), 7.751 (3.04), 8.372 (3.53), 8.644 (0.79), 8.657 (1.41), 8.669 (0.78), 11.247 (1.32).

Example 309

Ent-5-(Difluoromethyl)-N-{[4-(1-Methyl-1H-Pyrazol-5-Yl)-2,5-Dioxoimidazolidin-4-Yl]Methyl}-4'-(Trifluoromethyl)[Biphenyl]-2-Carboxamide

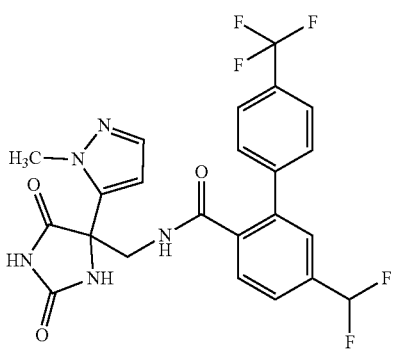 [SMILES: Cn1nccc1C1(CNC(=O)c2ccc(C(F)F)cc2-c2ccc(C(F)(F)F)cc2)NC(=O)NC1=O]

5-(difluoromethyl)-4'-(trifluoromethyl)[1,1'-biphenyl]-2-carboxylic acid (53.0 mg, 168 µmol) dissolved in 1.5 ml DMF was treated with N,N-diisopropylethylamine (150 µl, 840 µmol), 1-ethyl-3-(3-dimethylaminopropyl)carbodiimide hydrochloride (41.8 mg, 218 µmol) and 1-hydroxybenzotriazole hydrate (33.4 mg, 218 µmol) and stirred for 5 min at room temperature before ent-5-(aminomethyl)-5-(1-methyl-1H-pyrazol-5-yl)imidazolidine-2,4-dione hydrochloride (41.2 mg, 168 µmol) was added. The mixture was stirred at room temperature for 4 h. Purification was done by preparative HPLC (column: Chromatorex C18 10 µm, 250×30 mm; eluent A=water with 0.1% formic acid, B=acetonitrile; gradient: 0.0 min 30% B, 4.5 min 50% B, 11.5 min 70% B, 12 min 100% B, 14.75 min 30% B; flow: 50 ml/min). Further purification was needed and done by preparative HPLC (Instrument: Waters Prep LC/MS System; column: Phenomenex Kinetex C18 5 µm 100×30 mm; eluent A: water, eluent B: acetonitrile, eluent C: 2% formic acid in water, eluent D: acetonitrile/water (80 Vol. %/20 Vol %); flow: 80 ml/min; room temperature; UV 200-400 nm, At-Column Injektion. Gradient: eluent A 0 to 2 min 55 ml, eluent B 0 to 2 min 15 ml, eluent A 2 to 10 min from 55 ml to 31 ml and eluent B from 15 ml to 39 ml, 10 to 12 min 0 ml eluent A and 70 ml eluent B. Eluent C and eluent D constant flow each 5 ml/min over the whole time). Product containing samples were united, the solvents were evaporated and the residue was lyophylized. 38.0 mg (100% purity, 45% yield) of the title compound were obtained.

LC-MS (Method 7): $R_t$=1.62 min; MS (ESIpos): m/z=508 [M+H]$^+$ $^1$H-NMR (400 MHz, DMSO-d6) δ [ppm]: 2.072 (0.60), 3.791 (16.00), 3.870 (0.50), 3.885 (0.58), 3.905 (1.41), 3.920 (1.30), 3.934 (1.31), 3.951 (1.35), 3.968 (0.53), 3.985 (0.50), 6.475 (3.44), 6.480 (3.43), 6.986 (1.20), 7.125 (2.52), 7.264 (1.05), 7.384 (3.55), 7.388 (3.44), 7.543 (1.96), 7.563 (5.40), 7.583 (3.58), 7.630 (2.88), 7.690 (1.62), 7.710 (1.27), 7.783 (3.73), 7.803 (3.10), 8.446 (2.67), 8.884 (0.77), 8.900 (1.56), 8.915 (0.75), 11.272 (2.43).

Example 310

Ent-6-Chloro-N-{[4-(1-Methyl-1H-Pyrazol-5-Yl)-2,5-Dioxoimidazolidin-4-Yl]Methyl}-4'-(Trifluoromethyl)[Biphenyl]-2-Carboxamide

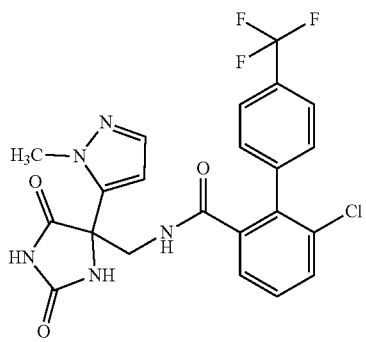 [SMILES: Cn1nccc1C1(CNC(=O)c2cccc(Cl)c2-c2ccc(C(F)(F)F)cc2)NC(=O)NC1=O]

6-chloro-4'-(trifluoromethyl)[1,1'-biphenyl]-2-carboxylicacid (51.0 mg, 170 µmol) dissolved in 1.5 ml DMF was treated with N,N-diisopropylethylamine (150 µl, 850 µmol), 1-ethyl-3-(3-dimethylaminopropyl)carbodiimide hydrochloride (42.3 mg, 221 µmol) and 1-hydroxybenzotriazole hydrate (33.8 mg, 221 µmol) and stirred for 5 min at room temperature before ent-5-(aminomethyl)-5-(1-methyl-1H-pyrazol-5-yl)imidazolidine-2,4-dione hydrochloride (41.7 mg, 170 µmol) was added. The mixture was stirred at room temperature for 4 h. Purification was done by preparative HPLC (column: Chromatorex C18 10 µm, 250×30 mm; eluent A=water with 0.1% formic acid, B=acetonitrile; gradient: 0.0 min 30% B, 4.5 min 50% B, 11.5 min 70% B, 12 min 100% B, 14.75 min 30% B; flow: 50 ml/min). Further purification was needed and done by preparative HPLC (Instrument: Waters Prep LC/MS System; column: Phenomenex Kinetex C18 5 µm 100×30 mm; eluent A: water, eluent B: acetonitrile, eluent C: 2% formic acid in water, eluent D: acetonitrile/water (80 Vol. %/20 Vol %); flow: 80 ml/min; room temperature; UV 200-400 nm, At-Column Injektion. Gradient: eluent A 0 to 2 min 55 ml, eluent B 0 to 2 min 15 ml, eluent A 2 to 10 min from 55 ml to 31 ml and eluent B from 15 ml to 39 ml, 10 to 12 min 0 ml eluent A and 70 ml eluent B. Eluent C and eluent D constant flow each 5 ml/min over the whole time). Product containing samples were united, the solvents were evaporated and the residue was lyophylized. 33.0 mg (100% purity, 40% yield) of the title compound were obtained.

LC-MS (Method 7): $R_t$=1.62 min; MS (ESIpos): m/z=492 [M+H]$^+$ $^1$H-NMR (400 MHz, DMSO-d6) δ [ppm]: 2.072 (0.52), 3.746 (16.00), 3.764 (2.58), 3.781 (2.34), 3.814 (1.30), 6.433 (3.50), 6.438 (3.51), 7.338 (1.73), 7.340 (1.77), 7.356 (5.01), 7.360 (5.03), 7.433 (1.45), 7.451 (1.61), 7.503 (1.72), 7.523 (2.97), 7.542 (1.71), 7.681 (2.09), 7.684 (2.12), 7.701 (1.73), 7.704 (1.63), 7.761 (2.80), 7.781 (2.51), 8.367 (2.62), 8.714 (0.73), 8.730 (1.59), 8.745 (0.74), 11.251 (2.28).

Example 311

Ent-3',4'-Dichloro-N-{[4-(1-Methyl-1H-Pyrazol-5-Yl)-2,5-Dioxoimidazolidin-4-Yl]Methyl}[Biphenyl]-2-Carboxamide

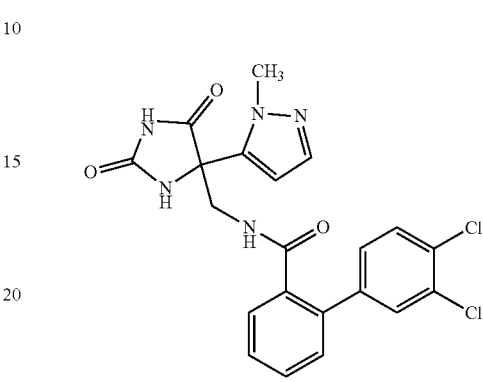

3',4'-dichloro[1,1'-biphenyl]-2-carboxylic acid (109 mg, 407 µmol) dissolved in 2.5 ml DMF was treated with N,N-diisopropylethylamine (350 µl, 2.0 mmol), 1-ethyl-3-(3-dimethylaminopropyl)carbodiimide hydrochloride (101 mg, 529 µmol) and 1-hydroxybenzotriazole hydrate (81.0 mg, 529 µmol) and stirred for 5 min at room temperature before ent-5-(aminomethyl)-5-(1-methyl-1H-pyrazol-5-yl)imidazolidine-2,4-dione hydrochloride (100 mg, 407 µmol) was added. The mixture was stirred at room temperature for 4 h. Purification was done by preparative HPLC (Instrument: Waters Prep LC/MS System; column: Phenomenex Kinetex C18 5 µm 100×30 mm; eluent A: water, eluent B: acetonitrile, eluent C: 2% formic acid in water, eluent D: acetonitrile/water (80 Vol. %/20 Vol %); flow: 80 ml/min; room temperature; UV 200-400 nm, At-Column Injektion. Gradient: eluent A 0 to 2 min 63 ml, eluent B 0 to 2 min 7 ml, eluent A 2 to 10 min from 63 ml to 39 ml and eluent B from 7 ml to 31 ml, 10 to 12 min 0 ml eluent A and 70 ml eluent B. Eluent C and eluent D constant flow each 5 ml/min over the whole time). Product containing samples were united, the solvents were evaporated and the residue was lyophylized. 83.0 mg (99% purity, 44% yield) of the title compound were obtained.

LC-MS (Method 7): $R_t$=1.56 min; MS (ESIpos): m/z=458 [M+H]$^+$ $^1$H-NMR (600 MHz, DMSO-d6) δ [ppm]: 3.791 (16.00), 3.844 (0.74), 3.854 (0.80), 3.866 (1.36), 3.876 (1.24), 3.914 (1.26), 3.925 (1.33), 3.936 (0.74), 3.948 (0.71), 6.460 (3.21), 6.464 (3.22), 7.239 (1.56), 7.242 (1.59), 7.253 (1.63), 7.256 (1.68), 7.374 (3.26), 7.378 (3.33), 7.382 (1.66), 7.395 (2.06), 7.423 (1.74), 7.435 (2.17), 7.456 (0.97), 7.468 (1.91), 7.480 (1.02), 7.526 (1.20), 7.538 (1.71), 7.551 (0.68), 7.604 (3.08), 7.607 (3.04), 7.627 (3.11), 7.641 (2.89), 8.355 (2.62), 8.664 (0.81), 8.674 (1.55), 8.685 (0.80), 11.221 (2.25).

Example 312

Ent-4'-Chloro-3-Fluoro-N-{[4-(1-Methyl-1H-Pyrazol-5-Yl)-2,5-Dioxoimidazolidin-4-Yl]Methyl}[Biphenyl]-2-Carboxamide

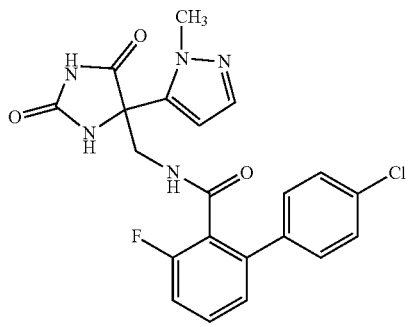 [SMILES: Cn1nccc1C1(CNC(=O)c2c(F)cccc2-c2ccc(Cl)cc2)NC(=O)NC1=O]

4'-chloro-3-fluoro[1,1'-biphenyl]-2-carboxylic acid (102 mg, 407 µmol) dissolved in 2.5 ml DMF was treated with N,N-diisopropylethylamine (350 µl, 2.0 mmol), 1-ethyl-3-(3-dimethylaminopropyl)carbodiimide hydrochloride (101 mg, 529 µmol) and 1-hydroxybenzotriazole hydrate (81.0 mg, 529 µmol) and stirred for 5 min at room temperature before ent-5-(aminomethyl)-5-(1-methyl-1H-pyrazol-5-yl) imidazolidine-2,4-dione hydrochloride (100 mg, 407 µmol) was added. The mixture was stirred at room temperature for 4 h. Purification was done by preparative HPLC (Instrument: Waters Prep LC/MS System; column: Phenomenex Kinetex C18 5 µm 100×30 mm; eluent A: water, eluent B: acetonitrile, eluent C: 2% formic acid in water, eluent D: acetonitrile/water (80 Vol. %/20 Vol %); flow: 80 ml/min; room temperature; UV 200-400 nm, At-Column Injektion. Gradient: eluent A 0 to 2 min 63 ml, eluent B 0 to 2 min 7 ml, eluent A 2 to 10 min from 63 ml to 39 ml and eluent B from 7 ml to 31 ml, 10 to 12 min 0 ml eluent A and 70 ml eluent B. Eluent C and eluent D constant flow each 5 ml/min over the whole time). Product containing samples were united, the solvents were evaporated and the residue was lyophylized. 75.0 mg (100% purity, 41% yield) of the title compound were obtained.

LC-MS (Method 7): $R_t$=1.39 min; MS (ESIpos): m/z=442 [M+H]$^+$ $^1$H-NMR (600 MHz, DMSO-d6) δ [ppm]: 3.788 (16.00), 3.826 (0.83), 3.837 (0.87), 3.849 (1.16), 3.860 (1.08), 3.944 (1.13), 3.954 (1.21), 3.967 (0.87), 3.977 (0.79), 6.421 (3.23), 6.424 (3.21), 7.215 (1.99), 7.228 (2.15), 7.269 (0.90), 7.284 (1.76), 7.298 (1.01), 7.359 (3.20), 7.363 (3.13), 7.392 (3.65), 7.395 (1.26), 7.403 (1.53), 7.406 (5.12), 7.410 (0.64), 7.468 (0.69), 7.471 (5.19), 7.475 (1.43), 7.486 (3.80), 7.500 (0.69), 7.510 (0.79), 7.514 (1.15), 7.524 (1.13), 7.527 (0.70), 7.537 (0.59), 8.309 (3.40), 8.897 (0.75), 8.907 (1.55), 8.917 (0.74), 11.153 (0.68).

Example 313

Ent-4'-Chloro-2'-Fluoro-N-{[4-(1-Methyl-1H-Pyrazol-5-Yl)-2,5-Dioxoimidazolidin-4-Yl]Methyl}[Biphenyl]-2-Carboxamide

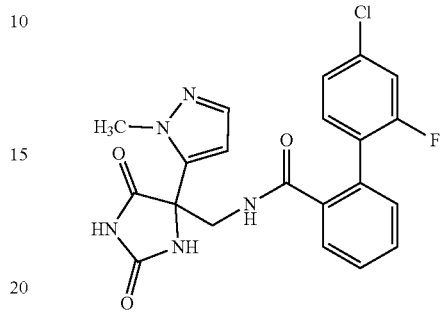

4'-chloro-2'-fluoro[1,1'-biphenyl]-2-carboxylic acid (102 mg, 407 µmol) dissolved in 2.5 ml DMF was treated with N,N-diisopropylethylamine (350 µl, 2.0 mmol), 1-ethyl-3-(3-dimethylaminopropyl)carbodiimide hydrochloride (101 mg, 529 µmol) and 1-hydroxybenzotriazole hydrate (81.0 mg, 529 µmol) and stirred for 5 min at room temperature before ent-5-(aminomethyl)-5-(1-methyl-1H-pyrazol-5-yl) imidazolidine-2,4-dione hydrochloride (100 mg, 407 µmol) was added. The mixture was stirred at room temperature for 4 h. Purification was done by preparative HPLC (Instrument: Waters Prep LC/MS System; column: Phenomenex Kinetex C18 5 µm 100×30 mm; eluent A: water, eluent B: acetonitrile, eluent C: 2% formic acid in water, eluent D: acetonitrile/water (80 Vol. %/20 Vol %); flow: 80 ml/min; room temperature; UV 200-400 nm, At-Column Injektion. Gradient: eluent A 0 to 2 min 63 ml, eluent B 0 to 2 min 7 ml, eluent A 2 to 10 min from 63 ml to 39 ml and eluent B from 7 ml to 31 ml, 10 to 12 min 0 ml eluent A and 70 ml eluent B. Eluent C and eluent D constant flow each 5 ml/min over the whole time). Product containing samples were united, the solvents were evaporated and the residue was lyophylized. 88.0 mg (99% purity, 48% yield) of the title compound were obtained.

LC-MS (Method 7): $R_t$=1.43 min; MS (ESIpos): m/z=442 [M+H]$^+$ $^1$H-NMR (600 MHz, DMSO-d6) δ [ppm]: 3.780 (16.00), 3.829 (0.79), 3.839 (0.88), 3.852 (1.30), 3.861 (1.19), 3.914 (1.20), 3.926 (1.27), 3.937 (0.79), 3.948 (0.75), 6.462 (3.18), 6.466 (3.29), 7.273 (0.72), 7.287 (1.97), 7.299 (2.24), 7.302 (2.86), 7.305 (2.73), 7.316 (0.64), 7.319 (0.80), 7.360 (1.88), 7.371 (4.08), 7.374 (5.22), 7.402 (1.42), 7.405 (1.40), 7.419 (1.43), 7.476 (0.51), 7.485 (4.19), 7.489 (2.64), 7.494 (2.08), 7.507 (0.50), 7.545 (1.05), 7.549 (0.95), 7.558 (1.09), 7.562 (0.93), 7.568 (0.67), 7.572 (0.60), 8.274 (3.31), 8.599 (0.81), 8.610 (1.54), 8.620 (0.80), 11.190 (1.37).

Example 314

Ent-4'-Chloro-2'-Methoxy-N-{[4-(1-Methyl-1H-Pyrazol-5-Yl)-2,5-Dioxoimidazolidin-4-Yl]Methyl}[Biphenyl]-2-Carboxamide

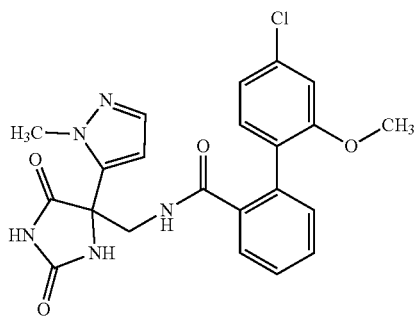 [SMILES: COc1cc(Cl)ccc1-c1ccccc1C(=O)NCC1(c2ccnn2C)NC(=O)NC1=O]

4'-chloro-2'-methoxy[1,1'-biphenyl]-2-carboxylic acid (107 mg, 407 µmol) dissolved in 2.5 ml DMF was treated with N,N-diisopropylethylamine (350 µl, 2.0 mmol), 1-ethyl-3-(3-dimethylaminopropyl)carbodiimide hydrochloride (101 mg, 529 µmol) and 1-hydroxybenzotriazole hydrate (81.0 mg, 529 µmol) and stirred for 5 min at room temperature before ent-5-(aminomethyl)-5-(1-methyl-1H-pyrazol-5-yl)imidazolidine-2,4-dione hydrochloride (100 mg, 407 µmol) was added. The mixture was stirred at room temperature for 4 h. Purification was done by preparative HPLC (Instrument: Waters Prep LC/MS System; column: Phenomenex Kinetex C18 5 µm 100×30 mm; eluent A: water, eluent B: acetonitrile, eluent C: 2% formic add in water, eluent D: acetonitrile/water (80 Vol. %/20 Vol %); flow: 80 ml/min; room temperature; UV 200-400 nm, At-Column Injektion. Gradient: eluent A 0 to 2 min 63 ml, eluent B 0 to 2 min 7 ml, eluent A 2 to 10 min from 63 ml to 39 ml and eluent B from 7 ml to 31 ml, 10 to 12 mi n 0 ml eluent A and 70 ml eluent B. Eluent C and eluent D constant flow each 5 ml/min over the whole time). Product containing samples were united, the solvents were evaporated and the residue was lyophylized. 93.0 mg (98% purity, 49% yield) of the title compound were obtained.

LC-MS (Method 7): $R_t$=1.44 min; MS (ESIpos): m/z=454 [M+H]$^+$ $^1$H-NMR (500 MHz, DMSO-d6) δ [ppm]: 2.071 (0.47), 3.680 (15.36), 3.776 (16.00), 3.822 (0.44), 3.840 (0.59), 3.851 (0.54), 3.907 (0.52), 6.469 (3.38), 6.472 (3.35), 7.016 (1.37), 7.020 (1.62), 7.032 (1.72), 7.036 (2.26), 7.053 (3.52), 7.057 (2.73), 7.124 (3.58), 7.140 (2.65), 7.265 (1.86), 7.280 (2.08), 7.361 (1.04), 7.372 (4.59), 7.375 (5.59), 7.385 (1.51), 7.399 (1.88), 7.414 (0.74), 7.473 (1.11), 7.476 (1.06), 7.488 (1.62), 7.491 (1.56), 7.503 (0.72), 7.506 (0.69), 8.258 (3.62), 8.338 (0.80), 8.351 (1.61), 8.363 (0.79), 11.219 (1.09).

Example 315

Rac-N-{[2,5-Dioxo-4-(1-Phenyl-1H-Pyrazol-5-Yl)Imidazolidin-4-Yl]Methyl}-5,6-Difluoro-4'-(Trifluoromethyl)[Biphenyl]-2-Carboxamide

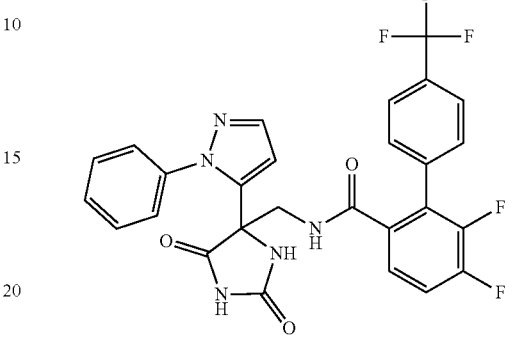

5,6-difluoro-N-[2-oxo-2-(1-phenyl-1H-pyrazol-5-yl)ethyl]-4'-(trifluoromethyl)[biphenyl]-2-carboxamide (444 mg, 66% purity, 604 µmol) was dissolved in 3.8 ml of ethanol. Ammonium carbonate (580 mg, 6.04 mmol) and potassium cyanide (157 mg, 2.41 mmol), dissolved in 7.5 ml of water, were added. The vial was sealed and the mixture was stirred at 80° C. over night. The reaction was concentrated in vacuo and extracted between water and ethyl acetate. The combined organic layers were dried over sodium sulfate, filtered and concentrated. The crude product was purified by preparative HPLC (Instrument: Waters Prep LC/MS System; column: Phenomenex Kinetex C18 5 µm 100×30 mm; eluent A: water, eluent B: acetonitrile, eluent C: 2% formic acid in water, eluent D: acetonitrile/water (80 Vol. %/20 Vol %); flow: 80 ml/min; room temperature; UV 200-400 nm, At-Column Injektion. Gradient: eluent A 0 to 2 min 63 ml, eluent B 0 to 2 min 7 ml, eluent A 2 to 10 min from 63 ml to 39 ml and eluent B from 7 ml to 31 ml, 10 to 12 min 0 ml eluent A and 70 ml eluent B. Eluent C and eluent D constant flow each 5 ml/min over the whole time). Product containing samples were united, the solvents were evaporated and the residue was lyophylized. 26.0 mg (97% purity, 8% yield) of the title compound were obtained.

LC-MS (Method 7): $R_t$=1.70 min; MS (ESIpos): m/z=556 [M+H]$^+$ $^1$H-NMR (600 MHz, DMSO-d6) δ [ppm]: 2.157 (0.49), 2.382 (0.93), 2.421 (1.22), 2.610 (0.82), 2.649 (0.94), 3.248 (1.32), 3.259 (1.46), 3.757 (3.38), 3.767 (3.61), 3.780 (4.82), 3.789 (4.42), 3.907 (4.45), 3.918 (4.71), 3.929 (3.67), 3.941 (3.28), 6.695 (12.80), 6.698 (11.80), 7.214 (3.22), 7.227 (15.38), 7.239 (16.00), 7.391 (1.27), 7.432 (6.32), 7.443 (14.55), 7.456 (10.31), 7.476 (6.41), 7.488 (7.06), 7.501 (2.31), 7.527 (12.00), 7.540 (12.97), 7.563 (4.05), 7.578 (4.14), 7.593 (2.43), 7.605 (13.80), 7.608 (12.11), 7.759 (0.74), 7.786 (13.75), 7.800 (12.66), 7.811 (2.42), 7.825 (1.72), 8.075 (14.38), 8.689 (3.23), 8.700 (6.37), 8.711 (3.38), 10.496 (2.30).

Example 316

Rac-N-{[4-(1,5-Dimethyl-1H-Pyrazol-4-Yl)-2,5-Dioxoimidazolidin-4-Yl]Methyl}-5,6-Difluoro-4'-(Trifluoromethyl)[Biphenyl]-2-Carboxamide

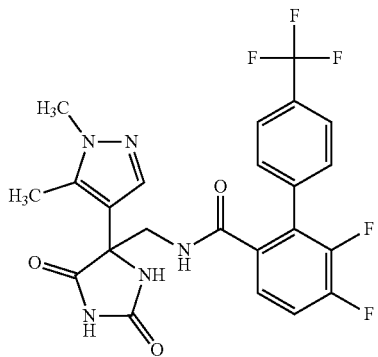 [SMILES: Cc1c(C2(CNC(=O)c3ccc(F)c(F)c3-c3ccc(C(F)(F)F)cc3)NC(=O)NC2=O)cnn1C]

N-[2-(1,5-dimethyl-1H-pyrazol-4-yl)-2-oxoethyl]-5,6-difluoro-4'-(trifluoromethyl)[biphenyl]-2-carboxamide (253 mg, 578 µmol) was dissolved in 4 ml of ethanol. Ammonium carbonate (556 mg, 5.78 mmol) and potassium cyanide (151 mg, 2.31 mmol), dissolved in 8 ml of water, were added. The vial was sealed and the mixture was stirred at 80° C. for 4 d. The reaction was concentrated in vacuo and extracted between water and ethyl acetate. The combined organic layers were dried over sodium sulfate, filtered and concentrated. The crude product was purified by preparative HPLC (column: Chromatorex C18 10 µm, 250×30 mm; eluent A=water with 0.1% formic acid, B=acetonitrile; gradient: 0.0 min 30% B, 4.5 min 50% B, 11.5 min 70% B, 12 min 100% B, 14.75 min 30% B; flow: 50 ml/min). Product containing samples were united, the solvents were evaporated and the residue was lyophylized. 4.00 mg (100% purity, 1% yield) of the title compound were obtained.

LC-MS (Method 7): $R_t$=1.57 min; MS (ESIpos): m/z=508 [M+H]$^+$ $^1$H-NMR (500 MHz, DMSO-d6) δ [ppm]: 2.228 (15.25), 3.658 (0.56), 3.671 (0.66), 3.685 (1.90), 3.693 (16.00), 3.711 (1.39), 3.723 (1.46), 3.739 (0.61), 3.751 (0.52), 7.255 (0.68), 7.263 (0.75), 7.271 (0.82), 7.280 (0.78), 7.351 (5.34), 7.537 (2.57), 7.553 (2.81), 7.587 (0.49), 7.604 (0.88), 7.623 (0.91), 7.640 (0.49), 7.798 (3.37), 7.814 (2.95), 8.172 (2.40), 8.175 (2.35), 8.667 (0.77), 8.680 (1.52), 8.692 (0.75), 10.879 (2.11).

Experimental Section—Evaluation of Pharmacological Activity

Example B1: Production of Human ADAMTS-7

Figure 2A:
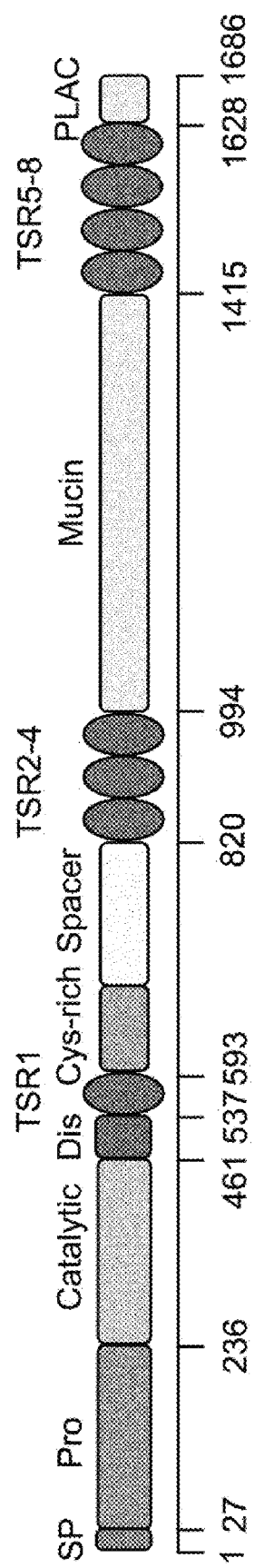

To study the activity of human ADAMTS-7 (hADAMTS-7), the inventors generated multiple constructs for the production of active ADAMTS-7 in E coli cells. These constructs contain the catalytic domain alone or catalytic domain with the Prodomain (Pro), Disintegrin domain (Dis), or TSR1 (FIG. 2 panel A). Different tags such as 6×His, GST, MBP, SUMO or Trigger factor (TF) were incorporated to the N-terminus of the constructs to improve the solubility of the protein and to facilitate protein purification, but none of these constructs produced soluble and active ADAMTS-7 to support further studies. Therefore, we tested catalytic domain containing constructs along with secretion signals in Expi293 mammalian cells. ADAMTS-7 proteins secreted into culture media were captured by affinity column and analyzed by analytical size exclusion column (SEC). A construct containing the secretion signal peptide (SP), Pro and CD domains of hADAMTS-7 (residues 1-537, now referred to as "hPro-hCD" in light of the later discovered hybrids in which the prodomain can be from a non-human species) with an affinity tag at the C-terminus was eluted largely in the void volume from SEC and yielded ~0.2 mg/L of soluble ADAMTS-7 proteins in the elution fractions 3-6 (FIG. 1 panel A). Based on the size and N-terminal sequencing results of the bands on the SDS-page, the soluble ADAMTS-7 is confirmed to be a mixture of amino acid (aa) 28-537 (hPro-hCD, unprocessed ADAMTS-7), aa 237-537 (hCD domain only, furin processed ADAMTS-7), and fragments from Pro. The mixture was dominated by the unprocessed ADAMTS-7, which accounts for ~90% of the population. A construct containing the secretion SP, an affinity/solubility tag and only hADAMTS-7 CD domain (residues 237-537) yielded mostly soluble aggregates (void). Soluble ADAMTS-7 proteins were only detectible by western blot (fractions B8-B12) (FIG. 3 panel A). Another construct that ends at TSR1 (hSP-hPro-hCD-hTSR1, residues 1-593), instead failed to overexpress soluble ADAMTS-7 proteins. Neither SDS-PAGE nor western blot can detect significant ADAMTS-7 proteins (FIG. 3 panel B). In comparison, rat ADAMTS-7 (rADAMTS-7) residues 1-575 (rSP-rPro-rCD-rTSR1) produced~0.6 mg/L soluble proteins (fractions1-6) from Expi293 cells with negligible aggregates (void) eluted from SEC. Purified rat ADAMTS-7 contains ~1:1 molar ratio of unprocessed (aa 25-575) and processed (aa 218-575) ADAMTS-7, and some fragments from Pro (FIG. 1 panel B).

Example B2: Hybrid Molecules to Improve the Production of Soluble hADAMTS-7

To improve the production of hADAMTS-7 protein, we also explored various other options. For example, we compared and analyzed the sequences of rat and human ADAMTS-7 in the Pro and CD domains (FIG. 2 panel B). CD domain sequence is well conserved. The amino acid sequence in the CD domain of rat and human is 84% identical (97% similar), compared to Prodomain which is 70% identical (89% similar). The rest of the sequences are different (i.e., neither identical nor similar) between the two species. Specifically, the CD domain has only 10 different residues between rat and human over 302 residues, while Pro has 22 different ones over 202 residues (FIG. 2 panel B). To test whether rat Pro played a role in facilitating protein folding and yielding more soluble ADAMTS-7 proteins, we designed hybrid molecules of rat SP-Pro (1-217) followed by human CD (237-537), named rPro-hCD (FIG. 1 panel C). The hybrid molecule was purified by Ni affinity column and analyzed by SEC as done to hADAMTS-7 (1-537). Little was eluted as aggregates in the void volume preceding the soluble peak (fractions 2-8). The soluble proteins were analyzed as a mixture of the unprocessed (aa 25-537) and processed (aa 237-537) ADAMTS-7, and Pro (FIG. 1 panel C). The yield of ADAMTS-7 protein after affinity and SEC two-step purification was 2.2 mg/L for rPro-hCD. This is in contrast with ~0.2 mg/L yield of the hPro-hCD, namely hADAMTS-7 (1-537). Our result suggests that the rat Pro is more effective in driving effective folding of the CD domain, therefore improving the yield of the soluble ADAMTS-7 proteins ~10 fold. Therefore, this example demonstrates a solution for the problem of protein solubility as well as for the problem of expression yield, both of which were lower for the fully human construct (hPro-hCD) as compared to the hybrid construct (rPro-hCD).

Example B3: Engineering Furin Cleavage Site to Manipulate the Production Ratio of the Processed and Unprocessed ADAMTS-7

We hypothesized multiple furin cleavage sites in rat Pro (FIG. 4 panel A), one after residue R58 or R60 (RVLR$^{58}$↓KR$^{60}$↓D) of Pro, and another between Pro and CD domains after R217 (RQQR$^{217}$↓S). These cleavage sites were found conserved in rat, mouse and human Pro. Sequential cleavage or processing at these furin sites by cellular furin enzyme leading to a complete removal of the Pro domain from the rest of the protein is likely a necessary step to a fully active or mature ADAMTS-7. Recombinant production of hPro-hCD and rPro-hCD revealed an inefficient furin processing in the mammalian cell culture (FIG. 1 panels A and C). Both constructs yielded a mixture of processed and unprocessed ADAMTS-7. We hypothesized that this could be attributed to a less sufficient amount of endogenous furin produced by mammalian cells or less optimal furin recognition sequence in current ADAMTS-7 constructs. We tested the idea of co-transfection DNAs of rPro-hCD and furin protease into Expi293 cells to coexpress the two proteins. That yielded overexpression of furin in the media but significantly reduced the production of ADAMTS-7 proteins without increasing the ratio of processed versus unprocessed ADAMTS-7. Next, we focused on the optimization of furin recognition site. We introduced mutation Q216K into rPro-hCD to convert $^{214}$RQQR$^{217}$ to $^{214}$RQKR$^{217}$, and named it rPro-hCD-FM2 (SEQ ID No. 2) (FIG. 4 panel A). Q216K mutation significantly increased furin cleavage efficiency of ADAMTS-7 in the same mammalian cell culture compared to the wild type (WT). The ratio of hCD or processed ADAMTS-7 in the raw expression media versus rPro-hCD or unprocessed ADAMTS-7 increased at least 6 fold (FIG. 4 panel B). As a control, a triple mutation R58A/R60A/R217A was introduced into rPro-hCD to silent predicted furin cleavage sites (FIG. 4 panel A). rPro-hCD-3RA completely abolished furin processing and yielded only the unprocessed ADAMTS-7 (FIG. 4 panel B). We conclude that manipulating the sequence of predicted furin recognition site has proved capable of changing the amount of processed and unprocessed of ADAMTS-7 molecules produced in mammalian cell culture. Thus, both the polypeptide of SEQ ID NO: 01 and that of SEQ ID NO: 02 are working solutions for the problems of protein solubility and expression yield, although the polypeptide of SEQ ID NO: 02 achieves a particularly improved ratio for the furin-processed polypeptide.

Example B4: Expression Constructs for Production of Recombinant Hybrid ADAMTS-7 Enzymes The human ADAMTS-7 catalytic domain with the endogenous human prodomain did not yield well folded secreted protein with enzymatic activity. Exchange of the human prodomain with the rat prodomain dramatically increased production of the human catalytic domain from hybrid rat-human constructs. Rat/human ADAMTS-7 chimera sequence (rPro-hCD (Rat 1-217/Human 237-537)-TEV-2Strep-6His, SEQ ID No. 01) encoding rat pro-domain of ADAMTS-7 (amino acids 1-217 of rat sequence UniProt Q1EHB3, which also includes the signal peptide) and catalytic domain of human ADAMTS-7 (amino acids 237-537 of human sequence UniProt Q9UKP4, which also includes a disintegrin domain) followed by TEV cleavage sequence, 2×Strep tag and a His Tag was cloned into the mammalian pcDNA6mycHis (ThermoFischer Scientific) expression vector (or into pcDNA3.4 vector in some embodiments).

Rat/human ADAMTS-7 chimera sequence (rPro-hCD-FM2 (Rat 1-217/Human 237-537 FM2 (Q216K))-TEV-2Strep-6His, SEQ ID No. 02) encoding rat pro-domain of ADAMTS-7 (amino acids 1-217 of rat sequence UniProt Q1EHB3, which also includes the signal peptide) and catalytic domain of human ADAMTS-7 (amino acids 237-537 of human sequence UniProt Q9UKP4, which also includes a disintegrin domain) followed by TEV cleavage sequence, 2×Strep tag and a His Tag was cloned into the mammalian pcDNA6mycHis (ThermoFischer Scientific) expression vector (or into pcDNA3.4 vector in some embodiments). SEQ ID No. 02 contains an additional mutation Glutamine 216 to Lysine within the rat pro-domain sequence (RQQR2171↓S to RQKR2171↓S), which improved cleavage by Furin for zymogen processing.

These expression constructs allow production of recombinant ADAMTS-7 enzyme—either containing at least parts of both domains (e.g., prodomain plus catalytic domain as encoded, in which the prodomain can optionally be preceded by a signal peptide and/or the catalytic domain can optionally be followed by a disintegrin domain) or containing primarily the catalytic domain (e.g., catalytic domain as encoded, for example as generated after furin cleavage between the prodomain and the catalytic domain, which catalytic domain can optionally be followed by a disintegrin domain).

Example B5 Recombinant Production of Active ADAMTS-7 Enzyme

Expi293 cells (A14635, ThermoFischer Scientific) were grown and transfected in accordance to the manufacturer instruction. In brief, at the final cell density of 2.5×10$^6$ cells/mL with >95% viability Expi 293 cells were transfected with 1 mg/liter of vector plasmid DNA as generated according to example 4 using Expifectamine transfection reagent (Thermo Fischer Scientific).

Approximately 96 hours post transfection, Expi293 cell culture was centrifuged at 4000 rpm (~3700 rcf) for 10 mins, and supernatant was collected. Supernatant was neutralized with 50 mM Tris pH8.0, 5 mM CaCl$_2$, 10 uM ZnCl$_2$ and 5 mM imidazole pH 8.0 and filtered through 0.22 μm filter.

The filtered supernatant was loaded on Ni-NTA column (GE healthcare #17-3712-06), equilibrated with buffer A (50 mM Tris pH 8.0, 300 mM NaCl, 10% glycerol, 5 mM CaCl$_2$, 10 μM ZnCl2 and 5 mM Imidazole (pH 8.0)) on Acta FPLC system. The column was washed with 20 volumes of buffer A and the bound proteins were eluted by linear gradient of 20 column volumes up to 100% buffer B (50 mM Tris pH 8.0, 300 mM NaCl, 10% glycerol, 5 mM CaCl2, 10 μM ZnCl2 and 500 mM Imidazole (pH 8.0)). The collected fractions were analyzed on the SDS gel and the fractions containing ADAMTS-7 protein were combined and concentrated 10 times.

The concentrated material from the Ni-NTA purification was loaded onto superdex S200 (SEC) column equilibrated in column buffer: 50 mM Tris pH 8.0, 300 mM NaCl, 10% glycerol, 5 mM CaCl2 and 10 μM ZnCl2. The collected fractions were analyzed on the SDS gel and the fractions containing ADAMTS-7 protein were combined and concentrated 10 times.

The concentrated material from the Ni-NTA purification was loaded onto superdex S200 (SEC) column equilibrated in column buffer: 50 mM Tris pH 8.0, 300 mM NaCl, 10% glycerol, 5 mM $CaCl_2$ and 10 µM $ZnCl_2$. The collected fractions were analyzed on the SDS gel and the fractions containing ADAMTS-7 protein were combined.

Combined S200 fractions were loaded to strep-tactin column (Qiagen #1057981) equilibrated in Buffer A (50 mM Tris 8.0, 300 mM NaCl, 10% glycerol, 5 mM $CaCl_2$, 10 µM $ZnCl_2$). The column was washed with 20 column volumes of the buffer A and the bound proteins were eluted by linear gradient of 20 column volumes up to 100% buffer B (50 mM Tris 8.0, 300 mM NaCl, 10% glycerol, 5 mM $CaCl_2$, 10 uM $ZnCl_2$ and 2.5 mM D-desthiobiotin). The collected fractions were analyzed on the SDS gel and the fractions containing ADAMTS-7 protein were combined. Combined fractions were dialysed overnight at +4° C. against the storage buffer (20 mM Tris pH 8.0, 300 mM NaCl, 10% glycerol, 5 mM CaCl2 and 10 µM $ZnCl_2$).

Dialyzed protein was concentrated to 1 mg/ml, aliquoted, flash frozen in dry ice/ethanol and stored at −80° C. The final yield of purified ADAMTS-7 was 0.5-1 mg per liter of Expi293 cell culture.

In some embodiments, the produced polypeptide is further processed (e.g., by TEV protease) to remove some of the parts C-terminal to the catalytic domain.

Example B6: Identification of ADAMTS-7 Substrates and Cleavage Assay Development Based on the interaction mapping data and the apparent fragment size in reducing and non-reducing conditions, the results were consistent with a ADAMTS-7 cleavage site near the second EGF repeat of COMP, however the substrate cleavage site has not been defined.

Figure 7B:
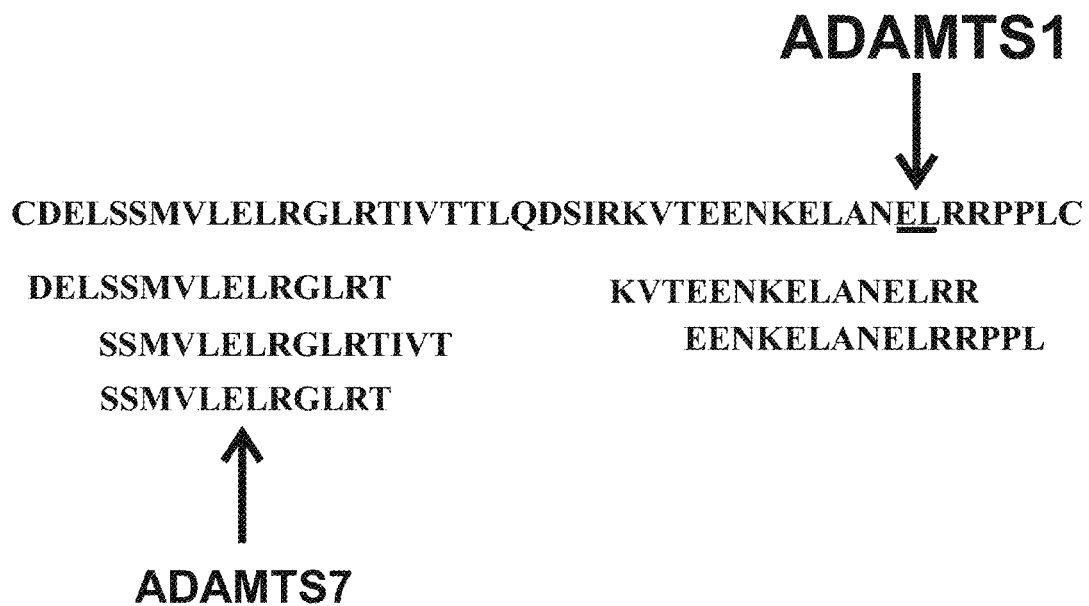

In an attempt to identify ADAMTS-7 substrate cleavage sites, we scanned the potential regions of COMP and TSP1 to identify ADAMTS consensus sites and generated a series of internally-quenched fluorescently-labeled peptides for use with our purified ADAMTS-7 enzyme (FIG. 7). Since ADAMTS-7 was reported to produce the 100 kDA COMP fragment resolvable on a gel under reducing and non-reducing conditions, we hypothesized that cleavage site would not be internal to a disulfide bond. Given the 1-3, 2-4, 5-6 ensemble of disulfide bonds within the EGF repeats, only the E152↓A153 site between the 4$^{th}$ and 5$^{th}$ cysteines committed to separate disulfide bonds was considered, which we attempted to emulate using acetamidomethyl (Acm) modified cysteines in the COMP candidate peptide (See FIG. 7) A second peptide from COMP (amino acids 73-84 GMQQ↓SVRTGLPS) was chosen based on observed ADAMTS cleavage of full-length COMP identified by N-terminal sequencing (data not shown). TSP1 contained a potential E↓LRG upstream from the ADAMTS1 cleavage site at E311↓L312. We chose to analyze this portion of TSP1 using a series of overlapping peptides. The COMP and TSP1 candidate regions contained a modified rhodamine AF488 dye coupled to the N-terminus and a local acceptor QXL520 quencher at the C-terminus that prevents fluorescence in the uncleaved configuration (FIG. 7). Following endopeptidic cleavage, the quencher is released to allow fluorescence signal detection from the substrate's amino terminus. Purified recombinant ADAMTS-7 (as of SEQ ID No. 01 or SEQ ID No. 02) and purified recombinant rADAMTS-7 (rat ADAMTS-7 residues 1-575 with a carboxyl terminal Flag, SEQ ID No. 03) were used to identify substrates from the TSP1 and COMP candidate peptides. ADAMTS-7 was diluted in reaction buffer (20 mM HEPES pH 8.0, 150 mM NaCl, 5 mM $CaCl_2$, 0.004% Brij, 10 µM $ZnCl_2$) for a concentration of approximately 100 nM and pre-incubated for 2 hr at room temperature prior to reaction start with 10 µM candidate peptide substrates. There were some differences between optimized buffer data and reported 2 mM $Zn^{2+}$ buffer data (Liu 2006 FASEB J); for example, the published amount of Zinc in assay buffer caused the purified ADAMTS-7 proteins to precipitate. Candidate FRET substrates based on SEQ ID No. 04 to 10 were generated through custom synthesis by Anaspec-AnaSpec, EGT (34801 Campus Drive, Fremont, CA 94555, USA); as explained by the manufacturer; AnaSpec, EGT Group's pH insensitive HiLyte™ Fluor dyes are a series of fluorescent labeling dyes with fluorescence emissions that span the full visible and near infrared spectrum. HiLyte™ Fluor dyes and AnaSpec's proprietary quenchers QXL™ have been used as fluorophore and quencher pairs for fluorescence resonance energy transfer (FRET) in our examples) in the reaction buffer. Activity data plotted as Relative Fluorescence Units overtime and as a calculated rate (RFU/min) are shown in FIG. 8. Significant activity was not observed with substrates in buffer alone (FIG. 8) or with incubation with purified ADAMTS-7 E389Q catalytic inactive proteins (data not shown).

ADAMTS-7 human catalytic domain constructs rPro-hCD hybrid (SEQ ID No. 01) and optimized furin site construct FM2 (SEQ ID No. 02) demonstrated the greatest specificity for the TSP1 S1 (amino acids 275-289: DELSSMVLELRGLRT, SEQ ID No. 04). ADAMTS-7 human catalytic domain constructs also cleaved the overlapping TSP1 S2 substrate (amino acids 278-292: SSMVLELRGLRTIVT, SEQ ID No. 05). Substrates S1 and S2 are overlapping at candidate site to E289↓L290 (FIG. 7). Cleavage at this site was confirmed by mass spec using an unlabeled peptide (data not shown). No significant activity was detected at the defined ADAMTS1 cleavage site E311↓L312 from TSP1 S3 (amino acids 300-314: KVTEENKELANERR, SEQ ID No. 06) or TSP1 S4 (amino acids 303-317 EENKELANERRPPL, SEQ ID No. 07). This suggests that the ADAMTS-7 substrate is distinct from ADAMTS1. To confirm the TSP1 E289↓L290 substrate site, a minimum overlap between the S1 and S2 peptides was tested as TSP1 S5 substrate (amino acids 278-289: SSMVLELRGLRT, SEQ ID No. 08). Activity was observed for the S5 substrate with ADAMTS-7 human catalytic domain constructs compared to buffer alone, however the removal of the amino DEL sequence greatly reduced the signal for activity compared to the S1 substrate DELSSMVLELRGLRT, SEQ ID No. 04. No activity was observed with COMP candidate peptides COMP1 amino acids 73-84: GMQQSVRTGLPS, SEQ ID No. 09 or COMP2 amino acids 146-159: SPGFRCEACPPGYS, SEQ ID No. 10.

Activity data from the rat ADAMTS-7 construct identified TSP1 S1 (SEQ ID No. 04) as the preferred substrate, along with S2 and S5 peptides containing the E2891L290 cleavage site (FIG. 8). S1 relative fluorescence signal was not as strong for rat ADAMTS-7 compared to the ADAMTS-7 human catalytic domain constructs, resulting in a lower ratio of S1 to S2 activity. TSP1 S2 substrate (SSMVLELR-GLRTIVT, SEQ ID No. 05) presented limited solubility compared to the preferred TSP1 S1 substrate (DELSSMVLELRGLRT, SEQ ID No. 04), potentially due to the additional hydrophobic residues at the carboxyl terminal side (data not shown). To further improve solubility of the S1 peptide, which contained a number of internal hydrophobic residues, modified versions of the S1 peptide ending in -K(QXL520)-NH2 were generated to include an additional hydrophilic moiety: -K(QXL520)-E-NH2 (SEQ ID No. 11), -K(QXL520)-K-NH2 (SEQ ID No. 12) and -K(QXL520)-OH (SEQ ID No. 13). Activity profiles for these substrates were not significantly affected, however the substrate solubility profile was improved with the additional carboxyl glutamic acid (i.e., a glutamic acid that has been conjugated at a carboxyl position on the peptide) added after the QXL520 quencher for SEQ ID No. 11 (data not shown).

Example B7 Assay for ADAMTS-7 Enzymatic Activity and Testing of Inhibitory Compounds Purified recombinant ADAMTS-7 (as of SEQ ID No. 01 or SEQ ID No. 02) was diluted in reaction buffer (20 mM HEPES pH 8.0, 150 mM NaCl, 5 mM $CaCl_2$, 0.004% Brij, 10 μM ZnCl2) fora concentration of approximately 20 nM. 25 μl of the solution were transferred into each well of a 384-well white microtiter plate (Greiner Bio-One 781075) and 1 μl test compound solution (modulator/inhibitor dissolved in DMSO, at the corresponding concentration) or pure DMSO as a control were added per well. The enzymatic reaction was initiated by addition of 25 μl of a 1 μM solution of the FRET substrate, HiLyteFluor-488 DELSSMVLELR-GLRT-K(QXL520)-E-NH2; (SEQ ID No. 11, custom synthesis by Anaspec) in the reaction buffer. Amino acids DELSSMVLELRGLRT are derived from Thrombospondin-1 sequence (275-289). An additional carboxyl glutamic acid was added after the QXL520 quencher to increase substrate solubility. The microtiter plate was incubated for 120 min at the temperature of 32° C. The increase of fluorescence intensity was measured in appropriate fluorescence plate reader (e.g. TECAN Ultra) using excitation wavelength of 485 nm and emission wavelength of 520 nm. IC50 values were calculated from percentage of inhibition of ADAMTS-7 activity as a function of test compound concentration. IC50 values derived using functional ADAMTS-7 according to SEQ ID No. 01 or SEQ ID No. 02, respectively, were not distinguishable, both laying within the experimental error.

Example B8: Expression Constructs for Production of Recombinant ADAMTS-12 Enzymes Rat/human ADAMTS-12 chimera sequence (rPro-hCD (Rat 1-244/Human 241-543)-3×FLAG, SEQ ID 15) encoding rat pro-domain of ADAMTS-12 (amino acids 1-244 of rat sequence UniProt D3ZTJ3, which also includes the signal peptide) and catalytic domain of human ADAMTS-12 (amino acids 241-543 of human sequence UniProt P58397, which also includes a disintegrin domain) followed by 3×FLAG Tag was cloned into the mammalian pcDNA3.4 expression vector.

Figure 6:
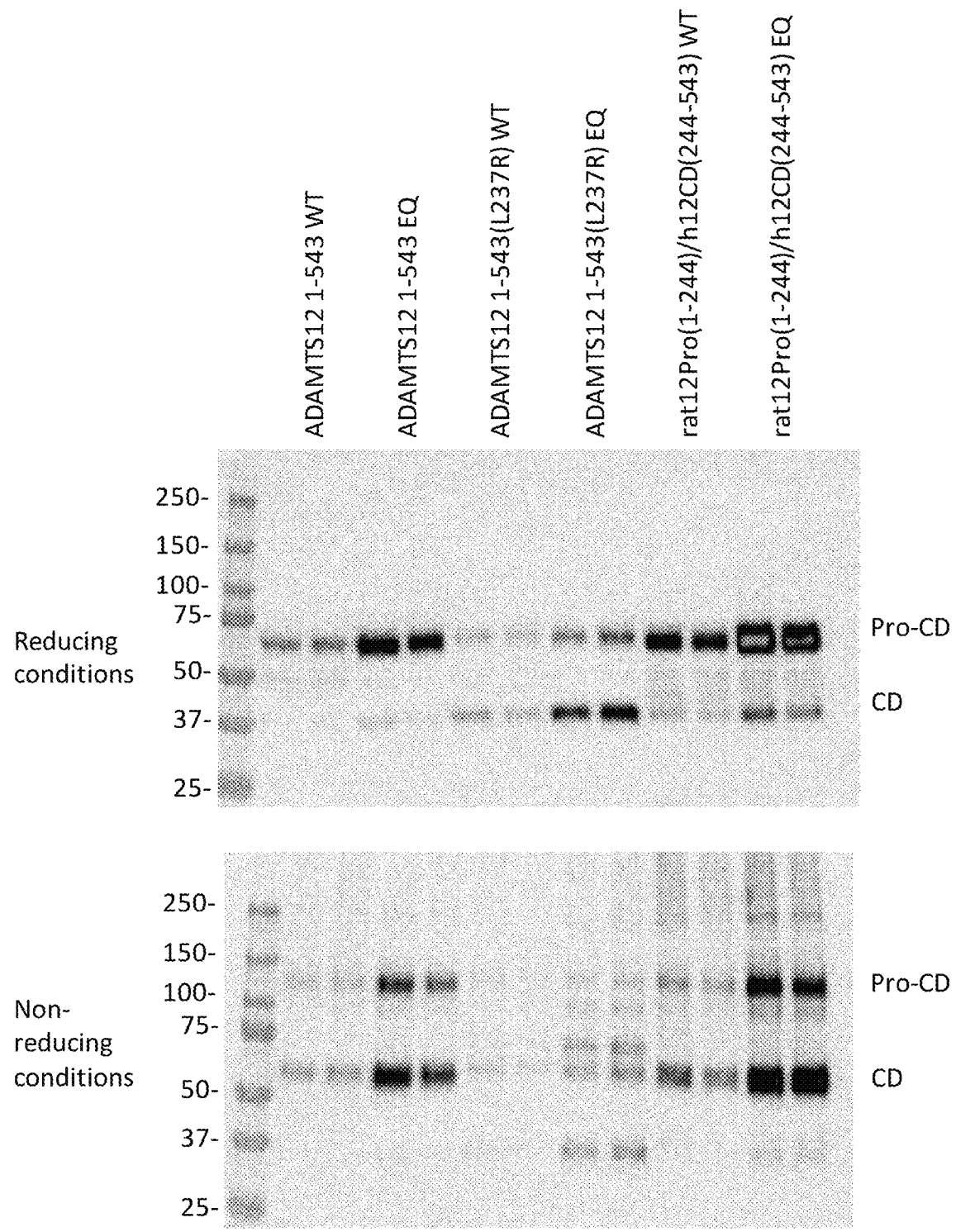
FIG. 6 shows that ADAMTS-12 expression is improved when rat prodomain is used. The first gel was run under non-reducing conditions, whereas the second gel was run under reducing conditions. E393Q substitution (EQ) resulted in increased protein yield. Mutation numbering E393Q follows the species based positions for the human ADAMTS12 region of the construct, i.e. rat ADAMTS12 SP-Pro (1-244) followed by human ADAMTS12 CD (241-544).

Rat/human ADAMTS-12 WT demonstrated a better expression profile compared to human ADAMTS-12 (1-543) WT with a human prodomain (FIG. 6). Optimization of the furin cleavage site (L237R) in the context of the human prodomain did not improve the yield of processed CD proteins compared to the rat/human ADAMTS-12 construct. Each ADAMTS-12 construct was mutated in parallel at the catalytic site with an E393Q substitution (EQ) resulting in increased protein yield similar to ADAMTS-7 catalytic mutations. Corresponding yield for the rat/human ADAMTS-12 EQ construct was also higher compared to ADAMTS-12 (1-543) EQ containing the human prodomain.

This expression construct allows production of recombinant ADAMTS-12 enzymes—either containing at least parts of both domains (e.g., prodomain plus catalytic domain as encoded, in which the prodomain can optionally be preceded by a signal peptide and/or the catalytic domain can optionally be followed by a disintegrin domain) or containing primarily the catalytic domain (e.g., catalytic domain as encoded, which can optionally be followed by a disintegrin domain).

Example B9: Recombinant Production of Active ADAMTS-12 Enzyme

Expi293 cells (Life technologies, A14635) were grown and transfected in accordance to the manufacturer instruction. Briefly, the Expi 293 cells at the final cell density of $2.5 \times 10^6$ cells/mL with >95% viability were transfected by the 1 mg/liter of vector plasmid DNA using Expifectamine transfection reagent (Life technologies, A14525). The overall purification scheme was similar to that used for rat ADAMTS-7 (SEQ ID NO: 03).

Approximately 72 hours post transfection, Expi293 cell culture was centrifuged at 4000 rpm (~3700 rcf) for 10 mins. Supernatant was collected and neutralized with 50 mM Tris pH 8.0, 5 mM $CaCl_2$, 10 μM $ZnCl_2$ before centrifuged again at 4000 rpm (~3700 rcf) for 10 min. Final supernatant was filtered through 0.22 μm filter.

The filtered supernatant was incubated overnight at 4° C. with anti-FLAG M2 affinity gel (Sigma-Aldrich A2220) equilibrated with buffer A (50 mM Tris pH 8.0, 300 mM NaCl, 10% glycerol, 5 mM CaCl2, 10 μM ZnCl2). The gel was collected and washed with 10 bed volumes of buffer A. The bound proteins were eluted by 100% buffer B (50 mM Tris pH 8.0, 300 mM NaCl, 10% glycerol, 5 mM $CaCl_2$, 10 μM ZnCl2, 150 ng/μl FLAG peptide (Sigma-Aldrich F4799)). The collected fractions were analyzed on the SDS gel. The fractions containing ADAMTS-12 protein were combined and concentrated 10 times.

The concentrated material from the FLAG affinity purification was loaded onto superdex S200 (SEC) column equilibrated in column buffer 20 mM Tris pH 8.0, 300 mM NaCl, 10% glycerol, 5 mM $CaCl_2$ and 10 μM $ZnCl_2$. The collected fractions were analyzed on the SDS gel. Fractions containing ADAMTS-12 protein were combined and concentrated to 0.5 mg/ml. Aliquoted proteins were flash frozen in liquid nitrogen and stored at −80° C.

Example B10: Assay for ADAMTS-12 Enzymatic Activity and Testing of Inhibitory Compounds Purified recombinant ADAMTS-12 was diluted in the reaction buffer (20 mM HEPES pH 8.0; 10 mM NaCl; 7.5 mM CaCl2; 0.004% Brij; 7.5 μM ZnCl2; 0.1% SmartBlock (Candor Bioscience 113125)) to the concentration of approximately 20 nM and 25 μl were transferred into each single well of 384-well white microtiter plate (Greiner Bio One 781075). 1 μl of the inhibitor compound solution (dissolved in DMSO, at the corresponding concentration) or pure DMSO as a control was added to the same wells. The enzymatic reaction was initiated by addition of 25 μl of 2 μM solution of the FRET substrate HiLyte Fluor488-DELSSMVLELRGLRT-K(QXL520)E-NH2; (cf. SEQ ID No. 11) in the reaction buffer. It was surprisingly found that the same substrate could be used for the paralogs ADAMTS-7 and ADAMTS-12. The microtiter plate was incubated for 120 min at the temperature of 32° C. The increase of fluorescence intensity was measured in appropriate fluorescence plate reader (e.g. TECAN Ultra) using excitation wavelength of 485 nm and emission wavelength of 520 nm. IC50 values were calculated from percentage of inhibition of ADAMTS-12 activity as a function of test compound concentration.

Example B11: Selectivity Assay for ADAMTS-7 and/or ADAMTS-12 Modulators

The respective enzyme (see table 2 below) was diluted in reaction buffer (50 mM Tris, 2.5 µM $ZnCl_2$, 0.05% BSA, 0.001% Brij, pH 7.5 for ADAM17; 50 mM Tris 7.5, 150 mM NaCl, 10 mM $CaCl_2$, 0.05% Brij for all other enzymes) to the respective concentration and 25 µl were transferred into each well of a 384-well white microtiter plate (Greiner Bio One 781075). 1 µl test compound solution (dissolved in DMSO, at the corresponding concentration) or pure DMSO as a control was added per well. The enzymatic reaction was initiated by addition of 25 µl of the respective concentration of the respective FRET substrate (see table 2 below) in reaction buffer.

The microtiter plate was incubated for 120 min at the temperature of 32° C. The increase of fluorescence intensity was measured in appropriate fluorescence plate reader (e.g. TECAN Ultra) using the respective wavelengths for excitation and emission. IC50 values were calculated from percentage of inhibition of enzyme activity as a function of test compound concentration.

TABLE 2

Assay conditions for the evaluation of the selectivity of ADAMTS-7 modulators.

| Enzyme | Source Enzyme | Conc. Enzyme | FRET substrate | Conc. Substrate | Source Substrate | Excitation Wavelength | Emission Wavelength |
|---|---|---|---|---|---|---|---|
| ADAMTS4 | R&D 4307-AD | 50 nM | Dabcyl-EEVKAKVQPY-Glu(Edans)-NH2 (cf. SEQ ID No. 14) | 1 µM | Jerini Peptide Technologies | 340 nm | 480 nm |
| ADAMTS5 | R&D 2198-AD | 100 nM | Dabcyl-EEVKAKVQPY-Glu(Edans)-NH2 (cf. SEQ ID No. 14) | 25 µM | Jerini Peptide Technologies | 340 nm | 480 nm |
| MMP12 | R&D 917-MPB, activated according to manufacturers instruction | 1 nM | Mca-PLGLEEA-Dap(Dnp)-NH2 (cf. SEQ ID No. 17) | 10 µM | Bachem M-2670 | 325 nm | 393 nm |
| MMP15 | R&D 916-MP, activated according to manufacturers instruction | 6 nM | Mca-KPLGL-Dpa-AR-NH2 (cf. SEQ ID No. 18) (Neumann, U. et al., 2004, Anal. Biochem. 328: 166-173) | 20 µM | R&D ES010 | 320 nm | 405 nm |
| MMP2 | R&D 902-MP, activated according to manufacturers instruction | 0.06 nM | Mca-PLGL -Dpa-AR-NH2 (cf. SEQ ID No. 19) | 20 µM | R&D ES001 | 320 nm | 405 nm |
| ADAM17 | R&D 930-ADB | 20 nM | Mca-PLAQAV-Dap(Dnp)-RSSSR-NH2 (cf. SEQ ID No. 20) | 20 µM | Bachem M-2255 | 320 nm | 405 nm |

Abbreviations: Dabcyl: e.g. Dabcyl quencher in 3-DAB form N-[4-(4-dimethylamino)phenylazo]benzoic acid; Glu(Edans): e.g. EDANS fluor (5-((2-Aminoethyl)amino)naphthalene-1-sulfonic acid) at modified Glutamic acid; Mca: (7-Methoxycoumarin-4-yl)acetyl; Dap(Dnp): e.g. N-beta-(2,4-dinitrophenyl)-L-2,3-diaminopropionic acid; Dpa: N-3-(2, 4-Dinitrophenyl)-L-2,3-diaminopropionyl.

TABLE 3

| Example Number | ADAMTS7-IC50 [mol/l] | ADAMTS4-IC50 [mol/l] |
|---|---|---|
| 1 | 1.10E-8 | 6.50E-6 |
| 2 | 8.70E-7 | >5.00E-5 |
| 3 | 4.30E-9 | 4.80E-6 |
| 4 | 7.35E-8 | 1.90E-5 |
| 5 | 7.80E-8 | 1.20E-5 |
| 6 | 5.40E-8 | 6.20E-6 |
| 7 | 1.50E-8 | 3.70E-6 |
| 8 | 1.85E-8 | 3.80E-6 |
| 9 | 4.30E-8 | 4.80E-6 |
| 10 | 5.70E-8 | 8.90E-6 |
| 11 | 9.10E-8 | 5.90E-6 |
| 12 | 2.50E-7 | >5.00E-5 |
| 13 | 1.90E-7 | >5.00E-5 |
| 14 | 6.60E-8 | 1.70E-5 |
| 15 | 1.80E-7 | 7.75E-6 |
| 16 | 4.15E-9 | 3.50E-6 |
| 17 | 9.35E-9 | 7.10E-6 |
| 18 | 6.30E-7 | 4.10E-5 |
| 19 | 9.80E-7 | >5.00E-5 |
| 20 | 2.90E-7 | 2.80E-5 |
| 21 | 8.70E-8 | >5.00E-5 |
| 22 | 4.50E-8 | 3.90E-6 |
| 23 | 3.20E-8 | 1.25E-5 |
| 24 | 3.90E-7 | >5.00E-5 |
| 25 | 4.60E-8 | >5.00E-5 |
| 26 | 3.90E-8 | >5.00E-5 |
| 27 | 2.20E-8 | 9.10E-6 |
| 28 | 6.00E-8 | 1.10E-5 |
| 29 | 3.80E-7 | >5.00E-5 |
| 30 | 1.60E-7 | 4.50E-5 |
| 31 | 4.55E-8 | 6.50E-6 |
| 32 | 1.30E-7 | 3.50E-5 |
| 33 | 1.70E-8 | 5.20E-6 |
| 34 | 3.60E-7 | 8.90E-6 |
| 35 | 1.40E-7 | 1.00E-5 |
| 36 | 1.20E-7 | >5.00E-5 |
| 37 | 8.90E-8 | 8.70E-6 |
| 38 | 7.10E-8 | 2.10E-5 |
| 39 | 8.50E-8 | 1.00E-5 |
| 40 | 7.20E-8 | 2.10E-5 |
| 41 | 2.30E-7 | 3.00E-5 |

TABLE 3-continued

| Example Number | ADAMTS7-IC50 [mol/l] | ADAMTS4-IC50 [mol/l] |
|---|---|---|
| 42 | 2.30E−7 | >5.00E−5 |
| 43 | 2.50E−7 | 2.80E−5 |
| 44 | 5.80E−8 | 1.10E−5 |
| 46 | 1.63E−8 | 4.80E−6 |
| 47 | 5.65E−8 | 4.15E−6 |
| 48 | 1.50E−7 | >5.00E−5 |
| 49 | 2.10E−7 | 2.20E−5 |
| 50 | 2.50E−7 | 4.30E−5 |
| 51 | 2.90E−7 | 2.50E−5 |
| 52 | 3.40E−7 | 1.90E−5 |
| 53 | 3.70E−7 | 4.10E−5 |
| 54 | 4.40E−7 | 3.20E−5 |
| 55 | 6.80E−7 | 3.00E−5 |
| 56 | 8.50E−7 | 3.10E−5 |
| 57 | 9.50E−7 | >5.00E−5 |
| 58 | 8.50E−7 | >5.00E−5 |
| 59 | 2.70E−7 | 2.30E−5 |
| 60 | 2.10E−7 | 1.50E−5 |
| 61 | 1.20E−7 | 7.40E−6 |
| 62 | 8.70E−8 | 2.60E−5 |
| 63 | 3.50E−8 | 1.30E−5 |
| 64 | 1.40E−7 | 1.20E−5 |
| 65 | 1.80E−7 | 2.00E−5 |
| 66 | 2.27E−8 | 8.20E−6 |
| 68 | 9.10E−8 | 1.10E−5 |
| 69 | 8.80E−9 | 4.90E−6 |
| 70 | 3.40E−8 | 4.50E−6 |
| 71 | 2.43E−8 | 1.63E−5 |
| 72 | 5.40E−8 | 6.90E−6 |
| 73 | 1.10E−7 | 2.00E−5 |
| 74 | 3.50E−7 | 5.20E−6 |
| 75 | 1.30E−7 | 1.00E−5 |
| 76 | 2.15E−7 | 1.40E−5 |
| 77 | 1.20E−6 | 4.00E−5 |
| 78 | 3.60E−7 | 1.40E−5 |
| 79 | 6.60E−9 | 2.10E−6 |
| 80 | 1.75E−8 | 5.73E−6 |
| 81 | 2.10E−7 | >5.00E−5 |
| 82 | 3.60E−7 | >5.00E−5 |
| 83 | 6.00E−7 | 3.60E−5 |
| 84 | 8.70E−7 | 5.00E−5 |
| 85 | 2.80E−8 | 1.30E−5 |
| 86 | 3.20E−8 | 7.60E−6 |
| 87 | 7.60E−8 | 6.90E−6 |
| 88 | 1.30E−7 | 9.10E−6 |
| 89 | 9.10E−8 | 7.60E−6 |
| 90 | 7.10E−7 | 5.00E−5 |
| 91 | 2.30E−7 | 3.00E−5 |
| 92 | 4.50E−8 | 1.90E−5 |
| 93 | 1.30E−8 | 3.40E−6 |
| 94 | 5.20E−8 | 5.40E−6 |
| 95 | 1.10E−6 | >5.00E−5 |
| 96 | 3.20E−7 | 4.60E−5 |
| 97 | 6.60E−8 | 7.20E−6 |
| 98 | 6.00E−8 | 2.10E−5 |
| 99 | 4.40E−8 | 4.50E−6 |
| 100 | 4.50E−8 | 8.10E−6 |
| 101 | 5.50E−8 | 3.20E−6 |
| 102 | 5.50E−8 | 6.60E−6 |
| 103 | 5.90E−8 | 7.10E−6 |
| 104 | 6.30E−8 | 8.70E−6 |
| 105 | 6.60E−8 | 4.90E−6 |
| 106 | 6.60E−8 | 5.40E−6 |
| 107 | 6.60E−8 | 6.20E−6 |
| 108 | 6.60E−8 | 1.90E−5 |
| 109 | 7.10E−8 | 8.70E−6 |
| 110 | 7.20E−8 | 7.90E−6 |
| 111 | 7.40E−8 | 7.90E−6 |
| 112 | 8.10E−8 | 2.20E−6 |
| 113 | 8.30E−8 | 1.20E−5 |
| 114 | 9.85E−8 | 1.02E−5 |
| 115 | 8.90E−8 | 7.80E−6 |
| 116 | 9.10E−8 | 1.20E−5 |
| 117 | 9.30E−8 | 6.10E−5 |
| 118 | 1.00E−7 | 7.60E−6 |
| 119 | 1.00E−7 | 9.10E−6 |
| 120 | 1.00E−7 | 3.50E−5 |
| 121 | 1.20E−7 | 5.90E−6 |
| 122 | 1.20E−7 | 7.90E−6 |
| 123 | 1.20E−7 | 1.90E−5 |
| 124 | 1.20E−7 | 4.20E−5 |
| 125 | 1.30E−7 | 8.70E−6 |
| 126 | 1.30E−7 | 1.10E−5 |
| 127 | 1.90E−7 | 1.30E−5 |
| 128 | 2.10E−7 | 1.30E−5 |
| 129 | 2.40E−7 | 8.70E−6 |
| 130 | 2.85E−7 | 1.73E−5 |
| 131 | 3.30E−7 | 8.70E−6 |
| 132 | 9.30E−7 | 3.60E−5 |
| 133 | 6.95E−9 | 1.60E−6 |
| 134 | 9.15E−9 | 1.40E−6 |
| 135 | 2.70E−9 | 1.30E−6 |
| 136 | 5.60E−8 | 7.10E−6 |
| 137 | 1.10E−8 | 1.30E−5 |
| 138 | 5.20E−8 | 4.90E−6 |
| 139 | 5.85E−9 | 2.10E−6 |
| 140 | 1.60E−7 | 1.10E−5 |
| 141 | 5.65E−9 | 3.60E−6 |
| 142 | 1.20E−7 | 1.80E−5 |
| 143 | 5.60E−9 | 4.60E−6 |
| 144 | 1.90E−7 | 2.50E−5 |
| 145 | 4.90E−8 | 2.80E−6 |
| 146 | 5.90E−9 | 1.90E−6 |
| 147 | 4.20E−9 | 1.70E−6 |
| 148 | 3.28E−9 | 1.84E−06 |
| 149 | 4.25E−9 | 1.15E−06 |
| 150 | 4.55E−9 | 1.85E−06 |
| 151 | 1.70E−9 | 1.02E−6 |
| 152 | 2.80E−9 | 7.05E−7 |
| 153 | 2.40E−9 | 5.10E−7 |
| 154 | 3.70E−9 | 3.95E−6 |
| 155 | 1.90E−8 | 5.90E−6 |
| 156 | 2.50E−7 | 2.50E−5 |
| 157 | 3.10E−9 | 3.00E−6 |
| 158 | 5.93E−9 | 3.05E−6 |
| 159 | 7.13E−9 | 3.75E−6 |
| 160 | 3.10E−9 | 8.30E−7 |
| 161 | 3.23E−9 | 7.28E−07 |
| 162 | 2.75E−9 | 4.63E−7 |
| 163 | 2.50E−9 | 1.30E−6 |
| 164 | 7.20E−8 | 1.40E−5 |
| 165 | 9.30E−9 | 6.60E−6 |
| 166 | 7.77E−9 | 3.25E−6 |
| 167 | 3.50E−9 | 4.40E−6 |
| 168 | 4.60E−9 | 1.90E−6 |
| 169 | 9.30E−9 | 8.50E−6 |
| 170 | 4.95E−9 | 4.90E−6 |
| 171 | 1.10E−8 | 6.90E−6 |
| 172 | 5.95E−9 | 3.10E−6 |
| 173 | 1.37E−8 | 7.90E−6 |
| 174 | 5.55E−9 | 2.60E−6 |
| 175 | 4.05E−9 | 4.90E−6 |
| 176 | 6.60E−9 | 4.13E−6 |
| 177 | 1.80E−8 | 1.20E−5 |
| 178 | 1.85E−8 | 5.37E−6 |
| 179 | 9.10E−9 | 1.20E−5 |
| 180 | 1.07E−8 | 1.78E−05 |
| 181 | 1.20E−8 | 1.20E−5 |
| 182 | 9.78E−9 | 4.03E−6 |
| 183 | 2.50E−8 | 1.90E−5 |
| 184 | 1.94E−8 | 9.37E−6 |
| 185 | 1.15E−8 | 1.65E−5 |
| 186 | 7.90E−8 | 2.40E−5 |
| 187 | 9.70E−9 | 3.55E−6 |
| 188 | 5.27E−9 | 2.73E−6 |
| 189 | 1.46E−8 | 3.65E−6 |
| 190 | 6.30E−8 | 1.20E−5 |
| 191 | 5.78E−9 | 6.48E−6 |
| 192 | 1.72E−8 | 7.13E−6 |
| 193 | 3.90E−9 | 1.57E−6 |
| 194 | 1.13E−8 | 8.90E−6 |
| 195 | 4.45E−9 | 4.63E−6 |
| 196 | 3.90E−8 | 3.00E−5 |
| 197 | 1.35E−8 | 1.30E−5 |
| 198 | 3.20E−8 | 3.90E−5 |
| 199 | 1.13E−8 | 1.60E−5 |

TABLE 3-continued

| Example Number | ADAMTS7-IC50 [mol/l] | ADAMTS4-IC50 [mol/l] |
|---|---|---|
| 200 | 1.10E−7 | 2.80E−5 |
| 201 | 2.70E−8 | 8.10E−6 |
| 202 | 7.40E−8 | 3.80E−5 |
| 203 | 1.40E−8 | 4.60E−5 |
| 204 | 8.70E−8 | 2.20E−5 |
| 205 | 4.50E−8 | 1.20E−5 |
| 206 | 8.90E−8 | >5.00E−5 |
| 207 | 6.05E−8 | >5.00E−5 |
| 208 | 1.40E−7 | >5.00E−5 |
| 209 | 7.37E−8 | 3.65E−05 |
| 210 | 1.30E−8 | 2.30E−5 |
| 211 | 1.10E−7 | 2.80E−5 |
| 212 | 5.60E−8 | 1.30E−5 |
| 213 | 4.30E−8 | 3.00E−5 |
| 214 | 8.97E−9 | 3.75E−05 |
| 215 | 1.70E−8 | 3.50E−6 |
| 216 | 7.60E−8 | 9.10E−6 |
| 217 | 8.70E−8 | 1.60E−5 |
| 218 | 2.40E−8 | 4.00E−6 |
| 219 | 6.50E−8 | 2.80E−6 |
| 220 | 6.55E−8 | 7.80E−6 |
| 221 | 1.10E−7 | 8.10E−6 |
| 222 | 1.70E−7 | 3.00E−6 |
| 223 | 2.10E−7 | 2.60E−5 |
| 224 | 2.20E−7 | 1.90E−5 |
| 225 | 2.50E−7 | 2.10E−5 |
| 226 | 3.30E−7 | >5.00E−5 |
| 227 | 3.40E−7 | 4.10E−5 |
| 228 | 9.30E−7 | 2.00E−5 |
| 229 | 8.70E−7 | 2.00E−5 |
| 230 | 7.60E−7 | 3.30E−5 |
| 231 | 1.50E−7 | 5.20E−6 |
| 232 | 2.55E−8 | 3.70E−6 |
| 233 | 1.70E−7 | 6.50E−6 |
| 234 | 2.30E−7 | 1.60E−5 |
| 235 | 2.97E−8 | 7.83E−6 |
| 236 | 8.50E−8 | 1.50E−5 |
| 237 | 7.40E−8 | >5.00E−5 |
| 238 | 5.40E−8 | 2.00E−6 |
| 239 | 5.10E−8 | >5.00E−5 |
| 240 | 1.00E−7 | >5.00E−5 |
| 241 | 2.10E−7 | 4.10E−5 |
| 242 | 3.30E−7 | 2.90E−5 |
| 243 | 1.10E−7 | 4.50E−5 |
| 244 | 9.80E−8 | 1.00E−5 |
| 245 | 8.70E−7 | >5.00E−5 |
| 246 | 1.00E−6 | >5.00E−5 |
| 247 | 3.80E−7 | >5.00E−5 |
| 248 | 2.60E−7 | >5.00E−5 |
| 249 | 1.90E−7 | 3.50E−5 |
| 250 | 1.60E−7 | 3.10E−5 |
| 251 | 6.50E−8 | 1.10E−5 |
| 252 | 2.00E−7 | 4.10E−5 |
| 253 | 4.30E−8 | 1.10E−5 |
| 254 | 1.80E−7 | 2.60E−5 |
| 255 | 4.30E−8 | 1.00E−5 |
| 256 | 3.90E−8 | 2.80E−5 |
| 257 | 2.50E−7 | 1.10E−5 |
| 258 | 3.20E−7 | 1.20E−5 |
| 259 | 6.90E−8 | 5.80E−6 |
| 260 | 1.60E−7 | 1.70E−5 |
| 261 | 8.90E−7 | >5.00E−5 |
| 262 | 1.60E−7 | 1.90E−5 |
| 263 | 3.00E−7 | 3.20E−5 |
| 264 | 7.20E−8 | 1.10E−5 |
| 265 | 1.60E−7 | 9.10E−6 |
| 266 | 1.00E−7 | 1.00E−5 |
| 267 | 1.20E−7 | 1.90E−5 |
| 268 | 6.10E−8 | 2.70E−5 |
| 269 | 1.30E−7 | 9.50E−6 |
| 270 | 2.00E−8 | 6.90E−6 |
| 271 | 6.65E−9 | 2.70E−6 |
| 272 | 1.40E−8 | 7.80E−6 |
| 273 | 6.03E−7 | 2.68E−05 |
| 274 | 2.20E−8 | 3.80E−6 |
| 275 | 1.80E−7 | 9.10E−6 |
| 276 | 8.10E−8 | 1.50E−5 |
| 277 | 1.60E−8 | 1.60E−5 |
| 278 | 3.65E−9 | 8.60E−6 |
| 279 | 8.50E−8 | 1.30E−5 |
| 280 | 2.50E−8 | 7.10E−6 |
| 281 | 2.15E−7 | 2.60E−5 |
| 282 | 8.90E−8 | 1.60E−5 |
| 283 | 5.40E−8 | 6.30E−6 |
| 284 | 6.30E−8 | 8.50E−6 |
| 285 | 1.48E−7 | 6.60E−6 |
| 286 | 2.30E−7 | 9.80E−6 |
| 287 | 1.50E−9 | 1.60E−7 |
| 288 | 4.10E−7 | 2.10E−5 |
| 289 | 3.80E−8 | 6.30E−6 |
| 290 | 3.30E−7 | 2.10E−5 |
| 291 | 5.60E−8 | 1.40E−5 |
| 292 | 3.00E−8 | 9.50E−6 |
| 293 | 3.70E−7 | >5.00E−5 |
| 294 | 1.30E−7 | 3.70E−5 |
| 295 | 5.00E−8 | >5.00E−5 |
| 296 | 1.30E−7 | 9.50E−6 |
| 297 | 4.80E−8 | 4.10E−6 |
| 298 | 7.90E−9 | 9.30E−6 |
| 299 | 9.80E−8 | 1.90E−5 |
| 300 | 3.10E−8 | 2.30E−5 |
| 301 | 1.00E−7 | 1.50E−5 |
| 302 | 4.00E−8 | 7.60E−6 |
| 303 | 6.50E−7 | 3.80E−5 |
| 304 | 4.80E−9 | 3.30E−6 |
| 305 | 1.10E−8 | 2.80E−6 |
| 306 | 1.20E−8 | 1.60E−5 |
| 307 | 1.10E−8 | 2.30E−5 |
| 308 | 6.30E−9 | 4.20E−6 |
| 309 | 1.10E−8 | 2.70E−6 |
| 310 | 1.60E−8 | 1.90E−6 |
| 311 | 4.20E−8 | 1.10E−5 |
| 312 | 5.40E−8 | 2.00E−5 |
| 313 | 6.50E−8 | 2.30E−5 |
| 314 | 9.50E−7 | >5.00E−5 |
| 315 | 1.30E−8 | 1.30E−6 |
| 316 | 4.10E−8 | 1.20E−5 |

Example B12 Rat Carotid Artery Balloon Injury Model

The balloon injury model is an important method to study the molecular and cellular mechanisms involved in vascular smooth muscle dedifferentiation, neointima formation and vascular remodeling.

The left carotid is injured using a balloon catheter with the right carotid serving as a negative control; the inflated balloon denudes the endothelium and distends the vessel wall. Following injury, potential therapeutic strategies such as the use of pharmacological compounds can be evaluated.

Following sedation to a surgical plane, male Sprague-Dawley rats are laid supine on a sterile surface, the neck area is shaved, cleansed and the surgical area aseptically draped to prevent contamination at the surgical site. A straight incision is made centrally in the neck region from below the chin to the top of the sternum. With continued blunt dissection, the left common carotid artery and the distal aspect of the carotid artery cephalic to the internal and external bifurcation are isolated and made free of overlying fascia and adjacent nerves. Sterile sutures and an arterial clamp are used to control blood flow in order to perform the injury. Isolating a section on the internal carotid artery and using sterile small microscissors, a transverse arteriotomy on the branch is performed. The uninflated 2 French arterial balloon catheter (Edwards Life Sciences, Germany) is inserted through the arteriotomy, inflated and moved down the entire length of the common carotid artery to the aortic arch. The balloon is inflated to a predetermined volume, deflated and withdrawn through the arteriotomy. Following adequate hemostasis, all remaining sutures are removed and the operational field is closed up. Neointimal thickening representing proliferative vascular smooth muscle cells usually peaks at 2 weeks after injury. Vessels are harvested at this time point for histological assessment of neointimal development, vascular growth, molecular analysis as well as gene and protein expression.

CLAUSES

The following clauses refer to further embodiments disclosed herein:
1. A compound of general formula (I):

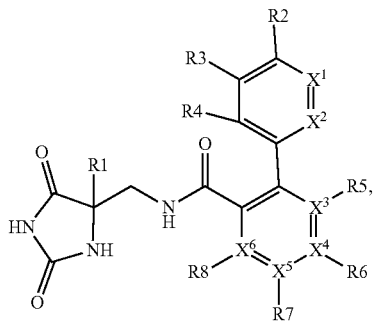

(I)

in which
$R^1$ represents a group selected from hydrogen, $(C_1-C_6)$-alkyl, $(C_3-C_6)$-cycloalkyl, 5- to 6-membered heterocycloalkyl, 5- to 10-membered heteroaryl, and phenyl
wherein said $(C_1-C_6)$-alkyl, $(C_3-C_6)$-cycloalkyl, 5- to 6-membered heterocycloalkyl, and 6- to 10-membered heteroaryl, phenyl are optionally substituted with one or two groups independently selected from cyano, halogen, amino, hydroxy, oxo, $C_1-C_3$-alkyl, $(C_1-C_4)$-alkoxy, $(C_1-C_4)$-alkylcarbonyl, mono-$(C_1-C_4)$-alkylamino, di-$(C_1-C_4)$-alkylamino, phenyl, $(C_1-C_4)$-alkylsulfonyl, and $(C_3-C_6)$-cycloalkyl,
wherein each said $C_1-C_3$-alkyl, $(C_3-C_6)$-cycloalkyl, and $(C_1-C_4)$-alkoxy is optionally substituted with up to 5 fluorine atoms
$R^2$ represents a group independently selected from hydrogen, cyano, halogen, $(C_1-C_4)$-alkylsulfonyl, $(C_1-C_4)$-alkyl, $(C_3-C_6)$-cycloalkyl, and $(C_1-C_4)$-alkoxy
wherein said $(C_1-C_4)$-alkyl, $(C_3-C_6)$-cycloalkyl, and $(C_1-O4)$-alkoxy each is optionally independently substituted with up to five fluorine atoms, cyano, or $(C_1-C_2)$alkyl, wherein said $(C_1-C_2)$alkyl is optionally substituted with up to five fluorine atoms
$R^3$, $R^4$, $R^5$, $R^6$, $R^7$ and $R^8$ represent a group independently selected from hydrogen, halogen, $(C_1-C_4)$-alkyl and $(C_1-C_4)$-alkoxy
wherein said $(C_1-C_4)$-alkyl and $(C_1-C_4)$-alkoxy each is optionally independently substituted with up to five fluorine atoms,
with the provisio that at least one of $R^2$, $R^3$, $R^4$ represents H,
$X^1$, $X^2$, $X^3$, $X^4$, $X^5$, $X^6$, represent N or C with the provisio that in each ring system maximal one X stands for N and $R^5$, $R^6$, $R^7$ and Ra are present provided that the designated atom's normal valency under the existing circumstances is not exceeded, and pharmaceutically acceptable salts thereof, solvates thereof and the solvates of the salts thereof.
2. A compound of general formula (I) according to Clause 1, in which
$R^1$ represents a group selected from hydrogen, $(C_1-C_6)$-alkyl, $(C_3-C_6)$-cycloalkyl, 5- to 6-membered heterocycloalkyl, 5- to 10-membered heteroaryl and phenyl
wherein said $(C_1-C_6)$-alkyl, $(C_3-C_6)$-cycloalkyl, 5- to 6-membered heterocycloalkyl, and 5- to 10-membered heteroaryl, phenyl are optionally substituted with one or two groups independently selected from cyano, halogen, amino, hydroxy, oxo, $C_1-C_3$-alkyl, $(C_1-C_4)$-alkoxy, $(C_1-C_4)$-alkylcarbonyl, mono-$(C_1-C_4)$-alkylamino, di-$(C_1-C_4)$-alkylamino, phenyl, $(C_1-C_4)$-alkylsulfonyl, and $(C_3-C_6)$-cycloalkyl,
wherein each said $C_1-C_3$-alkyl, $(C_3-C_6)$-cycloalkyl, and $(C_1-C_4)$-alkoxy is optionally substituted with up to 5 fluorine atoms
$R^2$ represents a group independently selected from hydrogen cyano, halogen, $(C_1-C_4)$-alkylsulfonyl, $(C_1-C_4)$-alkyl, $(C_3-C_6)$-cycloalkyl and $(C_1-C_4)$-alkoxy
wherein said $(C_1-C_4)$-alkyl$(C_3-C_6)$-cycloalkyl and $(C_1-C_4)$-alkoxy each is optionally independently substituted with up to five fluorine atoms, cyano, or $(C_1-C_2)$alkyl, wherein said $(C_1-C_2)$alkyl is optionally substituted with up to five fluorine atoms
$R^3$ and $R^4$ represent hydrogen and
$R^5$, $R^6$, $R^7$ and $R^8$ represent a group independently selected from hydrogen, halogen, $(C_1-C_4)$-alkyl and $(C_1-C_4)$-alkoxy
wherein said $(C_1-C_4)$-alkyl and $(C_1-C_4)$-alkoxy each is optionally independently substituted with up to five fluorine atoms,
$X^1$, $X^2$, $X^3$, $X^4$, $X^5$, $X^6$, represent N or C with the provisio that in each ring system maximal one X stands for N and $R^5$, $R^6$, $R^7$ and Ra are present provided that the designated atom's normal valency under the existing circumstances is not exceeded, and pharmaceutically acceptable salts thereof, solvates thereof and the solvates of the salts thereof.
3. A compound of general formula (I) according to Clause 1 or 2, in which
$R^1$ represents a group selected from hydrogen, $(C_1-C_6)$-alkyl, $(C_3-C_6)$-cycloalkyl, 5- to 6-membered heterocycloalkyl, 5- to 10-membered heteroaryl and phenyl
wherein said $(C_1-C_6)$-alkyl, $(C_3-C_6)$-cycloalkyl, 5- to 6-membered heterocycloalkyl, and 5- to 10-membered heteroaryl, phenyl are optionally substituted with one or two groups independently selected from cyano, halogen, amino, hydroxy, oxo, $C_1-C_3$-alkyl, $(C_1-C_4)$-alkoxy, $(C_1-C_4)$-alkylcarbonyl, mono-$(C_1-C_4)$-alkylamino, di-$(C_1-C_4)$-alkylamino, phenyl, $(C_1-C_4)$-alkylsulfonyl, and $(C_3-C_6)$-cycloalkyl,
wherein each said $C_1-C_3$-alkyl, $(C_3-C_6)$-cycloalkyl, and $(C_1-C_4)$-alkoxy is optionally substituted with up to 5 fluorine atoms
$R^2$ represents a group independently selected from hydrogen cyano, halogen, $(C_1-C_4)$-alkylsulfonyl, $(C_1-C_4)$-alkyl, $(C_3-C_6)$-cycloalkyl and $(C_1-C_4)$-alkoxy
wherein said $(C_1-C_4)$-alkyl$(C_3-C_6)$-cycloalkyl and $(C_1-O4)$-alkoxy each is optionally independently substituted with up to five fluorine atoms, cyano, or $(C_1-C_2)$alkyl, wherein said $(C_1-C_2)$alkyl is optionally substituted with up to five fluorine atoms.
$R^3$, $R^4$, $R^5$, $R^6$, $R^7$ and $R^8$ represent a group independently selected from hydrogen, halogen, $(C_1-C_4)$-alkyl and $(C_1-C_4)$-alkoxy wherein said $(C_1-C_4)$-alkyl and $(C_1-C_4)$-alkoxy each is optionally independently substituted with up to five fluorine atoms, with the provision that at least two from $R^5$, $R^6$, $R^7$ and $R^8$ represent hydrogen, $X^1$, $X^2$, $X^3$, $X^4$, $X^5$, $X^6$, represent N or C with the provisio that in each ring system maximal one X stands for N and $R^5$, $R^6$, $R^7$ and Ra are present provided that the designated atom's normal valency under the existing circumstances is not exceeded, and pharmaceutically acceptable salts thereof, solvates thereof and the solvates of the salts thereof.

4. Compound of the formula (I) according to Clause 1, 2 or 3 represented by the formula (Ia), (Ib), (Ic), (Id) and (Ie)

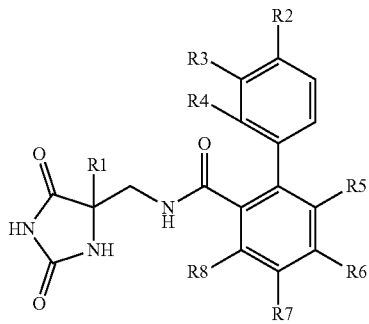
(Ia)

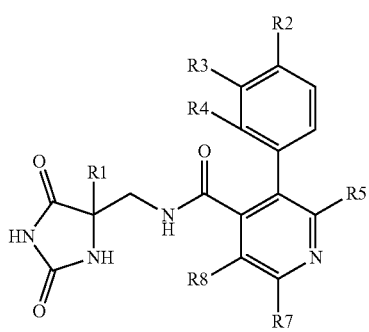
(Ib)

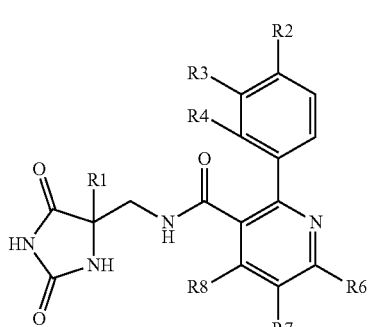
(Ic)

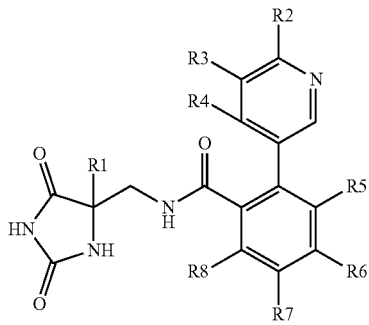
(Id)

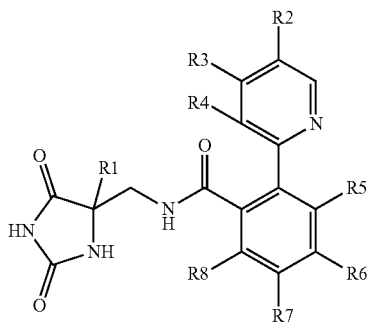
(Ie)

In which $R^1$ represents a group selected from hydrogen, $(C_1-C_6)$-alkyl, $(C_3-C_6)$-cycloalkyl, 5- to 6-membered heterocycloalkyl, 5- to 10-membered heteroaryl and phenyl wherein said $(C_1-C_6)$-alkyl, $(C_3-C_6)$-cycloalkyl, 5- to 6-membered heterocycloalkyl, and 5- to 10-membered heteroaryl, phenyl are optionally substituted with one or two groups independently selected from cyano, halogen, amino, hydroxy, oxo, $C_1-C_3$-alkyl, $(C_1-C_4)$-alkoxy, $(C_1-C_4)$-alkylcarbonyl, mono-$(C_1-C_4)$-alkylamino, di-$(C_1-C_4)$-alkylamino, phenyl, $(C_1-C_4)$-alkylsulfonyl, and $(C_3-C_6)$-cycloalkyl, wherein each said $C_1-C_3$-alkyl, $(C_3-C_6)$-cycloalkyl, and $(C_1-C_4)$-alkoxy is optionally substituted with up to 5 fluorine atoms $R^2$ represents a group independently selected from hydrogen cyano, halogen, $(C_1-C_4)$-alkylsulfonyl, $(C_1-C_4)$-alkyl, $(C_3-C_6)$-cycloalkyl and $(C_1-C_4)$-alkoxy wherein said $(C_1-C_4)$-alkyl$(C_3-C_6)$-cycloalkyl and $(C_1-04)$-alkoxy each is optionally independently substituted with up to five fluorine atoms, cyano, or $(C_1-C_2)$alkyl, wherein said $(C_1-C_2)$alkyl is optionally substituted with up to five fluorine atoms.

$R^3$, $R^4$, $R^5$, $R^6$, $R^7$ and $R^8$ represent a group independently selected from hydrogen, halogen, $(C_1-C_4)$-alkyl and $(C_1-C_4)$-alkoxy wherein said $(C_1-C_4)$-alkyl and $(C_1-C_4)$-alkoxy each is optionally independently substituted with up to five fluorine atoms, with the provision that at least two from $R^5$, $R^6$, $R^7$ and $R^8$ represent hydrogen, and pharmaceutically acceptable salts thereof, solvates thereof and the solvates of the salts thereof.

5. The compound of any one of clauses 1-4, wherein said $R^2$ is $(C_3-C_6)$-cycloalkyl substituted with a trifluoromethyl group.

6. Compound of the formula (I) according to Clause 1 to 5 selected from the group consisting of ent-6-fluoro-N-{[4-(1-methyl-1H-pyrazol-5-yl)-2,5-dioxo-imidazolidin-4-yl]methyl}-4'-(trifluoromethyl)[biphenyl]-2-carboxamide

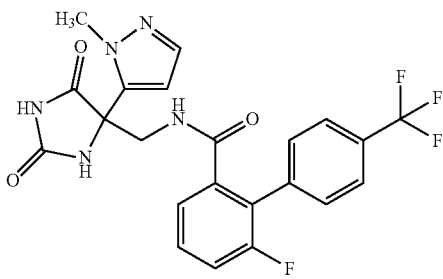 [SMILES: Cn1nccc1C1(CNC(=O)c2cccc(F)c2-c2ccc(C(F)(F)F)cc2)NC(=O)NC1=O]

ent-5,6-difluoro-N-{[4-(1-methyl-1H-pyrazol-5-yl)-2,5-dioxoimidazolidin-4-yl]methyl}-4'-(trifluoromethyl)[biphenyl]-2-carboxamide

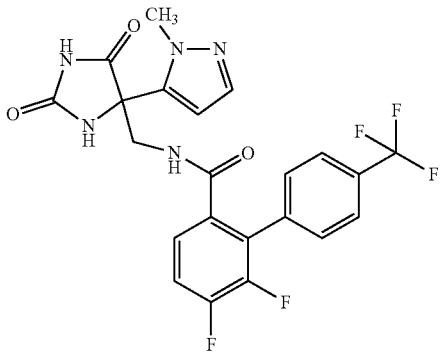 [SMILES: Cn1nccc1C1(CNC(=O)c2ccc(F)c(F)c2-c2ccc(C(F)(F)F)cc2)NC(=O)NC1=O]

ent-4'-chloro-N-{[4-(1-methyl-1H-pyrazol-5-yl)-2,5-dioxoimidazolidin-4-yl]methyl}[biphenyl]-2-carboxamide

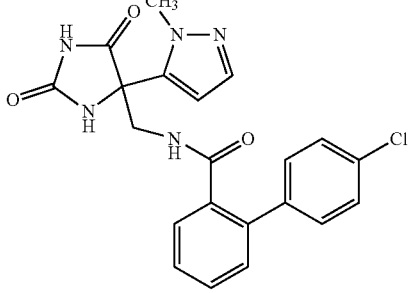

ent-4'-chloro-5-fluoro-N-{[4-(1-methyl-1H-pyrazol-5-yl)-2,5-dioxoimidazolidin-4-yl]methyl}[biphenyl]-2-carboxamide

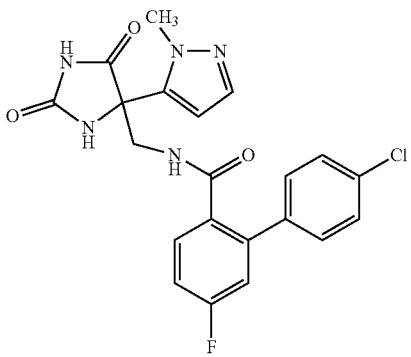 [SMILES: Cn1nccc1C1(CNC(=O)c2ccc(F)cc2-c2ccc(Cl)cc2)NC(=O)NC1=O]

ent-N-{[4-(1-methyl-1H-pyrazol-5-yl)-2,5-dioxoimidazolidin-4-yl]methyl}-4'-(trifluoromethyl)[biphenyl]-2-carboxamide

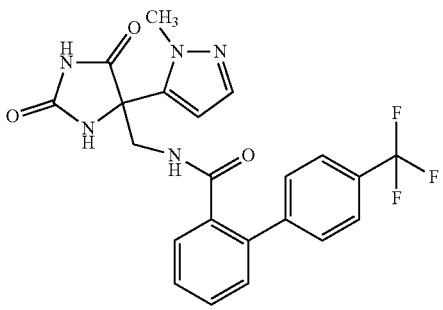 [SMILES: Cn1nccc1C1(CNC(=O)c2ccccc2-c2ccc(C(F)(F)F)cc2)NC(=O)NC1=O]

ent-4,5-difluoro-N-{[4-(1-methyl-1H-pyrazol-5-yl)-2,5-dioxoimidazolidin-4-yl]methyl}-4'-(trifluoromethyl)[biphenyl]-2-carboxamide

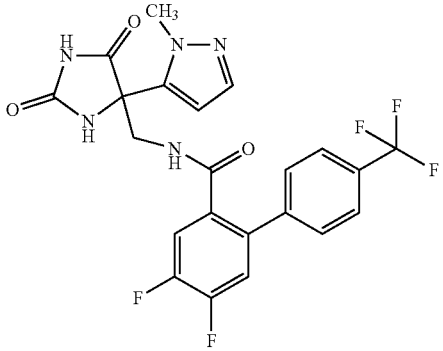 [SMILES: Cn1nccc1C1(CNC(=O)c2cc(F)c(F)cc2-c2ccc(C(F)(F)F)cc2)NC(=O)NC1=O]

ent-N-{[4-(4-methyl-1,2-oxazol-3-yl)-2,5-dioxoimidazolidin-4-yl]methyl}-4'-(trifluoromethyl)[biphenyl]-2-carboxamide

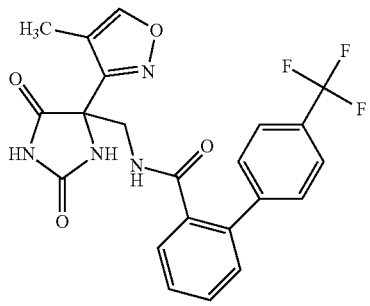 [SMILES: Cc1conc1C1(CNC(=O)c2ccccc2-c2ccc(C(F)(F)F)cc2)NC(=O)NC1=O]

7. Compound of formula (I) for the treatment and/or prevention of diseases.
8. Compound of formula (I) for use in a method for the treatment and/or prevention of heart diseases, vascular diseases, and/or cardiovascular diseases, lung diseases, inflammatory diseases, fibrotic diseases, metabolic diseases, cardiometabolic diseases.
9. Compound of formula (I) for use in a method for the treatment and/or prevention of atherosclerosis, atherosclerosis-related diseases such as coronary artery disease or peripheral vascular disease/arterial occlusive disease as well as post-surgery complications of these diseases such as restenosis after angioplasty.
10. Use of a compound according to formula (I) for the manufacture of a pharmaceutical composition for the treatment and/or prevention of atherosclerosis, atherosclerosis-related diseases such as coronary artery disease or peripheral vascular disease/arterial occlusive disease as well as post-surgery complications of these diseases such as restenosis after angioplasty
11. Use of a compound as defined in any of Clauses 1 to 6 for the manufacture of a pharmaceutical composition for the treatment and/or prevention of atherosclerosis, atherosclerosis-related diseases such as coronary artery disease or peripheral vascular disease/arterial occlusive disease as well as post-surgery complications of these diseases such as restenosis after angioplasty
12. Pharmaceutical composition comprising a compound as defined in any of Clauses 1 to 6 and one or more pharmaceutically acceptable excipients.
13. Pharmaceutical composition of Clause 10 comprising one or more first active ingredients, in particular compounds of general formula (I) according to any one of clauses 1 to 6, and one or more further active ingredients, in particular one or more additional therapeutic agents selected from the group consisting of angiotensin-converting enzyme inhibitors, angiotensin-receptor blockers, mineralocorticoid-receptor antagonists, endothelin antagonists, renin inhibitors, calcium blockers, beta-receptor blockers, vasopeptidase inhibitors, Sodium-Glucose-Transport-Antagonists, Metformin, Pioglitazones and Dipeptidyl-peptidase-IV inhibitors.
14. The pharmaceutical composition as defined in Clause 12 or 13 for the treatment and/or prevention of atherosclerosis, atherosclerosis-related diseases such as coronary artery disease or peripheral vascular disease/arterial occlusive disease as well as post-surgery complications of these diseases such as restenosis after angioplasty
15. Method for the treatment and/or prevention atherosclerosis, athersclerosis-related diseases such as coronary artery disease or peripheral vascular disease/arterial occlusive disease as well as post-surgery complications of these diseases such as restenosis after angioplastyin a human or other mammal, comprising administering to a human or other mammal in need thereof a therapeutically effective amount of one or more compounds as defined in any of Clauses 1 to 6, or of a pharmaceutical composition as defined in any of clauses 12 to 13.
16. A recombinant nucleic acid for expression of an ADAMTS-7 polypeptide that comprises a rodent prodomain of ADAMTS-7 as a first portion and a functional human ADAMTS-7 as a second portion
17. A recombinant nucleic acid for expression of an ADAMTS-7 polypeptide, wherein the polypeptide comprises
   a first portion having a sequence identity of >80% with the sequence of residues 1-217 of SEQ ID NO: 1 or with the sequence of residues 1-217 of SEQ ID NO: 2; and
   a second portion having a sequence identity of >80% with the sequence of residues 218-518 of SEQ ID NO: 1.
18. The recombinant nucleic acid of any one of clauses 16 or 17, wherein the first portion of the polypeptide comprises residues 1-217 of SEQ ID NO: 1 or residues 1-217 of SEQ ID NO: 2, and/or wherein the second portion amino acid sequence comprises residues 218-518 of SEQ ID NO: 1.
19. A recombinant nucleic acid for expression of an ADAMTS-7 polypeptide, wherein the recombinant nucleic acid encodes for a recombinant polypeptide that comprises
   a first portion having an amino acid sequence that aligns with a segment of an ADAMTS-7 prodomain amino acid sequence from a first species with a Needleman-Wunsch score greater than 700 when BLOSUM62 matrix, a gap opening penalty of 11, and a gap extension penalty of 1 are used; and
   a second portion having an amino acid sequence that aligns with a segment of an ADAMTS-7 catalytic domain amino acid sequence from a second species with a Needleman-Wunsch score greater than 1000 when BLOSUM62 matrix, a gap opening penalty of 11, and a gap extension penalty of 1 are used,
   wherein optionally the first species is rat and the second species is human.
20. The recombinant nucleic acid of any one of clauses 16 to 19, wherein the motif RQQR within the first portion of the polypeptide is altered, preferably into RQKR.
21. A recombinant nucleic acid for expression of an ADAMTS-12 polypeptide that comprises a rodent prodomain of ADAMTS-12 as a first portion and afunctional human ADAMTS-12 as a second portion.
22. A recombinant nucleic acid for expression of an ADAMTS-12 polypeptide that comprises
   a first portion having a sequence identity of >80% with the sequence of residues 1-244 of SEQ ID NO: 15, and
   a second portion having a sequence identity of >80% with the sequence of residues 245-547 of SEQ ID NO: 15.
23. The recombinant nucleic acid of any one of clauses 21 or 22, wherein the first portion comprises residues 1-244 of SEQ ID NO: 15, and/or wherein the second portion amino acid sequence comprises residues 245-547 of SEQ ID NO: 15.

24. A recombinant nucleic acid for expression of an ADAMTS-12 polypeptide, wherein the recombinant nucleic acid encodes for a recombinant polypeptide that comprises
   a first portion having an amino acid sequence that aligns with a segment of an ADAMTS-12 prodomain amino acid sequence from a first species with a Needleman-Wunsch score greater than 800 when BLOSUM62 matrix, a gap opening penalty of 11, and a gap extension penalty of 1 are used; and
   a second portion having an amino acid sequence that aligns with a segment of an ADAMTS12 catalytic domain amino acid sequence from a second species with a Needleman-Wunsch score greater than 1000 when BLOSUM62 matrix, a gap opening penalty of 11, and a gap extension penalty of 1 are used
   wherein optionally the first species is rat and the second species is human.
25. The recombinant nucleic acid of any one of clauses 21 to 24, wherein the second portion comprises an E393Q mutation.
26. The recombinant nucleic acid of any of clauses 16 to 25, wherein the encoded polypeptide or the second portion thereof is suited to cleave a peptide comprising standard residues 1-15 of the amino acid sequence of SEQ ID NO: 4, preferably with a kcat/KM of at least 20% of a corresponding kcat/KM of human ADAMTS-7 or human ADAMTS-12.
27. A recombinant polypeptide encoded by the recombinant nucleic acid according to any of clauses 16 to 26, or a fragment of that recombinant polypeptide, wherein said recombinant polypeptide or fragment thereof is suited to cleave a peptide substrate comprising standard residues 1-15 of SEQ ID NO: 4.
28. A peptide substrate for ADAMTS-7 and/or ADAMTS-12, the peptide substrate comprising
   residues 1-15 of the amino acid sequence of SEQ ID NO: 4, or
   residues 1-15 of the amino acid sequence of SEQ ID NO: 5, or
   residues 1-13 of the amino acid sequence of SEQ ID NO: 8, or
   a fragment of any of the sequences according to a), b) or c), the fragment comprising the amino acid sequence EL.
29. The peptide substrate of clause 28, wherein the peptide substrate comprises a first moiety conjugated to a residue that is N-terminal to sequence fragment EL comprised within SEQ ID No. 4, 5, or 8 or the fragment thereof, and a second moiety conjugated to a residue that is C-terminal to said sequence fragment EL.
30. The peptide substrate of clause 29, wherein the first moiety comprises a fluorophore and the second moiety comprises a quencher, or wherein the first moiety comprises a quencher and the second moiety comprises a fluorophore.
31. A method for the identification or characterization of an ADAMTS-7 and/or ADAMTS-12 modulator comprising the steps of
   contacting a recombinant polypeptide or a fragment thereof according to clause 27 with at least one test compound;
   contacting said recombinant polypeptide or fragment thereof with a peptide substrate according to any one of clauses 28 to 30, wherein the peptide substrate comprises a fluorophore and a quencher; and
   detecting fluorescence as a measure for the activity of said recombinant polypeptide or a fragment thereof.
32. A modulator of ADAMTS-7 and/or ADAMTS-12 identified by a method according to clause 31 for use in the treatment of coronary artery disease (CAD), peripheral vascular disease (PAD) and myocardial infarction (MI).
33. A method of producing a recombinant polypeptide according to clause 27, the method comprising
   cultivating a recombinant host cell comprising a recombinant nucleic acid according to any of clauses 16 to 26
   recovering the recombinant polypeptide of a fragment thereof according to clause 27.
34. Kit of parts comprising at least one recombinant nucleic acid according to any of clauses 16 to 26 or at least one polypeptide according to clause 27 and a peptide substrate according to any of clauses 28 to 30.

The invention claimed is:
1. A compound of formula (I):

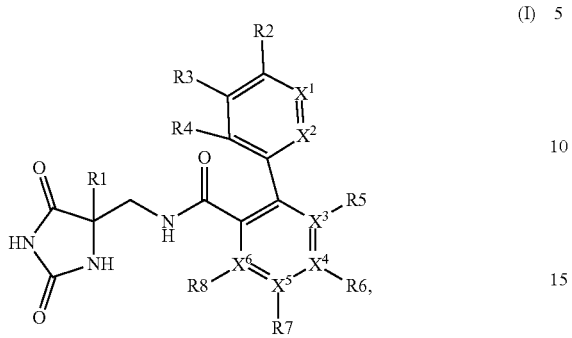

wherein,
R¹ is selected from the group consisting of hydrogen, $(C_1-C_6)$-alkyl, $(C_3-C_6)$-cycloalkyl, 5- to 6-membered heterocycloalkyl, 5- to 10-membered heteroaryl, and phenyl,
  wherein said $(C_1-C_6)$-alkyl, $(C_3-C_6)$-cycloalkyl, 5- to 6-membered heterocycloalkyl,5- to 10-membered heteroaryl, or phenyl is optionally substituted with one or two groups independently selected from the group consisting of cyano, halogen, amino, hydroxy, oxo, $C_1-C_3$-alkyl, $(C_1-C_4)$-alkoxy, $(C_1-C_4)$-alkylcarbonyl, mono-$(C_1-C_4)$-alkylamino, di-$(C_1-C_4)$-alkylamino, phenyl, $(C_1-C_4)$-alkylsulfonyl, and $(C_3-C_6)$-cycloalkyl,
  wherein each said $C_1-C_3$-alkyl, $(C_3-C_6)$-cycloalkyl, or $(C_1-C_4)$-alkoxy is optionally substituted with up to 5 fluorine atoms;
R² is selected from the group consisting of hydrogen, cyano, halogen, $(C_1-C_4)$-alkylsulfonyl, $(C_1-C_4)$-alkyl, $(C_3-C_6)$-cycloalkyl, and $(C_1-C_4)$-alkoxy,
  wherein said $(C_1-C_4)$-alkyl, $(C_3-C_6)$-cycloalkyl, or $(C_1-C_4)$-alkoxy is optionally independently substituted with up to five fluorine atoms, cyano, or $(C_1-C_2)$ alkyl,
  wherein said $(C_1-C_2)$alkyl is optionally substituted with up to five fluorine atoms;
R³ and R⁴are each independently selected from the group consisting of hydrogen, halogen, $(C_1-C_4)$-alkyl and $(C_1-C_4)$-alkoxy, wherein each said $(C_1-C_4)$-alkyl and $(C_1-C_4)$-alkoxy is optionally independently substituted with up to five fluorine atoms,
  provided that at least one of R², R³, and R⁴ represents H;
X¹, X², X³, X⁴, X⁵, and X⁶ are each independently N or C, provided that in each ring system maximally one X stands for N; and
R⁵, R⁶, R⁷ and R⁸ are each absent when the X atom to which they are attached is N, or
R⁵, R⁶, R⁷ and R⁸ are each independently selected from the group consisting of hydrogen, halogen, $(C_1-C_4)$-alkyl and $(C_1-C_4)$-alkoxy when the X atom to which they are attached is C,
  wherein each said $(C_1-C_4)$-alkyl and $(C_1-C_4)$-alkoxy is optionally independently substituted with up to five fluorine atoms present,
or a pharmaceutically acceptable salt thereof, a solvate thereof, or a solvate of a pharmaceutically acceptable salt thereof.

2. The compound of claim 1, wherein
R¹ is selected from the group consisting of hydrogen, $(C_1-C_6)$-alkyl, $(C_3-C_6)$-cycloalkyl, 5- to 6-membered heterocycloalkyl, 5- to 10-membered heteroaryl, and phenyl,
  wherein said $(C_1-C_6)$-alkyl, $(C_3-C_6)$-cycloalkyl, 5- to 6-membered heterocycloalkyl, 5- to 10-membered heteroaryl, or phenyl is optionally substituted with one or two groups independently selected from from the group consisting of cyano, halogen, amino, hydroxy, oxo, $C_1-C_3$-alkyl, $(C_1-C_4)$-alkoxy, $(C_1-C_4)$-alkylcarbonyl, mono-$(C_1-C_4)$-alkylamino, di-$(C_1-C_4)$-alkylamino, phenyl, $(C_1-C_4)$-alkylsulfonyl, and $(C_3-C_6)$-cycloalkyl,
  wherein each said $C_1-C_3$-alkyl, $(C_3-C_6)$-cycloalkyl, and $(C_1-C_4)$-alkoxy is optionally substituted with up to 5 fluorine atoms;
R² is selected from the group consisting of hydrogen, cyano, halogen, $(C_1-C_4)$-alkylsulfonyl, $(C_1-C_4)$-alkyl, $(C_3-C_6)$-cycloalkyl and $(C_1-C_4)$-alkoxy,
  wherein said $(C_1-C_4)$-alkyl$(C_3-C_6)$-cycloalkyl or $(C_1-C_4)$-alkoxy is optionally independently substituted with up to five fluorine atoms, cyano, or $(C_1-C_2)$ alkyl,
  wherein said $(C_1-C_2)$alkyl is optionally substituted with up to five fluorine atoms;
R³ and R⁴ are hydrogen; and
R⁵, R⁶, R⁷ and R⁸, when present, are each independently selected from the group consisting of hydrogen, halogen, $(C_1-C_4)$-alkyl and $(C_1-C_4)$-alkoxy,
  wherein each said $(C_1-C_4)$-alkyl and $(C_1-C_4)$-alkoxy is optionally independently substituted with up to five fluorine atoms,
or a pharmaceutically acceptable salt thereof, a solvate thereof, or a solvate of a pharmaceutically acceptable salt thereof.

3. The compound of claim 1, wherein
R¹ is selected from the group consisting of hydrogen, $(C_1-C_6)$-alkyl, $(C_3-C_6)$-cycloalkyl, 5- to 6-membered heterocycloalkyl, 5- to 10-membered heteroaryl, and phenyl,
  wherein said $(C_1-C_6)$-alkyl, $(C_3-C_6)$-cycloalkyl, 5- to 6-membered heterocycloalkyl, 5- to 10-membered heteroaryl, or phenyl is optionally substituted with one or two groups independently selected from the group consist of cyano, halogen, amino, hydroxy, oxo, $C_1-C_3$-alkyl, $(C_1-C_4)$-alkoxy, $(C_1-C_4)$-alkylcarbonyl, mono-$(C_1-C_4)$-alkylamino, di-$(C_1-C_4)$-alkylamino, phenyl, $(C_1-C_4)$-alkylsulfonyl, and $(C_3-C_6)$-cycloalkyl,
  wherein each said $C_1-C_3$-alkyl, $(C_3-C_6)$-cycloalkyl, and $(C_1-C_4)$-alkoxy is optionally substituted with up to 5 fluorine atoms;
R² represents a group independently selected from hydrogen cyano, halogen, $(C_1-C_4)$-alkylsulfonyl, $(C_1-C_4)$-alkyl, $(C_3-C_6)$-cycloalkyl and $(C_1-C_4)$-alkoxy
  wherein said $(C_1-C_4)$-alkyl$(C_3-C_6)$-cycloalkyl and $(C_1-C_4)$-alkoxy is optionally independently substituted with up to five fluorine atoms, cyano, or $(C_1-C_2)$ alkyl,
  wherein said $(C_1-C_2)$alkyl is optionally substituted with up to five fluorine atoms,
R³ and R⁴ are each independently selected from the group consisting of hydrogen, halogen, $(C_1-C_4)$-alkyl and $(C_1-C_4)$-alkoxy, wherein each said $(C_1-C_4)$-alkyl and $(C_1-C_4)$-alkoxy is optionally independently substituted with up to five fluorine atoms, $R^5$, $R^6$, $R^7$, and $R^8$, when present, are each independently selected from the group consisting of hydrogen, halogen, $(C_1\text{-}C_4)$-alkyl and $(C_1\text{-}C_4)$-alkoxy, wherein each said $(C_1\text{-}C_4)$-alkyl and $(C_1\text{-}C_4)$-alkoxy is optionally independently substituted with up to five fluorine atoms, and provided that at least two of $R^5$, $R^6$, $R^7$ and $R^8$ are hydrogen, or a pharmaceutically acceptable salt thereof, a solvate thereof, or a solvate of a pharmaceutically acceptable salt thereof.

4. The compound of claim 1, wherein the compound is of formula (Ia), (Ib), (Ic), (Id) or (Ie):

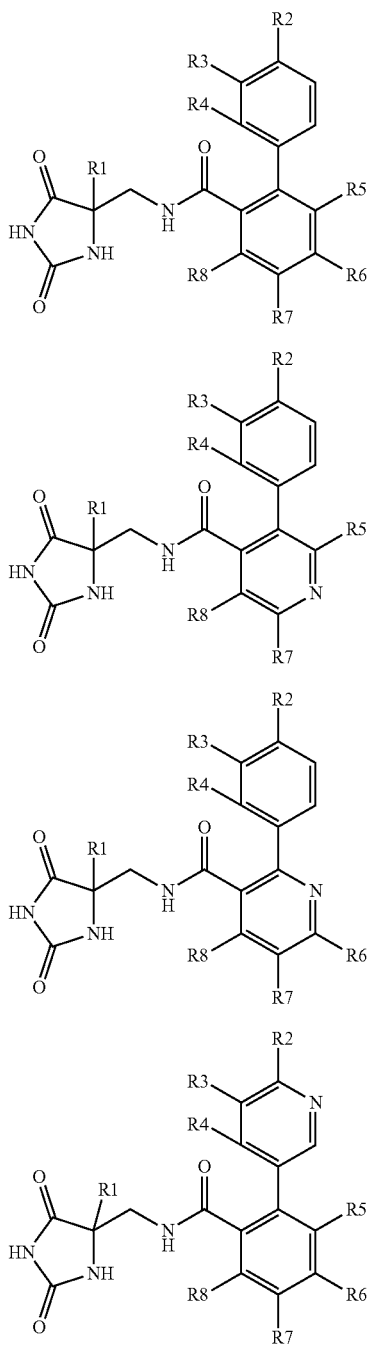

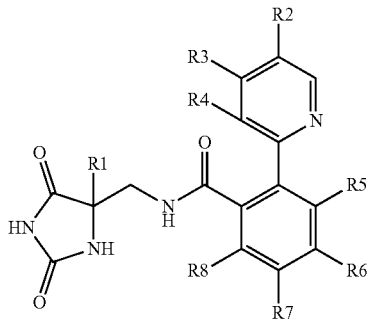

wherein $R^1$ is selected from the group consisting of hydrogen, $(C_1\text{-}C_6)$-alkyl, $(C_3\text{-}C_6)$-cycloalkyl, 5- to 6-membered heterocycloalkyl, 5- to 10-membered heteroaryl, and phenyl, wherein said $(C_1\text{-}C_6)$-alkyl, $(C_3\text{-}C_6)$-cycloalkyl, 5- to 6-membered heterocycloalkyl, 5- to 10-membered heteroaryl, or phenyl is optionally substituted with one or two groups independently selected from the group consisting of cyano, halogen, amino, hydroxy, oxo, $C_1\text{-}C_3$-alkyl, $(C_1\text{-}C_4)$-alkoxy, $(C_1\text{-}C_4)$-alkylcarbonyl, mono-$(C_1\text{-}C_4)$-alkylamino, di-$(C_1\text{-}C_4)$-alkylamino, phenyl, $(C_1\text{-}C_4)$-alkylsulfonyl, and $(C_3\text{-}C_6)$-cycloalkyl, wherein each said $C_1\text{-}C_3$-alkyl, $(C_3\text{-}C_6)$-cycloalkyl, and $(C_1\text{-}C_4)$-alkoxy is optionally substituted with up to 5 fluorine atoms;

$R^2$ is selected from the group consisting of hydrogen, cyano, halogen, $(C_1\text{-}C_4)$-alkylsulfonyl, $(C_1\text{-}C_4)$-alkyl, $(C_3\text{-}C_6)$-cycloalkyl and $(C_1\text{-}C_4)$-alkoxy, wherein said $(C_1\text{-}C_4)$-alkyl, $(C_3\text{-}C_6)$-cycloalkyl, or $(C_1\text{-}C_4)$-alkoxy is optionally independently substituted with up to five fluorine atoms, cyano, or $(C_1\text{-}C_2)$ alkyl, wherein said $(C_1\text{-}C_2)$alkyl is optionally substituted with up to five fluorine atoms;

$R^3$ and $R^4$ are independently selected from the group consisting of hydrogen, halogen, $(C_1\text{-}C_4)$-alkyl, and $(C_1\text{-}C_4)$-alkoxy, wherein each said $(C_1\text{-}C_4)$-alkyl and $(C_1\text{-}C_4)$-alkoxy is optionally independently substituted with up to five fluorine atoms;

$R^5$, $R^6$ $R^7$, and $R^8$, when present, are each independently selected from the group consisting of hydrogen, halogen, $(C_1\text{-}C_4)$-alkyl, and $(C_1\text{-}C_4)$-alkoxy, wherein each said $(C_1\text{-}C_4)$-alkyl and $(C_1\text{-}C_4)$-alkoxy is optionally independently substituted with up to five fluorine atoms, provided that at least two of $R^5$, $R^6$, $R^7$ and $R^8$ are hydrogen, or a pharmaceutically acceptable salt thereof, a solvate thereof, or a solvate of a pharmaceutically acceptable salt thereof.

5. The compound of claim 1, wherein $R^2$ is $(C_3\text{-}C_6)$-cycloalkyl substituted with a trifluoromethyl group.

6. The compound of claim 1, wherein the compound is selected from the group consisting of ent-6-fluoro-N-{[4-(1-methyl-1H-pyrazol-5-yl)-2,5-dioxoimidazolidin-4-yl] methyl}-4'-(trifluoromethyl) [biphenyl]-2-carboxamide

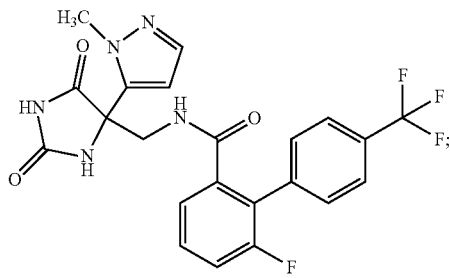 [SMILES: Cn1nccc1C1(CNC(=O)c2cccc(F)c2-c2ccc(C(F)(F)F)cc2)NC(=O)NC1=O]

ent-5,6-difluoro-N-{[4-(1-methyl-1H-pyrazol-5-yl)-2,5-dioxoimidazolidin-4-yl] methyl}-4'-(trifluoromethyl) [biphenyl]-2-carboxamide

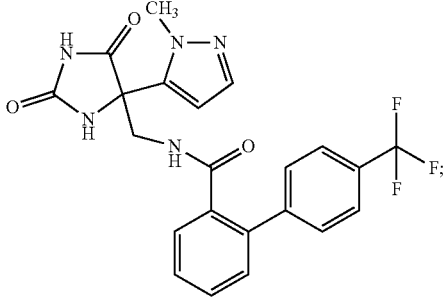

ent-4'-chloro-N-{[4-(1-methyl-1H-pyrazol-5-yl)-2,5-dioxoimidazolidin-4-yl] methyl} [biphenyl]-2-carboxamide

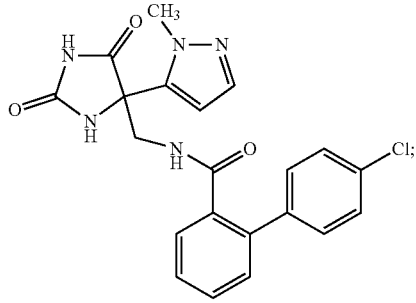 [SMILES: Cn1nccc1C1(CNC(=O)c2ccccc2-c2ccc(Cl)cc2)NC(=O)NC1=O]

ent-4'-chloro-5-fluoro-N-{[4-(1-methyl-1H-pyrazol-5-yl)-2,5-dioxoimidazolidin-4-yl] methyl} [biphenyl]-2-carboxamide

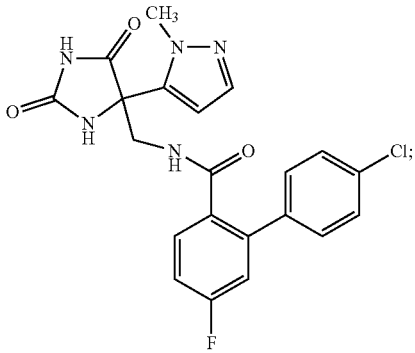 [SMILES: Cn1nccc1C1(CNC(=O)c2ccc(F)cc2-c2ccc(Cl)cc2)NC(=O)NC1=O]

ent-N-{[4-(1-methyl-1H-pyrazol-5-yl)-2,5-dioxoimidazolidin-4-yl] methyl}-4'-(trifluoromethyl) [biphenyl]-2-carboxamide ent-4,5-difluoro-N-{[4-(1-methyl-1H-pyrazol-5-yl)-2,5-dioxoimidazolidin-4-yl] methyl}-4'-(trifluoromethyl) [biphenyl]-2-carboxamide

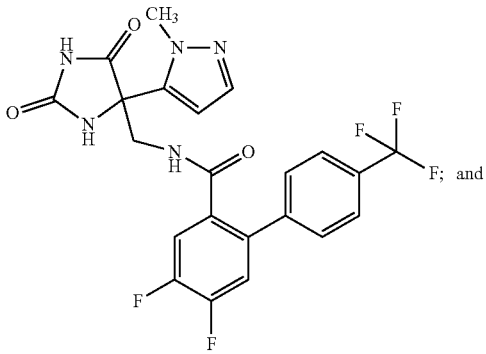 [SMILES: Cn1nccc1C1(CNC(=O)c2cc(F)c(F)cc2-c2ccc(C(F)(F)F)cc2)NC(=O)NC1=O]

ent-N-{[4-(4-methyl-1,2-oxazol-3-yl)-2,5-dioxoimidazolidin-4-yl] methyl}-4'-(trifluoromethyl) [biphenyl]-2-carboxamide

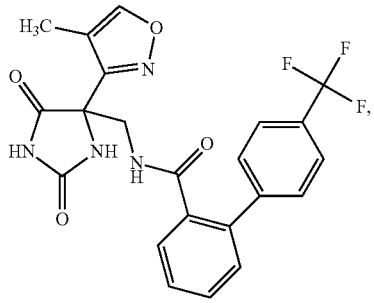 [SMILES: Cc1conc1C1(CNC(=O)c2ccccc2-c2ccc(C(F)(F)F)cc2)NC(=O)NC1=O]

or a pharmaceutically acceptable salt thereof, a solvate thereof, or a solvate of a pharmaceutically acceptable salt thereof.

7. A pharmaceutical composition comprising the compound of claim 1, a pharmaceutically acceptable salt thereof, a solvate thereof, or a solvate of a pharmaceutically acceptable salt thereof, and one or more pharmaceutically acceptable excipients.

8. The pharmaceutical composition of claim 7, further comprising one or more further active ingredients.

9. A method for the treatment of heart disease, vascular disease, cardiovascular disease, lung disease, inflammatory disease, fibrotic disease, metabolic disease or cardiometabolic disease, comprising administering to a mammal in need thereof a therapeutically effective amount of the compound of claim 1.

10. The method of claim 9, wherein the disease is atherosclerosis, coronary artery disease, peripheral vascular disease, arterial occlusive disease, or a post-surgery complication of any of the foregoing.

11. The method of claim 10, wherein the disease is restenosis after angioplasty.

12. The method of claim 9, wherein the mammal is a human.

13. The pharmaceutical composition of claim 7, further comprising one or more therapeutic agents selected from the group consisting of angiotensin-converting enzyme inhibitors, angiotensin-receptor blockers, mineralocorticoid-receptor antagonists, endothelin antagonists, renin inhibitors, calcium blockers, beta-receptor blockers, vasopeptidase inhibitors, sodium-glucose-transport-antagonists, metformin, pioglitazones and dipeptidyl-peptidase-IV inhibitors.

14. A method for the treatment of atherosclerosis or an atherosclerosis-related disease, comprising administering to a mammal in need thereof a therapeutically effective amount of the composition of claim 7.

15. The method of claim 14, wherein the treatment is for an atherosclerosis-related disease selected from the group consisting of coronary artery disease, peripheral vascular disease, arterial occlusive disease, and a post-surgery complication of any of the foregoing.

16. The method of claim 15, wherein the atheroschlerosis-related disease is restenosis after angioplasty.

17. The method of claim 14, wherein the mammal is a human.

\* \* \* \* \*

SEQUENCE LISTING

```
<160> NUMBER OF SEQ ID NOS: 33

<210> SEQ ID NO 1
<211> LENGTH: 562
<212> TYPE: PRT
<213> ORGANISM: Artificial Sequence
<220> FEATURE:
<223> OTHER INFORMATION: rPro-hCD (Rat 1-217/Human 237-537)-TEV-2Strep-
      6His
<220> FEATURE:
<221> NAME/KEY: ADAMTS7 rat prodomain (wild-type)
<222> LOCATION: (1)..(217)
<220> FEATURE:
<221> NAME/KEY: ADAMTS7 human catalytic domain
<222> LOCATION: (218)..(518)
<220> FEATURE:
<221> NAME/KEY: TEV cleavage site, 2xStrep tag, and a His tag
<222> LOCATION: (519)..(562)

<400> SEQUENCE: 1

Met His Arg Gly Leu Asn Leu Leu Ile Leu Cys Ala Leu Ala Pro
1               5                   10                  15

His Val Leu Gly Pro Ala Ser Gly Leu Pro Thr Glu Gly Arg Ala Gly
            20                  25                  30
```

```
Leu Asp Ile Val His Pro Val Arg Val Asp Ala Gly Gly Ser Phe Leu
        35                  40                  45

Ser Tyr Glu Leu Trp Pro Arg Val Leu Arg Lys Arg Asp Val Ser Ala
    50                  55                  60

Ala Gln Ala Ser Ser Ala Phe Tyr Gln Leu Gln Tyr Gln Gly Arg Glu
65              70                  75                  80

Leu Leu Phe Asn Leu Thr Thr Asn Pro Tyr Leu Leu Ala Pro Gly Phe
                85                  90                  95

Val Ser Glu Ile Arg Arg Arg Ser Asn Leu Ser Asn Val His Ile Gln
                100                 105                 110

Thr Ser Val Pro Thr Cys His Leu Leu Gly Asp Val Gln Asp Pro Glu
            115                 120                 125

Leu Glu Gly Gly Phe Ala Ala Ile Ser Ala Cys Asp Gly Leu Arg Gly
        130                 135                 140

Val Phe Gln Leu Ser Asn Glu Asp Tyr Phe Ile Glu Pro Leu Asp Glu
145                 150                 155                 160

Val Pro Ala Gln Pro Gly His Ala Gln Pro His Met Val Tyr Lys His
                165                 170                 175

Lys Arg Ser Gly Gln Gln Asp Asp Ser Arg Thr Ser Gly Thr Cys Gly
                180                 185                 190

Val Gln Gly Ser Pro Glu Leu Lys His Gln Arg Glu His Trp Glu Gln
        195                 200                 205

Arg Gln Gln Lys Arg Arg Gln Gln Arg Ser Val Ser Lys Glu Lys Trp
    210                 215                 220

Val Glu Thr Leu Val Val Ala Asp Ala Lys Met Val Glu Tyr His Gly
225                 230                 235                 240

Gln Pro Gln Val Glu Ser Tyr Val Leu Thr Ile Met Asn Met Val Ala
                245                 250                 255

Gly Leu Phe His Asp Pro Ser Ile Gly Asn Pro Ile His Ile Thr Ile
                260                 265                 270

Val Arg Leu Val Leu Leu Glu Asp Glu Glu Asp Leu Lys Ile Thr
    275                 280                 285

His His Ala Asp Asn Thr Leu Lys Ser Phe Cys Lys Trp Gln Lys Ser
    290                 295                 300

Ile Asn Met Lys Gly Asp Ala His Pro Leu His His Asp Thr Ala Ile
305                 310                 315                 320

Leu Leu Thr Arg Lys Asp Leu Cys Ala Ala Met Asn Arg Pro Cys Glu
                325                 330                 335

Thr Leu Gly Leu Ser His Val Ala Gly Met Cys Gln Pro His Arg Ser
                340                 345                 350

Cys Ser Ile Asn Glu Asp Thr Gly Leu Pro Leu Ala Phe Thr Val Ala
            355                 360                 365

His Glu Leu Gly His Ser Phe Gly Ile Gln His Asp Gly Ser Gly Asn
    370                 375                 380

Asp Cys Glu Pro Val Gly Lys Arg Pro Phe Ile Met Ser Pro Gln Leu
385                 390                 395                 400

Leu Tyr Asp Ala Ala Pro Leu Thr Trp Ser Arg Cys Ser Arg Gln Tyr
                405                 410                 415

Ile Thr Arg Phe Leu Asp Arg Gly Trp Gly Leu Cys Leu Asp Asp Pro
                420                 425                 430

Pro Ala Lys Asp Ile Ile Asp Phe Pro Ser Val Pro Pro Gly Val Leu
            435                 440                 445
```

```
Tyr Asp Val Ser His Gln Cys Arg Leu Gln Tyr Gly Ala Tyr Ser Ala
    450                 455                 460

Phe Cys Glu Asp Met Asp Asn Val Cys His Thr Leu Trp Cys Ser Val
465                 470                 475                 480

Gly Thr Thr Cys His Ser Lys Leu Asp Ala Ala Val Asp Gly Thr Arg
                    485                 490                 495

Cys Gly Glu Asn Lys Trp Cys Leu Ser Gly Glu Cys Val Pro Val Gly
                500                 505                 510

Phe Arg Pro Glu Ala Val Gly Ser Glu Asn Leu Tyr Phe Gln Ser Gly
            515                 520                 525

Trp Ser His Pro Gln Phe Glu Lys Gly Gly Ser Gly Gly Gly Ser
530                 535                 540

Gly Gly Gly Ser Trp Ser His Pro Gln Phe Glu Lys His His His His
545                 550                 555                 560

His His

<210> SEQ ID NO 2
<211> LENGTH: 562
<212> TYPE: PRT
<213> ORGANISM: Artificial Sequence
<220> FEATURE:
<223> OTHER INFORMATION: rPro-hCD-FM2 (Rat 1-217/Human 237-537 FM2
      (Q216K))-TEV-2Strep-6His
<220> FEATURE:
<221> NAME/KEY: ADAMTS7 rat prodomain (furin mutant Q216K)
<222> LOCATION: (1)..(217)
<220> FEATURE:
<221> NAME/KEY: ADAMTS7 human catalytic domain
<222> LOCATION: (218)..(518)
<220> FEATURE:
<221> NAME/KEY: TEV cleavage site, 2xStrep tag, and a His tag
<222> LOCATION: (519)..(562)

<400> SEQUENCE: 2

Met His Arg Gly Leu Asn Leu Leu Ile Leu Cys Ala Leu Ala Pro
1               5                   10                  15

His Val Leu Gly Pro Ala Ser Gly Leu Pro Thr Glu Gly Arg Ala Gly
                20                  25                  30

Leu Asp Ile Val His Pro Val Arg Val Asp Ala Gly Gly Ser Phe Leu
                35                  40                  45

Ser Tyr Glu Leu Trp Pro Arg Val Leu Arg Lys Arg Asp Val Ser Ala
50                  55                  60

Ala Gln Ala Ser Ser Ala Phe Tyr Gln Leu Gln Tyr Gln Gly Arg Glu
65                  70                  75                  80

Leu Leu Phe Asn Leu Thr Thr Asn Pro Tyr Leu Leu Ala Pro Gly Phe
                85                  90                  95

Val Ser Glu Ile Arg Arg Arg Ser Asn Leu Ser Asn Val His Ile Gln
                100                 105                 110

Thr Ser Val Pro Thr Cys His Leu Leu Gly Asp Val Gln Asp Pro Glu
                115                 120                 125

Leu Glu Gly Gly Phe Ala Ala Ile Ser Ala Cys Asp Gly Leu Arg Gly
                130                 135                 140

Val Phe Gln Leu Ser Asn Glu Asp Tyr Phe Ile Glu Pro Leu Asp Glu
145                 150                 155                 160

Val Pro Ala Gln Pro Gly His Ala Gln Pro His Met Val Tyr Lys His
                165                 170                 175

Lys Arg Ser Gly Gln Gln Asp Asp Ser Arg Thr Ser Thr Cys Gly
                180                 185                 190
```

```
Val Gln Gly Ser Pro Glu Leu Lys His Gln Arg Glu His Trp Glu Gln
            195                 200                 205

Arg Gln Gln Lys Arg Arg Gln Lys Arg Ser Val Ser Lys Glu Lys Trp
210                 215                 220

Val Glu Thr Leu Val Val Ala Asp Ala Lys Met Val Glu Tyr His Gly
225                 230                 235                 240

Gln Pro Gln Val Glu Ser Tyr Val Leu Thr Ile Met Asn Met Val Ala
                245                 250                 255

Gly Leu Phe His Asp Pro Ser Ile Gly Asn Pro Ile His Ile Thr Ile
            260                 265                 270

Val Arg Leu Val Leu Leu Glu Asp Glu Glu Asp Leu Lys Ile Thr
        275                 280                 285

His His Ala Asp Asn Thr Leu Lys Ser Phe Cys Lys Trp Gln Lys Ser
    290                 295                 300

Ile Asn Met Lys Gly Asp Ala His Pro Leu His His Asp Thr Ala Ile
305                 310                 315                 320

Leu Leu Thr Arg Lys Asp Leu Cys Ala Ala Met Asn Arg Pro Cys Glu
                325                 330                 335

Thr Leu Gly Leu Ser His Val Ala Gly Met Cys Gln Pro His Arg Ser
            340                 345                 350

Cys Ser Ile Asn Glu Asp Thr Gly Leu Pro Leu Ala Phe Thr Val Ala
355                 360                 365

His Glu Leu Gly His Ser Phe Gly Ile Gln His Asp Gly Ser Gly Asn
        370                 375                 380

Asp Cys Glu Pro Val Gly Lys Arg Pro Phe Ile Met Ser Pro Gln Leu
385                 390                 395                 400

Leu Tyr Asp Ala Ala Pro Leu Thr Trp Ser Arg Cys Ser Arg Gln Tyr
                405                 410                 415

Ile Thr Arg Phe Leu Asp Arg Gly Trp Gly Leu Cys Leu Asp Asp Pro
            420                 425                 430

Pro Ala Lys Asp Ile Ile Asp Phe Pro Ser Val Pro Pro Gly Val Leu
        435                 440                 445

Tyr Asp Val Ser His Gln Cys Arg Leu Gln Tyr Gly Ala Tyr Ser Ala
    450                 455                 460

Phe Cys Glu Asp Met Asp Asn Val Cys His Thr Leu Trp Cys Ser Val
465                 470                 475                 480

Gly Thr Thr Cys His Ser Lys Leu Asp Ala Ala Val Asp Gly Thr Arg
                485                 490                 495

Cys Gly Glu Asn Lys Trp Cys Leu Ser Gly Glu Cys Val Pro Val Gly
            500                 505                 510

Phe Arg Pro Glu Ala Val Gly Ser Glu Asn Leu Tyr Phe Gln Ser Gly
        515                 520                 525

Trp Ser His Pro Gln Phe Glu Lys Gly Gly Gly Ser Gly Gly Gly Ser
    530                 535                 540

Gly Gly Gly Ser Trp Ser His Pro Gln Phe Glu Lys His His His His
545                 550                 555                 560

His His

<210> SEQ ID NO 3
<211> LENGTH: 573
<212> TYPE: PRT
<213> ORGANISM: Artificial Sequence
<220> FEATURE:
<223> OTHER INFORMATION: rADAMTS7 (Rat 1-575)-Flag
```

```
<400> SEQUENCE: 3

Met Pro Cys Ala Gln Gly Asn Trp Met Ala Lys Leu Ser Met Val Ala
1               5                   10                  15

Gln Leu Leu Asn Phe Gly Ala Phe Cys His Gly Arg Gln Ala Gln Pro
            20                  25                  30

Trp Pro Val Arg Phe Pro Asp Pro Lys Gln Glu His Phe Ile Lys Ser
        35                  40                  45

Leu Pro Glu Tyr His Ile Val Ser Pro Val Gln Val Asp Ala Ser Gly
    50                  55                  60

His Phe Leu Ser Tyr Gly Leu His His Pro Val Thr Gly Ser Arg Lys
65                  70                  75                  80

Lys Arg Ala Ala Gly Gly Ser Gly Asp Gln Val Tyr Tyr Arg Ile Ser
                85                  90                  95

His Glu Glu Lys Asn Leu Phe Phe Asn Leu Thr Val Asn Trp Glu Phe
            100                 105                 110

Leu Ser Asn Gly Tyr Val Val Glu Arg Arg Tyr Gly Asn Leu Ser His
        115                 120                 125

Val Lys Met Ala Ala Ser Ser Gly Gln Pro Cys His Leu Arg Gly Thr
    130                 135                 140

Val Leu Gln Gln Gly Pro Thr Ile Arg Met Gly Thr Ala Ala Leu Ser
145                 150                 155                 160

Ala Cys Gln Gly Leu Thr Gly Phe Phe His Leu Pro His Gly Asp Phe
                165                 170                 175

Phe Ile Glu Pro Val Lys Lys His Pro Leu Thr Glu Glu Gly Tyr Gln
            180                 185                 190

Pro His Val Ile Tyr Arg Arg Gln Ser Tyr Arg Val Pro Glu Thr Lys
        195                 200                 205

Glu Pro Thr Cys Gly Leu Lys Asp Ser Leu Asp Asn Ser Val Lys Gln
    210                 215                 220

Glu Leu Gln Arg Glu Lys Trp Glu Arg Lys Asn Trp Pro Ser Arg Ser
225                 230                 235                 240

Leu Ser Arg Arg Ser Ile Ser Lys Glu Arg Trp Val Glu Thr Leu Val
                245                 250                 255

Val Ala Asp Thr Lys Met Ile Glu Tyr His Gly Ser Glu Asn Val Glu
            260                 265                 270

Ser Tyr Ile Leu Thr Ile Met Asn Met Val Thr Gly Leu Phe His Asn
        275                 280                 285

Pro Ser Ile Gly Asn Ala Ile His Ile Val Val Arg Leu Ile Leu
    290                 295                 300

Leu Glu Glu Glu Glu Gln Gly Leu Lys Ile Val His Ala Glu Lys
305                 310                 315                 320

Thr Leu Ser Ser Phe Cys Lys Trp Gln Lys Ser Ile Asn Pro Lys Ser
                325                 330                 335

Asp Leu Asn Pro Val His His Asp Val Ala Val Leu Leu Thr Arg Lys
            340                 345                 350

Asp Ile Cys Ala Gly Phe Asn Arg Pro Cys Glu Thr Leu Gly Leu Ser
        355                 360                 365

His Leu Ser Gly Met Cys Gln Pro His Arg Ser Cys Asn Ile Asn Glu
    370                 375                 380

Asp Ser Gly Leu Pro Leu Ala Phe Thr Ile Ala His Glu Leu Gly His
385                 390                 395                 400

Ser Phe Gly Ile Gln His Asp Gly Lys Glu Asn Asp Cys Glu Pro Val
                405                 410                 415
```

```
Gly Arg His Pro Tyr Ile Met Ser Arg Gln Leu Gln Tyr Asp Pro Thr
            420                 425                 430

Pro Leu Thr Trp Ser Lys Cys Ser Glu Glu Tyr Ile Thr Arg Phe Leu
            435                 440                 445

Asp Arg Gly Trp Gly Phe Cys Leu Asp Asp Ile Pro Lys Lys Lys Gly
            450                 455                 460

Leu Lys Ser Lys Val Ile Ala Pro Gly Val Ile Tyr Asp Val His His
465                 470                 475                 480

Gln Cys Gln Leu Gln Tyr Gly Pro Asn Ala Thr Phe Cys Gln Glu Val
                485                 490                 495

Glu Asn Val Cys Gln Thr Leu Trp Cys Ser Val Lys Gly Phe Cys Arg
            500                 505                 510

Ser Lys Leu Asp Ala Ala Ala Asp Gly Thr Gln Cys Gly Glu Lys Lys
            515                 520                 525

Trp Cys Met Ala Gly Lys Cys Ile Thr Val Gly Lys Lys Pro Glu Ser
            530                 535                 540

Ile Pro Gly Gly Gly Gly Ser Asp Tyr Lys Asp His Asp Gly Asp Tyr
545                 550                 555                 560

Lys Asp His Asp Ile Asp Tyr Lys Asp Asp Asp Lys
                565                 570
```

```
<210> SEQ ID NO 4
<211> LENGTH: 16
<212> TYPE: PRT
<213> ORGANISM: Artificial Sequence
<220> FEATURE:
<223> OTHER INFORMATION: Test substrate for ADAMTS7/12: (HiLyteFluor-488
      )-DELSSMVLELRGLRT-K(QXL520)-NH2

<400> SEQUENCE: 4

Asp Glu Leu Ser Ser Met Val Leu Glu Leu Arg Gly Leu Arg Thr Lys
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: Test Substrate for ADAMTS7/12:
      (HiLyteFluor-488)-SSMVLELRGLRTIVT-K(QXL520)-NH2

<400> SEQUENCE: 5

Ser Ser Met Val Leu Glu Leu Arg Gly Leu Arg Thr Ile Val Thr Lys
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: Test substrate for ADAMTS7/12:
      (HiLyteFluor-488)-KVTEENKELANELRR-K(QXL520)-NH2

<400> SEQUENCE: 6

Lys Val Thr Glu Glu Asn Lys Glu Leu Ala Asn Glu Leu Arg Arg Lys
1               5                   10                  15

<210> SEQ ID NO 7
<211> LENGTH: 16
<212> TYPE: PRT
<213> ORGANISM: Artificial Sequence
<220> FEATURE:
```

```
<223> OTHER INFORMATION: Test Substrate for ADAMTS7/12:
      (HiLyteFluor-488)-EENKELANELRRPPL-K(QXL520)-NH2

<400> SEQUENCE: 7

Glu Glu Asn Lys Glu Leu Ala Asn Glu Leu Arg Arg Pro Pro Leu Lys
1               5                   10                  15

<210> SEQ ID NO 8
<211> LENGTH: 13
<212> TYPE: PRT
<213> ORGANISM: Artificial Sequence
<220> FEATURE:
<223> OTHER INFORMATION: Test Substrate for ADAMTS7/12:
      (HiLyteFluor-488)-SSMVLELRGLRT-K(QXL520)-NH2

<400> SEQUENCE: 8

Ser Ser Met Val Leu Glu Leu Arg Gly Leu Arg Thr Lys
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Test Substrate for ADAMTS7/12: (Donor)
      GMQQSVRTGLPS (K-Quencher)

<400> SEQUENCE: 9

Gly Met Gln Gln Ser Val Arg Thr Gly Leu Pro Ser
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Test Substrate for ADAMTS7/12: (Donor)
      SPGFRCEACPPGYS (K-Quencher)

<400> SEQUENCE: 10

Ser Pro Gly Phe Arg Cys Glu Ala Cys Pro Pro Gly Tyr Ser
1               5                   10

<210> SEQ ID NO 11
<211> LENGTH: 16
<212> TYPE: PRT
<213> ORGANISM: Artificial Sequence
<220> FEATURE:
<223> OTHER INFORMATION: Substrate for ADAMTS7 and for ADAMTS12:
      (HiLyteFluor-488)-DELSSMVLELRGLRT-K(QXL520)-E-NH2

<400> SEQUENCE: 11

Asp Glu Leu Ser Ser Met Val Leu Glu Leu Arg Gly Leu Arg Thr Lys
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: Test Substrate for ADAMTS7/12:
      (HiLyteFluor-488)-DELSSMVLELRGLRT-K(QXL520)-K-NH2

<400> SEQUENCE: 12

Asp Glu Leu Ser Ser Met Val Leu Glu Leu Arg Gly Leu Arg Thr Lys
1               5                   10                  15
```

```
<210> SEQ ID NO 13
<211> LENGTH: 16
<212> TYPE: PRT
<213> ORGANISM: Artificial Sequence
<220> FEATURE:
<223> OTHER INFORMATION: Test Substrate for ADAMTS7/12:
      (HiLyteFluor-488)-DELSSMVLELRGLRT-K(QXL520)-OH

<400> SEQUENCE: 13

Asp Glu Leu Ser Ser Met Val Leu Glu Leu Arg Gly Leu Arg Thr Lys
1               5                   10                  15

<210> SEQ ID NO 14
<211> LENGTH: 10
<212> TYPE: PRT
<213> ORGANISM: Artificial Sequence
<220> FEATURE:
<223> OTHER INFORMATION: Substrate for ADAMTS4 and for ADAMTS5:
      Dabcyl-EEVKAKVQPY-Glu(Edans)-NH2

<400> SEQUENCE: 14

Glu Glu Val Lys Ala Lys Val Gln Pro Tyr
1               5                   10

<210> SEQ ID NO 15
<211> LENGTH: 573
<212> TYPE: PRT
<213> ORGANISM: Artificial Sequence
<220> FEATURE:
<223> OTHER INFORMATION: rPro-hCD for ADAMTS12

<400> SEQUENCE: 15

Met Pro Cys Ala Gln Gly Asn Trp Met Ala Lys Leu Ser Met Val Ala
1               5                   10                  15

Gln Leu Leu Asn Phe Gly Ala Phe Cys His Gly Arg Gln Ala Gln Pro
            20                  25                  30

Trp Pro Val Arg Phe Pro Asp Pro Lys Gln Glu His Phe Ile Lys Ser
        35                  40                  45

Leu Pro Glu Tyr His Ile Val Ser Pro Val Gln Val Asp Ala Ser Gly
    50                  55                  60

His Phe Leu Ser Tyr Gly Leu His His Pro Val Thr Gly Ser Arg Lys
65                  70                  75                  80

Lys Arg Ala Ala Gly Gly Ser Gly Asp Gln Val Tyr Tyr Arg Ile Ser
                85                  90                  95

His Glu Glu Lys Asn Leu Phe Phe Asn Leu Thr Val Asn Trp Glu Phe
            100                 105                 110

Leu Ser Asn Gly Tyr Val Val Glu Arg Arg Tyr Gly Asn Leu Ser His
        115                 120                 125

Val Lys Met Ala Ala Ser Ser Gly Gln Pro Cys His Leu Arg Gly Thr
    130                 135                 140

Val Leu Gln Gln Gly Pro Thr Ile Arg Met Gly Thr Ala Ala Leu Ser
145                 150                 155                 160

Ala Cys Gln Gly Leu Thr Gly Phe Phe His Leu Pro His Gly Asp Phe
                165                 170                 175

Phe Ile Glu Pro Val Lys Lys His Pro Leu Thr Glu Glu Gly Tyr Gln
            180                 185                 190

Pro His Val Ile Tyr Arg Arg Gln Ser Tyr Arg Val Pro Glu Thr Lys
        195                 200                 205

Glu Pro Thr Cys Gly Leu Lys Asp Ser Leu Asp Asn Ser Val Lys Gln
    210                 215                 220
```

```
Glu Leu Gln Arg Glu Lys Trp Glu Arg Lys Asn Trp Pro Ser Arg Ser
225                 230                 235                 240

Leu Ser Arg Arg Ser Ile Ser Lys Glu Arg Trp Val Glu Thr Leu Val
            245                 250                 255

Val Ala Asp Thr Lys Met Ile Glu Tyr His Gly Ser Glu Asn Val Glu
        260                 265                 270

Ser Tyr Ile Leu Thr Ile Met Asn Met Val Thr Gly Leu Phe His Asn
    275                 280                 285

Pro Ser Ile Gly Asn Ala Ile His Ile Val Val Arg Leu Ile Leu
290                 295                 300

Leu Glu Glu Glu Gln Gly Leu Lys Ile Val His His Ala Glu Lys
305                 310                 315                 320

Thr Leu Ser Ser Phe Cys Lys Trp Gln Lys Ser Ile Asn Pro Lys Ser
            325                 330                 335

Asp Leu Asn Pro Val His His Asp Val Ala Val Leu Leu Thr Arg Lys
            340                 345                 350

Asp Ile Cys Ala Gly Phe Asn Arg Pro Cys Glu Thr Leu Gly Leu Ser
        355                 360                 365

His Leu Ser Gly Met Cys Gln Pro His Arg Ser Cys Asn Ile Asn Glu
370                 375                 380

Asp Ser Gly Leu Pro Leu Ala Phe Thr Ile Ala His Glu Leu Gly His
385                 390                 395                 400

Ser Phe Gly Ile Gln His Asp Gly Lys Glu Asn Asp Cys Glu Pro Val
            405                 410                 415

Gly Arg His Pro Tyr Ile Met Ser Arg Gln Leu Gln Tyr Asp Pro Thr
        420                 425                 430

Pro Leu Thr Trp Ser Lys Cys Ser Glu Glu Tyr Ile Thr Arg Phe Leu
        435                 440                 445

Asp Arg Gly Trp Gly Phe Cys Leu Asp Asp Ile Pro Lys Lys Lys Gly
        450                 455                 460

Leu Lys Ser Lys Val Ile Ala Pro Gly Val Ile Tyr Asp Val His His
465                 470                 475                 480

Gln Cys Gln Leu Gln Tyr Gly Pro Asn Ala Thr Phe Cys Gln Glu Val
            485                 490                 495

Glu Asn Val Cys Gln Thr Leu Trp Cys Ser Val Lys Gly Phe Cys Arg
        500                 505                 510

Ser Lys Leu Asp Ala Ala Ala Asp Gly Thr Gln Cys Gly Glu Lys Lys
        515                 520                 525

Trp Cys Met Ala Gly Lys Cys Ile Thr Val Gly Lys Lys Pro Glu Ser
        530                 535                 540

Ile Pro Gly Gly Gly Gly Ser Asp Tyr Lys Asp His Asp Gly Asp Tyr
545                 550                 555                 560

Lys Asp His Asp Ile Asp Tyr Lys Asp Asp Asp Lys
                565                 570
```

<210> SEQ ID NO 16
<211> LENGTH: 14
<212> TYPE: PRT
<213> ORGANISM: Artificial Sequence
<220> FEATURE:
<223> OTHER INFORMATION: ADAMTS Catalytic Motif Consensus Sequence
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature

```
<222> LOCATION: (6)..(6)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 16

His Glu Xaa Xaa His Xaa Asx Gly Asn Ser Asx Xaa His Asp
1               5                   10

<210> SEQ ID NO 17
<211> LENGTH: 7
<212> TYPE: PRT
<213> ORGANISM: Artificial Sequence
<220> FEATURE:
<223> OTHER INFORMATION: Substrate for MMP12: Mca-Pro-Leu-Gly-Leu-Glu-
      Glu-Ala-Dap(Dnp)-NH2

<400> SEQUENCE: 17

Pro Leu Gly Leu Glu Glu Ala
1               5

<210> SEQ ID NO 18
<211> LENGTH: 8
<212> TYPE: PRT
<213> ORGANISM: Artificial Sequence
<220> FEATURE:
<223> OTHER INFORMATION: Substrate for MMP15: MCA-Lys-Pro-Leu-Gly-Leu-
      DPA-Ala-Arg-NH2
<220> FEATURE:
<221> NAME/KEY: X
<222> LOCATION: (6)..(6)
<223> OTHER INFORMATION: DPA

<400> SEQUENCE: 18

Lys Pro Leu Gly Leu Xaa Ala Arg
1               5

<210> SEQ ID NO 19
<211> LENGTH: 7
<212> TYPE: PRT
<213> ORGANISM: Artificial Sequence
<220> FEATURE:
<223> OTHER INFORMATION: Substrate for MMP2: MCA-Pro-Leu-Gly-Leu-DPA-
      Ala-Arg-NH2
<220> FEATURE:
<221> NAME/KEY: X
<222> LOCATION: (5)..(5)
<223> OTHER INFORMATION: DPA

<400> SEQUENCE: 19

Pro Leu Gly Leu Xaa Ala Arg
1               5

<210> SEQ ID NO 20
<211> LENGTH: 12
<212> TYPE: PRT
<213> ORGANISM: Artificial Sequence
<220> FEATURE:
<223> OTHER INFORMATION: Substrate for ADAM17:
      Mca-Pro-Leu-Ala-Gln-Ala-Val-Dap(Dnp)-Arg-Ser-Ser-Ser-Arg-NH2
<220> FEATURE:
<221> NAME/KEY: X
<222> LOCATION: (7)..(7)
<223> OTHER INFORMATION: Dap(Dnp)

<400> SEQUENCE: 20

Pro Leu Ala Gln Ala Val Xaa Arg Ser Ser Ser Arg
1               5                   10
```

-continued

```
<210> SEQ ID NO 21
<211> LENGTH: 1686
<212> TYPE: PRT
<213> ORGANISM: Artificial Sequence
<220> FEATURE:
<223> OTHER INFORMATION: Human ADAMTS7 from Q9UKP4

<400> SEQUENCE: 21
```

| | | | | | | | | | | | | | | |
|---|---|---|---|---|---|---|---|---|---|---|---|---|---|---|
| Met | Pro | Gly | Gly | Pro | Ser | Pro | Arg | Ser | Pro | Ala | Pro | Leu | Leu | Arg | Pro |
| 1 | | | | 5 | | | | | 10 | | | | | 15 | |
| Leu | Leu | Leu | Leu | Leu | Cys | Ala | Leu | Ala | Pro | Gly | Ala | Pro | Gly | Pro | Ala |
| | | | 20 | | | | | 25 | | | | | 30 | | |
| Pro | Gly | Arg | Ala | Thr | Glu | Gly | Arg | Ala | Ala | Leu | Asp | Ile | Val | His | Pro |
| | | 35 | | | | | 40 | | | | | 45 | | | |
| Val | Arg | Val | Asp | Ala | Gly | Gly | Ser | Phe | Leu | Ser | Tyr | Glu | Leu | Trp | Pro |
| 50 | | | | | 55 | | | | | 60 | | | | | |
| Arg | Ala | Leu | Arg | Lys | Arg | Asp | Val | Ser | Val | Arg | Arg | Asp | Ala | Pro | Ala |
| 65 | | | | | 70 | | | | | 75 | | | | | 80 |
| Phe | Tyr | Glu | Leu | Gln | Tyr | Arg | Gly | Arg | Glu | Leu | Arg | Phe | Asn | Leu | Thr |
| | | | | 85 | | | | | 90 | | | | | 95 | |
| Ala | Asn | Gln | His | Leu | Leu | Ala | Pro | Gly | Phe | Val | Ser | Glu | Thr | Arg | Arg |
| | | | 100 | | | | | 105 | | | | | 110 | | |
| Arg | Gly | Gly | Leu | Gly | Arg | Ala | His | Ile | Arg | Ala | His | Thr | Pro | Ala | Cys |
| | | 115 | | | | | 120 | | | | | 125 | | | |
| His | Leu | Leu | Gly | Glu | Val | Gln | Asp | Pro | Glu | Leu | Glu | Gly | Gly | Leu | Ala |
| | 130 | | | | | 135 | | | | | 140 | | | | |
| Ala | Ile | Ser | Ala | Cys | Asp | Gly | Leu | Lys | Gly | Val | Phe | Gln | Leu | Ser | Asn |
| 145 | | | | | 150 | | | | | 155 | | | | | 160 |
| Glu | Asp | Tyr | Phe | Ile | Glu | Pro | Leu | Asp | Ser | Ala | Pro | Ala | Arg | Pro | Gly |
| | | | | 165 | | | | | 170 | | | | | 175 | |
| His | Ala | Gln | Pro | His | Val | Val | Tyr | Lys | Arg | Gln | Ala | Pro | Glu | Arg | Leu |
| | | | 180 | | | | | 185 | | | | | 190 | | |
| Ala | Gln | Arg | Gly | Asp | Ser | Ser | Ala | Pro | Ser | Thr | Cys | Gly | Val | Gln | Val |
| | | 195 | | | | | 200 | | | | | 205 | | | |
| Tyr | Pro | Glu | Leu | Glu | Ser | Arg | Arg | Glu | Arg | Trp | Glu | Gln | Arg | Gln | Gln |
| | 210 | | | | | 215 | | | | | 220 | | | | |
| Trp | Arg | Arg | Pro | Arg | Leu | Arg | Arg | Leu | His | Gln | Arg | Ser | Val | Ser | Lys |
| 225 | | | | | 230 | | | | | 235 | | | | | 240 |
| Glu | Lys | Trp | Val | Glu | Thr | Leu | Val | Val | Ala | Asp | Ala | Lys | Met | Val | Glu |
| | | | | 245 | | | | | 250 | | | | | 255 | |
| Tyr | His | Gly | Gln | Pro | Gln | Val | Glu | Ser | Tyr | Val | Leu | Thr | Ile | Met | Asn |
| | | | 260 | | | | | 265 | | | | | 270 | | |
| Met | Val | Ala | Gly | Leu | Phe | His | Asp | Pro | Ser | Ile | Gly | Asn | Pro | Ile | His |
| | | 275 | | | | | 280 | | | | | 285 | | | |
| Ile | Thr | Ile | Val | Arg | Leu | Val | Leu | Leu | Glu | Asp | Glu | Glu | Asp | Leu |
| | 290 | | | | | 295 | | | | | 300 | | | | |
| Lys | Ile | Thr | His | His | Ala | Asp | Asn | Thr | Leu | Lys | Ser | Phe | Cys | Lys | Trp |
| 305 | | | | | 310 | | | | | 315 | | | | | 320 |
| Gln | Lys | Ser | Ile | Asn | Met | Lys | Gly | Asp | Ala | His | Pro | Leu | His | His | Asp |
| | | | | 325 | | | | | 330 | | | | | 335 | |
| Thr | Ala | Ile | Leu | Leu | Thr | Arg | Lys | Asp | Leu | Cys | Ala | Ala | Met | Asn | Arg |
| | | | 340 | | | | | 345 | | | | | 350 | | |
| Pro | Cys | Glu | Thr | Leu | Gly | Leu | Ser | His | Val | Ala | Gly | Met | Cys | Gln | Pro |
| | | 355 | | | | | 360 | | | | | 365 | | | |

-continued

```
His Arg Ser Cys Ser Ile Asn Glu Asp Thr Gly Leu Pro Leu Ala Phe
    370                 375                 380

Thr Val Ala His Glu Leu Gly His Ser Phe Gly Ile Gln His Asp Gly
385                 390                 395                 400

Ser Gly Asn Asp Cys Glu Pro Val Gly Lys Arg Pro Phe Ile Met Ser
                405                 410                 415

Pro Gln Leu Leu Tyr Asp Ala Ala Pro Leu Thr Trp Ser Arg Cys Ser
            420                 425                 430

Arg Gln Tyr Ile Thr Arg Phe Leu Asp Arg Gly Trp Gly Leu Cys Leu
        435                 440                 445

Asp Asp Pro Pro Ala Lys Asp Ile Ile Asp Phe Pro Ser Val Pro Pro
    450                 455                 460

Gly Val Leu Tyr Asp Val Ser His Gln Cys Arg Leu Gln Tyr Gly Ala
465                 470                 475                 480

Tyr Ser Ala Phe Cys Glu Asp Met Asp Asn Val Cys His Thr Leu Trp
                485                 490                 495

Cys Ser Val Gly Thr Thr Cys His Ser Lys Leu Asp Ala Ala Val Asp
            500                 505                 510

Gly Thr Arg Cys Gly Glu Asn Lys Trp Cys Leu Ser Gly Glu Cys Val
        515                 520                 525

Pro Val Gly Phe Arg Pro Glu Ala Val Asp Gly Gly Trp Ser Gly Trp
    530                 535                 540

Ser Ala Trp Ser Ile Cys Ser Arg Ser Cys Gly Met Gly Val Gln Ser
545                 550                 555                 560

Ala Glu Arg Gln Cys Thr Gln Pro Thr Pro Lys Tyr Lys Gly Arg Tyr
                565                 570                 575

Cys Val Gly Glu Arg Lys Arg Phe Arg Leu Cys Asn Leu Gln Ala Cys
            580                 585                 590

Pro Ala Gly Arg Pro Ser Phe Arg His Val Gln Cys Ser His Phe Asp
        595                 600                 605

Ala Met Leu Tyr Lys Gly Gln Leu His Thr Trp Val Pro Val Val Asn
    610                 615                 620

Asp Val Asn Pro Cys Glu Leu His Cys Arg Pro Ala Asn Glu Tyr Phe
625                 630                 635                 640

Ala Glu Lys Leu Arg Asp Ala Val Val Asp Gly Thr Pro Cys Tyr Gln
                645                 650                 655

Val Arg Ala Ser Arg Asp Leu Cys Ile Asn Gly Ile Cys Lys Asn Val
            660                 665                 670

Gly Cys Asp Phe Glu Ile Asp Ser Gly Ala Met Glu Asp Arg Cys Gly
        675                 680                 685

Val Cys His Gly Asn Gly Ser Thr Cys His Thr Val Ser Gly Thr Phe
    690                 695                 700

Glu Glu Ala Glu Gly Leu Gly Tyr Val Asp Val Gly Leu Ile Pro Ala
705                 710                 715                 720

Gly Ala Arg Glu Ile Arg Ile Gln Glu Val Ala Glu Ala Ala Asn Phe
                725                 730                 735

Leu Ala Leu Arg Ser Glu Asp Pro Glu Lys Tyr Phe Leu Asn Gly Gly
            740                 745                 750

Trp Thr Ile Gln Trp Asn Gly Asp Tyr Gln Val Ala Gly Thr Thr Phe
        755                 760                 765

Thr Tyr Ala Arg Arg Gly Asn Trp Glu Asn Leu Thr Ser Pro Gly Pro
    770                 775                 780
```

```
Thr Lys Glu Pro Val Trp Ile Gln Leu Leu Phe Gln Glu Ser Asn Pro
785                 790                 795                 800

Gly Val His Tyr Glu Tyr Thr Ile His Arg Glu Ala Gly Gly His Asp
                805                 810                 815

Glu Val Pro Pro Pro Val Phe Ser Trp His Tyr Gly Pro Trp Thr Lys
                820                 825                 830

Cys Thr Val Thr Cys Gly Arg Gly Val Gln Arg Gln Asn Val Tyr Cys
                835                 840                 845

Leu Glu Arg Gln Ala Gly Pro Val Asp Glu Glu His Cys Asp Pro Leu
    850                 855                 860

Gly Arg Pro Asp Asp Gln Gln Arg Lys Cys Ser Glu Gln Pro Cys Pro
865                 870                 875                 880

Ala Arg Trp Trp Ala Gly Glu Trp Gln Leu Cys Ser Ser Cys Gly
                885                 890                 895

Pro Gly Gly Leu Ser Arg Arg Ala Val Leu Cys Ile Arg Ser Val Gly
                900                 905                 910

Leu Asp Glu Gln Ser Ala Leu Glu Pro Pro Ala Cys Glu His Leu Pro
                915                 920                 925

Arg Pro Pro Thr Glu Thr Pro Cys Asn Arg His Val Pro Cys Pro Ala
930                 935                 940

Thr Trp Ala Val Gly Asn Trp Ser Gln Cys Ser Val Thr Cys Gly Glu
945                 950                 955                 960

Gly Thr Gln Arg Arg Asn Val Leu Cys Thr Asn Asp Thr Gly Val Pro
                965                 970                 975

Cys Asp Glu Ala Gln Gln Pro Ala Ser Glu Val Thr Cys Ser Leu Pro
                980                 985                 990

Leu Cys Arg Trp Pro Leu Gly Thr Leu Gly Pro Glu Gly Ser Gly Ser
            995                 1000                 1005

Gly Ser Ser Ser His Glu Leu Phe Asn Glu Ala Asp Phe Ile Pro
    1010                 1015                 1020

His His Leu Ala Pro Arg Pro Ser Pro Ala Ser Ser Pro Lys Pro
    1025                 1030                 1035

Gly Thr Met Gly Asn Ala Ile Glu Glu Glu Ala Pro Glu Leu Asp
    1040                 1045                 1050

Leu Pro Gly Pro Val Phe Val Asp Asp Phe Tyr Tyr Asp Tyr Asn
    1055                 1060                 1065

Phe Ile Asn Phe His Glu Asp Leu Ser Tyr Gly Pro Ser Glu Glu
    1070                 1075                 1080

Pro Asp Leu Asp Leu Ala Gly Thr Gly Asp Arg Thr Pro Pro Pro
    1085                 1090                 1095

His Ser His Pro Ala Ala Pro Ser Thr Gly Ser Pro Val Pro Ala
    1100                 1105                 1110

Thr Glu Pro Pro Ala Ala Lys Glu Glu Gly Val Leu Gly Pro Trp
    1115                 1120                 1125

Ser Pro Ser Pro Trp Pro Ser Gln Ala Gly Arg Ser Pro Pro Pro
    1130                 1135                 1140

Pro Ser Glu Gln Thr Pro Gly Asn Pro Leu Ile Asn Phe Leu Pro
    1145                 1150                 1155

Glu Glu Asp Thr Pro Ile Gly Ala Pro Asp Leu Gly Leu Pro Ser
    1160                 1165                 1170

Leu Ser Trp Pro Arg Val Ser Thr Asp Gly Leu Gln Thr Pro Ala
    1175                 1180                 1185

Thr Pro Glu Ser Gln Asn Asp Phe Pro Val Gly Lys Asp Ser Gln
```

-continued

|  | 1190 |  |  |  | 1195 |  |  |  | 1200 |  |
| Ser | Gln | Leu | Pro | Pro | Pro | Trp | Arg | Asp | Arg | Thr | Asn | Glu | Val | Phe |
|  | 1205 |  |  |  | 1210 |  |  |  | 1215 |  |

Lys Asp Asp Glu Glu Pro Lys Gly Arg Gly Ala Pro His Leu Pro
  1220              1225              1230

Pro Arg Pro Ser Ser Thr Leu Pro Pro Leu Ser Pro Val Gly Ser
  1235              1240              1245

Thr His Ser Ser Pro Ser Pro Asp Val Ala Glu Leu Trp Thr Gly
  1250              1255              1260

Gly Thr Val Ala Trp Glu Pro Ala Leu Glu Gly Gly Leu Gly Pro
  1265              1270              1275

Val Asp Ser Glu Leu Trp Pro Thr Val Gly Val Ala Ser Leu Leu
  1280              1285              1290

Pro Pro Pro Ile Ala Pro Leu Pro Glu Met Lys Val Arg Asp Ser
  1295              1300              1305

Ser Leu Glu Pro Gly Thr Pro Ser Phe Pro Thr Pro Gly Pro Gly
  1310              1315              1320

Ser Trp Asp Leu Gln Thr Val Ala Val Trp Gly Thr Phe Leu Pro
  1325              1330              1335

Thr Thr Leu Thr Gly Leu Gly His Met Pro Glu Pro Ala Leu Asn
  1340              1345              1350

Pro Gly Pro Lys Gly Gln Pro Glu Ser Leu Ser Pro Glu Val Pro
  1355              1360              1365

Leu Ser Ser Arg Leu Leu Ser Thr Pro Ala Trp Asp Ser Pro Ala
  1370              1375              1380

Asn Ser His Arg Val Pro Glu Thr Gln Pro Leu Ala Pro Ser Leu
  1385              1390              1395

Ala Glu Ala Gly Pro Pro Ala Asp Pro Leu Val Val Arg Asn Ala
  1400              1405              1410

Gly Trp Gln Ala Gly Asn Trp Ser Glu Cys Ser Thr Thr Cys Gly
  1415              1420              1425

Leu Gly Ala Val Trp Arg Pro Val Arg Cys Ser Ser Gly Arg Asp
  1430              1435              1440

Glu Asp Cys Ala Pro Ala Gly Arg Pro Gln Pro Ala Arg Arg Cys
  1445              1450              1455

His Leu Arg Pro Cys Ala Thr Trp His Ser Gly Asn Trp Ser Lys
  1460              1465              1470

Cys Ser Arg Ser Cys Gly Gly Gly Ser Ser Val Arg Asp Val Gln
  1475              1480              1485

Cys Val Asp Thr Arg Asp Leu Arg Pro Leu Arg Pro Phe His Cys
  1490              1495              1500

Gln Pro Gly Pro Ala Lys Pro Pro Ala His Arg Pro Cys Gly Ala
  1505              1510              1515

Gln Pro Cys Leu Ser Trp Tyr Thr Ser Ser Trp Arg Glu Cys Ser
  1520              1525              1530

Glu Ala Cys Gly Gly Gly Glu Gln Gln Arg Leu Val Thr Cys Pro
  1535              1540              1545

Glu Pro Gly Leu Cys Glu Glu Ala Leu Arg Pro Asn Thr Thr Arg
  1550              1555              1560

Pro Cys Asn Thr His Pro Cys Thr Gln Trp Val Val Gly Pro Trp
  1565              1570              1575

Gly Gln Cys Ser Gly Pro Cys Gly Gly Gly Val Gln Arg Arg Leu
  1580              1585              1590

```
Val Lys Cys Val Asn Thr Gln Thr Gly Leu Pro Glu Glu Asp Ser
    1595                1600                1605

Asp Gln Cys Gly His Glu Ala Trp Pro Glu Ser Ser Arg Pro Cys
    1610                1615                1620

Gly Thr Glu Asp Cys Glu Pro Val Glu Pro Pro Arg Cys Glu Arg
    1625                1630                1635

Asp Arg Leu Ser Phe Gly Phe Cys Glu Thr Leu Arg Leu Leu Gly
    1640                1645                1650

Arg Cys Gln Leu Pro Thr Ile Arg Thr Gln Cys Cys Arg Ser Cys
    1655                1660                1665

Ser Pro Pro Ser His Gly Ala Pro Ser Arg Gly His Gln Arg Val
    1670                1675                1680

Ala Arg Arg
    1685

<210> SEQ ID NO 22
<211> LENGTH: 1595
<212> TYPE: PRT
<213> ORGANISM: Artificial Sequence
<220> FEATURE:
<223> OTHER INFORMATION: Rat ADAMTS7 from Q1EHB3

<400> SEQUENCE: 22

Met His Arg Gly Leu Asn Leu Leu Ile Leu Cys Ala Leu Ala Pro
1               5                   10                  15

His Val Leu Gly Pro Ala Ser Gly Leu Pro Thr Glu Gly Arg Ala Gly
                20                  25                  30

Leu Asp Ile Val His Pro Val Arg Val Asp Ala Gly Gly Ser Phe Leu
                35                  40                  45

Ser Tyr Glu Leu Trp Pro Arg Val Leu Arg Lys Arg Asp Val Ser Ala
                50                  55                  60

Ala Gln Ala Ser Ser Ala Phe Tyr Gln Leu Gln Tyr Gln Gly Arg Glu
65                  70                  75                  80

Leu Leu Phe Asn Leu Thr Thr Asn Pro Tyr Leu Leu Ala Pro Gly Phe
                85                  90                  95

Val Ser Glu Ile Arg Arg Arg Ser Asn Leu Ser Asn Val His Ile Gln
                100                 105                 110

Thr Ser Val Pro Thr Cys His Leu Leu Gly Asp Val Gln Asp Pro Glu
                115                 120                 125

Leu Glu Gly Gly Phe Ala Ala Ile Ser Ala Cys Asp Gly Leu Arg Gly
                130                 135                 140

Val Phe Gln Leu Ser Asn Glu Asp Tyr Phe Ile Glu Pro Leu Asp Glu
145                 150                 155                 160

Val Pro Ala Gln Pro Gly His Ala Gln Pro His Met Val Tyr Lys His
                165                 170                 175

Lys Arg Ser Gly Gln Gln Asp Asp Ser Arg Thr Ser Gly Thr Cys Gly
                180                 185                 190

Val Gln Gly Ser Pro Glu Leu Lys His Gln Arg Glu His Trp Glu Gln
                195                 200                 205

Arg Gln Gln Lys Arg Arg Gln Gln Arg Ser Ile Ser Lys Glu Lys Trp
                210                 215                 220

Val Glu Thr Leu Val Val Ala Asp Ser Lys Met Val Glu Tyr His Gly
225                 230                 235                 240

Gln Pro Gln Val Glu Ser Tyr Val Leu Thr Ile Met Asn Met Val Ala
                245                 250                 255
```

Gly Leu Tyr His Asp Pro Ser Ile Gly Asn Pro Ile His Ile Thr Val
            260                 265                 270

Val Arg Leu Ile Ile Leu Glu Asp Glu Lys Asp Leu Lys Ile Thr
        275                 280                 285

His His Ala Asp Asp Thr Leu Lys Asn Phe Cys Arg Trp Gln Lys Asn
290                 295                 300

Val Asn Met Lys Gly Asp His Pro Gln His Asp Thr Ala Ile
305                 310                 315                 320

Leu Leu Thr Arg Lys Asp Leu Cys Ala Thr Met Asn His Pro Cys Glu
            325                 330                 335

Thr Leu Gly Leu Ser His Val Ala Gly Leu Cys His Pro Gln Leu Ser
            340                 345                 350

Cys Ser Val Ser Glu Asp Thr Gly Leu Pro Leu Ala Phe Thr Val Ala
            355                 360                 365

His Glu Leu Gly His Ser Phe Gly Ile Gln His Asp Gly Thr Gly Asn
    370                 375                 380

Asp Cys Glu Ser Ile Gly Lys Arg Pro Phe Ile Met Ser Pro Gln Leu
385                 390                 395                 400

Leu Tyr Asp Arg Gly Ile Pro Leu Thr Trp Ser Arg Cys Ser Arg Glu
            405                 410                 415

Tyr Ile Thr Arg Phe Leu Asp Arg Gly Trp Gly Leu Cys Leu Asp Asp
            420                 425                 430

Arg Pro Ser Lys Gly Val Ile Asn Phe Pro Ser Val Leu Pro Gly Val
435                 440                 445

Leu Tyr Asp Val Asn His Gln Cys Arg Leu Gln Tyr Gly Pro Ser Ser
    450                 455                 460

Ala Tyr Cys Glu Asp Val Asp Asn Val Cys Tyr Thr Leu Trp Cys Ser
465                 470                 475                 480

Val Gly Thr Thr Cys His Ser Lys Met Asp Ala Ala Val Asp Gly Thr
            485                 490                 495

Ser Cys Gly Lys Asn Lys Trp Cys Leu Asn Gly Glu Cys Val Pro Glu
        500                 505                 510

Gly Phe Gln Pro Glu Thr Val Asp Gly Gly Trp Ser Gly Trp Ser Ala
        515                 520                 525

Trp Ser Val Cys Ser Arg Ser Cys Gly Val Gly Val Arg Ser Ser Glu
        530                 535                 540

Arg Gln Cys Thr Gln Pro Val Pro Lys Asn Lys Gly Lys Tyr Cys Val
545                 550                 555                 560

Gly Glu Arg Lys Arg Tyr Arg Leu Cys Asn Leu Gln Ala Cys Pro Pro
            565                 570                 575

Asp Arg Pro Ser Phe Arg His Thr Gln Cys Ser Gln Phe Asp Ser Met
            580                 585                 590

Leu Tyr Lys Gly Lys Leu His Lys Trp Val Pro Val Leu Asn Asp Glu
            595                 600                 605

Asn Pro Cys Glu Leu His Cys Arg Pro Phe Asn Tyr Ser Asn Arg Glu
            610                 615                 620

Lys Leu Arg Asp Ala Val Met Asp Gly Thr Pro Cys Tyr Gln Gly Arg
625                 630                 635                 640

Ile Ser Arg Asp Ile Cys Ile Asp Gly Ile Cys Lys Lys Val Gly Cys
                645                 650                 655

Asp Phe Glu Leu Asp Ser Gly Ala Glu Glu Asp Arg Cys Gly Val Cys
            660                 665                 670

```
Arg Gly Asp Gly Ser Thr Cys His Thr Val Ser Arg Thr Phe Lys Glu
            675                 680                 685

Ala Glu Gly Met Gly Tyr Val Asp Val Gly Leu Ile Pro Ala Gly Ala
    690                 695                 700

Arg Glu Ile Leu Ile Glu Glu Val Ala Glu Ala Ala Asn Phe Leu Ala
705                 710                 715                 720

Leu Arg Ser Glu Asp Pro Asp Lys Tyr Phe Leu Asn Gly Gly Trp Thr
                725                 730                 735

Ile Gln Trp Asn Gly Asp Tyr Gln Val Ala Gly Thr Thr Phe Thr Tyr
            740                 745                 750

Thr Arg Lys Gly Asn Trp Glu Thr Leu Thr Ser Pro Gly Pro Thr Thr
        755                 760                 765

Glu Pro Val Trp Ile Gln Leu Leu Phe Gln Glu Arg Asn Pro Gly Val
    770                 775                 780

His Tyr Lys Tyr Thr Ile Gln Arg Ala Ser His Ser Glu Ala Gln Pro
785                 790                 795                 800

Pro Glu Phe Ser Trp His Tyr Gly Pro Trp Ser Lys Cys Pro Val Thr
                805                 810                 815

Cys Gly Thr Gly Val Gln Arg Gln Ser Leu Tyr Cys Met Glu Lys Gln
            820                 825                 830

Ala Gly Ile Val Asp Glu Gly His Cys Asp His Leu Ser Arg Pro Arg
        835                 840                 845

Asp Arg Lys Arg Lys Cys Asn Glu Glu Pro Cys Pro Ala Arg Trp Trp
    850                 855                 860

Val Gly Asp Trp Gln Pro Cys Ser Arg Ser Cys Gly Pro Gly Gly Phe
865                 870                 875                 880

Phe Arg Arg Ala Val Phe Cys Thr Arg Ser Val Gly Leu Asp Glu Gln
                885                 890                 895

Arg Ala Leu Glu Pro Ser Ala Cys Gly His Leu Pro Arg Pro Leu Ala
            900                 905                 910

Glu Ile Pro Cys Tyr His Tyr Val Ala Cys Pro Ser Ser Trp Gly Val
        915                 920                 925

Gly Asn Trp Ser Gln Cys Ser Val Thr Cys Gly Ala Gly Ile Arg Gln
    930                 935                 940

Arg Ser Val Leu Cys Ile Asn Asn Thr Gly Val Pro Cys Asp Gly Ala
945                 950                 955                 960

Glu Arg Pro Ile Thr Glu Thr Phe Cys Phe Leu Gln Pro Cys Gln Tyr
                965                 970                 975

Ser Thr Tyr Ile Val Asp Thr Gly Ala Ser Gly Ser Gly Ser Ser
            980                 985                 990

Pro Glu Leu Phe Asn Glu Val Asp Phe Asp Pro His Gln Pro Val Pro
        995                 1000                1005

Arg Pro Ser Pro Ala Ser Ser Pro Lys Pro Val Ser Ile Ser Asn
    1010                1015                1020

Ala Ile Asp Glu Glu Asp Pro Glu Leu Asp Pro Pro Gly Pro Val
    1025                1030                1035

Phe Val Asp Asp Phe Tyr Tyr Asp Tyr Asn Phe Ile Asn Phe His
    1040                1045                1050

Glu Asp Leu Ser Tyr Gly Ser Phe Glu Glu Ser His Ser Asp Leu
    1055                1060                1065

Val Asp Ile Gly Gly Gln Thr Val Pro Pro His Ile Arg Pro Thr
    1070                1075                1080

Glu Pro Pro Ser Asp Ser Pro Val Pro Thr Ala Gly Ala Pro Gly
```

```
                1085                1090                1095

Ala Glu Glu Glu Gly Ile Gln Gly Ser Trp Ser Pro Ser Pro Leu
        1100                1105                1110

Leu Ser Glu Ala Ser His Ser Pro Pro Val Leu Leu Glu Asn Thr
        1115                1120                1125

Pro Val Asn Pro Leu Ala Asn Phe Leu Thr Glu Glu Glu Ser Pro
        1130                1135                1140

Ile Gly Ala Pro Glu Leu Gly Leu Pro Ser Val Ser Trp Pro Pro
        1145                1150                1155

Ala Ser Val Asp Gly Met Val Thr Ser Val Ala Pro Gly Asn Pro
        1160                1165                1170

Asp Glu Leu Leu Val Arg Glu Asp Thr Gln Ser Gln Pro Ser Thr
        1175                1180                1185

Pro Trp Ser Asp Arg Asn Lys Leu Ser Lys Asp Gly Asn Pro Leu
        1190                1195                1200

Gly Pro Thr Ser Pro Ala Leu Pro Lys Ser Pro Phe Pro Thr Gln
        1205                1210                1215

Pro Ser Ser Pro Ser Asn Ser Thr Thr Gln Ala Ser Leu Ser Pro
        1220                1225                1230

Asp Ala Val Glu Val Ser Thr Gly Trp Asn Val Ala Leu Asp Pro
        1235                1240                1245

Val Leu Glu Ala Asp Leu Lys Pro Val His Ala Pro Thr Asp Pro
        1250                1255                1260

Gly Leu Leu Asp Gln Ile Gln Thr Pro His Thr Glu Gly Thr Gln
        1265                1270                1275

Ser Pro Gly Leu Leu Pro Arg Pro Ala Gln Glu Thr Gln Thr Asn
        1280                1285                1290

Ser Ser Lys Asp Pro Ala Val Gln Pro Leu Gln Pro Ser Leu Val
        1295                1300                1305

Glu Asp Gly Ala Pro Thr Asp Leu Leu Pro Ala Lys Asn Ala Ser
        1310                1315                1320

Trp Gln Val Gly Asn Trp Ser Gln Cys Ser Thr Thr Cys Gly Leu
        1325                1330                1335

Gly Ala Ile Trp Arg Leu Val Arg Cys Ser Ser Gly Asn Asp Glu
        1340                1345                1350

Asp Cys Thr Leu Ser Ser Arg Pro Gln Pro Ala Arg His Cys His
        1355                1360                1365

Leu Arg Pro Cys Ala Ala Trp Arg Ala Gly Asn Trp Ser Lys Cys
        1370                1375                1380

Ser Arg Asn Cys Gly Gly Gly Ser Ala Thr Arg Asp Val Gln Cys
        1385                1390                1395

Val Asp Thr Arg Asp Leu Arg Pro Leu Arg Pro Phe His Cys Gln
        1400                1405                1410

Pro Gly Pro Thr Lys Pro Pro Thr Arg Gln Leu Cys Gly Thr Gln
        1415                1420                1425

Pro Cys Leu Pro Trp Tyr Thr Ser Ser Trp Arg Glu Cys Ser Glu
        1430                1435                1440

Ala Cys Gly Gly Gly Glu Gln Arg Leu Val Thr Cys Pro Glu
        1445                1450                1455

Pro Gly Leu Cys Glu Glu Ser Leu Arg Pro Asn Asn Thr Arg Pro
        1460                1465                1470

Cys Asn Thr His Pro Cys Thr Gln Trp Val Val Gly Pro Trp Gly
        1475                1480                1485
```

```
Gln Cys Ser Ala Pro Cys Gly Gly Val Gln Arg Arg Leu Val
    1490            1495                1500

Lys Cys Val Asn Thr Gln Thr Gly Leu Ala Glu Glu Asp Ser Asp
    1505            1510                1515

Leu Cys Ser His Glu Ala Trp Pro Glu Ser Ser Arg Pro Cys Ala
    1520            1525                1530

Thr Glu Asp Cys Glu Leu Val Glu Pro Ser Arg Cys Glu Arg Asp
    1535            1540                1545

Arg Leu Pro Phe Asn Phe Cys Glu Thr Leu Arg Leu Leu Gly Arg
    1550            1555                1560

Cys Gln Leu Pro Thr Ile Arg Ala Gln Cys Cys Arg Ser Cys Pro
    1565            1570                1575

Pro Leu Ser Arg Gly Val Pro Ser Arg Gly His Gln Arg Val Ala
    1580            1585                1590

Arg Arg
    1595

<210> SEQ ID NO 23
<211> LENGTH: 1657
<212> TYPE: PRT
<213> ORGANISM: Artificial Sequence
<220> FEATURE:
<223> OTHER INFORMATION: Mouse ADAMTS7 from Q68SA9

<400> SEQUENCE: 23

Met His Arg Gly Pro Ser Leu Leu Leu Ile Leu Cys Ala Leu Ala Ser
1               5                   10                  15

Arg Val Leu Gly Pro Ala Ser Gly Leu Val Thr Glu Gly Arg Ala Gly
                20                  25                  30

Leu Asp Ile Val His Pro Val Arg Val Asp Ala Gly Gly Ser Phe Leu
            35                  40                  45

Ser Tyr Glu Leu Trp Pro Arg Val Leu Arg Lys Arg Asp Val Ser Thr
    50                  55                  60

Thr Gln Ala Ser Ser Ala Phe Tyr Gln Leu Gln Tyr Gln Gly Arg Glu
65                  70                  75                  80

Leu Leu Phe Asn Leu Thr Thr Asn Pro Tyr Leu Met Ala Pro Gly Phe
                85                  90                  95

Val Ser Glu Ile Arg Arg His Ser Thr Leu Gly His Ala His Ile Gln
                100                 105                 110

Thr Ser Val Pro Thr Cys His Leu Leu Gly Asp Val Gln Asp Pro Glu
            115                 120                 125

Leu Glu Gly Gly Phe Ala Ala Ile Ser Ala Cys Asp Gly Leu Arg Gly
        130                 135                 140

Val Phe Gln Leu Ser Asn Glu Asp Tyr Phe Ile Glu Pro Leu Asp Gly
145                 150                 155                 160

Val Ser Ala Gln Pro Gly His Ala Gln Pro His Val Val Tyr Lys His
                165                 170                 175

Gln Gly Ser Arg Lys Gln Ala Gln Gln Gly Asp Ser Arg Pro Ser Gly
                180                 185                 190

Thr Cys Gly Met Gln Val Pro Pro Asp Leu Glu Gln Gln Arg Glu His
            195                 200                 205

Trp Glu Gln Gln Gln Lys Arg Arg Gln Gln Arg Ser Val Ser Lys
        210                 215                 220

Glu Lys Trp Val Glu Thr Leu Val Val Ala Asp Ser Lys Met Val Glu
225                 230                 235                 240
```

```
Tyr His Gly Gln Pro Gln Val Glu Ser Tyr Val Leu Thr Ile Met Asn
                245                 250                 255

Met Val Ala Gly Leu Phe His Asp Pro Ser Ile Gly Asn Pro Ile His
                260                 265                 270

Ile Ser Ile Val Arg Leu Ile Ile Leu Glu Asp Glu Glu Lys Asp Leu
                275                 280                 285

Lys Ile Thr His His Ala Glu Glu Thr Leu Lys Asn Phe Cys Arg Trp
            290                 295                 300

Gln Lys Asn Ile Asn Ile Lys Gly Asp Asp His Pro Gln His His Asp
305                 310                 315                 320

Thr Ala Ile Leu Leu Thr Arg Lys Asp Leu Cys Ala Ser Met Asn Gln
                325                 330                 335

Pro Cys Glu Thr Leu Gly Leu Ser His Val Ser Gly Leu Cys His Pro
                340                 345                 350

Gln Leu Ser Cys Ser Val Ser Glu Asp Thr Gly Met Pro Leu Ala Phe
            355                 360                 365

Thr Val Ala His Glu Leu Gly His Ser Phe Gly Ile Gln His Asp Gly
            370                 375                 380

Thr Gly Asn Asp Cys Glu Ser Ile Gly Lys Arg Pro Phe Ile Met Ser
385                 390                 395                 400

Pro Gln Leu Leu Tyr Asp Arg Gly Ile Pro Leu Thr Trp Ser Arg Cys
                405                 410                 415

Ser Arg Glu Tyr Ile Thr Arg Phe Leu Asp Arg Gly Trp Gly Leu Cys
                420                 425                 430

Leu Asp Asp Arg Pro Ser Lys Asp Val Ile Ala Leu Pro Ser Val Leu
            435                 440                 445

Pro Gly Val Leu Tyr Asp Val Asn His Gln Cys Arg Leu Gln Tyr Gly
            450                 455                 460

Ser His Ser Ala Tyr Cys Glu Asp Met Asp Asp Val Cys His Thr Leu
465                 470                 475                 480

Trp Cys Ser Val Gly Thr Thr Cys His Ser Lys Leu Asp Ala Ala Val
                485                 490                 495

Asp Gly Thr Ser Cys Gly Lys Asn Lys Trp Cys Leu Lys Gly Glu Cys
            500                 505                 510

Val Pro Glu Gly Phe Gln Pro Glu Ala Val Asp Gly Gly Trp Ser Gly
            515                 520                 525

Trp Ser Ala Trp Ser Asp Cys Ser Arg Ser Cys Gly Val Gly Val Arg
530                 535                 540

Ser Ser Glu Arg Gln Cys Thr Gln Pro Val Pro Lys Asn Arg Gly Lys
545                 550                 555                 560

Tyr Cys Val Gly Glu Arg Lys Arg Ser Gln Leu Cys Asn Leu Pro Ala
                565                 570                 575

Cys Pro Pro Asp Arg Pro Ser Phe Arg His Thr Gln Cys Ser Gln Phe
            580                 585                 590

Asp Gly Met Leu Tyr Lys Gly Lys Leu His Lys Trp Val Pro Val Pro
            595                 600                 605

Asn Asp Asp Asn Pro Cys Glu Leu His Cys Arg Pro Ser Asn Ser Ser
            610                 615                 620

Asn Thr Glu Lys Leu Arg Asp Ala Val Val Asp Gly Thr Pro Cys Tyr
625                 630                 635                 640

Gln Ser Arg Ile Ser Arg Asp Ile Cys Leu Asn Gly Ile Cys Lys Asn
                645                 650                 655
```

```
Val Gly Cys Asp Phe Val Ile Asp Ser Gly Ala Glu Glu Asp Arg Cys
            660                 665                 670

Gly Val Cys Arg Gly Asp Gly Ser Thr Cys Gln Thr Val Ser Arg Thr
            675                 680                 685

Phe Lys Glu Thr Glu Gly Gln Gly Tyr Val Asp Ile Gly Leu Ile Pro
            690                 695                 700

Ala Gly Ala Arg Glu Ile Leu Ile Glu Glu Val Ala Glu Ala Asn
705                 710                 715                 720

Phe Leu Ala Leu Arg Ser Glu Pro Asp Lys Tyr Phe Leu Asn Gly
                725                 730                 735

Gly Trp Thr Ile Gln Trp Asn Gly Asp Tyr Arg Val Ala Gly Thr Thr
            740                 745                 750

Phe Thr Tyr Ala Arg Lys Gly Asn Trp Glu Asn Leu Thr Ser Pro Gly
            755                 760                 765

Pro Thr Ser Glu Pro Val Trp Ile Gln Leu Leu Phe Gln Glu Lys Asn
            770                 775                 780

Pro Gly Val His Tyr Gln Tyr Thr Ile Gln Arg Asp Ser His Asp Gln
785                 790                 795                 800

Val Arg Pro Pro Glu Phe Ser Trp His Tyr Gly Pro Trp Ser Lys Cys
                805                 810                 815

Thr Val Thr Cys Gly Thr Gly Val Gln Arg Gln Ser Leu Tyr Cys Met
            820                 825                 830

Glu Arg Gln Ala Gly Val Val Ala Glu Glu Tyr Cys Asn Thr Leu Asn
                835                 840                 845

Arg Pro Asp Glu Arg Gln Arg Lys Cys Ser Glu Pro Cys Pro Pro
850                 855                 860

Arg Trp Trp Ala Gly Glu Trp Gln Pro Cys Ser Arg Ser Cys Gly Pro
865                 870                 875                 880

Glu Gly Leu Ser Arg Arg Ala Val Phe Cys Ile Arg Ser Met Gly Leu
                885                 890                 895

Asp Glu Gln Arg Ala Leu Glu Leu Ser Ala Cys Glu His Leu Pro Arg
                900                 905                 910

Pro Leu Ala Glu Thr Pro Cys Asn Arg His Val Ile Cys Pro Ser Thr
            915                 920                 925

Trp Gly Val Gly Asn Trp Ser Gln Cys Ser Val Thr Cys Gly Ala Gly
            930                 935                 940

Ile Arg Gln Arg Ser Val Leu Cys Ile Asn Asn Thr Asp Val Pro Cys
945                 950                 955                 960

Asp Glu Ala Glu Arg Pro Ile Thr Glu Thr Phe Cys Phe Leu Gln Pro
                965                 970                 975

Cys Gln Tyr Pro Met Tyr Ile Val Asp Thr Gly Ala Ser Gly Ser Gly
            980                 985                 990

Ser Ser Ser Pro Glu Leu Phe Asn Glu Val Asp Phe Ile Pro Asn Gln
            995                 1000                1005

Leu Ala Pro Arg Pro Ser Pro Ala Ser Ser Pro Lys Pro Val Ser
        1010                1015                1020

Ile Ser Asn Ala Ile Asp Glu Glu Glu Leu Asp Pro Pro Gly Pro
        1025                1030                1035

Val Phe Val Asp Asp Phe Tyr Tyr Asp Tyr Asn Phe Ile Asn Phe
        1040                1045                1050

His Glu Asp Leu Ser Tyr Gly Ser Phe Glu Glu Pro His Pro Asp
        1055                1060                1065

Leu Val Asp Asn Gly Gly Trp Thr Ala Pro Pro His Ile Arg Pro
```

-continued

```
               1070                1075                1080
Thr Glu Ser Pro Ser Asp Thr Pro Val Pro Thr Ala Gly Ala Leu
        1085                1090                1095
Gly Ala Glu Ala Glu Asp Ile Gln Gly Ser Trp Ser Pro Ser Pro
        1100                1105                1110
Leu Leu Ser Glu Ala Ser Tyr Ser Pro Pro Gly Leu Glu Gln Thr
        1115                1120                1125
Ser Ile Asn Pro Leu Ala Asn Phe Leu Thr Glu Glu Asp Thr Pro
        1130                1135                1140
Met Gly Ala Pro Glu Leu Gly Phe Pro Ser Leu Pro Trp Pro Pro
        1145                1150                1155
Ala Ser Val Asp Asp Met Met Thr Pro Val Gly Pro Gly Asn Pro
        1160                1165                1170
Asp Glu Leu Leu Val Lys Glu Asp Glu Gln Ser Pro Pro Ser Thr
        1175                1180                1185
Pro Trp Ser Asp Arg Asn Lys Leu Ser Thr Asp Gly Asn Pro Leu
        1190                1195                1200
Gly His Thr Ser Pro Ala Leu Pro Gln Ser Pro Ile Pro Thr Gln
        1205                1210                1215
Pro Ser Pro Pro Ser Ile Ser Pro Thr Gln Ala Ser Pro Ser Pro
        1220                1225                1230
Asp Val Val Glu Val Ser Thr Gly Trp Asn Ala Ala Trp Asp Pro
        1235                1240                1245
Val Leu Glu Ala Asp Leu Lys Pro Gly His Gly Glu Leu Pro Ser
        1250                1255                1260
Thr Val Glu Val Ala Ser Pro Pro Leu Leu Pro Met Ala Thr Val
        1265                1270                1275
Pro Gly Ile Trp Gly Arg Asp Ser Pro Leu Glu Pro Gly Thr Pro
        1280                1285                1290
Thr Phe Ser Ser Pro Glu Leu Ser Ser Gln His Leu Lys Thr Leu
        1295                1300                1305
Thr Met Pro Gly Thr Leu Leu Leu Thr Val Pro Thr Asp Leu Arg
        1310                1315                1320
Ser Pro Gly Pro Ser Gly Gln Pro Gln Thr Pro Asn Leu Glu Gly
        1325                1330                1335
Thr Gln Ser Pro Gly Leu Leu Pro Thr Pro Ala Arg Glu Thr Gln
        1340                1345                1350
Thr Asn Ser Ser Lys Asp Pro Glu Val Gln Pro Leu Gln Pro Ser
        1355                1360                1365
Leu Glu Glu Asp Gly Asp Pro Ala Asp Pro Leu Pro Ala Arg Asn
        1370                1375                1380
Ala Ser Trp Gln Val Gly Asn Trp Ser Gln Cys Ser Thr Thr Cys
        1385                1390                1395
Gly Leu Gly Ala Ile Trp Arg Leu Val Ser Cys Ser Ser Gly Asn
        1400                1405                1410
Asp Glu Asp Cys Thr Leu Ala Ser Arg Pro Gln Pro Ala Arg His
        1415                1420                1425
Cys His Leu Arg Pro Cys Ala Ala Trp Arg Thr Gly Asn Trp Ser
        1430                1435                1440
Lys Cys Ser Arg Asn Cys Gly Gly Gly Ser Ser Thr Arg Asp Val
        1445                1450                1455
Gln Cys Val Asp Thr Arg Asp Leu Arg Pro Leu Arg Pro Phe His
        1460                1465                1470
```

Cys Gln Pro Gly Pro Thr Lys Pro Pro Asn Arg Gln Leu Cys Gly
        1475                1480                1485

Thr Gln Pro Cys Leu Pro Trp Tyr Thr Ser Ser Trp Arg Glu Cys
        1490                1495                1500

Ser Glu Ala Cys Gly Gly Gly Glu Gln Gln Arg Leu Val Thr Cys
        1505                1510                1515

Pro Glu Pro Gly Leu Cys Glu Glu Ser Leu Arg Pro Asn Asn Ser
        1520                1525                1530

Arg Pro Cys Asn Thr His Pro Cys Thr Gln Trp Val Val Gly Pro
        1535                1540                1545

Trp Gly Gln Cys Ser Ala Pro Cys Gly Gly Gly Val Gln Arg Arg
        1550                1555                1560

Leu Val Arg Cys Val Asn Thr Gln Thr Gly Leu Ala Glu Glu Asp
        1565                1570                1575

Ser Asp Leu Cys Ser His Glu Ala Trp Pro Glu Ser Ser Arg Pro
        1580                1585                1590

Cys Ala Thr Glu Asp Cys Glu Leu Val Glu Pro Pro Arg Cys Glu
        1595                1600                1605

Arg Asp Arg Leu Ser Phe Asn Phe Cys Gly Thr Leu Arg Leu Leu
        1610                1615                1620

Gly Arg Cys Gln Leu Pro Thr Ile Arg Ala Gln Cys Cys Arg Ser
        1625                1630                1635

Cys Pro Pro Leu Ser Arg Gly Val Pro Ser Arg Gly His Gln Arg
        1640                1645                1650

Val Ala Arg Arg
        1655

<210> SEQ ID NO 24
<211> LENGTH: 1594
<212> TYPE: PRT
<213> ORGANISM: Artificial Sequence
<220> FEATURE:
<223> OTHER INFORMATION: Human ADAMTS12 from P58397

<400> SEQUENCE: 24

Met Pro Cys Ala Gln Arg Ser Trp Leu Ala Asn Leu Ser Val Val Ala
1               5                   10                  15

Gln Leu Leu Asn Phe Gly Ala Leu Cys Tyr Gly Arg Gln Pro Gln Pro
            20                  25                  30

Gly Pro Val Arg Phe Pro Asp Arg Arg Gln Glu His Phe Ile Lys Gly
        35                  40                  45

Leu Pro Glu Tyr His Val Val Gly Pro Val Arg Val Asp Ala Ser Gly
    50                  55                  60

His Phe Leu Ser Tyr Gly Leu His Tyr Pro Ile Thr Ser Ser Arg Arg
65                  70                  75                  80

Lys Arg Asp Leu Asp Gly Ser Glu Asp Trp Val Tyr Tyr Arg Ile Ser
                85                  90                  95

His Glu Glu Lys Asp Leu Phe Phe Asn Leu Thr Val Asn Gln Gly Phe
            100                 105                 110

Leu Ser Asn Ser Tyr Ile Met Glu Lys Arg Tyr Gly Asn Leu Ser His
        115                 120                 125

Val Lys Met Met Ala Ser Ser Ala Pro Leu Cys His Leu Ser Gly Thr
    130                 135                 140

Val Leu Gln Gln Gly Thr Arg Val Gly Thr Ala Ala Leu Ser Ala Cys
145                 150                 155                 160

```
His Gly Leu Thr Gly Phe Phe Gln Leu Pro His Gly Asp Phe Phe Ile
            165                 170                 175

Glu Pro Val Lys Lys His Pro Leu Val Glu Gly Gly Tyr His Pro His
            180                 185                 190

Ile Val Tyr Arg Arg Gln Lys Val Pro Glu Thr Lys Glu Pro Thr Cys
            195                 200                 205

Gly Leu Lys Asp Ser Val Asn Ile Ser Gln Lys Gln Glu Leu Trp Arg
210                 215                 220

Glu Lys Trp Glu Arg His Asn Leu Pro Ser Arg Ser Leu Ser Arg Arg
225                 230                 235                 240

Ser Ile Ser Lys Glu Arg Trp Val Glu Thr Leu Val Val Ala Asp Thr
            245                 250                 255

Lys Met Ile Glu Tyr His Gly Ser Glu Asn Val Glu Ser Tyr Ile Leu
            260                 265                 270

Thr Ile Met Asn Met Val Thr Gly Leu Phe His Asn Pro Ser Ile Gly
            275                 280                 285

Asn Ala Ile His Ile Val Val Arg Leu Ile Leu Leu Glu Glu Glu
            290                 295                 300

Glu Gln Gly Leu Lys Ile Val His His Ala Glu Lys Thr Leu Ser Ser
305                 310                 315                 320

Phe Cys Lys Trp Gln Lys Ser Ile Asn Pro Lys Ser Asp Leu Asn Pro
            325                 330                 335

Val His His Asp Val Ala Val Leu Leu Thr Arg Lys Asp Ile Cys Ala
            340                 345                 350

Gly Phe Asn Arg Pro Cys Glu Thr Leu Gly Leu Ser His Leu Ser Gly
            355                 360                 365

Met Cys Gln Pro His Arg Ser Cys Asn Ile Asn Glu Asp Ser Gly Leu
            370                 375                 380

Pro Leu Ala Phe Thr Ile Ala His Glu Leu Gly His Ser Phe Gly Ile
385                 390                 395                 400

Gln His Asp Gly Lys Glu Asn Asp Cys Glu Pro Val Gly Arg His Pro
            405                 410                 415

Tyr Ile Met Ser Arg Gln Leu Gln Tyr Asp Pro Thr Pro Leu Thr Trp
            420                 425                 430

Ser Lys Cys Ser Glu Glu Tyr Ile Thr Arg Phe Leu Asp Arg Gly Trp
            435                 440                 445

Gly Phe Cys Leu Asp Asp Ile Pro Lys Lys Gly Leu Lys Ser Lys
450                 455                 460

Val Ile Ala Pro Gly Val Ile Tyr Asp Val His His Gln Cys Gln Leu
465                 470                 475                 480

Gln Tyr Gly Pro Asn Ala Thr Phe Cys Gln Glu Val Glu Asn Val Cys
            485                 490                 495

Gln Thr Leu Trp Cys Ser Val Lys Gly Phe Cys Arg Ser Lys Leu Asp
            500                 505                 510

Ala Ala Ala Asp Gly Thr Gln Cys Gly Glu Lys Lys Trp Cys Met Ala
            515                 520                 525

Gly Lys Cys Ile Thr Val Gly Lys Lys Pro Glu Ser Ile Pro Gly Gly
            530                 535                 540

Trp Gly Arg Trp Ser Pro Trp Ser His Cys Ser Arg Thr Cys Gly Ala
545                 550                 555                 560

Gly Val Gln Ser Ala Glu Arg Leu Cys Asn Asn Pro Glu Pro Lys Phe
            565                 570                 575
```

-continued

```
Gly Gly Lys Tyr Cys Thr Gly Glu Arg Lys Arg Tyr Arg Leu Cys Asn
            580                 585                 590

Val His Pro Cys Arg Ser Glu Ala Pro Thr Phe Arg Gln Met Gln Cys
        595                 600                 605

Ser Glu Phe Asp Thr Val Pro Tyr Lys Asn Glu Leu Tyr His Trp Phe
    610                 615                 620

Pro Ile Phe Asn Pro Ala His Pro Cys Glu Leu Tyr Cys Arg Pro Ile
625                 630                 635                 640

Asp Gly Gln Phe Ser Glu Lys Met Leu Asp Ala Val Ile Asp Gly Thr
                645                 650                 655

Pro Cys Phe Glu Gly Gly Asn Ser Arg Asn Val Cys Ile Asn Gly Ile
        660                 665                 670

Cys Lys Met Val Gly Cys Asp Tyr Glu Ile Asp Ser Asn Ala Thr Glu
    675                 680                 685

Asp Arg Cys Gly Val Cys Leu Gly Asp Gly Ser Ser Cys Gln Thr Val
        690                 695                 700

Arg Lys Met Phe Lys Gln Lys Glu Gly Ser Gly Tyr Val Asp Ile Gly
705                 710                 715                 720

Leu Ile Pro Lys Gly Ala Arg Asp Ile Arg Val Met Glu Ile Glu Gly
                725                 730                 735

Ala Gly Asn Phe Leu Ala Ile Arg Ser Glu Asp Pro Glu Lys Tyr Tyr
            740                 745                 750

Leu Asn Gly Gly Phe Ile Ile Gln Trp Asn Gly Asn Tyr Lys Leu Ala
        755                 760                 765

Gly Thr Val Phe Gln Tyr Asp Arg Lys Gly Asp Leu Glu Lys Leu Met
    770                 775                 780

Ala Thr Gly Pro Thr Asn Glu Ser Val Trp Ile Gln Leu Leu Phe Gln
785                 790                 795                 800

Val Thr Asn Pro Gly Ile Lys Tyr Glu Tyr Thr Ile Gln Lys Asp Gly
                805                 810                 815

Leu Asp Asn Asp Val Glu Gln Gln Met Tyr Phe Trp Gln Tyr Gly His
            820                 825                 830

Trp Thr Glu Cys Ser Val Thr Cys Gly Thr Gly Ile Arg Arg Gln Thr
        835                 840                 845

Ala His Cys Ile Lys Lys Gly Arg Gly Met Val Lys Ala Thr Phe Cys
    850                 855                 860

Asp Pro Glu Thr Gln Pro Asn Gly Arg Gln Lys Lys Cys His Glu Lys
865                 870                 875                 880

Ala Cys Pro Pro Arg Trp Trp Ala Gly Glu Trp Glu Ala Cys Ser Ala
                885                 890                 895

Thr Cys Gly Pro His Gly Glu Lys Lys Arg Thr Val Leu Cys Ile Gln
            900                 905                 910

Thr Met Val Ser Asp Glu Gln Ala Leu Pro Pro Thr Asp Cys Gln His
        915                 920                 925

Leu Leu Lys Pro Lys Thr Leu Leu Ser Cys Asn Arg Asp Ile Leu Cys
    930                 935                 940

Pro Ser Asp Trp Thr Val Gly Asn Trp Ser Glu Cys Ser Val Ser Cys
945                 950                 955                 960

Gly Gly Gly Val Arg Ile Arg Ser Val Thr Cys Ala Lys Asn His Asp
                965                 970                 975

Glu Pro Cys Asp Val Thr Arg Lys Pro Asn Ser Arg Ala Leu Cys Gly
            980                 985                 990

Leu Gln Gln Cys Pro Ser Ser Arg  Arg Val Leu Lys Pro  Asn Lys Gly
```

```
              995                 1000                1005
    Thr Ile Ser Asn Gly Lys Asn Pro Pro Thr Leu Lys Pro Val Pro
        1010                1015                1020

Pro Pro Thr Ser Arg Pro Arg Met Leu Thr Thr Pro Thr Gly Pro
        1025                1030                1035

Glu Ser Met Ser Thr Ser Thr Pro Ala Ile Ser Ser Pro Ser Pro
        1040                1045                1050

Thr Thr Ala Ser Lys Glu Gly Asp Leu Gly Gly Lys Gln Trp Gln
        1055                1060                1065

Asp Ser Ser Thr Gln Pro Glu Leu Ser Ser Arg Tyr Leu Ile Ser
        1070                1075                1080

Thr Gly Ser Thr Ser Gln Pro Ile Leu Thr Ser Gln Ser Leu Ser
        1085                1090                1095

Ile Gln Pro Ser Glu Glu Asn Val Ser Ser Ser Asp Thr Gly Pro
        1100                1105                1110

Thr Ser Glu Gly Gly Leu Val Ala Thr Thr Thr Ser Gly Ser Gly
        1115                1120                1125

Leu Ser Ser Ser Arg Asn Pro Ile Thr Trp Pro Val Thr Pro Phe
        1130                1135                1140

Tyr Asn Thr Leu Thr Lys Gly Pro Glu Met Glu Ile His Ser Gly
        1145                1150                1155

Ser Gly Glu Glu Arg Glu Gln Pro Glu Asp Lys Asp Glu Ser Asn
        1160                1165                1170

Pro Val Ile Trp Thr Lys Ile Arg Val Pro Gly Asn Asp Ala Pro
        1175                1180                1185

Val Glu Ser Thr Glu Met Pro Leu Ala Pro Pro Leu Thr Pro Asp
        1190                1195                1200

Leu Ser Arg Glu Ser Trp Trp Pro Pro Phe Ser Thr Val Met Glu
        1205                1210                1215

Gly Leu Leu Pro Ser Gln Arg Pro Thr Thr Ser Glu Thr Gly Thr
        1220                1225                1230

Pro Arg Val Glu Gly Met Val Thr Glu Lys Pro Ala Asn Thr Leu
        1235                1240                1245

Leu Pro Leu Gly Gly Asp His Gln Pro Glu Pro Ser Gly Lys Thr
        1250                1255                1260

Ala Asn Arg Asn His Leu Lys Leu Pro Asn Asn Met Asn Gln Thr
        1265                1270                1275

Lys Ser Ser Glu Pro Val Leu Thr Glu Glu Asp Ala Thr Ser Leu
        1280                1285                1290

Ile Thr Glu Gly Phe Leu Leu Asn Ala Ser Asn Tyr Lys Gln Leu
        1295                1300                1305

Thr Asn Gly His Gly Ser Ala His Trp Ile Val Gly Asn Trp Ser
        1310                1315                1320

Glu Cys Ser Thr Thr Cys Gly Leu Gly Ala Tyr Trp Arg Arg Val
        1325                1330                1335

Glu Cys Ser Thr Gln Met Asp Ser Asp Cys Ala Ala Ile Gln Arg
        1340                1345                1350

Pro Asp Pro Ala Lys Arg Cys His Leu Arg Pro Cys Ala Gly Trp
        1355                1360                1365

Lys Val Gly Asn Trp Ser Lys Cys Ser Arg Asn Cys Ser Gly Gly
        1370                1375                1380

Phe Lys Ile Arg Glu Ile Gln Cys Val Asp Ser Arg Asp His Arg
        1385                1390                1395
```

```
Asn Leu Arg Pro Phe His Cys Gln Phe Leu Ala Gly Ile Pro Pro
    1400            1405                1410

Pro Leu Ser Met Ser Cys Asn Pro Glu Pro Cys Glu Ala Trp Gln
    1415            1420                1425

Val Glu Pro Trp Ser Gln Cys Ser Arg Ser Cys Gly Gly Gly Val
    1430            1435                1440

Gln Glu Arg Gly Val Phe Cys Pro Gly Gly Leu Cys Asp Trp Thr
    1445            1450                1455

Lys Arg Pro Thr Ser Thr Met Ser Cys Asn Glu His Leu Cys Cys
    1460            1465                1470

His Trp Ala Thr Gly Asn Trp Asp Leu Cys Ser Thr Ser Cys Gly
    1475            1480                1485

Gly Gly Phe Gln Lys Arg Thr Val Gln Cys Val Pro Ser Glu Gly
    1490            1495                1500

Asn Lys Thr Glu Asp Gln Asp Gln Cys Leu Cys Asp His Lys Pro
    1505            1510                1515

Arg Pro Pro Glu Phe Lys Lys Cys Asn Gln Gln Ala Cys Lys Lys
    1520            1525                1530

Ser Ala Asp Leu Leu Cys Thr Lys Asp Lys Leu Ser Ala Ser Phe
    1535            1540                1545

Cys Gln Thr Leu Lys Ala Met Lys Lys Cys Ser Val Pro Thr Val
    1550            1555                1560

Arg Ala Glu Cys Cys Phe Ser Cys Pro Gln Thr His Ile Thr His
    1565            1570                1575

Thr Gln Arg Gln Arg Arg Gln Arg Leu Leu Gln Lys Ser Lys Glu
    1580            1585                1590

Leu

<210> SEQ ID NO 25
<211> LENGTH: 1599
<212> TYPE: PRT
<213> ORGANISM: Artificial Sequence
<220> FEATURE:
<223> OTHER INFORMATION: Rat ADAMTS12 from D3ZTJ3

<400> SEQUENCE: 25

Met Pro Cys Ala Gln Gly Asn Trp Met Ala Lys Leu Ser Met Val Ala
1               5                   10                  15

Gln Leu Leu Asn Phe Gly Ala Phe Cys His Gly Arg Gln Ala Gln Pro
            20                  25                  30

Trp Pro Val Arg Phe Pro Asp Pro Lys Gln Glu His Phe Ile Lys Ser
        35                  40                  45

Leu Pro Glu Tyr His Ile Val Ser Pro Val Gln Val Asp Ala Ser Gly
    50                  55                  60

His Phe Leu Ser Tyr Gly Leu His Pro Val Thr Gly Ser Arg Lys
65                  70                  75              80

Lys Arg Ala Ala Gly Gly Ser Gly Asp Gln Val Tyr Tyr Arg Ile Ser
                85                  90                  95

His Glu Glu Lys Asn Leu Phe Phe Asn Leu Thr Val Asn Trp Glu Phe
            100                 105                 110

Leu Ser Asn Gly Tyr Val Val Glu Arg Arg Tyr Gly Asn Leu Ser His
        115                 120                 125

Val Lys Met Ala Ala Ser Ser Gly Gln Pro Cys His Leu Arg Gly Thr
    130                 135                 140
```

-continued

Val Leu Gln Gln Gly Pro Thr Ile Arg Met Gly Thr Ala Ala Leu Ser
145                 150                 155                 160

Ala Cys Gln Gly Leu Thr Gly Phe Phe His Leu Pro His Gly Asp Phe
            165                 170                 175

Phe Ile Glu Pro Val Lys Lys His Pro Leu Thr Glu Glu Gly Tyr Gln
        180                 185                 190

Pro His Val Ile Tyr Arg Arg Gln Ser Tyr Arg Val Pro Glu Thr Lys
    195                 200                 205

Glu Pro Thr Cys Gly Leu Lys Asp Ser Leu Asp Asn Ser Val Lys Gln
210                 215                 220

Glu Leu Gln Arg Glu Lys Trp Glu Arg Lys Asn Trp Pro Ser Arg Ser
225                 230                 235                 240

Leu Ser Arg Arg Ser Ile Ser Lys Glu Arg Trp Val Glu Thr Leu Val
            245                 250                 255

Val Ala Asp Thr Lys Met Val Glu Tyr His Gly Ser Glu Asn Val Glu
        260                 265                 270

Ser Tyr Ile Leu Thr Ile Met Asn Met Val Thr Gly Leu Phe His Asn
    275                 280                 285

Pro Ser Ile Gly Asn Ala Val His Ile Val Val Arg Leu Ile Leu
290                 295                 300

Leu Glu Glu Glu Glu Gln Gly Leu Lys Ile Val His His Ala Glu Lys
305                 310                 315                 320

Thr Leu Ser Ser Phe Cys Lys Trp Gln Lys Ser Ile Asn Pro Lys Ser
            325                 330                 335

Asp Leu Asn Pro Val His His Asp Val Ala Val Leu Ile Thr Arg Lys
        340                 345                 350

Asp Ile Cys Ala Gly Val Asn Arg Pro Cys Glu Thr Leu Gly Leu Ser
    355                 360                 365

Gln Leu Ser Gly Met Cys Gln Pro His Arg Ser Cys Asn Ile Asn Glu
370                 375                 380

Asp Ser Gly Leu Pro Leu Ala Phe Thr Ile Ala His Glu Leu Gly His
385                 390                 395                 400

Ser Phe Gly Ile Gln His Asp Gly Lys Glu Asn Asp Cys Glu Pro Val
            405                 410                 415

Gly Arg His Pro Tyr Ile Met Ser Gln Gln Ile Gln Tyr Asp Pro Thr
        420                 425                 430

Pro Leu Thr Trp Ser Lys Cys Ser Lys Glu Tyr Ile Thr Arg Phe Leu
    435                 440                 445

Asp Arg Gly Arg Gly Phe Cys Leu Asp Asp Val Pro Arg Lys Lys Gly
450                 455                 460

Leu Lys Ser Asn Val Ile Ala Pro Gly Val Ile Tyr Asp Val His His
465                 470                 475                 480

Gln Cys Gln Leu Gln Tyr Gly Pro Asn Ala Thr Phe Cys Gln Glu Val
            485                 490                 495

Glu Asn Val Cys Gln Thr Leu Trp Cys Ser Val Lys Gly Phe Cys Arg
        500                 505                 510

Ser Lys Leu Asp Ala Ala Asp Gly Thr Arg Cys Gly Glu Lys Lys
    515                 520                 525

Trp Cys Met Ala Gly Lys Cys Ile Thr Val Gly Lys Lys Pro Glu Ser
530                 535                 540

Ile Pro Gly Gly Trp Gly Arg Trp Ser Pro Trp Ser His Cys Ser Arg
545                 550                 555                 560

Thr Cys Gly Ala Gly Ala Gln Ser Ala Glu Arg Leu Cys Asn Asn Pro

-continued

```
            565                 570                 575
Glu Pro Lys Phe Gly Lys Tyr Cys Thr Gly Glu Arg Lys Arg Tyr
            580                 585                 590
Arg Leu Cys Asn Val His Pro Cys Arg Ser Asp Thr Pro Thr Phe Arg
            595                 600                 605
Gln Met Gln Cys Ser Glu Phe Asp Thr Val Pro Tyr Lys Asn Gln Phe
            610                 615                 620
Tyr Arg Trp Phe Pro Val Phe Asn Pro Ala His Pro Cys Glu Leu Tyr
625                 630                 635                 640
Cys Arg Pro Ile Asp Glu Gln Phe Ser Glu Arg Met Leu Glu Ala Val
                    645                 650                 655
Ile Asp Gly Thr Pro Cys Phe Glu Gly Gly Asn Ser Arg Asn Val Cys
                    660                 665                 670
Ile Asn Gly Ile Cys Lys Arg Val Gly Cys Asp Tyr Glu Ile Asp Ser
                    675                 680                 685
Asn Ala Thr Glu Asp Arg Cys Gly Val Cys Leu Gly Asp Gly Ser Ala
            690                 695                 700
Cys Gln Thr Val Lys Lys Val Phe Arg Gln Lys Glu Gly Ser Gly Tyr
705                 710                 715                 720
Ile Asp Ile Gly Leu Ile Pro Lys Gly Ala Arg Asp Ile Arg Val Met
                    725                 730                 735
Glu Ile Lys Ala Ala Gly Asn Phe Leu Ala Ile Arg Ser Glu Asp Pro
            740                 745                 750
Glu Lys Tyr Tyr Leu Asn Gly Gly Phe Ile Ile Gln Trp Asn Gly Asn
            755                 760                 765
Tyr Lys Leu Ala Gly Thr Val Phe Gln Tyr Asp Arg Lys Gly Asp Leu
            770                 775                 780
Glu Arg Leu Met Ala Pro Gly Pro Thr Asn Glu Ser Val Trp Leu Gln
785                 790                 795                 800
Leu Leu Phe Gln Val Thr Asn Pro Gly Ile Lys Tyr Glu Tyr Thr Val
                    805                 810                 815
Arg Lys Asp Gly Leu Asp Asn Asp Val Glu Lys Leu Leu Tyr Phe Trp
            820                 825                 830
Gln Phe Gly Arg Trp Thr Glu Cys Ser Val Thr Cys Gly Thr Gly Ile
            835                 840                 845
Arg Arg Gln Thr Ala His Cys Val Lys Lys Gly His Gly Ile Val Lys
            850                 855                 860
Thr Thr Phe Cys Asn Pro Glu Thr Gln Pro Ser Val Arg Gln Lys Lys
865                 870                 875                 880
Cys Tyr Glu Lys Asp Cys Pro Pro Arg Trp Trp Ala Gly Glu Trp Glu
                    885                 890                 895
Ala Cys Ser Met Thr Cys Gly Pro Tyr Gly Glu Lys Lys Arg Thr Val
                    900                 905                 910
Leu Cys Ile Gln Thr Met Gly Ser Asp Glu Gln Ala Leu Pro Ala Thr
            915                 920                 925
Asp Cys Gln His Leu Leu Lys Pro Lys Thr Leu Val Ser Cys Asn Arg
            930                 935                 940
Asp Ile Leu Cys Pro Ser Asp Trp Thr Val Gly Asn Trp Ser Glu Cys
945                 950                 955                 960
Ser Val Ser Cys Gly Gly Gly Val Arg Ile Arg Ser Val Thr Cys Ala
                    965                 970                 975
Lys Asn Leu Asn Glu Pro Cys Asp Lys Thr Arg Lys Pro Asn Ser Arg
            980                 985                 990
```

-continued

```
Ala Leu Cys Gly Leu Gln Gln Cys  Pro Phe Ser Arg Arg  Val Leu Lys
        995              1000                  1005

Pro Asn Lys Asp Thr Val Pro  Ser Gly Lys Asn Pro  Thr Thr Ser
    1010             1015                 1020

Glu His Asp His Phe Lys Pro  Ile Pro Ala Ser Thr  Ser Arg Pro
    1025             1030                 1035

Thr Pro Leu Ser Thr Pro Thr  Val Pro Glu Ser Val  Ser Thr Ser
    1040             1045                 1050

Thr Pro Thr Ile Asn Ser Leu  Gly Ser Thr Ile Thr  Ser Gln Glu
    1055             1060                 1065

Glu Pro Asp Gly Ile Gly Trp  Gln Asn Asn Ser Thr  Gln Ala Glu
    1070             1075                 1080

Glu Asp Ser His Ile Pro Thr  Ser Val Gly Ser Thr  Ser Gln Thr
    1085             1090                 1095

Pro Leu Thr Ser Trp Ser Trp  Ser Met Gln Pro Asp  Asp Glu Asn
    1100             1105                 1110

Val Ser Ser Ser Ala Ile Gly  Pro Thr Ser Glu Ser  Asp Phe Trp
    1115             1120                 1125

Ala Thr Thr Ser Asp Ser Gly  Leu Ser Ser Ser Asn  Ala Met Thr
    1130             1135                 1140

Trp Gln Val Thr Pro Phe Tyr  Ser Thr Ala Thr Thr  Glu Pro Glu
    1145             1150                 1155

Val Glu Ile His Ser Gly Ser  Gly Glu Asp Ser Asp  Gln Pro Leu
    1160             1165                 1170

Asn Lys Glu Glu Asn Asn Ser  Val Leu Trp Asn Lys  Ile Arg Val
    1175             1180                 1185

Pro Glu Arg Asp Ala Pro Met  Glu Met Asp Ala Glu  Ile Pro Leu
    1190             1195                 1200

Gly Pro Pro Pro Thr Ser Tyr  Val Thr Glu Glu Ser  Ser Trp Pro
    1205             1210                 1215

Pro Phe Ser Thr Met Met Lys  Ser Ser Leu Pro Ala  Trp Ser Phe
    1220             1225                 1230

Lys Asn Glu Thr Pro Arg Asp  Glu Gly Met Ile Thr  Glu Lys Ser
    1235             1240                 1245

Gly Asn Ile Pro Leu Pro Leu  Gly Gly Asp His Gln  Thr Thr Ser
    1250             1255                 1260

Pro Glu Lys Leu Gly Asn Asn  Asp Gln Leu Ala Ser  Ala Asn Ser
    1265             1270                 1275

Thr Asn Pro Thr Gln Gly Ser  Gly Pro Val Leu Thr  Glu Glu Asp
    1280             1285                 1290

Ala Ser Thr Leu Ile Glu Glu  Gly Phe Leu Leu Asn  Ala Ser Asn
    1295             1300                 1305

Tyr Lys His Leu Met Lys Asp  His Ser Pro Ala His  Trp Ile Val
    1310             1315                 1320

Gly Asn Trp Ser Lys Cys Ser  Thr Thr Cys Gly Leu  Gly Ala Tyr
    1325             1330                 1335

Trp Arg Ser Val Glu Cys Ser  Thr Gly Met Asn Ala  Asp Cys Ala
    1340             1345                 1350

Ala Ile Gln Arg Pro Asp Pro  Ala Lys Lys Cys His  Leu Arg Pro
    1355             1360                 1365

Cys Ala Gly Trp Arg Val Gly  Asn Trp Ser Lys Cys  Ser Arg Asn
    1370             1375                 1380
```

```
Cys Ser Gly Gly Phe Lys Ile Arg Glu Val Gln Cys Met Asp Gly
        1385                1390                1395

Val Asp His His Arg Ser Leu Arg Pro Phe His Cys Gln Phe Leu
1400                1405                1410

Ala Gly Val Pro Pro Leu Ser Met Ser Cys Asn Leu Glu Pro
    1415                1420                1425

Cys Glu Glu Trp Lys Val Glu Pro Trp Ser Gln Cys Ser Arg Ser
    1430                1435                1440

Cys Gly Gly Gly Val Gln Glu Arg Gly Val Phe Cys Pro Gly Gly
    1445                1450                1455

Leu Cys Asp Trp Thr Lys Arg Pro Ala Ser Thr Val Pro Cys Asn
    1460                1465                1470

Arg His Leu Cys Cys His Trp Ala Thr Gly Asn Trp Glu Leu Cys
    1475                1480                1485

Thr Thr Ser Cys Gly Gly Gly Ser Gln Lys Arg Thr Val His Cys
    1490                1495                1500

Ile Pro Ser Glu Asn Ser Thr Thr Glu Asp Gln Asp Gln Cys Phe
    1505                1510                1515

Cys Asp His Gln Ala Arg Pro Pro Glu Phe Gln Asn Cys Asn Gln
    1520                1525                1530

Gln Ala Cys Arg Lys Ser Ala Asp Leu Thr Cys Thr Lys Asp Arg
    1535                1540                1545

Leu Ser Thr Ser Phe Cys Gln Thr Leu Lys Ser Met Lys Lys Cys
    1550                1555                1560

Ser Val Pro Ser Val Arg Val Gln Cys Cys Leu Ser Cys Pro Gln
    1565                1570                1575

Thr Gln Ser Ile His Thr Gln Arg Gln Arg Lys Gln Gln Met Leu
    1580                1585                1590

Gln Asn His Asp Thr Leu
    1595

<210> SEQ ID NO 26
<211> LENGTH: 1600
<212> TYPE: PRT
<213> ORGANISM: Artificial Sequence
<220> FEATURE:
<223> OTHER INFORMATION: Mouse ADAMTS12 from Q811B3

<400> SEQUENCE: 26

Met Pro Cys Ala Arg Gly Ser Trp Leu Ala Lys Leu Ser Ile Val Ala
1               5                   10                  15

Gln Leu Ile Asn Phe Gly Ala Phe Cys His Gly Arg Gln Thr Gln Pro
                20                  25                  30

Trp Pro Val Arg Phe Pro Asp Pro Arg Gln Glu His Phe Ile Lys Ser
            35                  40                  45

Leu Pro Glu Tyr His Ile Val Ser Pro Val Gln Val Asp Ala Gly Gly
        50                  55                  60

His Val Leu Ser Tyr Gly Leu His Pro Val Thr Ser Ser Arg Lys
65                  70                  75                  80

Lys Arg Ala Ala Gly Gly Ser Gly Asp Gln Leu Tyr Tyr Arg Ile Ser
                85                  90                  95

His Glu Glu Lys Asp Leu Phe Phe Asn Leu Thr Val Asn Trp Glu Phe
                100                 105                 110

Leu Ser Asn Gly Tyr Val Val Glu Lys Arg Tyr Gly Asn Leu Ser His
            115                 120                 125
```

-continued

```
Val Lys Met Val Ala Ser Ser Gly Gln Pro Cys His Leu Arg Gly Thr
130                 135                 140
Val Leu Gln Gln Gly Thr Thr Val Gly Ile Gly Thr Ala Ala Leu Ser
145                 150                 155                 160
Ala Cys Gln Gly Leu Thr Gly Phe Phe His Leu Pro His Gly Asp Phe
                165                 170                 175
Phe Ile Glu Pro Val Lys Lys His Pro Leu Thr Glu Glu Gly Ser Tyr
            180                 185                 190
Pro His Val Val Tyr Arg Arg Gln Ser Ile Arg Ala Pro Glu Thr Lys
        195                 200                 205
Glu Pro Ile Cys Gly Leu Lys Asp Ser Leu Asp Asn Ser Val Lys Gln
    210                 215                 220
Glu Leu Gln Arg Glu Lys Trp Glu Arg Lys Thr Leu Arg Ser Arg Ser
225                 230                 235                 240
Leu Ser Arg Arg Ser Ile Ser Lys Glu Arg Trp Val Glu Thr Leu Val
                245                 250                 255
Val Ala Asp Thr Lys Thr Val Glu Tyr His Gly Ser Glu Asn Val Glu
            260                 265                 270
Ser Tyr Ile Leu Thr Ile Met Asn Met Val Thr Gly Leu Phe His Ser
        275                 280                 285
Pro Ser Ile Gly Asn Leu Val His Ile Val Val Val Arg Leu Ile Leu
    290                 295                 300
Leu Glu Glu Glu Gln Gly Leu Lys Ile Val His His Ala Glu Lys
305                 310                 315                 320
Thr Leu Ser Ser Phe Cys Lys Trp Gln Lys Ser Ile Asn Pro Lys Ser
                325                 330                 335
Asp Leu Asn Pro Val His His Asp Val Ala Val Leu Ile Thr Arg Lys
            340                 345                 350
Asp Ile Cys Ala Gly Val Asn Arg Pro Cys Glu Thr Leu Gly Leu Ser
        355                 360                 365
Gln Leu Ser Gly Met Cys Gln Pro His Arg Ser Cys Asn Ile Asn Glu
    370                 375                 380
Asp Ser Gly Leu Pro Leu Ala Phe Thr Ile Ala His Glu Leu Gly His
385                 390                 395                 400
Ser Phe Gly Ile Gln His Asp Gly Lys Glu Asn Asp Cys Glu Pro Val
                405                 410                 415
Gly Arg His Pro Tyr Ile Met Ser Gln Gln Ile Gln Tyr Asp Pro Thr
            420                 425                 430
Pro Leu Thr Trp Ser Lys Cys Ser Lys Glu Tyr Ile Thr Arg Phe Leu
        435                 440                 445
Asp Arg Gly Arg Gly Phe Cys Leu Asp Asp Ile Pro Ser Lys Lys Gly
    450                 455                 460
Leu Lys Ser Asn Val Ile Ala Pro Gly Val Ile Tyr Asp Val His His
465                 470                 475                 480
Gln Cys Gln Leu Gln Tyr Gly Pro Asn Ala Thr Phe Cys Gln Glu Val
                485                 490                 495
Glu Asn Val Cys Gln Thr Leu Trp Cys Ser Val Lys Gly Phe Cys Arg
            500                 505                 510
Ser Lys Leu Asp Ala Ala Asp Gly Thr Arg Cys Gly Glu Lys Lys
        515                 520                 525
Trp Cys Met Ala Gly Lys Cys Ile Thr Val Gly Lys Lys Pro Glu Ser
    530                 535                 540
Ile Pro Gly Gly Trp Gly Arg Trp Ser Pro Trp Ser His Cys Ser Arg
```

-continued

```
           545                 550                 555                 560
Thr Cys Gly Ala Gly Ala Gln Ser Ala Glu Arg Leu Cys Asn Asn Pro
                    565                 570                 575
Glu Pro Lys Phe Gly Lys Tyr Cys Thr Gly Glu Arg Lys Arg Tyr
                580                 585                 590
Arg Leu Cys Asn Val His Pro Cys Arg Ser Asp Thr Pro Thr Phe Arg
                595                 600                 605
Gln Met Gln Cys Ser Glu Phe Asp Thr Val Pro Tyr Lys Asn Gln Phe
            610                 615                 620
Tyr Arg Trp Phe Pro Val Phe Asn Ala Ala His Pro Cys Glu Leu Tyr
625                 630                 635                 640
Cys Arg Pro Ile Asp Glu Gln Phe Ser Glu Arg Met Leu Glu Ala Val
                    645                 650                 655
Ile Asp Gly Thr Pro Cys Phe Glu Gly Gly Asn Ser Arg Asn Val Cys
                660                 665                 670
Ile Asn Gly Ile Cys Lys Arg Val Gly Cys Asp Tyr Glu Ile Asp Ser
                675                 680                 685
Asn Ala Thr Glu Asp Arg Cys Gly Val Cys Leu Gly Asp Gly Ser Ala
            690                 695                 700
Cys Gln Thr Val Lys Lys Leu Phe Arg Gln Lys Glu Gly Ser Gly Tyr
705                 710                 715                 720
Val Asp Ile Gly Leu Ile Pro Lys Gly Ala Arg Asp Ile Arg Val Met
                    725                 730                 735
Glu Ile Lys Ala Ala Gly Asn Phe Leu Ala Ile Arg Ser Glu Asp Pro
                740                 745                 750
Glu Lys Tyr Tyr Leu Asn Gly Gly Phe Ile Ile Gln Trp Asn Gly Asn
                755                 760                 765
Tyr Lys Leu Ala Gly Thr Val Phe Gln Tyr Asp Arg Lys Gly Asp Leu
            770                 775                 780
Glu Lys Leu Ile Ala Pro Gly Pro Thr Asn Glu Ser Val Trp Leu Gln
785                 790                 795                 800
Leu Leu Phe Gln Val Thr Asn Pro Gly Ile Lys Tyr Glu Tyr Thr Val
                    805                 810                 815
Arg Lys Asp Gly Leu Asp Asn Asp Val Glu Lys Leu Leu Tyr Phe Trp
                820                 825                 830
Gln Phe Gly Arg Trp Thr Glu Cys Ser Val Thr Cys Gly Thr Gly Ile
                835                 840                 845
Arg Arg Gln Ala Ala His Cys Val Lys Lys Gly His Gly Ile Val Lys
850                 855                 860
Thr Thr Phe Cys Asn Pro Glu Thr Gln Pro Ser Val Arg Gln Lys Lys
865                 870                 875                 880
Cys His Glu Lys Asp Cys Pro Pro Arg Trp Trp Ala Gly Glu Trp Glu
                885                 890                 895
Ala Cys Ser Thr Thr Cys Gly Pro Tyr Gly Glu Lys Lys Arg Thr Val
                900                 905                 910
Leu Cys Ile Gln Thr Met Gly Ser Asp Glu Gln Ala Leu Pro Ala Thr
            915                 920                 925
Asp Cys Gln His Leu Leu Lys Pro Lys Ala Leu Val Ser Cys Asn Arg
            930                 935                 940
Asp Ile Leu Cys Pro Ser Asp Trp Thr Val Gly Asn Trp Ser Glu Cys
945                 950                 955                 960
Ser Val Ser Cys Gly Gly Gly Val Arg Ile Arg Ser Val Thr Cys Ala
                    965                 970                 975
```

-continued

```
Lys Asn Leu Asn Glu Pro Cys Asp Lys Thr Arg Lys Pro Asn Ser Arg
            980                 985                 990

Ala Leu Cys Gly Leu Gln Gln Cys Pro Phe Ser Arg Arg Val Leu Lys
            995                1000                1005

Pro Asn Lys Asp Ile Ala Pro Ser Gly Lys Asn Gln Ser Thr Ala
        1010                1015                1020

Glu His Asp Pro Phe Lys Pro Ile Pro Ala Pro Thr Ser Arg Pro
        1025                1030                1035

Thr Pro Leu Ser Thr Pro Thr Val Pro Glu Ser Met Ser Thr Ser
        1040                1045                1050

Thr Pro Thr Ile Asn Ser Leu Gly Ser Thr Ile Ala Ser Gln Glu
        1055                1060                1065

Asp Ala Asn Gly Met Gly Trp Gln Asn Asn Ser Thr Gln Ala Glu
        1070                1075                1080

Glu Gly Ser His Phe Pro Thr Ser Ser Gly Ser Thr Ser Gln Val
        1085                1090                1095

Pro Val Thr Ser Trp Ser Leu Ser Ile Gln Pro Asp Asp Glu Asn
        1100                1105                1110

Val Ser Ser Ser Ala Ile Gly Pro Thr Ser Glu Gly Asp Phe Trp
        1115                1120                1125

Ala Thr Thr Thr Ser Asp Ser Gly Leu Ser Ser Ser Asp Ala Met
        1130                1135                1140

Thr Trp Gln Val Thr Pro Phe Tyr Ser Thr Met Thr Thr Asp Pro
        1145                1150                1155

Glu Val Glu Ile His Ser Gly Ser Gly Glu Asp Ser Asp Gln Pro
        1160                1165                1170

Leu Asn Lys Asp Lys Ser Asn Ser Val Ile Trp Asn Lys Ile Gly
        1175                1180                1185

Val Pro Glu His Asp Ala Pro Met Glu Thr Asp Ala Glu Leu Pro
        1190                1195                1200

Leu Gly Pro Pro Pro Thr Ser Tyr Met Gly Glu Glu Pro Ser Trp
        1205                1210                1215

Pro Pro Phe Ser Thr Lys Met Glu Gly Ser Leu Pro Ala Trp Ser
        1220                1225                1230

Phe Lys Asn Glu Thr Pro Arg Asp Asp Gly Met Ile Ala Glu Lys
        1235                1240                1245

Ser Arg Lys Ile Pro Leu Pro Leu Ala Gly Asp His His Pro Ala
        1250                1255                1260

Thr Ser Glu Lys Leu Glu Asn His Asp Lys Leu Ala Leu Pro Asn
        1265                1270                1275

Thr Thr Asn Pro Thr Gln Gly Phe Gly Pro Val Leu Thr Glu Glu
        1280                1285                1290

Asp Ala Ser Asn Leu Ile Ala Glu Gly Phe Leu Leu Asn Ala Ser
        1295                1300                1305

Asp Tyr Lys His Leu Met Lys Asp His Ser Pro Ala Tyr Trp Ile
        1310                1315                1320

Val Gly Asn Trp Ser Lys Cys Ser Thr Thr Cys Gly Leu Gly Ala
        1325                1330                1335

Tyr Trp Arg Ser Val Glu Cys Ser Ser Gly Val Asp Ala Asp Cys
        1340                1345                1350

Thr Thr Ile Gln Arg Pro Asp Pro Ala Lys Lys Cys His Leu Arg
        1355                1360                1365
```

```
Pro Cys Ala Gly Trp Arg Val Gly Asn Trp Ser Lys Cys Ser Arg
    1370                1375                1380

Asn Cys Ser Gly Gly Phe Lys Ile Arg Glu Val Gln Cys Met Asp
    1385                1390                1395

Ser Leu Asp His His Arg Ser Leu Arg Pro Phe His Cys Gln Phe
    1400                1405                1410

Leu Ala Gly Ala Pro Pro Leu Ser Met Ser Cys Asn Leu Glu
    1415                1420                1425

Pro Cys Gly Glu Trp Gln Val Glu Pro Trp Ser Gln Cys Ser Arg
    1430                1435                1440

Ser Cys Gly Gly Gly Val Gln Glu Arg Gly Val Ser Cys Pro Gly
    1445                1450                1455

Gly Leu Cys Asp Trp Thr Lys Arg Pro Ala Thr Thr Val Pro Cys
    1460                1465                1470

Asn Arg His Leu Cys Cys His Trp Ala Thr Gly Asn Trp Glu Leu
    1475                1480                1485

Cys Asn Thr Ser Cys Gly Gly Ser Gln Lys Arg Thr Ile His
    1490                1495                1500

Cys Ile Pro Ser Glu Asn Ser Thr Thr Glu Asp Gln Asp Gln Cys
    1505                1510                1515

Leu Cys Asp His Gln Val Lys Pro Pro Glu Phe Gln Thr Cys Asn
    1520                1525                1530

Gln Gln Ala Cys Arg Lys Ser Ala Asp Leu Thr Cys Leu Lys Asp
    1535                1540                1545

Arg Leu Ser Ile Ser Phe Cys Gln Thr Leu Lys Ser Met Arg Lys
    1550                1555                1560

Cys Ser Val Pro Ser Val Arg Ala Gln Cys Cys Leu Ser Cys Pro
    1565                1570                1575

Gln Ala Pro Ser Ile His Thr Gln Arg Gln Arg Lys Gln Gln Leu
    1580                1585                1590

Leu Gln Asn His Asp Met Leu
    1595                1600

<210> SEQ ID NO 27
<211> LENGTH: 202
<212> TYPE: PRT
<213> ORGANISM: Artificial Sequence
<220> FEATURE:
<223> OTHER INFORMATION: Human ADAMTS7 Pro Domain (hADAMTS7_Pro)

<400> SEQUENCE: 27

Arg Ala Thr Glu Gly Arg Ala Ala Leu Asp Ile Val His Pro Val Arg
1               5                   10                  15

Val Asp Ala Gly Gly Ser Phe Leu Ser Tyr Glu Leu Trp Pro Arg Ala
                20                  25                  30

Leu Arg Lys Arg Asp Val Ser Val Arg Arg Asp Ala Pro Ala Phe Tyr
            35                  40                  45

Glu Leu Gln Tyr Arg Gly Arg Glu Leu Arg Phe Asn Leu Thr Ala Asn
        50                  55                  60

Gln His Leu Leu Ala Pro Gly Phe Val Ser Glu Thr Arg Arg Arg Gly
65                  70                  75                  80

Gly Leu Gly Arg Ala His Ile Arg Ala His Thr Pro Ala Cys His Leu
                85                  90                  95

Leu Gly Glu Val Gln Asp Pro Leu Glu Gly Leu Ala Ala Ile
            100                 105                 110
```

Ser Ala Cys Asp Gly Leu Lys Gly Val Phe Gln Leu Ser Asn Glu Asp
            115                 120                 125

Tyr Phe Ile Glu Pro Leu Asp Ser Ala Pro Ala Arg Pro Gly His Ala
    130                 135                 140

Gln Pro His Val Val Tyr Lys Arg Gln Ala Pro Glu Arg Leu Ala Gln
145                 150                 155                 160

Arg Gly Asp Ser Ser Ala Pro Ser Thr Cys Gly Val Gln Val Tyr Pro
                165                 170                 175

Glu Leu Glu Ser Arg Arg Glu Arg Trp Glu Gln Arg Gln Trp Arg
                180                 185                 190

Arg Pro Arg Leu Arg Arg Leu His Gln Arg
        195                 200

<210> SEQ ID NO 28
<211> LENGTH: 193
<212> TYPE: PRT
<213> ORGANISM: Artificial Sequence
<220> FEATURE:
<223> OTHER INFORMATION: Rat ADAMTS7 Pro Domain (rADAMTS7_Pro)

<400> SEQUENCE: 28

Leu Pro Thr Glu Gly Arg Ala Gly Leu Asp Ile Val His Pro Val Arg
1               5                   10                  15

Val Asp Ala Gly Gly Ser Phe Leu Ser Tyr Glu Leu Trp Pro Arg Val
            20                  25                  30

Leu Arg Lys Arg Asp Val Ser Ala Ala Gln Ala Ser Ser Ala Phe Tyr
        35                  40                  45

Gln Leu Gln Tyr Gln Gly Arg Glu Leu Leu Phe Asn Leu Thr Thr Asn
    50                  55                  60

Pro Tyr Leu Leu Ala Pro Gly Phe Val Ser Glu Ile Arg Arg Arg Ser
65                  70                  75                  80

Asn Leu Ser Asn Val His Ile Gln Thr Ser Val Pro Thr Cys His Leu
                85                  90                  95

Leu Gly Asp Val Gln Asp Pro Glu Leu Glu Gly Gly Phe Ala Ala Ile
            100                 105                 110

Ser Ala Cys Asp Gly Leu Arg Gly Val Phe Gln Leu Ser Asn Glu Asp
        115                 120                 125

Tyr Phe Ile Glu Pro Leu Asp Glu Val Pro Ala Gln Pro Gly His Ala
    130                 135                 140

Gln Pro His Met Val Tyr Lys His Lys Arg Ser Gly Gln Asp Asp
145                 150                 155                 160

Ser Arg Thr Ser Gly Thr Cys Gly Val Gln Gly Ser Pro Glu Leu Lys
                165                 170                 175

His Gln Arg Glu His Trp Glu Arg Gln Lys Arg Arg Gln Gln
            180                 185                 190

Arg

<210> SEQ ID NO 29
<211> LENGTH: 301
<212> TYPE: PRT
<213> ORGANISM: Artificial Sequence
<220> FEATURE:
<223> OTHER INFORMATION: Human ADAMTS7 CD domain (hADAMTS7_CD)

<400> SEQUENCE: 29

Ser Val Ser Lys Glu Lys Trp Val Glu Thr Leu Val Val Ala Asp Ala
1               5                   10                  15

Lys Met Val Glu Tyr His Gly Gln Pro Gln Val Glu Ser Tyr Val Leu
            20                  25                  30

Thr Ile Met Asn Met Val Ala Gly Leu Phe His Asp Pro Ser Ile Gly
            35                  40                  45

Asn Pro Ile His Ile Thr Ile Val Arg Leu Val Leu Leu Glu Asp Glu
    50                  55                  60

Glu Glu Asp Leu Lys Ile Thr His His Ala Asp Asn Thr Leu Lys Ser
65                  70                  75                  80

Phe Cys Lys Trp Gln Lys Ser Ile Asn Met Lys Gly Asp Ala His Pro
                85                  90                  95

Leu His His Asp Thr Ala Ile Leu Leu Thr Arg Lys Asp Leu Cys Ala
            100                 105                 110

Ala Met Asn Arg Pro Cys Glu Thr Leu Gly Leu Ser His Val Ala Gly
            115                 120                 125

Met Cys Gln Pro His Arg Ser Cys Ser Ile Asn Glu Asp Thr Gly Leu
            130                 135                 140

Pro Leu Ala Phe Thr Val Ala His Glu Leu Gly His Ser Phe Gly Ile
145                 150                 155                 160

Gln His Asp Gly Ser Gly Asn Asp Cys Glu Pro Val Gly Lys Arg Pro
                165                 170                 175

Phe Ile Met Ser Pro Gln Leu Leu Tyr Asp Ala Ala Pro Leu Thr Trp
            180                 185                 190

Ser Arg Cys Ser Arg Gln Tyr Ile Thr Arg Phe Leu Asp Arg Gly Trp
            195                 200                 205

Gly Leu Cys Leu Asp Asp Pro Pro Ala Lys Asp Ile Ile Asp Phe Pro
210                 215                 220

Ser Val Pro Pro Gly Val Leu Tyr Asp Val Ser His Gln Cys Arg Leu
225                 230                 235                 240

Gln Tyr Gly Ala Tyr Ser Ala Phe Cys Glu Asp Met Asp Asn Val Cys
                245                 250                 255

His Thr Leu Trp Cys Ser Val Gly Thr Thr Cys His Ser Lys Leu Asp
            260                 265                 270

Ala Ala Val Asp Gly Thr Arg Cys Gly Glu Asn Lys Trp Cys Leu Ser
            275                 280                 285

Gly Glu Cys Val Pro Val Gly Phe Arg Pro Glu Ala Val
            290                 295                 300

<210> SEQ ID NO 30
<211> LENGTH: 302
<212> TYPE: PRT
<213> ORGANISM: Artificial Sequence
<220> FEATURE:
<223> OTHER INFORMATION: Rat ADAMTS7 CD domain (rADAMTS7_CD)

<400> SEQUENCE: 30

Ser Ile Ser Lys Glu Lys Trp Val Glu Thr Leu Val Val Ala Asp Ser
1               5                   10                  15

Lys Met Val Glu Tyr His Gly Gln Pro Gln Val Glu Ser Tyr Val Leu
            20                  25                  30

Thr Ile Met Asn Met Val Ala Gly Leu Tyr His Asp Pro Ser Ile Gly
            35                  40                  45

Asn Pro Ile His Ile Thr Val Val Arg Leu Ile Ile Leu Glu Asp Glu
    50                  55                  60

Glu Lys Asp Leu Lys Ile Thr His His Ala Asp Asp Thr Leu Lys Asn
65                  70                  75                  80

```
Phe Cys Arg Trp Gln Lys Asn Val Asn Met Lys Gly Asp Asp His Pro
                85                  90                  95

Gln His His Asp Thr Ala Ile Leu Leu Thr Arg Lys Asp Leu Cys Ala
            100                 105                 110

Thr Met Asn His Pro Cys Glu Thr Leu Gly Leu Ser His Val Ala Gly
            115                 120                 125

Leu Cys His Pro Gln Leu Ser Cys Ser Val Ser Glu Asp Thr Gly Leu
        130                 135                 140

Pro Leu Ala Phe Thr Val Ala His Glu Leu Gly His Ser Phe Gly Ile
145                 150                 155                 160

Gln His Asp Gly Thr Gly Asn Asp Cys Glu Ser Ile Gly Lys Arg Pro
                165                 170                 175

Phe Ile Met Ser Pro Gln Leu Leu Tyr Asp Arg Gly Ile Pro Leu Thr
            180                 185                 190

Trp Ser Arg Cys Ser Arg Glu Tyr Ile Thr Arg Phe Leu Asp Arg Gly
            195                 200                 205

Trp Gly Leu Cys Leu Asp Asp Arg Pro Ser Lys Gly Val Ile Asn Phe
        210                 215                 220

Pro Ser Val Leu Pro Gly Val Leu Tyr Asp Val Asn His Gln Cys Arg
225                 230                 235                 240

Leu Gln Tyr Gly Pro Ser Ser Ala Tyr Cys Glu Asp Val Asp Asn Val
                245                 250                 255

Cys Tyr Thr Leu Trp Cys Ser Val Gly Thr Thr Cys His Ser Lys Met
            260                 265                 270

Asp Ala Ala Val Asp Gly Thr Ser Cys Gly Lys Asn Lys Trp Cys Leu
        275                 280                 285

Asn Gly Glu Cys Val Pro Glu Gly Phe Gln Pro Glu Thr Val
290                 295                 300

<210> SEQ ID NO 31
<211> LENGTH: 562
<212> TYPE: PRT
<213> ORGANISM: Artificial Sequence
<220> FEATURE:
<223> OTHER INFORMATION: rPro-hCD (Rat 1-217/Human 237-537
      (R58A/R60A/R217A))-TEV-2Strep-6His

<400> SEQUENCE: 31

Met His Arg Gly Leu Asn Leu Leu Ile Leu Cys Ala Leu Ala Pro
1               5                   10                  15

His Val Leu Gly Pro Ala Ser Gly Leu Pro Thr Glu Gly Arg Ala Gly
            20                  25                  30

Leu Asp Ile Val His Pro Val Arg Val Asp Ala Gly Gly Ser Phe Leu
        35                  40                  45

Ser Tyr Glu Leu Trp Pro Arg Val Leu Ala Lys Ala Asp Val Ser Ala
    50                  55                  60

Ala Gln Ala Ser Ser Ala Phe Tyr Gln Leu Gln Tyr Gln Gly Arg Glu
65                  70                  75                  80

Leu Leu Phe Asn Leu Thr Thr Asn Pro Tyr Leu Leu Ala Pro Gly Phe
                85                  90                  95

Val Ser Glu Ile Arg Arg Arg Ser Asn Leu Ser Asn Val His Ile Gln
            100                 105                 110

Thr Ser Val Pro Thr Cys His Leu Leu Gly Asp Val Gln Asp Pro Glu
        115                 120                 125

Leu Glu Gly Gly Phe Ala Ala Ile Ser Ala Cys Asp Gly Leu Arg Gly
    130                 135                 140
```

```
Val Phe Gln Leu Ser Asn Glu Asp Tyr Phe Ile Glu Pro Leu Asp Glu
145                 150                 155                 160

Val Pro Ala Gln Pro Gly His Ala Gln Pro His Met Val Tyr Lys His
            165                 170                 175

Lys Arg Ser Gly Gln Gln Asp Asp Ser Arg Thr Ser Gly Thr Cys Gly
            180                 185                 190

Val Gln Gly Ser Pro Glu Leu Lys His Gln Arg Glu His Trp Glu Gln
            195                 200                 205

Arg Gln Gln Lys Arg Arg Gln Gln Ala Ser Val Ser Lys Glu Lys Trp
        210                 215                 220

Val Glu Thr Leu Val Val Ala Asp Ala Lys Met Val Glu Tyr His Gly
225                 230                 235                 240

Gln Pro Gln Val Glu Ser Tyr Val Leu Thr Ile Met Asn Met Val Ala
                245                 250                 255

Gly Leu Phe His Asp Pro Ser Ile Gly Asn Pro Ile His Ile Thr Ile
                260                 265                 270

Val Arg Leu Val Leu Leu Glu Asp Glu Glu Asp Leu Lys Ile Thr
            275                 280                 285

His His Ala Asp Asn Thr Leu Lys Ser Phe Cys Lys Trp Gln Lys Ser
290                 295                 300

Ile Asn Met Lys Gly Asp Ala His Pro Leu His His Asp Thr Ala Ile
305                 310                 315                 320

Leu Leu Thr Arg Lys Asp Leu Cys Ala Ala Met Asn Arg Pro Cys Glu
            325                 330                 335

Thr Leu Gly Leu Ser His Val Ala Gly Met Cys Gln Pro His Arg Ser
            340                 345                 350

Cys Ser Ile Asn Glu Asp Thr Gly Leu Pro Leu Ala Phe Thr Val Ala
            355                 360                 365

His Glu Leu Gly His Ser Phe Gly Ile Gln His Asp Gly Ser Gly Asn
        370                 375                 380

Asp Cys Glu Pro Val Gly Lys Arg Pro Phe Ile Met Ser Pro Gln Leu
385                 390                 395                 400

Leu Tyr Asp Ala Ala Pro Leu Thr Trp Ser Arg Cys Ser Arg Gln Tyr
                405                 410                 415

Ile Thr Arg Phe Leu Asp Arg Gly Trp Gly Leu Cys Leu Asp Asp Pro
            420                 425                 430

Pro Ala Lys Asp Ile Ile Asp Phe Pro Ser Val Pro Pro Gly Val Leu
            435                 440                 445

Tyr Asp Val Ser His Gln Cys Arg Leu Gln Tyr Gly Ala Tyr Ser Ala
            450                 455                 460

Phe Cys Glu Asp Met Asp Asn Val Cys His Thr Leu Trp Cys Ser Val
465                 470                 475                 480

Gly Thr Thr Cys His Ser Lys Leu Asp Ala Ala Val Asp Gly Thr Arg
            485                 490                 495

Cys Gly Glu Asn Lys Trp Cys Leu Ser Gly Glu Cys Val Pro Val Gly
            500                 505                 510

Phe Arg Pro Glu Ala Val Gly Ser Glu Asn Leu Tyr Phe Gln Ser Gly
            515                 520                 525

Trp Ser His Pro Gln Phe Glu Lys Gly Gly Gly Ser Gly Gly Gly Ser
        530                 535                 540

Gly Gly Gly Ser Trp Ser His Pro Gln Phe Glu Lys His His His His
545                 550                 555                 560
```

His His

<210> SEQ ID NO 32
<211> LENGTH: 196
<212> TYPE: PRT
<213> ORGANISM: Artificial Sequence
<220> FEATURE:
<223> OTHER INFORMATION: Mouse ADAMTS-7 prodomain (Mouse_Pro)

<400> SEQUENCE: 32

```
Leu Val Thr Glu Gly Arg Ala Gly Leu Asp Ile Val His Pro Val Arg
1               5                   10                  15

Val Asp Ala Gly Gly Ser Phe Leu Ser Tyr Glu Leu Trp Pro Arg Val
            20                  25                  30

Leu Arg Lys Arg Asp Val Ser Thr Thr Gln Ala Ser Ser Ala Phe Tyr
        35                  40                  45

Gln Leu Gln Tyr Gln Gly Arg Glu Leu Leu Phe Asn Leu Thr Thr Asn
    50                  55                  60

Pro Tyr Leu Met Ala Pro Gly Phe Val Ser Glu Ile Arg Arg His Ser
65                  70                  75                  80

Thr Leu Gly His Ala His Ile Gln Thr Ser Val Pro Thr Cys His Leu
                85                  90                  95

Leu Gly Asp Val Gln Asp Pro Glu Leu Glu Gly Gly Phe Ala Ala Ile
            100                 105                 110

Ser Ala Cys Asp Gly Leu Arg Gly Val Phe Gln Leu Ser Asn Glu Asp
        115                 120                 125

Tyr Phe Ile Glu Pro Leu Asp Gly Val Ser Ala Gln Pro Gly His Ala
    130                 135                 140

Gln Pro His Val Val Tyr Lys His Gln Gly Ser Arg Lys Gln Ala Gln
145                 150                 155                 160

Gln Gly Asp Ser Arg Pro Ser Gly Thr Cys Gly Met Gln Val Pro Pro
                165                 170                 175

Asp Leu Glu Gln Gln Arg Glu His Trp Glu Gln Gln Gln Gln Lys Arg
            180                 185                 190

Arg Gln Gln Arg
        195
```

<210> SEQ ID NO 33
<211> LENGTH: 45
<212> TYPE: PRT
<213> ORGANISM: Artificial Sequence
<220> FEATURE:
<223> OTHER INFORMATION: TSP-1 candidate region

<400> SEQUENCE: 33

```
Cys Asp Glu Leu Ser Ser Met Val Leu Glu Leu Arg Gly Leu Arg Thr
1               5                   10                  15

Ile Val Thr Thr Leu Gln Asp Ser Ile Arg Lys Val Thr Glu Glu Asn
            20                  25                  30

Lys Glu Leu Ala Asn Glu Leu Arg Arg Pro Pro Leu Cys
        35                  40                  45
```